United States Patent
Kiyama et al.

(10) Patent No.: US 9,572,813 B2
(45) Date of Patent: *Feb. 21, 2017

(54) ANTIVIRAL AGENT

(71) Applicant: SHIONOGI & CO., LTD., Osaka (JP)

(72) Inventors: Ryuichi Kiyama, Osaka (JP); Yasuhiko Kanda, Osaka (JP); Yukio Tada, Osaka (JP); Toshio Fujishita, Osaka (JP); Takashi Kawasuji, Osaka (JP); Shozo Takechi, Osaka (JP); Masahiro Fuji, Osaka (JP)

(73) Assignee: Shionogi & Co., Ltd., Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/603,979

(22) Filed: Jan. 23, 2015

(65) Prior Publication Data

US 2015/0202208 A1    Jul. 23, 2015

Related U.S. Application Data

(63) Continuation of application No. 10/485,394, filed as application No. PCT/JP02/08108 on Aug. 8, 2002.

(30) Foreign Application Priority Data

Aug. 10, 2001 (JP) ............................ 2001-245071
Dec. 5, 2001 (JP) ............................ 2001-370860
Jun. 28, 2002 (JP) ............................ 2002-191483

(51) Int. Cl.
*A61K 31/4015* (2006.01)
*A61K 31/4412* (2006.01)
*A61K 31/351* (2006.01)
*A61K 31/37* (2006.01)
*A61K 31/341* (2006.01)
(Continued)

(52) U.S. Cl.
CPC ......... *A61K 31/5377* (2013.01); *A61K 31/351* (2013.01); *A61K 31/4025* (2013.01); *A61K 31/4155* (2013.01); *A61K 31/4178* (2013.01); *A61K 31/4196* (2013.01); *A61K 31/422* (2013.01); *A61K 31/427* (2013.01); *A61K 31/4245* (2013.01); *A61K 31/433* (2013.01); *A61K 31/4427* (2013.01); *A61K 31/4433* (2013.01); *A61K 31/4439* (2013.01); *A61K 31/4709* (2013.01); *A61K 31/497* (2013.01); *A61K 31/501* (2013.01); *A61K 31/506* (2013.01); *A61K 31/513* (2013.01); *A61K 31/53* (2013.01); *C07D 207/38* (2013.01); *C07D 307/46* (2013.01); *C07D 401/04* (2013.01); *C07D 403/04* (2013.01); *C07D 403/06* (2013.01); *C07D 405/04* (2013.01); *C07D 405/06* (2013.01); *C07D 407/06* (2013.01); *C07D 409/06* (2013.01); *C07D 413/04* (2013.01); *C07D 413/06* (2013.01); *C07D 417/04* (2013.01); *C07D 417/06* (2013.01)

(58) Field of Classification Search
None
See application file for complete search history.

(56) References Cited

U.S. PATENT DOCUMENTS 6,333,323 B1   12/2001  Fujishita et al.
7,148,237 B2   12/2006  Fuji et al.
(Continued)

FOREIGN PATENT DOCUMENTS

EP    1 142 872    10/2001
EP    1 441 735     2/2006
(Continued)

OTHER PUBLICATIONS (J. G. Cannon, Chapter Nineteen in Burger's Medicinal Chemistry and Drug Discovery, Fifth Edition, vol. I: Principles and Practice, Wiley-Interscience 1995, pp. 783-802).*

(Continued)

*Primary Examiner* — Marcos Sznaidman
*Assistant Examiner* — Rayna B Rodriguez
(74) *Attorney, Agent, or Firm* — Morrison & Foerster LLP

(57) ABSTRACT

The present invention provides an integrase inhibitor. The inventors have found the following compound of formula (I) possessing an integrase inhibitory activity.

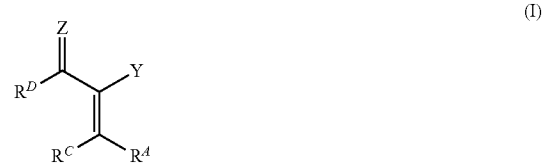

(I)

(wherein, $R^C$ and $R^D$ taken together with the neighboring carbon atoms form a ring which may be a condensed ring, Y is hydroxyl, mercapto or amino; Z is O, S or NH; $R^A$ is a group shown by

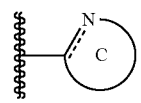

(wherein, C ring is N-containing aromatic heterocycle) or the like).

11 Claims, No Drawings

(51) Int. Cl.

| | |
|---|---|
| *A61K 31/5377* | (2006.01) |
| *A61K 31/4025* | (2006.01) |
| *A61K 31/4155* | (2006.01) |
| *A61K 31/4178* | (2006.01) |
| *A61K 31/422* | (2006.01) |
| *A61K 31/4245* | (2006.01) |
| *A61K 31/427* | (2006.01) |
| *A61K 31/433* | (2006.01) |
| *A61K 31/4427* | (2006.01) |
| *A61K 31/4433* | (2006.01) |
| *A61K 31/4439* | (2006.01) |
| *A61K 31/4709* | (2006.01) |
| *A61K 31/497* | (2006.01) |
| *A61K 31/501* | (2006.01) |
| *A61K 31/506* | (2006.01) |
| *A61K 31/53* | (2006.01) |
| *C07D 207/38* | (2006.01) |
| *C07D 307/46* | (2006.01) |
| *C07D 401/04* | (2006.01) |
| *C07D 403/04* | (2006.01) |
| *C07D 403/06* | (2006.01) |
| *C07D 405/04* | (2006.01) |
| *C07D 405/06* | (2006.01) |
| *C07D 407/06* | (2006.01) |
| *C07D 409/06* | (2006.01) |
| *C07D 413/04* | (2006.01) |
| *C07D 413/06* | (2006.01) |
| *C07D 417/04* | (2006.01) |
| *C07D 417/06* | (2006.01) |
| *A61K 31/4196* | (2006.01) |
| *A61K 31/513* | (2006.01) |

(56) References Cited

U.S. PATENT DOCUMENTS

| | | | |
|---|---|---|---|
| 7,576,198 | B1 | 8/2009 | Kawasuji et al. |
| 7,745,453 | B2 | 6/2010 | Mikamiyama et al. |
| 2002/0019434 | A1 | 2/2002 | Fujishita et al. |
| 2003/0181499 | A1 | 9/2003 | Fujishita et al. |
| 2004/0039060 | A1 | 2/2004 | Kiyama et al. |
| 2004/0229909 | A1 | 11/2004 | Kiyama et al. |
| 2005/0025774 | A1 | 2/2005 | Crescenzi et al. |
| 2010/0068695 | A1 | 3/2010 | Kiyama et al. |

FOREIGN PATENT DOCUMENTS

| | | |
|---|---|---|
| EP | 1 422 218 | 3/2012 |
| GB | 2 345 058 | 6/2000 |
| JP | 6-100445 | 4/1994 |
| JP | 2001-270884 | 10/2001 |
| WO | WO-92/06954 | 4/1992 |
| WO | WO-98/11889 | 3/1998 |
| WO | WO-99/50245 | 10/1999 |
| WO | WO-99/62513 | 12/1999 |
| WO | WO-99/62520 | 12/1999 |
| WO | WO-99/62897 | 12/1999 |
| WO | WO-00/39086 | 7/2000 |
| WO | WO-01/00578 | 1/2001 |
| WO | WO-01/17968 | 3/2001 |
| WO | WO-01/95905 | 12/2001 |
| WO | WO-02/30426 | 4/2002 |
| WO | WO-02/30930 | 4/2002 |
| WO | WO-02/30931 | 4/2002 |
| WO | WO-02/36734 | 5/2002 |
| WO | WO-02/070486 | 9/2002 |
| WO | WO-02/070491 | 9/2002 |
| WO | WO-03/016275 | 2/2003 |
| WO | WO-03/030897 | 4/2003 |
| WO | WO-03/035076 | 5/2003 |
| WO | WO-03/035077 | 5/2003 |
| WO | WO-2004/004657 | 1/2004 |
| WO | WO-2005/074513 | 8/2005 |
| WO | WO-2012/151567 | 11/2012 |

OTHER PUBLICATIONS

Agrawal et al., "Probing chelation motifs in HIV integrase inhibitors," PNAS (2012) 109(7):2251-2256.

Al-Mawsasi et al., "Allosteric Inhibitor Development Targeting HIV-1 Integrase," Chem. Med. Chem. (2011) 6:228-241.

Andreichlkov et al., "Five-Membered 2,3-Dioxoheterocycles XVI. Synthesis of 1,4-Disubstituted 5-Aryltetrahydropyrrole-2,3-Diones Based on the Reaction of Diethoxalylacetone with Azomethines," Perm Pharmaceutical Institute, pp. 2238-2243, translated from Zh. Org. Khim. (1989) 25(12):2494-2500.

Annex to the communication Opposition issued Jun. 18, 2014 in corresponding European Patent Application No. 02 749 384.

Balzarini et al., "Concomitant combination therapy for HIV infection preferable over sequential therapy with 3TC and non-nucleoside reverse transcriptase inhibitors," Proc. Natl. Acad. Sci. USA (1996) 93:13152-13157.

Betail et al., "Induction of antinuclear antibodies. Study of new molecules with a hydrazine structure or their analogs in mice," Ann. Pharm. Fr. (1978) 36(7-8):317-322.

Boers et al., "Synthesis and antiviral activity of 7-O-(ω-substituted)-alkyl-3-O-methyl-quercetin derivatives," Pharmazie (1998) 53(8):512-517.

Botta et al., "Researches on Antiviral Agents. 4[1]. Studies on the Chemistry of 6-Mehtyl-2-methoxy-4-O-acyloxy and 6-Methyl-2,4-di-O-acyloxypyrimidine Derivatives as New Acylation Reagents and Inhibitors of Uracil DNA Glycosylases," Tetrahedron (1994) 50(11):3603-3618.

Chanh et al., "Pharmacological Aspects of Pyrazoline Derivatives from 2-Hydroxy-butenolides," Arzneim.-Forsch. (Drug Res.) (1976) 26(11):2050-2052.

Cohen et al., "The spread, treatment, and prevention of HIV-1: evolution of a global pandemic," The Journal of Clinical Investigation (2008) 118(4):1244-1254.

Database CA Chemical Abstracts (STN accession No. 1978:169921) [abstract of Hsu et al., "Synthesis of 2-(2-quinolyl) chromone derivatives," Taiwan Kexue (1977) 31(3-4):130-135.

DeJong et al., "Adenovirus DNA replication: protein priming, jumping back and the role of the DNA binding protein DBP," Current Topics in Microbiology and Immunology (2003) 272:187-211.

Delelis et al., "Integrase and integration: biochemical activities of HIV-1 integrase," Retrovirology (2008) 5:114, 13 pages.

Elben et al., "'Cryptomycins'—Crown Ether Analogues of the Actinomycins," J. Chem. Research (S) (1978) 316-317.

European Patent Office Communication dated Feb. 24, 2009 in European Patent Application No. 02 749 384.0 corresponding to the present application.

European Search Report for EP 09177978.5, issued Mar. 24, 2010, 5 pages.

Fukai et al., "Cytotoxic Activity of Low Molecular Weight Polyphenols against Human Oral Tumor Cell Lines," Anitcancer Research (2000) 20:2525-2536.

Gein et al., "Synthesis of 4-substituted 1-methyl-5-aryl- and 1,5-diaryltetrahydropyrrole-2,3-diones and their antiviral action," Pharmaceutical Chemistry Journal (1991) 25(12):884-887.

Goldgur et al., "Structure of the HIV-1 integrase catalytic domain complexed with an inhibitor: A platform for antiviral drug design," PNAS (1999) 96(23):13040-13043.

Grobler et al., "Diketo acid inhibitor mechanism and HIV-1 integrase: Implications for metal binding in the active site of phosphotransferase enzymes," PNAS (2002) 99(10):6661-6666.

Grounds of Opposition issued Dec. 21, 2012 in corresponding European Application No. 02749384.0.

Hazuda et al., "Discovery and Analysis of Inhibitors of the Human Immunodeficiency Integrase," Drug Design and Discovery (1997) 15:17-24.

(56) References Cited

OTHER PUBLICATIONS

Hazuda et al., "Inhibitors of Strand Transfer That Prevent Integration and Inhibit HIV-1 Replication in Cells," Science (2000) 287:646-650.
Hesketh et al., "Regulatory signals in messenger RNA: determinants of nutrient-gene interaction and metabolic compartmentation," British Journal of Nutrition (1998) 80:307-321.
Hsu et al., "Synthesis of 2-(2-Quinolyl) Chromone Derivatives," T'ai-wan K'o Hsueh (1977) 31(3-4):130-135.
Interlocutory decision in Opposition proceedings (Art. 101(3)(a) and 106(2) EPC) for EP 02 749 384.0, issued Mar. 31, 2015, 17 pages.
International Search Report for PCT/JP02/08108, mailed Oct. 1, 2002, 4 pages.
Kadin, "Synthesis and Antiinflammatory Properties of N-Substituted 4,5-Dioxopyrrolidine-3-carboxanilides," Journal of Medicinal Chemistry (1976) 19(1):172-173.
Kanda et al., "Human papillomavirus and cervical cancer," Uirusu (2006) 56(2):219-230, PubMed abstract 17446671.
Kawasuji et al., "3-Hydroxy-1,5-dihydro-pyrrol-2-one derivatives as advanced inhibitors of HIV integrase," Bioorganic & Medicinal Chemistry (2007) 15:5487-5492.
Kawasuji et al., "Carbamoyl Pyridone HIV-1 Intergrase Inhibitors. 1. Molecular Design and Establishment of an Advanced Two-Metal Binding Pharmacophore," Journal of Medicinal Chemistry (2012) 55:8735-8744.
Lopez et al., "Solution and solid state (CPMAS) NMR studies of the tautomerism of six-membered heterocyclic compounds related to 2-pyridones," Spectroscopy (2000) 14:121-126.
Luke et al., "Properties of the OH Adducts of Hydroxy-, Methyl-, Methoxy-, and Amino-Substituted Pyrimidines: Their Dehydration Reactions and End-Product Analysis," J. Phys. Chem. A. (2002) 106:2497-2504.
Meragelman et al., "Anti-HIV Prenylated Flavonoids from Monotes africanus," J. Nat. Prod. (2001) 64:546-548.
Neamati, "Structure-based HIV-1 integrase inhibitor design: a future perspective," Exp. Opin. Invest. Drugs (2001) 10(2):281-296.
Nizi et al., "Solid Phase Synthesis of 2,6-Disubstituted-4(3H)-pyrimidinones Targeting HIV-1 Reverse Transcriptase," Tetrahedron Letters (1998) 39:3307-3310.
Notice of Opposition issued Dec. 21, 2012 in corresponding European Application No. 02749384.0.
Pace et al., "Dihydroxypyrimidine-4-carboxamides as Novel Potent and Selective HIV Integrase Inhibitors," J. Med. Chem. (2007) 50:2225-2239.
Pauwels et al., "Rapid and automated tetrazolium-based colorimetric assay for the detection of anti-HIV compounds," Journal of Virological Methods (1988) 20:309-321.
Petrocchi et al., "From dihydroxypyrimidine carboxylic acids to carboxamide HIV-1 integrase inhibitors: SAR around the amide moiety," Bioorganic & Medicinal Chemistry Letters (2007) 17:350-353.
Pyrimidine—IUPAC Gold Book 1995.
Reply of the Patent Proprietor to the Notice of Opposition issued Jun. 28, 2013 in corresponding European U.S. Pat. No. 1 422 218.
Response to Patentee's Observations Filed on behalf of Merck & Co., Inc. against European U.S. Pat. No. 1 422 218 (2013).
Rooney et al., "Inhibitors of Glycolic Acid Oxidase. 4-substututed 3-Hydroxy-1H-pyrrole-2,5-dione Derivatives," J. Med. Chem. (1983) 26:700-714.
Schafer et al., "Failure is an option: learning from unsuccessful proof-of-concept trials," Drug Discovery Today (2008) 13(21/22):913-916.
Silhankova et al., "Condensation Reactions of 2,4- and 2,6-Dimethylpyridines and their 1-Oxides," Collect. Czech. Chem. Commun. (1989) 54:1687-1704.
Skylarova et al., "Synthesis of Actinomycin Analogs. XVII. Actinocin Amides Containing Benzimidazole Fragments," Lensovet Leningrad Technological Institute, pp. 169-171, translated from Zh. Org. Khim. (1989) 25(1):186-189.
Sofan, "Synthesis of some new pyrrolo heterocycles: condensation of 4-carbomethoxy-1-methyl-2,3-dioxopyrrolidine with primary amines," Pharmazie (1997) 52(4):276-278.
Summa et al., "4,5-Dihydroxypyrimidine Carboxamides and N-Alkyl-5-hydroxypyrimidinone Carboxamides Are Potent, Selective HIV Integrase Inhibitors with Good Pharmacokinetic Profiles in Preclinical Species," J. Med. Chem. (2006) 49:6646-6649.
Sunderland et al., "6-Carboxamido-5,4-Hydroxypyrimidinones: A New Class of Heterocyclic Ligands and Their Evaluation as Gadolinium Chelating Agents," Inorg. Chem. (2001) 40:6746-6756.
Wai et al., "Dihydroxypyridopyrazine-1,6-dione HIV-1 integrase inhibitors," Bioorganic & Medicinal Chemistry Letters (2007) 17:5595-5599.
Sugden et al., "Antiinflammatory activity of some N-substituted-3-carboxamido-4-hydroxy-5-oxo-3-pyrrolines," Eur. J. Med. Chem. (1997) 14(2):189-190.
Additional Data for Compound D-9 for EP 1 422 218, dated Jun. 28, 2013.
Appendices 1 to 8, re EP 1 422 218, dated Mar. 3, 2015.
Assay results (Mouse MT4, MWPA Mg(nM), MTT) of Compounds C-31-b, B12-b, B29-b, B29-c and X3, re EP 1 422 218, dated Dec. 28, 2015.
Assay results (Potency Shift in presence of %HSA) for Compounds B-29-b, B29-c, E-16, A-141-g, E-24, E-26, E-37-b, X-3, and X-14, re EP 1 422 218, dated Dec. 28, 2015.
Assay results, re EP 1 422 218, dated Dec. 28, 2015.
Cheng et al., "Structure-based maximal affinity model predicts small-molecule druggability," Nat Biotechnol (2007) 25(1):71-75.
Consolidated list of compounds of formula (1), re EP 1 422 218, dated Feb. 12, 2015.
Corrected 'Table A' Data using the MWPA Mn Method for EP 1 422 218, dated Jun. 28, 2013.
Declaration and Curriculum Vita for Jay A. Grobler, re EP 1 422 218, dated Jan. 27, 2014.
Declaration and Curriculum Vita for John A. McCauley re EP 1 422 218, dated Jan. 27, 2014.
Declaration and Curriculum Vita for Nouri Neamati, re EP 1 422 218, Aug. 10, 2015.
Declaration of Yoshinaga, under 37 CFR 1.132, re U.S. Appl. No. 10/485,394 dated Aug. 5, 2014, 17 pages.
Declaration of Yoshinaga, under 37 CFR 1.132, re U.S. Appl. No. 10/485,394 dated Oct. 4, 2013, 7 pages.
Dicker et al., "Simple and accurate In Vitro method for predicting serum protein binding of HIV integrase strand transfer inhibitors" in: HIV-1 Integrase Mechanism and Inhibitor Design, First Edition, Neamati (ed.) John Wiley & Sons Inc. (2011) Ch.19, pp. 275-286.
Egbertson et al., "HIV integrase inhibitors: From diketo acids to heterocyclic templates: History of HIV integrase medicinal chemistry at Merck West Point and Merck Rome (IRBM)Leading to discovery of raltegravir," HIV-I Integrase: Mechanism and Inhibitor Design, First Edition, Neamati (ed.) John Wiley & Sons Inc. (2011) Ch.14, pp. 197-229.
Hare et al., "Retroviral intasome assembly and inhibition of DNA strand transfer," Nature (2010) 464(7286):232-236.
Highlights of Prescribing Information for STRIBILD (elvitegravir), US Approval 2012, 48 pages.
Highlights of Prescribing Information for TIVICAY (dolutegravir), US Approval 2013, 37 pages.
Highlights of Prescribing Information for ISENTRESS (Raltegravir) US Approval 2007, 23 pages.
Presentation Material in relation to in-vitro and in-vivo activity of FUMDIP, re EP 1 422 218, dated Dec. 28, 2015.
Statement of grounds for Appeal for EP 1 422 218, dated Aug. 10, 2015, 20 pages.
Reply to Appeal for EP 1 422 218, dated Dec. 28, 2015, 26 pages.
Sato et al., "A simple and rapid method for preliminary evaluation of in vivo efficacy of anti-HIV compounds in mice," Antiviral Res (1995) 27(1-2):151-163.
Sato et al "Evaluation of an SIV-infected rhesus monkey model via integrase inhibition" Dec. 28, 2015 (Abstract).
Table B—Data using the 'MWPA-Mg (nM) Method' for EP 1 422 218, dated Jun. 28, 2013.

(56) References Cited

OTHER PUBLICATIONS

Table C Data using the 'MWPA-Mg (nM) Method' for EP 1 422 218, dated Jun. 28, 2013.
Takashi et al., "3-Hydroxy-1,5-dihydro-pyrrol-2-one derivatives as advanced inhibitors of HIV integrase," Bioorganic & Medicinal Chemistry, (2007) 15:5487-5492.
Yoshinaga et al., "Antiviral characteristics of GSK1265744, an HIV integrase inhibitor dosed orally or by long-acting injection," Antimicrob Agents Chemother (2015) 59(1):397-406.
U.S. Appl. No. 60/400,807, Aug. 1, 2002.
U.S. Appl. No. 60/339,568, Oct. 26, 2001.
Office Action for CA 2,452,769, mailed Oct. 12, 2010, 3 pages.
Response to Office Action for CA 2,452,769, filed Aug. 5, 2011, 13 pages.
First Office Action for CN 02819869.7, issued Nov. 18, 2005, 10 pages.
Response to the First Office Action for CN 02819869.7, Mar. 30, 2006, 3 pages.
First Office Action for CN 200910128280.3, issued Aug. 12, 2010, 7 pages.
Response to the First Office Action for CN 200910128280.3, filed Dec. 24, 2010, 6 pages.
Second Office Action for CN 02819869.7, issued Aug. 1, 2008, 5 pages.
Response to Second Office Action, mailed on Aug. 1, 2008, for CN 02819869.7, 3 pages.
Second Office Action for CN 200910128280.3, issued Aug. 2, 2011, 3 pages.
Response to Second Office Action for CN 200910128280.3, Sep. 8, 2011, 5 pages.
First Office Action for KR 10-2004-7002062, mailed Jan. 24, 2009, 6 pages (Machine translation).
Second Office Action for KR 10-2004-7002062, mailed Jun. 23, 2009, 6 pages (Machine translation).
Final Office Action for KR 10-2004-7002062, mailed Mar. 19, 2010, 4 pages (Machine translation).
Response to Office Action for KR 10-2004-7002062, filed Nov. 18, 2009, 30 pages (Machine translation).
Response to Office Action for KR 10-2004-7002062, filed Nov. 18, 2009, 37 pages.
Response to Office Action for KR 10-2004-7002062, filed Nov. 18, 2009, 46 pages.
Appeal against Final Rejection for KR-2004-7002062, filed Jun. 9, 2010, 36 pages (Machine translation).
Office Action for MX PA/a/2004/000646, May 3, 2008, 6 pages.
Response to Office Action for MX PA/a/2004/000646, filed Aug. 29, 2008, 52 pages (Machine translation).
Patani et al., "Bioisosterim: A rational approach in Drug Design," Chem Rev (1996) 96:3147-3176.
Sato et al., "Evaluation of an SIV-infected rhesus monkey model via integrase inhibition," The XV International AIDS Conference, Jul. 11-16, 2004, 19 pages.
Sato et al., "Evaluation of an SIV-infected rhesus monkey model via integrase inhibition," The XV International AIDS Conference, Jul. 11-16, 2004, 1 page (Abstract).
Restriction Requirement for U.S. Appl. No. 10/485,394, mailed Jul. 2, 2007, 8 pages.
Response to Restriction Requirement for U.S. Appl. No. 10/485,394, filed Aug. 1, 2007, 2 pages.
Non-final Rejection for U.S. Appl. No. 10/485,394, mailed Nov. 16, 2007, 6 pages.
Response to Non-final Rejection for U.S. Appl. No. 10/485,394, filed Jan. 23, 2008, 28 pages.
Non-final Rejection for U.S. Appl. No. 10/485,394, mailed Jun. 4, 2008, 14 pages.
Response to Non-final Rejection for U.S. Appl. No. 10/485,394, filed Aug. 1, 2008, 26 pages.
Non-final Rejection for U.S. Appl. No. 10/485,394, mailed Dec. 5, 2008, 13 pages.
Response to Non-final Rejection for U.S. Appl. No. 10/485,394, filed Mar. 5, 2009, 26 pages.
Non-final Rejection for U.S. Appl. No. 10/485,394, mailed Jun. 23, 2009, 11 pages.
Response to Non-final Rejection for U.S. Appl. No. 10/485,394, filed Sep. 23, 2009, 33 pages.
Final Rejection for U.S. Appl. No. 10/485,394, mailed Dec. 8, 2009, 6 pages.
Response to Final Rejection for U.S. Appl. No. 10/485,394, filed Mar. 24, 2010, 4 pages.
Advisory Action for U.S. Appl. No. 10/485,394, mailed Apr. 6, 2010, 3 pages.
Request for Continued Examination for U.S. Appl. No. 10/485,394, filed Apr. 8, 2010, 2 pages.
Non-final Rejection for U.S. Appl. No. 10/485,394, mailed Jun. 17, 2010, 8 pages.
Response to Non-final Rejection for U.S. Appl. No. 10/485,394, filed Nov. 17, 2010, 8 pages.
Non-final Rejection for U.S. Appl. No. 10/485,394, mailed Feb. 15, 2011, 17 pages.
Response to Non-final Rejection for U.S. Appl. No. 10/485,394, filed May 13, 2011, 35 pages.
Final Rejection for U.S. Appl. No. 10/485,394, mailed Jul. 1, 2011, 14 pages.
Response to Final Rejection for U.S. Appl. No. 10/485,394, filed Aug. 25, 2011, 30 pages.
Advisory Action for U.S. Appl. No. 10/485,394, mailed Oct. 18, 2011, 3 pages.
Request for Continued Examination for U.S. Appl. No. 10/485,394, filed Nov. 30, 2011, 30 pages.
Non-final Rejection for U.S. Appl. No. 10/485,394, mailed May 2, 2013, 21 pages.
Response to Non-final Rejection for U.S. Appl. No. 10/485,394, filed Oct. 31, 2013, 17 pages.
Affidavit-traversing rejections or objections rule 132, filed Oct. 31, 2013, 7 pages.
Final Rejection for U.S. Appl. No. 10/482,394, mailed Feb. 11, 2014, 36 pages.
Notice of Appeal for U.S. Appl. No. 10/482,394, filed May 12, 2014, 1 page.
Request for Continued Examination, filed Aug. 12, 2014, 21 pages.
Affidavit-traversing rejections or objections rule 132, filed Aug. 12, 2014, 17 pages.
Restriction Requirement for U.S. Appl. No. 10/482,394, mailed Apr. 3, 2015, 12 pages.
Response to Restriction Requirement for U.S. Appl. No. 10/482,394, filed Jun. 17, 2015, 5 pages.
Notice of Non-Responsive Amendment for U.S. Appl. No. 10/482,394, mailed Aug. 26, 2015, 5 pages.
Response to Restriction Requirement for U.S. Appl. No. 10/482,394, filed Sep. 25, 2015, 2 pages.
Non-final Rejection for U.S. Appl. No. 10/482,394, mailed Nov. 30, 2015, 16 pages.
Response to Non-final Rejection for U.S. Appl. No. 10/482,394, mailed Feb. 29, 2016, 8 pages.
Final Rejection for U.S. Appl. No. 10/482,394, mailed Jun. 10, 2016, 24 pages.
Response to Final Rejection for U.S. Appl. No. 10/482,394, filed Aug. 10, 2016, 10 pages.
Affidavit-traversing rejections or objections rule 132, filed Aug. 10, 2016, 17 pages.
Supplementary European Search Report, mailed Oct. 18, 2005, 3 pages.
Communication pursuant to Article 96(2) EPC for EP 02749384.0, mailed Oct. 23, 2007, 9 pages.
Response to Communication pursuant to Article 96(2) EPC for EP 02749384.0, filed Jan. 9, 2008, 30 pages.
Communication pursuant to Article 94(3) EPC for EP 02749384.0, mailed Feb. 24, 2009, 6 pages.
Response to Communication pursuant to Article 94(3) EPC for EP 02749384.0, filed Aug. 17, 2009, 31 pages.
Communication pursuant to Article 94(3) EPC for EP 02749384.0, mailed Oct. 2, 2009, 4 pages.

(56) References Cited

OTHER PUBLICATIONS

Response to Communication pursuant to Article 94(3) EPC for EP 02749384.0, filed Nov. 13, 2009, 4 pages.
Communication pursuant to Article 94(3) EPC for EP 02749384.0, mailed Mar. 23, 2010, 4 pages.
Response to Communication pursuant to Article 94(3) EPC for EP 02749384.0, filed May 10, 2010, 2 pages.
Communication pursuant to Article 94(3) EPC for EP 02749384.0, mailed Sep. 2, 2010, 3 pages.
Response to Communication pursuant to Article 94(3) EPC for EP 02749384.0, filed Jan. 11, 2011, 47 pages.
Communication under Rule 71(3) EPC for EP 02749384.0, mailed Mar. 4, 2011, 4 pages.
Response to Communication under Rule 71(3) for EP 02749384.0, filed Jul. 14, 2011, 14 pages.
Communication pursuant to Article 94(3) EPC for EP 02749384.0, mailed Oct. 18, 2011, 4 pages.
Response to Communication pursuant to Article 94(3) EPC for EP 02749384.0, filed Nov. 28, 2011, 6 pages.
Decision to grant a European patent pursuant to Article 97(1) EPC for EP 02749384.0, mailed Feb. 23, 2012, 2 pages.
Notice of Appeal for EP 1 422 218, filed Jun. 8, 2015, 1 page.
Statement of grounds of appeal for EP 1 422 218, filed Aug. 10, 2015, 21 pages.
Letter relating to appeal procedure for EP 1 422 218, mailed Aug. 17, 2015, 17 pages.
Response to Letter relating to appeal procedure for EP 1 422 218, filed Dec. 28, 2015, 26 pages.
European Search Report for EP 15 18 7654, mailed Jun. 13, 2016, 9 pages.
Communication pursuant to Article 94(3) EPC for EP 10178132.6, mailed Feb. 9, 2015, 3 pages.
Response to Communication pursuant to Article 94(3) EPC for EP 10178132.6, filed May 6, 2015, 6 pages.
Communication pursuant to Article 94(3) EPC for EP 10178132.6, mailed Oct. 12, 2015, 6 pages.
Response to Communication pursuant to Article 94(3) EPC for EP 10178132.6, filed Feb. 19, 2016, 7 pages.
Communication pursuant to Article 94(3) EPC for EP 10178132.6, mailed May 9, 2016, 3 pages.
Response to Communication pursuant to Article 94(3) EPC for EP 10178132.6, filed Jul. 6, 2016, 12 pages.
Communication pursuant to Article 94(3) EPC for EP 10178132.6, mailed Jul. 22, 2016, 4 pages.
European Search Report for EP 09 177 978.5, mailed Mar. 24, 2010, 4 pages.
Communication under rule 71(3) EPC for EP 09 177 978.5, mailed Apr. 7, 2011, 4 pages.
Response to Communication under rule 71(3) EPC for EP 09 177 978.5, filed Aug. 12, 2011, 10 pages.
Amendment or correction of the text intended for grant for EP 09177978.5, mailed Sep. 8, 2011, 1 page.
Decision to grant a European patent pursuant to Article 97(1) EPC, mailed Sep. 29, 2011, 2 pages.
Butler et al., "A quantitative assay for HIV DNA integration *in vivo*," Nature Medicine (2001) 7(5):631-634.
Cherepanov et al., "Mode of Interaction of G-Quartets with the Integrase of Human Immunodeficiency Virus Type 1," Molecular Pharmacology (1997) 52:771-780.
Debyser et al., "In search of authentic inhibitors of HIV-1 integration," Antiviral Chemistry and Chemotherapy (2002) 13:1-15.
Desideri et al., "Synthesis and anti-human immunodeficiency virus type 1 integrase activity of hydroxybenzoic and hydroxycinnamic acid flavon-3-yl esters," Antiviral Chemistry and Chemotherapy (1998) 9:497-509.
Espeseth et al., "HIV-1 integrase inhibitors that compete with the target DNA substrate define a unique strand transfer conformation for integrase," PNAS USA (2000) 97(21):1124411249.

Fesen et al., "Inhibition of HIV-1 Integrase by Flavones, Caffeic Acid Phenethyl Ester (Cape) and Related Compounds," Biochemical Pharmacology (1994) 48(3):595-608.
Hare et al., "3'-Processing and strand transfer catalyzed by retroviral integrase in crystallo," EMBO Journal (2012) 31:3020-3028.
Lafemina et al., "Inhibition of Human Immunodeficiency Virus Integrase by Bis-Catechols," Antimircrobial Agents and Chemotherapy (1995) 39(2):320-324.
Lesbats et al., "Retroviral DNA integration," Chem Rev (2016) 116(20):12730-12757.
Lodi et al., "Solution Structure of the DNA Binding Domain of HIV-1 Integrase," Biochemistry (1995) 34(31):9826-9833.
Lubkowski et al., "Structure of the catalytic domain of avian sarcoma virus integrase with a bound HIV-1 integrase-targeted inhibitor," PNAS USA (1998) 95:4831-4836.
Maurer et al., "Carbonyl J Derivatives: A New Class of HIV-1 Integrase Inhibitors," Bioorganic Chemistry (2000) 28:140-155.
Molla et al., "Human Serum Attenuates the Activity of Protease Inhibitors toward Wild-Type and Mutant Human Immunodeficiency Virus," Virology (1998) 250:255-262.
Molteni et al., "A New Class of HIV-1 Integrase Inhibitors: the 3,3,3',3'-Tetramethyl-1,1'- spirobi (indan)-5,5',6,6'-tetrol Family," J. Med. Chem (2000) 43:2031-2039.
Pace et al., "The role of oxidative stress in HIV disease," Free Radic Biol Med (1995) 19(4):523-528.
Pais et al., "Structure Activity of 3-Aryl-1, 3-diketo-Containing Compounds as HIV-1 Integrase Inhibitors," J Med Chem (2002) 45:3184-3194.
Pani et al., "Anti-HIV-1 integrase drugs: how far from the shelf?" Curr Pharm Des (2000) 6(5):569-584.
Pannecouque et al., "New Class of HIV Integrase Inhibitors that Block Viral Replication in Cell Culture," Current Biology (2002) 12:1169-1177.
Pluymers et al., "HIV-1 Integration as a Target for Antiretroviral Therapy: A Review," Current Drug Targets-Infectious Disorders (2001) 1:133-149.
Pommier et al., "HIV-1 integrase as a target for antiviral drugs," Antiviral Chemistry and Chemotherapy (1997) 8(6):463-483.
Pommier et al., "Inhibitors of Human Immunodeficiency virus integrase," Advances in Virus Research (1999) 52:427-458.
Wai et al., "4-Aryl-2, 4-dioxobutanoic Acid Inhibitors of HIb-1 Integrase and Viral Replication in Cells," (2000) 43(26):4923-4926.
Yang et al., "Metalloprotein Inhibitors for the Treatment of Human Diseases," Current Topics in Medicinal Chemistry (2016) 16:384-396.
Non-final Rejection for U.S. Appl. No. 10/485,394, mailed Nov. 23, 2016, 22 pages.
Affidavit-traversing rejections or objections rule 132 for U.S. Appl. No. 10/485,394, filed Oct. 31, 2013, 7 pages.
Final Rejection for U.S. Appl. No. 10/485,394, mailed Feb. 11, 2014, 36 pages.
Notice of Appeal for U.S. Appl. No. 10/485,394, filed May 12, 2014, 1 page.
Request for Continued Examination for U.S. Appl. No. 10/485,394, filed Aug. 12, 2014, 21 pages.
Affidavit-traversing rejections or objections rule 132 for U.S. Appl. No. 10/485,394, filed Aug. 12, 2014, 17 pages.
Restriction Requirement for U.S. Appl. No. 10/485,394, mailed Apr. 3, 2015, 12 pages.
Response to Restriction Requirement for U.S. APpl. No. 10/485,394, filed Jun. 17, 2015, 5 pages.
Notice of Non-Responsive Amendment for U.S. Appl. No 10/485,394, mailed Aug. 26, 2015, 5 pages.
Response to Restriction Requirement for U.S. Appl. No. 10/485,394, filed Sep. 25, 2015, 2 pages.
Non-final Rejection for U.S. Appl. No. 10/485,394, mailed Nov. 30, 2015, 16 pages.
Response to Non-final Rejection for U.S. Appl. No. 10/485,394, mailed Feb. 26, 2016, 8 pages.
Final Rejection for U.S. Appl. No. 10/485,394, mailed Jun. 10, 2016, 24 pages.

(56) References Cited

OTHER PUBLICATIONS

Response to Final Rejection for U.S. Appl. No. 10/485,394, filed Aug. 10, 2016, 10 pages.
Affidavit-traversing rejections or objections rule 132 for U.S. Appl. No. 10/485,394, filed Aug. 10, 2016, 17 pages.
Supplementary European Search Report for EP 02749384.0, mailed Oct. 18, 2005, 3 pages.
Decision of Invalidity in the High Court of Justice, Chancery Division, Patents Court, Case ANo. HP-2015-000040, issued Nov. 25, 2016, 72 pages.
Order from the Regional Court Düsseldorf in the legal dispute of Shionogi & Co. Ltd. versus Merck Sharp & Dohme Ltd. et al. (translation), involving European Patent EP 1 422 218, order issued Nov. 7, 2016, 13 pages.

* cited by examiner

ANTIVIRAL AGENT

CROSS-REFERENCE TO RELATED APPLICATIONS

This application is a continuation of U.S. application Ser. No. 10/485,394 having an international filing date of 8 Aug. 2002 which is the national phase of PCT application PCT/JP2002/008108 having an international filing date of 8 Aug. 2002, which claims priority from Japanese application numbers 2001-245071 filed 10 Aug. 2001, 2001-370860 filed 5 Dec. 2001 and 2002-191483 filed 28 Jun. 2002. The contents of these documents are incorporated herein by reference.

TECHNICAL FIELD

The present invention relates to an antiviral agent, especially, a compound having an α-hydroxy-α,β unsaturated keone as a partial structure, and a pharmaceutical composition as an integrase inhibitor containing the same.

BACKGROUND ART

Among viruses, human immunodeficiency virus (HIV), a kind of retrovirus, is known to cause acquired immunodeficiency syndrome (AIDS). The therapeutic agent for AIDS is mainly selected from the group of reverse transcriptase inhibitors (e.g., AZT, 3TC) and protease inhibitors (e.g., Indinavir), but they are proved to be accompanied by side effects such as nephropathy and the emergence of resistant viruses. Thus, the development of anti-HIV agents having the other mechanism of action has been desired.

On the other hand, a combination therapy is reported to be effective in the treatment for acquired immunodeficiency syndrome because of the frequent emergence of the resistant mutant in Balzarini, J. et al, Proc. Natl. Acad. Sci. USA 1996, 93, p. 13152-13157. Reverse transcriptase inhibitors and protease inhibitors are clinically used as an anti-HIV agent, however, agents having the same mechanism of action often show the cross-resistance or only an additional activity. Therefore, anti-HIV agents having the other mechanism of action are desired.

Examples of the integrase inhibitor include 1,3-dioxobutanoic acids and 1,3-propanediones described in WO99/50245, WO99/62520, WO99/62897, WO99/62513, WO00/39086 and WO01/00578. Anther integrase inhibitor is acrylic acid derivative described in WO01/17968. The other recently reported types are aza- or polyazanaphthalenylcarboamide derivative described in WO2002/30426, WO2002/30930, WO2002/30931 and WO2002/36734.

A compound having a similar structure to the present invention compound is N-substituted-3-carboamide-4-hydroxy-5-oxo-3-pyrroline derivative with an anti-inflammatory effect described in Eur. J. Med. Chemical-Chim. Ther. (1979), 14 (2), 189-190. Pharmazie (1997), 52 (4), 276-278 discloses 1-methyl-4-arylcarbamido-2,3-dioxopyrrolidine derivative as an intermediate. WO92/06954 discloses pyrolizinedione derivative with an inhibitory effect on aldose reductase. J. Med. Chemical (1976), 19 (1), 172-173 discloses N-substituted-4,5-dioxopyrrolidine-3-carboxanilide derivative with anti-inflammatory effect. Journal of Physical Chemistry A (2002), 106 (11), 2497-2504 discloses pyrimidine derivative without mentioning any pharmaceutical use.

T'ai-wan K'o Hsueh (1997), 31 (3-4), 130-135 discloses 3-hydroxy-7-(phenylmethoxy)-2-(2-quinolinyl)-4H-1-benzopyrane-4-one. Examples of a compound having a structure of "4H-1-benzopyrane-4-one" include flavonoid derivative with anti-HIV activity described in ① J. Nat. Prod. (2001), 64 (4), 546-548, ② Anticancer Res. (2000), 20 (4), 2525-2536, ③ WO98/11889, ④ Pharmazie (1998), 53 (8), 512-517, though the action of mechanism is not mentioned therein.

DISCLOSURE OF INVENTION

Under the above circumstance, the development of a novel integrase inhibitor has been desired.

The present inventors have intensively studied to find a novel antiviral agent, the following compound (I), its prodrug, or a pharmaceutically acceptable salt or solvate thereof, possessing an integrase inhibitory activity;

(I)

(wherein, $R^C$ and $R^D$ taken together with the neighboring carbon atoms may form a ring, and the ring may be a condensed ring; Y is hydroxy, mercapto or amino; Z is O, S or NH; $R^A$ is shown by

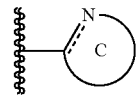

(wherein, C ring is N-containing aromatic heterocycle, wherein at least one atom neighboring to the atom at the bonding-position is N atom; the broken line shows the presence or absence of a bond.) or by

(wherein, X is O, S or NH; $R^D$ is a substituent selected from substitution group A); at least one of the ring formed by $R^C$ and $R^D$, C ring or $R^B$ is substituted with a group of —$Z^1$—$Z^2$—$Z^3$—$R^1$ (wherein, $Z^1$ and $Z^3$ are each independently a bond, optionally substituted alkylene or optionally substituted alkenylene; $Z^2$ is a bond, optionally substituted alkylene, optionally substituted alkenylene, —CH(OH)—, —S—, —SO—, —$SO_2$—, —$SO_2NR^2$—, —$NR^2SO_2$—, —O—, —$NR^2$—, —$NR^2CO$—, —$CONR^2$—, —C(=O)—O—, —O—C(=O) or —CO—; $R^2$ is hydrogen, optionally substituted alkyl, optionally substituted alkenyl, optionally substituted aryl or optionally substituted heteroaryl; $R^1$ is optionally substituted aryl, optionally substituted heteroaryl, optionally substituted cycloalkyl, optionally substituted cycloalkenyl or optionally substituted heterocycle); the ring formed by $R^C$ and $R^D$, C ring or $R^B$ is optionally substituted with a non-interfering substituent at any position other than that where the group of —$Z^1$—$Z^2$—$Z^3$—$R^1$ (wherein, $Z^1$, $Z^2$, $Z^3$ and $R^1$ are the same as defined above) locates;

substitution group A: hydrogen, halogen, alkoxycarbonyl, carboxy, alkyl, alkoxy, alkoxyalkyl, nitro, hydroxy, alkenyl, alkynyl, alkylsulfonyl, optionally substituted amino, alkylthio, alkylthioalkyl, haloalkyl, haloalkoxy, haloalkoxyalkyl, optionally substituted cycloalkyl, optionally substituted cycloalkenyl, optionally substituted heterocycle, nitroso, azide, amidino, guanidino, cyano, isocyano, mercapto, optionally substituted carbamoyl, sulfamoyl, sulfoamino, formyl, alkylcarbonyl, alkylcarbonyloxy, hydrazino, morpholino, optionally substituted aryl, optionally substituted heteroaryl, optionally substituted aralkyl, optionally substituted heteroarylalkyl, optionally substituted aryloxy, optionally substituted heteroaryloxy, optionally substituted aryl thio, optionally substituted heteroarylthio, optionally substituted aralkyloxy, optionally substituted heteroarylalkyloxy, optionally substituted aralkylthio, optionally substituted heteroarylalkyl thio, optionally substituted aryloxyalkyl, optionally substituted heteroaryloxyalkyl, optionally substituted arylthio alkyl, optionally substituted heteroarylthio alkyl, optionally substituted aryl sulfonyl, optionally substituted heteroarylsulfonyl, optionally substituted aralkylsulfonyl and optionally substituted heteroarylalkylsulfonyl.) (hereafter referred to as "the present invention compound").

The present inventors further found that the present invention compound and a pharmaceutical composition containing the same are useful as antivirus agent, anti-retrovirus agent, anti-HIV agent, anti-HTLV-1 (Human T cell leukemia virus type 1) agent, anti-FIV (Feline immunodeficiency virus) agent, and anti-SIV (Simian immunodeficiency virus) agent, esp., anti-HIV agent and an integrase inhibitor, whereby to achieve the present invention.

The present invention provides the present invention compound, its prodrug, a pharmaceutically acceptable salt or solvate thereof, a pharmaceutical composition containing the same as an active ingredient, antivirus agent, anti-HIV agent, an integrase inhibitor, and anti-HIV mixture. These are useful as anti-HIV agent as well as anti-AIDS agent for diseases such as AIDS, its related clinical syndrome, e.g., AIDS related complication (ARC), persistent generalized lymphadenopath) (PGL), Kaposi sarcoma, pneumocystis carini pneumonia, sudden thrombocytopenic purpura, AIDS related neurological symptom, for example, AIDS dementia complications AIDS-associated encephalopathy multiple sclerosis or tropical spastic paraparesis, and anti-HIV antibody positive and HIV positive symptom in asymptomatic patients.

The present invention relates to:

(1) a pharmaceutical composition containing as an active ingredient a compound of formula (I):

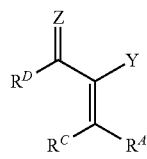

(I)

(wherein, $R^C$ and $R^D$ taken together with the neighboring carbon atoms form a ring which may be a condensed ring, Y is hydroxy, mercapto or amino; Z is O, S or NH; $R^A$ is a group shown by

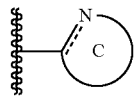

(wherein, C ring is N-containing aromatic heterocycle, wherein at least one atom neighboring to the atom at the bonding-position is non-substituted N atom; the broken line shows the presence or absence of a bond.) or by

(wherein, X is O, S or NH; $R^B$ is a substituent selected from substitution group A); at least one of the ring formed by $R^C$ and $R^D$, C ring or $R^B$ is substituted with a group of $—Z^1—Z^2—Z^3—R^1$ (wherein, $Z^1$ and $Z^3$ are each independently a bond, optionally substituted alkylene or optionally substituted alkenylene; $Z^2$ is a bond, optionally substituted alkylene, optionally substituted alkenylene, —CH(OH)—, —S—, —SO—, —SO$_2$—, —SO$_2$NR$^2$—, —NR$^2$SO$_2$—, —O—, —NR$^2$—, —NR$^2$CO—, —CONR$^2$—, —C(=O)—O—, —O—C(=O)— or —CO—; $R^2$ is, hydrogen, optionally substituted alkyl, optionally substituted alkenyl, optionally substituted aryl or optionally substituted heteroaryl; $R^1$ is optionally substituted aryl, optionally substituted heteroaryl, optionally substituted cycloalkyl, optionally substituted cycloalkenyl or optionally substituted heterocycle); the ring formed by $R^C$ and $R^D$, C ring or $R^B$ is optionally substituted with a non-interfering substituent at any position other than that where the group of $—Z^1—Z^2—Z^3—R^1$ (wherein, $Z^1$, $Z^2$, $Z^3$ and $R^1$ are the same as defined above) locates; substitution group A consists of: hydrogen, halogen, alkoxycarbonyl, carboxy, alkyl, alkoxy, alkoxyalkyl, nitro, hydroxy, alkenyl, alkynyl, alkylsulfonyl, optionally substituted amino, alkylthio, alkylthioalkyl, haloalkyl, haloalkoxy, haloalkoxyalkyl, optionally substituted cycloalkyl, optionally substituted cycloalkenyl, optionally substituted heterocycle, nitroso, azide, amidino, guanidino, cyano, isocyano, mercapto, optionally substituted carbamoyl, sulfamoyl, sulfoamino, formyl, alkyl carbonyl, alkyl carbonyloxy, hydrazino, morpholino, optionally substituted aryl, optionally substituted heteroaryl, optionally substituted aralkyl, optionally substituted heteroarylalkyl, optionally substituted aryl oxy, optionally substituted heteroaryl oxy, optionally substituted aryl thio, optionally substituted heteroaryl thio, optionally substituted aralkyloxy, optionally substituted heteroaryl alkyl oxy, optionally substituted aralkylthio, optionally substituted heteroaryl alkylthio, optionally substituted aryl oxyalkyl, optionally substituted heteroaryl oxyalkyl, optionally substituted aryl thioalkyl, optionally substituted heteroaryl thioalkyl, optionally substituted arylsulfonyl, optionally substituted heteroarylsulfonyl, optionally substituted aralkylsulfonyl and optionally substituted heteroarylalkylsulfonyl), its prodrug, or a pharmaceutically acceptable salt or solvate thereof, for use as an integrase inhibitor. In detail, the invention relates to the following (2) to (120).

(2) A pharmaceutical composition of above (1) wherein the ring formed by $R^C$ and $R^D$ is a 5- to 6-membered ring which may contain a heteroatom (s) and be condensed with.

(3) A pharmaceutical composition of above (2) wherein the ring formed by $R^C$ and $R^D$ is a 5- to 6-membered ring which may contain a heteroatom (s) of O and/or N and be condensed with a benzene ring.

(4) A pharmaceutical composition of above (3) wherein the ring formed by $R^C$ and $R^D$ is a 5-membered ring which contains a heteroatom (s) of N.

(5) A pharmaceutical composition of above (3) wherein the ring formed by $R^C$ and $R^D$ is a 6-membered ring which contains a heteroatom (s) of O and is condensed with a benzene ring.

(6) A pharmaceutical composition of above (3) wherein the ring formed by $R^C$ and $R^D$ is a 6-membered ring which contains a heteroatom (s) of N and is condensed with a benzene ring.

(7) A pharmaceutical composition of above (3) wherein the ring formed by $R^C$ and $R^D$ is a 6-membered ring which contains a heteroatom (s) of O.

(8) A pharmaceutical composition of above (3) wherein the ring formed by $R^C$ and $R^D$ is a 6-membered ring which contains a heteroatom (s) of N.

(9) A pharmaceutical composition of above (1) wherein the ring formed by $R^C$ and $R^D$ is a 6-membered carbocycle.

(10) A pharmaceutical composition of above (4) which contains as an active ingredient a compound of formula (II-1):

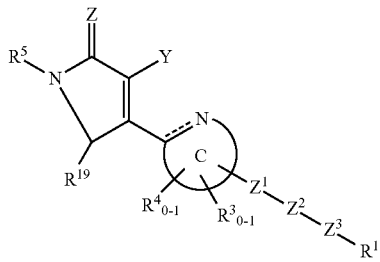

(II-1)

(wherein, Y, Z, C ring, $Z^1$, $Z^2$, $Z^3$, $R^1$ and the broken line is the same as above (1); $R^3$, $R^4$, $R^5$ and $R^{19}$ are each independently a non-interfering substituent), its prodrug or pharmaceutically acceptable salt or solvate thereof.

(11) A pharmaceutical composition of above (4) which contains as an active ingredient a compound of formula (III-1):

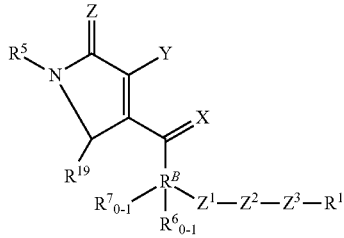

(III-1)

(wherein, X, Y, Z, $R^B$, $Z^1$, $Z^2$, $Z^3$ and $R^1$ are the same as above (1); $R^5$, $R^6$, $R^7$ and $R^{19}$ are each independently a non-interfering substituent), its prodrug or pharmaceutically acceptable salt or solvate thereof.

(12) A pharmaceutical composition of above (3) which contains as an active ingredient a compound of formula (II-2):

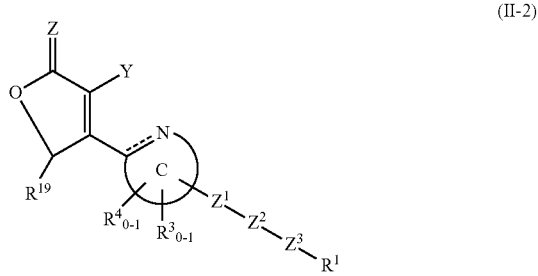

(II-2)

(wherein Y, Z, C ring, $Z^1$, $Z^2$, $Z^3$, $R^1$ and the broken line is the same as above (1); $R^3$, $R^4$ and $R^{19}$ are each independently a non-interfering substituent), its prodrug or pharmaceutically acceptable salt or solvate thereof.

(13) A pharmaceutical composition of above (3) which contains as an active ingredient a compound of formula (III-2):

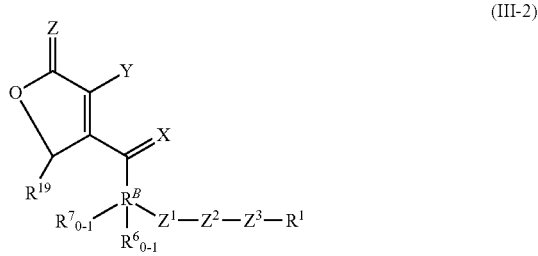

(III-2)

(wherein, X, Y, Z, $R^B$, $Z^1$, $Z^2$, $Z^3$ and $R^1$ is the same as above (1); $R^6$, $R^7$ and $R^{19}$ are each independently a non-interfering substituent), its prodrug or pharmaceutically acceptable salt or solvate thereof.

(14) A pharmaceutical composition of above (3) which contains as an active ingredient a compound of formula (IV-1):

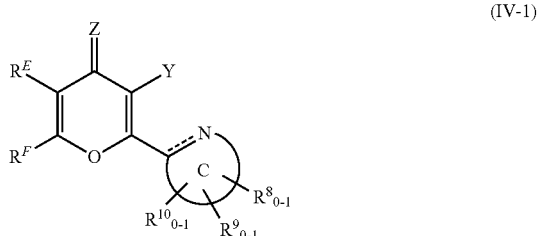

(IV-1)

(wherein, Y, Z, C ring and the broken line are the same as above (1); $R^8$, $R^9$ and $R^{10}$ are each independently a non-interfering substituent; at least one of $R^E$ and $R^F$ is shown by $-Z^1-Z^2-Z^3-R^1$ (wherein, $Z^1$, $Z^2$, $Z^3$ and $R^1$ are the same as above (1)) and the other is a non-interfering substituent, or $R^E$ and $R^F$ taken together with the neighboring carbon atoms may form a ring shown by:

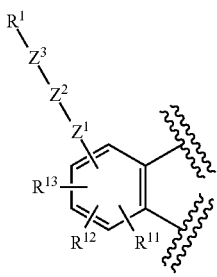

(wherein, $R^{11}$ to $R^{13}$ are each independently a non-interfering substituent, $Z^1$, $Z^2$, $Z^3$ and $R^1$ are the same as above (1)), its prodrug or pharmaceutically acceptable salt or solvate thereof.

(15) A pharmaceutical composition of above (5) which contains as an active ingredient a compound of formula (IV-2):

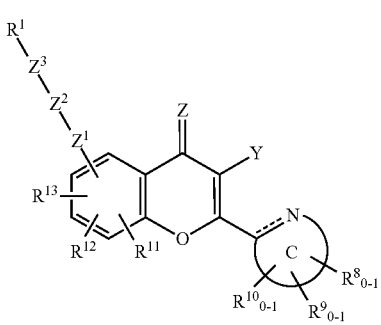

(IV-2)

(wherein, Y, Z, C ring, $Z^1$, $Z^2$, $Z^3$, $R^1$ and the broken line are the same as above (1); $R^8$ to $R^{13}$ are each independently a non-interfering substituent), its prodrug or pharmaceutically acceptable salt or solvate thereof.

(16) A pharmaceutical composition of above (3) which contains as an active ingredient a compound of formula (V-1):

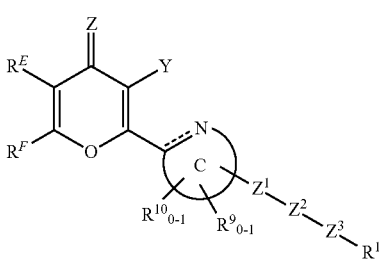

(V-1)

(wherein, Y, Z, C ring, $Z^1$, $Z^2$, $Z^3$, $R^1$ and the broken line are the same as above (1); $R^9$ and RP are each independently a non-interfering substituent; $R^E$ and $R^F$ are each independently a non-interfering substituent or taken together with the neighboring carbon atoms may form a ring shown by:

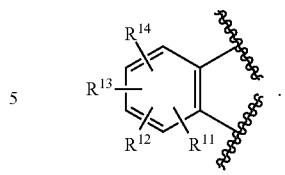

(wherein, $R^{11}$ to $R^{14}$ are each independently a non-interfering substituent), its prodrug or pharmaceutically acceptable salt or solvate thereof.

(17) A pharmaceutical composition of above (5) which contains as an active ingredient a compound of formula (V-2):

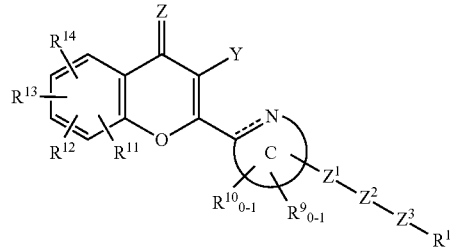

(V-2)

(wherein, Y, Z, C ring, $Z^1$, $Z^2$, $Z^3$, $R^1$ and the broken line are the same as above (1); $R^9$ to $R^{14}$ are each independently a non-interfering substituent), its prodrug or pharmaceutically acceptable salt or solvate thereof.

(18) A pharmaceutical composition of above (3) which contains as an active ingredient a compound of formula (VI-1):

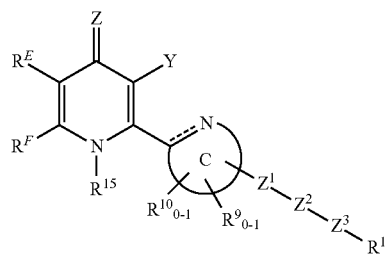

(VI-1)

(wherein, Y, Z, C ring, $Z^1$, $Z^2$, $Z^3$, $R^1$ and the broken line are the same as above (1); $R^9$, $R^{10}$ and $R^{15}$ are each independently a non-interfering substituent; $R^E$ and $R^F$ are each independently a non-interfering substituent or taken together with the neighboring carbon atoms may form a ring shown by

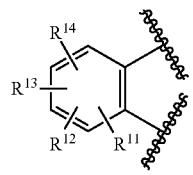

(wherein, $R^{11}$ to $R^{14}$ are each independently a non-interfering substituent), its prodrug or pharmaceutically acceptable salt or solvate thereof.

(19) A pharmaceutical composition of above (6) which contains as an active ingredient a compound of formula (VI-2):

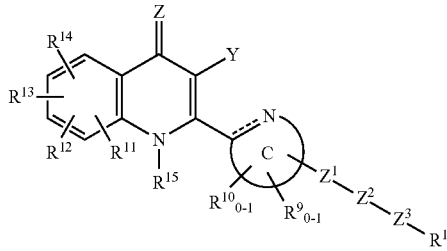

(VI-2)

(wherein, Y, Z, C ring, $Z^1$, $Z^2$, $Z^3$, $R^1$ and the broken line are the same as above (1); $R^9$ to $R^{15}$ are each independently a non-interfering substituent), its prodrug or pharmaceutically acceptable salt or solvate thereof).

(20) A pharmaceutical composition of above (3) which contains as an active ingredient a compound of formula (VII-1):

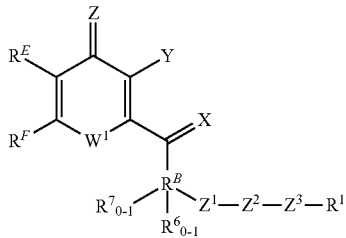

(VII-1)

(wherein, X, Y, Z, $R^B$, $Z^1$, $Z^2$, $Z^3$ and $R^1$ are the same as above (1); $W^1$ is —O— or —N(—$R^G$)—; $R^G$ is a non-interfering substituent; $R^6$ and $R^7$ are each independently a non-interfering substituent; $R^E$ and $R^F$ are each independently a non-interfering substituent or taken together with the neighboring carbon atoms form a ring shown by

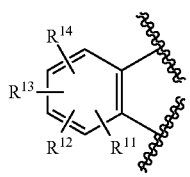

(wherein, $R^{11}$ to $R^{14}$ are each independently a non-interfering substituent)), its prodrug or pharmaceutically acceptable salt or solvate thereof.

(21) A pharmaceutical composition of above (3) which contains as an active ingredient a compound of formula (VII-2):

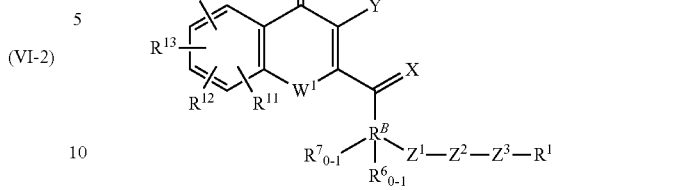

(VII-2)

(wherein, X, Y, Z, $R^B$, $Z^1$, $Z^2$, $Z^3$ and $R^1$ are the same as above (1); $W^1$ is —O— or —N(—$R^G$)—; $R^G$ is a non-interfering substituent; $R^6$, $R^7$, $R^{11}$ to $R^{14}$ are each independently a non-interfering substituent), its prodrug or pharmaceutically acceptable salt or solvate thereof.

(22) A pharmaceutical composition of above (3) which contains as an active ingredient a compound of formula (VII-3):

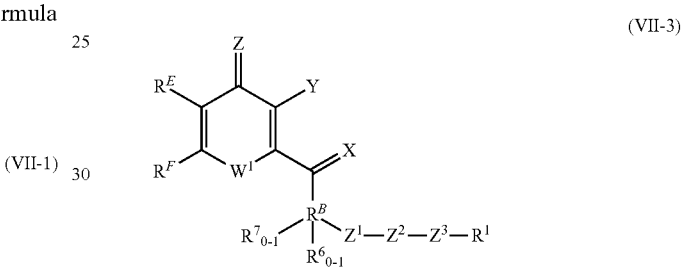

(VII-3)

(wherein, X, Y, Z, $R^B$, $Z^1$, $Z^2$, $Z^3$ and $R^1$ are the same as above (1); $W^1$ is —O— or —N(—$R^G$)—; $R^G$ is a non-interfering substituent; $R^6$ and $R^7$ are each independently a non-interfering substituent; $R^E$ and $R^F$ are each independently a non-interfering substituent), its prodrug or pharmaceutically acceptable salt or solvate thereof.

(23) A pharmaceutical composition of above (9) which contains as an active ingredient a compound of formula (VIII-1):

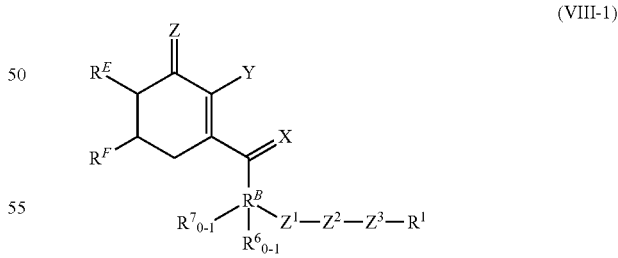

(VIII-1)

(wherein, X, Y, Z, $R^B$, $Z^1$, $Z^2$, $Z^3$ and $R^1$ are the same as above (1); $R^6$ and $R^7$ are each independently a non-interfering substituent; $R^E$ and $R^F$ are each independently a non-interfering substituent), its prodrug or pharmaceutically acceptable salt or solvate thereof.

(24) A pharmaceutical composition of above (9) which contains as an active ingredient a compound of formula (VIII-2):

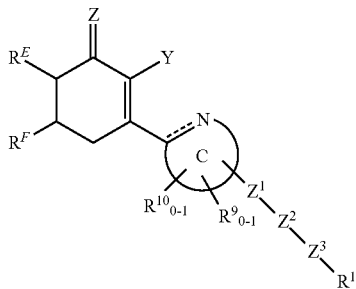

(wherein, Y, Z, C ring, $Z^1$, $Z^2$, $Z^3$, $R^1$ and the broken line are the same as above (1); $R^E$ and $R^F$ are each independently a non-interfering substituent; $R^9$ and $R^{10}$ are each independently a non-interfering substituent), its prodrug or pharmaceutically acceptable salt or solvate thereof.

(25) A pharmaceutical composition of above (8) which contains as an active ingredient a compound of formula (IX-1):

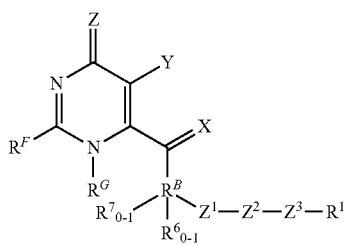

(wherein, X, Y, Z, $R^B$, $Z^1$, $Z^2$, $Z^3$ and $R^1$ are the same as above (1); $R^6$ and $R^7$ are each independently a non-interfering substituent; $R^F$ and $R^G$ are each independently a non-interfering substituent), its prodrug or pharmaceutically acceptable salt or its solvate thereof.

(26) A pharmaceutical composition of above (8) which contains as an active ingredient a compound of formula (IX-2):

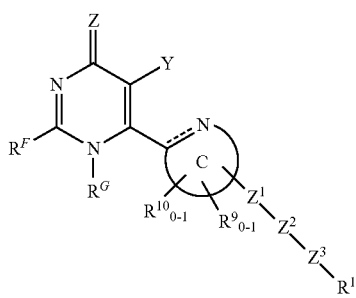

(wherein, Y, Z, C ring, $Z^1$, $Z^2$, $Z^3$, $R^1$ and the broken line are the same as above (1); $R^9$ and $R^{10}$ are each independently a non-interfering substituent; $R^F$ and $R^G$ are each independently a non-interfering substituent), its prodrug or pharmaceutically acceptable salt or solvate thereof.

(27) A pharmaceutical composition of above (4) which contains as an active ingredient a compound of formula (X-1):

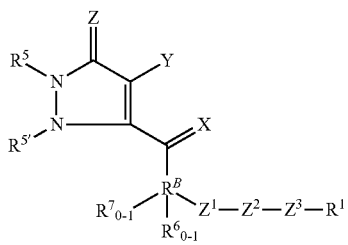

(wherein, X, Y, Z, $R^B$, $Z^1$, $Z^2$, $Z^3$ and $R^1$ are the same as above (1); $R^5$, $R^{5'}$, $R^6$ and $R^7$ are each independently a non-interfering substituent), its prodrug or pharmaceutically acceptable salt or solvate thereof.

(28) A pharmaceutical composition of above (4) which contains as an active ingredient a compound of formula (X-2):

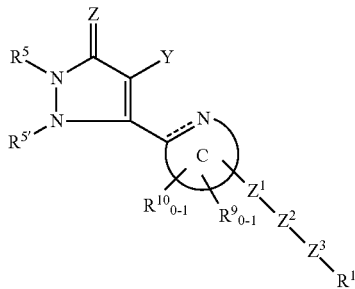

(wherein, Y, Z, C ring, $Z^1$, $Z^2$, $Z^3$, $R^1$ and the broken line are the same as above (1); $R^5$, $R^{5'}$, $R^9$ and $R^{19}$ are each independently a non-interfering substituent), its prodrug or pharmaceutically acceptable salt or solvate thereof.

(29) A pharmaceutical composition of above (7) which contains as an active ingredient a compound of formula (XI-1):

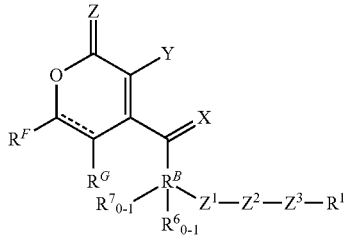

(wherein, X, Y, Z, $R^B$, $Z^1$, $Z^2$, $Z^3$ and $R^1$ are the same as above (1); $R^6$, $R^7$, $R^F$ and $R^G$ are each independently a non-interfering substituent; the broken line (---) shows the presence or absence of a bond), its prodrug or pharmaceutically acceptable salt or solvate thereof.

(30) A pharmaceutical composition of above (7) which contains as an active ingredient a compound of formula (XI-2):

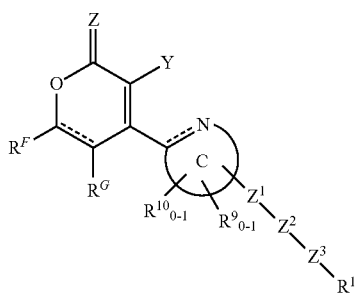

(XI-2)

(wherein, Y, Z, C ring, $Z^1$, $Z^2$, $Z^3$, $R^1$ and the broken line are the same as above (1); $R^9$, $R^{10}$, $R^F$ and $R^G$ are each independently a non-interfering substituent; the broken line (---) shows the presence or, absence of a bond), its prodrug or pharmaceutically acceptable salt or solvate thereof.

(31) A pharmaceutical composition of above (8) which contains as an active ingredient a compound of formula (XII-1):

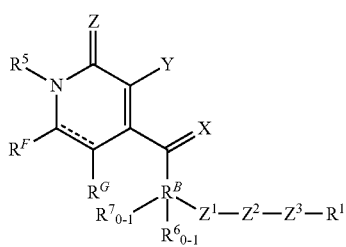

(XII-1)

(wherein, X, Y, Z, $R^B$, $Z^1$, $Z^2$, $Z^3$ and $R^1$ are the same as above (1); $R^5$, $R^6$, $R^7$, $R^F$ and $R^G$ are each independently a non-interfering substituent; the broken line (---) shows the presence or absence of a bond), its prodrug or pharmaceutically acceptable salt or solvate thereof.

(32) A pharmaceutical composition of above (8) which contains as an active ingredient a compound of formula (XII-2):

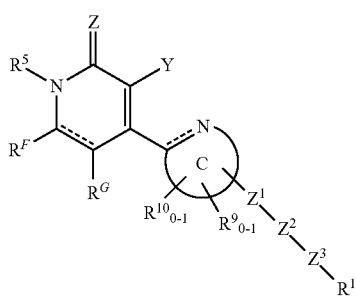

(XII-2)

(wherein, Y, Z, C ring, $Z^1$, $Z^2$, $Z^3$, and $R^1$ are the same as above (1); $R^5$, $R^9$, $R^{10}$, $R^F$ and $R^G$ are each independently a non-interfering substituent; the broken line (---) shows the presence or absence of a bond), its prodrug or pharmaceutically acceptable salt or solvate thereof.

(33) A pharmaceutical composition of above, (8) which contains as an active ingredient a compound of formula (XIII-1):

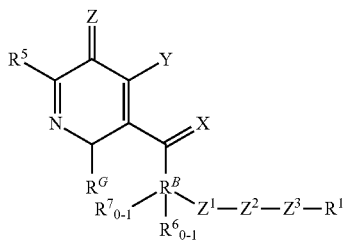

(XIII-1)

(wherein, X, Y, Z, $R^B$, $Z^1$, $Z^2$, $Z^3$ and $R^1$ are the same as above (1); $R^5$, $R^6$, $R^7$ and $R^G$ are each independently a non-interfering substituent), its prodrug or pharmaceutically acceptable salt or solvate thereof.

(34) A pharmaceutical composition of above (8) which contains as an active ingredient a compound of formula (XIII-2):

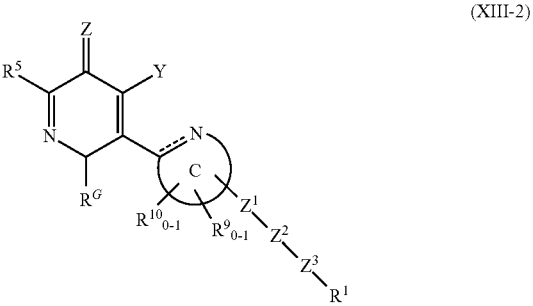

(XIII-2)

(wherein, Y, Z, C ring, $Z^1$, $Z^2$, $Z^3$ and $R^1$ are the same as above (1); $R^5$, $R^9$, $R^{10}$ and $R^G$ are each independently a non-interfering substituent), its prodrug or pharmaceutically acceptable salt or solvate thereof.

(35) A pharmaceutical composition of any one of (1) to (34), wherein the non-interfering substituents are independently selected from hydrogen, halogen, alkoxycarbonyl, carboxy, alkyl, alkoxy, alkoxyalkyl, nitro, hydroxy, hydroxyalkyl, alkenyl, alkynyl, alkylsulfonyl, optionally substituted amino, alkylthio, alkylthioalkyl, haloalkyl, haloalkoxy, haloalkoxyalkyl, optionally substituted cycloalkyl, optionally substituted cycloalkenyl, optionally substituted heterocycle, oxo, thioxo, nitroso, azide, amidino, guanidino, cyano, isocyano, mercapto, optionally substituted carbamoyl, sulfamoyl, sulfoamino, formyl, alkylcarbonyl, alkylcarbonyloxy, hydrazino, morpholino, optionally substituted aryl, optionally substituted heteroaryl, optionally substituted aralkyl, optionally substituted heteroarylalkyl, optionally substituted aryloxy, optionally substituted heteroaryloxy, optionally substituted arylthio, optionally substituted heteroarylthio, optionally substituted aralkyloxy, optionally substituted heteroarylalkyloxy, optionally substituted aralkylthio, optionally substituted heteroarylalkylthio, optionally substituted aryloxyalkyl, optionally substituted heteroaryloxyalkyl, optionally substituted arylthioalkyl, optionally substituted heteroarylthioalkyl, optionally substituted arylsulfonyl, optionally substituted heteroarylsulfonyl, optionally substituted aralkylsulfonyl and optionally substituted heteroarylalkylsulfonyl.

(36) A method for prevention or treatment of AIDS or AIDS-related complication, comprising administration of a pharmaceutical composition of any one of above (1) to (35).

(37) Use of a compound of any one of above (1) to (35) for preparing pharmaceutical composition as an integrase inhibitor.

(38) A compound of formula (I-Q): Q-$Z^1$—$Z^2$—$Z^3$—$R^1$, its prodrug or pharmaceutically acceptable salt or solvate thereof, wherein, $Z^1$, $Z^2$, $Z^3$ and $R^1$ are the same as above (1); Q is shown by any one of the following formulae:

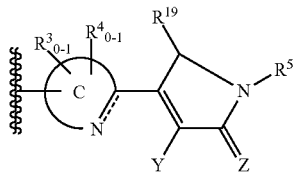

(wherein, C ring is the same as above (1); Y is hydroxy; Z is O; $R^3$, $R^4$, $R^5$ and $R^{19}$ are the same as above (10)),

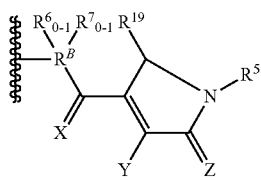

(wherein, X is O; Y and Z are the same as above; $R^5$, $R^6$, $R^7$ and $R^{19}$ are the same as above (11); $R^B$ is optionally substituted aryl, optionally substituted heteroaryl, optionally substituted cycloalkyl, optionally substituted cycloalkenyl or optionally substituted heterocycle),

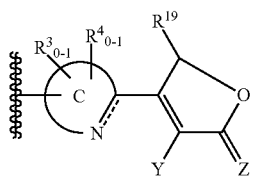

(wherein, C ring is the same as above (1); Y and Z are the same as above; $R^3$, $R^4$ and $R^{19}$ are the same as above (10)),

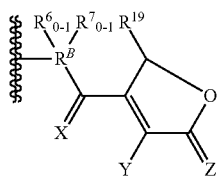

(wherein, X, Y, Z and $R^B$ are the same as above; $R^6$, $R^7$ and $R^{19}$ are the same as above (11)),

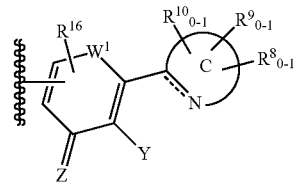

(wherein, C ring is the same as above (1); Y and Z are the same as above; $R^8$ to $R^{10}$ are the same as above (14); $W^1$ is the same as above (20); $R^{16}$ is a non-interfering substituent),

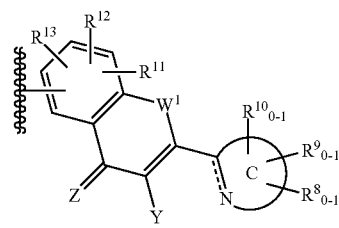

(wherein, C ring is the same as above (1); Y and Z are the same as above; $R^8$ to $R^{13}$ are the same as above (14); $W^1$ is the same as above (20)),

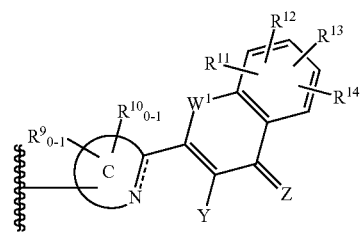

(wherein, C ring is the same as above (1); Y and Z are the same as above; $R^9$ to $R^{14}$ is the same as above (16); $W^1$ is the same as above (20)),

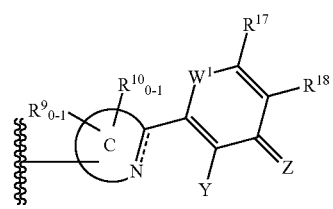

(wherein, C ring is the same as above (1); Y and Z are the same as above; $W^1$ is the same as above (20); $R^9$ and $R^{16}$ are the same as above (14); $R^{17}$ and $R^{18}$ are each independently a non-interfering substituent),

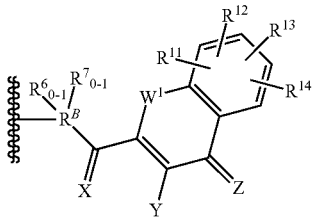

(wherein, X, Y, Z and $R^B$ are the same as above; $W^1$ is the same as above (20); $R^6$ and $R^7$ are the same as above (11); $R^{11}$ to $R^{14}$ are the same as above (16)),

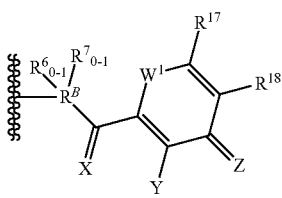

(wherein, X, Y, Z and $R^B$ are the same as above; W' is the same as above (20); $R^6$ and $R^7$ are the same as above (11); $R^{17}$ and $R^{18}$ are each independently a non-interfering substituent):

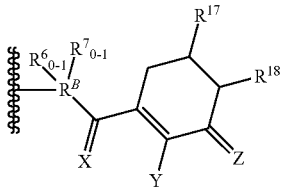

(wherein, X, Y, Z and $R^B$ are the same as above; $R^6$ and $R^7$ are the same as above. (11); $R^{17}$ and $R^{18}$ are each independently a non-interfering substituent),

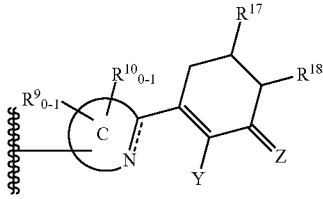

(wherein, C ring is the same as above (1); Y and Z are the same as above; $R^9$ and $R^7$ are the same as above (14); $R^{17}$ and $R^{18}$ are as defined above),

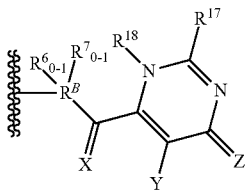

(wherein, X, Y, Z and $R^B$ are the same as above; $R^5$ is the same as above (10); $R^6$ and $R^7$ are the same as above (11); $R^{17}$ and $R^{18}$ are the same as defined above),

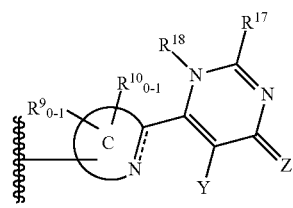

(wherein, C ring is the same as above (1); Y and Z are the same as above; $R^5$ is the same as above (10); $R^9$ and $R^{10}$ are the same as above (14); $R^{17}$ and $R^{18}$ are the same as defined above),

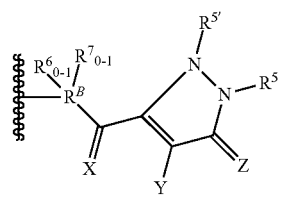

(wherein, X, Y, Z and $R^B$ are the same as above; $R^5$ and $R^{5'}$ are the same as above (27); $R^6$ and $R^7$ are the same as above (11)),

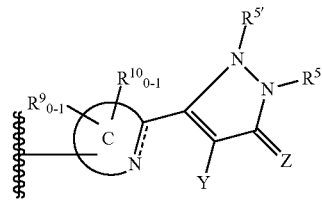

(wherein, C ring is the same as above (1); Y and Z are the same as above; $R^5$ and $R^{5'}$ are the same as above (27); $R^9$ and $R^{10}$ are the same as above (14)):

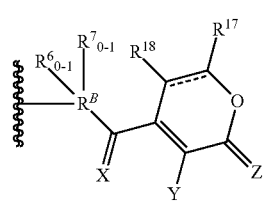

(wherein, X, Y, Z and $R^B$ are the same as above; $R^6$ and $R^7$ are the same as above (11); $R^{17}$ and $R^{18}$ are the same as above, the broken line (---) shows the presence or absence of a bond),

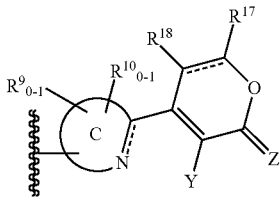

(wherein, C ring is the same as above (1); Y and Z are the same as above; $R^9$ and $R^{10}$ are the same as above (14); $R^{17}$ and $R^{18}$ are the same as above, the broken line (---) shows the presence or absence of a bond),

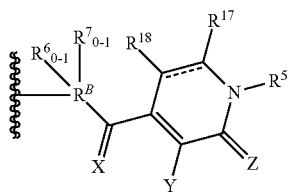

(wherein, X, Y, Z and $R^B$ are the same as above; $R^5$, $R^6$ and $R^7$ are the same as above (11); $R^{17}$ and $R^{18}$ are the same as above, the broken line (---) shows the presence or absence of a bond),

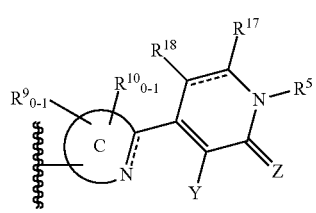

(wherein, C ring is the same as above (1); Y and Z are the same as above; $R^5$ is the same as above (10); $R^9$ and $R^{10}$ are the same as above (14); $R^{17}$ and $R^{18}$ are the same as above, the broken line (---) shows the presence or absence of a bond),

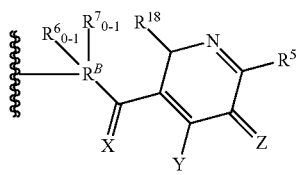

(wherein, X, Y, Z and $R^B$ are the same as above; $R^5$, $R^6$ and $R^7$ are the same as above (11); $R^{18}$ is the same as defined above), and

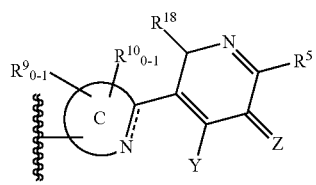

(wherein, C ring is the same as above (1); Y and Z are the same as above; $R^5$ is the same as above (10); $R^9$ and $R^{10}$ are the same as above (14); $R^{18}$ is the same as defined above); provided that excluded are compounds, wherein $Z^1$ is a bond, $Z^2$ is —O—, $Z^3$ is methylene, $R^1$ is phenyl, and Q is a group of the formula:

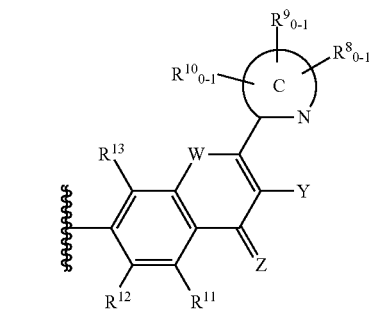

(wherein, $R^8$ to $R^{13}$ are hydrogens, Y is hydroxy, Z is O, W is —O—, and C ring is quinoline-2-yl) or the formula:

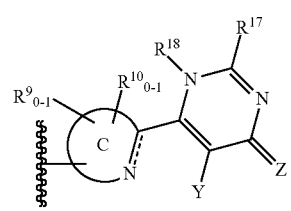

wherein, $R^9$ and $R^{10}$ are the same as above, $R^{17}$ is alkyl, $R^{18}$ is hydrogen, Y is hydroxy, Z is O, C ring is dihydropyrimidine).

(39) A compound of above (38), shown by formula (II-1):

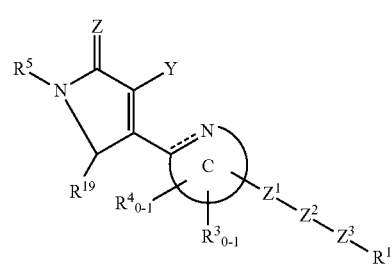

(II-1)

(wherein, Y is hydroxy; Z is O; C ring, $Z^1$, $Z^2$, $Z^3$ and $R^1$ are the same as above (1); $R^3$, $R^4$, $R^5$ and $R^{19}$ are each independently a non-interfering substituent), its prodrug or pharmaceutically acceptable salt or solvate thereof.

(40) A compound of above (39), wherein $Z^1$ and $Z^3$ are each independently a bond or alkylene; $Z^2$ is a bond or —O—; $R^1$ is optionally substituted aryl or optionally substituted heteroaryl, its prodrug or pharmaceutically acceptable salt or solvate thereof.

(41) A compound of above (39), wherein C ring is pyrimidine-4-yl or 1,3,4-oxadiazole-2-yl; $Z^1$ is a bond; $Z^2$ is —O or alkylene; $Z^3$ is a bond or alkylene; $R^1$ is aryl optionally substituted with halogen; $R^3$, $R^4$ and $R^{19}$ are hydrogens; $R^5$ is alkyl, aralkyl, cycloalkyl, aryl or alkoxy, its prodrug or pharmaceutically acceptable salt or solvate thereof.

(42) A compound of above (38), shown by formula (III-1):

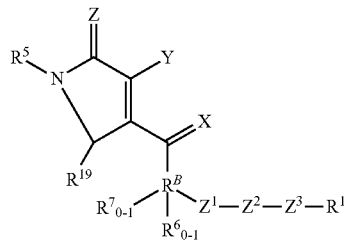

(III-1)

(wherein, X is O; Y is hydroxy; Z is O; $R^B$ is optionally substituted aryl, optionally substituted heteroaryl, optionally substituted cycloalkyl, optionally substituted cycloalkenyl or optionally substituted heterocycle; $Z^1$, $Z^2$, $Z^3$ and $R^1$ are the same as above (1); $R^5$, $R^6$, $R^7$ and $R^{19}$ are each independently a non-interfering substituent), its prodrug or pharmaceutically acceptable salt or solvate thereof.

(43) A compound of above (39) or (42), wherein, $R^5$ is hydrogen, alkyl, aralkyl, cycloalkyl, optionally substituted aryl, alkoxy, alkoxyalkyl, optionally substituted amino, hydroxyalkyl, alkenyl, alkoxycarbonylalkyl or heteroarylalkyl, its prodrug or pharmaceutically acceptable salt or solvate thereof.

(44) A compound of above (42), wherein $R^B$ is fran-2-yl, its prodrug or pharmaceutically acceptable salt or solvate thereof.

(45) A compound of above (42), wherein $R^B$ is aryl or fran-2-yl; $Z^1$ and $Z^3$ are bonds; $Z^2$ is alkylene; $R^1$ is aryl optionally substituted with halogen; $R^6$, $R^7$ and $R^{19}$ are hydrogens; $R^5$ is alkyl, cycloalkyl, alkoxy, aryl optionally substituted with alkoxy, hydroxyalkyl, alkenyl, aralkyl, alkoxycarbonylalkyl, or pyridine-2-ylmethyl, its prodrug or pharmaceutically acceptable salt or solvate thereof.

(46) A compound of above (38), shown by formula (II-2):

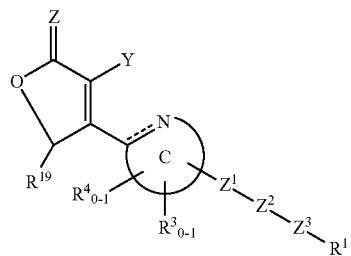

(II-2)

(wherein, Y is hydroxy; Z is O; C ring, $Z^1$, $Z^2$, $Z^3$ and $R^1$ are the same as above (1); $R^3$, $R^4$ and $R^{19}$ are each independently a non-interfering substituent), its prodrug or pharmaceutically acceptable salt or solvate thereof.

(47) A compound of above (46), wherein $Z^1$ and $Z^3$ are each independently a bond or alkylene; $Z^2$ is a bond or —O—; $R^1$ is optionally substituted aryl or optionally substituted heteroaryl, its prodrug or pharmaceutically acceptable salt or solvate thereof.

(48) A compound of above (46), wherein C ring is pyrimidine-4-yl or 1,3,4-oxadiazole-2-yl; $Z^1$ is a bond; $Z^2$ is —O or alkylene; $Z^3$ is a bond or alkylene; $R^1$ is aryl optionally substituted with halogen; $R^3$, $R^4$ and $R^{19}$ are hydrogens, its prodrug or pharmaceutically acceptable salt or solvate thereof.

(49) A compound of above (38) shown by formula (III-2):

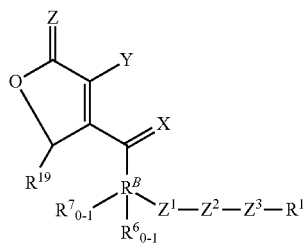

(III-2)

(wherein, X is O; Y is hydroxy; Z is O; $R^B$ is optionally substituted aryl, optionally substituted heteroaryl, optionally substituted cycloalkyl, optionally substituted cycloalkenyl or optionally substituted heterocycle; $Z^1$, $Z^2$, $Z^3$ and $R^1$ are the same as above (1); $R^6$, $R^7$ and $R^{19}$ are each independently a non-interfering substituent), its prodrug or pharmaceutically acceptable salt or solvate thereof.

(50) A compound of above (49), wherein $R^B$ is fran-2-yl, its prodrug or pharmaceutically acceptable salt or solvate thereof.

(51) A compound of above (49), wherein $R^B$ is aryl or fran-2-yl; $Z^1$ and $Z^3$ are bonds; $Z^2$ is alkylene; $R^1$ is aryl optionally substituted with halogen; $R^6$, $R^7$ and $R^{19}$ are hydrogens, its prodrug or pharmaceutically acceptable salt or solvate thereof.

(52) A compound of above (38), shown by formula (IV-2):

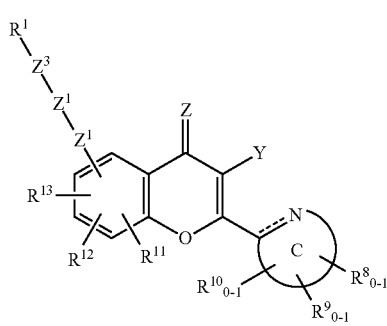

(IV-2)

(wherein, Y is hydroxy; Z is O; C ring, $Z^1$, $Z^2$, $Z^3$ and W are the same as above (1); $R^8$ to $R^{13}$ are each independently a non-interfering substituent), its prodrug or pharmaceutically acceptable salt or solvate thereof.

(53) A compound of above (52), wherein C ring is pyridine-2-yl, 1,2,4-triazole-3-yl or imidazole-2-yl optionally substituted with alkyl; $Z^1$ is a bond; $Z^2$ is —O—; $Z^3$ is alkylene; $R^1$ is aryl optionally substituted with halogen; $R^3$ to $R^{13}$ are hydrogens, its prodrug or pharmaceutically acceptable salt or solvate thereof.

(54) A compound of above (38), shown by formula (V-2):

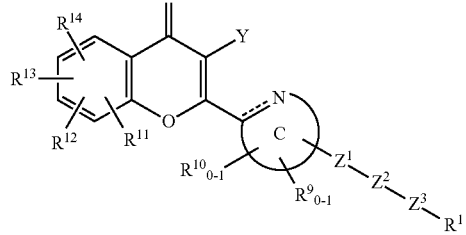

(V-2)

(wherein, Y is hydroxy; Z is O; C ring, $Z^1$, $Z^2$, $Z^3$ and $R^1$ are the same as above (1); $R^9$ to $R^{14}$ are each independently a non-interfering substituent), its prodrug or pharmaceutically acceptable salt or solvate thereof.

(55) A compound of above (52) or (54), wherein $Z^1$ and $Z^3$ are each independently a bond or alkylene; $Z^2$ is a bond or —O—; $R^1$ is optionally substituted aryl or optionally substituted heteroaryl, its prodrug or pharmaceutically acceptable salt or solvate thereof.

(56) A compound of above (54), wherein C ring is 1,3,4-oxadiazole-2-yl; $Z^1$ and $Z^3$ are bonds; $Z^2$ is alkylene; W is aryl optionally substituted with halogen; $R^9$ to $R^{14}$ are hydrogens, its prodrug or pharmaceutically acceptable salt or solvate thereof.

(57) A compound of above (38), shown by formula (VI-2):

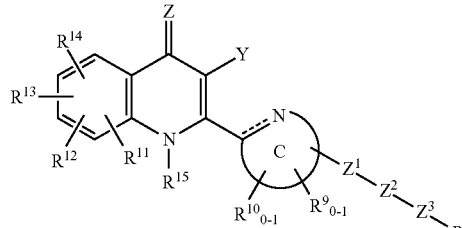

(VI-2)

(wherein, Y is hydroxy; Z is O; C ring, $Z^1$, $Z^2$, $Z^3$ and $R^1$ are the same as above (1); $R^9$ to $R^{15}$ are each independently a non-interfering substituent), its prodrug or pharmaceutically acceptable salt or solvate thereof.

(58) A compound of above (57), wherein $R^{15}$ is hydrogen or alkyl, its prodrug or pharmaceutically acceptable salt or solvate thereof.

(59) A compound of above (57), wherein C ring is 1,3,4-oxadiazole-2-yl; $Z^1$ and $Z^3$ are bonds; $Z^2$ is alkylene; $R^1$ is aryl optionally substituted with halogen; $R^9$ to $R^{14}$ are hydrogens; $R^{15}$ is hydrogen or alkyl, its prodrug or pharmaceutically acceptable salt or solvate thereof.

(60) A compound of above (38), shown by formula (VII-4):

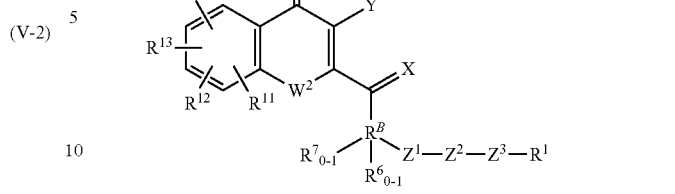

(VII-4)

(wherein, X is O; Y is hydroxy; Z is O; $W^2$ is —O— or —NH—; $R^B$ is optionally substituted aryl, optionally substituted heteroaryl, optionally substituted cycloalkyl, optionally substituted cycloalkenyl or optionally substituted heterocycle; $Z^1$, $Z^2$, $Z^3$ and $R^1$ are the same as above (1); $R^6$, $R^7$, $R^{11}$ to $R^{14}$ are each independently a non-interfering substituent), its prodrug or pharmaceutically acceptable salt or solvate thereof.

(61) A compound of above (60), wherein $R^B$ is fran-2-yl, its prodrug or pharmaceutically acceptable salt or solvate thereof.

(62) A compound of above (60), wherein $R^B$ is fran-2-yl; $Z^1$ and $Z^3$ are bonds; $Z^2$ is alkylene; $R^1$ is aryl optionally substituted with halogen; $R^6$, $R^7$, $R^{11}$ to $R^{14}$ are hydrogens, its prodrug or pharmaceutically acceptable salt or solvate thereof.

(63) A compound of above (38), shown by formula (VII-5):

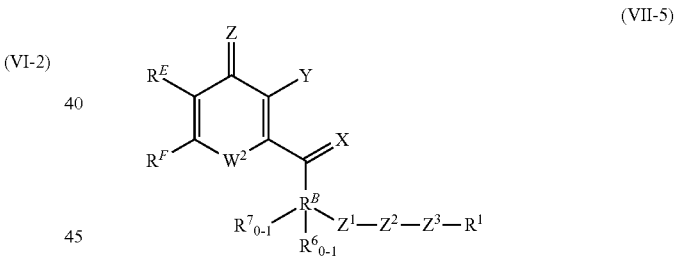

(VII-5)

(wherein, X is O; Y is hydroxy; Z is O; $W^2$ is —O— or —NH—; $R^B$ is optionally substituted aryl, optionally substituted heteroaryl, optionally substituted cycloalkyl, optionally substituted cycloalkenyl or optionally substituted heterocycle; $Z^1$, $Z^2$, $Z^3$ and $R^1$ are the same as above (1); $R^6$, $R^7$, $R^E$ and $R^F$ are each independently a non-interfering substituent), its prodrug or pharmaceutically acceptable salt or solvate thereof.

(64) A compound of above (63), wherein $R^B$ is fran-2-yl, its prodrug or pharmaceutically acceptable salt or solvate thereof.

(65) A compound of above (63), wherein $R^B$ is fran-2-yl; $Z^1$ and $Z^3$ are bonds; $Z^2$ is alkylene; $R^1$ is aryl optionally substituted with halogen; $R^6$, $R^7$, $R^E$ and $R^F$ are hydrogens, its prodrug or pharmaceutically acceptable salt or solvate thereof.

(66) A compound of above (38), shown by formula (VIII-1):

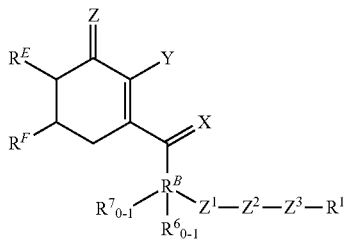

(VIII-1)

(wherein, X is O; Y is hydroxy; Z is O; $R^B$ is optionally substituted aryl, optionally substituted heteroaryl, optionally substituted cycloalkyl, optionally substituted cycloalkenyl or optionally substituted heterocycle; $Z^1$, $Z^2$, $Z^3$ and $R^1$ are the same as above (1); $R^E$ and $R^F$ are each independently a non-interfering substituent), its prodrug or pharmaceutically acceptable salt or solvate thereof.

(67) A compound of above (66), wherein $R^B$ is fran-2-yl, its prodrug or pharmaceutically acceptable salt or solvate thereof.

(68) A compound of above (66), wherein $R^B$ is fran-2-yl; $Z^1$ and $Z^3$ are bonds; $Z^2$ is alkylene; $R^1$ is aryl optionally substituted with halogen; $R^6$, $R^7$, $R^E$ and $R^F$ are hydrogens, its prodrug or pharmaceutically acceptable salt or solvate thereof.

(69) A compound of above (38), shown by formula (VIII-2):

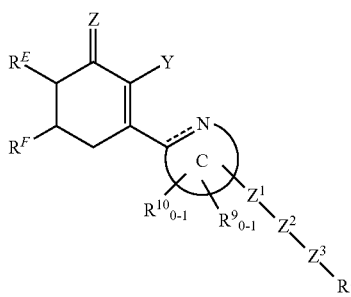

(VIII-2)

(wherein, Y is hydroxy; Z is O; C ring, $Z^1$, $Z^2$, $Z^3$ and $R^1$ are the same as above (1); $R^E$ and $R^F$ are each independently a non-interfering substituent), its prodrug or pharmaceutically acceptable salt or solvate thereof.

(70) A compound of above (38), shown by formula (IX-1):

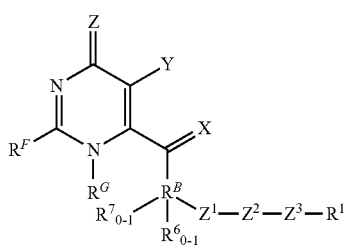

(IX-1)

(wherein, X is O; Y is hydroxy; Z is b; $R^B$ is optionally substituted aryl, optionally substituted heteroaryl, optionally substituted cycloalkyl, optionally substituted cycloalkenyl or optionally substituted heterocycle; $Z^1$, $Z^2$, $Z^3$ and $R^1$ are the same as above (1); $R^6$, $R^7$, $R^F$ and $R^G$ are each independently a non-interfering substituent), its prodrug or pharmaceutically acceptable salt or solvate thereof.

(71) A compound of above (70), wherein $R^B$ is fran-2-yl, its prodrug or pharmaceutically acceptable salt or solvate thereof.

(72) A compound of above (70), wherein $R^B$ is fran-2-yl; $Z^1$ and $Z^3$ are bonds; $Z^2$ is alkylene; $R^1$ is aryl optionally substituted with halogen; $R^6$, $R^7$, $R^F$ and $R^G$ are hydrogens, its prodrug or pharmaceutically acceptable salt or solvate thereof.

(73) A compound of above (38), shown by formula (IX-2):

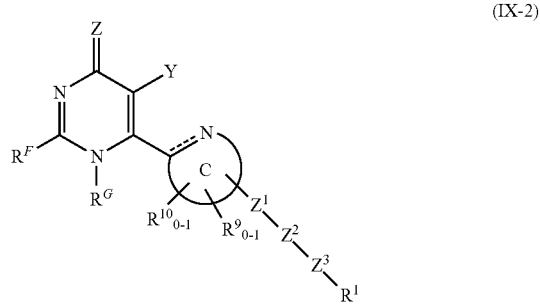

(IX-2)

(wherein, Y is hydroxy; Z is O; C ring, $Z^1$, $Z^2$, $Z^3$ and $R^1$ are the same as above (1); $R^9$, $R^{10}$, $R^F$ and $R^G$ are each independently a non-interfering substituent, provided that when $R^G$ is hydrogen and $R^F$ is alkyl, C ring is not dihydropirimidine), its prodrug or pharmaceutically acceptable salt or solvate thereof.

(74) A compound of above (38), shown by formula (X-1):

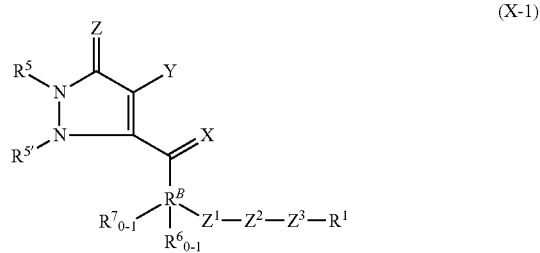

(X-1)

(wherein, X is O; Y is hydroxy; Z is O; $R^B$ is optionally substituted aryl, optionally substituted heteroaryl, optionally substituted cycloalkyl, optionally substituted cycloalkenyl or optionally substituted heterocycle; $Z^1$, $Z^2$, $Z^3$ and $R^1$ are the same as above (1); $R^5$, $R^{5'}$, $R^6$ and $R^7$ are each independently a non-interfering substituent), its prodrug or pharmaceutically acceptable salt or solvate thereof.

(75) A compound of above (74), wherein $R^B$ is fran-2-yl, its prodrug or pharmaceutically acceptable salt or solvate thereof.

(76) A compound of above (74), wherein $R^B$ is fran-2-yl; $Z^1$ and $Z^3$ are bonds; $Z^2$ is alkylene; $R^1$ is aryl optionally substituted with halogen; $R^6$, $R^7$, $R^5$ and $R^{5'}$ are hydrogens, its prodrug or pharmaceutically acceptable salt or solvate thereof.

(77) A compound of above (38), shown by formula (X-2):

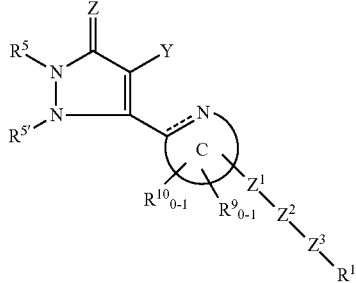

(X-2)

(wherein, Y is hydroxy; Z is O; C ring, $Z^1$, $Z^2$, $Z^3$ and $R^1$ are the same as above (1); $R^5$, $R^{5'}$, $R^9$ and $R^{10}$ are each independently a non-interfering substituent), its prodrug or pharmaceutically acceptable salt or solvate thereof.

(78) A compound of above (38), shown by formula (XI-1):

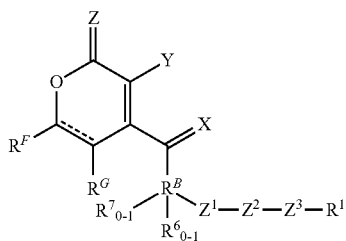

(XI-1)

(wherein, X is O; Y is hydroxy; Z is O; $R^B$ is optionally substituted aryl, optionally substituted heteroaryl, optionally substituted cycloalkyl, optionally substituted cycloalkenyl or optionally substituted heterocycle; $Z^1$, $Z^2$, $Z^3$ and $R^1$ are the same as above (1); $R^6$, $R^7$, $R^F$ and $R^G$ are each independently a non-interfering substituent, the broken line (---) shows the presence or absence of a bond), its prodrug or pharmaceutically acceptable salt or solvate thereof.

(79) A compound of above (78), wherein, $R^B$ is fran-2-yl, its prodrug or pharmaceutically acceptable salt or solvate thereof.

(80) A compound of above (78), wherein, $R^B$ is fran-2-yl; $Z^1$ and $Z^3$ are bonds; $Z^2$ is alkylene; $R^1$ is aryl optionally substituted with halogen; $R^6$, $R^7$, $R^F$ and $R^G$ are hydrogens, its prodrug or pharmaceutically acceptable salt or solvate thereof.

(81) A compound of above (38), shown by (XI-2):

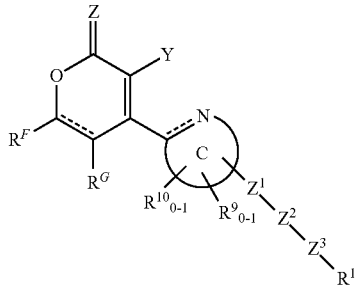

(XI-2)

(wherein, Y is hydroxy; Z is O; C ring, $Z^1$, $Z^2$, $Z^3$ and $R^1$ are the same as above (1); $R^9$, $R^{10}$, $R^F$ and $R^G$ are each independently a non-interfering substituent, the broken line (---) shows the presence or absence of a bond), its prodrug or pharmaceutically acceptable salt or solvate thereof.

(82) A compound of above (38), shown by (XII-1):

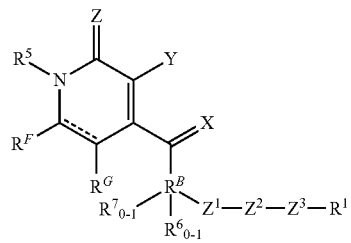

(XII-1)

(wherein, X is O; Y is hydroxy; Z is O; $R^B$ is optionally substituted aryl, optionally substituted heteroaryl, optionally substituted cycloalkyl, optionally substituted cycloalkenyl or optionally substituted heterocycle; $Z^1$, $Z^2$, $Z^3$ and $R^1$ are the same as above (1); $R^5$, $R^6$, $R^7$, $R^F$ and $R^G$ are each independently a non-interfering substituent, the broken line (---) shows the presence or absence of a bond), its prodrug or pharmaceutically acceptable salt or solvate thereof.

(83) A compound of above (82), wherein, $R^B$ is fran-2-yl, its prodrug or pharmaceutically acceptable salt or solvate thereof.

(84) A compound of above (82), wherein, $R^B$ is fran-2-yl; $Z^1$ and $Z^3$ are bonds; $Z^2$ is alkylene; $R^1$ is aryl optionally substituted with halogen; $R^6$, $R^7$, $R^F$ and $R^G$ are hydrogens, its prodrug or pharmaceutically acceptable salt or solvate thereof.

(85) A compound of above (38), shown by formula (XII-2):

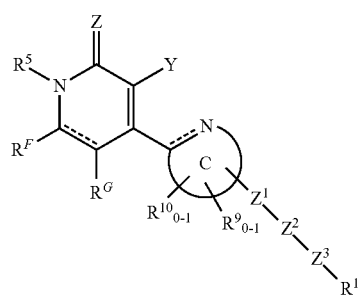

(XII-2)

(wherein, Y is hydroxy; Z is O; C ring, $Z^1$, $Z^2$, $Z^3$ and $R^1$ are the same as above (1); $R^5$, $R^9$, $R^{10}$, $R^F$ and $R^G$ are each independently a non-interfering substituent, the broken line (---) shows the presence or absence of a bond), its prodrug or pharmaceutically acceptable salt or solvate thereof.

(86) A compound of above (38), shown by formula (XIII-1):

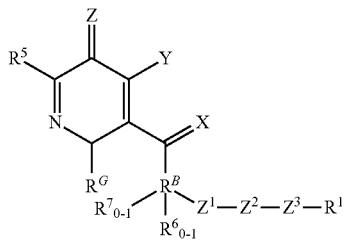

(XIII-1)

(wherein, X is O; Y is hydroxy; Z is O; $R^B$ is optionally substituted aryl, optionally substituted heteroaryl, optionally substituted cycloalkyl, optionally substituted cycloalkenyl or optionally substituted heterocycle; $Z^1$, $Z^2$, $Z^3$ and $R^1$ are the same as above (1); $R^5$, $R^6$, $R^7$ and $R^G$ are each independently a non-interfering substituent), its prodrug or pharmaceutically acceptable salt or solvate thereof.

(87) A compound of above (86), wherein $R^B$ is fran-2-yl, its prodrug or pharmaceutically acceptable salt or solvate thereof.

(88) A compound of above (86), wherein $R^B$ is fran-2-yl; $Z^1$ and $Z^3$ are bonds; $Z^2$ is alkylene; $R^1$ is aryl optionally substituted with halogen; $R^6$, $R^7$ and $R^G$ are hydrogens, its prodrug or pharmaceutically acceptable salt or solvate thereof.

(89) A compound of above (38), shown by formula (XIII-2):

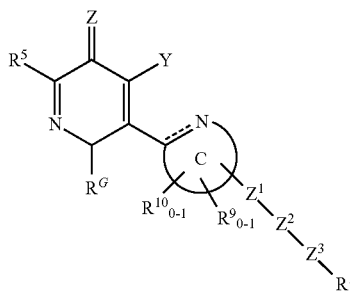

(XIII-2)

(wherein, Y is hydroxy; Z is O; C ring, $Z^1$, $Z^2$, $Z^3$ and $R^1$ are the same as above (1); $R^5$, $R^9$, $R^{10}$ and $R^G$ are each independently a non-interfering substituent), its prodrug or pharmaceutically acceptable salt or solvate thereof.

(90) A compound of above (38), (39), (46), (52), (54), (57), (69), (73), (77), (81), (85) or (89), wherein C ring is optionally substituted pyridine-2-yl, optionally substituted pyrimidine-4-yl, optionally substituted 1,3,4-oxadiazole-2-yl, optionally substituted 1,2,4-triazole-3-yl or optionally substituted imidazole-2-yl, its prodrug or pharmaceutically acceptable salt or solvate thereof.

(91) A compound of above (38), (39), (46), (52), (54), (57), (69), (73), (77), (81), (85) or (89), wherein $Z^1$ and $Z^3$ are each independently a bond or alkylene; $Z^2$ is a bond or —O—; $R^1$ is optionally substituted aryl or optionally substituted heteroaryl, its prodrug or pharmaceutically acceptable salt or solvate thereof.

(92) A compound of above (38), (39), (46), (52), (54), (57), (69), (73), (77), (81), (85) or (89), wherein C ring is pyrimidine-4-yl or 1,3,4-oxadiazole-2-yl; $Z^1$ is a bond; $Z^2$ is —O or alkylene; $Z^3$ is a bond or alkylene; $R^1$ is aryl optionally substituted with halogen; $R^3$, $R^4$ and $R^{19}$ are hydrogens, its prodrug or pharmaceutically acceptable salt or solvate thereof.

(93) A compound of above (38), (39), (42), (46), (49), (52), (54), (57), (60). (63), (66), (69), (70), (73), (74), (77), (78), (81), (82), (85), (86) or (89), wherein each non-interfering substituent is independently selected from hydrogen, halogen, alkoxycarbonyl, carboxy, alkyl, alkoxy, alkoxy alkyl, nitro, hydroxy, alkenyl, alkynyl, alkylsulfonyl, optionally substituted amino, alkylthio, alkylthio alkyl, haloalkyl, haloalkoxy, haloalkoxyalkyl, optionally substituted cycloalkyl, optionally substituted cycloalkenyl, optionally substituted heterocycle, oxo, thioxo, nitroso, azide, amidino, guanidino, cyano, isocyano, mercapto, optionally substituted carbamoyl, sulfamoyl, sulfoamino, formyl, alkyl carbonyl, alkyl carbonyloxy, hydrazino, morpholino, optionally substituted aryl, optionally substituted heteroaryl, optionally substituted aralkyl, optionally substituted heteroarylalkyl, optionally substituted aryl oxy, optionally substituted heteroaryl oxy, optionally substituted aryl thio, optionally substituted heteroaryl thio, optionally substituted aralkyloxy, optionally substituted heteroaryl alkyloxy, optionally substituted aralkylthio, optionally substituted heteroaryl alkylthio, optionally substituted aryl oxyalkyl, optionally substituted heteroaryl oxyalkyl, optionally substituted aryl thioalkyl, optionally substituted heteroaryl thioalkyl, optionally substituted arylsulfonyl, optionally substituted heteroarylsulfonyl, optionally substituted aralkylsulfonyl and optionally substituted heteroaryl alkylsulfonyl, its prodrug or pharmaceutically acceptable salt or solvate thereof.

(94) A compound of above (38), (39), (42), (46), (49), (52), (54), (57), (60). (63), (66), (69), (70), (73), (74), (77), (78), (81), (82), (85), (86) or (89), wherein $Z^1$, $Z^2$ and $Z^3$ are not bonds at the same, its prodrug or pharmaceutically acceptable salt or solvate thereof.

(95) A compound of above (94), wherein $R^1$ is phenyl optionally substituted with halogen, $Z^1$ is a bond, $Z^2$ is alkylene or —O—, $Z^3$ is a bond or alkylene, its prodrug or pharmaceutically acceptable salt or solvate thereof.

(96) A compound of above (95), wherein $R^1$ is 4-fluorophenyl, its prodrug or pharmaceutically acceptable salt or solvate thereof.

(97) A compound of the formula (I):

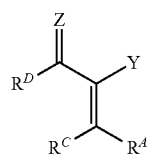

(I)

(wherein, $R^C$ and $R^D$ taken together with the neighboring carbon atoms form 5- or 6-membered heterocycle which may contain O and/or N atom and be condensed with a benzene ring; Y is hydroxy, mercapto or amino; Z is O, S or NH;

$R^A$ is shown of the formula:

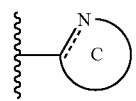

(wherein, C ring is N-containing aromatic heterocycle, wherein at least one atom neighboring to the atom at the bonding-position is unsubstituted N atom. The broken line shows the presence or absence of a bond.) or the formula:

(wherein, X is O, S or NH; $R^B$ is optionally substituted aryl, optionally substituted heteroaryl, optionally substituted cycloalkyl, optionally substituted cycloalkenyl or optionally substituted heterocycle);
at least one of the ring formed by $R^C$ and $R^D$, C ring and $R^B$ is substituted with a group of the formula: $-Z^1-Z^2-Z^3-R^1$ (wherein, $Z^1$ and $Z^3$ are each independently a bond, optionally substituted alkylene or optionally substituted alkenylene; $Z^2$ is a bond, optionally substituted alkylene, optionally substituted alkenylene, $-CH(OH)-$, $-S-$, $-SO-$, $-SO_2-$, $-SO_2N(R^2)-$, $-N(R^2)SO_2-$, $-O-$, $-N(R^2)-$, $-N(R^2)CO-$, $-CON(R^2)-$, $-C(=O)-O-$, $-O-C(=O)$ or $-CO-$; $R^2$ is hydrogen, optionally substituted alkyl, optionally substituted alkenyl, optionally substituted aryl or optionally substituted heteroaryl; $R^1$ is optionally substituted aryl, optionally substituted heteroaryl, optionally substituted cycloalkyl, optionally substituted cycloalkenyl or optionally substituted heterocycle); and
the ring formed by $R^C$ and $R^D$, C ring or $R^B$ is optionally substituted with 1 to 3 substituents selected from hydrogen, alkyl, aralkyl, cycloalkyl, optionally substituted aryl, alkoxy, alkoxyalkyl, optionally substituted amino, hydroxyalkyl, alkenyl, alkoxycarbonylalkyl, heteroarylalkyl and hydroxy, at any position except where the above the formula: $-Z^1-Z^2-Z^3-R^1$ (wherein, $Z^1$, $Z^2$, $Z^3$ and $R^1$ are the same as defined above) locates, its prodrug or pharmaceutically acceptable salt or solvate thereof.

(98) A compound of above (97), wherein the ring formed by $R^C$ and $R^D$ is 0.5- or 6-membered heterocycle which may contain O and/or N atom and be condensed with benzene ring; Y is hydroxy; Z is O; X is O; the ring formed by $R^C$ and $R^D$ is optionally substituted with 1 to 3 substituents selected from hydrogen, alkyl, aralkyl, cycloalkyl, optionally substituted aryl, alkoxy, alkoxyalkyl, optionally substituted amino, hydroxyalkyl, alkenyl, alkoxycarbonylalkyl and heteroaryl alkyl, and C ring and $R^B$ are each independently optionally substituted with 1 to 3 substituents selected from alkyl, amino, halogen and hydroxy, its prodrug or pharmaceutically acceptable salt or solvate thereof.

(99) A compound of above (97) or (98), wherein at least one of the ring formed by $R^C$ and $R^D$, C ring and $R^B$ is substituted with a group of the formula: $-Z^1-Z^2-Z^3-R^1$ (wherein $Z^1$ is a bond or alkylene; $Z^2$ is alkylene or $-O-$; $Z^3$ is a bond or alkylene; $R^1$ is optionally substituted aryl or optionally substituted heteroaryl), its prodrug or pharmaceutically acceptable salt or solvate thereof.

(100) A pharmaceutical composition comprising a compound of any one of above (38) to (99), its prodrug or pharmaceutically acceptable salt or solvate thereof.

(101) A pharmaceutical composition of above (100) which is an enzyme inhibitor.

(102) A pharmaceutical composition of above (100) which is a nucleic acid-related enzyme inhibitor.

(103) A pharmaceutical composition of above (100) which is an HIV integrase inhibitor.

(104) A pharmaceutical composition of above (100) which is an anti-HIV agent.

(105) A pharmaceutical composition of above (100) which is a critical prevention or treatment agent for AIDS or a AIDS-related complication.

(106) A mixture of a pharmaceutical composition of above (103) in combination with a reverse transcriptase inhibitor and/or a protease inhibitor.

(107) A pharmaceutical composition of above (100) which can enhance the anti-HIV activity of a reverse transcriptase inhibitor and/or a protease inhibitor.

(108) A method for prevention or treatment of AIDS or a AIDS-related complication which comprises administration of a compound of any one of (38) to (99).

(109) Use of a compound of any one of (38) to (99) for preparing a pharmaceutical composition as an integrase inhibitor.

(110) A process for preparing a compound of the formula (III-1):

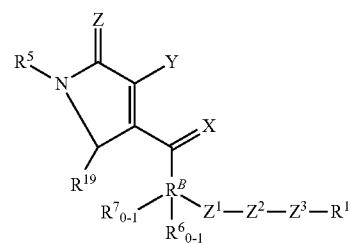

(wherein, X, Y, Z, $R^B$, $R^5$ to $R^7$, $R^{19}$, $Z^1$ to $Z^3$ and $R^1$ are the same as defined below) which comprises reacting a compound of the formula (K):

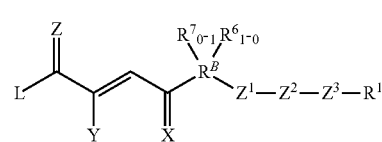

(wherein, X is O; Y is hydroxy; Z is O; L is a leaving group; $R^B$, $Z^1$, $Z^2$, $Z^3$ and $R^1$ are the same as above (1); $R^6$ and $R^7$ are the same as above (11)) with a compound of the formula: $R^5NH_2$ (wherein, $R^5$ is a non-interfering substituent) and a compound of the formula: $R^{19}CHO$ (wherein, $R^{19}$ is a non-interfering substituent).

(111) A process for preparing a compound of the formula (III-1) of above (110), wherein, $R^B$ is heteroaryl; $R^6$ and $R^7$ do not substitute on $R^B$; L is alkoxy; $Z^1$ and $Z^3$ are bonds; $Z^2$ is alkylene; $R^1$ is optionally substituted phenyl.

(112) A process for preparing a compound of the formula (III-1) of above (110), wherein $Z^2$ is methylene; $R^1$ is 4-fluorophenyl.

(113) A process for preparing a compound of the formula (III-1) of above (112), wherein the compound of the formula (K) is 4-[5-(4-fluorobenzyl)fran-2-yl]-2-hydroxy-4-oxo-2-butenoic acid alkyl ester.

(114) A process for preparing a compound of the formula (III-1) of above (110) to (113), wherein compounds shown of the formula: $R^5NH_2$ and $R^{19}CHO$ are selected from the following groups;

compound of the formula: $R^5NH_2$ cyclopropylamine, cyclobutylamine, cyclopentylamine, cycloleucine, cyclohexylamine, 1-aminocyclohexan carboxylic acid, 1-ethynylcyclohexylamine, 1,2-diaminocyclohexan, 2-methylcyclohexylamine, 2,3-dimethylcyclohexylamine, 4-methylcyclohexylamine, aminomethylcyclohexan, 1,3-cyclohexan bis(methylamine), 1-amino-5,6,7,8-tetrahydronaphthalene, 1,2,3,4-tetrahydro-1-naphthylamine cyclooctylamine, 2-amino-1-propene-1,1, 3-tricarbonitril, diaminomaleonitril, S-methylL-csteine, L-aspartic acid, L-leucine, DL-homoserine, D-methionine, L-allylglycine, L-glutamic acid, 2-amino-1,3,4-thiadiazole, 2-amino-5-mercapto-1,3,4-thiadiazole, 2-amino-5-ethyl-1,3,4-thiadiazole, 3,5-dimethylpyrazole-1-carboamide, 5-amino-3-methylisoxazole, 3-amino-5-methylisoxazole, 2-(2-amino ethyl)-1-methylpyrrolidine, 1-(2-amino ethyl) pyrrolidine, 1-(3-amino propyl)-2-pyrolidinone, furfurylamine, 1-aminoindan, 5-aminoindan, 1-naphthyl amine, 2-naphthyl amine, cycloheptylamine, D-tert-leucine, DL-valine, DL-isoleucine, D-serine, guanidoacetic acid, creatine, D-allothreonine, 2-amino-2-methyl-1,3-propanediol, tris(hydroxy methyl)aminomethane, DL-2-amino-3-methyl-1-butanol, L-isoleucinol, D-leucinol, L-methioninol, DL-penicillamine, DL-cysteine, DL-homocysteine, 1-acetyl-3-thiosemicarbazide, 1-acetyl-2-thiourea, N-methylthiourea, ethylthiourea, allylthiourea, dithioxamide, histamine, 3-amino-1,2,4-triazole, 3-amino-5-mercapto-1,2,4-triazole, 3-amino-5-methylthio 1,2,4-triazole, 3,5-diamino-1,2,4-triazole, 3-aminopyrazole, 3-amino-4-cyanopyrazole, 3-aminopyrazole-4-carboxylic acid, L-prolineamide, 2-amino-2-thiazoline, 2-aminothiazole, 2-amino-5-nitrothiazole, 2-amino-4-methylthiazole, D-cycloserine, tetrahydrofurfurylamine, 2-aminopurine, 2-aminobenzimidazole, 5-amino indole, 4-aminopyrazolo[3,4-D]pyrimidine, 6-aminoindazole, 8-azaadenine, 3,4-methylenedioxyaniline, N-(2-aminoethyl)piperazine, nipecotamide, 4-(aminomethyl) piperidine, 5-aminouracil, 5-azacytosine, cytosine, 5-fluorocytosine, 4-amino-2,6-dihydroxypyrimidine, 2-aminopyrimidine, 2-amino-4-chloro-6-methylpyrimidine, 2-amino-4,6-dihydroxypyrimidine, 2-amino-4-hydroxy-6-methylpyrimidine, 4-chloro-2,6-diaminopyrimidine, 2,4-diamino-6-hydroxypyrimidine, 2,4,6-triaminopyrimidine, 2-amino-4-methylpyrimidine, 2-amino-4,6-dimethylpyrimidine, 2-amino-5-nitro pyrimidine, 4-aminopyrimidine, 4,5-diaminopyrimidine, 4,5-diamino-6-hydroxy pyrimidine, pyrazineamide, aminopyrazine, 3-aminopyrazine E-2-carboxylic acid, 4-(2-aminoethyl)morpholine, N-(3-aminopropyl)morpholine, nicotineamide N-oxide, 3-amino-2-chloro-pyridine, 5-amino-2-chloropyridine, 5-amino-2-methoxypyridine, 3-hydroxypicolineamide, 2-aminopyridine, 2-amino-3-nitropyridine, 2-amino-3-hydroxy pyridine, 2-aminonicotinic acid, 2,3-diaminopyridine, 2-amino-3-methylpyridine, 2-amino-4-methylpyridine, 2-amino-4,6-dimethylpyridine, 2-amino-5-chloropyridine, 2-amino-5-nitropyridine, 6-aminonicotinic acid, 6-aminonicotinamide, 2-amino-5-methylpyridine, 2,6-diaminopyridine, 2-amino-6-methylpyridine, 6-methylnicotinamide, 2-(aminomethyl)pyridine, 2-(2-aminoethyl)pyridine, nicotinamide, thionicotinamide, 3-aminopyridine, 3,4-diaminopyridine, 3-(aminomethyl)pyridine, isonicotinamide, 4-aminopyridine, 4-(aminomethyl)pyridine, 3-amino-1,2,4-triazine, 3-amino-5,6-dimethyl-1,2,4-triazine, 1-(2-amino-ethyl)piperidine, 3-aminoquinoline, 5-aminoquinoline, 6-aminoquinoline, 8-aminoquinoline, 5-aminoisoquinoline, nitroguanidine, cyanamide, thiosemicarbazide, aniline, 2-aminobenzonitril, 2-fluoroaniline, 2,4-difluoroaniline, 2,4,5-trifluoroaniline, 2,4,6-trifluoroaniline, 2,5-difluoroaniline, 2-fluoro-5-methylaniline, 2,6-difluoroaniline, 2-chloroaniline, 2-chloro-4-methylaniline, 2-chloro-5-methylaniline, 2-chloro-6-methylaniline, O-nitroaniline, anisidine, O-phenetidine, 2-aminophenol, 6-amino-m-cresol, 2-amino-4-chlorophenol, 2-amino-4-methylphenol, 2-aminothiophenol, 2-(methylthio)aniline, anthranilic acid, 2'-aminoacetophenone, 2-isopropenylaniline, 2-isopropylaniline, o-phenylenediamine, 3,4-diaminotoluene, 4,5-dimethyl-1,2-phenylenediamine, o-toluidine, 2,3-dimethylaniline, 4-methoxy-2-methylaniline, 2,4-dimethylaniline, 2,4,6-trimethylartiline, 2,5-dimethylaniline, 2-isopropyl-6-methylaniline, 2,6-dimethylaniline, 2-aminobenzyl alcohol, 2-ethylaniline, 2-ethyl-6-methylaniline, 2,6-diethyl aniline, 2-aminophenetyl alcohol, 3-aminobenzonitril, 3-fluoroaniline, 3-fluoro-o-anisidine, 3-fluoro-2-methylaniline, 3,4-difluoroaniline, 3-fluoro-4-methylaniline, 3,5-difluoroaniline, 5-fluoro-2-methylaniline, 3-chloroaniline, 3-chloro-2-methylaniline, 3-chloro-4-fluoroaniline, 3-chloro-4-methylaniline, 5-chloro-2-methylaniline, m-nitroaniline, m-anisidine, m-phenetidine, 3-aminophenol, 3-amino-o-cresol, 3-aminothiophenol, 3-(methylthio)aniline, 3-aminobenzoic acid, 3-aminoacetophenone, 3-(1-hydroxy ethyl)aniline, m-phenylenediamine, 2,6-diaminotoluene, 2,4-diaminotoluene, m-toluidine, 3,4-dimethylaniline, 3,5-dimethylaniline, 2-methoxy-5-methylaniline, 3-aminobenzyl alcohol, 3-ethylaniline, 4-aminobenzonitril, 4-fluoroaniline, 4-fluoro-2-methylaniline, 4-chloro aniline, 4-chloro-2-methylaniline, p-nitroaniline, N,N-dimethylp-phenylene diamine, p-anisidine, p-phenetidine, 4-aminophenol, 4-amino-m-cresol, 4-amino-2,5-dimethylphenol, 4-amino-o-cresol, 4-aminothiophenol, 4-(methylthio)aniline, 4-aminobenzoic acid, 4-aminoacetophenone, 4-tert-butylaniline, 4-isopropylaniline, p-phenylenediamine, p-toluidine, 4-aminophenylacetonitrile, 4-ethylaniline, 4-aminophenetyl alcohol, 4-propylaniline, 4-N-butylaniline, formamide, hydroxyurea, phenylurea, cyanoacetylurea, methylurea, ethylurea, allylurea, N-butylurea, N,N-dimethylurea, 1,1-diethylurea, phenylcarbamate, tert-butylcarbamate, methylcarbamate, ethylcarbamate, butylcarbamate, benzamide, 2-fluorobenzamide, salicylamide, 2-aminobenzamide, O-toluamide, 3-fluorobenzamide, 3-aminobenzamide, m-toluamide, 4-fluorobenzamide, 4-hydroxybenzamide, 4-aminobenzamide, p-toluamide, ethyl oxamate, oxamide, 2,2,2-trifluoroacetamide, trimethylacetamide, 2,2-dichloroacetamide, 2-chloropropioneamide, lactamide, methacrylamide, isobutylamide, urea, acetamide, cyanoacetamide, 2-bromoacetamide, fluoroacetamide, 2-chloro acetamide, N-acetylglycine amide, acrylic amide, cinnamamide, malonamide, propioneamide, 3-chloropropioneamide, 2-aminoisobutanoic acid, tert-utylamine, 2-amino-2-methyl-1-propanol, tert-octylamine, 1,2-diamino-2-methylpropane, tert-amyl amine, 1,1-diethylpropargylamine, thiobenzamide, (R)-(−)-2-phenylglycinol, thiourea, DL-α-methylbenzylamine, thioacetamide, 3-aminocrotonitril, methyl 3-aminocrotonate, ethyl 3-aminocrotonate, D-alanine, 1,2-dimethylpropylamine, isopropylamine, 2-amino-1-methoxypropane, DL-2-amino-1-propanol, ethyl 3-aminobutylate, DL-β-amino-n-butanoic acid, 1,3-dimethylbutylamine, 1,2-diaminopropane, 1-methyl-3-phenylpropylamine, 2-amino-6-methylheptane, DL-2-aminobutanoic acid, sec-butylamine, (+/−)-2-amino-1-butanol, 3-amino pentane, D-norvaline, D-norleucine, 2-aminoheptane, 2-aminooctane, methylamine, benzylamine, 2-fluorobenzylamine, 2-chlorobenzylamine, 2-methoxybenzylamine, 2-methylbenzylamine, 3-fluorobenzyl amine, 3-methoxybenzylamine, 3-methylbenzylamine, m-xylylenediamine, 4-fluorobenzylamine, 4-chlorobenzylamine, 4-methoxybenzylamine, 4-methylbenzyl amine, glycine, 2,2,2-trifluoroethyl amine, aminoacetoaldehyde dimethyl acetal, amino acetoaldehyde diethyl acetal, 2-amino-1-phenylethanol, DL-isoserine, 1-amino-2-propanol, 3-amino-1,2-propanediol, DL-4-amino-3-hydroxybutanoic acid, 1,3-diamino-2-hydroxypropane, 2-phenylpropylamine, DL-3-aminoisobutanoic acid, isobutylamine, 2-methylbutylamine, 2-ethylhexylamine, ethylamine, N-phenylethylenediamine, N-acetylethylenediamine, N-isopropylethylenediamine, N-methylethylenediamine, N-ethylethylene diamine, 2-(2-aminoethylamino)ethanol, diethylenediamine, N-(n-propyl)ethylenediamine, N,N-dimethylethylene diamine N,N-diethylethylenediamine, tris(2-aminoethyl)amine, 2-methoxyethylamine, 2-(2-aminoethoxy)ethanol, ethanolamine, phenetylamine, thyramine, 2-(4-aminophenyl)ethylamine, 2-(p-tril)ethylamine, taurine, propargylamine, allylamine, β-alanine, 3,3-dimethylbutylamine, isoamylamine, ethylenediamine, propylamine, N-isopropyl-1,3-propanediamine, N-methyl-1,3-propane diamine, N-(2-aminoethyl)-1,3-propane diamine, N-propyl-1,3-propanediamine, 3,3'-diaminodipropylamine, N,N-dimethyl-1,3-propanediamine, N,N-bis(3-aminopropyl)methylamine, N,N-diethyl-1,3-propanediamine, 3-isopropoxypropylamine, 3-ethoxypropylamine, 3-amino-1-propanol, 3-phenylpropylamine, 4-aminobutanoic acid, 1,3-diaminopropane, 4-amino-1-butanol, 4-phenylbutylamine, 5-aminovalerianic acid, 1,4-diaminobutane, N-amylamine, 5-amino-1-pentanol, 6-aminocaproic acid, 1,5-diaminopentane, hexylamine, 6-amino-1-haxanol, 7-aminoheptanoic acid, 1,6-hexandiamine, n-heptylamine, 1,7-diaminoheptane, octylamine, 1,8-diaminooctane, nonylamine, cyclohexane carboamide, 2,2-dimethyl-1,3-propanediamine, 2-n-propylaniline, DL-2-amino-1-pentanol, DL-2-amino-1-haxanol, 1-(3-aminopropyl)imidazole, p-xylylene diamine, 1-aminocyclopropane-1-carboxylic acid, cyanothioacetamide, 2,4-difluorobenzylamine, 2,5-difluorobenzylamine, 2,6-difluorobenzylamine, 3,4-difluorobenzylamine, 2-methyl-3-thiosemicarbazide, 5-amino-2-methoxyphenol, 4-sec-butylaniline, 2,3-difluoroaniline, thiophene-2-carboamide, 1-amino-1-cyclopentanemethanol, 3-methyladenine, 1-methyladenine, 4-chloro-2-fluoroaniline, 5-amino-1-ethylpyrazole, 2,3-diaminotoluene, butylamine, 4-chloro-o-phenylene diamine, 1-(trimethylsilylmethyl)urea, 2,3,4-trifluoroaniline, 2-(1-cyclohexanyl)ethyl amine, 3-amino-2-butenethioamide, 2,3,6-trifluoroaniline, 1,5-diamino-2-methylpentane, amidinothiourea, 3-ethynylaniline, N,N-bis(2-hydroxyethyl)ethylenediamine, 3-methoxypropylamine, 4-aminostyrene, 2-amino-6-fluorobenzonitrile, 3-amino-5-hydroxypyrazole, 2,4-diamino-6-methyl-1,3,5-triazine, pyridine-2-carboamide, 1-aminoisoquinoline, 4-chloro-1,3-phenylenediamine, 2-chloro ethylcarbamate, amide fumarate, acetoacetamide, N—N-butylethylenediamine, 3-butoxypropylamine, cyclopropanemethylamine, 5-aminoindazole, 2,4-diamino pyrimidine, α-ethylbenzylamine, 3-aminoisoxazole, chlorodifluoroacetamide, 1,8-diamino-3,6-dioxaoctane, 2-sec-butylaniline, 3-chlorobenzylamine, 2-fluoro-4-methylaniline, 1-(4-fluorophenyl)ethylamine, 4-aminophthalonitrile, adenine, 2-chloro-4-fluoroaniline, semicarbazide, (R)-(−)-1-cyclohexylethylamine, 5-amino-o-cresol, N,N, 2,2-tetramethyl-1,3-propanediamine, 2,2-diethoxyacetamide, 3-amino-5,5-dimethyl-2-cyclohexane-1-one, propylcarbamate, glycolamide, 2-amino-1,3-propanediol, thiophene-2-ethylamine, 2,5-dimethyl-1,4-phenylene diamine, 2-amino-4-methoxy-6-methyl-1,3,5-triazine, 2-phenoxyethylamine, 4-amino-2-mercaptopyrimidine, creatinine, 2-amino-4-methoxy-6-methylpyrimidine, 3,5-difluorobenzylamine, (1R,2R)-(−)-1,2-diaminocyclohexane, (1S,2S)-(+)-1,2-diaminocyclohexan, D-asparatic acid, DL-asparatic acid, DL-leucine, D-leucine, L-homoserine, DL-methionine, L-methionine, DL-allylglycine, D-glutamic acid, L-leucinol, DL-threonine, cis-1,2-diaminocyclohexane, trans-1,2-cyclohexanediamine, L-tert-leucine, D-valine, L-valine, D-iso leucine, L-isoleucine, DL-serine, L-serine, L-allo-threonine, D-threonine, L-threonine, L-valinol, D-valinol, L-cysteine, DL-cycloserine, L-cycloserine, L-asparagine, (S-(+)-2-phenylglycinol, (R-(+)-1-phenylethylamine, L-(−)-α-methylbenzylamine, DL-alanine, L-alanine, L-alaninol, D-alaninol, D-(−)-2-aminobutanoic acid, L-α-amino-n-butanoic acid, (R-(−)-2-aminobutane, (S-(+)-2-aminobutane, (S-(+)-2-amino-1-butanol, (R-(−)-2-amino-1-butanol, DL-norvaline, L-norvaline, DL-norleucine, L-norleucine, (R-(−)-1-amino-2-propanol, (5-(+)-1-amino-2-propanol, (S-(−)-2-methylbutylamine, DL-lysine, L-lysine, DL-tert-leucine, (S-(+)-1-cyclohexylethylamine, ethyl thiooxamate, 2-amino-5-methylbenzyl alcohol, 2-amino-3-methylbenzyl alcohol, 3-amino-2-methylbenzyl alcohol, 3-fluoro-4-methoxyaniline, 3-amino-4-methylbenzyl alcohol, 5-methoxy-2-methylaniline, 2-amino-m-cresol, trans-1,4-diaminocyclohexan, 3-amino-5-methylpyrazole, 2,3-diaminophenol, 1-piperidinecarboamide, 6-amino-1-methyluracil, 3-fluorophenetylamine, 2-aminobenzylamine, 2-methoxy-6-methylaniline, 2-fluoro phenetylamine, 4-aminobenzylamine, 1-acetylguanidine, D-homoserine, 2-amino-5-methylthiazole, maleamine acid, (S-(+)-tetrahydrofurfurylamine, 2-aminobenzyl cyanide, 4-amino-2-chlorophenol, 2-amino-4,5-dicyanoimidazole, 4-amino-6-methoxypyrimidine, 2-tert-butylaniline, 2-(4-fluorophenyl)ethylamine, 1,3-diamino pentane, 2-amino-1-methylbenzimidazole, 5-methylfurfurylamine, (R-(+)-1-(p-tril)ethylamine, (S-(−)-1-(p-tril)ethylamine, 3-amino-1,2,4-triazole-5-carboxylic acid, muscimol, 4-ethynlaniline, 2-amino-4-methylbenzonitril, 2-amino-5-methylthio-1,3,4-thiadiazole, 1-(aminocarbonyl)-1-cyclopropanecarboxylic acid, cis-4-aminocyclohexan carboxylic acid, (S-(+)-2-(aminomethyl)pyrrolidine, 5-amino-4-nitroimidazole, 3-amino-1-propanolvinyl aether, thioethylenediamine, isopropyldiethylene triamine, L-tert-leucinol, N-methyl-1,2-phenylenediamine, (R-(−)-tetrahydrofurfurylamine, L-(−)-lactamide, (R-(+)-lactamide, (S-(+)-2,2-dimethylcyclopropanecarboamide, (1S,2R)-(−)-cis-1-amino-2-indanol, (1R,2S)-(+)-cis-1-amino-2-indanol, (R-(−)-1-aminoindane, (S-(+)-1-aminoindane, (R)-2-phenyl-1-propylamine, (S)-2-phenyl-1-propylamine, D-methioninol, (R)-2-amino-1-phenylethanol, 2-amino-4,5-dimethyl-3-furancarbonitrile, N-hexylethylenediamine, (S-(−)-4-amino-2-hydroxybutanoic acid, (S)-3-amino-1,2-propanediol, (R)-3-amino-1,2-propanediol, 4-aminoindole, (R-(−)-tert-leucinol and 2-amino-5-fluoropyridine.

compound of the formula: $R^{19}CHO$ formaldehyde, ethyl 2-formyl-1-cyclopropanecarboxylate, cyclohexancarboaldehyde, 1,2,3,6-tetrahydrobenzaldehyde, 1-methylpyrrole-2-carboaldehyde, furfural, 5-nitro-2-furaldehyde, 5-methylfurfural, 5-hydroxymethyl-2-furaldehyde, 3-(2-furyl)acrolein, benzaldehyde, 2-fluorobenzaldehyde, 2-chloro benzaldehyde, o-anise aldehyde, salicyl aldehyde, 3-fluoro-2-hydroxybenzaldehyde, 2,3-dihydroxybenzaldehyde, 2,5-dihydroxybenzaldehyde, o-naphthalaldehyde, o-tolaldehyde, 2,4-dimethylbenzaldehyde, mesitaldehyde, 2,5-dimethylbenzaldehyde, 3-cyanobenzaldehyde, 3-fluorobenzaldehyde, 3-chlorobenzaldehyde, 3-methoxybenzaldehyde, 3-hydroxybenzaldehyde, 3,4-dihydroxybenzaldehyde, isonaphthalaldehyde, m-tolaldehyde, 4-cyanobenzaldehyde, 4-fluorobenzaldehyde, 4-chlorobenzaldehyde, 4-dimethylaminobenzaldehyde, p-anise aldehyde, imidazole-2-carboaldehyde, pyrrole-2-carboaldehyde, 2-thiophenecarboaldehyde, 3-methylthiophene-2-carboaldehyde, 5-methyl-2-thiophenecarboaldehyde, 3-thiophenecarboaldehyde, indole-3-carboaldehyde, 2-pyridinecarboaldehyde, 6-methyl-2-pyridinecarboaldehyde, 3-pyridinecarboaldehyde, 4-pyridinecarboaldehyde, 4-hydroxybenzaldehyde, terenaphthalaldehyde, cuminaldehyde, p-tolaldehyde, 4-ethyl benzaldehyde, glyoxal, glyoxylic acid, methyl glyoxal, trimethylacetoaldehyde, D-(−)-erythrose, 2-phenylpropionaldehyde, methacrolein, 3-ethoxymethacrolein, alpha-methylcinnamaldehyde, trans-2-methyl-2-butenal, 2-methyl-2-pentenal, isobutylaldehyde, 2,6-dimethyl-5-hepten-1-ol, 2-methylbutylaldehyde, 2-ethylbutylaldehyde, 2-methylpentanal, 2-ethylhaxanal, acetoaldehyde, chloro acetoaldehyde, phenylacetoaldehyde, phenylpropargyl aldehyde, acrolein, 3-(dimethylamino)acrolein, trans-cinnamaldehyde, crotonaldehyde, 2,4-haxadienal, trans,trans-2,4-heptadienal, trans,trans-2,4-nonadienal, trans-2-hexanal, trans-2,cis-6-nonadien-1-al, trans-2-heptenal, trans-2-octanal, trans-2-nonenal, isovaleralaldehyde, propionaldehyde, 3-phenylpropionaldehyde, 3-(methylthio)propionaldehyde, butylaldehyde, glutaralaldehyde, valeraldehyde, haxanal, heptalaldehyde, octanal, nonanal, trans-2-pentenal, 2,4-dimethyl-2,6-heptadienal, 2,6-pyridinedicarboaldehyde, 2-ethylacrolein, 3-methyl-2-butenal, 2,3-difluorobenzaldehyde, 2,6-difluorobenzaldehyde, 2,4-difluorobenzaldehyde, 2,5-difluorobenzaldehyde, 3,4-difluorobenzaldehyde, 3,5-difluorobenzaldehyde, 3-furaldehyde, 3,5,5-trimethylhaxanal, 3-phenylbutylaldehyde, 2,2-dimethyl-4-pentenal, 2,4-dihydroxybenzaldehyde, cyclopropanecarboaldehyde, 4-hydroxy-3-methylbenzaldehyde, benzo[b]furan-2-carboaldehyde, 3,5-dihydroxybenzaldehyde, 3,4-dimethylbenzaldehyde, 2-cyanobenzaldehyde, 5-ethyl-2-furaldehyde, 2-hydroxy-3-methylbenzaldehyde, 3,3-dimethylbutylaldehyde, 5-chloro-2-thiophenecarboaldehyde, 3,4-dihydro-2H-pyrane-2-carboaldehyde, D-glyceroaldehyde, DL-glyceroaldehyde, 3-fluoro-2-methylbenzaldehyde, 3-dimethylamino-2-methyl-2-propenal, 3,5-dimethylbenzaldehyde, 4,5-dimethyl-2-furancarboaldehyde, 4-vinylbenzaldehyde, 2,6-dimethylbenzaldehyde, 2-octanal, dimethoxyacetoaldehyde, 2-deoxy-D-ribose, 2-formyl thiazole, 5-ethyl-2-thiophenecarboaldehyde, glyoxylic acid, 4-pyridinecarboaldehyde-N-oxide, 5-norbornene-2-carboaldehyde, 4-formylimidazole, 5-methylimidazole-4-carboaldehyde, 5-formyluracil, 2,3-thiophenedicarboaldehyde, thiophene-2,5-dicarboaldehyde, 2,3-o-isopropylidene-D-glyceroaldehyde, 2-hydroxy-5-methylbenzaldehyde, 1-cyclohexane-1-carbo aldehyde, 2,3-dimethylbenzaldehyde, 1-methyl-2-imidazolecarboaldehyde, vinylbenzaldehyde, 4-fluoro-3-methylbenzaldehyde, 3-fluoro-4-methylbenzaldehyde, tetrahydrofran-3-carboaldehyde, 2-fluoro-5-formyl benzonitrile, indole-5-carboaldehyde, 4-acetylbenzaldehyde, 3-vinylbenzaldehyde and 2-fluoro-5-methylbenzaldehyde.

(115) A process for preparing a compound of the formula (III-1) of above (110), wherein the compound of formula (K) is 4-[5-(4-fluorobenzyl)fran-2-yl]-2-hydroxy-4-oxo-2-butenoic acid alkyl ester and compounds shown of the formula: $R^5NH_2$ and $R^{19}CHO$ are each selected from the groups of above (114).

(116) A compound of formula (III-1) prepared by the process of any one of above (110) to (114).

(117) A compound of formula (III-1) prepared by the process of (115).

(118) A library of compounds prepared by the process of above (115).

(119) A pharmaceutical composition comprising as an effective ingredient a compound of above (117).

(120) A pharmaceutical composition as an integrase inhibitor comprising as an effective ingredient a compound of above (117).

The present invention is explained in detail below.
Characteristics of a compound of the formula (I):

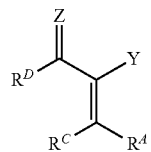

(wherein, $R^C$, $R^D$, Y, Z and $R^A$ are the same as defined above) includes the followings:
1) $R^C$ and $R^D$ taken together with the neighboring carbon atoms may form a ring, and the ring may be a condensed ring,
2) Y is hydroxy, mercapto or amino,
3) Z is O, S or NH,
4) $R^A$ is shown by the formula:

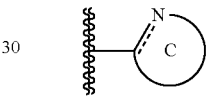

(wherein, C ring is the same as defined above) or the formula:

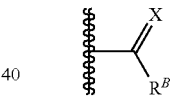

(wherein, X and $R^B$ are the same as defined above),
5) C ring is N-containing aromatic heterocycle, wherein at least one atom neighboring to the atom at the bonding-position is N atom,
6) X is O, S or NH,
7) $R^B$ is a substituent selected from substitution group A,
8) at least one of the ring formed by $R^C$ and $R^D$, C ring or $R^B$ is substituted with a group of the formula: $-Z^1-Z^2-Z^3-R^1$ (wherein, $Z^1$ and $Z^3$ are each independently a bond, optionally substituted alkylene or optionally substituted alkenylene; $Z^2$ is a bond, optionally substituted alkylene, optionally substituted alkenylene, $-CH(OH)-$, $-S-$, $-SO-$, $-SO_2-$, $-SO_2NR^2-$, $-NR^2SO_2-$, $-O-$, $-NR^2-$, $-NR^2CO-$, $-CONR^2-$, $-C(=O)-O-$, $-O-C(=O)-$ or $-CO-$; $R^2$ is hydrogen, optionally substituted alkyl, optionally substituted alkenyl, optionally substituted aryl or optionally substituted heteroaryl; $R^1$ is optionally substituted aryl, optionally substituted heteroaryl, optionally substituted cycloalkyl, optionally substituted cycloalkenyl or optionally substituted heterocycle),
9) the ring formed by $R^C$ and $R^D$, C ring or $R^B$ is optionally substituted with a non-interfering substituent at any position other than that where the group of $-Z^1-Z^2-Z^3-R^1$ (wherein, $Z^1$, $Z^2$, $Z^3$ and $R^1$ is the same as defined above) locates, 10) substitution group A consists of: hydrogen, halogen, alkoxycarbonyl, carboxy, alkyl, alkoxy, alkoxyalkyl, nitro, hydroxy, alkenyl, alkynyl, alkylsulfonyl, optionally substituted amino, alkylthio, alkylthioalkyl, haloalkyl, haloalkoxy, haloalkoxyalkyl, optionally substituted cycloalkyl, optionally substituted cycloalkenyl, optionally substituted heterocycle, nitroso, azide, amidino, guanidino, cyano, isocyano, mercapto, optionally substituted carbamoyl, sulfamoyl, sulfoamino, formyl, alkylcarbonyl, alkyl carbonyloxy, hydrazino, morpholino, optionally substituted aryl, optionally substituted heteroaryl, optionally substituted aralkyl, optionally substituted heteroaryl alkyl, optionally substituted aryloxy, optionally substituted heteroaryloxy, optionally substituted arylthio, optionally substituted heteroarylthio, optionally substituted aralkyloxy, optionally substituted heteroarylalkyloxy, optionally substituted aralkylthio, optionally substituted heteroaryl alkylthio, optionally substituted aryl oxyalkyl, optionally substituted heteroaryl oxyalkyl, optionally substituted aryl thioalkyl, optionally substituted heteroaryl thioalkyl, optionally substituted arylsulfonyl, optionally substituted heteroarylsulfonyl, optionally substituted aralkylsulfonyl and optionally substituted heteroarylalkylsulfonyl, The ring formed by $R^C$ and $R^D$ includes a 4- to 9-membered carbocycle or heterocycle, which may be condensed with the other ring (e.g., 4- to 9-membered carbocycle or heterocycle, or a condensed ring thereof). Preferred is a 5- to 7-membered carbocycle or heterocycle, more preferred is 5- or 6-membered carbocycle or heterocycle, and their condensed ring with the other ring (e.g., 5- or 6-membered carbocycle or heterocycle). Further preferred rings formed by $R^C$ and $R^D$ are the following cases. The heteroaryl used below refers to a ring containing 1 to 4 hetero atom (s) (O, O or S).

1) The ring is 5- or 6-membered one which may contain a heteroatom (s),
2) The ring is 5- or 6-membered heterocycle containing a heteroatom (s),
3) The ring is 5- or 6-membered heterocycle which may contain O and/or N atom,
4) The ring is 5- or 6-membered heterocycle which contains O and/or N atom,
5) The ring is 5- or 6-membered heterocycle which contains N atom,
6) The ring is 5- or 6-membered heterocycle which contains O atom,
7) The ring is 5-membered heterocycle which contains N atom,
8) The ring is 6-membered heterocycle which contains O atom,
9) The ring is 6-membered carbocycle, and
10) The ring is one of above 1) to 9) which is condensed with the other ring,
10) The ring is heterocycle which consists of the ring of above 1) to 9) condensed with a benzene ring.

Examples of the ring formed by $R^C$ and $R^D$ include the followings:

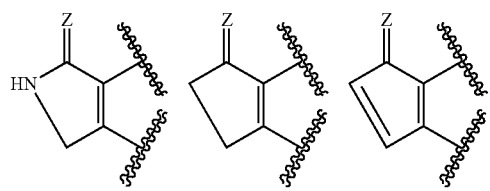

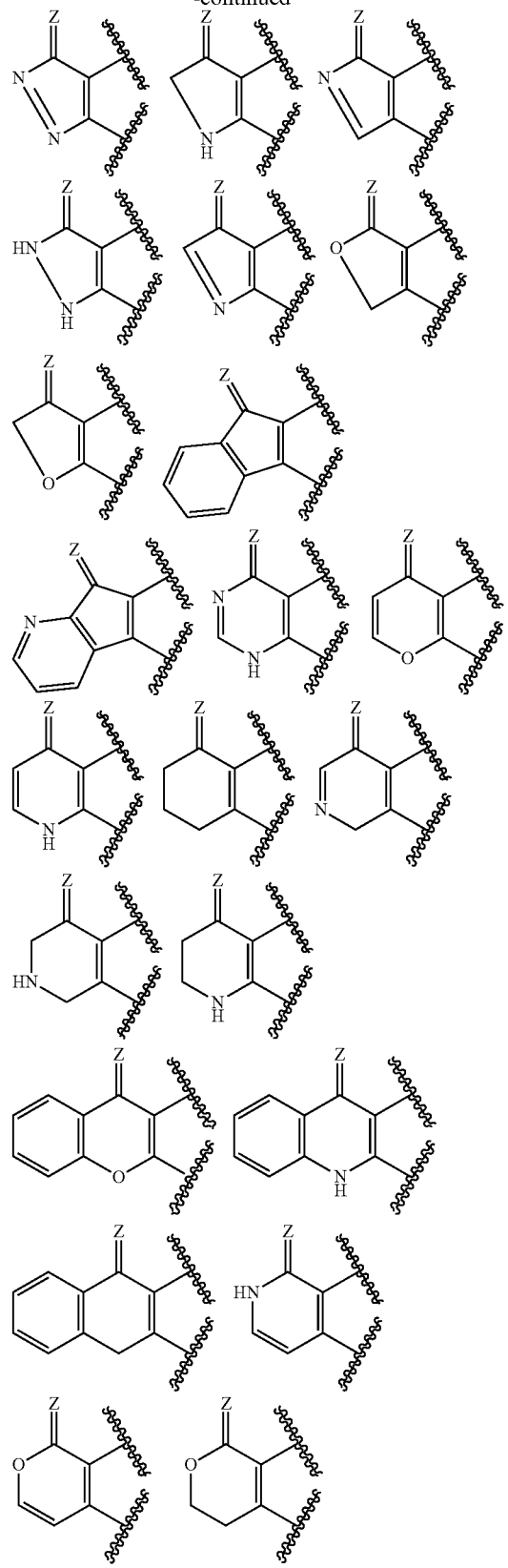

(wherein, Z is the same as above (1))

Among the above, preferred are the followings:
1) The ring is 5-membered N-containing heterocycle,
2) The ring is 6-membered O-containing heterocycle, 3) The ring is 6-membered N-containing heterocycle,
4) The ring is 6-membered O-containing heterocycle condensed with benzene ring, and
5) The ring is 6-membered N-containing heterocycle condensed with benzene ring, Further preferred rings are shown below

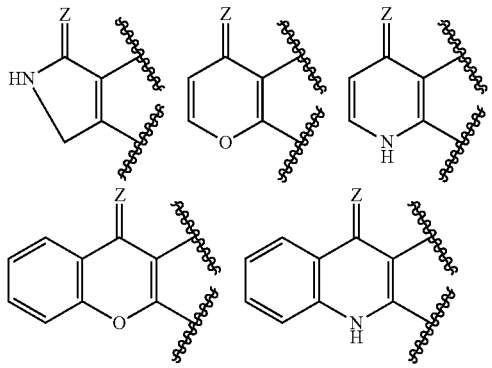

The ring formed by $R^C$ and $R^D$ may be substituted, at any substitutable position of C atom or N atom constructing the ring, with a group of the formula: $-Z^1-Z^2-Z^3-R^1$ (wherein, $Z^1$, $Z^2$, $Z^3$ and $R^1$ are the same as defined above.) or a non-interfering substituent.

The compound of the formula (I) is characterized in that at least one of the ring formed by $R^C$ and $R^D$, C ring and $R^B$ is substituted with a group of the formula: $-Z^1-Z^2-Z^3-R^1$ (wherein, $Z^1$, $Z^2$, $Z^3$ and $R^1$ are the same as defined above.).

Examples of the formula: $-Z^1-Z^2-Z^3-R^1$ (wherein, $Z^1$, $Z^2$, $Z^3$, and $R^1$ are the same as defined above.) include $-R^1$, $-CH_2-R^{one\ or\ 1}$, $-CH=CH-R^1$, $-CH(OH)-R^1$, $-SO-R^1$, $-SO_2-R^1$, $-SO_2NH-R^1$, $-NHSO_2-R^{one\ or\ 1}$, $-NH-R^1$, $-NHCO-R^1$, $-CONH-R^1$, $-C(=O)-O-R^1$, $-O-C(=O)-R^1$, $-CO-R^1$, $-C_2H_4-R^1$, $-CH=CH-CH_2-R^1$, $-CH(OH)-CH_2-R^1$, $-S-CH_2-R^1$, $-SO-CH_2-R^1$, $-SO_2-CH_2-R^1$, $-SO_2NH-CH_2-R^1$, $-NHSO_2-CH_2-R^1$, $-O-CH_2-R^1$, $-NH-CH_2-R^1$, $-NHCO-CH_2-R^1$, $-CONH-CH_2-R^1$, $-C(=O)-O-CH_2-R^1$, $-O-C(=O)-CH_2-R^1$, $-CO-CH_2-R^1$, $-CH=CH-CH=CH-R^1$, $-CH=CH-CH(OH)-R^1$, $-CH=CH-S-R^1$, $-CH=CH-SO-R^1$, $-CH=CH-SO_2-R^1$, $-CH=CH-SO_2NH-R^1$, $-CH=CH-NHSO_2-R^1$, $-CH=CH-O-R^1$, $-CH=CH-NH-R^1$, $-CH=CH-NHCO-R^1$, $-CH=CH-CONH-R^1$, $-CH=CH-C(=O)-O-R^1$, $-CH=CH-O-C(=O)-R^1$, $-CH=CH-CO-R^1$, $-CH_2-CH=CH-R^1$, $-CH_2-CH(OH)-R^1$, $-CH_2-S-R^1$, $-CH_2-SO-R^1$, $-CH_2-SO_2-R^1$, $-CH_2-SO_2NH-R^1$, $-CH_2-NHSO_2-R^1$, $-CH_2-O-R^1$, $-CH_2-NH-R^1$, $-CH_2-NHCO-R^1$, $-CH_2-CONH-R^1$, $-CH_2-C(=O)-O-R^1$, $-CH_2-O-C(=O)-R^1$, $-CH_2-CO-R^1$, $-CH(OH)-CH=CH-R^1$, $-S-CH=CH-R^1$, $-SO-CH=CH-R^1$, $-SO_2-CH=CH-R^1$, $-SO_2NH-CH=CH-R^1$, $-NHSO_2-CH=CH-R^1$, $-O-CH=CH-R^1$, $-NH-CH=CH-R^1$, $-NHCO-CH=CH-R^1$, $-CONH-CH=CH-R^1$, $-C(=O)-O-CH=CH-R^1$, $-O-C(=O)-CH=CH-R^1$, $-CO-CH=CH-R^1$, $-CH_2-CH=CH-CH_2-R^1$, $-CH_2-CH(OH)-CH_2-R^1$, $-CH_2-S-CH_2-R^1$, $-CH_2-SO-CH_2-R^1$, $-CH_2-SO_2-CH_2-R^1$, $-CH_2-SO_2NH-CH_2-R^1$, $-CH_2-NHSO_2-CH_2-R^1$, $-CH_2-O-CH_2-R^1$, $-CH_2-NH-CH_2-R^1$, $-CH_2-NHCO-CH_2-R^1$, $-CH_2-CONH-CH_2-R^1$, $-CH_2-C(=O)-O-CH_2-R^1$, $-CH_2-O-C(=O)-CH_2-R^1$, $-CH_2-CO-CH_2-R^1$, $-C_2H_4-CH=CH-R^1$, $-CH_2-CH=CH-CH-R^1$, $-CH_2-S-CH=CH-R^1$, $-CH_2-SO-CH=CH-R^1$, $-CH_2-SO_2-CH=CH-R^1$, $-CH_2-SO_2NH-CH=CH-R^1$, $-CH_2-NHSO_2-CH=CH-R^1$, H=CH-R^1, $-CH_2-NH-CH=CH-R^1$, $-CH_2-NHCO-CH=CH-R^1$, $-CH_2-CONH-CH=CH-R^1$, $-CH_2-C(=O)-O-CH=CH-R^1$, $-CH_2-O-C(=O)-CH=CH-R^1$, $-CH_2-CO-CH=CH-R^1$, $-CH=CH-C_2H_4-R^1$, $-CH=CH-CH=CH-CH_2-R^1$, $-CH=CH-CH(OH)-CH_2-R^1$, $-CH=CH-S-CH_2-R^1$, $-CH=CH-SO-CH_2-R^1$, $-CH=CH-SO_2-CH_2-R^1$, $-CH=CH-SO_2NH-CH_2-R^1$, $-CH=CH-NHSO_2-CH_2-R^1$, $-CH=CH-O-CH_2-R^1$, $-CH=CH-NH-CH_2-R^1$, $-CH=CH-NHCO-CH_2-R^1$, $-CH=CH-CONH-CH_2-R^1$, $-CH=CH-C(=O)-O-CH_2-R^1$, $-CH=CH-O-C(=O)-CH_2-R^{one}$ or $-CH=CH-CO-CH_2-R^1$ (wherein, $R^1$ is optionally substituted aryl, optionally substituted heteroaryl, optionally substituted cycloalkyl, optionally substituted cycloalkenyl, or optionally substituted heterocycle).

Preferable examples of $-Z^1-Z^2-Z^3-R^1$ (wherein, $Z^1$, $Z^2$, $Z^3$, and $R^1$ are the same as defined above.) are shown below.

1) $Z^1$ and $Z^3$ are bonds,
2) $Z^1$ and $Z^3$ are bonds, $Z^2$ is a bond, $-CO-$, $-O-S-$, $-SO_2$ or lower alkylene (esp., $-CH_2-$, $-(CH_2)_2-$))
3) $Z^1$ and $Z^3$ are bonds, $Z^2$ is a bond, $-CO-$, $-O-$, $-S-$, $-SO_2$ or lower alkylene (esp., $-CH_2-$, $-(CH_2)_2-$), $R^1$ is optionally substituted aryl or optionally substituted heteroaryl,
4) $Z^1$ and $Z^3$ are bonds, $Z^2$ is $-SO_2-$, $-CH_2$ or $-C_2H_4-$, $R^1$ is optionally substituted aryl (esp., phenyl),
5) $Z^1$ is a bond or alkylene, $Z^3$ is a bond, $Z^2$ is optionally substituted alkylene, alkenylene or $-O-$, $R^1$ is optionally substituted aryl, optionally substituted heteroaryl or optionally substituted cycloalkyl,
6) $Z^1$ is a bond or alkylene,
7) $Z^1$ is a bond,
8) $Z^2$ is a bond, alkylene, $-SO_2$ or $-O-$,
9) $Z^2$ is a bond, alkylene or $-O-$,
10) $Z^2$ is alkylene or $-O-$,
11) $Z^3$ is a bond or alkylene,
12) $R^1$ is optionally substituted cycloalkyl, optionally substituted aryl or optionally substituted heteroaryl,
13) $R^1$ is optionally substituted cycloalkyl, optionally substituted cycloalkenyl, optionally substituted heterocycle or optionally substituted aryl,
14) $R^1$ is optionally substituted cycloalkyl, optionally substituted aryl, optionally substituted heteroaryl or optionally substituted heterocycle,
15) $R^1$ is optionally substituted aryl,
16) $Z^1$ and $Z^3$ are bonds, $Z^2$ is alkylene, $R^1$ is optionally substituted aryl,
17) $Z^1$ is a bond or alkylene, $Z^3$ is a bond, $Z^2$ is optionally substituted alkylene, alkenylene, $-S$ or $-O-$, $R^1$ is optionally substituted aryl, optionally substituted heteroaryl or optionally substituted cycloalkyl,
18) $Z^1$ and $Z^3$ are each independently a bond or alkylene; $Z^2$ is a bond or $-O-$; $R^1$ is optionally substituted aryl or optionally substituted heteroaryl,
19) $Z^1$, $Z^2$ and $Z^3$ are not bonds at the same time, 20) R¹ is phenyl optionally substituted with halogen, Z¹ is a bond, Z² is alkylene or —O—, Z³ is a bond or alkylene,
21) R¹ is 4-fluorophenyl, Z¹ is a bond, Z² is alkylene or —O—, Z³ is a bond or alkylene.

Examples of the formula: —Z¹—Z²—Z³—R¹ include phenyl, 2-fluorophenyl, 3-fluorophenyl, 4-fluorophenyl, 2-chlorophenyl, 3-chlorophenyl, 4-chlorophenyl 2,4-difluorophenyl, 2,6-difluorophenyl, 2,5-difluorophenyl, 3,4-difluorophenyl, 4-methylphenyl, 3-trifluoromethylphenyl, 4-trifluoromethylphenyl, 4-hydroxyphenyl, 4-methoxyphenyl, 4-bromophenyl, 4-biphenyl, benzyl, 2-fluorobenzyl, 3-fluorobenzyl, 4-fluorobenzyl, 2-chlorobenzyl, 3-chlorobenzyl, 4-chlorobenzyl, 2,4-difluorobenzyl, 2,6-difluorobenzyl, 2,5-difluorobenzyl, 3,4-difluorobenzyl, 3,6-difluorobenzyl, 4-methylbenzyl, 3-trifluoromethylbenzyl, 4-trifluoromethylbenzyl, 4-hydroxybenzyl, 4-methoxybenzyl, 4-bromobenzyl, 4-phenylbenzyl, 2-phenylethyl, 2-(2-fluorophenyl)ethyl, 2-(3-fluorophenyl)ethyl, 2-(4-fluorophenyl)ethyl, 2-(2-chlorophenyl)ethyl, 2-(3-chlorophenyl)ethyl, 2-(4-chlorophenypethyl, 2-(2,4-difluorophenyl)ethyl, 2-(2,6-difluorophenypethyl, 2-(2,5-difluorophenyl)ethyl, 2-(3,4-difluorophenyl)ethyl, 2-(4-methylphenyl)ethyl, 2-(3-trifluoromethylphenyl)ethyl, 2-(4-trifluoromethylphenyl)ethyl, 2-(4-hydroxy phenyl)ethyl, 2-(4-methoxyphenyl)ethyl, 2-(4-bromophenyl)ethyl, 2-(4-biphenyl)ethyl, benzene sulfonyl, 2-fluorobenzenesulfonyl, 3-fluorobenzenesulfonyl, 4-fluorobenzene sulfonyl, 2-chlorobenzene sulfonyl, 3-chlorobenzene sulfonyl, 4-chlorobenzene sulfonyl, 2,4-difluorobenzene sulfonyl, 2,6-difluorobenzenesulfonyl, 2,5-difluorobenzene sulfonyl, 3,4-difluorobenzene sulfonyl, 4-methylbenzene sulfonyl, 3-trifluoromethylbenzenesulfonyl, 4-trifluoromethylbenzenesulfonyl, 4-hydroxybenzene sulfonyl, 4-methoxybenzene sulfonyl, 4-bromobenzene sulfonyl, 4-phenylbenzene sulfonyl, phenylthio, 2-fluorophenylthio, 3-fluorophenylthio, 4-fluorophenylthio, 2-chlorophenylthio, 3-chlorophenylthio, 4-chlorophenylthio, 2,4-difluorophenylthio, 2,6-difluorophenylthio, 2,5-difluorophenylthio, 3,4-difluorophenylthio, 4-methylphenylthio, 3-trifluoromethylphenylthio, 4-trifluoromethylphenylthio, 4-hydroxyphenylthio, 4-methoxyphenylthio, 4-bromophenylthio, 4-biphenylthio, phenoxy, 2-fluorophenoxy, 3-fluorophenoxy, 4-fluorophenoxy, 2-chlorophenoxy, 3-chlorophenoxy, 4-chlorophenoxy, 2,4-difluorophenoxy, 2,6-difluorophenoxy, 2,5-difluorophenoxy, 3,4-difluorophenoxy, 4-methylphenoxy, 3-trifluoromethylphenoxy, 4-trifluoromethylphenoxy, 4-hydroxy phenoxy, 4-methoxyphenoxy, 4-bromophenoxy, 4-phenylphenoxy, benzoyl, 2-fluorobenzoyl, 3-fluorobenzoyl, 4-fluorobenzoyl, 2-chlorobenzoyl, 3-chlorobenzoyl, 4-chlorobenzoyl, 2,4-difluorobenzoyl, 2,6-difluorobenzoyl, 2,5-difluorobenzoyl, 3,4-difluorobenzoyl, 4-methylbenzoyl, 3-trifluoromethylbenzoyl, 4-trifluoromethylbenzoyl, 4-hydroxybenzoyl, 4-methoxybenzoyl, 4-bromobenzoyl, 4-phenylbenzoyl, 2-thienyl, 3-thienyl, furfuryl, 3-furylmethyl, (2-chlorothiophene-3-yl)methyl, 2-picolyl, 3-picolyl, 4-picolyl, (2-fluoropyridine-3-yl)methyl, (2-fluoropyridine-5-yl)methyl, (5-fluoropyridine-2-yl)methyl, benzyloxy, 4-fluorobenzyloxy, 2-phenylethyloxy, and 2-(4-fluorophenyl)ethyl oxy.

A group of the formula:

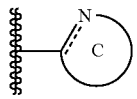

(wherein, C ring is N-containing aromatic heterocycle wherein at least one atom neighboring to the atom at the bonding-position is N atom. The broken line shows the presence or absence of a bond) means heteroaryl wherein at least one atom neighboring to the atom at the bonding-position is non-substituted N atom.

C ring may contain a heteroatom (s) other than the N atom shown in the above formula. The atoms constituting C ring include C, O, N and S. The bonds constituting C ring include a single bond or double bond. C ring is a monocyclic ring or condensed ring (e.g., di- to penta-cyclic condensed ring) and preferred is a monocyclic ring or di-cyclic condensed ring, and more preferred is a monocyclic ring.

A monocyclic heteroaryl of C ring means 5- to 8-membered heteroaryl wherein one atom neighboring to the atom at the bonding-position is non-substituted N atom and which may contain further 1 to 4 of O, S and/or N atom, and preferably 5- or 6-membered heteroaryl. The examples include imidazole-2-yl, imidazole-4-yl, pyrazole-3-yl, triazole3-yl, tetrazole-5-yl, oxazole-2-yl, oxazole-4-yl, isoxazole-3-yl, thiazole-2-yl, thiazole-4-yl, 1,3,4-thiadiazole-2-yl, 1,2,4-thiadiazole-5-yl, 1,2,4-thiadiazole-3-yl, 1,3,4-oxadiazole-2-yl, 1,2,4-oxadiazole-5-yl, 1,2,4-oxadiazole-3-yl, isothiazole-3-yl, pyridine-2-yl, pyridazine-3-yl, pyradine-2-yl, pyrimidine-2-yl; pyrimidine-4-yl, and furazan-3-yl.

Preferred is imidazole-2-yl, 1,2,4-triazole-3-yl, tetrazole-5-yl, oxazole-2-yl, thiazole-2-yl, 1,3,4-thiadiazole-2-yl, 1,2,4-thiadiazole-5-yl, 1,2,4-thiadiazole-3-yl, 1,3,4-oxadiazole-2-yl, 1,2,4-oxadiazole-5-yl, 1,2,4-oxadiazole-3-yl, pyrimidine-2-yl, and pyridine-2-yl, more preferred is pyridine-2-yl, pyrimidine-2-yl, 1,3,4-oxadiazole-2-yl, 1,2,4-triazole-3-yl, and imidazole-2-yl.

A condensed heteroaryl of C ring means the above monocyclic heteroaryl which is condensed with 1 to 4 of 5- to 8-membered aromatic carbocycle and/or with another 5- to 8-membered aromatic heterocycle optionally containing 1 to 4 of O, S, and/or N atom (s). The aromatic ring to be condensed is preferably 5- or 6-membered one, such as benzimidazole-2-yl, benzooxazole-2-yl, quinoxaline-2-yl, cinnoline-3-yl, quinazoline-2-yl, quinazoline-4-yl, quinoline-2-yl, phthalazine-1-yl, isoquinoline-1-yl, isoquinoline-3-yl, purine-2-yl, purine-6-yl, purine-8-yl, pteridine-2-yl, pteridine-4-yl, pteridine-6-yl, pteridine-7-yl, and phenantridine-6-yl. Preferred is benzimidazole-2-yl, benzooxazole-2-yl, quinazoline-2-yl, purine-2-yl, purine-8-yl, pteridine-2-yl, quinoline-2-yl, isoquinoline-1-yl, and isoquinoline-3-yl, and more preferred is quinoline-2-yl, isoquinoline-1-yl, and isoquinoline-3-yl. More preferred is of the formula:

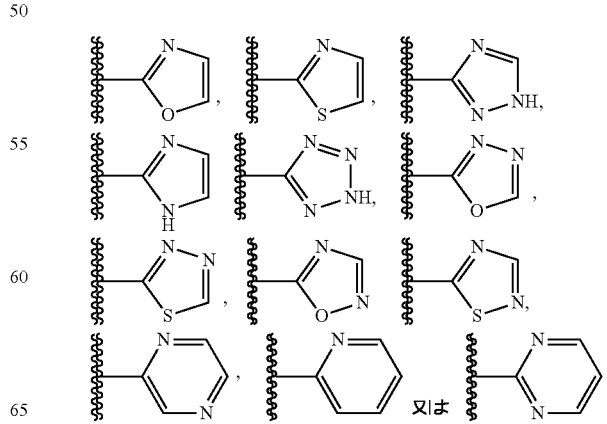

C ring may be substituted with a group of the formula: —$Z^1$—$Z^2$—$Z^3$—$R^1$ (wherein, $Z^1$, $Z^2$, $Z^3$ and $R^1$ are the same as above) or a non-interfering substituent.

$R''_{0-1}$ (n is an integer more than 0) is $R''_0$ or $R''_1$. $R''_0$ means "non-substituted with $R'''$", and $R''_1$ means "substituted with $R'''$".

Preferred compounds of the formula (I) are shown below.
A compound of the formula (I):

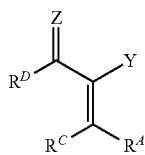

(I)

(wherein, $R^C$ and $R^D$ taken together with the neighboring carbon atoms may form 5- to 6-membered heterocycle which may contain O and/or N atom and may be condensed with benzene ring; Y is hydroxy, mercapto or amino; Z is O, S or NH; $R^A$ is the formula:

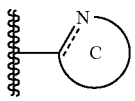

(wherein, C ring is N-containing aromatic heterocycle, wherein at least one atom neighboring to the atom at the bonding-position is N atom, and the broken line shows the presence or absence of a bond) or the formula:

(wherein, X is O, S or NH; $R^B$ is optionally substituted aryl, optionally substituted heteroaryl, optionally substituted cycloalkyl, optionally substituted cycloalkenyl or optionally substituted heterocycle);
at least one of the ring formed by $R^C$ and $R^D$, C ring or $R^B$ is substituted with a group of the formula; —$Z^1$—$Z^2$—$Z^3$—$R^1$ (wherein, $Z^1$ and $Z^3$ are each independently a bond, optionally substituted alkylene or optionally substituted alkenylene; $Z^2$ is a bond, optionally substituted alkylene, optionally substituted alkenylene CH(OH)—, —S—, —SO—, —SO$_2$—, —SO$_2$NR$^2$—, —NR$^2$SO$_2$—, —O—, —NR$^2$—, —NR$^2$CO—, —CONR$^2$—, —C(=O)—O—, —O—C(=O) or —CO—; $R^2$ is hydrogen, optionally substituted alkyl, optionally substituted alkenyl, optionally substituted aryl or optionally substituted heteroaryl; $R^1$ is optionally substituted aryl, optionally substituted heteroaryl, optionally substituted cycloalkyl, optionally substituted cycloalkenyl or optionally substituted heterocycle); the ring formed by $R^C$ and $R^D$, C ring or $R^E$ may be substituted, at any position other than that which is substituted with the formula: —$Z^1$—$Z^2$—$Z^3$—$R^1$ (wherein, $Z^1$, $Z^2$, $Z^3$ and $R^1$ are the same as defined above) locates, with 1 to 3 groups selected from hydrogen, alkyl, aralkyl, cycloalkyl, optionally substituted aryl, alkoxy, alkoxyalkyl, optionally substituted amino, hydroxyalkyl, alkenyl, alkoxycarbonyl alkyl, heteroarylalkyl and hydroxy.

A compound of the above formula (I), wherein the ring formed by $R^C$ and $R^D$ is a 5- or 6-membered heterocycle which contains O and/or N atom and my be condensed with a benzene ring; Y is hydroxy; Z is O; X is O; the ring formed by $R^C$ and $R^D$ is substituted, at any possible position other than that which is substituted with a group of the formula: —$Z^1$—$Z^2$—$Z^3$—$R^1$ (wherein, $Z^1$, $Z^2$, $Z^3$ and $R^1$ are the same as defined above), with 1 to 3 of substituents selected from hydrogen, alkyl, aralkyl, cycloalkyl, optionally substituted aryl, alkoxy, alkoxyalkyl, optionally substituted amino, hydroxyalkyl, alkenyl, alkoxycarbonylalkyl and heteroaryl alkyl, C ring and $R^E$ are each independently substituted with 1 to 3 of substituents selected from alkyl, amino, halogen and hydroxy.

A compound wherein at least one of the ring formed by $R^C$ and $R^D$, C ring or $R^B$ is substituted with a group of the formula: —$Z^1$—$Z^2$—$Z^3$—$R^1$ (wherein, $Z^1$ is a bond or alkylene; $Z^2$ is alkylene or —O—; $Z^3$ is a bond or alkylene; $R^1$ is optionally substituted aryl or optionally substituted heteroaryl).

Further preferred compounds are as follows.
A compound of the formula (I-Q): Q-$Z^1$— $R^2$—$Z^3$—$R^1$ (wherein, $Z^1$, $Z^2$, $Z^3$ and $R^1$ are the same as above (1); Q is a group of the formula:

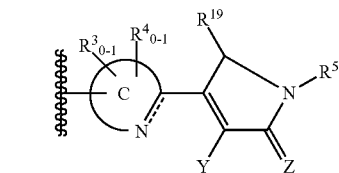

of the formula:

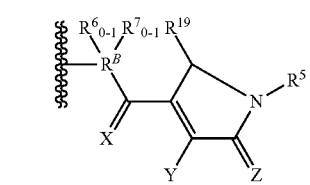

of the formula:

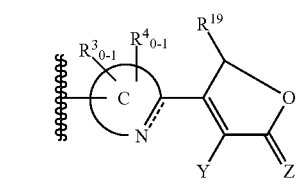

of the formula:

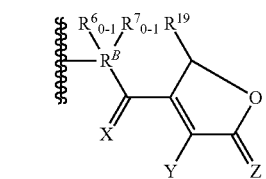

of the formula:
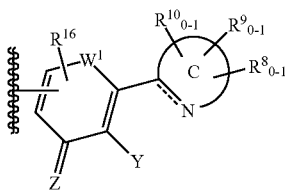
of the formula:
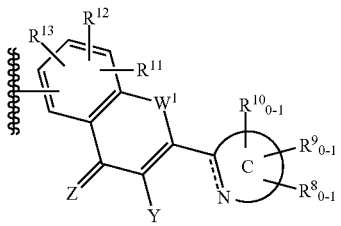
of the formula:
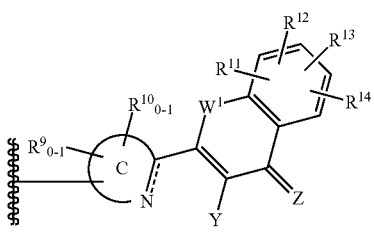
of the formula:
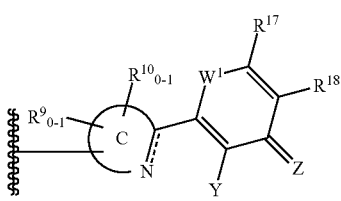
of the formula:
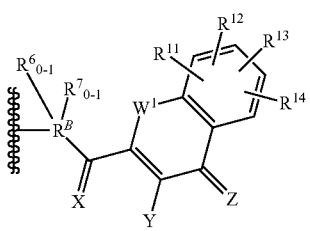
of the formula:
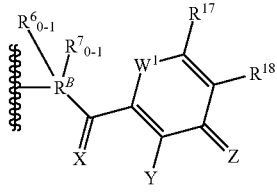
of the formula:
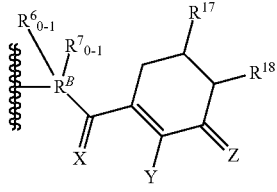
of the formula:
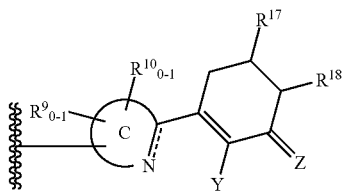
of the formula:
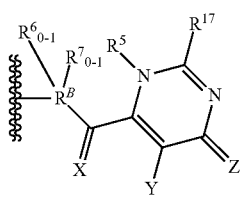
of the formula:
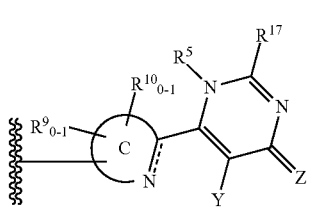

of the formula:
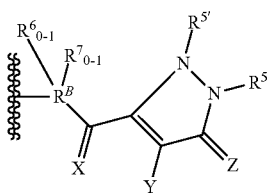
of the formula:
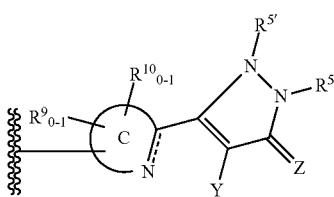
of the formula:
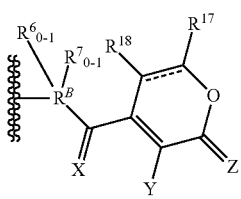
of the formula:
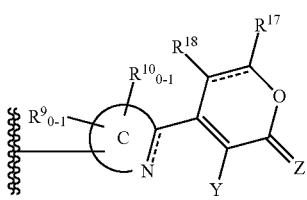
of the formula:
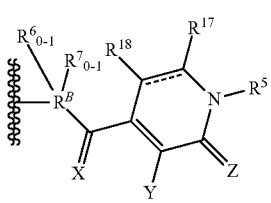
of the formula:
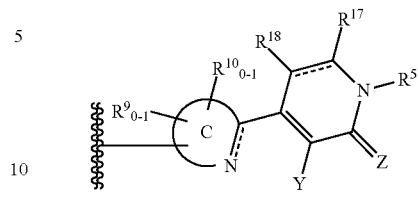
of the formula:
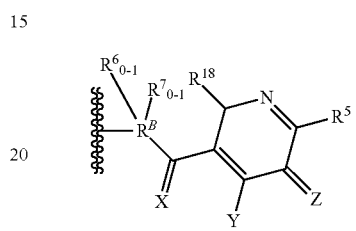
or of the formula:
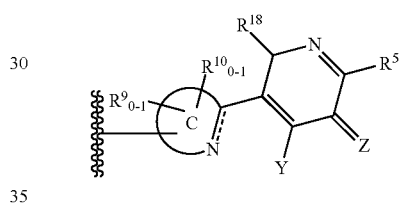
Further preferred are the followings:
A compound of the formula:
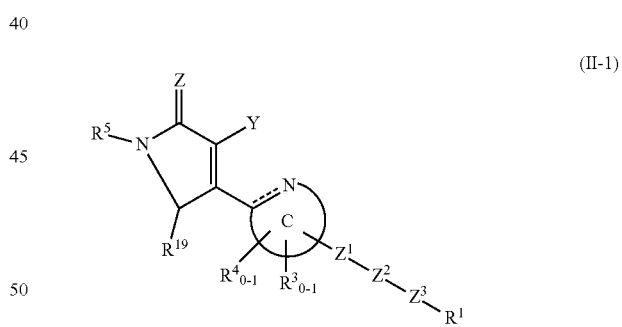
(II-1)
A compound of the formula:
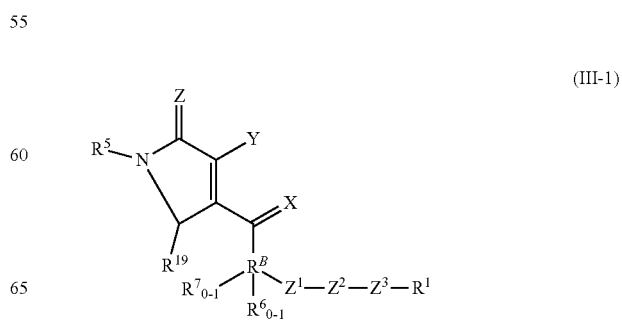
(III-1)

A compound of the formula:

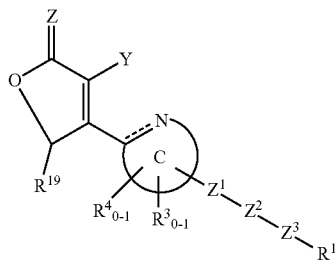

(II-2)

A compound of the formula:

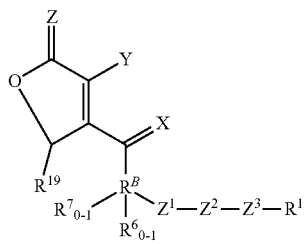

(III-2)

A compound of the formula:

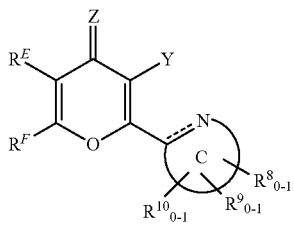

(IV-1)

(wherein, at least one of $R^E$ and $R^F$ is a group of the formula: —$Z^1$—$Z^2$—$Z^3$—$R^1$, the other is a non-interfering substituent or $R^E$ and $R^F$ taken together with the neighboring carbon atoms may form a ring of the formula:

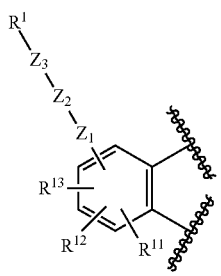

A compound of the formula:

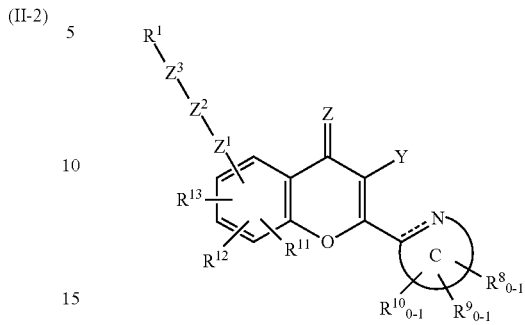

(IV-2)

A compound of the formula:

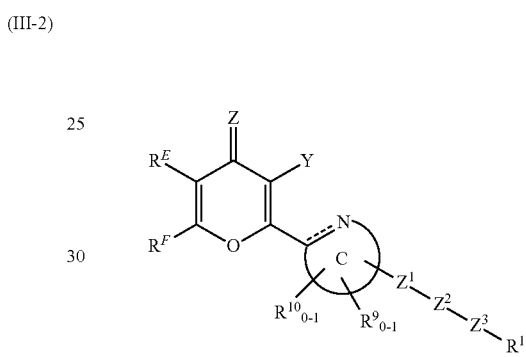

(V-1)

(wherein, $R^E$ and $R^F$ are each independently a non-interfering substituent or taken together with the neighboring carbon atoms may form a ring of the formula:

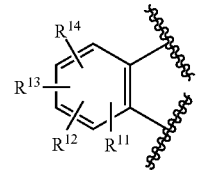

A compound of the formula:

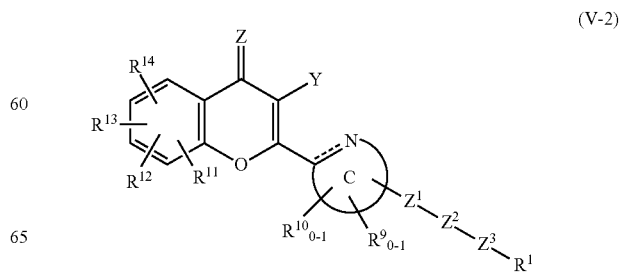

(V-2)

A compound of the formula:

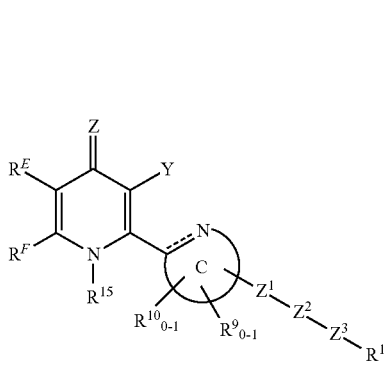

(VI-1)

(wherein, $R^E$ and $R^F$ are each independently a non-interfering substituent or taken together with the neighboring carbon atoms may form a ring of the formula:

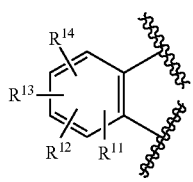

A compound of the formula:

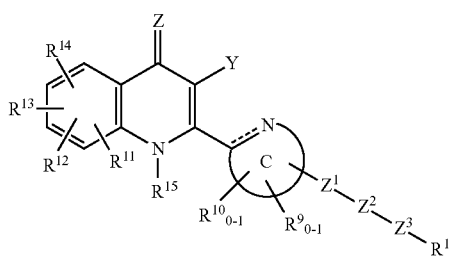

(VI-2)

A compound of the formula:

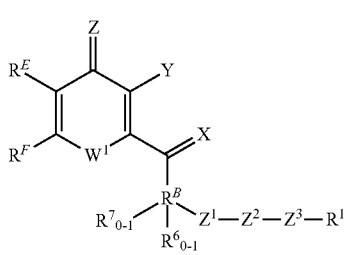

(VII-1)

(wherein, $R^E$ and $R^F$ are each independently a non-interfering substituent or taken together with the neighboring carbon atoms may form a ring of the formula:

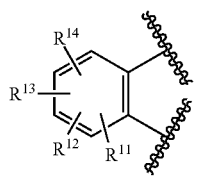

A compound of the formula:

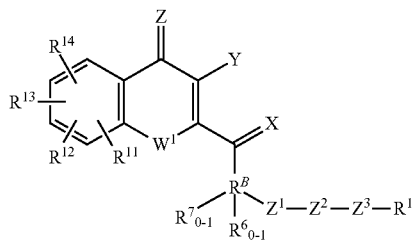

(VII-2)

A compound of the formula:

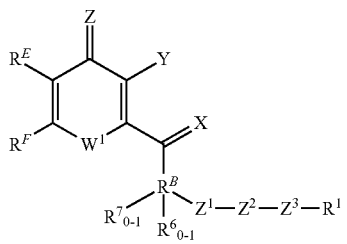

(VII-3)

(wherein, $R^E$ and $R^F$ are each independently a non-interfering substituent)

A compound of the formula:

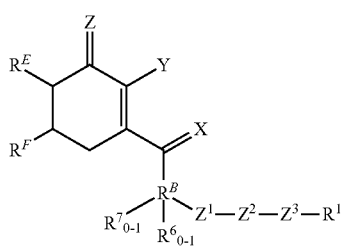

(VIII-1)

(wherein, $R^E$ and $R^F$ are each independently a non-interfering substituent)

A compound of the formula:

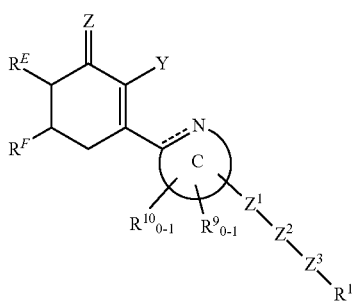

(VIII-2)

(wherein, $R^E$ and $R^F$ are each independently a non-interfering substituent)

A compound of the formula:

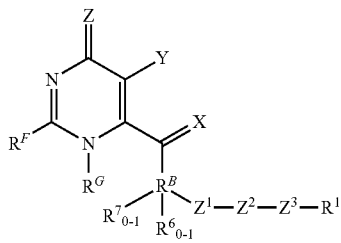

(IX-1)

(wherein, $R^F$ and $R^G$ are each independently a non-interfering substituent)

A compound of the formula:

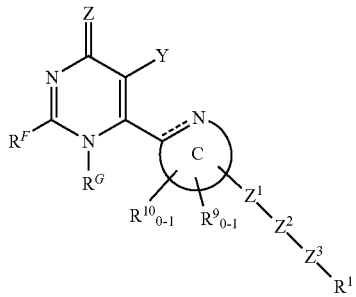

(IX-2)

(wherein, $R^F$ and $R^G$ are each independently a non-interfering substituent)

A compound of the formula:

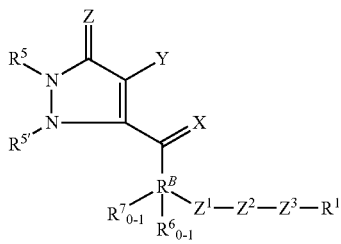

(X-1)

A compound of the formula:

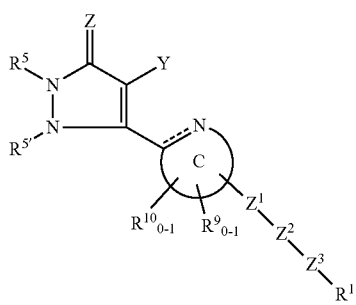

(X-2)

A compound of the formula:

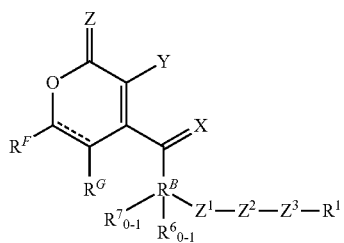

(XI-1)

(wherein, $R^F$ and $R^G$ are each independently a non-interfering substituent)

A compound of the formula:

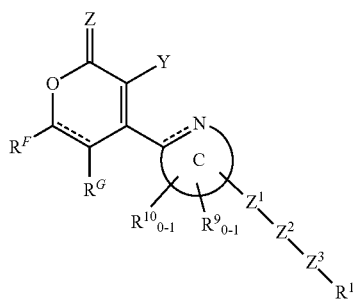

(XI-2)

(wherein, $R^F$ and $R^G$ are each independently a non-interfering substituent)

A compound of the formula:

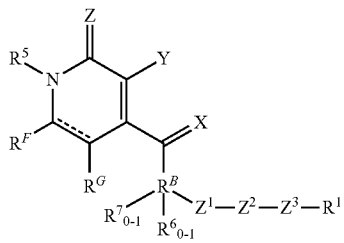

(XII-1)

(wherein, $R^F$ and $R^G$ are each independently a non-interfering substituent)

A compound of the formula:

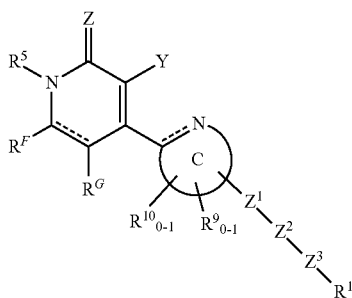

(XII-2)

(wherein, $R^F$ and $R^G$ are each independently a non-interfering substituent)

A compound of the formula:

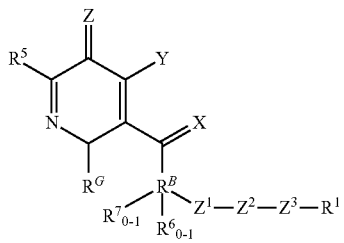

(XIII-1)

(wherein, $R^G$ is a non-interfering substituent)

A compound of the formula:

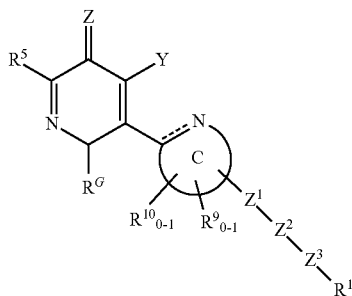

(XIII-2)

(wherein, $R^G$ is a non-interfering substituent)

In the above shown compounds, $R^6$, $R^7$ and a group of the formula: $-Z^1-Z^2-Z^3-R^1$ are substituents on $R^B$. The definition of each symbol is explained below.

X is O, S or NH and preferred is O,

Y is hydroxy, mercapto or amino and preferred is hydroxy,

Z is O, S or NH and preferred is O,

C ring is N-containing aromatic heterocycle, wherein at least one atom neighboring to the atom at the bonding-position is N atom and preferred is optionally substituted pyridine-2-yl, optionally substituted pyrimidine-4-yl or optionally substituted 1,3,4-oxadiazole 2-yl, $R^B$ is a substituent selected from substitution group A and preferred is optionally substituted aryl, optionally substituted heteroaryl, optionally substituted cycloalkyl, optionally substituted cycloalkenyl or optionally substituted heterocycle, $R^1$ is optionally substituted aryl, optionally substituted heteroaryl, optionally substituted cycloalkyl, optionally substituted cycloalkenyl or optionally substituted heterocycle, $Z^1$ and $Z^3$ are each independently a bond, optionally substituted alkylene or optionally substituted alkenylene, $Z^2$ is a bond, optionally substituted alkylene, optionally substituted alkenylene, $-CH(OH)-$, $-S-$, $-SO-$, $-SO_2-$, $-SO_2NR^2-$, $-NR^2SO_2-$, $-O-$, $-NR^2-$, $-NR^2CO-$, $-CONR^2-$, $-C(=O)-O-$, $-O-C(=O)$ or $-CO-$, $R^2$ is hydrogen, optionally substituted alkyl, optionally substituted alkenyl, optionally substituted aryl or optionally substituted heteroaryl, $W^1$ is $-O-$ or $-N(-R^G)-$, $R^3$ to $R^{19}$ and $R^G$ are each independently a non-interfering substituent, $R^G$ is preferably hydrogen or alkyl.

Examples of $R^B$ include a substituent selected from substitution group A.

substitution group A:

hydrogen, halogen, alkoxycarbonyl, carboxy, alkyl, alkoxy, alkoxyalkyl, nitro, hydroxy, alkenyl, alkynyl, alkylsulfonyl, optionally substituted amino, alkylthio, alkylthioalkyl, haloalkyl, haloalkoxy, haloalkoxyalkyl, optionally substituted cycloalkyl, optionally substituted cycloalkenyl, optionally substituted heterocycle, nitroso, azide, amidino, guanidino, cyano, isocyano, mercapto, optionally substituted carbamoyl, sulfamoyl, sulfoamino, formyl, alkylcarbonyl, alkyl carbonyloxy, hydrazino, morpholino, optionally substituted aryl, optionally substituted heteroaryl, optionally substituted aralkyl, optionally substituted heteroarylalkyl, optionally substituted aryloxy, optionally substituted heteroaryloxy, optionally substituted arylthio, optionally substituted heteroarylthio, optionally substituted aralkyloxy, optionally substituted heteroarylalkyloxy, optionally substituted aralkylthio, optionally substituted heteroarylalkylthio, optionally substituted aryloxyalkyl, optionally substituted heteroaryloxy alkyl, optionally substituted arylthio alkyl, optionally substituted heteroarylthio alkyl, optionally substituted aryl sulfonyl, optionally substituted heteroarylsulfonyl, optionally substituted aralkylsulfonyl and optionally substituted heteroarylalkylsulfonyl.

Preferred are alkoxycarbonyl, carboxy, alkyl, alkoxy, alkoxyalkyl, hydroxy, alkenyl, alkynyl, alkylsulfonyl, optionally substituted amino, alkylthio, alkylthioalkyl, haloalkyl, haloalkoxy, haloalkoxyalkyl, optionally substituted cycloalkyl, optionally substituted cycloalkenyl, optionally substituted heterocycle, alkylcarbonyl, alkyl carbonyloxy, optionally substituted aryl, optionally substituted heteroaryl, optionally substituted aralkyl, optionally substituted heteroarylalkyl, optionally substituted aryl oxy, optionally substituted heteroaryl oxy, optionally substituted aryl thio, optionally substituted heteroaryl thio, optionally substituted aralkyloxy, optionally substituted heteroarylalkyl oxy, optionally substituted aralkylthio, optionally substituted heteroarylalkylthio, optionally substituted aryl oxyalkyl, optionally substituted heteroaryl oxyalkyl, optionally substituted arylthio alkyl, optionally substituted heteroarylthioalkyl, optionally substituted aryl sulfonyl, optionally substituted heteroarylsulfonyl, optionally substituted aralkylsulfonyl, optionally substituted heteroarylalkylsulfonyl. More preferred are alkyl, hydroxy, alkoxy, optionally substituted amino, optionally substituted aryl, optionally substituted heteroaryl, optionally substituted cycloalkyl, optionally substituted cycloalkenyl or optionally substituted heterocycle. Most preferred are optionally substituted aryl, optionally substituted heteroaryl, optionally substituted cycloalkyl, optionally substituted cycloalkenyl or optionally substituted heterocycle.

Preferable $R^B$ of the above formula (III-1), (III-2), (VII-1), (VII-2), (VII-3), (VII-4), (VII-5), (VIII-1), (IX-1), (X-1), (XI-1), (XII-1) and (XIII-1) includes optionally substituted cycloalkyl, optionally substituted cycloalkenyl, optionally substituted heterocycle, optionally substituted aryl, optionally substituted heteroaryl, optionally substituted aralkyl, optionally substituted heteroarylalkyl, optionally substituted aryl oxy, optionally substituted heteroaryloxy, optionally substituted arylthio, optionally substituted heteroarylthio, optionally substituted aralkyloxy, optionally substituted heteroarylalkyloxy, optionally substituted aralkylthio, optionally substituted heteroarylalkylthio, optionally substituted aryloxyalkyl, optionally substituted heteroaryloxyalkyl, optionally substituted arylthio alkyl, optionally substituted heteroarylthioalkyl, optionally substituted arylsulfonyl, optionally substituted heteroarylsulfonyl, optionally substituted aralkylsulfonyl, optionally substituted heteroarylalkylsulfonyl. More preferred are optionally substituted aryl, optionally substituted heteroaryl, optionally substituted cycloalkyl, optionally substituted cycloalkenyl or optionally substituted heterocycle. Most preferred are optionally substituted aryl, optionally substituted heteroaryl, optionally substituted cycloalkyl, optionally substituted cycloalkenyl or optionally substituted heterocycle.

The ring formed by $R^C$ and $R^D$, C ring and $R^B$ are optionally substituted with a non-interfering substituent (s). The substituent may locate at one or more, preferably one to five, any substitutable positions.

The non-interfering substituent means any substituent not interfering with the integrase inhibitory activity. The non-interfering substituent can be selected based on the determined integrase inhibitory activity and drug design using computer, as well as molecular weight, an der Waals' radius, electrostatic characteristic of the substituent.

Preferred examples of the non-interfering substituent include hydrogen, halogen, alkoxycarbonyl, carboxy, alkyl, alkoxy, alkoxyalkyl, nitro, hydroxy, alkenyl, alkynyl, alkylsulfonyl, optionally substituted amino, alkylthio, alkylthio alkyl, haloalkyl, haloalkoxy, haloalkoxyalkyl, optionally substituted cycloalkyl, optionally substituted cycloalkenyl, optionally substituted heterocycle, oxo, thioxo, nitroso, azide, amidino, guanidino, cyano, isocyano, mercapto, optionally substituted carbamoyl, sulfamoyl, sulfoamino, formyl, alkylcarbonyl, alkylcarbonyloxy, hydrazino, morpholino, optionally substituted aryl, optionally substituted heteroaryl, optionally substituted aralkyl, optionally substituted heteroarylalkyl, optionally substituted aryl oxy, optionally substituted heteroaryl oxy, optionally substituted aryl thio, optionally substituted heteroaryl thio, optionally substituted aralkyloxy, optionally substituted heteroaryl alkyl oxy, optionally substituted aralkylthio, optionally substituted heteroarylalkylthio, optionally substituted aryl oxyalkyl, optionally substituted heteroaryl oxyalkyl, optionally substituted aryl thioalkyl, optionally substituted heteroaryl thioalkyl, optionally substituted arylsulfonyl, optionally substituted heteroarylsulfonyl, optionally substituted aralkylsulfonyl and optionally substituted heteroarylalkyl sulfonyl.

More preferred non-interfering substituents include hydrogen, halogen, alkoxycarbonyl, carboxy, alkyl, alkoxy, alkoxyalkyl, nitro, hydroxy, alkenyl, alkynyl, alkylsulfonyl, optionally substituted amino, alkylthio, alkylthio alkyl, haloalkyl, haloalkoxy, haloalkoxyalkyl, optionally substituted cycloalkyl, optionally substituted cycloalkenyl, optionally substituted heterocycle, oxo, thioxo, nitroso, azide, amidino, guanidino, cyano, isocyano, mercapto, optionally substituted carbamoyl, sulfamoyl, sulfoamino, formyl, alkylcarbonyl, alkylcarbonyloxy, hydrazino, morpholino, optionally substituted aryl, optionally substituted heteroaryl, optionally substituted aralkyl, optionally substituted heteroarylalkyl, optionally substituted aryloxy, optionally substituted heteroaryloxy, optionally substituted arylthio, optionally substituted heteroarylthio, optionally substituted aralkyloxy, optionally substituted heteroaryl alkyloxy, optionally substituted aralkylthio, optionally substituted heteroarylalkylthio, optionally substituted aryloxyalkyl, optionally substituted heteroaryl oxyalkyl, optionally substituted arylthio alkyl, optionally substituted heteroaryl thioalkyl, optionally substituted arylsulfonyl, optionally substituted heteroarylsulfonyl, optionally substituted aralkylsulfonyl and optionally substituted heteroarylalkylsulfonyl.

Most preferred non-interfering substituents include hydrogen, halogen, alkoxycarbonyl, carboxy, alkyl, alkoxy, alkoxyalkyl, nitro, hydroxy, alkenyl, alkynyl, alkylsulfonyl, optionally substituted amino, alkylthio, alkylthioalkyl, haloalkyl, haloalkoxy, haloalkoxyalkyl, optionally substituted cycloalkyl, optionally substituted cycloalkenyl, optionally substituted heterocycle, oxo, thioxo, cyano, mercapto, optionally substituted carbamoyl, formyl, alkylcarbonyl, alkylcarbonyloxy, optionally substituted aryl, optionally substituted heteroaryl, optionally substituted aralkyl, optionally substituted heteroarylalkyl, optionally substituted aryloxy, optionally substituted heteroaryloxy, optionally substituted arylthio, optionally substituted heteroarylthio, optionally substituted aralkyloxy, optionally substituted heteroarylalkyloxy, optionally substituted aralkylthio, optionally substituted heteroarylalkylthio, optionally substituted aryl oxyalkyl, optionally substituted heteroaryl oxyalkyl, optionally substituted aryl thioalkyl, optionally substituted heteroaryl thioalkyl, optionally substituted arylsulfonyl, optionally substituted heteroarylsulfonyl, optionally substituted aralkylsulfonyl and optionally substituted heteroarylalkylsulfonyl.

Examples of non-interfering substituent on the ring formed by $R^C$ and $R^D$ (e.g., non-interfering substituent of $R^{19}$, $R^E$, $R^F$, $R^{11}$, $R^{12}$, $R^{13}$, $R^{14}$, $R^{15}$ and $R^G$) are preferably hydrogen, halogen, alkyl, aralkyl, cycloalkyl, optionally substituted aryl, alkoxy, alkoxyalkyl, optionally substituted amino, hydroxyalkyl, alkenyl, alkoxycarbonylalkyl, heteroarylalkyl or hydroxy.

$R^5$ and $R^{5'}$ are each preferably hydrogen, alkyl, aralkyl, cycloalkyl, optionally substituted aryl, alkoxy, alkoxyalkyl, optionally substituted amino, hydroxyalkyl, alkenyl, alkoxycarbonylalkyl or heteroarylalkyl.

Examples of non-interfering substituent on C ring (e.g., non-interfering substituent of $R^3$, $R^4$, $R^8$, $R^9$ and $R^{10}$) are preferably halogen, alkyl, aralkyl, cycloalkyl, optionally substituted aryl, alkoxy, alkoxyalkyl, optionally substituted amino, hydroxy alkyl, alkenyl, alkoxycarbonylalkyl, heteroarylalkyl or hydroxy, and more preferred is hydrogen, alkyl, amino, halogen or hydroxy.

Examples of non-interfering substituent on $R^B$ (e.g., non-interfering substituent of $R^6$ and $R^7$) are preferably halogen, alkyl, aralkyl, cycloalkyl, optionally substituted aryl, alkoxy, alkoxyalkyl, optionally substituted amino, hydroxyalkyl, alkenyl, alkoxycarbonylalkyl, heteroarylalkyl or hydroxy, and more preferred is hydrogen, alkyl, amino, halogen, hydroxy.

Terms used herein are explained below. Each term, by itself or in combination with others, is defined as follows.

"alkylene" means C1 to C6 straight or branched chain alkylene, for example, methylene, ethylene, trimethylene, propylene, tetramethylene, ethylethylene, pentamethylene or hexamethylene. Preferred is C1 to C4 straight alkylene, for example, methylene, ethylene, trimethylene or tetramethylene.

"alkenylene" is C2 to C6 straight or branched chain alkenylene derived from the above "alkylene" having one or more of double bond, for example, vinylene, propenylene or butenylene. Preferred is C2 to C3 straight alkenylene, for example, vinylene or propenylene.

"alkyl" means C1 to C10 straight or branched chain alkyl, for example, methyl, ethyl, n-propyl, isopropyl, n-butyl, isobutyl, sec-butyl, tert-butyl, n-pentyl, isopentyl, neopentyl, tert-pentyl, n-hexyl, isohexyl, n-heptyl, n-octyl, n-nonyl, n-decyl. Preferred is C1 to C6 alkyl, for example, methyl, ethyl, n-propyl, isopropyl, n-butyl, isobutyl, sec-butyl, tert-butyl, n-pentyl, isopentyl, neopentyl, tert-pentyl, n-hexyl, isohexyl.

"alkenyl" means C2 to C8 straight or branched chain alkenyl derived from the above "alkyl" having one or more double, for example, vinyl, 1-propenyl, 2-propenyl, 1-butenyl, 2-butenyl, 3-butenyl, 1,3-butadienyl, 3-methyl-2-butenyl.

"aryl" means monocyclic aromatic hydrocarbon group (e.g., phenyl) or polycyclic aromatic hydrocarbon group (e.g., 1-naphthyl, 2-naphthyl, 1-anthoryl, 2-anthoryl, 9-anthoryl, 1-phenantryl, 2-phenantryl, 3-phenantryl, 4-phenantryl, 9-phenantryl). Preferred is phenyl or naphthyl (e.g., 1-naphthyl, 2-naphthyl).

"heteroaryl" means monocyclic aromatic heterocyclic group and condensed aromatic heterocyclic group.

"monocyclic aromatic heterocyclic group" means 5- to 8-membered aromatic ring which may contain 1 to 4 of O, S and/or N atom and has a bonding radical at any substitutable position.

"condensed aromatic heterocyclic group" is a condensed ring formed by condensing a 5- to 8-membered aromatic ring which may contain 1 to 4 of O, S and/or N atom with a 1 to 4 of 5- to 8-membered aromatic carbocycle or the other 5- to 8-membered aromatic heterocycle, and the condensed ring has a bonding radical at any substitutable position.

Examples of "heteroaryl" include furyl (e.g., 2-furyl, 3-furyl), thienyl (e.g., 2-thienyl, 3-thienyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1,2,4-triazole-1-yl, 1,2,4-triazole-3-yl, 1,2,4-triazole-4-yl), tetrazolyl (e.g., 1-tetrazolyl, 2-tetrazolyl, 5-tetrazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), thiadiazolyl, isothiazolyl (e.g., 3-isothiazolyl, 4-isothiazolyl, 5-isothiazolyl), pyridyl (e.g., 2-pyridyl, 3-pyridyl, 4-pyridyl), pyridazinyl (e.g., 3-pyridazinyl, 4-pyridazinyl), pirimidinyl (e.g., 2-pirimidinyl, 4-pirimidinyl, 5-pirimidinyl), furazanyl (e.g., 3-furazanyl), pyradinyl (e.g., 2-pyradinyl), oxadiazolyl (e.g., 1,3,4-oxadiazole-2-yl), benzofuryl (e.g., 2-benzo[b]furyl, 3-benzo[b]furyl, 4-benzo[b]furyl, 5-benzo[b]furyl, 6-benzo[b]furyl, 7-benzo[b]furyl), benzo thienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyl (e.g., 1-benzo imidazolyl, 2-benzoimidazolyl, 4-benzoimidazolyl, 5-benzoimidazolyl), dibenzo furyl, benzooxazolyl, quinoxalinyl (e.g., 2-quinoxalinyl, 5-quinoxalinyl, 6-quinoxalinyl), cinnolinyl (e.g., 3-cinnolinyl, 4-cinnolinyl, 5-cinnolinyl, 6-cinnolinyl, 7-cinnolinyl, 8-cinnolinyl), quinazolil (e.g., 2-quinazolinyl, 4-quinazolinyl, 5-quinazolinyl, 6-quinazolinyl, 7-quinazolinyl, 8-quinazolinyl), quinolil (e.g., 2-quinolil, 3-quinolil, 4-quinolil, 5-quinolil, 6-quinolil, 7-quinolil, 8-quinolil), phthalazinyl (e.g., 1-phthalazinyl, 5-phthalazinyl, 6-phthalazinyl), isoquinolil (e.g., 1-isoquinolil, 3-isoquinolil, 4-isoquinolil, 5-isoquinolil, 6-isoquinolil, 7-isoquinolil, 8-isoquinolil), puril, pteridinyl (e.g., 2-pteridinyl, 4-pteridinyl, 6-pteridinyl, 7-pteridinyl), carbazolyl, phenantridinyl, acridinyl (e.g., 1-acridinyl, 2-acridinyl, 3-acridinyl, 4-acridinyl, 9-acridinyl), indolyl (e.g., 1-indolyl, 2-indolyl, 3-indolyl, 4-indolyl, 5-indolyl, 6-indolyl, 7-indolyl), isoindolyl, phenazinyl (e.g., 1-phenazinyl, 2-phenazinyl) or phenothiadinyl (e.g., 1-phenothiadinyl, 2-phenothiadinyl, 3-phenothiadinyl, 4-phenothiadinyl).

"cycloalkyl" means C3 to C10 cyclic saturated hydrocarbon group, for example, cyclopropyl, cyclobutyl, cyclopentyl, cyclohexyl, cycloheptyl, cyclooctyl. Preferred is C3 to C6 cycloalkyl, for example, cyclopentyl, cyclohexyl.

"cycloalkenyl" means C3 to C10 cyclic non-aromatic hydrocarbon group, for example, cyclopropenyl (e.g., 1-cyclopropenyl), cyclobutenyl (e.g., 1-cyclobutenyl), cycloheptenyl (e.g., 1-cyclopenten-1-yl, 2-cyclopenten-1-yl, 3-cyclopenten-1-yl), cyclohexenyl (e.g., 1-cyclohexene-1-yl, 2-cyclohexene-1-yl, 3-cyclohexene-1-yl), cycloheptenyl (e.g., 1-cycloheptenyl), cyclooctenyl (e.g., 1-cyclooctenyl). Preferred is 1-cyclohexene-1-yl, 2-cyclohezene-1-yl, 3-cyclohezene-1-yl.

"heterocycle" means non-aromatic heterocyclic group which contains at least one of N, O, and S atom and has a bonding radical at any substitutable position, for example, 1-pyrrolinyl, 2-pyrrolinyl, 3-pyrrolinyl, 1-pyrrolidinyl, 2-pyrrolidinyl, 3-pyrrolidinyl, 1-imidazolyl, 2-imidazolyl, 4-imidazolyl, 1-pyrazolinyl, 3-pyrazolinyl, 4-pyrazolinyl, 1-pyrazolidinyl, 3-pyrazolidinyl, 4-pyrazolidinyl, piperidino, 2-piperidino, 3-piperidil, 4-piperidil, 1-piperazinyl, 2-piperazinyl, 2-morpholinyl, 3-morpholinyl, morpholino, tetrahydropyranyl. The "non-aromatic heterocyclic group" is saturated or unsaturated.

The alkyl of "alkoxy" is the same as above "alkyl", and "alkoxy" includes for example, methoxy, ethoxy, n-propoxy, isopropoxy, n-butoxy, isobutoxy, tert-butoxy. Preferred is methoxy, ethoxy.

"alkoxycarbonyl" means carbonyl substituted with the above "alkoxy", including for example, methoxycarbonyl, ethoxycarbonyl, n-propoxycarbonyl, isopropoxycarbonyl, n-butoxycarbonyl, isobutoxycarbonyl, tert-butoxycarbonyl.

"alkoxyalkyl" means the above "alkyl" substituted with the above "alkoxy", including for example, methoxymethyl, ethoxymethyl, n-propoxymethyl, isopropoxymethyl, n-butoxymethyl, isobutoxymethyl, tert-butoxymethyl, methoxyethyl, ethoxyethyl, n-propoxyethyl, isopropoxyethyl, n-butoxyethyl, isobutoxyethyl, tert-butoxyethyl.

"alkynyl" means C2 to C8 alkynyl derived from the above "alkyl" having one or more of triple bond, including for example, ethynyl, 1-propynyl, 2-propynyl, 1-butynyl, 2-butynyl, 3-butynyl.

"alkylsulfonyl" means sulfonyl substituted with the above "alkyl", including for example, methylsulfonyl, ethylsulfonyl, n-propylsulfonyl, isopropylsulfonyl, butylsulfonyl, isobutylsulfonyl, sec-butylsulfonyl, tert-butylsulfonyl, n-pentylsulfonyl, isopentylsulfonyl, neopentylsulfonyl, tert-pentylsulfonyl, n-hexylsulfonyl, isohexylsulfonyl, n-heptylsulfonyl, n-octylsulfonyl, n-nonylsulfonyl, n-desylsulfonyl.

"optionally substituted amino" is substituted or unsubstituted amino.

"optionally substituted carbamoyl" is substituted or unsubstituted carbamoyl.

Examples of the substituent of "optionally substituted amino" and "optionally substituted carbamoyl" includes alkyl (e.g., methyl, ethyl, dimethyl), alkoxyalkyl (e.g., ethoxymethyl, ethoxyethyl), acyl (e.g., formyl, acetyl, benzoyl, toluoyl), aralkyl (e.g., benzyl, trityl), hydroxy.

"alkylthio" means sulfur atom substituted with the above "alkyl", including for example, methylthio, ethylthio, n-propylthio, isopropylthio, n-butylthio, isobutylthio, sec-butylthio, tert-butylthio, n-pentylthio, isopentylthio, neopentylthio, tert-pentylthio, n-hexylthio, isohexylthio, n-heptylthio, n-octylthio, n-nonylthio, n-desylthio. Preferred is sulfur atom substituted with C1 to C6 alkyl.

"alkylthioalkyl" means the above "alkyl" substituted with the above "alkylthio", including for example, methylthiomethyl, ethylthiomethyl, n-propylthiomethyl, isopropylthiomethyl, n-butylthiomethyl, isobutylthiomethyl, sec-butylthiomethyl, tert-butylthiomethyl, n-pentylthiomethyl, isopentyl thiomethyl, neopentylthiomethyl, tert-pentylthiomethyl, n-hexylthiomethyl, isohexylthiomethyl, n-heptylthiomethyl, n-octylthiomethyl, n-nonylthiomethyl, n-desylthiomethyl, methylthioethyl, ethylthio ethyl, n-propylthioethyl, isopropylthioethyl, n-butylthioethyl, isobutylthioethyl, sec-butylthioethyl, tert-butylthio ethyl, n-pentylthioethyl, isopentylthioethyl, neopentylthioethyl, tert-pentylthioethyl, n-hexylthioethyl, isohexylthioethyl, n-heptylthioethyl, n-octylthioethyl, n-nonylthioethyl, n-desylthioethyl. Preferred is C1 to C2 alkyl substituted with C1 to C6 alkylthio.

"haloalkyl" means the above "alkyl" substituted with one or more of halogen. Preferred is halogenated C1 to C3 alkyl, for example, trifluoromethyl, chloromethyl, dichloromethyl, 1,1-dichloroethyl, 2,2,2-tri chloroethyl.

"haloalkoxy" means O substituted with the above "haloalkyl", including for example, trifluoromethoxy, chloromethoxy, dichloromethoxy, 1,1-dichloro ethoxy, 2,2,2-trichloroethoxy.

"haloalkoxyalkyl" means the above "alkyl" substituted with the above "haloalkoxy", including for example, trifluoromethoxymethyl, chloro methoxymethyl, dichloromethoxymethyl, 1,1-dichloroethoxymethyl, 2,2,2-trichloro ethoxymethyl, trifluoromethoxyethyl, chloromethoxyethyl, dichloromethoxyethyl, 1,1-dichloro ethoxyethyl, 2,2,2-trichloroethoxyethyl.

"alkylcarbonyl" means carbonyl substituted with the above "alkyl", including for example, acetyl, propionyl, butyryl, isobutyryl, valeryl, isovaleryl, pivaroyl, haxanoyl, octanoyl, lauroyl.

"alkylcarbonyloxy" means O substituted with the above "alkylcarbonyl", including for example, acetyloxy, propionyloxy, butyryloxy, isobutyryloxy, valeryloxy, isovaleryloxy, pivaroyloxy, haxanoyloxy, octanoyloxy, lauroyloxy.

"aralkyl" means the above "alkyl" substituted with 1 to 3 of the above "aryl", including for example, benzyl, diphenylmethyl, triphenylmethyl, phenetyl, 1-naphthyl methyl, 2-naphthylmethyl.

"heteroarylalkyl" means the above "alkyl" substituted with 1 to 3 of the above "heteroaryl". Preferred is heteroarylalkyl having C1 to C4 alkyl, esp., C1 or C2 alkyl, for example, furylmethyl, thienylmethyl, pyrrolylmethyl, imidazolyl methyl, pyrazolylmethyl, triazolylmethyl, tetrazolylmethyl, oxazolylmethyl, isoxazolylmethyl, thiazolylmethyl, thiadiazolylmethyl, isothiazolylmethyl, pyridyl methyl, pyridazinylmethyl, pirimidinylmethyl, furazanylmethyl, pyrazinylmethyl, ozadiazolylmethyl, benzofurylmethyl, benzothienylmethyl, benzimidazolyl methyl, dibenzofurylmethyl, benzoxazolylmethyl, quinoxalilmethyl, cinnolinylmethyl, quinazolilmethyl, quinolilmethyl, phthalazinylmethyl, isoquinolylmethyl, purilmethyl, pteridinylmethyl, carbazolylmethyl, phenantridinylmethyl, acridinylmethyl, indolyl methyl, isoindolylmethyl, phenadinylmethyl, phenothiadinylmethyl, furylethyl, thienylethyl, pyrrolylethyl, imidazolylethyl, pyrazolylethyl, triazolylethyl, tetrazolylethyl, oxazolylethyl, isoxazolylethyl, thiazolylethyl, thiadiazolylethyl, isothiazolylethyl, pyridylethyl, pyridazinylethyl, pirimidinylethyl, furazanylethyl, pyrazinylethyl, oxadiazolylethyl, benzofurylethyl, benzothienylethyl, benzimidazolyl ethyl, dibenzofurylethyl, benzooxazolylethyl, quinoxalylethyl, cinnolinylethyl, quinazolilethyl, quinolilethyl, phthalazinylethyl, isoquinolilethyl, purilethyl, pteridinyl ethyl, carbazolylethyl, phenantridinylethyl, acridinylethyl, indolyl ethyl, isoindolylethyl, phenadinylethyl or phenothiadinylethyl.

In the definitions of "aryloxy", "heteroaryloxy", "arylthio", "heteroarylthio", "aralkyloxy", "heteroarylalkyloxy", "aralkylthio", "heteroarylalkylthio", "aryloxyalkyl", "heteroaryloxyalkyl", "arylthioalkyl", "heteroarylthioalkyl", "arylsulfonyl", "heteroarylsulfonyl", "aralkylsulfonyl" and "heteroarylalkylsulfonyl", each term of "aryl", "aralkyl", "heteroaryl", "heteroarylalkyl" and "alkyl" is the same as mentioned above.

Each group of "optionally substituted alkylene", "optionally substituted alkenylene", "optionally substituted alkyl", "optionally substituted alkenyl", "optionally substituted aryl", "optionally substituted heteroaryl", "optionally substituted cyclo alkyl", "optionally substituted cycloalkenyl", "optionally substituted heterocycle", "optionally substituted aralkyl", "optionally substituted heteroarylalkyl", "optionally substituted aryloxy", "optionally substituted heteroaryloxy", "optionally substituted arylthio", "optionally substituted heteroarylthio", "optionally substituted aralkyloxy", "optionally substituted heteroarylalkyloxy", "optionally substituted aralkylthio", "optionally substituted heteroarylalkylthio", "optionally substituted aryl oxyalkyl", "optionally substituted heteroaryloxyalkyl", "optionally substituted aryl thioalkyl", "optionally substituted heteroarylthio alkyl", "optionally substituted arylsulfonyl", "optionally substituted heteroarylsulfonyl", "optionally substituted aralkylsulfonyl" and "optionally substituted heteroarylalkylsulfonyl" may have 1 to 4, same or different substituent at any substitutable position. The substituent is selected from those which do not interfer with the integraseinhibitory activity, as well as the case of above mentioned "non-interfering substituent". Examples of the substituent include hydroxy, carboxy, halogen (F, Cl, Br, I), haloalkyl (e.g., $CF_3$, $CH_2CF_3$, $CH_2CCl_3$), alkyl (e.g., methyl, ethyl, isopropyl, tert-butyl), alkenyl (e.g., vinyl), alkynyl (e.g., ethynyl), cycloalkyl (e.g., cyclopropyl), cycloalkenyl (e.g., cyclopropenyl), alkoxy (e.g., methoxy, ethoxy, propoxy, butoxy), alkoxycarbonyl (e.g., methoxycarbonyl, ethoxycarbonyl, tert-butoxycarbonyl), nitro, nitroso, optionally substituted amino (e.g., alkylamino (e.g., methylamino, ethylamino, dimethylamino), acylamino (e.g., acetyl amino, benzoylamino), aralkylamino (e.g., benzylamino, tritylamino), hydroxy amino), azide, aryl (e.g., phenyl), aralkyl (e.g., benzyl), cyano, isocyano, isocyanate, thiocyanate, isothiocyanate, mercapto, alkylthio (e.g., methylthio), alkylsulfonyl (e.g., methane sulfonyl, ethane sulfonyl), optionally substituted carbamoyl, sulfamoyl, acyl (e.g., formyl, acetyl), formyloxy, haloformyl, oxazolo, thioformyl, thiocarboxy, dithio carboxy, thiocarbamoyl, sulfino, sulfoamino, hydrazino, azide, ureido, amidino, guanidino.

In the definition of $R^1$, the substituent of "optionally substituted aryl", "optionally substituted heteroaryl", "optionally substituted cycloalkyl", "optionally substituted cycloalkenyl", and "optionally substituted heterocycle" is preferably hydroxy, carboxy, halogen (F, Cl, Br, I), haloalkyl (e.g., CF$_3$, CH$_2$CF$_3$, CH$_2$CCl$_3$), alkyl (e.g., methyl, ethyl, isopropyl, tert-butyl), alkenyl (e.g., vinyl), alkynyl (e.g., ethynyl), cycloalkyl (e.g., cyclopropyl), cycloalkenyl (e.g., cyclopropenyl), alkoxy (e.g., methoxy, ethoxy, propoxy, butoxy), alkoxycarbonyl (e.g., methoxycarbonyl, ethoxycarbonyl, tert-butoxycarbonyl), nitro, optionally substituted amino (e.g., alkylamino (e.g., methylamino, ethylamino, dimethylamino), acylamino (e.g., acetyl amino, benzoylamino), aralkylamino (e.g., benzylamino, tritylamino), hydroxy amino), azide, aryl (e.g., phenyl), aralkyl (e.g., benzyl), cyano, mercapto, alkylthio (e.g., methylthio), alkylsulfonyl (e.g., methanesulfonyl, ethanesulfonyl), optionally substituted carbamoyl, sulfamoyl, acyl (e.g., formyl, acetyl), formyl oxy, thiocarbamoyl, sulfoamino, hydrazino, azide, ureido, amidino, guanidino. More preferred is alkyl, haloalkyl, halogen (e.g., F, Cl, Br), alkoxy and further preferred is methoxy. Preferred is mono- or disubstituted one.

In the definition of $Z^1$, $Z^2$ and $Z^3$, the substituent of "optionally substituted alkylene" and "optionally substituted alkenylene" is preferably hydroxy, carboxy, halogen (e.g., F, Cl, Br, I), haloalkyl (e.g., CF$_3$, CH$_2$CF$_3$, CH$_2$CCl$_3$), alkyl (e.g., methyl, ethyl, isopropyl, tert-butyl), alkenyl (e.g., vinyl), alkynyl (e.g., ethynyl), cycloalkyl (e.g., cyclopropyl), cycloalkenyl (e.g., cyclopropenyl), alkoxy (e.g., methoxy, ethoxy, propoxy, butoxy), alkoxycarbonyl (e.g., methoxycarbonyl, ethoxycarbonyl, tert-butoxycarbonyl), optionally substituted amino (e.g., alkylamino (e.g., methylamino, ethyl amino, dimethylamino), acylamino (e.g., acetylamino, benzoylamino), aralkylamino (e.g., benzylamino, tritylamino), hydroxyamino), aryl (e.g., phenyl), aralkyl (e.g., benzyl), cyano, mercapto, alkylthio (e.g., methylthio), alkylsulfonyl (e.g., methanesulfonyl, ethanesulfonyl), optionally substituted carbamoyl, sulfamoyl, acyl (e.g., formyl, acetyl), formyloxy, thiocarbamoyl, sulfoamino, hydrazino, azide, ureido, amidino, guanidino.

When a non-interfering substituent is "optionally substituted aryl", "optionally substituted heteroaryl", "optionally substituted cycloalkyl", "optionally substituted cycloalkenyl", "optionally substituted heterocycle", "optionally substituted aralkyl", "optionally substituted heteroarylalkyl", "optionally substituted aryloxy", "optionally substituted heteroaryloxy", "optionally substituted arylthio", "optionally substituted heteroarylthio", "optionally substituted aralkyloxy", "optionally substituted heteroaryl alkyloxy", "optionally substituted aralkylthio", "optionally substituted heteroaryl alkylthio", "optionally substituted aryl oxyalkyl", "optionally substituted heteroaryl oxyalkyl", "optionally substituted aryl thioalkyl", "optionally substituted heteroaryl thioalkyl", "optionally substituted arylsulfonyl", "optionally substituted heteroarylsulfonyl", "optionally substituted aralkylsulfonyl" or "optionally substituted heteroarylalkylsulfonyl", the substituent is preferably hydroxy, carboxy, halogen (e.g., F, Cl, Br, I), haloalkyl (e.g., CF$_3$, CH$_2$CF$_3$, CH$_2$CCl$_3$), alkyl (e.g., methyl, ethyl, isopropyl, tert-butyl), alkenyl (e.g., vinyl), alkynyl (e.g., ethynyl), cycloalkyl (e.g., cyclopropyl), cycloalkenyl (e.g., cyclopropenyl), alkoxy (e.g., methoxy, ethoxy, propoxy, butoxy), alkoxycarbonyl (e.g., methoxycarbonyl, ethoxycarbonyl, tert-butoxycarbonyl), nitro, optionally substituted amino (e.g., alkylamino (e.g., methylamino, ethyl amino, dimethylamino), acylamino (e.g., acetylamino, benzoylamino), aralkylamino (e.g., benzylamino, tritylamino), hydroxyamino), azide, aryl (e.g., phenyl), aralkyl (e.g., benzyl), cyano, mercapto, alkylthio (e.g., methylthio), alkylsulfonyl (e.g., methanesulfonyl, etahnesulfonyl), optionally substituted carbamoyl, sulfamoyl, acyl (e.g., formyl, acetyl), formyloxy, thiocarbamoyl, sulfoamino, hydrazino, azide, ureido, amidino, guanidino. More preferred is alkyl, haloalkyl, halogen (e.g., F, Cl, Br), alkoxy (e.g., methoxy). Preferred is mono- or di-substituted one.

The present invention includes the above mentioned compounds, prodrug, pharmaceutically acceptable salt and solvate thereof, as well as all tautomers and geometrical isomers. For example, ketoenol tautomers of the formula (I) are included in the present invention compounds. The compounds of formula (XIII-1) and (XIII-2) may include the following tautomers:

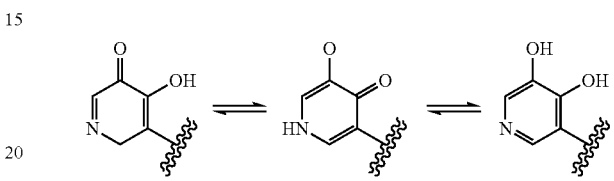

A prodrug is a derivative of a compound of the present invention having a group which can be decomposed chemically or metabolically, and such a prbdrug is converted to a pharmaceutically active compound of the present invention by means of solvolysis or by placing the compound in vivo under a physiological condition. Method for the selection and process of an appropriate prodrug derivative are described in the literature such as Design of Prodrugs, Elsevier and Amsterdam 1985.

It is known that HIV multiplies vigorously in a lymph node even in the asymptomatic term. Thus a prodrug of a compound of the present invention is preferably a lymph-directivity one. The diseases caused by HIV include AIDS cerebrum symptom. Thus a preferable prodrug of a compound of the present invention is a brain-directivity one. As these lymph-directivity prodrug and brain-directivity prodrug, the following prodrugs with high lipophilicity are preferable.

When a compound of the present invention has a carboxyl group, an ester derivative prepared by reacting a basal acid compound with a suitable alcohol or an amide derivative prepared by reacting a basal acid compound with a suitable amine is exemplified as a prodrug. A especially preferred ester derivative as an prodrug is methylester, ethylester, n-propylester, isopropylester, n-butylester, isobutylester, tert-butylester, morpholinoethylester or N,N-diethylglycolamidoester.

When a compound of the present invention has a hydroxy group, an acyloxy derivative prepared by reacting a compound having a hydroxyl group with a suitable acylhalide or a suitable acid anhydride is exemplified as a prodrug. A especially preferred acyloxy derivative as a prodrug is —O(=O)—CH$_3$, —OC(=O)—C$_2$H$_5$, —OC(=O)-(tert-Bu), —OC(=O)—C$_{15}$H$_{31}$, —OC(=O)-(m-COONa-Ph), —OC(=O)—CH$_2$CH$_2$COONa, —O(C=O)—CH(NH$_2$)CH$_3$ or —OC(=O)—CH$_2$—N(CH$_3$)$_2$.

When a compound of the present invention has an amino group, an amide derivative prepared by reacting a compound having amino with a suitable acid halide or a suitable acid anhydride is exemplified as a prodrug. A especially preferred amide derivative as a prodrug is —NHC(=O)—(CH$_2$)$_{20}$CH$_3$ or —NHC(=O)—CH(NH$_2$)CH$_3$.

For example, a prodrug can be produced by the chemical modification of Y. For example, Y is substituted with acyl and it is examined whether the prodrug is converted to a compound of the present invention by means of solvolysis or by placing the compound under a physiological condition or not. Therefore, even if Y is a substituent except for hydroxy, mercapto or amino, a compound converted to hydroxy, mercapto or amino by means of solvolysis or by placing the compound under a physiological condition is contained in prodrugs of the present invention and the present invention. For example, a compound converted to the present invention compound in phosphate buffer (pH7.4)-ethanol or plasma is a compound of the present invention.

Pharmaceutically acceptable salts of a compound of the present invention include, as basic salts, for example, alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine or procaine salts; aralkyl amine salts such as N,N-dibenzylethylenediamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts. Acid salts include, for example, mineral acid salts such as hydrochloride, sulfates salts, nitrate salts, phosphates salts, carbonates salts, hydrogencarbonates or perchlorate; organic acid salts such as acetates, propionates, lactates, maleates, fumarates, tararic acid salts, malates, citrates salts, or ascorbates; sulfonates such as methane sulfonates, isethionates, benzenesulfonates, or p-toluenesulfonates; and acidic amino acid salts such as aspartates or glutamates.

Furthermore, various solvates of a compound of the present invention, for example, monosolvate, disolvate, monohydrate or dihydrate are also within the scope of the present invention.

The term "inhibit" means that a compound of the present invention suppresses the action of integrase.

The term "pharmaceutically acceptable" means harmless with respect to the prevention and the treatment.

BEST MODE FOR CARRYING OUT THE INVENTION

The general method for the production of a compound of the present invention is explained below.

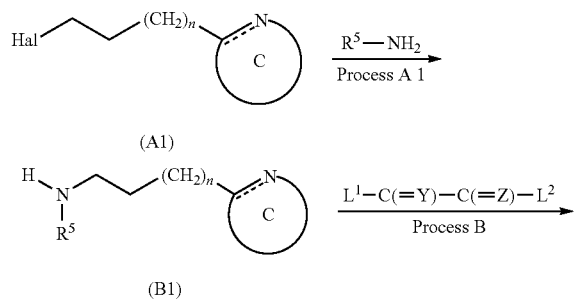

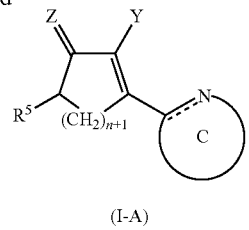

(wherein, C ring, $R^5$, Y, Z and the broken line are the same as above; $L^1$ and $L^2$ are leaving groups such as alkoxy; Hal is halogen; n is an integer of 0 or more, C ring may be substituted with a group of the formula: $-Z^1-Z^2-Z^3-R^1$ (wherein $Z^1$, $Z^2$, $Z^3$ and $R^1$ are the same as above) and/or a non-interfering substituent.)

Process A1

This process is for reacting compound of the formula (A1) with compound of the formula: $R^5NH_2$ to give compound of the formula (B1).

Examples of compound of the formula (A1) include heteroarylalkyl halides.

Examples of compound of the formula: $R^5NH_2$ include alkylamine (e.g., methylamine, ethylamine, n-propylamine, isopropylamine, n-butylamine, tert-butylamine, 2-ethylpropyl), cycloalkylamine (e.g., cyclohexylamine), arylamine (e.g., aniline), alkoxyamine (e.g., tert-butoxyamine), aralkylamine (e.g., benzylamine).

Examples of solvent include dimethylformamide, alcohol (e.g., methanol, ethanol).

This process may be conducted in the presence of base (e.g. sodium hydrogencarbonate, potassium carbonate).

Process B

This process is for reacting compound of the formula (B1) with compound of the formula: $L^1-C(=Y)-C(=Z)-L^2$ in the presence of base to give compound of, the formula (I-A).

Examples of compound of the formula: $L^1-C(=Y)-C(=Z)$-12 include oxalic acid dimethyl, oxalic acid diethyl.

Examples of base include metal alcolate (e.g. sodium methoxide, sodium ethoxide).

Examples of reaction solvent include alcohol (e.g., methanol, ethanol).

Compound (B1) can be prepared by the following process.

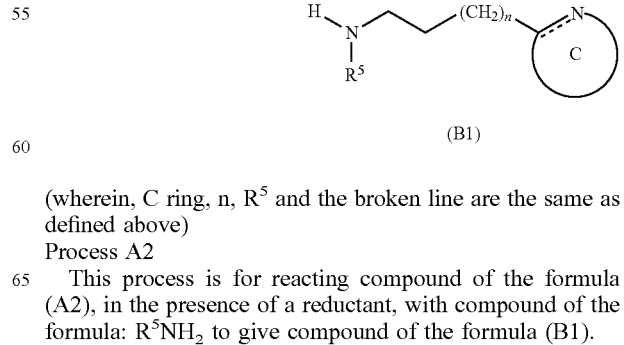

(wherein, C ring, n, $R^5$ and the broken line are the same as defined above)

Process A2

This process is for reacting compound of the formula (A2), in the presence of a reductant, with compound of the formula: $R^5NH_2$ to give compound of the formula (B1).

Examples of compound of the formula (A2) include heteroarylalkyl.

Examples of compound of the formula: $R^5NH_2$ include amine as used in Process A1

Examples of reductant include $NaBH_3CN$.

Examples of reaction solvent include alcohol (e.g., methanol, ethanol).

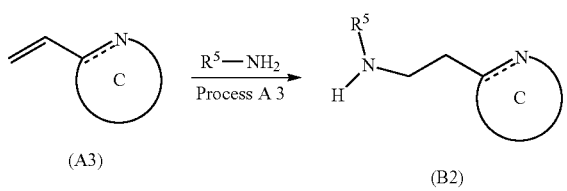

(A3)     (B2)

(wherein, C ring, $R^5$ and the broken line are the same as above)

Process A3

This process is for reacting compound of the formula (A3) with compound of the formula: $R^5NH_2$ to give compound of the formula (B2).

Examples of compound of the formula (A3) include vinyl pyrimidine (e.g., 4-vinyl-6-phenethylpyrimidine).

Examples of compound of the formula: $R^5NH_2$ include amine as used in Process A1.

Examples of reaction solvent include alcohol (e.g., methanol, ethanol).

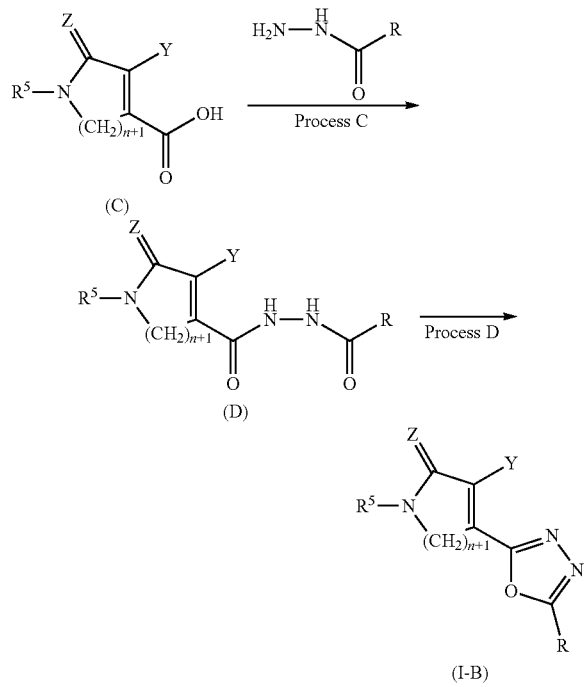

(wherein, Y, Z, $R^5$, n are the same as above; R is of the formula: $-Z^1-Z^2-Z^3-R^1$ (wherein, $Z^1, Z^2, Z^3$ and $R^1$ are the same as above) or a non-interfering substituent)

Process C

This process is for condensing compound of the formula (C) with compound of the formula: $R-C(=O)-NH-NH_2$ to give compound of the formula (D). Y is preferably protected in advance.

Examples of compound of the formula (C) include 2,5-dihydro-1-isopropyl-5-oxo-4-hydroxy-1H-pyrrole-3-carboxylic acid, and examples of its protected type include 2,5-dihydro-1-isopropyl-5-oxo-4-methoxy-1H-pyrrole-3-carboxylic acid.

Examples of compound of the formula: $R-C(=O)-NH-NH_2$ include acetyl hydrazine (e.g., phenylacetyl hydrazine, p-fuluorophenylacetyl hydrazine).

Examples of condensing agent include DCC (dicyclohexylcarbodiimide), WSCD (1-ethyl-3-(3-dimethylaminopropyl)carbodiimide), HOBt (1-hydroxybenzotriazole).

Examples of reaction solvent include tetrahydrofran, dimethylformamide.

Process D

This process is for halogenating compound of the formula (D), followed by treating with a base, to give compound of the formula (I-B).

Halogenation can be conducted by reacting compound of the formula (D) with bromine or the like in the presence of triphenylphosphine.

Examples of base include triethylamine.

Examples of reaction solvent include methylene chloride.

In Process C and D where Y is protected in advance, deprotection of Y can be conducted by reacting trimethylsilil chloride in the presence of NaI in acetonitrile.

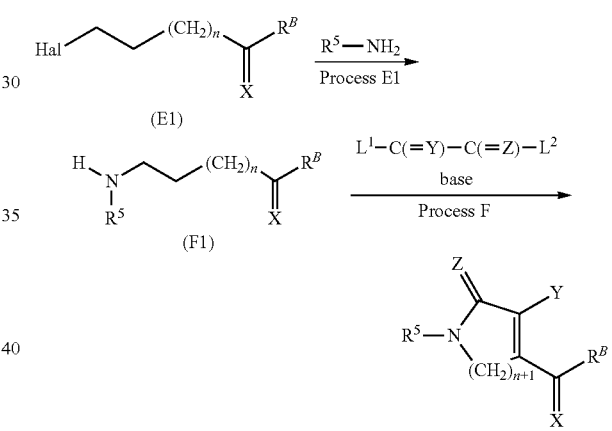

(wherein, $R^5$, Y, Z, n, $R^B$ and Hal are the same as defined above. $R^{13}$ is optionally substituted with a group of the formula: $-Z^1-Z^2-Z^3-R^1$ (wherein, $Z^1, Z^2, Z^3$ and $R^1$ are the same as above) and/or a non-interfering substituent.)

Process E1

This process is for reacting compound of the formula (E1) with compound of the formula: $R^5NH_2$ to give compound of the formula (F1), according to Process A1.

Process F

This process is for reacting compound of the formula (F1) with compound of the formula: $L^1-C(=Y)-C(=Z)-L^2$ in the presence of a base to give compound of the formula (I-C), according to Process B.

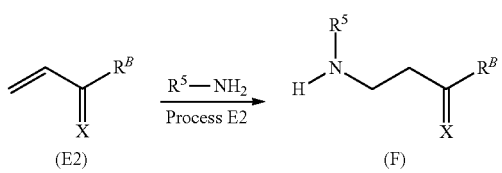

(E2)     (F)

(wherein, $R^B$, $R^5$ and X are the same as defined above)
Process E2

This process is for reacting compound of the formula (E2) with compound of the formula: $R^5NH_2$ to give compound of the formula (F), according to Process A3.

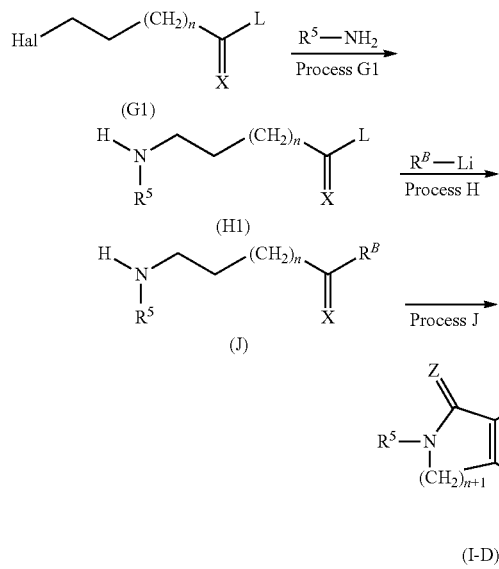

(wherein, n, $R^5$, X, $R^B$, Hal and Y are the same as above; L is a leaving group)
Process G1

This process is for reacting compound of the formula (G1) with compound of the formula: $R^5NH_2$ to give compound of the formula (H1), according to Process E1.
Process H This process is for reacting compound of the formula (H1) with compound of the formula $R^BLi$ to give compound of the formula (H1). The amino group in the formula (H1) is preferably protected in advance.

Examples of compound of the formula (H1) include 3-alkylamino propanic acid methylmethoxyamide (e.g., 3-methylamino propanic acid methylmethoxyamide, 3-ethyl amino propanic acid methylmethoxyamide, 3-n-propylamino propanic acid methylmethoxyamide, 3-n-butylamino propanic acid methylmethoxyamide, 3-ethyl propylamino propanic acid methylmethoxyamide, 3-tert-butylamino propanic acid methylmethoxyamide), 3-cycloalkyl amino propanic acid methylmethoxyamide (e.g., 3-cyclopropylaminopropanic acid methylmethoxyamide, 3-cyclopentylaminopropanic acid methylmethoxyamide, 3-cyclohexylaminopropanic acid methylmethoxyamide), 3-alkoxyaminopropanic acid methylmethoxyamide (e.g., 3-(2-methoxyethyl amino)propanic acid methylmethoxyamide), 3-alkenyl amino propanic acid methylmethoxyamide (e.g., 3-allylamino propanic acid methylmethoxyamide), 3-heterocyclealkylamino propanic acid methylmethoxyamide (e.g., 3-pyrrolidilpropanic acid methylmethoxyamide, 3-morpholil ethyl propanic acid methylmethoxyamide). Examples of its protected type include compounds wherein the amino group is protected with Boc group (tert-butoxycarbonyl). The protection can be conducted by reacting compound of the formula (H1) with $Boc_2O$ in an alcohol (e.g., methanol, ethanol).

Examples of compound of the formula: $R^BLi$ include 5-(p-fluorobenzyl)fran-2-yllithium. Compound of the formula: $R^BLi$ can be prepared by reacting compound of the formula: $R^BBr$ with butyl lithium.
Process J This process is for reacting compound of the formula (J) with compound of the formula: $L^1$-C(=Y)—C(=Z)-$L^2$ in the presence of a base to give compound of the formula (I-D), according to Process B and Process F

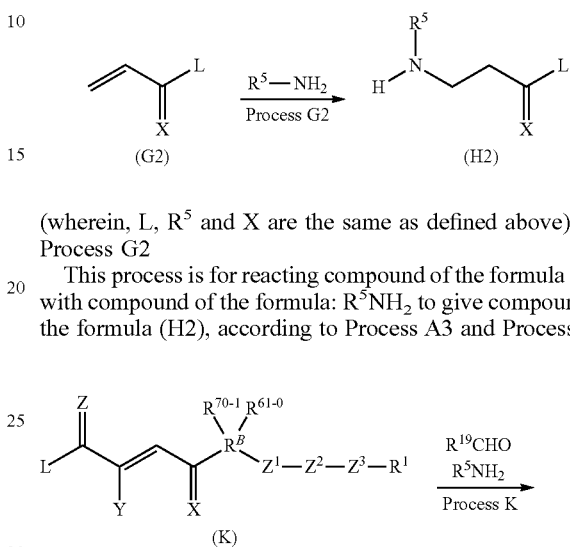

(wherein, L, $R^5$ and X are the same as defined above)
Process G2

This process is for reacting compound of the formula (G2) with compound of the formula: $R^5NH_2$ to give compound of the formula (H2), according to Process A3 and Process E2.

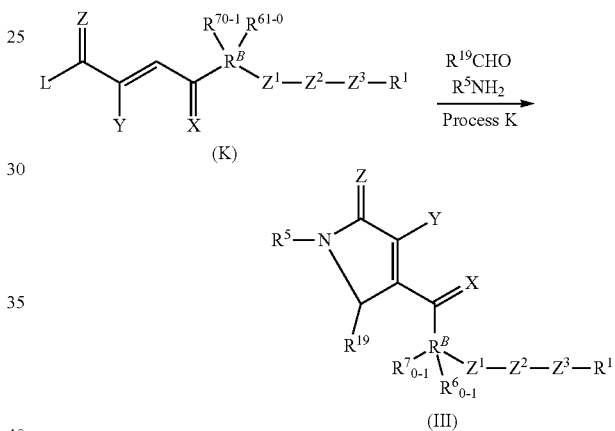

(wherein, X is O; Y is hydroxy; Z is O; $R^6$, $R^7$, $R^5$ and $R^{19}$ are non-interfering substituents; L is a leaving group; $R^B$, $Z^1$, $Z^2$, $Z^3$ and $R^1$ are the same as above (1))
Process K This process is for reacting compound of the formula (K) with compound of the formula: $R^5NH_2$ and compound of the formula: $R^{19}CHO$ to give compound of the formula (III), according to Zhurnal Organicheskoi Khimii, Vol. 22, No. 8, pp. 1749-1756.

Examples of compound of the formula (K) include that wherein, $R^B$ is optionally substituted aryl, optionally substituted heteroaryl, optionally substituted cycloalkyl, optionally substituted cycloalkenyl, or optionally substituted heterocycle, such as 2-hydroxy-4-oxo4-aryl-2-butenic acid alkyl ester, 2-hydroxy-4-oxo4-heteroaryl-2-butenic acid alkyl ester, 2-hydroxy-4-oxo4-cycloalkyl-2-butenic acid alkyl ester, 2-hydroxy-4-oxo-4-cycloalkenyl-2-butenic acid alkyl ester, 2-hydroxy-4-oxo4-heterocycle-2-butenic acid alkyl ester wherein the aryl, heteroaryl, cycloalkyl, cycloalkenyl, heterocycle are substituted with a group of the formula: —$Z^1$—$Z^2$—$Z^3$—$R^1$ (wherein, $Z^1$, $Z^2$, $Z^3$ and $R^1$ are the same as defined above). Examples thereof include 4-(4-benzyloxybenzyl)-2-hydroxy-4-oxo-2-butenoic acid methylester, 4-[4-(4-fluorobenzyloxyl)benzyl]-2-hydroxy-4-oxo-2-butenoic acid methylester, 4-(5-benzylfran-2-yl)-2-hydroxy-4-oxo-2-butenoic acid methylester, 4-[5-(4- fluorobenzyl)fran-2-yl]-2-hydroxy-4-oxo-2-butenoic acid methylester. These compounds can be prepared according to the method described in WO00/39086.

Examples of compound of the formula: $R^5NH_2$ include alkylamine (e.g., methylamine, ethyl amine, n-propylamine, isopropylamine, n-butylamine, tert-butylamine, 2-ethyl propyl), cycloalkylamine (e.g., cyclohexylamine), arylamine (e.g., aniline), alkoxyamine (e.g., tert-butoxyamine), aralkylamine (e.g., benzylamine). Compound of the formula: $R^5NH_2$ may be used in an amount of 1 to 3 mol equivalent, preferably 1 to 2 mol equivalent per compound of the formula (K).

Examples of compound of the formula: $R^{19}CHO$ include optionally substituted arylaldehyde (e.g., benzaldehyde), optionally substituted heteroarylaldehyde (e.g., furfural), alkylaldehyde (e.g., acetoaldehyde), alkenylaldehyde, cycloalkyl aldehyde (e.g., cyclopropylaldehyde, cyclohexylaldehyde), formaldehyde and/or polymer thereof (formalin aqueous solution can be used.).

Compound of the formula: $R^{19}CHO$ can be used in an amount of 1 to 3 mol equivalent, preferably 1 to 2 mol equivalent per compound of the formula (K).

Examples of leaving group include alkoxy.

The reaction temperature is 0° C. to 100° C., preferably room temperature to 50° C., more preferably room temperature to 30° C.

Examples of reaction solvent include dioxane, ethanol, dimethylformamide, tetrahydrofran, acetonitrile, or a mixture thereof. Preferred is dioxane. This process may be conducted in the presence of a base. This process is conducted for example as follows. To a solution or suspension of compound of the formula (K) in an organic solvent, were added compound of the formula: $R^5NH_2$ and compound of the formula: $R^{19}CHO$ succesively or simultaneously, and the mixture was stirred for several hours (preferably, 0.5 to 24 hours, more preferably 0.5 to 5 hour) at room temperature to 50° C. The reaction mixture was added to dil. hydrochloric acid, which was extracted with an organic solvent such as ethyl acetate, washed with saturated saline, dried, and evaporated under reduced pressure to give crystals of compound of the formula (III). Alternatively, addition of an organic solvent such as methanol or aether can give the crystal of compound of the formula (III). In case such a crystal can not obtained, purification with silica gel chromatography gives compound of the formula (III). In addition, the adding order of each compound of the formula: $R^5NH_2$, formula: $R^{19}CHO$ and the formula (K) is optional.

In this process, the present invention compound of the formula (III) can be readily prepared. Compound of the formula: $R^5NH_2$ or $R^{19}CHO$ can be synthesized or commercially available.

This process can be conducted by the method used in the combinatorial chemistry (e.g., parallel synthesis). For example, to each well of a plate with 96 holes, are added an organic solvent (e.g., dioxane), compound of the formula (K), compound of the formula: $R^5NH_2$ and compound of the formula: $R^{19}CHO$, which is shaken at room temperature to 50° C., then evaporated to remove the organic solvent to give a library of compounds of the formula (III). In this process, generation of by-products can be controlled at low level, thus the evaporation of the used organic solvent readily give an sample for the bioassay.

This process can be conducted as a routine work, thus useful for preparing lots of compounds having various substituents in a short period of time. Namely, reaction of various kinds of compounds of the formula (K), the formula: $R^5NH_2$ and the formula: $R^{19}CHO$, each basic structure being fixed, gives several ten to several ten thousands of compounds, from which a compound having the most suitable substituent is selected to give a compound of the present invention with high activity.

The library of the present invention compound can consists of 2 or more compounds obtained by the above method. The library means a group consisting of 2 or more compounds having a common partial structure. Examples of the common partial structure include a pyrrolinone structure. The pyrrolinone structure is preferably substituted with hydroxy and a group of the formula: $-C(=O)-R^B-Z^1-Z^2-Z^3-R^1$. A compound having such a common partial structure possesses an HIV integrase inhibitory activity and a library consisting of such compounds is useful for screening an anti-HIV agent, AIDS-treating agent etc., as well as other medicines. In orer to obtain a particularly useful information on Structure Activity Relationship (SAR), the library is a group preferably consisting of 10 or more compounds, more preferably 50 or more. The library of the present invention comprises at least one compound of the present invention. Thus, a compound included in the library is very useful for screening a compound possessing a potent HIV integrase inhibitory activity.

A preferable starting material is of the formula (K):

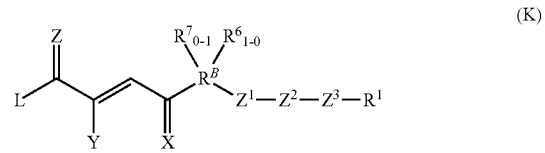

(K)

(wherein, X is O; Y is hydroxy; Z is O; $R^B$ is heteroaryl; $R^B$ is not substituted with $R^6$ and $R^7$; L is alkoxy; $Z^1$ and $Z^3$ are bonds; $Z^2$ is alkylene; $R^1$ is optionally substituted phenyl)

A more preferable starting material of the formula (K) is a compound wherein X is O; Y is hydroxy; Z is O; $R^B$ is heteroaryl; $R^B$ is not substituted with $R^6$ and $R^7$; L is alkoxy; $Z^1$ and $Z^3$ are bonds; $Z^2$ is methylene; $R^1$ is 4-fluorophenyl. Further preferred is 4-[5-(4-fluorobenzyl)fran-2-yl]-2-hydroxy-4-oxo2-butenoic acid alkyl ester.

For use to the production of the present compound, the following compounds of the formula: $R^5NH_2$ or $R^{19}CHO$ can be selected from commercially available amine and aldehyde with reference to molecular weight thereof. Compound of the formula: $R^5NH_2$ can be selected from amine shown below:

cyclopropylamine, cyclobutylamine, cyclopentylamine, cycloroleucine, cyclohexylamine, 1-aminocyclohexan carboxylic acid, 1-etynylcyclohexylamine, 1,2-diaminocyclohexan, 2-methylcyclohexylamine, 2,3-dimethylcyclohexylamine, 4-methylcyclohexylamine, amino methylcyclohexan, 1,3-cyclohexan bis(methylamine), 1-amino-5,6,7,8-tetrahydronaphthalene, 1,2,3,4-tetrahydro-1-naphthylamine, cycloctylamine, 2-amino-1-propene-1,1,3-tricarbonitryl, diaminomaleonitryl, S-methyl L-cystein, L-aspartic acid, L-leucine, DL-homoserine, D-methionine, L-allylglycine, L-glutamic acid, 2-amino-1,3,4-thiadiazole, 2-amino-5-mercapto-1,3,4-thiadiazole, 2-amino-5-ethyl-1,3,4-thiadiazole, 3,5-dimethylpyrazole-1-carboamide, 5-amino-3-methylisoxazole, 3-amino-5-methylisoxazole, 2-(2-aminoethyl)-1-methylpyrrolidine, 1-(2-aminoethyl) pyrrolidine, 1-(3-aminopropyl)-2-pyrrolidinone, furfurylamine, 1-amino indan, 5-aminoindan, 1-naphthylamine, 2-naphthylamine, cycloheptylamine, D-tert-leucine, DL-valine, DL-isoleucine, D-serine, guanidoacetic acid, creatine, D-allothreonine, 2-amino-2-methyl-1,3-propane diol, tris (hydroxymethyl)aminomethane, DL-2-amino-3-methyl-1-nutaol, L-isoleucinol, D-leucinol, L-methioninol, DL-penicilamine, DL-cysteine, DL-homocysteine, 1-acetyl-3-thiosemicarbazide, 1-acetyl-2-thiourea, N-methylthiourea, ethyl thiourea, allylthiourea, dithioxamide, histamine, 3-amino-1,2,4-triazole, 3-amino-5-mercapto-1,2,4-triazole, 3-amino-5-methylthio-1,2,4-triazole, 3,5-diamino-1,2,4-triazole, 3-aminopyrazole, 3-amino-4-cyanopyrazole, 3-aminopyrazole-4-carboxylic acid, L-prolineamide, 2-amino-2-thiazoline, 2-amino thiazole, 2-amino-5-nitrothiazole, 2-amino-4-methylthiazole, D-cycloserine, tetra hydrofurfurylamine, 2-aminopurine, 2-aminobenzimidazole 5-amino indole, 4-amino pyrazolo[3,4-D]pyrimidine, 6-aminoindazole, 8-azaadenine, 3,4-methylenedioxyaniline, N-(2-aminoethyl)piperazine, nipecotamide, 4-(aminomethyl)piperidine, 5-aminouracil, 5-azacytosine, cytosine, 5-fluorocytosine, 4-amino-2,6-dihydroxypyrimidine, 2-amino pyrimidine, 2-amino-4-chloro-6-methylpyrimidine, 2-amino-4,6-dihydroxypyrimidine, 2-amino-4-hydroxy-6-methylpyrimidine, 4-chloro-2,6-diaminopyrimidine, 2,4-diamino-6-hydroxypyrimidine, 2,4,6-triaminopyrimidine, 2-amino-4-methylpyrimidine, 2-amino-4,6-dimethylpyrimidine, 2-amino-5-nitropyrimidine, 4-aminopyrimidine, 4,5-diaminopyrimidine, 4,5-diamino-6-hydroxypyrimidine, pyrazine amide, aminopyrazine, 3-aminopyrazine E-2-carboxylic acid, 4-(2-aminoethyl)morpholine, N-(3-aminopropyl) morpholine, nicotinamide N-oxide, 3-amino-2-chloropyridine, 5-amino-2-chloro pyridine, 5-amino-2-methoxypyridine, 3-hydroxypicolineamide, 2-aminopyridine, 2-amino-3-nitropyridine, 2-amino-3-hydroxypyridine, 2-aminonicotinic acid, 2,3-diamino pyridine, 2-amino-3-methylpyridine, 2-amino-4-methylpyridine, 2-amino-4,6-di methylpyridine, 2-amino-5-chloropyridine, 2-amino-5-nitropyridine, 6-aminonicotinic acid, 6-aminonicotinamide, 2-amino-5-methylpyridine, 2,6-diaminopyridine, 2-amino-6-methylpyridine, 6-methylnicotinamide, 2-(amino methyl)pyridine, 2-(2-aminoethyl) pyridine, nicotinamide, thionicotinamide, 3-aminopyridine, 3,4-diaminopyridine, 3-(aminomethyl)pyridine, isonicotinamide, 4-aminopyridine, 4-(aminomethyl)pyridine, 3-amino-1,2,4-triazine, 3-amino-5,6-dimethyl-1,2,4-triazine, 1-(2-amino ethyl)piperidine, 3-amino quinoline, 5-amino quinoline, 6-amino quinoline, 8-amino quinoline, 5-aminoisoquinoline nitroguanidine, cyanamide, thiosemicarbazide, aniline, 2-aminobenzonitryl, 2-fluoroaniline, 2,4-difluoroaniline, 2,4,5-trifluoroaniline, 2,4,6-trifluoroaniline, 2,5-difluoroaniline, 2-fluoro-5-methylaniline, 2,6-difluoroaniline, 2-chloro aniline, 2-chloro-4-methyl aniline, 2-chloro-5-methylaniline, 2-chloro-6-methylaniline, O-nitroaniline, O-anisidine, O-phenetidine, 2-aminophenol, 6-amino-m-cresol, 2-amino-4-chlorophenol, 2-amino-4-methylphenol, 2-aminothiophenol, 2-(methylthio)aniline, anthranilic acid, 2'-aminoacetophenone, 2-isopropenylaniline, 2-isopropylaniline, o-phenylenediamine, 3,4-diaminotoluene, 4,5-dimethyl-1,2-phenylenediamine, 2,3-dimethylaniline, 4-methoxy-2-methylaniline, 2,4-dimethylaniline, 2,4,6-trimethylaniline, 2,5-dimethylaniline, 2-isopropyl-6-methylaniline, 2,6-dimethylaniline, 2-aminobenzyl alcohol, 2-ethylaniline, 2-ethyl-6-methylaniline, 2,6-diethylaniline, 2-aminophenetyl alcohol, 3-aminobenzonitryl, 3-fluoroaniline, 3-fluoro-o-anisidine, 3-fluoro-2-methylaniline, 3,4-difluoroaniline, 3-fluoro-4-methylaniline, 3,5-difluoroaniline, 5-fluoro-2-methylaniline, 3-chloroaniline, 3-chloro-2-methyl aniline, 3-chloro-4-fluoroaniline, 3-chloro-4-methyl aniline, 5-chloro-2-methylaniline, m-nitro aniline, m-anisidine, m-phenetidine, 3-aminophenol, 3-amino-o-cresol, 3-aminothiophenol, 3-(methylthio)aniline, 3-aminobenzoic acid, 3-amino acetophenone, 3-(1-hydroxyethyl)aniline, m-phenylenediamine, 2,6-diaminotoluene, 2,4-diaminotoluene, m-toluidine, 3,4-dimethylaniline, 3,5-dimethylaniline, 2-methoxy-5-methylaniline, 3-aminobenzyl alcohol, 3-ethylandine, 4-aminobenzonitryl, 4-fluoro aniline, 4-fluoro-2-methylandine, 4-chloro aniline, 4-chloro-2-methyl aniline, p-nitro aniline, N,N-dimethyl-p-phenylene diamine, p-anisidine, p-phenetidine, 4-amino phenol, 4-amino-m-cresol, 4-amino-2,5-dimethylphenol, 4-amino-o-cresol, 4-amino thiophenol, 4-(methylthio)aniline, 4-aminobenzoic acid, 4-amino acetophenone, 4-tert-butylaniline, 4-isopropylaniline, p-phenylenediamine, p-toluidine, 4-amino phenylacetonitrile, 4-ethylaniline, 4-aminophenetyl alcohol, 4-propylaniline, 4-N-butylaniline, formamide, hydroxyurea, phenylurea, cyanoacetylurea, methylurea, ethylurea, arylurea, N-butylurea, N,N-dimethylurea, 1,1-diethylurea, phenylcarbamate, tert-butylcarbamate, methylcarbamate, ethylcarbamate, butylcarbamate, benzamide, 2-fluorobenzamide, salicylamide, 2-aminobenzamide, O-toluamide, 3-fluorobenzamide, 3-aminobenzamide, m-toluamide, 4-fluorobenzamide, 4-hydroxybenzamide, 4-aminobenzamide, p-toluamide, ethyl oxamate, oxamide, 2,2,2-trifluoroacetamide, trimethylacetamide, 2,2-dichloroacetamide, 2-chloropropionamide, lactamide, methacrylamide, isobutylamide, urea, acetamide, cyano acetamide, 2-bromo acetamide, fluoroacetamide, 2-chloroacetamide, N-acetylglycineamide, acrylamide, cinnamamide, malonamide, propione amide, 3-chloropropione amide, 2-aminoisobutanoic acid, tert-butylamine, 2-amino-2-methyl-1-propanol, tert-octylamine, 1,2-diamino-2-methylpropane, tert-amylamine, 1,1-diethylpropargylamine, thiobenzamide, (R)-(−)-2-phenylglycinol, thiourea, DL-α-methylbenzylamine, thioacetamide, 3-aminocrotonitryl, methyl-3-aminocrotonate, ethyl 3-aminocrotonate, D-alanine, 1,2-dimethylpropylamine, isopropylamine, 2-amino-1-methoxypropane, DL-2-amino-1-propanol, ethyl 3-aminobutylate, DL-β-amino-n-butanoic acid, 1,3-dimethylbutylamine, 1,2-diaminopropane, 1-methyl-3-phenylpropylamine, 2-amino-6-methylhaptane, DL-2-aminobutanoic acid, sec-butylamine, (+/−)-2-amino-1-butanol, 3-aminopentan, D-norvaline, D-norleucine, 2-aminoheptane, 2-aminooctane, methylamine, benzylamine, 2-fluorobenzylamine, 2-chlorobenzylamine, 2-methoxybenzylamine, 2-methylbenzylamine, 3-fluorobenzylamine, 3-methoxybenzylamine, 3-methylbenzylamine, m-xylendiamine, 4-fluorobenzyl amine, 4-chlorobenzylamine, 4-methoxybenzylamine, 4-methylbenzylamine, glycine, 2,2,2-trifluoroethylamine, aminoacetoaldehyde dimethyl acetal, aminoacetoaldehyde diethyl acetal, 2-amino-1-phenylethanol, DL-isoserine, 1-amino-2-propanol, 3-amino-1,2-propane diol, DL-4-amino-3-hydroxybutanoic acid, 1,3-diamino-2-hydroxypropane, 2-phenylpropylamine, DL-3-amino isobutanoic acid, isobutylamine, 2-methylbutylamine, 2-ethylhexylamine, ethylamine, N-phenylethylenediamine, N-acetylethylenediamine, N-isopropylethylenediamine, N-methylethylenediamine, N-ethylethylenediamine, 2-(2-aminoethylamino) ethanol, diethylenediamine, N-(n-propyl)ethylenediamine, N,N-dimethylethylenediamine, N,N-diethylethylenediamine, tris(2-aminoethyl)amine, 2-methoxyethylamine, 2-(2-aminoethoxyl)ethanol, ethanolamine, phenetylamine, thyramine, 2-(4-aminophenyl)ethylamine, 2-(p-tril)ethylamine, taurine, propargylamine, allylamine, β-alanine, 3,3-dimethylbutylamine, isoamylamine, ethylenediamine, propylamine, N-isopropyl-1,3-propane diamine, N-methyl-1,3-propanediamine, N-(2-aminoethyl)-1,3-propanediamine, N-propyl-1,3-propanediamine, 3,3'-diaminodipropylamine, N,N-dimethyl-1,3-propanediamine, N,N-bis(3-aminopropyl)methylamine, N,N-diethyl-1,3-propanediamine, 3-isopropoxypropylamine, 3-ethoxypropylamine, 3-amino-1-propanol, 3-phenylpropylamine, 4-aminobutanoic acid, 1,3-diaminopropane, 4-amino-1-butanol, 4-phenylbutylamine, 5-aminovalerianic acid, 1,4-diaminobutane, N-amylamine, 5-amino-1-pentanol, 6-aminocaproic acid, 1,5-diaminopentane, hexylamine, 6-amino-1-haxanol, 7-aminoheptanoic acid 1,6-hexandiamine, n-heptylamine, 1,7-diaminoheptane, octylamine, 1,8-diaminooctane, nonylamine, cyclohexancarboamide, 2,2-dimethyl-1,3-propane diamine, 2-n-propylaniline, DL-2-amino-1-pentanol, DL-2-amino-1-haxanol, 1-(3-aminopropyl)imidazole, p-xylendiamine, 1-aminocyclopropane-1-carboxylic acid, cyanothioacetamide, 2,4-difluorobenzylamine, 2,5-difluorobenzyl amine, 2,6-difluorobenzylamine, 3,4-difluorobenzylamine, 2-methyl-3-thiosemicarbazide, 5-amino-2-methoxyphenol, 4-sec-butylaniline, 2,3-difluoroaniline, thiophene-2-carboamide, 1-amino-1-cyclopentanmethanol, 3-methyladenine, 1-methyladenine, 4-chloro-2-fluoroaniline, 5-amino-1-ethylpyrazole, 2,3-diaminotoluene, butylamine, 4-chloro-o-phenylene diamine, 1-(trimethylsilylmethyl)urea, 2,3,4-trifluoroaniline, 2-(1-cyclohexenyl)ethylamine, 3-amino-2-butenethioamide, 2,3,6-trifluoroaniline, 1,5-diamino-2-methylpentane, amidinothiourea, 3-ethynylaniline, N,N-bis(2-hydroxyethyl)ethylenediamine, 3-methoxypropylamine, 4-aminostyrene, 2-amino-6-fluorobenzonitryl, 3-amino-5-hydroxypyrazole, 2,4-diamino-6-methyl-1,3,5-triazine, pyridine-2-carboamide, 1-aminoisoquinoline, 4-chloro-1,3-phenylenediamine, 2-chloroethylcarbamate, fumaramide, acetoamide, N—N-butylethylenediamine, 3-butoxypropylamine, cyclopropanemethylamine, 5-aminoindazole, 2,4-diamino pyrimidine, α-ethylbenzylamine, 3-aminoisoxazole, chlorodifluoroacetamide, 1,8-diamino-3,6-dioxaoctane, 2-sec-butylaniline, 3-chlorobenzylamine, 2-fluoro-4-methylaniline, 1-(4-fluorophenyl)ethylamine, 4-aminophthaloitrile, adenine, 2-chloro-4-fluoroaniline, semicarbazide, (R-(−)-1-cyclohexylethylamine, 5-amino-o-cresol, N,N,2,2-tetramethyl-1,3-propanediamine, 2,2-diethoxyacetamide, 3-amino-5,5-dimethyl-2-cyclohexene-1-one, propylcarbamate, glycolamide, 2-amino-1,3-propanediol, thiophene-2-ethyl amine, 2,5-dimethyl-1,4-phenylene diamine, 2-amino-4-methoxy-6-methyl-1,3,5-tri azine, 2-phenoxyethylamine, 4-amino-2-mercaptopyrimidine, creatinine, 2-amino-4-methoxy-6-methylpyrimidine, 3,5-difluorobenzylamine, (1R,2R)-(−)-1,2-diamino cyclohexan, (1S,2S)-(+)-1,2-diaminocyclohexan, D-aspartic acid, DL-aspartic acid, DL-leucine, D-leucine, L-homoserine, DL-methionine, L-methionine, DL-allylglycine, D-glutamic acid, L-leucinol, DL-threonine, cis-1,2-diaminocyclohexan, trans-1,2-cyclohexandiamine, L-tert-leucine, D-valine, L-valine, D-iso leucine, L-iso leucine, DL-serine, L-serine, L-allothreonine, D-threonine, L-threonine, L-valinol, D-valinol, L-cysteine, DL-cycloserine, L-cycloserine, L-asparagine, (S)-(+)-2-phenylglycinol, (R)-(+)-1-phenylethylamine, L-(−)-α-methylbenzylamine, DL-alanine, L-alanine, L-alaninol, D-alaninol, D-(−)-2-aminobutanoic acid, L-α-amino-n-butanoic acid, (R)-(−)-2-aminobutane, (S-(+)-2-aminobutane, (S)-(+)-2-amino-1-butanol, (R)-(−)-2-amino-1-butanol, DL-norvaline, L-norvaline, DL-norleucine, L-norleucine, (R)-(−)-1-amino-2-propanol, (S)-(+)-1-amino-2-propanol, (S)-(−)-2-methylbutylamine, DL-lysine, L-lysine, DL-tert-leucine, (S)-(+)-1-cyclohexylethylamine, ethyl thiooxamate, 2-amino-5-methylbenzyl alcohol, 2-amino-3-methylbenzyl alcohol, 3-amino-2-methylbenzyl alcohol, 3-fluoro-4-methoxy aniline, 3-amino-4-methylbenzyl alcohol, 5-methoxy-2-methyl aniline, 2-amino-m-cresol, trans-1,4-diaminocyclohexan, 3-amino-5-methylpyrazole, 2,3-diaminophenol, 1-piperidinecarboamide, 6-amino-1-methyluracil, 3-fluorophenetylamine, 2-aminobenzylamine, 2-methoxy-6-methylaniline, 2-fluorophenetylamine, 4-aminobenzylamine, 1-acetylguanidine, D-homoserine, 2-amino-5-methylthiazole, (S-(+)-tetrahydrofurfurylamine, 2-amino benzylcyanide, 4-amino-2-chlorophenol, 2-amino-4,5-dicyanoimidazole, 4-amino-6-methoxypyrimidine, 2-tert-butyl aniline, 2-(4-fluorophenyl)ethylamine, 1,3-diamino pentane, 2-amino-1-methylbenzimidazole, 5-methylfurfuryl amine, (R-(+)-1-(p-tril)ethyl amine, (S-(−)-1-(p-tril)ethyl amine, 3-amino-1,2,4-triazole-5-carboxylic acid, muscimol, 4-ethynylaniline, 2-amino-4-methylbenzonitryl, 2-amino-5-methylthio-1,3,4-thiadiazole, 1-(amino carbonyl)-1-cyclopropanecarboxylic acid, cis-4-aminocyclohexancarboxylic acid, (S-(+)-2-(aminomethyl)pyrrolidine, 5-amino-4-nitro imidazole, 3-amino-1-propanol vinyl aether, thioethylenediamine, isopropyldiethylene triamine, L-tert-leucinol, N-methyl-1,2-phenylenediamine, (R-(−)-tetra hydrofurfurylamine, N-(−)-lactamide, (R-(+)-lactamide, (S-(+)-2,2-dimethylcyclopropanecarboamide, (1S,2R)-(−)-cis-1-amino-2-indanol, (1R,2S)-(+)-cis-1-amino-2-danol, (R-(−)-1-aminoindane, (S-(+)-1-aminoindane, (R)-2-phenyl-1-propylamine, (S)-2-phenyl-1-pr op ylamine, D-methioninol, (R)-2-amino-1-phenylethanol, 2-amino-4,5-dimethyl-3-furancarbonitrile, N-hexylethylenediamine, (S-(−)-4-amino-2-hydroxybutanoic acid, (S)-3-amino-1,2-propandiol, (R)-3-amino-1,2-propandiol, 4-aminoindole, (R-(−)-tert-leucinol and 2-amino-5-fluoro pyridine.

Compound of the formula: $R^{19}CHO$ can be selected from aldehyde shown below. formaldehyde, ethyl 2-formyl-1-cyclopropancarboxylate, cyclohexancarboaldehyde, 1,2,3,6-tetrahydrobenzaldehyde, 1-methylpyrrole-2-carboaldehyde, furfural, 5-nitro-2-fulaldehyde, 5-methylfurfural, 5-hydroxymethyl-2-fulaldehyde, 3-(2-furyl)acrolein, benzaldehyde, 2-fluorobenzaldehyde, 2-chlorobenzaldehyde, o-anise aldehyde, salicylaldehyde, 3-fluoro-2-hydroxybenzaldehyde, 2,3-dihydroxybenzaldehyde, 2,5-dihydroxybenzaldehyde, o-naphthalaldehyde, o-tolaldehyde, 2,4-dimethylbenzaldehyde, mesitaldehyde, 2,5-dimethylbenzaldehyde, 3-cyano benzaldehyde, 3-fluorobenzaldehyde, 3-chlorobenzaldehyde, 3-methoxybenzaldehyde, 3-hydroxybenzaldehyde, 3,4-dihydroxybenzaldehyde, isonaphthalaldehyde, m-tolaldehyde, 4-cyanobenzaldehyde, 4-fluorobenzaldehyde, 4-chlorobenzaldehyde, 4-dimethylaminobenzaldehyde, p-anisealdehyde, imidazole-2-carboaldehyde, pyrrole-2-carboaldehyde, 2-thiophenecarboaldehyde, 3-methylthiophene-2-carboaldehyde, 5-methyl-2-thiophenecarboaldehyde, 3-thiophenecarboaldehyde, indole-3-carboaldehyde, 2-pyridinecarboaldehyde, 6-methyl-2-pyridinecarboaldehyde, 3-pyridinecarboaldehyde, 4-pyridinecarboaldehyde, 4-hydroxybenzaldehyde, terenaphthalaldehyde, cuminaldehyde, p-tolaldehyde, 4-ethylbenzaldehyde, glyoxal, glyoxalic acid, methylglyoxal, trimethylacetoaldehyde, D-(−)-erythrose, 2-phenylpropionaldehyde, methacrolein, 3-ethoxy methacrolein, alpha-methylcinnamaldehyde, trans-2-methyl-2-butenal, 2-methyl-2-pentenal, isobutylaldehyde, 2,6-dimethyl-5-hepten-1-al, 2-methylbutylaldehyde, 2-ethylbutylaldehyde, 2-methylpental, 2-ethylhaxal, acetoaldehyde, chloroacetoaldehyde, phenylacetoaldehyde, phenylpropargylaldehyde, acrolein, 3-(dimethylamino)acrolein, trans-cinnamaldehyde, crotonaldehyde, 2,4-haxadienal, trans,trans-2,4-heptadienal, trans,trans-2,4-nonadienal, trans-2-hexanal, trans-2,cis-6-nonadien-1-al, trans-2-heptanal, trans-2-octanal, trans-2-nonenal, isovaleraldehyde, propionaldehyde, 3-phenylpropionaldehyde, 3-(methylthio) propionaldehyde, butylaldehyde, glutaraldehyde, valeraldehyde, haxanal, heptaldehyde, octanal, naval, trans-2-pentenal, 2,4-dimethyl-2,6-heptadienal, 2,6-pyridine dicarboaldehyde, 2-ethylacrolein, 3-thethyl-2-butenal, 2,3-difluoro benzaldehyde, 2,6-difluorobenzaldehyde, 2,4-difluorobenzaldehyde, 2,5-difluoro benzaldehyde, 3,4-difluorobenzaldehyde, 3,5-difluorobenzaldehyde, 3-fulaldehyde, 3,5,5-trimethylhaxanal, 3-phenylbutylaldehyde, 2,2-dimethyl-4-pentenal, 2,4-dihydroxybenzaldehyde, cyclopropanecarboaldehyde, 4-hydroxy-3-methylbenzaldehyde, benzo[b]furan-2-carboaldehyde, 3,5-dihydroxybenz aldehyde, 3,4-dimethylbenz aldehyde, 2-cyanobenzaldehyde, 5-ethyl-2-fulaldehyde, 2-hydroxy-3-methylbenzaldehyde, 3,3-dimethylbutylaldehyde, 5-chloro-2-thiophenecarboaldehyde, 3,4-dihydro-2H-pyran-2-carboaldehyde, D-glyceroaldehyde, DL-glyceroaldehyde, 3-fluoro-2-methylbenzaldehyde, 3-dimethylamino-2-methyl-2-propenal, 3,5-dimethylbenzaldehyde, 4,5-dimethyl-2-furancarboaldehyde, 4-vinylbenzaldehyde, 2,6-dimethylbenzaldehyde, 2-octynal, dimethoxyacetoaldehyde, 2-deoxy-D-ribose, 2-formyl thiazole, 5-ethyl-2-thiophenecarboaldehyde, glyoxylic acid, 4-pyridinecarboaldehyde-N-oxide, 5-norbornen-2-carboaldehyde, 4-formylimidazole, 5-methylimidazole-4-carboaldehyde, 5-formyluracil, 2,3-thiophene dicarboaldehyde, thiophene-2,5-dicarboaldehyde, 2,3-o-isopropylidene-D-glyceroaldehyde, 2-hydroxy-5-methylbenzaldehyde, 1-cyclohexene-1-carboaldehyde, 2,3-dimethylbenzaldehyde, 1-methyl-2-imidazolecarboaldehyde, vinylbenzaldehyde, 4-fluoro-3-methylbenzaldehyde, 3-fluoro-4-methylbenzaldehyde, tetrahydrofran-3-carboaldehyde, 2-fluoro-5-formyl benzonitryl, indole-5-carboaldehyde, 4-acetylbenzaldehyde, 3-vinylbenzaldehyde and 2-fluoro-5-methylbenzaldehyde.

propenyl)phenol, 4-(phenetyl)-2-(1-oxo-3-(2-pyridyl)-2-propenyl)phenol, 4-(p-fluorophenetyl)-2-(1-oxo-3-(2-pyridyl)-2-propennyl)phenol.

Examples of base include 2N NaOH aq. solution.

Examples of hydrogen peroxide include 30% hydrogen peroxide.

Examples of reaction solvent include alcohol (e.g., methanol, ethanol).

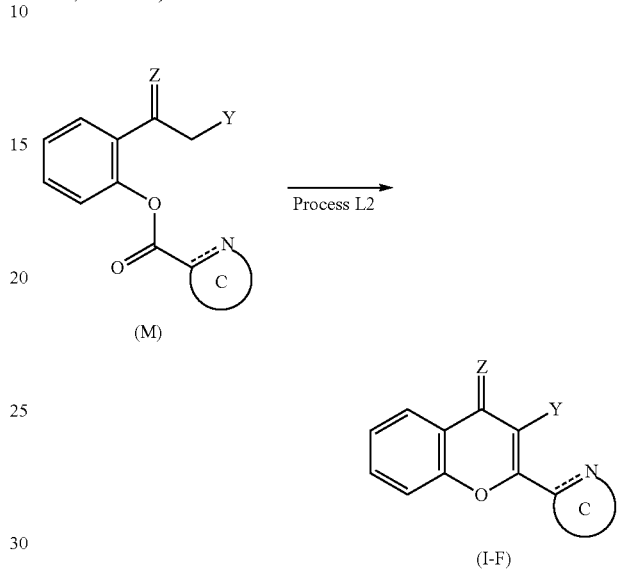

(wherein, Y, Z, C ring are the same as above; benzene ring and/or C ring of the formula (M) or (I-F) is optionally substituted with a group of the formula: —$Z^1$—$Z^2$—$Z^3$—$R^1$ (wherein, $Z^1$, $Z^2$, $Z^3$ and $R^1$ are the same as above) and/or a non-interfering substituent.)

Process L 2

This process is for reacting compound of the formula (M) with a base to give compound of the formula (I-F). Y is preferably protected in, advance. Examples of compound of the formula (M) include 2-(2-benzoyloxyl-oxoethyl)-3-methoxyphenyl-2-picolilate.

Examples of base include NaH.

Examples of solvent include dimethylformamide.

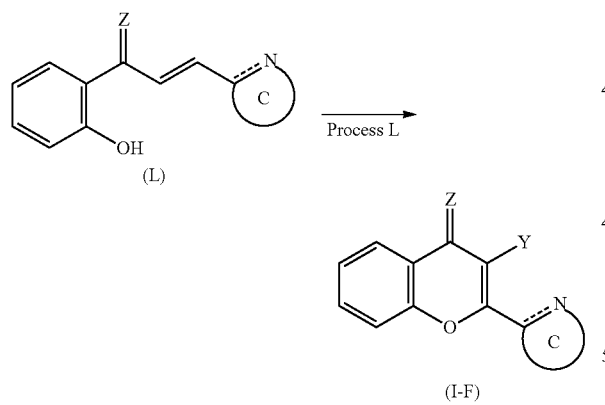

(wherein, C ring, Z and Y are the same as above; benzene ring and/or C ring of the formula (L) and or (IV) are optionally substituted with a group of the formula: —$Z^1$—$Z^2$—$Z^3$—$R^1$ (wherein, $Z^1$, $Z^2$, $Z^3$ and $R^1$ are the same as above) and/or a non-interfering substituent.)

Process L

This process is for reacting compound of the formula (L) with hydrogen peroxide in the presence of a base to give compound of the formula (I-F).

Examples of compound of the formula (L) include 4-(benzyloxy)-2-(1-oxo-3-(2-pyridyl)-2-propenyl)phenol, 4-(p-fluorobenzyloxy)-2-(1-oxo-3-(2-pyridyl)-2-propenyl)phenol, 4-(phenetyloxy)-2-(1-oxo-3-(2-pyridyl)-2-propenyl) phenol, 4-(p-fluoro phenetyloxy)-2-(1-oxo-3-(2-pyridyl)-2-

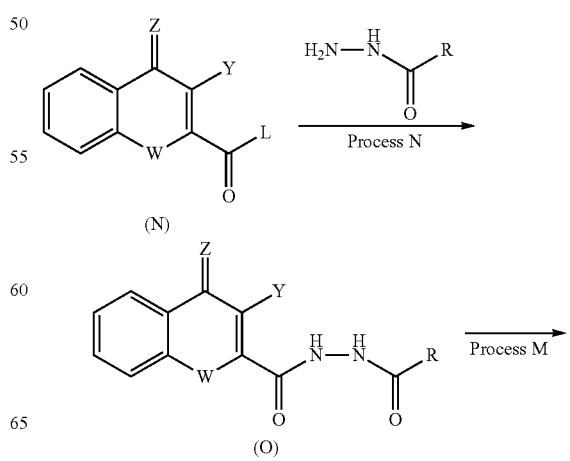

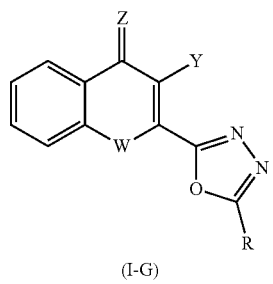

(I-G)

(wherein, W is —O or —N(—R$^{15}$)—; L is a leaving group such as alkoxy; Y, Z and R are the same as defined above)

Process N

This process is for reacting compound of the formula (N) with compound of the formula: R—C(=O)—NH—NH$_2$ in the presence of a condensing agent to give compound of the formula (O). Y and or Z is preferably protected in advance. The process may be conducted as well as Process C.

Examples of compound of the formula (N) include 3-hydroxy-4-oxo-1H-quinoline-2-carboxylic acid, 3-hydroxy-4-oxo-1-methyl-1H-quinoline-2-carboxylic acid, 3-hydroxy-4-oxo-4H-chromene-2-carboxylic acid. Examples of its protected type include 2-ethoxycarbonyl-3-methoxy-1H-quinoline-4-one, 2-ethoxycarbonyl-3-methoxy-1-methyl-1H-quinoline-4-one, 3-benzyloxy-4-oxo-4H-chromene-2-carboxylic acid ethyl ester, 3-methoxy-4-oxo-4H-chromene-2-carboxylic acid ethyl ester. These compounds can be prepared according to the method of J. Heterocyclic Chem, 24, p 1649, 1987.

Process M

This process is for preparing compound of the formula (I-G) from compound of the formula (O). The process, oxadiazole ring formation from diacylhydrazine, can be conducted by heating diacylhydrazine together with phosphorus oxychloride or thionyl chloride.

The reaction temperature is 50 to 100° C., preferably 80 to 100° C.

The process can also be conducted in the presence of triethylamine dibromotri phenylphospholan. In this case, the reaction temperature is 0 to 100° C., preferably 0 to 30° C. The reaction solvents include dichloromethane and tetrahydrofran.

Process O

This process is for halogenating compound of the formula (N), followed by treating with a base, to give compound of the formula (I-G), as well as Process O.

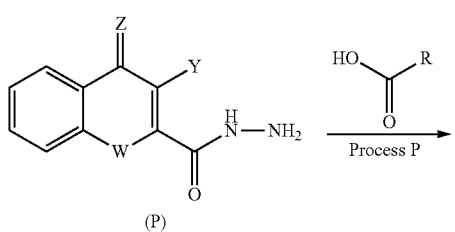 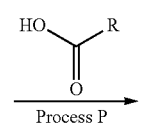

(P)  Process P

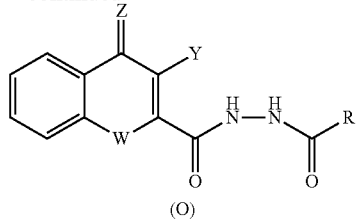

(O)

(wherein W is —O or —N(—R$^{15}$)—; Y, Z and R are the same as defined above; the benzene ring of the formula (N) or (O) is optionally substituted with a group of the formula: —Z$^1$—Z$^2$—Z$^3$—R$^1$ (wherein, Z$^1$, Z$^2$, Z$^3$ and R$^1$ are the same as above) and/or a non-interfering substituent.

Process P

This process is for reacting compound of the formula (P) with compound of the formula: R—C(=O)—OH in the presence of a condensing agent to give compound of the formula (O). Y and Z are preferably protected in advance. The process can be conducted as well as Process C and Process N.

Examples of compound of the formula (P) include 2-hydrazinocarbonyl-3,4-dihydroxyquinoline. Protected types thereof include 2-hydrazinocarbonyl-3,4-dimethoxyquinoline.

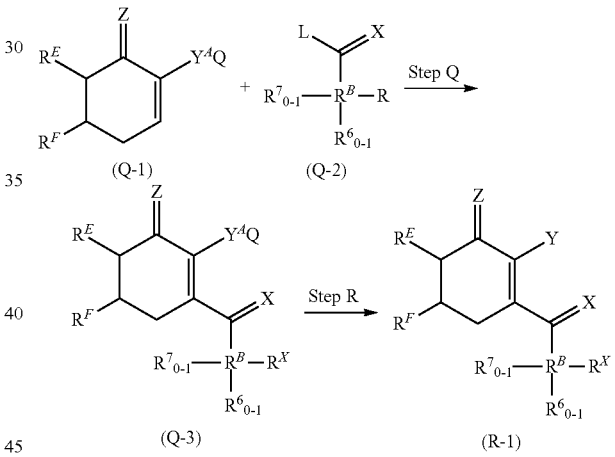

(wherein, R$^6$, R$^7$, R$^B$, R$^E$, R$^F$, X and Y are the same as above; L is a leaving group; Q is a protecting group; Y$^A$ is O, S or NH$_2$; R$^X$ is the formula: —Z$^1$—Z$^2$—Z$^3$—R$^1$ (wherein, Z$^1$, Z$^2$, Z$^3$ and R$^1$ are the same as above))

Process Q

This process is for reacting compound of the formula (Q-1) with compound of the formula (Q-2) to give compound of the formula (Q-3).

Examples of compound of the formula (Q-1) include cyclohexenon which can be prepared by the known method (Tetrahedron, 1997, 53, p 8963).

Examples of compound of the formula (Q-2) include furan-2-carboxylic acid halides which can be prepared by the known method (Zhurnal Organicheskoi Khimii, Vol. 22, No. 8, pp. 1749-1756).

Examples of reaction solvent include aethers (e.g., tetrahydrofran, dioxane) and N,N-dimethylformamide, which can be used by itself or in combination.

The process can be conducted in the presence of a base (e.g., lithium bistri methylsililamide) or an acid (e.g., ZnCl$_2$, TiCl$_4$, HCl).

Process R

This process is for deprotecting compound of the formula (Q-3) in the presence of an acid to give compound of the formula (R-1).

Examples of acid include hydrochloric acid and sulfuric acid.

Examples of reaction solvent include aethers (e.g., tetrahydrofran, dioxane), alcohols (e.g., methanol, ethanol), which can be used by itself or in combination.

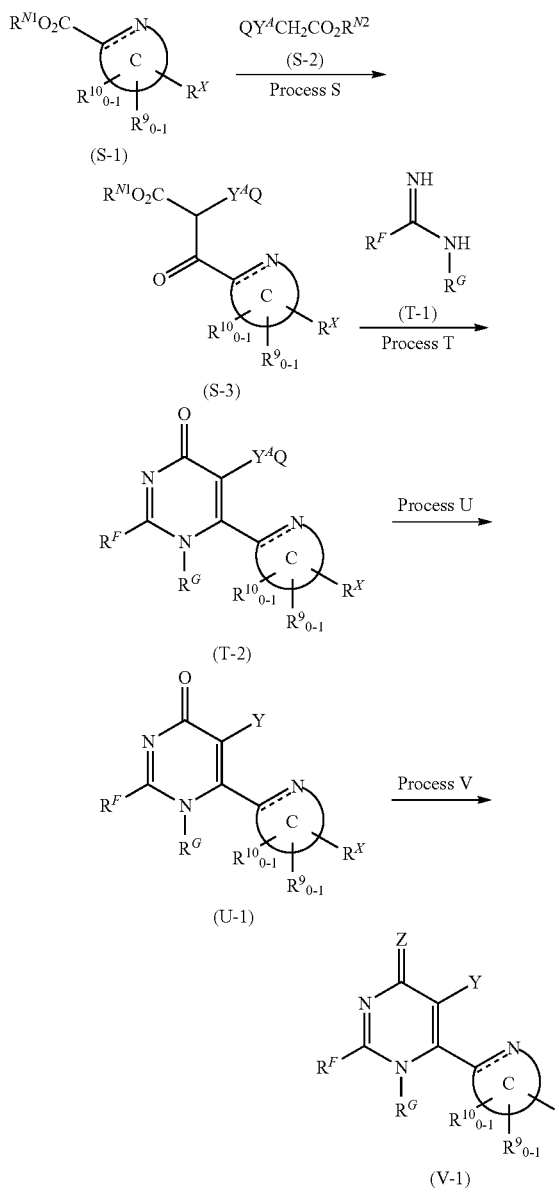

(wherein, $R^9$, $R^{10}$, $R^F$, $R^G$, $R^X$; and Y are the same as above; $Y^A$ is O, S or $NH_2$; $R^{N1}$ and $R^{N2}$ are alkyl; Q is a protecting group)

Process S

This process is for reacting compound of the formula (S-1) with compound of the formula (S-2) to give compound of the formula (S-3).

Examples of compound of the formula (S-1) include pyridine carboxylic acid which can be prepared from picoline by oxidation with selenium dioxide and esterification.

Examples of compound of the formula (S-2) include protected 2-hydroxyacetic acid esters.

Examples of reaction solvent include aether (e.g., tetrahydrofran, dioxane), N,N-dimethylformamide, which can be used by itself or in combination.

The process can be conducted in the presence of a base (e.g., lithium bistri methylsililamide).

Process T

This process is for reacting compound the formula (S-3) with compound of the formula (T-1) to give compound of the formula (T-2).

Examples of compound of the formula (T-1) include amidines.

Examples of reaction solvent include alcohol (e.g., methanol, ethanol).

The process can be conducted in the presence of a base (e.g., sodium methoxide).

Process U

This process is for deprotecting compound of the formula (T-2) to give compound of the formula (U-1).

Examples of reaction solvent include alcohol (e.g., methanol, ethanol), aether (e.g., tetrahydrofran, dioxane), which can be used by itself or in combination.

The process can be conducted in the presence of an acid (e.g., hydrochloric acid, p-toluene sulfonic acid) or by adding hydrogen.

Process V

This process is for reacting compound of the formula (U-1) with a sulfurizing reagent or an amine to give compound of the formula (V-1).

Examples of sulfurizing reagent include Lawson's reagent and phosphorus pentasulfide.

Examples of amine include methylamine and morpholine.

Examples of reaction solvent include aromatichydrocarbon (e.g., toluene, xylene), aether (e.g., tetrahydrofran, dioxane) which can be used by itself or in combination.

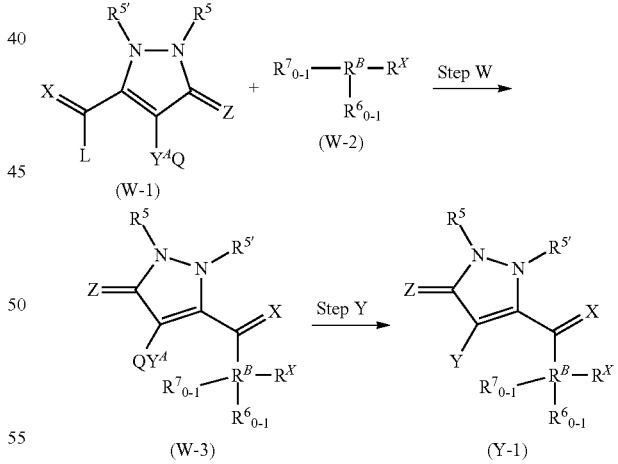

(wherein, $R^5$, $R^{5'}$, $R^6$, $R^7$, $R^B$, $R^X$, L, Q, X, Y and $Y^A$ are the same as above)

Process W

This process is for reacting compound of the formula (W-1) with compound of the formula (W-2) to give compound of the formula (W-3).

Examples of compound of the formula (W-1) include pyrazolones.

Examples of compound of the formula (W-2) include those exemplified as compound of the formula (Q-2).

Examples of reaction solvent include aether (e.g., tetrahydrofran, dioxane), N,N-dimethylformamide, which can be used by itself or in combination.

The process can be conducted in the presence of a base (e.g., n-butyllithium).

Process X

This process is for deprotecting compound of the formula (W-3) to give compound the formula (Y-1).

Examples of reaction solvent include alcohol (e.g., methanol, ethanol), aether (e.g., tetrahydrofran, dioxane), which can be used by itself or in combination.

The process can be conducted in the presence of an acid (e.g., hydrochloric acid, O-toluenesulfonic acid or by adding hydrogen.

The present invention compounds can also be prepared according to the general organic synthesis method of heterocyclyl compounds descrived in literatures e.g., (1) Alan R. Katriszly et al., Comprehensive Heterocyclic Chemistry, (2) Alan R. Katriszly et al., Comprehensive Heterocyclic Chemistry II, (3) RODD'S CHEMISTRY OF CARBON COMPOUNDS VOLUME IV HETEROCYCLIC COMPOUNDS.

Introduction of a group of the formula: $-Z^1-Z^2-Z^3-R^1$ (wherein, $Z^1$, $Z^2$, $Z^3$ and $R^1$ are the same as above) may be conducted before or after each of the above processes, according to the method of WO 00/39086.

Examples of compound of the formula (AA-1) include Boc-protected pyrrolidine 2-one which can be prepared by the known method (Tetrahedron Lett., 36, 8949-8952 (1995)).

The process can be conducted as well as Process H.

Process AB

This process is for cyclizing compound of the formula (AA-3), optionally followed by Retroclaisen Reaction, to give compound of the formula (AB). The cyclization can be conducted as well as Process B.

The Retroclaisen Reaction can be conducted by treating with a base such as LiOH in a solvent such as tetrahydrofran.

Process AC

This process is for reacting compound of the formula (AB) with compound of the formula: $R^5$-L (wherein L is a leaving group) in the presence of a base to give compound of the formula (AC). The process can be conducted according to the conventional N-alkylation. For example, compound of the formula (AB) is reacted with bromoethane etc. in the presence of a base such as potassium bis(trimethylsilil)amide in a solvent such as tetrahydrofran.

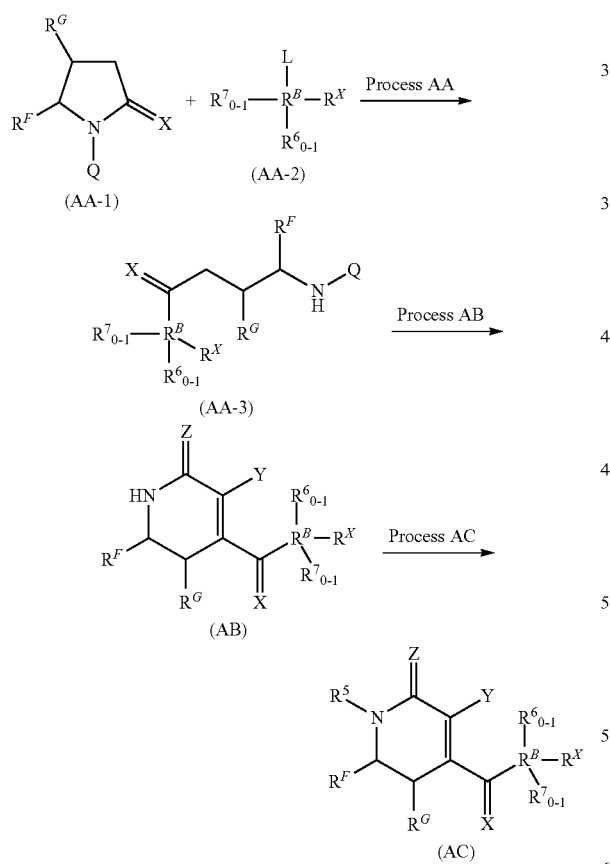

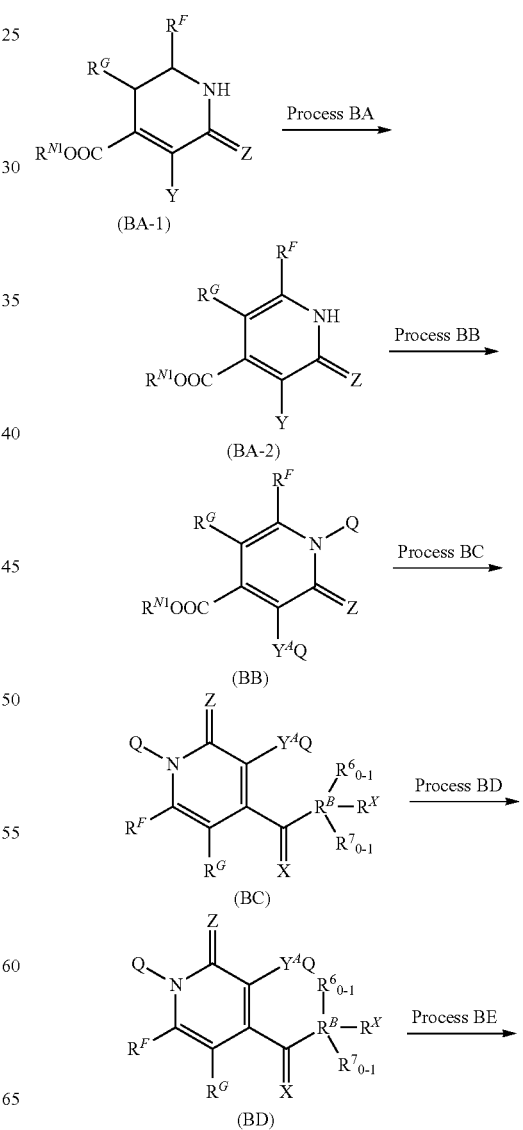

(wherein, $R^6$, $R^7$, $R^B$, $R^F$, $R^G$, $R^X$, L, Q, X, Y and Z are the same as above)

Process AA

This process is for reacting compound of the formula (AA-1) with compound of the formula (AA-2) in the presence of a base to give compound of the formula (AA-3).

-continued

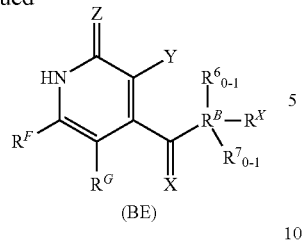

(BE)

(wherein, $R^6$, $R^7$, $R^B$, $R^F$, $R^G$, $R^{N1}$, $R^X$, L, Q, X, Y, $Y^A$ and Z are the same as above)

Process BA

This process is for dehydrating compound of the formula (BA-1) to give compound of the formula (BA-2).

Examples of compound of the formula (BA-1) include 5-hydroxy-6-oxo-1,2,3,6-tetrahydropyridine-4-carboxylic acid ethyl ester, which can be prepared by the known method (Org. Prep. Proced. Int., 29, 330-335 (1997)).

The process can be conducted by treating compound of the formula (BA-1) with a catalytic amount of paradium carbon in a solvent such as oxylene.

Process BB

This process is for protecting a reactive substituent of compound of the formula (BA-2) to give compound of the formula (BB).

Examples of a protecting group include alkyl and alkoxyalkyl, which can be introduced by the conventional protection reaction (Protective Groups in Organic Synthesis, Theodora W. Greene).

Process BC

This process is for converting compound of the formula (BB) into compound of the formula (BC), according to the method of Process H and Process AA.

Process BD and BE

These processes are for deprotecting compound of the formula (BC) to give compound of the formula (BD), followed by deprotection to give compound the formula (BE). Depending on the reaction conditions, both deprotections can be conducted at the same time. These deprotections can be conducted according to the conventional method (Protective Groups in Organic Synthesis, Theodora W. Greene).

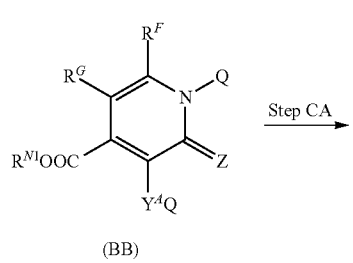

(BB)

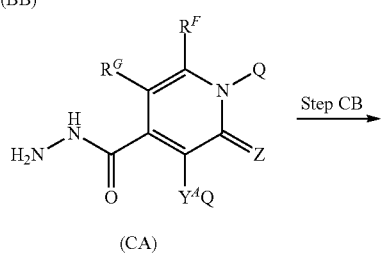

(CA)

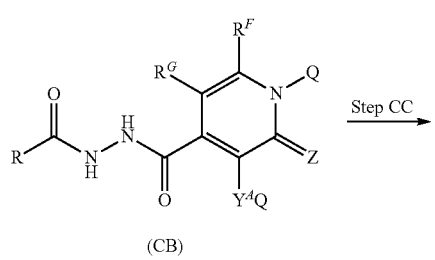

(CB)

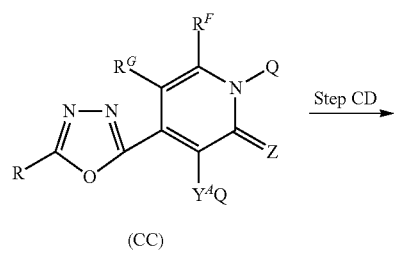

(CC)

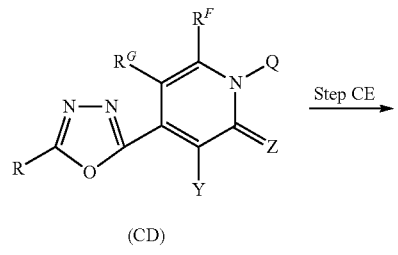

(CD)

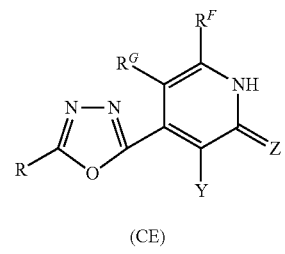

(CE)

(wherein, R, $R^F$, $R^G$, $R^{N1}$, L, Q, X, Y, $Y^A$ and Z are the same as above)

Process CA

This process is for reacting compound of the formula (BB) with hydrazine to give compound of the formula (CA). The process can be conducted by reaction with hydrazine in a solvent such as ethanol.

Process CB

This process is for converting compound of the formula (CA) into compound of the formula (CB) according to the methods of Process N and Process P.

Process CC

This process is for converting compound of the formula (CB) into compound of the formula (CC) according to the method of Process M.

Process CD and CE

This process is for deprotecting compounds of the formula (CC) and (CD) according to the method of Process CD and CE.

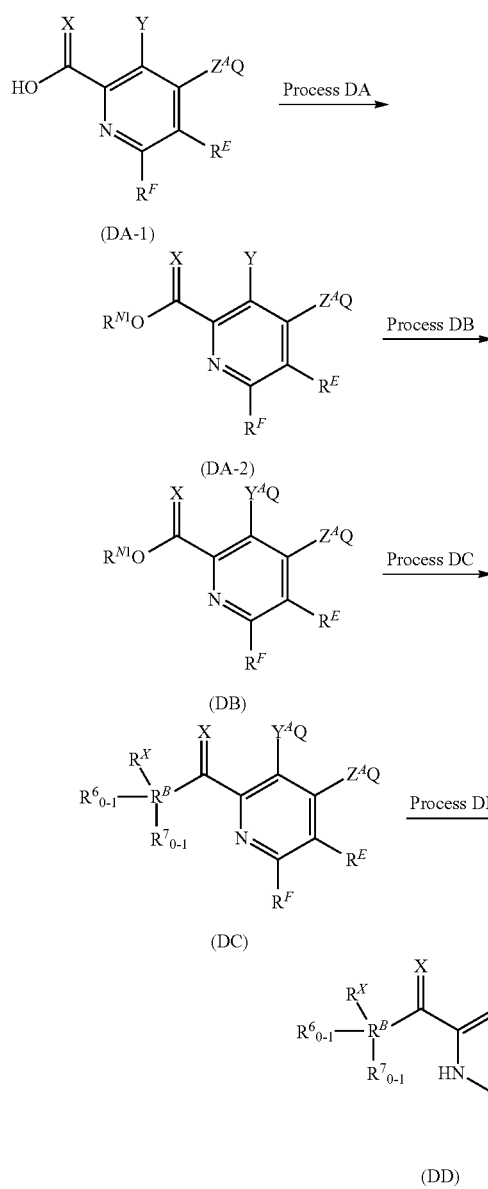

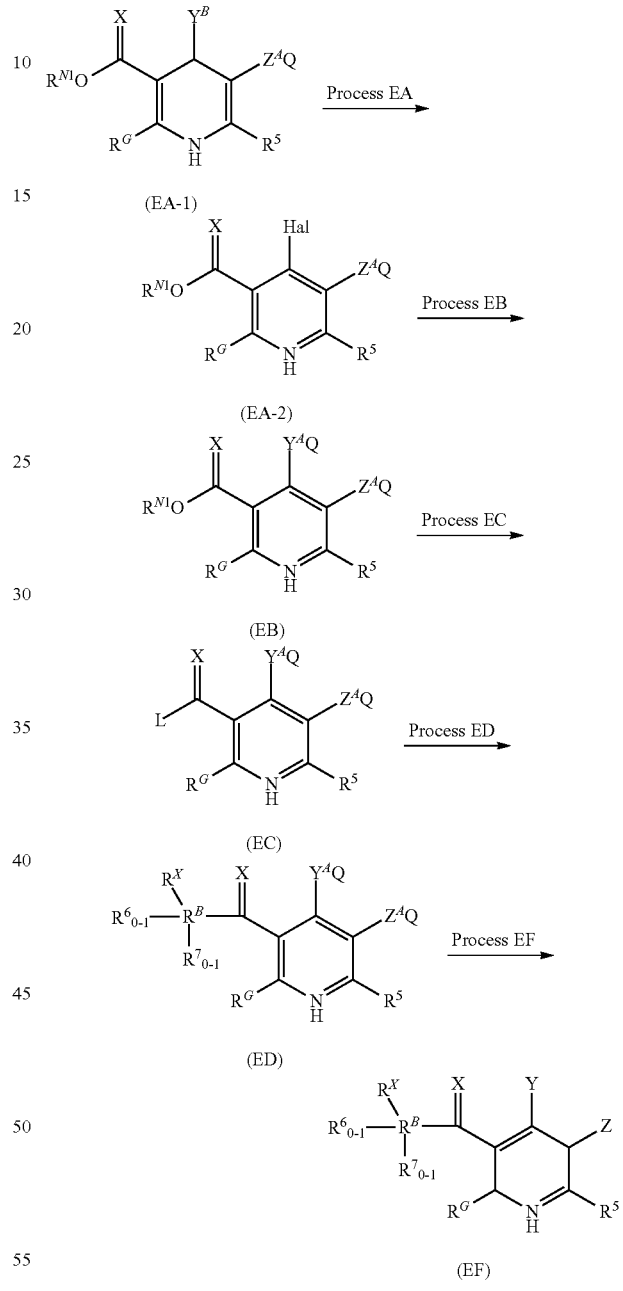

(wherein, $R^6$, 13.7, $R^B$, $R^E$, $R^F$, $R^{N1}$, $R^X$, Q, X, Y, $Y^A$ and Z are the same as above, $Z^A$ is O, S or $NH_2$)

Process DA

This process is for esterifying compound of the formula (DA-1) to give compound of the formula (DA-2).

Examples of compound of the formula (DA-1) include 3-hydroxy-4-methoxypyridine-2-carboxylic acid which can be obtained by the known method (Tetrahedron, 54, 12745-12774 (1998)). The esterification can be conducted by the conventional method.

Process DB

This process is for protecting a reactive substituent of compound of the formula (DA-2) to give compound of the formula (DB). The protecting group is preferably alkyl. The protection can be conducted according to the conventional method (Protective Groups in Organic Synthesis, Theodora W. Greene).

Process DC

This process is for converting compound of the formula (DB) into compound of the formula (DC) according to Process BC:

Process DD

This process is for deprotecting compound of the formula (DC) to give compound of the formula (DD), according to the conventional method (Protective Groups in Organic Synthesis, Theodora W. Greene).

(wherein, $R^5$, $R^6$, $R^7$, $R^B$, $R^G$, $R^{N1}$, $R^X$, Q, L, X, Y, $Y^A$, Z and $Z^A$ are the same as above, Hal is halogen)

Process EA

This process is for halogenating compound of the formula (EA-1) to give compound of the formula (EA-2). Examples of compound of the formula (EA-1) include 5-methoxy-6-methyl-4-oxo-1,4-dihydro-pyridine-3-carboxylic acid methyl ester which can be obtained by the known method (WO92/02523). The halogenation can be conventionally conducted, for example, compound of the formula (EA-1) is heated in phosphorus oxychloride.

Process EB

This process is for substituting halogen of compound of the formula (EA-2) with a group of $Y^4Q$ to give compound of the formula (EB). Compound of the formula (EA-2) is reacted with sodium methoxide in a solvent such as methanol.

Process EC

This process is for substituting $OR^{N1}$ of compound of the formula (EB) with a leaving group L to give compound of the formula (EC).

Process ED

This process is for converting compound of the formula (EC) into compound of the formula (ED) according to Process BC.

Process EF

This process is for deprotecting compound of the formula (ED) to give compound of the formula (EF) according to the conventional method (Protective Groups in Organic Synthesis, Theodora W. Greene).

Use of the present invention compounds is explained below.

The present invention compound is useful for preparing a pharmaceutical composition such as antivirus agent. The present invention compound, possessing a remarkable inhibitory activity on integrase of virus, is expected to exhibit a preventing or treating effect for diseases caused by viruses which grow at least via production of integrase in infected animal cells, thus being useful as an integrase inhibitor against a retro-virus (e.g., HIV-1, HIV-2, HTLV-1, SIV, FIV) as well as an anti-HIV agent.

Further, the present invention compound can be used in combination with other anti-HIV agents having a different action of mechanisum such as a reverse transcriptase inhibitor and/or a protease inhibitor. Since any of the integrase inhibitors have not been on sale, a combination therapy of the present invention compound with a reverse transcriptase inhibitor and/or a protease inhibitor is very useful.

Further, the present invention compound can be used as a combined agent for enhancing the anti-HIV activity of other HIV agents, as shown in the cocktail therapy.

Further, the present invention compound can be used in gene therapy in order to prevent a retrovirus vector derived from HIV or MLV from spreading over non-targeted tissues. In particular, in a case that cells infected with a vector in vitro is put back to a body, administration of the present invention compound in advance can prevent an unnecessary infection in the body.

The compounds of the present invention can be administered orally or parenterally. For oral administration, the compounds of the present invention can be used in any form of usual formulations, for example, solid formulations such as tablets, powders, granules, capsules; aqueous formulations; oleaginous suspensions; solutions such as syrup or elixir. For parenteral administration, the compounds of the present invention can be used as an aqueous or oleaginous suspension injection, or nose drops. In the preparation of such formulations, conventional excipients, binding agents, lubricants, aqueous solvents, oleaginous solvents, emulsifying agents, suspending agents, preservatives, stabilizers, and the like can be optionally used. Preferred is an oral agent as an HIV-agent.

A formulation according to the present invention may be manufactured by combining (for example, admixing) a curatively effective amount of a compound of the present invention with a pharmaceutically acceptable carrier or diluent. The formulation of the present invention may be manufactured with well-known and easily available ingredients in accordance with a known method.

In the case of manufacturing a pharmaceutical composition according to the present invention, an active ingredient is admixed or diluted with a carrier, or they are contained in a carrier in the form of capsule, sacheier, paper, or another container. In the case of functioning a carrier as a diluent, the carrier is a solid, semi-solid, or liquid material which functions as a medium. Accordingly, a formulation according to the present invention may be produced in the form of tablet, pill, powder medicine, intraoral medicine, elixir agent, suspending agent, emulsifier, dissolving agent, syrup agent, aerosol agent (solid in liquid medium), and ointment. Such a formulation may contain up to 10% of an active compound. It is preferred to formulate a compound of the present invention prior to administration.

Any suitable carrier well known to those skilled in the art may be used for the formulation. In such formulation, a carrier is in the form of solid, liquid, or a mixture of solid and liquid. For instance, a compound of the present invention is dissolved into 4% dextrose 0.5% sodium citrate aqueous solution so as to be 2 mg/ml concentration for intravenous injection. Solid formulation includes powder, tablet, and capsule. Solid carrier consists of one or more of material (s) for serving also as fragrant, lubricant, dissolving agent, suspension, binder, tablet disintegrator, capsule. A tablet for oral administration contains a suitable excipient such as calcium carbonate, sodium carbonate, lactose, calcium phosphate and the like together with a disintegrator such as corn starch, alginic acid and the like and/or a binder such as gelatin, acacia and the like, and a lubricant such as magnesium stearate, stearic acid, talc and the like.

In a powder medicine, a carrier is a finely pulverized solid which is blended with finely pulverized active ingredients. In a tablet, active ingredients are admixed with a carrier having required binding power in a suitable ratio, and it is solidified in a desired shape and size. Powder medicine and tablet contain about 1 to about 99% by weight of the active ingredients being novel compounds according to the present invention. Example of suitable solid carriers include magnesium carbonate, magnesium stearate, talc, sugar, lactose, pectin, dextrin, starch, gelatin, tragacanth gum, methyl cellulose, sodium carboxymethylcellulose, low-melting wax, and cocoa butter.

A liquid formulation includes suspending agent, emulsifier, syrup agent, and elixir agent. Active ingredients may be dissolved or suspended into a pharmaceutically acceptable carrier such as sterile water, a sterile organic solvent, a mixture thereof and the like. Active ingredients may be dissolved frequently into a suitable organic solvent such as propylene glycol aqueous solution. When finely pulverized active ingredients are dispersed into aqueous starch, sodium carboxylmethylcellulose solution, or suitable oil, the other compositions can be prepared.

Although an appropriate dosage of the compound of the present invention varies depending on the administration route, age, body weight, conditions of the patient, and kind of disease, in the case of oral administration, the daily dosage can be between approximately 0.05-3000 mg, preferably approximately 0.1-1000 mg, for an adult. The daily dosage can be administered in divisions. In the case of parenteral administration, the daily dosage for an adult can be between approximately 0.01-1000 mg, preferably approximately 0.05-500 mg.

Examples

The production method and physical data of the synthesized products are shown below. Reactions are usually carried out under nitrogen atmosphere, and reaction solvents are used as dried over molecular sieve and the like. Extracts are dried over sodium sulfate or magnesium sulfate and the like.

A Group Compounds

Compound A-7

4-[5-(4-Fluorobenzyl)furan-2-carbonyl]-3-hydroxyl-1-isopropyl-1,5-dihydropyrrole-2-one

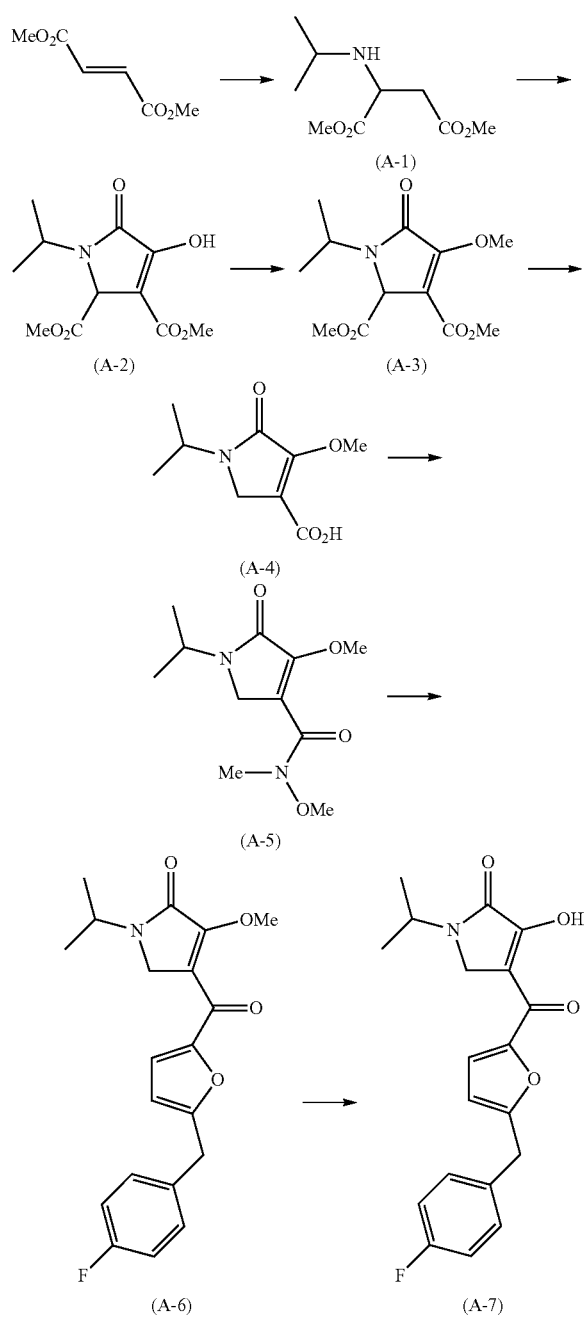

(A-1) Dimethyl fumarate (30 g, 0.21 mol) was dissolved in acetonitrile (200 ml) under heating and isopropylamine (25 g, 0.42 mol) was added thereto under ice cooling, then the mixture was stirred for 16 hours at room temperature. Evaporation of the solvent and the excess isopropylamine under reduced pressure gave dimethyl 2-isopropylaminosuccinate (42 g, yield: 100%). NMR (CDCl$_3$) δ: 1.01 (3H, d, J=6.0 Hz), 1.05 (3H, d, J=6.3 Hz), 2.67 (1H, t, J=9.9 Hz), 2.79 (1H, m), 3.69 (3H, s), 3.74 (3H, s), 3.68-3.75 (2H, m).

(A-2) According to the method of the reference (J. Org. Chem., 1968, 33, p 2051), the above-mentioned compound A-1 (42 g, 0.21 mol) was reacted with sodium methoxide (33 g, 0.6 mol) and dimethyl oxalate (25 g, 0.21 mol). After stirring for 16 hours at room temperature and further refluxing under heating for 2 hours, the solvent was evaporated. The dilute hydrochloric acid was added to the residue, then the precipitated crystal was filtered to give 4-hydroxylisopropyl-5-oxo-2,5-dihydro-1H-pyrrole-2,3-dicarboxylic acid dimethyl (33.6 g, yield: 65%).

NMR (CDCl$_3$) δ: 1.20 (3H, d, J=6.9 Hz), 1.32 (3H, d, J=6.9 Hz), 3.77 (3H, s), 3.85 (3H, s), 4.39 (1H, m), 4.78 (1H, s).

(A-3) To a suspension of the above-mentioned compound A-2 (10 g, 39 mmol) in diethyl ether (200 ml), a diethyl ether solution of diazomethane was added. After the reaction was stopped by adding acetic acid, the reaction mixture was washed and dried. The solvent was evaporated to give 1-isopropyl-4-methoxy-5-oxo-2,5-dihydro-1H-pyrrole-2,3-dicarboxylic acid dimethyl (10.2 g, yield: 97%).

NMR (CDCl$_3$) δ: 1.18 (3H, d, J=6.9 Hz), 1.31 (3H, d, J=6.9 Hz), 3.77 (3H, s), 3.78 (3H, s), 4.36 (3H, s), 4.30-4.40 (1H, m), 4.76 (1H, s).

(A-4) The above-mentioned compound A-3 (10.2 g, 38 mmol) was dissolved in methyl alcohol (50 ml) and was added thereto the aqueous sodium hydroxide solution (sodium hydroxide 8 g, water 50 ml). The reaction mixture was refluxed for 1 hour. After the solvent was evaporated, water (50 ml) was added to the residue. The solution was acidified with the concentrated hydrochloric acid and extracted with diethyl ether. The extract was washed and dried. The solvent was evaporated and the residue was Crystallized with diisopropylether to give 1-isopropyl-4-methoxy-5-oxo-2,5-dihydro-1H-pyrrole-3-carboxylic acid (3.9 g, yield: 52%).

NMR (CDCl$_3$) δ: 1.24 (6H, d, J=6.9 Hz), 3.97 (2H, s), 4.38 (3H, s), 4.40-4.50 (1H, m).

(A-5) The above-mentioned compound A-4 (1.6 g, 8.0 mmol) was dissolved in methylene chloride (30 ml) and to which was added 1-ethyl-3-(3-dimethylaminopropyl)carbodiimide (1.5 g, 9.8 mmol), N,O-dimethylhydroxylamine hydrochloride (940 mg, 9.6 mmol), hydroxybenzimidazole (110 mg, 0.8 mmol) and triethylamine (1.0 g, 9.9 mmol). The mixture was stirred for 2 hours at room temperature. The solution was dilute d with chloroform, washed and dried. The solvent was evaporated under reduced pressure and the residue was purified with silica gel column chromatography (ethyl acetate) to give 1-isopropyl-4-methoxy-5-oxo-2,dihydro-1H-pyrrole-3-carboxylic acid methoxymethylamide (1.5 g, yield: 77%).

NMR (CDCl$_3$) δ: 1.22 (6H, d, J=6.9 Hz), 3.30 (3H, s), 3.71 (3H, s), 3.98 (2H, s), 4.04 (3H, s), 4.40-4.50 (1H, m).

(A-6) Aluminum chloride (1.36 g, 10 mmol) was suspended in tetrahydrofuran (20 ml), to which was added sodium borohydride (650 mg, 17 mmol) under ice cooling. After the mixture was stirred for 10 minutes, (5-bromofuran-2-yl)-(4-fluorophenyl)metanone (900 mg, 3.4 mmol) was added to the mixture and refluxed for 30 minutes under heating. After cooling, the reaction solution was poured into the ice water and extracted with diethyl ether. The extract was washed, dried, and evaporated to give 2-bromo-5-(4-fluorobenzyl)

furan. This residue was dissolved in tetrahydrofuran, to which was added n-butyllithium (2.5 ml, 4 mmol) at −78° C. 10 Minutes later, the compound A-5 (820 mg, 3.4 mmol) was added to the mixture and stirred for 1 hour. Water was added to the solution and the mixture was extracted with ethyl acetate. After the ethyl acetate solution was washed and dried, the solvent was evaporated under reduced pressure and the residue was purified with silica gel column chromatography (n-hexane:ethyl acetate=2:1) to give 4-[5-(4-fluorobenzyl)furan-2-carbonyl]-1-isopropyl-3-methoxy-1,5-dihydropyrrole-2-one (80 mg, yield: 7%).

NMR (CDCl$_3$) δ: 1.23 (6H, d, J=6.9 Hz), 4.05 (2H, s), 4.08 (2H, s), 4.15 (3H, s), 4.40-4.50 (1H, m), 6.17 (1H, d, J=3.6 Hz), 6.90-7.06 (2H, m), 7.20-7.26 (2H, m), 7.35 (1H, d, J=3.6 Hz).

(A-7) The above-mentioned compound A-6 (80 mg, 0.22 mmol) was dissolved in acetonitri (5 ml), to which was added chlorotrimethylsilane (200 mg, 1.8 mmol) and sodium iodide (270 mg, 1.8 mmol), and the mixture was stirred for 30 minutes at room temperature. Sodium sulfite was added to the solution, which was acidified with the 1 N hydrochloric acid aqueous solution and extracted with ethyl acetate. The extract was washed, dried and was evaporated and the residue was Crystallized with diethylether to give 4-[5-(4-fluorobenzyl)furan-2-carbonyl]-3-hydroxy-1-isopropyl-1,5-dihydropyrrole-2-one (50 mg, yield: 68%).

Melting point: 155-157° C.

Elementary analysis as $C_{19}H_{18}FNO_4 \cdot 0.2H_2O$

Calcd. (%): C, 65.77; H, 5.35; N, 4.04; F, 5.48.

Found (%): C, 65.72; H, 5.27; N, 3.97; F, 5.26.

NMR (CDCl$_3$) δ: 1.23 (6H, d, J=6.9 Hz), 4.08 (2H, s), 4.13 (2H, s), 4.50-4.60 (1H, m), 6.33 (1H, d, J=3.6 Hz), 7.02-7.10 (2H, m), 7.20-7.26 (2H, m), 7.33 (1H, d, J=3.6 Hz).

Compound A-12

4-[5-(4-Fluorobenzyl)furan-2-carbonyl]-3-hydroxy-1-methyl-1,5-dihydropyrrole-2-one

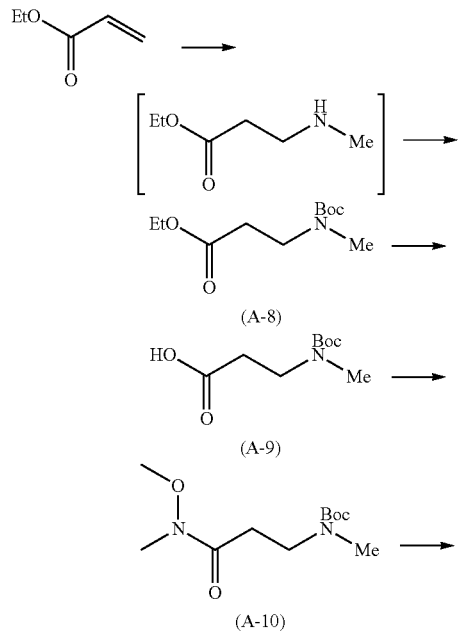

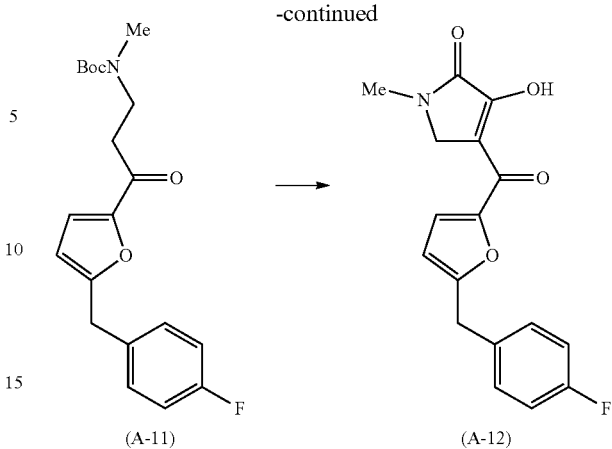

(A-8) Acrylic acid ethyl ester (2.0 g, 20 mmol) was dissolved in ethanol (20 ml), to which was added dropwise methylamine (20 mmol, 20% ethanol solution) under ice cooling. Di-tert-butyldicarbonate (4.4 g, 20 mmol) was added thereto and the mixture was warmed to room temperature. The solvent was evaporated under reduced pressure and the residue was purified with silica gel column chromatography (n-hexane:ethyl acetate=5:1-3:1) to give 3-(tert-butoxycarbonylmethylamino)propionic acid ethyl ester (3.1 g, yield: 66%).

NMR (CDCl$_3$) δ: 1.26 (3H, t, J=7.2 Hz), 1.46 (9H, s), 2.54 (2H, t, J=7.0 Hz), 2.87 (3H, s), 3.50 (2H, t, J=7.0 Hz), 4.14 (2H, q, J=7.2 Hz).

(A-9) 1N Lithium hydroxide aqueous solution (17.5 ml) was added to the above-mentioned compound A-8 (4.05 g, 17.5 mmol) in methyl alcohol (35 ml) and the mixture was stirred for 5 hours. Methyl alcohol was evaporated under reduced pressure and the solution was acidified with citric acid and extracted with ethyl acetate. The extract was washed, dried and was evaporated to give 3-(tert-butoxycarbonylmethylamino)propionic acid (3.57 g, yield: 100%).

NMR (CD$_3$OD) δ: 1.45 (9H, s), 2.51 (2H, t, J=7.0 Hz), 2.87 (3H, s), 3.50 (2H, d, J=7.0 Hz).

(A-10) The above-mentioned compound A-9 (3.82 g, 18.8 mmol) was dissolved in a chloroform (20 ml)-acetonitrile (10 ml) solution and to which was added O,N-dimethylhydroxylamine hydrochloride (2.02 g, 20.7 mmol), 1-hydroxybenzotriazole (254 mg, 1.88 mmol), 1-ethyl-3-(3-dimethylaminopropyl)carbodiimide (3.50 g, 22.6 mmol) and triethylamine (2.09 g, 20.7 mmol) and the mixture was stirred for 3 hours. Water was added to the solution and extracted with chloroform. The extract was washed, dried, and evaporated under reduced pressure and the residue was purified with silica gel column chromatography (n-hexane:ethyl acetate=1:1-2:1) to give [2-(methoxymethylcarbamoyl)ethyl]methylcarbamic acid tert-butyl ester (3.94 g, yield: 85%).

NMR (CDCl$_3$) δ: 1.46 (9H, s), 2.67 (2H, t, J=7.0 Hz), 2.89 (3H, s), 3.19 (3H, s), 3.52 (2H, t, J=7.0 Hz), 3.69 (3H, s).

(A-11) N-butyllithium (5 mmol) was added dropwise to 2-bromo-5-(4-fluorobenzyl)furan (1.30 g, 5 mmol) in THF (10 ml) at −78° C. The above-mentioned compound A-10 (1.23 g, 5 mmol) in THF (5 ml) was added to the mixture and stirred for 30 minutes, then an ammonium chloride aqueous solution was added to the solution and the solution was extracted with ethyl acetate. The extract was washed, dried, and evaporated under reduced pressure and the residue was purified with silica gel column chromatography (n-hexane:

ethyl acetate=3:1-2:1) to give {3-[5-(4-fluorobenzyl)furan-2-yl]-3-oxopropyl}methylcarbamic acid tert-butyl ester (1.02 g, yield: 56%).

NMR (CDCl₃) δ: 1.42 (9H, s), 2.87 (3H, s), 3.00 (2H, t, J=7.0 Hz), 3.58 (2H, t, J=7.0 Hz), 4.01 (2H, s), 6.10 (1H, d, J=3.7 Hz), 6.98-7.05 (2H, m), 7.13 (1H, d, J=4.0 Hz), 7.19-7.26 (2H, m).

The following compound was synthesized by the same method as above using 3-(4-fluorobenzyl)-bromobenzene which was synthesized according to the method of the reference (Journal of Medicinal Chemistry, 2000, 43, 26, p 4923).

{3-[3-(4-Fluorobenzyl)phenyl]-3-oxopropyl}methylcarbamic acid tert-butyl ester

NMR (CDCl₃) δ: 1.43 (9H, s), 2.89 (3H, s), 3.18 (2H, t, J=6.7 Hz), 3.61 (2H, t, J=6.7 Hz), 4.01 (2H, s), 6.95-7.01 (2H, m), 7.11-7.16 (2H, m), 7.37-7.40 (2H, m), 7.81-7.82 (2H, m).

(A-12) A 4N hydrochloric acid dioxane solution (5 ml) was added to the above-mentioned compound A-11 (1.00 g, 2.77 mmol) and the mixture was stirred for 30 minutes. The excess hydrochloric acid and solvent were evaporated under reduced pressure, to which was added oxalic acid diethyl (485 mg, 3.32 mmol) in ethanol (5 ml) After sodium ethoxide (8.31 mmol, 20% ethanol solution) was added under ice cooling, the solution was warmed to room temperature and stirred for 1 hour. Water was added to the solution and extracted with ethyl acetate. The extract was washed, dried and evaporated. The precipitated crystal was washed with methyl alcohol and dried under reduced pressure to give 4-[5-(4-fluorobenzyl)furan-2-carbonyl]-3-hydroxyl-methyl-1,5-dihydropyrrole-2-one (641 mg, yield: 73%).

Melting point: 141-143° C.
Elementary analysis as $C_{17}H_{14}FNO_4 \cdot 0.1H_2O$
Calcd. (%): C, 64.39; H, 4.51; N, 4.42; F, 5.99.
Found (%): C, 64.24; H, 4.29; N, 4.43; F, 5.92.
NMR (CDCl₃) δ: 3.14 (3H, s), 4.07 (2H, s), 4.19 (2H, s), 6.29 (1H, d, J=3.7 Hz), 7.03-7.09 (2H, m), 7.20-7.26 (2H, m), 7.32 (1H, d, J=3.7 Hz).

The following compound was synthesized by the above-mentioned method.

(A-12-a) 4-[3-(4-Fluorobenzyl)benzoyl]-3-hydroxy-1-methyl-1,5-dihydropyrrole-2-one Melting point: 135-137° C.
Elementary analysis as $C_{19}H_{16}FNO_3 \cdot 0.2H_2O$
Calcd. (%): C, 69.38; H, 5.03; N, 4.26; F, 5.78.
Found (%): C, 69.53; H, 4.83; N, 4.21; F, 5.61.
NMR (CDCl₃) δ: 3.16 (3H, s), 4.04 (2H, s), 4.23 (2H, s), 6.99-7.04 (2H, m), 7.13-7.18 (2H, m), 7.42-7.44 (2H, m), 7.56 (1H, s), 7.62-7.65 (1H, m).

Compound A-17

1-Cyclopropyl-4-[5-(4-fluorobenzyl)furan-2-carbonyl]-3-hydroxy-1,5-dihydropyrrole-2-one

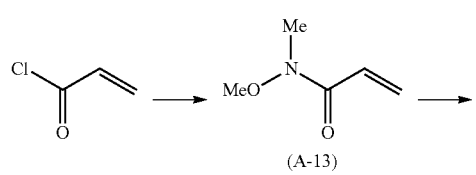

(A-13)

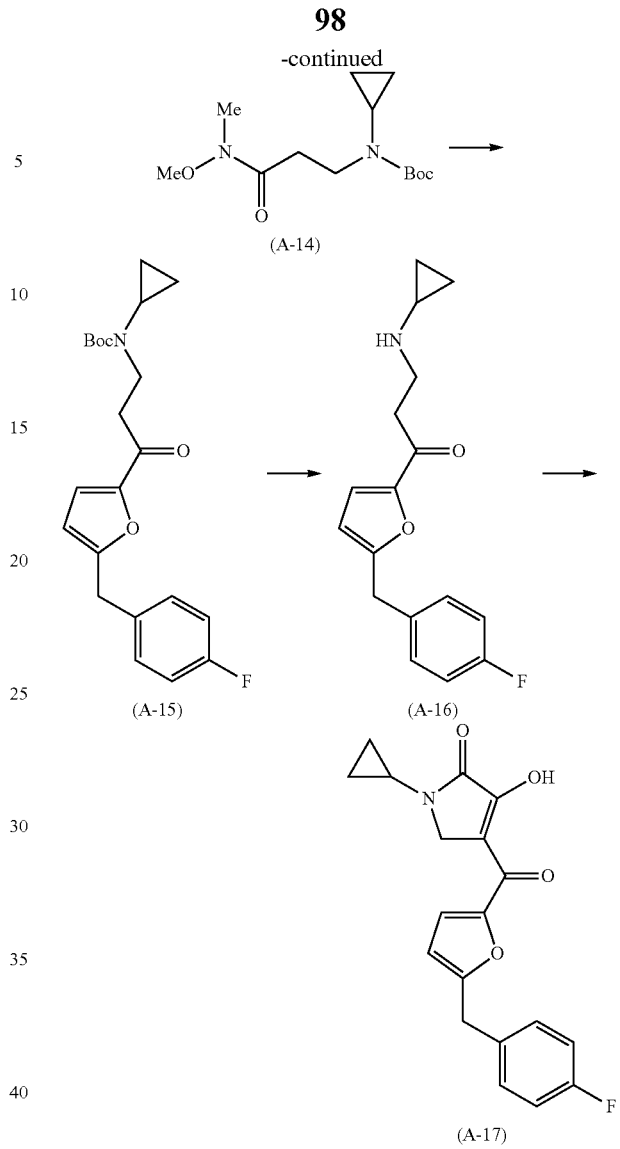

(A-13) Sodium hydrogen carbonate (54 g, 0.64 mol) was added to N,O-dimethylhydroxylamine hydrochloride (32 g, 0.32 mol) in methylene chloride (1 L), and the mixture was stirred for 30 minutes at room temperature. Acryloyl chloride (30 g, 0.32 mol) in methylene chloride was added dropwise to the solution under ice cooling and stirred for 1 hour at room temperature. The solution was dried, filtered and evaporated to give N-methoxy-N-methylacrylamide (34 g, yield: 92%).

NMR (CDCl₃) δ: 3.27 (3H, s), 3.72 (3H, s), 5.75 (1H, dd, J=10.2, 1.8 Hz), 6.43 (1H, dd, J=17.1, 1.8 Hz), 6.73 (1H, dd, J=17.1, 10.2 Hz).

(A-14) The above-mentioned compound A-13 (2.0 g, 17.4 mmol) and cyclopropylamine (1.0 g, 17.5 mmol) were dissolved in ethanol (20 ml), and the mixture was refluxed for 1 hour under heating. After di-tert-butyldicarbonate (4.5 g, 20 mmol) was added to the solution under ice cooling, and the mixture was stirred for 30 minutes at room temperature. The solvent was evaporated under reduced pressure and the residue was purified with silica gel column chromatography (n-hexane:ethyl acetate=1:2) to give cyclopropyl[2-(methoxymethylcarbamoyl)ethyl]carbamic acid tert-butyl ester (2.9 g, yield: 60%).

NMR (CDCl$_3$) δ: 0.58-0.65 (2H, m), 0.70-0.78 (2H, m), 1.46 (9H, s), 2.50-2.56 (1H, m), 2.68 (2H, t, J=7.4 Hz), 3.18 (3H, s), 3.52 (2H, t, J=7.4 Hz), 3.70 (3H, s).

The following compounds were synthesized by the above-mentioned method.

Ethyl[2-(methoxymethylcarbamoyl)ethyl]carbamic acid tert-butyl ester

NMR (CDCl$_3$) δ: 1.09 (3H, t, J=7.0 Hz), 1.46 (9H, s), 2.68 (2H, t, J=6.8 Hz), 3.18 (3H, s), 3.26 (2H, q, J=7.0 Hz), 3.48 (2H, t, J=6.8 Hz), 3.69 (3H, s).

[2-(Methoxymethylcarbamoyl)ethyl]propylcarbamic acid tert-butyl ester

NMR (CDCl$_3$) δ: 0.87 (3H, t, J=7.5 Hz), 1.45-1.59 (2H, m), 1.46 (9H, s), 2.69 (2H, s), 3.14-3.20 (2H, m), 3.18 (3H, s), 3.49 (2H, t, J=7.1 Hz), 3.69 (3H, s).

Butyl[2-(methoxymethylcarbamoyl)ethyl]carbamic acid tert-butyl ester

NMR (CDCl$_3$) δ: 0.92 (3H, t, J=7.4 Hz), 1.23-1.34 (2H, m), 1.44-1.53 (2H, m), 1.46 (9H, s), 2.69 (2H, s), 3.18 (3H, s), 3.20 (2H, t, J=7.5 Hz), 3.48 (2H, t, J=7.1 Hz), 3.69 (3H, s).

(2-Methoxyethyl)[2-(methoxymethylcarbamoyl)ethyl]carbamic acid tert-butyl ester

NMR (CDCl$_3$) δ: 1.46 (9H, s), 2.71 (2H, brs), 3.18 (3H, s), 3.34 (3H, s), 3.42 (2H, brs), 3.45 (2H, brs), 3.55 (2H, t, J=6.7 Hz), 3.69 (3H, s).

(1-Ethylpropyl)[2-(methoxymethylcarbamoyl)ethyl]carbamic acid tert-butyl ester

NMR (CDCl$_3$) δ: 0.85 (6H, t, J=7.5 Hz), 1.46 (9H, s), 2.65-2.80 (2H, m), 3.18 (3H, s), 3.25-3.40 (2H, m), 3.63 (0.5H, brs), 3.69 (3H, s), 3.88 (0.5H, brs).

(A-15) N-butyllithium (1.55M solution, 3.3 ml, 5.1 mmol) was added to 2-bromo-5-(4-fluorobenzyl)furan (1.3 g, 5.1 mmol) in tetrahydrofuran (10 ml) at −78° C. After the mixture was stirred for 5 minutes, the compound A-14 (1.36 g, 5 mmol) was added and stirred for 30 minutes. A saturated ammonium chloride aqueous solution was added to the solution and was extracted with ethyl acetate. The extract was washed, dried, and evaporated under reduced pressure, then the residue was purified with silica gel column chromatography (ethyl acetate:n-hexane=4:1) to give cyclopropyl{3-[5-(4-fluorobenzyl)furan-2-yl]-3-oxopropyl}carbamic acid tert-butyl ester (1.12 g, yield: 58%).

NMR (CDCl$_3$) δ: 0.55-0.62 (2H, m), 0.66-0.7 (2H, m), 1.44 (9H, s), 2.45-2.52 (1H, m), 3.00 (2H, t, J=7.1 Hz), 3.60 (2H, t, J=7.1 Hz), 4.01 (2H, s), 6.10 (1H, d, J=3.6 Hz), 6.96-7.05 (2H, m), 7.14 (1H, d, J=3.6 Hz), 7.16-7.23 (2H, m).

The following compounds were synthesized by the above-mentioned method.

Ethyl{3-[5-(4-fluorobenzyl)furan-2-yl]-3-oxopropyl}carbamic acid tert-butyl ester NMR (CDCl$_3$) δ: 1.08 (3H, t, J=7.1 Hz), 1.43 (9H, s), 3.01 (2H, t, J=6.8 Hz), 3.24 (2H, q, J=7.1 hz), 3.54 (2H, t, J=6.8 Hz), 4.01 (2H, s), 6.10 (1H, d, J=3.6 Hz), 7.00-7.04 (2H, m), 7.14 (1H, s), 7.18-7.24 (2H, m).

{3-[5-(4-Fluorobenzyl)furan-2-yl]-3-oxopropyl}propylcarbamic acid tert-butyl ester NMR (CDCl$_3$) δ: 0.86 (3H, t, J=7.4 Hz), 1.42-1.58 (2H, m), 1.43 (9H, s), 3.01 (2H, t, J=6.9 Hz), 3.14 (2H, t, J=7.4 Hz), 3.54 (2H, t, J=6.9 Hz), 4.01 (3H, s), 6.10 (1H, d, J=3.3 Hz), 6.97-7.04 (2H, m), 7.14 (1H, s), 7.18-7.24 (2H, m).

Butyl{3-[5-(4-fluorobenzyl)furan-2-yl]-3-oxopropyl}carbamic acid tert-butyl ester NMR (CDCl$_3$) δ: 0.91 (3H, t, J=7.4 Hz), 1.21-1.35 (2H, m), 1.42-1.52 (2H, m), 1.43 (9H, s), 3.01 (2H, t, J=7.0 Hz), 3.18 (2H, t, J=7.5 Hz), 3.54 (2H, t, J=7.0 Hz), 4.01 (2H, s), 6.10 (1H, d, J=3.3 Hz), 6.97-7.04 (2H, m), 7.15 (1H, s), 7.18-7.23 (2H, m).

{3-[5-(4-Fluorobenzyl)furan-2-yl]-3-oxopropyl}-(2-methoxyethyl)carbamic acid tert-butyl ester NMR (CDCl$_3$) δ: 1.42 (9H, s), 3.02 (2H, brs), 3.32 (3H, s), 3.39 (2H, brs), 3.46 (2H, brs), 3.61 (2H, t, J=6.9 Hz), 4.00 (2H, s), 6.09 (1H, d, J=2.3 Hz), 6.98-7.05 (2H, m), 7.13 (1H, brs), 7.18-7.28 (2H, m).

(1-Ethylpropyl)-{3-[5-(4-fluorobenzyl)furan-2-yl]-3-oxopropyl}-carbamic acid tert-butyl ester NMR (CDCl$_3$) δ: 0.85 (6H, brs), 1.45 (9H, s), 3.02-3.11 (2H, m), 3.32-3.43 (2H, m), 3.63 (0.5H, brs), 3.88 (0.5H, brs), 4.01 (2H, s), 6.08-6.11 (1H, m), 6.98-7.03 (2H, m), 7.11 (1H, brs), 7.17-7.28 (2H, m).

(A-16) The above-mentioned compound A-15 (1.12 g, 2.9 mmol) was dissolved in a 4N hydrochloric acid/dioxane solution (4 ml) and the mixture was stirred for 30 minutes at room temperature. The solution was poured into a sodium hydrogen carbonate solution and extracted with ethyl acetate. The extract was washed, dried, and evaporated under reduced pressure, then the residue was purified with silica gel column chromatography (chloroform:methyl alcohol=10:1) to give 3-cyclopropylamino-1-[5-(4-fluorobenzyl)furan-2-yl]propane-1-one (810 mg, yield: 98%).

NMR (CDCl$_3$) δ: 0.30-0.37 (2H, m), 0.41-0.48 (2H, m), 2.11-2.20 (1H, m), 2.95-3.01 (2H, m), 3.05-3.11 (2H, m), 4.01 (2H, s), 6.10 (1H, d, J=3.6 Hz), 6.96-7.05 (2H, m), 7.12 (1H, d, J=3.6 Hz), 7.16-7.23 (2H, m).

The following compounds were synthesized by the above-mentioned method.

3-Ethylamino1-[5-(4-fluorobenzyl)furan-2-yl]propane-1-one

NMR (CDCl$_3$) δ: 1.48 (3H, t, J=7.2 Hz), 3.04-3.18 (2H, m), 3.33-3.41 (2H, m), 3.53 (2H, t, J=6.6 Hz), 3.98 (2H, s), 6.10 (1H, d, J=3.6 Hz), 6.97-7.04 (2H, m), 7.15-7.21 (2H, m), 7.23 (1H, d, J=3.6 Hz), 9.57 (1H, s).

1-[5-(4-Fluorobenzyl)furan-2-yl]-3-propylaminopropane-1-one

NMR (CDCl$_3$) δ: 1.05 (3H, t, J=7.4 Hz), 1.85-1.99 (2H, m), 2.90-3.05 (2H, m), 3.29-3.40 (2H, m), 3.55 (2H, t, J=6.5

Hz), 3.99 (2H, s), 6.12 (1H, d, J=3.5 Hz), 6.98-7.06 (2H, m), 7.17-7.23 (2H, m), 7.24 (1H, d, J=3.5 Hz), 9.50 (1H, s).

3-Butylamino-1-[5-(4-fluorobenzyl)furan-2-yl]propane-1-one

NMR (CDCl$_3$) δ: 0.95 (3H, t, J=7.4 Hz), 1.37-1.51 (2H, m), 1.80-1.93 (2H, m), 2.94-3.08 (2H, m), 3.30-3.41 (2H, m), 3.54 (2H, t, J=7.1 Hz), 3.98 (2H, s), 6.10 (1H, d, J=3.6 Hz), 6.96-7.05 (2H, m), 7.15-7.22 (2H, m), 7.25 (1H, d, J=3.6 Hz), 9.51 (1H, s).

1-[5-(4-Fluorobenzyl)furan-2-yl]-3-(2-methoxyethylamino)propane-1-one

NMR (CDCl$_3$) δ: 2.86 (2H, t, J=5.2 Hz), 3.05 (4H, dd, J=2.7, 2.7 Hz), 3.36 (3H, s), 3.52 (2H, t, J=5.2 Hz), 4.00 (2H, s), 6.11 (1H, d, J=3.6 Hz), 6.98-7.04 (2H, m), 7.13 (1H, d, J=3.4 Hz), 7.18-7.26 (2H, m).

3-(1-Ethylpropylamino)-1-[5-(4-fluorobenzyl)furan-2-yl]propane-1-one

NMR (CDCl$_3$) δ: 0.90 (6H, brs), 1.45 (4H, brs), 2.90-3.15 (4H, m), 4.00 (2H, s), 6.12 (1H, d, J=3.7 Hz), 6.95-7.08 (2H, m), 7.15 (1H, d, J=3.7 Hz), 7.20-7.28 (2H, m).

(A-17) The above-mentioned compound A-16 (300 mg, 1 mmol) and oxalic acid dimethyl (140 mg, 1.2 mmol) were dissolved in methyl alcohol (2 ml), then 3N-sodium methoxidemethyl alcohol (0.7 ml, 2 mmol) was added to the mixture and stirred for 1 hour at room temperature. The solution was poured into an ammonium chloride aqueous solution and extracted with chloroform. The extract was washed, dried, and evaporated under reduced pressure. The residue was recrystallized from methyl alcohol to give 1-cyclopropyl-4-[5-(4-fluorobenzyl)furan-2-carbonyl]-3-hydroxy-1,5-dihydropyrrole-2-one (110 mg, yield: 32%).

Melting point: 158-159° C.
Elementary analysis as C$_{19}$H$_{16}$FNO$_4$
Calcd. (%): C, 66.86; H, 4.72; N, 4.10; F, 5.57.
Found (%): C, 66.84; H, 4.62; N, 4.09; F, 5.24.
NMR (CDCl$_3$) δ: 0.76-0.85 (2H, m), 0.90-0.98 (2H, m), 2.84-2.92 (1H, m), 4.07 (2H, s), 4.10 (2H, d, J=0.6 Hz), 6.31 (1H, dt, J=3.6, 0.6 Hz), 7.03-7.10 (2H, m), 7.20-7.26 (2H, m), 7.32 (1H, d, J=3.6 Hz).

The following compounds were synthesized by the above-mentioned method.

(A-17-a) 1-Ethyl-4-[5-(4-fluorobenzyl)furan-2-carbonyl]-3-hydroxy-1,5-dihydropyrrole-2-one NMR (CDCl$_3$) δ: 1.23 (3H, t, J=7.3 Hz), 3.58 (2H, q, J=7.3 Hz), 4.08 (2H, s), 4.18 (2H, s), 6.31 (1H, d, J=3.6 Hz), 7.02-7.10 (2H, m), 7.21-7.26 (2H, m), 7.33 (1H, d, J=3.6 Hz).

(A-17-b) 4-[5-(4-Fluorobenzyl)furan-2-carbonyl]-3-hydroxy-1-propyl-1,5-dihydropyrrole-2-one NMR (CDCl$_3$) δ: 0.96 (3H, t, J=7.4 Hz), 1.56-1.70 (2H, m), 3.48 (2H, t, J=7.4 Hz), 4.08 (2H, s), 4.16 (2H, s), 6.31 (1H, d, J=3.3 Hz), 7.00-7.10 (2H, m), 7.20-7.26 (2H, m), 7.33 (1H, d, J=3.3 Hz).

(A-17-c) 1-Butyl-4-[5-(4-fluorobenzyl)furan-2-carbonyl]-3-hydroxy-1,5-dihydropyrrole-2-one NMR (CDCl$_3$) δ: 0.97 (3H, t, J=7.2 Hz), 1.30-1.44 (2H, m), 1.53-1.64 (2H, m), 3.52 (2H, t, J=7.4 Hz), 4.08 (2H, s), 4.16 (2H, s), 6.31 (1H, d, J=3.5 Hz), 7.01-7.10 (2H, m), 7.20-7.26 (2H, m), 7.33 (1H, d, J=3.5 Hz).

(A-17-d) 4-[5-(4-Fluorobenzyl)furan-2-carbonyl]-3-hydroxy-1-(2-methoxyethyl)-1,5-dihydropyrrole-2-one Melting point: 105-106° C.
NMR (CDCl$_3$) δ: 3.35 (3H, s), 3.60 (2H, t, J=4.3 Hz), 3.72 (2H, t, J=4.6 Hz), 4.06 (2H, s), 4.40 (2H, s), 6.29 (1H, d, J=3.7 Hz), 7.03-7.08 (2H, m), 7.21-7.24 (2H, m), 7.31 (1H, d, J=3.7 Hz).

(A-17-e) 1-(1-Ethylpropyl)-4-[5-(4-fluorobenzyl)furan-2-carbonyl]-3-hydroxy-1,5-dihydropyrrole-2-one Melting point: 140-141° C.
NMR (CDCl$_3$) δ: 0.86 (6H, t, J=7.3 Hz), 1.42-1.73 (4H, m), 4.02 (2H, s), 4.06-4.15 (3H, m), 6.33 (1H, d, J=3.7 Hz), 7.02-7.08 (2H, m), 7.20-7.27 (2H, m) 7.34 (1H, d, J=3.1 Hz).

Compound A-19

1-Cyclohexyl-4-[5-(4-fluorobenzyl)furan-2-carbonyl]-3-hydroxy-1,5-dihydropyrrole-2-one

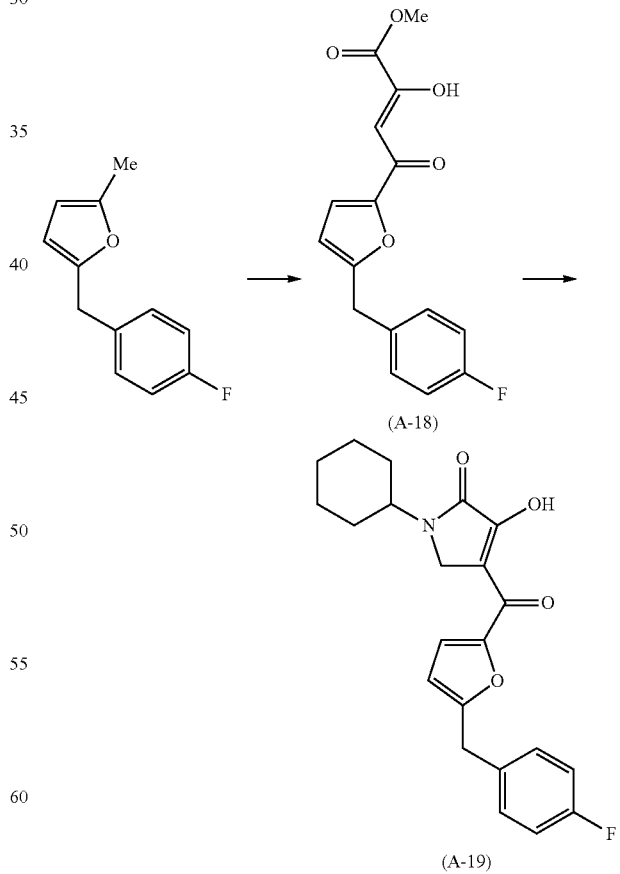

(A-18) 4-[5-(4-Fluorobenzyl)furan-2-yl]-2-hydroxy-4-oxo-2-butenoic acid methyl ester was synthesized according to the method of the reference (WO00/39086).

(A-19) The above-mentioned compound A-18 (300 mg, 1 mmol) was dissolved in dioxane (3 ml), to which were added cyclohexylamine (200 mg, 2 mmol) and paraformaldehyde (80 mg) under ice cooling. After the mixture was stirred for 3 hours at room temperature, the solution was poured into a dilute hydrochloric acid-ice water and extracted with ethyl acetate. The extract was washed, dried, and evaporated under reduced pressure. The residue was recrystallized from diethyl ether to give 1-cyclohexyl-4-[5-(4-fluorobenzyl) furan-2-carbonyl]-3-hydroxy-1,5-dihydropyrrole-2-one (280 mg, yield: 73%).

Melting point: 41-142° C.
Elementary analysis as $C_{22}H_{22}FNO_4$
Calcd. (%): C, 68.92; H, 5.78; N, 3.65; F, 4.96.
Found (%): C, 68.73; H, 5.77; N, 3.60; F, 4.80.
NMR (CDCl$_3$) δ: 1.15-1.51 (5H, m), 1.70-1.91 (5H, m), 4.08 (2H, s), 4.12 (2H, s), 4.10-4.20 (1H, m), 6.33 (1H, d, J=3.6 Hz), 7.03-7.10 (2H, m), 7.20-7.26 (2H, m), 7.33 (1H, d, J=3.6 Hz).

The following compounds were synthesized by the above-mentioned method.

(A-19-a) 1-Cyclopentyl-4-[5-(4-fluorobenzyl)furan-2-carbonyl]-3-hydroxy-1,5-dihydropyrrole-2-one Melting point: 157-159° C.
Elementary analysis as $C_{21}H_{20}FNO_4$
Calcd. (%): C, 68.28; H, 5.46; N, 3.79; F, 5.14.
Found (%): C, 67.94; H, 5.48; N, 3.72; F, 5.13.
NMR (CDCl$_3$) δ: 1.44-1.60 (2H, m), 1.60-1.82 (4H, m), 1.90-2.02 (2H, m), 4.07 (2H, s), 4.15 (2H, s), 4.56-4.68 (1H, m), 6.33 (1H, d, J=3.6 Hz), 7.03-7.10 (2H, m), 7.18-7.26 (2H, m), 7.33 (1H, d, J=3.6 Hz).

(A-19-b) 4-[5-(4-Fluorobenzyl)furan-2-carbonyl]-3-hydroxy-(4-methoxyphenyl)-1,5-dihydropyrrole-2-one Melting point: 225-227° C.
Elementary analysis as $C_{23}H_{18}FNO_5 \cdot 0.1H_2O$
Calcd. (%): C, 67.51; H, 4.48; N, 3.42; F, 4.64.
Found (%): C, 67.31; H, 4.46; N, 3.38; F, 4.38.
NMR (CDCl$_3$) δ: 3.85 (3H, s), 4.10 (2H, s), 4.60 (2H, s), 6.36 (1H, d, J=3.6 Hz), 6.97 (2H×2, Abq, J=9.0 Hz), 7.02-7.10 (2H, m), 7.20-7.26 (2H, m), 7.38 (1H, d, J=3.6 Hz), 7.57 (2H×2, Abq, J=9.0 Hz).

(A-19-c) 4-[5-(4-Fluorobenzyl)furan-2-carbonyl]-3-hydroxy-(2-hydroxyl-methylethyl)-1,5-dihydropyrrole-2-one Melting point: 168-169° C.
Elementary analysis as $C_{19}H_{18}FNO_5$
Calcd. (%): C, 63.50; H, 5.05; N, 3.90; F, 5.29.
Found (%): C, 63.17; H, 4.99; N, 3.83; F, 5.13.
NMR (DMSO-d$_6$) δ: 1.07 (3H, d, J=6.3 Hz), 3.32-3.38 (2H, m), 3.89-3.96 (1H, m), 4.09 (2H, s), 4.27 (2H, s), 4.60 (1H, bs), 6.41 (1H, d, J=3.6 Hz), 7.00-7.15 (2H, m), 7.30-7.36 (2H, m), 7.50 (1H, d, J=3.6 Hz).

(A-19-d) 1-Allyl-4-[5-(4-fluorobenzyl)furan-2-carbonyl]-3-hydroxy-1,5-dihydropyrrole-2-one Melting point: 95-96.5° C.
Elementary analysis as $C_{19}H_{16}FNO_4$
Calcd. (%): C, 66.86; H, 4.72; N, 4.10; F, 5.57.
Found (%): C, 66.69; H, 4.65; N, 4.07; F, 5.36.
NMR (CDCl$_3$) δ: 4.05 (2H, s), 4.15 (2H, d, J=6.1 Hz), 4.18 (2H, s), 5.24 (1H, dd, J=16.7, 1.1 Hz), 5.29 (1H, dd, J=10.1, 1.1 Hz), 5.81 (1H, ddt, J=16.7, 10.1, 6.1 Hz), 6.31 (1H, d, J=3.5 Hz), 7.00-7.08 (2H, m), 7.17-7.25 (2H, m), 7.32 (1H, d, J=3.5 Hz).

(A-19-e) 1-Benzyl-4-[5-(4-fluorobenzyl)furan-2-carbonyl]-3-hydroxy-1,5-dihydropyrrole-2-one Melting point: 129-130° C.
Elementary analysis as $C_{23}H_{18}FNO_4$
Calcd. (%): C, 70.58; H, 4.64; N, 3.58; F, 4.85.
Found (%): C, 70.42; H, 4.56; N, 3.60; F, 4.74.
NMR (CDCl$_3$) δ: 3.99 (2H, s), 4.13 (2H, s), 4.71 (2H, s), 6.27 (1H, d, J=3.6 Hz), 6.91-7.00 (2H, m), 7.08-7.16 (2H, m), 7.23-7.30 (3H, m), 7.33-7.42 (3H, m).

(A-19-f) 4-[5-(4-Fluorobenzyl)furan-2-carbonyl]-3-hydroxy-(2-hydroxyethyl)-1,5-dihydropyrrole-2-one Melting point: 144-145.5° C.
Elementary analysis as $C_{18}H_{16}FNO_5$
Calcd. (%): C, 62.61; H, 4.67; N, 4.06; F, 5.50.
Found (%): C, 62.39; H, 4.61; N, 4.01; F, 5.42.
NMR (CDCl$_3$) δ: 3.68 (2H, t, J=4.9 Hz), 3.89 (2H, t, J=4.9 Hz), 4.07 (2H, s), 4.37 (2H, s), 6.29 (1H, d, J=3.6 Hz), 7.01-7.10 (2H, m), 7.20-7.28 (2H, m), 7.32 (1H, d, J=3.6 Hz).

(A-19-g) 4-[5-(4-Fluorobenzyl)furan-2-carbonyl]-3-hydroxy-1-(2-hydroxypropyl)-1,5-dihydropyrrole-2-one Melting point: 172° C.
Elementary analysis as $C_{19}H_{18}NO_5F$
Calcd. (%) C, 65.50; H, 5.05; N, 3.90; F, 5.29.
Found (%) C, 63.32; H, 5.09; N, 3.88; F, 4.94.
NMR (CDCl$_3$) δ: 1.27 (d, 3H, J=6.0 Hz), 3.40-3.60 (m, 3H), 4.07 (s, 2H), 4.00-4.20 (m, 1H), 4.25-4.50 (m, 2H), 6.29 (d, 1H, J=3.6 Hz), 7.02-7.10 (m, 2H), 7.20-7.26 (m, 2H), 7.32 (d, 1H, J=3.6 Hz).

(A-19-h) 4-[5-(4-Fluorobenzyl)furan-2-carbonyl]-3-hydroxy-1-(2-hydroxybutyl)-1,5-dihydropyrrole-2-one Melting point: 132-133° C.
Elementary analysis as $C_{20}H_{20}NO_5F$
Calcd. (%) C, 64.34; H, 5.40; N, 3.75; F, 5.09.
Found (%) C, 64.18; H, 5.39; N, 3.74; F, 4.71.
NMR (CDCl$_3$) δ: 1.03 (t, 3H, J=7.2 Hz), 1.45-1.65 (m, 2H), 3.48 (dd, 1H, J=14.1 Hz, 8.1 Hz), 3.61 (dd, 1H, J=14.4 Hz, 2.7 Hz), 3.75-3.90 (m, 1H), 4.07 (s, 2H), 4.33 (d, 1H, J=18.0 Hz), 4.43 (d, 1H, J=18.0 Hz), 6.29 (d, 1H, J=3.6 Hz), 7.02-7.10 (m, 2H), 7.20-7.28 (m, 2H), 7.32 (d, 1H, J=3.6 Hz).

(A-19-i) 4-[5-(4-Fluorobenzyl)furan-2-carbonyl]-3-hydroxy-1-(2-hydroxypentyl)-1,5-dihydropyrrole-2-one Melting point: 171° C.
Elementary analysis as $C_{21}H_{22}NO_5F$
Calcd. (%) C, 65.11; H, 5.72; N, 3.62; F, 4.90.
Found (%) C, 64.82; H, 5.68; N, 3.58; F, 4.42.
NMR (CDCl$_3$) δ: 0.95 (t, 3H, J=7.2 Hz), 1.20-140 (m, 2H), 1.50-1.70 (m, 2H), 3.65-3.76 (m, 1H), 3.80-3.90 (m, 1H), 4.07 (s, 2H), 4.13 (d, 1H, J=18.0 Hz), 4.31 (d, 1H, J=18.0 Hz), 6.32 (d, 1H, J=3.6 Hz), 7.02-7.10 (m, 2H), 7.20-7.28 (m, 2H), 7.34 (d, 1H, J=3.6 Hz).

(A-19-j) 1-(2,3-Dihydroxypropyl)-4-[5-(4-fluorobenzyl)furan-2-carbonyl]-3-hydroxy-1,5-dihydropyrrole-2-one Melting point: 119-120° C.
Elementary analysis as $C_{19}H_{18}NO_6F$
Calcd. (%) C, 60.80; H, 4.83; N, 3.73; F, 5.06.
Found (%) C, 60.56; H, 4.81; N, 3.70; F, 4.66.
NMR (CDCl$_3$) δ: 3.54-3.72 (m, 4H), 3.90-4.02 (m, 1H), 4.07 (s, 2H), 4.35 (d, 1H, J=18.0 Hz), 4.43 (d, 1H, J=18.0 Hz), 6.30 (d, 1H, J=3.6 Hz), 7.02-7.10 (m, 2H), 7.20-7.28 (m, 2H), 7.34 (d, 1H, J=3.6 Hz).

(A-19-k) 4-[5-(4-Fluorobenzyl)furan-2-carbonyl]-3-hydroxy-1,5-dihydropyrrole-2-one Melting point: 178-179° C.
Elementary analysis as $C_{16}H_{12}NO_4F$
Calcd. (%) C, 63.79; H, 4.01; N, 4.65; F, 6.31.
Found (%) C, 62.87; H, 4.29; N, 4.17; F, 5.92.
NMR (CDCl$_3$) δ: 4.05 (s, 2H), 4.39 (s, 2H), 6.31 (d, 1H, J=3.6 Hz), 7.00-7.10 (m, 2H), 7.16-7.24 (m, 2H), 7.26-7.32 (m, 1H), 7.35 (d, 1H, J=3.6 Hz).

(A-19-l) 4-[5-(4-Fluorobenzyl)furan-2-carbonyl]-3-hydroxy-1-(2-morpholine-4-ylethyl)-1,5-dihydropyrrole-2-one Melting point: 189-190° C. (decomp.)
Elementary analysis as $C_{22}H_{23}N_2O_5F0.3H_2O$
Calcd. (%) C, 62.94; H, 5.67; N, 6.67; F, 4.53.
Found (%) C, 62.91; H, 5.61; N, 6.64; F, 4.25.
NMR (DMSO-d$_6$) δ: 2.58 (m), 3.55 (m), 4.08 (s, 2H), 4.14 (s, 2H), 6.37 (d, 1H, J=3.6 Hz), 7.13-7.20 (m, 2H), 7.30-7.35 (m, 2H), 7.85 (bs, 1H).

(A-19-m) 4-[5-(4-Fluorobenzyl)furan-2-carbonyl]-3-hydroxy-1-(2-piperidine-1-ylethyl)-1,5-dihydropyrrole-2-one Melting point: 228-232° C. (decomp.)
Elementary analysis as $C_{23}H_{25}N_2O_4F.0.1H_2O$
Calcd. (%) C, 66.68; H, 6.13; N, 6.76; F, 4.59.
Found (%) C, 66.55; H, 6.06; N, 6.76; F, 4.38.
NMR (DMSO-d$_6$) δ: 1.40-1.60 (m, 6H), 2.40-2.80 (m), 3.20-3.60 (m), 3.93 (s, 2H), 4.01 (s, 2H), 6.19 (bs, 1H), 7.11-7.20 (m, 2H), 7.28-7.35 (m, 2H), 8.58 (bs, 1H).

(A-19-n) 4-[5-(4-Fluorobenzyl)furan-2-carbonyl]-3-hydroxy-5H-furan-2-one

Melting point: 178-179° C.
Elementary analysis as $C_{16}H_{12}NO_4F$
Calcd. (%) C, 63.79; H, 4.01; N, 4.65; F, 6.31.
Found (%) C, 62.87; H, 4.29; N, 4.17; F, 5.92.
NMR (CDCl$_3$) δ: 4.06 (s, 2H), 5.18 (d, 2H, J=0.6 Hz), 6.35 (dd, 1H, J=3.6 Hz, 0.6 Hz), 7.02-7.10 (m, 2H), 7.18-7.24 (m, 2H), 7.41 (d, 1H, J=3.6 Hz).
(A-19-O) 4-[5-(4-Fluorobenzyl)furan-2-carbonyl]-3-hydroxy-1-isopropyl-5-methyl-1,5-dihydropyrrole-2-one was synthesized by using acetaldehyde instead of paraformaldehyde.
Melting point: 120-122° C.

NMR (CDCl$_3$) δ: 1.25 (3H, d, J=6.4 Hz), 1.38 (3H, d, J=6.9 Hz), 1.41 (3H, d, J=6.9 Hz), 4.07 (2H, d, J=2.1 Hz), 4.12 (1H, sep, J=6.9 Hz), 4.55 (1H, q, J=6.4 Hz), 6.32 (1H, d, J=3.6 Hz), 7.01-7.10 (2H, m), 7.19-7.28 (2H, m), 7.36 (1H, d, J=3.6 Hz).

Compound A-29

4-[5-(4-Fluorobenzyl)oxazole-2-carbonyl]-3-hydroxy-1-isopropyl-1,5-dihydropyrrole-2-one (A-29-a)

4-[5-(4-Fluorobenzyl)oxazole-2-carbonyl]-3-hydroxy-1-methyl-1,5-dihydropyrrole-2-one (A-29-b)

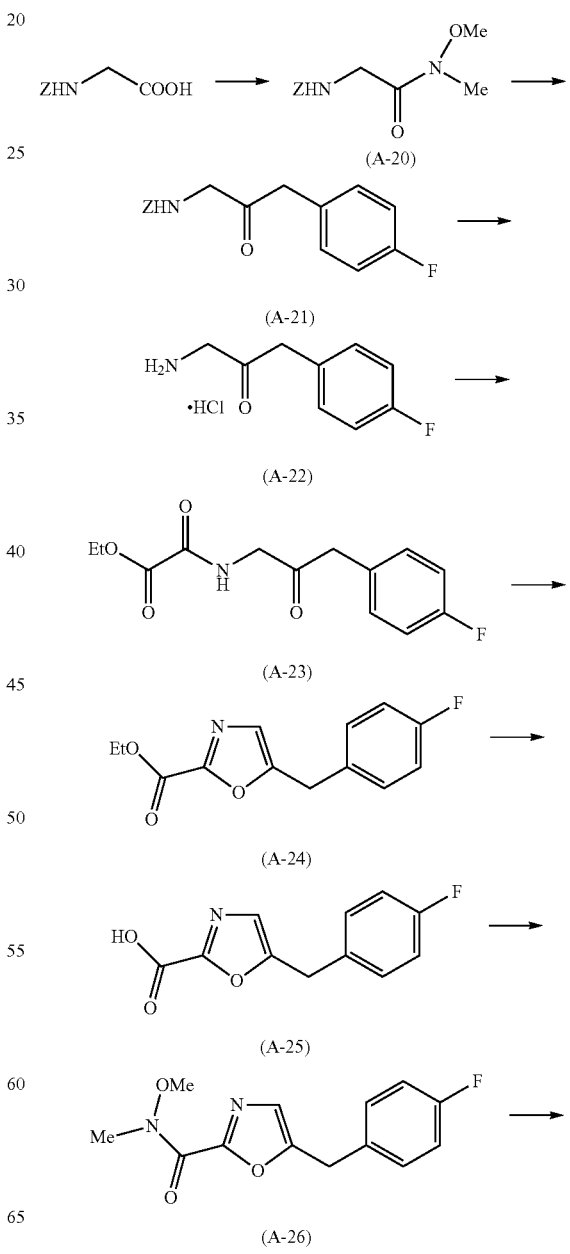

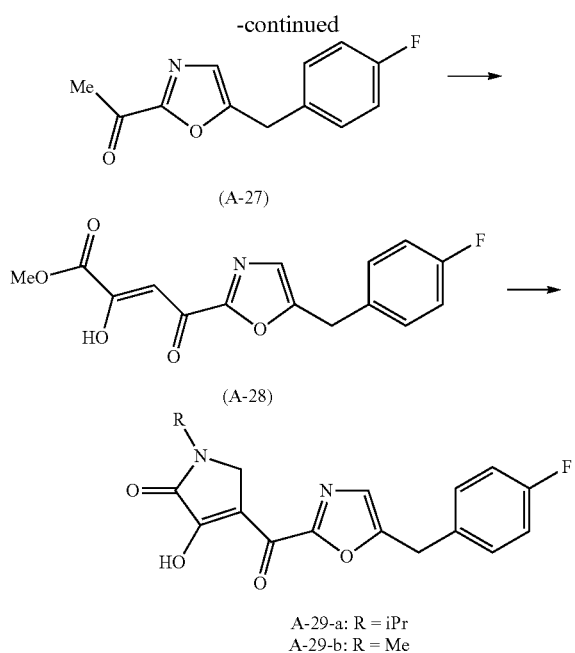

A-29-a: R = iPr
A-29-b: R = Me (A-20) To a solution of benzyloxycarbonylaminoacetic acid (102.5 g, 0.49 mol), 1-ethyl-3-(3-dimethylaminopropyl)carbodiimide hydrochloric acid (112.7 g, 0.588 mol), hydroxybenztriazole (6.62 g, 0.049 mol) and N,O-dimethylhydroxylamine hydrochloric acid (57.35 g, 0.588 mol) in dichloromethane (1 L), was added triethylamine (82 ml, 0.588 mol) and stirred for 10 minutes under water cooling, 10 minutes later, the mixture was stirred at room temperature for 1 hour. The solution was allowed to stand overnight at room temperature. The mixture was evaporated under reduced pressure, to which were added ethyl acetate (500 ml), 2N hydrochloric acid (70 ml) and water (300 ml) and the solution was shaken and separated. The solution was washed with water (200 ml), a saturated sodium bicarbonate aqueous solution (100 ml) and water (100 ml), and water (200 ml) successively. The water solution was extracted with ethyl acetate (300 ml), the ethyl acetate was Collected, dried with magnesium sulfate and evaporated under reduced pressure to give [(methoxymethylcarbamoypmethyl]carbamic acid benzyl ester (108.92 g, yield: 88.1%).

Melting point: 77-78° C.

NMR (CDCl$_3$) δ: 3.21 (3H, s), 3.72 (3H, s), 4.15 (2H, d, J=4.2 Hz), 5.13 (2H, s), 5.55 (1H, bs), 7.30-7.40 (5H, m).

(A-21) A metal sheet of magnesium (21.89 g, 900 mmol) and diethyl ether (120 ml) were added in 2 L 3 necked flask under nitrogen atmosphere, to which was added a small amount of iodine. After a small portion of 4-fluorobenzylbromide (112.2 ml, 900 mmol) in diethyl ether (150 ml) was added dropwise and diluted with diethyl ether (930 ml), the reaction mixture was Cooled with ice-NaCl. When the reaction mixture was Come to 1° C., the remaining 4-fluorobenzylbromide was added dropwise for 3 hours 40 minutes and the reaction mixture was stirred for 40 minutes.

The above-mentioned compound A-20 (75.68 g, 300 mmol) in tetrahydrofuran (720 ml) was added to 3 L 3 necked flask under nitrogen atmosphere, then the reaction mixture was Cooled with ice-NaCl, to which was added dropwise for 1.5 hours a diethyl ether solution of Grignard reagent which was previously prepared. The solution was kept from -1° C. to 3° C., and further stirred for 1 hour. (the temperature of the end of the reaction was at 3° C.). The reaction mixture was poured into an ice water, to which were added ethyl acetate (800 ml) and 2N hydrochloric acid (600 ml) and extracted. The water solution was reextracted with ethyl acetate (400 ml). The ethyl acetate solution was washed one time with water (600 ml), dried with magnesium sulfate and evaporated under reduced pressure. N-hexane and diethyl ether (2:1, 720 ml) were added to a crystal residue (130.7 g), to give crude crystal (71.15 g, 78.7%) of A-21 which was recrystallized from dichloromethane and n-hexane to give A-21 (47.82 g, yield: 52.9%). The filtrate was purified with silica gel column chromatography (toluene:acetone=98:2) to give A-21 (11.85 g, 13.1%).

Melting point: 92-93° C.

NMR (CDCl$_3$) δ: 3.71 (2H, s), 4.13 (2H, d, J=4.5 Hz), 5.10 (2H, s), 5.43 (1H, bs), 7.00-7.05 (2H, m), 7.15-7.19 (2H, m), 7.35 (5H, bs).

(A-22) The above-mentioned compound A-21 (113.88 g, 378 mmol) was suspended in methyl alcohol (756 ml), to which were added 10% Pd—C (7.56 g), water (76 ml) and 5N hydrochloric acid (114 ml). The mixture was reduced under atmosphere pressure. 3 Hours later, methyl alcohol (160 ml), water (40 ml) and 10% Pd—C (3.83 g) were added to the mixture and further reduced for 4.7 hours (6.05 L, hydrogen). The catalyst was filtered, washed with methyl alcohol and then the solution was evaporated under reduced pressure. Diethyl ether (400 ml) was added to a crystal residue and the crystal was Crushed to give 1-amino-3-(4-fluorophenyl)propane-2-one hydrochloride (74.67 g, yield: 97%).

Melting point: 190-192° C.

NMR (DMSO-d$_6$) δ: 3.91 (2H, s), 4.01 (2H, s), 7.13-7.21 (2H, m), 7.22-7.28 (2H, m), 8.24 (2H, bs).

(A-23) The above-mentioned compound A-22 (69.50 g, 341.3 mmol) was suspended to toluene (535 ml), to which was added chloroglyoxylic acid ethyl (77 ml, 689 mmol), then the mixture was stirred and heated at 90° C. for 2 hours. The reaction mixture was Cooled by ice, then ethyl acetate (500 ml) and water were added to the mixture and shaken (the precipitated crystal was not dissolved). The water layer and the precipitate were extracted 3 times with chloroform (400 ml) each chloroform solution was washed, dried with sodium sulfate and evaporated under reduced pressure. Diethyl ether and n-hexane (1:1, 200 ml) were added to a crystal residue and the crystal was Crushed to give N-[3-(4-fluorophenyl)-2-oxopropyl]oxamic acid ethyl ester (80.0 g, yield: 87.7%).

Melting point: 126-127° C.

NMR (CDCl$_3$) δ: 1.38 (3H, t, J=7.2 Hz), 3.76 (2H, s), 4.25 (2H, d, J=4.8 Hz), 4.36 (2H, q, J=7.2 Hz), 7.01-7.08 (2H, m), 7.17-7.22 (2H, m), 7.70 (1H, bs).

(A-24) The above-mentioned compound A-23 (74.90 g, 280 mmol) was suspended to toluene (784 ml), to which was added phosphorus oxychloride (144 ml, 1.545 mol), then the mixture was stirred and heated at 120° C. for 2 hours. The solution was evaporated under reduced pressure and then the residue was dissolved in ethyl acetate. The solution was poured into ice water, then extracted one time with ethyl acetate and washed 2 times and dried with magnesium sulfate. The solution was evaporated under reduced pressure to give a crude product (70.15 g). The crude product was purified with silica gel column chromatography (chloroform) to give 5-(4-fluorobenzyl)oxazole-2-carboxylic acid ethyl ester (66.70 g, yield: 95.6%) as a red oil.

NMR (CDCl$_3$) δ: 1.42 (3H, t, J=7.2 Hz), 4.05 (2H, s), 4.45 (2H, q, J=7.2 Hz), 6.92 (1H, s), 6.99-7.07 (2H, m), 7.18-7.24 (2H, m).

(A-25) The above-mentioned compound A-24 (54.70 g, 219.5 mmol) was dissolved in ethanol (640 ml) and the mixture was stirred under ice cooling, to which was added dropwise 4N lithium hydroxide (110 ml, 440 mmol) for 15 minutes and stirred for 1.5 hours. 1N hydrochloric acid (444 ml) was added dropwise for 30 minutes and then water (500 ml) was added. The mixture was stirred for 10 minutes and the precipitated crystal was separated to give 5-(4-fluorobenzyl)oxazole-2-carboxylic acid (43.74 g, yield: 90.1%).

Melting point: 84-85° C.

NMR (DMSO-d6) δ: 4.13 (2H, s), 7.12-7.21 (3H, m), 7.27-7.35 (2H, m).

(A-26) According to the method of the example A-20, 5-(4-fluorobenzyl)oxazole-2-carboxylic acid methoxymethylamide was synthesized from the above-mentioned compound A-25.

NMR (CDCl$_3$) δ: 3.46 (3H, bs), 3.83 (3H, s), 4.04 (2H, s), 6.86 (1H, s), 6.98-7.05 (2H, m), 7.16-7.28 (2H, m).

(A-27) According to the method of the example A-21, 1-[5-(4-fluorobenzyl)oxazole-2-yl]etanone was synthesized from the above-mentioned compound A-26.

Melting point: 51-52° C.

NMR (CDCl$_3$) δ: 2.63 (3H, s), 4.05 (2H, s), 6.91 (1H, m), 7.00-7.06 (2H, m), 7.19-7.24 (2H, m).

(A-28) According to the method of the example A-18, 4-[5-(4-fluorobenzyl)oxazole-2-yl]-2-hydroxy-4-oxo-2-butenoic acid methyl ester was synthesized from the above-mentioned compound A-27.

Melting point: 115-116° C.

NMR (CDCl$_3$) δ: 3.94 (3H, s), 4.09 (2H, s), 7.00-7.07 (3H, m), 7.24-7.27 (3H, m).

(A-29-a) According to the method of the example A-19, 4-[5-(4-fluorobenzyl)oxazole-2-carbonyl]-3-hydroxyl-isopropyl-1,5-dihydropyrrole-2-one was synthesized from the above-mentioned compound A-28.

Melting point: 217-219° C.

Elementary analysis as C$_1$H$_{17}$FN$_2$O$_4$

Calcd. (%): C, 62.79; H, 4.98; N, 8.14; F, 5.52.

Found (%): C, 62.31; H, 4.89; N, 8.00; F, 5.51.

NMR (CDCl$_3$) δ: 1.27 (6H, d, J=6.9 Hz), 4.10 (2H, s), 4.14 (2H, s), 4.55 (1H, m), 7.03-7.09 (3H, m), 7.23-7.28 (2H, m), 15.08 (1H, bs).

According to the same method, A-29-b, 4-[5-(4-fluorobenzyl)oxazole-2-carbonyl]-3-hydroxyl-methyl-1,5-dihydropyrrole-2-one was synthesized.

Melting point: 218-220° C.

Elementary analysis as C$_{16}$H$_{13}$FN$_2$O$_4$

Calcd. (%): C, 60.76; H, 4.14; N, 8.86; F, 6.01.

Found (%): C, 60.46; H, 4.08; N, 8.78; F, 5.97.

NMR (CDCl$_3$) δ: 3.16 (3H, s), 4.14 (4H, s), 7.02-7.09 (3H, m), 7.22-7.28 (2H, m), 15.21 (1H, bs).

Compound A-33

4-[5-(4-Fluorobenzyl)thiazole-2-carbonyl]-3-hydroxy-1-methyl-1,5-dihydropyrrole-2-one

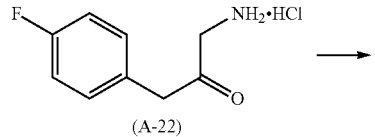

(A-22)

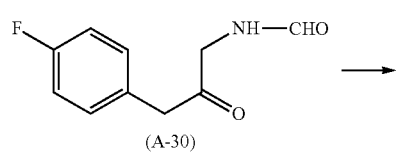

(A-30)

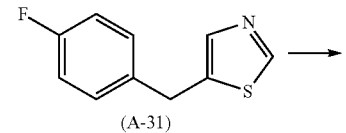

(A-31)

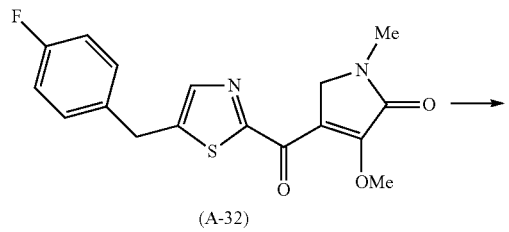

(A-32)

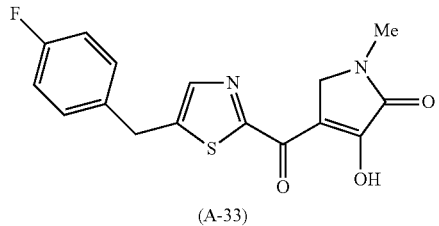

(A-33)

(A-30) formic acid (2 ml) was added to acetic anhydride (4 ml) under ice cooling and stirred at 50° C. for 15 minutes. The solution was stirred for 3 minutes under ice cooling, to which was added sodium formate (0.91 g, 13.4 mmol) and then the mixture was stirred at room temperature for 5 minutes. 1-Amino-3-(4-fluorophenyl)propane-2-one hydrochloride A-22 (2.04 g, 10 mmol) was added to the solution and stirred at room temperature for 40 minutes. Then water was added to the solution which was extracted with methylene chloride. The extract was washed, dried and evaporated under reduced pressure to give a crude crystal (1.85 g) of N-[3-(4-fluorophenyl)-2-oxopropyl]formamide.

NMR (CDCl$_3$) δ: 3.75 (2H, s), 4.24 (2H, d, J=5.4 Hz), 6.34 (1H, br.s), 7.04 (2H, t like, J=8.7 Hz), 7.16-7.22 (2H, m), 8.23 (1H, s).

(A-31) A crude crystal (1.85 g) of the above-mentioned compound A-30 was dissolved in toluene (40 ml), to which was added Lawesson's reagent (4.05 g, 10 mmol) and the mixture stirred at room temperature for 15 minutes, 60° C. for 15 minutes and 100° C. for 1.5 hours. The solution was Cooled to room temperature, then the insoluble matter was separated and washed with toluene. The filtrate and the toluene solution were concentrated under reduced pressure. The residue was purified with silica gel column chromatography (chloroform:methyl alcohol=1:0-49:1,n-hexane:ethyl acetate=2:1) to give 5-(4-fluorobenzyl)thiazole (1.47 g, 2 step yield: 76%).

NMR (CDCl$_3$) δ: 4.14 (2H, s), 7.00 (2H, t like, J=8.7 Hz), 7.14-7.20 (2H, m), 7.72 (1H, s), 8.86 (1H, s).

(A-32) A n-butyllithium-hexane solution (1.5 mmol) was added dropwise to the above-mentioned compound A-31

(290 mg, 1.5 mmol) in tetrahydrofuran (8 ml) at −78° C. and the mixture was stirred for 20 minutes, to which was added dropwise 4-methoxy-1-methyl-5-oxo-2,5-dihydro-1H-pyrrole-3-carboxylic acid methoxymethylamide (321 mg, 1.5 mmol) in tetrahydrofuran (1.5 ml) which was synthesized according to the method of A-5 and stirred for 55 minutes. A saturated ammonium chloride aqueous solution was added to the solution, then extracted with ethyl acetate. The extract was washed, dried and evaporated under reduced pressure. The residue was Crystallized from ethyl acetate-diisopropylether to give 4-[5-(4-fluorobenzyl)thiazole-2-carbonyl]-3-methoxy-1-methyl-1,5-dihydropyrrole-2-one (226 mg, yield: 44%).

NMR (CDCl$_3$) δ: 3.12 (3H, s), 4.19 (2H, s), 4.31 (3H, s), 4.60 (2H, s), 7.03 (2H, t, like, J=8.7 Hz), 7.17-7.23 (2H, m), 7.66 (1H, t, J=0.9 Hz).

The following compounds were synthesized by the above-mentioned method using 1-isopropyl-4-methoxy-5-oxo-2,5-dihydro-1H-pyrrole-3-carboxylic acid methoxymethylamide.

4-[5-(4-Fluorobenzyl)thiazole-2-carbonyl]-1-isopropyl-3-methoxy-1,5-dihydropyrrole-2-one NMR (CDCl$_3$) δ: 1.28 (6H, d, J=6.6 Hz), 4.19 (2H, s), 4.29 (3H, s), 4.52 (2H, s), 4.45-4.54 (1H, m), 7.26 (2H, t, like, J=8.7 Hz), 7.18-7.23 (2H, m), 7.68 (1H, s).

(A-33) 5N hydrochloric acid (2 ml) was added to the above-mentioned compound A-32 (219 mg, 0.63 mmol) in methyl alcohol (10 ml), and the mixture was stirred at 50° C. for 14 hours, then stirred for 30 minutes under ice cooling. The precipitated crystal was filtered out, then washed with methyl alcohol to give 164 mg of the crystal which was recrystallized from methyl alcohol-ethyl acetate to give 4-[5-(4-fluorobenzyl)thiazole-2-carbonyl]-3-hydroxy-1-methyl-1,5-dihydropyrrole-2-one (145 mg, yield: 69%).

Melting point: 230-231° C.

Elementary analysis as C$_{16}$H$_{13}$FN$_2$O$_3$S

Calcd. (%): C, 57.82; H, 3.94; N, 8.43; F, 5.72; S, 9.65.

Found (%): C, 57.91; H, 3.89; N, 8.34; F, 5.71; S, 9.47.

NMR (CDCl$_3$) δ: 3.16 (3H, s), 4.11 (2H, s), 4.23 (2H, s), 7.06 (2H, t like, J=8.7 Hz), 7.20-7.25 (2H, m), 7.76 (1H, s).

The following compound was synthesized by the above-mentioned method.

4-[5-(4-Fluorobenzyl)thiazole-2-carbonyl]-1-isopropyl-3-hydroxy-1,5-dihydropyrrole-2-one Melting point: 201-202° C.

Elementary analysis as C$_{18}$H$_{17}$FN$_2$O$_3$S

Calcd. (%): C, 59.99; H, 4.75; N, 7.77; F, 5.27; S, 8.90.

Found (%): C, 60.04; H, 4.70; N, 7.70; F, 5.30; S, 8.84.

NMR (CDCl$_3$) δ: 1.26 (6H, d, J=6.6 Hz), 4.08 (2H, s), 4.24 (2H, s), 4.50-4.62 (1H, m), 7.06 (2H, t like, J=8.7 Hz), 7.20-7.26 (2H, m), 7.56 (1H, s).

Compound A-39

4-[2-(4-Fluorobenzyl)furan-3-carbonyl]-3-hydroxy-1-methyl-1,5-dihydropyrrole-2-one

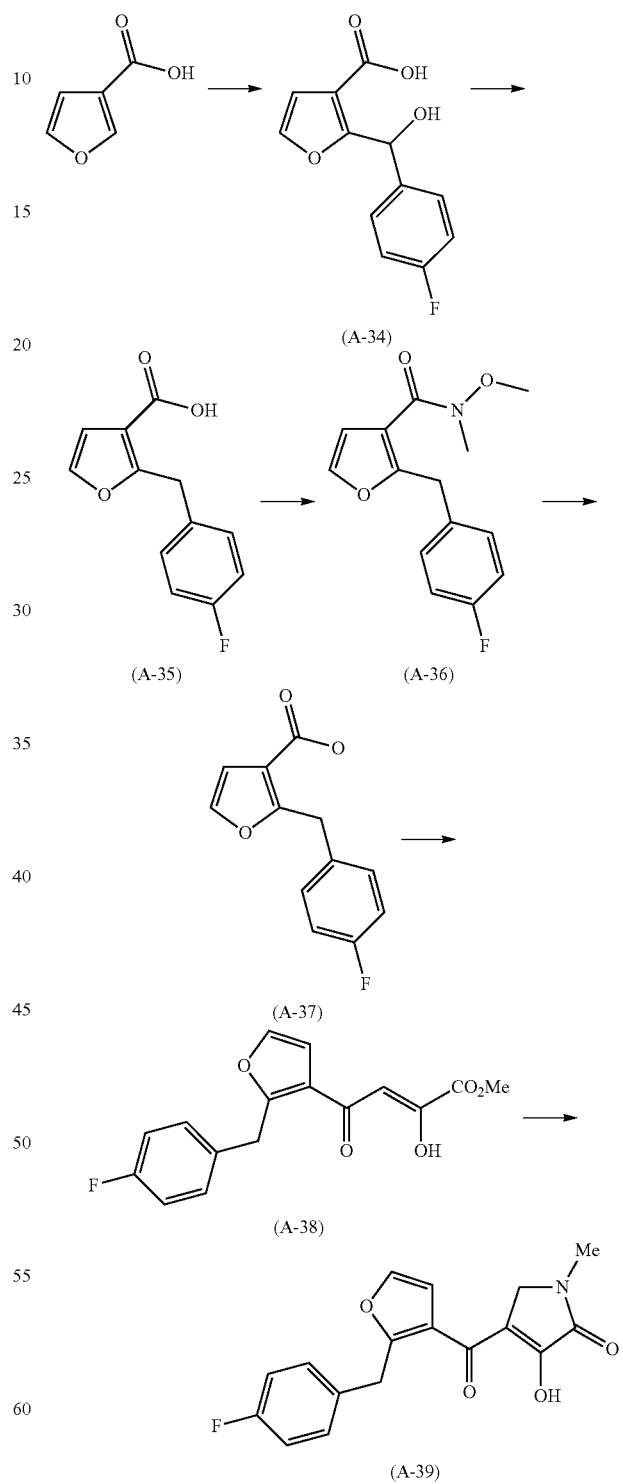

(A-34) To a lithium diisopropylamide solution prepared from diisopropylamine (22.0 ml, 157 mmol) and n-butyllithium (157 mmol) in tetrahydrofuran (150 ml), was added dropwise 3-furancarboxylic acid (8.79 g, 78.5 mmol) in tetrahydrofuran (80 ml) at −78° C. The mixture was stirred at the same temperature for 1 hour 10 minutes, to which was added 4-fluorobenzaldehyde (10.7 g, 86.4 mmol) in tetrahydrofuran (30 ml). The temperature was warmed to 0° C. for 30 minutes, then water (100 ml) was added to the solution and the organic layer was extracted with 1N sodium hydroxide aqueous solution. The water solution was acidified with concentrated hydrochloric acid, then extracted with ethyl acetate. The extract was washed, dried and evaporated under reduced pressure to give the residue which was Crystallized from diisopropylether-n-hexane to afford 2-[(4-fluorophenyl)hydroxymethyl]furan-3-carboxylic acid (13.5 g, yield: 73%).

(A-35) The above-mentioned compound A-34 (13.5 g, 57.2 mmol) in acetonitrile (75 ml) was added dropwise to sodium iodide (34.3 g) and chlorotrimethylsilane (29.1 ml) in acetonitrile (60 ml) under ice cooling, then stirred for 15 minutes, to which was added 10% sodium hydrogen sulfite aqueous solution (200 ml) and stirred for 15 minutes. The solution was extracted with ethyl acetate, washed and dried, then evaporated under reduced pressure to give the residue which was Crystallized from isopropylether-n-hexane to afford 2-(4-fluorobenzyl)furan-3-carboxylic acid (9.73 g, yield: 77%).

NMR (CDCl$_3$) δ: 4.35 (2H, s), 6.72 (1H, d, J=2.1 Hz), 6.98 (2H, t like, J=8.7 Hz), 7.22-7.28 (2H, m), 7.30 (1H, d, J=2.1 Hz).

(A-36) To a mixture of the above-mentioned compound A-35 (3.00 g, 13.6 mmol), N,O-dimethylhydroxylamine hydrochloride (1.60 g, 16.4 mmol) and 1-hydroxy-1H-benzotriazole1 hydrate (0.21 g, 1.4 mmol) in tetrahydrofuran (40 ml), was added triethylamine (2.27 ml, 16.4 mmol) and stirred for 10 minutes, to which was added 1-ethyl-3-(3-dimethylaminopropyl)carbodiimide hydrochloride (3.14 g, 16.4 mmol) and stirred overnight. Water and 2N hydrochloric acid (10 ml) were added to the solution and extracted with ethyl acetate. The extract was washed, dried and evaporated under reduced pressure, then the residue was purified with silica gel column chromatography (n-hexane:ethyl acetate=3:1) to give 2-(4-fluorobenzyl)furan-3-carboxylic acid methoxymethylamide (2.29 g, yield: 64%).

NMR (CDCl$_3$) δ: 3.33 (3H, s), 3.61 (3H, s), 4.27 (2H, s), 6.70 (1H, d, J=1.8 Hz), 6.96 (2H, t like, J=8.7 Hz), 7.24-7.31 (3H, m).

(A-37) To the above-mentioned compound A-36 (2.29 g, 8.71 mmol) in tetrahydrofuran (40 ml), was added dropwise a tetrahydrofuran solution of methyl magnesium bromide (26.1 mmol) under ice cooling, and the mixture was stirred for 1 hour 10 minutes, to which was added a saturated ammonium chloride aqueous solution and extracted with ethyl acetate.

The extract was washed, dried and evaporated under reduced pressure. The residue was purified with silica gel column chromatography (n-hexane:ethyl acetate=5:1) to give 1-[2-(4-fluorobenzyl)furan-3-yl]etanone (1.83 g, yield: 97%).

NMR (CDCl$_3$) δ: 2.43 (3H, s), 4.32 (2H, s), 6.63 (1H, d, J=1.8 Hz), 6.96 (2H, t like, J=8.7 Hz), 7.24-7.39 (3H, m).

(A-38) According to the method of the example A-18, 4-[2-(4-fluorobenzyl)furan-3-yl]-2-hydroxy-4-oxo-2-butenoic acid methyl (557 mg, yield: 79%) was synthesized by using the above-mentioned compound A-37 (504 mg, 2.31 mmol).

Melting point: 61-62° C. (diisopropylether)
NMR (CDCl$_3$) δ: 3.93 (3H, s), 4.38 (2H, s), 6.67 (1H, d, J=2.1 Hz), 6.70 (1H, s), 6.98 (2H, t like, J=8.7 Hz), 7.23-7.29 (2H, m), 7.34 (1H, J=2.1 Hz), 15.23 (1H, br.s).

(A-39) According to the method of the example A-19, 4-[2-(4-fluorobenzyl)furan-3-carbonyl]-3-hydroxy-1-methyl-1,5-dihydropyrrole-2-one (85 mg, yield: 40%) was synthesized by using the above-mentioned compound 21 (203 mg, 0.67 mmol).

Melting point: 171-172° C.
Elementary analysis as C$_{17}$H$_{14}$FNO$_4$
Calcd. (%): C, 64.76; H, 4.48; N, 4.44; F, 6.03.
Found (%): C, 64.74; H, 4.43; N, 4.41; F, 5.88.
NMR (CDCl$_3$) δ: 3.18 (3H, s), 4.30 (2H, s), 4.38 (2H, s), 6.56 (1H, d, J=2.1 Hz), 6.98 (2H, t J=8.7 Hz), 7.26-7.31 (2H, m), 7.38 (1H, d, J=2.1 Hz).

According to the same method, 4-[2-(4-fluorobenzyl)furan-3-carbonyl]-3-hydroxy-1-isopropyl-1,5-dihydropyrrole-2-one was synthesized.

Melting point: 180-182° C.
Elementary analysis as C$_{19}$H$_{18}$FNO$_4$
Calcd. (%): C, 66.46; H, 5.28; N, 4.08; F, 5.53.
Found (%): C, 66.45; H, 5.26; N, 4.08; F, 5.46.
NMR (CDCl$_3$) δ: 1.29 (6H, d, J=6.6 Hz), 4.23 (2H, s), 4.38 (2H, s), 4.54-4.63 (1H, m), 6.61 (1H, d, J=2.1 Hz), 6.98 (2H, t like, J=9 Hz), 7.26-7.31 (2H, m), 7.39 (1H, d, J=2.1 Hz).

Compound A-50

4-[3-(4-Fluorobenzyl)furan-2-carbonyl]-3-hydroxy-1-methyl-1,5-dihydropyrrole-2-one

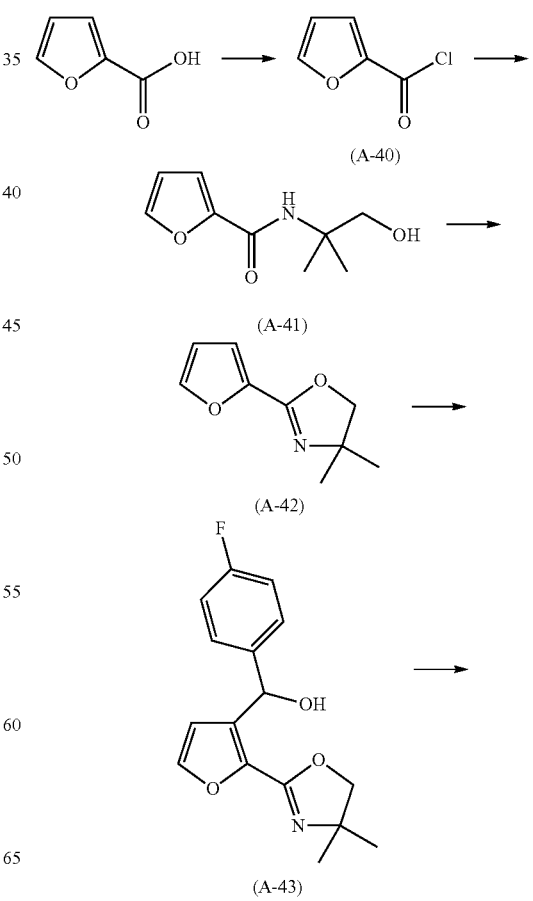

-continued

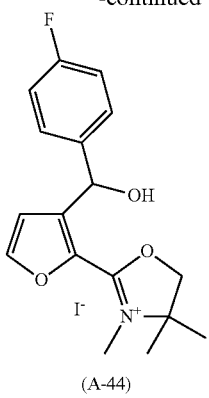

(A-44)

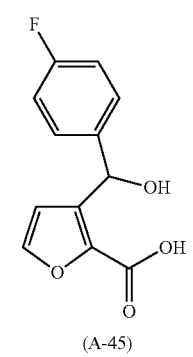

(A-45)

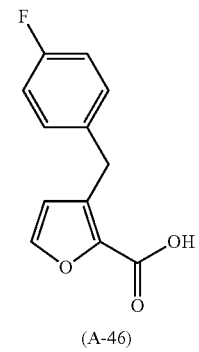

(A-46)


(A-47)

-continued

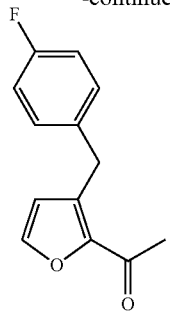

(A-48)

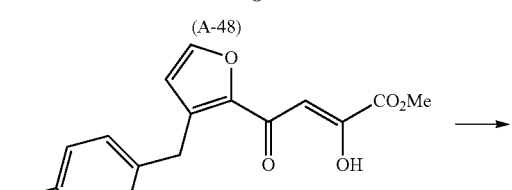

(A-49)

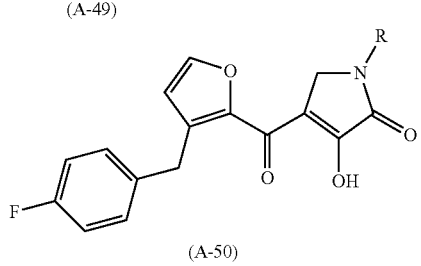

(A-50)

(A-40) To a toluene (60 ml) solution of 2-furancarboxylic acid (11.2 g, 100 mmol), were added thionyl chloride (8.76 ml, 120 mmol) and two drops of N,N-dimethylformamide, and stirred at 80° C. for 4 hours. The solution was Concentrated to give a crude product of 2-furancarboxylic acid chloride, which was used without purification to the following reaction.

(A-41) The above-mentioned A-40 was added to 2-amino-2-methyl-1-propylalcohol (22.3 g, 250 mmol) in methylene chloride (100 ml) under ice cooling, the mixture was stirred for 21 minutes, then water was added and the solution was extracted with methylene chloride after salting-out. The extract was dried, then evaporated under reduced pressure to give a crude product (18 g) of 2-furancarboxylic acid (2-hydroxy-1,1-dimethylethyl)amide. The crude product was used without purification to the following reaction.

(A-42) To a toluene (150 ml) solution of the above-mentioned crude product A-41, was added thionyl chloride (9.48 ml, 130 mmol) under ice cooling and stirred at room temperature for 1 hour 20 minutes, to which was Carefully added water (50 ml) and sodium hydroxide (26 g) aqueous solution (100 ml) under ice cooling. The solution was extracted with toluene, washed and dried, then evaporated under reduced pressure. The residue was distilled under reduced pressure to give 2-furan-2-yl-4,4-dimethyl-4,5-dihydroxazole (12.6 g, total yield of 3 steps: 76%).

Boiling point: 67-70° C. (3 mmHg)

NMR (CDCl$_3$) δ: 1.39 (6H, s), 4.10 (2H, s), 6.47-6.50 (1H, m), 6.94 (1H, J=3.3 Hz), 7.53 (1H, br. s).

(A-43) To the above-mentioned compound A-42 (11.6 g, 70.3 mmol) in 1,2-dimethoxyethane (290 ml) at −60° C., was added dropwise n-butyllithium (73.8 mmol) in n-hexane and stirred for 15 minutes, to which was added dropwise 4-fluorobenzaldehyde (9.15 g, 73.8 mmol) in 1,2-dimethoxyethane (20 ml). The mixture was stirred for 1 hour 10 minutes, then added 1N hydrochloric acid (200 ml) evaporated under reduced pressure and washed with toluene. The water layer was alkalinized with 2N sodium hydroxide aqueous solution (100 ml) and extracted with toluene. The extract was washed, dried and evaporated under reduced pressure to give the residue, purified with silica gel column chromatography (toluene:acetone=9:1) to give [2-(4,4-dimethyl-4,5-dihydroxazole-2-yl)furan-3-yl]-(4-fluorophenyl)methyl alcohol (15.1 g, yield: 74%).

NMR (CDCl$_3$) δ: 1.35 (3H, s), 1.40 (3H, s), 4.17 (2H, s), 5.88 (1H, s) 6.13 (1H, d, J=1.8 Hz), 7.03 (2H, t like, J=8.7 Hz), 7.37-7.43 (3H, m).

(A-44) To the above-mentioned compound A-43 (14.6 g, 50.5 mmol) in nitromethane (100 ml), added iodomethane (15.7 ml) and the mixture was stirred at 50° C. for 50 hours, to which was added diethyl ether (400 ml) at room temperature. The solution was stirred under ice cooling, then the precipitated crystal was filtered to give iodo[2-[3-[(4-fluorophenyl)hydroxy]furan-2-yl]-3,4,4-trimethyl-4,5-dihydroxazole-3-ium].

Immediately, this crystal was used to the following reaction.

(A-45) To the above-mentioned compound A-44 in methyl alcohol (200 ml), was added 2N sodium hydroxide aqueous solution (101 ml), and the mixture was stirred at room temperature for 1 hour and evaporated under reduced pressure. Water (150 ml) was added to the residue, then washed with toluene. The water layer was acidified with 2N hydrochloric acid (130 ml), and extracted with ethyl acetate. The extract was washed, dried and evaporated under reduced pressure to give a crude product (15.0 g) of 3-[(4-fluorophenyl)hydroxymethyl]furan-2-carboxylic acid.

NMR (CDCl$_3$) δ: 5.6 (2H, br, s), 6.23 (1H, s) 6.42 (1H, d, J=1.8 Hz), 0.7.04 (2H, t like, J=8.7 Hz), 7.37-7.43 (2H, m), 7.53 (1H, d, J=1.8 Hz).

(A-46) According to the method of A-35, 3-(4-fluorobenzyl)-2-furancarboxylic acid (7.72 g: total yield of 3 steps 70%) was synthesized by using the above-mentioned crude product A-45 (15.0 g).

Melting point: 144° C.

NMR (CDCl$_3$) δ: 4.18 (2H, s), 6.31 (1H, d, J=1.8 Hz), 6.99 (21-1, t like, J=8.7 Hz), 7.18-7.23 (2H, m), 7.53 (1H, d, J=1.8 Hz).

(A-47) According to the method of A-36, 3-(4-fluorobenzyl)-2-furancarboxylic acid methoxymethylamide (1.87 g: 71%) was synthesized by using the above-mentioned compound A-46 (2.20 g).

NMR (CDCl$_3$) δ: 3.33 (3H, s), 3.82 (3H, s), 4.11 (2H, s), 6.24 (1H, d, J=1.8 Hz), 6.96 (2H, t like, J=8.7 Hz), 7.20-7.25 (2H, m), 7.37 (1H, d, J=1.8 Hz).

(A-48) According to the method of A-37, 1-[3-(4-fluorobenzyl)furan-2-yl]etanone (1.99 g:96%) was synthesized by using the above-mentioned compound A-47 (2.50 g).

NMR (CDCl$_3$) δ: 2.51 (3H, s), 4.17 (2H, s), 6.29 (1H, d, J=1.8 Hz), 6.96 (2H, t like, J=8.7 Hz), 7.17-7.23 (2H, m), 7.39 (1H, d, J=1.8 Hz).

(A-49) According to the method of A-18, 4-[3-(4-fluorobenzyl)furan-2-yl]-2-hydroxy-4-oxo-2-butenoic acid methyl (2.48 g, yield: 90%) was synthesized by using the above-mentioned compound A-48 (1.98 g, 9.08 mmol).

Melting point: 100-101° C.

NMR (CDCl$_3$) δ: 3.94 (3H, s), 4.24 (2H, s), 6.36 (1H, d, J=1.5 Hz), 6.98 (2H, t like, J=8.7 Hz), 7.05 (1H, s), 7.18-7.24 (2H, m), 7.51 (1H, d, J=1.5 Hz), 14.73 (1H, br.s).

(A-50) According to the method of A-19, 4-[3-(4-fluorobenzyl)furan-2-carbonyl]-3-hydroxy-1-methyl-1,5-dihydropyrrole-2-one (112 mg, yield: 54%) was synthesized by using above-mentioned compound 32 (200 mg, 0.66 mmol).

Melting point: 208-210° C.
Elementary analysis as $C_{17}H_{14}FNO_4$
Calcd. (%): C, 64.76; H, 4.48; N, 4.44; F, 6.03.
Found (%): C, 64.67; H, 4.38; N, 4.33; F, 5.96.
NMR (CDCl$_3$) δ: 3.18 (3H, s), 4.27 (2H, s), 4.47 (2H, s), 6.40 (1H, d, J=1.8 Hz), 6.99 (2H, t like, J=8.7 Hz), 7.20-7.26 (2H, m), 7.58 (1H, d, J=1.8 Hz).

The following compounds were synthesized by the above-mentioned method.

(A-50-a) 4-[3-(4-Fluorobenzyl)furan-2-carbonyl]-3-hydroxy-1-isopropyl-1,5-dihydropyrrole-2-one Melting point: 197-199° C.
Elementary analysis as $C_{19}H_{18}FNO_4$
Calcd. (%): C, 66.46; H, 5.28; N, 4.08; F, 5.53.
Found (%): C, 66.40; H, 5.24; N, 4.04; F, 5.52.
NMR (CDCl$_3$) δ: 1.30 (6H, d, J=7.2 Hz), 4.27 (2H, s), 4.41 (2H, s), 4.55-4.66 (1H, m), 6.41 (1H, d, J=1.5 Hz), 6.99 (2H, t like, J=8.7 Hz), 7.20-7.26 (2H, m), 7.56 (1H, d, J=1.5 Hz).

(A-50-b) 4-[3-(4-Fluorobenzyl)furan-2-carbonyl]-3-hydroxy-1-(2-hydroxyethyl)-1,5-dihydropyrrole-2-one Melting point: 195-196° C.
Elementary analysis as $C_{18}H_{16}NO_6F$
Calcd. (%) C, 62.61; H, 4.67; N, 4.06; F, 5.50.
Found (%) C, 62.48; H, 4.52; N, 4.05; F, 5.45.
NMR (DMSO-d$_6$) δ: 3.52 (m, 2H), 3.58 (m, 2H), 4.19 (s, 2H), 4.47 (s, 2H), 6.62 (d, 1H, J=1.2 Hz), 7.05-7.15 (m, 2H), 7.28-7.35 (m, 2H), 7.91 (d, 1H, J=1.2 Hz).

(A-50-c) 4-[3-(4-Fluorobenzyl)furan-2-carbonyl]-3-hydroxy-1-(2-methoxyethyl)-1,5-dihydropyrrole-2-one Melting point: 170° C.
Elementary analysis as $C_{19}H_{18}NO_5F$
Calcd. (%) C, 63.50; H, 5.05; N, 3.90; F, 5.29.
Found (%) C, 63.35; H, 4.93; N, 3.91; F, 5.21.
NMR (DMSO-d$_6$) δ: 3.26 (s, 2H), 3.52 (m, 2H), 3.60 (m, 2H), 4.18 (s, 2H), 4.43 (s, 2H), 6.62 (d, 1H, J=1.2 Hz), 7.05-7.14 (m, 2H), 7.28-7.35 (m, 2H), 7.91 (d, 1H, J=1.2 Hz).

(A-50-d) 1-Ethyl-4-[3-(4-fluorobenzyl)furan-2-carbonyl]-3-hydroxy-1,5-dihydropyrrole-2-one Melting point: 167° C.
Elementary analysis as $C_{18}H_{16}NO_4F$
Calcd. (%) C, 65.65; H, 4.90; N, 4.25; F, 5.77.
Found (%) C, 65.65; H, 4.77; N, 4.25; F, 5.69.
NMR (DMSO-d$_6$) δ: 1.15 (t, 3H, J=7.2 Hz), 3.48 (q, 2H, J=7.2 Hz), 4.18 (s, 2H), 4.40 (s, 2H), 6.62 (d, 1H, J=1.2 Hz), 7.05-7.14 (m, 2H), 7.28-7.35 (m, 2H), 7.90 (d, 1H, J=1.2 Hz).

(A-50-e) 1-(2,3-Dihydroxypropyl)-4-[3-(4-fluorobenzyl)furan-2-carbonyl]-3-hydroxy-1,5-dihydropyrrole-2-one Melting point: 208-210° C.
Elementary analysis as $C_{19}H_{18}NO_6F.0.1H_2O$ Calcd. (%) C, 60.51; H, 4.86; N, 3.71; F, 5.04.

Found (%) C, 60.36; H, 4.64; N, 3.67; F, 4.95.

NMR (DMSO-$d_6$) δ: 3.29-3.36 (m, 3H), 3.60 (dd, 1H, J=14.1 Hz, 3.6 Hz), 3.72 (m, 1H), 4.19 (s, 2H), 4.45 (d, 1H, J=18.6 Hz), 4.55 (d, 1H, J=18.6 Hz), 4.68 (m, 1H), 4.98 (m, 1H), 6.62 (d, 1H, J=1.2 Hz), 7.05-7.14 (m, 2H), 7.28-7.35 (m, 2H), 7.91 (d, 1H, J=1.2 Hz).

Compound A-56

4-[3-(4-Fluorobenzyl)-5-methylfuran-2-carbonyl]-3-hydroxy-1-methyl-1,5-dihydropyrrole-2-one

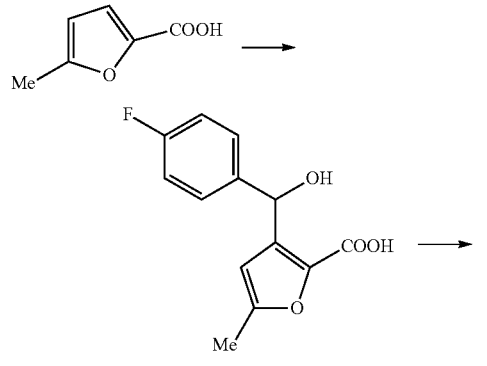

(A-51)

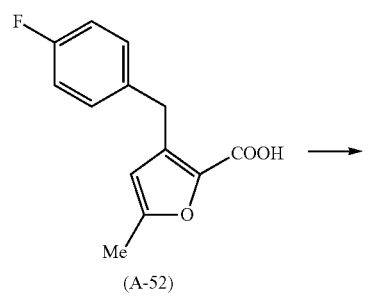

(A-52)

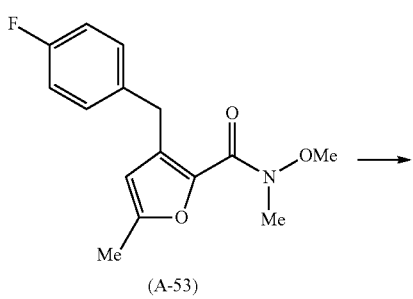

(A-53)

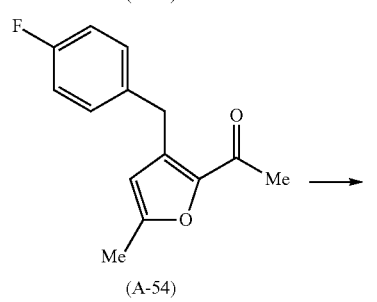

(A-54)

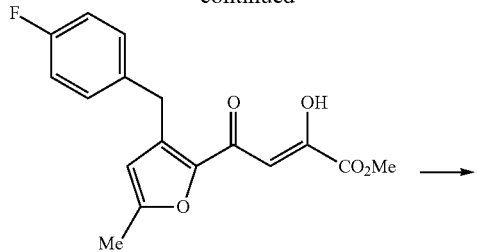

(A-55)

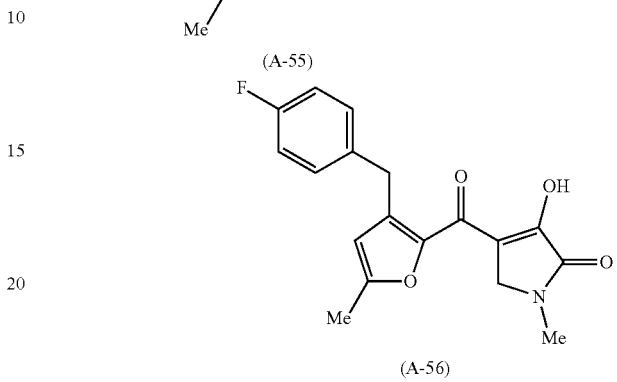

(A-56)

(A-51) According to the method of the reference (Tetrahedron Lett. 1985, 26, p 1777), 5-methyl-2-furoin acid (2.64 g, 20.9 mmol) was reacted with 4-fluorobenzaldehyde (2.7 ml, 25 mmol).

(A-52) According to the method of the reference (Tetrahedron 1995, 51, p 11043), the above-mentioned crude product was reacted with trimethylsilyl chloride (10.2 ml, 80 mmol) and sodium iodide (12.0 g, 80 mmol).

(A-53) According to the method of the example A-36, the above-mentioned crude product was reacted with N,O-dimethylhydroxylamine hydrochloride (2.05 g, 21 mmol) to give 3-(4-fluorobenzyl)-5-methyl-2-furoinacid methoxymethylamide (3.38 g, yield: 58%).

(A-54) According to the method of the example A-37, the above-mentioned compound A-53 (3.35 g, 12.1 mmol) was reacted with 1M methylmagnesium bromide (24 ml, 24 mmol) to give 1-[3-(4-fluorobenzyl)-5-methylfuran-2-yl]etanone (2.44 g, yield: 87%).

NMR (CDCl$_3$) δ: 2.30 (3H, d, J=0.6 Hz), 2.46 (3H, s), 4.12 (2H, s), 5.92 (1H, s), 6.93-6.99 (2H, m), 7.17-7.22 (2H, m).

The following compounds were synthesized by the above-mentioned method.

1-[3,5-Bis(4-fluorobenzyl)-5-methylfuran-2-yl]etanone

NMR (CDCl$_3$) δ: 2.45 (3H, s), 3.92 (2H, s), 4.11 (2H, s), 5.90 (1H, s), 6.92-7.03 (4H, m), 7.15-7.20 (4H, m).

1-[5-Tert-butyl-3-(4-fluorobenzyl)furan-2-yl]etanone

NMR (CDCl$_3$) δ: 1.28 (9H, s), 2.47 (3H, s), 4.13 (2H, s), 5.90 (1H, s), 6.93-6.99 (2H, m), 7.19-7.24 (2H, m).

1-[3-(4-Fluorobenzyl)-5-p-tolylfuran-2-yl]etanone

NMR (CDCl$_3$) δ: 2.37 (3H, s), 2.58 (3H, s), 4.21 (2H, s), 6.47 (1H, s), 6.95-7.01 (2H, m), 7.20-7.27 (4H, m), 7.60 (2H, d, J=8.1 Hz).

1-[3-(4-Fluorobenzyl)-4,5-dimethylfuran-2-yl]etanone

NMR (CDCl$_3$) δ: 1.82 (3H, s), 2.26 (3H, s), 2.45 (3H, s), 4.13 (2H, s), 6.89-6.95 (2H, m), 7.15-7.20 (2H, m).

(A-55) According to the method of the example A-38, the above-mentioned compound A-54 was reacted to give 4-[3-(4-fluorobenzyl)-5-methylfuran-2-yl]-2-hydroxy-4-oxo-2-butenoic acid methyl ester.

NMR (CDCl$_3$) δ: 2.35 (3H, d, J=0.6 Hz), 3.94 (3H, s), 4.19 (2H, s), 6.01 (1H, s), 6.95-7.01 (2H, m), 7.00 (1H, s), 7.19-7.23 (2H, m).

The following compounds were synthesized by the above-mentioned method.

4-[3,5-Bis(4-fluorobenzyl)-5-methylfuran-2-yl]-2-hydroxy-4-oxo-2-butenoic acid methyl ester NMR (CDCl$_3$) δ: 3.93 (3H, s), 3.95 (2H, s), 4.17 (2H, s), 5.96 (1H, s), 6.93-7.04 (4H, m), 6.97 (1H, s), 7.15-7.21 (4H, m), 14.84 (1H, brs).

4-[5-Tert-butyl-3-(4-fluorobenzyl)furan-2-yl]-2-hydroxy-4-oxo-2-butenoic acid methyl ester NMR (CDCl$_3$) δ: 1.30 (9H, s), 3.94 (3H, s), 4.20 (2H, s), 5.99 (1H, s), 6.96-7.02 (2H, m), 6.96 (1H, s), 7.20-7.25 (2H, m).

4-[3-(4-Fluorobenzyl)-5-p-tolylfuran-2-yl]-2-hydroxy-4-oxo-2-butenoic acid methyl ester NMR (CDCl$_3$) δ: 2.39 (3H, s), 3.96 (3H, s), 4.27 (2H, s), 6.54 (1H, s), 6.98-7.03 (2H, m), 7.11 (1H, s), 7.22-7.28 (4H, m), 7.63 (2H, d, J=8.1 Hz).

4-[3-(4-Fluorobenzyl)-4,5-dimethylfuran-2-yl]-2-hydroxy-4-oxo-2-butenoic acid methyl ester NMR (CDCl$_3$) δ: 1.84 (3H, s), 2.31 (3H, s), 3.93 (3H, s), 4.20 (2H, s), 6.91-6.97 (2H, m), 7.01 (1H, s), 7.15-7.20 (2H, m), 14.88 (1H, brs).

(A-56) According to the method of the example A-39, the above-mentioned compound A-55 was reacted to give 4-[3-(4-fluorobenzyl)-5-methylfuran-2-carbonyl]-3-hydroxy-1-methyl-1,5-dihydropyrrole-2-one.

Melting point: 154-156° C.
Elementary analysis as $C_{18}H_{16}FNO_4$
Calcd. (%): C, 65.65; H, 4.90; N, 4.25; F, 5.77.
Found (%): C, 65.30; H, 4.83; N, 4.05; F, 5.59.
NMR (CDCl$_3$) δ: 2.37 (3H, s), 3.18 (3H, s), 4.22 (2H, s), 4.43 (2H, s), 6.05 (1H, s), 6.96-7.01 (2H, m), 7.20-7.26 (2H, m).

The following compounds were synthesized by the above-mentioned method.

(A-56-a) 4-[3-(4-Fluorobenzyl)-5-methylfuran-2-carbonyl]-3-hydroxy-1-isopropyl-1,5-dihydropyrrole-2-one Melting point: 125-127° C.
Elementary analysis as $C_{20}H_{20}FNO_4$
Calcd. (%): C, 67.22; H, 5.64; N, 3.92; F, 5.32.
Found (%): C, 67.95; H, 5.64; N, 3.86; F, 5.64.
NMR (CDCl$_3$) δ: 1.30 (6H, d, J=6.7 Hz), 2.38 (3H, d, J=0.9 Hz), 4.22 (2H, s), 4.38 (2H, s), 4.59 (1H, sec, J=6.7 Hz), 6.05 (1H, d, J=0.9 Hz), 6.95-7.01 (2H, m), 7.20-7.24 (2H, m).

(A-56-b) 4-[3,5-Bis(4-fluorobenzyl)furan-2-carbonyl]-3-hydroxy-1-methyl-1,5-dihydropyrrole-2-one Melting point: 157-160° C.
Elementary analysis as $C_{24}H_{19}F_2NO_4$ 0.2H$_2$O
Calcd. (%): C, 67.51; H, 4.55; N, 3.28; F, 8.90.
Found (%): C, 67.45; H, 4.52; N, 3.21; F, 8.61.
NMR (CDCl$_3$) δ: 3.10 (3H, s), 3.98 (2H, s), 4.09 (2H, s), 4.20 (2H, s), 6.08 (1H, s), 6.95-7.08 (4H, m), 7.17-7.24 (4H, m).

(A-56-c) 4-[3,5-Bis(4-fluorobenzyl)furan-2-carbonyl]-3-hydroxy-1-isopropyl-1,5-dihydropyrrole-2-one Melting point: 159-161° C.
Elementary analysis as $C_{26}H_{23}F_2NO_4$
Calcd. (%): C, 69.17; H, 5.14; N, 3.10; F, 8.42.
Found (%): C, 68.94; H, 5.22; N, 3.06; F, 8.07.
NMR (CDCl$_3$) δ: 1.20 (6H, d, J=6.7 Hz), 3.98 (2H, s), 4.07 (2H, s), 4.21 (2H, s), 4.54 (1H, sec, J=6.7 Hz), 6.18 (1H, d, J=0.9 Hz), 6.96-7.08 (4H, m), 7.18-7.24 (4H, m).

(A-56-d) 4-[5-Tert-butyl-3-(4-fluorobenzyl)furan-2-carbonyl]-3-hydroxy-1-methyl-1,5-dihydropyrrole-2-one Melting point: 179-181° C.
Elementary analysis as $C_{21}H_{22}FNO_4$
Calcd. (%): C, 67.91; H, 5.97; N, 3.77; F, 5.12.
Found (%): C, 67.51; H, 5.88; N, 3.62; F, 4.96.
NMR (CDCl$_3$) δ: 1.31 (9H, s), 3.19 (3H, s), 4.22 (2H, s), 4.43 (2H, s), 6.02 (1H, s), 6.96-7.02 (2H, m), 7.21-7.26 (2H, m).

(A-56-e) 4-[3-(4-Fluorobenzyl)-5-p-tolylfuran-2-carbonyl]-3-hydroxy-1-methyl-1,5-dihydropyrrole-2-one Melting point: 242-245° C.
Elementary analysis as $C_{24}H_{20}FNO_4$ 0.1H$_2$O
Calcd. (%): C, 70.79; H, 5.00; N, 3.44; F, 4.67.
Found (%): C, 70.50; H, 5.17; N, 3.41; F, 4.58.
NMR (CDCl$_3$) δ: 2.41 (3H, s), 3.23 (3H, s), 4.30 (2H, s), 4.57 (2H, s), 6.58 (1H, s), 6.98-7.04 (2H, m), 7.25-7.30 (4H, m), 7.54 (2H, d, J=8.1 Hz).

(A-56-f) 4-[3-(4-Fluorobenzyl)-4,5-dimethylfuran-2-carbonyl]-3-hydroxy-1-methyl-1,5-dihydropyrrole-2-one Melting point: 202-204° C.
Elementary analysis as $C_{19}H_{18}FNO_4$ 0.2H$_2$O
Calcd. (%): C, 66.46; H, 5.28; N, 4.08; F, 5.53.
Found (%): C, 66.46; H, 5.20; N, 4.00; F, 5.44.
NMR (CDCl$_3$) δ: 1.87 (3H, s), 2.32 (3H, s), 3.18 (3H, s), 4.22 (2H, s), 4.43 (2H, s), 6.91-6.97 (2H, m); 7.17-7.22 (2H, m).

(A-56-g) 4-[5-Tert-butyl-3-(4-fluorobenzyl)furan-2-carbonyl]-1-ethyl-3-hydroxy-1,5-dihydropyrrole-2-one Melting point: 141-143° C.
Elementary analysis as $C_{22}H_{24}FNO_4$ Calcd. (%): C, 68.56; H, 6.28; N, 3.63; F, 4.93.
Found (%): C, 68.54; H, 6.36; N, 3.63; F, 4.87.
NMR (CDCl₃) δ: 1.21 (3H, t, J=7.4 Hz), 1.31 (9H, s), 3.65 (2H, q, J=7.2 Hz), 4.22 (2H, s), 4.44 (2H, s), 6.02 (1H, s), 6.96-7.02 (2H, m), 7.21-7.26 (2H, m).

(A-56-h) 4-[5-Tert-butyl-3-(4-fluorobenzyl)furan-2-carbonyl]-3-hydroxy-1-isopropyl-1,5-dihydropyrrole-2-one Melting point: 146-147° C.
Elementary analysis as $C_{23}H_{26}FNO_4$
Calcd. (%): C, 69.16; H, 6.56; N, 3.51; F, 4.76.
Found (%): C, 69.11; H, 6.62; N, 3.50; F, 4.77.
NMR (CDCl₃) δ: 1.30 (6H, d, J=6.6 Hz), 1.32 (9H, s), 4.22 (2H, s), 4.40 (2H, s), 4.59 (1H, seq, J=6.6 Hz), 6.03 (1H, s), 6.96-7.02 (2H, m), 7.21-7.26 (2H, m).

(A-56-i) 4-[5-Tert-butyl-3-(4-fluorobenzyl)furan-2-carbonyl]-1-cyclopropyl-3-hydroxy-1,5-dihydropyrrole-2-one Melting point: 148-150° C.
Elementary analysis as $C_{23}H_{24}FNO_4 \cdot 0.1H_2O$
Calcd. (%): C, 69.19; H, 6.11; N, 3.51; F, 4.76.
Found (%): C, 68.82; H, 6.17; N, 3.73; F, 4.61.
NMR (CDCl₃) δ: 0.83-0.99 (4H, m), 1.32 (9H, s), 2.92-3.00 (1H, m), 4.21 (2H, s), 4.36 (2H, s), 6.02 (1H, s), 6.96-7.02 (2H, m), 7.21-7.25 (2H, m).

Compound A-61

4-[3-(4-Fluorobenzyl)thiophene-2-carbonyl]-3-hydroxy-1-methyl-1,5-dihydropyrrole-2-one

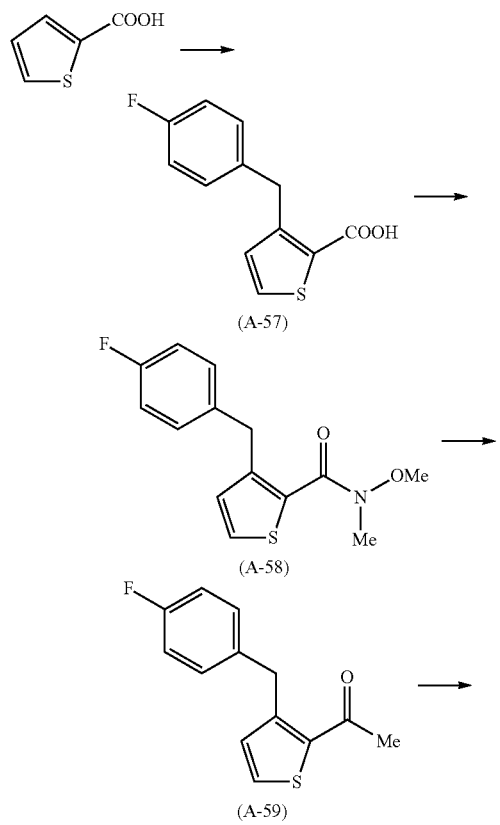

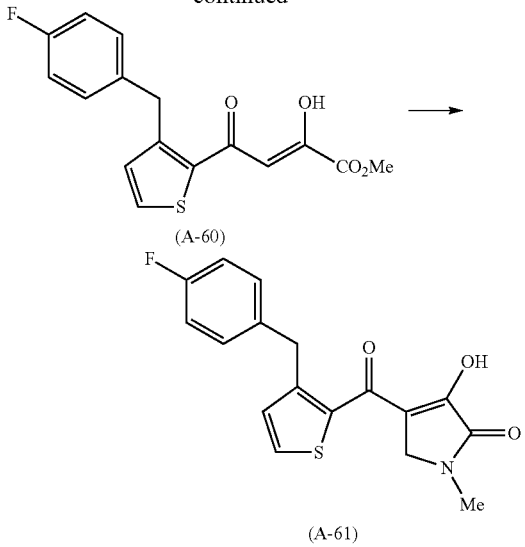

(A-57) According to the method of the reference (Tetrahedron Lett. 1985, 26, p 1777), 2-thiophenecarboxylic acid (3.84 g, 30 mmol) was reacted with 4-fluorobenzylbromide (5.6 ml, 45 mmol).

(A-58) According to the example A-36, the above-mentioned crude product A-57 was reacted with N,O-dimethylhydroxylamine hydrochloride (2.93 g, 30 mmol).

(A-59) According to the example A-37, the above-mentioned crude product A-58 was reacted with 1M methylmagnesium bromide (30 ml, 30 mmol) to give 1-[3-(4-fluorobenzyl)thiophene-2-yl]etanone (3.47 g, yield: 49%).

NMR (CDCl₃) δ: 2.55 (3H, s), 4.36 (2H, s), 6.86 (1H, d, J=4.9 Hz), 6.93-6.99 (2H, m), 7.15-7.20 (2H, m), 7.41 (1H, d, J=5.2 Hz).

(A-60) According to the example A-38, the above-mentioned crude product A-59 was reacted to give 4-[3-(4-fluorobenzyl)thiophene-2-yl]-2-hydroxy-4-oxo-2-butenoic acid methyl ester.

NMR (CDCl₃) δ: 3.93 (3H, s), 4.42 (2H, s), 6.83 (1H, s), 6.91 (1H, d, J=4.9 Hz), 6.95-7.01 (2H, m), 7.16-7.21 (2H, m), 7.55 (1H, d, J=5.2 Hz).

(A-61) According to the example A-39, the above-mentioned crude product A-60 was reacted to give 4-[3-(4-fluorobenzyl)thiophene-2-carbonyl]-3-hydroxy-1-methyl-1,5-dihydropyrrole-2-one.

Melting point: 181-183° C.
Elementary analysis as $C_{17}H_{14}FNO_3S$
Calcd. (%): C, 61.62; H, 4.26; N, 4.23; F, 5.73.
Found (%): C, 61.34; H, 4.35; N, 3.99; F, 5.59.
NMR (CDCl₃) δ: 3.19 (3H, s), 4.42 (4H, s), 6.96 (1H, d, J=5.1 Hz), 6.95-7.01 (2H, m), 7.18-7.22 (2H, m), 7.58 (1H, d, J=4.8 Hz).

The following compound was synthesized by the above-mentioned method.

4-[3-(4-Fluorobenzyl)thiophene-2-carbonyl]-3-hydroxy-1-isopropyl-1,5-dihydropyrrole-2-one Melting point: 174-175° C.
Elementary analysis as $C_{19}H_{18}FNO_3S \cdot 1H_2O$
Calcd. (%): C, 63.18; H, 5.08; N, 3.88; F, 5.26.
Found (%): C, 62.93; H, 5.03; N, 3.78; F, 5.08.

NMR (CDCl$_3$) δ: 1.31 (6H, d, J=6.7 Hz), 4.34 (2H, s), 4.42 (2H, s), 4.60 (1H, sec, J=6.7 Hz), 6.96 (1H, d, J=5.2 Hz), 6.95-7.01 (2H, m), 7.18-7.22 (2H, m), 7.58 (1H, d, H=4.9 Hz).

Compound A-69

4-[5-(4-Fluorobenzyl)-2-methyloxazole-4-carbonyl]-3-hydroxy-1-methyl-1,5-dihydropyrrole-2-one

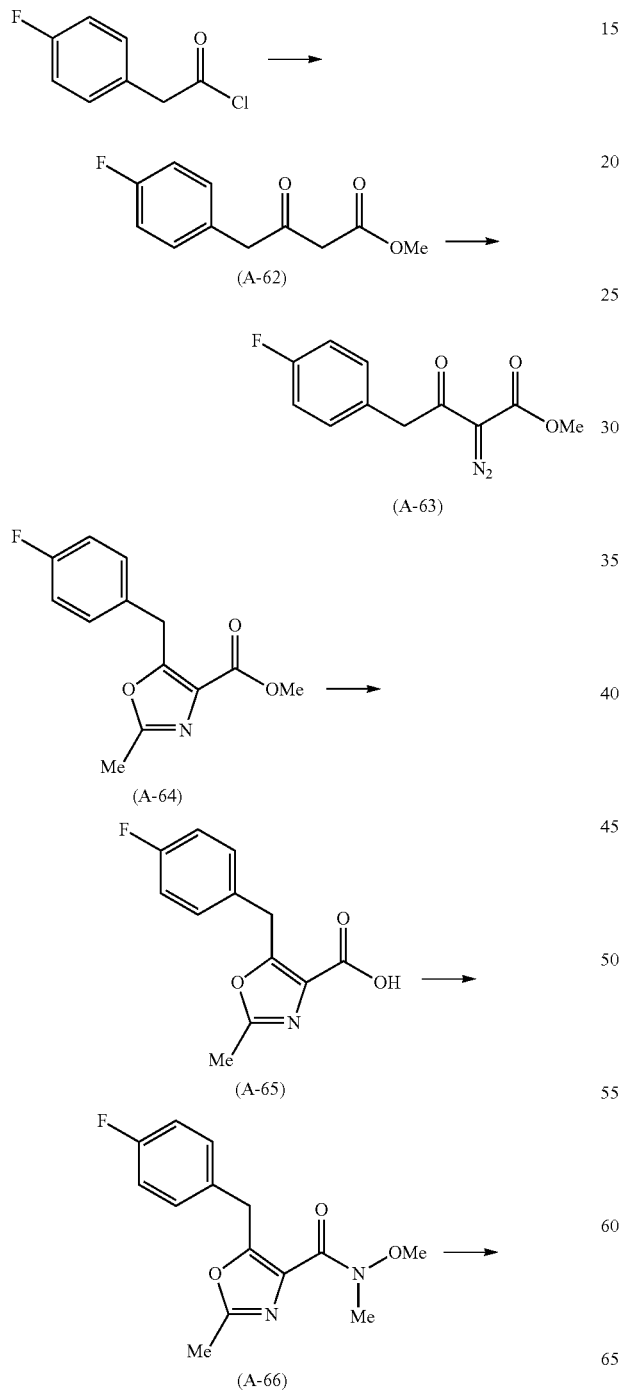

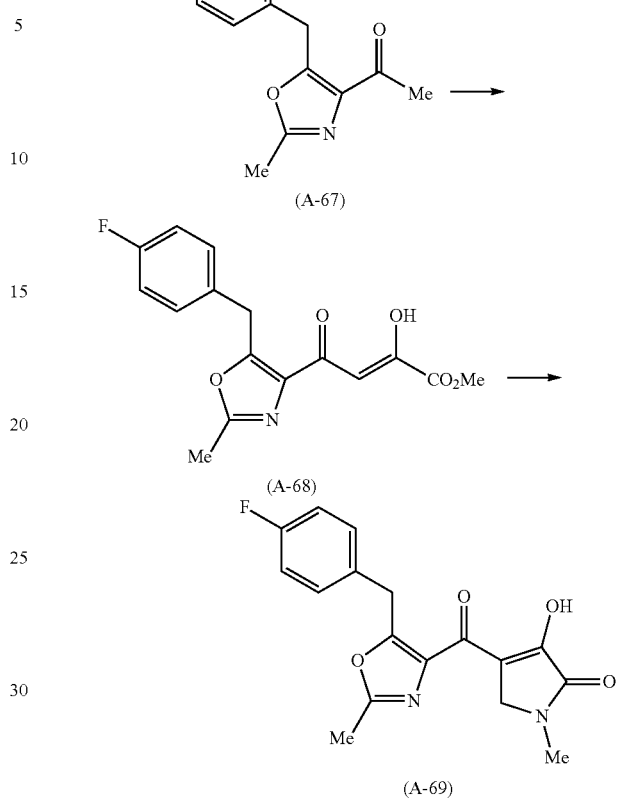

(A-62) According to the method of the reference (Org. Synth. Col. VII, 1990, p 359), 4-fluorophenylacetyl chloride (27.6 g, 160 mmol) was reacted with meldrum's acid in the presence of pyridine, then reacted with methyl alcohol to give 4-(4-fluorophenyl)-3-oxobutanoic acid methyl ester1 (28.9 g, yield: 86%).

NMR (CDCl$_3$) δ: 3.47 (2H, s), 3.72 (3H, s), 3.81 (2H, s), 7.00-7.06 (2H, m), 7.15-7.20 (2H, m).

(A-63) According to the method of the reference (Org. Synth. 1992, 70, p 93), the above-mentioned compound A-62 (4.20 g, 20 mmol) was reacted with 4-acetamidebenzenesulfonyl azide in the presence of triethylamine to give 2-diazo-4-(4-fluorophenyl)-3-oxobutanoic acid methyl ester 2a (3.67 g, yield: 78%).

NMR (CDCl$_3$) δ: 3.85 (3H, s), 4.16 (2H, s), 6.97-7.03 (2H, m), 7.23-7.28 (2H, m). According to the method of the reference (J. Org. Chem. 1962, 27, p 1717), 2-diazo-5-(4-fluorophenyl)-3-oxopentaiaoic acid methyl ester was prepared from the known compound 5-(4-fluorophenyl)-3-oxopentanoic acid methyl ester.

NMR (CDCl$_3$) δ: 2.93 (2H, t, J=7.5 Hz), 3.13-3.18 (2H, m), 3.83 (3H, s), 6.93-6.99 (2H, m), 7.17-7.21 (2H, m).

(A-64) According to the method of the reference (Synthesis, 1993, p 793), the above-mentioned compound A-63 (2.92 g, 12.4 mmol) was reacted with acetonitrile in the presence of boron trifluoride to give 5-(4-fluorobenzyl)-2-methyloxazole-4-carboxylic acid methyl ester (1.72 g, yield: 56%).

NMR (CDCl$_3$) δ: 2.43 (3H, s), 3.93 (3H, s), 4.31 (2H, s), 6.97-7.02 (2H, m), 7.23-7.28 (2H, m).

The following compound was synthesized by the above-mentioned method.

5-[2-(4-Fluorophenyl)ethyl]-2-methyloxazole-4-carboxylic acid methyl ester

NMR (CDCl$_3$) δ: 2.44 (3H, s), 2.95 (2H, t, J=7.8 Hz), 3.27 (2H, dd, J=6.9, 8.7 Hz), 3.87 (3H, s), 6.94-6.99 (2H, m), 7.12-7.17 (2H, m).

(A-65) The above-mentioned compound A-64 (1.70 g, 6.82 mmol) washedyhydrolyzed to give 5-(4-fluorobenzyl)-2-methyloxazole-4-carboxylic acid (1.27 g, yield: 79%).

NMR (CDCl$_3$) δ: 2.31 (3H, s), 4.29 (2H, s), 6.90-6.96 (2H, m), 7.22-7.26 (2H, m).

The following compound was synthesized by the above-mentioned method.

5-[2-(4-Fluorophenyl)ethyl]-2-methyloxazole-4-carboxylic acid

NMR (CDCl$_3$) δ: 2.49 (3H, s), 2.97 (2H, t, J=8.0 Hz), 3.30 (2H, dd, J=6.9, 8.7 Hz), 6.94-7.00 (2H, m), 7.12-7.17 (2H, m).

(A-66) According to the method of the example A-36, the above-mentioned compound A-65 (1.25 g, 5.31 mmol) was reacted with N,O-dimethylhydroxylamine hydrochloride (1.53 g, 8.0 mmol) to give 5-(4-fluorobenzyl)-2-methyloxazole-4-carboxylic acid methoxymethylamide (1.30 g, yield: 88%).

NMR (CDCl$_3$) δ: 2.40 (3H, s), 3.43 (3H, s), 3.80 (3H, s), 4.22 (2H, s), 6.95-7.01 (2H, m), 7.28-7.33 (2H, m).

The following compound was synthesized by the above-mentioned method.

5-[2-(4-Fluorophenyl)ethyl]-2-methyloxazole-4-carboxylic acid methoxymethylamide 5b NMR (CDCl$_3$) δ: 2.42 (3H, s), 2.94 (2H, t, J=8.1 Hz), 3.20 (2H, dd, J=6.8, 8.9 Hz), 3.37 (3H, s), 3.76 (3H, s), 6.92-6.98 (2H, m), 7.13-7.18 (2H, m).

(A-67) According to the method of the example A-37, the above-mentioned compound A-66 (1.28 g, 4.6 mmol) was reacted with 1M methylmagnesium bromide (9.2 ml, 9.2 mmol) to give 1-[5-(4-fluorobenzyl)-2-methyloxazole-4-yl]etanone A-7 (0.89 g, yield: 83%).

NMR (CDCl$_3$) δ: 2.42 (3H, s), 2.54 (3H, s), 4.30 (2H, s), 6.95-7.01 (2H, m), 7.24-7.29 (2H, m).

The following compound was synthesized by the above-mentioned method.

1-{5-[2-(4-Fluorophenyl)ethyl]-2-methyloxazole-4-yl}etanone

NMR (CDCl$_3$) δ: 2.43 (3H, s), 2.49 (3H, s), 2.93 (2H, t, J=8.0 Hz), 3.27 (2H, dd, J=7.1, 8.9 Hz), 6.93-6.99 (2H, m), 7.12-7.17 (2H, m).

(A-68) According to the method of the example A-38, the above-mentioned compound A-67 was reacted to give 4-[5-(4-fluorobenzyl)-2-methyloxazole4-carbonyl]-2-hydroxy4-oxo2-butenoic acidmethylester.

NMR (CDCl$_3$) δ: 2.44 (3H, s), 3.92 (3H, s), 4.36 (2H, s), 6.97-7.03 (2H, m), 7.19 (1H, s), 7.25-7.30 (2H, m), 14.82 (1H, brs).

The following compound was synthesized by the above-mentioned method.

4-{5-[2-(4-Fluorophenyl)ethyl]-2-methyloxazole-4-carbonyl}-2-hydroxy-4-oxo-2-butenoic acid methyl ester NMR (CDCl$_3$) δ: 2.45 (3H, s), 2.97 (2H, t, J=7.8 Hz), 3.33 (2H, dd, J=6.8, 8.9 Hz), 3.91 (3H, s), 6.94-7.00 (2H, m), 7.13-7.19 (2H, m), 7.14 (1H, s), 14.70 (1H, brs).

(A-69) According to the method of the example A-39, the above-mentioned compound A-68 was reacted to give 4-[5-(4-fluorobenzyl)-2-methyloxazole-4-carbonyl]-3-hydroxyl-methyl-1,5-dihydropyrrole-2-one.

Melting point: 170° C.
Elementary analysis as $C_{17}H_{15}FN_2O_4$
Calcd. (%): C, 61.82; H, 4.58; N, 8.48; F, 5.75.
Found (%): C, 61.66; H, 4.57; N, 8.45; F, 5.64.
NMR (CDCl$_3$) δ: 2.56 (3H, s), 3.15 (3H, s), 4.15 (2H, d, J=0.6 Hz), 4.41 (2H, s), 6.97-7.03 (2H, m), 7.26-7.31 (2H, m), 15.08 (1H, brs).

The following compound was synthesized by the above-mentioned method.

4-[5-(4-Fluorobenzyl)-2-methyloxazole-4-carbonyl]-3-hydroxy-1-isopropyl-1,5-dihydropyrrole-2-one Negative ESIMS m/z 357 (M−H)$^-$
Positive ESIMS m/z 359 (M+H)$^+$
NMR (CDCl$_3$) δ: 1.27 (6H, d, J=5.3 Hz), 2.57 (3H, s), 4.08 (2H, s), 4.14 (2H, s), 4.54 (1H, sec, J=6.6 Hz), 6.97-7.02 (2H, m), 7.27-7.32 (2H, m), 15.03 (1H, brs).

4-{5-[2-(4-Fluorophenyl)ethyl]-2-methyloxazole-4-carbonyl}-3-hydroxy-1-methyl1,5-dihydropyrrole-2-one Melting point: 184-185° C.
Elementary analysis as $C_{18}H_{17}FN_2O_4$
Calcd. (%): C, 62.79; H, 4.98; N, 8.14; F, 5.52.
Found (%): C, 62.57; H, 4.91; N, 8.03; F, 5.37.
NMR (CDCl$_3$) δ: 2.56 (3H, s), 2.98 (2H, t, J=7.2 Hz), 3.14 (3H, s), 3.38 (2H, dd, J=6.9, 8.7 Hz), 4.07 (2H, s), 6.94-7.00 (2H, m), 7.15-7.19 (2H, m), 15.11 (1H, brs).

Compound A-73

4-[2-(4-Fluorobenzyl)-1H-imidazole-4-carbonyl]-3-hydroxy-1-isopropyl-1,5-dihydropyrrole-2-one

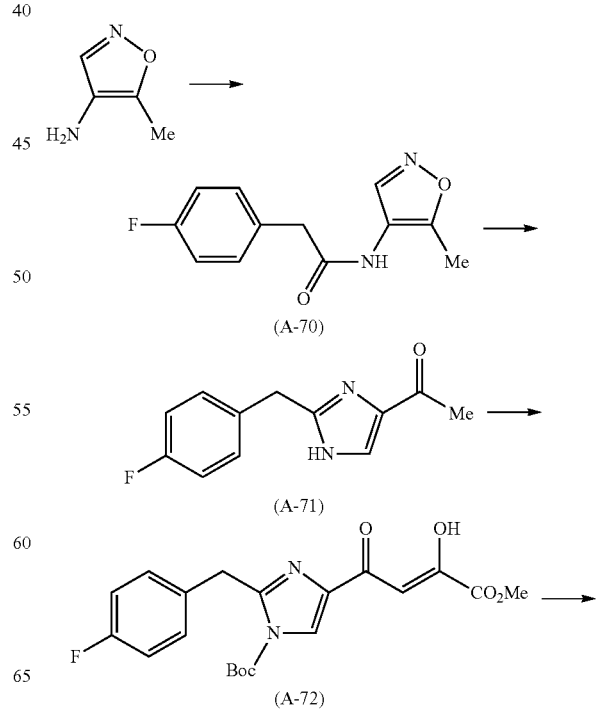

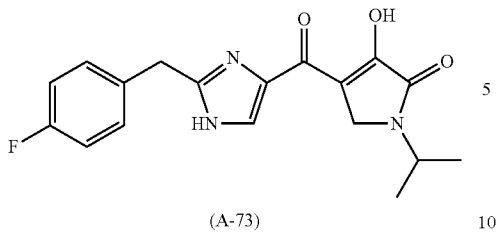

(A-73)

(A-70) According to the method of the reference (J. Org. Chem. 1987, 52, p 2714), (5-methylisoxazole-4-yl)amine hydrochloride (16.15 g, 120 mmol) was reacted with 4-fluorophenylacetyl chloride (20.8 g, 120 mmol) in the presence of triethylamine to give 2-(4-fluorophenyl)-N-(5-methylisoxazole-4-yl)acetamide (22.55 g, yield: 80%).

NMR (CDCl$_3$) δ: 2.28 (3H, s), 3.69 (3H, s), 6.71 (1H, brs), 7.06-7.20 (2H, m), 7.26-7.32 (2H, m), 8.46 (1H, s).

(A-71) The above-mentioned compound A-70 was reduced by hydrogenation, then treated with sodium hydroxide to give 1-[2-(4-fluorobenzyl)-1H-imidazole-4-yl]etanone (yield: 82%).

NMR (CDCl$_3$) δ: 2.45 (3H, s), 4.12 (2H, s), 6.96-7.01 (2H, m), 7.19-7.23 (2H, m), 7.64 (1H, s).

(A-72) The above-mentioned compound A-71 was protected with a BOC group, then according to the method of the example A-38, 2-(4-fluorobenzyl)-4-(3-hydroxy-3-methoxycarbonylacryloyl)imidazole-4-carboxylic acid tert-butyl ester was synthesized.

NMR (CDCl$_3$) δ: 1.55 (9H, s), 3.93 (3H, s), 4.41 (2H, s), 6.94-7.00 (2H, m), 7.17 (1H, s), 7.19-7.23 (2H, m), 8.06 (1H, s).

(A-73) A-72 was reacted according to the method of example A-39 to give a mixture comprising a de-protected product. The mixture was deprotected by using trifluoroacetic acid to give 4-[2-(4-fluorobenzyl)-1H-imidazole-4-carbonyl]-3-hydroxy-1-isopropyl-1,5-dihydropyrrole-2-one.

Melting point: 220° C.

Elementary analysis as C$_{18}$H$_{18}$FN$_3$O$_3$ 0.2H$_2$O

Calcd. (%): C, 62.31; H, 5.35; N, 12.11; F, 5.48.

Found (%): C, 62.13; H, 5.07; N, 11.94; F, 5.57.

NMR (CDCl$_3$) δ: 1.24 (6H, d, J=6.7 Hz), 4.05 (2H, s), 4.12 (2H, s), 4.52 (1H, sec, J=6.7 Hz), 6.98-7.03 (2H, m), 7.24-7.29 (2H, m), 7.64 (1H, s).

Compound A-78-a

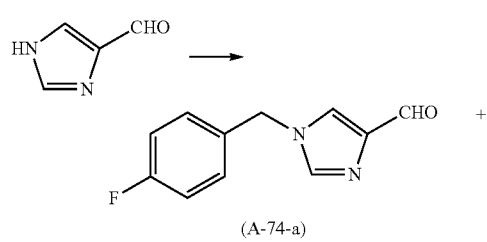

(A-74-a)

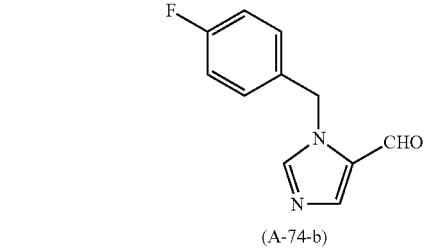

(A-74-b)

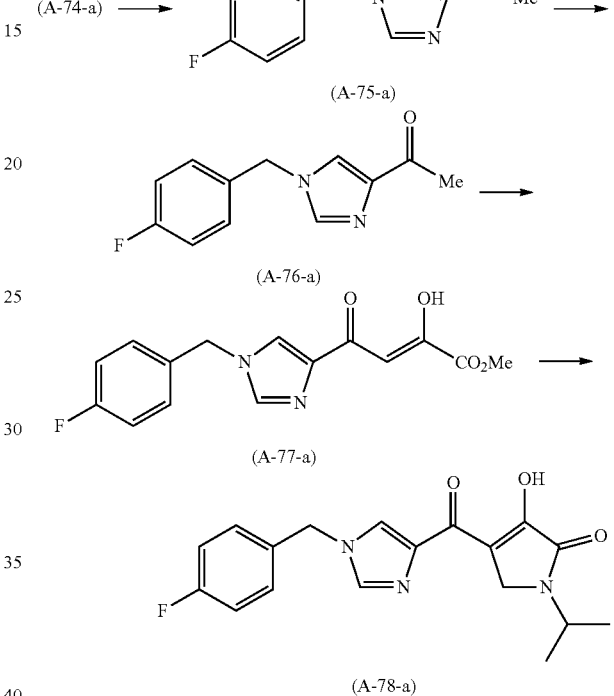

(A-74-a, A-74-b) To a dimethylformamide solution (30 ml) of 1H-imidazole-4-carboaldehyde (2.88 g, 30 mmol), potassium tert-butoxide (3.7 g, 33 mmol) and 4-fluorobenzylbromide (3.74 ml, 30 mmol) were added under ice cooling, then, the mixture was stirred for 1 hour. The solution was added a saturated ammonium chloride aqueous solution and extracted with ethyl acetate, washed with water and brine, dried and evaporated under reduced pressure. The residue was purified with silica gel column chromatography to give 1-(4-fluorobenzyl)-1H-imidazole-4-carboaldehyde A-74-a (2.7 g, yield: 44%); NMR (CDCl$_3$) δ: 5.18 (2H, s), 7.06-7.18 (2H, m), 7.20-7.23 (2H, m), 7.60 (1H, d, J=1.1 Hz), 7.62 (1H, s), 9.87 (1H, s) and 3-(4-fluorobenzyl)-3H-imidazole-4-carboaldehyde A-74-b (2.95 g, yield: 48%);

NMR (CDCl$_3$) δ: 5.49 (2H, s), 7.00-7.06 (2H, m), 7.21-7.24 (2H, m), 7.72 (1H, s), 7.84 (1H, s), 9.75 (1H, d, J=0.9 Hz).

(A-75-a) To a tetrahydrofuran solution (30 ml) of the above-mentioned compound A-74-a (2.7 g, 13.2 mmol), was added dropwise 1M methylmagnesium bromide (16 ml, 16 mmol) under ice cooling at room temperature, the mixture was stirred for 1.5 hours, then was added dropwise 1M methylmagnesium bromide (16 ml, 16 mmol). The solution was stirred for 1.5 hours, then was added a saturated ammonium chloride aqueous solution and extracted with ethyl acetate, washed with water and brine. The solution was dried and evaporated under reduced pressure. The residue was purified with silica gel column chromatography to give 1-[1-(4-fluorobenzyl)-1H-imidazole-4-yl]ethanol (2.75 g, yield: 95%).

NMR (CDCl$_3$) δ: 1.50 (3H, d, J=6.4 Hz), 3.04 (1H, brs), 4.86 (1H, q, J=6.6 Hz), 5.03 (2H, s), 6.76 (1H, s), 7.01-7.08 (2H, m), 7.13-7.17 (2H, m), 7.47 (1H, d, J=1.3 Hz).

(A-75-b) The following compound was synthesized by the above-mentioned method from the compound A-74-b.

1-[3-(4-Fluorobenzyl)-3H-imidazole-4-yl]ethanol

NMR (DMSO-d$_6$) δ: 1.36 (3H, d, J=6.7 Hz), 4.55 (1H, m), 5.18 (1H, q, J=6.1 Hz), 5.25 (2H, s), 6.81 (1H, t, J=0.9 Hz), 7.17-7.22 (4H, m), 7.65 (1H, d, J=1.2 Hz).

(A-76-a) To a tetrahydrofuran solution (60 ml) of the above-mentioned compound A-75-a (2.48 g, 11.3 mmol), was added manganese dioxide (9.56 g, 110 mmol) at room temperature, then the mixture was stirred for 2.5 hours. The solution was filtered by celite, then evaporated under reduced pressure and the residue was recrystallized with diisopropylether-ethyl acetate to give 1-[1-(4-fluorobenzyl)-1H-imidazole-4-yl]etanone (1.77 g, yield: 72%).

NMR (CDCl$_3$) δ: 2.55 (3H, s), 5.12 (2H, s), 7.05-7.10 (2H, m), 7.16-7.21 (2H, m), 7.54-7.56 (2H, m).

(A-76-b) The following compound was synthesized by the above-mentioned method from the compound A-75-b.

1-[3-(4-Fluorobenzyl)-3H-imidazole-4-yl]etanone

NMR (CDCl$_3$) δ: 2.55 (3H, s), 5.49 (2H, s), 6.99-7.04 (2H, m), 7.15-7.20 (2H, m), 7.64 (1H, s), 7.82 (1H, s).

(A-77-a) According to the method of the above-mentioned example A-39, 4-[1-(4-fluorobenzyl)-1H-imidazole-4-carbonyl]-2-hydroxy-4-oxo-2-butenoic acid methyl ester was synthesized from the compound A-76-a.

NMR (DMSO-d$_6$) δ: 3.65 (3H, s), 5.18 (2H, s), 7.12-7.18 (2H, m), 7.32-7.37 (2H, m), 7.54 (1H, brs), 7.67 (1H, brs).

(A-77-b) The following compound was synthesized by the above-mentioned method from the compound A-76-b.

4-[3-(4-Fluorobenzyl)-3H-imidazole-4-carbonyl]-2-hydroxy-4-oxo-2-butenoic acid methyl ester NMR (CDCl$_3$) δ: 3.71 (3H, s), 5.43 (2H, s), 6.46 (1H, s), 6.81-6.87 (2H, m), 7.06-7.10 (2H, m), 7.52 (1H, s), 7.65 (1H, s).

(A-78-a) According to the method of the above-mentioned example A-39, 4-[1-(4-fluorobenzyl)-1H-imidazole-4-carbonyl]-3-hydroxy-1-isopropyl-1,5-dihydropyrrole-2-one was synthesized from the compound A-77-a.

Melting point: 224-226° C.

Elementary analysis as C$_{18}$H$_{18}$FN$_3$O$_3$

Calcd. (%): C, 62.97; H, 5.28; N, 12.24; F, 5.53.

Found (%): C, 62.57; H, 5.15; N, 12.02; F, 5.27.

NMR (DMSO-d$_6$) δ: 1.18 (6H, d, J=6.7 Hz), 3.97 (2H, s), 4.25 (1H, sec, J=6.7 Hz), 5.37 (2H, s), 7.21-7.27 (2H, m), 7.47-7.52 (2H, m), 8.17 (1H, s), 8.48 (1H, s).

(A-78-b) The following compound was synthesized by the above-mentioned method from the compound A-77-b.

4-[3-(4-Fluorobenzyl)-3H-imidazole-4-carbonyl]-3-hydroxy-1-isopropyl-1,5-dihydropyrrole-2-one Melting point: 156-159° C.

Negative ESIMS m/z 342 (M−H)$^−$

Positive ESIMS m/z 344 (M+H)$^+$

NMR (DMSO-d$_6$) δ: 1.17 (6H, d, J=6.7 Hz), 4.02 (2H, s), 4.21 (1H, sec, J=6.7 Hz), 5.55 (2H, s), 7.03 (2H, brt), 7.21-7.25 (2H, m), 7.90 (1H, brs), 8.11 (1H, brs).

Compound A-84

4-[5-(4-Fluorobenzyl)-1H-pyrrole-2-carbonyl]-3-hydroxy-1-methyl-1,5-dihydropyrrole-2-one

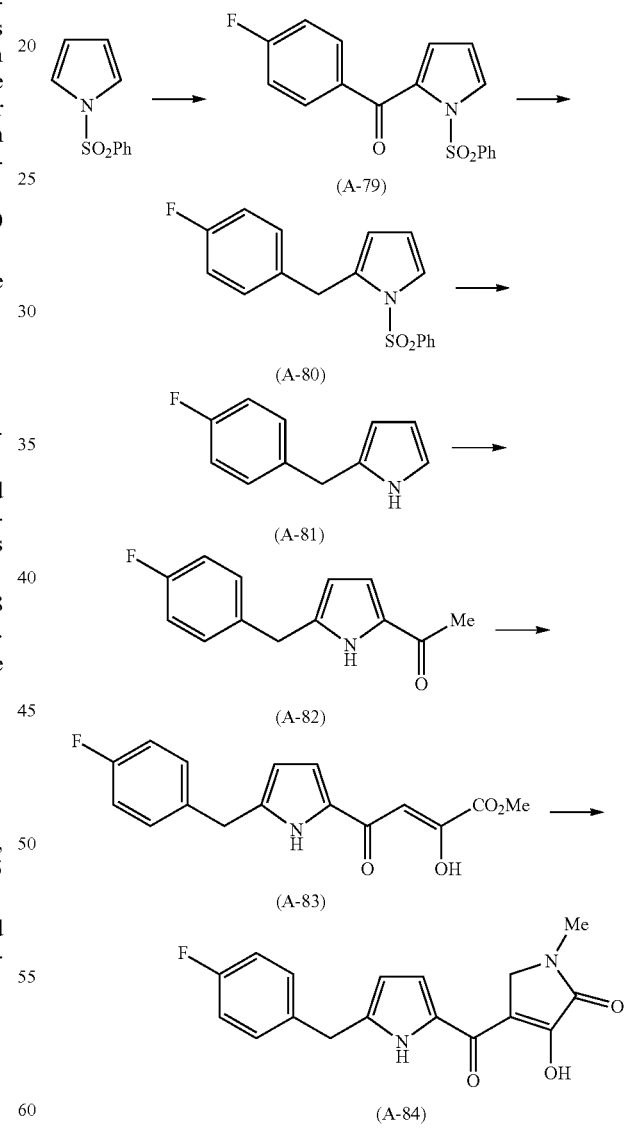

(A-79) According to the method of the reference (J. Org. Chem., 1983, 48, p 3214), 1-benzenesulfonyl 1H-pyrrole (J. Org. Chem., 1999, 64, p 3379) (45.0 g, 217 mmol) was reacted with 4-fluorobenzoyl chloride (103 g, 651 mmol) in the presence of boron trifluoride-diethyl ether complex (80.1 ml, 651 mmol) in methylene chloride (360 ml) to give 2-(4-fluorophenyl)-N-(5-methylisoxazole-4-yl)acetamide (22.55 g, yield: 80%).

The residue was Crystallized (diisopropylether-n-hexane) to give (1-benzenesulfonyl 1H-pyrrole-2-yl-(4-fluorophenyl)metanone (33 g, yield: 46%).

NMR (CDCl$_3$) δ: 6.36 (1H, dd, J=3.3, 3.6 Hz), 6.70 (1H, dd, J=1.5, 3.6 Hz), 7.08-7.15 (2H, m), 7.55-7.70 (3H, m), 7.78 (1H, dd, J=1.5, 3.3 Hz), 7.80-7.89 (2H, m), 8.00-8.14 (2H, m).

(A-80) According to the method of the reference (Synth. Comm., 1990, 20, p 1647), the above-mentioned compound A-79 (32.5 g, 98.7 mmol) was reduced by borane tert-butylamine complex (51.5 g, 0.59 mol) in the presence of aluminum chloride (39.5 g, 0.30 mol) in methylene chloride (150 ml). The residue was purified with column chromatography (ethyl acetate:n-hexane=1:4-1:3) to give 1-benzenesulfonyl-2-(4-fluorobenzyl)-1H-pyrrole (26.9 g, yield: 86%).

NMR (CDCl$_3$) δ: 4.05 (2H, s), 5.81 (1H, dd, J=1.5, 3.3 Hz), 6.21 (1H, t, J=1.5 Hz), 6.81-7.01 (4H, m), 7.34 (1H, dd, J=1.5, 3.3 Hz), 7.37-7.44 (2H, m), 7.52-7.61 (3H, m).

(A-81) To a methyl alcohol (400 ml) solution of the above-mentioned compound A-80 (26.9 g, 86.5 mmol), was added 5N sodium hydroxide aqueous solution 85 ml, and the reaction mixture was stirred for 6 hours under refluxing. The solution was Cooled at room temperature, to which was added 2N hydrochloric acid 185 ml, then extracted with ethyl acetate. The extract was washed with saturated NaCl aqueous solution, dried, then evaporated under reduced pressure. The residue was purified with column chromatography (ethyl acetate:n-hexane=1:3) to give 2-(4-fluorobenzyl)-1H-pyrrole (14.5 g, yield: 97%).

NMR (CDCl$_3$) δ: 3.95 (2H, s), 5.97 (1H, s), 6.15 (1H, dd, J=2.7, 5.7 Hz), 6.68 (1H, dd, J=2.7, 4.2 Hz), 6.94-7.02 (2H, m), 7.12-7.19 (2H, m), 7.82 (1H, brs).

(A-82) To phosphorus oxychloride (7.33 ml, 78.6 mmol) at room temperature, was added dropwise DMA (12.5 ml) for 20 minutes under stirring, to which was added dropwise a DMA (12.5 ml) solution of the above-mentioned compound A-81 (12.5 g, 71.3 mmol) at room temperature. The solution was stirred at 50° C. for 3 hours, to which was added 5N sodium hydroxide aqueous solution 86 ml under ice-water cooling, to which was added 6N hydrochloric acid 30 ml and extracted with ethyl acetate. The extract was washed with water, and saturated NaCl aqueous solution, dried, then evaporated under reduced pressure. The residue was Crystallized with diisopropylether 40 ml and filtered out, then washed with diisopropylether, dried to give 1-[5-(4-fluorobenzyl)-1H-pyrrole-2-yl]etanone (5.65 g, yield: 36%). The filtrate was Concentrated under reduced pressure, then the residue was purified with column chromatography (ethyl acetate:n-hexane=1:3-1:2) and recrystallized (diisopropylether) to give 1-[5-(4-fluorobenzyl)-1H-pyrrole-2-yl]etanone (3.85 g, yield: 25%).

NMR (CDCl$_3$) δ: 3.37 (3H, s), 3.96 (2H, s), 6.00-6.04 (1H, m), 6.82-6.86 (1H, m), 6.96-7.05 (2H, m), 7.12-7.18 (2H, m), 9.11 (1H, brs).

(A-83) According to the method of the above-mentioned example A-18, 4-[5-(4-fluorobenzyl)-1H-pyrrole-2-yl]-2-hydroxy-4-oxo-2-butenoic acid methyl ester was synthesized from the above-mentioned compound A-82.

NMR (CDCl$_3$) δ: 3.92 (3H, s), 4.00 (2H, s), 6.10-6.13 (1H, m), 6.75 (1H, s), 6.97-7.06 (3H, m), 7.12-7.19 (2H, m), 9.09 (1H, brs).

(A-84) According to the method of the above-mentioned example A-19, 4-[5-(4-fluorobenzyl)-1H-pyrrole-2-carbony-1]-3-hydroxy-1-methyl-1,5-dihydropyrrole-2-one was synthesized from the above-mentioned compound A-83.

NMR (DMSO-d$_6$) δ: 3.00 (3H, s), 3.95 (2H, s), 4.22 (2H, s), 5.97-6.03 (1H, m), 7.06-7.16 (3H, m), 7.26-7.34 (2H, m), 12.00 (1H, brs).

Melting point: 221-223° C.

Elementary analysis as C$_{17}$H$_{15}$FN$_2$O$_3$

Calcd. (%): C, 64.96; H, 4.81; N, 8.91; F, 6.04.

Found (%): C, 64.87; H, 4.68; N, 8.80; F, 6.10.

The following compound was synthesized by the above-mentioned method.

4-[5-(4-Fluorobenzyl)-1H-pyrrole-2-carbonyl]-3-hydroxy-1-isopropyl-1,5-dihydropyrrole-2-one NMR (DMSO-d$_6$) δ: 1.20 (6H, d, J=6.9 Hz), 3.95 (2H, s), 4.17 (2H, s), 4.19-4.31 (1H, m), 5.99-6.03 (1H, m), 7.07-7.18 (3H, m), 7.27-7.35 (2H, m), 11.96 (1H, brs).

Melting point: 222-224° C.

Elementary analysis as C$_{19}$H$_{19}$FN$_2$O$_3$

Calcd. (%): C, 66.66; H, 5.59; N, 8.18; F, 5.55.

Found (%): C, 66.66; H, 5.49; N, 8.12; F, 5.62.

Compound A-89

4-[4-(4-Fluorobenzyl)-1H-pyrrole-3-carbonyl]-3-hydroxy-1-methyl-1,5-dihydropyrrole-2-one

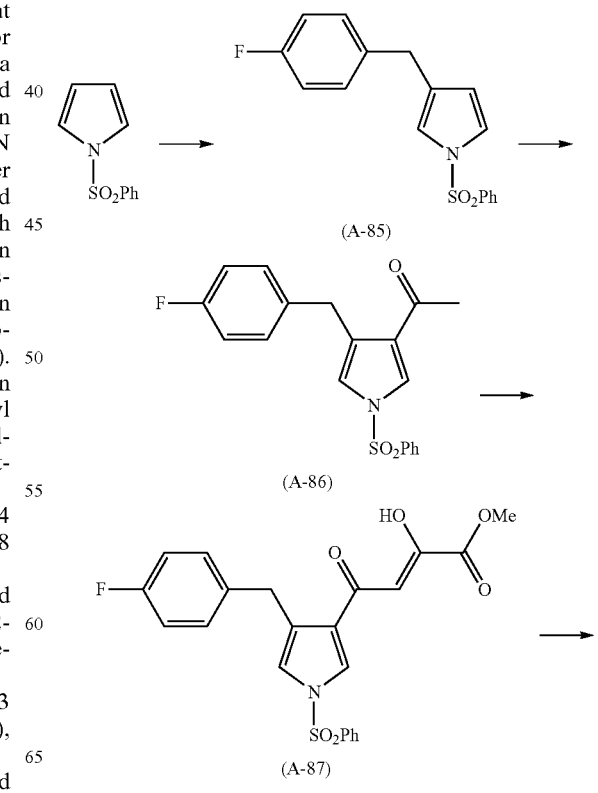

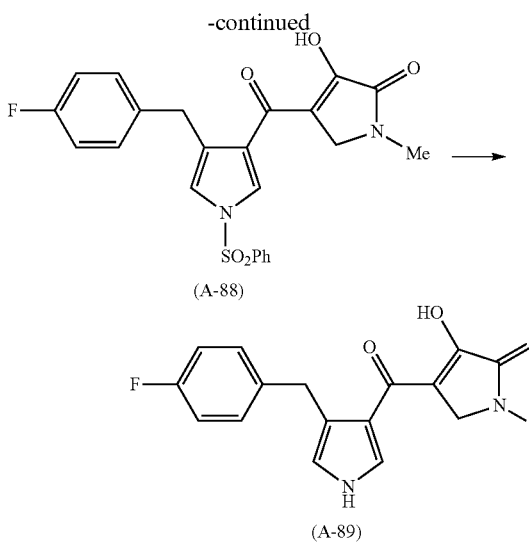

(A-85) According to the method of the reference (J. Org. Chem., 1983, 48, p 3214), 1-benzenesulfonyl-1H-pyrrole (J. Org. Chem., 1999, 64, p 3379) was reacted with 4-fluorobenzoyl chloride (2.88 ml, 26.5 mmol) in the presence of aluminum chloride (3.25 g, 26.5 mmol) in methylene chloride (40 ml) to give a crude ketone (9.15 g) which was reduced by borane tert-butylamine complex (11.6 g, 133 mmol) in the presence of aluminum chloride (8.88 g, 66.6 mmol) in methylene chloride (200 ml) according to the method of the reference (Synth. Comm., 1990, 20, p 1647). The residue was purified with column chromatography (ethyl acetate:n-hexane=1:4-1:3) to give 1-benzenesulfonyl-3-(4-fluorobenzyl)-1H-pyrrole (4.66 g, yield: 61%).

NMR (CDCl$_3$) δ: 3.70 (2H, s), 6.10 (1H, dd, J=1.5, 3.0 Hz), 6.86-7.12 (6H, m), 7.46-7.64 (3H, m), 7.80-7.85 (2H, m).

(A-86) To a methylene chloride (35 ml) suspension of aluminum chloride (4.33 g, 32.5 mmol) at room temperature, was added dropwise a methylene chloride (5 ml) solution of acetic anhydride (1.66 g, 16.3 mmol) for 15 minutes under stirring, to which a methylene chloride (10 ml) solution of the above-mentioned compound A-85 (4.66 g, 14.8 mmol) was added dropwise under ice cooling. The solution was stirred for 1 hour under ice cooling, then for 30 minutes at room temperature, to which was added ice water and extracted with ethyl acetate. The extract was washed with a saturated sodium hydrogen carbonate aqueous solution and a saturated NaCl aqueous solution, then dried and evaporated under reduced pressure. The residue was Crystallized by diisopropyl ether and n-hexane and filtered out. The filtrate was evaporated under reduced pressure, then the residue was purified with column chromatography (ethyl acetate:n-hexane=1:3-1:2) and crystallized with (diisopropyl ether-n-hexane) to give 1-[1-benzenesulfonyl-4-(4-fluorobenzyl)-1H-pyrrole-3-yl]etanone (3.57 g, yield: 68%).

NMR (CDCl$_3$) δ: 2.39 (3H, s), 3.98 (2H, s), 6.66-6.89 (1H, m), 6.91-7.15 (4H, m), 7.52-7.89 (6H, m).

(A-87) According to the method of the above-mentioned example A-18, 4-[1-benzenesulfonyl-4-(4-fluorobenzyl)-1H-pyrrole-3-yl]-2-hydroxy-4-oxo-2-butenoic acid methyl ester was synthesized from the above-mentioned compound A-86.

NMR (CDCl$_3$) δ: 3.93 (3H, s), 4.03 (2H, s), 6.72-6.74 (1H, m), 6.93-7.15 (4H, m), 7.53-7.92 (6H, m).

(A-88) According to the method of the above-mentioned example A-19, 4-[1-benzenesulfonyl-4-(4-fluorobenzyl)-1H-pyrrole-3-carbonyl]-3-hydroxy-1-methyl-1,5-dihydropyrrole-2-one was synthesized from the above-mentioned compound A-87.

NMR (DMSO-d$_6$) δ: 2.99 (3H, s), 3.90 (2H, s), 4.02 (2H, s), 7.00-7.21 (6H, m), 7.63-7.82 (3H, m), 7.97-8.14 (3H, m).

The following compound was synthesized by the above-mentioned method.

4-[1-Benzenesulfonyl-4-(4-fluorobenzyl)-1H-pyrrole-3-carbonyl]-3-hydroxy-1-isopropyl-1,5-dihydropyrrole-2-one NMR (DMSO-d$_6$) d: 1.18 (6H, d, J=6.7 Hz), 3.90 (2H, s), 3.97 (2H, s), 4.16-4.31 (1H, m), 7.05-7.15 (6H, m), 7.63-7.82 (5H, m), 8.13 (2H, brs).

(A-89) According to the method of the reference (J. Org. Chem., 1983, 48, p 3214), the protected NH group of the pyrrole ring of the above-mentioned compound A-88 was deprotected by hydrolysis to give 4-[4-(4-fluorobenzyl)-1H-pyrrole-3-carbonyl]-3-hydroxy-1-methyl-1,5-dihydropyrrole-2-one.

NMR (DMSO-d$_6$) δ: 2.99 (3H, s), 4.02 (2H, s), 4.19 (2H, s), 6.54 (1H, s), 7.00-7.27 (4H, m), 7.62 (1H, s), 11.41 (1H, brs).

Melting point: 265-267° C.
Elementary analysis as $C_{17}H_{15}FN_2O_3$ 0.1H$_2$O
Calcd. (%): C, 64.59; H, 4.85; N, 8.86; F, 6.01.
Found (%): C, 64.54; H, 4.72; N, 8.82; F, 5.89.

The following compound was synthesized by the above-mentioned method.

4-[4-(4-Fluorobenzyl)-1H-pyrrole-3-carbonyl]-3-hydroxy-1-isopropyl-1,5-dihydropyrrole-2-one NMR (DMSO-d$_6$) δ: 1.20 (6H, d, J=6.7 Hz), 4.02 (2H, s), 4.14 (2H, s), 4.18-4.32 (1H, m), 6.56 (1H, s), 7.00-7.26 (4H, m), 7.68 (1H, s), 11.39 (1H, brs).

Melting point: 255-258° C.
Elementary analysis as $C_{19}H_{19}FN_2O_3$ 0.2H$_2$O
Calcd. (%): C, 65.96; H, 5.65; N, 8.10; F, 5.49.
Found (%): C, 66.06; H, 5.45; N, 8.01; F, 5.42.

Compound A-92

4-[1-(4-Fluorobenzyl)-1H-pyrrole-2-carbonyl]-3-hydroxy-1-methyl-1,5-dihydropyrrole-2-one

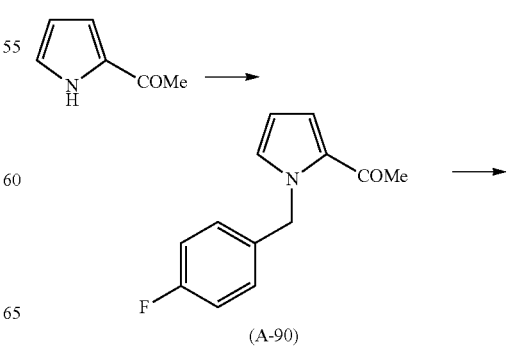

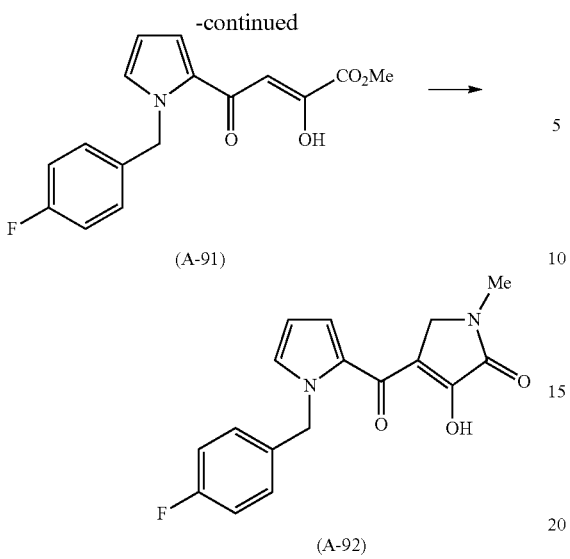

(A-90) Sodium hydride (5 g, 12.5 mmol) was washed with n-hexane, then dried and suspend in dimethylformamide 100 ml, to which were added 2-acetylpyrrole (10.9 g, 10 mmol) and 4-fluorobenzyl bromide (20 g, 10.6 mmol) under ice cooling. Then the mixture, was stirred at room temperature for 1 hour and added to an ammonium chloride solution. The solution was extracted with ethyl ether, then washed, dried and evaporated under reduced pressure. The residue was purified with column chromatography (ethyl acetate:n-hexane=1:10) to give the objective compound 21:4 g (yield 99%).

NMR (CDCl$_3$) δ: 2.41 (s, 3H), 5.53 (s, 2H), 6.20 (dd, 1H, J=3.9 Hz, 2.4 Hz), 6.90 (m, 1H), 6.92-7.02 (m, 3H), 7.07-7.12 (m, 2H).

(A-91) To a tetrahydrofuran 40 ml solution of the above-mentioned compound A-90 (4.35 g, 20 mmol), lithium hexamethyl disilazide (1N tetrahydrofuran solution, 24 ml) was added dropwise at −78° C. 10 Minutes later, oxalic acid dimethyl (2.83 g, 24 mmol) was added thereto and stirred at 0° C. for 30 minutes. The solution was added to ice water and acidified with hydrochloric acid, then extracted with ethyl acetate, washed, dried and evaporated under reduced pressure. The residue was Crystallized with n-hexane to give the objective compound 5.7 g (yield 94%).

NMR (CDCl$_3$) δ: 3.90 (s, 3H), 5.60 (s, 2H), 6.28 (dd, 1H, J=3.9 Hz, 2.4 Hz), 6.84 (s, 1H), 6.95-6.99 (m, 3H), 7.07-7.16 (m, 3H).

(A-92) To a dioxane 50 ml solution of the above-mentioned compound A-91 (1.0 g, 3.3 mmol), methylamine (40% methyl alcohol solution) and paraformaldehyde 300 mg were added at room temperature for 1 hour under stirring. The solvent was evaporated under reduced pressure, to which was added an ammonium chloride solution and extracted with chloroform, washed, dried and evaporated under reduced pressure. The residue was Crystallized by isopropyl alcohol to give 4-[1-(4-fluorobenzyl)-1H-pyrrole-2-carbonyl]-3-hydroxy-1-methyl-1,5-dihydropyrrole-2-one 720 mg (yield 69%).

Melting point: 150-151° C.
Elementary analysis as $C_{17}H_{15}N_2O_3F$
Calcd. (%) C, 64.96; H, 4.81; N, 8.91; F, 5.85.
Found (%) C, 65.81; H, 4.68; N, 8.74; F, 5.85.
NMR (CDCl$_3$) δ: 3.15 (s, 3H), 4.32 (s, 2H), 5.60 (s, 2H), 6.31 (dd, 1H, J=4.2 Hz, 2.4 Hz), 6.91 (dd, 1H, J=4.2 Hz, 1.5 Hz), 6.96-7.16 (m, 5H).

The following compound was synthesized by the above-mentioned method.

4-[1-(4-Fluorobenzyl)-1H-pyrrole-2-carbonyl]-3-hydroxy-1-isopropyl-1,5-dihydropyrrole-2-one Melting point: 132° C.
Elementary analysis as $C_{19}H_{19}N_2O_3F$
Calcd. (%) C, 66.66; H, 5.59; N, 8.18; F, 5.55.
Found (%) C, 66.46; H, 5.48; N, 8.14; F, 5.47.
NMR (CDCl$_3$) δ: 1.28 (d, 6H, J=6.6 Hz), 4.25 (s, 2H), 4.57 (m, 1H), 5.61 (s, 2H), 6.32 (dd, 1H, J=4.2 Hz, 2.4 Hz), 6.95-7.14 (m, 6H).

Compound A-98

4-[5-(4-Fluorobenzyl)oxazole-4-carbonyl]-3-hydroxy-1-methyl-1,5-dihydropyrrole-2-one

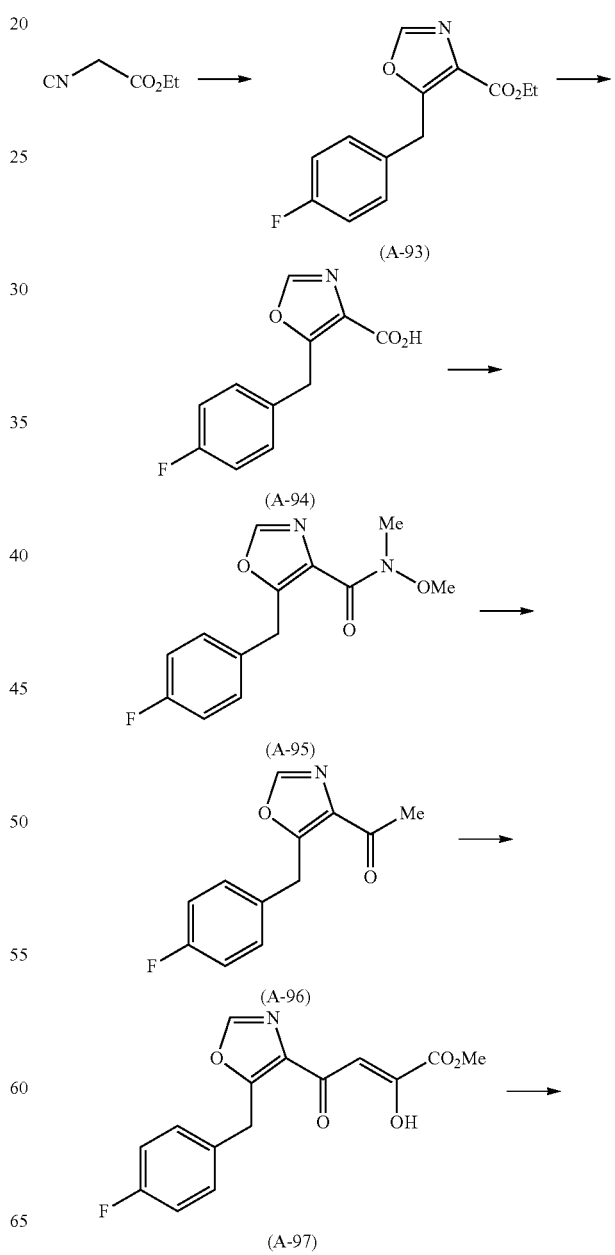

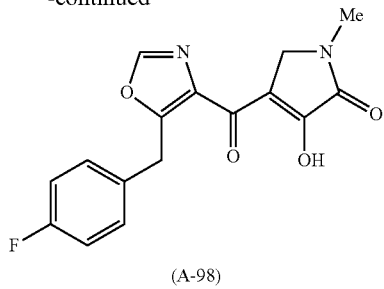

(A-98)

(A-93) To a tetrahydrofuran solution (20 ml) of potassium t-butoxide (3.4 g, 30 mmol), isocyanoacetic acid ethylester (3.4 g, 30 mmol) was added dropwise thereto under ice cooling. 10 minutes later, 4-phenylacetic acid chloride (5 g, 29 mmol) was added dropwise under ice cooling and stirred for 1 hour. The solution was added to the ammonium chloride solution and extracted with ethyl acetate, then washed, dried and evaporated under reduced pressure. The residue was purified with column chromatography (ethyl acetate:n-hexane=1:2) to give the objective compound 4.8 g (yield 65%).

NMR (CDCl$_3$) δ: 1.42 (t, 3H, J=7.1 Hz), 4.37 (s, 2H), 3.92 (q, 2H, J=7.1 Hz), 6.95-7.03 (m, 2H), 7.23-7.29 (m, 2H), 7.76 (s, 1H).

(A-94) To an ethanol 30 ml solution of the above-mentioned compound A-93 (4.8 g, 19.3 mmol), 1N lithium hydroxide solution 20 ml was added at room temperature for 1 hour under stirring, then the mixture was evaporated under reduced pressure and acidified with 1N hydrochloric acid. The solution was extracted with ethyl acetate, then washed, dried and evaporated under reduced pressure. The residue was Crystallized with isopropyl alcohol to give the objective compound 3.9 g (yield 91%).

NMR (DMSO-d$_6$) δ: 4.38 (s, 2H), 7.11-7.18 (m, 2H), 7.28-7.31 (m, 2H), 8.34 (s, 1H), 13.20 (bs, 1H).

(A-95) According to the method of the above-mentioned example A-20, 5-(4-fluorobenzyl) oxazole-4-carboxylic acid methoxymethylamide 4.4 g (yield 95%) was synthesized from the above-mentioned compound A-94 (3.9 g, 17.6 mmol).

NMR (CDCl$_3$) δ: 3.42 (s, 3H), 3.83 (s, 3H), 4.28 (s, 2H), 6.95-7.01 (m, 2H), 7.25-7.34 (m, 2H), 7.72 (s, 1H).

(A-96) According to the method of the above-mentioned example A-21, 1-[5-(4-fluorobenzyl)oxazole-4-yl]etanone 3.5 g (yield 96%) was synthesized from the above-mentioned compound A-95 (4.4 g, 16.7 mmol).

NMR (CDCl$_3$) δ: 2.59 (s, 3H), 4.36 (s, 2H), 6.95-7.01 (m, 2H), 7.25-7.34 (m, 2H), 7.71 (s, 1H).

(A-97) According to the method of the above-mentioned example A-18, 4-[5-(4-fluorobenzyl)oxazole-4-yl]-2-hydroxy-4-oxo-2-butenoic acid methylester 5.37 g (yield 90%) was synthesized from the above-mentioned compound A-96 (4.3 g, 19.6 mmol).

NMR (CDCl$_3$) δ: 3.93 (s, 3H), 4.43 (s, 2H), 6.95-7.04 (m, 2H), 7.26 (s, 1H), 7.25-7.31 (m, 2H), 7.77 (s, 1H).

(A-98) According to the method of the above-mentioned example A-19, 4-[5-(4-fluorobenzyl)oxazole-4-carbonyl]-3-hydroxy-1-methyl-1,5-dihydropyrrole-2-one 760 mg (yield 67%) was synthesized from the above-mentioned compound A-97 (1 g, 3.3 mmol).

NMR (CDCl$_3$) δ: 3.93 (s, 3H), 4.14 (s, 2H), 4.49 (s, 2H), 6.95-7.04 (m, 2H), 7.25-7.31 (m, 2H), 8.14 (s, 1H).

Melting point: 257° C.

Elementary analysis as C$_{16}$H$_{13}$N$_2$O$_4$F.0.2HCl

Calcd. (%) C, 59.39; H, 4.11; N, 8.66; F, 5.87 Cl: 2.19.

Found (%) C, 59.51; H, 4.01; N, 8.65; F, 5.69 Cl: 2.12.

The following compound was synthesized by the above-mentioned method.

4-[5-(4-Fluorobenzyl)oxazole-4-carbonyl]-3-hydroxy-1-isopropyl-1,5-dihydropyrrole-2-one NMR (CDCl$_3$) δ: 3.93 (s, 3H), 4.14 (s, 2H), 4.49 (s, 2H), 6.95-7.04 (m, 2H), 7.25-7.31 (m, 2H), 8.14 (s, 1H).

Melting point: 193° C.

Elementary analysis as C$_{18}$H$_{17}$N$_2$O$_4$F

Calcd. (%) C, 62.79; H, 4.98; N, 8.14; F, 5.52.

Found (%) C, 62.73; H, 4.91; N, 8.14; F, 5.42.

Compound A-102

4-[1-(4-Fluorobenzyl)-1H-pyrazole-4-carbonyl]-3-hydroxy-1-isopropyl-1,5-dihydropyrrole-2-one

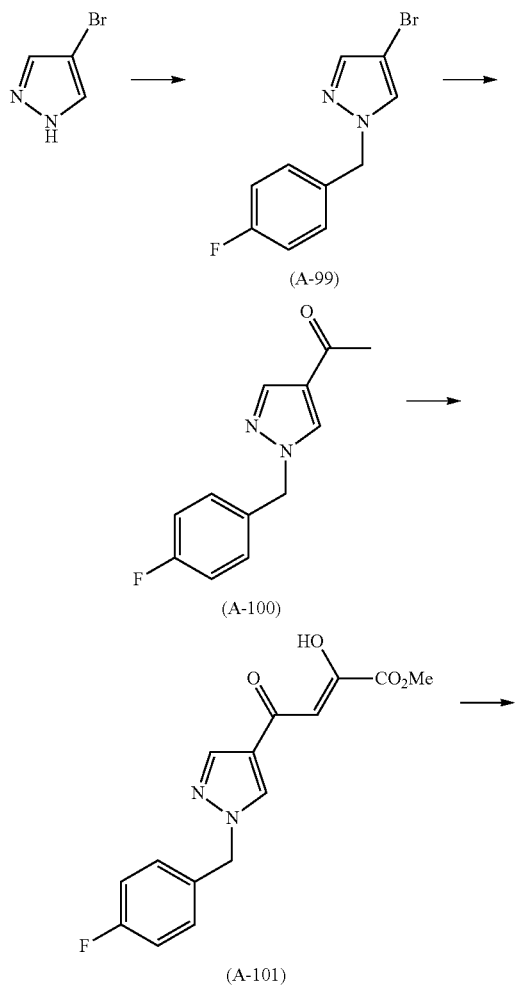

-continued

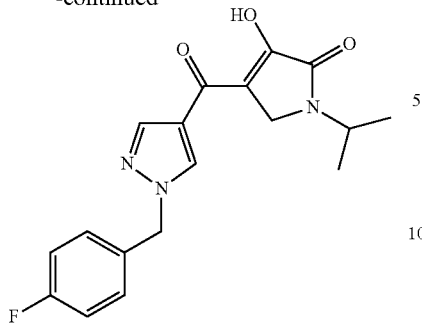
(A-102)

(A-99) To a N,N-dimethylformamide solution (20 ml) of 4-bromopyrazole (5.0 g, 34.0 mmol) at 0° C., sodium hydride (60%) (2.04 g, 51.0 mmol) was added, then the mixture was stirred for 20 minutes, to which was added 4-fluorobenzyl bromide (5.1 ml, 40.8 mmol) at room temperature for 1 hour. The solution was poured into ice water, then extracted with ether, washed, dried and evaporated under reduced pressure. The residue was purified with silica gel column chromatography (n-hexane/ethyl acetate=81) to give 4-bromo1-(4-fluorobenzyl)-1H-pyrazole (7.42 g, yield: 86%).

(A-100) A mixture of the above-mentioned compound A-99 (1.28 g, 5.00 mmol), acetic acid palladium (34 mg, 0.150 mmol), 1,3-diphenylphosphinopropane (136 mg, 0.330 mmol), butylvinylether (3.24 ml, 25.0 mmol) and potassium carbonate (829 mg, 6.00 mmol) in a solution of N,N-dimethylformamide (12.5 ml) and water (3 ml) was reacted in a shield tube at 100° C. for 24 hours. The solution was Cooled, then poured into 5% hydrochloric acid and stirred for 30 minutes, to which was added a saturated sodium bicarbonate aqueous solution, extracted with ethyl acetate, washed, dried, and evaporated under reduced pressure. The residue was purified with silica gel column chromatography (n-hexane/ethyl acetate=2/1) to give 1-[1-(4-fluorobenzyl)-1H-pyrazole-4-yl]etanone (555 mg, yield: 51%).

NMR (CDCl$_3$) δ:2.41 (3H, s), 5.28 (2H, s), 7.01-7.09 (2H, m), 7.21-7.28 (2H, m), 7.85 (1H, s), 7.93 (1H, s).

(A-101) According to the method of the above-mentioned example A-18, 4-[1-(4-fluorobenzyl)-1H-pyrazole-4-yl]-2-hydroxy-4-oxo-2-butenoic acid methyl (1.08 g, yield: 77%) was synthesized from the above-mentioned compound A-100 (1.00 g, 4.59 mmol).

NMR (CDCl$_3$) δ: 3.92 (3H, s), 5.31 (2H, s), 6.67 (1H, s), 7.03-7.12 (2H, m), 7.23-7.28 (2H, m), 7.94 (1H, s), 8.02 (1H, s).

(A-102) According to the method of the above-mentioned example A-19, 4-[1-(4-fluorobenzyl)-1H-pyrazole-4-carbonyl]-3-hydroxy-1-isopropyl-1,5-dihydropyrrole-2-one (122 mg, yield: 36%) was synthesized from the above-mentioned compound A-101 (304 mg, 1.00 mmol).

Melting point: 129.5-131° C.
Elementary analysis as $C_{18}H_{18}FN_3O_3$
Calcd. (%): C, 62.97; H, 5.28; N, 12.24; F, 5.53.
Found (%): C, 62.96; H, 5.22; N, 12.22; F, 5.49.
NMR (CDCl$_3$) δ: 1.30 (6H, d, J=6.7 Hz), 4.22 (2H, s), 4.56 (1H, sep, J=6.7 Hz), 5.33 (2H, s), 7.03-7.12 (2H, m), 7.23-7.31 (2H, m), 7.97 (1H, s), 8.05 (1H, s).

The following compound was synthesized by the above-mentioned method.

(4-1) 4-[1-(4-Fluorobenzyl)-1H-pyrazole-4-carbonyl]-3-hydroxy-1-methyl-1,5-dihydropyrrole-2-one Melting point: 150-151° C.
Elementary analysis as $C_{16}H_{14}FN_3O_3$
Calcd. (%): C, 60.95; H, 4.48; N, 13.33; F, 6.03.
Found (%): C, 60.73; H, 4.38; N, 13.25; F, 6.00.
NMR (CDCl$_3$) δ: 3.18 (3H, s), 4.29 (2H, s), 5.33 (2H, s), 7.03-7.13 (2H, m), 7.24-7.31 (2H, m), 7.92 (1H, s), 8.01 (1H, s).

Compound A-107

4-[2-(4-Fluorobenzyl)oxazole-5-carbonyl]-3-hydroxy-1-isopropyl-1,5-dihydropyrrole-2-one

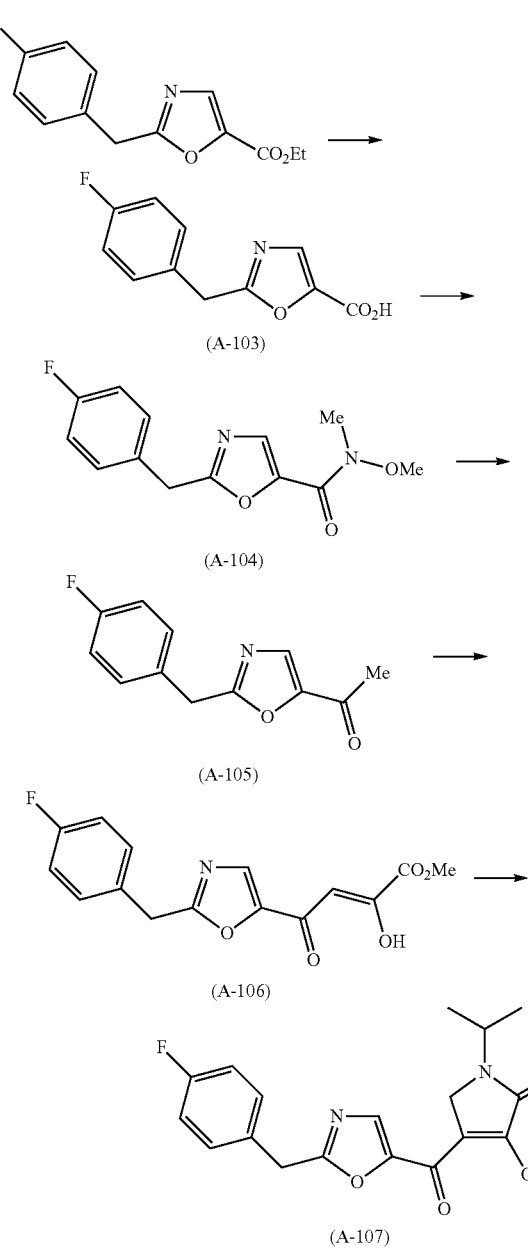

(A-103) To a dioxane solution (30 ml) of 2-(4-fluorobenzyl)oxazole-5-carboxylic acid ethyl (10 g, 40.1 mmol) which was prepared according to the method of the reference (J. Chem. Soc., Perkin Trans. 1,1997, p 2673), 1N lithium hydroxide aqueous solution (48 ml, 48.0 mmol) was added for 3 minutes at 0° C. The mixture was stirred at room temperature for 30 minutes, then 1N hydrochloric acid (55 ml, 55.0 mmol) was added and extracted with ethyl acetate, washed, dried and evaporated under reduced pressure. The residue was Crystallized using diisopropyl ether and hexane to give 2-(4-fluorobenzyl)oxazole-5-carboxylic acid (8.50 g, yield: 95%).

NMR (CDCl$_3$) δ: 4.19 (2H, s), 7.00-7.08 (2H, m), 7.25-7.34 (2H, m), 7.80 (1H, s).

The following compound was synthesized by the above-mentioned method using 2-(4-fluorobenzyl)oxazole-4-carboxylic acid ethyl which was prepared according to the method of the reference (J. Org. Chem., 1996, 61, p 1761).

NMR (CDCl$_3$) δ: 4.21 (2H, s), 6.97-7.06 (2H, m), 7.25-7.33 (2H, m), 8.24 (1H, s).

(A-104) According to the method of the above-mentioned example A-20, 2-(4-fluorobenzyl)oxazole-5-carboxylic acid methoxymethylamide (955 mg, yield: 76%) was synthesized from the above-mentioned compound A-103 (1.0 g, 4.70 mmol).

NMR (CDCl$_3$) δ: 3.33 (3H, s), 3.74 (3H, s), 4.16 (2H, s), 6.97-7.06 (2H, m), 7.25-7.34 (2H, m), 7.60 (1H, s).

The following compound was synthesized by the above-mentioned method.

2-(4-Fluorobenzyl)oxazole-4-carboxylic acid methoxymethylamide

NMR (CDCl$_3$) δ: 3.37 (3H, s), 3.73 (3H, s), 4.14 (2H, s), 6.96-7.05 (2H, m), 7.25-7.33 (2H, m), 8.08 (1H, s).

(A-105) According to the method of the above-mentioned example A-21, 1-[2-(4-fluorobenzyl)oxazole-5-yl]etanone (7) (730 mg, yield: 92%) was synthesized from the above-mentioned compound A-104 (950 mg, 3.60 mmol).

NMR (CDCl$_3$) δ: 2.46 (3H, s), 4.16 (2H, s), 6.69-7.08 (2H, m), 7.25-7.33 (2H, m), 7.68 (1H, s).

The following compound was synthesized by the above-mentioned method.

1-[2-(4-Fluorobenzyl)oxazole-4-yl]etanone

NMR (CDCl$_3$) δ: 2.51 (3H, s), 4.12 (2H, s), 6.98-7.06 (2H, m), 7.24-7.31 (2H, m), 8.11 (1H, s).

(A-106) According to the method of the above-mentioned example A-18, 4-[2-(4-fluorobenzyl)oxazole-5-yl]-2-hydroxy-4-oxo-2-butenoic acid methyl (1.43 g, yield: 86%) was synthesized from the above-mentioned compound A-105 (1.20 g, 5.48 mmol).

NMR (CDCl$_3$) δ: 3.94 (3H, s), 4.19 (2H, s), 6.80 (1H, s), 7.00-7.09 (2H, m), 7.26-7.34 (2H, m), 7.83 (1H, s).

The following compound was synthesized by the above-mentioned method.

4-[2-(4-Fluorobenzyl)oxazole-4-yl]-2-hydroxy-4-oxo-2-butenoic acid methyl (A-107) According to the method of the above-mentioned example A-19, 4-[2-(4-fluorobenzyl)oxazole-5-carbonyl]-3-hydroxy-1-isopropyl-1,5-dihydropyrrole-2-one (256 mg, yield: 75%) was synthesized from the above-mentioned compound (8) (305 mg, 1.00 mmol).

Melting point: 174-178° C.
Elementary analysis as $C_{18}H_{17}FN_2O_4$.
Calcd. (%): C, 62.79; H, 4.98; N, 8.14; F, 5.52.
Found (%): C, 62.41; H, 4.89; N, 7.98; F, 5.33.
NMR (CDCl$_3$) δ: 1.25 (6H, d, J=6.8 Hz), 4.10 (2H, s), 4.23 (2H, s), 4.54 (1H, sep, J=6.8 Hz), 7.03-7.12 (2H, m), 7.28-7.35 (2H, m), 7.95 (1H, s).

The following compound was synthesized by the above-mentioned method.

4-[2-(4-Fluorobenzyl)oxazole-4-carbonyl]-3-hydroxy-1-isopropyl-1,5-dihydropyrrole-2-one Melting point: 154-155° C.
NMR (CDCl$_3$) δ: 1.26 (6H, d, J=6.8 Hz), 4.05 (2H, s), 4.22 (2H, s), 4.54 (1H, sep, J=6.8 Hz), 7.03-7.12 (2H, m), 7.25-7.32 (2H, m), 8.27 (1H, s).

Compound A-111

4-[5-(4-Fluorobenzyl)thiophene-2-carbonyl]-3-hydroxy-1-isopropyl-1,5-dihydropyrrole-2-one

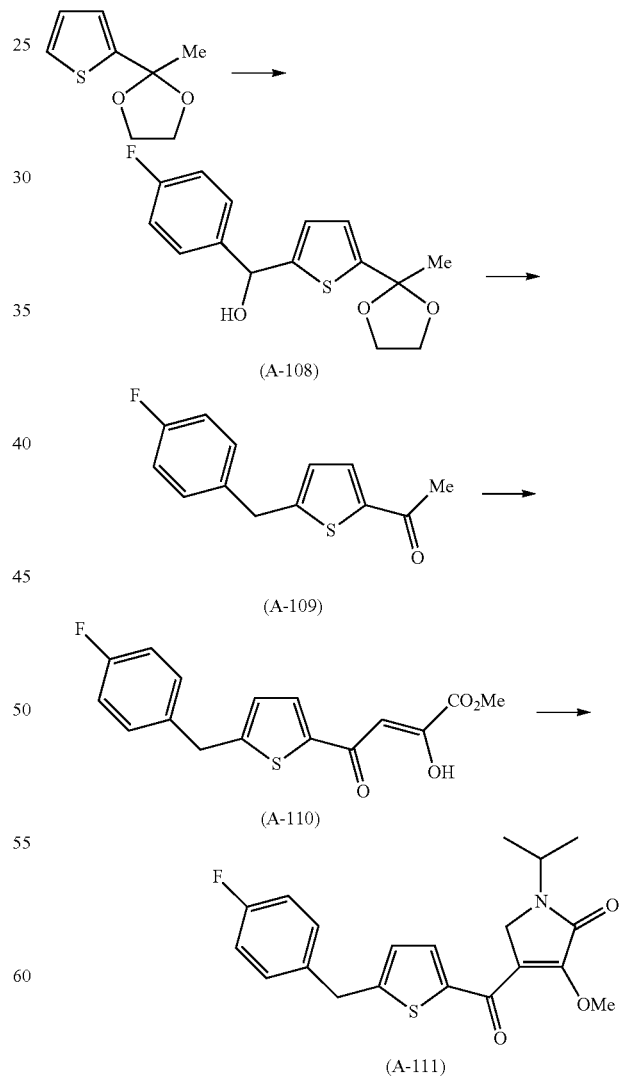

(A-108) To a tetrahydrofuran solution (25 ml) of 2-(2-methyl[1,3]dioxolane-2-yl)thiophene (2.0 g, 11.8 mmol) at −78° C., 1.55M n-butyllithium-hexane solution (9.1 ml, 14.1 mmol) was added dropwise for 10 minutes. The mixture was stirred at −78° C. for 1 hour, then a tetrahydrofuran solution (5 ml) of p-fluorobenzaldehyde (2.2 g, 17.7 mmol) was added and stirred for 15 minutes, to which was added a saturated ammonium chloride aqueous solution. The solution was extracted with ethyl acetate, washed, dried and evaporated. The residue was purified with silica gel column chromatography (n-hexane/ethyl acetate=31) to give (4-fluorophenyl)-[5-(2-methyl[1,3]dioxolane-2-yl)thiophene-2-yl]methyl alcohol (3.20 g, yield: 92%).

(A-109) To an acetonitrile solution (30 ml) of sodium iodide (7.85 g, 52.4 mmol), chlorotrimethylsilane (6.7 ml, 52.4 mmol) was added at 0° C., to which an acetonitrile solution (10 ml) of the above-mentioned compound A-108 (3.08 g, 10.5 mmol) was added and stirred for 1 hour. The saturated sodium bicarbonate and 0.5 M sodium thiosulfate aqueous solution were added to the reaction mixture and extracted with ethyl acetate, washed, dried and evaporated under reduced pressure. The residue was purified with silica gel column chromatography (n-hexane/ethyl acetate=31) to give 1-[5-(4-fluorobenzyl)thiophene-2-yl]etanone (1.34 g, yield: 55%).

NMR (CDCl$_3$) δ: 2.50 (3H, s), 4.13 (2H, s), 6.81 (1H, d, J=3.8 Hz), 6.97-7.05 (2H, m), 7.16-7.24 (2H, m), 7.53 (1H, d, J=3.8 Hz).

(A-110) According to the method of the above-mentioned example A-18, (4-[5-(4-fluorobenzyl)thiophene-2-yl]-2-hydroxy-4-oxo-2-butenoic acid methyl (1.27 g, yield: 76%) was synthesized from the above-mentioned compound A-109 (1.23 g, 5.26 mmol).

NMR (CDCl$_3$) δ: 3.93 (3H, s), 4.17 (2H, s), 6.85 (1H, s), 6.88 (1H, d, J=3.9 Hz), 6.98-7.07 (2H, m), 7.17-7.24 (2H, m), 7.69 (1H, d, J=3.9 Hz).

(A-111) According to the method of the above-mentioned example A-19, 4-[5-(4-fluorobenzyl)thiophene-2-carbonyl]-3-hydroxy-1-isopropyl-1,5-dihydropyrrole-2-one (181 mg, yield: 50%) was synthesized from the above-mentioned compound A-110 (320 mg, 1.00 mmol).

Melting point: 138-139° C.

NMR (CDCl$_3$) δ: 1.30 (6H, d, J=6.8 Hz), 4.19 (2H, s), 4.28 (2H, s), 4.58 (1H, sep, J=6.8 Hz), 6.91 (1H, d, J=3.9 Hz), 7.00-7.07 (2H, m), 7.19-7.25 (2H, m), 7.64 (1H, d, J=3.9 Hz).

Compound A-115

4-[2-(4-Fluorobenzyl)-2H-pyrazole-3-carbonyl]-3-hydroxy-1-methyl-1,5-dihydropyrrole-2-one

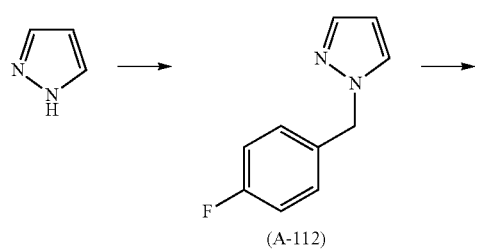

(A-112)

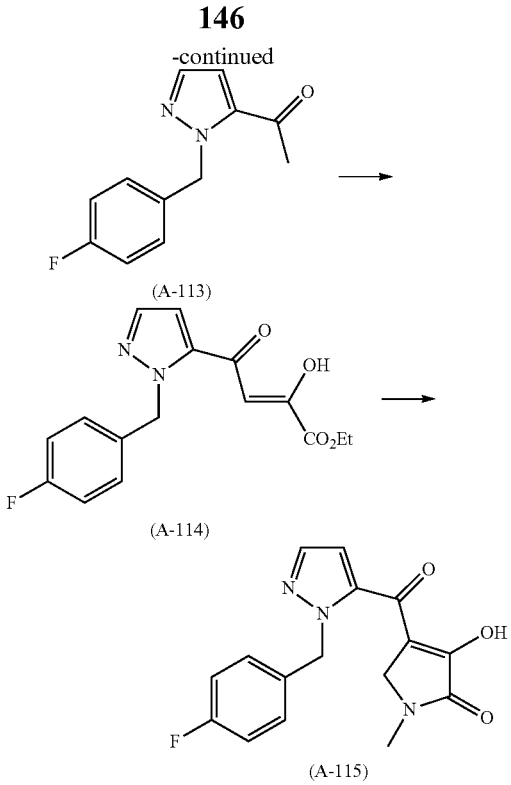

(A-112) To a dimethylformamide (57 ml) suspension of sodium hydride (purity 60%, 3.23 g, 80.7 mmol), the dimethylformamide (5 ml) solution of pyrazole (5.00 g, 73.4 mmol) was added dropwise. The mixture was stirred at room temperature for 1 hour, then to which was added a dimethylformamide (5 ml) solution of 4-fluorobenzylbromide (14.6 g, 77.1 mmol) and stirred for 1 hour. The mixture was poured into ice water, extracted with ethyl acetate, washed, dried and evaporated under reduced pressure to give a crude product of 1-(4-fluorobenzyl)-1H-pyrazole (14.2 g, yield: 100%).

NMR (CDCl$_3$) δ: 5.29 (2H, s), 6.29 (1H, dd, J=1.8 Hz, 2.1 Hz), 7.00-7.05 (2H, m), 7.17-7.21 (2H, m), 7.38 (1H, d, J=2.1 Hz), 7.55 (1H, d, J=1.8 Hz).

(A-113) To a solution of tetrahydrofuran (35 ml)-diethyl ether (23 ml) of the above-mentioned compound A-112 (2.00 g, 11.4 mol), n-butyllithium (7.90 ml, 12.5 mmol, 1.59M hexane solution) was added at −78° C., then the mixture was stirred for 1.5 hours, to which was added acetic anhydride (2.32 g, 22.7 mmol). The mixture was stirred for 1 hour under ice cooling, then sodium hydrogen carbonate aqueous solution was added and extracted with ethyl acetate, washed, dried and evaporated under reduced pressure. The residue was purified with silica gel column chromatography (n-hexane:ethyl acetate=4:1) to give 1-[2-(4-fluorobenzyl)-2H-pyrazole-3-yl]etanone (700 mg, yield: 28%).

NMR (CDCl$_3$) δ: 4.50 (3H, s), 5.71 (2H, s), 6.87 (1H, d, J=2.1 Hz), 6.95-7.00 (2H, m), 7.24-7.29 (2H, m), 7.55 (1H, d, J=2.1 Hz).

(A-114) To a tetrahydrofuran solution (8 ml) of the above-mentioned compound A-113 (1.00 g, 4.58 mmol), lithium hexamethyldisilazane (5.50 ml, 5.50 mmol, 1.0M tetrahydrofuran solution) was added dropwise at −78° C. for 10 minutes under stirring, to which was added oxalic acid diethyl (804 mg, 5.50 mmol). The mixture was stirred at 0° C. for 1 hour, then ammonium chloride aqueous solution was added, then extracted with ethyl acetate, washed, dried and evaporated under reduced pressure. The crystal was washed with isopropyl ether to give 4-[2-(4-fluorobenzyl)-2H-pyrazole-3-yl]-2-hydroxy-4-oxo-2-butenoic acid ethyl ester (754 mg, yield: 52%).

NMR (CDCl$_3$) δ: 1.40 (3H, q, J=6.9 Hz), 4.39 (2H, q, J=6.9 Hz), 5.78 (2H, s), 6.82 (1H, s), 6.96-7.01 (3H, m), 7.24-7.29 (2H, m), 7.61 (1H, d, J=2.1 Hz), 14.24 (1H, br).

(A-115) To a dioxane (13 ml) solution of the above-mentioned compound A-114 (318 mg, 1.00 mmol), methylamine (2.20 mmol, 40% ethanol solution) and paraformaldehyde (90 mg) were added. The mixture was stirred for 1 hour at room temperature and diluted with ammonium chloride aqueous solution and chloroform. An insoluble product was filtered out, then the filtrate was extracted with chloroform, washed, dried and evaporated under reduced pressure. The crude crystal was recrystallized by acetone-isopropylether to give 4-[2-(4-fluorobenzyl)-2H-pyrazole-3-carbonyl]-3-hydroxy-1-methyl-1,5-dihydropyrrole-2-one (161 mg, yield: 51%).

Melting point: 179-181° C.
Elementary analysis as C$_{16}$H$_{14}$FN$_2$O$_3$
Calcd. (%): C, 60.95; H, 4.48; N, 13.33; F, 6.03.
Found (%): C, 60.86; H, 4.24; N, 13.28; F, 5.78.
NMR (CDCl$_3$) δ: 3.17 (3H, s), 4.28 (2H, s), 5.77 (2H, s), 6.82 (1H, d, J=2.2 Hz), 6.98 (2H, t, J=8.7 Hz), 7.24-7.29 (2H, m), 7.63 (1H, d, J=2.2 Hz).

The following compound was synthesized by the above-mentioned method.

4-[2-(4-Fluorobenzyl)-2H-pyrazole-3-carbonyl]-3-hydroxy-1-isopropyl-1,5-dihydropyrrole-2-one (199 mg, yield: 58%)

Melting point: 170-171° C.
Elementary analysis as C$_{18}$H$_{18}$FN$_3$O$_3$
Calcd. (%): C, 62.97; H, 5.28; N, 12.24; F, 5.58.
Found (%): C, 62.95; H, 5.00; N, 12.25; F, 5.59.
NMR (CDCl$_3$) δ: 1.29 (6H, d, J=6.9 Hz), 4.20 (2H, s), 4.51-4.60 (1H, m), 5.77 (2H, s), 6.88 (1H, d, J=2.1 Hz), 6.96-7.02 (2H, m), 7.25-7.30 (2H, m), 7.65 (1H, d, J=2.1 Hz)

Compound A-124

4-[5-(4-Fluorobenzyl)furan-3-carbonyl]-3-hydroxy-1-methyl-1,5-dihydropyrrole-2-one

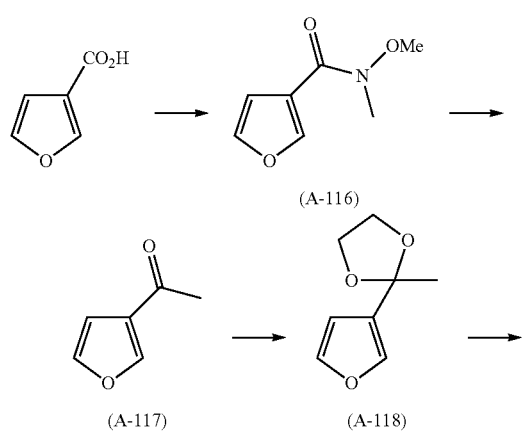

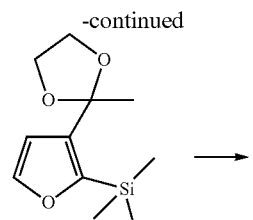
(A-119)

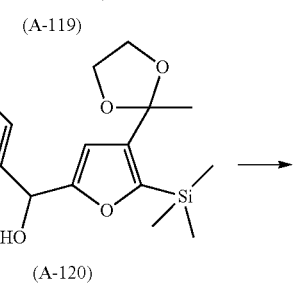
(A-120)

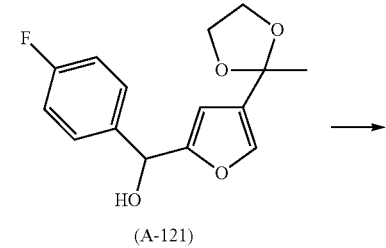
(A-121)

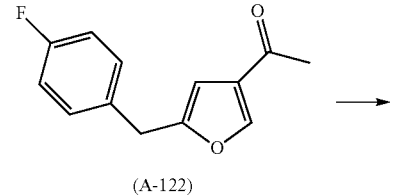
(A-122)

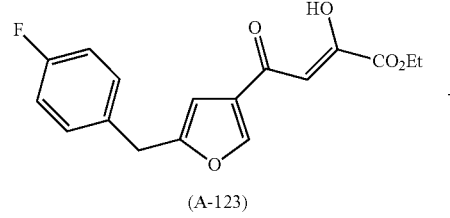
(A-123)

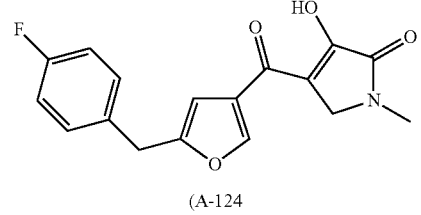
(A-124)

(A-116) To a diethylformamide (0.5 ml)-methylene chloride (200 ml) solution of furan-3-carboxylic acid (20.0 g, 178 mmol), oxalyl chloride (24.9 g, 196 mmol) was added dropwise. The mixture was stirred at room temperature for 1 hour and was evaporated under reduced pressure. The residue was dissolved into methylene chloride (200 ml), to which were added N,O-dimethylhydroxylamine hydrochloride (20.8 g, 214 mmol) and triethylamine (43.2 g, 427 mmol) at 0° C. The mixture was stirred at room temperature for 30 minutes, then was added water, which was extracted with chloroform, washed, dried and evaporated under reduced pressure to give a crude product of furan-3-carboxylic acid methoxymethylamide (31.3 g).

NMR (CDCl$_3$) δ: 3.34 (3H, s), 3.72 (3H, s), 6.87-6.88 (1H, m), 7.42-7.43 (1H, m), 8.03-8.04 (1H, m).

(A-117) To a tetrahydrofuran (300 ml) solution of the above-mentioned crude product A-116 (31.3 g), methyl magnesiumbromide (214 ml, 214 mmol, 1M tetrahydrofuran solution) was added at −50° C. The mixture was stirred at 0° C. for 2 hours, to which was added methyl magnesiumbromide (70 ml, 70 mmol, 1M tetrahydrofuran solution) and was stirred for 2 hours. 2N Hydrochloric acid (200 lm) was added to the mixture, which was extracted with diethyl ether and washed, dried and evaporated under reduced pressure to give 3-acetylfuran (15.9 g, yield: 81%).

NMR (CDCl$_3$) δ: 2.45 (3H, s), 6.77-6.78 (1H, m), 7.44-7.45 (1H, m), 8.02-8.03 (1H, m).

(A-118) A mixture of the above-mentioned compound A-117 (15.9 g, 144 mmol), p-toluenesulfonic acid mono hydrate (1.69 g, 8.90 mmol) and ethylene glycol (55.2 g, 890 mmol) was refluxed in benzene (500 ml) for 16 hours removing the produced water. Then, sodium hydrogen carbonate aqueous solution was added to the mixture, which was extracted with ethyl acetate, washed, dried and evaporated under reduced pressure to give 2-furan-3-yl-2-methyl[1,3]-dioxolane (20.9 g, yield: 94%).

NMR (CDCl$_3$) δ: 1.67 (3H, s), 3.89-4.05 (4H, m), 6.36-6.37 (1H, m), 7.36-7.37 (1H, m), 7.41-7.42 (1H, m).

(A-119) To a tetrahydrofuran (200 ml) solution of the above-mentioned compound A-118 (19.8 g, 128 mmol), n-butyllithium (90.0 ml, 141 mmol, 1.59M hexane solution) was added at −78° C. and the mixture was stirred at 0° C. for 30 minutes. Then chloro trimethylsilane (15.3 g, 141 mmol) was added at −78° C., which was stirred at 0° C. for 30 minutes, to which was added ammonium chloride aqueous solution and extracted with diethyl ether, washed, dried and evaporated under reduced pressure to give trimethyl[3-(2-methyl[1,3]dioxolane-2-yl)furan-2-yl]silane (26.7 g, yield: 92%).

NMR (CDCl$_3$) δ: 0.30 (9H, s), 1.63 (3H, s), 3.81-4.02 (4H, m), 6.39 (1H, d, J=1.8 Hz), 7.51 (1H, d, J=1.8 Hz).

(A-120) To a tetrahydrofuran (130 ml) solution of the above-mentioned compound A-119 (26.7 g, 118 mmol), n-butyllithium (89 ml, 142 mmol, 1.59M hexanesolution) was added at −78° C. and the mixture was stirred at 0° C. for 30 minutes, to which was added a tetrahydrofuran (60 ml) solution of p-fluorobenzaldehyde (17.6 g, 142 mmol) at −78° C. To the mixture was added ammonium chloride aqueous solution at room temperature, then extracted with diethyl ether, washed, dried and evaporated under reduced pressure. The residue was purified with silica gel column chromatography (n-hexane:ethyl acetate=4:1) to give (4-fluorophenyl)-[4-(2-methyl[1,3]dioxolane-2-yl)-5-trimethylsilanylfuran-2-yl]methyl alcohol (18.3 g, yield: 49%).

NMR (CDCl$_3$) δ: 0.29 (9H, S), 1.57 (3H, s), 3.78-3.99 (4H, m), 5.76 (1H, m), 6.02 (1H, s), 7.03-7.09 (2H, m), 7.41-7.46 (2H, m).

(A-121) Tetrabutylammonium fluoride (8 ml, 8 mmol, 1M tetrahydrofuran solution) was added to the above-mentioned compound A-120 (762 mg, 2.17 mmol) in tetrahydrofuran (8 ml), then the mixture was stirred at 60° C. for 30 minutes. The solution was diluted with diethyl ether, which was washed with 1N hydrochloric acid, water and saturated NaCl aqueous solution, successively, then dried and evaporated under reduced pressure to give (4-fluorophenyl)-[4-(2-methyl[1,3]dioxolane-2-yl)furan-2-yl]methyl alcohol (561 mg, yield: 93%).

NMR (CDCl$_3$) δ: 1.61 (3H, s), 3.86-4.03 (4H, m), 5.76 (1H, s), 6.06-6.07 (1H, m), 7.04-7.09 (2H, m), 7.37-7.44 (3H, m).

(A-122) A mixture of sodium iodide (1.90 g, 12.7 mmol) and chlorotrimethylsilane (1.39 g, 12.7 mmol) in acetonitrile (7 ml) was stirred at room temperature for 15 minutes, to which was added the above-mentioned compound A-121 (709 mg, 2.55 mmol) at 0° C., then the mixture was stirred at room temperature for 30 minutes. Water and 1N sodium hydroxide aqueous solution were added thereto successively, which was extracted with diethyl ether, washed, dried and evaporated under reduced pressure. The residue was purified with silica gel column chromatography (n-hexane:ethyl acetate=4:1) to give 3-acetyl-5-(4-fluorobenzyl)furan (307 mg, yield: 55%).

NMR (CDCl$_3$) δ: 2.39 (3H, s), 3.93 (2H, s), 6.36 (1H, d, J=0.9 Hz), 6.79-7.03 (2H, m), 7.16-7.21 (2H, m), 7.26 (1H, d, J=0.9 Hz).

(A-123) Lithium hexamethyldisilazane (4.30 ml, 4.30 mmol, 1M tetrahydrofuran solution) was added to the above-mentioned compound A-122 (773 mg, 3.54 mmol) in tetrahydrofuran (15 ml) at −78° C., then the mixture was stirred for 10 minutes. Oxalic acid diethyl (621 mg, 4.25 mmol) was added at −30° C., which was stirred for 30 minutes, to which was added water and 1N hydrochloric acid. The mixture was extracted with ethyl acetate, washed, dried and evaporated under reduced pressure. The crude crystal was washed with diisopropyl ether to give 4-[5-(4-fluorobenzyl)furan-3-yl]-2-hydroxy-4-oxo-2-butenoic acid ethyl ester (689 mg, yield: 61%).

NMR (CDCl$_3$) δ: 1.39 (3H, t, J=7.2 Hz), 3.96 (2H, s), 4.37 (2H, q, J=7.2 Hz), 6.40 (1H, d, J=0.9 Hz), 6.62 (1H, s), 6.99-7.04 (2H, m), 7.17-7.22 (2H, m), 8.03 (1H, d, J=0.9 Hz).

(A-124) To a dioxane (8 ml) solution of the above-mentioned compound A-123 (200 mg, 0.628 mmol), methylamine (1.38 mmol, 30% ethanol solution) and paraformaldehyde (57 mg) were added successively. The mixture was stirred at room temperature for 30 minutes, then diluted with ammonium chloride aqueous solution and chloroform. The insoluble product was filtered off, then the filtrate was extracted with chloroform, washed with 1N hydrochloric acid, water and saturated NaCl aqueous solution successively. The mixture was evaporated under reduced pressure, then the residue was Crystallized by acetone-diisopropyl ether to give 4-[5-(4-fluorobenzyl)furan-3-carbonyl]-3-hydroxy-1-methyl-1,5-dihydropyrrole-2-one (56 mg, yield: 28%).

Melting point: 158-160° C.
Elementary analysis as $C_{17}H_{14}FNO_4$
Calcd. (%): C, 64.76; H, 4.48; N, 4.44; F, 6.03.
Found (%): C, 64.54; H, 4.48; N, 4.41; F, 6.03.
NMR (CDCl$_3$) δ: 3.17 (3H, s), 3.98 (2H, s), 4.24 (2H, s), 6.43 (1H, s), 6.99-7.05 (2H, m), 7.18-7.23 (2H, m), 7.98 (1H, s).

The following compound was synthesized by the above-mentioned method.

4-[5-(4-Fluorobenzyl)furan-3-carbonyl]-3-hydroxy-1-isopropyl-1,5-dihydropyrrole-2-one (87 mg, yield: 43%)

Melting point: 162-164° C.
Elementary analysis as $C_{19}H_{18}FNO_4$
Calcd. (%): C, 66.46; H, 5.28; N, 4.08; F, 5.53.
Found (%): C, 66.42; H, 5.30; N, 3.96; F, 5.53.
NMR (CDCl$_3$) δ: 1.29 (6H, d, J=6.9 Hz), 3.98 (2H, s), 4.17 (2H, s), 4.51-4.60 (1H, m), 6.46 (1H, d, J=0.9 Hz), 6.98-7.04 (2H, m), 7.18-7.23 (2H, m), 8.03 (1H, d, J=0.9 Hz).

Compound A-130

4-[4-(4-Fluorobenzyl)oxazole-2-carbonyl]-3-hydroxy-1-methyl-1,5-dihydropyrrole-2-one

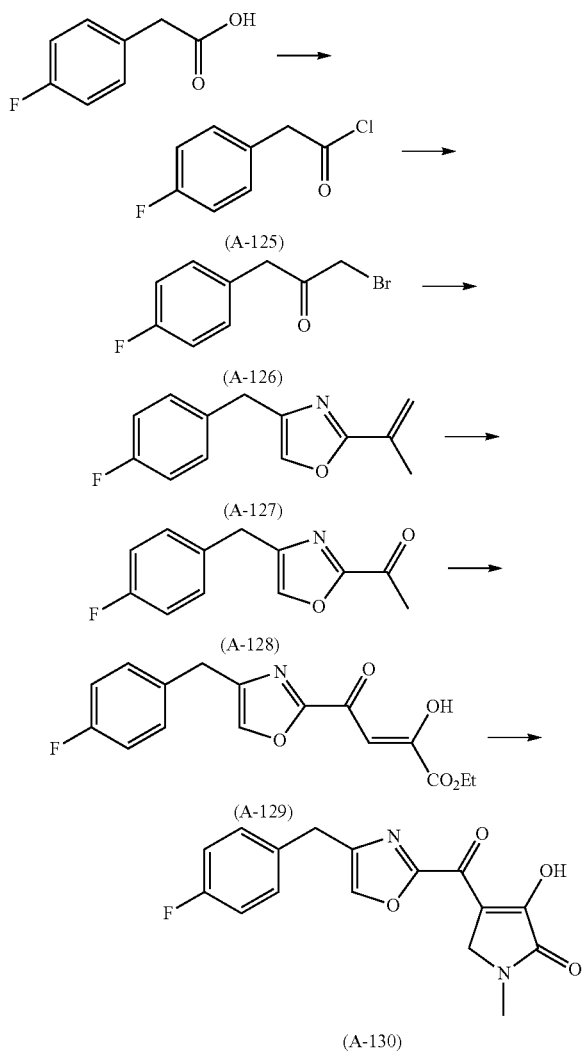

(A-125) To a methylene chloride (100 ml) solution of 4-fluorophenylacetic acid (10.0 g, 64.9 mmol) and dimethylformamide (0.5 ml), oxalyl chloride (9.06 g, 71.4 mmol) was added dropwise at room temperature and the mixture was stirred for 1 hour, which was evaporated under reduced pressure. The residue was distilled to give (4-fluorophenyl)acetyl chloride (8.44 g, yield: 75%).

Boiling point: 80° C./15 mmHg (A-126) N,N-Nitrosomethylurea (10.1 g, 97.8 mmol) was added to 50% potassium hydroxide aqueous solution (40 ml)-diethyl ether (250 ml), then the yellow ether layer was added to the above-mentioned compound A-125 (8.44 g, 48.9 mmol) in diethyl ether (80 ml) under ice cooling. The mixture was stirred at 0° C. for 15 minutes and at room temperature for 15 minutes. The solution was Cooled at −30° C., to which was added 48% hydrogen bromide (50 ml), then which was stirred at −30° C. for 30 minutes and at room temperature for 30 minutes. To the solution was added water, then which was extracted with diethyl ether, washed, dried and evaporated under reduced pressure to give 1-bromo-3-(4-fluorophenyl)propane-2-one (6.52 g, yield: 58%).

NMR (CDCl$_3$) δ: 3.91 (2H, s), 3.94 (2H, s), 7.01-7.07 (2H, m), 7.18-7.22 (2H, m).

(A-127) A solution mixture of the above-mentioned compound A-126 (6.52 g, 28.2 mmol) and 2-methylacrylamide (5.28 g, 62.1 mmol) in tetrahydrofuran (100 ml) was stirred for 3 days at 100° C. To the solution was added water and extracted with ethyl acetate, washed, dried and evaporated under reduced pressure. The residue was purified with silica gel column chromatography (chloroform) to give 4-(4-fluorobenzyl)-2-isopropenyloxazole (5.68 g, yield: 93%).

NMR (CDCl$_3$) δ: 2.15-2.16 (3H, m), 3.86 (2H, s), 5.35-5.36 (1H, m), 5.91-5.92 (1H, m), 6.97-7.03 (2H, m), 7.15-7.16 (1H, m), 7.22-7.24 (2H, m).

(A-128) To a dioxane (110 ml)-water (110 ml) solution of the above-mentioned compound A-127 (5.68 g, 26.1 mmol), 5% osmium tetroxide (0.44 ml) and sodium periodic acid (11.2 g, 52.5 mmol) were added at room temperature for 20 minutes under stirring. The solution was diluted with water, then extracted with ethyl acetate, washed, dried and evaporated under reduced pressure. The residue was purified with silica gel column chromatography (n-hexane:ethyl acetate=4:1) to give 1-[4-(4-fluorobenzyl)oxazole-2-yl]etanone (2.26 g, yield: 40%).

NMR (CDCl$_3$) δ: 2.65 (3H, m), 3.92 (2H, s), 6.99-7.05 (2H, m), 7.22-7.24 (2H, m), 7.43 (1H, m).

(A-129) To a tetrahydrofuran (2.5 ml) solution of the above-mentioned compound A-128 (110 mg, 0.50 mmol), lithium hexamethyldisilazane (0.60 mmol, 1M tetrahydrofuran solution) was added dropwise at −78° C., then the mixture was stirred for 30 minutes, to which was added a tetrahydrofuran (1 ml) solution of imidazole-1-yloxoethyl acetate ester (101 mg, 0.60 mmol) which was synthesized according to the method of the reference (J. Org. Chem., 1981, 46, 211-213). The mixture was stirred at −78° C. for 1 hour, to which was added 2N hydrochloric acid-ice water, which was extracted with diethyl ether, washed, dried and evaporated under reduced pressure to give 4-[4-(4-fluorobenzyl)oxazole-2-yl]-2-hydroxy-4-oxo-2-butenoic acid ethyl ester (152 mg, yield: 95%).

NMR (CDCl$_3$) δ: 1.41 (3H, t, J=7.2 Hz), 3.95 (2H, s), 4.40 (2H, q, J=7.2 Hz), 6.99-7.05 (2H, m), 7.22-7.26 (3H, m), 7.51-7.52 (1H, m).

(A-130) To a dioxane (8 ml) solution of the above-mentioned compound A-129 (199 mg, 0.623 mmol), methylamine (1.37 mmol, 40% ethanol solution) and paraformaldehyde (56 mg) were added, then the mixture was stirred at room temperature for 1 hour. The solution was diluted with ammonium chloride aqueous solution and chloroform, successively. The insoluble product was filtered out, then the filtrate was extracted with chloroform. The extract was washed with 1N hydrochloric acid, water and saturated NaCl aqueous solution, successively. The solvent was evaporated under reduced pressure, then the residue was Crystallized by isopropyl alcohol to give 4-[4-(4-fluorobenzyl)oxazole-2-carbonyl]-3-hydroxy-1-methyl-1,5-dihydropyrrole-2-one (36 mg, yield: 18%).

Melting point: 209-210° C.

Elementary analysis as $C_{16}H_{13}FN_2O_4$

Calcd. (%): C, 60.76; H, 4.14; N, 8.86; F, 6.01.

Found (%): C, 60.63; H, 4.13; N, 8.64; F, 5.91.

NMR (CDCl$_3$) δ: 3.16 (3H, s), 3.99 (2H, s), 4.14 (2H, s), 7.02-7.08 (2H, m), 7.23-7.27 (2H, m), 7.67 (1H, s).

The following compound was synthesized by the above-mentioned method.

4-[4-(4-Fluorobenzyl)oxazole-2-carbonyl]-3-hydroxy-1-isopropyl-1,5-dihydropyrrole-2-one (48 mg, yield: 29%)

Melting point: 184.5-185.5° C.
Elementary analysis as $C_{18}H_{17}FN_2O_4$
Calcd. (%): C, 62.79; H, 4.98; N, 8.14; F, 5.52.
Found (%): C, 62.70; H, 4.78; N, 8.26; F, 5.43.
NMR (CDCl$_3$) δ: 1.27 (6H, d, J=6.6 Hz), 3.99 (2H, s), 4.10 (2H, s), 4.51-4.60 (1H, m), 7.02-7.08 (2H, m), 7.22-7.27 (2H, m), 7.68 (1H, m).

Compound A-137

4-[4-(4-Fluorobenzyl)furan-2-carbonyl]-3-hydroxy-1-methyl-1,5-dihydropyrrole-2-one

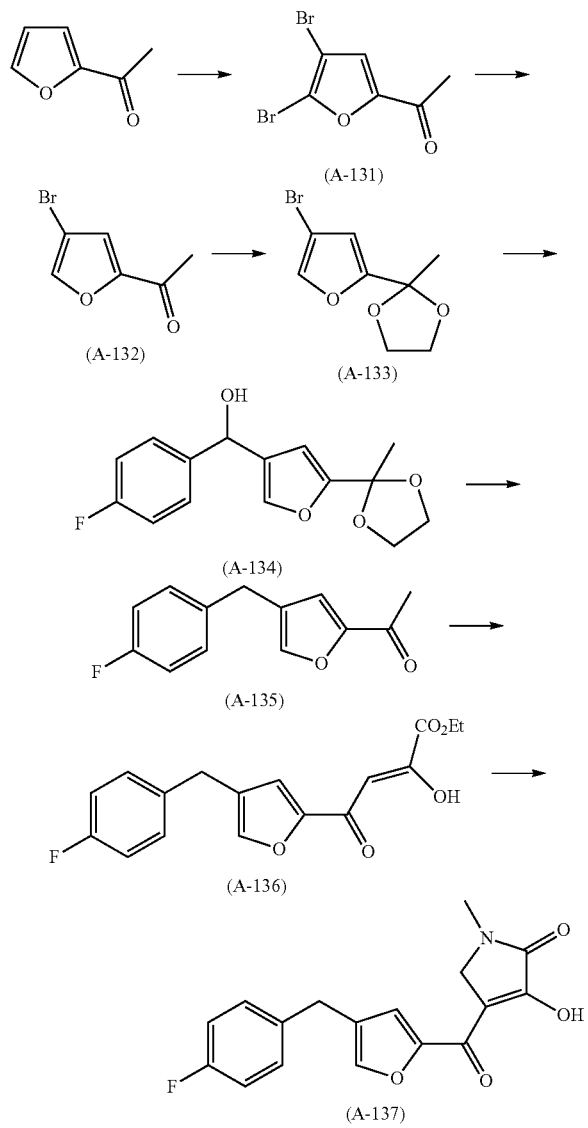

(A-131) 2-Acetylfuran (11.0 g, 100 mmol) and bromine (32.0 g, 200 mmol) were successively added dropwise to aluminum chloride (33.3 g, 250 mmol) at room temperature, then the mixture was stirred for 10 minutes. The solution was poured into ice-37% hydrochloric acid, then which was extracted with diethyl ether, washed, dried and evaporated under reduced pressure. The residue was purified with silica gel chromatography (n-hexane:ethyl acetate=4:1) to give 2-acetyl-4,5-dibromofuran (20.9 g, yield: 78%).
NMR (CDCl$_3$) δ: 2.46 (3H, s), 7.17 (1H, s).
(A-132) The above-mentioned compound A-131 (7.00 g, 26.1 mmol) in diethyl ether (3.5 L) was irradiated at 0° C. for 2 hours, then which was evaporated under reduced pressure. The residue was purified with silica gel chromatography (n-hexane:ethyl acetate=9:1) to give 2-acetyl-4-bromofuran (2.03 g, yield: 41%).
NMR (CDCl$_3$) δ: 2.47 (3H, s), 7.18 (1H, d, J=0.6 Hz), 7.59 (1H, d, J=0.6 Hz).
(A-133) A mixture of the above-mentioned compound A-132 (1.80 g, 9.52 mmol)ethylene glycol (3.00 g, 47.6 mmol) and p-toluenesulfonic acid (91 mg, 0.475 mmol) in benzene (100 ml) was refluxed for 5 hours removing the produced water. The solution was diluted with diethyl ether, then washed with water, saturated NaCl aqueous solution, successively. The mixture was dried and evaporated under reduced pressure. The residue was purified with silica gel column chromatography (n-hexane:ethyl acetate=9:1) to give 2-(4-bromofuran-2-yl)-2-methyl[1,3]dioxolane (1.96 g, yield: 88%).
NMR (CDCl$_3$) δ: 1.70 (3H, s), 3.95-4.08 (4H, m), 6.38 (1H, d, J=0.9 Hz), 7.37 (1H, d, J=0.9 Hz).
(A-134) To a tetrahydrofuran (30 ml) solution of the above-mentioned compound A-133 (1.50 g, 6.44 mmol), n-butyl-lithium (4.45 ml, 7.08 mmol, 1.59M hexane solution) was added dropwise at -78° C. The mixture was stirred at -78° C. for 10 minutes, then to which was added a tetrahydrofuran (8 ml) solution of p-fluorobenzaldehyde (959 mg, 7.73 mmol) and stirred for 1.5 hours. To the solution was added ammonium chloride aqueous solution, then extracted with ethyl acetate, washed, dried and evaporated under reduced pressure. The residue was purified with silica gel chromatography (n-hexane:ethyl acetate=2:1) to give (4-fluorophenyl)-[5-(2-methyl[1,3]dioxolane-2-yl)furan-3-yl]methyl alcohol (939 mg, yield: 53%).
NMR (CDCl$_3$) δ: 1.69 (3H, s), 3.98-4.04 (4H, m), 5.72 (1H, s), 6.25 (1H, d, J=0.9 Hz), 7.02-7.05 (2H, m), 7.22 (1H, d, J=0.9 Hz), 7.35-7.40 (2H, m).
(A-135) To an acetonitrile (20 ml) solution of sodium iodide (2.35 g, 15.7 mmol) and chlorotrimethylsilane (1.71 g, 15.7 mmol) was added, then which was stirred at room temperature for 15 minutes. To the mixture was added an acetonitrile (20 ml) solution of the above-mentioned compound A-134 (876 mg, 3.15 mmol) under ice cooling, which was stirred for 30 minutes, to which was added 1N sodium hydroxide aqueous solution, then extracted with diethyl ether. The extract was washed, dried and evaporated under reduced pressure. The residue was purified with silica gel chromatography (n-hexane:ethyl acetate=4:1) to give 1-[4-(4-fluorobenzyl)furan-2-yl]etanone (299 mg, yield: 44%).
NMR (CDCl$_3$) δ: 2.43 (3H, s), 3.77 (2H, s), 6.97-7.02 (3H, m), 7.13-7.18 (2H, m), 7.35 (1H, d, J=0.9 Hz).
(A-136) To a tetrahydrofuran (10 ml) solution of the above-mentioned compound A-135 (299 mg, 1.37 mmol), lithium hexamethyldisilazane (1.64 ml, 1.64 mmol, 1M tetrahydrofuran solution) was added dropwise at -78° C., then the mixture was stirred at -78° C. for 10 minutes. Oxalic acid diethyl (240 mg, 1.64 mmol) was added at -30° C. and was stirred for 1 hour, to which was added ammonium chloride aqueous solution and extracted with ethyl acetate. The extract was washed, dried and evaporated with reduced pressure to give 4-[4-(4-fluorobenzyl)furan-2-yl]-2-hydroxy-4-oxo-2-butenoic acid ethyl ester (436 mg, yield: 100%).

NMR (CDCl₃) δ: 1.40 (3H, t, J=6.9 Hz), 3.80 (2H, s), 4.38 (2H, q, J=6.9 Hz), 6.88 (1H, d, J=1.4 Hz), 6.99-7.04 (2H, m), 7.14-7.19 (3H, m), 7.44 (1H, br).

(A-137) To a dioxane (8 ml) solution of the above-mentioned compound A-136 (200 mg, 0.628 mmol), methylamine (1.38 mmol, 40% ethanol solution) and paraformaldehyde (57 mg) were added successively at room temperature and the mixture was stirred for 1 hour. The solution was diluted with ammonium chloride aqueous solution and chloroform, then insoluble product was filtered out, and the filtrate was extracted with chloroform. The extract was washed with 1N hydrochloric acid, water, saturated NaCl aqueous solution, successively, which was evaporated under reduced pressure. The residue was Crystallized with isopropyl alcohol to give 4-[4-(4-fluorobenzyl)furan-2-carbonyl]-3-hydroxy-1-methyl-1,5-dihydropyrrole-2-one (72 mg, yield: 36%).

Melting point: 143-145° C.

Elementary analysis as $C_{17}H_{14}FNO_4$

Calcd. (%): C, 64.76; H, 4.48; N, 4.44; F, 6.03.

Found (%): C, 64.56; H, 4.59; N, 4.35; F, 5.95.

NMR (CDCl₃) δ: 3.17 (3H, s), 3.81 (2H, s), 4.42 (2H, s), 6.99-7.04 (2H, m), 7.14-7.19 (2H, m), 7.22 (1H, s), 7.43 (1H, s).

The following compound was synthesized by the above-mentioned method.

4-[4-(4-Fluorobenzyl)furan-2-carbonyl]-3-hydroxy-1-isopropyl-1,5-dihydropyrrole-2-one (26 mg yield: 36%)

Melting point: 148-150° C.

Elementary analysis as $C_{19}H_{18}FNO_4$

Calcd. (%): C, 66.46; H, 5.28; N, 4.08; F, 5.53.

Found (%): C, 66.11; H, 5.23; N, 4.10; F, 5.37.

NMR (CDCl₃) δ: 1.29 (6H, d, J=6.6 Hz), 3.81 (2H, s), 4.36 (2H, s), 4.54-4.63 (1H, m), 6.98-7.04 (2H, m), 7.14-7.19 (2H, m), 7.23 (1H, br), 7.44 (1H, d, J=0.9 Hz).

Compound A-141

3-Hydroxy-1-isopropyl-4-[5-(2-methoxybenzyl) furan-2-carbonyl]-1,5-dihydropyrrole-2-one

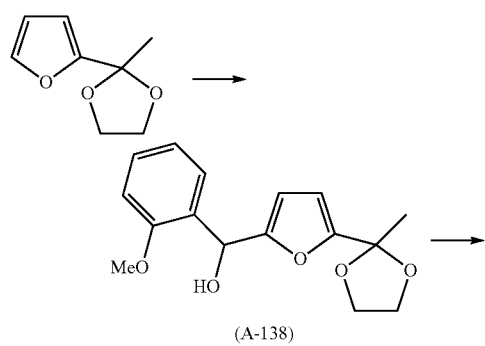

(A-138)

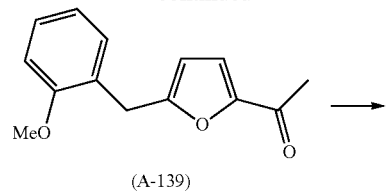

(A-139)

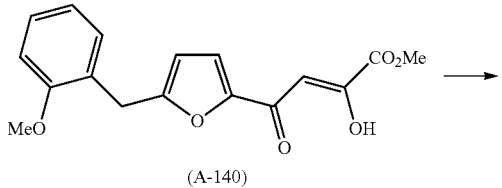

(A-140)

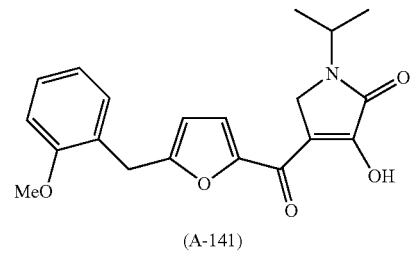

(A-141)

(A-138) To a tetrahydrofuran solution (25 ml) of 2-(2-methyl[1,3]dioxolane-2-yl)furan (2.50 g, 16.2 mmol), 1.58M n-butyllithium-hexane solution (11.3 ml, 17.9 mmol) was added dropwise for 10 minutes at −78° C., then the solution was stirred for 1 hour at −30° C. A tetrahydrofuran solution (20 ml) of o-isopropoxybenzaldehyde (2.06 g, 18.7 mmol) was added at −78° C. and the reaction mixture was stirred at 0° C. for 20 minutes, to which was added saturated ammonium chloride aqueous solution, which was extracted with ethyl acetate. The extract was washed, dried and evaporated, then the residue was purified with silica gel column chromatography (n-hexane/ethyl acetate=31) to give (2-methoxyphenyl)-[5-(2-methyl[1,3]dioxolane-2-yl)furan-2-yl]methyl alcohol (3.97 g, yield: 77%).

(A-139) To an acetonitrile solution (40 ml) of sodium iodide (4.65 g, 31.1 mmol), chlorotrimethylsilane (3.90 ml, 31.1 mmol) was added at 0° C., to which was added an acetonitrile solution (20 ml) of the above-mentioned compound A-138 (3.95 g, 12.5 mmol). To the reaction mixture were added saturated sodium bicarbonate and 0.5M sodium thiosulfate aqueous solution, then which was extracted with ethyl acetate. The extract was washed, dried and evaporated under reduced pressure. The residue was purified with silica gel column chromatography (n-hexane/ethyl acetate=81) to give 1-[5-(2-methoxybenzyl)furan-2-yl]etanone (1.82 g, yield: 57%).

NMR (CDCl₃) δ: 2.43 (3H, s), 3.82 (3H, s), 4.04 (2H, s), 6.05 (1H, d, J=3.6 Hz), 6.87-6.94 (2H, m), 7.08 (1H, d, J=3.6 Hz), 7.15 (1H, dd, J=7.4, 1.7 Hz), 7.25 (1H, td, J=7.8, 1.4 Hz). The following compounds were synthesized by the above-mentioned method.

1-(5-Benzo[1,3]dioxol-4-ylmethylfuran-2-yl)etanone

NMR (CDCl₃) δ: 2.43 (3H, s), 4.01 (2H, s), 5.96 (2H, s), 6.15 (1H, d, J=3.6 Hz), 6.68-6.81 (3H, m), 7.10 (1H, d, J=3.6 Hz).

1-(5-Naphthalene-1-ylmethylfuran-2-yl)etanone

NMR (CDCl$_3$) δ: 2.43 (3H, s), 4.49 (2H, s), 5.94 (1H, d, J=3.5 Hz), 7.05 (1H, d, J=3.5 Hz), 7.36-7.53 (4H, m), 7.81 (1H, d, J=8.1 Hz), 7.85-7.90 (1H, m), 7.93-7.98 (1H, m).

1-[5-(2-Isopropoxybenzyl)furan-2-yl]etanone

NMR (CDCl$_3$) δ: 1.29 (6H, d, J=6.1 Hz), 2.42 (3H, s), 4.02 (2H, s), 4.55 (1H, sep, J=6.1 Hz), 6.07 (1H, d, J=3.5 Hz), 6.84-6.91 (2H, m), 7.09 (1H, d, J=3.5 Hz), 7.14-7.25 (2H, m).

1-[5-(3-Isopropoxybenzyl)furan-2-yl]etanone

NMR (CDCl$_3$) δ: 1.32 (6H, d, J=6.0 Hz), 2.43 (3H, s), 4.00 (2H, s), 4.53 (1H, sep, J=6.0 Hz), 6.12 (1H, dd, J=4.0, 0.9 Hz), 6.75-6.83 (3H, m), 7.10 (1H, d, J=4.0 Hz), 7.17-7.24 (1H, m).

1-[5-(4-Fluoro-2-methoxybenzyl)furan-2-yl]etanone

NMR (CDCl$_3$) δ: 2.42 (3H, s), 3.80 (3H, s), 3.98 (2H, s), 6.04 (1H, d, J=3.6 Hz), 6.58-6.64 (2H, m), 7.06-7.12 (2H, m).

1-[5-(4-Fluoro-3-methoxybenzyl)furan-2-yl]etanone

NMR (CDCl$_8$) δ: 2.44 (3H, s), 3.87 (3H, s), 4.00 (2H, s), 6.12 (1H, d, J=3.6 Hz), 6.76 (1H, ddd, J=8.1, 4.1, 2.1 Hz), 6.85 (1H, dd, J=8.3, 2.1 Hz), 7.02 (1H, dd, J=11.0, 8.1 Hz), 7.11 (1H, d, J=3.6 Hz).

1-[5-(4-Fluoro-2-isopropoxybenzyl)furan-2-yl]etanone

NMR (CDCl$_3$) δ: 1.29 (6H, d, J=6.0 Hz), 2.42 (3H, s), 3.96 (2H, s), 4.49 (1H, sep, J=6.0 Hz), 6.04-6.06 (1H, m), 6.54-6.62 (2H, m), 7.07-7.13 (2H, m).

1-(5-Benzylfuran-2-yl)etanone

NMR (CDCl$_3$) δ: 2.43 (3H, s), 4.04 (2H, s), 6.10 (1H, d, J=3.5 Hz), 7.09 (1H, d, J=3.5 Hz), 7.23-7.36 (4H, m).

1-[5-(2-[1,3]Dioxolane-2-yl-4-fluorobenzyl)furan-2-yl]etanone

NMR (CDCl$_3$) δ: 2.43 (3H, s), 3.98-4.16 (4H, m), 4.17 (2H, s), 5.91 (1H, s), 6.02 (1H, d, J=3.5 Hz), 7.01 (1H, td, J=8.4, 2.9 Hz), 7.08 (1H, d, J=3.5 Hz), 7.17 (1H, dd, J=5.6, 2.9 Hz), 7.33 (1H, dd, J=9.6, 2.9 Hz).

1-[5-(2-[1,3]Dioxolane-2-ylbenzyl)furan-2-yl]etanone

NMR (CDCl$_3$) δ: 2.43 (3H, s), 3.99-4.16 (2H, m), 4.22 (2H, s), 5.93 (1H, s), 6.01 (1H, d, J=3.4 Hz), 7.08 (1H, d, J=3.4 Hz), 7.18-7.22 (1H, m), 7.29-7.34 (2H, m), 7.58-7.62 (1H, m)

(A-140) According to the method of the above-mentioned example A-18, 2-hydroxy-4-[5-(2-methoxybenzyl)furan-2-yl]-4-oxo-2-butenoic acid methyl (977 mg, yield: 88%) was synthesized from the above-mentioned compound A-139 (810 mg, 3.52 mmol).

NMR (CDCl$_3$) δ: 3.83 (3H, s), 3.93 (3H, s), 4.07 (2H, s), 6.15 (1H, d, J=3.6 Hz), 6.88 (1H, s), 6.89-6.95 (2H, m), 7.16 (1H, dd, 1.8 Hz) 7.23-7.30 (2H, m).

The following compounds were synthesized by the above-mentioned method.

4-(5-Benzo[1,3]dioxol-4-ylmethylfuran-2-yl)-2-hydroxy-4-oxo-2-butenoic acid methyl NMR (CDCl$_3$) δ: 3.93 (3H, s), 4.04 (2H, s), 5.97 (2H, s), 6.25 (1H, d, J=3.6 Hz), 6.67-6.84 (3H, m), 6.89 (1H, s), 7.27 (1H, d, J=3.6 Hz).

2-Hydroxy-4-(5-naphthalene-1-ylmethylfuran-2-yl)-4-oxo-2-butenoic acid methyl NMR (CDCl$_3$) δ: 3.93 (3H, s), 4.53 (2H, s), 6.05 (1H, d, J=3.6 Hz), 6.88 (1H, s), 7.22 (1H, d, J=3.6 Hz), 7.36-7.55 (1H, m), 7.80-7.97 (3H, m).

2-Hydroxy-4-[5-(2-isopropoxybenzyl)furan-2-yl]-4-oxo-2-butenoic acid methyl

NMR (CDCl$_3$) δ: 1.29 (6H, d, J=6.1 Hz), 3.93 (3H, s), 4.06 (2H, s), 4.57 (1H, sep, J=6.1 Hz), 6.17 (1H, d, J=3.9 Hz), 6.85-6.92 (3H, m), 7.15-7.28 (3H, m).

2-Hydroxy-4-[5-(3-isopropoxybenzyl)furan-2-yl]-4-oxo-2-butenoic acid methyl

NMR (CDCl$_3$) δ: 1.33 (6H, d, J=6.0 Hz), 3.93 (3H, s), 4.03 (2H, s), 4.54 (1H, sep, J=6.0 Hz), 6.22 (1H, d, J=3.6 Hz), 6.76-6.82 (3H, m), 6.88 (1H, s), 7.20-7.26 (1H, m), 7.27 (1H, d, J=3.6 Hz).

4-[5-(4-Fluoro-2-methoxybenzyl)furan-2-yl]-2-hydroxy-4-oxo-2-butenoic acid methyl NMR (CDCl$_3$) δ: 3.82 (3H, s), 3.93 (3H, s), 4.02 (2H, s), 6.14 (1H, d, J=3.3 Hz), 6.60-6.66 (2H, m), 6.88 (1H, s), 7.07-7.14 (1H, m), 7.26 (1H, d, J=3.3 Hz).

4-[5-(4-Fluoro-3-methoxybenzyl)furan-2-yl]-2-hydroxy-4-oxo-2-butenoic acid methyl NMR (CDCl$_3$) δ: 3.88 (3H, s), 3.93 (3H, s), 4.03 (2H, s), 6.22 (1H, d, J=3.5 Hz), 6.77 (1H, ddd, J=8.3, 4.1, 1.9 Hz), 6.84-6.88 (1H, m), 6.87 (1H, s), 7.03 (1H, dd, J=11.1, 8.3 Hz), 7.28 (1H, d, J=3.5 Hz).

4-[5-(4-Fluoro-2-isopropoxybenzyl)furan-2-yl]-2-hydroxy-4-oxo-2-butenoic acid methyl NMR (CDCl$_3$) δ: 1.30 (6H, d, J=6.0 Hz), 3.93 (3H, s), 4.00 (2H, s), 4.50 (1H, sep, J=6.0 Hz), 6.15 (1H, d, J=3.5 Hz), 6.55-6.62 (2H, m), 6.87 (1H, s), 7.08-7.14 (1H, s) 7.26 (1H, d, J=3.5 Hz).

4-(5-Benzylfuran-2-yl)-2-hydroxy-4-oxo-2-butenoic acid methyl

NMR (CDCl$_3$) δ: 3.93 (3H, s), 4.08 (2H, s), 6.20 (1H, d, J=3.6 Hz), 6.88 (1H, s), 7.23-7.37 (5H, m).

(A-141) According to the method of the above-mentioned example A-19, 3-hydroxy-1-isopropyl-4-[5-(2-methoxybenzyl)furan-2-carbonyl]-1,5-dihydropyrrole-2-one (168 mg, yield: 47%) was synthesized from the above-mentioned compound A-140 (316 mg, 1.00 mmol).

Melting point: 123-124° C.
Elementary analysis as $C_{20}H_{21}NO_5$
Calcd. (%): C, 67.59; H, 5.96; N, 3.94.
Found (%): C, 67.36; H, 5.94; N, 3.88.
NMR (CDCl$_3$) δ: 1.24 (6H, d, J=6.8 Hz), 3.81 (3H, s), 4.09 (2H, s), 4.15 (2H, s), 4.55 (1H, sep, J=6.8 Hz), 6.30 (1H, d, J=3.6 Hz), 6.89-6.98 (2H, m), 7.19-7.34 (3H, m).

The following compounds were synthesized by the above-mentioned method.

(A-141-a) 4-(5-Benzo[1,3]dioxyl-4-ylmethylfuran-2-carbonyl)-3-hydroxy-1-isopropyl-1,5-dihydropyrrole-2-one Melting point: 130-132° C.
NMR (CDCl$_3$) δ: 1.25 (6H, d, J=6.8 Hz), 4.06 (2H, s), 4.20 (2H, s), 4.56 (1H, sep, J=6.8 Hz), 5.96 (2H, s), 6.36 (1H, d, J=3.6 Hz), 6.72-6.87 (3H, m), 7.34 (1H, d, J=3.6 Hz).

(A-141-b) 4-(5-Benzo[1,3]dioxyl-4-ylmethylfuran-2-carbonyl)-3-hydroxy-1-methyl-1,5-dihydropyrrole-2-one Melting point: 169-170° C.
NMR (CDCl$_3$) δ: 3.14 (3H, s), 4.06 (2H, s), 4.23 (2H, s), 5.97 (2H, s), 6.34 (1H, d, J=3.6 Hz), 6.68-6.74 (1H, m), 6.77-6.87 (2H, m), 7.33 (1H, d, J=3.6 Hz).

(A-141-c) 3-Hydroxy-1-isopropyl-4-(5-naphthalene-1-ylmethylfuran-2-carbonyl)-1,5-dihydropyrrole-2-one Melting point: 165-166.5° C.
NMR (CDCl$_3$) δ: 1.14 (6H, d, J=6.8 Hz), 3.92 (2H, s), 4.47 (1H, sep, J=6.8 Hz), 4.55 (2H, s), 6.37 (1H, d, J=3.8 Hz), 7.33 (1H, d, J=3.8 Hz), 7.43-7.56 (4H, m), 7.83-7.96 (3H, m).

(A-141-d) 3-Hydroxy-4-[5-(2-isopropoxybenzyl)furan-2-carbonyl]-1-isopropyl-1,5-dihydropyrrole-2-one NMR (CDCl$_3$) δ: 1.22 (6H, d, J=3.6 Hz), 1.24 (6H, d, J=3.3 Hz), 4.06 (2H, s), 4.11 (2H, s), 4.50-4.61 (2H, m), 6.32 (1H, d, J=3.5 Hz), 6.87-6.95 (2H, m), 7.21-7.30 (2H, m), 7.34 (1H, d, J=3.5 Hz).

(A-141-e) 3-Hydroxy-4-[5-(3-isopropoxybenzyl)furan-2-carbonyl]-1-isopropyl-1,5-dihydropyrrole-2-one Melting point: 98-99° C.
Elementary analysis as $C_{22}H_{25}NO_5$
Calcd. (%): C, 68.91; H, 6.57; N, 3.65.
Found (%): C, 68.74; H, 6.49; N, 3.65.
NMR (CDCl$_3$) δ: 1.24 (6H, d, J=6.9 Hz), 1.32 (6H, d, J=6.0 Hz), 4.04 (2H, s), 4.18 (2H, s), 4.48-4.63 (2H, m), 6.35 (1H, d, J=3.8 Hz), 6.77-6.84 (3H, m), 7.22-7.29 (1H, m), 7.33 (1H, d, J=3.8 Hz).

(A-141-f) 4-[5-(4-Fluoro-2-methoxybenzyl)furan-2-carbonyl]-3-hydroxy-1-isopropyl-1,5-dihydropyrrole-2-one Melting point: 112-113° C.
Elementary analysis as $C_{20}H_{20}FNO_5$
Calcd. (%): C, 64.34; H, 5.40; N, 3.75; F, 5.09.
Found (%): C, 64.24; H, 5.45; N, 3.69; F, 4.97.
NMR (CDCl$_3$) δ: 1.25 (6H, d, J=6.8 Hz), 3.80 (3H, s), 4.04 (2H, s), 4.15 (2H, s), 4.56 (1H, sep, J=6.8 Hz), 6.28 (1H, d, J=3.8 Hz), 6.62-6.70 (2H, m), 7.13-7.19 (1H, m), 7.33 (1H, d, J=3.8 Hz).

(A-141-g) 4-[5-(4-Fluoro-2-methoxybenzyl)furan-2-carbonyl]-3-hydroxy-1-methyl-1,5-dihydropyrrole-2-one Melting point: 134-135° C.
Elementary analysis as $C_{18}H_{16}FNO_5$
Calcd. (%): C, 62.61; H, 4.67; N, 4.06; F, 5.50.
Found (%): C, 62.36; H, 4.64; N, 3.73; F, 5.43.
NMR (CDCl$_3$) δ: 3.13 (3H, s), 3.82 (3H, s), 4.04 (2H, s), 4.18 (2H, s), 6.25 (1H, d, J=3.6 Hz), 6.63-6.70 (2H, m), 7.10-7.16 (1H, m), 7.32 (1H, d, J=3.6 Hz).

(A-141-h) 4-[5-(4-Fluoro-3-methoxybenzyl)furan-2-carbonyl]-3-hydroxy-1-isopropyl-1,5-dihydropyrrole-2-one Melting point: 160-161° C.
Elementary analysis as $C_{20}H_{20}FNO_5$
Calcd. (%): C, 64.34; H, 5.40; N, 3.75; F, 5.09.
Found (%): C, 64.12; H, 5.42; N, 3.68; F, 5.04.
NMR (CDCl$_3$) δ: 1.24 (6H, d, J=6.7 Hz), 3.87 (3H, s), 4.06 (2H, s), 4.15 (2H, s), 4.55 (1H, sep, J=6.7 Hz), 6.33 (1H, d, J=3.6 Hz), 6.77-6.85 (2H, m), 7.06 (1H, dd, J=11.1, 8.1 Hz), 7.33 (1H, d, J=3.6 Hz).

(A-141-i) 4-[5-(4-Fluoro-3-methoxybenzyl)furan-2-carbonyl]-3-hydroxy-1-methyl-1,5-dihydropyrrole-2-one Melting point: 164-166° C.
Elementary analysis as $C_{18}H_{16}FNO_5$
Calcd. (%): C, 62.61; H, 4.67; N, 4.06; F, 5.50.
Found (%): C, 62.36; H, 4.61; N, 3.87; F, 5.38.
NMR (CDCl$_3$) δ: 3.13 (3H, s), 3.89 (3H, s), 4.05 (2H, s), 4.21 (2H, s), 6.30 (1H, d, J=3.6 Hz), 6.78 (1H, ddd, J=8.2, 4.1, 2.2 Hz), 6.84 (1H, dd, J=8.0, 2.2 Hz), 7.06 (1H, dd, J=11.1, 8.2 Hz), 7.32 (1H, d, J=3.6 Hz).

(A-141-j) 4-[5-(4-Fluoro-2-isopropoxybenzyl)furan-2-carbonyl]-3-hydroxy-1-isopropyl-1,5-dihydropyrrole-2-one Melting point: 98-100° C.
Elementary analysis as $C_{22}H_{24}FNO_5$
Calcd. (%): C, 65.82; H, 6.03; N, 3.49; F, 4.73.
Found (%): C, 65.68; H, 5.98; N, 3.49; F, 4.65.
NMR (CDCl$_3$) δ: 1.23 (6H, d, J=6.9 Hz), 1.25 (6H, d, J=6.3 Hz), 4.02 (2H, s), 4.11 (2H, s), 4.42-4.62 (2H, m), 6.29 (1H, d, J=3.6 Hz), 6.60-6.67 (2H, m), 7.14-7.20 (1H, m), 7.34 (1H, d, J=3.6 Hz).

(A-141-k) 4-[5-(4-Fluoro-2-isopropoxybenzyl)furan-2-carbonyl]-3-hydroxy-1-methyl-1,5-dihydropyrrole-2-one Melting point: 126-129° C.
NMR (CDCl$_3$) δ: 1.26 (6H, d, J=6.1 Hz), 3.12 (3H, s), 4.01 (2H, s), 4.15 (2H, s), 4.49 (1H, sep, J=6.1 Hz), 6.26 (1H, d, J=3.3 Hz), 6.60-6.67 (2H, m), 7.11-7.17 (1H, m), 7.32 (1H, d, J=3.3 Hz).

(A-141-l) 4-(5-Benzylfuran-2-carbonyl)-3-hydroxy-1-isopropyl-1,5-dihydropyrrole-2-one Melting point: 162-163° C.
Elementary analysis as $C_{19}H_{19}NO_4$
Calcd. (%): C, 70.14; H, 5.89; N, 4.31.
Found (%): C, 70.11; H, 5.81; N, 4.31.
NMR (CDCl$_3$) δ: 1.23 (6H, d, J=6.8 Hz), 4.10 (2H, s), 4.14 (2H, s), 4.55 (1H, sep, J=6.8 Hz), 6.34-6.36 (1H, m), 7.25-7.31 (2H, m), 7.32-7.40 (3H, m).

(A-141-m) 4-(5-Benzylfuran-2-carbonyl)-3-hydroxy-1-methyl-1,5-dihydropyrrole-2-one Melting point: 116-118° C.
NMR (CDCl$_3$) δ: 3.12 (3H, s), 4.10 (2H, s), 4.18 (2H, s), 6.32 (1H, d, J=3.6 Hz), 7.24-7.29 (2H, m), 7.31-7.41 (3H, m).

Compound A-145

5-Fluoro-2-[5-(4-hydroxy-1-isopropyl-5-oxo-2,5-dihydro-1H-pyrrole-3-carbonyl)furan-2-ylmethyl]benzamide

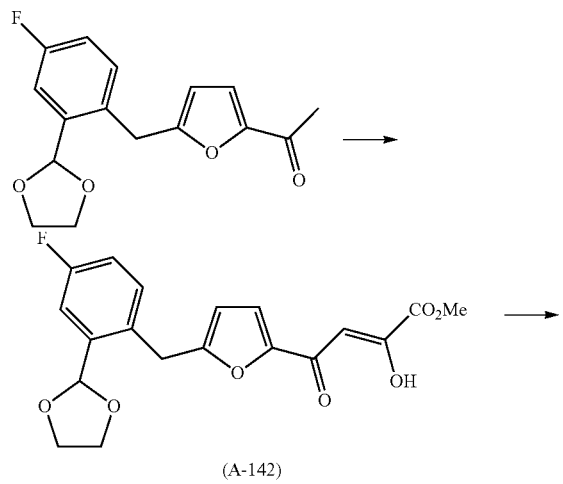

(A-142)

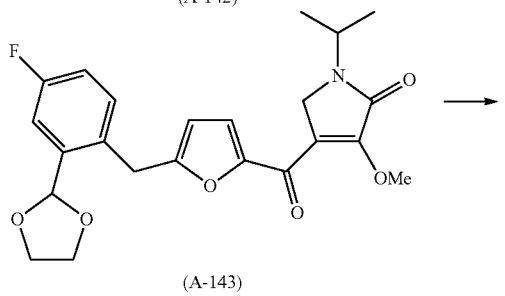

(A-143)

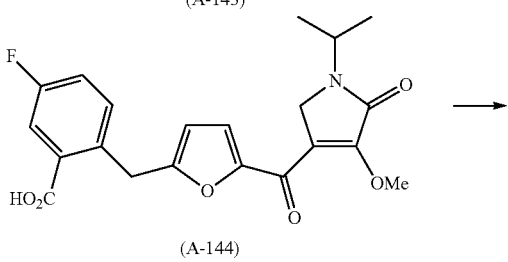

(A-144)

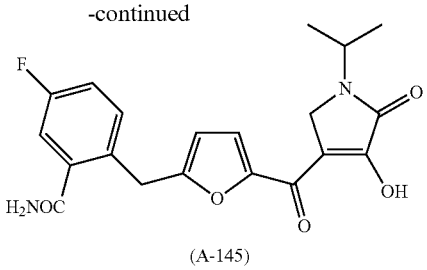

(A-145)

(A-142) According to the method of the above-mentioned example A-18, a crude product (2.78 g) of 4-[5-(2-[1,3]dioxolane-2-yl-4-fluorobenzyl)furan-2-yl]-2-hydroxy-4-oxo-2-butenoic acid methyl was synthesized from the above-mentioned compound; 1-[5-(2-[1,3]dioxolane-2-yl-4-fluorobenzyl)furan-2-yl]ethane (2.03 g, 7.00 mmol).
NMR (CDCl$_3$) δ: 3.93 (3H, s), 4.02-4.15 (4H, m), 4.21 (2H, s), 5.92 (1H, s), 6.12 (1H, d, J=3.6 Hz), 6.88 (1H, s), 7.03 (1H, td, J=8.3, 2.8 Hz), 7.18 (1H, dd, J=8.3, 5.6 Hz), 7.26 (1H, d, J=3.6 Hz), 7.34 (1H, dd, J=9.8, 2.8 Hz).

The following compound was synthesized by the above-mentioned method.

4-[5-(2-[1,3]Dioxolane-2-ylbenzyl)furan-2-yl]-2-hydroxy-4-oxo-2-butenoic acid methyl NMR (CDCl$_3$) δ: 3.93 (3H, s), 4.00-4.17 (4H, m), 4.26 (2H, s), 5.94 (1H, s), 6.12 (1H, d, J=3.8 Hz), 6.89 (1H, s), 7.18-7.22 (1H, m), 7.26 (1H, d, J=3.8 Hz), 7.31-7.35 (2H, m), 7.58-7.62 (1H, m).

(A-143) To a methyl alcohol (3 ml)-ether (10 ml) solution of a crude product (1.51 g) of 4-[5-(2-[1,3]dioxolane-2-yl-4-fluorobenzyl)furan-2-carbonyl]-3-hydroxy-1-isopropyl-1,5-dihydropyrrole-2-one which was produced from the above-mentioned compound A-142 (1.39 g), an ether solution of diazomethane was added at 0° C. until the foam disappeared. According to the method of the above-mentioned example A-19, the reaction mixture was stirred for 10 minutes, then which was evaporated under reduced pressure. The residue was purified with silica gel column chromatography (n-hexane/ethyl acetate=11) to give 4-[5-(2-[1,3]dioxolane-2-yl-4-fluorobenzyl)furan-2-carbonyl]-1-isopropyl-3-methoxy-1,5-dihydropyrrole-2-one (880 mg, yield: 59% (from 2-9)).
NMR (CDCl$_3$) δ: 1.23 (6H, d, J=6.8 Hz), 4.00-4.15 (4H, m), 4.07 (2H, s), 4.16 (3H, s), 4.21 (2H, s), 4.45 (1H, sep, J=6.8 Hz), 5.91 (1H, s), 6.09 (1H, dd, J=3.6, 0.9 Hz), 7.02 (1H, td, J=8.3, 2.7 Hz), 7.20 (1H, dd, J=8.3, 5.4 Hz), 7.30-7.37 (1H, m), 7.33 (1H, d, J=3.6 Hz).

The following compound was synthesized by the above-mentioned method.

4-[5-(2-[1,3]Dioxolane-2-ylbenzyl)furan-2-carbonyl]-1-isopropyl-3-methoxy-1,5-dihydropyrrole-2-one NMR (CDCl$_3$) δ: 1.22 (6H, d, J=6.7 Hz), 3.99-4.16 (4H, m), 4.08 (2H, s), 4.15 (3H, s), 4.26 (2H, s), 4.45 (1H, sep, J=6.7 Hz), 5.93 (1H, s), 6.10 (1H, d, J=3.9 Hz), 7.22-7.27 (1H, m), 7.31-7.36 (3H, m), 7.59-7.63 (1H, m)

(A-144) To a tetrahydrofuran (10 ml)-methyl alcohol (10 ml) solution of the above-mentioned compound A-143 (880 mg, 2.05 mmol), 2N hydrochloric acid (1.0 ml) was added at 50° C., then the reaction mixture was stirred for 3 hours, to which was added a saturated sodium bicarbonate aqueous solution under cooling. The mixture was extracted with ethyl acetate, washed, dried and evaporated under reduced pressure to give a crude product (764 mg, yield: 97%) of 5-fluoro-2-[5-(1-isopropyl-4-methoxy-5-oxo-2,5-dihydro-1H-pyrrole-3-carbonyl)furan-2-ylmethyl]benzaldehyde, which was dissolved into dioxane (10 ml)-methyl alcohol (5 ml), then 2-methyl-2-butene (2.1 ml, 19.8 mmol) was added thereto. Sodium chlorite (538 mg, 5.94 mmol) was added to the reaction mixture at 0° C., to which was added a sodium dihydrogen phosphate dihydrate (929 mg, 5.94 mmol) aqueous solution (10 ml) for 5 minutes. The reaction mixture was stirred at the same temperature for 1 hour, then 2N hydrochloric acid was added and the mixture was extracted with ethyl acetate. The extract was washed, dried and evaporated under reduced pressure to give 5-fluoro-2-[5-(1-isopropyl-4-methoxy-5-oxo-2,5-dihydro-1H-pyrrole-3-carbonyl)furan-2-ylmethyl]benzoic acid (609 mg, yield: 77%).

NMR (CDCl$_3$) δ: 1.23 (6H, d, J=6.7 Hz), 4.08 (2H, s), 4.11 (3H, s), 4.46 (1H, sep, J=6.7 Hz), 4.52 (2H, s), 6.15 (1H, d, J=3.3 Hz), 7.20-7.27 (1H, m), 7.30-7.36 (2H, m), 7.78 (1H, dd, J=9.3, 2.7 Hz).

The following compound was synthesized by the above-mentioned method.

2-[5-(1-Isopropyl-4-methoxy-5-oxo-2,5-dihydro-1H-pyrrole-3-carbonyl)furan-2-ylmethyl]benzoic acid NMR (CDCl$_3$) δ: 1.23 (6H, d, J=6.8 Hz), 4.03-4.16 (4H, m), 4.08 (2H, s), 4.10 (3H, s), 4.45 (1H, sep, J=6.8 Hz), 4.56 (2H, s), 6.15 (1H, d, J=3.6 Hz), 7.32 (1H, d, J=3.6 Hz), 7.34-7.42 (2H, m), 7.54 (1H, td, J=7.5, 1.5 Hz), 8.11 (1H, dd, J=7.2, 1.2 Hz).

(A-145) To a N,N-dimethylformamide solution (5 ml) of the above-mentioned compound A-144 (300 mg, 0.748 mmol), 1-ethyl-3-(3-dimethylaminopropyl)carbodiimide hydrochloride (215 mg, 1.12 mmol), 1-hydroxy-1H-benzotriazole monohydrate (127 mg, 0.898 mmol) and ammonium chloride (60 mg, 1.12 mmol), triethylamine (0.16 ml, 1.12 mmol) was added at 0° C., then the reaction mixture was stirred for overnight at room temperature. 2N Hydrochloric acid was added to the solution, which was extracted with ethyl acetate. The extract was washed, dried and evaporated under reduced pressure. The residue was purified with silica gel column chromatography (chloroform/methyl alcohol=401) to give 5-fluoro-2-[5-(1-isopropyl-4-methoxy-5-oxo-2,5-dihydro-1H-pyrrole-3-carbonyl)furan-2-ylmethyl] benzamide (82 mg, yield: 27%) from which compound (82 mg, 0.205 mmol), 5-fluoro-2-[5-(4-hydroxy-1-isopropyl-5-oxo-2,5-dihydro-1H-pyrrole-3-carbonyl)furan-2-ylmethyl] benzamide (39 mg, yield: 49%) was produced according to the synthetic method of compound (16).

Melting point: 215-218° C.

Elementary analysis as C$_{20}$H$_{19}$FN$_2$O$_5$

Calcd. (%): C, 62.17; H, 4.96; N, 7.25; F, 4.92.

Found (%): C, 62.14; H, 5.03; N, 7.18; F, 4.92.

NMR (DMSO) (5:1.19 (6H, d, J=6.6 Hz), 4.10 (2H, s), 4.25 (1H, sep, J=6.6 Hz), 4.31 (2H, s), 6.29 (1H, d, J=3.5 Hz), 7.23-7.31 (2H, m), 7.35-7.40 (2H, m), 7.52 (1H, s), 7.55 (1H, d, J=3.5 Hz), 7.90 (1H, s).

The following compound was synthesized by the above-mentioned method.

2-[5-(4-Hydroxy-1-isopropyl-5-oxo-2,5-dihydro-1H-pyrrole-3-carbonyl)furan-2-ylmethyl]benzamide Melting point: 195-197° C.

NMR (CDCl$_3$) δ: 1.26 (6H, d, J=7.0 Hz), 4.20 (2H, s), 4.41 (2H, s), 4.56 (1H, sep, J=7.0 Hz), 5.60 (1H, br s), 5.83 (1H, br s), 6.35 (1H, d, J=3.9 Hz), 7.31-7.39 (3H, m), 7.43-7.50 (1H, m), 7.53-7.58 (1H, m).

Compound A-146

5-Fluoro-2-[5-(4-hydroxy-1-isopropyl-5-oxo-2,5-dihydro-1H-pyrrole-3-carbonyl)furan-2-ylmethyl] benzoic acid methyl

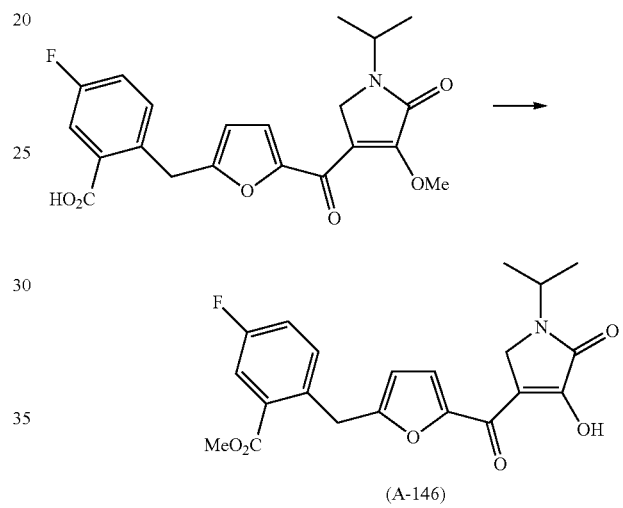

(A-146)

(A-146) To a methyl alcohol (2 ml)-ether (4 ml) solution of the above-mentioned compound, 5-fluoro-2-[5-(1-isopropyl-4-methoxy-5-oxo-2,5-dihydro-1H-pyrrole-3-carboxy)furan-2-ylmethyl]benzoic acid, an ether solution of diazomethane was added at 0° C., until the foam disappeared. The reaction mixture was stirred for 10 minutes, then which was evaporated under reduced pressure. The residue was purified with silica gel column chromatography (n-hexane/ethyl acetate=2/1-1/1) to give 5-fluoro-2-[5-(1-isopropyl-4-methox-5-oxo-2,5-dihydro-1H-pyrrole-3-carbonyl) furan-2-ylmethyl]benzoic acid methyl (187 mg, yield: 60%) from which compound (187 mg, 0.451 mmol), 5-fluoro-2-[5-(4-hydroxy-1-isopropyl-5-oxo-2,5-dihydro-1H-pyrrole-3-carbonyl)furan-2-ylmethyl]benzoic acid methyl (121 mg, yield: 70%) was produced according to the synthetic method of the compound (16).

Melting point: 110-111° C.

Elementary analysis as C$_{21}$H$_{20}$FNO$_6$

Calcd. (%): C, 62.84; H, 5.02; N, 3.49; F, 4.73.

Found (%): C, 62.99; H, 5.15; N, 3.43; F, 4.66.

NMR (CDCl$_3$) δ: 1.25 (6H, d, J=6.8 Hz), 3.87 (3H, s), 4.14 (2H, s), 4.50 (2H, s), 4.56 (1H, sep, J=6.8 Hz), 6.30 (1H, d, J=3.4 Hz), 7.20-7.29 (1H, m), 7.31-7.37 (1H, m), 7.33 (1H, d, J=3.4 Hz), 7.72 (1H, dd, J=9.1, 2.7 Hz).

Compound A-152

4-[5-Cyclohexyl-3-(4-fluorobenzyl)furan-2-carbonyl]-3-hydroxy-1-methyl-1,5-dihydropyrrole-2-one

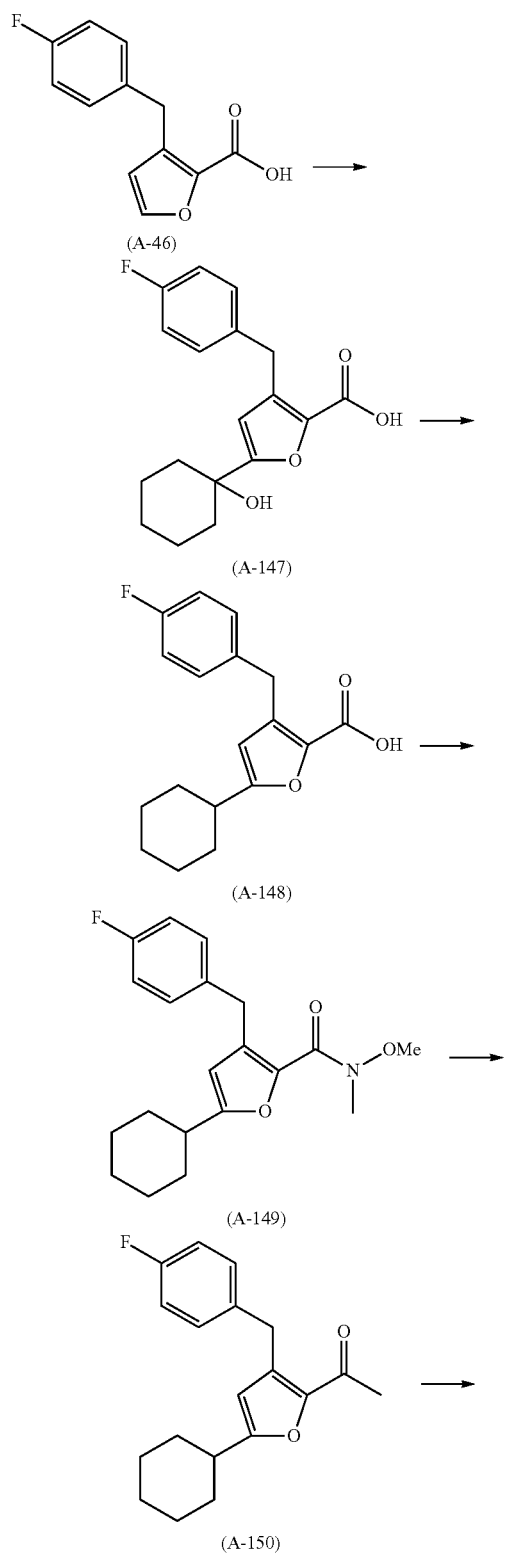

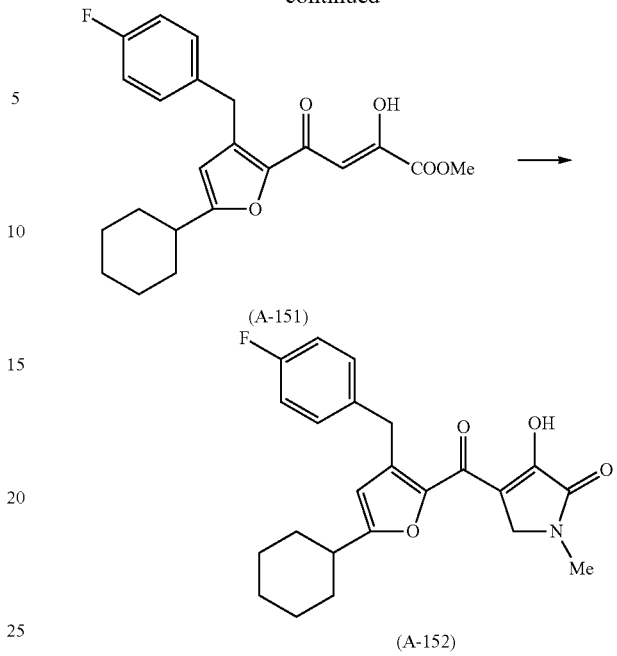

(A-(147)) To a tetrahydrofuran solution (14 ml) of diisopropylamine (1.54 ml, 11 mmol) under dry ice cooling, 1.58M n-butyllithium (7.0 ml, 11 mmol) was added, then the reaction mixture was stirred for 30 minutes, to which was added dropwise a tetrahydrofuran solution (7 ml) of the above-mentioned compound A-46 (1.10 g, 5.0 mmol) for 10 minutes.

The reaction mixture was stirred for 1 hour, then to which was added cyclohexanone (0.62 ml, 6.0 mmol) and stirred for 30 minutes. 2N Hydrochloric acid was added to the reaction mixture, then which was extracted 2 times with ethyl acetate. The organic layer was washed with 2N hydrochloric acid and brine, successively, then dried with anhydrosodium sulfate, which was evaporated to give a crude product (1.8 g) of 3-(4-fluorobenzyl)-5-(1-hydroxycyclohexyl)-2-furoin acid.

(A-148) According to the method of A-35, a crude product (1.6 g) of 5-cyclohexyl-3-(4-fluorobenzyl)-2-furoin acid was synthesized from the above-mentioned crude product A-147.

(A-149) According to the method of A-36, 5-cyclohexyl-3-(4-fluorobenzyl)-2-furoin acid methoxymethylamide (1.05 g, total yield of 3 process: 61%) was synthesized from the above-mentioned product A-148.

NMR (CDCl$_3$) δ: 1.1-2.1 (10H, m), 2.5-2.6 (1H, m), 3.32 (3H, s), 3.84 (3H, s), 4.08 (2H, s), 5.83 (1H, d, J=0.9 Hz), 6.93-6.98 (2H, m), 7.21-7.25 (2H, m).

(A-150) According to the method of A-37, 1-[5-cyclohexyl-3-(4-fluorobenzyl)furan-2-yl]etanone (860 mg, yield: 99%) was synthesized from the above-mentioned compound A-149 (1.0 g, 2.9 mmol).

NMR (CDCl$_3$) δ: 1.2-2.1 (10H, m), 2.46 (3H, s), 2.5-2.7 (1H, m), 4.13 (2H, s), 5.89 (1H, s), 6.93-6.98 (2H, m), 7.18-7.22 (2H, m).

(A-151) According to the method of A-18, 4-[5-cyclohexyl-3-(4-fluorobenzyl)furan-2-yl]-2-hydroxy-4-oxo-2-butenoic acid methyl ester (709 mg, yield: 65%) was synthesized from the above-mentioned compound A-150 (850 mg, 2.83 mmol).

NMR (CDCl₃) δ: 1.1-2.1 (10H, m), 2.64 (1H, m), 3.94 (3H, s), 4.20 (2H, s), 5.97 (1H, s), 6.95-7.01 (2H, m), 6.98 (1H, s), 7.19-7.24 (2H, m).

(A-152) According to the method of A-19, 4-[5-cyclohexyl-3-(4-fluorobenzyl)furan-2-carbonyl]-3-hydroxy-1-methyl-1,5-dihydropyrrole-2-one (102 mg, yield: 34%) was synthesized from the above-mentioned compound A-151 (290 mg, 0.75 mmol).

Melting point: 175-176° C.

Elementary analysis as $C_{23}H_{24}FNO_4$

Calcd. (%): C, 69.51; H, 6.09; N, 3.52; F, 4.78.

Found (%): C, 69.45; H, 6.11; N, 3.57; F, 4.69.

NMR (CDCl₃) δ: 1.20-2.05 (10H, m), 2.65 (1H, m), 3.20 (3H, s), 4.22 (2H, s), 4.42 (2H, s), 6.02 (1H, s), 6.96-7.02 (2H, m), 7.21-7.25 (2H, m).

Compound A-158

4-[3-(4-Fluorobenzyl)-5-(1-methoxy-1-methylethyl)furan-2-carbonyl]-3-hydroxy-1-methyl-1,5-dihydropyrrole-2-one

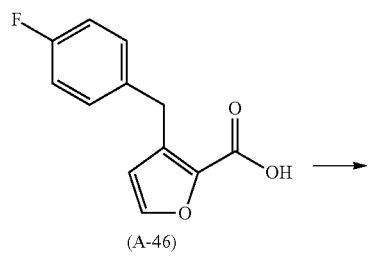

(A-46)

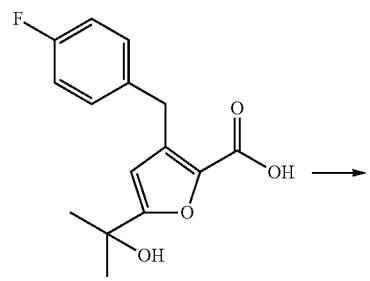

(A-153)

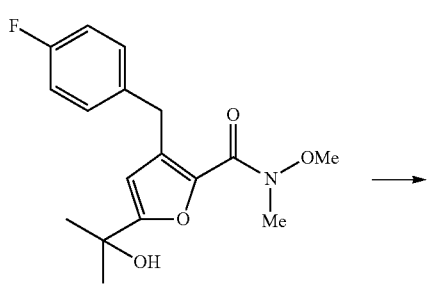

(A-154)

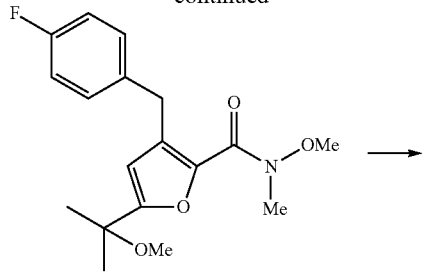

(A-155)

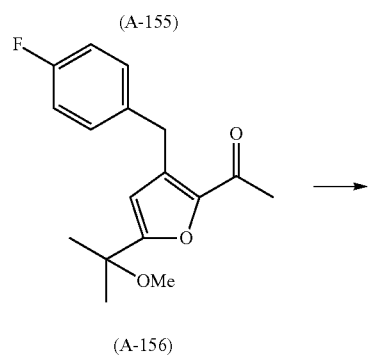

(A-156)

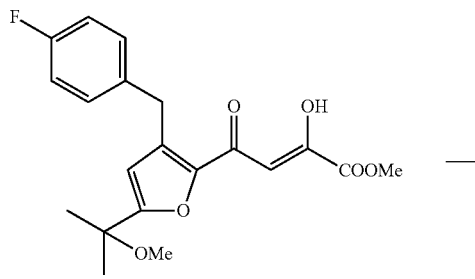

(A-157)

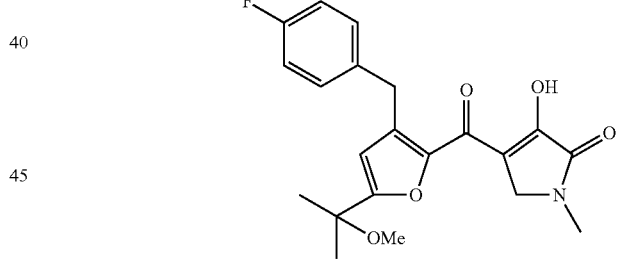

(A-158)

(A-153) To a tetrahydrofuran solution (28 ml) of diisopropylamine (3.1 ml, 22 mmol) under dry ice cooling, 1.58M n-butyllithium (14 ml, 22 mmol) was added, then the reaction mixture was stirred for 30 minutes, to which was added dropwise a tetrahydrofuran solution (7 ml) of the above-mentioned compound A-46 (2.2 g, 10 mmol) for 10 minutes. The reaction mixture was stirred for 1 hour, then to which was added acetone (1 ml) and stirred for 30 minutes. 2N Hydrochloric acid was added to the reaction mixture, then which was extracted 2 times with ethyl acetate. The organic layer was washed with 2N hydrochloric acid and brine, successively, then dried with anhydrosodium sulfate, which was evaporated to give a crude product (3.07 g) of 3-(4-fluorobenzyl)-5-(1-hydroxy-1-methylethyl)-2-furoin acid.

(A-154) According to the method of A-36, 3-(4-fluorobenzyl)-5-(1-hydroxy-1-methyl ethyl)-2-furoin acid methoxymethylamide (1.97 g, total yield of 2 process: 61%) was synthesized from the above-mentioned crude product A-153.

NMR (CDCl$_3$) δ: 1.56 (6H, s), 3.31 (3H, s), 3.84 (3H, s), 4.07 (2H, s), 6.06 (1H, s), 6.93-6.99 (2H, m), 7.21-7.25 (2H, m).

(A-155) To a N,N-dimethylformamide solution (8 ml) of the above-mentioned compound A-154 (964 mg, 3.0 mmol), 60% sodium hydride (144 mg, 3.6 mmol) and iodomethane (0.28 ml, 4.5 mmol) were successively added under ice cooling, then the reaction mixture was stirred at room temperature for 3 hours, to which was added water and 2N hydrochloric acid, successively. The reaction mixture was extracted 2 times with ethyl acetate, then the organic layer was washed with water and brine, successively, which was dried with anhydro magnesium sulfate. The reaction mixture was evaporated, then the crude product was treated with silica gel column chromatography to give 3-(4-fluorobenzyl)-5-(1-methoxy1-methylethyl)-2-furoin acid methoxymethylamide (774 mg, yield: 77%).

NMR (CDCl$_3$) δ: 1.50 (6H, s), 3.07 (3H, s), 3.32 (3H, s), 3.87 (3H, s), 4.09 (2H, s), 6.09 (1H, s), 6.94-7.00 (2H, m), 7.21-7.26 (2H, m).

(A-156) According to the method of A-37, 1-[3-(4-fluorobenzyl)-5-(1-methoxy-1-methylethyl)furan-2-yl]etanone (624 mg, yield: 95%) was synthesized from the above-mentioned A-155 (760 mg, 2.27 mmol).

NMR (CDCl$_3$) δ: 1.52 (6H, s), 2.51 (3H, s), 3.10 (3H, s), 4.15 (2H, s), 6.15 (1H, s), 6.94-7.00 (2H, m), 7.18-7.23 (2H, m).

(A-157) According to the method of A-18, a crude product (822 mg) of 4-[3-(4-fluorobenzyl)-5-(1-methoxy-1-methylethyl)furan-2-yl]-2-hydroxy-4-oxo-2-butenoic acid methyl ester was synthesized from the above-mentioned compound A-156 (620 mg, 2.10 mmol).

NMR (CDCl$_3$) δ: 1.54 (6H, s), 3.11 (3H, s), 3.94 (3H, s), 4.22 (2H, s), 6.22 (1H, s), 6.97-7.02 (2H, m), 7.01 (1H, s), 7.20-7.24 (2H, m).

(A-158) According to the method of A-19, 4-[3-(4-fluorobenzyl)-5-(1-methoxy-1-methylethyl)furan-2-carbonyl]-3-hydroxy-1-methyl-1,5-dihydropyrrole-2-one (143 mg, yield: 34%) was synthesized from the above-mentioned crude product A-157 (410 mg, 1.09 mmol).

Melting point: 144-145° C.

Elementary analysis as C$_{21}$H$_{22}$FNO$_5$

Calcd. (%): C, 65.11; H, 5.72; N, 3.62; F, 4.90.

Found (%): C, 65.00; H, 5.63; N, 3.62; F, 4.67.

NMR (CDCl$_3$) δ: 1.54 (6H, s), 3.09 (3H, s), 3.19 (3H, s), 4.24 (2H, s), 4.45 (2H, d, J=0.6 Hz), 6.25 (1H, s), 6.97-7.03 (2H, m), 7.21-7.26 (2H, m).

1-Ethyl-4-[3-(4-fluorobenzyl)-5-(1-methoxy-1-methylethyl)furan-2-carbonyl]-3-hydroxy-1,5-dihydropyrrole-2-one (187 mg, yield: 47%) was synthesized from the above-mentioned crude product A-157 (376 mg, 1.0 mmol).

Melting point: 146-148° C.

Elementary analysis as C$_{22}$H$_{24}$FNO$_5$

Calcd. (%): C, 65.82; H, 6.03; N, 3.49; F, 4.73.

Found (%): C, 65.78; H, 6.00; N, 3.45; F, 4.55.

NMR (CDCl$_3$) δ: 1.27 (3H, t, J=7.2 Hz), 1.54 (6H, s), 3.09 (3H, s), 3.65 (2H, q, J=7.2 Hz), 4.24 (2H, s), 4.45 (2H, s), 6.24 (1H, s), 6.97-7.02 (2H, m), 7.21-7.25 (2H, m).

Compound A-164

1-Ethyl-4-[3-(4-fluorobenzyl)-5-methanesulfonyl-furan-2-carbonyl]-3-hydroxy-1,5-dihydropyrrole-2-one

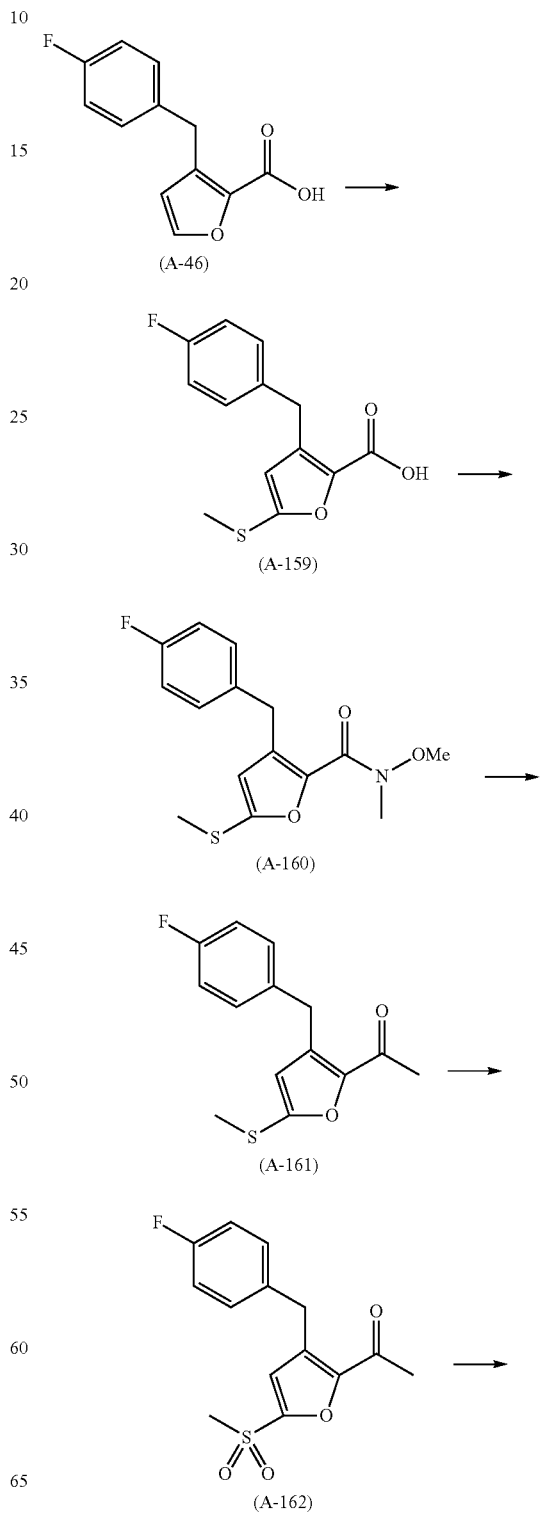

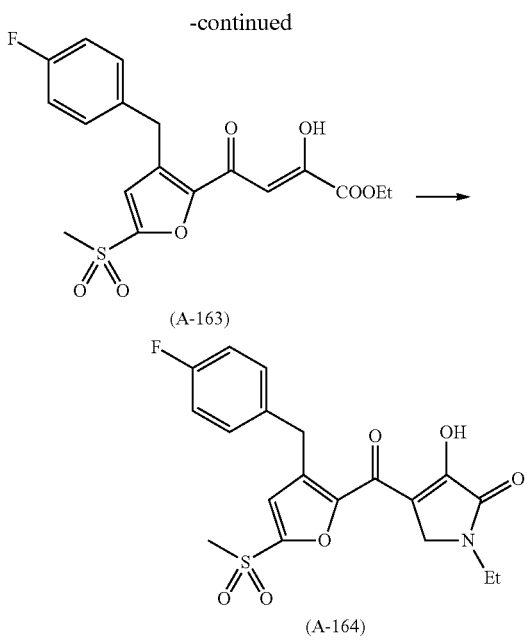

(A-163)

(A-164)

(A-159) To a tetrahydrofuran solution (30 ml) of diisopropylamine (3.4 ml, 24 mmol) under dry ice cooling, 1.58M n-butyllithium (15 ml, 24 mmol) was added, then the reaction mixture was stirred for 30 minutes, to which was added dropwise a tetrahydrofuran solution (10 ml) of the above-mentioned compound A-46 (2.2 g, 10 mmol) for 10 minutes. The reaction mixture was stirred for 1 hour, then to which was added dimethyl disulfide (0.9 ml, 10 mmol) and stirred for 30 minutes. 2N Hydrochloric acid was added to the reaction mixture, then which was extracted 2 times with ethyl acetate. The organic layer was washed with 2N hydrochloric acid and brine, successively, then dried with anhydrosodium sulfate, which was evaporated to give a crude product (2.82 g) of 3-(4-fluorobenzyl)-5-methylsulfanil-2-furoin acid.

(A-160) According to the method of A-36, 3-(4-fluorobenzyl)-5-methylsulfanil-2-furoin acid methoxymethylamide (3.14 g) was synthesized from the above-mentioned crude product A-159.

(A-161) According to the method of A-37, 1-[3-(4-fluorobenzyl)-5-methylsulfanilfuran-2-yl]etanone (2.44 g) was synthesized from the above-mentioned crude product A-160.

(A-162) To a methylene chloride solution (6 ml) of the above-mentioned crude product A-161 (1.06 g, 4 mmol) under ice cooling, a methylene chloride solution (8 ml) of 80% m-chloroperbenzoic acid (1.73 g, 8 mmol) was added dropwise for 10 minutes, then the reaction mixture was stirred for 30 minutes, to which was added 80% m-chloroperbenzoic acid (863 mg, 4 mmol). The reaction mixture was stirred for 2 hours, then the crystal was filtered out. The filtrate was evaporated, then the residue was dissolved in ethyl acetate, which was washed 3 times with saturated sodium hydrogen carbonate aqueous solution and 1 time with brine, which was then dried with anhydro magnesium sulfate. The reaction mixture was evaporated to give a crude product, which was treated with silica gel column chromatography to give 1-[3-(4-fluorobenzyl)-5-methane sulfonylfuran-2-yl]etanone (942 mg, total yield of 4 process: 64%).

NMR (CDCl$_3$) δ: 2.59 (3H, s), 3.19 (3H, s), 4.17 (2H, s), 6.95 (1H, s), 6.97-7.03 (2H, m), 7.17-7.21 (2H, m).

(A-163) According to the method of A-18, a crude product (213 mg) of 4-[3-(4-fluorobenzyl)-5-methane sulfonylfuran-2-yl]-2-hydroxy-4-oxo-2-butenoic acid ethyl ester was synthesized from the above-mentioned compound A-162 (148 mg, 0.5 mmol).

NMR (CDCl$_3$) δ: 1.42 (3H, t, J=7.1 Hz), 3.21 (3H, s), 4.25 (2H, s), 4.43 (2H, q, J=7.2 Hz), 6.99-7.05 (2H, m), 6.99 (1H, s), 7.05 (1H, s), 7.18-7.23 (2H, m).

(A-164) According to the method of A-19, 1-ethyl-4-[3-(4-fluorobenzyl)-5-methanesulfonylfuran-2-carbonyl]-3-hydroxy-1,5-dihydropyrrole-2-one (69 mg yield: 34%) was synthesized from the above-mentioned crude product 15 (213 mg, 0.5 mmol).

Melting point: 154-157° C.

Elementary analysis as $C_{19}H_{18}FNO_6S$

Calcd. (%): C, 56.01; H, 4.45; N, 3.44; F, 4.66; S, 7.87.

Found (%): C, 55.77; H, 4.36; N, 3.39; F, 4.43; S, 7.69.

NMR (CDCl$_3$) δ: 1.28 (3H, t, J=7.1 Hz), 3.19 (3H, s), 3.65 (2H, q, J=7.2 Hz), 4.27 (2H, s), 4.48 (2H, s), 7.00-7.05 (2H, m), 7.02 (1H, s), 7.20-7.25 (2H, m).

Compound A-171

4-[3-(4-Fluorobenzyl)-5-(1,1-dioxotetrahydrothiopyran-4-yl)furan-2-carbonyl]-3-hydroxy-1-methyl-1,5-dihydropyrrole-2-one

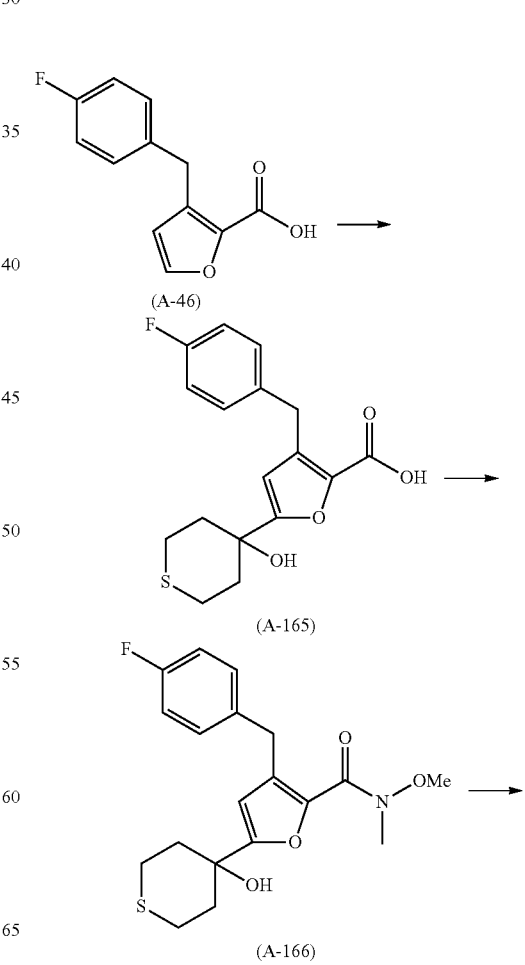

(A-46)

(A-165)

(A-166)

-continued

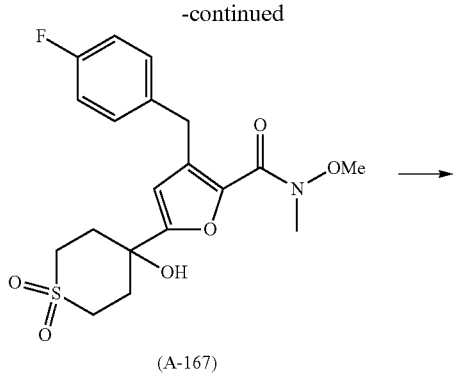

(A-167)

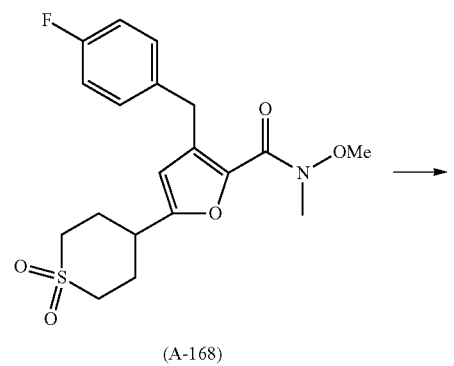

(A-168)

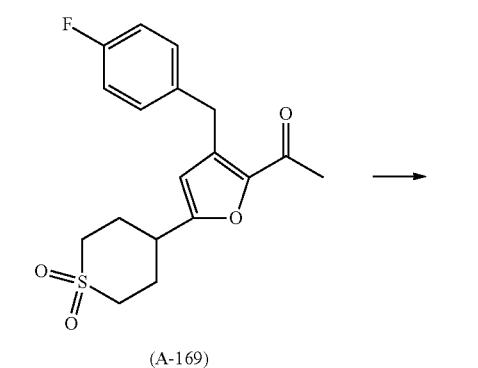

(A-169)

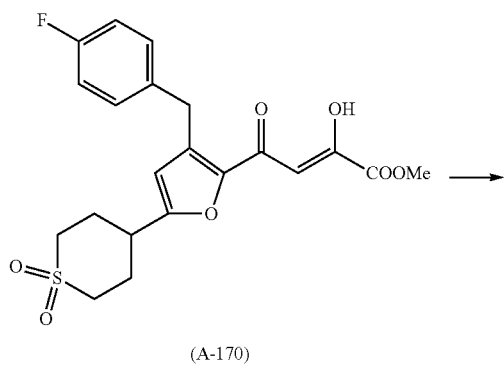

(A-170)

-continued

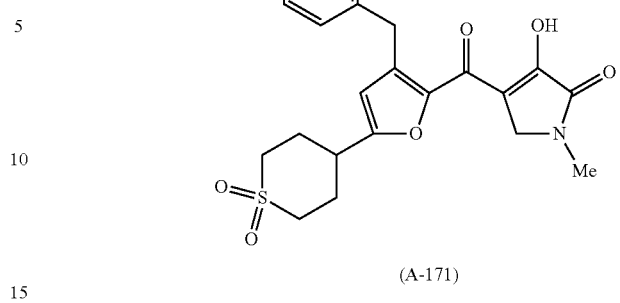

(A-171)

(A-165) To a tetrahydrofuran solution (30 ml) of diisopropylamine (3.08 ml, 22 mmol) under dry ice cooling, 1.57M n-butyllithium (14 ml, 22 mmol) was added, then the reaction mixture was stirred for 30 minutes, to which was added dropwise a tetrahydrofuran solution (10 ml) of the above-mentioned compound A-46 (2.2 g, 10 mmol) for 10 minutes. The reaction mixture was stirred for 1 hour, then to which was added tetrahydrothiopyran-4-one (1.39 g, 12 mmol) and stirred for 30 minutes. 2N Hydrochloric acid was added to the reaction mixture, then which was extracted 2 times with ethyl acetate. The organic layer was washed with 2N hydrochloric acid and brine, successively, then dried with anhydrosodium sulfate, which was evaporated to give a crude product (3.95 g) of 3-(4-fluorobenzyl)-5-(4-hydroxytetrahydrothiopyran-4-yl)-2-furoin acid.

(A-166) According to the method of A-36, 3-(4-fluorobenzyl)-5-(4-hydroxytetrahydrothiopyran-4-yl)-2-furoin acid methoxymethylamide (2.97 g, total yield of 2 process: 78%) was synthesized from the above-mentioned compound A-165.

NMR (CDCl$_3$) δ: 2.15-2.19 (4H, m), 2.43-2.51 (2H, m), 3.00-3.09 (2H, m), 3.31 (3H, s), 3.83 (3H, s), 4.07 (2H, s), 6.07 (1H, s), 6.93-6.99 (2H, m), 7.19-7.24 (2H, m).

(A-167) To a methylene chloride solution (20 ml) of the above-mentioned crude product A-166 (2.86 g, 7.54 mmol) under ice cooling, a methylene chloride solution (20 ml) of 80% m-chloroperbenzoic acid (3.11 g, 18 mmol) was added dropwise for 15 minutes, then the reaction mixture was stirred for 2 hours, to which was added 80% m-chloroperbenzoic acid (650 mg, 3.77 mmol). The reaction mixture was stirred for 1 hour, then the crystal was filtered out. The filtrate was evaporated, then the residue was dissolved in ethyl acetate, which was washed 3 times with saturated sodium hydrogen carbonate aqueous solution and 1 time with brine, which was then dried with anhydro magnesium sulfate. The reaction mixture was evaporated to give a crude product, which was crystallized with diisopropyl ether-acetone to give 3-(4-fluorobenzyl)-5-(4-hydroxy-1,1-dioxotetrahydrothiopyran-4-yl)-2-furoin acid methoxymethylamide (2.63 g, yield: 85%).

NMR (CDCl$_3$) δ: 2.30-2.37 (2H, m), 2.51-2.61 (2H, m), 2.88-2.94 (2H, m), 3.30 (3H, s), 3.46 (2H, dt, J=3.3, 13.5 Hz), 3.81 (3H, s), 4.03 (2H, s), 6.12 (1H, s), 6.94-6.99 (2H, m), 7.17-7.22 (2H, m).

(A-168) According to the method of A-35, 3-(4-fluorobenzyl)-5-(1,1-dioxotetrahydrothiopyran-4-yl)-2-furoin acid methoxymethylamide (1.53 g, yield: 97%) was synthesized from the above-mentioned compound A-167 (1.65 g, 4.0 mmol).

NMR (CDCl₃) δ: 2.29-2.43 (4H, m), 2.90-3.16 (5H, m), 3.32 (3H, s), 3.81 (3H, s), 4.07 (2H, s), 5.95 (1H, s), 6.94-7.00 (2H, m), 7.19-7.24 (2H, m).

(A-169) According to the method of A-37, 1-[3-(4-fluorobenzyl)-5-(1,1-dioxotetrahydrothiopyran-4-yl)furan-2-yl]etanone (1.14 g, yield: 92%) was synthesized from the above-mentioned compound A-168 (1.40 g, 3.54 mmol).

NMR (CDCl₃) δ: 2.31-2.43 (4H, m), 2.47 (3H, s), 2.91-3.17 (5H, m), 4.13 (2H, s), 6.00 (1H, s), 6.94-7.00 (2H, m), 7.16-7.21 (2H, m).

(A-170) According to the method of A-18, 4-[3-(4-fluorobenzyl)-5-(1,1-dioxotetrahydrothiopyran-4-yl)furan-2-yl]-2-hydroxy-4-oxo-2-butenoic acid ethyl ester (286 mg, yield: 66%) was synthesized from the above-mentioned compound A-169 (350 mg, 1.0 mmol).

NMR (CDCl₃) δ: 2.28-2.48 (4H, m), 2.94-3.18 (5H, m), 3.95 (3H, s), 4.20 (2H, s), 6.07 (1H, s), 6.94 (1H, s), 6.97-7.02 (2H, m), 7.18-7.23 (2H, m).

(A-171) According to the method of A-19, 4-[3-(4-fluorobenzyl)-5-(1,1-dioxotetrahydrothiopyran-4-yl)furan-2-carbonyl]-3-hydroxy-1-methyl-1,5-dihydropyrrole-2-one (69 mg, yield: 34%) was synthesized from the above-mentioned compound A-170 (175 mg, 0.4 mmol).

Melting point: 200-203° C.

Elementary analysis as $C_{22}H_{22}FNO_6S$

Calcd. (%): C, 59.05; H, 4.96; N, 3.13; F, 4.25; S, 7.17.

Found (%): C, 58.67; H, 4.85; N, 2.95; F, 4.06; S, 7.05.

NMR (CDCl₃) δ: 2.29-2.45 (4H, m), 2.93-3.15 (5H, m), 3.20 (3H, s), 4.23 (2H, s), 4.40 (2H, s), 6.12 (1H, s), 6.97-7.03 (2H, m), 7.19-7.24 (2H, m).

According to the same method, 1-ethyl-4-[3-(4-fluorobenzyl)-5-(1,1-dioxotetrahydrothiopyran-4-yl)furan-2-carbonyl]-3-hydroxy-1,5-dihydropyrrole-2-one (55 mg, yield: 52%) was synthesized from the above-mentioned compound A-170 (100 mg, 0.23 mmol).

Melting point: 213-216° C.

Elementary analysis as $C_{23}H_{24}FNO_6S \cdot 0.2H_2O$

Calcd. (%): C, 59.39; H, 5.29; N, 3.01; F, 4.08; S, 6.89.

Found (%): C, 59.22; H, 5.20; N, 2.91; F, 3.95; S, 6.76.

NMR (CDCl₃) δ: 1.29 (3H, t, J=7.2 Hz), 2.35-2.43 (4H, m), 2.95-3.19 (5H, m), 3.65 (2H, q, J=7.2 Hz), 4.23 (2H, s), 4.40 (2H, s), 6.12 (1H, s), 6.97-7.03 (2H, m), 7.19-7.24 (2H, m).

Compound A-178

4-[3-(4-Fluorobenzyl)-5-(morpholine-4-carbonyl)furan-2-carbonyl]-3-hydroxy-1-methyl-1,5-dihydropyrrole-2-one

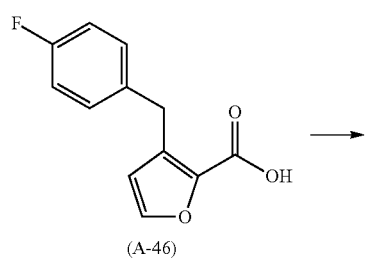

(A-46)

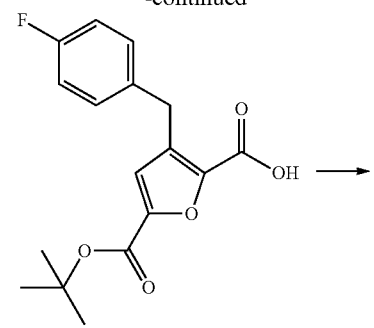

(A-172)

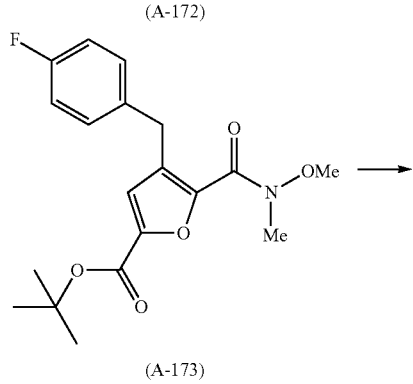

(A-173)

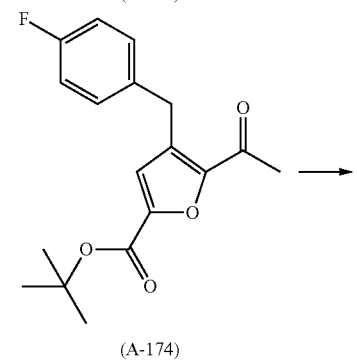

(A-174)

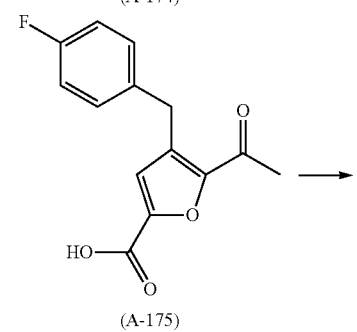

(A-175)

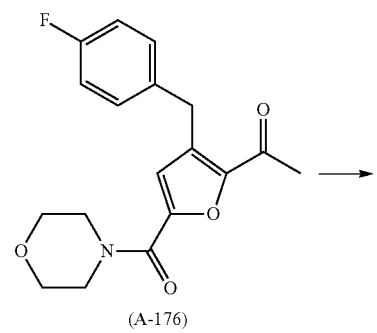

(A-176)

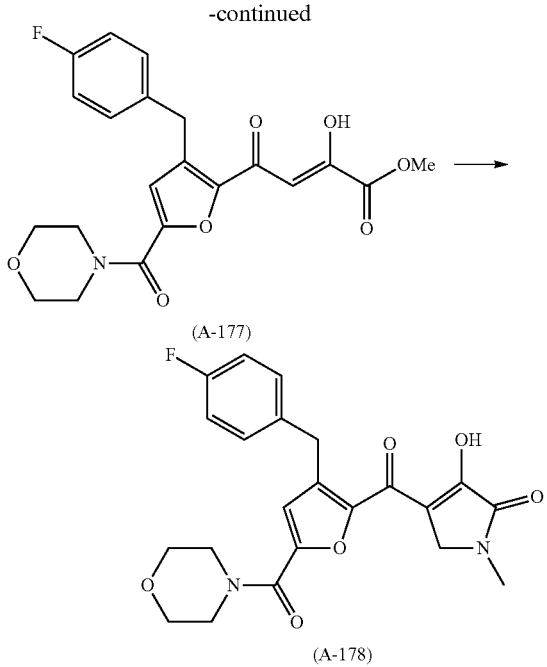

(A-172) To a tetrahydrofuran (75 ml) solution of diisopropylamine (8.41 ml, 60 mmol) in nitrogen gas under dry ice acetone cooling (−70° C.), n-butyllithium-hexane solution (1.58M) (38 ml, 60 mmol) was added dropwise (LDA preparation) for 20 minutes, then the reaction mixture was stirred for 30 minutes, to which was added dropwise a tetrahydrofuran (35 ml) solution of 3-(4-fluorobenzyl)furan-2-carboxylic acid (A-46) (5.505 g, 25 mmol) for 20 minutes. The reaction mixture was stirred for 1 hour, then a tetrahydrofuran (25 ml) solution of carbonic acid di-t-butyl ester (19.3 g, 88.4 mmol) was added dropwise for 15 minutes, which was stirred for 1.5 hours. The reaction mixture was stirred for 15 minutes under ice cooling, then water (100 ml) was added dropwise and stirred for 20 minutes. The reaction mixture was extracted with diethyl ether (300 ml)-water (200 ml), then the ether layer was extracted 4 times with 2N sodium hydroxide (15 ml) and water (50 ml). The alkali layer was cooled with ice, to which was added 2N hydrochloric acid (105 ml), then which was extracted with ethyl acetate (300 ml), washed with water (100 ml) and dried with magnesium sulfate. The reaction mixture was evaporated under reduced pressure to give a crude product of 3-(4-fluorobenzyl)furan-2,5-dicarboxylic acid-5-tert-butyl ester (A-172) (7.70 g, yield: 96.1%).

(A-173) A mixture of 3-(4-fluorobenzyl)furan-2,5-dicarboxylic acid 5-tert-butyl ester (A-172) (7.70 g, 24.04 mmol), N,O-dimethylhydroxylamine hydrochloric acid (2.93 g, 30 mmol) and hydroxybenztriazole (4.05 g, 30 mmol) was suspended in dichloromethane (250 ml) at room temperature, to which were added triethylamine (4.25 ml, 30.5 mmol) and 1-ethyl-3-(3-dimethylaminopropyl)carbodiimide hydrochloric acid (5.75 g, 30 mmol), successively. The reaction mixture was stirred, then allowed to stand overnight at room temperature, to which was added ethyl acetate, then dichloromethane was evaporated under reduced pressure. To the ethyl acetate solution, ice water and saturated sodium bicarbonate aqueous solution (80 ml) were added, and the mixture was extracted, washed and dried with magnesium sulfate. The reaction mixture was evaporated under reduced pressure, then the residue was purified with silica gel column chromatography (n-hexane:acetone=19:1) to give 4-(4-fluorobenzyl)-5-(methoxymethylcarbamoyl)furan-2-carboxylic acid tert-butyl ester (3.901 g, yield: 44.6%) from the n-hexane eluent.

Melting point: 103-107° C.

NMR (CDCl$_3$) δ: 1.55 (9H, s), 3.33 (3H, s), 3.93 (3H, s), 4.09 (2H, s), 6.83 (1H, s), 6.94-7.01 (2H, m), 7.20-7.25 (2H, m).

(A-174) To a tetrahydrofuran (40 ml) solution of the above-mentioned compound A-173 (3.80 g, 10.46 mmol) in nitrogen gas under dry ice acetone cooling (−30° C.), methylmagnesium bromide tetrahydrofuran solution (1M) (15.7 ml, 15.7 mmol) was added dropwise for 10 minutes, then the reaction mixture was stirred for 40 minutes, to which was added dropwise methylmagnesium bromide tetrahydrofuran solution (1M) (18.8 ml, 18.8 mmol). The reaction mixture was stirred for 1.5 hours, then the reaction mixture was poured into ice water, to which was added ethyl acetate and 2N hydrochloric acid (17.3 ml, 34.5 mmol), then extracted. The extract was washed with water, then dried with magnesium sulfate, which was evaporated under reduced pressure. N-hexane (8 ml) was added to the crystalline residue (3.375 g) under ice cooling to give a crystalline colorless powder of 5-acetyl-4-(4-fluorobenzyl)furan-2-carboxylic acid tert-butyl ester (2.906 g, yield: 87.3%). The filtrate was purified with silica gel column chromatography (n-hexane:acetone=24:1) to give A-174 (200 mg, yield: 6.0%) which was similarly treated with n-hexane.

Melting point: 102-103° C.

NMR (CDCl$_3$) δ: 1.56 (9H, s), 2.58 (3H, s), 4.16 (2H, s), 6.83 (1H, s), 6.95-7.01 (2H, m), 7.16-7.21 (2H, m).

(A-175) To a dichloromethane (20 ml) solution of the above-mentioned compound A-174 (1.273 g, 4.0 mmol) at room temperature, trifluoroacetic acid (12 ml) was added. The reaction mixture was stirred for 1.5 hours, then evaporated under reduced pressure. Toluene was added to the residue and evaporated. This operation was done for 2 times. N-hexane was added to the crystalline residue to give a colorless powder of 5-acetyl-4-(4-fluorobenzyl)furan-2-carboxylic acid (1.004 g, yield: 95.7%).

Melting point: 143-144° C.

NMR (CDCl$_3$) δ: 2.61 (3H, s), 4.18 (2H, s), 6.96-7.02 (2H, m), 7.07 (1H, s), 7.17-7.22 (2H, m).

(A-176) To a dichloromethane (10 ml) suspension of the above-mentioned compound A-175 (262 mg, 1.0 mmol) and hydroxybenztriazole (162 mg, 1.2 mmol) at room temperature, morpholine (0.105 ml, 1.2 mmol) and 1-ethyl-3-(3-dimethylaminopropyl)carbodiimide hydrochloric acid (230 mg, 1.2 mmol) were added. The reaction mixture was stirred for 3 hours, then evaporated under reduced pressure. Ice water and ethyl acetate were added to the residue (776 mg), which was washed with 2N hydrochloric acid (0.5 ml, 1 mmol), saturated sodium bicarbonate aqueous solution and water, successively. The reaction mixture was dried with magnesium sulfate, then evaporated under reduced pressure to give a yellow green oil of 1-[3-(4-fluorobenzyl)-5-(morpholine-4-carbonyl)furan-2-yl]etanone (343 mg, 103%).

NMR (CDCl$_3$) δ: 2.53 (3H, s), 3.70-3.85 (8H, m), 4.16 (2H, s), 6.81 (1H, s), 6.94-7.00 (2H, m), 7.17-7.22 (2H, m).

5-Acetyl-4-(4-fluorobenzyl)furan-2-carboxylic acid diethylamide (yield: 91.8%) was synthesized, by the above-mentioned method.

Melting point: 74-75° C.

NMR (CDCl$_3$) δ: 1.15-1.40 (6H, m), 2.53 (3H, s), 3.40-3.65 (4H, m), 4.16 (2H, s), 6.85 (1H, s), 6.94-6.99 (2H, m), 7.18-7.22 (2H, m).

(A-177) According to the method of A-18, a yellow crystal of 4-[3-(4-fluorobenzyl)-5-(morpholine-4-carbonyl)furan-2-yl]-2-hydroxy-4-oxo-2-butenoic acid methyl ester (407 mg, yield: 97.6%) was synthesized from the above-mentioned compound A-176 (343 mg, 1.0 mmol).

Melting point: 143-146° C.

NMR (CDCl$_3$) δ: 3.73-3.83 (8H, m), 3.95 (3H, s), 4.23 (2H, s), 6.84 (1H, s), 6.97-7.03 (3H, m), 7.18-7.25 (2H, m).

A yellow powder crystal of 4-[5-diethylcarbamoyl-3-(4-fluorobenzyl)furan-2-yl]-2-hydroxy-4-oxo-2-butenoic acid methyl ester (yield: 93.1%) was synthesized, by the above-mentioned method.

Melting point: 128-130° C.

NMR (CDCl$_3$) δ: 1.15-1.45 (6H, m), 3.45-3.65 (4H, m), 3.94 (3H, s), 4.23 (2H, s), 6.91 (1H, s), 6.96-7.03 (3H, m), 7.19-7.24 (2H, m).

(A-178) According to the method of A-19, a yellow crystal of 4-[3-(4-fluorobenzyl)-5-(morpholine-4-carbonyl)furan-2-carbonyl]-3-hydroxy-1-methyl-1,5-dihydropyrrole-2-one (237 mg, yield: 57.5%) was synthesized from the above-mentioned compound A-177 (401 mg, 0.961 mmol).

Melting point: 209-211° C. (dec)

Elementary analysis as $C_{22}H_{21}FN_2O_6$

Calcd. (%): C, 61.68; H, 4.94; N, 6.54; F, 4.43.
Found (%): C, 61.33; H, 4.92; N, 6.36; F, 4.34.

NMR (CDCl$_3$) δ: 3.19 (3H, s), 3.75 (8H, bs), 4.27 (2H, s), 4.47 (2H, s), 6.69 (1H, s), 6.98-7.03 (2H, m), 7.20-7.25 (2H, m).

(A-178-a) An ocher prism crystal of 4-(4-fluorobenzyl)-5-(4-hydroxy-1-methyl-5-oxo-2,5-dihydro-1H-pyrrole-3-carbonyl)furan-2-carboxylic acid diethylamide (yield: 36.5%) was synthesized, by the above-mentioned method.

Melting point: 122-123° C.

Elementary analysis as $C_{22}H_{23}FN_2O_5$

Calcd. (%): C, 63.76; H, 5.59; N, 6.76; F, 4.58.
Found (%): C, 63.63; H, 5.58; N, 6.61; F, 4.44.

NMR (CDCl$_3$) δ: 1.25 (6H, t, J=6.9 Hz), 3.18 (3H, s), 3.53 (4H, q, J=6.9 Hz), 4.27 (2H, s), 4.51 (2H, s), 6.64 (1H, s), 6.97-7.03 (2H, m), 7.20-7.27 (2H, m).

Compound A-184

2-(4-Fluorobenzyl)-5-(4-hydroxy-1-methyl-5-oxo-2,5-dihydro-1H-pyrrole-3-carbonyl)furan-3-carboxylic acid ethylamide

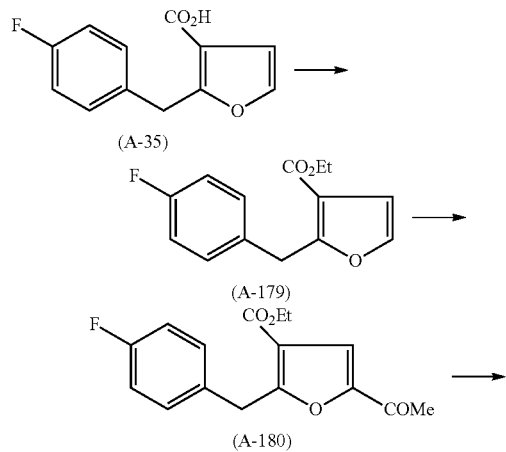
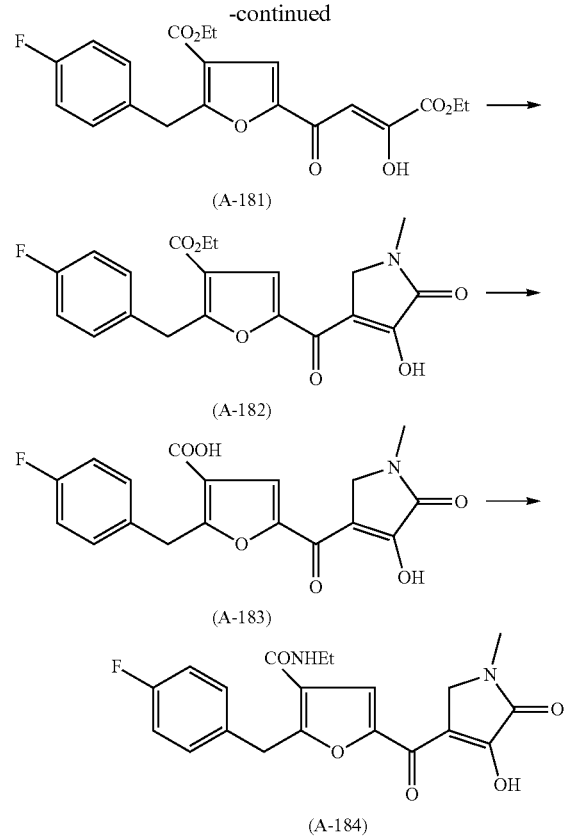

(A-179) To an ethanol (40 ml) solution of the above-mentioned compound A-35 (3.55 g, 16.1 mmol), conc-sulfuric acid (0.1 ml) was added, then dehydration was performed for 9 hours under refluxing. The reaction mixture was allowed to stand overnight at room temperature, then evaporated. The residue was dissolved to ethyl acetate, which was washed with saturated sodium hydrogen carbonate solution, dried and evaporated under reduced pressure to give a crude product of 2-(4-fluorobenzyl)furan-3-carboxylic acid ethyl ester (4.18 g, yield: 100%).

NMR (CDCl$_3$) δ: 1.35 (3H, t, J=7.2 Hz), 4.31 (2H, q, J=7.2 Hz), 4.32 (2H, s), 6.67 (1H, d, J=2.1 Hz), 6.94-7.00 (2H, m), 7.22-7.27 (3H; m).

(A-180) Aluminum chloride (11.2 g, 84 mmol) was added to methylene chloride (30 ml), then a methylene chloride solution (5 ml) of the above-mentioned compound A-179 (4.18 g, 16.8 mmol) was added thereto under ice cooling. The reaction mixture was stirred for 30 minutes, to which was added acetyl chloride (6.6 g, 84 mmol), then which was stirred at room temperature for 15 minutes. The reaction mixture was poured into ice water, which was extracted with methylene chloride, washed with 1N hydrochloric acid and saturated sodium hydrogen carbonate aqueous solution, successively. The reaction mixture was dried, then which was evaporated under reduced pressure to give a crude product of 5-acetyl-2-(4-fluorobenzyl)furan-3-carboxylic acid ethyl ester (4.54 g, yield: 93%).

NMR (CDCl$_3$) δ: 1.37 (3H, t, J=7.2 Hz), 2.44 (3H, s), 4.35 (2H, q, J=7.2 Hz), 4.38 (2H, s), 6.94-7.00 (2H, m), 7.26-7.31 (2H, m), 7.41 (1H, s).

(A-181) According to the method of the example A-18, 5-(3-ethoxycarbonyl-3-hydroxyacryloyl)-2-(4-fluorobenzyl)furan-3-carboxylic acid ethyl ester (1.1 g, yield: 82%) was synthesized from the above-mentioned compound A-180 (1.0 g, 3.44 mmol).

NMR (CDCl₃) δ: 1.38 (3H, t, J=7.2 Hz), 1.41 (3H, t, J=7.2 Hz), 4.35 (2H, q, J=7.2 Hz), 4.39 (2H, q, J=7.2 Hz), 4.41 (2H, s), 6.84 (1H, s), 6.97-7.03 (2H, m), 7.26-7.31 (2H, m), 7.57 (1H, s).

(A-182) According to the method of the example A-19, 2-(4-fluorobenzyl)-5-(4-hydroxy-1-methyl-5-oxo-2,5-dihydro-1H-pyrrole-3-carbonyl)furan-3-carboxylic acid ethyl ester (850 mg, yield: 86%) was synthesized from the above-mentioned compound A-181 (1.0 g, 2.56 mmol).

Melting point: 172-173° C.
Elementary analysis as $C_{20}H_{18}FNO_6$
Calcd. (%): C, 62.01; H, 4.68; N, 3.62; F, 4.90.
Found (%): C, 61.95; H, 4.45; N, 3.60; F, 4.73.
NMR (CDCl₃) δ: 1.40 (3H, t, J=7.2 Hz), 3.10 (3H, s), 4.02 (2H, s), 4.38 (2H, q, J=7.2 Hz), 4.45 (2H, s), 7.03-7.10 (2H, m), 7.26-7.31 (2H, m), 7.61 (1H, s).

(A-183) To a dioxane (20 ml) solution of the above-mentioned compound A-182 (500 mg, 1.29 mmol), 1N lithium hydroxide solution (3 ml) was added at 50° C. for 30 minutes, then the reaction mixture was concentrated, diluted with water, which was acidified with hydrochloric acid. The reaction mixture was extracted with chloroform, washed, dried and evaporated under reduced pressure to give a crude product (420 mg, yield: 91%), which was crystallized from methyl alcohol to give 2-(4-fluorobenzyl)-5-(4-hydroxy-1-methyl-5-oxo-2,5-dihydro-1H-pyrrole-3-carbonyl)furan-3-carboxylic acid.

Melting point: 255-258° C. (decomp.)
Elementary analysis as $C_{18}H_{14}FNO_6$
Calcd. (%): C, 60.17; H, 3.93; N, 3.90; F, 5.29.
Found (%): C, 59.86; H, 3.86; N, 3.80; F, 5.04.
NMR (DMSO-d₆): 2.99 (3H, s), 4.09 (2H, s), 4.42 (2H, s), 7.13-7.19 (2H, m), 7.29-7.34 (2H, m), 7.85 (1H, s), 13.22 (1H, bs).

(A-184) To a DMF (5 ml) solution of the above-mentioned compound A-183 (359 mg, 1 mmol), HOBt (13.5 mg, 0.1 mmol) and WSCD (575 mg, 3 mmol) in ethylamine (2 mol/l in THF, 1.5 ml, 3 mmol) was added under ice cooling. The reaction mixture was stirred at room temperature for 20 hours, then water was added to stop the reaction, which was extracted with chloroform, washed with water, dried and evaporated under reduced pressure. The crystalline residue was recrystallized from isopropyl alcohol to give 2-(4-fluorobenzyl)-5-(4-hydroxy-1-methyl-5-oxo-2,5-dihydro-1H-pyrrole-3-carbonyl)furan-3-carboxylic acid ethylamide (91 mg, yield: 24%).

Melting point: 169-170° C.
Elementary analysis as $C_{20}H_{19}O_5FN_2$
Calcd. (%) C, 62.17; H, 4.96; F, 4.92; N, 7.25.
Found (%) C, 62.05; H, 4.89; F, 4.75; N, 7.22.
¹H-NMR (CDCl₃) δ: 1.26 (3H, t, J=7.2 Hz), 3.10 (3H, s), 3.40-3.53 (2H, m), 4.01 (2H, s), 4.49 (2H, s), 5.93 (1H, bs), 7.03-7.08 (2H, m), 7.25-7.33 (2H, m), 7.41 (1H, s).

The following compound was synthesized by the above-mentioned method.

(A-184-a) 2-(4-Fluorobenzyl)-5-(4-hydroxy-1-methyl-5-oxo-2,5-dihydro-1H-pyrrole-3-carbonyl)furan-3-carboxylic acid benzylamide Melting point: 181-184° C.
Elementary analysis as $C_{25}H_{21}O_5FN_2$
Calcd. (%) C, 66.96; H, 4.72; F, 4.24; N, 6.25.
Found (%) C, 66.63; H, 4.64; F, 4.06; N, 6.12.

¹H NMR (CDCl₃) δ: 3.9 (3H, s), 4.00 (2H, s), 4.51 (2H, s), 4.62 (2H, d, J=5.5 Hz), 6.28 (1H, bs), 7.02-7.08 (2H, m), 7.26-7.42 (8H, m).

B Group Compound

Compound B-6

3-Hydroxy-1-isopropyl-4-(6-phenethylpyrimidine-4-yl)-1,5-dihydropyrrole-2-one

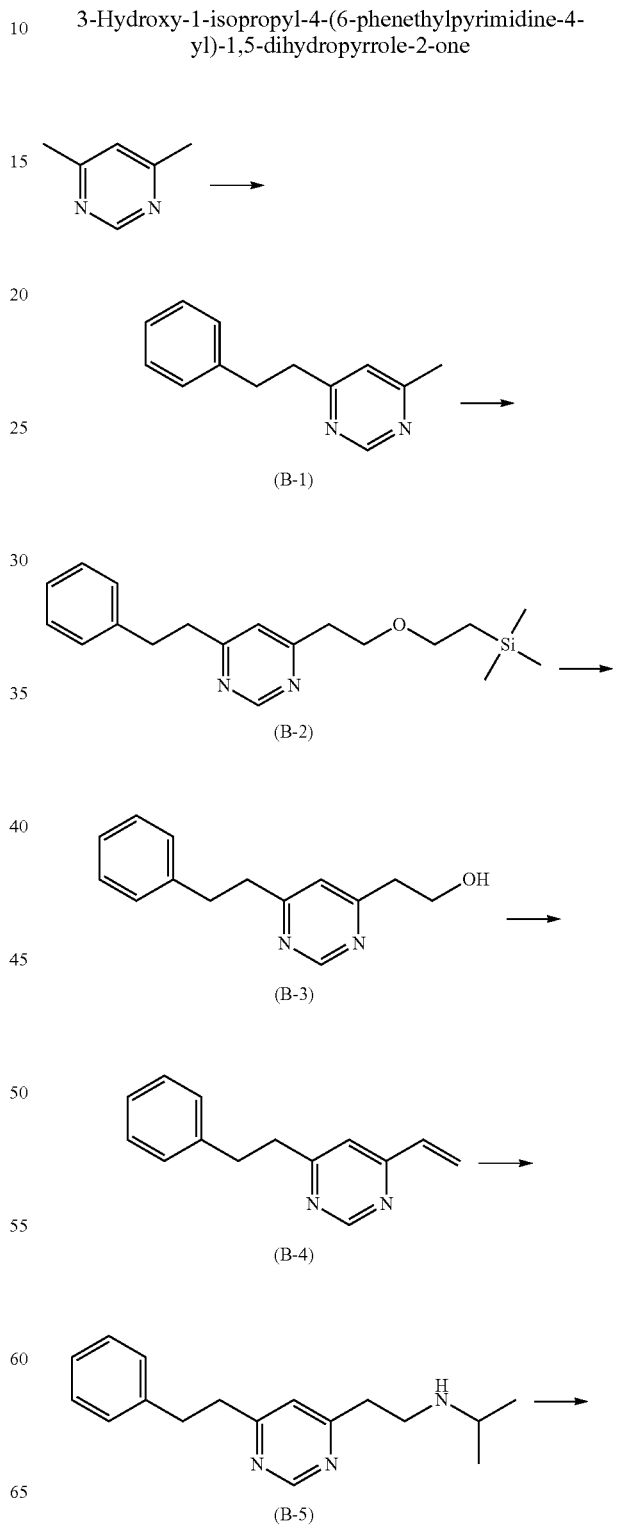

-continued

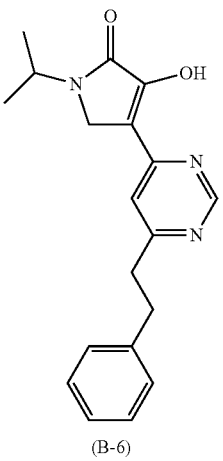

(B-6)

(B-1) According to the method of the reference (WO01/17968), 4-methyl-6-phenethylpyrimidine was synthesized.
(B-2) To a THF (100 ml) solution of the above-mentioned compound B-1 (19.8 g, 100 mmol) at −78° C., n-butyllithium solution (100 mmol) was added dropwise, then a THF (50 ml) solution of 2-(trimethylsilyl)ethoxymethyl chloride (16.7 g, 100 mmol) was added thereto. The reaction mixture was stirred at 0° C. for 30 minutes, to which was added ammonium chloride aqueous solution, then extracted with ethyl acetate. The extract was washed, dried and evaporated to give a 9:1 mixture (32.7 g, yield: 100%) of 4-phenethyl-6-[2-(2-trimethylsilanylethoxy)ethyl]pyrimidine and 4-methyl-6-[2-phenyl-1-(2-trimethylsilanylethoxymethyl)ethyl]pyrimidine.

4-phenethyl-6-[2-(2-trimethylsilanylethoxy)ethyl]pyrimidine

NMR (CDCl$_3$) δ: −0.03 (9H, s), 0.89 (2H, dd, J=8.0, 8.0 Hz), 2.95 (2H, t, J=6.5 Hz), 3.04 (4H, s), 3.50 (2H, dd, J=8.0, 8.0 Hz), 3.75 (2H, t, J=6.5 Hz), 7.03 (1H, d, J=1.2 Hz), 7.18-7.31 (5H, m), 9.05 (1H, d, J=1.2 Hz).
(B-3) To a 1,4-dioxane (50 ml) solution of the above-mentioned compound B-2 (32.7 g, 100 mmol), 5N-hydrochloric acid aqueous solution (100 ml) was added, then the reaction mixture was stirred at 60° C. for 1 hour, to which was added sodium carbonate until the solution became alkali, then extracted with ethyl acetate. The extract was washed, dried, and evaporated to give a crude mixture product (23.6 g) of 2-(6-phenethylpyrimidine-4-yl)ethanol and 2-(6-methylpyrimidine-4-yl)-3-phenylpropane-1-ol.

NMR (CDCl$_3$) δ: 2.94 (2H, t, J=5.5 Hz), 3.06 (4H, s), 4.00 (2H, t, J=5.5 Hz), 6.97 (1H, d, J=1.2 Hz), 7.16-7.31 (5H, m), 9.05 (1H, d, J=1.2 Hz).
(B-4) To a chloroform (100 ml) solution of the above-mentioned crude product B-3 (23.6 g), pyridine (15.8 g, 200 mmol) was added, to which was added trifluoromethanesulfonic acid anhydride (28.2 g, 100 mmol) under ice cooling. The reaction mixture was stirred for 10 minutes, then sodium hydrogen carbonate aqueous solution (100 ml) was added thereto and chloroform was evaporated under reduced pressure. 1,4-Dioxane (50 ml) was added to the residue, then was added 5N-sodium hydroxide aqueous solution (50 ml) under ice cooling. The reaction mixture was stirred for 30 minutes, which was extracted with diethyl ether. The extract was washed, dried and evaporated under reduced pressure, then the residue was purified with silica gel column chromatography (n-hexane ethyl acetate=5:1-1:1) to give 4-phenethyl-6-vinylpyrimidine (3.7 g, yield: 18%).

NMR (CDCl$_3$) δ: 3.07 (4H, s), 5.67 (1H, dd, J=10.7, 1.2 Hz), 6.42 (1H, dd, J=17.4, 1.2 Hz), 6.68 (1H, dd, J=10.4, 17.4 Hz), 7.03 (1H, d, J=1.2 Hz), 7.17-7.32 (5H, m), 9.09 (1H, d, J=1.2 Hz).
(B-5) To an ethanol (3 ml) solution of the above-mentioned compound B-4 (316 mg, 1.5 mmol), acetic acid (90 mg, 1.5 mmol) and isopropylamine (266 mg, 4.5 mmol) were added, then the reaction mixture was refluxed for 3 hours. Sodium hydrogen carbonate aqueous solution was added thereto, then extracted with chloroform. The extract was washed, dried and evaporated under reduced pressure, then the residue was purified with silica gel column chromatography (chloroform:methyl alcohol=9:1) to give isopropyl[2-(6-phenethylpyrimidine-4-571)ethyl]amine (309 mg, yield: 76%).

NMR (CDCl$_3$) δ: 1.07 (6H, d, J=6.3 Hz), 2.85-3.06 (9H, m), 6.96 (1H, d, J=1.2 Hz), 7.16-7.31 (5H, m), 9.05 (1H, d, J=1.2 Hz).

The following compounds were synthesized by the above-mentioned method.

Methyl[2-(6-phenethylpyrimidine-4-yl)ethyl]amine

NMR (CDCl$_3$) δ: 2.45 (3H, s), 2.86-3.04 (4H, m), 3.06 (4H, s), 6.94 (1H, d, J=1.2 Hz), 7.16-7.31 (5H, m), 9.05 (1H, d, J=1.2 Hz).

Benzyl[2-(6-phenethylpyrimidine-4-yl)ethyl]amine

NMR (CDCl$_3$) δ: 2.90-3.05 (8H, m), 3.84 (2H, s), 6.93 (1H, d, J=0.9 Hz), 7.15-7.33 (5H, m), 9.03 (1H, d, J=1.3 Hz).

(1-Ethylpropyl)[2-(6-phenethylpyrimidine-4-yl)ethyl]amine

NMR (CDCl$_3$) δ: 0.87 (6H, t, J=7.5 Hz), 1.45 (4H, dq, J=7.6, 7.0 Hz), 2.44 (1H, tt, J=6.1, 5.8 Hz), 2.89-3.06 (8H, m), 6.99 (1H, d, J=1.2 Hz), 7.17-7.31 (5H, m), 9.04 (1H, d, J=1.2 Hz).

Cyclohexyl[2-(6-phenethylpyrimidine-4-yl)ethyl]amine

NMR (CDCl$_3$) δ: 1.07-1.28 (6H, m), 1.60-1.91 (4H, m), 2.48 (1H, m), 2.90 (2H, t, J=6.7 Hz), 3.01-3.06 (6H, m), 6.96 (1H, d, J=1.2 Hz), 7.16-7.31 (5H, m), 9.05 (1H, d, J=1.2 Hz).

[2-(6-Phenethylpyrimidine-4-yl)ethyl]phenylamine

NMR (CDCl$_3$) δ: 2.97-3.05 (6H, m), 3.53 (2H, t, J=6.4 Hz), 6.65 (2H, d, J=7.3 Hz), 6.75 (1H, t, J=7.3 Hz), 6.92 (1H, d, J=0.9 Hz), 7.14-7.30 (7H, m), 9.08 (1H, d, J=1.2 Hz).

Tert-butyl[2-(6-phenethylpyrimidine-4-yl)ethyl]amine

NMR (CDCl$_3$) δ: 1.19 (9H, s), 2.99-3.06 (8H, m), 6.97 (1H, d, J=1.2 Hz), 7.16-7.31 (5H, m), 9.04 (1H, d, J=1.2 Hz).

O-tert-butyl N-[2-(6-phenethylpyrimidine-4-yl)ethyl]hydroxylamine

NMR (CDCl$_3$) δ: 1.20 (9H, s), 2.95 (2H, brs), 3.04 (4H, s), 3.27 (2H, brs), 6.99 (1H, d, J=1.2 Hz), 7.16-7.31 (5H, m), 9.04 (1H, d, J=1.2 Hz).

(B-6) To an ethanol (1.5 ml) solution of the above-mentioned compound B-5 (269 mg, 1 mmol), oxalic acid diethyl (175 mg, 1.2 mmol) and sodium ethoxide (4.5 mmol, 20% ethanol solution) were added, then the reaction mixture was heated at 60° C. for 5 hours. Ammonium chloride aqueous solution was added to the solution, which was extracted with chloroform. The extract was washed, dried and evaporated under reduced pressure. The precipitated crystal was washed with methyl alcohol, which was dried with reduced pressure to give 3-hydroxy-1-isopropyl-4-(6-phenethylpyrimidine-4-yl)-1,5-dihydropyrrole-2-one (209 mg, yield: 65%).

Melting point: 229-231° C.
Elementary analysis as $C_{19}H_{21}N_3O_2$ $0.2H_2O$
Calcd. (%): C, 69.79; H, 6.60; N, 12.85.
Found (%): C, 69.85; H, 6.46; N, 12.83.
NMR (CDCl$_3$) δ: 1.28 (6H, d, J=6.7 Hz), 3.09 (4H, s), 4.05 (2H, s), 4.57 (1H, qq, J=6.9, 6.7 Hz), 6.93 (1H, s), 7.18-7.32 (5H, m), 9.02 (1H, s).

The following compounds were synthesized by the above-mentioned method.

(B-6-a) 3-Hydroxy-1-methyl-4-(6-phenethylpyrimidine-4-yl)-1,5-dihydropyrrole-2-one Melting point: 211-213° C.
Elementary analysis as $C_{17}H_{17}N_3O_2$
Calcd. (%): C, 69.14; H, 5.80; N, 14.23.
Found (%): C, 69.09; H, 5.61; N, 14.23.
NMR (CDCl$_3$) δ: 3.09 (4H, s), 3.16 (3H, s), 4.07 (2H, s), 6.79 (1H, s), 7.16-7.29 (5H, m), 9.01 (1H, s).

(B-6-b) 1-Benzyl-3-hydroxy-4-(6-phenethylpyrimidine-4-yl)-1,5-dihydropyrrole-2-one Melting point: 222-223° C.
Elementary analysis as $C_{23}H_{21}N_3O_2$ $0.3H_2O$
Calcd. (%): C, 73.31; H, 5.78; N, 11.15.
Found (%): C, 73.37; H, 5.49; N, 11.19.
NMR (CDCl$_3$) δ: 3.05 (4H, s), 3.93 (3H, s), 4.73 (2H, s), 6.70 (1H, s), 7.13-7.39 (10H, m), 9.00 (1H, s).

(B-6-c) 1-(1-Ethylpropyl)-3-hydroxy-4-(6-phenethylpyrimidine-4-yl)-1,5-dihydropyrrole-2-one Melting point: 182-183° C.
Elementary analysis as $C_{21}H_{25}N_3O_2$
Calcd. (%): C, 71.77; H, 7.17; N, 11.96.
Found (%): C, 71.69; H, 7.13; N, 11.90.
NMR (CDCl$_3$) δ: 0.88 (6H, t, J=7.3 Hz), 1.48-1.74 (4H, m), 3.10 (4H, s), 3.96 (2H, s), 4.10 (1H, m), 6.94 (1H, s), 7.19-7.33 (5H, m), 9.06 (1H, s).

(B-6-d) 1-Cyclohexyl-3-hydroxy-4-(6-phenethylpyrimidine-4-yl)-1,5-dihydropyrrole-2-one Melting point: 248-250° C.
Elementary analysis as $C_{22}H_{25}N_3O_2$ $0.1H_2O$
Calcd. (%): C, 72.34; H, 6.95; N, 11.50.
Found (%): C, 72.28; H, 6.92; N, 11.55.
NMR (CDCl$_3$) δ: 1.41-1.51 (4H, m), 1.71-1.88 (6H, m), 3.10 (4H, s), 4.07 (2H, 4.15 (1H, m), 6.92 (1H, s), 7.18-7.32 (5H, m), 9.03 (1H, s).

(B-6-e) 1-Hydroxy-4-(6-phenethylpyrimidine-4-yl)-1-phenyl-1,5-dihydropyrrole-2-one Melting point: 253-255° C.
Elementary analysis as $C_{22}H_{19}N_3O_2$ $0.1H_2O$
Calcd. (%): C, 73.56; H, 5.39; N, 11.70.
Found (%): C, 73.37; H, 5.16; N, 11.65.
NMR (CDCl$_3$) δ: 3.13 (4H, s), 4.56 (2H, s), 6.98 (1H, s), 7.18-7.33 (6H, m), 7.44 (2H, t, J=7.6 Hz), 7.81 (2H, d, J=7.6 Hz), 9.08 (1H, s).

(B-6-f) 1-Tert-butyl-3-hydroxy-4-(6-phenethylpyrimidine-4-yl)-1,5-dihydropyrrole-2-one Melting point: 199-200° C.
Elementary analysis as $C_{20}H_{23}N_3O_2$
Calcd. (%): C, 71.19; H, 6.87; N, 12.45.
Found (%): C, 70.84; H, 6.81; N, 12.30.
NMR (CDCl$_3$) δ: 1.53 (9H, s), 3.09 (4H, s), 4.16 (2H, s), 7.03 (1H, s), 7.19-7.32 (5H, m), 9.03 (1H, s).

(B-6-g) 1-Tert-butoxy-3-hydroxy-4-(6-phenethylpyrimidine-4-yl)-1,5-dihydropyrrole-2-one Melting point: 230-232° C.
Elementary analysis as $C_{20}H_{23}N_3O_2$ $0.1H_2O$,
Calcd. (%): C, 67.62; H, 6.58; N, 11.83.
Found (%): C, 67.51; H, 6.42; N, 11.83.
NMR (CDCl$_3$) δ: 1.39 (9H, s), 3.10 (4H, s), 4.27 (2H, s), 6.76 (1H, s), 7.17-7.32 (5H, m), 9.02 (1H, s).

Compound B-9

4-[5-(4-Fluorobenzyl)-[1,3,4]oxadiazole-2-yl]-3-hydroxy-1-isopropyl-1,5-dihydropyrrole-2-one

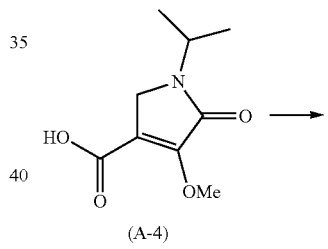
(A-4)

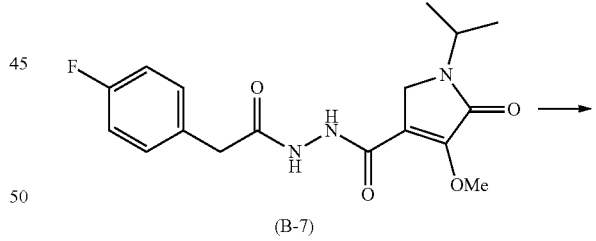
(B-7)

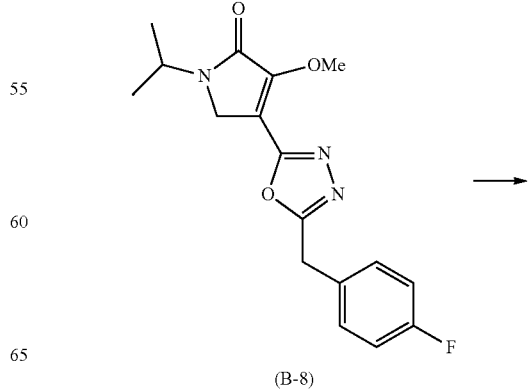
(B-8)

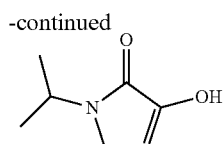

(B-9)

(B-7) To a THF (10 ml) solution of 4-hydroxy-1-isopropyl-5-oxo-2,5-dihydro-1H-pyrrole-3-carboxylic acid A-4 (995 mg, 5 mmol), (4-fluorophenyl) acetic acid hydrazide (924 mg, 5.5 mmol), 1-hydroxybenzotriazole (67 mg, 0.5 mmol) and 1-ethyl-3-(3-dimethylaminopropyl)carbodiimide (931 mg, 6 mmol) were added, then the reaction mixture was stirred for 2 hours. The reaction was stopped with water, which was extracted with ethyl acetate. The extract was washed, dried and evaporated under reduced pressure. The residue was purified with silica gel column chromatography (n-hexane:ethyl acetate=1:4-0:1) to give 1-isopropyl-4-methoxy-5-oxo-2,5-dihydro-1H-pyrrole-3-carboxylic acid N'-[2-(4-fluorophenyl)acetyl]hydrazide (1.46 g, yield: 84%).

Melting point: 157-158° C.

NMR (CDCl$_3$) δ: 1.21 (6H, d, J=6.9 Hz), 3.63 (2H, s), 3.94 (2H, s), 4.36-4.45 (4H, m), 7.00-7.08 (2H, m), 7.26-7.32 (2H, m), 8.38 (1H, s), 9.26 (1H, s).

(B-8) To a methylene chloride (3 ml) solution of triphenylphosphine (629 mg, 2.4 mmol), bromine (2.4 mmol, 1M methylene chloride solution) was added dropwise under ice cooling, then the reaction mixture was stirred at room temperature for 30 minutes, to which triethylamine (506 mg, 5 mmol) and the above-mentioned compound B-7 (699 mg, 2 mmol) were added at room temperature, successively. The reaction mixture was warmed, then the reaction was stopped with water, which was extracted with chloroform. The extract was washed, dried and evaporated under reduced pressure. The residue was purified with silica gel column chromatography (n-hexane:ethyl acetate=1:1-1:3) to give 4-[5-(4-fluorobenzyl)-[1,3,4]oxadiazole-2-yl]-1-isopropyl-3-methoxy-1,5-dihydropyrrole-2-one (595 mg, yield: 90%).

NMR (CDCl$_3$) δ: 1.24 (6H, d, J=6.7 Hz), 4.16 (2H, s), 4.22 (2H, s), 4.30 (3H, s), 4.46 (1H, qq, J=6.7 Hz), 7.00-7.08 (2H, m), 7.27-7.34 (2H, m).

(B-9) To an acetonitrile solution (5 ml) of the above-mentioned compound B-8 (550 mg, 1.66 mmol), sodium iodide (1.99 g, 13.3 mmol) was added, to which was added chlorotrimethylsilane (1.44 g, 13.3 mmol) under ice cooling. The reaction mixture was stirred at 50° C. for 2 hours, to which were added water and 10% sodium sulfite aqueous solution (2 ml), successively. The precipitated crystal was washed with water and ethyl acetate, successively, then dried under reduced pressure to give 4-[5-(4-fluorobenzyl)-[1,3,4]oxadiazole-2-yl]-3-hydroxy-1-isopropyl-1,5-dihydropyrrole-2-one (441 mg, yield: 84%).

Melting point: 204-206° C.

Elementary analysis as C$_{16}$H$_{16}$N$_3$O$_3$

Calcd. (%): C, 60.56; H, 5.08; N, 13.24; F, 5.99.

Found (%): C, 60.43; H, 4.93; N, 13.14; F, 5.93.

NMR (CDCl$_3$) δ: 1.28 (6H, d, J=6.7 Hz), 4.22 (2H, s), 4.24 (2H, s), 4.50 (1H, qq, J=6.7 Hz), 6.99-7.07 (2H, m), 7.26-7.34 (2H, m).

Compound B-12

4-(6-Benzyloxypyrimidine-4-yl)-3-hydroxy-1-methyl-1,5-dihydropyrrole-2-one

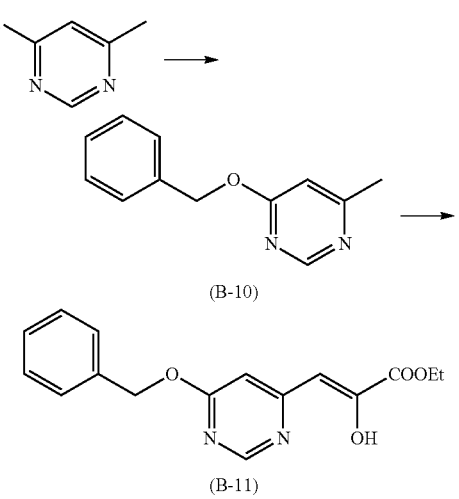

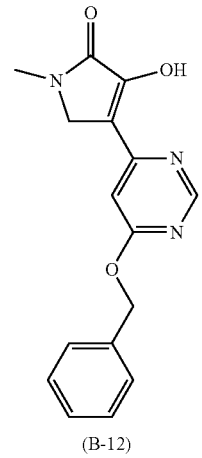

(B-12)

(B-10) To a dimethylformamide (5 ml) solution of sodium hydride (192 mg, 8 mmol), a dimethylformamide (3 ml) solution of benzyl alcohol was added for 30 minutes, to which was added for 10 minutes 4-chloro-6-methylpyrimidine (1.03 g, 8 mmol) which was synthesized according to the method of the reference (WO01/17968). The reaction was quenched by adding ammonium chloride aqueous solution, then the reaction mixture was extracted with diethyl ether. The extract was washed, dried and evaporated under reduced pressure. The residue was purified with silica gel column chromatography (n-hexane:ethyl acetate=3:1-2:1) to give 4-benzyloxy-6-methylpyrimidine (1.49 g, yield: 93%).

NMR (CDCl$_3$) δ: 2.45 (3H, s), 5.42 (2H, s), 6.64 (1H, s), 7.36-7.43 (5H, m), 8.69 (1H, s).

(B-11) To a tetrahydrofuran (10 ml) solution of the above-mentioned compound B-10 (601 mg, 3 mmol), oxalic acid diethyl (2.2 g, 15 mmol) and potassium tert-butoxide (672 mg, 6 mmol) were added at 60° C. for 30 minutes, successively. The reaction was quenched by adding ammonium chloride aqueous solution, then extracted with ethyl acetate. The extract was washed, dried and evaporated under reduced pressure. The precipitated crystal was washed with n-hexane, then dried under reduced pressure to give 3-(6-benzyloxypyrimidine-4-yl)-2-hydroxyacrylic acid ethyl ester (694 mg, yield: 77%).

Melting point: 136-137° C.

NMR (CDCl$_3$) δ: 1.39 (3H, t, J=7.2 Hz), 4.36 (2H, q, J=7.2 Hz), 5.46 (2H, s), 6.42 (1H, s), 6.57 (1H, s), 7.35-7.46 (5H, m), 8.69 (1H, s).

(B-12) To a dioxane (1 ml) solution of the above-mentioned compound B-11 (100 mg, 0.33 mmol), paraformaldehyde (50 mg, 1.65 mmol) and methylamine (0.66 mmol. 30% ethanolsolution) were added at room temperature for 1 hour, successively. The reaction was quenched by adding ammonium chloride aqueous solution, then the reaction mixture was extracted with ethyl acetate. The extract was washed, dried and evaporated under reduced pressure. The precipitated crystal was washed with diethyl ether, then dried under reduced pressure to give 4-(6-benzyloxypyrimidine-4-yl)-3-hydroxy-1-methyl-1,5-dihydropyrrole-2-one (83 mg, yield: 85%).

Melting point: 203-204° C.
Elementary analysis as $C_{16}H_{15}N_3O_3$ 0.1$H_2O$
Calcd. (%): C, 64.25; H, 5.12; N, 14.05.
Found (%): C, 64.09; H, 4.94; N, 13.99.

NMR (CDCl$_3$) δ: 1.15 (3H, s), 4.07 (2H, s), 5.47 (2H, s), 6.47 (1H, s), 7.30-7.48 (5H, m), 8.72 (1H, s).

The following compounds were synthesized by the above-mentioned method.

(B-12-a) 4-(6-Benzyloxypyrimidine-4-yl)-3-hydroxy-1-isopropyl-1,5-dihydropyrrole-2-one Melting point: 177-178° C.
Elementary analysis as $C_{18}H_{19}N_3O_3$ 0.1$H_2O$
Calcd. (%): C, 66.08; H, 5.92; N, 12.84.
Found (%): C, 65.99; H, 5.80; N, 12.68.

NMR (CDCl$_3$) δ: 1.26 (6H, d, J=6.7 Hz), 4.04 (2H, s), 4.56 (1H, sept), 5.47 (2H, s), 6.55 (1H, s), 7.30-7.47 (5H, m), 8.72 (1H, s).

(B-12-b) 4-[6-(4-Fluorobenzyloxyl)pyrimidine-4-yl]-3-hydroxy-1-methyl-1,5-dihydropyrrole-2-one H-NMR (CDCl$_3$) δ: 3.15 (s, 3H), 4.08 (s, 2H), 5.43 (s, 2H), 6.47 (d, 1H, J=1.2 Hz), 7.05-7.15 (m, 2H), 7.40-7.50 (m, 2H), 8.71 (d, 1H, J=1.2 Hz).

Melting point: 232-234° C.
Elementary analysis as $C_{16}H_{14}N_3O_3F$
Calcd. (%) C, 60.95; H, 4.48; N, 13.33; F, 6.03.
Found (%) C, 60.89; H, 4.36; N, 13.27; F, 6.14.

(B-12-c) 4-[6-(4-Fluorobenzyloxyl)pyrimidine-4-yl]-3-hydroxy-1-isopropyl-1,5-dihydropyrrole-2-one H-NMR (CDCl$_3$) δ: 1.26 (d, 6H, J=6.9 Hz), 4.05 (s, 2H), 4.55 (m, 1H), 5.43 (s, 2H), 6.50 (d, 1H, J=1.2 Hz), 7.05-7.15 (m, 2H), 7.40-7.50 (m, 2H), 8.71 (d, 1H, J=1.2 Hz).

Melting point: 191° C.
Elementary analysis as $C_{18}H_{18}N_3O_3F$.0.3$H_2O$
Calcd. (%) C, 61.99; H, 5.38; N, 12.05; F, 5.45.
Found (%) C, 61.87; H, 5.11; N, 12.05; F, 5.35.

(B-12-d) 4-[6-(2-Fluorobenzyloxyl)pyrimidine-4-yl]-3-hydroxy-1-methyl-1,5-dihydropyrrole-2-one H-NMR (CDCl$_3$) δ: 3.15 (s, 3H), 4.07 (s, 2H), 5.53 (s, 2H), 6.48 (d, 1H, J=1.2 Hz), 7.10-7.20 (m, 2H), 7.34 (m, 1H), 7.48 (m, 1H), 8.72 (d, 1H, J=1.2 Hz).

Melting point: 215-217° C.
Elementary analysis as $C_{16}H_{14}N_3O_3F$.0.3$H_2O$
Calcd. (%) C, 59.92; H, 4.59; N, 13.10; F, 5.92.
Found (%) C, 60.10; H, 4.51; N, 13.05; F, 5.64.

(B-12-e) 4-[6-(2-Fluorobenzyloxyl)pyrimidine-4-yl]-3-hydroxy-1-isopropyl-1,5-dihydropyrrole-2-one H-NMR (CDCl$_3$) δ: 1.26 (d, 6H, J=6.91 Hz), 4.06 (s, 2H), 4.55 (m, 1H), 5.54 (s, 2H), 6.63 (d, 1H, J=1.2 Hz), 7.05-7.20 (m, 2H), 7.35 (m, 1H), 7.48 (m, 1H), 8.72 (d, 1H, J=1.2 Hz).

Melting point: 170-171° C.
Elementary analysis as $C_{18}H_{18}N_3O_3F$
Calcd. (%) C, 62.97; H, 5.28; N, 12.24; F, 5.53.
Found (%) C, 62.94; H, 5.33; N, 12.21; F, 5.31.

(B-12-f) 3-Hydroxy-4-[6-(3-isopropylbenzyloxyl)pyrimidine-4-yl]-1-methyl-1,5-dihydropyrrole-2-one H-NMR (CDCl$_3$) δ: 1.27 (d, 6H, J=6.6 Hz), 2.93 (m, 1H), 3.15 (s, 3H), 4.08 (s, 2H), 5.45 (s, 2H), 6.48 (d, 1H, J=1.2 Hz), 7.20-7.36 (m, 4H), 8.73 (d, 1H, J=1.2 Hz).

Melting point: 149-150° C.
Elementary analysis as $C_{19}H_{21}N_3O_3$
Calcd. (%) C, 67.24; H, 6.24; N, 12.38.
Found (%) C, 67.17; H, 6.08; N, 12.38.

(B-12-g) 3-Hydroxy-4-[6-(3-isopropylbenzyloxyl)pyrimidine-4-yl]-1-isopropyl-1,5-dihydropyrrole-2-one H-NMR (CDCl$_3$) δ: 1.26 (d, 6H, J=6.6 Hz), 1.27 (d, 6H, J=6.9 Hz), 2.93 (m, 1H), 4.05 (s, 3H), 4.56 (m, 1H), 5.45 (s, 2H), 6.58 (d, 1H, J=1.2 Hz), 7.20-7.36 (m, 4H), 8.73 (d, 1H, J=1.2 Hz).

Melting point: 191° C.
Elementary analysis as $C_{21}H_{25}N_3O_3$
Calcd. (%) C, 68.64; H, 6.86; N, 11.44.
Found (%) C, 68.63; H, 6.64; N, 11.38.

(B-12-h) 1-Ethyl-4-[6-(4-fluorobenzyloxy)pyrimidine-4-yl]-3-hydroxy-1,5-dihydropyrrole-2-one H-NMR (CDCl$_3$) δ: 1.24 (t, 3H, J=7.2 Hz), 3.61 (q, 2H, J=7.2H), 4.10 (s, 2H), 5.43 (s, 2H), 6.57 (d, 1H, J=1.2 Hz), 7.05-7.11 (m, 2H), 7.40-7.46 (m, 2H), 8.70 (d, 1H, J=1.2 Hz).

Melting point: 171-173° C.
Elementary analysis as $C_{17}H_{16}N_3O_3F$
Calcd. (%) C, 62.00; H, 4.90; N, 12.76; F, 5.77.
Found (%) C, 61.97; H, 4.83; N, 12.69; F, 5.77.

(B-12-i) 4-[6-(4-Fluorobenzyloxyl)pyrimidine-4-yl]-3-hydroxy-1-propyl-1,5-dihydropyrrole-2-one H-NMR (CDCl$_3$) δ: 0.95 (t, 3H, J=7.5 Hz), 1.65 (m, 2H), 3.51 (t, 2H, J=7.5H), 4.08 (s, 2H), 5.43 (s, 2H), 6.52 (d, 1H, J=1.2 Hz), 7.05-7.11 (m, 2H), 7.40-7.45 (m, 2H), 8.71 (d, 1H, J=1.2 Hz).

Melting point: 159-160° C.
Elementary analysis as $C_{18}H_{18}N_3O_3F$

Calcd. (%) C, 62.97; H, 5.28; N, 12.24; F, 5.53.
Found (%) C, 63.00; H, 5.24; N, 12.21; F, 5.65.

(B-12-j) 4-[6-(4-Fluorobenzyloxyl)pyrimidine-4-yl]-3-hydroxy-1-(2-hydroxyethyl)-1,5-dihydropyrrole-2-one H-NMR (DMSO-$d_6$) δ: 3.50 (m, 2H), 3.59 (m, 2H), 4.29 (s, 2H), 4.85 (bs, 2H), 5.42 (s, 2H), 7.19-7.28 (m, 3H), 7.50-7.58 (m, 2H), 8.75 (m, 1H).
Melting point: 178-180° C.
Elementary analysis as $C_{17}H_{16}N_3O_4F$
Calcd. (%) C, 59.13; H, 4.67; N, 12.17; F, 5.50.
Found (%) C, 59.07; H, 4.64; N, 12.07; F, 5.55.

(B-12-k) 4-[6-(4-Fluorobenzyloxyl)pyrimidine-4-yl]-3-hydroxy-1-(2-methoxyethyl)-1,5-dihydropyrrole-2-one H-NMR (CDCl$_3$) δ: 3.35 (s, 3H), 3.59 (t, 2H, J=4.8 Hz), 3.72 (t, 2H, J=4.8 Hz), 4.23 (s, 2H), 5.43 (s, 2H), 6.48 (d, 1H, J=1.2 Hz), 7.05-7.11 (m, 2H), 7.40-7.46 (m, 2H), 8.71 (d, 1H, J=1.2 Hz).
Melting point: 153-154° C.
Elementary analysis as $C_{18}H_{18}N_3O_4F$
Calcd. (%) C, 60.16; H, 5.05; N, 11.69; F, 5.29.
Found (%) C, 60.17; H, 5.01; N, 11.64; F, 5.37.

(B-12-l) 4-[6-(4-Fluorobenzyloxyl)pyrimidine-4-yl]-3-hydroxy-1,5-dihydropyrrole-2-one H-NMR (DMSO-$d_6$) δ: 4.11 (s, 2H), 5.42 (s, 2H), 7.18-7.28 (m, 3H), 7.50-7.56 (m, 2H), 8.73 (s, 1H), 8.76 (m, 1H).
Melting point: 194-196° C.
Elementary analysis as $C_{15}H_{12}N_3O_3F$
Calcd. (%) C, 59.80; H, 4.01; N, 13.95; F, 6.31.
Found (%) C, 59.53; H, 4.00; N, 13.83; F, 6.21.

(B-12-m) 4-[6-(4-Fluorobenzyloxyl)pyrimidine-4-yl]-3-hydroxy-1-(4-methoxybenzyl)-1,5-dihydropyrrole-2-one H-NMR (CDCl$_3$) δ: 3.80 (s, 3H), 3.91 (s, 2H), 4.66 (s, 2H), 5.40 (s, 2H), 6.38 (d, 1H, J=1.2 Hz), 6.87 and 7.20 (ABq, 2H×2, J=8.4 Hz), 7.02-7.09 (m, 2H), 7.37-7.41 (m, 2H), 8.69 (d, 1H, J=1.2 Hz).
Melting point: 227-228° C.
Elementary analysis as $C_{23}H_{20}N_3O_4F \cdot 0.1H_2O$
Calcd. (%) C, 65.27; H, 4.81; N, 9.93; F, 4.49.
Found (%) C, 65.06; H, 4.52; N, 9.94; F, 4.43.

(B-12-n) 1-Allyl-4-[6-(4-fluorobenzyloxy)pyrimidine-4-yl]-3-hydroxy-1,5-dihydropyrrole-2-one H-NMR (CDCl$_3$) δ: 4.05 (s, 2H), 4.16 (m, 2H), 5.20-5.23 (m, 1H), 5.26 (m, 1H), 5.43 (s, 2H), 5.75-5.90 (m, 1H), 6.48 (d, 1H, J=1.2 Hz), 7.04-7.10 (m, 2H), 7.37-7.44 (m, 2H), 8.71 (d, 1H, J=1.2 Hz).
Melting point: 167-168° C.
Elementary analysis as $C_{18}H_{16}N_3O_3F$
Calcd. (%) C, 63.34; H, 4.72; N, 12.31; F, 5.57.
Found (%) C, 63.43; H, 4.59; N, 12.37; F, 5.62.

(B-12-o) 3-Hydroxy-4-[6-(2-isopropylbenzyloxy)-pyrimidine-4-yl]-1-methyl-1,5-dihydropyrrole-2-one Melting point: 240-241° C.
Elementary analysis as $C_{19}H_{21}N_3O_3$ Calcd. (%): C, 67.24; H, 6.24; N, 12.38.
Found (%): C, 67.03; H, 6.07; N, 12.31.
NMR (CDCl$_3$) δ: 1.28 (6H, d, J=6.7 Hz), 3.15 (3H, s), 3.22 (1H, m), 4.08 (2H, s), 5.52 (2H, s), 6.42 (1H, s), 7.19-7.23 (1H, m), 7.37-7.42 (3H, m), 8.73 (1H, s).

Compound B-14

4-{6-[2-(4-Fluorophenyl)ethyl]pyrimidine-4-yl}-3-hydroxy-1-methyl-1,5-dihydropyrrole-2-one

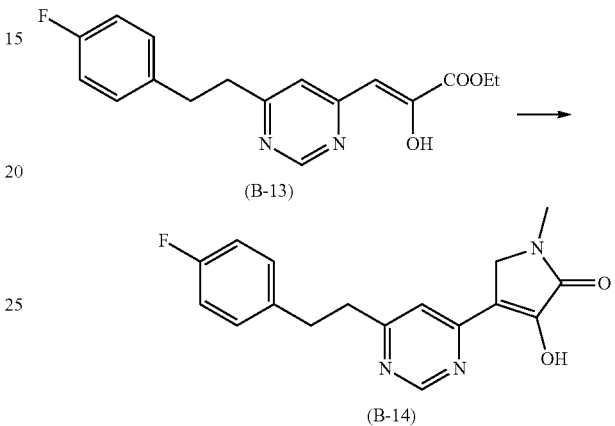

(B-13) According to the method of the reference (WO01/17968), 3-{6-[2-(4-fluorophenyl)ethyl]pyrimidine-4-yl}-2-hydroxyacrylic acid ethyl ester was synthesized.
Melting point: 139-141° C.
NMR (CDCl$_3$) δ: 1.39 (3H, t, J=7.3 Hz), 3.04 (4H, s), 4.37 (2H, q, J=7.3 Hz), 6.39 (1H, s), 6.86 (1H, s), 6.93-6.99 (2H, m), 7.10-7.18 (2H, m), 8.95 (1H, s).
(B-14) To a dioxane (2 ml) solution of the above-mentioned compound B-13 (100 mg, 0.33 mmol), paraformaldehyde (20 mg, 0.66 mmol) and methylamine (0.66 mmol. 30% ethanol solution) were added, successively at room temperature for 2 hours. The reaction was quenched with ammonium chloride aqueous solution, then the reaction mixture was extracted with ethyl acetate. The extract was washed, dried and evaporated under reduced pressure. The precipitated crystal was washed with methyl alcohol and dried under reduced pressure to give 4-{6-[2-(4-fluorophenyl)ethyl]pyrimidine-4-yl}-3-hydroxy-1-methyl-1,5-dihydropyrrole-2-one (72 mg, yield: 72%).
Melting point: 225-228° C.
Elementary analysis as $C_{17}H_{16}FN_3O_2$
Calcd. (%): C, 65.17; H, 5.15; N, 13.41; F, 6.06.
Found (%): C, 65.03; H, 5.31; N, 13.37; F, 5.93.
NMR (CDCl$_3$) δ: 3.06 (3H, s), 3.16 (2H, s), 4.08 (2H, s), 6.78 (1H, s), 6.94-7.00 (2H, m), 7.10-7.15 (2H, m), 9.01 (1H, d, J=1.2 Hz).
The following compound was synthesized by the above-mentioned method.

(B-14-a) 4-{6-[2-(4-Fluorophenyl)ethyl]pyrimidine-4-yl}-3-hydroxy-1-isopropyl-1,5-dihydropyrrole-2-one Melting point: 225-228° C.
Elementary analysis as $C_{19}H_{20}FN_3O_2$ Calcd. (%): C, 66.85; H, 5.91; N, 12.31; F, 5.57.

Found (%): C, 66.61; H, 6.10; N, 12.25; F, 5.43.

NMR (CDCl$_3$) δ: 1.28 (6H, d, J=6.7 Hz), 3.06 (4H, s), 4.05 (2H, s), 4.57 (1H, sept), 6.89 (1H, d, J=1.2 Hz), 6.91-6.99 (2H, m), 7.00-7.16 (2H, m), 9.02 (1H, d, H=1.2 Hz).

Compound 16

4-{6-[1-(4-Fluorobenzyl)-2-(4-fluorophenyl)ethyl]pyrimidine-4-yl}-3-hydroxy-1-methyl-1,5-dihydropyrrole-2-one

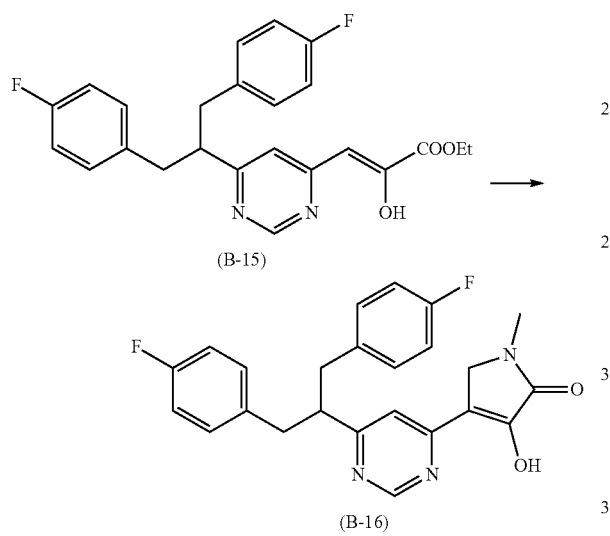

(B-15) According to the method of the reference (WO01/17968), 3-{6-[1-(4-fluorobenzyl)-2-(4-fluorophenyl)ethyl]pyrimidine-4-yl}-2-hydroxyacrylic acid ethyl ester was synthesized.

Melting point: 132-133° C.

NMR (CDCl$_3$) δ: 1.36 (3H, t, J=7.0 Hz), 2.95-3.15 (5H, m), 4.33 (2H, q, J=7.0 Hz), 6.22 (1H, s), 6.42 (1H, d, J=1.4 Hz), 6.85-7.00 (8H, m), 8.97 (1H, s).

(B-16) To a dioxane (2 ml) solution of the above-mentioned compound B-15 (100 mg, 0.24 mmol), paraformaldehyde (14 mg, 0.48 mmol) and methylamine (0.48 mmol. 30% ethanol solution) were added successively at room temperature for 2 hours. The reaction was quenched with ammonium chloride aqueous solution, then the reaction mixture was extracted with ethyl acetate. The extract was washed, dried and evaporated under reduced pressure. The precipitated crystal was washed with diethyl ether, which was dried to give 4-{6-[1-(4-fluorobenzyl)-2-(4-fluorophenyl)ethyl]pyrimidine-4-yl}-3-hydroxy-1-methyl-1,5-dihydropyrrole-2-one (60 mg, yield: 59%).

Melting point: 162-164° C.

Elementary analysis as C$_{24}$H$_{21}$F$_2$N$_3$O$_2$ 0.2H$_2$O

Calcd. (%): C, 67.82; H, 5.07; N, 9.89; F, 8.94.

Found (%): C, 67.82; H, 5.09; N, 9.87; F, 8.79.

NMR (CDCl$_3$) δ: 2.99-3.15 (8H, m), 3.89 (2H, s), 6.28 (1H, s), 6.85-6.99 (8H, m), 9.04 (1H, s).

The following compound was synthesized by the above-mentioned method.

(B-16-a) 4-{6-[1-(4-Fluorobenzyl)-2-(4-fluorophenyl)ethyl]pyrimidine-4-yl}-3-hydroxy-1-isopropyl-1,5-dihydropyrrole-2-one Melting point: 181-183° C.

Elementary analysis as C$_{26}$H$_{25}$F$_2$N$_3$O$_2$

Calcd. (%): C, 69.47; H, 5.61; N, 9.35; F, 8.45.

Found (%): C, 69.49; H, 5.65; N, 9.32; F, 8.32.

NMR (CDCl$_3$) δ: 1.23 (6H, d, J=6.7 Hz), 3.00-3.20 (5H, m), 3.87 (2H, s), 4.53 (1H, sept), 6.42 (1H, s), 6.86-7.00 (8H, m), 9.05 (1H, s).

Compound B-19

3-Hydroxy-1-methyl-4-(6-phenoxypyrimidine-4-yl)-1,5-dihydropyrrole-2-one

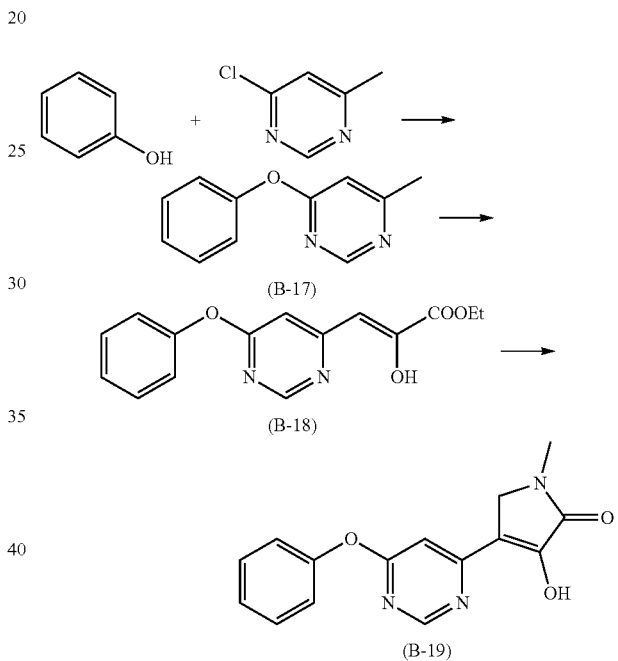

(B-17) According to the synthetic method of (B-10), 4-methyl-6-phenoxypyrimidine was synthesized.

NMR (CDCl$_3$) δ: 2.50 (3H, s), 6.72 (1H, s), 7.13-7.17 (2H, m), 7.25-7.31 (1H, m), 7.42-7.47 (2H, m), 8.68 (1H, s).

(B-18) According to the synthetic method of (B-11), 2-hydroxy-3-(6-phenoxy pyrimidine-4-yl)acrylic acid ethyl ester was synthesized from the above-mentioned compound (B-17).

NMR (CDCl$_3$) δ: 1.40 (3H, t, J=7.0 Hz), 4.37 (2H, q, J=7.0 Hz), 6.46 (1H, s), 6.64 (1H, s), 7.14-7.18 (2H, m), 7.29-7.34 (1H, m), 7.44-7.49 (2H, m), 8.69 (1H, s).

(B-19) According to the synthetic method of (B-12), 3-hydroxy-1-methyl-4-(6-phenoxy pyrimidine-4-yl)-1,5-dihydropyrrole-2-one was synthesized from the above-mentioned compound (B-18).

Melting point: 235-236° C.

Elementary analysis as C$_{15}$H$_{13}$N$_3$O$_3$0.3H$_2$O

Calcd. (%): C, 62.41; H, 4.75; N, 14.56.

Found (%): C, 62.48; H, 4.41; N, 14.49.

NMR (DMSO-d$_6$) δ: 3.02 (3H, s), 4.20 (2H, s), 7.21-7.32 (3H, m), 7.39 (1H, d, J=1.0 Hz), 7.44-7.49 (2H, m), 8.67 (1H, d, J=1.0 Hz).

Compound B-22

N-[6-(4-Hydroxy-1-methyl-5-oxo-2,5-dihydro-1H-pyrrole-3-yl)pyrimidine-4-yl]-benzenesulfoneamide

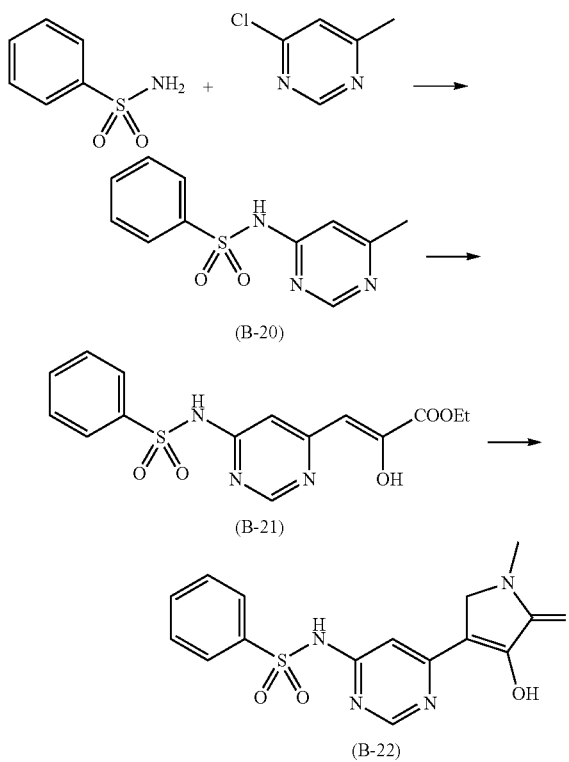

(B-20) To a DMSO (2 ml) solution of 4-chloro-6-methylpyrimidine (128 mg, 1 mmol) which was synthesized according to the method of the reference (WO01/17968), benzenesulfone amide (236 mg, 1.5 mmol) and potassium carbonate (207 mg, 1.5 mmol) were added, successively. The reaction mixture was heated at 120° C. for 3 hours. The reaction was quenched with ammonium chloride aqueous solution, then the reaction mixture was extracted with chloroform. The extract was dried and evaporated under reduced pressure. The precipitated crystal was washed with ethyl acetate and diethyl ether, successively, which was dried to give N-(6-methylpyrimidine-4-yl)benzenesulfoneamide (151 mg, yield: 61%).

Melting point: 188-189° C.

NMR (CDCl$_3$) δ: 2.45 (3H, s), 7.11 (1H, s), 7.45-7.63 (3H, m), 7.92-7.95 (2H, m), 8.71 (1H, s).

(B-21) According to the synthetic method of (B-11), 3-(6-benzenesulfonylaminopyrimidine-4-yl)-2-hydroxyacrylic acid ethyl ester was synthesized from the above-mentioned compound (13-20).

Melting point: 205-208° C.

NMR (CDCl$_3$) δ: 1.40 (3H, t, J=7.0 Hz), 4.37 (2H, q, J=7.0 Hz), 6.44 (1H, s), 7.08 (1H, s), 7.52-7.67 (3H, m), 7.93-8.00 (2H, m), 8.84 (1H, s), 10.82 (1H, bs), 13.81 (1H, bs), 8.69 (1H, s).

(B-22) According to the synthetic method of (B-12), N-[6-(4-hydroxy-1-methyl-5-oxo-2,5-dihydro-1H-pyrrole-3-yl)-pyrimidine-4-yl]-benzenesulfoneamide was synthesized from the above-mentioned compound (B-21).

Melting point: >300° C.

Elementary analysis as $C_{16}H_{14}N_4O_4S0.9H_2O$

Calcd. (%): C, 49.69; H, 4.39; N, 15.45; S, 8.84.

Found (%): C, 49.67; H, 4.17; N, 15.32; S, 8.82.

NMR (DMSO-d$_6$) δ: 3.00 (3H, s), 4.12 (2H, s), 7.54-7.65 (3H, m), 7.69 (1H, s), 7.90 (2H, m), 8.53 (1H, s).

The following compound was synthesized by the above-mentioned method.

(B-22-a) N-[6-(4-Hydroxy-1-isopropyl-5-oxo-2,5-dihydro-1H-pyrrole-3-yl)pyrimidine-4-yl]benzenesulfoneamide Melting point: 255-260° C.

Elementary analysis as $C_{17}H_{18}N_4O_4S0.5H_2O$

Calcd. (%): C, 53.25; H, 4.99; N, 14.61; S, 8.36.

Found (%): C, 53.55; H, 4.72; N, 14.61; S, 8.09.

NMR (DMSO-d$_6$) δ: 1.18 (6H, d, J=6.7 Hz), 4.05 (2H, s), 4.25 (1H, m), 7.52-7.62 (4H, m), 7.89-7.92 (2H, m), 8.48 (1H, s).

Compound B-25

3-Hydroxy-1-methyl-4-(5-phenoxypyridine-2-yl)-1, 5-dihydropyrrole-2-one (B-23) According to the method of the reference (J. Am. Chem. Soc. 1997, 119 (43), 10539-10540), 2-methyl-5-phenoxypyridine was synthesized using 6-methylpyridine-3-ol and iodobenzene.

NMR (CDCl$_3$) δ: 2.54 (3H, s), 6.67-7.01 (2H, m), 7.09-7.15 (2H, m), 7.21-7.24 (1H, m), 7.31-7.38 (2H, m), 8.30 (1H, d, J=2.7 Hz).

The following compound was synthesized by the above-mentioned method.

5-(4-Fluorophenoxy)-2-methylpyridine

NMR (CDCl$_3$) δ: 2.54 (3H, s), 6.94-7.07 (4H, m), 7.11 (1H, d, J=8.4 Hz), 7.18 (1H, dd, J=2.8, 5.6 Hz), 8.26 (1H, d, J=2.8 Hz).

(B-24) According to the method of the reference (WO01/17968), 2-hydroxy-3-(5-phenoxy pyridine-2-yl)acrylic acid ethyl ester was synthesized using the above-mentioned compound B-23.

Melting point: 73-75° C.

NMR (CDCl$_3$) δ: 1.39 (3H, t, J=7.0 Hz), 4.36 (2H, q, J=7.0 Hz), 6.58 (1H, s), 7.04-7.08 (2H, m), 7.17-7.22 (2H, m), 7.35-7.43 (3H, m), 8.24 (1H, d, J=2.7 Hz).

The following compound was synthesized by the above-mentioned method.

3-[5-(4-Fluorophenoxyl)pyridine-2-yl]-2-hydroxy-acrylic acid ethyl ester

Melting point: 99-101° C.

NMR (CDCl$_3$) δ: 1.39 (3H, t, J=7.0 Hz), 4.36 (2H, q, J=7.0 Hz), 6.58 (1H, s), 7.01-7.13 (4H, m), 7.21 (1H, d, J=8.9 Hz), 7.33 (1H, dd, J=2.7, 8.5 Hz), 8.22 (1H, d, J=2.7 Hz).

(B-25) According to the synthetic method of (B-12), 3-hydroxy-1-methyl-4-(5-phenoxypyridine-2-yl)-1,5-dihydropyrrole-2-one was synthesized from the above-mentioned compound (B-24).

Melting point: 200-202° C.

Elementary analysis as C$_{16}$H$_{14}$N$_2$O$_3$ 0.2H$_2$O
Calcd. (%): C, 67.22; H, 5.08; N, 9.80.
Found (%): C, 67.22; H, 4.97; N, 9.74.

NMR (CDCl$_3$) δ: 3.15 (3H, s), 4.15 (2H, s), 7.03-7.07 (2H, m), 7.15-7.22 (2H, m), 7.36-7.43 (3H, m), 8.32 (1H, d, J=2.3 Hz).

The following compounds were synthesized by the above-mentioned method.

(B-25-a) 3-Hydroxy-1-isopropyl-4-(5-phenoxypyridine-2-yl)-1,5-dihydropyrrole-2-one Melting point: 181-183° C.
Elementary analysis as C$_{18}$H$_{18}$N$_2$O$_3$ 0.2H$_2$O
Calcd. (%): C, 68.86; H, 5.91; N, 8.92.
Found (%): C, 68.65; H, 5.65; N, 8.89.
NMR (CDCl$_3$) δ: 1.27 (6H, d, J=6.7 Hz), 4.12 (2H, s), 4.57 (1H, sept), 7.02-7.07 (2H, m), 7.17-7.28 (2H, m), 7.37-7.43 (3H, m), 8.32 (1H, dd, J=0.6, 2.7 Hz).

(B-25-b) 4-[5-(4-Fluorophenoxyl)pyridine-2-yl]-3-hydroxy-1-methyl-1,5-dihydropyrrole-2-one Melting point: 229-230° C.
Elementary analysis as C$_{16}$H$_{13}$FN$_2$O$_3$
Calcd. (%): C, 64.00; H, 4.36; N, 9.33; F, 6.33.
Found (%): C, 63.90; H, 4.27; N, 9.32; F, 6.13.
NMR (CDCl$_3$) δ: 3.15 (3H, s), 4.16 (2H, s), 7.01-7.13 (4H, m), 7.19 (1H, d, J=8.9 Hz), 7.35 (1H, dd, J=2.7, 8.5 Hz), 8.30 (1H, d, J=2.7 Hz).

(B-25-c) 4-[5-(4-Fluorophenoxyl)pyridine-2-yl]-3-hydroxy-1-isopropyl-1,5-dihydropyrrole-2-one Melting point: 178-179° C.
Elementary analysis as C$_{18}$H$_{17}$FN$_2$O$_3$ Calcd. (%): C, 65.84; H, 5.22; N, 8.49; F, 5.79.
Found (%): C, 65.63; H, 5.14; N, 8.49; F, 5.58.
NMR (CDCl$_3$) δ: 1.28 (6H, d, J=7.0 Hz), 4.12 (2H, s), 4.56 (1H, sept), 7.00-7.13 (4H, m), 7.27 (1H, d, J=8.9 Hz), 7.35 (1H, dd, J=2.7, 8.8 Hz), 8.30 (1H, dd, J=0.6, 2.7 Hz).

Compound B-29

4-[5-(4-Fluorobenzyl)-pyridine-2-yl]-3-hydroxy-1-methyl-1,5-dihydropyrrole-2-one

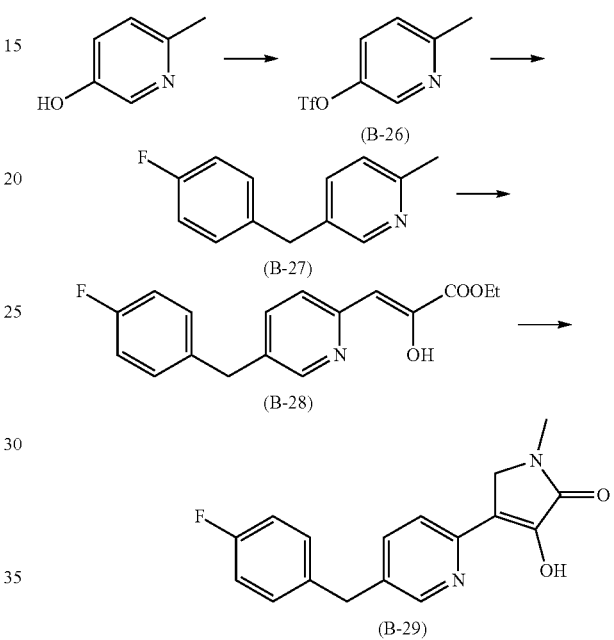

(B-26) To a methylene chloride (100 ml) solution of 5-hydroxy-2-methylpyridine (10.9 g, 100 mmol) and pyridine (12.2 ml, 150 mmol), trifluoromethanesulfonic acid anhydride (18.5 ml, 120 mmol) was added dropwise under ice cooling, then the reaction mixture was stirred for 1.5 hours, to which were added methyl alcohol (2 ml) and saturated sodium hydrogen carbonate aqueous solution (150 ml), successively. Then the reaction mixture was extracted with methylene chloride. The extract was washed, dried and evaporated under reduced pressure. The residue was purified with silica gel column chromatography (n-hexane:ethyl acetate=9:1-4:1) to give 2-methyl-5-(trifluoromethanesulfonyloxy)pyridine (23.0 g, yield: 95%).

(B-27) To a tetrahydrofuran (130 ml) solution of the above-mentioned compound B-26 (10.4 g, 43.2 mmol), 4-fluorobenzylzine bromide in tetrahydrofuran (65 mmol) synthesized according to the method of the reference (J. Org. Chem., 1994, 59, p 2671) and tetrakis(triphenylphosphine) palladium (2.4 g) were added, then the reaction mixture was refluxed for 5 hours. The reaction mixture was evaporated under reduced pressure, to which were added water and ethyl acetate, then insoluble product was filtered with celite. The filtrate was extracted with ethyl acetate, then washed with water. The ethyl acetate solution was extracted with 1N hydrochloric acid, then the hydrochloric acid extract was alkalized with 2N sodium hydroxide aqueous solution. The alkali solution was extracted with ethyl acetate, then washed, dried and evaporated. The residue was purified with silica gel column chromatography (n-hexane:ethyl acetate=2:1) to give 5-(4-fluorobenzyl)-2-methylpyridine (5.42 g, yield: 62%).

NMR (CDCl$_3$) δ: 2.53 (3H, s), 3.91 (2H, s), 6.96 (2H, t like, J=8.7 Hz), 7.06-7.15 (3H, m), 7.34 (1H, dd, J=8.1 Hz, 1.5 Hz), 7.36 (1H, d, J=1.5 Hz).

(B-28) To a tetrahydrofuran (30 ml) solution of the above-mentioned compound B-27 (2.88 g, 14.3 mmol), n-butyllithium solution (15.7 mmol) was added dropwise at −78° C., and oxalic acid diethyl (6.27 g, 42.9 mmol) was added thereto, then the reaction mixture was stirred for 30 minutes, then stirred at 0° C. for 30 minutes. The reaction was quenched with ammonium chloride aqueous solution, extracted with ethyl acetate. The extract was washed, dried and evaporated under reduced pressure. The precipitated crystal was washed with n-hexane, which was dried to give 3-[5-(4-fluorobenzyl)pyridine-2-yl]-2-hydroxyacrylic acid ethyl ester (2.72 g, yield: 63%).

Melting point: 94-96° C.
Elementary analysis as C$_{17}$H$_{16}$FNO$_3$
Calcd. (%): C, 67.76; H, 5.35; N, 4.65; F, 6.31.
Found (%): C, 67.83; H, 5.21; N, 4.63; F, 6.13.
NMR (CDCl$_3$) δ: 1.39 (3H, t, J=7.1 Hz), 3.96 (2H, s), 4.36 (2H, q, J=7.1 Hz), 6.56 (1H, s), 6.98-7.04 (2H, m), 7.11-7.18 (3H, m), 7.51 (1H, dd, J=2.0, 8.3 Hz), 8.29 (1H, d, J=2.0 Hz).

(B-29) To a dioxane (7.5 ml) solution of the above-mentioned compound B-28 (151 mg, 0.50 mmol), paraformaldehyde (40 mg, 1.0 mmol) and methylamine (1.0 mmol. 40% methyl alcohol solution) were added, successively, then the reaction mixture was stirred at room temperature for 2 hours. The solvent was evaporated in vacuum and an ammonium chloride aqueous solution, water and chloroform were added thereto, followed by filtration. The filtrate was washed, dried and evaporated in vacuum. The precipitated crystal was recrystallized from 2-propyl alcohol and dried in vacuum to give 4-[5-(4-fluorobenzyl)-pyridine2-yl]-3-hydroxy-1-methyl-1,5-dihydropyrrole-2-one (55 mg, yield: 37%).

Melting point: 204-206° C.
Elementary analysis as C$_{17}$H$_{15}$FN$_2$O$_2$
Calcd. (%): C, 68.45; H, 5.07; N, 9.39; F, 6.37.
Found (%): C, 68.14; H, 5.14; N, 9.09; F, 6.00.
NMR (CDCl$_3$) δ: 3.14 (3H, s), 3.97 (2H, s), 4.12 (2H, s), 6.98-7.16 (5H, m), 7.53 (1H, dd, J=2.1, 8.2 Hz), 8.37 (1H, d, J=1.5 Hz).

The following compounds were prepared as well as above.

(B-29-a) 4-[5-(4-fluorobenzyl)-pyridine2-yl]-3-hydroxyl-isopropyl-1,5-dihydro-pyrrole-2-one Melting point: 162-164° C.
Elementary analysis as C$_{19}$H$_{19}$FN$_2$O$_2$
Calcd. (%): C, 69.92; H, 5.87; N, 8.58; F, 5.82.
Found (%): C, 69.77; H, 5.81; N, 8.57; F, 5.58.
NMR (CDCl$_3$) δ: 1.27 (6H, d, J=6.7 Hz), 3.98 (2H, s), 4.08 (2H, s), 4.57 (1H, sept, J=6.7 Hz), 6.98-7.16 (5H, m), 7.53 (1H, dd, J=2.4, 8.2 Hz), 8.37-8.38 (1H, m).

(B-29-b) 4-[5-(4-fluorobenzyl)-pyridine2-yl]-3-hydroxy-(2-hydroxyethyl)-1,5-dihydropyrrole2-one Melting point: 202-204° C.
Elementary analysis as C$_{18}$H$_{17}$FN$_2$O$_3$
Calcd. (%): C, 65.84; H, 5.22; N, 8.53; F, 5.79.
Found (%): C, 60.49; H, 4.89; N, 7.66; F, 5.09.

NMR (CDCl$_3$) δ: 3.70 (2H, t, J=5.1 Hz), 3.90 (2H, t, J=5.0 Hz), 3.98 (2H, s), 4.27 (2H, s), 6.98-7.04 (3H, m), 7.11-7.16 (2H, m), 7.53 (1H, dd, J=1.9, 8.9 Hz), 8.37 (1H, d, J=1.9 Hz).

(B-29-c) 4-[5-(4-fluorobenzyl)-pyridine2-yl]-3-hydroxy-(2-methoxyethyl)-1,5-dihydropyrrole2-one Melting point: 202-204° C.
Elementary analysis as C$_{20}$H$_{23}$FN$_2$O$_3$
Calcd. (%): C, 67.02; H, 6.47; N, 7.82; F, 5.30.
Found (%): C, 66.23; H, 5.52; N, 8.02; F, 5.33.
NMR (CDCl$_3$) δ: 3.35 (3H, s), 3.60 (2H, t, J=4.9 Hz), 3.73 (2H, t, J=4.9 Hz), 3.97 (2H, s), 4.26 (2H, s), 6.98-7.05 (3H, m), 7.11-7.15 (2H, m), 7.52 (1H, dd, J=2.3, 8.1 Hz), 8.37 (1H, d, J=1.4 Hz).

(B-29-d) 4-[5-(4-fluorobenzyl)-pyridine-2-yl]-3-hydroxy-1-(4-methoxybenzyl)-1,5-dihydropyrrole-2-one Melting point: 164-166° C.
Elementary analysis as C$_{24}$H$_{21}$FN$_2$O$_3$
Calcd. (%): C, 71.27; H, 5.23; N, 6.93; F, 4.70.
Found (%): C, 70.28; H, 5.15; N, 6.93; F, 4.38.
NMR (CDCl$_3$) δ: 3.79 (3H, s), 3.94 (2H, s), 3.96 (2H, s), 4.66 (2H, s), 6.85-6.89 (2H, 6.96-7.02 (3H, m), 7.08-7.13 (2H, m), 7.20-7.25 (2H, m), 7.46 (1H, dd, J=2.2, 8.0 Hz), 8.34 (1H, d, J=2.3 Hz).

Compound B-34

4-{4-[2-(4-fluorophenyl)ethyl]pyridine-2-yl}-3-hydroxy-1-methyl-1,5-dihydropyrrole-2-one

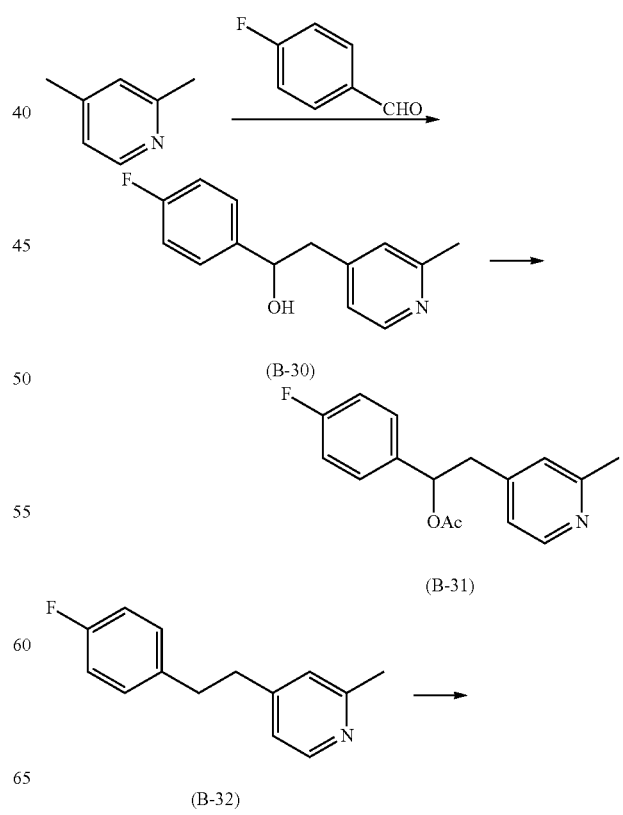

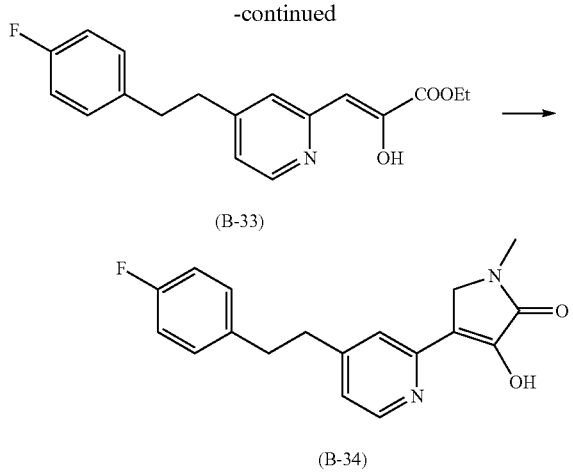

(B-30) To a solution of diisopropylamine (5.06 g, 50 mmol) in THF (20 ml), was added a n-butyllithium solution (50 mmol) at 0° C. After stirring for 5 minutes, a solution of 2,4-dimethylpyridine (5.35 g, 50 mmol) in THF (10 ml) was added dropwise thereto at −78° C. The mixture was stirred at −78° C. for 30 minutes, warmed to 10° C., and 4-fluorobenzaldehyde (6.8 g, 55 mmol) was added thereto, whereby the temperature rose to 35° C. After stirring for 10 minutes, an ammonium chloride aqueous solution was added to terminate the reaction, followed by extraction with ethyl acetate. The extract was washed, dried, and evaporated under reduced pressure. The residue was purified with silica gel column chromatography using ethyl acetate to give 1-(4-fluorophenyl)-2-(2-methylpyridine4-yl)ethanol (6.2 g, yield: 54%).

(B-31) To a solution of the above-mentioned compound B-30 (6.15 g, 26.6 mmol), triethylamine (4.03 g, 39.9 mmol), and dimethylaminopyridine (200 mg, 1.6 mmol) in THF (20 ml), was added dropwise acetic anhydride (4.07 g, 36 mmol) under ice cooling. After stirring for 45 minutes, ice water was added to terminate the reaction, followed by extraction with ethyl acetate. The extract was washed, dried, and evaporated under reduced pressure, to give acetic acid 1-(4-fluorophenyl)-2-(2-methylpyridine-4-yl)ethylester (7.25 g, yield: 99%).

(B-32) To a solution of the above-mentioned compound B-31 (7.25 g, 26.5 mmol) in ethanol (250 ml), were added triethylamine (5.37 g, 53 mmol) and 10% palladium carbon (1 g) and the mixture was stirred under hydrogen atmosphere at room temperature. After removing palladium carbon, the solvent was evaporated under reduced pressure and the residue was purified with silica gel column chromatography (ethyl acetate) to give 4-[2-(4-fluorophenyl)ethyl]-2-methylpyridine (5.23 g, yield: 92%).

NMR (CDCl$_3$) δ: 2.52 (3H, s), 2.90-3.00 (4H, m), 6.88 (1H, dd, J=5.5, 1.2 Hz), 6.90-7.00 (3H, m), 7.04-7.14 (2H, m), 8.37 (1H, d, J=5.1 Hz).

(B-33) To a solution of isopropylamine (1.01 g, 10 mmol) in THF (10 ml), was added a n-butyllithium solution (10 mmol) under ice-cooling. After stirring the mixture for 5 minutes, a solution of B-32 (2.15 g, 10 mmol) in THF (5 ml) was added dropwise at −78° C., then the mixture was stirred for 20 minutes and oxalic acid diethyl (5.84 g, 40 mmol) was added dropwise with stirring for 45 minutes. The mixture was further stirred at room temperature for 1 hour, then an ammonium chloride aqueous solution was added to terminate the reaction, followed by extraction with ethyl acetate. The extract was washed, dried, and evaporated under reduced pressure. The residue was purified with silica gel column chromatography (ethyl acetate) to give 3-{4-[2-(4-fluorophenyl)ethyl]pyridine-2-yl}-2-hydroxyacrylic acid ethylester (224 mg, yield: 11%).

Melting point: 129-130° C.

NMR (CDCl$_3$) δ: 1.39 (3H, t, J=6.9 Hz), 2.92 (4H, s), 4.36 (2H, q, J=6.9), 6.48 (1H, s), 5.47 (2H, s), 6.90-7.04 (3H, m), 7.04-7.14 (2H, m), 8.25 (1H, d, J=5.1 Hz).

Elementary analysis as C$_{18}$H$_{18}$NFO$_3$

Calcd. (%): C, 68.56; H, 5.75; N, 4.44; F, 6.02.

Found (%): C, 68.85; H, 5.55; N, 4.57; F, 5.93.

(B-34) To a solution of the above-mentioned compound B-33 (200 mg, 0.635 mmol) and 95% paraformaldehyde (52 mg, 1.73 mmol) in dioxane (3 ml), was added a 30% methylamine ethanol solution (250 μl) at room temperature and the mixture was stirred for 2 hours 30 minutes. An ammonium chloride aqueous solution was added thereto to terminate the reaction, which was extracted with ethyl acetate. The extract was washed, dried, and evaporated under reduced pressure. The precipitated crystal was washed with diethyl ether to give 4-{4-[2-(4-fluorophenyl)ethyl]pyridine-2-yl}-3-hydroxy-1-methyl-1,5-dihydropyrrole-2-one (108 mg, yield: 55%).

Melting point: 167-168° C.

NMR (CDCl$_3$) δ: 2.92 (4H, s), 3.15 (3H, s), 4.07 (2H, s), 6.74 (1H, s), 6.93 (1H, dd, J=5.7, 2.1 Hz), 6.98 (2H, t, J=8.4 Hz), 7.08-7.14 (2H, m), 8.33 (1H, d, J=6.7 Hz).

Elementary analysis as C$_{18}$H$_{17}$N$_2$FO$_2$

Calcd. (%): C, 69.22; H, 5.49; N, 8.97; F, 6.08.

Found (%): C, 69.08; H, 5.39; N, 8.58; F, 6.00.

The following compound was prepared as well as above.

(B-34-a) 4-{4-[2-(4-fluorophenyl)ethyl]pyridine-2-yl}-3-hydroxy-1-isopropyl-1,5-dihydropyrrole-2-one Melting point: 167-168° C.

NMR (CDCl$_3$) δ: 1.27 (6H, d, J=6.6 Hz), 2.93 (4H, s), 4.03 (2H, s), 4.58 (1H, m), 6.82 (1H, s), 6.93 (1H, dd, J=6.0, 1.5 Hz), 6.98 (2H, t, J=8.7 Hz), 7.05-7.14 (2H, m), 8.35 (1H, d, J=6.0 Hz).

Elementary analysis as C$_{20}$H$_{21}$N$_2$FO$_2$

Calcd. (%): C, 70.57; H, 6.22; N, 8.23; F, 5.58.

Found (%): C, 70.10; H, 6.10; N, 8.11; F, 5.50.

Compound B-38

4-[5-(4-fluorobenzyloxy)-pyridine-2-yl]-3-hydroxy-1-methyl-1,5-dihydropyrrole-2-one

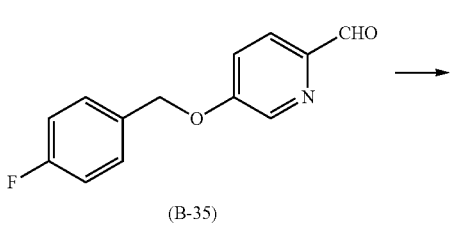

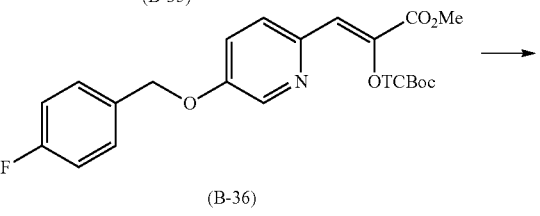

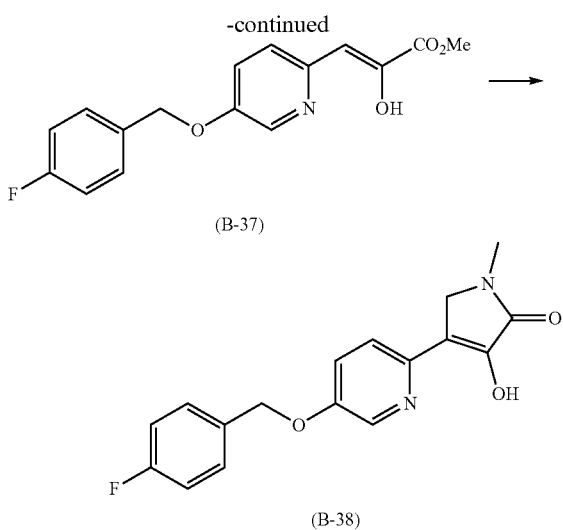

(B-35) According to the reference (J. Med. Chem. 20, 1258, 1977), 5-(4-fluorobenzyloxy)-pyridine-2-carboaldehyde was synthesized.

(B-36) To a THF (50 ml) solution containing (dimethoxy-phosphoryl-(2,2,2-trichloro-1,1-dimethylethoxycarbony-loxy)-acetic acid methyl ester (1.91 g, 4.76 mmol) prepared according to the reference (Tetrahedron Lett. 25, 3529, 1984), lithium bistrimethylsilylamine (1M-THF solution, 5.62 mmol) was added at −78° C. and the mixture was stirred for 30 minutes. The above-mentioned compound B-35 (1 g, 4.3 mmol) was slowly added thereto and the mixture was stirred for 15 minutes, warmed to 0° C., and further stirred for 30 minutes. An ammonium chloride aqueous solution was added to terminate the reaction, which was extracted with ethyl acetate. The extract was washed, dried, and evaporated under reduced pressure. The residue was purified with silica gel column chromatography (ethyl acetatehexane=1:1) to give 3-[5-(4-fluorobenzyloxy)-pyridine-2-yl]-2-(2,2,2-trichloro-1,1-dimethylethoxycarbony-loxy)-acrylic acid methyl ester (1.096 g, 50%).

(B-37) To a solution of the above-mentioned compound B-36 (1.2 g, 2.36 mmol) in methyl alcohol (25 ml), 28% sodium methoxide (910 mg, 4.72 mmol) was added at 0° C. and the mixture was at room temperature for 1 hour. An ammonium chloride aqueous solution was added to terminate the reaction, which was extracted with ethyl acetate. The extract was washed, dried, and evaporated under reduced pressure.

The residue was purified with silica gel column chromatography (ethyl acetate) to give 3-[5-(4-fluorobenzyloxy)-pyridine2-yl]-2-hydroxyacrylic acid methyl ester (233 mg, yield: 32%).

Melting point: 131-132° C.

NMR (CDCl$_3$) δ: 3.89 (3H, s), 5.10 (2H, s), 6.56 (1H, s), 7.10 (2H, t, J=8.4 Hz), 7.18 (1H, d, J=8.4 Hz), 7.33 (1H, dd, J=8.4, 2.7 Hz), 7.36-7.45 (2H, m), 8.13 (1H, d, J=2.7 Hz).

Elementary analysis as $C_{16}H_{14}NFO_4$

Calcd. (%): C, 60.36; H, 4.65; N, 4.62; F, 6.26.
Found (%): C, 60.63; H, 4.57; N, 4.66; F, 6.06.

(B-38) To a solution of the above-mentioned compound B-37 (150 mg, 0.495 mmol) and 95% paraformaldehyde (40 mg, 1.33 mmol) in dioxane (5 ml), was added a 30% methylamine ethanol solution (150 μl) and the mixture was stirred at room temperature for 5 hours. An ammonium chloride aqueous solution was added to terminate the reaction, followed by extraction with ethyl acetate stirred. The extract was washed, dried, and evaporated under reduced pressure. The precipitated crystal was washed with diethyl ether to give 4-[5-(4-fluorobenzyloxy)-pyridine-2-yl]-3-hydroxyl-methyl-1,5-dihydropyrrole-2-one (70 mg, yield: 45%).

Melting point: 210-211° C.

NMR (CDCl$_3$) δ: 3.14 (3H, s), 4.11 (2H, s), 5.10 (2H, s), 7.10 (2H, t, J=8.7 Hz), 7.11 (1H, d, J=8.4 Hz), 7.32 (1H, dd, J=9.0, 3.0 Hz), 7.41 (2H, dd, J=8.7, 5.4 Hz), 8.29 (1H, d, J=3.0 Hz).

Elementary analysis as $C_{17}H_{15}N_2FO_3$

Calcd. (%): C, 64.96; H, 4.81; N, 8.91; F, 6.04.
Found (%): C, 64.68; H, 4.77; N, 8.78; F, 5.81.

The following compound was prepared as well as above.

(B-38-a) 4-[5-(4-fluorobenzyloxy)-pyridine-2-yl]-3-hydroxyl-isopropyl-1,5-dihydropyrrole-2-one Melting point: 195-196° C.

NMR (CDCl$_3$) δ: 1.26 (6H, d, J=6.6), 4.09 (2H, s), 4.56 (1H, m), 5.10 (2H, s), 7.10 (2H, t, J=8.7 Hz), 7.20 (1H, d, J=8.7 Hz), 7.32 (1H, dd, J=8.7, 3.0 Hz), 7.41 (2H, dd, J=8.4, 5.4 Hz), 8.30 (1H, d, J=3.0 Hz).

Elementary analysis as $C_{19}H_{19}N_2FO_3$

Calcd. (%) C, 66.66; H, 5.59; N, 8.18; F, 5.55.
Found (%): C, 66.46; H, 5.61; N, 8.20; F, 5.54.

Compound B-42

4-[5-(4-fluorophenylsulfanil)-pyridine-2-yl]-3-hydroxy-1-methyl-1,5-dihydropyrrol-2-one

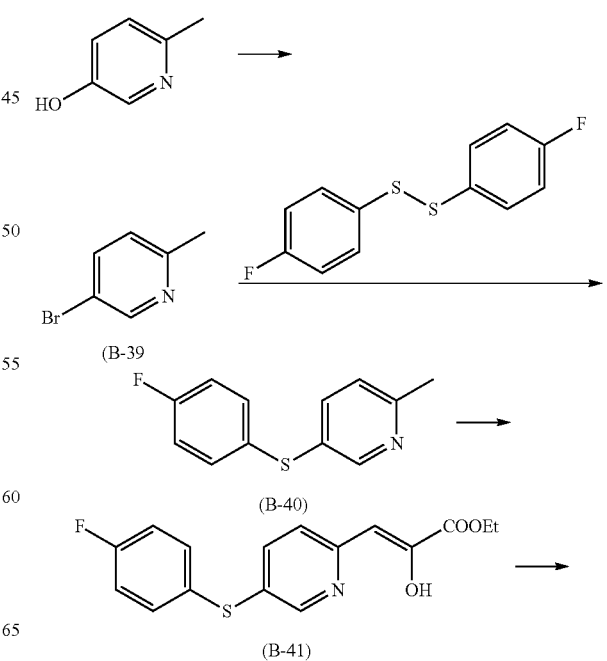

-continued

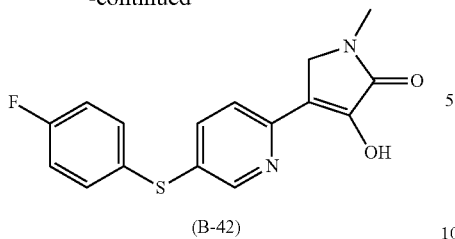

(B-42)

(B-39) Using 6-methylpyridine-3-ol, with reference to J. Org. Chem. 1967, 32, 1607, 5-bromo-2-methylpyridine was synthesized.

NMR (CDCl$_3$) δ: 2.51 (3H, s), 7.05 (1H, d, J=8.3 Hz), 7.68 (1H, d, J=2.5, 8.3 Hz), 8.55 (1H, d, J=2.3 Hz).

(B-40) To a solution of the above-mentioned compound B-39 (6.0 g, 35 mmol) in tetrahydrofuran (100 ml), was added n-butyllithium (35 mmol) at −78° C., then 4-fluorophenyldisulphide (8.9 g, 35 mmol) synthesized according to Tetrahedron Lett. 1990, 31, 5007 was added thereto and the mixture was stirred for 30 minutes. Water was added to terminate the reaction, followed by extraction with ethyl acetate. The extract was washed, dried, and evaporated under reduced pressure. The residue was purified with silica gel column chromatography (n-hexane/ethyl acetate=6:1) to give 5-(4-fluorophenylsulfanil)-2-methylpyridine (2.8 g, yield: 34%).

NMR (CDCl$_3$) δ: 2.54 (3H, s), 6.98-7.04 (2H, m), 7.09 (1H, d, J=8.1 Hz), 7.31-7.36 (2H, m), 7.49 (1H, dd, J=2.3, 8.1 Hz), 8.46 (1H, d, 2.3 Hz).

(B-41) Using the above-mentioned compound B-40, according to the method of (B-11), 3-[5-(4-fluorophenylsulfinyl)-pyridine-2-yl]-2-hydroxyacrylic acid ethyl ester was synthesized.

Melting point: 96-98° C.

NMR (CDCl$_3$) δ: 1.39 (3H, t, J=7.0 Hz), 4.36 (2H, q, J=7.0 Hz), 6.54 (1H, s), 7.06-7.13 (3H, m), 7.42-7.46 (2H, m), 7.55 (1H, dd, J=2.4, 8.5 Hz), 8.32 (1H, d, J=2.4 Hz).

(B-42) Using the above-mentioned compound B-41, according to the method of (B-12), 4-[5-(4-fluorophenylsulfinyl)-pyridine-2-yl]-3-hydroxy-1-methyl-1,5-dihydropyrrole-2-one was synthesized.

Melting point: 210-212° C.

Elementary analysis as C$_{16}$H$_{13}$FN$_2$O$_2$S

Calcd. (%): C, 60.75; H, 4.14; N, 8.86; F, 6.01; S, 10.14.

Found (%): C, 60.44; H, 4.01; N, 8.66; F, 5.75; S, 9.97.

NMR (CDCl$_3$) δ: 1.14 (3H, s), 4.11 (2H, s), 7.02-7.11 (3H, m), 7.41-7.46 (2H, m), 7.58 (1H, dd, J=2.3, 8.2 Hz), 8.38 (1H, d, J=1.6 Hz).

The following compound was prepared as well as above.

(B-42-a) 4-[5-(4-fluorophenylsulfinyl)-pyridine-2-yl]-3-hydroxy-1-isopropyl-1,5-dihydropyrrole-2-one Melting point: 163-164° C.

Elementary analysis as C$_{18}$H$_{17}$FN$_2$O$_2$S

Calcd. (%): C, 62.77; H, 4.98; N, 8.13; F, 5.52; S, 9.31.

Found (%): C, 62.62; H, 4.74; N, 7.98; F, 5.28; S, 9.10.

NMR (CDCl$_3$) δ: 1.27 (6H, d, J=6.9 Hz), 4.08 (2H, s), 4.56 (1H, sept), 7.05-7.11 (2H, m), 7.13 (1H, dd, J=0.6, 8.3 Hz), 7.39-7.45 (2H, m), 7.59 (1H, dd, J=2.3, 8.4 Hz), 8.38 (1H, dd, J=0.6, 2.3 Hz).

Compound B-44

4-[5-(4-fluorobenzenesulfinyl)-pyridine-2-yl]-3-hydroxy-1-methyl-1,5-dihydropyrrole-2-one

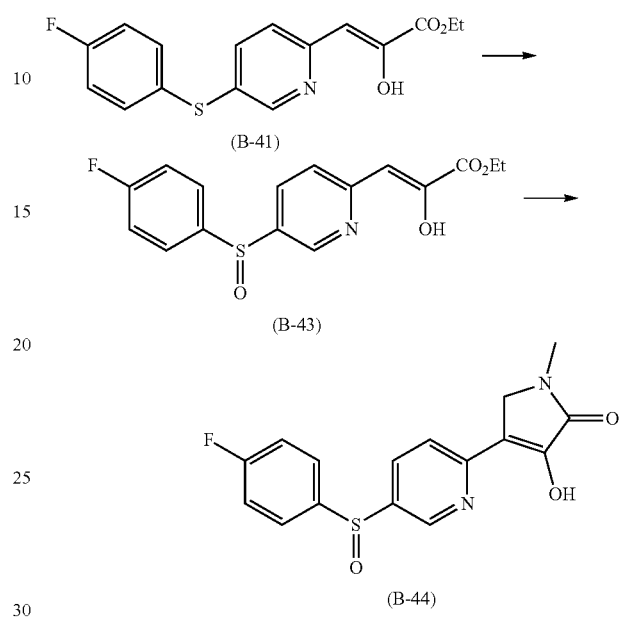

(B-43) To a solution of B-41 (640 mg, 2 mmol) in chloroform (6 ml), was added mCPBA (690 mg, 4 mmol) under ice-cooling. After 30 minutes stirring, a saturated sodium hydrogen carbonate aqueous solution was added to terminate the reaction, which was extracted with chloroform. The extract was washed and dried, then the solvent was evaporated under reduced pressure. The residue was purified with silica gel column chromatography (n-hexane/ethyl acetate=4:1) to give 3-[5-(4-fluorobenzenesulfinyl)-pyridine-2-yl]-2-hydroxyacrylic acid ethyl ester (400 mg, yield: 60%).

Melting point: 148-150° C.

NMR (CDCl$_3$) δ: 1.39 (3H, t, J=7.2 Hz), 4.36 (2H, q, J=7.2 Hz), 6.58 (1H, s), 7.20-7.26 (2H, m), 7.29 (1H, d, J=8.4 Hz), 7.66-7.71 (2H, m), 7.93 (1H, dd, J=2.3, 8.4 Hz), 8.64 (1H, d, J=2.3 Hz).

(B-44) Using the above-mentioned compound B-43, according to the method of B-12, 4-[5-(4-fluorobenzenesulfinyl)-pyridine-2-yl]-3-hydroxy-1-methyl-1,5-dihydropyrrole-2-one was synthesized.

Melting point: 228-230° C.

Elementary analysis as C$_{16}$H$_{13}$FN$_2$O$_3$S

Calcd. (%): C, 57.82; H, 3.94; N, 8.43; F, 5.72; S, 9.65.

Found (%): C, 57.56; H, 3.74; N, 8.20; F, 5.52; S, 9.49.

NMR (CDCl$_3$) δ: 3.16 (3H, s), 4.16 (2H, s), 7.19-7.26 (2H, m), 7.30 (1H, dd, J=0.9, 8.5 Hz), 7.66-7.71 (2H, m), 8.02 (1H, dd, J=2.4, 8.5 Hz), 8.67 (1H, dd, J=0.9, 2.4 Hz).

The following compound was prepared as well as above.

(B-44-a) 4-[5-(4-fluorobenzenesulfinyl)-pyridine-2-yl]-3-hydroxy-1-isopropyl-1,5-dihydropyrrole-2-one Melting point: 205-207° C.

Elementary analysis as C$_{18}$H$_{17}$FN$_2$O$_3$S

Calcd. (%): C, 59.99; H, 4.75; N, 7.77; F, 5.27; S, 8.90.

Found (%): C, 59.75; H, 4.57; N, 7.58; F, 5.08; S, 8.84.

NMR (CDCl$_3$) δ: 1.27 (6H, d, J=7.0 Hz), 4.12 (2H, s), 4.56 (1H, sept), 7.19-7.26 (2H, m), 7.38 (1H, d, J=8.5 Hz), 7.65-7.71 (2H, m), 8.01 (1H, dd, J=2.4, 8.5 Hz), 8.67 (1H, dd, 2.4 Hz).

Compound B-55

4-[5-(4-fluorobenzyl)-pyrimidine-2-yl]-3-hydroxy-1-methyl-1,5-dihydropyrrole-2-one

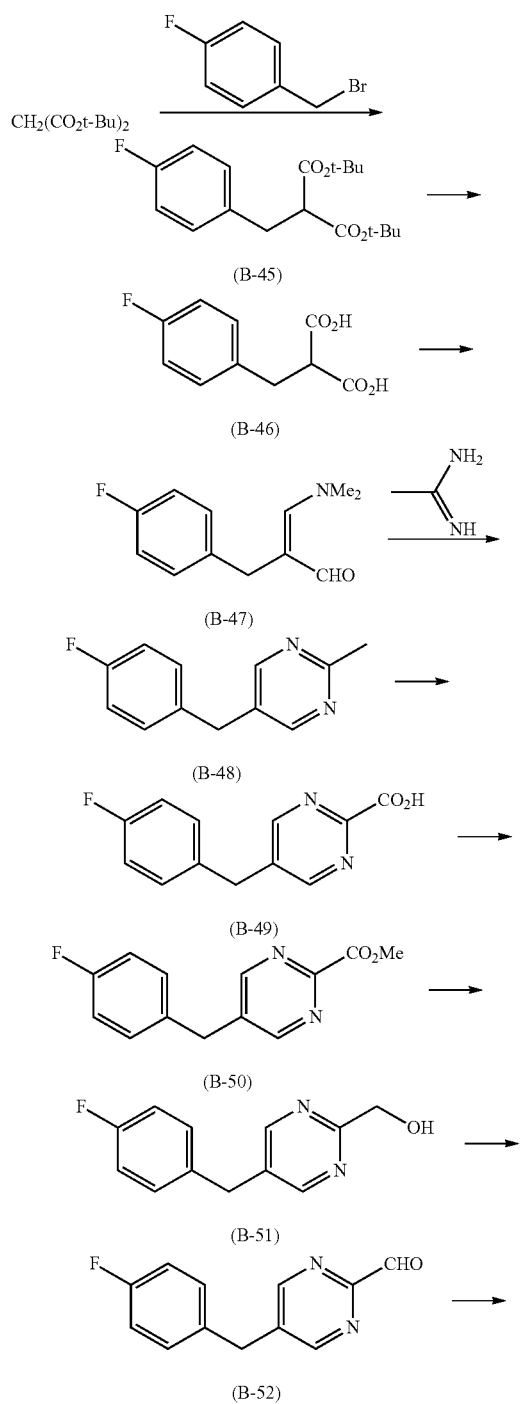

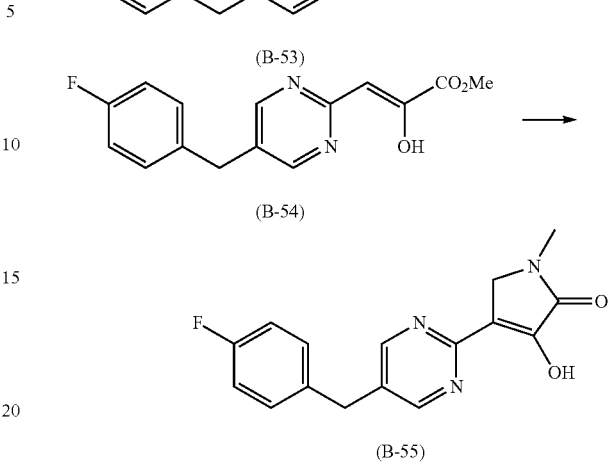

(B-45) According to J. Org. Chem. vol. 64, No. 3, (1999), p 992, experimental (25), using 4-fluorobenzylbromide and di-t-butyl malonate, 2-(4-fluorobenzyl)-malonic acid t-butyl ester was synthesized.

NMR (CDCl$_3$) δ: 1.41 (18H, s), 3.09 (2H, d, J=7.9 Hz), 3.42 (1H, t, J=7.9 Hz), 6.93-6.98 (2H, m), 7.15-7.19 (2H, m).

(B-46) To a solution of the above-mentioned compound B-45 (16.4 g, 50.6 mmol) in dichloromethane (15 ml), trifluoroacetic acid (15 ml) was added and the mixture was stirred at room temperature for 1 hour. The solvent was evaporated under reduced pressure and the residue was recrystallized with ethylether and n-hexane to give 2-(4-fluorobenzyl)malonic acid (8.90 g, yield: 83%).

NMR (CDCl$_3$) δ: 3.13 (2H, d, J=7.6 Hz), 3.60 (1H, t, J=7.8 Hz), 6.95-7.01 (2H, m), 7.22-7.27 (2H, m).

(B-47) According to Collection Czechoslov. Chem. Commun. vol. 32 (1967), p 3792-3793, using the above-mentioned compound B-46, 3-dimethylamino-2-(4-fluorobenzyl)-propenal was synthesized.

(B-48) To a solution of the above-mentioned compound B-47 (1.42 g, 7.5 mmol) and actoamide hydrochloride (1.42 g, 15 mmol) in methyl alcohol (5 ml), was added a solution of sodium methylate in methyl alcohol (15 ml) and the mixture was refluxed for 4 hours. An ammonium chloride aqueous solution was added thereto, which was extracted with ethyl acetate. The extract was washed and dried, then the solvent was evaporated. The residue was purified with silica gel column chromatography (n-hexane:ethyl acetate=1:2-1:3) to give 5-(4-fluorobenzyl)-2-methylpyrimidine (956 mg, yield: 69%).

NMR (CDCl$_3$) δ2.71 (3H, s), 3.90 (2H, s), 6.97-7.03 (2H, m), 7.12-7.15 (2H, m), 8.46 (2H, s).

(B-49) To a solution of the above-mentioned compound B-48 (3.01 g, 15 mmol) in pyridine (22 ml), was added selenium dioxide (11.0 g, 99 mmol) and the mixture was refluxed for 17.5 hours. Chloroform and water were added thereto, followed by celite-filtration. The filtrate was washed and dried, then the solvent was evaporated to give crude 5-(4-fluorobenzyl)-pyrimidine-2-carboxylic acid (3.57 g).

NMR (CDCl$_3$) δ: 4.07 (2H, s), 6.99-7.06 (2H, m), 7.13-7.18 (2H, m), 8.83 (2H, s).

(B-50) To a solution of the above-mentioned crude product B-49 (3.57 g) in tetrahydrofuran (43 ml), was added a solution of diazomethane in ethylether (30 mmol) and the mixture was stirred at 0° C. for 10 minutes. The solution was warmed to room temperature and stirred for 10 minutes. Acetic acid was added thereto under ice-cooling, which was neutralized with a sodium hydrogen carbonate aqueous solution, then extracted with ethyl acetate.

The extract was washed and dried, then the solvent was evaporated. The residue was purified with silica gel column chromatography (n-hexane:ethyl acetate=2:3) to give 5-(4-fluorobenzyl)-pyrimidine-2-carboxylic acid methyl ester (1.98 g, yield: 54%).

NMR (CDCl$_3$) δ: 4.05 (2H, s), 4.07 (3H, s), 7.01-7.06 (2H, m), 7.12-7.17 (2H, m), 8.75 (2H, s).

(B-51) To a solution of the above-mentioned compound B-50 (1.98 g, 8.04 mmol) in tetrahydrofuran (26 ml) and t-butanol (13 ml), was added at −30° C. sodium borohydride (338 mg, 8.04 mmol), then the mixture was warmed to room temperature and stirred for 4 hours. An ammonium chloride aqueous solution was added to terminate the reaction, followed by extraction with ethyl acetate. The extract was washed and dried, then the solvent was evaporated under reduced pressure. The residue was purified with silica gel column chromatography (n-hexane:ethyl acetate=1:2) to give [5-(4-fluorobenzyl)-pyrimidine-2-yl]-methyl alcohol (470 mg, yield: 27%).

NMR (CDCl$_3$) δ: 4.05 (2H, s), 4.07 (3H, s), 7.01-7.06 (2H, m), 7.12-7.17 (2H, m), 8.75 (2H, s).

(B-52) To a solution of oxalyl chloride (281 ul, 3.23 mmol) in methylene chloride (5 ml), was added dropwise a solution of dimethylsulfoxide (457 ul, 6.45 mmol) in methylene chloride (1 ml) at −78° C. with stirring for 10 minutes. A solution of the above-mentioned compound B-51 (470 mg, 2.15 mmol) in methylene chloride (1.5 ml) was added dropwise thereto with stirring for 30 minutes. Triethylamine (1.79 ml, 12.9 mmol) was added dropwise to the mixture, which was warmed to 0° C. and stirred for 30 minutes. The solution was diluted with chloroform, washed, and dried, then the solvent was evaporated under reduced pressure. The residue was purified with silica gel column chromatography (n-hexane:ethyl acetate=1:2) to give 5-(4-fluorobenzyl)-pyrimidine-2-carboaldehyde (337 mg, yield: 72%).

NMR (CDCl$_3$) δ: 4.08 (2H, s), 7.01-7.07 (2H, m), 7.15-7.20 (2H, m), 8.81 (2H, s), 10.09 (1H, s).

(B-53) To a solution of lithiumbis(trimethylsilyl)amide solution (1.87 ml), was added dropwise at −78° C. a tetrahydrofuran (2 ml) solution containing (dimethoxyphosphoryl-(2,2,2-trichloro-1,1-dimethylethoxycarbonyloxy)-acetic acid methyl ester (688 mg, 1.71 mmol) prepared according to Tetrahedron Lett. 25, 3529, 1984, and the mixture was stirred for 10 minutes. A solution of the above-mentioned compound B-52 (337 mg, 1.56 mmol) in tetrahydrofuran (2 ml) was added thereto and the mixture was stirred for 5 minutes, which was warmed to 0° C. and stirred for 30 minutes. An ammonium chloride aqueous solution was added to terminate the reaction, followed by extraction with ethyl acetate. The extract was washed, dried, and evaporated under reduced pressure. The residue was purified with silica gel column chromatography (n-hexane:ethyl acetate=2:1) to give 3-[5-(4-fluorobenzyl)-pyrimidine-2-yl]-2-(2,2,2-trichloro-1,1-dimethylethoxycarbonyloxy)-acrylic acid methyl ester (500 mg, yield: 66%).

NMR (CDCl$_3$) δ: 1.98 (6H, s), 3.76 (2H, s), 3.94 (3H, s), 6.88 (1H, s), 6.99-7.04 (2H, m), 7.10-7.16 (2H, m), 8.52 (2H, s).

(B-54) To a solution of the above-mentioned compound B-53 (380 mg, 0.77 mmol) in methyl alcohol (12 ml), a solution of sodium methylate in methanol (376 ul) was added under ice-cooling, which was warmed to room temperature and stirred for 30 minutes. Triethylamine (1.79 ml, 12.9 mmol) was added dropwise and the mixture was warmed to 0° C. and stirred for 30 minutes. An ammonium chloride aqueous solution was added to terminate the reaction, followed by extraction with ethyl acetate. The extract was washed, dried, and the solvent was evaporated under reduced pressure. The precipitated crystal was washed with diisopropylether and dried under reduced pressure to give 3-[5-(4-fluorobenzyl)-pyrimidine-2-yl]-2-hydroxyacrylic acid methylester (129 mg, yield: 58%).

Melting point: 132-134° C.
Elementary analysis as $C_{15}H_{13}FN_2O_3$
Calcd. (%): C, 62.50; H, 4.55; N, 9.72; F, 6.59.
Found (%): C, 60.81; H, 4.55; N, 9.69; F, 6.42.
NMR (CDCl$_3$) δ: 3.91 (3H, s), 3.97 (2H, s), 6.75 (1H, s), 7.01-7.06 (2H, m), 7.13-7.18 (2H, m), 8.54 (2H, s).

According to the method of (B-55) (B-12), 4-[5-(4-fluorobenzyl)-pyrimidine-2-yl]-3-hydroxyl-methyl-1,5-dihydropyrrole-2-one was obtained.

Melting point: 163-165° C.
Elementary analysis as $C_{16}H_{14}FN_3O_2$
Calcd. (%): C, 64.21; H, 4.71; N, 14.04; F, 6.35.
Found (%): C, 63.05; H, 4.82; N, 13.48; F, 6.07.
NMR (CDCl$_3$) δ: 3.16 (3H, s), 3.97 (2H, s), 4.22 (2H, s), 7.01-7.06 (2H, m), 7.13-7.18 (2H, m), 8.53 (2H, s).

The following compound was prepared as well as above.

(B-55-a) 4-[5-(4-fluorobenzyl)-pyrimidine-2-yl]-3-hydroxy-1-isopropyl-1,5-dihydropyrrole-2-one Melting point: 155-157° C.
Elementary analysis as $C_{18}H_{18}FN_3O_2$
Calcd. (%): C, 66.04; H, 5.54; N, 12.84; F, 5.80.
Found (%): C, 65.09; H, 5.44; N, 12.35; F, 5.67.
NMR (CDCl$_3$) δ: 1.27 (6H, d, J=6.7 Hz), 3.97 (2H, s), 4.19 (2H, s), 4.58 (1H, sept, J=6.9 Hz), 7.01-7.06 (2H, m), 7.13-7.17 (2H, m), 8.53 (2H, s).

Compound B-59

3-hydroxy-1-methyl-4-(5-phenoxypyrimidine-2-yl)-1,5-dihydropyrrole-2-one

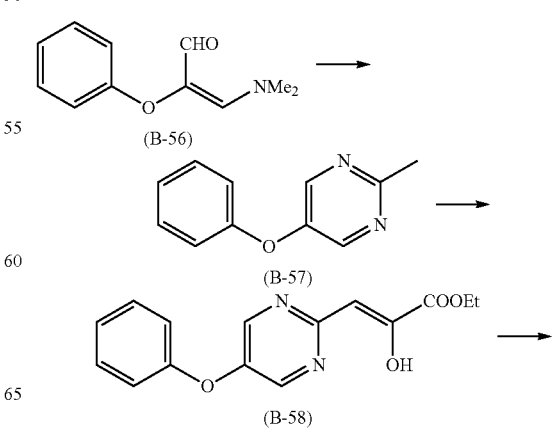

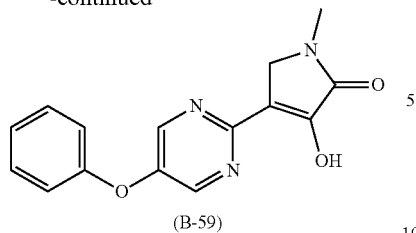

(B-56) According to J. Med. Chem. 1980, 23, 1016, 3-dimethylamino-2-phenoxypropenal was synthesized.

NMR (CDCl$_3$) δ: 3.10 (6H, s), 6.57 (1H, s), 6.93-6.99 (3H, m), 7.24-7.30 (2H, m), 8.83 (1H, s).

The following compound was prepared as well as above.

3-dimethylamino-2-(4-fluorophenoxy)-propenal

NMR (CDCl$_3$) δ: 3.11 (6H, s), 6.57 (1H, s), 6.86-6.98 (4H, m), 8.81 (1H, s).

(B-57) To a solution of the above-mentioned compound B-56 (17.9 g, 97 mmol) and acetoamidine hydrochloride (17.7 g, 187 mmol) in methyl alcohol (200 ml), was added sodium methoxide (562 mmol) and the mixture was refluxed for 3 hours. Ammonium chloride (20 g) was added thereto at room temperature the mixture was stirred 1 for hours. The solvent was evaporated under reduced pressure and to the residue was added chloroform (200 ml), then insoluble products were filtered off. The solvent was evaporated and the residue was purified with silica gel column chromatography (ethyl acetate) to give 2-methyl-5-phenoxypyrimidine (13.2 g, yield: 76%).

NMR (CDCl$_3$) δ: 2.73 (3H, s), 7.01-7.05 (2H, m), 7.16-7.21 (1H, m), 7.36-7.42 (2H, m), 8.40 (2H, s).

The following compound was prepared as well as above.

5-(4-fluorophenoxy)-2-methylpyrimidine

NMR (CDCl$_3$) δ: 2.72 (3H, s), 6.99-7.12 (4H, m), 8.37 (2H, s).

(B-58) Using the above-mentioned compound B-57, according to the method of (B-11), 2-hydroxy-3-(5-phenoxypyrimidine-2-yl)-acrylic acid ethyl ester was synthesized.

Melting point: 52-53° C.

NMR (CDCl$_3$) δ: 1.39 (3H, t, J=7.3 Hz), 4.37 (2H, q, J=7.3 Hz), 6.78 (1H, s), 7.07-7.11 (2H, m), 7.24-7.28 (1H, m), 7.41-7.46 (2H, m), 8.47 (2H, s).

The following compound was prepared as well as above.

3-[5-(4-fluorophenoxy)-pyrimidine-2-yl]-2-hydroxy-acrylic acid ethyl ester

Melting point: 92-93° C.

NMR (CDCl$_3$) δ: 1.39 (3H, t, J=7.3 Hz), 4.37 (2H, q, J=7.3 Hz), 6.78 (1H, s), 7.05-7.16 (4H, m), 8.44 (2H, s).

(B-59) Using the above-mentioned compound B-58, according to (B-12), 3-hydroxy-1-methyl-4-(5-phenoxypyrimidine-2-yl)-1,5-dihydropyrrole-2-one was synthesized.

Melting point: 207-208° C.

Elementary analysis as C$_{15}$H$_{13}$N$_3$O$_3$

Calcd. (%): C, 63.60; H, 4.63; N, 14.83.

Found (%): C, 63.53; H, 4.47; N, 14.82.

NMR (CDCl$_3$) δ: 3.17 (3H, s), 4.23 (2H, s), 7.07-7.10 (2H, m), 7.22-7.27 (1H, m), 7.41-7.46 (2H, m), 8.47 (2H, s).

The following compound was prepared as well as above.

(B-59-a) 3-hydroxyl-isopropyl-4-(5-phenoxypyrimidine-2-yl)-1,5-dihydropyrrole-2-one Melting point: 164-165° C.

Elementary analysis as C$_{17}$H$_{17}$N$_3$O$_3$ 0.2H$_2$O

Calcd. (%): C, 64.83; H, 5.57; N, 13.34.

Found (%): C, 64.98; H, 5.48; N, 13.22.

NMR (CDCl$_3$) δ: 1.28 (6H, d, J=7.0 Hz), 4.20 (2H, s), 4.59 (1H, sept), 7.05-7.10 (2H, m), 7.22-7.27 (1H, m), 7.40-7.47 (2H, m), 8.47 (2H, s).

(B-59-b) 4-[5-(4-fluorophenoxy)-pyrimidine-2-yl]-3-hydroxy-1-methyl-1,5-dihydropyrrole-2-one Melting point: 230-232° C.

Elementary analysis as C$_{15}$H$_{12}$FN$_3$O$_3$

Calcd. (%): C, 59.80; H, 4.01; N, 13.95; F, 6.31.

Found (%): C, 59.60; H, 3.89; N, 13.81; F, 6.05.

NMR (CDCl$_3$) δ: 3.17 (3H, s), 4.22 (2H, s), 7.04-7.16 (4H, m), 8.44 (2H, s).

(B-59-c) 4-[5-(4-fluorophenoxy)-pyrimidine-2-yl]-3-hydroxy-1-isopropyl-1,5-dihydropyrrole-2-one Melting point: 165-166° C.

Elementary analysis as C$_{17}$H$_{16}$FN$_3$O$_3$

Calcd. (%): C, 62.00; H, 4.90; N, 12.76; F, 5.77.

Found (%): C, 62.00; H, 4.91; N, 12.71; F, 5.51.

NMR (CDCl$_3$) δ: 1.28 (6H, d, J=7.0 Hz), 4.19 (2H, s), 4.59 (1H, m), 7.04-7.16 (4H, m), 8.45 (2H, s).

Compound B-64

4-(4-benzyloxypyrimidine-2-yl)-3-hydroxy-1-methyl-1,5-dihydropyrrole-2-one

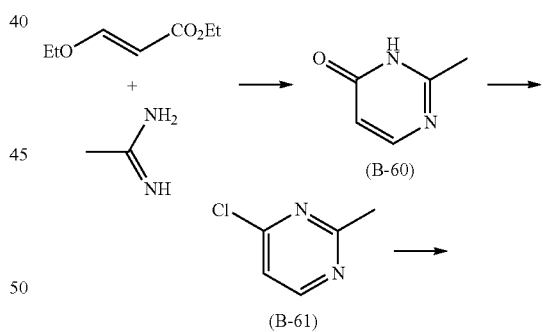

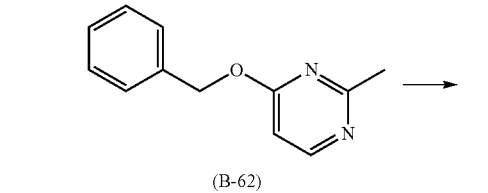

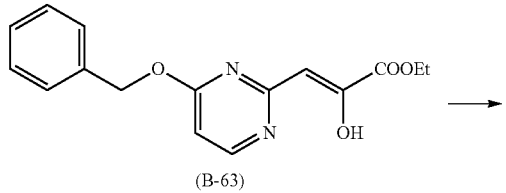

-continued

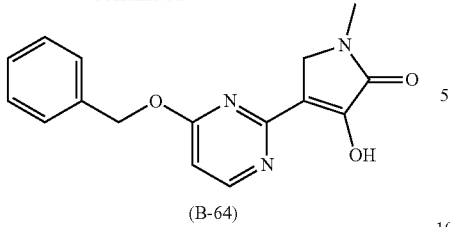

(B-64)

(B-60) To a solution of 3-ethoxyacrylic acid ethyl ester (12.95 g, 89.82 mmol) and acetoamidine hydrochloride (25.44 g, 269.1 mmol) in ethanol (130 ml), was added potassium carbonate (37.23 g, 269.4 mmol) and the mixture was refluxed for 2.5 hours. After filtrating, the solvent was evaporated under reduced pressure and the precipitated crystals were washed with chloroform and dried under reduced pressure to give crude 2-methyl-3H-pyrimidine-4-one.

(B-61) To the crude above-mentioned compound B-60, was added phosphorus oxychloride (60 ml) and the mixture was stirred at 80° C. for 1.5 hours. The solvent was evaporated under reduced pressure and to the residue was added ice (120 g), then the mixture was neutralized with a 5N sodium hydroxide aqueous solution and extracted with ethyl acetate. The extract was washed and dried, then the solvent was evaporated under reduced pressure. The residue was diluted with ethyl acetate and diethyl ether, and a 4N hydrochloric acid ethyl acetate solution (20 ml) was added thereto. The precipitated crystals were washed with ethyl acetate and dried under reduced pressure to give 4-chloro-2-methylpyrimidine hydrochloride (8.08 g, yield: 55%).

NMR (DMSO-$d_6$) δ: 2.62 (3H, s), 7.55 (1H, d, J=5.7 Hz), 8.69 (1H, d, J=5.7 Hz).

(B-62) To a solution of sodium hydride (973 mg, 24.3 mmol) in dimethylformamide (10 ml), was added benzylalcohol (2.50 ml, 24.2 mmol) under ice-cooling and the mixture was stirred at room temperature for 30 minutes. The above-mentioned compound B-xx (2.02 g, 12.2 mmol) was added thereto under ice-cooling, and the mixture was stirred at room temperature for 1 hour. Water was added to terminate the reaction, and the mixture was extracted with ethyl acetate. The extract was washed, dried, and evaporated under reduced pressure, then the residue was purified with silica gel column chromatography (n-hexane:ethyl acetate=5:1) to give 4-benzyloxy-2-methylpyrimidine (2.45 g, yield: 100%).

NMR (CDCl$_3$) δ: 2.64 (3H, s), 5.42 (2H, s), 6.58 (1H, d, J=5.9 Hz), 7.29-7.48 (5H, m), 8.33 (1H, d, J=5.9 Hz).

The following compound was prepared as well as above.

4-(4-fluorobenzyloxy)-2-methylpyrimidine

NMR (CDCl$_3$) δ: 2.63 (3H, s), 5.38 (2H, s), 6.57 (1H, d, J=5.7 Hz), 7.07 (2H, m), 7.43 (2H, m), 8.34 (1H, d, J=5.7 Hz).

(B-63) To a solution of the above-mentioned compound B-62 (1.00 g, 4.99 mmol) in tetrahydrofuran (20 ml), were added oxalic acid diethyl (3.40 ml, 25.0 mmol) and potassium tert-butoxide (1.12 g, 9.98 mmol) under ice-cooling and the mixture was stirred at 50° C. for 45 minutes. An ammonium chloride aqueous solution was added to terminate the reaction, followed by extraction with ethyl acetate. The extract was washed and dried, then the solvent was evaporated under reduced pressure. The precipitated crystals were recrystallized from ethyl acetate n-hexane to give 3-(4-benzyloxypyrimidine-2-yl)-2-hydroxyacrylic acid ethyl ester (911 mg, yield: 61%).

Melting point: 124-126° C.
Elementary analysis as $C_{16}H_{16}N_2O_4$ 0.1H$_2$O
Calcd. (%): C, 63.61; H, 5.40; N, 9.27.
Found (%): C, 63.51; H, 5.21; N, 9.13.
NMR (CDCl$_3$) δ: 1.40 (3H, t, J=7.2 Hz), 4.38 (2H, q, J=7.2 Hz), 5.45 (2H, s), 6.57 (1H, d, J=6.0 Hz), 6.60 (1H, s), 7.34-7.48 (5H, m), 8.29 (1H, d, J=6.0 Hz).

The following compound was prepared as well as above.

3-[4-(4-fluorobenzyloxy)pyrimidine-2-yl]-2-hydroxyacrylic acid ethyl ester

Melting point: 150-151° C.
Elementary analysis as $C_{16}H_{15}FN_2O_4$
Calcd. (%): C, 60.37; H, 4.75; N, 8.80; F, 5.97.
Found (%): C, 60.28; H, 4.61; N, 8.78; F, 5.81.
NMR (CDCl$_3$) δ: 1.41 (3H, t, J=7.5 Hz), 4.38 (2H, q, J=7.5 Hz), 5.42 (2H, s), 6.57 (1H, d, J=5.9 Hz), 6.60 (1H, s), 7.08 (2H, m), 7.43 (2H, m), 8.29 (1H, d, J=5.9 Hz).

(B-64) To a solution of the above-mentioned compound B-63 (150 mg, 0.50 mmol) in dioxane (7.5 ml), were added paraformaldehyde (80.5 mg, 2.01 mmol) and methylamine (2.00 mmol, 40% methyl alcohol solution) and the mixture was stirred at room temperature for 18 hours.

An ammonium chloride aqueous solution was added to terminate the reaction, followed by extraction with chloroform. The extract was washed and dried, then the solvent was evaporated under reduced pressure. The precipitated crystals were recrystallized from methyl alcohol to give 4-(4-benzyloxypyrimidine-2-yl)-3-hydroxy-1-methyl-1,5-dihydropyrrole-2-one (86.0 mg, yield: 58%).

Melting point: 222-224° C.
Elementary analysis as $C_{16}H_{15}N_3O_3$0.1CH$_3$OH0.2H$_2$O
Calcd. (%): C, 63.59; H, 5.24; N, 13.82.
Found (%): C, 63.58; H, 5.03; N, 13.75.
NMR (CDCl$_3$) δ: 3.17 (3H, s), 4.21 (2H, s), 5.44 (2H, s), 6.59 (1H, d, J=5.9 Hz), 7.33-7.47 (5H, m), 8.34 (1H, d, J=5.9 Hz).

The following compound was prepared as well as above.

(B-64-a) 4-(4-benzyloxypyrimidine-2-yl)-3-hydroxy-1-isopropyl-1,5-dihydropyrrole-2-one Melting point: 155-157° C.
Elementary analysis as $C_{18}H_{19}N_3O_3$ 0.3H$_2$O
Calcd. (%): C, 65.36; H, 5.97; N, 12.70.
Found (%): C, 65.31; H, 5.84; N, 12.62.
NMR (CDCl$_3$) δ: 1.29 (6H, d, J=6.6 Hz), 4.15 (2H, s), 4.60 (1H, sept), 5.45 (2H, s), 6.60 (1H, d, J=6.0 Hz), 7.35-7.48 (5H, m), 8.36 (1H, d, J=6.0 Hz).

(B-64-b) 4-[4-(4-fluorobenzyloxy)pyrimidine-2-yl]-3-hydroxy-1-methyl-1,5-dihydropyrrole-2-one Melting point: 227-230° C.
Elementary analysis as $C_{16}H_{14}FN_3O_3$
Calcd. (%): C, 60.95; H, 4.48; N, 13.33; F, 6.03.
Found (%): C, 60.82; H, 4.30; N, 13.12; F, 5.78.
NMR (CDCl$_3$) δ: 3.18 (3H, s), 4.21 (2H, s), 5.40 (2H, s), 6.58 (1H, d, J=6.2 Hz), 7.09 (2H, m), 7.42 (2H, m), 8.35 (1H, d, J=6.2 Hz).

(B-64-c) 4-[4-(4-fluorobenzyloxy)pyrimidine-2-yl]-3-hydroxy-1-isopropyl-1,5-dihydropyrrole-2-one Melting point: 148-149° C.
Elementary analysis as $C_{18}H_{18}FN_3O_3$0.3H$_2$O Calcd. (%): C, 61.99; H, 5.38; N, 12.05; F, 5.45.
Found (%): C, 61.95; H, 5.17; N, 11.78; F, 5.23.
NMR (CDCl$_3$) δ: 1.29 (6H, d, J=6.6 Hz), 4.16 (2H, s), 4.60 (1H, sept), 5.41 (2H, s), 6.59 (1H, d, J=6.0 Hz), 7.09 (2H, m), 7.43 (2H, m), 8.37 (1H, d, J=6.0 Hz).

Compound B-68

4-[5-(4-fluorobenzyloxy)pyrimidine-2-yl]-3-hydroxy-1-methyl-1,5-dihydropyrrole-2-one

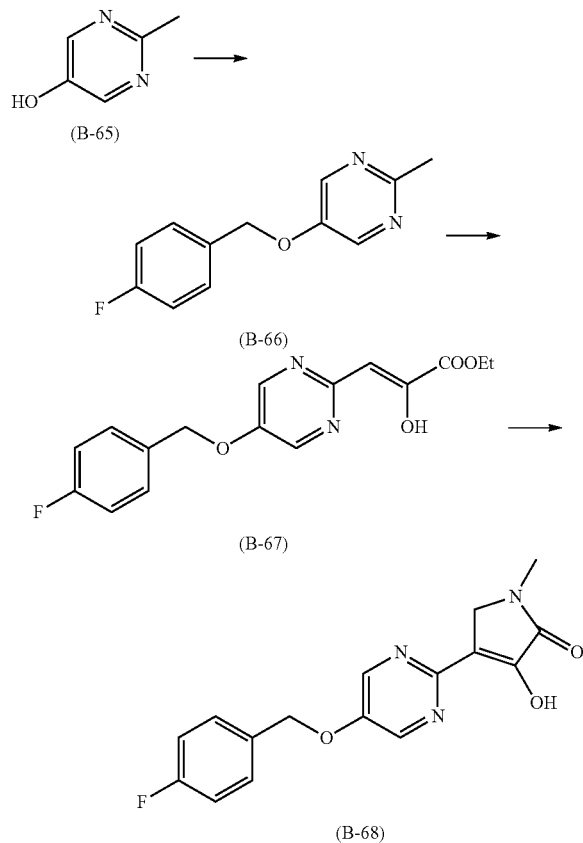

(B-65) According to the method described in U.S. Pat. No. 5,010,193, 2-methylpyrimidine-5-ol was synthesized.
(B-66) To a solution of the above-mentioned compound B-65 (640 mg, 5.81 mmol) and potassium carbonate (1.20 g, 8.68 mmol) in acetone (20 ml), was added 4-fluorobenzyl bromide (1.10 ml, 8.83 mmol) and the mixture was stirred at room temperature for 15 hours.

After filtrating, the solvent was evaporated under reduced pressure, then the residue was purified with silica gel column chromatography (n-hexane:ethyl acetate=1:1) to give 5-(4-fluorobenzyloxy)-2-methylpyrimidine (758 mg, yield: 60%).
NMR (CDCl$_3$) δ: 2.68 (3H, s), 5.09 (2H, s), 7.10 (2H, m), 7.40 (2H, m), 8.36 (2H, s).
(B-67) To a solution of the above-mentioned compound B-66 (699 mg, 3.20 mmol) and 18-crown-6 (94.0 mg, 0.355 mmol) in tetrahydrofuran (15 ml), were added oxalic acid diethyl (4.35 ml, 32.0 mmol) and potassium tert-butoxide (1.44 g, 12.8 mmol) and the mixture was stirred at 60° C. for 1 hour. An ammonium chloride aqueous solution was added to terminate the reaction, followed by extraction with ethyl acetate. The extract was washed and dried, then the solvent was evaporated under reduced pressure. The residue was subjected to silica gel column chromatography with ethyl acetate, giving the elution comprising the objective compound, from which the solvent was evaporated under reduced pressure. The precipitated crystals were recrystallized from isopropyl alcohol to give 3-[5-(4-fluorobenzyloxy)pyrimidine-2-yl]-2-hydroxyacrylic acid ethyl ester (530 mg, yield: 52%).
Melting point: 134-135° C.
Elementary analysis as C$_{16}$H$_{15}$FN$_2$O$_4$
Calcd. (%): C, 60.37; H, 4.75; N, 8.80; F, 5.97.
Found (%): C, 59.95; H, 4.66; N, 8.68; F, 5.70.
NMR (CDCl$_3$) δ: 1.39 (3H, t, J=7.1 Hz), 4.36 (2H, q, J=7.1 Hz), 5.15 (2H, s), 6.75 (1H, s), 7.12 (2H, m), 7.41 (2H, m), 8.45 (2H, s), 12.74 (1H, brs).
(B-68) To a solution of the above-mentioned compound B-67 (151 mg, 0.474 mmol) in dioxane (7.5 ml), were added paraformaldehyde (75.7 mg, 1.89 mmol) and methylamine (3.86 mmol. 30% ethanol solution) and the mixture was stirred at room temperature for 22 hours. An ammonium chloride aqueous solution was added to terminate the reaction, followed by extraction with chloroform. The extract was washed and dried, then the solvent was evaporated under reduced pressure. The precipitated crystals were recrystallized from isopropyl alcohol to give 4-[5-(4-fluorobenzyloxy)pyrimidine-2-yl]-3-hydroxy-1-methyl-1,5-dihydropyrrole-2-one (104 mg, yield: 70%).
Melting point: 185-187° C.
Elementary analysis as C$_{16}$H$_{14}$FN$_3$O$_3$
Calcd. (%): C, 60.95; H, 4.48; N, 13.33; F, 6.03.
Found (%): C, 60.82; H, 4.44; N, 13.20; F, 5.78.
NMR (CDCl$_3$) δ: 3.15 (3H, s), 4.20 (2H, s), 5.16 (2H, s), 7.12 (2H, m), 7.42 (2H, m), 8.44 (2H, s), 10.53 (1H, brs).
The following compound was prepared as well as above.

(B-68-a) 4-[5-(4-fluorobenzyloxy)pyrimidine-2-yl]-3-hydroxy-1-isopropyl-1,5-dihydropyrrole-2-one Melting point: 219-221° C.
Elementary analysis as C$_{18}$H$_{18}$FN$_3$O$_3$
Calcd. (%): C, 62.97; H, 5.28; N, 12.24; F, 5.53.
Found (%): C, 62.71; H, 4.85; N, 12.10; F, 5.36.
NMR (CDCl$_3$) δ: 1.27 (6H, d, J=6.9 Hz), 4.17 (2H, s), 4.58 (1H, m), 5.16 (2H, s), 7.12 (2H, m), 7.42 (2H, m), 8.44 (2H, s), 10.43 (1H, brs).

Compound B-73

4-{5-[2-(4-fluorophenyl)ethyl]pyrimidine-2-yl}-3-hydroxy-1-methyl-1,5-dihydropyrrole-Z-one

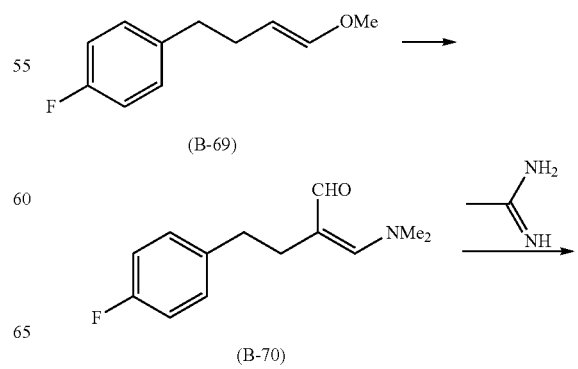

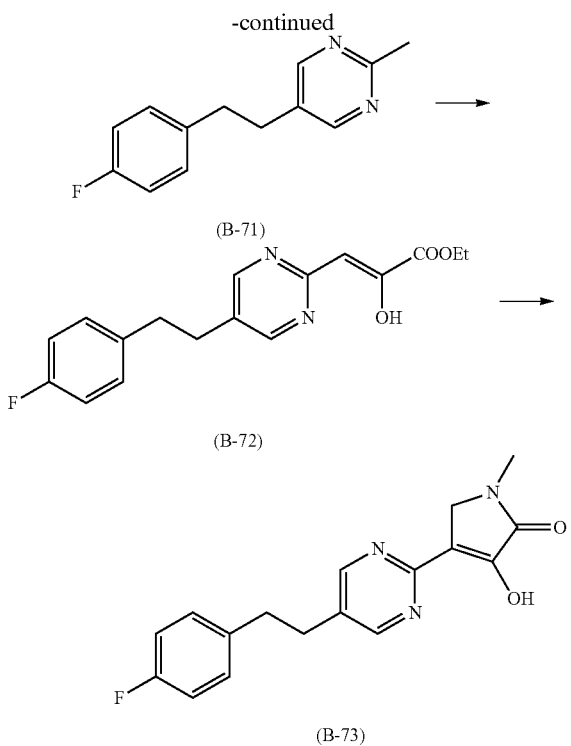

(B-71)

(B-72)

(B-73)

(B-69) According to J. Org. Chem. 1993, 58, 1696-1701, 1-fluoro-4-(4-methoxy-3-butenyl)benzene was synthesized.
(B-70) To dimethylformamide (3.35 ml, 43.3 mmol), was added dropwise phosphorus oxychloride (4.00 ml, 42.9 mmol) under ice-cooling and the mixture was stirred at 50° C. for 45 minutes. The mixture was diluted with chloroform (6 ml), to which was added at 75° C. a solution of the above-mentioned compound B-69 (2.60 g, 14.4 mmol) in chloroform (3 ml) and the mixture was refluxed for 5 hours. The reaction mixture was added dropwise to a solution of potassium carbonate (40 g) in water-toluene-ethanol (10:9:1, 80 ml), and the mixture was stirred for 1 hour. After filtrating, the filtrate was extracted with chloroform, washed, and dried, then the solvent was evaporated under reduced pressure to give crude 2-dimethylaminomethylene-4-(4-fluorophenyl)butylaldehyde
(B-71) To a solution of the above-mentioned crude compound B-70 in methyl alcohol (15 ml), were added acetoamidine hydrochloride (2.61 g, 27.6 mmol) and sodium methoxide (83 mmol, 28% methyl alcohol solution) and the mixture was refluxed for 3 hours. An ammonium chloride aqueous solution was added to terminate the reaction, followed by extraction with chloroform. The extract was washed and dried, then the solvent was evaporated under reduced pressure. The residue was purified with silica gel column chromatography (n-hexane:ethyl acetate=5:1) to give 5-[2-(4-fluorophenyl)ethyl]-2-methylpyrimidine (764 mg, yield: 25%).
NMR (CDCl$_3$) δ: 2.70 (3H, s), 2.88 (4H, m), 6.97 (2H, m), 7.06 (2H, m), 8.37 (2H, s).
(B-72) To a solution of the above-mentioned compound B-71 (759 mg, 3.51 mmol) in tetrahydrofuran (15 ml), were added oxalic acid diethyl (2.40 ml, 17.7 mmol) and potassium tert-butoxide (787 mg, 7.01 mmol) under ice-cooling, and the mixture was stirred at 50° C. for 2.5 hours and refluxed for 1.5 hours. An ammonium chloride aqueous solution was added to terminate the reaction, followed by extraction with ethyl acetate. The extract was washed and dried, then the solvent was evaporated under reduced pressure. The precipitated crystals were recrystallized from ethyl acetate isopropyl ether to 3-{5-[2-(4-fluorophenyl)ethyl]pyrimidine-2-yl}-2-hydroxyacrylic acid ethyl ester (704 mg, yield: 63%).
Melting point: 133-134° C.
Elementary analysis as $C_{17}H_{17}FN_2O_3$
Calcd. (%): C, 64.55; H, 5.42; N, 8.86; F, 6.01.
Found (%): C, 64.38; H, 5.35; N, 8.73; F, 6.06.
NMR (CDCl$_3$) δ: 1.39 (3H, t, J=7.2 Hz), 2.93 (4H, s), 4.37 (2H, q, J=7.2 Hz), 6.74 (1H, s), 6.98 (2H, m), 7.07 (2H, m), 8.44 (2H, s), 13.25 (1H, brs).
(B-73) To a solution of the above-mentioned compound B-72 (152 mg, 0.481 mmol) in dioxane (7.5 ml), were added paraformaldehyde (76.9 mg, 1.92 mmol) and methylamine (1.93 mmol. 30% ethanol solution) and the mixture was stirred at room temperature for 14 hours. An ammonium chloride aqueous solution was added to terminate the reaction, followed by extraction with chloroform. The extract was washed and dried, then the solvent was evaporated under reduced pressure. The precipitated crystals were recrystallized from isopropyl alcohol to give 4-{5-[2-(4-fluorophenyl)ethyl]pyrimidine-2-yl}-3-hydroxy-1-methyl-1,5-dihydropyrrole-2-one (86.9 mg, yield: 58%).
Melting point: 158-160° C.
Elementary analysis as $C_{17}H_{16}FN_3O_2$
Calcd. (%): C, 65.17; H, 5.15; N, 13.41; F, 6.06.
Found (%): C, 65.10; H, 5.17; N, 13.19; F, 6.06.
NMR (CDCl$_3$) δ: 2.93 (4H, s), 3.16 (3H, s), 4.21 (2H, s), 6.98 (2H, m), 7.07 (2H, m), 8.41 (2H, s).
The following compound was prepared as well as above.

(B-73-a) 4-{5-[2-(4-fluorophenyl)ethyl]pyrimidine-2-yl}-3-hydroxy-1-isopropyl-1,5-dihydropyrrole-2-one Melting point 143-144° C.
Elementary analysis as $C_{19}H_{20}FN_8O_2$
Calcd. (%): C, 66.85; H, 5.91; N, 12.31; F, 5.57.
Found (%): C, 66.71; H, 5.87; N, 12.18; F, 5.57.
NMR (CDCl$_3$) δ: 1.27 (6H, d, J=6.9 Hz), 2.93 (4H, s), 4.18 (2H, s), 4.58 (1H, sept), 6.98 (2H, m), 7.07 (2H, m), 8.41 (2H, s).

Compound B-79

3-hydroxy-1-methyl-4-(4-phenethylpyrimidine-2-yl)-1,5-dihydropyrrole-2-one

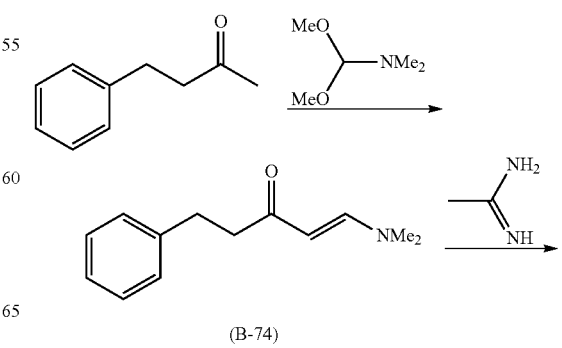

(B-74)

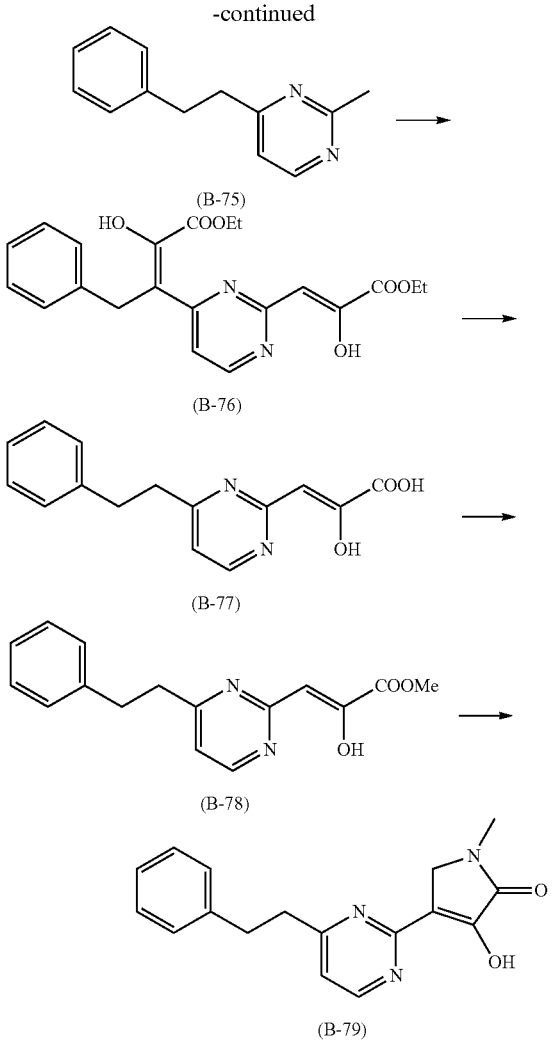

(B-74) A solution of 4-phenylbutan-2-one (74 g, 500 mmol) and N,N-dimethylformamidedimethylacetal (60 g, 500 mmol) in DMF (50 ml) was refluxed for 3 hours. The solvent was evaporated under reduced pressure and the oily residue was purified with silica gel column chromatography (ethyl acetatehexane=1:1) to give 1-dimethylamino-5-phenylpent-1-en-3-one (23.11 g, yield: 27.6%).

(B-75) To a solution of the above-mentioned compound B-74 (23.11 g, 113.7 mmol) and acetoamidine hydrochloride (12.89 g, 227.4 mmol) in methyl alcohol (50 ml), was added sodium methoxide (3N-methyl alcohol solution, 564 mmol) and the mixture was refluxed for 6 hours. The methyl alcohol was evaporated under reduced pressure, to which was added water to terminate the reaction. After adding hydrochloric acid and an ammonium chloride aqueous solution for neutralization, the mixture was extracted with ethyl acetate, which was washed and dried. The solvent was evaporated under reduced pressure and the residue was purified with silica gel column chromatography (ethyl acetate) to give 2-methyl-4-phenethylpyrimidine.

NMR (CDCl$_3$) δ: 2.73 (3H, s), 3.03 (4H, s), 6.87 (1H, d, J=5.1 Hz), 7.14-7.32 (5H, m), 8.47 (1H, d, J=5.1 Hz).

(B-76) To a solution of the above-mentioned compound B-75 (1 g, 5 mmol) and oxalic acid diethyl (3.68 g, 25 mmol) in THF (15 ml), was added at room temperature potassium tert-butoxide (2.24 g, 20 mmol) and the mixture was stirred at 80° C. for 2 hours 30 minutes. An ammonium chloride aqueous solution was added to terminate the reaction, then the mixture was extracted with ethyl acetate. The extract was washed and dried, and the solvent was evaporated under reduced pressure. The residue was purified with silica gel column chromatography (hexane/ethyl acetate=1:1) to give 3-{2-(2-ethoxycarbonyl-2-hydroxyvinyl)-3-methyl-2,3-dihydropyridine-4-yl}-2-hydroxy-4-phenyl-2-butenoic acid ethyl ester (520 mg, 26%).

(B-77) To a solution of the above-mentioned compound B-76 (628 mg, 1.58 mmol) in methylalcohol (20 ml) and water (5 ml), was added lithium hydroxide (1N-aqueous solution, 1.6 mmol) and the mixture was stirred at 60° C. for 1.5 hours. Methylalcohol was evaporated under reduced pressure and water was added thereto, then the mixture was washed with chloroform. Citric acid was added to the aqueous layer, which was extracted with ethyl acetate. The extract was washed and dried, then the solvent was evaporated under reduced pressure to give 2-hydroxy-3-(4-phenethylpyrimidine-2-yl)-acrylic acid (510 mg, 99%).

(B-78) To the above-mentioned compound B-77 (510 mg, 1.9 mmol) was added a hydrochloric acid methyl alcohol solution (8 ml) and the mixture was stirred at room temperature for 2.5 hours. The solvent was evaporated under reduced pressure and the residue was added to a sodium hydrogen carbonate aqueous solution, which was extracted with ethyl acetate. The extract was washed and dried, then the solvent was evaporated under reduced pressure to give 2-hydroxy-3-(4-phenethylpyrimidine-2-yl)-acrylic acid methyl ester (511 mg, 94%).

NMR (CDCl$_3$) δ: 3.09 (4H, s), 3.93 (3H, s), 6.76 (1H, s), 6.90 (1H, d, J=5.4 Hz), 7.15-7.35 (5H, m), 8.55 (1H, d, J=5.4 Hz), 13.8 (1H, bs).

(B-79) To a solution of the above-mentioned compound B-78 (230 mg, 0.8195 mmol) and 95% paraformaldehyde (51 mg, 1.7 mmol) in dioxane (5 ml), was added a 30% methylamine/ethanol solution (170 µl), and the mixture was stirred at room temperature for 2.5 hours. An ammonium chloride aqueous solution was added to terminate the reaction, then the mixture was extracted with ethyl. The extract was washed and dried, and the solvent was evaporated under reduced pressure. The precipitated crystals were recrystallized from ethanol to give 3-hydroxy-1-methyl-4-(4-phenethylpyrimidine-2-yl)-1,5-dihydropyrrole-2-one (120 mg, yield: 50%).

Melting point: 118-119° C.

NMR (CDCl$_3$) δ: 3.10 (4H, s), 3.17 (3H, s), 4.24 (2H, s), 6.90 (1H, d, J=6.0 Hz), 7.20-7.35 (5H, m), 8.52 (1H, d, J=5.2 Hz).

Elementary analysis as $C_{17}H_{17}N_3O_2$

Calcd. (%): C, 69.14; H, 5.80; N, 14.32.

Found (%): C, 69.04; H, 5.54; N, 14.18.

The following compound was prepared as well as above.

(B-79-a) 3-hydroxy-1-isopropyl-4-(4-phenethylpyrimidine-2-yl)-1,5-dihydropyrrole-2-one Melting point: 126-127° C.

NMR (CDCl$_3$) δ: 1.29 (6H, d, J=6.6 Hz), 3.00-3.15 (4H, m), 4.20 (2H, s), 4.60 (1H, sept), 6.90 (1H, d, J=5.4 Hz), 7.15-7.35 (5H, m), 8.53 (1H, d, J=5.1 Hz).

Elementary analysis as $C_{19}H_{21}N_3O_3$

Calcd. (%): C, 70.57; H, 6.55; N, 12.99.

Found (%): C, 70.39; H, 6.55; N, 12.93.

Compound B-84

3-hydroxy-1-methyl-4-(6-phenoxypyridazine-3-yl)-1,5-dihydropyrrole-2-one

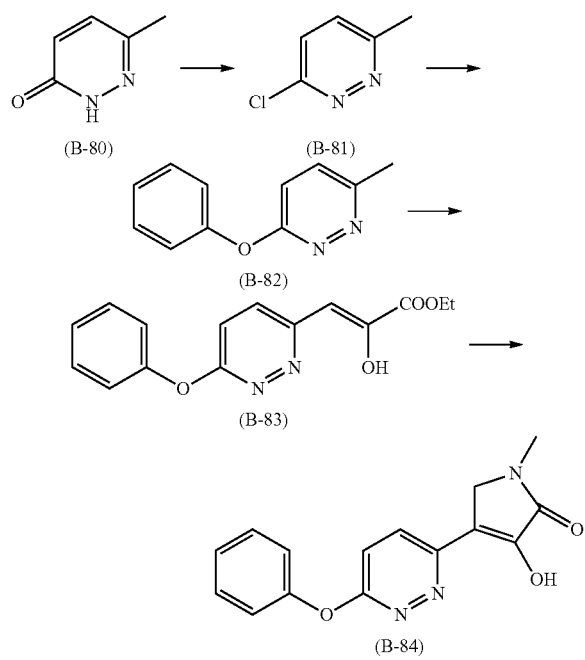

(B-80) According to the method of J. Chem. Soc. 1947, 239, 6-methyl-2H-pyridazine-3-one was synthesized.

NMR (CDCl$_3$) δ: 2.34 (3H, s), 6.92 (1H, d, J=9.7 Hz), 7.16 (1H, d, J=9.5 Hz), 11.97 (1H, bs).

(B-81) Using the above-mentioned compound (B-80), according to the method of WO 01/17968, 3-chloro-6-methylpyridazine was synthesized.

NMR (CDCl$_3$) δ: 2.72 (3H, s), 7.32 (1H, d, J=8.9 Hz), 7.42 (1H, d, J=8.9 Hz).

(B-82) Using the above-mentioned compound B-81, according to the method of (B-10), 3-methyl-6-phenoxypyridazine was synthesized.

NMR (CDCl$_3$) δ: 2.66 (3H, s), 7.07 (1H, d, J=8.9 Hz), 7.17-7.25 (3H, m), 7.34 (1H, d, J=8.9 Hz), 7.37-7.43 (2H, m).

The following compound was prepared as well as above.

3-(4-fluorophenoxy)-6-methylpyridazine

NMR (CDCl$_3$) δ: 2.65 (3H, s), 7.05-7.19 (5H, m), 7.34 (1H, d, J=8.9 Hz).

(B-83) Using the above-mentioned compound B-82, according to the method of (B-11). 2-hydroxy-3-(6-phenoxy-pyridazine-3-yl)-acrylic acid ethyl ester was synthesized.

Melting point: 127-128° C.

NMR (CDCl$_3$) δ: 1.39 (3H, t, J=7.2 Hz), 4.36 (2H, q, J=7.2 Hz), 6.47 (1H, s), 7.19-7.32 (4H, m), 7.41-7.49 (3H, m).

The following compound was prepared as well as above.

3-[6-(4-fluorophenoxy)-pyridazine-3-yl]-2-hydroxy-acrylic acid ethyl ester

Melting point: 164-165° C.
NMR (CDCl$_3$) δ: 1.39 (3H, t, J=7.0 Hz), 4.36 (2H, q, J=7.0 Hz), 6.48 (1H, s), 7.11-7.26 (5H, m), 7.44 (1H, dd, J=0.6, 9.1 Hz).

(B-84) Using the above-mentioned compound B-83, according to the method of (B-12), 3-hydroxy-1-methyl-4-(6-phenoxypyridazine-3-yl)-1,5-dihydropyrrole-2-one was synthesized.

Melting point: 220-225° C.
Elementary analysis as C$_{15}$H$_{13}$N$_3$O$_3$
Calcd. (%): C, 63.60; H, 4.63; N, 14.83.
Found (%): C, 63.49; H, 4.36; N, 14.54.
NMR (CDCl$_3$) δ: 3.17 (3H, s), 4.29 (2H, s), 7.20-7.30 (4H, m), 7.42-7.48 (2H, m), 7.85 (1H, d, J=9.5 Hz).

The following compound was prepared as well as above.

(B-84-a) 3-hydroxy-1-isopropyl-4-(6-phenoxy-pyridazine-3-yl)-1,5-dihydropyrrole-2-one Melting point: 203-205° C.
Elementary analysis as C$_{17}$H$_{17}$N$_3$O$_3$ 0.1H$_2$O
Calcd. (%): C, 65.21; H, 5.54; N, 13.42.
Found (%): C, 65.17; H, 5.22; N, 13.17.
NMR (CDCl$_3$) δ: 1.28 (6H, d, J=6.7 Hz), 4.31 (2H, s), 4.53 (1H, sept), 7.20-7.29 (4H, m), 7.41-7.47 (2H, m), 8.03 (1H, d, J=9.2 Hz).

(B-84-b) 4-[6-(4-fluorophenoxy)-pyridazine-3-yl]-3-hydroxy-1-methyl-1,5-dihydropyrrole-2-one Melting point: 240-243° C.
Elementary analysis as C$_{16}$H$_{12}$FN$_3$O$_3$ 0.2H$_2$O
Calcd. (%): C, 59.09; H, 4.10; N, 13.78; F, 6.23.
Found (%): C, 59.06; H, 3.70; N, 13.72; F, 6.02.
NMR (CDCl$_3$) δ: 3.17 (3H, s), 4.30 (2H, s), 7.09-7.27 (5H, m), 7.94 (1H, d, J=9.2 Hz).

(B-84-c) 4-[6-(4-fluorophenoxy)-pyridazine-3-yl]-3-hydroxy-1-isopropyl-1,5-dihydropyrrole-2-one Melting point: 204-206° C.
Elementary analysis as C$_{17}$H$_{16}$FN$_3$O$_3$
Calcd. (%): C, 62.00; H, 4.90; N, 12.76; F, 5.77.
Found (%): C, 61.95; H, 4.61; N, 12.67; F, 5.58.
NMR (CDCl$_3$) δ: 1.28 (6H, d, J=6.7 Hz), 4.31 (2H, s), 4.50 (1H, m), 7.09-7.23 (5H, m), 8.06 (1H, d, J=9.2 Hz).

Compound B-90

3-hydroxy-1-methyl-4-(5-phenethylpyridazine-3-yl)-1,5-dihydropyrrole-2-one

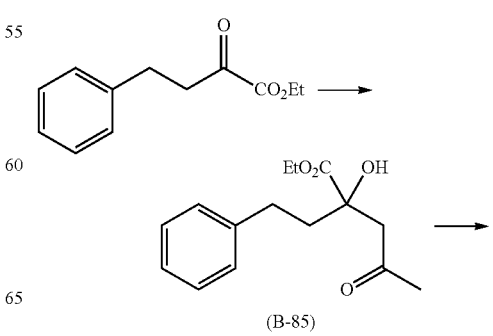

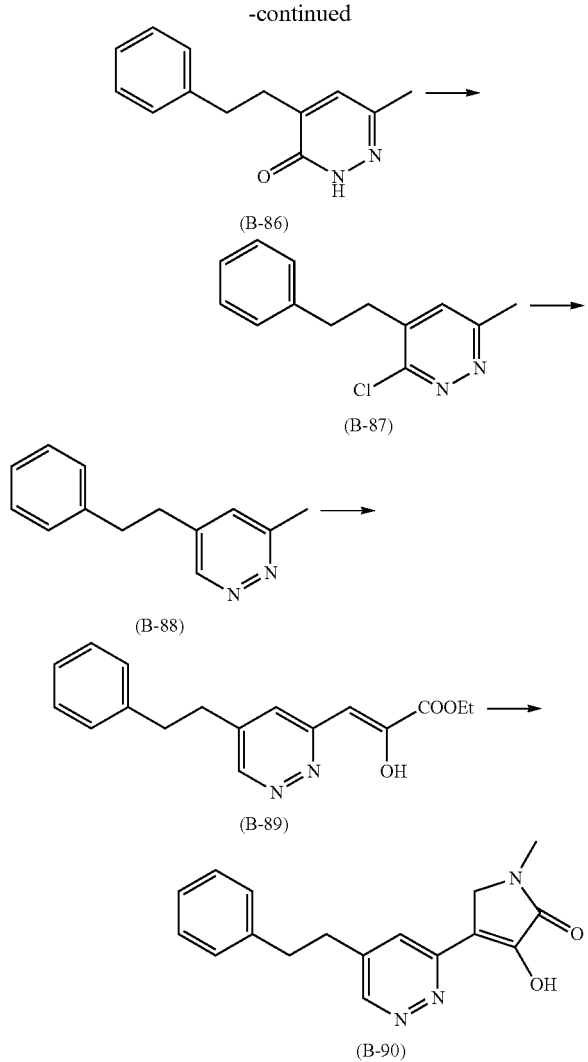

(B-85) To a solution of diisopropylamine (11.5 ml, 82.1 mmol) in tetrahydrofuran (100 ml), was added dropwise a n-butyl lithium solution (79.5 mmol) under ice-cooling and the mixture was stirred for 20 minutes. Acetone (5.85 ml, 79.7 mmol) was added dropwise thereto at −78° C. and the mixture was stirred for 30 minutes. A solution of 2-oxo-4-phenylbutanoic acid ethyl ester (15.0 g, 72.7 mmol) in tetrahydrofuran (50 ml) was added dropwise thereto and the mixture was stirred for 1 hour. An ammonium chloride aqueous solution was added to terminate the reaction, then the mixture was extracted with ethyl acetate. The extract was washed and dried, and the solvent was evaporated under reduced pressure. The residue was purified with silica gel column chromatography (n-hexane:ethyl acetate=5:1-2:1) to give 2-hydroxy-4-oxo-2-phehethylpentanoic acid ethyl ester (16.7 g, yield: 87%)

NMR (CDCl$_3$) δ: 1.29 (3H, t, J=7.2 Hz), 1.96 (2H, m), 2.16 (3H, s), 2.49 (1H, m), 2.79 (1H, m), 2.88 (1H, d, J=17.4 Hz), 3.07 (1H, d, J=17.4 Hz), 3.81 (1H, brs), 4.23 (2H, q, J=7.2 Hz), 7.13-7.31 (5H, m).

(B-86) To a solution of the above-mentioned compound B-85 (16.7 g, 63.2 mmol) in 95% ethanol (35 ml), was added hydrazine-hydrate (4.70 ml, 95.0 mmol) and the mixture was refluxed for 2 hours. The solvent was evaporated under reduced pressure, then the precipitated crystals were washed with water and dried under reduced pressure to give 6-methyl-4-phenethyl-2H-pyridazine-3-one (8.71 g, yield: 64%).

NMR (CDCl$_3$) δ: 2.25 (3H, s), 2.92 (4H, m), 6.82 (1H, s), 7.16-7.33 (5H, m), 11.03 (1H, brs).

(B-87) To a solution of the above-mentioned compound B-86 (4.29 g, 20.0 mmol), was added phosphorus oxychloride (10 ml) and the mixture was stirred at 80° C. for 30 minutes. The solvent was evaporated and to the residue was added ice (40 g), then the mixture was neutralized with a 5N sodium hydroxide aqueous solution and extracted with ethyl acetate. The extract was washed and dried, then the solvent was evaporated under reduced pressure to give crude 3-chloro-6-methyl-4-phenethylpyridazine.

(B-88) A suspension of the above-mentioned crude compound B-87, 28% aqueous ammonia (4 g), and 10% palladium-carbon (0.80 g) in 95% ethanol (400 ml) was stirred in hydrogen atmosphere at 4 atm at room temperature for 30 minutes. The reaction mixture was filtered and the solvent was evaporated under reduced pressure. The residue was extracted with ethyl acetate and the extract was washed and dried, then the solvent was evaporated under reduced pressure. The residue was purified with silica gel column chromatography (ethyl acetate) to give 3-methyl-5-phenethyl-pyridazine (3.49 g, yield: 88%).

NMR (CDCl$_3$) δ: 2.66 (3H, s), 2.93 (4H, m), 7.05 (1H, d, J=2.3 Hz), 7.10-7.33 (5H, m), 8.84 (1H, d, J=2.3 Hz).

(B-89) To a solution of the above-mentioned compound B-88 (3.00 g, 15.1 mmol) in tetrahydrofuran (60 ml), was added dropwise a n-butyl lithium solution (16.7 mmol) at −78° C. Oxalic acid diethyl (6.20 ml, 45.6 mmol) was added thereto and the mixture was stirred for 1 hour, to which was added an ammonium chloride aqueous solution under ice-cooling to terminate the reaction, followed by extraction with ethyl acetate. The extract washed and dried, then the solvent was evaporated under reduced pressure. The residue was subjected to silica gel column chromatography and the portion eluted with ethyl acetate was evaporated under reduced pressure. The precipitated crystals were recrystallized from ethyl acetate-isopropylether-n-hexane to give 2-hydroxy-3-(5-phenethylpyridazine-3-yl)-acrylic acid ethylester (954 mg, yield: 21%).

Melting point: 94-95° C.
Elementary analysis as $C_{17}H_{18}N_2O_3$
Calcd. (%): C, 68.44; H, 6.08; N, 9.39.
Found (%): C, 68.35; H, 5.88; N, 9.36.
NMR (CDCl$_3$) δ: 1.39 (3H, t, J=7.1 Hz), 2.88-3.02 (4H, m), 4.35 (2H, q, J=7.1 Hz), 6.02 (1H, s), 7.00 (1H, s), 7.10-7.16 (2H, m), 7.21-7.35 (3H, m), 8.31 (1H, s).

(B-90) To a solution of the above-mentioned compound B-89 (149 mg, 0.50 mmol) in dioxane (7.5 ml), were added paraformaldehyde (79.8 mg, 2.00 mmol) and methylamine (2.01 mmol. 40% methyl alcohol solution) and the mixture was stirred at room temperature for 3.5 hours. An ammonium chloride aqueous solution was added thereto to terminate the reaction, and the mixture was extracted with chloroform. The extract was washed and dried, then the solvent was evaporated under reduced pressure. The precipitated crystals were recrystallized from ethanol to give 3-hydroxy-1-methyl-4-(5-phenethylpyridazine-3-yl)-1,5-dihydropyrrole-2-one (119 mg, yield: 81%).

Melting point: 203-205° C.
Elementary analysis as $C_{17}H_{17}N_3O_2$
Calcd. (%): C, 69.14; H, 5.80; N, 14.23.
Found (%): C, 68.76; H, 5.68; N, 14.04.

NMR (CDCl₃) δ: 2.99 (4H, s), 3.17 (3H, s), 4.15 (2H, s), 7.11-7.18 (3H, m), 7.21-7.37 (3H, m), 8.62 (1H, d, J=1.5 Hz).

The following compound was prepared as well as above.

(B-90-a) 3-hydroxy-1-isopropyl-4-(5-phenethyl-pyridazine-3-yl)-1,5-dihydropyrrole-2-one Melting point: 182-184° C.
Elementary analysis as $C_{19}H_{21}N_3O_2·0.1C_3H_7OH$
Calcd. (%): C, 70.37; H, 6.67; N, 12.76.
Found (%): C, 70.06; H, 6.40; N, 12.64.
NMR (CDCl₃) δ: 1.29 (6H, d, J=6.9 Hz), 3.00 (4H, s), 4.17 (2H, s), 4.57 (1H, m), 7.12-7.17 (2H, m), 7.21-7.37 (5H, m), 8.67 (1H, d, J=2.1 Hz).

Compound B-95

3-hydroxy-1-methyl-4-(5-phenoxypyrazine-2-yl)-1,5-dihydropyrrole-2-one

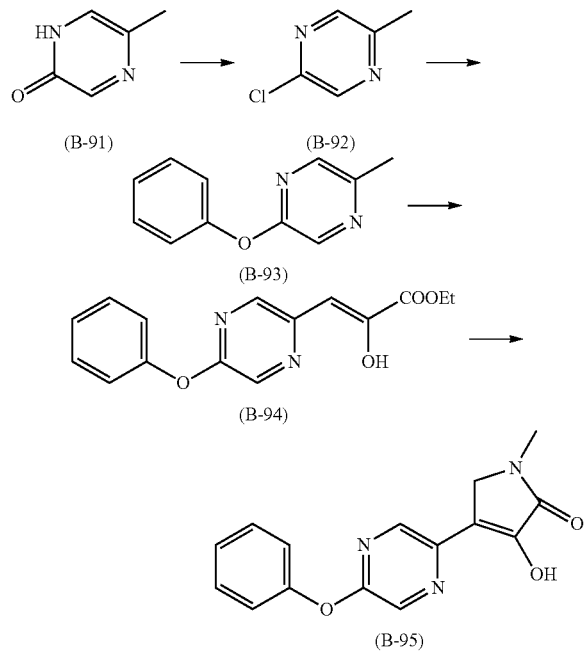

(B-91) According to the method of J. Am. Chem. Soc. 1952, 74, 1580, 5-methyl-1H-pyrazine-2-one was synthesized.
NMR (CDCl₃) δ: 2.34 (3H, s), 7.08 (1H, s), 8.21 (1H, s).
(B-92) Using the above-mentioned compound B-91, according to WO 01/17968, 2-chloro-5-methyl pyrazine was synthesized.
NMR (CDCl₃) δ: 2.56 (3H, s), 8.24 (1H, s), 8.49 (1H, s).
(B-93) Using the above-mentioned compound B-92, according to the method of (B-10), 2-methyl-5-phenoxypyrazine was synthesized.
NMR (CDCl₃) δ: 2.51 (3H, s), 7.12-7.26 (3H, m), 7.39-7.44 (2H, m), 7.98 (1H, s), 8.31 (1H, s).

The following compound was prepared as well as above.

2-(4-fluorophenoxy)-5-methylpyrazine

NMR (CDCl₃) δ: 2.51 (3H, s), 7.09-7.12 (4H, m), 7.95 (1H, s), 8.32 (1H, s).

(B-94) Using the above-mentioned compound B-93, according to the method of (B-11), 2-hydroxy-3-(5-phenoxypyrazine-2-yl)-acrylic acid ethyl ester was synthesized.
Melting point: 128-129° C.
NMR (CDCl₃) δ: 1.40 (3H, t, J=7.0 Hz), 4.37 (2H, q, J=7.0 Hz), 6.63 (1H, s), 7.16-7.19 (2H, m), 7.26-7.31 (1H, m), 7.43-7.48 (2H, m), 8.13 (1H, d, J=1.5 Hz), 8.29 (1H, d, J=1.2 Hz).

The following compound was prepared as well as above.

3-[5-(4-fluorophenoxy)-pyrazine-2-yl]-2-hydroxy-acrylic acid ethyl ester

Melting point: 139-140° C.
NMR (CDCl₃) δ: 1.40 (3H, t, J=7.0 Hz), 4.37 (2H, q, J=7.0 Hz), 6.63 (1H, s), 7.12-7.14 (4H, m), 8.11 (1H, d, J=1.1 Hz), 8.30 (1H, d, J=0.9 Hz).

(B-95) Using the above-mentioned compound B-94, according to the method of (B-12), 3-hydroxy-1-methyl-4-(5-phenoxypyrazine-2-yl)-1,5-dihydropyrrole-2-one was synthesized.
Melting point: 233-235° C.
Elementary analysis as $C_{15}H_{13}N_3O_3·0.3H_2O$
Calcd. (%): C, 62.41; H, 4.75; N, 14.56.
Found (%): C, 62.52; H, 4.48; N, 14.61.
NMR (CDCl₃) δ: 3.16 (3H, s), 4.19 (2H, s), 7.16-7.18 (2H, m), 7.25-7.31 (1H, m), 7.42-7.48 (2H, m), 8.27 (1H, d, J=1.2 Hz), 8.35 (1H, d, J=1.5 Hz).

The following compound was prepared as well as above.

(B-95-a) 3-hydroxy-1-isopropyl-4-(5-phenoxypyrazine-2-yl)-1,5-dihydropyrrole-2-one Melting point: 216-217° C.
Elementary analysis as $C_{17}H_{17}N_3O_3$
Calcd. (%): C, 65.58; H, 5.50; N, 13.50.
Found (%): C, 65.27; H, 5.35; N, 13.47.
NMR (CDCl₃) δ: 1.29 (6H, d, J=7.0 Hz), 4.17 (2H, s), 4.51 (1H, sept), 7.15-7.20 (2H, m), 7.24-7.30 (1H, m), 7.41-7.47 (2H, m), 8.34 (1H, d, J=1.5 Hz), 8.40 (1H, d, J=1.2 Hz), 8.78 (1H, bs).

(B-95-b) 4-[5-(4-fluorophenoxy)-pyrazine-2-yl]-3-hydroxy-1-methyl-1,5-dihydropyrrole-2-one Melting point: 237-238° C.
Elementary analysis as $C_{15}H_{12}FN_3O_3·0.1H_2O$
Calcd. (%): C, 59.44; H, 4.06; N, 13.86; F, 6.27.
Found (%): C, 59.34; H, 4.01; N, 13.95; F, 6.31.
NMR (CDCl₃) δ: 3.16 (3H, s), 4.19 (2H, s), 7.11-7.15 (4H, m), 8.26 (1H, d, J=0.9 Hz), 8.36 (1H, d, J=0.9 Hz), 8.93 (1H, bs).

(B-95-c) 4-[5-(4-fluorophenoxy)-pyrazine-2-yl]-3-hydroxy-1-isopropyl1,5-dihydropyrrole-2-one Melting point: 227-229° C.
Elementary analysis as $C_{17}H_{16}FN_3O_3$
Calcd. (%): C, 62.00; H, 4.90; N, 12.76; F, 5.77.
Found (%): C, 62.05; H, 4.81; N, 12.75; F, 5.72.

NMR (CDCl₃) δ: 1.29 (6H, d, J=6.7 Hz), 4.17 (2H, s), 4.51 (1H, sept), 7.09-7.16 (4H, m), 8.35 (1H, s), 8.40 (1H, s), 8.69 (1H, bs).

Compound B-106

4-[5-(4-fluorobenzyl)-pyrazine-2-yl]-3-hydroxy-1-methyl-1,5-dihydropyrrole-2-one

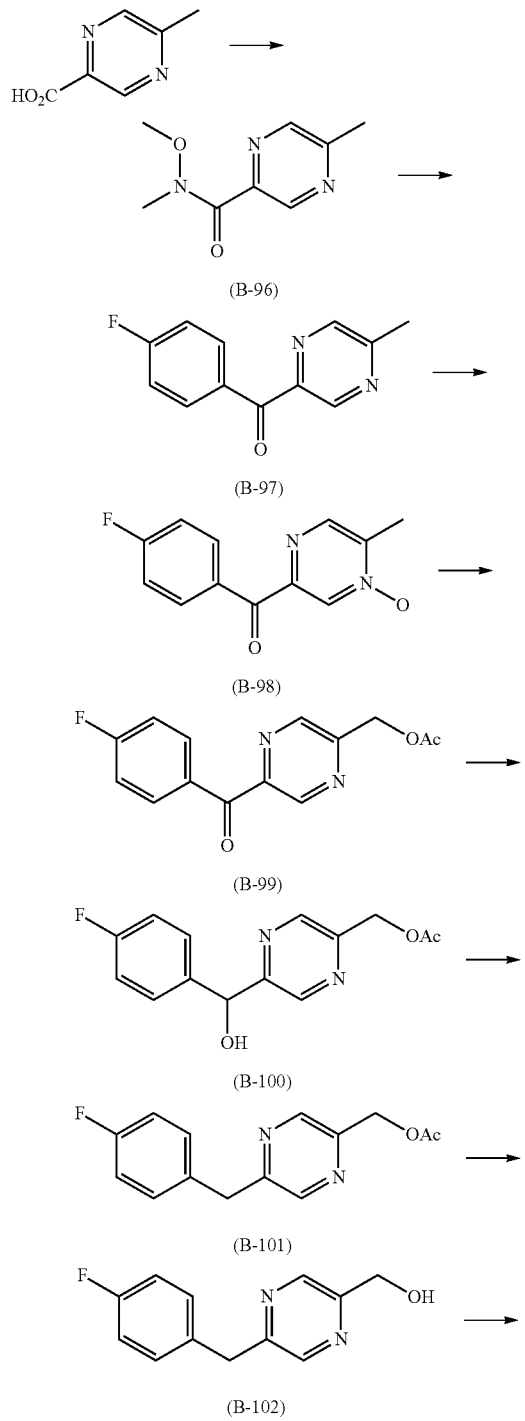

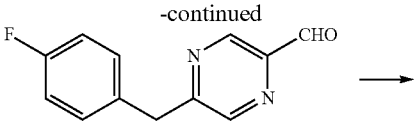

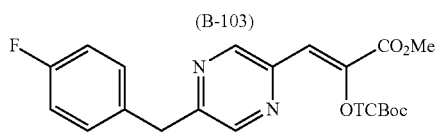

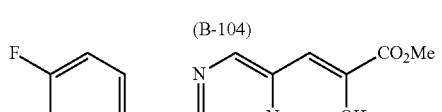

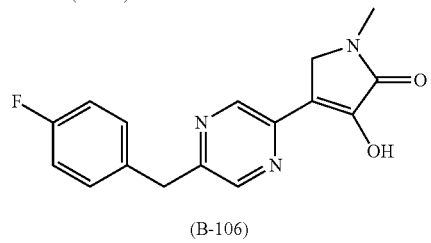

(B-96) To a solution of 5-methyl-2-pyrazine carboxylic acid (25 g, 180 mmol), HOBt (4.9 g, 36 mmol), and N,O-dimethylhydroxyamine hydrochloride (21 g, 220 mmol) in methylene chloride (100 ml) and chloroform (400 ml), were added triethylamine (30 ml, 220 mmol) and WSCD (41 g, 220 mmol) and the mixture was stirred at room temperature for 2 hours. The solution was washed and dried, then the solvent was evaporated under reduced pressure to give crude 5-methylpyrazine-2-carboxylic acid methoxymethylamide (30.5 g).

NMR (CDCl₃) δ: 2.63 (3H, s), 3.41 (3H, s), 3.75 (3H, s), 8.47 (1H, s), 8.82 (1H, s).

(B-97) To a solution of the above-mentioned crude product B-96 (16.3 g, 90 mmol) in tetrahydrofuran (220 ml), was added dropwise 4-fluorophenylmagnesium bromide (99 ml) at −40° C. and the mixture was stirred at −20° C. for 30 minutes. An ammonium chloride aqueous solution was added to terminate the reaction, which was extracted with ethyl acetate. The extract was washed and dried, then the solvent was evaporated under reduced pressure. The precipitated crystals were washed with n-hexane and dried to give 4-fluorophenyl-5-methylpyrazine-2-yl-metanone (16.8 g, yield: 86%).

NMR (CDCl₃) δ: 2.70 (3H, s), 7.15-7.21 (2H, m), 8.16-8.20 (2H, m), 8.54 (1H, s), 9.17 (1H, s).

(B-98) To a solution of the above-mentioned compound B-97 (16.8 g, 78 mmol) in chloroform (250 ml), was added m-chloroperbenzoic acid (22.7 g, 86 mmol) and the mixture was stirred at room temperature overnight. Sodium hydrogen carbonate was added thereto to alkalify the solution and the mixture washed and dried, then the solvent was evaporated under reduced pressure. The precipitated crystals were washed with diisopropylether and dried under reduced pressure to give (4-fluorophenyl-(5-methyl-4-oxypyrazine-2-yl)-metanone (15.8 g, yield: 88%).

NMR (CDCl₃) δ: 2.56 (3H, s), 7.14-7.22 (2H, m), 8.18-8.24 (2H, m), 8.53 (1H, s), 8.77 (1H, s).

(B-99) A solution of the above-mentioned compound B-98 (15.8 g, 78 mmol) in acetic anhydride (160 ml) was stirred at 135° C. for 3 hours, which was cooled to room temperature, then water (500 ml) was added thereto with stirring overnight. The reaction solution was extracted with ethyl acetate, then the extract was washed and dried. The solvent was evaporated under reduced pressure and the residue was purified with silica gel column chromatography (n-hexane:ethyl acetate=3:1) to give acetic acid 5-(4-fluorobenzoyl)-pyrazine-2-ylmethyl ester (8.0 g, yield: 43%)

NMR (CDCl$_3$) δ: 2.22 (3H, s), 5.37 (2H, s), 7.16-7.22 (2H, m), 8.17-8.22 (2H, m), 8.72 (1H, s), 9.24 (1H, s).

(B-100) To a solution of the above-mentioned compound B-99 (8.0 g, 29 mmol) in methyl alcohol (60 ml), was added sodium borohydrate (491 mg, 11.7 mmol) under ice-cooling and the mixture was stirred for 2 hours, which was warmed to room temperature, followed by stirring for 30 minutes. An ammonium chloride aqueous solution was added to terminate the reaction, and the mixture was extracted with ethyl acetate. The extract was washed and dried, then the solvent was evaporated under reduced pressure to give crude acetic acid 5-[(4-fluorophenyl)-hydroxymethyl]-pyrazine-2-ylmethyl ester (8.0 g).

NMR (CDCl$_3$) δ: 2.15 (3H, s), 5.25 (2H, s), 5.87 (1H, s), 7.02-7.08 (2H, m), 8.34-8.39 (2H, m), 8.53 (1H, s), 8.58 (1H, s).

(B-101) To a solution of the above-mentioned crude product B-100 (8.0 g) in trifluoroacetic acid (200 ml), was added triethylsilane (40 ml, 250 mmol) under ice-cooling and the mixture was stirred at room temperature for 4 days. The solvent was evaporated under reduced pressure and an aqueous solution of sodium hydrogen carbonate was added to neutralize the solution, which was extracted with ethyl acetate. The extract was washed and dried, then the solvent was evaporated under reduced pressure and the residue was purified with silica gel column chromatography (n-hexane:ethyl acetate=1:1) to give acetic acid 5-(4-fluorobenzyl)-pyrazine-2-ylmethyl ester (4.5 g, yield: 60%).

NMR (CDCl$_3$) δ: 2.15 (3H, s), 4.14 (2H, s), 5.22 (2H, s), 6.97-7.03 (2H, m), 7.20-7.25 (2H, m), 8.43 (1H, s), 8.57 (1H, s).

(B-102) To a solution of the above-mentioned compound B-101 (4.5 g, 17.3 mmol) in methyl alcohol (50 ml), was added a 2N sodium hydroxide aqueous solution (26 ml) and the mixture was stirred at room temperature for 1 hour. Hydrochloric acid and an ammonium chloride aqueous solution were added to neutralize the reaction solution, which was extracted with ethyl acetate. The extract was washed and dried, then the solvent was evaporated under reduced pressure. The residue was purified with silica gel column chromatography (n-hexane:ethyl acetate=1:2) to give [5-(4-fluorobenzyl)-pyrazine-2-yl]-methyl alcohol (3.1 g, yield: 82%).

NMR (CDCl$_3$) δ: 3.15 (1H, brs), 4.14 (2H, s), 4.79 (2H, s), 6.97-7.02 (2H, m), 7.19-7.24 (2H, m), 8.39 (1H, s), 8.55 (1H, s).

(B-103) To a solution of the above-mentioned compound B-102 (3.0 g, 13.7 mmol) in chloroform (90 ml), was added manganese dioxide (12.0 g, 137 mmol) and the mixture was refluxed for 3 hours. The reaction mixture was filtered with celite and the solvent was evaporated under reduced pressure to give crude 5-(4-fluorobenzyl)-pyrazine-2-carboaldehyde (2.46 g).

NMR (CDCl$_3$) δ: 4.25 (2H, s), 7.00-7.06 (2H, m), 7.23-7.28 (2H, m), 8.60 (1H, s), 9.09 (1H, s), 10:11 (1H, s).

(B-104) (B-105) −78° C. に cool 下 To a lithium bis(trimethylsilyl)amide solution (13.6 ml), was added dropwise a tetrahydrofuran (15 ml) solution containing (dimethoxyphosphoryl-(2,2,2-trichloro-1,1-dimethylethoxycarbonyloxy)-acetic acid methyl ester (5.03 g, 12.5 mmol) synthesized according to Tetrahedron Lett. 25, 3529, 1984) and the mixture was stirred for 10 minutes. A solution of the above-mentioned compound B-103 (337 mg, 1.56 mmol) in tetrahydrofuran (2 ml) was added thereto and the mixture was stirred for 10 minutes, which was warmed to 0° C. and stirred for 20 minutes. An ammonium chloride aqueous solution was added to terminate the reaction and the mixture was extracted with ethyl acetate. The extract was washed and dried, then the solvent was evaporated under reduced pressure. The residue was purified with silica gel column chromatography (n-hexane:ethyl acetate=2:1-1:2) to give 3-[5-(4-fluorobenzyl)-pyrazine-2-yl]-2-(2,2,2-trichloro-1,1-dimethylethoxycarbonyloxy)-acrylic acid methyl ester (3.46 g, yield: 62%) and 3-[5-(4-fluorobenzyl)-pyrazine-2-yl]-2-hydroxy acrylic acid methyl ester (0.70 g, yield: 21%).

3-[5-(4-fluorobenzyl)-pyrazine-2-yl]-2-(2,2,2-trichloro-1,1-dimethylethoxycarbonyloxy)-acrylic acid methyl ester NMR (CDCl$_3$) δ: 1.98 (6H, s), 3.76 (2H, s), 4.15 (3H, s), 6.93 (1H, s), 6.98-7.04 (2H, m), 7.20-7.25 (2H, m), 8.42 (1H, d, J=1.5 Hz), 8.69 (1H, d, J=1.5 Hz).

3-[5-(4-fluorobenzyl)-pyrazine-2-yl]-2-hydroxy-acrylic acid methyl ester

Melting point: 122-123° C.
Elementary analysis as C$_{15}$H$_{13}$FN$_2$O$_3$
Calcd. (%): C, 62.50; H, 4.55; N, 9.72; F, 6.59.
Found (%): C, 62.45; H, 4.35; N, 9.72; F, 6.45.
NMR (CDCl$_3$) δ: 3.91 (3H, s), 4.16 (2H, s), 6.64 (1H, s), 6.99-7.05 (2H, m), 7.22-7.25 (2H, m), 8.28 (1H, s), 8.50 (1H, s).

(B-106) Using the above-mentioned compound B-105, by a similar method to (B-12), 4-[5-(4-fluorobenzyl)-pyrazine-2-yl]-3-hydroxy-1-methyl-1,5-dihydropyrrole-2-one was obtained.

Melting point: 223-225° C.
Elementary analysis as C$_{16}$H$_{14}$FN$_3$O$_2$
Calcd. (%): C, 64.21; H, 4.71; N, 14.04; F, 6.35.
Found (%): C, 63.65; H, 4.31; N, 13.89; F, 6.19; Cl, 0.82.
NMR (CDCl$_3$) δ: 3.16 (3H, s), 4.16 (2H, s), 4.21 (2H, s), 6.98-7.04 (2H, m), 7.21-7.27 (2H, m), 8.35 (1H, s), 8.60 (1H, s).

The following compound was prepared as well as above.

(B-106-a) 4-[5-(4-fluorobenzyl)-pyrazine-2-yl]-3-hydroxy-1-isopropyl-1,5-dihydropyrrole-2-one Melting point: 207-209° C.
Elementary analysis as C$_{18}$H$_{18}$FN$_3$O$_2$
Calcd. (%): C, 66.04; H, 5.54; N, 12.84; F, 5.80.
Found (%): C, 65.25; H, 5.38; N, 12.46; F, 5.51.
NMR (CDCl$_3$) δ: 1.29 (6H, d, J=6.9 Hz), 4.16 (2H, s), 4.18 (2H, s), 4.55 (1H, sept, J=6.9 Hz), 6.98-7.04 (2H, m), 7.21-7.26 (2H, m), 8.34 (1H, s), 8.74 (1H, s).

Compound B-110

4-[4-(4-fluorobenzyloxy)-[1,3,5]triazine-2-yl]-3-hydroxy-1-methyl-1,5-dihydropyrrole-2-one

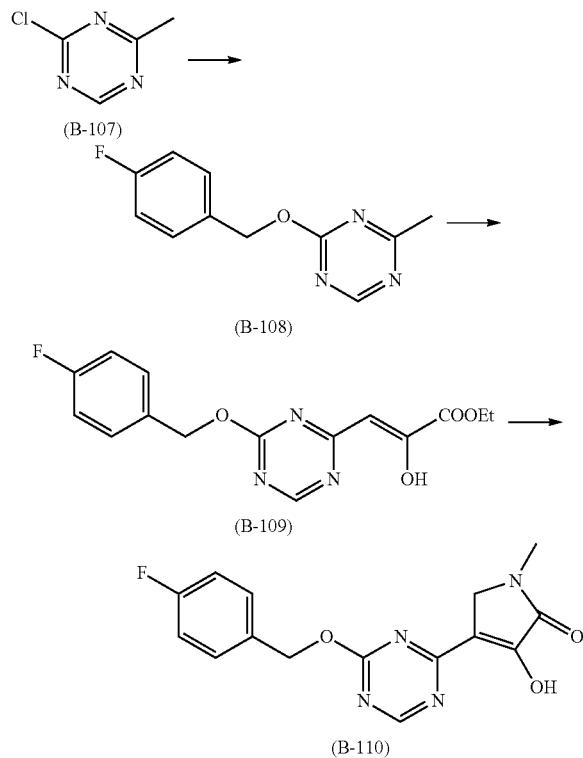

(B-107) According to Synthesis 1981, 907, 2-chloro-4-methyl[1,3,5]triazine was synthesized.
NMR (CDCl$_3$) δ: 2.71 (3H, s), 8.92 (1H, s).
(B-108) To a solution of calcium carbonate (7.8 g, 57 mmol) in 4-fluorobenzyl alcohol (15 ml), was added the above-mentioned compound (B-107) (7.4 g, 57 mmol) and the mixture was stirred at 90° C. for 3 hours. Water was added to terminate the reaction, which was extracted with ethyl acetate. The extract was washed and dried, then the solvent was evaporated under reduced pressure. The residue was purified with silica gel column chromatography (n-hexane: ethyl acetate=3:1-1:1) to give 2-(4-fluorobenzyloxy)-4-methyl[1,3,5]triazine (3.3 g, yield: 26%).
NMR (CDCl$_3$) δ: 2.60 (3H, s), 5.44 (2H, s), 7.32-7.36 (2H, m), 7.43-7.48 (2H, m), 8.77 (1H, s).
(B-109) Using the above-mentioned compound B-108, according to the method of (B-11), 3-[4-(4-fluorobenzyloxy)-[1,3,5]triazine-2-yl]-2-hydroxyacrylic acid ethyl ester was synthesized.
Melting point: 142-143° C.
NMR (CDCl$_3$) δ: 1.40 (3H, t, J=7.0 Hz), 4.38 (2H, q, J=7.0 Hz), 5.47 (2H, s), 6.54 (1H, s), 7.05-7.11 (2H, m), 7.44-7.48 (2H, m), 8.80 (1H, s).
(B-110) Using the above-mentioned compound B-109, according to the method of (B-12), 4-[4-(4-fluorobenzyloxy)-[1,3,5]triazine-2-yl]-3-hydroxy-1-methyl-1,5-dihydropyrrole-2-one was synthesized.
Melting point: 169-171° C.
Elementary analysis as C$_{15}$H$_{13}$FN$_4$O$_3$ 0.3H$_2$O
Calcd. (%): C, 56.00; H, 4.26; N, 17.42; F, 5.91.
Found (%): C, 55.92; H, 3.89; N, 17.58; F, 5.62.
NMR (CDCl$_3$) δ: 3.17 (3H, s), 4.20 (2H, s), 5.47 (2H, s), 7.05-7.11 (2H, m), 7.44-7.48 (2H, m), 8.82 (1H, s).
The following compound was prepared as well as above.

(B-110-a) 4-[4-(4-fluorobenzyloxy)-[1,3,5]triazine-2-yl]-3-hydroxy-1-isopropyl-1,5-dihydropyrrole-2-one Melting point: 105-106° C.
Elementary analysis as C$_{17}$H$_{17}$FN$_4$O$_3$
Calcd. (%): C, 59.30; H, 4.98; N, 16.27; F, 5.52.
Found (%): C, 59.12; H, 4.68; N, 16.29; F, 5.36.
NMR (CDCl$_3$) δ: 1.27 (6H, d, J=6.7 Hz), 4.15 (2H, s), 4.57 (1H, sept), 5.48 (2H, s), 7.03-7.11 (2H, m), 7.44-7.48 (2H, m), 8.82 (1H, s).

Compound B-112

4-{5-[2-(4-fluorophenyl)ethyl]-thiazole-2-yl}-3-hydroxy-1-methyl-1,5-dihydropyrrole-2-one

(B-111) According to WO 01/17968, 3-{5-[2-(4-fluorophenyl)ethyl]-thiazole-2-yl}-2-hydroxyacrylic acid ethyl ester was synthesized.
Melting point: 146-148° C.
Elementary analysis as C$_{16}$H$_{16}$FNO$_3$S
Calcd. (%): C, 59.80; H, 5.02; N, 4.36; F, 5.91; S, 9.98.
Found (%): C, 59.85; H, 4.90; N, 4.32; F, 5.82; S, 10.03.
NMR (CDCl$_3$) δ: 1.38 (3H, t, J=7.1 Hz), 2.95 (2H, t, J=7.5 Hz), 3.14 (2H, t, J=7.5 Hz), 4.36 (2H, q, J=7.1 Hz), 6.69 (1H, s), 6.95-7.01 (2H, m), 7.09-7.14 (2H, m), 7.41 (1H, s).
(B-112) Using the above-mentioned compound B-111, by a similar method to (B-12), 4-{5-[2-(4-fluorophenyl)ethyl]-thiazole-2-yl}-3-hydroxy-1-methyl-1,5-dihydropyrrole-2-one was obtained.
Melting point: 214-216° C.
Elementary analysis as C$_{16}$H$_{15}$FN$_2$O$_2$S
Calcd. (%): C, 60.36; H, 4.75; N, 8.80; F, 5.97; S, 10.07.
Found (%): C, 59.98; H, 4.59; N, 8.59; F, 5.77; S, 9.95.
NMR (CDCl$_3$) δ: 2.93 (2H, t, J=7.6 Hz), 2.98 (3H, s), 3.15 (2H, t, J=7.4 Hz), 4.21 (2H, s), 7.07-7.12 (2H, m), 7.25-7.29 (2H, m), 7.48 (1H, s).
The following compound was prepared as well as above.

(B-112-a) 4-{5-[2-(4-fluorophenyl)ethyl]-thiazole-2-yl}-3-hydroxy-1-isopropyl-1,5-dihydropyrrole-2-one Melting point: 208-210° C.
Elementary analysis as C$_{18}$H$_{19}$FN$_2$O$_2$S Calcd. (%): C, 62.41; H, 5.53; N, 8.09; F, 5.48; S, 9.26.
Found (%): C, 62.21; H, 5.51; N, 8.02; F, 5.39; S, 9.24.
NMR (CDCl$_3$) δ: 1.28 (6H, d, J=6.7 Hz), 2.96 (2H, t, J=7.4 Hz), 3.16 (2H, t, J=7.4 Hz), 4.23 (2H, s), 4.53 (1H, sept, J=6.7 Hz), 6.95-7.00 (2H, m), 7.10-7.14 (2H, m), 7.41 (1H, s).

Compound B-117

4-[5-(4-fluorobenzyl)-thiazole-2-yl]-3-hydroxy-1-methyl-1,5-dihydropyrrole-2-one

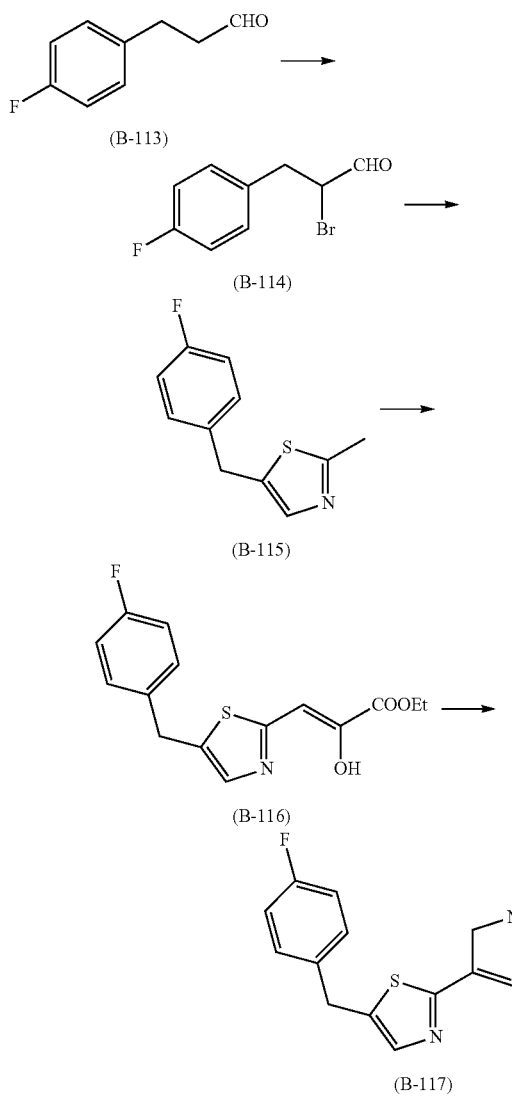

(B-113) According to J. Org. Chem. 1993, 58, 1696-1701, 3-(4-fluorophenyl)-propionic aldehyde was synthesized.
(B-114) To a solution of the above-mentioned compound B-113 (4.6 g, 30 mmol) in acetonitrile (120 ml), tetrabutylammonium tribromide (14.5 g, 30 mmol) was added and the mixture was stirred at room temperature for 30 minutes. The solvent was evaporated under reduced pressure and water was added thereto, which was extracted with diethyl ether. The extract was washed and dried, then the solvent was evaporated under reduced pressure to give crude 2-bromo-3-(4-fluorophenyl)-propionic aldehyde (6.0 g).
NMR (CDCl$_3$) δ: 3.14 (1H, dd, J=7.8, 14.8 Hz), 3.46 (1H, dd, J=6.6, 14.8 Hz), 4.41 (1H, dt, J=2.4, 6.7 Hz), 6.98-7.04 (2H, m), 7.17-7.21 (2H, m), 9.49 (1H, s).
(B-115) To a solution of the above-mentioned crude product B-114 (6.0 g) in acetonitrile (60 ml), was added thioacetoamide (3.9 g, 52 mmol) and the mixture was refluxed for 1 hour. A sodium hydrogen carbonate aqueous solution was added to neutralize the solution, which was extracted with diethyl ether. The extract was washed and dried, then the solvent was evaporated under reduced pressure. The residue was purified with silica gel column chromatography (n-hexane:ethyl acetate=3:1) to give 5-(4-fluorobenzyl)-2-methylthiazole (3.8 g, yield: 71%).
NMR (CDCl$_3$) δ: 2.64 (3H, s), 4.06 (2H, s), 6.96-7.02 (2H, m), 7.15-7.20 (2H, m), 7.32 (1H, s).
(B-116) Using the above-mentioned compound B-115, by a similar method to (B-11), 3-[5-(4-fluorobenzyl)-thiazole-2-yl]-2-hydroxyacrylic acid ethyl ester was obtained.
Melting point: 160-162° C.
Elementary analysis as C$_{15}$H$_{14}$FNO$_3$S
Calcd. (%): C, 58.62; H, 4.59; N, 4.56; F, 6.18; S, 10.43.
Found (%): C, 58.84; H, 4.32; N, 4.76; F, 6.45; S, 10.90.
NMR (CDCl$_3$) δ: 1.38 (3H, t, J=7.1 Hz), 4.13 (2H, s), 4.35 (2H, q, J=7.1 Hz), 6.68 (1H, s), 7.00-7.05 (2H, m), 7.17-7.21 (2H, m), 7.48 (1H, s).
(B-117) Using the above-mentioned compound B-116, by a similar method to (B-12), 4-[5-(4-fluorobenzyl)-thiazole-2-yl]-3-hydroxy-1-methyl-1,5-dihydropyrrole-2-one was obtained.
Melting point: 222-224° C.
Elementary analysis as C$_{15}$H$_{13}$FN$_2$O$_2$S
Calcd. (%): C, 59.20; H, 4.31; N, 9.20; F, 6.24; S, 10.54.
Found (%): C, 57.01; H, 4.08; N, 8.68; F, 5.91; S, 10.06.
NMR (CDCl$_3$) δ: 2.98 (3H, s), 4.19 (2H, s), 4.22 (2H, s), 7.11-7.17 (2H, m), 7.30-7.35 (2H, m), 7.60 (1H, s).
The following compound was prepared as well as above.

(B-117-a) 4-[5-(4-fluorobenzyl)-thiazole-2-yl]-3-hydroxy-1-isopropyl-1,5-dihydropyrrole-2-one Melting point: 212-214° C.
Elementary analysis as C$_{17}$H$_{17}$FN$_2$O$_2$S
Calcd. (%): C, 61.43; H, 5.16; N, 8.43; F, 5.72; S, 9.65.
Found (%): C, 61.17; H, 5.06; N, 8.30; F, 5.62; S, 9.58.
NMR (CDCl$_3$) δ: 1.26 (6H, d, J=6.7 Hz), 4.16 (2H, s), 4.22 (2H, s), 4.51 (1H, sept, J=6.7 Hz), 6.98-7.03 (2H, m), 7.17-7.22 (2H, m), 7.53 (1H, s).

C Group Compound

Compound C-8

2-[5-(4-fluorobenzyl)furan-2-carbonyl]-3-hydroxy-4H-1-benzopyrane-4-one

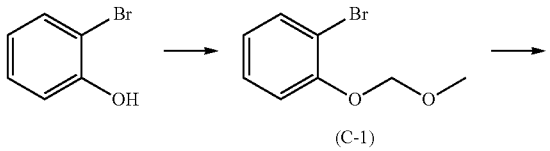

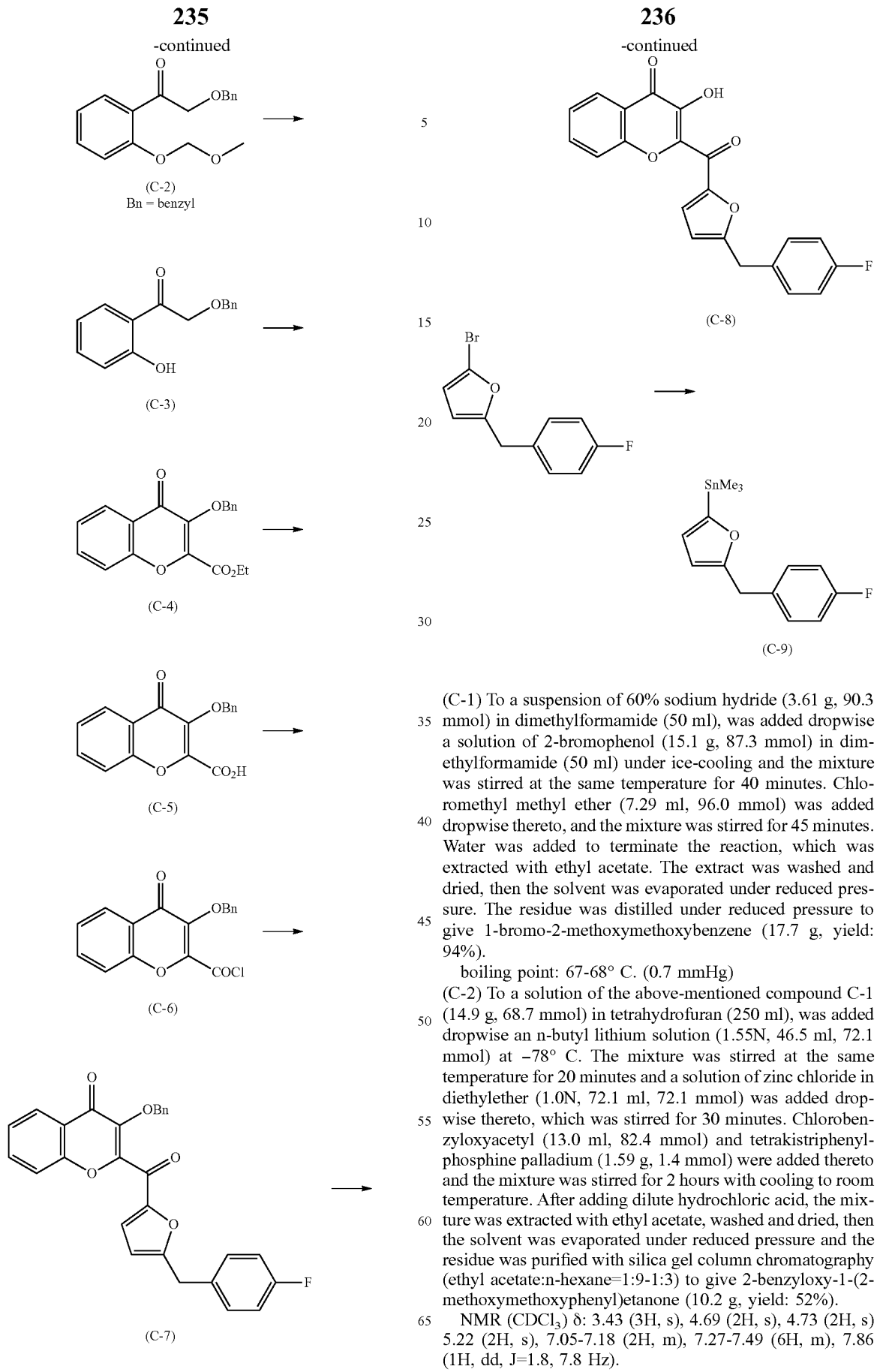

(C-1) To a suspension of 60% sodium hydride (3.61 g, 90.3 mmol) in dimethylformamide (50 ml), was added dropwise a solution of 2-bromophenol (15.1 g, 87.3 mmol) in dimethylformamide (50 ml) under ice-cooling and the mixture was stirred at the same temperature for 40 minutes. Chloromethyl methyl ether (7.29 ml, 96.0 mmol) was added dropwise thereto, and the mixture was stirred for 45 minutes. Water was added to terminate the reaction, which was extracted with ethyl acetate. The extract was washed and dried, then the solvent was evaporated under reduced pressure. The residue was distilled under reduced pressure to give 1-bromo-2-methoxymethoxybenzene (17.7 g, yield: 94%).

boiling point: 67-68° C. (0.7 mmHg)

(C-2) To a solution of the above-mentioned compound C-1 (14.9 g, 68.7 mmol) in tetrahydrofuran (250 ml), was added dropwise an n-butyl lithium solution (1.55N, 46.5 ml, 72.1 mmol) at −78° C. The mixture was stirred at the same temperature for 20 minutes and a solution of zinc chloride in diethylether (1.0N, 72.1 ml, 72.1 mmol) was added dropwise thereto, which was stirred for 30 minutes. Chlorobenzyloxyacetyl (13.0 ml, 82.4 mmol) and tetrakistriphenylphosphine palladium (1.59 g, 1.4 mmol) were added thereto and the mixture was stirred for 2 hours with cooling to room temperature. After adding dilute hydrochloric acid, the mixture was extracted with ethyl acetate, washed and dried, then the solvent was evaporated under reduced pressure and the residue was purified with silica gel column chromatography (ethyl acetate:n-hexane=1:9-1:3) to give 2-benzyloxy-1-(2-methoxymethoxyphenyl)etanone (10.2 g, yield: 52%).

NMR (CDCl$_3$) δ: 3.43 (3H, s), 4.69 (2H, s), 4.73 (2H, s) 5.22 (2H, s), 7.05-7.18 (2H, m), 7.27-7.49 (6H, m), 7.86 (1H, dd, J=1.8, 7.8 Hz).

(C-3) To a solution of the above-mentioned compound C-2 (10.2 g, 35.7 mmol) in methyl alcohol (100 ml), was added 2N hydrochloric acid (25 ml) and the mixture was stirred at 50° C. for 4 hours 30 minutes. Water (100 ml) was added thereto, and the mixture was extracted with ethyl acetate, washed and dried, then the solvent was evaporated under reduced pressure and the residue was purified with silica gel column chromatography (ethyl acetate:n-hexane=1:4) to give 2-benzyloxy-1-(2-hydroxyphenyl)etanone (7.89 g, yield: 91%).

NMR (CDCl$_3$) δ: 4.70 (2H, s), 4.77 (2H, s), 6.83-6.90 (1H, m), 7.00 (1H, dd, J=1.2, 8.4 Hz), 7.28-7.51 (6H, m), 7.63 (1H, dd, J=1.5, 8.1 Hz), 11.9 (1H, s).

(C-4) To a solution of the above-mentioned compound C-3 (7.64 g, 31.6 mmol) in pyridine (76 ml), was added ethyl chloro glyoxylic acetate (5.29 ml, 47.4 mmol) under ice-cooling. The mixture was stirred for 20 minutes while allowing to be at room temperature, then further stirred at 100° C. for 37 hours. Water (5 ml) was added thereto and the mixture was stirred at room temperature for 15 minutes and evaporated under reduced pressure, to which was added 1N hydrochloric acid, followed by extraction with ethyl acetate. The extract was washed and dried, then the solvent was evaporated under reduced pressure. The residue was purified with silica gel column chromatography (ethyl acetate:n-hexane=1:3) to give 3-benzyloxy4-oxo-4H-chromene-2-carboxylic acid ethyl ester (3.48 g, yield: 34%).

NMR (CDCl$_3$) δ: 1.36 (3H, t, J=7.2 Hz), 4.40 (2H, q, J=7.2 Hz), 5.28 (2H, s), 7.30-7.76 (8H, m), 8.23-8.27 (1H, m).

(C-5) To the above-mentioned compound C-4 (1.73 g, 5.34 mmol) in ethanol (16 ml), was added 2N sodium hydroxide aqueous solution (3 ml) and the mixture was stirred at room temperature for 1 hour. The mixture was concentrated under reduced pressure and 2N hydrochloric acid (3.2 ml) and water were added thereto, which was extracted with ethyl acetate, washed, and dried. The solvent was evaporated under reduced pressure and the residue was crystallized from ethyl acetate n-hexane to give 3-benzyloxy-4-oxo-4H-chromene-2-carboxylic acid (1.24 g, yield: 79%).

Melting point: 145-146° C.

NMR (CDCl$_3$) δ: 5.63 (2H, s), 7.36-7.52 (6H, m), 7.62-7.66 (1H, m), 7.75-7.82 (1H, m), 8.25 (1H, dd, J=2.1, 7.8 Hz).

(C-6) To a solution of the above-mentioned compound C-5 (157 mg, 0.53 mmol) in methylene chloride (3 ml), were added oxalylchloride (50 μl, 0.69 mmol) and dimethylformamide (2 μl) under ice-cooling and the mixture was stirred for 20 minutes while allowing to be at room temperature. The solution was concentrated under reduced pressure to give crude 3-benzyloxy-4-oxo-4H-chromene-2-carboxylic acid chloride.

(C-7) To a solution of the above-mentioned compound C-6 in chloroform (1 ml), were added dichlorobis(acetonitrile) palladium (II) (12 mg, 0.046 mmol) and trimethylzinc compound (250 mg) prepared below at room temperature and the mixture was stirred at the same temperature for 5 minutes and at 50° C. for 20 minutes. Water was added thereto and the mixture was extracted with ethyl acetate, washed and dried. The solvent was evaporated and the residue was purified with silica gel column chromatography (ethyl acetate:n-hexane=1:4). Crystallization from ethyl acetate n-hexane gave 3-benzyloxy-2-[5-(4-fluorobenzyl)furan-2-carbonyl]chromene-4-one (82 mg, yield: 21%).

Melting point: 158° C.

NMR (CDCl$_3$) δ: 4.02 (2H, s), 5.24 (2H, s), 6.96-7.76 (13H, m), 8.30 (1H, dd, J=1.5, 8.1 Hz).

(C-8) To a solution of the above-mentioned compound C-7 (79 mg, 0.17 mmol) in ethanol (2 ml) and tetrahydrofuran (6 ml), was added 10% palladium-carbon (20 mg) and the mixture was stirred at room temperature for 10 minutes under hydrogen atmosphere. After filtrating off the palladium-carbon, the filtrate was concentrated under reduced pressure and the residue was crystallized from tetrahydrofuran methyl alcohol to give 2-[5-(4-fluorobenzyl)furan-2-carbonyl]-3-hydroxy-4H-1-benzopyrane-4-one (45 mg, yield: 71%).

Melting point: 226-227° C.

Elementary analysis as $C_{21}H_{13}FO_5$

Calcd. (%): C, 69.23; H, 3.60; F, 5.21.

Found (%): C, 69.00; H, 3.53; F, 5.15.

NMR (CDCl$_3$) δ: 4.14 (2H, s), 6.32 (1H, d, J=3.6 Hz), 7.01-7.79 (7H, m), 7.90 (1H, d, J=3.6 Hz), 8.30 (1H, dd, J=1.5, 8.1 Hz), 11.86 (1H, s).

(C-9) To a solution of bromofuran (500 mg, 1.96 mmol) in tetrahydrofuran (250 ml), was added dropwise a n-butyl lithium solution (1.55N, 1.3 ml, 2.02 mmol) at −78° C. and the mixture was stirred for 5 minutes. To the mixture was added dropwise a solution of trimethyltin chloride (423 mg, 2.06 mmol) in tetrahydrofuran (0.5 ml) and the mixture was stirred at −78° C. for 30 minutes and further stirred with warming to room temperature. Water was added thereto and the mixture was extracted with ethyl acetate, washed, and dried. The solvent was evaporated under reduced pressure to give the crude trimethyltin compound.

NMR (CDCl$_3$) δ: 0.20-0.40 (9H, m), 3.98 (2H, s), 5.92-5.96 (1H, m), 6.46-6.50 (1H, m), 6.94-7.22 (4H, m).

Compound C-12

6-[(4-fluorobenzyl)oxy]-3-hydroxy(2-pyridine-2-yl)-4H-1-benzopyrane-4-one

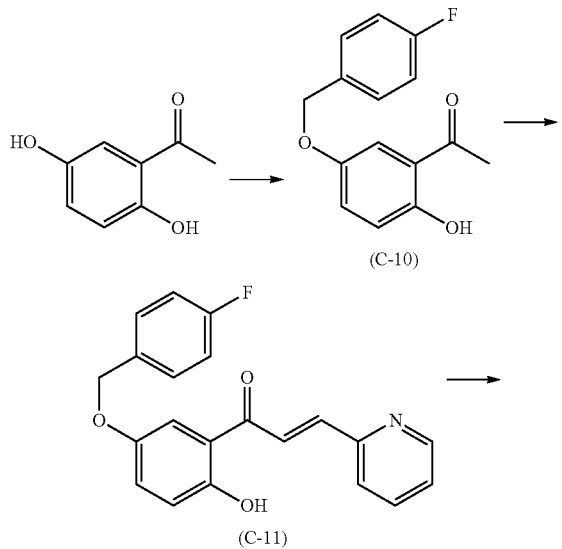

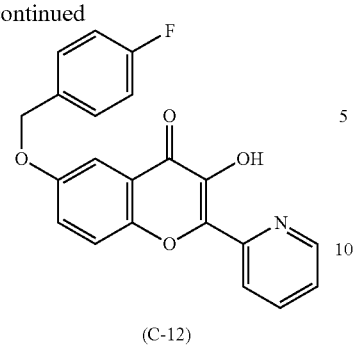

(C-12)

(C-10) To a suspension of 2',5'-dihydroxyacetophenone (23.1 g, 152 mmol) and powder potassium carbonate (23.1 g, 167 mmol) in acetonitrile (400 ml), was added 4-fluorobenzylbromide (18.9 ml, 152 mmol) at room temperature and the mixture was refluxed for 3 hours. The solution cooled to room temperature was filtered and the obtained solid products were washed with ethyl acetate. The filtrate and the ethyl acetate solution after washing were combined and concentrated under reduced pressure, to which was added an ammonium chloride aqueous solution, followed by extraction with ethyl acetate. The extract was washed and dried, then active carbon (10 g) was added thereto, followed by filtration and concentration under reduced pressure. The residue was crystallized from methyl alcohol (100 ml) to give 1-[5-(4-fluorobenzyloxy)-2-hydroxyphenyl]etanone (30.3 g, yield: 77%).

Melting point: 88-89° C.

NMR (CDCl$_3$) δ: 2.60 (3H, s), 5.00 (2H, s), 6.90-7.45 (7H, m), 11.87 (1H, s).

(C-11) To a solution of the above-mentioned compound C-10 (470 mg, 1.81 mmol) in ethanol (14 ml), were added pyridine-2-aldehyde (202 mg, 1.90 mmol), and a 50% sodium hydroxide aqueous solution (0.490 ml) and the mixture was stirred at room temperature for 43 hours. The solution was neutralized with 2N hydrochloric acid, which was extracted with ethyl acetate. The extract was washed and dried, then the solvent was evaporated under reduced pressure. The residue was purified with silica gel column chromatography (ethyl acetate:n-hexane=1:4) and crystallized from methyl alcohol diisopropylether to give 1-[5-(4-fluorobenzyloxy)-2-hydroxyphenyl]-3-pyridine-2-yl propenone (157 mg, yield: 25%).

Melting point: 118° C.

NMR (CDCl$_3$) δ: 5.04 (2H, s), 6.96-7.89 (11H, m), 8.20 (1H, d, J=15.3 Hz), 8.70-8.75 (1H, m).

(C-12) To a suspension of the above-mentioned compound C-11 (155 mg, 0.44 mmol) in methyl alcohol (7.5 ml), were added 2N sodium hydroxide aqueous solution (0.89 ml) and 30% hydrogen peroxide solution (0.151 ml) and the mixture was stirred at room temperature for 30 minutes. The solution was neutralized with 2N hydrochloric acid, to which was added water and methyl alcohol. The precipitated crystals were filtered off. The crude crystals were washed with water, dried, and crystallized from methyl alcohol to give 6-[(4-fluorobenzyl)oxy]-3-hydroxy(2-pyridine-2-yl)-4H-1-benzopyrane-4-one (31 mg, yield: 19%).

Melting point: 204-205° C.

Elementary analysis as C$_{19}$H$_{18}$FNO$_4$

Calcd. (%): C, 69.42; H, 3.88; N, 3.86; F, 5.23.

Found (%): C, 69.39; H, 3.81; N, 3.86; F, 5.01.

NMR (CDCl$_3$) δ: 5.13 (2H, s), 7.05-7.54 (7H, m), 7.76 (1H, d, J=3.0 Hz), 8.00 (1H, dd, J=1.5, 8.1 Hz), 8.11-8.17 (1H, m), 8.62-8.63 (1H, m), 13.02 (1H, his).

Compound C-22

5-[(4-fluorobenzyl)oxy]-3-hydroxy(2-pyridine-2-yl)-4H-1-benzopyrane-4-one

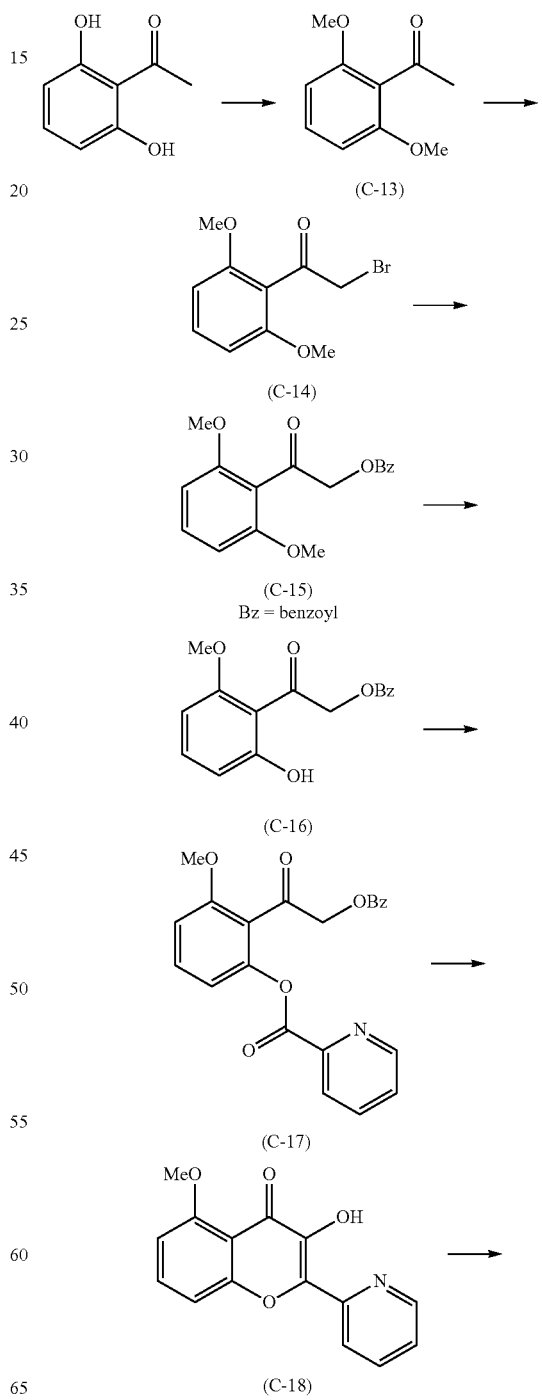

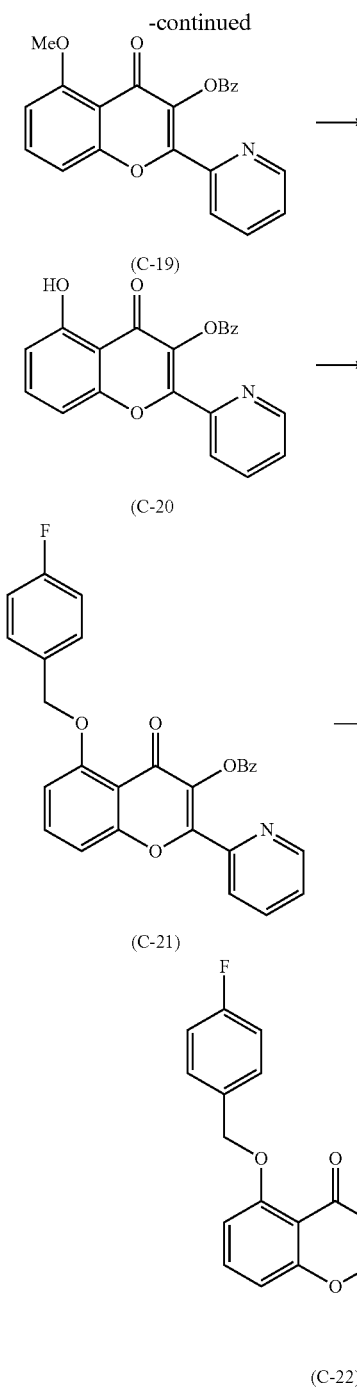

(C-13) To a suspension of 2',6'-dihydroxyacetophenone (5.0 g, 32.9 mmol) and powder potassium carbonate (10.0 g, 72.4 mmol) in dimethylformamide (30 ml), was added iodomethane (7.1 ml, 114 mmol) at room temperature and the mixture was stirred at the same temperature overnight. To the solution was added 2N hydrochloric acid (45 ml) and water (45 ml) and the precipitated crystals were filtered off. The crude crystals were washed with water and dried, then crystallized from ethyl acetate n-hexane to give 1-(2,6-dimethoxyphenyl)etanone (4.2 g, yield: 71%).

Melting point: 69° C.

NMR (CDCl$_3$) δ: 2.48 (3H, s), 3.81 (6H, s), 6.55 (2H, d, J=8.1 Hz), 7.26 (1H, t, J=8.1 Hz).

(C-14) To a solution of the above-mentioned compound C-13 (4.0 g, 22.2 mmol) in tetrahydrofuran (40 ml), was added phenyltrimethylammoniumtribromide (8.34 g, 22.2 mmol) over 10 minutes at room temperature and the mixture was stirred at the same temperature for 1 hour. Water was added thereto, and the mixture was extracted with ethyl acetate, washed, and dried, then the solvent was evaporated under reduced pressure. The residue was purified with silica gel column chromatography (ethyl acetate:n-hexane=1:4). After allowing to stand at room temperature, the obtained solid residue was washed with diisopropylether to give 2-bromo-1-(2,6-dimethoxyphenyl)etanone (4.22 g, yield: 70%).

Melting point: 78-82° C.

NMR (CDCl$_3$) δ: 3.82 (6H, s), 4.38 (2H, s), 6.57 (2H, d, J=8.4 Hz), 7.32 (1H, t, J=8.4 Hz).

(C-15) A suspension of benzoic acid (1.13 g, 9.3 mmol) and powder potassium carbonate (0.91 g, 6.56 mmol) in dimethylformamide (30 ml) was stirred at 90° C. for 1 hour and cooled to room temperature. The above-mentioned compound C-14 (2.0 g, 7.7 mmol) was added thereto and the mixture was stirred at 100° C. for 30 minutes. To the solution cooled to room temperature, was added water (120 ml), then the precipitated crystals were filtered off, washed with water, and dried to give benzoic acid 2-(2,6-dimethoxyphenyl)-2-oxoethyl ester (2.0 g, yield: 86%).

NMR (CDCl$_3$) δ: 3.82 (6H, s), 5.25 (2H, s), 6.58 (2H, d, J=8.4 Hz), 7.33 (1H, t, J=8.4 Hz), 7.41-7.61 (3H, m), 8.06-8.12 (2H, m).

(C-16) To a solution of the above-mentioned compound C-15 (1.5 g, 4.99 mmol) in methylene chloride (250 ml), was added dropwise a tribromoborane-methylene chloride solution (1.0N, 4.99 ml, 4.99 mmol) at −78° C. and the mixture was stirred at the same temperature for 15 minutes. To the solution was added water, which was extracted with ethyl acetate, washed, and dried. The solvent was evaporated under reduced pressure. After allowing to stand at room temperature, the obtained solid residue was washed with diisopropylether to give benzoic acid 2-(2-hydroxy-6-methoxyphenyl)-2-oxoethyl ester (1.14 g, yield: 80%).

NMR (CDCl$_3$) δ: 3.97 (3H, s), 5.51 (2H, s), 6.43 (1H, d, J=8.1 Hz), 6.61 (1H, dd, J=1.2, 8.4 Hz), 7.37-7.63 (4H, m), 8.13-8.19 (2H, m), 12.76 (1H, s).

(C-17) To a solution of the above-mentioned compound C-18 (1.14 g, 3.98 mmol) in dimethylformamide (15 ml), were added picolyl chloride hydrochloride (0.92 g, 5.18 mmol) and triethylamine (1.36 ml, 9.75 mmol) under ice-cooling and the mixture was stirred at room temperature for 30 minutes. Water was added thereto, and the mixture was extracted with ethyl acetate, washed, and dried, then the solvent was evaporated under reduced pressure. The residue was purified with silica gel column chromatography (ethyl acetate:n-hexane=1:2-1:1) to give pyridine-2-carboxylic acid 2-(2-benzoyloxyacetyl)-3-methoxyphenyl ester (1.17 g, yield: 75%).

NMR (CDCl$_3$) δ: 3.90 (3H, s), 5.34 (2H, s), 6.90 (1H, d, J=8.4 Hz), 6.99 (1H, d, J=7.5 Hz), 7.35-7.58 (5H, m), 7.88 (1H, dt, J=1.8, 7.8 Hz), 7.95-8.01 (2H, m), 8.26 (1H, d, J=7.8 Hz), 8.80-8.85 (1H, m).

(C-18) To a solution of the above-mentioned compound C-17 (805 mg, 2.06 mmol) in dimethylformamide (8 ml), was added 60% sodium hydride (205 mg, 5.15 mmol) under ice-cooling and the mixture was stirred at 55° C. for 15 minutes. After cooling, the solution was poured into 2N hydrochloric acid (2.6 ml) and ice water, then the mixture was extracted with ethyl acetate. The extract was washed and dried, then the solvent was evaporated under reduced pressure. The residue was dissolved into acetic acid (6 ml), to which was added sulfuric acid (0.16 ml) and the mixture was stirred at 60° C. for 2 hours. After cooling, the solution was poured into ice water, which was neutralized with a saturated sodium hydrogen carbonate aqueous solution. The mixture was extracted with ethyl acetate and chloroform, washed, and dried. The residue was purified with silica gel column chromatography (chloroform:methyl alcohol=20:1) to give 3-hydroxy-5-methoxy-2-pyridine-2-ylchromene-4-one (234 mg, yield: 42%).

NMR (CDCl$_3$) δ: 4.02 (3H, s), 6.77 (1H, d, J=8.1 Hz), 7.11 (1H, d, J=8.1 Hz), 7.40 (1H, ddd, J=1.2, 5.1, 7.5 Hz), 7.56 (1H, t, J=8.1 Hz), 7.97 (1H, dt, J=1.8, 8.1 Hz), 8.07-8.12 (1H, m), 8.61-8.66 (1H, m), 12.48 (1H, brs).

(C-19) To a suspension of the above-mentioned compound C-18 (234 mg, 0.87 mmol) and powder potassium carbonate (240 mg, 1.74 mmol) in dimethylformamide (7 ml), was added chlorobenzoyl (0.20 ml, 1.74 mmol) at room temperature and the mixture was stirred at 115° C. for 10 minutes. To the solution cooled to room temperature, was added water, and the mixture was extracted ethyl acetate. The extract was washed and dried, then the solvent was evaporated under reduced pressure. The residue was purified with silica gel column chromatography (chloroform:methyl alcohol=20:1) to give benzoic acid 5-methoxy-4-oxo-2-pyridine-2-yl-4H-chromene-3-yl ester (213 mg, yield: 66%).

NMR (CDCl$_3$) δ: 3.98 (3H, s), 6.84 (1H, d, J=7.8 Hz), 7.21 (1H, dd, J=0.9, 8.4 Hz), 7.33-7.67 (5H, m), 7.80 (1H, dt, J=1.8, 7.8 Hz), 7.91-7.96 (1H, m), 8.17-8.23 (1H, m), 8.69-8.73 (1H, m).

(C-20) To a solution of the above-mentioned compound C-19 (213 mg, 0.57 mmol) in methylene chloride (10 ml), was added dropwise a solution of boron tribromide in methylene chloride (1.0N, 0.685 ml, 0.685 mmol) at −78° C. and the mixture was stirred at the same temperature for 10 minutes. Water was added thereto and the mixture was extracted with ethyl acetate, washed, and dried. The solvent was evaporated under reduced pressure and the residue was purified with silica gel column chromatography (ethyl acetate:n-hexane=1:1) to give benzoic acid 5-hydroxy-4-oxo-2-pyridine-2-yl-4H-chromene-3-yl ester (66 mg, yield: 32%).

NMR (CDCl$_3$) δ: 6.87 (1H, d, J=8.4 Hz), 7.10 (1H, d, J=8.7 Hz), 7.35-7.70 (5H, m), 7.84 (1H, dt, J=1.8, 7.8 Hz), 7.98 (1H, d, J=8.1 Hz), 8.18-8.24 (1H, m), 8.61-8.66 (1H, m), 12.04 (1H, s).

(C-21) To a suspension of the above-mentioned compound C-20 (91 mg, 0.25 mmol) and powder potassium carbonate (53 mg, 0.38 mmol) in dimethylformamide (2 ml), was added 4-fluorobenzylbromide (40 μl, 0.32 mmol) at room temperature and the mixture was stirred for 3 hours. Water was added thereto and and the mixture was extracted with ethyl acetate, washed, and dried. The solvent was evaporated under reduced pressure and the residue was purified with silica gel column chromatography (ethyl acetate:n-hexane=1:1-1:2) to give benzoic acid 5-(4-fluorobenzyloxy)-4-oxo-2-pyridine-2-yl-4H-chromene-3-yl ester (108 mg).

(C-22) To a suspension of the above-mentioned compound C-21 (105 mg, 0.23 mmol) in ethanol (5 ml), was added 2N sodium hydroxide aqueous solution (0.124 ml) at 60° C. and the mixture was stirred for 25 minutes. After cooling, the reaction mixture was neutralized with 2N hydrochloric acid. The precipitated crystals were filtered off, washed with water and ethanol and dried. The crude crystals were crystallized from methyl alcohol to give 5-[(4-fluorobenzyl)oxy]-3-hydroxy(2-pyridine-2-yl)-4H-1-benzopyrane-4-one (30 mg, yield: 33%).

Melting point: 213° C.

Elementary analysis as $C_{21}H_{14}FNO_4 \cdot 0.1H_2O$

Calcd. (%): C, 69.08; H, 3.92; N, 3.84; F, 5.20.

Found (%): C, 68.98; H, 3.81; N, 3.85; F, 5.01.

NMR (CDCl$_3$) δ: 5.24 (1H, s), 6.82 (1H, d, J=8.1 Hz), 7.06-7.17 (3H, m), 7.38-7.44 (1H, m), 7.55 (1H, t, J=8.1 Hz), 7.70-7.78 (2H, m), 7.98 (1H, dt, J=1.8, 8.1 Hz), 8.10 (1H, d, J=8.1 Hz), 8.62-8.67 (1H, m), 12.79 (1H, brs).

Compound C-26

2-[5-(4-fluorobenzyl)-[1,3,4]-oxadiazole-2-yl]-3-hydroxy-4H-1-benzopyrane-4-one

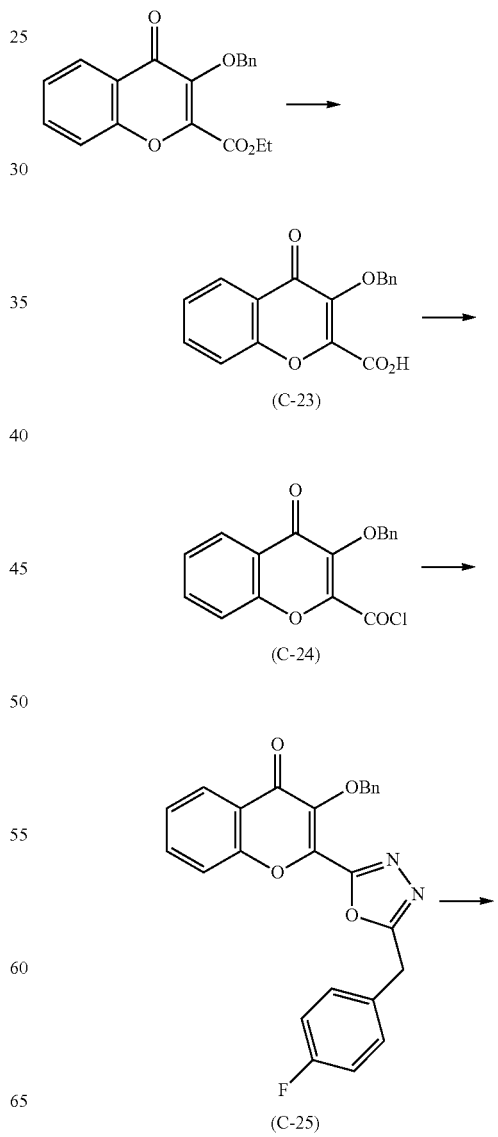

-continued

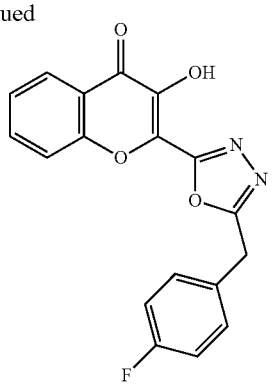

(C-26)

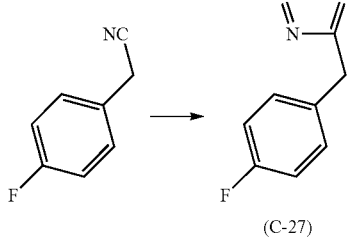

(C-27)

(C-23) To a solution of compound C-4 (1.73 g, 5.34 mmol) in methyl alcohol (16 ml), was added a 2N sodium hydroxide aqueous solution (3 ml) and the mixture was stirred at room temperature for 1 hour. The solution was neutralized with 2N hydrochloric acid, to which was added water, and the mixture was extracted with ethyl acetate. The extract was washed and dried, then the solvent was evaporated under reduced pressure to give crude 3-benzyloxybenzyloxy-4-oxo-4H-chromene-2-carboxylic acid (48 mg).

(C-24) To a solution of the above-mentioned compound C-23 (48 mg) in diglyme (1 ml), were added oxalylchloride (14 μl, 0.16 mmol) and dimethylformamide (2 μl) under ice-cooling. The mixture was cooled to room temperature with stirring for 30 minutes to give a crude 3-benzyloxy-4-oxo-4H-chromene-2-carboxylic acid chloride solution.

(C-25) To the above-mentioned solution of (C-24), were added a tetrazole (25 mg, 0.14 mmol) mentioned below and pyridine (47 μl, 0.58 mmol) and the mixture was stirred at room temperature for 30 minutes and at 130° C. for 15 minutes. After cooling, water was added thereto, then the precipitated crystals were filtered off, washed with water, and dried to give 3-benzyloxy-2-[5-(4-fluorobenzyl)-[1,3,4]-oxadiazole-2-yl]chromene-4-one (37 mg, yield: 62%).

NMR (CDCl₃) δ: 4.23 (2H, s), 5.36 (2H, s), 6.98-7.78 (12H, m), 8.25-8.30 (1H, m).

(C-26) To a solution of compound C-25 (34 mg, 0.079 mmol) in ethanol (2 ml) and tetrahydrofuran (4 ml), was added 10% palladium-carbon (8 mg) and the mixture was stirred under hydrogen atmosphere at room temperature for 10 minutes. After removing the palladium-carbon by filtration, the solution was evaporated under reduced pressure. The residue was crystallized from methyl alcohol to give 2-[5-(4-fluorobenzyl)-[1,3,4]-oxadiazole-2-yl]-3-hydroxy-4H-1-benzopyrane-4-one (19 mg, yield: 70%).

Melting point: 221° C.

Elementary analysis as $C_{18}H_{11}FN_2O_4$

Calcd. (%): C, 63.91; H, 3.28; N, 8.28; F, 5.62.

Found (%): C, 63.84; H, 3.23; N, 8.18; F, 5.48.

NMR (CDCl₃) δ: 4.36 (2H, s), 7.04-7.13 (2H, m), 7.34-7.60 (5H, m), 8.13 (1H, brs), 8.29 (1H, dd, J=1.2, 7.8 Hz).

(C-27) To a solution of 4-fluorobenzylcyanide (7.5 g, 55.5 mmol) in dimethylformamide (75 ml), were added ammonium chloride (5.9 g, 111.0 mmol) and sodium azide (7.2 g, 111.0 mmol) at room temperature and the mixture was stirred at 130° C. for 3 hours. The mixture was cooled to room temperature and water was added thereto, followed by extraction with ethyl acetate. The extract was washed and dried, and then the solvent was evaporated under reduced pressure. The residue was washed with diisopropylether/n-hexane and dried to give 5-(4-fluorobenzyl)-2H-tetrazole (5.45 g, yield: 55%).

Melting point: 158-159° C.

NMR (CDCl₃) δ: 4.29 (2H, s), 7.13-7.36 (4H, m).

Compound C-31a and C-31b

6-[(4-fluorobenzyl)oxy]-3-hydroxy-2-(1H-[1,2,4]triazole-3-yl)-4H-1-benzopyrane-4-one and 6-[(4-fluorobenzyl)oxy]-3-hydroxy-2-(1-methyl-1H-imidazole-2-yl)-4H-1-benzopyrane-4-one

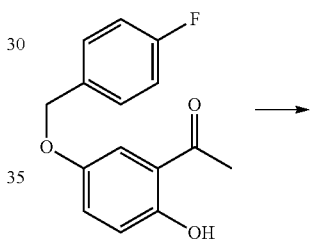

(C-28)

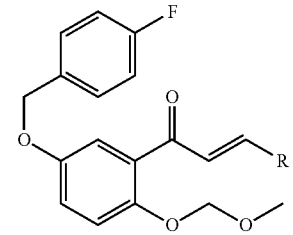

(C-29a)) R =

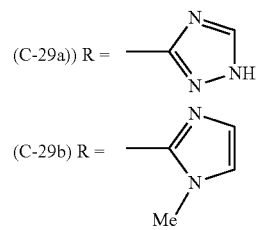

(C-29b) R =

-continued

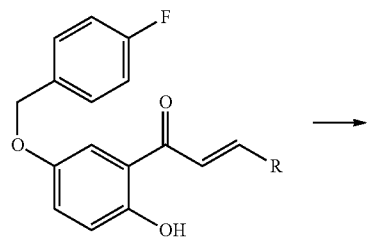

(C-30a) R =

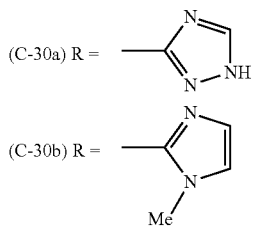

(C-30b) R =

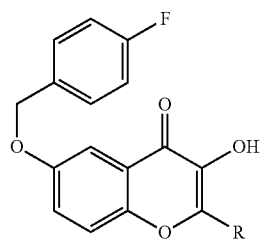

(C-31a) R =

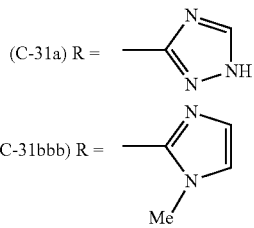

(C-31bbb) R =

(C-28) To a suspension of 60% sodium hydride (0.45 g, 11.3 mmol) in dimethylformamide (25 ml), was added dropwise a solution of C-10 (2.64 g, 10.2 mmol) in dimethylformamide (25 ml) under ice-cooling and the mixture was stirred at the same temperature for 20 minutes. Chloromethyl methyl ether (0.93 ml, 12.3 mmol) was added dropwise thereto and the mixture was stirred for 5 minutes, and further 25 minutes while warming to room temperature. Water was added thereto and the mixture was extracted with ethyl acetate, washed, and dried. The solvent was evaporated under reduced pressure and the residue was purified with silica gel column chromatography (ethyl acetate:n-hexane=1:5-1:3) to give 1-[5-(4-fluorobenzyloxy)-2-methoxymethoxyphenyl]etanone (2.93 g, yield: 95%).

NMR (CDCl$_3$) δ: 2.65 (3H, s), 3.51 (3H, s), 5.01 (2H, s), 5.22 (2H, s), 7.03-7.16 (4H, m), 7.33-7.42 (3H, m).

(C-29a) To a solution of the above-mentioned compound C-28 (304 mg, 1.0 mmol) and 1H-[1,2,4]triazole-2-aldehyde (145 mg, 1.5 mmol) in dioxane (4 ml) and 99% ethanol (6 ml), was added a 1N sodium hydroxide aqueous solution (2 ml) and the mixture was refluxed for 3 hours 20 minutes. An ammonium chloride aqueous solution was added thereto and the mixture was extracted with ethyl acetate, washed, and dried. The solvent was evaporated under reduced pressure and the residue was purified with silica gel column chromatography(methyl alcohol:chloroform=3:97). Crystallization from ethyl acetate and diisopropylether gave 1-[5-(4-fluorobenzyloxy)-2-methoxymethoxyphenyl]-3-(1H-[1,2,4]triazole-3-yl)propenone (260 mg, yield: 68%).

Melting point: 114-116° C.

NMR (CDCl$_3$) δ: 3.47 (3H, s), 5.01 (2H, s), 5.19 (2H, s), 7.02-7.27 (5H, m), 7.37-7.43 (2H, m), 7.61 (1H, d, J=15.6 Hz), 7.88 (1H, d, J=15.6 Hz), 8.32 (1H, br.s).

(C-29b) Using the above-mentioned compound C-28 (304 mg, 1.0 mmol) and 1-methyl-2-imidazole-2-aldehyde (166 mg, 1.5 mmol), according to the method of C-29a, crude 1-[5-(4-fluorobenzyloxy)-2-methoxymethoxyphenyl]-3-(1-methyl-1H-imidazole-2-yl)propenone (434 mg) was obtained, which was used in the next reaction without purification.

(C-30a) To a solution of the above-mentioned compound C-29a (202 mg, 0.527 mmol) in methyl alcohol (6 ml), was added 2N hydrochloric acid (1.5 ml) and the mixture was stirred at 50° C. for 3 hours 20 minute. A sodium hydrogen carbonate aqueous solution was added thereto and the mixture was extracted with ethyl acetate, washed and dried. The solvent was evaporated under reduced pressure to give crude crystals of 1-[5-(4-fluorobenzyloxy)-2-hydroxyphenyl]-3-(1H-[1,2,4]triazole-3-yl)propenone (183 mg).

(C-30b) Using the above-mentioned compound C-29b (434 mg), according to the method of C-30a, crude crystals of 1-[5-(4-fluorobenzyloxy)-2-hydroxyphenyl]-3-(1-methyl-1H-imidazole-2-yl)propenone (355 mg) was obtained, which was used in the next reaction without purification.

(C-31a) To a suspension of the above-mentioned compound C-30a (180 mg, 0.53 mmol) in methyl alcohol (8 ml), were added a 2N sodium hydroxide aqueous solution (1.06 ml) and 30% hydrogen peroxide solution (0.18 ml) and the mixture were stirred at room temperature for 1 hour. A 2N hydrochloric acid (1.06 ml) was added thereto and the mixture was stirred for 2 hours 20 minutes. The precipitated crystals were filtered off and washed with water to give crude crystals (121 mg). Recrystallization from dimethylformamide/water gave 6-[(4-fluorobenzyl)oxy]-3-hydroxy-2-(1H-[1,2,4]triazole-3-yl)-4H-1-benzopyrane-4-one (110 mg yield: 59%).

Melting point: 277° C. (comp.)

Elementary analysis as C$_{18}$H$_{12}$FN$_3$O$_4$0.4H$_2$O

Calcd. (%): C, 59.97; H, 3.58; N, 11.66; F, 5.27.

Found (%): C, 59.91; H, 3.63; N, 11.60; F, 5.13.

NMR (DMSO-d$_6$) δ: 5.23 (2H, s), 7.22-7.28 (2H, m), 7.48-7.59 (5H, m), 7.69 (1H, d, J=9.3 Hz), 8.79 (1H, br.s).

(C-31b) Using the above-mentioned compound C-30b (355 mg), according to C-31a, 6-[(4-fluorobenzyl)oxy]-3-hydroxy-2-(1-methyl-1H-imidazole-2-yl)-4H-1-benzopyrane-4-one (169 mg, total yield of 3 processes: 47%).

Melting point: 239-242° C. (methylene chloride/methyl alcohol).

Elementary analysis as C$_{20}$H$_{15}$FN$_2$O4

Calcd. (%): C, 65.57; H, 4.13; N, 7.65; F, 5.19.

Found (%): C, 65.64; H, 4.08; N, 7.65; F, 5.09.

NMR (CDCl$_3$) δ: 4.16 (3H, s), 5.11 (2H, s), 7.04 (1H, d, J=0.9 Hz), 7.06-7.12 (2H, m), 7.21 (1H, d, J=0.9 Hz), 7.31 (1H, dd, J=3.0, 9.3 Hz), 7.39-7.46 (3H, m), 7.75 (1H, d, J=3.0 Hz).

Compound C-35 and C-36

6-[(4-fluorobenzyl)oxy]-3-hydroxy-4H-1-benzopyrane-4-one-2-carboxylate ethyl ester and 6-[(4-fluorobenzyl)oxy]-3-hydroxy-4H-1-benzopyrane-4-one-2-carboxylic acid

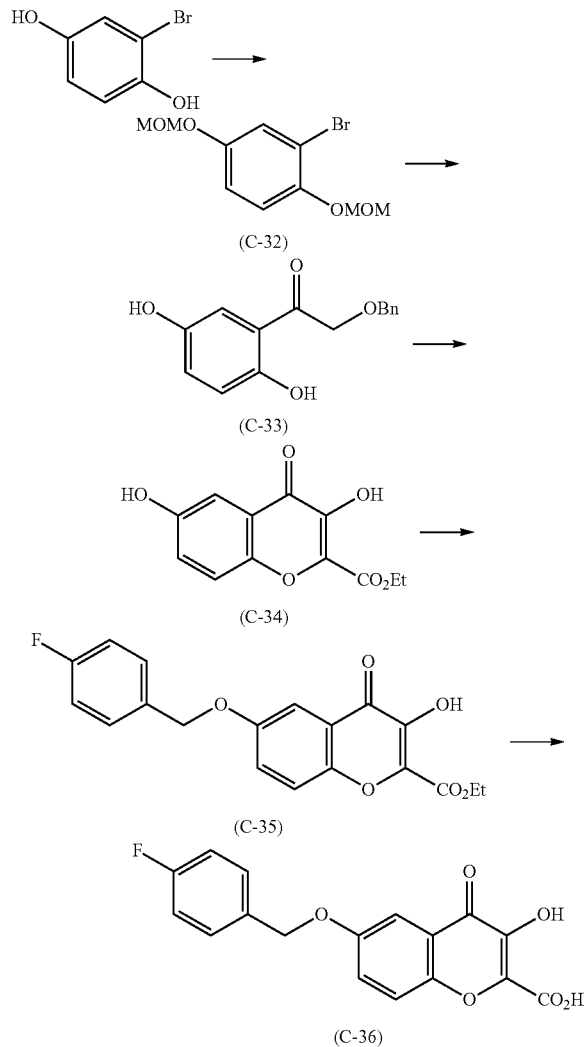

(C-32) To a solution of bromo hydroquinon (10.0 g, 52.9 mmol) in DMF (50 ml), was added 60% sodium hydride (4.44 g, 111.1 mmol) under ice-cooling and the mixture was stirred at room temperature for 30 minutes. Chloromethyl methyl ether (8.44 ml, 111.1 mmol) was added dropwise thereto under ice-cooling and the mixture was stirred at room temperature for 30 minutes. Water and 2N hydrochloric acid were added thereto and the mixture was extracted with ethyl acetate. The extract was washed with water and saturated brine, washed, and dried. The solvent was evaporated under reduced pressure and the residue was purified with column chromatography (ethyl acetate:n-hexane=1:19-1:9) to give 2-bromo-1,4-bismethoxymethylbenzene (11.4 g, yield: 83%).

NMR (CDCl$_3$) δ: 3.47 (3H, s), 3.52 (3H, s), 5.10 (2H, s), 5.17 (2H, s), 6.93 (1H, dd, J=2.7, 9.0 Hz), 7.07 (1H, d, J=9.0 Hz), 7.27 (1H, d, J=2.7 Hz).

(C-33) To a solution of the above-mentioned compound C-32 (2.0 g, 7.22 mmol) in tetrahydrofuran (40 ml), was added dropwise a n-butyl lithium-hexane solution (1.55N, 4.7 ml, 7.22 mmol) at −78° C. and the mixture was stirred at the same temperature for 15 minutes. A zincchloride-tetrahydrofuran solution (1.3N, 5.6 ml, 7.22 mmol) was added dropwise and the mixture was stirred for 30 minutes. To the solution were added chloro(benzyloxy)acetyl (1.25 ml, 7.94 mmol) and tetrakistriphenylphosphine palladium (0.83 g, 0.72 mmol) and the mixture was stirred for 1.5 hours under cooling to room temperature. Water and 2N hydrochloric acid were added thereto and the mixture was extracted with ethyl acetate, water and a sodium hydrogen carbonate aqueous solution, After washing with saturated brine, the mixture was dried and evaporated under reduced pressure. The residue was purified with column chromatography (ethyl acetate:n-hexane=1:9-1:3) to give a crude ketone (845 mg), which was dissolved into methyl alcohol 10 ml and 2N hydrochloric acid 3.0 ml was added thereto. The mixture was stirred at 60° C. for 2 hours 30 minutes. After allowing to stand for cooling, water was added thereto, then the precipitated crystals were filtered off, washed with water, and dried to give 2-benzyloxy-(2,5-dihydroxyphenyl)etanone (376 mg, yield: 20%).

NMR (CDCl$_3$) δ: 4.69 (2H, s), 4.71 (2H, s), 6.88-7.42 (8H, m), 11.5 (1H, s).

(C-34) To a solution of the above-mentioned compound C-33 (370 mg, 1.43 mmol) in pyridine (6 ml), was added ethyl chloroglyoxylacetate (0.57 ml, 5.10 mmol) under ice-cooling and the mixture was stirred for 1 hour under cooling to room temperature and further stirred for 1 hour 30 minutes at 100° C. After cooling, water and 2N hydrochloric acid were added thereto and the mixture was extracted with ethyl acetate. The extract was washed with water, a sodium hydrogen carbonateaqueous solution, and saturated brine, and dried. The solvent was evaporated under reduced pressure and the residue was purified with column chromatography (ethyl acetate:n-hexane=1:2) to give 3,6-dihydroxy-4H-1-benzopyrane-4-one-2-carboxylate ethyl ester (109 mg, yield: 22%).

NMR (CDCl$_3$) δ: 1.36 (3H, t, J=6.9 Hz), 4.40 (2H, q, J=6.9 Hz), 5.25 (2H, s), 7.18 (1H, brs), 7.30-7.76 (7H, m), 7.83 (1H, d, J=3.0 Hz).

(C-35) To a solution of the above-mentioned compound C-34 (120 mg, 0.35 mmol) in methyl alcohol (6 ml) and tetrahydrofuran (2 ml), was added 10% palladium-carbon (15 mg) under 1 atm hydrogen atmosphere. The mixture was stirred at room temperature for 1 hour and filtered, then the solvent was evaporated under reduced pressure to give a residue (93 mg). The residue (33 mg) was dissolved in DMF 1 ml, and 60% sodium hydride (12 mg, 0.30 mmol) was added thereto under ice-cooling. The mixture was stirred at room temperature for 30 minutes and at 50° C. for 30 minutes, then 4-fluorobenzylbromide (12 μl, 96.3 μmol) was added dropwise under ice-cooling.

The mixture was stirred at room temperature for 1 hour 30 minutes, then water and 2N hydrochloric acid were added thereto. The precipitated crystals were filtered off, washed with water, and dried. The crude crystals were recrystallized from chloroform/methyl alcohol to give 6-[(4-fluorobenzyl)oxy]-3-hydroxy-4H-1-benzopyrane-4-one-2-carboxylate ethyl ester (33 mg, yield: 70%).

NMR (CDCl$_3$) δ: 1.49 (3H, t, J=7.2 Hz), 4.54 (2H, q, J=7.2 Hz), 5.11 (2H, s), 7.06-7.13 (2H, m), 7.37-7.53 (4H, m), 7.66 (1H, d, J=3.0 Hz), 9.43 (1H, s).

Melting point: 190-192° C.

Elementary analysis as $C_{19}H_{15}FO_6 \cdot 0.1H_2O$

Calcd. (%): C, 63.37; H, 4.25; F, 5.28.
Found (%): C, 63.31; H, 4.18; F, 5.43.

(C-36) To a solution of the above-mentioned compound C-35 (31 mg, 86.5 μmol) in DMSO (1.5 ml), was added a 2N sodium hydroxide aqueous solution 108 μl and the mixture was stirred at room temperature for 1 hour. 2N hydrochloric acid and water were added thereto and the precipitated crystals were filtered off, washed with water, and dried. The crude crystals were recrystallized from diisopropylether and methyl alcohol to give 6-[(4-fluorobenzyl)oxy]-3-hydroxy-4H-1-benzopyrane-4-one-2-carboxylic acid (18 mg, yield: 62%).

NMR (DMSO-$d_6$) δ:5.21 (2H, s), 7.21-7.67 (7H, m).
Melting point: 219-220° C.
Elementary analysis as $C_{19}H_{15}FO_6$ 1.3$H_2O$
Calcd. (%): C, 57.73; H, 3.88; F, 5.37.
Found (%): C, 57.75; H, 3.90; F, 5.11.

Compound C-39

5-[(4-fluorobenzyl)oxy]-3-hydroxy-2-(2-methyl-2H-[1,2,4]triazole-3-yl)-4H-1-benzopyrane-4-one

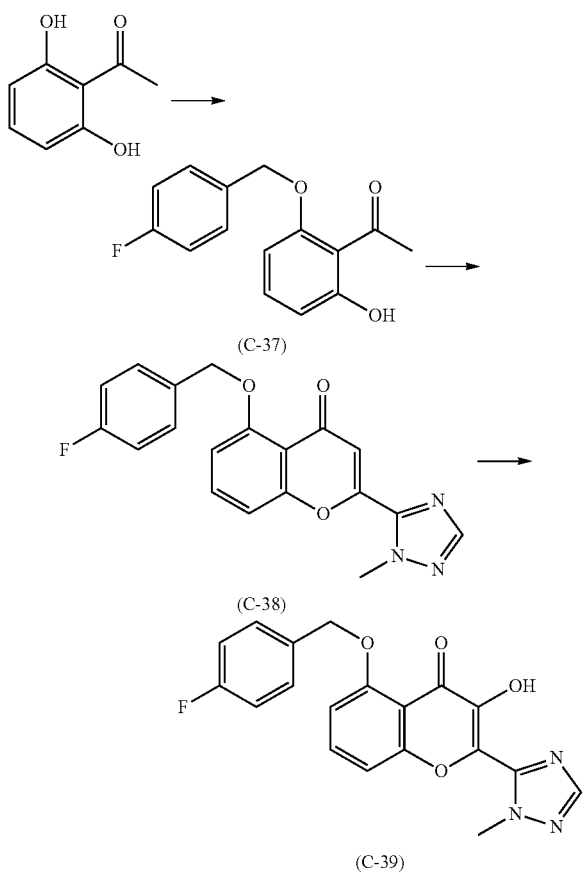

(C-37) To a suspension of 2',6'-dihydroxyacetophenone (5.0 g, 32.9 mmol) and powder potassium carbonate (9.1 g, 65.7 mmol) in DMF (30 ml), was added 4-fluorobenzyl bromide (4.1 ml, 32.9 mmol) under ice-cooling and the mixture was stirred at room temperature for 4 hour. Water 30 ml and 2N hydrochloric acid 60 ml were added thereto and the precipitated crystals were filtered off, washed with water, methyl alcohol, and diisopropylether, and dried to give 1-[2-(4-fluorobenzyloxy)-6-hydroxyphenyl]etanone (5.52 g, yield: 65%).

NMR (CDCl$_3$) δ: 2.59 (3H, s), 5.09 (2H, s), 6.45 (1H, d, J=8.4 Hz), 6.60 (1H, d, J=8.4 Hz), 7.07-7.45 (5H, m), 13.24 (1H, s).

(C-38) To a solution of the above-mentioned compound C-37 (1.0 g, 3.84 mmol) and 2-methyl 2H-[1,2,4]triazole-3-carboxylate ethyl ester (J. Am. Chem. Soc., 1972, 94, p 5894, Heterocycles, 1990, 31, p 1629) (1.2 g, 7.68 mmol) in DMF (20 ml), was added potassium tert-butoxide (1.72 mg, 15.4 mmol) under ice-cooling and the mixture was stirred at room temperature for 20 minutes. After ice-cooling the mixture, 2N hydrochloric acid 7.5 ml and water 33 ml were added thereto and the precipitated crystals were filtered off, washed with water, and dried. The obtained crystals were suspended to a mixture of tetrahydrofuran (15 ml) and methyl alcohol (6 ml), then a solution of concentrated hydrochloric acid 1.3 ml in methyl alcohol (15 ml) was added thereto at room temperature and the mixture was stirred at 60° C. for 40 minutes. After allowing to stand the mixture for cooling, 2N sodium hydroxide 7.7 ml and water 125 ml were added thereto, then the precipitated crystals were filtered off, washed with water, and dried to give 5-[(4-fluorobenzyl)oxy]-2-(2-methyl-2H-[1,2,4]triazole-3-yl)-4H-1-benzopyrane-4-one (1.16 g, yield: 86%).

NMR (CDCl$_3$) δ: 4.29 (3H, s), 5.25 (2H, s), 6.92 (1H, d, J=8.1 Hz), 7.04 (1H, s), 7.07-7.14 (2H, m), 7.56-7.65 (5H, m), 7.99 (1H, s).

According to the method mentioned above, the following compounds were prepared.

(C-38a) 5-[(4-fluorobenzyl)oxy]-2-(1-methyl-1H-[1,2,4]triazole-3-yl)-4H-1-benzopyrane-4-one NMR (DMSO-$d_6$) δ: 4.00 (3H, s), 5.25 (2H, s), 6.75 (1H, s), 7.12 (1H, d, J=8.1 Hz), 7.21-7.29 (3H, m), 7.65-7.76 (3H, m), 8.72 (1H, s).

(C-38b) 5-[(4-fluorobenzyl)oxy]-2-(5-methyl-1H-[1,2,4]triazole-3-yl)-4H-1-benzopyrane-4-one NMR (DMSO-$d_6$) δ: 2.45 (3H, s), 5.25 (2H, s), 6.72 (1H, s), 7.11 (1H, d, J=8.1 Hz), 7.21-7.29 (3H, m), 7.65-7.76 (3H, m).

(C-38c) 5-[(4-fluorobenzyl)oxy]-2-(1H-[1,2,4]triazole-3-yl)-4H-1-benzopyrane-4-one NMR (DMSO-$d_6$) δ: 5.26 (2H, s), 6.79 (1H, s), 7.12 (1H, d, J=8.4 Hz), 7.21-7.29 (3H, m), 7.66-7.77 (3H, m), 8.78 (1H, s).

(C-38d) 5-[(4-fluorobenzyl)oxy]-2-(pyrimidine-2-yl)-4H-1-benzopyrane-4-one

NMR (CDCl$_3$) δ: 5.25 (2H, s), 6.89 (1H, s), 7.12 (1H, d, J=8.4 Hz), 7.07-7.14 (2H, m), 7.31-7.43 (3H, m), 7.51 (1H, s), 7.56-7.66 (3H, m), 8.95 (2H, d, J=4.8 Hz).

(C-39) To a solution of the above-mentioned compound C-38 (500 mg, 1.42 mmol) in methylene chloride (25 ml), was added, under ice-cooling, an acetone solution containing dimethyldioxylane (0.076N, 18.7 ml, 1.42 mmol) prepared by the method mentioned in Chem. Ber., 1991, 124, p 2377) and the mixture was stirred at room temperature for 28 hours. The solvent was evaporated under reduced pressure and the residue was dissolved in methylene chloride 25 ml, and p-toluenesulfonic acid 1 hydrate (325 mg, 1.87 mmol) was added thereto under ice-cooling and the mixture was stirred at room temperature for 1 hour. The solvent was evaporated under reduced pressure and the residue was suspended in methyl alcohol 25 ml, to which were added 2N sodium hydroxide 0.8 ml, saturated sodium hydrogen carbonate aqueous solution 4.0 ml, and water 20 ml under ice-cooling. The precipitated crystals were filtered off, washed with water, and dried to give 5-[(4-fluorobenzyl)oxy]-3-hydroxy-2-(2-methyl-2H-[1,2,4]triazole-3-yl)-4H-1-benzopyrane-4-one (280 mg, yield: 54%).

NMR (CDCl$_3$) δ: 3.97 (3H, s), 5.29 (2H, s), 7.10 (1H, d, J=8.1 Hz), 7.20-7.30 (3H, m), 7.70-7.77 (5H, m), 8.21 (1H, s), 10.12 (1H, brs).

Melting point: 215-216° C.

The following compounds were prepared according to the method mentioned above.

(C-39a) 5-[(4-fluorobenzyl)oxy]-3-hydroxy-2-(1-methyl-1H-[1,2,4]triazole-3-yl)-4H-1-benzopyrane-4-one NMR (DMSO-d$_6$) δ: 4.01 (3H, s), 5.27 (2H, s), 7.06 (1H, d, J=8.1 Hz), 7.17-7.30 (3H, m), 7.66-7.77 (3H, m), 8.78 (1H, s), 9.56 (1H, brs).

Melting point: 264-266° C.

(C-39b) 5-[(4-fluorobenzyl)oxy]-3-hydroxy-2-(5-methyl-1H-[1,2,4]triazole-3-yl)-4H-1-benzopyrane-4-one NMR (DMSO-d$_6$) δ: 2.47 (3H, s), 5.27 (2H, s), 7.05 (1H, d, J=8.4 Hz), 7.17-7.30 (3H, m), 7.66-7.77 (3H, m).

Melting point: 289-292° C.

(C-39c) 5-[(4-fluorobenzyl)oxy]-3-hydroxy-2-(1H-[1,2,4]triazole-3-yl)-4H-1-benzopyran-4-one NMR (DMSO-d$_6$) δ: 5.28 (2H, s), 7.07 (1H, d, J=7.8 Hz), 7.20-7.30 (3H, m), 7.68-7.78 (3H, m), 8.66 (1H, brs).

Melting point: 254-256° C.

(C-39d) 5-[(4-fluorobenzyl)oxy]-3-hydroxy-2-(pyrimidine-2-yl)-4H-1-benzopyrane-4-one NMR (CDCl$_3$) δ: 5.28 (2H, s), 7.05 (1H, d, J=8.1 Hz), 7.22-7.31 (3H, m), 7.65-7.80 (4H, m), 9.10 (2H, d, J=5.7 Hz), 11.96 (1H, brs).

Melting point: 252-254° C.

Compound C-41

3-hydroxy-2-(5-phenoxypyrimidine-2-yl)-4H-1-benzopyrane-4-one

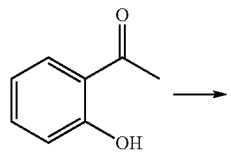

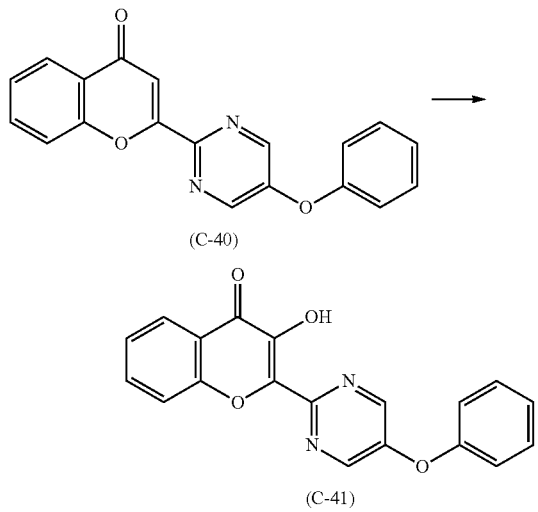

(C-40) According to the method of compound C-38, 2'-hydroxyacetophenone (150 mg, 1.10 mmol) and 5-phenoxypyrimidine-2-carboxylic acid (380 mg, 1.65 mmol) were subjected to cyclization reaction to give 2-(5-phenoxypyrimidine-2-yl)-4H-1-benzopyrane-4-one (296 mg, yield: 85%).

NMR (CDCl$_3$) δ: 7.12-7.75 (9H, m), 8.24-8.28 (1H, m), 8.63 (2H, s).

(C-41) According to the method of compound C-39, the above-mentioned compound C-40 (150 mg, 0.42 mmol) was oxidized with dimethyldioxylane to give 3-hydroxy-2-(5-phenoxypyrimidine-2-yl)-4H-1-benzopyrane-4-one (32 mg, yield: 20%).

NMR (CDCl$_3$) δ: 7.14-7.72 (8H, m), 8.31-8.35 (1H, m), 8.68 (2H, s), 11.63 (1H, s).

Melting point: 212° C.

Compound C-48

5-[(4-fluorobenzyl)oxy]-3-hydroxy-2-(2-methyl-2H-[1,2,4]triazole-3-yl)-4H-1-benzopyrane-4-one-7-carboxylic acid dimethylamide

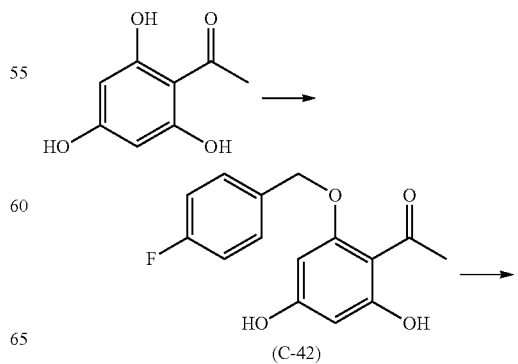

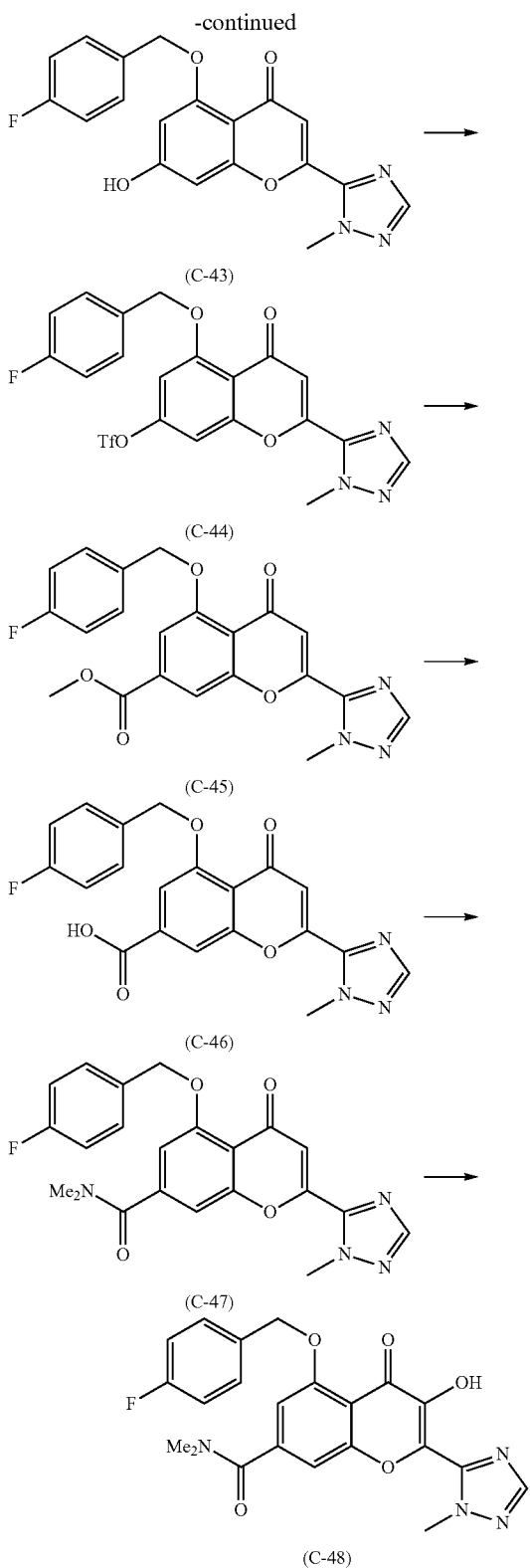

(C-43)

(C-44)

(C-45)

(C-46)

(C-47)

(C-48)

(C-42) To a suspension of 2',4',6'-trihydroxyacetophenone (18.6 g, 100 mmol) and powder potassium carbonate (20.7 g, 150 mmol) in DMF (140 ml), was added 4-fluorobenzyl bromide (13.7 ml, 110 mmol) under ice-cooling and the mixture was stirred at room temperature for 1 hour 15 minutes. Water and 2N hydrochloric acid were added thereto and the mixture was extracted with ethyl acetate. The extract was washed with water and saturated brine, and dried, then the solvent was evaporated under reduced pressure.

The residue was purified with column chromatography (ethyl acetate:n-hexane=1:3-1:2) to give crude crystals, which were washed with diisopropylether to give 1-[2-(4-fluorobenzyloxy)-4,6-dihydroxyphenyl]etanone (2.62 g, yield: 10%).

NMR (CDCl$_3$) δ: 2.45 (3H, s), 5.13 (2H, s), 5.88 (1H, d, J=1.5 Hz), 6.07 (1H, d, J=1.5 Hz), 7.21-7.28 (2H, m), 7.54-7.61 (2H, m), 10.59 (1H, brs), 13.81 (1H, s).

(C-43) According to the method of compound C-38, the above-mentioned compound C-42 (2.05 g, 7.42 mmol) and 2-methyl-2H-[1,2,4]triazole-3-carboxylate ethyl ester (2.30 g, 14.8 mmol) were subjected to cyclization reaction to give 5-[(4-fluorobenzyl)oxy]-7-hydroxy-2-(2-methyl-2H-[1,2,4]triazole-3-yl)-4H-1-benzopyrane-4-one (0.90 g, yield: 33%).

NMR (DMSO-d$_6$) δ: 4.21 (3H, s), 5.19 (2H, s), 6.52-6.67 (3H, m), 7.21-7.29 (2H, m), 7.63-7.70 (2H, m), 8.14 (1H, s), 11.1 (1H, brs).

(C-44) To a suspension of the above-mentioned compound C-43 (0.90 g, 2.45 mmol) and triethylamine (1.02 ml, 7.35 mmol) in methylene chloride (140 ml), was added anhydrous trifluoromethanesulfonic acid (0.62 ml, 3.68 mmol) under ice-cooling and the mixture was stirred for 40 minutes. Ice water was added thereto and the mixture was extracted with ethyl acetate. The extract was washed with water and saturated brine, and dried, then the solvent was evaporated under reduced pressure. The residue was purified with column chromatography (ethyl acetate:n-hexane=1:1-2:1) to give trifluoromethanesulfonic acid 5-[(4-fluorobenzyl)oxy]-2-(2-methyl-2H-[1,2,4]triazole-3-yl)-4H-1-benzopyrane-4-one-7-yl ester (1.13 g, yield: 93%).

NMR (CDCl$_3$) δ: 4.28 (3H, s), 5.26 (2H, s), 6.81 (1H, d, J=2.4 Hz), 7.05-7.16 (4H, m), 7.56-7.62 (2H, m), 8.01 (1H, s).

(C-45) To a suspension of the above-mentioned compound C-44 (1.06 g, 2.12 mmol), acetic acid palladium (II) (48 mg, 0.21 mmol) and 1,3-bis(diphenylphosphino)propane (109 mg, 0.27 mmol) in DMSO (30 ml), were added at room temperature triethylamine (3.0 ml, 15.1 mmol), and methyl alcohol (10 ml) successively, and the mixture was stirred under added 1 atm CO atmosphere at 70° C. for 55 minutes. After cooling, 2N hydrochloric acid 10 ml and water 70 ml were added thereto, and the precipitated crystals were filtered off, washed with water, and dried. The crude crystals were recrystallized from ethyl acetate/methyl alcohol to give 5-[(4-fluorobenzyl)oxy]-2-(2-methyl-2H-[1,2,4]triazole-3-yl)-4H-1-benzopyrane-4-one-7-carboxylate methyl ester (486 mg, yield: 56%).

NMR (CDCl$_3$) δ: 4.00 (3H, s), 4.32 (3H, s), 5.30 (2H, s), 7.08-7.15 (2H, m), 7.10 (1H, s), 7.56 (1H, d, J=1.5 Hz), 7.61-7.67 (2H, m), 7.77 (1H, d, J=1.5 Hz), 8.00 (1H, s).

(C-46) To a solution of the above-mentioned compound C-45 (325 mg, 0.79 mmol) in DMSO (16 ml), was added 2N sodium hydroxide aqueous solution 437 μl and the mixture was stirred at room temperature for 2 hours. To the solution were added 2N hydrochloric acid and water, then the precipitated crystals were filtered, washed with water, and dried to give 5-[(4-fluorobenzyl)oxy]-2-(2-methyl-2H-[1,2,4]triazole-3-yl)-4H-1-benzopyrane-4-one-7-carboxylic acid (300 mg, yield: 86%).

NMR (DMSO-d$_6$) δ: 4.29 (3H, s), 5.35 (2H, s), 6.86 (1H, d, J=1.2 Hz), 7.23-7.31 (2H, m), 7.57 (1H, s), 7.68-7.77 (2H, m), 7.83 (1H, s), 8.18 (1H, d, J=1.2 Hz).

(C-47) To a solution of the above-mentioned compound C-46 (140 mg, 0.35 mmol) in DMF (7 ml), were added at room temperature 1-ethyl-3-(3-dimethylaminopropyl)carbodiimide hydrochloride (75 mg, 0.40 mmol) and 1-hydroxybenzotriazole (55 mg, 0.35 mmol) and the mixture was stirred for 10 minutes. A 2N dimethylamine THF solution (195 μl, 0.40 mmol) was added thereto, and the mixture was stirred for 40 minutes. To the solution were added 2N hydrochloric acid and ice water, and the mixture was extracted with ethyl acetate. The extract was washed with water and saturated brine and dried, then the solvent was evaporated under reduced pressure. The residue was purified with column chromatography (chloroform:methyl alcohol=50:1-20:1) to give 5-[(4-fluorobenzyl)oxy]-2-(2-methyl-2H-[1,2,4]triazole-3-yl)-4H-1-benzopyrane-4-one-7-carboxylic acid dimethylamide (104 mg, yield: 90%).

NMR (CDCl$_3$) δ: 2.93 (3H, s), 3.14 (3H, s), 4.28 (3H, s), 5.27 (2H, s), 6.91 (1H, d, J=1.5 Hz), 7.06 (1H, s), 7.07-7.14 (2H, m), 7.15 (1H, d, J=1.5 Hz), 7.57-7.63 (2H, m), 8.00 (1H, s).

(C-48) According to the method of compound C-39, the above-mentioned compound C-47 (103 mg, 0.24 mmol) was oxidized with dimethyldioxylane to give 5-[(4-fluorobenzyl)oxy]-3-hydroxy-2-(2-methyl-2H-[1,2,4]triazole-3-yl)-4H-1-benzopyrane-4-one-7-carboxylic acid dimethylamide (15 mg, yield: 14%).

NMR (DMSO-d$_6$) δ: 2.90 (3H, s), 3.02 (3H, s), 4.00 (3H, s), 5.33 (2H, s), 7.05 (1H, s), 7.23-7.31 (3H, m), 7.70-7.76 (2H, m), 8.21 (1H, s), 10.22 (1H, brs).

Melting point: 227-229° C.

The following compounds were prepared according to the method above.

(C-48a) 5-[(4-fluorobenzyl)oxy]-3-hydroxy-2-(2-methyl-2H-[1,2,4]triazole-3-yl)-4H-1-benzopyrane-4-one-7-carboxylate methyl ester NMR (DMSO-d$_6$) δ: 3.94 (3H, s), 4.02 (3H, s), 5.39 (2H, s), 7.24-7.32 (2H, m), 7.51 (1H, s), 7.72-7.82 (3H, m), 8.24 (1H, s), 10.36 (1H, brs).

Melting point: 253-255° C.

(C-48b) 5-[(4-fluorobenzyl)oxy]-3-hydroxy-2-(2-methyl-2H-[1,2,4]triazole-3-yl)-4H-1-benzopyrane-4-one-7-carboxylic acid NMR (DMSO-d$_6$) δ: 4.01 (3H, s), 5.38 (2H, s), 7.24-7.32 (2H, m), 7.51 (1H, s), 7.69 (1H, s), 7.74-7.82 (2H, m), 8.23 (1H, s), 10.34 (1H, brs).

Melting point: 280-282° C.

Compound C-53

5-[(4-fluorobenzyl)oxy]-3-hydroxy-2-(2-methyl-2H-[1,2,4]triazole-3-yl)-4H-1-benzopyrane-4-one-8-carboxylate methyl ester

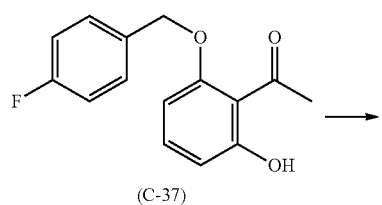

(C-37)

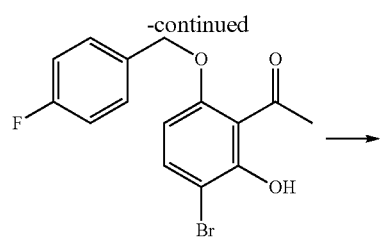

(C-49)

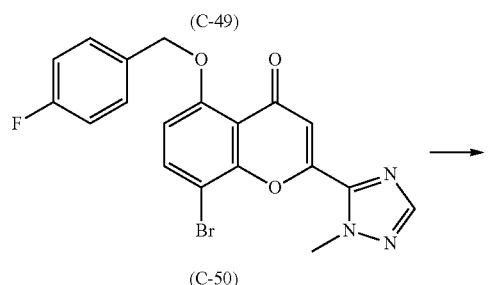

(C-50)

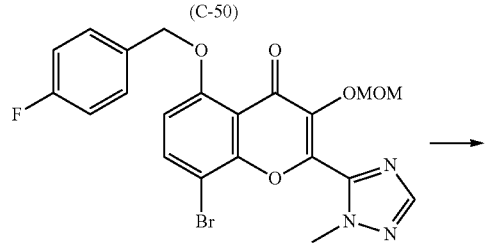

(C-51)

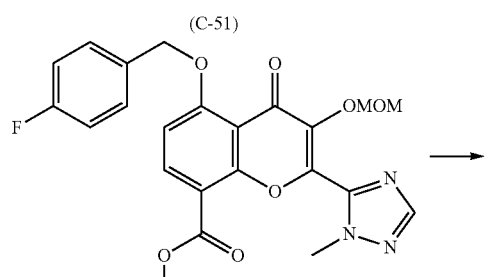

(C-52)

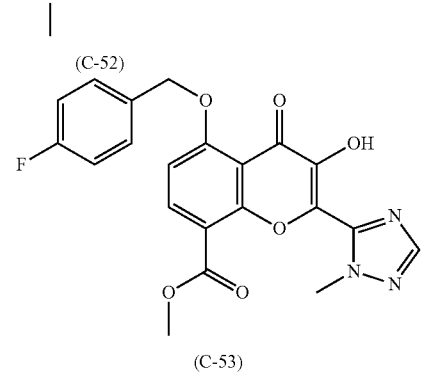

(C-53)

(C-49) To a solution of compound C-37 (10.0 g, 38.4 mmol) in methylene chloride (150 ml), was added phenyltrimethylammonium tribromide (14.4 g, 384 mmol) under ice-cooling and the mixture was stirred for 2 hours 20 minutes. A 10% sodium hydrogen sulfate aqueous solution was added thereto and methylene chloride was evaporated under reduced pressure, to which was added water, followed by extraction with ethyl acetate. The extract was washed with water and saturated brine, and dried, then the solvent was evaporated under reduced pressure. The residue was crystallized from diisopropylether/ethyl acetate to give 1-[3-bromo-6-(4-fluorobenzyloxy)-2-hydroxyphenyl]etanone (9.88 g, yield: 76%).

NMR (CDCl$_3$) δ: 2.60 (3H, s), 5.09 (2H, s), 6.42 (1H, d, J=9.0 Hz), 7.07-7.14 (2H, m), 7.37-7.43 (2H, m), 7.60 (1H, d, J=9.0 Hz), 14.02 (1H, s).

(C-50) According to the method of compound C-38, cyclization using as starting materials the above-mentioned compound C-49 (150 mg, 11.8 mmol) and 2-methyl-2H-[1,2,4]triazole-3-carboxylate ethyl ester (3.66 g, 23.6 mmol) gave 8-bromo-5-[(4-fluorobenzyl)oxy]-2-(2-methyl-2H-[1,2,4]triazole-3-yl)-4H-1-benzopyrane-4-one (296 mg, yield: 85%).

NMR (CDCl$_3$) δ: 4.46 (3H, s), 5.23 (2H, s), 6.85 (1H, d, J=9.0 Hz), 7.06-7.14 (2H, m), 7.18 (1H, s), 7.55-7.62 (2H, m), 7.81 (1H, d, J=9.0 Hz), 7.99 (1H, s).

(C-51) According to the method of compound C-39, the above-mentioned compound C-50 (1.0 g, 0.42 mmol) as a starting material was oxydized with dimethyldioxysilane to give crude substituted 3-hydroxybenzopyranone (550 mg). The obtained compound was dissolved to DMF (15 ml) and 60% sodium hydride (54 mg, 1.35 mmol) was added thereto under ice-cooling. The mixture was stirred at room temperature for 15 minutes and chloromethyl methyl ether (93 μl, 1.35 mmol) was added dropwise under ice-cooling, and the mixture was stirred at room temperature for 30 minutes. To the solution was added ice water, and the mixture was extracted with ethyl acetate. The extract was washed with water and saturated brine, dried, then the solvent was evaporated under reduced pressure. The residue was purified with column chromatography (ethyl acetate:n-hexane=1:2) to give 8-bromo-5-[(4-fluorobenzyl)oxy]-3-methoxymethoxy-2-(2-methyl-2H-[1,2,4]triazole-3-yl)-4H-1-benzopyrane-4-one (119 mg, yield: 13%).

NMR (CDCl$_3$) δ: 3.05 (3H, s), 4.11 (3H, s), 5.22 (2H, s), 5.25 (2H, s), 6.80 (1H, d, J=9.0 Hz), 7.07-7.14 (2H, m), 7.56-7.61 (2H, m), 7.80 (1H, d, J=9.0 Hz), 8.11 (1H, s).

(C-52) To a suspension of the above-mentioned compound C-51 (100 mg, 0.20 mmol), acetic acid palladium (II) (4.6 mg, 0.02 mmol) and 1,3-bis(diphenylphosphino)propane (10.5 mg, 0.025 mmol) in DMF (3 ml), were added at room temperature triethylamine (0.28 ml, 2.04 mmol) and methyl alcohol (1.0 ml) successively, then the mixture was stirred under 1 atm CO atmosphere at 70° C. for 18 hours. After cooling, water 6 ml was added thereto, and the precipitated crystals were filtered off, washed with water, and dried. The crude crystals were purified with column chromatography (ethyl acetate:n-hexane=1:2-1:3) to give 5-[(4-fluorobenzyl)oxy]-3-methoxymethoxy-2-(2-methyl-2H-[1,2,4]triazole-3-yl)-4H-1-benzopyrane-4-one-8-carboxylate methyl ester (53 mg, yield: 55%).

NMR (CDCl$_3$) δ: 3.03 (3H, s), 3.90 (3H, s), 4.11 (3H, s), 5.22 (2H, s), 5.33 (2H, s), 6.91 (1H, d, J=9.0 Hz), 7.09-7.15 (2H, m), 7.57-7.63 (2H, m), 8.09 (1H, s), 8.25 (1H, d, J=9.0 Hz).

(C-53) To a suspension of the above-mentioned compound C-52 in tetrahydrofuran (1 ml) and methyl alcohol (1 ml), was added a solution of concentrated hydrochloric acid 36 μl in methyl alcohol (0.5 ml) at room temperature, and the mixture was stirred at 50° C. for 10 minutes. The mixture was ice-cooled, and saturated sodium hydrogen carbonate aqueous solution 0.5 ml and water 2 ml were added thereto, then the precipitated crystals were filtered off, washed with water, and dried to give 5-[(4-fluorobenzyl)oxy]-3-hydroxy-2-(2-methyl-2H-[1,2,4]triazole-3-yl)-4H-1-benzopyrane-4-one-8-carboxylate methyl ester (38 mg, yield: 84%).

NMR (CDCl$_3$) δ: 3.93 (3H, s), 4.48 (3H, s), 5.32 (2H, s), 6.90 (1H, d, J=9.0 Hz), 7.09-7.15 (2H, m), 7.66-7.72 (2H, m), 8.05 (1H, s), 8.25 (1H, d, J=9.0 Hz), 10.94 (1H, brs).

Melting point: 236-237° C.

Elementary analysis as $C_{21}H_{16}FN_3O_6 \cdot 0.1H_2O$

Calcd. (%): C, 59.05; H, 3.82; N, 9.84; F, 4.45.

Found (%): C, 58.92; H, 3.78; N, 9.62; F, 4.45.

The following compound was prepared as well as above.

(C-53a) 8-bromo-5-[(4-fluorobenzyl)oxy]-3-hydroxy-2-(2-methyl-2H-[1,2,4]triazole-3-yl)-4H-1-benzopyrane-4-one NMR (CDCl$_3$) δ: 4.53 (3H, s), 5.24 (2H, s), 6.81 (1H, d, J=9.0 Hz), 7.08-7.14 (2H, m), 7.65-7.70 (2H, m), 7.82 (1H, d, J=9.0 Hz), 8.06 (1H, s), 10.86 (1H, brs).

Melting point: 220-223° C.

Compound C-57

5-[(4-fluorobenzyl)oxy]-3-hydroxy-2-(2-methyl-2H-[1,2,4]triazole-3-yl)-4H-1-benzopyrane-4-one-7-carboxylic acid amide

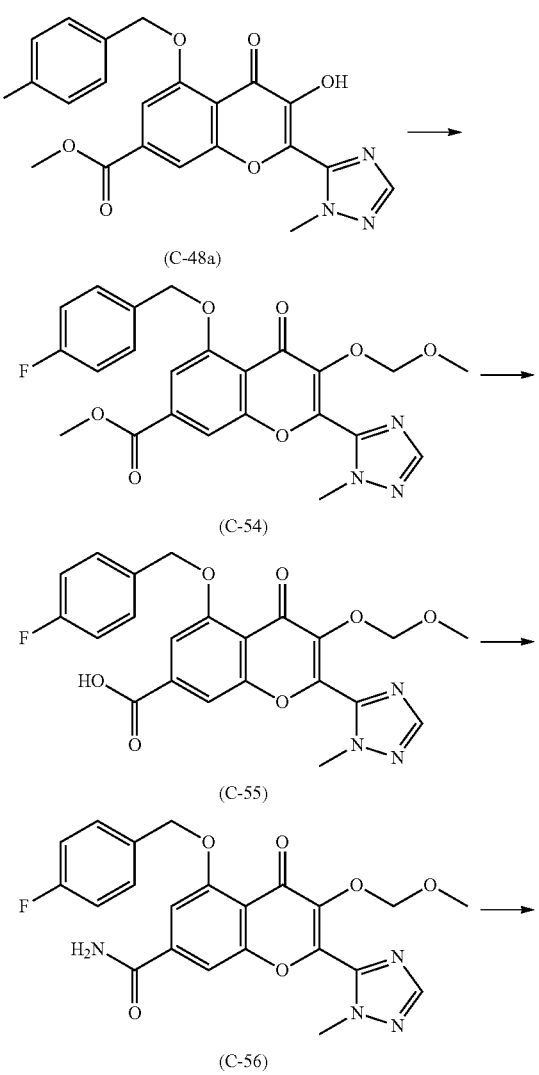

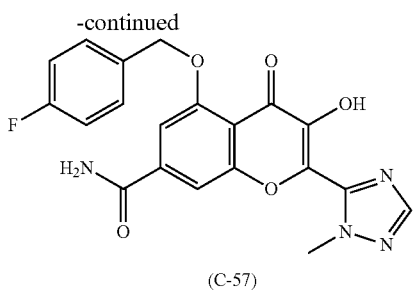

(C-57)

(C-54) To a solution of compound C-48a (520 mg, 1.22 mmol) in DMF (10.4 ml), were added dropwise triethylamine (0.77 ml, 5.52 mmol) and chloromethyl methyl ether (0.28 ml, 3.69 mmol) at room temperature and the mixture was stirred for 1 hour 30 minute. Water 15 ml was added thereto and the precipitated crystals were filtered off and dried to give 5-[(4-fluorobenzyl)oxy]-3-methoxymethoxy-2-(2-methyl-2H-[1,2,4]triazole-3-yl)-4H-1-benzopyrane-4-one-7-carboxylate methyl ester (543 mg, yield: 95%).

NMR (CDCl$_3$) δ: 2.99 (3H, s), 3.97 (3H, s), 4.03 (3H, s), 5.20 (2H, s), 5.31 (2H, s), 7.08-7.16 (2H, m), 7.52 (1H, d, J=1.2 Hz), 7.60-7.67 (2H, m), 7.78 (1H, d, J=1.2 Hz), 8.10 (1H, s).

(C-55) To a solution of the above-mentioned compound C-54 (100 mg, 0.21 mmol) in DMSO (4 ml), was added a 2N sodium hydroxide aqueous solution 128a 1 and the mixture was stirred at room temperature for 30 minutes. 2N hydrochloric acid and water were added thereto and the mixture was extracted with ethyl acetate. The extract was washed with water and saturated brine and dried, then the solvent was evaporated under reduced pressure. To the residue were added methyl alcohol (2 ml) and diisopropylether (4 ml) and the precipitated crystals were filtered off, washed with isopropylether, and dried to give 5-[(4-fluorobenzyl)oxy]-3-methoxymethoxy-2-(2-methyl2H-[1,2,4]triazole-3-yl)-4H-1-benzopyrane-4-one-7-carboxylic acid (78 g, yield: 80%).

NMR (DMSO-d$_6$) δ: 2.91 (3H, s), 3.99 (3H, s), 5.08 (2H, s), 5.37 (2H, s), 7.24-7.33 (2H, m), 7.55 (1H, s), 7.65-7.76 (3H, m), 8.25 (1H, s).

(C-56) To a solution of the above-mentioned compound C-55 (140 mg, 0.16 mmol) in DMF (3 ml), were added at room temperature 1-ethyl-3-(3-dimethylaminopropyl)carbodiimide hydrochloride (38 mg, 0.20 mmol) and 1-hydroxybenzotriazole (25 mg, 0.16 mmol) and the mixture was stirred for 10 minutes. To the mixture were added ammonium chloride (26 mg, 0.49 mmol) and triethylamine (92 µl, 0.66 mmol) and the mixture was stirred for 45 hours. Water was added thereto and the mixture was extracted with ethyl acetate. The extract was washed with water and saturated brine, and dried, then the solvent was evaporated under reduced pressure. The residue was purified column chromatography (chloroform:methyl alcohol=20:1-15:1) to give 5-[(4-fluorobenzyl)oxy]-3-methoxymethoxy-2-(2-methyl-2H-[1,2,4]triazole-3-yl)-4H-1-benzopyrane-4-one-7-carboxylic acid amide (62 mg, yield: 83%).

NMR (DMSO-d$_6$) δ: 2.89 (3H, s), 3.98 (3H, s), 5.07 (2H, s), 5.35 (2H, s), 7.25-7.33 (2H, m), 7.56 (1H, s), 7.68-7.75 (3H, m), 8.25 (1H, s), 8.27 (1H, brs).

The following compound was prepared as well as above.

(C-56a) 5-[(4-fluorobenzyl)oxy]-3-methoxymethoxy-2-(2-methyl-2H-[1,2,4]triazole-3-yl)-4H-1-benzopyrane-4-one-7-carboxylic acid methoxymethylamide NMR (CDCl$_3$) δ: 2.99 (3H, s), 3.38 (3H, s), 3.50 (3H, s), 4.03 (3H, s), 5.20 (2H, s), 5.29 (2H, s), 7.07-7.15 (2H, m), 7.17 (1H, d, J=1.2 Hz), 7.43 (1H, d, J=1.2 Hz), 7.57-7.64 (2H, m), 8.10 (1H, s).

(C-57) According to the method of compound C-53, the above-mentioned compound C-56 (61 mg, 0.13 mmol) as a starting material was deprotected to give 5-[(4-fluorobenzyl)oxy]-3-hydroxy-2-(2-methyl-2H-[1,2,4]triazole-3-yl)-4H-1-benzopyrane-4-one-7-carboxylic acid amide (37 mg, yield: 67%).

NMR (DMSO-d$_6$) δ: 4.00 (3H, s), 5.35 (2H, s), 7.23-7.33 (2H, m), 7.52 (1H, s), 7.70-7.83 (4H, m), 8.22 (1H, s), 8.26 (1H, brs), 10.28 (1H, brs).

Melting point: 257-258° C.

The following compound was prepared as well as above.

(C-57a) 5-[(4-fluorobenzyl)oxy]-3-hydroxy-2-(2-methyl-2H-[1,2,4]triazole-3-yl)-4H-1-benzopyrane-4-one-7-carboxylic acid methoxymethylamide NMR (CDCl$_3$) δ: 3.40 (3H, s), 3.51 (3H, s), 4.31 (3H, s), 5.28 (2H, s), 7.07-7.28 (3H, m), 7.40 (1H, s), 7.63-7.72 (2H, m), 8.06 (1H, s), 10.07 (1H, brs).

Melting point: 220-221° C.

Compound C-60

5-[(4-fluorobenzyl)oxy]-3-hydroxy-2-(2-methyl-2H-[1,2,4]triazole-3-yl)-4H-1-benzopyrane-4-one-8-carboxylic acid dimethylamide

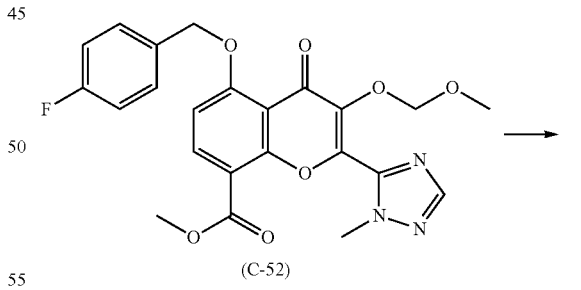

(C-52)

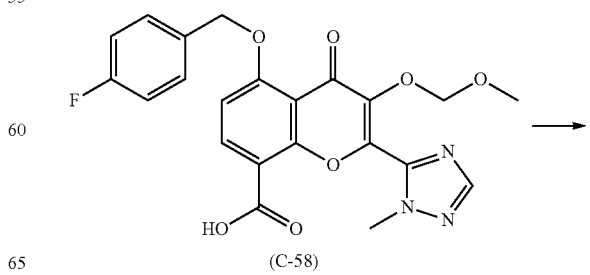

(C-58)

263
-continued

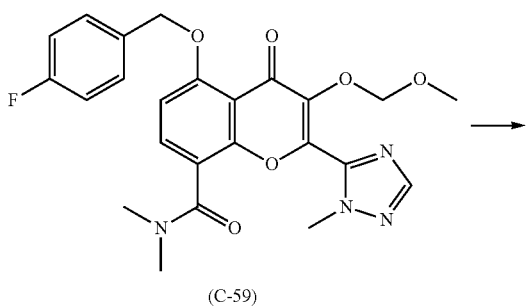

(C-59)

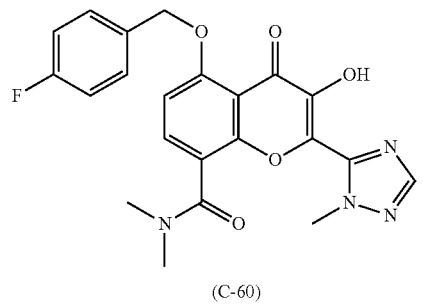

(C-60)

(C-58) According to the method of compound C-55, compound C-52 (120 mg, 0.26 mmol) as a starting material was hydrolyzed at the ester moiety to give 5-[(4-fluorobenzyl)oxy]-3-methoxymethoxy-2-(2-methyl-2H-[1,2,4]triazole-3-yl)-4H-1-benzopyrane-4-one-8-carboxylic acid (57 mg, yield: 49%).

NMR (CDCl₃) δ: 3.05 (3H, s), 4.09 (3H, s), 5.23 (2H, s), 5.32 (2H, s), 6.90 (1H, d, J=9.0 Hz), 7.08-7.17 (2H, m), 7.56-7.64 (2H, m), 8.14 (1H, s), 8.27 (1H, d, J=9.0 Hz).

(C-59) According to the method of compound C-56, the above-mentioned compound C-58 (56 mg, 0.12 mmol) as a starting material was subjected to amidation to give 5-[(4-fluorobenzyl)oxy]-3-methoxymethoxy-2-(2-methyl-2H-[1,2,4]triazole-3-yl)-4H-1-benzopyrane-4-one-8-carboxylic acid dimethylamide (52 mg, yield: 88%).

NMR (CDCl₃) δ: 3.00 (3H, s), 3.01 (3H, s), 3.11 (3H, s), 4.01 (3H, s), 5.21 (2H, s), 5.29 (2H, s), 6.92 (1H, d, J=8.7 Hz), 7.07-7.17 (2H, m), 7.55-7.64 (3H, m), 8.06 (1H, s).

(C-60) According to the method of compound C-53, the above-mentioned compound C-59 (51 mg, 0.11 mmol) as a starting material was deprotected to give 5-[(4-fluorobenzyl)oxy]-3-hydroxy-2-(2-methyl-2H-[1,2,4]triazole-3-yl)-4H-1-benzopyrane-4-one-8-carboxylic acid dimethylamide (34 mg, yield: 74%).

NMR (CDCl₃) δ: 2.95 (3H, s), 3.16 (3H, s), 4.21 (3H, s), 5.27 (2H, s), 6.91 (1H, d, J=8.7 Hz), 7.07-7.16 (2H, m), 7.53 (1H, d, J=8.7 Hz), 7.64-7.72 (2H, m), 8.06 (1H, s), 10.41 (1H, brs).

Melting point: 246-247° C.

264
Compound C-63

5-[2-(4-fluorophenyl)ethoxy]-3-hydroxy-2-(2-methyl-2H-[1,2,4]triazole-3-yl)-4H-1-benzopyrane-4-one

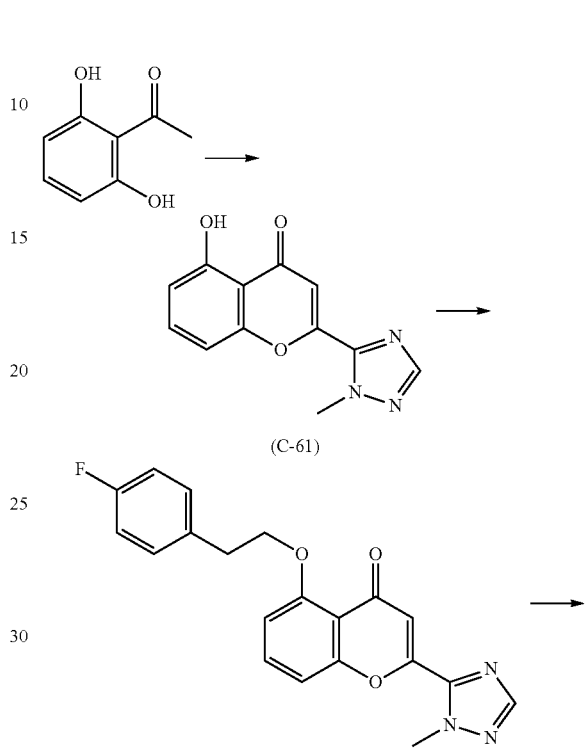

(C-61)

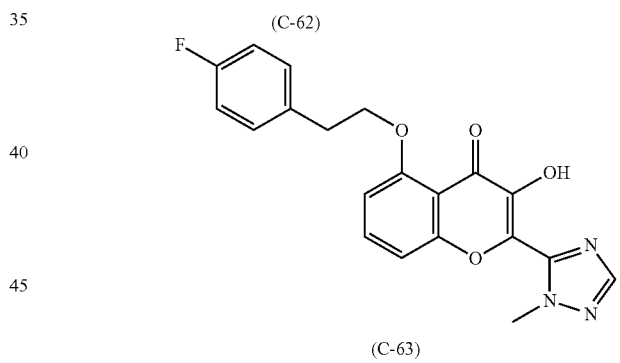

(C-62)

(C-63)

(C-61) According to the method of compound C-38, 2',6'-dihydroxyacetophenone (1.0 g, 6.57 mmol) and 2-methyl-2H-[1,2,4]triazole-3-carboxylate ethyl ester (2.0 g, 12.9 mmol) as starting materials, were subjected to cyclization to give 5-hydroxy-2-(2-methyl-2H-[1,2,4]triazole-3-yl)-4H-1-benzopyrane-4-one (1.13 g, yield: 71%).

NMR (CDCl₃) δ: 4.32 (3H, s), 6.89 (1H, dd, J=0.9, 8.4 Hz), 6.98 (1H, dd, J=0.9, 8.4 Hz), 7.14 (1H, s), 7.61 (1H, t, J=8.4 Hz), 8.00 (1H, s), 12.34 (1H, s).

(C-62) To a suspension of the above-mentioned compound C-62 (500 mg, 2.06 mmol), 2-(4-fluorophenyl)ethanol (0.52 ml, 4.16 mmol), and triphenylphosphine (1.08 g, 4.12 mmol) in tetrahydrofuran (10 ml), was added azodicarboxylic acid diisopropyl (0.81 ml, 4.11 mmol) under ice-cooling and the mixture was stirred at room temperature for 2 hours. To the solution were added water and ethyl acetate, and the precipitated crystals were filtered off, washed with water and ethyl acetate, and dried to give 5-[2-(4-fluorophenyl)

ethoxy]-2-(2-methyl-2H-[1,2,4]triazole-3-yl)-4H-1-benzopyrane-4-one (523 mg, yield: 70%). The filtrate was extracted with ethyl acetate, and the extract was washed with saturated brine and water, and dried, then the solvent was evaporated under reduced pressure. To the residue was added ethyl acetate and the precipitated crystals were filtered off, washed with diisopropylether, and dried to give 5-[2-(4-fluorophenyl)ethoxy]-2-(2-methyl2H-[1,2,4]triazole-3-yl)-4H-1-benzopyrane-4-one (122 mg, yield: 16%).

NMR (CDCl$_3$) δ: 3.23 (2H, t, J=6.6 Hz), 4.25 (2H, t, J=6.6 Hz), 4.28 (3H, s), 6.82 (1H, d, J=7.5 Hz), 6.07-7.09 (4H, m), 7.40-7.60 (3H, m), 7.99 (1H, s).

(C-63) According to the method of compound C-39, the above-mentioned compound C-62 (200 mg, 0.55 mmol) as a starting material was oxidized with dimethyldioxylane to give 5-[2-(4-fluorophenyl)ethoxy]-3-hydroxy-2-(2-methyl-2H-[1,2,4]triazole-3-yl)-4H-1-benzopyrane-4-one (86 mg, yield: 41%).

NMR (CDCl$_3$) δ: 3.24 (2H, t, J=6.3 Hz), 4.26 (2H, t, J=6.3 Hz), 4.29 (3H, s), 6.75 (1H, d, J=8.1 Hz), 6.97-7.08 (3H, m), 7.44-7.58 (3H, m), 8.05 (1H, s), 9.72 (1H, brs).

Melting point: 215-217° C.

Compound C-66

5-[2-(4-fluorophenyl)ethyl]-3-hydroxy-2-(2-methyl2H-[1,2,4]triazole-3-yl)-4H-1-benzopyrane-4-one

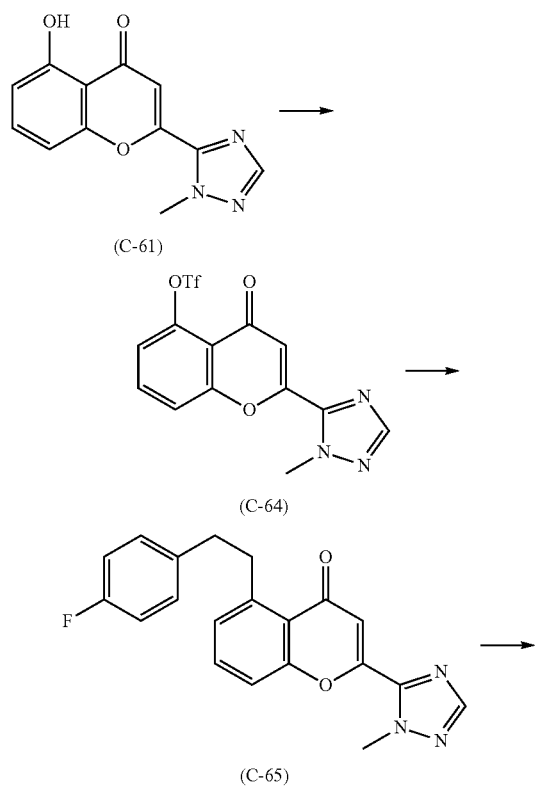

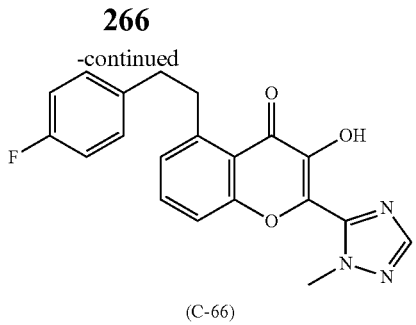

(C-64) To a solution of compound C-61 (500 mg, 2.06 mmol) and triethylamine (1.15 ml, 8.25 mmol) in methylene chloride (10 ml), was added anhydrous trifluoromethanesulfonic acid (0.69 ml, 4.10 mmol) under ice-cooling and the mixture was stirred for 1 hour 30 minutes. To the solution was added ice water and the mixture was extracted with ethyl acetate. The extract was washed with saturated brine and dried, and the solvent was evaporated under reduced pressure. The residue was purified with column chromatography (ethyl acetate:n-hexane=1:1) and recrystallized from acetone/hexane to give trifluoromethanesulfonic acid 2-(2-methyl-2H-[1,2,4]triazole-3-yl)-4H-1-benzopyrane-4-one-5-yl ester (495 mg, yield: 64%).

NMR (CDCl$_3$) δ: 4.31 (3H, s), 7.14 (1H, s), 7.31 (1H, d, J=7.8 Hz), 7.63 (1H, dd, J=0.9, 8.7 Hz), 7.77-7.83 (1H, m), 8.02 (1H, s).

(C-65) To a suspension of zinc (310 mg, 4.74 mmol) in tetrahydrofuran (2.0 ml), was added chlorotrimethylsilane (25 μl, 0.27 mmol) at room temperature for 5 minutes.

To the mixture was added a tetrahydrofuran (2.0 ml) solution containing 1-fluoro-4-(2-iodoethyl)benzene (1.0 g, 4.0 mmol), synthesized from 2-(4-fluorophenyl)ethanol according to the method of J. Org. Chem., 1979, 44, p 1247, and the mixture was stirred at 40° C. for 4 hour and allowed to stand at room temperature overnight. To a solution of compound C-64 (417 mg, 1.11 mmol) in tetrahydrofuran (8.3 ml), were added HMPA (1.0 ml), tetrakistriphenylphosphine palladium (64 mg, 0.06 mmol) and the above-mentioned alkylzinc solution (2.8 ml) at 60° C. for 2.5 hour. After cooling, water was added thereto, and the mixture was extracted with ethyl acetate. The extract was washed with saturated brine, and dried, then the solvent was evaporated under reduced pressure. The residue was purified with column chromatography (ethyl acetate:n-hexane=1:1) and recrystallized from ethyl acetate/hexane to give 5-[2-(4-fluorophenyl)ethyl]-2-(2-methyl-2H-[1,2,4]triazole-3-yl)-4H-1-benzopyrane-4-one (256 mg, yield: 66%).

NMR (CDCl$_3$) δ: 2.90 (2H, t, J=8.1 Hz), 3.55 (2H, t, J=8.1 Hz), 4.32 (3H, s), 6.93-7.02 (2H, m), 7.09-7.14 (3H, m), 7.22-7.29 (2H, m), 7.41 (1H, dd, J=1.2, 8.4 Hz), 7.57 (1H, dd, J=7.5, 8.4 Hz), 8.01 (1H, s).

(C-66) According to the method of compound C-39, the above-mentioned compound C-65 (200 mg, 0.57 mmol) was oxidized with dimethyldioxylane to give 5-[2-(4-fluorophenyl)ethyl]-3-hydroxy-2-(2-methyl-2H-[1,2,4]triazole-3-yl)-4H-1-benzopyrane-4-one (99 mg, yield: 47%).

NMR (CDCl$_3$) δ: 2.91 (2H, t, J=8.1 Hz), 3.57 (2H, t, J=8.1 Hz), 4.36 (3H, s), 6.93-7.02 (2H, m), 7.10 (1H, dd, J=1.2, 7.5 Hz), 7.28-7.36 (2H, m), 7.38 (1H, dd, J=1.2, 8.7 Hz), 7.56 (1H, dd, J=7.5, 8.7 Hz), 8.07 (1H, s), 10.15 (1H, brs).

Melting point: 192-193° C.

Compound C-69

3-hydroxy-2-[1-(4-fluorobenzyl)-1H-[1,2,4]triazole-3-yl]-4H-1-benzopyrane-4-one

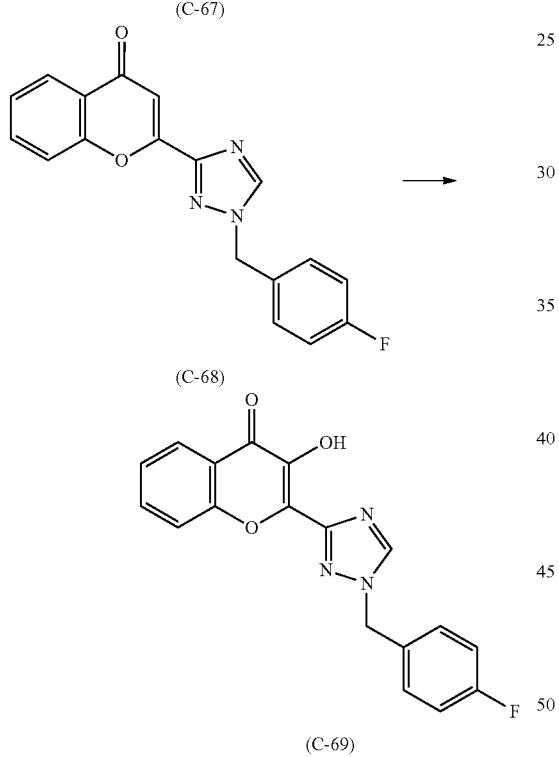

(C-67) To a suspension of 1H-[1,2,4]triazole-3-carboxylate ethyl ester (Farmako, 1997, 52, p 429) (1.0 g, 7.09 mmol) in ethanol (25 ml), were added 20% sodium ethoxide ethanol solution 3.3 ml and 4-fluorobenzylbromide (0.93 ml, 7.46 mmol) under ice-cooling and the mixture was stirred for 1.5 hour, Further, the mixture was stirred at room temperature for 30 minutes and at 80° C. for 40 minutes. After cooling, water was added to the solution and the mixture was extracted with ethyl acetate. The extract was washed with saturated brine and dried, then the solvent was evaporated under reduced pressure. The residue was purified with silica gel column chromatography (ethyl acetate:n-hexane=1:1-1:3) to give 1-(4-fluorobenzyl)-1H-[1,2,4]triazole-3-carboxylate ethyl ester (754 mg, yield: 42%).

NMR (CDCl$_3$) δ: 1.44 (3H, t, J=7.2 Hz), 4.48 (2H, t, J=7.2 Hz), 5.39 (2H, s), 7.00-7.13 (2H, m), 7.25-7.34 (2H, m), 8.08 (1H, s).

(C-68) According to the method of compound C-38, 2'-hydroxyacetophenone (145 mg, 1.07 mmol) and the above-mentioned compound C-67 (533 mg, 2.14 mmol) as starting materials were subjected to cyclization to give 2-[1-(4-fluorobenzyl)-1H-[1,2,4]triazole-3-yl]-4H-1-benzopyrane-4-one (205 mg, yield: 60%).

NMR (CDCl$_3$) δ: 5.43 (2H, s), 7.07-7.16 (2H, m), 7.31-7.47 (3H, m), 7.64-7.75 (2H, m), 8.14 (1H, s), 8.22-8.27 (1H, m).

(C-69) According to the method of compound C-39, the above-mentioned compound C-68 (204 mg, 0.63 mmol) as a starting material was oxidized with dimethyldioxylane to give 3-hydroxy-2-[1-(4-fluorobenzyl)-1H-[1,2,4]triazole-3-yl]-4H-1-benzopyrane-4-one (137 mg, yield: 64%).

NMR (CDCl$_3$) δ: 5.49 (2H, s), 7.09-7.18 (2H, m), 7.34-7.46 (3H, m), 7.63-7.75 (2H, m), 8.22 (1H, s), 8.30-8.36 (1H, m), 9.45 (1H, brs).

Melting point: 260-262° C.

Compound C-71

3-hydroxy-4H-1-benzopyrane-4-one-2-carboxylic acid 4-fluorobenzylamide

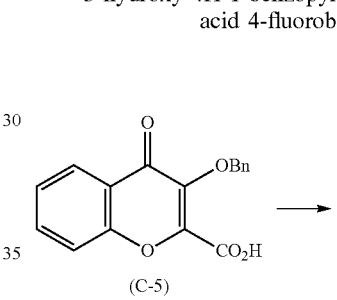

(C-70) To a solution of compound C-5 (200 mg, 0.68 mmol) in DMF (4 ml), were added at room temperature 1-ethyl-3-(3-dimethylaminopropyl)carbodiimide hydrochloride (155 mg, 0.81 mmol), 4-fluorobenzylamine (85 μl, 0.74 mmol) and 1-hydroxybenzotriazole (10 mg, 0.07 mmol) and the mixture was stirred at room temperature for 3 hour. To the solution was added water and 2N hydrochloric acid and the mixture was extracted with ethyl acetate. The extract was washed with a saturated sodium hydrogen carbonate aqueous solution and saturated brine, and dried. The solvent was evaporated under reduced pressure, to which was added diisopropylether (6 ml) and hexane (3 ml), then the precipitated crystals were filtered off, washed with diisopropylether, and dried to give 3-benzyloxy-4-oxo-4H-chromene-2-carboxylic acid 4-fluorobenzylamide (231 mg, yield: 85%).

NMR (DMSO-$d_6$) δ: 4.45 (2H, d, J=6.0 Hz), 5.15 (2H, s), 7.07-7.16 (2H, m), 7.30-7.46 (7H, m), 7.51-7.58 (1H, m), 7.70-7.76 (1H, m), 7.84-7.91 (1H, m), 8.14 (1H, d, J=7.8 Hz), 9.33 (1H, d, J=6.0 Hz).

(C-71) According to the method of compound C-8, the above-mentioned compound C-70 (120 mg, 0.30 mmol) as a starting material was deprotected to give 3-hydroxy-4H-1-benzopyrane-4-one-2-carboxylic acid 4-fluorobenzylamide (62 mg, yield: 67%).

NMR (CDCl$_3$) δ: 4.67 (2H, d, J=6.0 Hz), 7.04-7.14 (2H, m), 7.34-7.49 (4H, m), 7.67-7.75 (1H, m), 7.84-7.91 (1H, m), 8.28 (1H, dd, J=1.5, 8.1 Hz), 10.72 (1H, brs).

Melting point: 235-236° C.

D Group Compound

Compound D-5

2-[5-(4-fluorobenzyl)-[1,3,4]oxadiazole-2-yl]-3-hydroxy-1H-quinoline-4-one

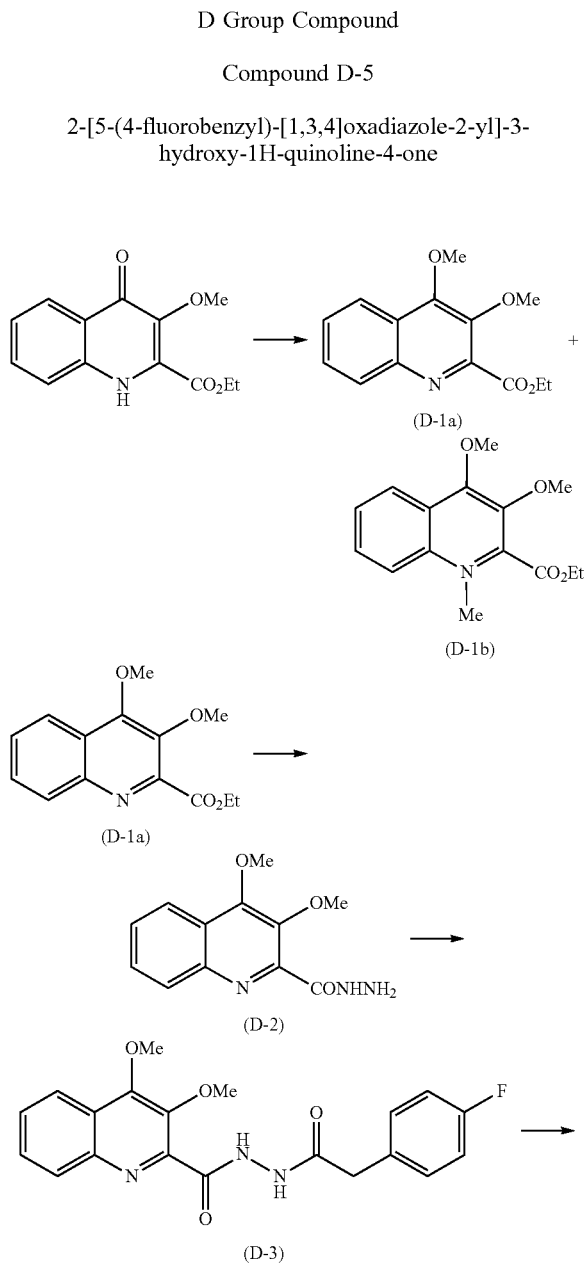

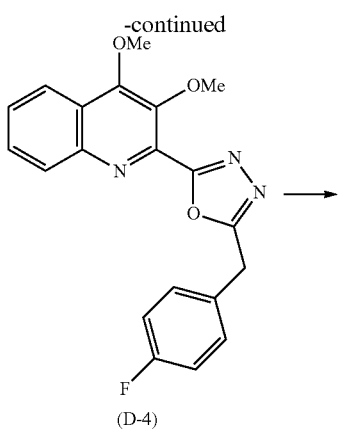

(D-4)

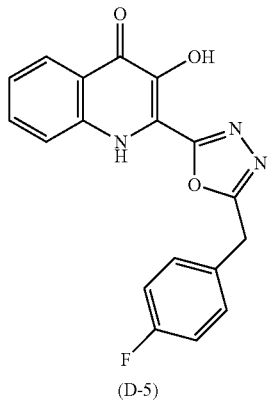

(D-5)

(D-1a,D-1b) To a solution of 2-ethoxycarbonyl3-methoxy1H-quinoline4-one (1.236 g, 5 mmol), synthesized according to J. Heterocyclic Chem, 24, p 1649, 1987, in dimethylformamide (10 ml), was added potassium carbonate (691 mg, 5 mmol) and the mixture was stirred at room temperature for 5 minutes. Iodomethane (0.63 ml, 10.1 mmol) was added thereto, and the mixture was stirred for 2 hours. To the mixture was poured ice water, which was extracted with ethyl acetate 3 times. The extract was washed and dried, then the solvent was evaporated under reduced pressure. The residue was purified with silica gel column chromatography (lober column B, toluene:acetone=24:1) to give 2-ethoxycarbonyl-3,4-dimethoxyquinoline (890 mg, yield: 34.1%) and 2-ethoxycarbonyl-3-methoxy-1-methylquinoline-4-one (1.583 g, yield: 60.6%).

D-1a: oily product

NMR (CDC$_3$) δ: 1.47 (3H, t, J=7.2 Hz), 3.98 (3H, s), 4.22 (3H, s), 4.54 (2H, q, J=7.2 Hz), 7.54-7.59 (1H, m), 7.65-7.70 (1H, m), 8.09-8.15 (2H, m).

D-1b: Melting point: 103° C.

NMR (CDCl$_3$) δ:1.46 (3H, t, J=7.2 Hz), 3.72 (3H, s), 3.97 (3H, s), 4.53 (2H, q, J=7.2 Hz), 7.40 (1H, m), 7.47 (1H, d, J=8.7 Hz), 7.70 (1H, m), 8.52 (1H, m).

(D-2) To a solution of the above-mentioned compound D-1a (885 mg, 3.39 mmol) in ethanol (4.5 ml), was added hydrazine hydrate (0.34 ml, 7.0 mmol) and the mixture was stirred for 30 minutes and allowed to stand at room temperature overnight. The mixture was stirred at 90° C. for 4 hour and water was added thereto, then the mixture was concentrated under reduced pressure and extracted with ethyl acetate. The extract was washed and dried, then the solvent was evaporated under reduced pressure to give 3,4-dimethoxyquinolinecarboxylic acid hydrazide (832 mg, yield: 99.3%).

NMR (CDCl₃) δ:2.79 (3H, bs), 4.02 (3H, s), 4.24 (3H, s), 7.55-7.60 (1H, m), 7.65-7.71 (1H, m), 8.02 (1H, d, J=8.4 Hz), 8.14 (1H, d, J=7.8 Hz).

(D-3) To a solution of the above-mentioned compound D-2 (826 mg, 3.34 mmol) and 4-fluorophenylacetic acid (592 mg, 3.84 mmol) in tetrahydrofuran (10 ml), were added 1-hydroxybenztriazole (90 mg, 0.67 mmol) and 1-ethyl-3-(3-dimethylaminopropyl)-carbodiimide hydrochloric acid (768 mg, 4 mmol) and the mixture was stirred for 6 hours. To the solution was added ice water and the mixture was extracted with ethyl acetate, washed, dried, and concentrated under reduced pressure. Diethyl ether was added thereto and the precipitated crystals were filtered off to give 3,4-dimethoxyquinoline-2-carboxylic acid N-[2-(4-fluorophenyl)acetyl]hydrazide (968 mg, yield: 75.6%).

Melting point: 172-173° C.

NMR (CDCl₃) δ: 3.73 (2H, s), 3.99 (3H, s), 4.23 (3H, s), 7.02-7.08 (2H, m), 7.33-7.38 (2H, m), 7.55-7.60 (1H, m), 7.65-7.70 (1H, m), 8.04 (1H, d, J=8.4 Hz), 8.12 (1H, d, J=8.4 Hz), 8.83 (1H, bs), 10.35 (1H, bs).

(D-4) To a solution of triphenylphosphine (738 mg, 2.81 mmol) in methylene chloride (15 ml), was added a solution of bromine (0.144 ml, 2.81 mmol) in methylene chloride (2 ml) under ice-cooling, and the mixture was stirred at room temperature for 30 minutes. After ice-cooling, a solution of triethylamine (0.82 ml, 5.87 mmol) in methylene chloride (2 ml) was added dropwise, followed by adding the above-mentioned compound D-3 (769 mg, 2.01 mmol), and the mixture was stirred for 1 hour 20 minutes. After further stirring at room temperature for 15 minutes, the solution was poured into ice water, and the mixture was extracted with chloroform. The extract was washed and dried, and the solvent was evaporated under reduced pressure. The residue was purified with silica gel column chromatography (lober column B, toluene:acetone=7:1) to give 2-[5-(4-fluorobenzyl)-[1,3,4]oxadiazole-2-yl]-3,4-dimethoxyquinoline (615 mg, yield: 83.9%).

Melting point: 126° C.

NMR (CDCl₃) δ: 3.99 (3H, s), 4.27 (3H, s), 4.36 (2H, s), 7.02-7.08 (2H, m), 7.36-7.41 (2H, m), 7.57-7.63 (1H, m), 7.68-7.74 (1H, m), 8.12-8.19 (2H, m).

(D-5) To a solution of sodium iodide (4.12 g, 27.5 mmol) in acetonitrile (116 ml), was added trimethylchlorosilane (3.49 ml, 27.5 mmol) and the mixture was stirred for 20 minutes, followed by adding the above-mentioned compound D-4 (628 mg, 1.72 mmol). After stirring for 40 minutes, the mixture was refluxed for 2 hours. The reaction mixture was poured into ice water, which was stirred at room temperature for 1 hour. The precipitated yellow crystals were filtered off and the obtained crude crystals (532 mg, yield: 91.7%) were dissolved into dimethylformamide (100 ml) under heating. The mixture was filtered and concentrated to the volume of 30 ml, to which was added water (20 ml) and the mixture was allowed to stand at room temperature overnight. The precipitated crystals were filtered off to give 2-[5-(4-fluorobenzyl)-[1,3,4]oxadiazole-2-yl]-3-hydroxy-1H-quinoline-4-one (505 mg, yield: 87%).

Melting point: >300° C.

Elementary analysis as $C_{18}H_{12}FN_3O_3$
Calcd. (%): C, 64.09; H, 3.59; N, 12.46; F, 5.63.
Found (%): C, 64.05; H, 3.49; N, 12.54; F, 5.46.

NMR (DMSO-d) δ: 4.46 (2H, s), 7.19-7.31 (3H, m), 7.43-7.48 (2H, m), 7.61-7.67 (1H, m), 7.88 (1H, d, J=8.7 Hz), 8.13 (1H, dd, J=1.2, 8.4 Hz).

Compound D-9

2-[5-(4-fluorobenzyl)-[1,3,4]oxadiazole-2-yl]-3-hydroxy-1-methyl-1H-quinoline-4-one

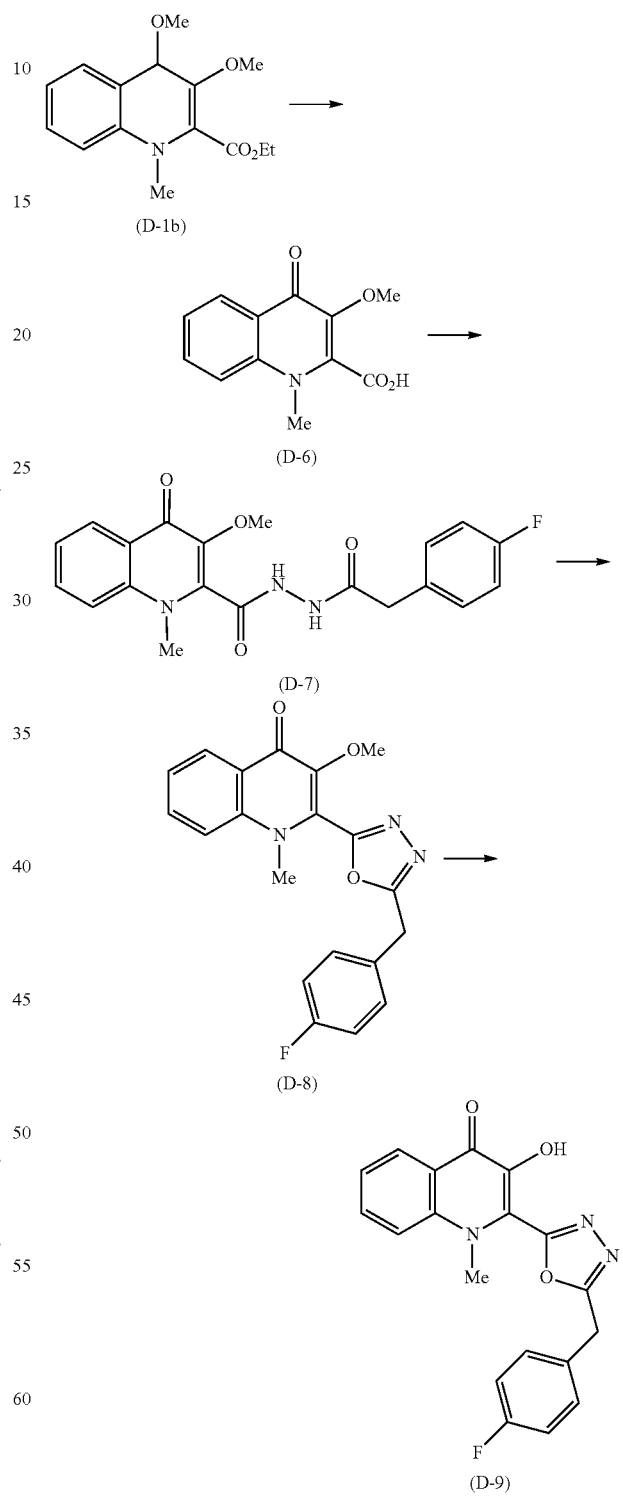

(D-6) To a solution of D-1b (1.21 g, 4.63 mmol) in ethanol (15.3 ml), was added a 1N sodium hydroxide aqueous solution (15.3 ml, 15.3 mmol), and the mixture was refluxed for 2 hours. After ice-cooling, water (25 ml) and a 1N hydrochloric acid aqueous solution (18.5 ml, 18.5 mmol) were added to make the pH 1 to 2, and the precipitated crystals were filtered off and washed with water to give 3-methoxy-1-methyl-4-oxo-1,4-dihydroquinoline-2-carboxylic acid (1.122 g, yield: 100%).

Melting point: 155-156° C. (decomp.)

NMR (DMSO-$d_6$) δ: 3.76 (3H, s), 3.78 (3H, s), 7.41-7.46 (1H, m), 7.78-7.80 (2H, m), 8.24-8.27 (1H, m).

(D-7) To a solution of the above-mentioned compound D-7 (997 mg, 4.28 mmol) and 4-fluorophenylacetic acid hydrazide (1.08 g, 6.41 mmol) in dimethylformamide (17 ml), were added 1-hydroxybenztriazole (866 mg, 6.41 mmol) and 1-ethyl-3-(3-dimethylaminopropyl)carbodiimide hydrochloric acid (1.23 g, 6.41 mmol) and the mixture was stirred for 3 hours. 4-Fluorophenylacetic acid hydrazide (1.08 g, 6.41 mmol) was added thereto and the mixture was allowed to stand at room temperature overnight. To the solution was added ice water and the precipitated crystals were filtered off, washed with water to give 3-methoxy-1-methyl-4-oxo-1,4-dihydroquinoline-2-carboxylic acid N'-[2-(4-fluorophenyl)acetyl]hydrazide (969 mg, yield: 59%).

Melting point: 140-142-(solid)-212-213° C.

NMR (CDCl$_3$) δ: 3.75 (2H, s), 3.77 (3H, s), 3.79 (3H, s), 7.03-7.08 (2H, m), 7.26-7.47 (5H, m), 8.17 (1H, dd, J=1.2, 8.4 Hz), 8.44 (1H, bs), 10.73 (1H, bs).

(D-8) To a solution of triphenylphosphine (929 mg, 3.54 mmol) in methylene chloride (35 ml) was added a solution of bromine (0.182 ml, 3.54 mmol) in methylene chloride (2 ml) under ice-cooling, and the mixture was stirred at room temperature for 30 minutes. After ice-cooling, a solution of triethylamine (1.03 ml, 7.37 mmol) in methylene chloride (2 ml) was added dropwise, and the above-mentioned compound D-7 (905 mg, 2.36 mmol) was added thereto, and the mixture was stirred for 1 hour 30 minutes. The solution was poured into ice water, which was extracted with chloroform, and then the precipitated unreacted materials were filtered off. The extract was washed and dried, and then the solvent was evaporated under reduced pressure. The residue was purified with silica gel column chromatography (lober column B, toluene:acetone=6:1) to give 2-[5-(4-fluorobenzyl)-[1,3,4]oxadiazole-2-yl]-3-methoxy-1-methyl-1H-quinoline-4-one (527 mg, yield: 55.1%).

Melting point: 156-157° C.

NMR (CDCl$_3$) δ: 3.60 (3H, s), 3.84 (3H, s), 4.33 (2H, s), 7.04-7.10 (2H, m), 7.32-7.36 (2H, m), 7.40-7.46 (1H, m), 7.51 (1H, d, J=8.7 Hz), 7.71-7.77 (1H, m), 8.53 (1H, dd, J=1.5, 8.1 Hz).

(D-9) To a solution of sodium iodide (1.62 g, 10.8 mmol) in acetonitrile (90 ml), was added trimethylchlorosilane (1.36 ml, 10.7 mmol) at room temperature and the mixture was stirred for 30 minutes. The above-mentioned compound D-8 (490 mg, 1.34 mmol) was added thereto and the mixture was stirred for 30 minutes and refluxed for 2 hours. After cooling, the reaction mixture was poured to ice water and the mixture was stirred at room temperature for 1 hour. The precipitated yellow crystals were filtered off as crude crystals (412 mg, yield: 87.5%). The crystals were dissolved to methylene chloride, which was filtered with a millipore filter, and then the methylene chloride was concentrated in water bath while adding methyl alcohol thereto. After ice-cooling, the precipitated crystals were filtered off and washed with methyl alcohol to give 2-[5-(4-fluorobenzyl)-[1,3,4]oxadiazole-2-yl]-3-hydroxy-1-methyl-1H-quinoline-4-one (360 mg, yield: 76.4%).

Melting point: 222° C.

Elementary analysis as $C_{19}H_{14}FN_3O_3$

Calcd. (%): C, 64.95; H, 4.02; N, 11.96; F, 5.41.
Found (%): C, 64.96; H, 3.91; N, 11.96; F, 5.23.

NMR (CDCl$_3$) δ: 3.78 (3H, s), 4.35 (2H, s), 7.04-7.10 (2H, m), 7.35-7.45 (3H, m), 7.57 (1H, d, J=8.7 Hz), 7.73-7.78 (1H, m), 8.47-8.50 (1H, m).

E Group Compound

Compound E-8

2-[5-(4-fluorobenzyl)furan-2-carbonyl]-3-hydroxy-pyrane-4-one

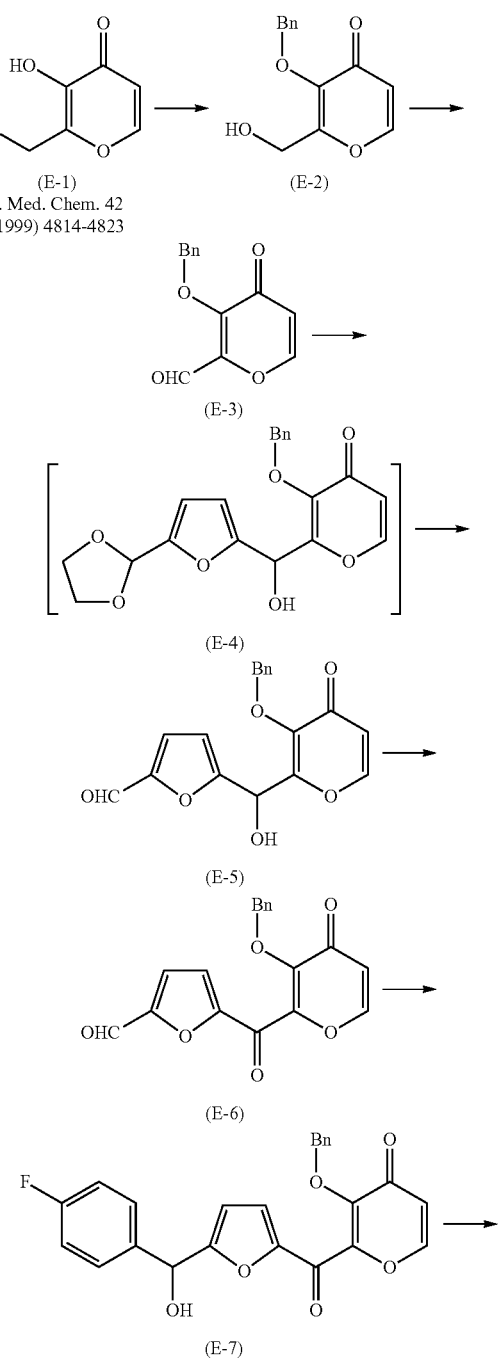

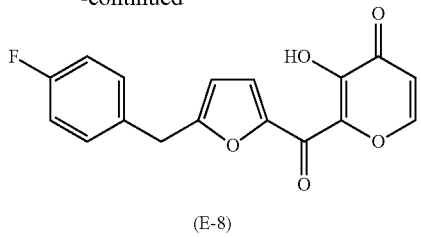

(E-8)

(E-2) Hydroxymethyl product (E-1) (2.2 g, 15.5 mm) was dissolved in acetone (33 ml). To the solution, were added potassium carbonate (6.4 g, 46 mm) and benzylbromide (3.2 g, 18.7 mm) and the mixture was refluxed under heating for 3 hours. After evaporating acetone, water was added thereto. The mixture was extracted with ethyl acetate, washed with water, dried with sodium sulfate, and then concentrated under reduced pressure. The residue was isolated and purified with silica gel column chromatography (ethyl acetate: n-hexane=3:1) to give compound E-2 as oily product (1.4 g, yield: 39%).

$^1$H-NMR (CDCl$_3$) δ 4.32 (s, 2H), 5.21 (s, 2H), 6.40 (d, J=5.4 Hz, 1H), 7.37-7.38 (m, 5H), 7.69 (d, J=6.0 Hz, 1H)

(E-3) Oxalylchloride (1.64 g, 13 mm) was dissolved in methylene chloride (15 ml) and the solution cooled to −78° C. To this solution, was added dropwise a solution of dimethylsulfoxide (2.1 g, 26.9 mm) in methylene chloride (10 ml). After stirring at −78° C. for 15 minutes, a solution which alcohol product (E-2) (1.5 g, 6.5 mm) was dissolved in methylene chloride (10 ml) was added thereto. After 30 minutes, triethylamine (5.3 g, 42 mm) was added thereto and the mixture stirred for 15 minutes. After warming to room temperature, ice water was added thereto and the mixture was extracted with ethyl acetate, washed with water, dried with sodium sulfate, and then concentrated under reduced pressure. The residue was isolated and purified with silica gel column chromatography (ethyl acetate:n-hexane=1:1) to give compound E-3 as oily product (1.39 g, yield: 93%).

$^1$H-NMR (CDCl$_3$) δ 5.52 (s, 2H), 6.50 (d, J=5.4 Hz, 1H), 7.36 (s, 5H), 7.75 (d, J=5.7 Hz, 1H), 9.88 (s, 1H)

(E-5) 2-Furan-2-yl-[1.3]dioxolane (920 mg, 6.6 mm) was dissolved in dried tetrahydrofuran (20 ml), and the solution cooled to −78° C. To this solution, was added dropwise a solution of 1.57 mol/l n-butyl lithium-hexane solution (5.4 ml, 8.5 mm). After 15 minutes, a solution of γ-pyrone product (E-3) (1.5 g, 6.5 mm) in tetrahydrofuran (15 ml) was added thereto. After 30 minutes, the mixture was warmed to 0° C. After saturated ammonium chloride aqueous solution was added thereto, the mixture was extracted with ethyl acetate, washed with water, and then concentrated under reduced pressure. The obtained residue was dissolved in methyl alcohol (10 ml). 6N hydrochloric acid (2 ml) was added thereto and the mixture was stirred at room temperature for 1 hour. The mixture was neutralized with sodium hydrogen carbonate, extracted with ethyl acetate, washed with water, dried with sodium sulfate, and then concentrated under reduced pressure. The residue was purified with silica gel column chromatography (ethyl acetate:n-hexane=1:1) to give compound E-5 as oily product (730 mg, yield: 35%).

$^1$H-NMR (CDCl$_3$) δ 5.22 (d, J=11.1 Hz, 1H), 5.27 (d, J=11.1 Hz, 1H), 5.90 (s, 1H), 6.42 (d, J=5.7 Hz, 1H), 6.44 (d, J=3.6 Hz, 1H), 7.17 (d, J=3.6 Hz, 1H), 7.35-7.38 (m, 5H), 7.66 (d, J=5.7 Hz, 1H), 9.58 (s, 1H)

(E-6) Oxalylchloride (570 mg, 4.5 mm) was dissolved in methylene chloride (10 ml) and the solution was cooled to −78° C. A solution which dimethyl sulfoxide (700 mg, 9 mm) was dissolved in methylene chloride (5 ml) was added dropwise and the mixture was stirred for 15 minutes. A solution of alcohol product (E-5) (730 mg, 2.2 mm) in methylene chloride (10 ml) was added. After stirring for 30 minutes, triethylamine (1.8 g, 18 mm) was added dropwise thereto. After 15 minutes, the mixture was put to be 0° C. and a saline solution was added thereto. The mixture was extracted with ethyl acetate, washed with water, dried with sodium sulfate, and then concentrated under reduced pressure. The residue was purified with silica gel column chromatography (ethyl acetate:n-hexane=2:1) to give product E-6 as oily product (610 mg, yield: 84%).

$^1$H-NMR (d6-DMSO) δ 5.19 (s, 2H), 6.66 (d, J=5.7 Hz, 1H), 7.20-7.27 (m, 5H), 7.64 (d, J=3.6 Hz, 1H), 7.71 (d, J=3.9 Hz, 1H), 8.29 (d, J=5.7 Hz, 1H), 9.79 (s, 1H)

(E-7) Aldehyde product (E-6) (550 mg, 1.7 mm) was dissolved in dried tetrahydrofuran (22 ml) and a solution of 1 mol/l parafluorophenyl magnesium bromide in tetrahydrofuran (1.6 ml, 1.7 mm) were added thereto under ice-cooling. After stirring at room temperature for 15 minutes, ammonium chloride aqueous solution was added thereto. The mixture was extracted with ethyl acetate, washed with water, dried with sodium sulfate, and then concentrated under reduced pressure. The residue was purified with silica gel column chromatography (ethyl acetate:n-hexane=1:1) to give compound E-7 as oily product (413 mg, yield: 58%).

$^1$H-NMR (d6-DMSO) δ 5.06 (s, 2H), 5.82 (s, 1H), 6.53 (d, J=3.6 Hz, 1H), 6.58 (d, J=5.4 Hz, 1H), 7.13-7.25 (m, 7H), 7.40-7.45 (m, 2H), 7.50 (d, J=3.6 Hz, 1H), 8.20 (d, J=5.7 Hz, 1H)

(E-8) Alcohol product (E-7) (290 mg, 0.7 mm) was dissolved in trifluoroacetic acid (6 ml) and triethylsilane (0.7 ml) added thereto under ice-cooling. After 30 minutes, the mixture was stirred at room temperature for 30 minutes. After concentrating under reduced pressure, the mixture was neutralized with sodium hydrogen carbonate, extracted with ethyl acetate, washed with water, dried with sodium sulfate, and then concentrated under reduced pressure. The residue was dissolved in acetone, treated with active carbon, and then recrystallized with ethyl acetate/isopropylether to give compound E-8 as pale yellow crystal (83 mg, yield: 39%) of mp 157-9.

$^1$H-NMR (d6-DMSO) δ 4.15 (s, 1H), 6.50 (d, J=3.9 Hz, 1H), 6.51 (d, J=5.4 Hz, 1H), 7.15-7.21 (m, 2H), 7.32-7.37 (m, 2H), 7.70 (d, J=3.6 Hz, 1H), 8.22 (d, J=5.7 Hz, 1H), 10.77 (brs, 1H)

Elementary analysis as (C$_{17}$H$_1$FO$_5$/0.3H$_2$O)
Calcd. (%) C, 63.87; H, 3.66; F, 5.94.
Found (%) C, 63.85; H, 3.27; F, 6.27.
m/z 313 [M−H]−, m/z 315 [M+H]+, m/z 359 [M+2Na−H]+
IR (nujol) (cm-1) 3400, 1646, 1608

Compound E-16

2-[5-(4-fluorobenzyl)furan-2-carbonyl]-3-hydroxy-6-methylpyrane-4-one

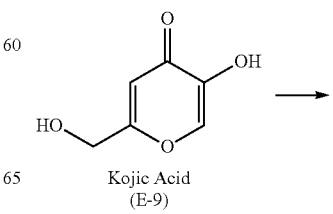

Kojic Acid
(E-9)

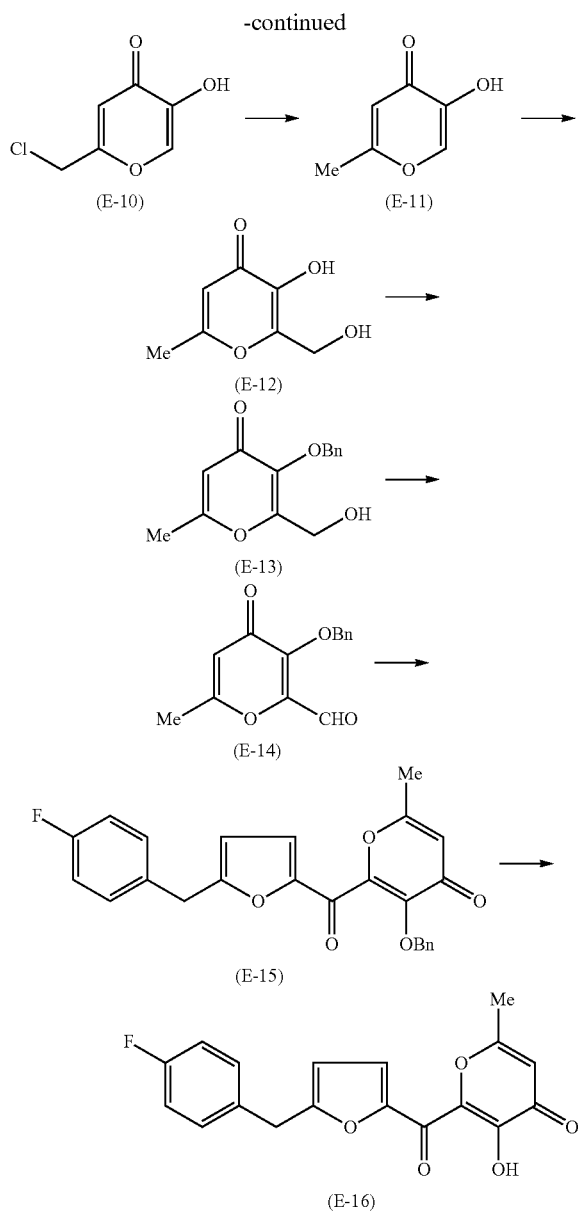

(E-10) Kojic acid product E-9 (14.2 g, 0.1 mol) was dissolved in thionyl chloride (24 g) and the solution was stirred at room temperature. After 10 minutes, solid content was washed with hexane to give white crystal (16.5 g, yield: 100%).

$^1$H-NMR (CDCl$_3$) δ: 4.36 (s, 2H), 6.58 (s, 1H), 7.89 (s, 1H).

(E-11) The above-mentioned compound E-10 (16.5 g, 0.1 mol) was suspended in water (400 ml). Zinc powder (13 g, 0.2 mol) and concentrated hydrochloric acid (10 ml) were added thereto and the mixture was stirred at 75° C. for 1 hour. After cooling, zinc powder was removed by suction filtration and the filtrate was extracted with chloroform. After washing and drying, the solvent was evaporated under reduced pressure and the residue was crystallized with ether to give the compound (10.4 g, yield: 82%).

$^1$H-NMR (CDCl$_3$) δ: 2.31 (s, 3H), 6.28 (s, 1H), 6.61 (bs, 1H), 7.79 (s, 1H).

(E-12) The above-mentioned compound E-11 (10.4 g, 82 mmol) was dissolved in methyl alcohol (54 ml). Sodium hydroxide solution (sodium hydroxide (4.2 g) was dissolved in water (11 ml)) and 37% formaldehyde solution (17 ml) were added thereto and the mixture was stirred at room temperature for 25 hours. Methyl alcohol was evaporated under reduced pressure. The solution was acidified with concentrated hydrochloric acid and then sodium sulfate was added thereto. The mixture was diluted with tetrahydrofuran. To the solution, was added molecular sieve and the mixture was dried and filtered. The solvent was evaporated under reduced pressure and the residue was crystallized with chloroform to give the compound (8.1 g, yield: 64%).

H-NMR (DMSO-d$_6$) δ: 2.26 (s, 3H), 4.39 (s, 2H), 5.36 (bs, 1H), 6.22 (s, 1H), 8.91 (bs, 1H).

(E-13) The above-mentioned compound E-12 (7.0 g, 45 mmol) was dissolved in acetone (150 ml). Potassium carbonate (20 g, 145 mmol) and benzyl bromide (9.6 g, 56 mmol) were added thereto and the mixture was refluxed for 16 hours. After cooling, acetone was evaporated under reduced pressure and the residue was extracted with ethyl acetate. After washing and drying, the solvent was evaporated under reduced pressure and the residue was crystallized with ether to give the compound (8.5 g, yield: 76%).

$^1$H-NMR (CDCl$_3$) δ: 2.26 (s, 3H), 4.28 (s, 2H), 5.21 (s, 2H), 6.21 (s, 1H), 7.38 (m, 5H).

(E-14) Oxalylchloride (8.6 g, 67 mmol) was dissolved in methylene chloride (80 ml). To the solution, was added dropwise a solution of dimethyl sulfoxide (10.5 g, 135 mmol) in methylene chloride (50 ml) at −78° C. After 15 minutes, a solution of the above-mentioned compound E-13 (8.3 g, 34 mmol) in methylene chloride (50 ml) was added dropwise thereto at −78° C. and the mixture was stirred at the same temperature for 30 minutes. Triethylamine (27 g, 270 mmol) was added thereto and warmed to room temperature. Water was added thereto and the mixture was extracted with chloroform. After washing and drying, the solvent was evaporated under reduced pressure and the residue was crystallized with isopropylether to give the compound (7.4 g, yield: 90%).

$^1$H-NMR (CDCl$_3$) δ: 2.32 (s, 3H), 5.49 (s, 2H), 6.30 (s, 1H), 7.35 (m, 5H), 9.84 (s, 1H).

(E-15) To a solution of 2-(4-fluorobenzyl)furanlithium salt synthesized as the synthetic method of A-6 in tetrahydrofuran (5 mmol), added a solution of the above-mentioned compound E-14 (1.22 g, 5 mmol) in tetrahydrofuran at −78° C. The mixture was stirred at the same temperature for 30 minutes. The solution was added to ammonium chloride solution and extracted with ethyl acetate. After washing and drying, the solvent was evaporated under reduced pressure and the residue was dissolved in chloroform (30 ml). To the solution, was added manganese dioxide (20 g) and the mixture was stirred at 60° C. for 15 minutes. The solution was filtered and the filtrate was dried and evaporated under reduced pressure. The residue was purified with column chromatography (ethyl acetate:n-hexane=1:1) to give the compound (1.15 g, yield: 55%).

$^1$H-NMR (CDCl$_3$) δ: 2.29 (s, 3H), 4.00 (s, 2H), 5.21 (s, 2H), 6.13 (d, 1H, J=3.9 Hz), 6.30 (d, 1H, J=0.6 Hz), 6.98-7.04 (m, 2H), 7.14 (d, 1H, J=3.6 Hz), 7.15-7.24 (m, 7H).

(E-16) The above-mentioned compound E-15 (3.78 g, 9.0 mmol) was dissolved in trifluoroacetic acid (30 ml) and the mixture was stirred at room temperature for 30 minutes. The solvent was evaporated under reduced pressure. Ice water was added thereto and extracted with ethyl acetate. After washing and drying, the solvent evaporated under reduced pressure and the residue was recrystallized with methyl alcohol to give compound (1.8 g, yield: 62%).

$^1$H-NMR (DMSO-d$_6$) δ: 2.36 (s, 3H), 4.15 (s, 2H), 6.41 (s, 1H), 6.52 (d, 1H, J=3.6 Hz), 7.14-7.22 (m, 2H), 7.30-7.38 (m, 2H), 7.63 (d, 1H, J=3.6 Hz).
Melting point: 173-175° C.
Elementary analysis as C$_{18}$H$_{13}$O$_5$F
Calcd. (%) C, 65.85; H, 3.99; F, 5.79.
Found (%) C, 65.64; H, 3.96; F, 5.69.

Compound E-24

2-[5-(4-fluorobenzyl)furan-2-carbonyl]-3-hydroxy-6-hydroxymethlpyrane-4-one

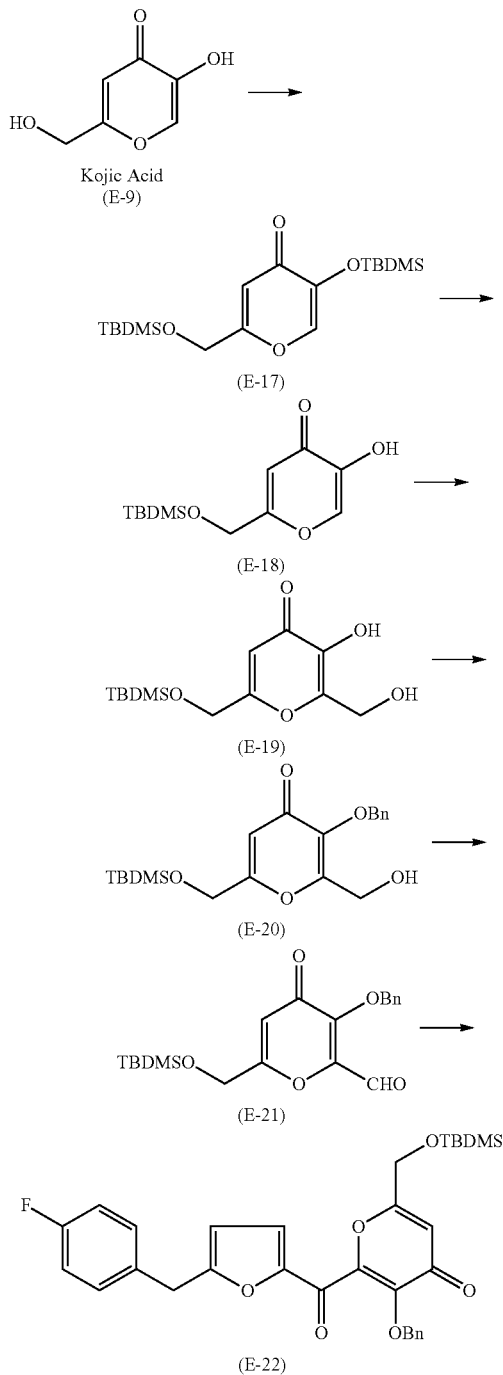

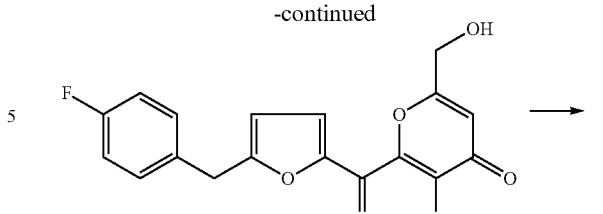

(E-23)

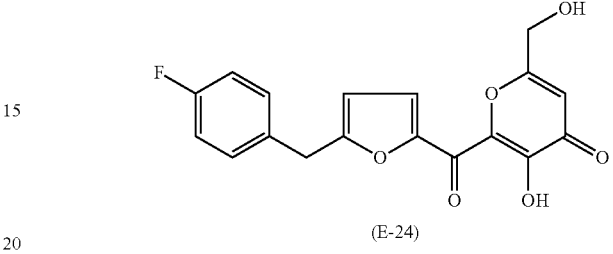

(E-24)

(E-17) To a solution of kojic acid compound E-9 (44.9 g, 316 mmol) in DMF (400 ml), were added imidazole (45.1 g, 663 mmol) and then chlorotert-butyldimethylsilane (100 g, 663 mmol) under ice-cooling. The mixture was warmed to room temperature and stirred for 30 minutes. Water was added thereto to stop the reaction and the mixture was extracted with diethyl ether. After washing with water and drying, the solvent was evaporated under reduced pressure to give 5-(tert-butyldimethylsilanyloxy)-2-(tert-butyldimethylsilanyloxymethyl)-pyrane-4-one.

H-NMR (CDCl$_3$) δ: 0.11 (6H, s), 0.23 (6H, s), 0.93 (9H, s), 0.96 (9H, s), 4.45 (2H, s), 6.45 (s, 1H), 7.62 (s, 1H).

(E-18) To the above-mentioned compound E-17, was added 30% formic acid-chloroform solution (300 ml) and the mixture was stirred for 1 hour. Water (300 ml) was added thereto, extracted with chloroform, washed with water and dried. The solvent was evaporated under reduced pressure and precipitated crystal was washed with n-hexane to give 2-(tert-butyldimethylsilanyloxymethyl)-5-hydroxypyrane-4-one (76.22 g, yield: 94%).

Melting point: 121-122° C.
$^1$H-NMR (CDCl$_3$) δ: 0.12 (6H, s), 0.93 (9H, s), 4.49 (2H, s), 6.50 (1H, bs), 6.57 (s, 1H), 7.80 (s, 1H).

(E-19) To a solution of the above-mentioned compound E-18 (76.22 g, 297 mmol) in methyl alcohol (500 ml), were added sodium hydroxide solution (5N-aqueous solution, 59.4 ml, 297 mmol) and 37% formaldehyde aqueous solution (72.3 g, 891 mmol) under ice-cooling. Then the mixture was warmed to room temperature and stirred for 5 hours. Saturated ammonium chloride aqueous solution was added thereto to stop the reaction and methyl alcohol was evaporated under reduced pressure. The solution was extracted with chloroform, washed with water and dried. The precipitated crystal was washed with n-hexane to give 6-(tert-butyldimethylsilanyloxymethyl)-3-hydroxy2-hydroxymethylpyrane-4-one (74.47 g, yield: 88%).

Melting point: 133-134° C.
$^1$H-NMR (CDCl$_3$) δ: 0.12 (6H, s), 0.94 (9H, s), 4.53 (2H, s), 4.70 (2H, s), 6.56 (111H, bs), 6.57 (1H, s).

(E-20) The above-mentioned compound E-19 (74.47 g, 260 mmol) was dissolved in acetone (350 ml). Potassium carbonate (35.9 g, 260 mmol) and benzyl bromide (44.5 g, 260 mmol) were added thereto and the mixture was refluxed for 2 hours. After cooling, acetone was evaporated under reduced pressure and the residue was extracted with ethyl acetate. After washing and drying, the solvent was evaporated under reduced pressure and the precipitated crystal was washed with n-hexane to give 3-benzyloxy-6-(tert-butyl-dimethylsilanyloxymethyl)-2-hydroxymethylpyrane-4-one (89.08 g, yield: 91%).

Melting point: 87-90° C.

$^1$H-NMR (CDCl$_3$) δ: 0.11 (6H, s), 0.93 (9H, s), 4.26 (2H, s), 4.46 (2H, s), 5.22 (2H, s), 6.51 (1H, s), 7.38 (5H, s).

(E-21) To a solution of the above-mentioned compound E-20 (89.08 g, 237 mmol) in chloroform (400 ml), was added manganese dioxide (103 g, 1.18 mmol). The mixture was refluxed under heating for 2 hours. Manganese dioxide was filtered and dried. The solvent was evaporated under reduced pressure to give 3-benzyloxy6-(tert-butyl-dimethylsilanyloxymethyl)-4-oxo-4H-pyrane-2-carboaldehyde (87.7 g, yield: 99%).

$^1$H-NMR (CDCl$_3$) δ: 0.11 (6H, s), 0.93 (9H, s), 4.51 (2H, s), 5.51 (2H, s), 6.63 (1H, s), 7.36 (s, 1H), 9.84 (1H, s).

(E-22) With using the above-mentioned compound E-21 (34.8 g, 93 mmol) according to the synthetic method of E-15, 3-benzyloxy-6-(tert-butyldimethylsilanyloxymethyl)-2-[5-(4-fluorobenzyl)furan-2-carbonyl]-pyrane-4-one (34.0 g, yield: 67%) was given.

$^1$H-NMR (CDCl$_3$) δ: 0.11 (6H, s), 0.93 (9H, s), 4.00 (2H, s), 4.47 (2H, s), 5.23 (2H, s), 6.13 (1H, d, J=3.7 Hz), 6.59 (1H, s), 6.99-7.04 (2H, m), 7.14-7.23 (8H, m).

(E-23) The above-mentioned compound E-22 (34.0 g, 62 mmol) was dissolved in dioxane (300 ml). 3N-hydrochloric acid aqueous solution (150 ml) was added thereto. After stirring for 30 minutes, the mixture was extracted with ethyl acetate, washed and dried. The solvent was evaporated under reduced pressure. The precipitated crystal was washed with diethyl ether to give 3-benzyloxy-2-[5-(4-fluorobenzyl)furan-2-carbonyl]-6-hydroxymethylpyrane-4-one (26.2 g, yield: 97%).

Melting point: 104-106° C.

$^1$H-NMR (CDCl$_3$) δ: 3.99 (2H, s), 4.48 (2H, s), 5.21 (2H, s), 6.12 (1H, d, J=3.7 Hz), 6.58 (1H, s), 6.98-7.04 (2H, m), 7.12-7.22 (8H, m).

(E-24) With using the above-mentioned compound E-23 according to the synthetic method of E-16, 2-[5-(4-fluorobenzyl)furan-2-carbonyl]-3-hydroxy-6-hydroxymethyl-pyrane-4-one was synthesized.

Melting point: 193-195° C.

Elementary analysis as C$_{18}$H$_{31}$O$_6$F

Calcd. (%) C, 62.79; H, 3.81; F, 5.52.

Found (%) C, 62.73; H, 3.75; F, 5.32.

$^1$H-NMR (CD$_3$OD) δ: 4.13 (2H, s), 4.55 (2H, s), 6.44 (1H, d, J=3.7 Hz), 6.57 (1H, s), 7.03-7.09 (2H, m), 7.30-7.35 (2H, m), 7.86 (1H, d, J=3.7 Hz).

Compound E-26

2-[5-(4-fluorobenzyl)furan-2-carbonyl]-3-hydroxy-6-methoxymethylpyrane-4-one

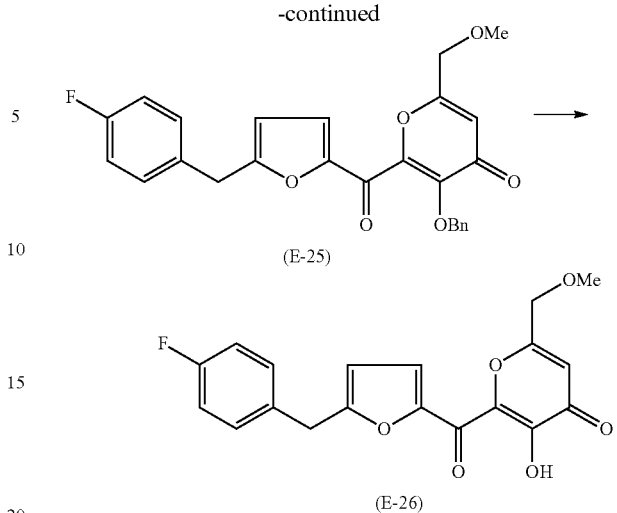

(E-25) To a solution of compound E-23 (217 mg, 0.5 mmol) in THF (1 ml), added diazomethane ether solution under ice-cooling and then silica gel (100 mg). Acetic acid was added thereto to stop the reaction. The solvent was evaporated under reduced pressure and the residue was purified with silica gel column chromatography (ethyl acetate:n-hexane=1:1) to give 3-benzyloxy2-[5-(4-fluorobenzyl)furan-2-carbonyl]-6-methoxymethylpyrane-4-one (118 mg, yield: 53%).

$^1$H-NMR (CDCl$_3$) δ: 3.44 (3H, s), 4.00 (2H, s), 4.24 (2H, s), 5.23 (2H, s), 6.13 (1H, d, J=3.6 Hz), 6.54 (1H, s), 6.98-7.04 (2H, m), 7.16-7.26 (8H, m).

(E-26) With using the above-mentioned compound E-25 according to the synthetic method of E-16, 2-[5-(4-fluorobenzyl)furan-2-carbonyl]-3-hydroxy-6-methoxymethyl-pyrane-4-one was synthesized.

Melting point: 147-148

Elementary analysis as C$_{19}$H$_{15}$O$_6$F

Calcd. (%) C, 63.69; H, 4.22; F, 5.30.

Found (%) C, 63.72; H, 4.27; F, 5.14.

$^1$H-NMR (CDCl$_3$) δ: 3.47 (3H, s), 4.11 (2H, s), 4.36 (2H, s), 6.26 (1H, d, J=3.7 Hz), 6.50 (1H, s), 7.01-7.07 (2H, m), 7.22-7.26 (2H, m), 7.76 (1H, d, J=3.7 Hz).

Compound E-28

6-[5-(4-fluorobenzyl)furan-2-carbonyl]-5-hydroxy-4-oxo-4H-pyrane-2-carboxylic acid

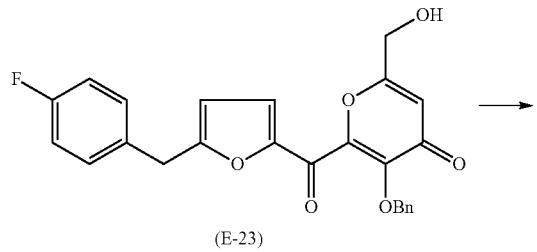

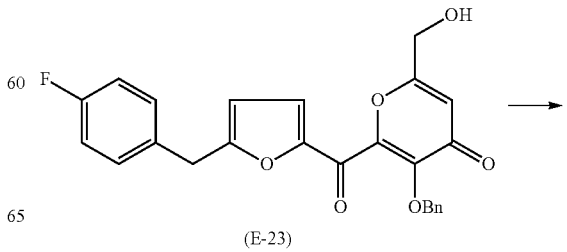

-continued

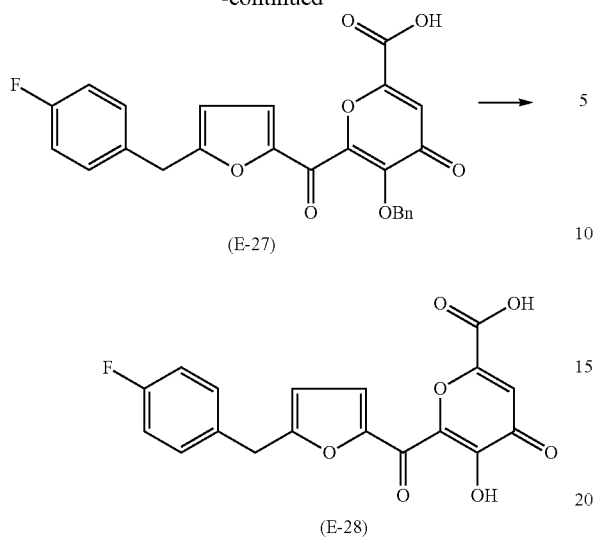

(E-27) To a solution of compound E-23 (10 g, 10 mmol) in acetone (100 ml), added dropwise 8N-Jones reagent aqueous solution (CrO$_3$—H$_2$SO$_4$, 13.8 ml, 110 mmol) under ice-cooling for 30 minutes and the mixture was warmed to room temperature. After stirring for 1 hour, isopropylalcohol was added thereto to stop the reaction and the insoluble product was filtered. Water was added thereto and the mixture was extracted with ethyl acetate, washed and dried. The solvent was evaporated under reduced pressure to give 5-benzyloxy-6-[5-(4-fluorobenzyl)furan-2-carbonyl]-4-oxo-4H-pyrane-2-carboxylic acid (8.29 g, yield: 80%).

H-NMR (DMSO-D) δ: 4.14 (2H, s), 5.12 (2H, s), 6.51 (1H, d, J=3.4 Hz), 7.09-7.35 (10H, m).

(E-28) With using the above-mentioned compound E-27 according to the synthetic method of E-16, 6-[5-(4-fluorobenzyl)furan-2-carbonyl]-5-hydroxy-4-oxo-4H-pyrane-2-carboxylic acid was synthesized.

Melting point: >200° C. decomp.

$^1$H-NMR (DMSO-D$_6$) δ: 4.17 (2H, s), 6.59 (1H, d, J=3.4 Hz), 7.03 (1H, s), 7.15-7.21 (2H, m), 7.32-7.37 (2H, m), 8.04 (1H, d, J=3.4 Hz).

Compound E-30

6-[5-(4-fluorobenzyl)furan-2-carbonyl]-5-hydroxy-4-oxo-4H-pyrane-2-carboxylate methyl

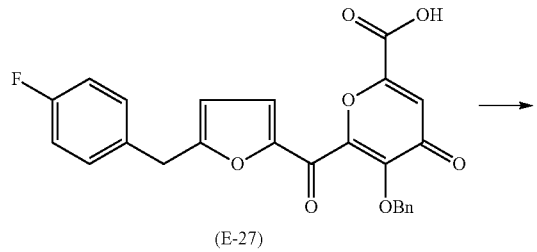

(E-29) To a solution of compound E-27 (400 mg, 0.89 mmol) in THF (3 ml), was added trimethylsilyldiazomethane (2.0 mol/l in THF, 0.53 ml, 1.07 mmol). Acetic acid was added thereto to stop the reaction. The solvent was evaporated under reduced pressure and the residue was purified with silica gel column chromatography (ethyl acetate:n-hexane=3:1) to give 5-benzyloxy-6-[5-(4-fluorobenzyl)furan-2-carbonyl]-4-oxo-4H-pyrane-2-carboxylate methyl ester (320 mg, yield: 78%).

$^1$H-NMR (CDCl$_3$) δ: 3.95 (3H, s), 4.02 (2H, s), 5.29 (2H, s), 6.16 (1H, d, J=3.8 Hz), 6.98-7.04 (2H, m), 7.17-7.34 (9H, m).

(E-30) With using the above-mentioned compound E-29 according to the synthetic method of E-16, 6-[5-(4-fluorobenzyl)furan-2-carbonyl]-5-hydroxy-4-oxo-4H-pyrane-2-carboxylate methyl ester was synthesized.

Melting point: 174-176° C.

Elementary analysis as C$_{19}$H$_{13}$O$_7$F

Calcd. (%) C, 61.30; H, 3.52; F, 5.10.

Found (%) C, 61.30; H, 3.52; F, 4.97.

$^1$H-NMR (CDCl$_3$) δ: 4.03 (3H, s), 4.13 (2H, s), 6.32 (1H, d, J=3.7 Hz), 7.01-7.07 (2H, m), 7.21-7.28 (3H, m), 8.23 (1H, d, J=3.7 Hz).

Compound E-32

6-[5-(4-fluorobenzyl)furan-2-carbonyl]-5-hydroxy-4-oxo-4H-pyrane-2-carboxylate benzylamide

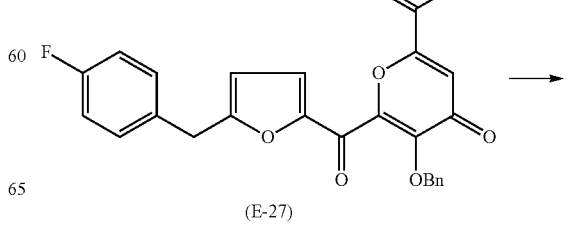

-continued

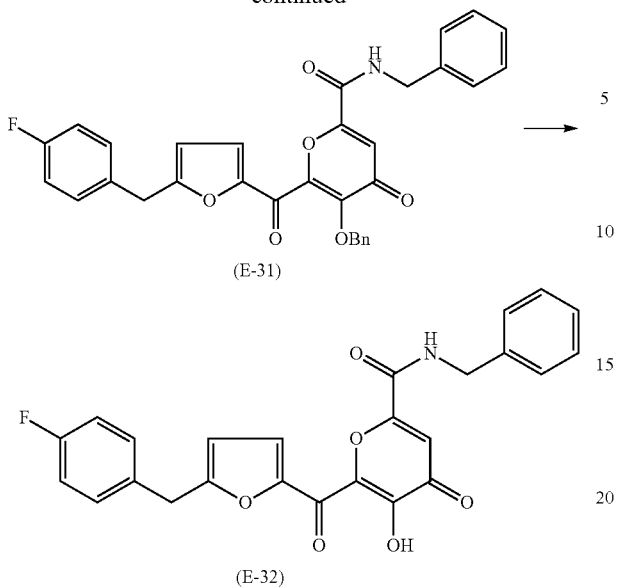

(E-31) To a solution of compound E-27 (224 mg, 0.5 mmol), HOBt (7 mg, 0.05 mmol) and WSCD (115 mg, 0.6 mmol) in DMF (3 ml), was added benzylamine (4 mg, 0.6 mmol) at room temperature. After stirring 20 hours, water was added thereto to stop the reaction. The mixture was extracted with ethyl acetate, washed with water and dried. The solvent was evaporated under reduced pressure and the residue was purified with silica gel column chromatography (ethyl acetate:n-hexane=2:1) to give 5-benzyloxy-6-[5-(4-fluorobenzyl)furan-2-carbonyl]-4-oxo-4H-pyrane-2-carboxylate benzylamide (112 mg, yield: 42%).

$^1$H-NMR (CDCl$_3$) δ: 3.92 (2H, s), 4.56 (2H, d, J=5.8 Hz), 5.24 (2H, s), 6.12 (1H, d, J=3.7 Hz), 6.97-7.35 (16H, m).

(E-32) Using the above-mentioned compound E-31 according to the synthetic method of E-16, 6-[5-(4-fluorobenzyl)furan-2-carbonyl]-5-hydroxy-4-oxo-4H-pyrane-2-carboxylate benzylamide was synthesized.

Melting point: 195-197° C.

Elementary analysis as C$_{25}$H$_{18}$O$_5$F$_1$N$_1$

Calcd. (%) C, 67.11; H, 4.06; F, 4.25; N, 3.13.

Found (%) C, 65.21; H, 4.06; F, 4.07; N, 3.04.

$^1$H-NMR (CDCl$_3$) δ: 3.72 (2H, s), 4.63 (2H, d, J=5.8 Hz), 6.14 (1H, d, J=3.7 Hz), 6.99-7.35 (10H, m), 7.70 (1H, d, J=3.7 Hz), 11.54 (1H, bs).

According to the same method, the following compounds were synthesized.

(E-32-a) 6-[5-(4-fluorobenzyl)furan-2-carbonyl]-5-hydroxy-4-oxo-4H-pyrane-2-carboxylate methyl amide Melting point: 231-232° C.

Elementary analysis as C$_{19}$H$_{14}$NO$_6$F

Calcd. (%) C, 61.46; H, 3.80; N, 3.77; F, 5.12.

Found (%) C, 61.26; H, 3.76; N, 3.71; F, 5.02.

$^1$H-NMR (CDCl$_3$) δ: 2.97 (d, 3H, J=4.8 Hz), 4.14 (s, 2H), 6.35 (d, 1H, J=3.6 Hz), 6.87 (1H, bs), 7.03-7.09 (m, 2H), 7.15 (s, 1H), 7.19-7.27 (m, 2H), 7.87 (d, 1H, J=3.6 Hz).

(E-32-b) 6-[5-(4-fluorobenzyl)furan-2-carbonyl]-5-hydroxy-4-oxo-4H-pyrane-2-carboxylate ethyl amide Melting point: 217-219° C.

Elementary analysis as C$_{20}$H$_{16}$O$_5$F$_1$N$_1$

Calcd. (%) C, 62.34; H, 4.19; F, 4.93; N, 3.63.

Found (%) C, 62.46; H, 4.15; F, 4.79; N, 3.56.

$^1$H-NMR (CDCl$_3$) δ: 1.25 (3H, t, J=7.3 Hz), 3.46 (2H, m), 4.13 (2H, s), 6.32 (1H, d, J=3.7 Hz), 6.78 (1H, bs), 7.03-7.09 (2H, m), 7.14 (1H, s), 7.21-7.26 (2H, m), 7.88 (1H, d, J=4.0 Hz), 11.30 (1H, bs).

(E-32-c) 6-[5-(4-fluorobenzyl)furan-2-carbonyl]-5-hydroxy-4-oxo-4H-pyrane-2-carboxylate isopropylamide Melting point: 208-210° C.

Elementary analysis as C$_{21}$H$_{18}$O$_6$F$_1$N$_1$

Calcd. (%) C, 63.16; H, 4.54; F, 4.76; N, 3.51.

Found (%) C, 63.19; H, 4.54; F, 4.55; N, 3.40.

$^1$H-NMR (CDCl$_3$) δ: 1.29 (6H, d, J=6.7 Hz), 4.12 (2H, s), 4.26 (1H, m), 6.29 (1H, d, J=3.7 Hz), 6.49 (1H, d, J=7.9 Hz), 7.02-7.09 (2H, m), 7.13 (1H, s), 7.21-7.27 (2H, m), 7.89 (1H, d, J=3.7 Hz), 11.32 (1H, bs).

(E-32-d) 6-[5-(4-fluorobenzyl)furan-2-carbonyl]-5-hydroxy-4-oxo-4H-pyrane-2-carboxylate phenylamide Melting point: 263-266° C.

$^1$H-NMR (DMSO-D$_6$) δ: 4.17 (2H, s), 6.58 (1H, d, J=3.7 Hz), 7.14-7.21 (3H, m), 7.32-7.42 (5H, m), 7.72 (2H, d, J=7.6 Hz), 7.98 (1H, d, J=3.7 Hz), 10.5 (1H, s), 11.00 (1H, bs).

(E-32-e) 6-[5-(4-fluorobenzyl)furan-2-carbonyl]-5-hydroxy-4-oxo-4H-pyrane-2-carboxylic acid (2-methoxyethyl)-amide Melting point: 177-179° C.

Elementary analysis as C$_{21}$H$_{18}$O$_7$F$_1$N$_1$

Calcd. (%) C, 60.72; H, 4.37; F, 4.57; N, 3.37.

Found (%) C, 60.94; H, 4.30; F, 4.44; N, 3.31.

$^1$H-NMR (CDCl$_8$) δ: 3.36 (3H, s), 3.53-3.56 (2H, m), 3.61-3.65 (2H, m), 4.17 (1H, s), 6.28 (1H, d, J=3.7 Hz), 7.02-7.08 (2H, m), 7.15 (1H, bs), 7.19-7.27 (2H, m), 7.81 (1H, d, J=3.7 Hz), 11.65 (1H, bs).

(E-32-f) 6-[5-(4-fluorobenzyl)furan-2-carbonyl]-5-hydroxy-4-oxo-4H-pyrane-2-carboxylate amide Melting point: 259-262° C.

$^1$H-NMR (DMSO-D$_6$) δ: 4.16 (2H, s), 6.57 (1H, d, J=3.7 Hz), 7.11 (1H, s), 7.15-7.20 (2H, m), 7.32-7.37 (2H, m), 7.97 (1H, d, J=3.7 Hz), 8.13 (1H, bs), 8.29 (1H, bs), 10.92 (1H, bs).

(E-32-g) 2-[5-(4-fluorobenzyl)furan-2-carbonyl]-3-hydroxy-6-(piperidine-1-carbonyl)-pyrane-4-one Melting point: 146-148° C.

Elementary analysis as C$_{23}$H$_{20}$O$_6$F$_1$N$_1$

Calcd. (%) C, 64.94; H, 4.74; F, 4.47; N, 3.29.

Found (%) C, 64.87; H, 4.82; F, 4.30; N, 3.17.

¹H-NMR (CDCl₃) δ: 1.50-1.80 (6H, m), 3.40-3.75 (4H, m), 4.10 (2H, s), 6.27 (1H, d, J=3.7 Hz), 6.57 (1H, s), 7.01-7.06 (2H, m), 7.21-7.26 (2H, m), 7.80 (1H, d, J=3.7 Hz), 11.82 (1H, bs).

(E-32-h) 6-[5-(4-fluorobenzyl)furan-2-carbonyl]-5-hydroxy-4-oxo-4H-pyrane-2-carboxylate dimethylamide Melting point: 182-183° C.
Elementary analysis as $C_{20}H_{16}NO_6F$
Calcd. (%) C, 62.34; H, 4.19; N, 3.63; F, 4.93.
Found (%) C, 62.19; H, 4.16; N, 3.64; F, 4.73.
¹H-NMR (CDCl₃) δ: 3.13 (m, 6H), 4.10 (s, 2H), 6.28 (d, 1H, J=3.6 Hz), 6.63 (s, 1H), 7.00-7.07 (m, 2H), 7.06-7.27 (m, 2H), 7.83 (d, 1H, J=3.6 Hz), 11.81 (s, 1H).

(E-32-i) ({6-[5-(4-fluorobenzyl)furan-2-carbonyl]-5-hydroxy-4-oxo-4H-pyrane-2-carbonyl}amino)ethyl acetate ester Melting point: 150-151° C.
Elementary analysis as $C_{22}H_{18}NO_8F \cdot 0.2H_2O$
Calcd. (%) C, 59.12; H, 4.15; N, 3.13; F, 4.25.
Found (%) C, 58.87; H, 4.00; N, 3.15; F, 4.13.
H-NMR (CDCl₃) δ: 1.32 (t, 3H, J=7.2 Hz), 4.14 (m, 4H), 7.27 (q, 2H, J=7.2 Hz), 6.34 (d, 1H, J=3.6 Hz), 7.01-7.07 (m, 2H), 7.19-7.26 (m, 3H), 7.85 (d, 1H, J=3.6 Hz).

Compound E-37

N-{6-[5-(4-fluorobenzyl)furan-2-carbonyl]-5-hydroxy-4-oxo-4H-pyrane-2-yl-methyl}-acetoamide

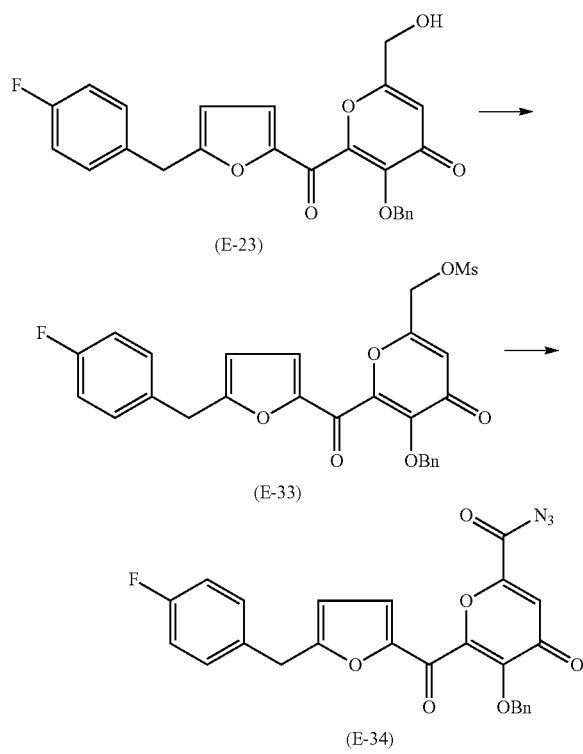

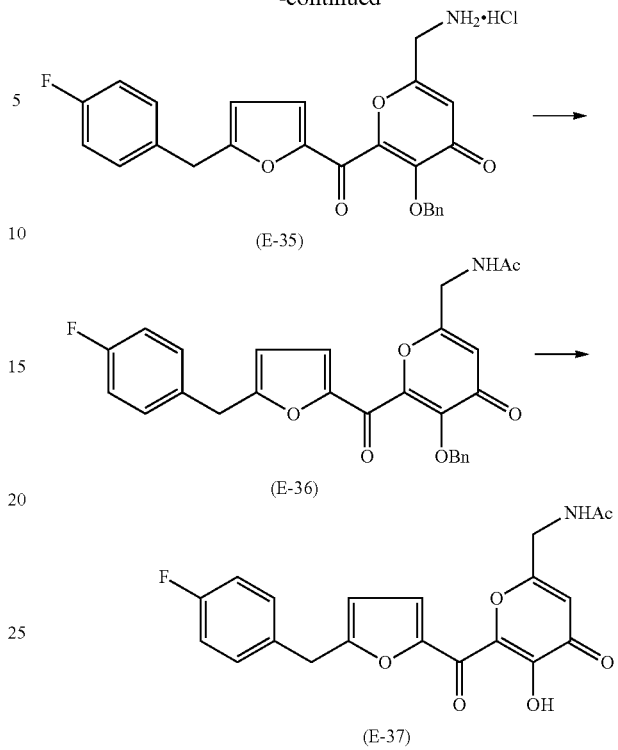

(E-33) To a solution of compound E-23 (434 mg, 1 mmol) in methylene chloride (4 ml), were added diisopropylethylamine (142 mg, 1.1 mmol) and then methane sulfonylchloride (126 mg, 1.1 mmol) under ice-cooling. After stirring for 10 minutes, water was added thereto to stop the reaction. The mixture was extracted with chloroform, washed and dried to give methanesulfonic acid 5-benzyloxy6-[5-(4-fluorobenzyl)furan-2-carbonyl]-4-oxo-4H-pyrane-2-yl-methyl-ester (521 mg, yield: 100%).
¹H-NMR (CDCl₃) δ: 3.09 (3H, s), 3.99 (2H, s), 4.99 (2H, s), 5.22 (2H, s), 6.15 (1H, d, J=3.6 Hz), 6.59 (1H, s), 6.98-7.04 (2H, m), 7.16-7.23 (8H, m).

(E-34) To a solution of the above-mentioned compound E-33 (256 mg, 0.5 mmol) in DMF (3 ml), was added sodium azide (49 mg, 0.75 mmol) and the mixture was stirred for 1 hour. Water was added thereto to stop the reaction and the mixture was extracted with ethyl acetate, washed and dried to give 6-azidemethyl-3-benzyloxy-2-[5-(4-fluorobenzyl)furan-2-carbonyl]-pyrane-4-one (228 mg, yield: 99%).
H-NMR (CDCl₃) δ: 3.99 (2H, s), 4.19 (2H, s), 5.22 (2H, s), 6.15 (1H, d, J=3.6 Hz), 6.50 (1H, s), 6.98-7.04 (2H, m), 7.15-7.26 (8H, m).

(E-35,36) To a solution of the above-mentioned compound E-34 (228 mg, 0.5 mmol) in THF (3 ml), were added water (0.3 ml) and then triphenylphosphine (292 mg, 1 mmol). After stirring at room temperature for 30 minutes, 4N-HCl/dioxane solution (0.25 ml) was added thereto and the solvent was evaporated under reduced pressure. To the mixture, were added methylene chloride (3 ml) and then acetic anhydride (102 mg, 1 mmol) under ice-cooling. To the mixture, was added triethylamine (101 mg, 1 mmol) at the same temperature. Water was added thereto to stop the reaction. The mixture was extracted with chloroform, washed and dried. The solvent was evaporated under reduced pressure and the residue was purified with silica gel column chromatography (ethyl acetate) to give N-{5-benzyloxy-6-[5-(4-fluorobenzyl)furan-2-carbonyl]-4-oxo-4H-pyrane-2-ylmethyl}-acetoamide (177 mg, yield: 74%).

¹H-NMR (CDCl₃) δ: 1.98 (3H, s), 3.99 (2H, s), 4.24 (2H, d, J=6.1 Hz), 5.16 (2H, s), 6.13 (1H, d, J=3.7 Hz), 6.33 (1H, s), 6.82 (1H, bs), 6.98-7.05 (2H, m), 7.15-7.35 (8H, m).

(E-37) Using the above-mentioned compound E-36 (170 mg, 0.36 mmol) according to the synthetic method of E-16, N-{6-[5-(4-fluorobenzyl)furan-2-carbonyl]-5-hydroxy-4-oxo-4H-pyrane-2-yl-methyl}-acetoamide (10 mg, 80%) was synthesized.

Melting point: 263-265° C.

¹H-NMR (DMSO-D₆) δ: 1.90 (3H, s), 4.16 (2H, s), 4.25 (2H, d, J=5.6 Hz), 6.39 (1H, s), 6.52 (1H, d, J=3.8 Hz), 7.14-7.20 (2H, m), 7.32-7.36 (2H, m), 7.66 (1H, d, J=3.4 Hz), 8.53 (1H, t, J=5.6 Hz).

According to the same method, the following compounds were synthesized.

(E-37-a) N-{6-[5-(4-fluorobenzyl)furan-2-carbonyl]-5-hydroxy-4-oxo-4H-pyrane-2-ylmethyl}-3-methyl-butylamide ¹H-NMR (CDCl₃) δ: 0.94 (6H, d, J=4.2 Hz), 2.10-2.18 (3H, m), 4.10 (2H, s), 4.23 (2H, d, J=6.1), 6.22 (1H, bs), 6.29 (1H, d, J=4.0 Hz), 6.37 (1H, s), 7.01-7.08 (2H, m), 7.22-7.26 (2H, m); 7.78 (1H, d, J=7 Hz), 11.90 (1H, s).

(E-37-b) N-{6-[5-(4-fluorobenzyl)furan-2-carbonyl]-5-hydroxy-4-oxo-4H-pyrane-2-ylmethyl}-2-methoxyacetoamide ¹H-NMR (CDCl₃) δ: 3.44 (3H, s), 3.97 (2H, s), 4.11 (2H, s), 4.45 (2H, d, J=6.4), 6.43 (1H, s), 7.01-7.08 (3H, m), 7.22-7.26 (2H, m), 7.75 (1H, d, J=3.7 Hz), 11.88 (1H, s).

(E-37-c) N-{6-[5-(4-fluorobenzyl)furan-2-carbonyl]-5-hydroxy-4-oxo-4H-pyrane-2-ylmethyl}-benzamide ¹H-NMR (DMSO-d₆) δ: 4.12 (2H, s), 4.49 (2H, d, J=5.8), 6.34 (1H, d, J=3.7 Hz), 6.48 (1H, s), 7.14-7.20 (2H, m), 7.29-7.33 (2H, m), 7.47-7.60 (3H, m), 7.64 (1H, d, J=3.7 Hz), 7.88-7.91 (2H, m), 9.18 (1H, t, J=5.5 Hz), 10.83 (1H, s).

(E-37-d) N-{6-[5-(4-fluorobenzyl)furan-2-carbonyl]-5-hydroxy-4-oxo-4H-pyrane-2-ylmethyl}-benzene sulfone amide ¹H-NMR (DMSO-d₆) δ: 4.09 (2H, d, J=5.8 Hz), 4.17 (2H, s), 6.42 (1H, s), 6.52 (1H, d, J=3.7 Hz), 7.15-7.21 (2H, m), 7.33-7.38 (2H, m), 7.47-7.60 (3H, m), 7.70 (1H, d, J=3.7 Hz), 7.75-7.78 (2H, m), 8.54 (1H, t, J=5.5 Hz), 10.81 (1H, bs).

Compound E-40

6-[5-(4-fluorobenzyl)furan-2-carbonyl]-5-hydroxy-4-oxo-4H-pyrane-2-carboaldehyde O-methyloxime

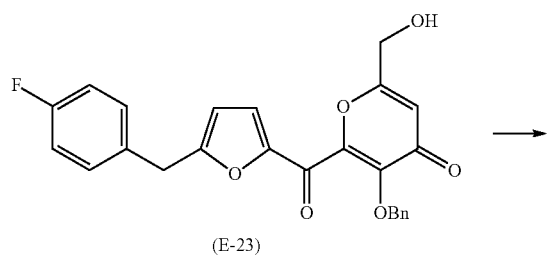

(E-23)

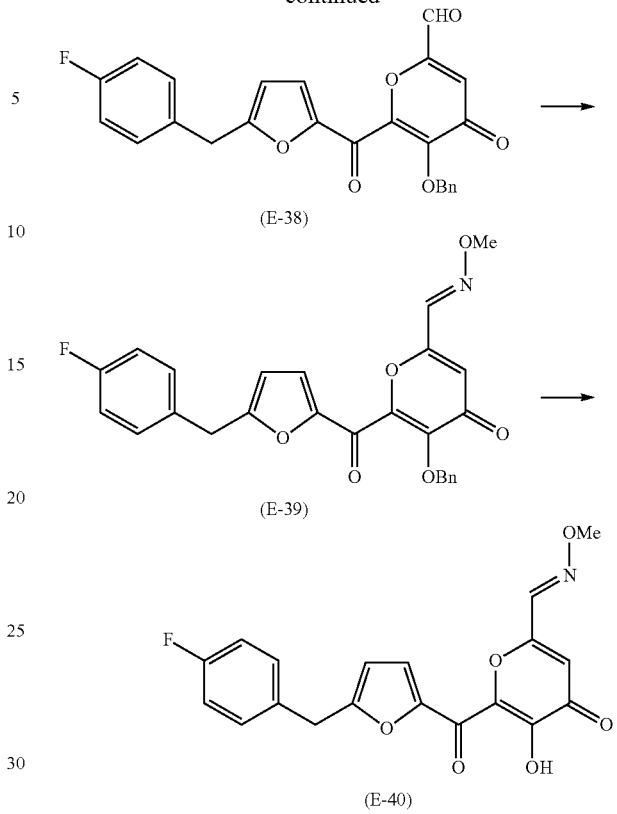

(E-38)

(E-39)

(E-40)

(E-38) To a solution of alcohol E-23 (1.00 g, 2.31 mmol) in chloroform (40 ml), was added manganese dioxide (4.02 g, 46.2 mmol) and the mixture was refluxed for 4 hours under heating. The insoluble product was separated with filtrate and the concentrated residue was dissolved in a solution of chloroform (40 ml) under reduced pressure. Manganese dioxide (4.02 g, 46.2 mmol) was added thereto and the mixture was refluxed for 2 hours under heating. The insoluble product was separated with filtrate. The concentrated residue under reduced pressure was purified with silica gel column chromatography (toluene:acetone=2:1) and crystallized from acetone-diisopropylether to give 5-benzyloxy6-[5-(4-fluorobenzyl)furan-2-carbonyl]-4-oxo-4H-pyrane-2-carboaldehyde (364 mg, yield: 36%).

Melting point: 69-72° C.

NMR (CDCl₃) δ: 4.01 (2H, s), 5.29 (2H, s), 6.17 (1H, d, J=3.6 Hz), 7.01 (2H, t like, J=8.7 Hz), 7.06 (1H, s), 7.16-7.30 (8H, m), 9.67 (1H, s).

(E-39) To a solution of the above-mentioned compound E-38 (150 mg, 0.346 mmol) in ethanol (5 ml)-water (1 ml), were added sodium acetate (85 mg) and hydrochloric acid O-methylhydroxylamine (35 mg) and the mixture was stirred at 80° C. for 5 hours. Water was added thereto and extracted with ethyl acetate. The extract was washed and dried. The solvent was evaporated under reduced pressure. The residue was purified with lober column (size B) (toluene:ethyl acetate=5:1) and crystallized from ethyl acetate-diisopropylether to give 5-benzyloxy6-[5-(4-fluorobenzyl)furan-2-carbonyl]-4-oxo-4H-pyrane-2-carboaldehyde O-methyloxime (103 mg, yield: 64%).

Melting point: 116-117° C.

NMR (CDCl₃) δ: 4.01 (2H, s), 4.02 (3H, s), 5.27 (2H, s), 6.14 (1H, d, J=3.6 Hz), 6.69 (1H, s), 7.00 (2H, t like, J=8.7 Hz), 7.15-7.30 (7H, m), 7.73 (1H, s).

(E-40) The above-mentioned compound E-39 (132 mg, 0.286 mmol) was dissolved in trifluoroacetic acid (1 ml) and the solution was stirred at room temperature for 35 minutes. The residue that trifluoroacetic acid was evaporated under reduced pressure was dissolved in chloroform, washed with water twice and dried. The solvent was evaporated under reduced pressure. The residue was crystallized from tetrahydrofuran-diisopropylether to give 6-[5-(4-fluorobenzyl)furan-2-carbonyl]-5-hydroxy-4-oxo-4H-pyrane-2-carboaldehyde O-methyloxime (100 mg, yield: 94%).

Melting point: 180-182° C.

NMR (CDCl$_3$) δ: 4.10 (3H, s), 4.12 (2H, s), 6.26 (1H, d, J=3.6 Hz), 6.54 (1H, s), 7.04 (2H, t like, J=8.7 Hz), 7.23-7.28 (2H, m), 7.80 (1H, s), 8.19 (1H, d, J=3.6 Hz), 11.97 (1H, br. s).

Compound E-43

6-[5-(4-fluorobenzyl)furan-2-carbonyl]-5-hydroxy-4-oxo-4H-pyrane-2-carbonitrile

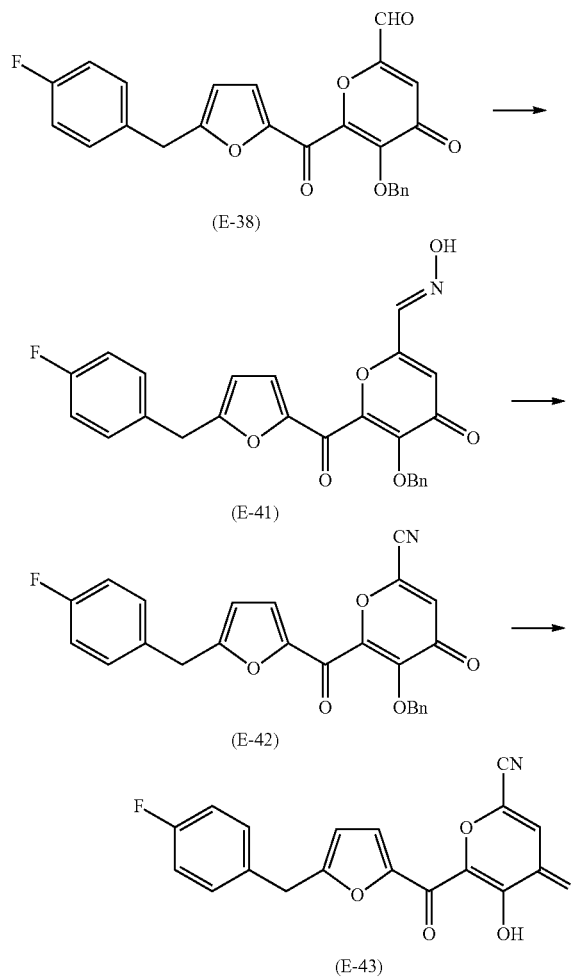

(E-41) To a solution of compound E-38 (264 mg, 0.611 mmol) in ethanol (5 ml)-water (1 ml), were added sodium acetate (150 mg) and hydroxylamine hydrochloride (51 mg) and the mixture was stirred at room temperature overnight. To a solution, water was added and the mixture was extracted with ethyl acetate. The extract was washed and dried. The solvent was evaporated under reduced pressure to give rude crystal (250 mg) of 5-benzyloxy6-[5-(4-fluorobenzyl)furan-2-carbonyl]-4-oxo-4H-pyrane-2-carboaldehyde oxime. This was used for the next reaction without purifying.

(E-42) To a solution of imidazole (250 mg) in methylene chloride (5 ml), was added thionyl chloride (0.067 ml) under ice-cooling and the mixture was stirred for 15 minutes. To the solution, was added a suspension of the above-mentioned compound E-41 (250 mg) in methylene chloride (10 ml) and the mixture was stirred under warming to room temperature for 51 minutes. Water was added to the solution and the mixture was extracted with chloroform. The extract was washed and dried. The solvent was evaporated under reduced pressure and the residue was purified with silica gel column chromatography (toluene:ethyl acetate=10:1) to give 5-benzyloxy-6-[5-(4-fluorobenzyl)furan-2-carbonyl]-4-oxo-4H-pyrane-2-carbonitrile (195 mg, 0.2 total yield of process: 74%).

NMR (CDCl$_3$) δ: 4.00 (2H, s), 5.26 (2H, s), 6.18 (1H, d, J=3.6 Hz), 6.95 (1H, s), 7.02 (2H, t like, J=8.7 Hz), 7.13-7.28 (8H, m).

(E-43) The above-mentioned compound E-42 (195 mg, 0.454 mmol) was dissolved in trifluoroacetic acid (2 ml) and the mixture was stirred at room temperature for 35 minutes. The residue which trifluoroacetic acid was evaporated under reduced pressure was dissolved in chloroform, washed with water twice and dried. The solvent was evaporated under reduced pressure. The residue was crystallized from tetrahydrofuran-diisopropylether to give 6-[5-(4-fluorobenzyl)furan-2-carbonyl]-5-hydroxy-4-oxo-4H-pyrane-2-carbonitrile (98 mg, yield: 64%).

Melting point: 190-194° C. (decomp.)

NMR (CDCl$_3$) δ: 4.12 (3H, s), 6.35 (1H, d, J=3.9 Hz), 6.95 (1H, s), 7.05 (2H, t like, J=8.7 Hz), 7.23-7.29 (2H, m), 7.67 (1H, d, J=3.9 Hz), 12.15 (1H, br. s).

Compound E-45

3-[6-[5-(4-fluorobenzyl)furan-2-carbonyl]-5-hydroxy-4-oxo-4H-pyrane-2-yl]ethyl acrylate

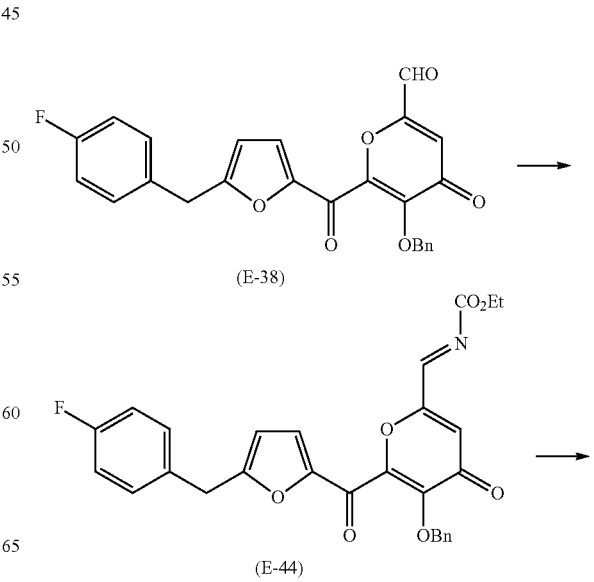

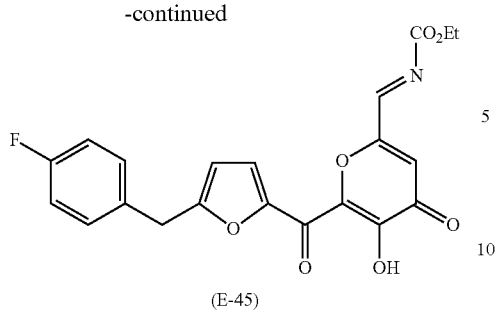

(E-45)

(E-44) To a suspension of 60% sodium hydride (20 mg, 0.5 mmol) in tetrahydrofuran (2 ml), was added diethylphosphonoethyl acetate (0.119 ml) and the mixture was stirred at room temperature for 10 minutes. To the solution, was added a solution of compound E-38 (220 mg, 0.506 mmol) in tetrahydrofuran (3 ml) under ice-cooling and the mixture was stirred for 35 minutes. The solution added ammonium chloride aqueous solution was extracted with ethyl acetate. The extract was washed and dried. The solvent was evaporated under reduced pressure and the residue was purified with lober column (size B) (toluene:ethyl acetate=5: 1) to give 3-[-5-benzyloxy[6-[5-(4-fluorobenzyl)furan-2-carbonyl]-4-oxo-4H-pyrane-2-yl]ethyl acrylate (149 mg, yield: 58%).

Melting point: 104-106° C.

NMR (CDCl$_3$) δ: 1.31 (3H, t, J=7.2 Hz), 4.00 (2H, s), 4.26 (2H, q, J=7.2 Hz), 5.25 (2H, s), 6.16 (1H, d, J=3.6 Hz), 6.56 (1H, d, J=15.3 Hz), 6.57 (1H, s), 7.00 (2H, t like, J=8.7 Hz), 7.13-7.29 (9H, m).

(E-45) The above-mentioned compound E-44 (149 mg, 0.297 mmol) was dissolved in trifluoroacetic acid (1 ml) and the mixture was stirred at room temperature for 35 minutes. The residue which trifluoroacetic acid was evaporated under reduced pressure was dissolved, washed with water twice and dried. The solvent was evaporated under reduced pressure. The residue was crystallized from tetrahydrofurandiisopropylether 3-[6-[5-(4-fluorobenzyl)furan-2-carbonyl]-5-hydroxy-4-oxo-4H-pyrane-2-yl]ethyl acrylate (99 mg, yield: 81%).

Melting point: 205-207° C.

NMR (CDCl$_3$) δ: 1.33 (3H, t, J=6.9 Hz), 4.17 (2H, s), 4.30 (2H, q, J=6.9 Hz), 6.32 (1H, d, J=3.6 Hz), 6.62 (1H, s), 6.83 (1H, d, J=15.6 Hz), 7.04 (2H, t like, J=8.7 Hz), 7.23-7.27 (2H, m), 7.30 (1H, d, J=15.6 Hz), 7.62 (1H, d, J=3.6 Hz), 11.85 (1H, br.s).

Compound E-50

5-bromo2-[5-(4-fluorobenzyl)furan-2-carbonyl]-3-hydroxypyrane-4-one

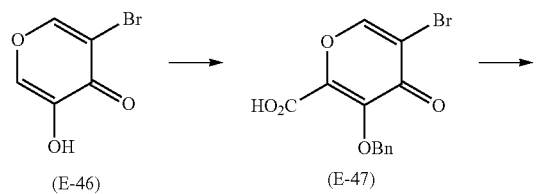

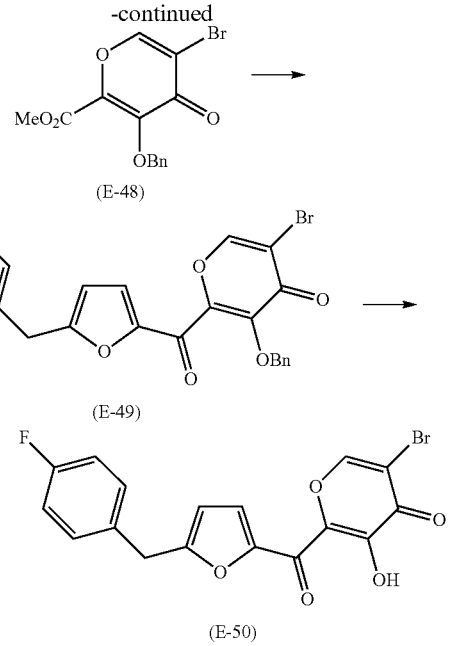

(E-47) To a solution of 3-bromo-5-hydroxypyrane-4-one E-46 (10.0 g, 52.4 mmol) synthesized according to the method described in reference (Heterocycles, 1992, 34, p 1803) in methyl alcohol (40 ml), was added sodium hydroxide (2.61 g, 65.3 mmol) aqueous solution (12 ml) and the mixture was stirred for 5 minutes. 37% formaldehyde aqueous solution (10.6 ml, 131 mmol) was added dropwise thereto over 40 minutes and the mixture was stirred overnight. After removing formaldehyde and methyl alcohol under reduced pressure, methyl alcohol (40 ml) and chlorobenzyl (7.2 ml, 62.9 mmol) were added to the residue and the mixture was stirred at 60° C. for 2 hours. After cooling, the mixture was neutralized with 2M hydrochloric acid and methyl alcohol was evaporated under reduced pressure. The water layer was extracted with ethyl acetate. The extract was washed and dried. The solvent was evaporated under reduced pressure to give crude product (12.2 g). To a solution of the obtained crude product (12.2 g) and 2,2,6,6-tetramethylpiperidine-1-oxyl, free radical (613 mg, 3.92 mmol) in ethyl acetate (80 ml), was added 1.0M sodium hydrogen carbonate aqueous solution (80 ml, 80 mmol). 10% sodium hyochlorite aqueous solution (58 ml, 78.5 mmol) was added dropwise thereto for 50 minutes with stirring hard under about 5° C. The water layer was divided, acidified with 2M hydrochloric acid and then extracted with ethyl acetate. The extract was washed and dried. The solvent was evaporated under reduced pressure to give 3-benzyloxy-5-bromo-4-oxo-4H-pyrane-2-carboxylic acid (6.26 g, yield: 37%).

(E-48) To a solution of the above-mentioned compound E-47 (685 mg, 2.11 mmol) in dimethylformamide (5 ml), were added 1,8-diazabicyclo[5,4,0]-7-undecen (0.35 ml, 2.32 mmol) and iodomethane (0.13 ml, 2.53 mmol) and the mixture was stirred at room temperature for 3 hours. Water was added to the solution and the mixture was extracted with ethyl acetate. The extract was washed and dried. The solvent was evaporated under reduced pressure to give 3-benzyloxy-5-bromo-4-oxo-4H-pyrane-2-carboxylate methyl ester (643 mg, yield: 90%).

NMR (CDCl$_3$) δ:3.89 (3H, s), 5.32 (2H, s), 7.32-7.40 (2H, m), 7.44-7.49 (2H, m), 8.11 (1H, s).

(E-49) A solution of 2-bromo-5-(4-fluorobenzyl)furan (181 mg, 0.708 mmol) in tetrahydrofuran (5 ml) was cooled to −78° C. 1.57M butyllithiumhexane solution (0.45 ml, 0.649 mmol) was added dropwise thereto. After stirring at the same temperature for 10 minutes, a solution of compound E-48 (200 mg, 0.59 mmol) in tetrahydrofuran (2 ml) was added thereto and the mixture was stirred for 80 minutes. The saturated ammonium chloride aqueous solution was added thereto and the mixture was extracted with ethyl acetate. The extract was washed and dried. The solvent was evaporated under reduced pressure and the residue was purified with silica gel column chromatography (n-hexane/ethyl acetate=3/1) to give 3-benzyloxy-5-bromo-2-[5-(4-fluorobenzyl)furan2-carbonyl]pyrane-4-one (109 mg, yield: 38%).

NMR (CDCl$_3$) δ: 3.99 (2H, s), 5.24 (2H, s), 6.14 (1H, d, J=3.6 Hz), 6.97-7.05 (2H, m), 7.13-7.21 (3H, m), 7.21-7.26 (5H, m), 8.11 (1H, s).

(E-50) The above-mentioned compound E-49 (100 mg, 0.207 mmol) was dissolved in trifluoroacetic acid (2 ml) and the mixture was stirred for 1 hour. The solvent was evaporated under reduced pressure. Water was added to the residue and the mixture was extracted with ethyl acetate. The extract was washed and dried. The solvent was evaporated under reduced pressure and the obtained solid was recrystallized with the acetone-methyl alcohol mixture to give 5-bromo-2-[5-(4-fluorobenzyl)furan-2-carbonyl]-3-hydroxypyrane-4-one (61 mg, yield: 75%).

Melting point: 191-192° C.

Elementary analysis as C$_{17}$H$_{10}$BrFO$_5$

Calcd. (%): C, 51.93; H, 2.56; Br, 20.32; F, 4.83.

Found (%): C, 52.12; H, 2.55; Br, 20.37; F, 4.66.

NMR (CDCl$_3$) δ:4.11 (2H, s), 6.28 (1H, d, J=3.7 Hz), 7.01-7.09 (2H, m), 7.21-7.29 (2H, m), 7.64 (1H, d, J=3.7 Hz), 8.16 (1H, s), 11.92 (1H, s).

Compound E-52

2-[5-(4-fluorobenzyl)furan-2-carbonyl]-3-hydroxy-5-phenylpyrane-4-one

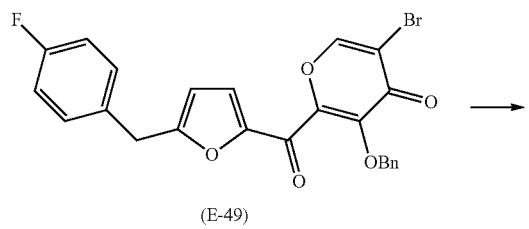

(E-49)

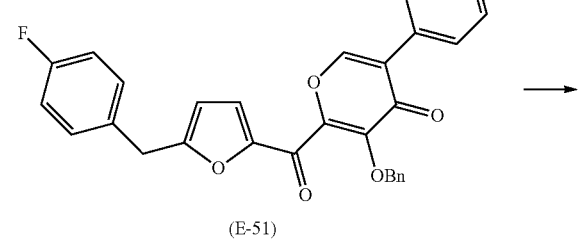

(E-51)

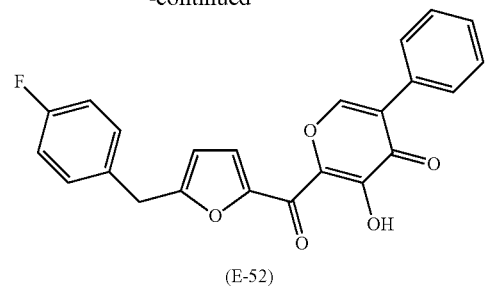

(E-52)

(E-51) To a solution of compound E-49 (250 mg, 0.518 mmol), phenylboronic acid (76 mg, 0.622 mmol) and tetrakistriphenylphosphine palladium (30 mg, 0.0259 mmol) in dimethoxyethane (4 ml) ethanol (1 ml), was added 2M sodium carbonate aqueous solution (0.93 ml, 1.86 mmol) and the mixture was fluxed under heating for 1 hour. After cooling, the saturated ammonium chloride aqueous solution was added thereto and the mixture was extracted with ethyl acetate. The extract was washed and dried. The solvent was evaporated under reduced pressure. The residue was purified with silica gel column chromatography (n-hexane/ethyl acetate=3/1) to give 3-benzyloxy-2-[5-(4-fluorobenzyl)furan-2-carbonyl]-5-phenylpyrane-4-one (67 mg, yield: 27%).

NMR (CDCl$_3$) δ: 4.02 (2H, s), 5.25 (2H, s), 6.15 (1H, d, J=3.6 Hz), 6.97-7.05 (2H, m), 7.17-7.38 (7H, m), 7.41-7.50 (4H, m), 7.52-7.58 (2H, m), 7.92 (1H, s).

(E-52) According to the same method of example E-16, 2-[5-(4-fluorobenzyl)furan-2-carbonyl]-3-hydroxy-5-phenylpyrane-4-one (28 mg, yield: 51%) was synthesized from the above-mentioned compound E-51 (67 mg, 0.140 mmol).

Melting point: 199-201° C.

NMR (CDCl$_3$) δ:4.12 (2H, s), 6.27 (1H, d, J=3.6 Hz), 7.01-7.09 (2H, m), 7.22-7.28 (2H, m), 7.40-7.50 (3H, m), 7.53-7.58 (2H, m), 7.69 (1H, d, J=3.6 Hz), 7.98 (1H, s), 11.68 (1H, s).

F Group Compound

Compound F-4

3-[5-(4-fluorobenzyl)furan-2-carbonyl]-2-hydroxy-2-cyclohexene-1-one

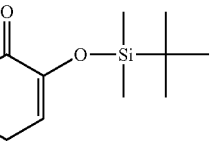

(F-1)

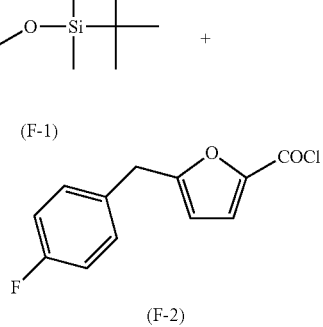

(F-2)

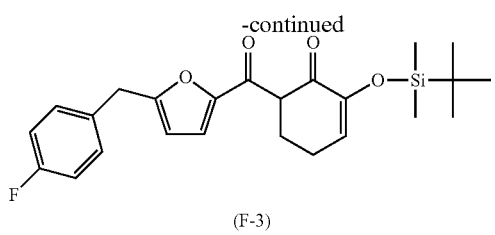

(F-3)

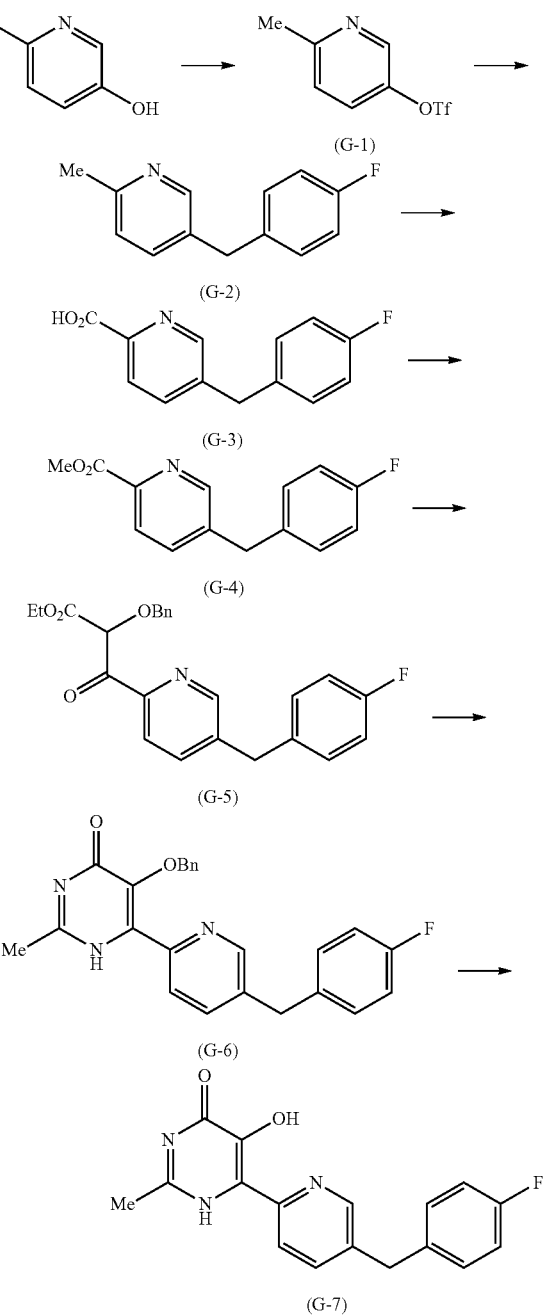

(F-4)

(F-3) To a lithiumbistrimethylsilylamide solution prepared from hexamethyldisilazane (0.23 ml) and n-butyllithium (1.1 mmol) in tetrahydrofuran (3 ml), was added dropwise a solution of 2-(tert-butyldimethylsilyloxy)-2-cyclohexene-1-one (F–1) (226 mg, 1.0 mmol) synthesized according to the method described in reference (Tetrahedron, 1997, 53, p 8963) in tetrahydrofuran (2 ml) under cooling at −78° C. After stirring at the same temperature for 19 minutes, a solution of 5-(4-fluorobenzyl)furan-2-carboxylate chloride (F-2) (WO-00039086, example 120) (120 mg, 0.5 mmol) in tetrahydrofuran (1 ml) was added dropwise thereto. After stirring for 1 hour, the mixture was warmed to 0° C. over 20 minutes. The ammonium chloride aqueous solution was added to the solution and the mixture was extracted with ethyl acetate. The extract was washed and dried. The solvent was evaporated under reduced pressure and the residue was purified with silica gel column chromatography (n-hexane: ethyl acetate=10:1-5:1) to give 2-(tert-butyldimethylsilyloxy)-6-[5-(4-fluorobenzyl)furan-2-carbonyl]-2-cyclohexene-1-one (189 mg, yield: 88%).

(F-4) To a solution of the above-mentioned compound F-3 (172 mg, 0.40 mmol) in tetrahydrofuran (1 ml)-methyl alcohol (4 ml), was added 2n-hydrochloric acid (1 ml) and the mixture was stirred at room temperature for 15 minutes and then at 50° C. for 1 hour. Ice water was added to the solution and the mixture was extracted with ethyl acetate. The extract was washed and dried. The solvent was evaporated under reduced pressure and the residue was crystallized from ethyl acetate diisopropylether to give 3-[5-(4-fluorobenzyl)furan-2-carbonyl]-2-hydroxy-2-cyclohexene-1-one (85 mg, yield: 68%).

Melting point: 133-134° C.

Elementary analysis as $C_{18}H_{15}FO_4$

Calcd. (%): C, 68.78; H, 4.81; F, 6.04.

Found (%): C, 68.56; H, 54.77; F, 5.90.

NMR (CDCl$_3$) δ:2.02-2.10 (2H, m), 2.61 (2H, t like, J=7 Hz), 2.87 (2H, t, J=6.0 Hz), 4.06 (2H, s), 6.22 (1H, J=3.6 Hz), 7.03 (2H, t like, J=9 Hz), 7.23 (2H, dd, J=8.3 Hz, 5.3 Hz), 7.30 (1H, d, J=3.6 Hz), 13.26 (1H, br.s). There was the mixture of three kinds of tautomers in CDCl$_3$ and the data of compound F-4, which had the highest presence ratio (70%), was shown.

G Group Compound

Compound G-7

6-[5-(4-fluorobenzyl)pyridine-2-yl]-5-hydroxy2-methyl-1H-pyrimidine-4-one (G-1) 5-hydroxy-2-methylpyridine (10.9 g, 100 mmol) and pyridine (12.2 ml, 150 mmol) was dissolved in methylene chloride (100 ml) and trifluoromethanesulfonic acid anhydride (18.5 ml, 120 mmol) was added dropwise thereto under ice-cooling. After stirring at the same temperature for 1.5 hours, methyl alcohol (2 ml) and then the saturated sodium hydrogen carbonate aqueous solution (150 ml) were added thereto and the mixture was extracted with methylene chloride. The extract was washed and dried. The solvent was evaporated under reduced pressure and the residue was purified with silica gel column chromatography (n-hexane: ethyl acetate=9:1-4:1) to give 2-methyl-5-(trifluoromethanesulfonyloxy)pyridine (23.0 g, yield: 95%).

(G-2) To a solution of the above-mentioned compound G-1 (10.4 g, 43.2 mmol) in tetrahydrofuran (130 ml), were added 4-fluorobenzyl bromidezinc-tetrahydrofuran solution (65 mmol) synthesized according to the method described in reference (J. Org. Chem., 1994, 59, p 2671) and tetrakis(triphenylphosphine)palladium (2.4 g) and the mixture was refluxed under heating for 5 hours. The solvent was evaporated under reduced pressure. Water and ethyl acetate was added to the residue and the insoluble product was filtrated with celite. The filtration was extracted with ethyl acetate and the residue was washed with water. The obtained solution of ethyl acetate was extracted with 1n-hydrochloric acid. The hydrochloric acid extract turned alkaline with 2n-sodium hydroxide aqueous solution. The solution was extracted with ethyl acetate, washed and dried. The residue which the solvent was evaporated was purified with silica gel column chromatography (n-hexane:ethyl acetate=2:1) to give 5-(4-fluorobenzyl)-2-methylpyridine (5.42 g, yield: 62%).

NMR (CDCl$_3$) δ:2.53 (3H, s), 3.91 (2H, s), 6.96 (2H, t like, J=8.7 Hz), 7.06-7.15 (3H, m), 7.34 (1H, dd, J=8.1 Hz, 1.5 Hz), 7.36 (1H, d, J=1.5 Hz).

(G-3) To a solution of the above-mentioned compound G-2 (4.64 g, 22.9 mmol) in pyridine (40 ml), was added selenium dioxide (15.3 g, 138 mmol) and the mixture was refluxed under heating for 36 hours. Water and chloroform were added to the residue, which pyridine was evaporated under reduced pressure. The insoluble product was separated with filtrate. The filtration was extracted with chloroform and the extract was washed and dried. The solvent was evaporated under reduced pressure. The residue was dissolved in toluene (50 ml) and the solution was treated with active carbon (4 g). The solvent was evaporated under reduced pressure to give crude product (5.6 g) of 5-(4-fluorobenzyl)pyridine-2-carboxylic acid.

Furthermore, using 5-(4-fluorophenyloxy)-2-methylpyridine synthesized according to the method described in reference (JP1979-125681), 5-(4-fluorophenyloxyl)pyridine-2-carboxylic acid was synthesized according to the same method.

(G-4) To a solution of the above-mentioned crude product G-3 (5.6 g) in methyl alcohol (50 ml), was added dropwise thionyl chloride (8.36 ml, 115 mmol) under ice-cooling. After adding dropwise, the mixture was refluxed under heating for 4 hours. Water and ethyl acetate were added thereto under ice-cooling. Sodium hydrogen carbonate (14 g) was added gradually at the same temperature and the mixture was extracted with ethyl acetate. The extract was washed and dried. The solvent was evaporated under reduced pressure and the residue was purified with silica gel column chromatography (n-hexane:acetone=2:1) to give 5-(4-fluorobenzyl)pyridine-2-carboxylate methyl (3.40 g, 2 total yield of process: 60%).

NMR (CDCl$_3$) δ:4.00 (3H, s), 4.04 (2H, s), 7.01 (2H, t like, J=8.7 Hz), 7.10-7.16 (2H, m), 7.58 (1H, dd, J=7.8 Hz, 2.4 Hz), 8.06 (1H, d, J=7.8 Hz), 8.62 (1H, d, J=2.4 Hz).

According to the same method, 5-(4-fluorophenyloxy) pyridine-2-carboxylate methyl was synthesized.

NMR (CDCl$_3$) δ:4.00 (3H, s), 7.03-7.16 (4H, m), 7.25 (1H, dd, J=8.7 Hz, 2.4 Hz), 8.10 (1H, dd, J=8.7 Hz), 8.47 (1H, d, J=2.4 Hz).

(G-5) To a solution of benzyloxyethyl acetate (521 mg, 2.7 mmol) in tetrahydrofuran (10 ml), was added dropwise lithium (bistrimethylsilyl)amidetetrahydrofuran solution (2.7 mmol) at −78° C. After stirring at the same temperature for 25 minutes, a solution of the above-mentioned compound G-4 (328 mg, 1.34 mmol) in tetrahydrofuran (5 ml) was added dropwise thereto and the mixture was stirred for 32 minutes. To the solution, was added saturated ammonium chloride aqueous solution and the mixture was extracted with ethyl acetate. The extract was washed and dried. The solvent was evaporated under reduced pressure and the residue was purified with silica gel column chromatography (n-hexane:acetone=3:1) to give 2-benzyloxy-3-[5-(4-fluorobenzyl)pyridine-2-yl]-3-oxo ethyl propionate (315 mg, yield: 58%).

According to the same method, 2-benzyloxy-3-[5-(4-fluorophenyloxyl)pyridine-2-yl]-3-oxo ethyl propionate was synthesized.

Furthermore, using [5-(4-fluorobenzyl)-[1,3,4]oxadiazole-2-carboxylate ethyl synthesized according to the method described in reference (Carbohydr. Res., 1994, 254, p 91), 2-benzyloxy-3-[5-(4-fluorobenzyl)-[1,3,4]oxadiazole-2-yl]-3-oxo ethyl propionate was synthesized.

(G-6) The above-mentioned compound G-5 (315 mg, 0.77 mmol) and acetoamidine hydrochloride (293 mg, 3.1 mmol) were dissolved in a solution of methyl alcohol (6 ml). 28% sodium methoxide-methyl alcohol solution (0.47 ml) was added thereto and the mixture was refluxed under heating for 2 hours 25 minutes. To the solution, which cooled to room temperature, was added the saturated ammonium chloride aqueous solution and the mixture was extracted with ethyl acetate. The extract was washed and dried. The solvent was evaporated under reduced pressure and the residue was crystallized from ethyl acetate isopropylether to give 5-benzyloxy-6-[5-(4-fluorobenzyl)pyridine-2-yl]-2-methyl-1H-pyrimidine-4-one (164 mg, yield: 53%).

NMR (CDCl$_3$) δ:2.57 (3H, s), 4.01 (2H, s), 5.20 (2H, s), 7.01 (2H, t like, J=8.7 Hz), 7.10-7.18 (2H, m), 7.20-7.27 (5H, m), 7.49 (1H, dd, J=8.1 Hz, 2.1 Hz), 7.88 (1H, d, J=8.1 Hz), 8.64 (1H, d, J=2.1 Hz).

The following compound was prepared as well as above.

5-benzyloxy-6-[5-(4-fluorophenyloxyl)pyridine-2-yl]-2-methyl-1H-pyrimidine-4-one NMR (CDCl$_3$) δ: 2.59 (3H, s), 5.21 (2H, s), 7.00-7.14 (4H, m), 7.21-7.31 (6H, m), 7.93 (1H, d, J=9.0 Hz), 8.49 (1H, d, J=2.7 Hz).

5-benzyloxy-6-[5-(4-fluorobenzyl)-[1,3,4]oxadiazole-2-yl]-2-methyl-1H-pyrimidine-4-one NMR (CDCl$_3$) δ: 2.55 (3H, s), 4.23 (2H, s), 5.36 (2H, s), 7.23-7.40 (6H, m), 12.61 (1H, br.s).

(G-7) To a solution of the above-mentioned compound G-6 (102 mg, 0.25 mmol) in tetrahydrofuran (2 ml)-methyl alcohol (2 ml), was added 10% palladium-carbon (13 mg) and the mixture was stirred under hydrogen atmosphere at room temperature for 10 minutes. Chloroform (8 ml) and methyl alcohol (3 ml) was added to the solution. The precipitated crystal was dissolved in the solution and catalyst was separated with filtrate. The solvent was evaporated under reduced pressure and the crystalline residue was recrystallized from N,N-dimethylformamide to give 6-[5-(4-fluorobenzyl)pyridine-2-yl]-5-hydroxy-2-methyl-1H-pyrimidine-4-one (47 mg, yield: 59%).

Melting point: >300° C.
Elementary analysis as $C_{17}H_{14}FN_3O_2$
Calcd. (%): C, 65.59; H, 4.53; N, 13.50; F, 6.10.
Found (%): C, 65.57; H, 4.44; N, 13.50; F, 5.82.
NMR (DMSO-$d_6$) δ:2.27 (3H, s), 4.07 (3H, s), 7.15 (2H, t like J=9 Hz), 7.30-7.38 (2H, m), 7.93 (1H, dd, J=1.8 Hz, 8.1 Hz), 8.23 (1H, d, J=8.1 Hz), 8.59 (1H, d, J=1.8 Hz), 12.41 (1H, br.s), 13.82 (1H, br.s).
The following compound was prepared as well as above.

6-[5-(4-fluorophenyloxyl)pyridine-2-yl]-5-hydroxy-2-methyl-1H-pyrimidine-4-one (G-7-a)

Melting point: 255-256° C.
Elementary analysis as $C_{16}H_{12}FN_3O_3 \cdot 0.5H_2O$
Calcd. (%): C, 59.63; H, 4.07; N, 13.04; F, 5.89.
Found (%): C, 59.71; H, 4.04; N, 12.93; F, 5.74.
NMR (DMSO-$d_6$) δ: 2.28 (3H, s), 7.22-7.36 (4H, m), 7.68 (1H, dd, J=3 Hz, 9 Hz), 8.29 (1H, d, J=9 Hz), 8.47 (1H, d, J=3 Hz), 12.43 (1H, br.s), 13.23 (1H, br.s).

6-[5-(4-fluorobenzyl)-[1,3,4]oxadiazole-2-yl]-5-hydroxy-2-methyl-1H-pyrimidine-4-one (G-7-b)

Melting point: 283-286° C.
Elementary analysis as $C_{14}H_{11}FN_4O_3$
Calcd. (%): C, 55.63; H, 3.67; N, 18.54; F, 6.29.
Found (%): C, 55.61; H, 3.69; N, 18.36; F, 5.99.
NMR (DMSO-$d_6$) δ:2.25 (3H, s), 4.37 (2H, s), 7.20 (2H, t like J=9 Hz), 7.36-7.42 (2H, m).

H Group Compound

Compound H-7

3-hydroxy-1-isopropyl-4-(6-phenethylpyrimidine-4-yl)-1,5-dihydropyrrole-2-one

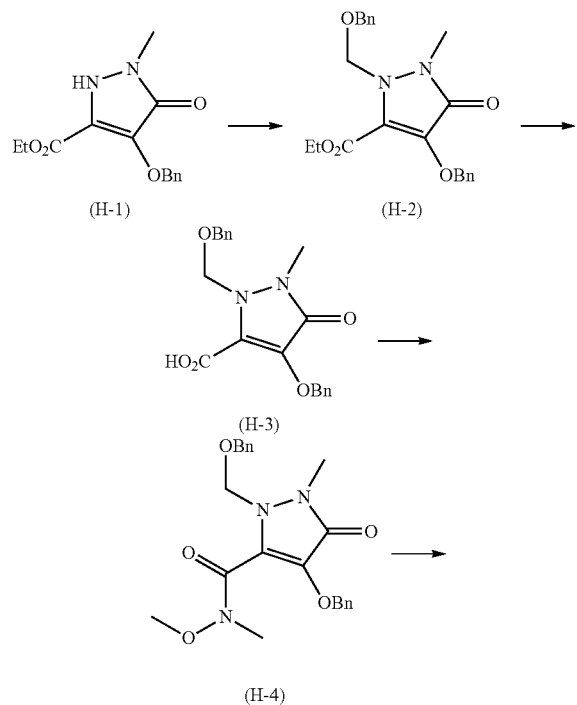

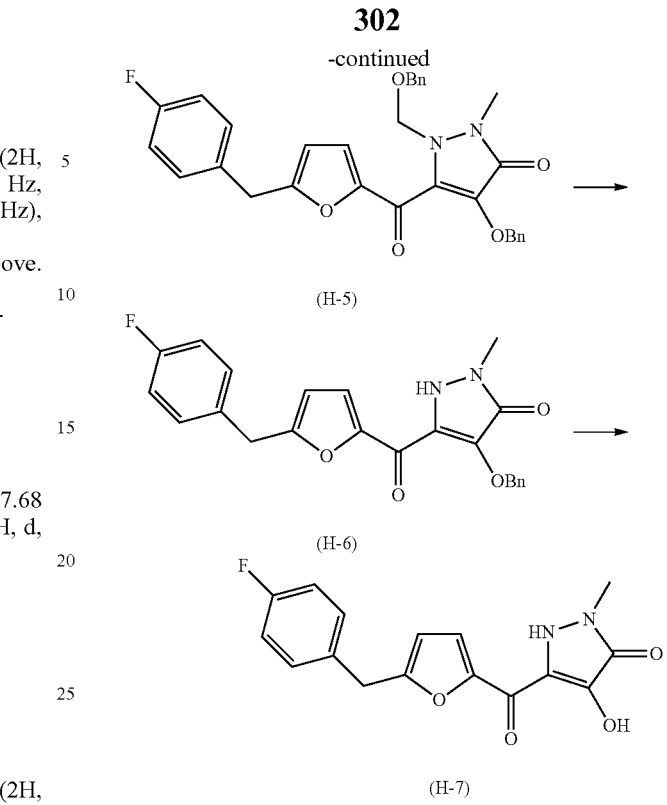

(H-1) According to the method described in reference (Tetrahedron 1997, 53 (15), 5617), 4-benzyloxy-1-methyl-5-oxo-2,5-dihydro-1H-pyrazole-3-carboxylate ethyl ester was synthesized.
Melting point: 131-133° C.
NMR (CDCl$_3$) δ: 1.39 (3H, t, J=7.0 Hz), 3.58 (3H, s), 4.40 (2H, q, J=7.0 Hz), 5.03 (2H, s), 7.33-7.39 (5H, m).
(H-2) To a solution of sodium hydride (856 mg, 21.4 mmol) and dimethylformamide (25 ml), was added the above-mentioned compound H-1 (4.93 g, 17.8 mmol) and the mixture was stirred for 30 minutes. Chloromethoxymethylbenzene (3.35 g, 21.4 mmol) was added thereto under ice-cooling and the mixture was warmed to room temperature and stirred for 30 minutes. The ammonium chloride aqueous solution was added thereto to stop the reaction and the mixture was extracted with diethyl ether. The extract was washed and dried. The solvent was evaporated under reduced pressure to give 4-benzyloxy-2-benzyloxymethyl-1-methyl-5-oxo-2,5-dihydro-1H-pyrazole-3-carboxylate ethyl ester (6.68 g, yield: 95%).
NMR (CDCl$_3$) δ: 1.40 (3H, t, J=7.0 Hz), 3.67 (3H, s), 4.42 (2H, q, J=7.0 Hz), 4.73 (2H, s), 5.05 (2H, s), 5.33 (2H, s), 7.26-7.44 (10H, m).
(H-3) To a solution of the above-mentioned compound H-2 (6.68 g, 16.8 mmol) in methyl alcohol (50 ml), was added 1N-lithium hydroxide aqueous solution (25.3 ml, 25.3 mmol). The mixture was warmed to 60° C. and stirred for 2 hours. Methyl alcohol was evaporated under reduced pressure and the water layer was washed with diethyl ether. The aqueous solution was acidified with citric acid and the mixture was extracted with ethyl acetate. The extract was washed and dried and the solvent was evaporated to give 4-benzyloxy-2-benzyloxymethyl-1-methyl-5-oxo-2,5-dihydro-1H-pyrazole-3-carboxylic acid (5.28 g, yield: 85%).
NMR (DMSO-$d_6$) δ: 3.63 (3H, s), 4.77 (2H, s), 4.98 (2H, s), 5.34 (2H, s), 7.25-7.38 (10H, m).

(H-4) A solution of the above-mentioned product H-3 (5.28 g, 14.3 mmol), 1-hydroxybenzotriazole (189 mg, 1.4 mmol), 1-ethyl-3-(3-dimethylaminopropyl)carbodiimidehydrochloride (3.3 g, 17.2 mmol),N,O-dimethylhydroxyamine (1.68 g, 17.2 mmol) and triethylamine (1.74 g, 17.2 mmol) in dimethylformamide (50 ml) was stirred at room temperature for 3 hours. Water was added thereto to stop the reaction and the mixture was extracted with ethyl acetate. The extract was washed and dried. The solvent was evaporated under reduced pressure and the residue was purified with silica gel column chromatography (n-hexane-ethyl acetate=1:1-1:2) to give 4-benzyloxy-2-benzyloxymethyl-1-methyl-5-oxo-2, 5-dihydro-1H-pyrazole-3-carboxylic acid methoxy-methylamide (3.89 g, yield: 66%).

NMR (CDCl$_3$) δ: 3.37 (3H, s), 3.63 (3H, s), 3.76 (3H, s), 4.75 (2H, s), 5.12 (2H, s), 5.32 (2H, s), 7.26-7.37 (10H, m).

(H-5) To a solution of 2-bromo-5-(4-fluorobenzyl)furan (2.41 g, 9.45 mmol) synthesized according to the method of example A-6 in THF (60 ml), were added n-butyllithium (9.45 mmol) at −78° C. and then a solution of the above-mentioned compound H-4 (3.89 g, 9.45 mmol) in THF (10 ml). The ammonium chloride aqueous solution was added thereto to stop the reaction and the mixture was extracted with ethyl acetate. The extract was washed and dried. The solvent was evaporated under reduced pressure and the residue was purified with silica gel column chromatography (n-hexane-ethyl acetate=3:1-1:2) to give 4-benzyloxy-1-benzyloxymethyl-5-[5-(4-fluorobenzyl)furan-2-carbonyl]-2-methyl-1,2-dihydropyrazole-3-one (2.36 g, yield: 47%).

NMR (CDCl$_3$) δ: 3.67 (3H, s), 4.07 (2H, s), 4.76 (2H, s), 5.10 (2H, s), 5.37 (2H, s), 6.10 (1H, d, J=3.6 Hz), 6.97-7.03 (2H, m), 7.21-7.36 (10H, m), 7.45-7.48 (2H, m), 7.69 (1H, d, J=3.4 Hz).

(H-6) To a solution of the above-mentioned compound H-5 (2.36 g, 4.48 mmol) in dioxane (205 ml), was added 6N hydrochloric acid aqueous solution (20 ml) and the mixture was stirred at room temperature for 1 hour. The solvent was evaporated under reduced pressure and the residue was purified with silica gel column chromatography (n-hexane-ethyl acetate=1:1-0:1) to give 4-benzyloxy-5-[5-(4-fluorobenzyl)furan-2-carbonyl]-2-methyl1,2-dihydropyrazole-3-one (1.56 g, yield: 86%).

NMR (CDCl$_3$) δ: 3.61 (3H, s), 4.06 (2H, s), 5.09 (2H, s), 6.11 (1H, d, J=3.7 Hz), 7.98-7.03 (2H, m), 7.21-7.42 (7H, m), 7.71 (1H, d, J=3.1 Hz).

(H-7) To a solution of the above-mentioned compound H-6 (837 mg, 2.1 mmol) in acetic acid (10 ml), was added 47% hydrogen bromide aqueous solution (10 ml) and the mixture was stirred at 50° C. for 1 hour. The solvent was evaporated under reduced pressure and the residue was dissolved in ethyl acetate, washed with water and dried. The precipitated crystal obtained by evaporating solvent under reduced pressure was washed with n-hexane-ethyl acetate (2:1) to give 3-hydroxy-1-isopropyl-4-(6-phenethylpyrimidine-4-yl)-1,5-dihydropyrrole-2-one (476 mg, yield: 72%).

Melting point: 156-159° C.

Elementary analysis as $C_{16}H_{13}FN_2O_4$

Calcd. (%): C, 60.76; H, 4.14; N, 8.86; F, 6.01.

Found (%): C, 60.94; H, 4.16; N, 8.66; F, 5.86.

NMR (CDCl$_3$) δ: 3.77 (3H, s), 4.09 (2H, s), 6.21 (1H, d, J=3.7 Hz), 6.99-7.05 (2H, m), 7.26-7.32 (2H, m), 8.00 (1H, d, J=3.7 Hz).

Compound H-13

5-[5-(4-fluorobenzyl)furan-2-carbonyl]-4-hydroxy-1,2-dimethyl-1,2-dihydropyrazole-3-one

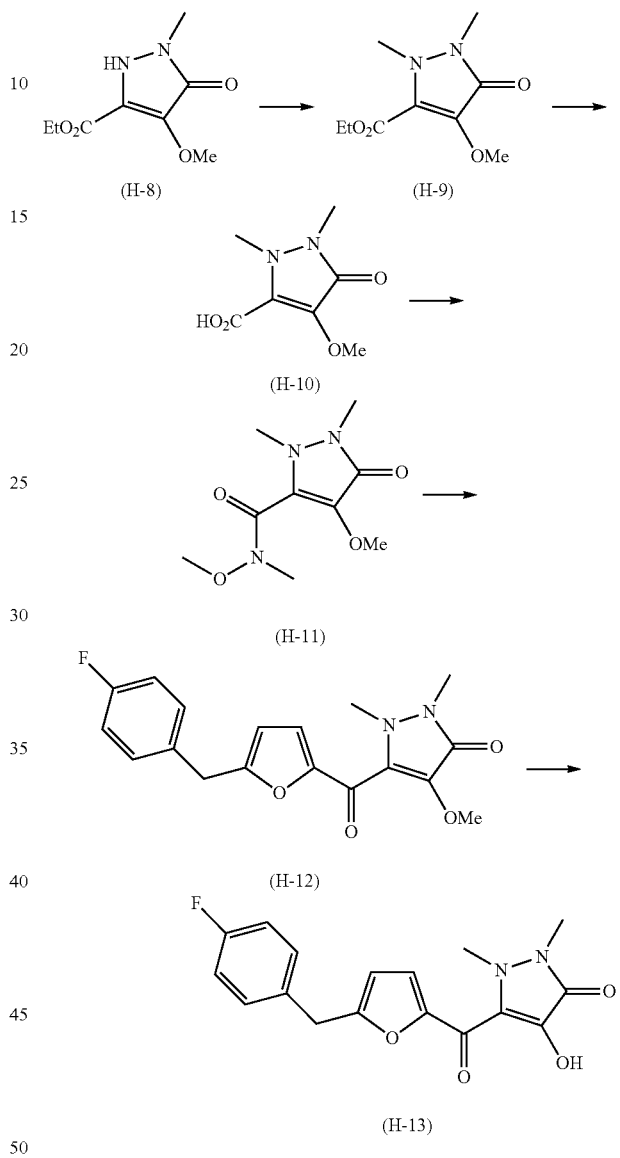

(H-8) According to the method described in reference (Tetrahedron 1997, 53 (15), 5617), 4-methoxy-1-methyl-5-oxo-2,5-dihydro-1H-pyrazole-3-carboxylate ethyl ester was synthesized.

Melting point: 99-100° C.

NMR (CDCl$_3$) δ: 1.37 (3H, t, J=7.0 Hz), 3.67 (3H, s), 3.84 (3H, s), 4.38 (2H, q, J=7.0 Hz).

(H-9) Using the above-mentioned compound H-8 and iodo methane according to the synthetic method of (H-2), 4-methoxy-1,2-dimethyl-5-oxo-2,5-dihydro-1H-pyrazole-3-carboxylate ethyl ester was synthesized.

NMR (CDCl$_3$) δ: 1.41 (3H, t, J=7.0 Hz), 3.68 (3H, s), 3.87 (3H, s), 4.09 (3H, s), 4.41 (2H, q, J=7.0 Hz).

(H-10). Using the above-mentioned compound H-9 according to the synthetic method of (H-3), the crude product of 4-methoxy-1,2-dimethyl-5-oxo-2,5-dihydro-1H-pyrazole-3-carboxylic acid was synthesized.

(H-11) Using the above-mentioned crude product H-10 according to the synthetic method of (H-4), 4-methoxy-1,2-dimethyl-5-oxo-2,5-dihydro-1H-pyrazole-3-carboxylic acid methoxy-methyl-amide was synthesized.

NMR (CDCl$_3$) δ: 3.39 (3H, s), 3.63 (3H, s), 3.77 (3H, s), 3.83 (3H, s), 4.07 (3H, s).

(H-12) Using the above-mentioned product H-11 according to the synthetic method of (H-5), 5-[5-(4-fluorobenzyl)furan-2-carbonyl]-4-methoxy-1,2-dimethyl-1,2-dihydropyrazole-3-one was synthesized.

Melting point: 111-113° C.

NMR (CDCl$_3$) δ: 3.69 (3H, s), 3.89 (3H, s), 4.06 (2H, s), 4.11 (3H, s), 6.09 (1H, d, J=3.7 Hz), 6.97-7.03 (2H, m), 7.21-7.26 (2H, m), 7.66 (1H, d, J=3.7 Hz).

(H-13) The above-mentioned compound H-12 (750 mg, 2.18 mmol) and pyridinehydrochloride (7.5 g) were heated to 150° C. for 12 minutes. Water was added thereto to stop the reaction and the mixture was extracted with ethyl acetate. The extract was washed and dried. The solvent was evaporated under reduced pressure and the precipitated crystal was recrystallized with n-hexane-ethyl acetate (2:1) to give (5-[5-(4-fluorobenzyl)furan-2-carbonyl]-4-hydroxy-1,2-dimethyl-1,2-dihydropyrazole-3-one (250 mg, yield: 35%).

Melting point: 110-111° C.

Elementary analysis as $C_{17}H_{15}FN_2O_4$

Calcd. (%): C, 61.82; H, 4.58; N, 8.48; F, 5.75.

Found (%): C, 61.82; H, 4.46; N, 8.41; F, 5.64.

NMR (CDCl$_3$) δ: 3.68 (3H, s), 3.92 (3H, s), 4.06 (2H, s), 6.12 (1H, d, J=3.4 Hz), 6.97-7.03 (2H, m), 7.21-7.26 (2H, m), 7.71 (1H, d, J=3.7 Hz).

I Group Compound

Compound I-3

4-[5-(4-fluorobenzyl)furan-2-carbonyl]-3-hydroxy-5,6-dihydro-1H-pyridine-2-one

Compound I-4

1-ethyl4-[5-(4-fluorobenzyl)furan-2-carbonyl]-3-hydroxy-5,6-dihydro-1H-pyridine-2-one

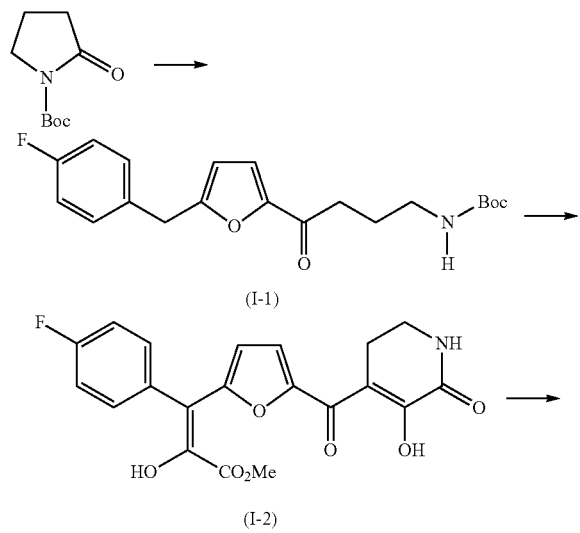

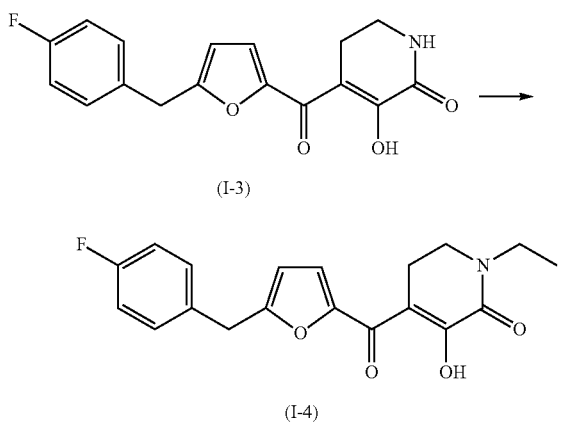

(I-1) Aluminum chloride (2.96 g, 22.2 mmol) was suspended in tetrahydrofuran (30 ml) and sodium borohydride (1.41 g, 37.3 mmol) was added thereto under ice-cooling. After stirring for 10 minutes, (5-bromofuran-2-yl-(4-fluorophenyl)metanone (2.00 g, 7.43 mmol) was added thereto and the mixture was refluxed under heating for 20 minutes. After cooling, water (60 ml) was added dropwise to the solution and the mixture was extracted with diethyl ether. The extract was washed and dried. The solvent was evaporated under reduced pressure to give 2-bromo-5-(4-fluorobenzyl)furan. This residue was dissolved in tetrahydrofuran (40 ml) and n-butyllithium (5.20 ml, 8.16 mmol) was added dropwise at −78° C. After 5 minutes, 2-oxo pyrrolidine-1-carboxylic acid tert-butylester (2.76 g, 14.9 mmol) in tetrahydrofuran (5 ml) known by reference (Tetrahedron Lett., 36, 8949-8952 (1995)) was added thereto and the mixture was stirred for 2 hours. The saturated ammonium chloride aqueous solution was added to the solution to stop the reaction and the mixture was extracted with ethyl acetate. The extract was washed and dried. The solvent was evaporated under reduced pressure and the residue was purified with silica gel column chromatography (n-hexane:ethyl acetate=3:1) to give {4-[5-(4-fluorobenzyl)furan-2-yl]-4-oxobutyl}carbamic acid tert-butylester (1.95 g, yield: 73%).

NMR (CDCl$_3$) δ: 1.42 (9H, s), 1.89 (2H, m), 2.81 (2H, t, J=7.2 Hz), 3.19 (2H, m), 4.01 (2H, s), 4.64 (1H, brs), 6.09 (1H, d, J=3.5 Hz), 7.01 (2H, m), 7.10 (1H, d, J=3.5 Hz), 7.21 (2H, m).

(I-2) To a solution of the above-mentioned compound I-1 (900 mg, 2.49 mmol) and dimethyl oxalate (881 mg, 7.46 mmol) in toluene (20 ml), was added sodium ethoxide (5.00 mmol, 28% methyl alcohol solution) and the mixture was stirred at room temperature for 4 hours. 5N hydrochloric acid (5 ml) was added to the solution to stop the reaction and the mixture was extracted with ethyl acetate-tetrahydrofuran. The extract was washed and dried and the solvent was evaporated under reduced pressure to give the crude product of 3-(4-fluorophenyl)-2-hydroxy-3-[5-(5-hydroxy-6-oxo-1,2,3,6-tetrahydropyridine-4-carbonyl)furan-2-yl]propenoic acid methylester.

(I-3) To a solution of the crude product of the above-mentioned compound I-2 in tetrahydrofuran (50 ml), was added 1N lithium hydroxide aqueous solution (20 ml) at 60°

C. and the mixture was stirred for 2 hours. 5N hydrochloric acid (4 ml) was added to the solution to stop the reaction and the mixture was extracted with ethyl acetate. The extract was washed and dried. The solvent was evaporated under reduced pressure. The obtained precipitated crystal was recrystallized with methyl alcohol to give 4-[5-(4-fluorobenzyl)furan-2-carbonyl]-3-hydroxy-5,6-dihydro-1H-pyridine-2-one (138 mg, yield: 18%).

Melting point: 166-168° C.

Elementary analysis as $C_{17}H_{14}FNO_4$

Calcd. (%): C, 64.76; H, 4.48; N, 4.44; F, 6.03.

Found (%): C, 64.51; H, 4.55; N, 4.41; F, 5.88.

NMR (CDCl$_3$) δ: 2.96 (2H, t, J=6.8 Hz), 3.46 (2H, dt, J=2.9, 6.8 Hz), 4.05 (2H, s), 6.22 (1H, d, J=3.5 Hz), 6.57 (1H, brs), 7.03 (2H, m), 7.21 (2H, m), 7.29 (1H, d, J=3.5 Hz), 14.75 (1H, brs).

(I-4) To a solution of the above-mentioned compound I-3 (336 mg, 1.07 mmol) and bromoethane (0.320 ml, 4.29 mmol) in tetrahydrofuran (27 ml), was added a solution of potassium bis(trimethylsilyl)amide (2.70 mmol, 0.5M toluene solution) and the mixture was refluxed under heating for 2.5 hours. 2N hydrochloric acid (30 ml) was added to the solution to stop the reaction and the mixture was extracted with ethyl acetate. The extract was washed and dried. The solvent was evaporated under reduced pressure and the residue was purified with silica gel column chromatography (chloroform:methyl alcohol=50:1) to give 1-ethyl-4-[5-(4-fluorobenzyl)furan-2-carbonyl]-3-hydroxy-5,6-dihydro-1H-pyridine-2-one (184 mg, yield: 50%).

NMR (CDCl$_3$) δ: 1.21 (3H, t, J=7.2 Hz), 2.92 (2H, t, J=6.8 Hz), 3.56 (2H, t, J=6.8 Hz), 3.56 (2H, q, J=7.2 Hz), 4.04 (2H, s), 6.21 (1H, d, J=3.3 Hz), 7.03 (2H, m), 7.21 (2H, m), 7.26 (1H, d, J=3.3 Hz), 14.51 (1H, brs).

The following compound was prepared as well as above.

(I-4-a) 4-[5-(4-fluorobenzyl)furan-2-carbonyl]-3-hydroxy-1-methyl-5,6-dihydro-1H-pyridine-2-one NMR (CDCl$_3$) δ: 2.94 (2H, t, J=6.6 Hz), 3.11 (3H, s), 3.46 (2H, t, J=6.6 Hz), 4.04 (2H, s), 6.21 (1H, d, J=3.3 Hz), 7.03 (2H, m), 7.21 (2H, m), 7.26 (1H, d, J=3.3 Hz), 14.55 (1H, brs).

(I-4-b) 4-[5-(4-fluorobenzyl)furan-2-carbonyl]-3-hydroxy-1-(2-methoxyethyl)-5,6-dihydro-1H-pyridine2-one NMR (CDCl$_3$) δ: 2.91 (2H, t, J=6.6 Hz), 3.55 (2H, t, J=6.6 Hz), 3.61 (3H, s), 3.56-3.70 (4H, m), 4.04 (2H, s), 6.20 (1H, d, J=4.5 Hz), 7.02 (2H, m), 7.21 (2H, m), 7.26 (1H, d, J=4.5 Hz), 14.64 (1H, brs).

(I-4-c) 4-[5-(4-fluorobenzyl)furan-2-carbonyl]-3-hydroxy-(2-hydroxyethyl)-5,6-dihydro-1H-pyridine-2-one NMR (CDCl$_3$) δ: 2.95 (2H, t, J=6.6 Hz), 3.56 (2H, t, J=6.6 Hz), 3.66 (2H, t, J=4.8 Hz), 3.86 (2H, t, J=4.8 Hz), 4.04 (2H, s), 6.21 (1H, d, J=3.3 Hz), 7.02 (2H, m), 7.21 (2H, m), 7.26 (1H, d, J=3.3 Hz), 14.71 (1H, brs).

J Group Compound

Compound J-4

4-[5-(4-fluorobenzyl)furan-2-carbonyl]-3-hydroxy-1-methyl-1H-pyridine-2-one

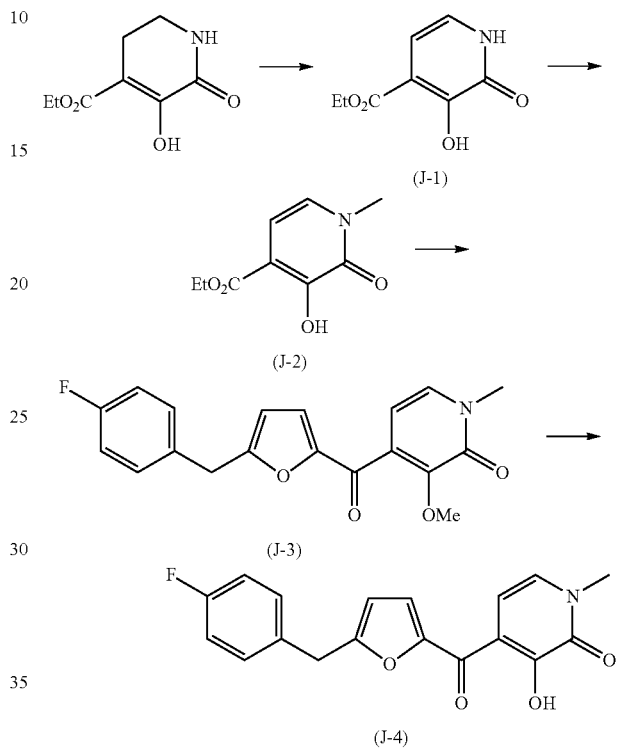

(J-1) A suspension of 5-hydroxy-6-oxo-1,2,3,6-tetrahydropyridine-4-carboxylate ethyl ester (5.32 g, 28.7 mmol) known by reference (Org. Prep. Proced. Int., 29, 330-335 (1997)) and 10% palladium carbon (1.18 g) in xylene (100 ml) was refluxed under heating for 21 hours. The solution was diluted with chloroform/methyl alcohol and palladium carbon was removed with filtrate. The solvent was evaporated under reduced pressure to give a crude product of 3-hydroxy-2-oxo-1,2-dihydropyridine-4-carboxylate ethyl ester.

(J-2) To a solution of crude product of the above-mentioned compound J-1 and potassium carbonate (20.28 g, 143.8 mmol) in dimethylformamide (90 ml), was added iodomethane (7.20 ml, 116 mmol) under ice-cooling and the mixture was stirred at 50° C. for 3 hours. 1N hydrochloric acid (135 ml) was added to the solution to stop the reaction and the mixture was extracted with ethyl acetate. The extract was washed and dried and the solvent was evaporated under reduced pressure to give 3-methoxy-1-methyl-2-oxo-1,2-dihydropyridine-4-carboxylate ethyl ester (2.69 g, yield: 44%).

NMR (CDCl$_3$) δ: 1.39 (3H, t, J=7.2 Hz), 3.57 (3H, s), 4.01 (3H, s), 4.36 (2H, q, J=7.2 Hz), 6.33 (1H, d, J=6.9 Hz), 7.07 (1H, d, J=6.9 Hz).

(J-3) Aluminum chloride (4.84 g, 36.3 mmol) was suspended in tetrahydrofuran (50 ml) and sodium borohydride (2.28 g, 60.3 mmol) was added thereto under ice-cooling. After stirring for 10 minutes, (5-bromofuran-2-yl-(4-fluorophenyl)metanone (3.25 g, 12.1 mmol) was added thereto and the mixture was refluxed under heating for 20 minutes. After cooling, water (100 ml) was added dropwise to the solution and the mixture was extracted with diethyl ether. The extract was washed and dried and the solvent was evaporated under reduced pressure to give 2-bromo-5-(4-fluorobenzyl)furan. This residue was dissolved in tetrahydrofuran (50 ml) and n-butyllithium (8.00 ml, 12.6 mmol) was added dropwise thereto at −78° C. After 10 minutes, the above-mentioned compound J-2 (2.55 g, 12.1 mmol) in tetrahydrofuran (25 ml) was added thereto and the mixture was stirred for 1 hour. The saturated ammonium chloride aqueous solution was added to the solution to stop the reaction and the mixture was extracted with ethyl acetate. The extract was washed and dried. The solvent was evaporated under reduced pressure and the residue was diluted with methyl alcohol (50 ml). 1N lithium hydroxide aqueous solution (25 ml) was added thereto and the mixture was stirred at room temperature for 1 hour. 1N hydrochloric acid (20 ml) was added to the solution to stop the reaction and the mixture was extracted with ethyl acetate. The extract was washed and dried. The solvent was evaporated under reduced pressure and the residue was purified with silica gel column chromatography (n-hexane:ethyl acetate=1:2) to give 4-[5-(4-fluorobenzyl)furan-2-carbonyl]-3-methoxy-1-methyl-1H-pyridine-2-one (1.09 g, yield: 27%).

NMR (CDCl$_3$) δ: 3.60 (3H, s), 3.90 (3H, s), 4.04 (2H, s), 6.11 (1H, d, J=6.9 Hz), 6.12 (1H, d, J=3.3 Hz), 7.02 (2H, m), 7.05 (1H, d, J=3.3 Hz), 7.12 (1H, d, J=6.9 Hz), 7.23 (2H, m).

(J-4) To a solution of the above-mentioned compound J-3 (518 mg, 1.52 mmol) in methylene chloride (25 ml), was added boron tribromide (4.50 mmol, 1.0M methylene chloride solution) at −78° C. and the mixture was stirred for 1.5 hours. Water (15 ml) was added to the solution to stop the reaction and the mixture was extracted with ethyl acetate. The extract was washed and dried. The solvent was evaporated under reduced pressure. The precipitated crystal was recrystallized with ethanol to give 4-[5-(4-fluorobenzyl)furan-2-carbonyl]-3-hydroxy-1-methyl-1H-pyridine-2-one (279 mg, yield: 56%).

Melting point: 145-147° C.

Elementary analysis as $C_{18}H_{14}FNO_4$

Calcd. (%): C, 66.05; H, 4.31; N, 4.28; F, 5.80.

Found (%): C, 65.87; H, 4.32; N, 4.13; F, 5.58.

NMR (CDCl$_3$) δ: 3.63 (3H, s), 4.07 (2H, s), 6.20 (1H, d, J=3.9 Hz), 6.57 (1H, d, J=7.2 Hz), 6.83 (1H, d, J=7.2 Hz), 7.03 (2H, m), 7.24 (2H, m), 7.29 (1H, d, J=3.9 Hz), 9.94 (1H, brs).

Compound J-7

4-[5-(4-fluorobenzyl)furan-2-carbonyl]-3-hydroxy-1-methoxymethyl-1H-pyridine-2-one

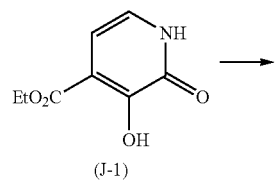

(J-1)

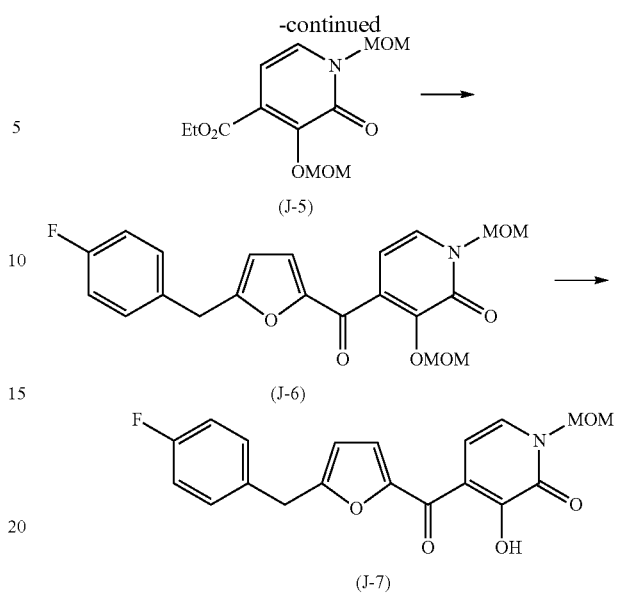

(J-5) To a solution of the above-mentioned compound J-1 (3.66 g, 20 mmol) in dimethylformamide (80 ml), was added sodium hydride (2.40 g, 60 mmol) under ice-cooling and the mixture was stirred for 20 minutes. Chloromethylmethylether (4.56 ml, 60 mmol) was added dropwise thereto. Then, the mixture was warmed to room temperature and stirred for 1 hour. To a mixture of ethyl acetate and sodium hydrogen carbonate aqueous solution, was added the solution under ice-cooling and the mixture was extracted with ethyl acetate. The extract was washed and dried. The solvent was evaporated and the residue was purified with silica gel column chromatography (n-hexane-ethyl acetate=3:1) to give 3-methoxymethoxy-1-methoxymethyl-2-oxo-1,2-dihydropyridine-4-carboxylate ethyl ester (1.47 g, yield: 26%).

NMR (CDCl$_3$) δ: 1.31 (3H, t, J=7.1 Hz), 3.31 (3H, s), 3.48 (3H, s), 4.30 (2H, q, J=7.1 Hz), 5.25 (2H, s), 5.32 (2H, s), 6.32 (1H, d, J=7.3 Hz), 7.12 (1H, d, J=7.3 Hz).

(J-6) Aluminum chloride (3.25 g, 24.4 mmol) was suspended in tetrahydrofuran (22 ml) and sodium borohydride (1.54 g, 40.7 mmol) was added thereto under ice-cooling. After stirring for 10 minutes, (5-bromofuran-2-yl-(4-fluorophenyl)metanone (2.19 g, 8.13 mmol) was added thereto and the mixture was refluxed under heating for 30 minutes. After cooling, water (40 ml) was added dropwise to the solution and the mixture was extracted with diethyl ether. The extract was washed and dried. The solvent was evaporated under reduced pressure to give the crude purified product (2.22 g) of 2-bromo-5-(4-fluorobenzyl)furan. This residue was dissolved in tetrahydrofuran (30 ml) and n-butyllithium (5.18 ml, 8.13 mmol) was added dropwise thereto at −78° C. After stirring for 10 minutes, a solution of the above-mentioned compound J-5 (1.47 g, 5.42 mmol) in tetrahydrofuran (3 ml) was added thereto and the mixture was stirred for 90 minutes. Ammonium chloride aqueous solution and water were added to the solution at −78° C. and the mixture was extracted with ethyl acetate. The extract was washed and dried. The solvent was evaporated under reduced pressure and the residue was purified with silica gel column chromatography (ethyl acetate from n-hexane-ethyl acetate=3:1) to give 4-[5-(4-fluorobenzyl)furan-2-carbonyl]-3-methoxymethoxy-1-methoxymethyl-1H-pyridine-2-one (735 mg, yield: 34%).

NMR (CDCl₃) δ: 3.25 (3H, s), 3.43 (3H, s), 4.05 (2H, s), 5.25 (2H, s), 5.35 (2H, s), 6.16 (1H, d, J=3.4 Hz), 6.20 (1H, d, J=7.0 Hz), 6.98-7.04 (2H, m), 7.11 (1H, d, J=3.7 Hz), 7.20-7.29 (3H, m).

(J-7) To a solution of the above-mentioned compound J-6 (141 mg, 0.35 mmol) in ethanol (5 ml), was added 3n-hydrochloric acid (5 ml) and the mixture was stirred for 1 hour. The solution was neutralized with sodium hydroxide aqueous solution and sodium hydrogen carbonate aqueous solution and the mixture was extracted with ethyl acetate. The extract was washed and dried. The solvent was evaporated under reduced pressure. The obtained precipitated crystal was recrystallized with diisopropylether and ethanol and dried under reduced pressure to give 4-[5-(4-fluorobenzyl)furan-2-carbonyl]-3-hydroxy-1-methoxymethyl-1H-pyridine-2-one (52 mg, yield: 42%).

Melting point: 128-130° C.
Elementary analysis as C₁₉H₁₆FNO₅
Calcd. (%): C, 63.86; H, 4.51; N, 3.92; F, 5.32.
Found (%): C, 63.35; H, 4.43; N, 3.79; F, 5.07.
NMR (CDCl₃) δ: 3.42 (3H, s), 4.08 (2H, s), 5.38 (2H, s), 6.21 (1H, d, J=3.7 Hz), 6.64 (1H, d, J=7.6 Hz), 6.95 (1H, d, J=7.6 Hz), 7.01-7.06 (2H, m), 7.22-7.27 (2H, m), 7.32 (1H, d, J=3.7 Hz).

Compound J-8

4-[5-(4-fluorobenzyl)furan-2-carbonyl]-3-hydroxy-1H-pyridine-2-one

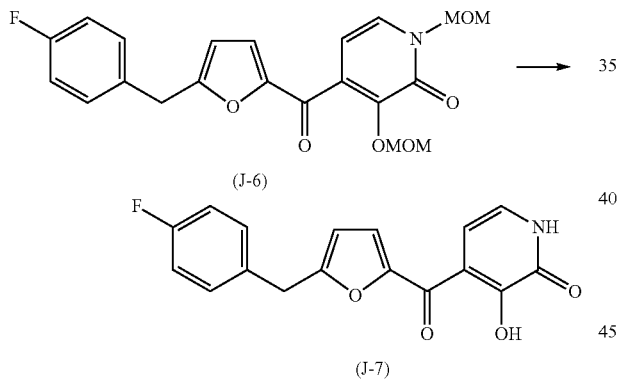

(J-8) To a solution of the above-mentioned compound J-6 (685 mg, 1.71 mmol) in methylene chloride (15 ml), was added boron tribromide methylene chloride solution (5.13 ml) at −78° C. The mixture was stirred for 90 minutes, warmed to 0° C. and then stirred for 20 minutes. Water was added to the solution under ice-cooling and the mixture was extracted with ethyl acetate. The extract was washed and dried. The solvent was evaporated. The obtained precipitated crystal was washed with chloroform, recrystallized with ethanol and dried under reduced pressure to give 4-[5-(4-fluorobenzyl)furan-2-carbonyl]-3-hydroxy-1H-pyridine-2-one (301 mg, yield: 56%).

Melting point: 229-231° C.
Elementary analysis as C₁₇H₁₂FNO₄
Calcd. (%): C, 65.18; H, 3.86; N, 4.47; F, 6.06.
Found (%): C, 63.80; H, 3.75; N, 4.37; F, 5.77; Cl, 0.87.
NMR (DMSO-d6) δ: 4.15 (2H, s), 6.14 (1H, d, J=6.7 Hz), 6.44 (1H, d, J=3.7 Hz), 6.97 (1H, d, J=6.7 Hz), 7.19-7.25 (3H, m), 7.35-7.40 (2H, m), 9.76 (1H, brs), 11.98 (1H, brs).

K Group Compound

Compound K-4

4-[5-(4-fluorobenzyl)-[1,3,4]oxadiazole-2-yl]-3-hydroxy-1-methyl-1H-pyridine-2-one

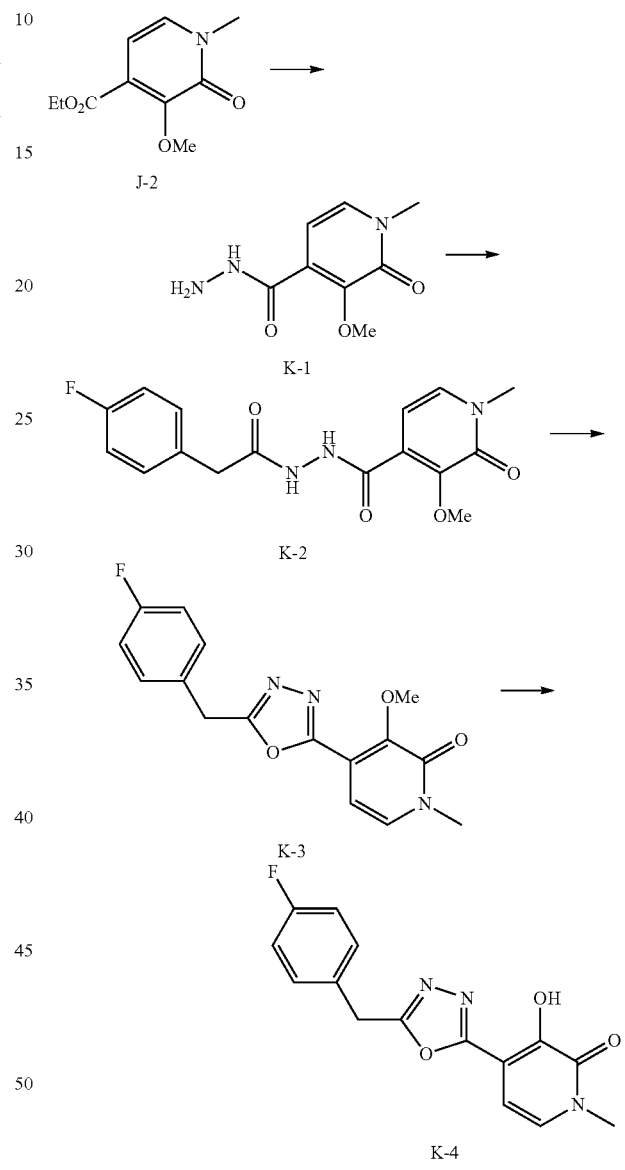

(K-1) To a solution of compound J-2 (1.00 g, 4.73 mmol) in ethanol (5 ml), was added hydrazine monohydrate (1 ml) and the mixture was refluxed under heating for 1 hour. The solvent was evaporated under reduced pressure to give crude product of 3-methoxy-1-methyl-2-oxo-1,2-dihydropyridine-4-carboxylic acid hydrazide.

(K-2) To a suspension of crude product of the above-mentioned compound K-1, 4-fluorophenylacetic acid (1.12 g, 7.12 mmol) and 1-hydroxybenzotriazole (132 mg, 0.977 mmol) in dimethylformamide (10 ml), was added 1-ethyl-3-(3-dimethylaminopropyl)carbodiimidehydrochloride (1.36 g, 7.09 mmol) and the mixture was stirred at room temperature for 20 hours. Water (20 ml) was added to the solution to stop the reaction and the mixture was extracted with chloroform. The extract was washed and dried. The solvent was evaporated under reduced pressure and the residue was purified with silica gel column chromatography (chloroform) to give 3-methoxy-1-methyl-2-oxo-1,2-dihydropyridine-4-carboxylic acid N'-[2-(4-fluorophenyl)acetyl]-hydrazide (919 mg, yield: 58%)

NMR (CDCl$_3$) δ: 3.57 (3H, s), 3.66 (3H, s), 4.22 (2H, s), 6.72 (1H, d, J=7.2 Hz), 7.04 (2H, m), 7.12 (1H, d, J=7.2 Hz), 7.30 (2H, m).

(K-3) To the above-mentioned compound K-2 (916 mg, 2.75 mmol), was added polyphosphoric acid (18 g) and the mixture was stirred at 150° C. for 1 hour. Ice water (50 g) was added to the solution and the obtained precipitated crystal was washed with water and recrystallized with ethanol to give 4-[5-(4-fluorobenzyl)-[1,3,4]oxadiazole-2-yl]-3-methoxy-1-methyl-1H-pyridine-2-one (498 mg, yield: 58%).

NMR (CDCl$_3$) δ: 3.59 (3H, s), 4.01 (3H, s), 4.28 (2H, s), 6.69 (1H, d, J=7.2 Hz), 7.05 (2H, m), 7.13 (1H, d, J=7.2 Hz), 7.35 (2H, m).

(K-4) To a solution of the above-mentioned compound K-3 (261 mg, 0.828 mmol) in methylene chloride (25 ml), was added boron tribromide (2.40 mmol, 1.0M methylene chloride solution) under ice-cooling and the mixture was stirred for 75 minutes. Water (10 ml) was added to the solution to stop the reaction and the mixture was extracted with chloroform. The extract was washed and dried. The solvent was evaporated under reduced pressure. The obtained precipitated crystal was recrystallized with chloroform/methyl alcohol to give 4-[5-(4-fluorobenzyl)-[1,3,4]oxadiazole-2-yl]-3-hydroxy-1-methyl-1H-pyridine-2-one (200 mg, yield: 80%).

Melting point: 216-218° C.

Elementary analysis as $C_{15}H_{12}FN_3O_3$ $(CHCl_3)_{0.04}$

Calcd. (%): C, 59.02; H, 3.97; N, 13.73; Cl, 1.39; F, 6.21.

Found (%): C, 59.10; H, 3.92; N, 13.68; Cl, 1.20; F, 6.13.

NMR (DMSO-d$_6$) δ: 3.52 (3H, s), 4.37 (2H, s), 6.56 (1H, d, J=7.5 Hz), 7.19 (2H, m), 7.27 (1H, d, J=7.5 Hz), 7.41 (2H, m), 10.37 (1H, brs).

L Group Compound

Compound L-4

2-[5-(4-fluorobenzyl)furan-2-carbonyl]-3-hydroxy-1H-pyridine-4-one

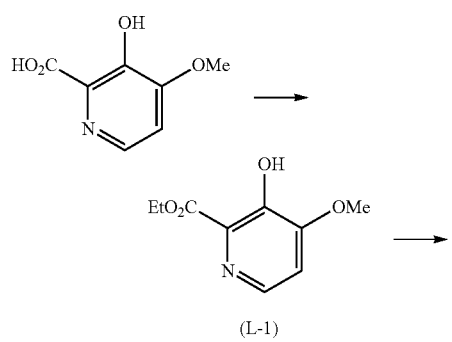

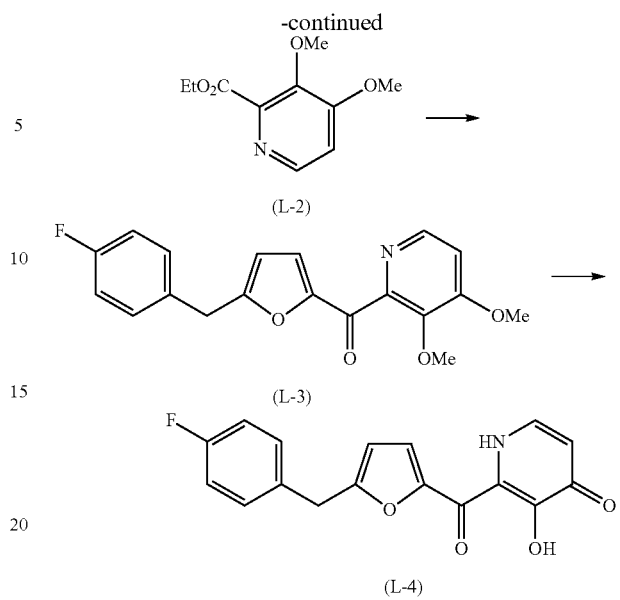

(L-1) To a solution of 3-hydroxy-4-methoxypyridine-2-carboxylic acid (2.85 g, 16.8 mmol) in ethanol (60 ml) known by reference (Tetrahedron, 54, 12745-12774 (1998)), was added strong sulfuric acid (1 ml) and the mixture was refluxed under heating for 75 hours. The solvent was evaporated under reduced pressure. Water (60 ml) and potassium carbonate (1.6 g) were added the obtained residue to neutralize and the mixture was extracted with chloroform. The extract was washed and dried. The solvent was evaporated under reduced pressure to give 3-hydroxy-4-methoxypyridine-2-carboxylate ethyl ester (2.06 g, yield: 62%).

NMR (CDCl$_3$) δ: 1.49 (3H, t, J=7.2 Hz), 3.97 (3H, s), 4.54 (2H, q, J=7.2 Hz), 6.94 (1H, d, J=5.1 Hz), 8.19 (1H, d, J=5.1 Hz), 11.01 (1H, brs).

(L-2) To a solution the above-mentioned compound L-1 (2.05 g, 10.4 mmol) and potassium carbonate (2.85 g, 20.6 mmol) in dimethylformamide (40 ml), was added dimethyl sulfate (1.45 ml, 15.3 mmol) and the mixture was stirred at 80° C. for 2 hours. 1N hydrochloric acid (30 ml) and water (50 ml) were added to the solution to stop the reaction and the mixture was extracted with ethyl acetate. The extract was washed and dried. The solvent was evaporated under reduced pressure and the residue was purified with silica gel column chromatography (n-hexane:ethyl acetate=1:1) to give 3,4-dimethoxypyridine-2-carboxylate ethyl ester (1.08 g, yield: 49%).

NMR (CDCl$_3$) δ: 1.43 (3H, t, J=7.2 Hz), 3.93 (3H, s), 3.95 (3H, s), 4.45 (2H, q, J=7.2 Hz), 6.95 (1H, d, J=5.4 Hz), 8.32 (1H, d, J=5.4 Hz).

(L-3) Aluminum chloride (3.06 g, 22.9 mmol) was suspended in tetrahydrofuran (30 ml). Sodium borohydride (1.45 g, 38.3 mmol) was added thereto under ice-cooling. The mixture was stirred for 10 minutes. (5-bromofuran-2-yl-(4-fluorophenyl)metanone (2.05 g, 7.62 mmol) was added thereto and the mixture was refluxed under heating for 20 minutes. After cooling, water (60 ml) was added dropwise to the solution and the mixture was extracted with diethyl ether. The extract was washed and dried. The solvent was evaporated under reduced pressure to give 2-bromo-5-(4-fluorobenzyl)furan. This residue was dissolved in tetrahydrofuran (35 ml). n-butyllithium (4.90 ml, 7.64 mmol) was added dropwise thereto at −78° C. After 10 minutes, tetrahydrofuran (15 ml) of the above-mentioned compound L-2

(1.07 g, 5.07 mmol) was added thereto and the mixture was stirred for 1 hour. The saturated ammonium chloride aqueous solution was added to the solution to stop the reaction and the mixture was extracted with ethyl acetate. The extract was washed and dried. The solvent was evaporated under reduced pressure and the residue was purified with silica gel column chromatography (n-hexane:ethyl acetate=1:1) to give (3,4-dimethoxypyridine-2-yl)-[5-(4-fluorobenzyl)furan-2-yl]metanone (1.53 g, yield: 90%).

NMR (CDCl$_3$) δ: 3.90 (3H, s), 3.96 (3H, s), 4.05 (2H, s), 6.09 (1H, d, J=3.5 Hz), 6.95 (1H, d, J=5.6 Hz), 7.00 (2H, m), 7.03 (1H, d, J=3.5 Hz), 7.22 (2H, m), 8.28 (1H, d, J=5.6 Hz).

(L-4) To a suspension of the above-mentioned compound L-3 (1.48 g, 4.34 mmol) and sodium iodide (5.22 g, 34.8 mmol) in acetonitrile (30 ml), was added chlorotrimethylsilane (4.40 ml, 34.7 mmol) and the mixture was refluxed under heating for 3 hours. Water (30 ml) and 10% sodium hydrogen sulfate aqueous solution (30 ml) were added to the solution to stop the reaction and the mixture was extracted with ethyl acetate. The extract was washed and dried. The solvent was evaporated under reduced pressure and the residue was purified with silica gel column chromatography. The solvent was evaporated from the fraction of the obtained product by eluting with ethyl acetate under reduced pressure and the obtained precipitated crystal was crystallized with toluene to give 2-[5-(4-fluorobenzyl)furan-2-carbonyl]-3-hydroxy-1H-pyridine-4-one (448 mg, yield: 33%).

NMR (CD$_3$OD) δ: 4.10 (2H, s), 6.35 (1H, d, J=3.6 Hz), 6.69 (1H, d, J=5.9 Hz), 7.05 (2H, m), 7.32 (2H, m), 7.81 (1H, d, J=5.9 Hz), 7.84 (1H, brs).

M Group Compound

Compound M-6

5-[5-(4-fluorobenzyl)furan-2-carbonyl]-3-hydroxy-2-methyl-1H-pyridine-4-one

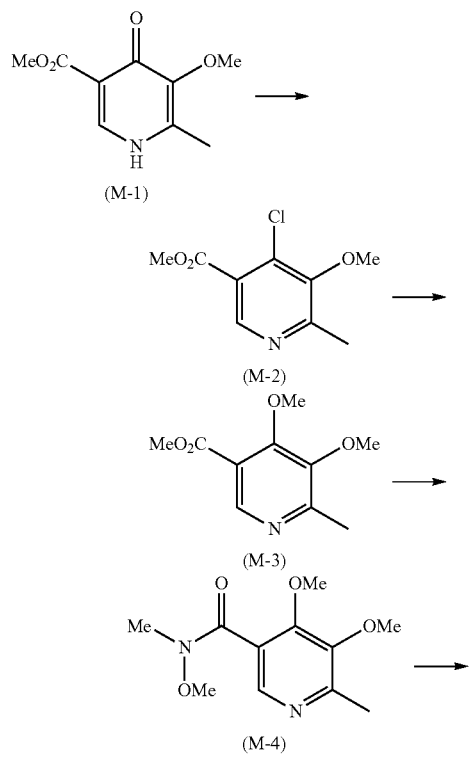

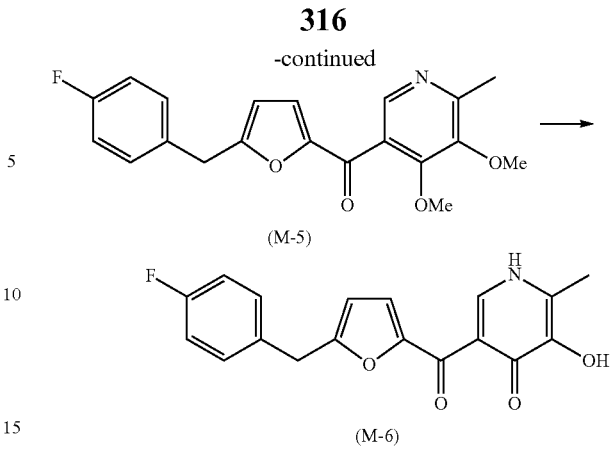

(M-1) According to the method described in WO92/02523, 5-methoxy-6-methyl-4-oxo-1,4-dihydropyridine-3-carboxylate methyl ester was synthesized.

(M-2) A solution of the above-mentioned compound M-1 (980 mg, 5.0 mmol) in phosphorus oxychloride (5 ml) was refluxed under heating for 30 minutes. The solvent was evaporated from the solution under reduced pressure and the residue was neutralized with sodium hydroxideaqueous solution. The mixture was extracted with ethyl acetate and the extract was washed and dried. The solvent was evaporated to give crude product (738 mg) of 4-chloro-5-methoxy-6-methyl-nicotinate methylester.

NMR (CDCl$_3$) δ: 2.61 (3H, s), 3.88 (3H, s), 3.96 (3H, s), 8.71 (1H, s).

(M-3) To a solution of the above-mentioned crude product M-2 (738 mg) in methyl alcohol (5 ml), was added sodium methylate methyl alcohol solution (2.49 ml) under ice-cooling. After stirring at room temperature for 2 hours, the mixture was warmed to 50° C. and stirred for 2 hours. The solution was neutralized with ammonium chloride aqueous solution. Methyl alcohol was evaporated under reduced pressure and the residue was extracted with ethyl acetate. The extract was washed and dried. The solvent was evaporated to give crude product (609 mg) of 4,5-dimethoxy-6-methyl-nicotinate methylester.

NMR (CDCl$_3$) δ: 2.53 (3H, s), 3.85 (3H, s), 3.92 (3H, s), 4.02 (3H, s), 8.61 (1H, s).

(M-4) A solution of the above-mentioned crude product M-3 (449 mg) in sodium hydroxide (10 ml) was refluxed under heating for 1 hour. The solution was neutralized with hydrochloric acid and the solvent was evaporated under reduced pressure. To a solution of the residue in methylene chloride (10 ml), were added N,O-dimethylhydroxyamine hydrochloride (249 mg, 2.56 mmol) and 1-hydroxybenztriazole (58 mg, 0.43 mmol). Triethylamine (357 ul, 2.56 mmol) and 1-ethyl3-(3-dimethylaminopropyl)carbodiimidehydrochloride (491 mg, 2.56 mmol) were added thereto under ice-cooling and the mixture was warmed and stirred for 2 hours. The ammonium chloride aqueous solution was added to the solution and the mixture was extracted with chloroform. The extract was washed and dried. The solvent was evaporated under reduced pressure and the residue was purified with silica gel column chromatography (n-hexane-ethyl acetate=1:1) to give 4,5,N-trimethoxy-6,N-dimethyl-nicotinamide (449 mg, yield: 80%).

NMR (CDCl$_3$) δ: 2.51 (3H, s), 3.34 (3H, brs), 3.52 (3H, brs), 3.83 (3H, s), 4.00 (3H, s), 8.13 (1H, s).

(M-5) Aluminum chloride (2.02 g, 15.0 mmol) was suspended in tetrahydrofuran (20 ml). Sodium borohydride (851 mg, 22.5 mmol) was added thereto under ice-cooling.

After stirring for 10 minutes, (5-bromofuran-2-yl-(4-fluorophenyl)metanone (2.02 g, 7.5 mmol) was added thereto and the mixture was refluxed under heating for 30 minutes. After cooling, water (20 ml) was added dropwise to the solution and the mixture was extracted with diethyl ether. The extract was washed and dried. The solvent was evaporated under reduced pressure to give 2-bromo-5-(4-fluorobenzyl)furan (1.74 g, yield: 91%). This residue (715 mg, 2.80 mmol) was dissolved in tetrahydrofuran (9 ml). n-butyllithium (1.79 ml, 2.80 mmol) was added dropwise thereto at −78° C. After stirring for 5 minutes, a solution of the above-mentioned compound M-4 (449 mg, 1.87 mmol) in tetrahydrofuran (1 ml) was added thereto and the mixture was stirred for 30 minutes. The ammonium chloride aqueous solution and water were added to the solution at −78° C. and the mixture was extracted with ethyl acetate. The extract was washed and dried. The solvent was evaporated under reduced pressure and the residue was purified with silica gel column chromatography (n-hexane-ethyl acetate=1:1) to give (4,5-dimethoxy-6-methylpyridine-3-yl)-[5-(4-fluorobenzyl)furan-2-yl]-metanone (348 mg, yield: 52%).

NMR (CDCl$_3$) δ: 2.54 (3H, s), 3.84 (3H, s), 3.91 (3H, s), 4.05 (2H, s), 6.15 (1H, d, J=3.7 Hz), 6.99-7.06 (3H, m), 7.21-7.26 (2H, m), 8.26 (1H, s).

(M-6) To a solution of the above-mentioned compound M-5 (289 mg, 0.81 mmol) in methylene chloride (6 ml), boron tribromidemethylene chloride solution (4.05 ml) was added under ice-cooling. The mixture was stirred at 0° C. for 30 minutes, warmed to room temperature and then stirred for 2 hours. 2n-hydrochloric acid (6 ml) was added to the solution and the mixture was stirred for 10 minutes and neutralized with sodium hydrogen carbonate. The mixture was extracted with ethyl acetate and the extract was washed and dried. The solvent was evaporated and the obtained precipitated crystal was washed with chloroform, recrystallized with ethanol and dried under reduced pressure to give 5-[5-(4-fluorobenzyl)furan-2-carbonyl]-3-hydroxy-2-methyl-1H-pyridine-4-one (123 mg, yield: 46%).

Melting point: 190-192° C.
Elementary analysis as C$_{18}$H$_{14}$FNO$_4$
Calcd. (%): C, 66.05; H, 4.31; N, 4.28; F, 5.80.
Found (%): C, 65.17; H, 4.18; N, 4.27; F, 5.56.
NMR (DMSO-d6) δ: 2.20 (3H, s), 4.08 (2H, s), 6.34 (1H, d, J=3.7 Hz), 7.14-7.20 (2H, m), 7.25 (1H, d, J=3.7 Hz), 7.30-7.35 (2H, m), 7.72 (1H, s).

The compounds of the present invention include the following compounds which can be synthesized with a manner similar to that of the above examples.

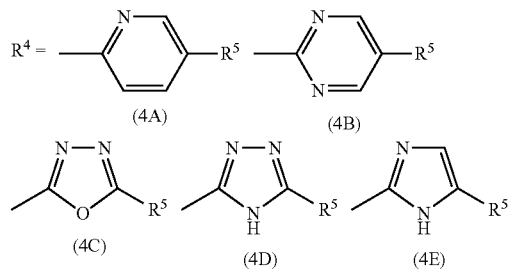

The substituents of $R^1$, $R^2$, X, $R^4$ and $R^5$ of above compound include the following substitution group.
$R^1$=H (1A), Me(1B), OMe(1C), Cl(1D), Ph(1E)
$R^2$=H (2A), Me(2B), OMe(2C), Cl(2D), Ph(2E)
X=O(3A), NH(3B)

$R^4$ = (4A), (4B), (4C), (4D), (4E)

$R^5$=H (5A), Me(5B), OMe(5C), Cl(5D), Ph(5E)

The preferable combinations ($R^1$, $R^2$, X, $R^4$, $R^5$) of the substituents of above compound include the followings.
(1A, 2A, 3A, 4A, 5A), (1A, 2A, 3A, 4A, 5B), (1A, 2A, 3A, 4A, 5C), (1A, 2A, 3A, 4A, 5D), (1A, 2A, 3A, 4A, 5E), (1A, 2A, 3A, 4B, 5A), (1A, 2A, 3A, 4B, 5B), (1A, 2A, 3A, 4B, 5C), (1A, 2A, 3A, 4B, 5D), (1A, 2A, 3A, 4B, 5E), (1A, 2A, 3A, 4C, 5A), (1A, 2A, 3A, 4C, 5B), (1A, 2A, 3A, 4C, 5C), (1A, 2A, 3A, 4C, 5D), (1A, 2A, 3A, 4C, 5E), (1A, 2A, 3A, 4D, 5A), (1A, 2A, 3A, 4D, 5B), (1A, 2A, 3A, 4D, 5C), (1A, 2A, 3A, 4D, 5D), (1A, 2A, 3A, 4D, 5E), (1A, 2A, 3A, 4E, 5A), (1A, 2A, 3A, 4E, 5), (1A, 2A, 3A, 4E, 5D), (1A, 2A, 3A, 4E, 5E), (1A, 2A, 3B, 4A, 5A), (1A, 2A, 3B, 4A, 5B), (1A, 2A, 3B, 4A, 5C), (1A, 2A, 3B, 4A, 5D), (1A, 2A, 3B, 4A, 5E), (1A, 2A, 3B, 4B, 5A), (1A, 2A, 3B, 4B, 5B), (1A, 2A, 3B, 4B, 5C), (1A, 2A, 3B, 4B, 5D), (1A, 2A, 3B, 4B, 5E), (1A, 2A, 3B, 4C, 5A), (1A, 2A, 3B, 4C, 5B), (1A, 2A, 3B, 4C, 5C), (1A, 2A, 3B, 4C, 5D), (1A, 2A, 3B, 4E, 5E), (1A, 2A, 3B, 4D, 5A), (1A, 2A, 3B, 4D, 5B), (1A, 2A, 3B, 4D, 5C), (1A, 2A, 3B, 4D, 5D), (1A, 2A, 3B, 4D, 5E), (1A, 2A, 3B, 4E, 5A), (1A, 2A, 3B, 4E, 5B), (1A, 2A, 3B, 4E, 5C), (1A, 2A, 3B, 4E, 5D), (1A, 2A, 3B, 4E, 5E), (1A, 2B, 3A, 4A, 5A), (1A, 2B, 3A, 4A, 5B), (1A, 2B, 3A, 4A, 5C), (1A, 2B, 3A, 4A, 5D), (1A, 2B, 3A, 4A, 5E), (1A, 2B, 3A, 4B, 5A), (1A, 2B, 3A, 4B, 5B), (1A, 2B, 3A, 4B, 5C), (1A, 2B, 3A, 4B, 5D), (1A, 2B, 3A, 4B, 5E), (1A, 2B, 3A, 4C, 5A), (1A, 2B, 3A, 4C, 5B), (1A, 2B, 3A, 4C, 5C), (1A, 2B, 3A, 4C, 5D), (1A, 2B, 3A, 4C, 5E), (1A, 2B, 3A, 4D, 5A), (1A, 2B, 3A, 4D, 5B), (1A, 2B, 3A, 4D, 5C), (1A, 2B, 3A, 4D, 5D), (1A, 2B, 3A, 4D, 5E), (1A, 2B, 3A, 4E, 5A), (1A, 2B, 3A, 4E, 5B), (1A, 2B, 3A, 4E, 5C), (1A, 2B, 3A, 4E, 5D), (1A, 2B, 3A, 4E, 5E), (1A, 2B, 3B, 4A, 5A), (1A, 2B, 3B, 4A, 5B), (1A, 2B, 3B, 4A, 5C), (1A, 2B, 3B, 4A, 5D), (1A, 2B, 3B, 4A, 5E), (1A, 2B, 3B, 4B, 5A), (1A, 2B, 3B, 4B, 5B), (1A, 2B, 3B, 4B, 5C), (1A, 2B, 3B, 4B, 5D), (1A, 2B, 3B, 4B, 5E), (1A, 2B, 3B, 4C, 5A), (1A, 2B, 3B, 4C, 5B), (1A, 2B, 3B, 4C, 5C), (1A, 2B, 3B, 4C, 5D), (1A, 2B, 3B, 4C, 5E), (1A, 2B, 3B, 4D, 5A), (1A, 2B, 3B, 4D, 5B), (1A, 2B, 3B, 4D, 5C), (1A, 2B, 3B, 4D, 5D), (1A, 2B, 3B, 4D, 5E), (1A, 2B, 3B, 4E, 5A), (1A, 2B, 3B, 4E, 5B), (1A, 2B, 3B, 4E, 5C), (1A, 2B, 3B, 4E, 5D), (1A, 2B, 3B, 4E, 5E), (1A, 2C, 3A, 4A, 5A), (1A, 2C, 3A, 4A, 5B), (1A, 2C, 3A, 4A, 5C), (1A, 2C, 3A, 4A, 5D), (1A, 2C, 3A, 4A, 5E), (1A, 2C, 3A, 4B, 5A), (1A, 2C, 3A, 4B, 5B), (1A, 2C, 3A, 4B, 5C), (1A, 2C, 3A, 4B, 5D), (1A, 2C, 3A, 4B, 5E), (1A, 2C, 3A, 4C, 5A), (1A, 2C, 3A, 4C, 5B), (1A, 2C, 3A, 4C, 5C), (1A, 2C, 3A, 4C, 5D), (1A, 2C, 3A, 4C, 5E), (1A, 2C, 3A, 4D, 5A), (1A, 2C, 3A, 4D, 5B), (1A, 2C, 3A, 4D, 5C), (1A, 2C, 3A, 4D, 5D), (1A, 2C, 3A, 4D, 5E), (1A, 2C, 3A, 4E, 5A), (1A, 2C, 3A, 4E, 5B), (1A, 2C, 3A, 4E, 5C), (1A, 2C, 3A, 4E, 5D), (1A, 2C, 3A, 4E, 5E), (1A, 2C, 3B, 4A, 5A), (1A, 2C, 3B, 4A, 5B), (1A, 2C, 3B, 4A, 5C), (1A, 2C, 3B, 4A, 5D), (1A, 2C, 3B, 4A, 5E), (1A, 2C, 3B, 4B, 5A), (1A, 2C, 3B, 4B, 5B), (1A, 2C, 3B, 4B, 5C), (1A, 2C, 3B, 4B, 5D), (1A, 2C, 3B, 4B, 5E), (1A, 2C, 3B, 4C, 5A), (1A, 2C, 3B, 4C, 5B), (1A, 2C, 3B, 4C, 5C), (1A, 2C, 3B, 4C, 5D), (1A, 2C, 3B, 4C, 5E), (1A, 2C, 3B, 4D, 5A), (1A, 2C, 3B, 4D, 5B), (1A, 2C, 3B, 4D, 5C), (1A, 2C, 3B, 4D, 5D), (1A, 2C, 3B, 4D, 5E), (1A, 2C, 3B, 4E, 5A), (1A, 2C, 3B, 4E, 5B), (1A, 2C, 3B, 4E, 5C), (1A, 2C, 3B, 4E, 5D), (1A, 2C, 3B, 4E, 5E), (1A, 2D, 3A, 4A, 5A), (1A, 2D, 3A, 4A, 5B), (1A, 2D, 3A, 4A, 5C), (1A, 2D, 3A, 4A, 5D), (1A, 2D, 3A, 4A, 5E), (1A, 2D, 3A, 4B, 5A), (1A, 2D, 3A, 4B, 5B), (1A, 2D, 3A, 4B, 5C), (1A, 2D, 3A, 4B, 5D), (1A, 2D, 3A, 4B, 5E), (1A, 2D, 3A, 4C, 5A), (1A, 2D, 3A, 4C, 5B), (1A, 2D, 3A, 4C, 5C), (1A, 2D, 3A, 4C, 5D), (1A, 2D, 3A, 4C, 5E), (1A, 2D, 3A, 4D, 5A), (1A, 2D, 3A, 4D, 5B), (1A, 2D, 3A, 4E, 5C), (1A, 2D, 3A, 4D, 5D), (1A, 2D, 3A, 4D, 5E), (1A, 2D, 3A, 4E, 5A), (1A, 2D, 3A, 4E, 5B), (1A, 2D, 3A, 4E, 5C), (1A, 2D, 3A, 4E, 5D), (1A, 2D, 3A, 4E, 5E), (1A, 2D, 3B, 4A, 5A), (1A, 2D, 3B, 4A, 5B), (1A, 2D, 3B, 4A, 5C), (1A, 2D, 3B, 4A, 5J), (1A, 2D, 3B, 4A, 5E), (1A, 2D, 3B, 4B, 5A), (1A, 2D, 3B, 4B, 5B), (1A, 2D, 3B, 4B, 5C), (1A, 2D, 3B, 4B, 5D), (1A, 2D, 3B, 4B, 5E), (1A, 2D, 3B, 4C, 5A), (1A, 2D, 3B, 4C, 5B), (1A, 2D, 3B, 4C, 5C), (1A, 2D, 3B, 4C, 5D), (1A, 2D, 3B, 4C, 5E), (1A, 2D, 3B, 4D, 5A), (1A, 2E, 3B, 4D, 5B), (1A, 2D, 3B, 4D, 5C), (1A, 2D, 3B, 4D, 5D), (1A, 2D, 3B, 4D, 5E), (1A, 2D, 3B, 4E, 5A), (1A, 2D, 3B, 4E, 5B), (1A, 2D, 3B, 4E, 5C), (1A, 2D, 3B, 4E, 5D), (1A, 2D, 3B, 4E, 5E), (1A, 2E, 3A, 4A, 5A), (1A, 2E, 3A, 4A, 5B), (1A, 2E, 3A, 4A, 5C), (1A, 2E, 3A, 4A, 5D), (1A, 2E, 3A, 4A, 5E), (1A, 2E, 3A, 4B, 5A), (1A, 2E, 3A, 4B, 5B), (1A, 2E, 3A, 4B, 5C), (1A, 2E, 3A, 4B, 5D), (1A, 2E, 3A, 4B, 5E), (1A, 2E, 3A, 4C, 5A), (1A, 2E, 3A, 4C, 5B), (1A, 2E, 3A, 4C, 5C), (1A, 2E, 3A, 4C, 5D), (1A, 2E, 3A, 4C, 5E), (1A, 2E, 3A, 4D, 5A), (1A, 2E, 3A, 4D, 5B), (1A, 2E, 3A, 4D, 5C), (1A, 2E, 3A, 4D, 5D), (A, 2E, 3A, 4D, 5E), (1A, 2E, 3A, 4E, 5A), (1A, 2E, 3A, 4E, 5B), (1A, 2E, 3A, 4E, 5C), (1A, 2E, 3A, 4E, 5D), (1A, 2E, 3A, 4E, 5E), (1A, 2E, 3B, 4A, 5A), (1A, 2E, 3B, 4A, 5B), (1A, 2E, 3B, 4A, 5C), (1A, 2E, 3B, 4A, 5D), (1A, 2E, 3B, 4A, 5E), (1A, 2E, 3B, 4B, 5A), (1A, 2E, 3B, 4B, 5B), (1A, 2E, 3B, 4B, 5C), (1A, 2E, 3B, 4B, 5D), (1A, 2E, 3B, 4B, 5E), (1A, 2E, 3B, 4C, 5A), (1A, 2E, 3B, 4C, 5B), (1A, 2E, 3B, 4C, 5C), (1A, 2E, 3B, 4C, 5D), (1A, 2E, 3B, 4C, 5E), (1A, 2E, 3B, 4D, 5A), (1A, 2E, 3B, 4D, 5B), (1A, 2E, 3B, 4D, 5C), (1A, 2E, 3B, 4D, 5D), (1A, 2E, 3B, 4D, 5E), (1A, 2E, 3B, 4E, 5A), (1A, 2E, 3B, 4E, 5B), (1A, 2E, 3B, 4E, 5C), (1A, 2E, 3B, 4E, 5D), (1A, 2E, 3B, 4E, 5E), (1B, 2A, 3A, 4A, 5A), (1B, 2A, 3A, 4A, 5B), (1B, 2A, 3A, 4A, 5C), (1B, 2A, 3A, 4A, 5D), (1B, 2A, 3A, 4A, 5E), (1B, 2A, 3A, 4B, 5A), (1B, 2A, 3A, 4B, 5B), (1B, 2A, 3A, 4B, 5C), (1B, 2A, 3A, 4B, 5D), (1B, 2A, 3A, 4B, 5E), (1B, 2A, 3A, 4C, 5A), (1B, 2A, 3A, 4C, 5B), (1B, 2A, 3A, 4C, 5C), (1B, 2A, 3A, 4C, 5D), (1B, 2A, 3A, 4C, 5E), (1B, 2A, 3A, 4D, 5A), (1B, 2A, 3A, 4D, 5B), (1B, 2A, 3A, 4D, 5C), (1B, 2A, 3A, 4D, 5D), (1B, 2A, 3A, 4D, 5E), (1B, 2A, 3A, 4E, 5A), (1B, 2A, 3A, 4E, 5B), (1B, 2A, 3A, 4E, 5C), (1B, 2A, 3A, 4E, 5D), (1B, 2A, 3A, 4E, 5E), (1B, 2A, 3B, 4A, 5A), (1B, 2A, 3B, 4A, 5B), (1B, 2A, 3B, 4A, 5C), (1B, 2A, 3B, 4A, 5D), (1B, 2A, 3B, 4A, 5E), (1B, 2A, 3B, 4B, 5A), (1B, 2A, 3B, 4B, 5B), (1B, 2A, 3B, 4B, 5C), (1B, 2A, 3B, 4B, 5D), (1B, 2A, 3B, 4B, 5E), (1B, 2A, 3B, 4C, 5A), (1B, 2A, 3B, 4C, 5B), (1B, 2A, 3B, 4C, 5C), (1B, 2A, 3B, 4C, 5D), (1B, 2A, 3B, 4C, 5E), (1B, 2A, 3B, 4D, 5A), (1B, 2A, 3B, 4D, 5B), (1B, 2A, 3B, 4D, 5C), (1B, 2A, 3B, 4D, 5D), (1B, 2A, 3B, 4D, 5E), (1B, 2A, 3B, 4E, 5A), (1B, 2A, 3B, 4E, 5B), (1B, 2A, 3B, 4E, 5C), (1B, 2A, 3B, 4E, 5D), (1B, 2A, 3B, 4E, 5E), (1B, 2B, 3A, 4A, 5A), (1B, 2B, 3A, 4A, 5B), (1B, 2B, 3A, 4A, 5C), (1B, 2B, 3A, 4A, 5D), (1B, 2B, 3A, 4A, 5E), (1B, 2B, 3A, 4B, 5A), (1B, 2B, 3A, 4B, 5B), (1B, 2B, 3A, 4B, 5C), (1B, 2B, 3A, 4B, 5D), (1B, 2B, 3A, 4B, 5E), (1B, 2B, 3A, 4C, 5A), (1B, 2B, 3A, 4C, 5B), (1B, 2B, 3A, 4C, 5C), (1B, 2B, 3A, 4C, 5D), (1B, 2B, 3A, 4C, 5E), (1B, 2B, 3A, 4D, 5A), (1B, 2B, 3A, 4D, 5B), (1B, 2B, 3A, 4D, 5C), (1B, 2B, 3A, 4D, 5D), (1B, 2B, 3A, 4D, 5E), (1B, 2B, 3A, 4E, 5A), (1B, 2B, 3A, 4E, 5B), (1B, 2B, 3A, 4E, 5C), (1B, 2B, 3A, 4E, 5D), (1B, 2B, 3A, 4E, 5E), (1B, 2B, 3B, 4A, 5A), (1B, 2B, 3B, 4A, 5B), (1B, 2B, 3B, 4A, 5C), (1B, 2B, 3B, 4A, 5D), (1B, 2B, 3B, 4A, 5E), (1B, 2B, 3B, 4B, 5A), (1B, 2B, 3B, 4B, 5B), (1B, 2B, 3B, 4B, 5C), (1B, 2B, 3B, 4B, 5D), (1B, 2B, 3B, 4B, 5E), (1B, 2B, 3B, 4C, 5A), (1B, 2B, 3B, 4C, 5B), (1B, 2B, 3B, 4C, 5C), (1B, 2B, 3B, 4C, 5D), (1B, 2B, 3B, 4C, 5E), (1B, 2B, 3B, 4D, 5A), (1B, 2B, 3B, 4D, 5B), (1B, 2B, 3B, 4D, 5C), (1B, 2B, 3B, 4D, 5D), (1B, 2B, 3B, 4D, 5E), (1B, 2B, 3B, 4E, 5A), (1B, 2B, 3B, 4E, 5B), (1B, 2B, 3B, 4E, 5C), (1B, 2B, 3B, 4E, 5D), (1B, 2B, 3B, 4E, 5E), (1B, 2C, 3A, 4A, 5A), (1B, 2C, 3A, 4A, 5B), (1B, 2C, 3A, 4A, 5C), (1B, 2C, 3A, 4A, 5D), (1B, 2C, 3A, 4A, 5E), (1B, 2C, 3A, 4B, 5A), (1B, 2C, 3A, 4B, 5B), (1B, 2C, 3A, 4B, 5C), (1B, 2C, 3A, 4B, 5D), (1B, 2C, 3A, 4B, 5E), (1B, 2C, 3A, 4C, 5A), (1B, 2C, 3A, 4C, 5B), (1B, 2C, 3A, 4C, 5C), (1B, 2C, 3A, 4C, 5D), (1B, 2C, 3A, 4C, 5E), (1B, 2C, 3A, 4D, 5A), (1B, 2C, 3A, 4D, 5B), (1B, 2C, 3A, 4D, 5C), (1B, 2C, 3A, 4D, 5D), (1B, 2C, 3A, 4D, 5E), (1B, 2C, 3A, 4E, 5A), (1B, 2C, 3A, 4E, 5B), (1B, 2C, 3A, 4E, 5C), (1B, 2C, 3A, 4E, 5D), (1B, 2C, 3A, 4E, 5E), (1B, 2C, 3B, 4A, 5A), (1B, 2C, 3B, 4A, 5B), (1B, 2C, 3B, 4A, 5C), (1B, 2C, 3B, 4A, 5D), (1B, 2C, 3B, 4A, 5E), (1B, 2C, 3B, 4B, 5A), (1B, 2C, 3B, 4B, 5B), (1B, 2C, 3B, 4B, 5C), (1B, 2C, 3B, 4B, 5D), (1B, 2C, 3B, 4B, 5E), (1B, 2C, 3B, 4C, 5A), (1B, 2C, 3B, 4C, 5B), (1B, 2C, 3B, 4C, 5C), (1B, 2C, 3B, 4C, 5D), (1B, 2C, 3B, 4C, 5E), (1B, 2C, 3B, 4D, 5A), (1B, 2C, 3B, 4D, 5B), (1B, 2C, 3B, 4D, 5C), (1B, 2C, 3B, 4D, 5D), (1B, 2C, 3B, 4D, 5E), (1B, 2C, 3B, 4E, 5A), (1B, 2C, 3B, 4E, 5B), (1B, 2C, 3B, 4E, 5C), (1B, 2C, 3B, 4E, 9D), (1B, 2C, 3B, 4E, 5E), (1B, 2D, 3A, 4A, 5A), (1B, 2D, 3A, 4A, 5B), (1B, 2D, 3A, 4A, 5C), (1B, 2D, 3A, 4A, 5D), (1B, 2D, 3A, 4A, 5E), (1B, 2D, 3A, 4B, 5A), (1B, 2D, 3A, 4B, 5B), (1B, 2D, 3A, 4B, 5C), (1B, 2D, 3A, 4B, 5D), (1B, 2D, 3A, 4B, 5E), (1B, 2D, 3A, 4C, 5A), (1B, 2D, 3A, 4C, 5B), (1B, 2D, 3A, 4C, 5C), (1B, 2D, 3A, 4C, 5D), (1B, 2D, 3A, 4C, 5E), (1B, 2D, 3A, 4D, 5A), (1B, 2D, 3A, 4D, 5B), (1B, 2D, 3A, 4D, 5C), (1B, 2D, 3A, 4D, 5D), (1B, 2D, 3A, 4D, 5E), (1B, 2D, 3A, 4E, 5A), (1B, 2D, 3A, 4E, 5B), (1B, 2D, 3A, 4E, 5C), (1B, 2D, 3A, 4E, 5D), (1B, 2D, 3A, 4E, 5E), (1B, 2D, 3B, 4A, 5A), (1B, 2D, 3B, 4A, 5B), (1B, 2D, 3B, 4A, 5C), (1B, 2D, 3B, 4A, 5D), (1B, 2D, 3B, 4A, 5E), (1B, 2D, 3B, 4B, 5A), (1B, 2D, 3B, 4B, 5B), (1B, 2D, 3B, 4B, 5C), (1B, 2D, 3B, 4B, 5D), (1B, 2D, 3B, 4B, 5E), (1B, 2D, 3B, 4C, 5A), (1B, 2D, 3B, 4C, 5B), (1B, 2D, 3B, 4C, 5C), (1B, 2D, 3B, 4C, 5D), (1B, 2D, 3B, 4C, 5E), (1B, 2D, 3B, 4D, 5A), (1B, 2D, 3B, 4D, 5B), (1B, 2D, 3B, 4D, 5C), (1B, 2D, 3B, 4D, 5D), (1B, 2D, 3B, 4D, 5E), (1B, 2D, 3B, 4E, 5A), (1B, 2D, 3B, 4E, 5B), (1B, 2D, 3B, 4E, 5C), (1B, 2D, 3B, 4E, 5D), (1B, 2D, 3B, 4E, 5E), (1B, 2E, 3A, 4A, 5A), (1B, 2E, 3A, 4A, 5B), (1B, 2E, 3A, 4A, 5C), (1B, 2E, 3A, 4A, 5D), (1B, 2E, 3A, 4A, 5E), (1B, 2E, 3A, 4B, 5A), (1B, 2E, 3A, 4B, 5B), (1B, 2E, 3A, 4B, 5C), (1B, 2E, 3A, 4B, 5D), (1B, 2E, 3A, 4B, 5E), (1B, 2E, 3A, 4C, 5A), (1B, 2E, 3A, 4C, 5B), (1B, 2E, 3A, 4C, 5C), (1B, 2E, 3A, 4C, 5D), (1B, 2E, 3A, 4C, 5E), (1B, 2E, 3A, 4D, 5A), (1B, 2E, 3A, 4D, 5B), (1B, 2E, 3A, 4D, 5C), (1B, 2E, 3A, 4D, 5D), (1B, 2E, 3A, 4D, 5E), (1B, 2E, 3A, 4E, 5A), (1B, 2E, 3A, 4E, 5B), (1B, 2E, 3A, 4E, 5C), (1B, 2E, 3A, 4E, 5D), (1B, 2E, 3A, 4E, 5E), (1B, 2E, 3B, 4A, 5A), (1B, 2E, 3B, 4A, 5B), (1B, 2E, 3B, 4A, 5C), (1B, 2E, 3B, 4A, 5D), (1B, 2E, 3B, 4A, 5E), (1B, 2E, 3B, 4B, 5A), (1B, 2E, 3B, 4B, 5B), (1B, 2E, 3B, 4B, 5C), (1B, 2E, 3B, 4B, 5D), (1B, 2E, 3B, 4B, 5E), (1B, 2E, 3B, 4C, 5A), (1B, 2E, 3B, 4C, 5B), (1B, 2E, 3B, 4C, 5C), (1B, 2E, 3B, 4C, 5D), (1B, 2E, 3B, 4C, 5E), (1B, 2E, 3B, 4D, 5A), (1B, 2E, 3B, 4D, 5B), (1B, 2E, 3B, 4D, 5C), (1B, 2E, 3B, 4D, 5D), (1B, 2E, 3B, 4D, 5E), (1B, 2E, 3B, 4E, 5A), (1B, 2E, 3B, 4E, 5B), (1B, 2E, 3B, 4E, 5C), (1B, 2E, 3B, 4E, 5D), (1B, 2E, 3B, 4E, 5E), (1C, 2A, 3A, 4A, 5A), (1C, 2A, 3A, 4A, 5B), (1C, 2A, 3A, 4A, 5C), (1C, 2A, 3A, 4A, 5D), (1C, 2A, 3A, 4A, 5E), (1C, 2A, 3A, 4B, 5A), (1C, 2A, 3A, 4B, 5B), (1C, 2A, 3A, 4B, 5C), (1C, 2A, 3A, 4B, 5D), (1C, 2A, 3A, 4B, 5E), (1C, 2A, 3A, 4C, 5A), (1C, 2A, 3A, 4C, 5B), (1C, 2A, 3A, 4C, 5C), (1C, 2A, 3A, 4C, 5D), (1C, 2A, 3A, 4C, 5E), (1C, 2A, 3A, 4D, 5A), (1C, 2A, 3A, 4D, 5B), (1C, 2A, 3A, 4D, 5C), (1C, 2A, 3A, 4D, 5D), (1C, 2A, 3A, 4D, 5E), (1C, 2A, 3A, 4E, 5A), (1C, 2A, 3A, 4E, 5B), (1C, 2A, 3A, 4E, 5C), (1C, 2A, 3A, 4E, 5D), (1C, 2A, 3A, 4E, 5E), (1C, 2A, 3B, 4A, 5A), (1C, 2A, 3B, 4A, 5B), (1C, 2A, 3B, 4A, 5C), (1C, 2A, 3B, 4A, 5D), (1C, 2A, 3B, 4A, 5E), (1C, 2A, 3B, 4B, 5A), (1C, 2A, 3B, 4B, 5B), (1C, 2A, 3B, 4B, 5C), (1C, 2A, 3B, 4B, 5D), (1C, 2A, 3B, 4B, 5E), (1C, 2A, 3B, 4C, 5A), (1C, 2A, 3B, 4C, 5B), (1C, 2A, 3B, 4C, 5C), (1C, 2A, 3B, 4C, 5D), (1C, 2A, 3B, 4C, 5E), (1C, 2A, 3B, 4D, 5A), (1C, 2A, 3B, 4D, 5B), (1C, 2A, 3B, 4D, 5C), (1C, 2A, 3B, 4D, 5D), (1C, 2A, 3B, 4D, 5E), (1C, 2A, 3B, 4E, 5A), (1C, 2A, 3B, 4E, 5B), (1C, 2A, 3B, 4E, 5C), (1C, 2A, 3B, 4E, 5D), (1C, 2A, 3B, 4E, 5E), (1C, 2B, 3A, 4A, 5A), (1C, 2B, 3A, 4A, 5B), (1C, 2B, 3A, 4A, 5C), (1C, 2B, 3A, 4A, 5D), (1C, 2B, 3A, 4A, 5E), (1C, 2B, 3A, 4B, 5A), (1C, 2B, 3A, 4B, 5B), (1C, 2B, 3A, 4B, 5C), (1C, 2B, 3A, 4B, 5D), (1C, 2B, 3A, 4B, 5E), (1C, 2B, 3A, 4C, 5A), (1C, 2B, 3A, 4C, 5B), (1C, 2B, 3A, 4C, 5C), (1C, 2B, 3A, 4C, 5D), (1C, 2B, 3A, 4C, 5E), (1C, 2B, 3A, 4D, 5A), (1C, 2B, 3A, 4D, 5B), (1C, 2B, 3A, 4D, 5C), (1C, 2B, 3A, 4D, 5D), (1C, 2B, 3A, 4D, 5E), (1C, 2B, 3A, 4E, 5A), (1C, 2B, 3A, 4E, 5B), (1C, 2B, 3A, 4E, 5C), (1C, 2B, 3A, 4E, 5D), (1C, 2B, 3A, 4E, 5E), (1C, 2B, 3B, 4A, 5A), (1C, 2B, 3B, 4A, 5B), (1C, 2B, 3B, 4A, 5C), (1C, 2B, 3B, 4A, 5D), (1C, 2B, 3B, 4A, 5E), (1C, 2B, 3B, 4B, 5A), (1C, 2B, 3B, 4B, 5B), (1C, 2B, 3B, 4B, 5C), (1C, 2B, 3B, 4B, 5D), (1C, 2B, 3B, 4B, 5E), (1C, 2B, 3B, 4C, 5A), (1C, 2B, 3B, 4C, 5B), (1C, 2B, 3B, 4C, 5C), (1C, 2B, 3B, 4C, 5D), (1C, 2B, 3B, 4C, 5E), (1C, 2B, 3B, 4D, 5A), (1C, 2B, 3B, 4D, 5B), (1C, 2B, 3B, 4D, 5C), (1C, 2B, 3B, 4D, 5D), (1C, 2B, 3B, 4D, 5E), (1C, 2B, 3B, 4E, 5A), (1C, 2B, 3B, 4E, 5B), (1C, 2B, 3B, 4E, 5C), (1C, 2B, 3B, 4E, 5D), (1C, 2B, 3B, 4E, 5E), (1C, 2C, 3A, 4A, 5A), (1C, 2C, 3A, 4A, 5B), (1C, 2C, 3A, 4A, 5C), (1C, 2C, 3A, 4A, 5D), (1C, 2C, 3A, 4A, 5E), (1C, 2C, 3A, 4B, 5A), (1C, 2C, 3A, 4B, 5B), (1C, 2C, 3A, 4B, 5C), (1C, 2C, 3A, 4B, 5D), (1C, 2C, 3A, 4B, 5E), (1C, 2C, 3A, 4C, 5A), (1C, 2C, 3A, 4C, 5B), (1C, 2C, 3A, 4C, 5C), (1C, 2C, 3A, 4C, 5D), (1C, 2C, 3A, 4C, 5E), (1C, 2C, 3A, 4D, 5A), (1C, 2C, 3A, 4D, 5B), (1C, 2C, 3A, 4D, 5C), (1C, 2C, 3A, 4D, 5D), (1C, 2C, 3A, 4D, 5E), (1C, 2C, 3A, 4E, 5A), (1C, 2C, 3A, 4E, 5B), (1C, 2C, 3A, 4E, 5C), (1C, 2C, 3A, 4E, 5D), (1C, 2C, 3A, 4E, 5E), (1C, 2C, 3B, 4A, 5A), (1C, 2C, 3B, 4A, 5B), (1C, 2C, 3B, 4A, 5C), (1C, 2C, 3B, 4A, 5D), (1C, 2C, 3B, 4A, 5E), (1C, 2C, 3B, 4B, 5A), (1C, 2C, 3B, 4B, 5B), (1C, 2C, 3B, 4B, 5C), (1C, 2C, 3B, 4B, 5D), (1C, 2C, 3B, 4B, 5E), (1C, 2C, 3B, 4C, 5A), (1C, 2C, 3B, 4C, 5B), (1C, 2C, 3B, 4C, 5C), (1C, 2C, 3B, 4C, 5D), (1C, 2C, 3B, 4C, 5E), (1C, 2C, 3B, 4D, 5A), (1C, 2C, 3B, 4D, 5B), (1C, 2C, 3B, 4D, 5C), (1C, 2C, 3B, 4D, 5D), (1C, 2C, 3B, 4D, 5E), (1C, 2C, 3B, 4E, 5A), (1C, 2C, 3B, 4E, 5B), (1C, 2C, 3B, 4E, 5C), (1C, 2C, 3B, 4E, 5D), (1C, 2C, 3B, 4E, 5E), (1C, 2D, 3A, 4A, 5A), (1C, 2D, 3A, 4A, 5B), (1C, 2D, 3A, 4A, 5C), (1C, 2D, 3A, 4A, 5D), (1C, 2D, 3A, 4A, 5E), (1C, 2D, 3A, 4B, 5A), (1C, 2D, 3A, 4B, 5B), (1C, 2D, 3A, 4B, 5C), (1C, 2D, 3A, 4B, 5D), (1C, 2D, 3A, 4B, 5E), (1C, 2D, 3A, 4C, 5A), (1C, 2D, 3A, 4C, 5B), (1C, 2D, 3A, 4C, 5C), (1C, 2D, 3A, 4C, 5D), (1C, 2D, 3A, 4C, 5E), (1C, 2D, 3A, 4D, 5A), (1C, 2D, 3A, 4D, 5B), (1C, 2D, 3A, 4D, 5C), (1C, 2D, 3A, 4D, 5D), (1C, 2D, 3A, 4D, 5E), (1C, 2D, 3A, 4E, 5A), (1C, 2D, 3A, 4E, 5B), (1C, 2D, 3A, 4E, 5C), (1C, 2D, 3A, 4E, 5D), (1C, 2D, 3A, 4E, 5E), (1C, 2D, 3B, 4A, 5A), (1C, 2D, 3B, 4A, 5B), (1C, 2D, 3B, 4A, 5C), (1C, 2D, 3B, 4A, 5D), (1C, 2D, 3B, 4A, 5E), (1C, 2D, 3B, 4B, 5A), (1C, 2D, 3B, 4B, 5B), (1C, 2D, 3B, 4B, 5C), (1C, 2D, 3B, 4B, 5D), (1C, 2D, 3B, 4B, 5E), (1C, 2D, 3B, 4C, 5A), (1C, 2D, 3B, 4C, 5B), (1C, 2D, 3B, 4C, 5C), (1C, 2D, 3B, 4C, 5D), (1C, 2D, 3B, 4C, 5E), (1C, 2D, 3B, 4D, 5A), (1C, 2D, 3B, 4D, 5B), (1C, 2D, 3B, 4D, 5C), (1C, 2D, 3B, 4D, 5D), (1C, 2D, 3B, 4D, 5E), (1C, 2D, 3B, 4E, 5A), (1C, 2D, 3B, 4E, 5B), (1C, 2D, 3B, 4E, 5C), (1C, 2D, 3B, 4E, 5D), (1C, 2D, 3B, 4E, 5E), (1C, 2E, 3A, 4A, 5A), (1C, 2E, 3A, 4A, 5B), (1C, 2E, 3A, 4A, 5C), (1C, 2E, 3A, 4A, 5D), (1C, 2E, 3A, 4A, 5E), (1C, 2E, 3A, 4B, 5A), (1C, 2E, 3A, 4B, 5B), (1C, 2E, 3A, 4B, 5C), (1C, 2E, 3A, 4B, 5D), (1C, 2E, 3A, 4B, 5E), (1C, 2E, 3A, 4C, 5A), (1C, 2E, 3A, 4C, 5B), (1C, 2E, 3A, 4C, 5C), (1C, 2E, 3A, 4C, 5D), (1C, 2E, 3A, 4C, 5E), (1C, 2E, 3A, 4D, 5A), (1C, 2E, 3A, 4D, 5B), (1C, 2E, 3A, 4D, 5C), (1C, 2E, 3A, 4D, 5D), (1C, 2E, 3A, 4D, 5E), (1C, 2E, 3A, 4E, 5A), (1C, 2E, 3A, 4E, 5B), (1C, 2E, 3A, 4E, 5C), (1C, 2E, 3A, 4E, 5D), (1C, 2E, 3A, 4E, 5E), (1C, 2E, 3B, 4A, 5A), (1C, 2E, 3B, 4A, 5B), (1C, 2E, 3B, 4A, 5C), (1C, 2E, 3B, 4A, 5D), (1C, 2E, 3B, 4A, 5E), (1C, 2E, 3B, 4B, 5A), (1C, 2E, 3B, 4B, 5B), (1C, 2E, 3B, 4B, 5C), (1C, 2E, 3B, 4B, 5D), (1C, 2E, 3B, 4B, 5E), (1C, 2E, 3B, 4C, 5A), (1C, 2E, 3B, 4C, 5B), (1C, 2E, 3B, 4C, 5C), (1C, 2E, 3B, 4C, 5J), (1C, 2E, 3B, 4C, 5E), (1C, 2E, 3B, 4D, 5A), (1C, 2E, 3B, 4D, 5B), (1C, 2E, 3B, 4D, 5C), (1C, 2E, 3B, 4D, 5D), (1C, 2E, 3B, 4D, 5E), (1C, 2E, 3B, 4E, 5A), (1C, 2E, 3B, 4E, 5B), (1C, 2E, 3B, 4E, 5C), (1C, 2E, 3B, 4E, 5D), (1C, 2E, 3B, 4E, 5E), (1D, 2A, 3A, 4A, 5A), (1D, 2A, 3A, 4A, 5B), (1D, 2A, 3A, 4A, 5C), (1D, 2A, 3A, 4A, 5D), (1D, 2A, 3A, 4A, 5E), (1D, 2A, 3A, 4B, 5A), (1D, 2A, 3A, 4B, 5B), (1D, 2A, 3A, 4B, 5C), (1D, 2A, 3A, 4B, 5D), (1D, 2A, 3A, 4B, 5E), (1D, 2A, 3A, 4C, 5A), (1D, 2A, 3A, 4C, 5B), (1D, 2A, 3A, 4C, 5C), (1D, 2A, 3A, 4C, 5D), (1D, 2A, 3A, 4C, 5E), (1D, 2A, 3A, 4D, 5A), (1D, 2A, 3A, 4D, 5B), (1D, 2A, 3A, 4D, 5C), (1D, 2A, 3A, 4D, 5D), (1D, 2A, 3A, 4D, 5E), (1D, 2A, 3A, 4E, 5A), (1D, 2A, 3A, 4E, 5B), (1D, 2A, 3A, 4E, 5C), (1D, 2A, 3A, 4E, 5D), (1D, 2A, 3A, 4E, 5E), (1D, 2A, 3B, 4A, 5A), (1D, 2A, 3B, 4A, 5B), (1D, 2A, 3B, 4A, 5C), (1D, 2A, 3B, 4A, 5D), (1D, 2A, 3B, 4A, 5E), (1D, 2A, 3B, 4B, 5A), (1D, 2A, 3B, 4B, 5B), (1D, 2A, 3B, 4B, 5C), (1D, 2A, 3B, 4B, 5D), (1D, 2A, 3B, 4B, 5E), (1D, 2A, 3B, 4C, 5A), (1D, 2A, 3B, 4C, 5B), (1D, 2A, 3B, 4C, 5C), (1D, 2A, 3B, 4C, 5D), (1D, 2A, 3B, 4C, 5E), (1D, 2A, 3B, 4D, 5A), (1D, 2A, 3B, 4D, 5B), (1D, 2A, 3B, 4D, 5C), (1D, 2A, 3B, 4D, 5D), (1D, 2A, 3B, 4D, 5E), (1D, 2A, 3B, 4E, 5A), (1D, 2A, 3B, 4E, 5B), (1D, 2A, 3B, 4E, 5C), (1D, 2A, 3B, 4E, 5D), (1D, 2A, 3B, 4E, 5E), (1D, 2B, 3A, 4A, 5A), (1D, 2B, 3A, 4A, 5B), (1D, 2B, 3A, 4A, 5C), (1D, 2B, 3A, 4A, 5D), (1D, 2B, 3A, 4A, 5E), (1D, 2B, 3A, 4B, 5A), (1D, 2B, 3A, 4B, 5B), (1D, 2B, 3A, 4B, 5C), (1D, 2B, 3A, 4B, 5D), (1D, 2B, 3A, 4B, 5E), (1D, 2B, 3A, 4C, 5A), (1D, 2B, 3A, 4C, 5B), (1D, 2B, 3A, 4C, 5C), (1D, 2B, 3A, 4C, 5D), (1D, 2B, 3A, 4C, 5E), (1D, 2B, 3A, 4D, 5A), (1D, 2B, 3A, 4D, 5B), (1D, 2B, 3A, 4D, 5C), (1D, 2B, 3A, 4D, 5D), (1D, 2B, 3A, 4D, 5E), (1D, 2B, 3A, 4E, 5A), (1D, 2B, 3A, 4E, 5B), (1D, 2B, 3A, 4E, 5C), (1D, 2B, 3A, 4E, 5D), (1D, 2B, 3A, 4E, 5E), (1D, 2B, 3B, 4A, 5A), (1D, 2B, 3B, 4A, 5B), (1D, 2B, 3B, 4A, 5C), (1D, 2B, 3B, 4A, 5D), (1D, 2B, 3B, 4A, 5E), (1D, 2B, 3B, 4B, 5A), (1D, 2B, 3B, 4B, 5B), (1D, 2B, 3B, 4B, 5C), (1D, 2B, 3B, 4B, 5D), (1D, 2B, 3B, 4B, 5E), (1D, 2B, 3B, 4C, 5A), (1D, 2B, 3B, 4C, 5B), (1D, 2B, 3B, 4C, 5C), (1D, 2B, 3B, 4C, 5D), (1D, 2B, 3B, 4C, 5E), (1D, 2B, 3B, 4D, 5A), (1D, 2B, 3B, 4D, 5B), (1D, 2B, 3B, 4D, 5C), (1D, 2B, 3B, 4D, 5D), (1D, 2B, 3B, 4D, 5E), (1D, 2B, 3B, 4E, 5A), (1D, 2B, 3B, 4E, 5B), (1D, 2B, 3B, 4E, 50), (1D, 2B, 3B, 4E, 5D), (1D, 2B, 3B, 4E, 5E), (1D, 2C, 3A, 4A, 5A), (1D, 2C, 3A, 4A, 5B), (1D, 2C, 3A, 4A, 5C), (1D, 2C, 3A, 4A, 5D), (1D, 2C, 3A, 4A, 5E), (1D, 2C, 3A, 4B, 5A), (1D, 2C, 3A, 4B, 5B), (1D, 2C, 3A, 4B, 5C), (1D, 2C, 3A, 4B, 5D), (1D, 2C, 3A, 4B, 5E), (1D, 2C, 3A, 4C, 5A), (1D, 2C, 3A, 4C, 5B), (1D, 2C, 3A, 4C, 5C), (1D, 2C, 3A, 4C, 5D), (1D, 2C, 3A, 4C, 5E), (1D, 2C, 3A, 4D, 5A), (1D, 2C, 3A, 4D, 5B), (1D, 2C, 3A, 4D, 5C), (1D, 2C, 3A, 4D, 5D), (1D, 2C, 3A, 4D, 5E), (1D, 2C, 3A, 4E, 5A), (1D, 2C, 3A, 4E, 5B), (1D, 2C, 3A, 4E, 5C), (1D, 2C, 3A, 4E, 5D), (1D, 2C, 3A, 4E, 5E), (1D, 2C, 3B, 4A, 5A), (1D, 2C, 3B, 4A, 5B), (1D, 2C, 3B, 4A, 5C), (1D, 2C, 3B, 4A, 5D), (1D, 2C, 3B, 4A, 5E), (1D, 2C, 3B, 4B, 5A), (1D, 2C, 3B, 4B, 5B), (1D, 2C, 3B, 4B, 5c), (1D, 2C, 3B, 4B, 5D), (1D, 2C, 3B, 4B, 5E), (1D, 2C, 3B, 4C, 5A), (1D, 2C, 3B, 4C, 5B), (1D, 2C, 3B, 4C, 5C), (1D, 2C, 3B, 4C, 5D), (1D, 2C, 3B, 4C, 5E), (1D, 2C, 3B, 4D, 5A), (1D, 2C, 3B, 4D, 5B), (1D, 2C, 3B, 4D, 5C), (1D, 2C, 3B, 4D, 5D), (1D, 2C, 3B, 4D, 5E), (1D, 2C, 3B, 4E, 5A), (1D, 2C, 3B, 4E, 5B), (1D, 2C, 3B, 4E, 5C), (1D, 2C, 3B, 4E, 5D), (1D, 2C, 3B, 4E, 5E), (1D, 2D, 3A, 4A, 5A), (1D, 2D, 3A, 4A, 5B), (1D, 2D, 3A, 4A, 5C), (1D, 2D, 3A, 4A, 5D), (1D, 2D, 3A, 4A, 5E), (1D, 2D, 3A, 4B, 5A), (1D, 2D, 3A, 4B, 5B), (1D, 2D, 3A, 4B, 5C), (1D, 2D, 3A, 4B, 5D), (1D, 2D, 3A, 4B, 5E), (1D, 2D, 3A, 4C, 5A), (1D, 2D, 3A, 4C, 5B), (1D, 2D, 3A, 4C, 5C), (1D, 2D, 3A, 4C, 5D), (1D, 2D, 3A, 4C, 5E), (1D, 2D, 3A, 4D, 5A), (1D, 2D, 3A, 4D, 5B), (1D, 2D, 3A, 4D, 5C), (1D, 2D, 3A, 4D, 5D), (1D, 2D, 3A, 4D, 5E), (1D, 2D, 3A, 4E, 5A), (1D, 2D, 3A, 4E, 5B), (1D, 2D, 3A, 4E, 5C), (1D, 2D, 3A, 4E, 5D), (1D, 2D, 3A, 4E, 5E), (1D, 2D, 3B, 4A, 5A), (1D, 2D, 3B, 4A, 5B), (1D, 2D, 3B, 4A, 5C), (1D, 2D, 3B, 4A, 5D), (1D, 2D, 3B, 4A, 5E), (1D, 2D, 3B, 4B, 5A), (1D, 2D, 3B, 4B, 5B), (1D, 2D, 3B, 4B, 5C), (1D, 2D, 3B, 4B, 5D), (1D, 2D, 3B, 4B, 5E), (1D, 2D, 3B, 4C, 5A), (1D, 2D, 3B, 4C, 5B), (1D, 2D, 3B, 4C, 5C), (1D, 2D, 3B, 4C, 5D), (1D, 2D, 3B, 4C, 5E), (1D, 2D, 3B, 4D, 5A), (1D, 2D, 3B, 4D, 5B), (1D, 2D, 3B, 4D, 5C), (1D, 2D, 3B, 4D, 5D), (1D, 2D, 3B, 4D, 5E), (1D, 2D, 3B, 4E, 5A), (1D, 2D, 3B, 4E, 5B), (1D, 2D, 3B, 4E, 5C), (1D, 2D, 3B, 4E, 5D), (1D, 2D, 3B, 4E, 5E), (1D, 2E, 3A, 4A, 5A), (1D, 2E, 3A, 4A, 5B), (1D, 2E, 3A, 4A, 5C), (1D, 2E, 3A, 4A, 5D), (1D, 2E, 3A, 4A, 5E), (1D, 2E, 3A, 4B, 5A), (1D, 2E, 3A, 4B, 5B), (1D, 2E, 3A, 4B, 5C), (1D, 2E, 3A, 4B, 5D), (1D, 2E, 3A, 4B, 5E), (1D, 2E, 3A, 4C, 5A), (1D, 2E, 3A, 4C, 5B), (1D, 2E, 3A, 4C, 5C), (1D, 2E, 3A, 4C, 5D), (1D, 2E, 3A, 4C, 5E), (1D, 2E, 3A, 4D, 5A), (1D, 2E, 3A, 4D, 5B), (1D, 2E, 3A, 4D, 5C), (1D, 2E, 3A, 4D, 5D), (1D, 2E, 3A, 4D, 5E), (1D, 2E, 3A, 4E, 5A), (1D, 2E, 3A, 4E, 5B), (1D, 2E, 3A, 4E, 5C), (1D, 2E, 3A, 4E, 5D), (1D, 2E, 3A, 4E, 5E), (1D, 2E, 3B, 4A, 5A), (1D, 2E, 3B, 4A, 5B), (1D, 2E, 3B, 4A, 5C), (1D, 2E, 3B, 4A, 5D), (1D, 2E, 3B, 4A, 5E), (1D, 2E, 3B, 4B, 5A), (1D, 2E, 3B, 4B, 5B), (1D, 2E, 3B, 4B, 5C), (1D, 2E, 3B, 4B, 5D), (1D, 2E, 3B, 4B, 5E), (1D, 2E, 3B, 4C, 5A), (1D, 2E, 3B, 4C, 5B), (1D, 2E, 3B, 4C, 5C), (1D, 2E, 3B, 4C, 5D), (1D, 2E, 3B, 4C, 5E), (1D, 2E, 3B, 4D, 5A), (1D, 2E, 3B, 4D, 5B), (1D, 2E, 3B, 4D, 5C), (1D, 2E, 3B, 4D, 5D), (1D, 2E, 3B, 4D, 5E), (1D, 2E, 3B, 4E, 5A), (1D, 2E, 3B, 4E, 5B), (1D, 2E, 3B, 4E, 5C), (1D, 2E, 3B, 4E, 5D), (1D, 2E, 3B, 4E, 5E), (1E, 2A, 3A, 4A, 5A), (1E, 2A, 3A, 4A, 5B), (1E, 2A, 3A, 4A, 5C), (1E, 2A, 3A, 4A, 5D), (1E, 2A, 3A, 4A, 5E), (1E, 2A, 3A, 4B, 5A), (1E, 2A, 3A, 4B, 5B), (1E, 2A, 3A, 4B, 5C), (1E, 2A, 3A, 4B, 5D), (1E, 2A, 3A, 4B, 5E), (1E, 2A, 3A, 4C, 5A), (1E, 2A, 3A, 4C, 5B), (1E, 2A, 3A, 4C, 5C), (1E, 2A, 3A, 4C, 5D), (1E, 2A, 3A, 4C, 5E), (1E, 2A, 3A, 4D, 5A), (1E, 2A, 3A, 4D, 5B), (1E, 2A, 3A, 4D, 5C), (1E, 2A, 3A, 4D, 5D), (1E, 2A, 3A, 4D, 5E), (1E, 2A, 3A, 4E, 5A), (1E, 2A, 3A, 4E, 5B), (1E, 2A, 3A, 4E, 5C), (1E, 2A, 3A, 4E, 5D), (1E, 2A, 3A, 4E, 5E), (1E, 2A, 3B, 4A, 5A), (1E, 2A, 3B, 4A, 5B), (1E, 2A, 3B, 4A, 5C), (1E, 2A, 3B, 4A, 5D), (1E, 2A, 3B, 4A, 5E), (1E, 2A, 3B, 4B, 5A), (1E, 2A, 3B, 4B, 5B), (1E, 2A, 3B, 4B, 5C), (1E, 2A, 3B, 4B, 5D), (1E, 2A, 3B, 4B, 5E), (1E, 2A, 3B, 4C, 5A), (1E, 2A, 3B, 4C, 5B), (1E, 2A, 3B, 4C, 5C), (1E, 2A, 3B, 4C, 5D), (1E, 2A, 3B, 4C, 5E), (1E, 2A, 3B, 4D, 5A), (1E, 2A, 3B, 4D, 5B), (1E, 2A, 3B, 4D, 5C), (1E, 2A, 3B, 4D, 5D), (1E, 2A, 3B, 4D, 5E), (1E, 2A, 3B, 4E, 5A), (1E, 2A, 3B, 4E, 5B), (1E, 2A, 3B, 4E, 5C), (1E, 2A, 3B, 4E, 5D), (1E, 2A, 3B, 4E, 5E), (1E, 2B, 3A, 4A, 5A), (1E, 2B, 3A, 4A, 5B), (1E, 2B, 3A, 4A, 5C), (1E, 2B, 3A, 4A, 5D), (1E, 2B, 3A, 4A, 5E), (1E, 2B, 3A, 4B, 5A), (1E, 2B, 3A, 4B, 5B), (1E, 2B, 3A, 4B, 5C), (1E, 2B, 3A, 4B, 5D), (1E, 2B, 3A, 4B, 5E), (1E, 2B, 3A, 4C, 5A), (1E, 2B, 3A, 4C, 5B), (1E, 2B, 3A, 4C, 5C), (1E, 2B, 3A, 4C, 5D), (1E, 2B, 3A, 4C, 5E), (1E, 2B, 3A, 4D, 5A), (1E, 2B, 3A, 4D, 5B), (1E, 2B, 3A, 4D, 5C), (1E, 2B, 3A, 4D, 5D), (1E, 2B, 3A, 4D, 5E), (1E, 2B, 3A, 4E, 5A), (1E, 2B, 3A, 4E, 5B), (1E, 2B, 3A, 4E, 5C), (1E, 2B, 3A, 4E, 5D), (1E, 2B, 3A, 4E, 5E), (1E, 2B, 3B, 4A, 5A), (1E, 2B, 3B, 4A, 5B), (1E, 2B, 3B, 4A, 5C), (1E, 2B, 3B, 4A, 5D), (1E, 2B, 3B, 4A, 5E), (1E, 2B, 3B, 4B, 5A), (1E, 2B, 3B, 4B, 5B), (1E, 2B, 3B, 4B, 5C), (1E, 2B, 3B, 4B, 5D), (1E, 2B, 3B, 4B, 5E), (1E, 2B, 3B, 4C, 5A), (1E, 2B, 3B, 4C, 5B), (1E, 2B, 3B, 4C, 5C), (1E, 2B, 3B, 4C, 5D), (1E, 2B, 3B, 4C, 5E), (1E, 2B, 3B, 4D, 5A), (1E, 2B, 3B, 4D, 5B), (1E, 2B, 3B, 4D, 5C), (1E, 2B, 3B, 4D, 5D), (1E, 2B, 3B, 4D, 5E), (1E, 2B, 3B, 4E, 5A), (1E, 2B, 3B, 4E, 5B), (1E, 2B, 3B, 4E, 5C), (1E, 2B, 3B, 4E, 5D), (1E, 2B, 3B, 4E, 5E), (1E, 2C, 3A, 4A, 5A), (1E, 2C, 3A, 4A, 5B), (1E, 2C, 3A, 4A, 5C), (1E, 2C, 3A, 4A, 5D), (1E, 2C, 3A, 4A, 5E), (1E, 2C, 3A, 4B, 5A), (1E, 2C, 3A, 4B, 5B), (1E, 2C, 3A, 4B, 5C), (1E, 2C, 3A, 4B, 5D), (1E, 2C, 3A, 4B, 5E), (1E, 2C, 3A, 4C, 5A), (1E, 2C, 3A, 4C, 5B), (1E, 2C, 3A, 4C, 5C), (1E, 2C, 3A, 4C, 5D), (1E, 2C, 3A, 4C, 5E), (1E, 2C, 3A, 4D, 5A), (1E, 2C, 3A, 4D, 5B), (1E, 2C, 3A, 4D, 5C), (1E, 2C, 3A, 4D, 5D), (1E, 2C, 3A, 4D, 5E), (1E, 2C, 3A, 4E, 5A), (1E, 2C, 3A, 4E, 5B), (1E, 2C, 3A, 4E, 5C), (1E, 2C, 3A, 4E, 5D), (1E, 2C, 3A, 4E, 5E), (1E, 2C, 3B, 4A, 5A), (1E, 2C, 3B, 4A, 5B), (1E, 2C, 3B, 4A, 5C), (1E, 2C, 3B, 4A, 5D), (1E, 2C, 3B, 4A, 5E), (1E, 2C, 3B, 4B, 5A), (1E, 2C, 3B, 4B, 5B), (1E, 2C, 3B, 4B, 5C), (1E, 2C, 3B, 4B, 5D), (1E, 2C, 3B, 4B, 5E), (1E, 2C, 3B, 4C, 5A), (1E, 2C, 3B, 4C, 5B), (1E, 2C, 3B, 4C, 5C), (1E, 2C, 3B, 4C, 5D), (1E, 2C, 3B, 4C, 5E), (1E, 2C, 3B, 4D, 5A), (1E, 2C, 3B, 4D, 5B), (1E, 2C, 3B, 4D, 5C), (1E, 2C, 3B, 4D, 5D), (1E, 2C, 3B, 4D, 5E), (1E, 2C, 3B, 4E, 5A), (1E, 2C, 3B, 4E, 5B), (1E, 2C, 3B, 4E, 5C), (1E, 2C, 3B, 4E, 5D), (1E, 2C, 3B, 4E, 5E), (1E, 2D, 3A, 4A, 5A), (1E, 2D, 3A, 4A, 5B), (1E, 2D, 3A, 4A, 5C), (1E, 2D, 3A, 4A, 5D), (1B, 2D, 3A, 4A, 5E), (1E, 2D, 3A, 4B, 5A), (1E, 2D, 3A, 4B, 5B), (1E, 2D, 3A, 4B, 5C), (1E, 2D, 3A, 4B, 5D), (1E, 2D, 3A, 4B, 5E), (1E, 2D, 3A, 4C, 5A), (1E, 2D, 3A, 4C, 5B), (1E, 2D, 3A, 4C, 5C), (1E, 2D, 3A, 4C, 5D), (1E, 2D, 3A, 4C, 5E), (1E, 2D, 3A, 4D, 5A), (1E, 2D, 3A, 4D, 5B), (1E, 2D, 3A, 4D, 5C), (1E, 2D, 3A, 4D, 5D), (1E, 2D, 3A, 4D, 5E), (1E, 2D, 3A, 4E, 5A), (1E, 2D, 3A, 4E, 5B), (1E, 2D, 3A, 4E, 5C), (1E, 2D, 3A, 4E, 5D), (1E, 2D, 3A, 4E, 5E), (1E, 2D, 3B, 4A, 5A), (1E, 2D, 3B, 4A, 5B), (1E, 2D, 3B, 4A, 5C), (1E, 2D, 3B, 4A, 5D), (1E, 2D, 3B, 4A, 5E), (1E, 2D, 3B, 4B, 5A), (1E, 2D, 3B, 4B, 5B), (1E, 2D, 3B, 4B, 5C), (1E, 2D, 3B, 4B, 5D), (1E, 2D, 3B, 4B, 5E), (1E, 2D, 3B, 4C, 5A), (1B, 2D, 3B, 4C, 5B), (1E, 2D, 3B, 4C, 5C), (1E, 2D, 3B, 4C, 5D), (1E, 2D, 3B, 4C, 5E), (1E, 2D, 3B, 4D, 5A), (1E, 2D, 3B, 4D, 5B), (1E, 2D, 3B, 4D, 5C), (1E, 2D, 3B, 4D, 5D), (1E, 2D, 3B, 4D, 5E), (1E, 2D, 3B, 4E, 5A), (1E, 2D, 3B, 4E, 5B), (1E, 2D, 3B, 45C), (1E, 2D, 3B, 4E, 5D), ((1E, 2D, 3B, 4E, 5E), (1E, 2E, 3A, 4A, 5A), (1E, 2E, 3A, 4A, 5B), (1E, 2E, 3A, 4A, 5C), (1E, 2E, 3A, 4A, 5D), (1E, 2E, 3A, 4A, 5E), (1E, 2E, 3A, 4B, 5A), (1E, 2E, 3A, 4B, 5B), (1E, 2E, 3A, 4B, 5C), (1E, 2E, 3A, 4B, 5D), (1E, 2E, 3A, 4B, 5E), (1E, 2E, 3A, 4C, 5A), (1E, 2E, 3A, 4C, 5B), (1E, 2E, 3A, 4C, 5C), (1E, 2E, 3A, 4C, 5D), (1E, 2E, 3A, 4C, 5E), (1E, 2E, 3A, 4D, 5A), (1E, 2E, 3A, 4D, 5B), (1E, 2E, 3A, 4D, 5C, 5D), (1E, 2E, 3A, 4D, 5E), (1E, 2E, 3A, 4E, 5A), (1E, 2E, 3A, 4E, 5B), (1E, 2E, 3A, 4E, 5C), (1E, 2E, 3A, 4E, 5D), (1E, 2E, 3A, 4E, 5E), (1E, 2E, 3B, 4A, 5A), (1E, 2E, 3B, 4A, 5B), (1E, 2E, 3B, 45C), (1E, 2E, 3B, 4A, 5D), (1E, 2E, 3B, 4A, 5E), (1E, 2E, 3B, 4B, 5A), (1E, 2E, 3B, 4B, 5B), (1E, 2E, 3B, 4B, 5B), (1E, 2E, 3B, 4B, 5C), (1E, 2E, 3B, 4B, 5E), (1E, 2E, 3B, 4C, 5A), (1E, 2E, 3B, 4C, 5B), (1E, 2E, 3B, 4C, 5C), (1E, 2E, 3B, 4C, 5D), (1E, 2E, 3B, 4C, 5E), (1E, 2E, 3B, 4D, 5A), (1E, 2E, 3B, 4D, 5B), (1E, 2E, 3B, 4D, 5C), (1E, 2E, 3B, 4D, 5D), (1E, 2E, 3B, 4D, 5E), (1E, 2E, 3B, 4E, 5A), (1E, 2E, 3B, 4E, 5B), (1E, 2E, 3B, 4E, 5C), (1E, 2E, 3B, 4E, 5D), (1E, 2E, 3B, 4E, 5E)

And $(R^1, R^2, X, R^4, R^5)=(1A, 2A, 3A, 4A, 5A)$ is the compound which $R^1$ is 1A, $R^2$ is 2A, X is 3A, $R^4$ is 4A and $R^5$ is 5A. The other combinations are the same.

The compounds of the present invention include the following compounds. The following compounds are synthesized with a same manner similar to the above examples.

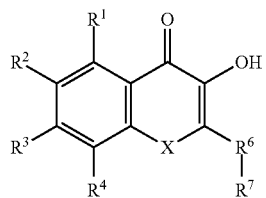

The substituents of $R^1$, $R^2$, $R^3$, $R^4$, X, $R^6$ and $R^7$ of above compound include the following substitution group.
$R^1$=H (1A), Me(1B), OMe(1C), Cl(1D), Ph(1E)
$R^2$=H (2A), Me(2B), OMe(2C), Cl(2D), Ph(2E)
$R^3$=H (2A), Me(3B), OMe(3C), Cl(3D), Ph(3E)
$R^4$=H (4A), Me(4B), OMe(40), Cl(4D), Ph(4E)
X=O(3A), NH(3B)

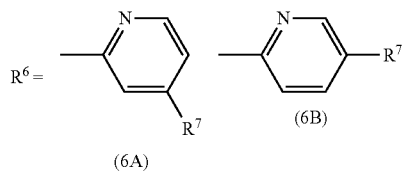

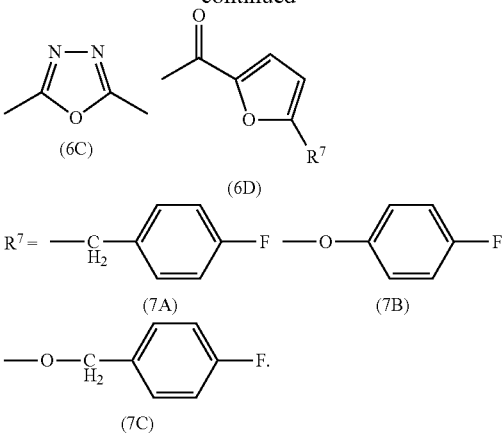

The preferable combinations $(R^1, R^2, R^3, R^4, X, R^6, R^7)$ of the substituents of above compound include the followings.

(1A, 2A, 3A, 4A, 5A, 6A, 7A), (1A, 2A, 3A, 4A, 5A, 6A, 7B), (1A, 2A, 3A, 4A, 5A, 6A, 7C), (1A, 2A, 3A, 4A, 5A, 6B, 7A), (1A, 2A, 3A, 4A, 5A, 6B, 7B), (1A, 2A, 3A, 4A, 5A, 6B, 7C), (1A, 2A, 3A, 4A, 5A, 6C, 7A), (1A, 2A, 3A, 4A, 5A, 6C, 7B), (1A, 2A, 3A, 4A, 5A, 6C, 7C), (1A, 2A, 3A, 4A, 5A, 6D, 7A), (1A, 2A, 3A, 4A, 5A, 6D, 7B), (1A, 2A, 3A, 4A, 5A, 6D, 7C), (1A, 2A, 3A, 4A, 5B, 6A, 7A), (1A, 2A, 3A, 4A, 5B, 6A, 7B), (1A, 2A, 3A, 4A, 5B, 6A, 7C), (1A, 2A, 3A, 4A, 5B, 6B, 7A), (1A, 2A, 3A, 4A, 5B, 6B, 7B), (1A, 2A, 3A, 4A, 5B, 6B, 7C), (1A, 2A, 3A, 4A, 5B, 6C, 7A), (1A, 2A, 3A, 4A, 5B, 6C, 7B), (1A, 2A, 3A, 4A, 5B, 6C, 7C), (1A, 2A, 3A, 4A, 5B, 6D, 7A), (1A, 2A, 3A, 4A, 5B, 6D, 7B), (1A, 2A, 3A, 4A, 5B, 6D, 7C), (1A, 2A, 3A, 4B, 5A, 6A, 7A), (1A, 2A, 3A, 4B, 5A, 6A, 7B), (1A, 2A, 3A, 4B, 5A, 6A, 7C), (1A, 2A, 3A, 4B, 5A, 6B, 7A), (1A, 2A, 3A, 4B, 5A, 6B, 7B), (1A, 2A, 3A, 4B, 5A, 6B, 7C), (1A, 2A, 3A, 4B, 5A, 6C, 7A), (1A, 2A, 3A, 4B, 5A, 6C, 7B), (1A, 2A, 3A, 4B, 5A, 6C, 7C), (1A, 2A, 3A, 4B, 5A, 6D, 7A), (1A, 2A, 3A, 4B, 5A, 6D, 7B), (1A, 2A, 3A, 4B, 5A, 6D, 7C), (1A, 2A, 3A, 4B, 5B, 6A, 7A), (1A, 2A, 3A, 4B, 5B, 6A, 7B), (1A, 2A, 3A, 4B, 5B, 6A, 7C), (1A, 2A, 3A, 4B, 5B, 6B, 7A), (1A, 2A, 3A, 4B, 5B, 6B, 7B), (1A, 2A, 3A, 4B, 5B, 6B, 7C), (1A, 2A, 3A, 4B, 5B, 6C, 7A), (1A, 2A, 3A, 4B, 5B, 6C, 7B), (1A, 2A, 3A, 4B, 5B, 6C, 7C), (1A, 2A, 3A, 4B, 5B, 6D, 7A), (1A, 2A, 3A, 4B, 5B, 6D, 7B), (1A, 2A, 3A, 4B, 5B, 6D, 7C), (1A, 2A, 3A, 4C, 5A, 6A, 7A), (1A, 2A, 3A, 4C, 5A, 6A, 7B), (1A, 2A, 3A, 4C, 5A, 6A, 7C), (1A, 2A, 3A, 4C, 5A, 6B, 7A), (1A, 2A, 3A, 4C, 5A, 6B, 7B), (1A, 2A, 3A, 4C, 5A, 6B, 7C), (1A, 2A, 3A, 4C, 5A, 6C, 7A), (1A, 2A, 3A, 4C, 5A, 6C, 7B), (1A, 2A, 3A, 4C, 5A, 6C, 7C), (1A, 2A, 3A, 4C, 5A, 6D, 7A), (1A, 2A, 3A, 4C, 5A, 6D, 7B), (1A, 2A, 3A, 4C, 5A, 6D, 7C), (1A, 2A, 3A, 4C, 5B, 6A, 7A), (1A, 2A, 3A, 4C, 5B, 6A, 7B), (1A, 2A, 3A, 4C, 5B, 6A, 7C), (1A, 2A, 3A, 4C, 5B, 6B, 7A), (1A, 2A, 3A, 4C, 5B, 6B, 7B), (1A, 2A, 3A, 4C, 5B, 6B, 7C), (1A, 2A, 3A, 4C, 5B, 6C, 7A), (1A, 2A, 3A, 4C, 5B, 6C, 7B), (1A, 2A, 3A, 4C, 5B, 6C, 7C), (1A, 2A, 3A, 4C, 5B, 6D, 7A), (1A, 2A, 3A, 4C, 5B, 6D, 7B), (1A, 2A, 3A, 4C, 5B, 6D, 7C), (1A, 2A, 3A, 4D, 5A, 6A, 7A), (1A, 2A, 3A, 4D, 5A, 6A, 7B), (1A, 2A, 3A, 4D, 5A, 6A, 7C), (1A, 2A, 3A, 4D, 5A, 6B, 7A), (1A, 2A, 3A, 4D, 5A, 6B, 7B), (1A, 2A, 3A, 4D, 5A, 6B, 7C), (1A, 2A, 3A, 4D, 5A, 6C, 7A), (1A, 2A, 3A, 4D, 5A, 6C, 7B), (1A, 2A, 3A, 4D, 5A, 6C, 7C), (1A, 2A, 3A, 4D, 5A, 6D, 7A), (1A, 2A, 3A, 4D, 5A, 6D, 7B), (1A, 2A, 3A, 4D, 5A, 6D, 7C), (1A, 2A, 3A, 4D, 5B, 6A, 7A), (1A, 2A, 3A, 4D, 5B, 6A, 7B), (1A, 2A, 3A, 4D, 5B, 6A, 7C), (1A, 2A, 3A, 4D, 5B, 6B, 7A), (1A, 2A, 3A, 4D, 5B, 6B, 7B), (1A, 2A, 3A, 4D, 5B, 6B, 7C), (1A, 2A, 3A, 4D, 5B, 6C, 7A), (1A, 2A, 3A, 4D, 5B, 6C, 7B), (1A, 2A, 3A, 4D, 5B, 6C, 7C), (1A, 2A, 3A, 4D, 5B, 6D, 7A), (1A, 2A, 3A, 4D, 5B, 6D, 7B), (1A, 2A, 3A, 4D, 5B, 6D, 7C), (1A, 2A, 3A, 4E, 5A, 6A, 7A), (1A, 2A, 3A, 4E, 5A, 6A, 7B), (1A, 2A, 3A, 4E, 5A, 6A, 7C), (1A, 2A, 3A, 4E, 5A, 6B, 7A), (1A, 2A, 3A, 4E, 5A, 6B, 7B), (1A, 2A, 3A, 4E, 5A, 6B, 7C), (1A, 2A, 3A, 4E, 5A, 6C, 7A), (1A, 2A, 3A, 4E, 5A, 6C, 7B), (1A, 2A, 3A, 4E, 5A, 6C, 7C), (1A, 2A, 3A, 4E, 5A, 6D, 7A), (1A, 2A, 3A, 4E, 5A, 6D, 7B), (1A, 2A, 3A, 4E, 5A, 6D, 7C), (1A, 2A, 3A, 4E, 5B, 6A, 7A), (1A, 2A, 3A, 4E, 5B, 6A, 7B), (1A, 2A, 3A, 4E, 5B, 6A, 7C), (1A, 2A, 3A, 4E, 5B, 6B, 7A), (1A, 2A, 3A, 4E, 5B, 6B, 7B), (1A, 2A, 3A, 4E, 5B, 6B, 7C), (1A, 2A, 3A, 4E, 5B, 6C, 7A), (1A, 2A, 3A, 4E, 5B, 6C, 7B), (1A, 2A, 3A, 4E, 5B, 6C, 7C), (1A, 2A, 3A, 4E, 5B, 6D, 7A), (1A, 2A, 3A, 4E, 5B, 6D, 7B), (1A, 2A, 3A, 4E, 5B, 6D, 7C), (1A, 2A, 3B, 4A, 5A, 6A, 7A), (1A, 2A, 3B, 4A, 5A, 6A, 7B), (1A, 2A, 3B, 4A, 5A, 6A, 7C), (1A, 2A, 3B, 4A, 5A, 6B, 7A), (1A, 2A, 3B, 4A, 5A, 6B, 7B), (1A, 2A, 3B, 4A, 5A, 6B, 7C), (1A, 2A, 3B, 4A, 5A, 6C, 7A), (1A, 2A, 3B, 4A, 5A, 6C, 7B), (1A, 2A, 3B, 4A, 5A, 6C, 7C), (1A, 2A, 3B, 4A, 5A, 6D, 7A), (1A, 2A, 3B, 4A, 5A, 6D, 7B), (1A, 2A, 3B, 4A, 5A, 6D, 7C), (1A, 2A, 3B, 4A, 5B, 6A, 7A), (1A, 2A, 3B, 4A, 5B, 6A, 7B), (1A, 2A, 3B, 4A, 5B, 6A, 7C), (1A, 2A, 3B, 4A, 5B, 6B, 7A), (1A, 2A, 3B, 4A, 5B, 6B, 7B), (1A, 2A, 3B, 4A, 5B, 6B, 7C), (1A, 2A, 3B, 4A, 5B, 6C, 7A), (1A, 2A, 3B, 4A, 5B, 6C, 7B), (1A, 2A, 3B, 4A, 5B, 6C, 7C), (1A, 2A, 3B, 4A, 5B, 6D, 7A), (1A, 2A, 3B, 4A, 5B, 6D, 7B), (1A, 2A, 3B, 4A, 5B, 6D, 7C), (1A, 2A, 3B, 4B, 5A, 6A, 7A), (1A, 2A, 3B, 4B, 5A, 6A, 7B), (1A, 2A, 3B, 4B, 5A, 6A, 7C), (1A, 2A, 3B, 4B, 5A, 6B, 7A), (1A, 2A, 3B, 4B, 5A, 6B, 7B), (1A, 2A, 3B, 4B, 5A, 6B, 7C), (1A, 2A, 3B, 4B, 5A, 6C, 7A), (1A, 2A, 3B, 4B, 5A, 6C, 7B), (1A, 2A, 3B, 4B, 5A, 6C, 7C), (1A, 2A, 3B, 4B, 5A, 6D, 7A), (1A, 2A, 3B, 4B, 5A, 6D, 7B), (1A, 2A, 3B, 4B, 5A, 6D, 7C), (1A, 2A, 3B, 4B, 5B, 6A, 7A), (1A, 2A, 3B, 4B, 5B, 6A, 7B), (1A, 2A, 3B, 4B, 5B, 6A, 7C), (1A, 2A, 3B, 4B, 5B, 6B, 7A), (1A, 2A, 3B, 4B, 5B, 6B, 7B), (1A, 2A, 3B, 4B, 5B, 6B, 7C), (1A, 2A, 3B, 4B, 5B, 6C, 7A), (1A, 2A, 3B, 4B, 5B, 6C, 7B), (1A, 2A, 3B, 4B, 5B, 6C, 7C), (1A, 2A, 3B, 4B, 5B, 6D, 7A), (1A, 2A, 3B, 4B, 5B, 6D, 7B), (1A, 2A, 3B, 4B, 5B, 6D, 7C), (1A, 2A, 3B, 4C, 5A, 6A, 7A), (1A, 2A, 3B, 4C, 5A, 6A, 7B), (1A, 2A, 3B, 4C, 5A, 6A, 7C), (1A, 2A, 3B, 4C, 5A, 6B, 7A), (1A, 2A, 3B, 4C, 5A, 6B, 7B), (1A, 2A, 3B, 4C, 5A, 6B, 7C), (1A, 2A, 3B, 4C, 5A, 6C, 7A), (1A, 2A, 3B, 4C, 5A, 6C, 7B), (1A, 2A, 3B, 4C, 5A, 6C, 7C), (1A, 2A, 3B, 4C, 5A, 6D, 7A), (1A, 2A, 3B, 4C, 5A, 6D, 7B), (1A, 2A, 3B, 4C, 5A, 6D, 7C), (1A, 2A, 3B, 4C, 5B, 6A, 7A), (1A, 2A, 3B, 4C, 5B, 6A, 7B), (1A, 2A, 3B, 4C, 5B, 6A, 7C), (1A, 2A, 3B, 4C, 5B, 6B, 7A), (1A, 2A, 3B, 4C, 5B, 6B, 7B), (1A, 2A, 3B, 4C, 5B, 6B, 7C), (1A, 2A, 3B, 4C, 5B, 6C, 7A), (1A, 2A, 3B, 4C, 5B, 6C, 7B), (1A, 2A, 3B, 4C, 5B, 6C, 7C), (1A, 2A, 3B, 4C, 5B, 6D, 7A), (1A, 2A, 3B, 4C, 5B, 6D, 7B), (1A, 2A, 3B, 4C, 5B, 6D, 7C), (1A, 2A, 3B, 4D, 5A, 6A, 7A), (1A, 2A, 3B, 4D, 5A, 6A, 7B), (1A, 2A, 3B, 4D, 5A, 6A, 7C), (1A, 2A, 3B, 4D, 5A, 6B, 7A), (1A, 2A, 3B, 4D, 5A, 6B, 7B), (1A, 2A, 3B, 4D, 5A, 6B, 7C), (1A, 2A, 3B, 4D, 5A, 6C, 7A), (1A, 2A, 3B, 4D, 5A, 6C, 7B), (1A, 2A, 3B, 4D, 5A, 6C, 7C), (1A, 2A, 3B, 4D, 5A, 6D, 7A), (1A, 2A, 3B, 4D, 5A, 6D, 7B), (1A, 2A, 3B, 4D, 5A, 6D, 7C), (1A, 2A, 3B, 4D, 5B, 6A, 7A), (1A, 2A, 3B, 4D, 5B, 6A, 7B), (1A, 2A, 3B, 4D, 5B, 6A, 7C), (1A, 2A, 3B, 4D, 5B, 6B, 7A), (1A, 2A, 3B, 4D, 5B, 6B, 7B), (1A, 2A, 3B, 4D, 5B, 6B, 7C), (1A, 2A, 3B, 4D, 5B, 6C, 7A), (1A, 2A, 3B, 4D, 5B, 6C, 7B), (1A, 2A, 3B, 4D, 5B, 6C, 7C), (1A, 2A, 3B, 4D, 5B, 6D, 7A), (1A, 2A, 3B, 4D, 5B, 6D, 7B), (1A, 2A, 3B, 4D, 5B, 6D, 7C), (1A, 2A, 3B, 4E, 5A, 6A, 7A), (1A, 2A, 3B, 4E, 5A, 6A, 7B), (1A, 2A, 3B, 4E, 5A, 6A, 7C), (1A, 2A, 3B, 4E, 5A, 6B, 7A), (1A, 2A, 3B, 4E, 5A, 6B, 7B), (1A, 2A, 3B, 4E, 5A, 6B, 7C), (1A, 2A, 3B, 4E, 5A, 6C, 7A), (1A, 2A, 3B, 4E, 5A, 6C, 7B), (1A, 2A, 3B, 4E, 5A, 6C, 7C), (1A, 2A, 3B, 4E, 5A, 6D, 7A), (1A, 2A, 3B, 4E, 5A, 6D, 7B), (1A, 2A, 3B, 4E, 5A, 6D, 7C), (1A, 2A, 3B, 4E, 5B, 6A, 7A), (1A, 2A, 3B, 4E, 5B, 6A, 7B), (1A, 2A, 3B, 4E, 5B, 6A, 7C), (1A, 2A, 3B, 4E, 5B, 6B, 7A), (1A, 2A, 3B, 4E, 5B, 6B, 7B), (1A, 2A, 3B, 4E, 5B, 6B, 7C), (1A, 2A, 3B, 4E, 5B, 6C, 7A), (1A, 2A, 3B, 4E, 5B, 6C, 7B), (1A, 2A, 3B, 4E, 5B, 6C, 7C), (1A, 2A, 3B, 4E, 5B, 6D, 7A), (1A, 2A, 3B, 4E, 5B, 6D, 7B), (1A, 2A, 3B, 4E, 5B, 6D, 7C), (1A, 2A, 3C, 4A, 5A, 6A, 7A), (1A, 2A, 3C, 4A, 5A, 6A, 7B), (1A, 2A, 3C, 4A, 5A, 6A, 7C), (1A, 2A, 3C, 4A, 5A, 6B, 7A), (1A, 2A, 3C, 4A, 5A, 6B, 7B), (1A, 2A, 3C, 4A, 5A, 6B, 7C), (1A, 2A, 3C, 4A, 5A, 6C, 7A), (1A, 2A, 3C, 4A, 5A, 6C, 7B), (1A, 2A, 3C, 4A, 5A, 6C, 7C), (1A, 2A, 3C, 4A, 5A, 6D, 7A), (1A, 2A, 3C, 4A, 5A, 6D, 7B), (1A, 2A, 3C, 4A, 5A, 6D, 7C), (1A, 2A, 3C, 4A, 5B, 6A, 7A), (1A, 2A, 3C, 4A, 5B, 6A, 7B), (1A, 2A, 3C, 4A, 5B, 6A, 7C), (1A, 2A, 3C, 4A, 5B, 6B, 7A), (1A, 2A, 3C, 4A, 5B, 6B, 7B), (1A, 2A, 3C, 4A, 5B, 6B, 7C), (1A, 2A, 3C, 4A, 5B, 6C, 7A), (1A, 2A, 3C, 4A, 5B, 6C, 7B), (1A, 2A, 3C, 4A, 5B, 6C, 7C), (1A, 2A, 3C, 4A, 5B, 6D, 7A), (1A, 2A, 3C, 4A, 5B, 6D, 7B), (1A, 2A, 3C, 4A, 5B, 6D, 7C), (1A, 2A, 3C, 4B, 5A, 6A, 7A), (1A, 2A, 3C, 4B, 5A, 6A, 7B), (1A, 2A, 3C, 4B, 5A, 6A, 7C), (1A, 2A, 3C, 4B, 5A, 6B, 7A), (1A, 2A, 3C, 4B, 5A, 6B, 7B), (1A, 2A, 3C, 4B, 5A, 6B, 7C), (1A, 2A, 3C, 4B, 5A, 6C, 7A), (1A, 2A, 3C, 4B, 5A, 6C, 7B), (1A, 2A, 3C, 4B, 5A, 6C, 7C), (1A, 2A, 3C, 4B, 5A, 6D, 7A), (1A, 2A, 3C, 4B, 5A, 6D, 7B), (1A, 2A, 3C, 4B, 5A, 6D, 7C), (1A, 2A, 3C, 4B, 5B, 6A, 7A), (1A, 2A, 3C, 4B, 5B, 6A, 7B), (1A, 2A, 3C, 4B, 5B, 6A, 7C), (1A, 2A, 3C, 4B, 5B, 6B, 7A), (1A, 2A, 3C, 4B, 5B, 6B, 7B), (1A, 2A, 3C, 4B, 5B, 6B, 7C), (1A, 2A, 3C, 4B, 5B, 6C, 7A), (1A, 2A, 3C, 4B, 5B, 6C, 7B), (1A, 2A, 3C, 4B, 5B, 6C, 7C), (1A, 2A, 3C, 4B, 5B, 6D, 7A), (1A, 2A, 3C, 4B, 5B, 6D, 7B), (1A, 2A, 3C, 4B, 5B, 6D, 7C), (1A, 2A, 3C, 4C, 5A, 6A, 7A), (1A, 2A, 3C, 4C, 5A, 6A, 7B), (1A, 2A, 3C, 4C, 5A, 6A, 7C), (1A, 2A, 3C, 4C, 5A, 6B, 7A), (1A, 2A, 3C, 4C, 5A, 6B, 7B), (1A, 2A, 3C, 4C, 5A, 6B, 7C), (1A, 2A, 3C, 4C, 5A, 6C, 7A), (1A, 2A, 3C, 4C, 5A, 6C, 7B), (1A, 2A, 3C, 4C, 5A, 6C, 7C), (1A, 2A, 3C, 4C, 5A, 6D, 7A), (1A, 2A, 3C, 4C, 5A, 6D, 7B), (1A, 2A, 3C, 4C, 5A, 6D, 7C), (1A, 2A, 3C, 4C, 5B, 6A, 7A), (1A, 2A, 3C, 4C, 5B, 6A, 7B), (1A, 2A, 3C, 4C, 5B, 6A, 7C), (1A, 2A, 3C, 4C, 5B, 6B, 7A), (1A, 2A, 3C, 4C, 5B, 6B, 7B), (1A, 2A, 3C, 4C, 5B, 6B, 7C), (1A, 2A, 3C, 4C, 5B, 6C, 7A), (1A, 2A, 3C, 4C, 5B, 6C, 7B), (1A, 2A, 3C, 4C, 5B, 6C, 7C), (1A, 2A, 3C, 4C, 5B, 6D, 7A), (1A, 2A, 3C, 4C, 5B, 6D, 7B), (1A, 2A, 3C, 4C, 5B, 6D, 7C), (1A, 2A, 3C, 4D, 5A, 6A, 7A), (1A, 2A, 3C, 4D, 5A, 6A, 7B), (1A, 2A, 3C, 4D, 5A, 6A, 7C), (1A, 2A, 3C, 4D, 5A, 6B, 7A), (1A, 2A, 3C, 4D, 5A, 6B, 7B), (1A, 2A, 3C, 4D, 5A, 6B, 7C), (1A, 2A, 3C, 4D, 5A, 6C, 7A), (1A, 2A, 3C, 4D, 5A, 6C, 7B), (1A, 2A, 3C, 4D, 5A, 6C, 7C), (1A, 2A, 3C, 4D, 5A, 6D, 7A), (1A, 2A, 3C, 4D, 5A, 6D, 7B), (1A, 2A, 3C, 4D, 5A, 6D, 7C), (1A, 2A, 3C, 4D, 5B, 6A, 7A), (1A, 2A, 3C, 4D, 5B, 6A, 7B), (1A, 2A, 3C, 4D, 5B, 6A, 7C), (1A, 2A, 3C, 4D, 5B, 6B, 7A), (1A, 2A, 3C, 4D, 5B, 6B, 7B), (1A, 2A, 3C, 4D, 5B, 6B, 7C), (1A, 2A, 3C, 4D, 5B, 6C, 7A), (1A, 2A, 3C, 4D, 5B, 6C, 7B), (1A, 2A, 3C, 4D, 5B, 6C, 7C), (1A, 2A, 3C, 4D, 5B, 6D,

7A), (1A, 2A, 3C, 4D, 5B, 6D, 7B), (1A, 2A, 3C, 4D, 5B, 6D, 7C), (1A, 2A, 3C, 4E, 5A, 6A, 7A), (1A, 2A, 3C, 4E, 5A, 6A, 7B), (1A, 2A, 3C, 4E, 5A, 6A, 7C), (1A, 2A, 3C, 4E, 5A, 6B, 7A), (1A, 2A, 3C, 4E, 5A, 6B, 7B), (1A, 2A, 3C, 4E, 5A, 6B, 7C), (1A, 2A, 3C, 4E, 5A, 6C, 7A), (1A, 2A, 3C, 4E, 5A, 6C, 7B), (1A, 2A, 3C, 4E, 5A, 6C, 7C), (1A, 2A, 3C, 4E, 5A, 6D, 7A), (1A, 2A, 3C, 4E, 5A, 6D, 7B), (1A, 2A, 3C, 4E, 5A, 6D, 7C), (1A, 2A, 3C, 4E, 5B, 6A, 7A), (1A, 2A, 3C, 4E, 5B, 6A, 7B), (1A, 2A, 3C, 4E, 5B, 6A, 7C), (1A, 2A, 3C, 4E, 5B, 6B, 7A), (1A, 2A, 3C, 4E, 5B, 6B, 7B), (1A, 2A, 3C, 4E, 5B, 6B, 7C), (1A, 2A, 3C, 4E, 5B, 6C, 7A), (1A, 2A, 3C, 4E, 5B, 6C, 7B), (1A, 2A, 3C, 4E, 5B, 6C, 7C), (1A, 2A, 3C, 4E, 5B, 6D, 7A), (1A, 2A, 3C, 4E, 5B, 6D, 7B), (1A, 2A, 3C, 4E, 5B, 6D, 7C), (1A, 2A, 3D, 4A, 5A, 6A, 7A), (1A, 2A, 3D, 4A, 5A, 6A, 7B), (1A, 2A, 3D, 4A, 5A, 6A, 7C), (1A, 2A, 3D, 4A, 5A, 6B, 7A), (1A, 2A, 3D, 4A, 5A, 6B, 7B), (1A, 2A, 3D, 4A, 5A, 6B, 7C), (1A, 2A, 3D, 4A, 5A, 6C, 7A), (1A, 2A, 3D, 4A, 5A, 6C, 7B), (1A, 2A, 3D, 4A, 5A, 6C, 7C), (1A, 2A, 3D, 4A, 5A, 6D, 7A), (1A, 2A, 3D, 4A, 5A, 6D, 7B), (1A, 2A, 3D, 4A, 5A, 6D, 7C), (1A, 2A, 3D, 4A, 5B, 6A, 7A), (1A, 2A, 3D, 4A, 5B, 6A, 7B), (1A, 2A, 3D, 4A, 5B, 6A, 7C), (1A, 2A, 3D, 4A, 5B, 6B, 7A), (1A, 2A, 3D, 4A, 5B, 6B, 7B), (1A, 2A, 3D, 4A, 5B, 6B, 7C), (1A, 2A, 3D, 4A, 5B, 6C, 7A), (1A, 2A, 3D, 4A, 5B, 6C, 7B), (1A, 2A, 3D, 4A, 5B, 6C, 7C), (1A, 2A, 3D, 4A, 5B, 6D, 7A), (1A, 2A, 3D, 4A, 5B, 6D, 7B), (1A, 2A, 3D, 4A, 5B, 6D, 7C), (1A, 2A, 3D, 4B, 5A, 6A, 7A), (1A, 2A, 3D, 4B, 5A, 6A, 7B), (1A, 2A, 3D, 4B, 5A, 6A, 7C), (1A, 2A, 3D, 4B, 5A, 6B, 7A), (1A, 2A, 3D, 4B, 5A, 6B, 7B), (1A, 2A, 3D, 4B, 5A, 6B, 7C), (1A, 2A, 3D, 4B, 5A, 6C, 7A), (1A, 2A, 3D, 4B, 5A, 6C, 7B), (1A, 2A, 3D, 4B, 5A, 6C, 7C), (1A, 2A, 3D, 4B, 5A, 6D, 7A), (1A, 2A, 3D, 4B, 5A, 6D, 7B), (1A, 2A, 3D, 4B, 5A, 6D, 7C), (1A, 2A, 3D, 4B, 5B, 6A, 7A), (1A, 2A, 3D, 4B, 5B, 6A, 7B), (1A, 2A, 3D, 4B, 5B, 6A, 7C), (1A, 2A, 3D, 4B, 5B, 6B, 7A), (1A, 2A, 3D, 4B, 5B, 6B, 7B), (1A, 2A, 3D, 4B, 5B, 6B, 7C), (1A, 2A, 3D, 4B, 5B, 6C, 7A), (1A, 2A, 3D, 4B, 5B, 6C, 7B), (1A, 2A, 3D, 4B, 5B, 6C, 7C), (1A, 2A, 3D, 4B, 5B, 6D, 7A), (1A, 2A, 3D, 4B, 5B, 6D, 7B), (1A, 2A, 3D, 4B, 5B, 6D, 7C), (1A, 2A, 3D, 4C, 5A, 6A, 7A), (1A, 2A, 3D, 4C, 5A, 6A, 7B), (1A, 2A, 3D, 4C, 5A, 6A, 7C), (1A, 2A, 3D, 4C, 5A, 6B, 7A), (1A, 2A, 3D, 4C, 5A, 6B, 7B), (1A, 2A, 3D, 4C, 5A, 6B, 7C), (1A, 2A, 3D, 4C, 5A, 6C, 7A), (1A, 2A, 3D, 4C, 5A, 6C, 7B), (1A, 2A, 3D, 4C, 5A, 6C, 7C), (1A, 2A, 3D, 4C, 5A, 6D, 7A), (1A, 2A, 3D, 4C, 5A, 6D, 7B), (1A, 2A, 3D, 4C, 5A, 6D, 7C), (1A, 2A, 3D, 4C, 5B, 6A, 7A), (1A, 2A, 3D, 4C, 5B, 6A, 7B), (1A, 2A, 3D, 4C, 5B, 6A, 7C), (1A, 2A, 3D, 4C, 5B, 6B, 7A), (1A, 2A, 3D, 4C, 5B, 6B, 7B), (1A, 2A, 3D, 4C, 5B, 6B, 7C), (1A, 2A, 3D, 4C, 5B, 6C, 7A), (1A, 2A, 3D, 4C, 5B, 6C, 7B), (1A, 2A, 3D, 4C, 5B, 6C, 7C), (1A, 2A, 3D, 4C, 5B, 6D, 7A), (1A, 2A, 3D, 4C, 5B, 6D, 7B), (1A, 2A, 3D, 4C, 5B, 6D, 7C), (1A, 2A, 3D, 4D, 5A, 6A, 7A), (1A, 2A, 3D, 4D, 5A, 6A, 7B), (1A, 2A, 3D, 4D, 5A, 6A, 7C), (1A, 2A, 3D, 4D, 5A, 6B, 7A), (1A, 2A, 3D, 4D, 5A, 6B, 7B), (1A, 2A, 3D, 4D, 5A, 6B, 7C), (1A, 2A, 3D, 4D, 5A, 6C, 7A), (1A, 2A, 3D, 4D, 5A, 6C, 7B), (1A, 2A, 3D, 4D, 5A, 6C, 7C), (1A, 2A, 3D, 4D, 5A, 6D, 7A), (1A, 2A, 3D, 4D, 5A, 6D, 7B), (1A, 2A, 3D, 4D, 5A, 6D, 7C), (1A, 2A, 3D, 4D, 5B, 6A, 7A), (1A, 2A, 3D, 4D, 5B, 6A, 7B), (1A, 2A, 3D, 4D, 5B, 6A, 7C), (1A, 2A, 3D, 4D, 5B, 6B, 7A), (1A, 2A, 3D, 4D, 5B, 6B, 7B), (1A, 2A, 3D, 4D, 5B, 6B, 7C), (1A, 2A, 3D, 4D, 5B, 6C, 7A), (1A, 2A, 3D, 4D, 5B, 6C, 7B), (1A, 2A, 3D, 4D, 5B, 6C, 7C), (1A, 2A, 3D, 4D, 5B, 6D, 7A), (1A, 2A, 3D, 4D, 5B, 6D, 7B), (1A, 2A, 3D, 4D, 5B, 6D, 7C), (1A, 2A, 3D, 4E, 5A, 6A, 7A), (1A, 2A, 3D, 4E, 5A, 6A, 7B), (1A, 2A, 3D, 4E, 5A, 6A, 7C), (1A, 2A, 3D, 4E, 5A, 6B, 7A), (1A, 2A, 3D, 4E, 5A, 6B, 7B), (1A, 2A, 3D, 4E, 5A, 6B, 7C), (1A, 2A, 3D, 4E, 5A, 6C, 7A), (1A, 2A, 3D, 4E, 5A, 6C, 7B), (1A, 2A, 3D, 4E, 5A, 6C, 7C), (1A, 2A, 3D, 4E, 5A, 6D, 7A), (1A, 2A, 3D, 4E, 5A, 6D, 7B), (1A, 2A, 3D, 4E, 5A, 6D, 7C), (1A, 2A, 3D, 4E, 5B, 6A, 7A), (1A, 2A, 3D, 4E, 5B, 6A, 7B), (1A, 2A, 3D, 4E, 5B, 6A, 7C), (1A, 2A, 3D, 4E, 5B, 6B, 7A), (1A, 2A, 3D, 4E, 5B, 6B, 7B), (1A, 2A, 3D, 4E, 5B, 6B, 7C), (1A, 2A, 3D, 4E, 5B, 6C, 7A), (1A, 2A, 3D, 4E, 5B, 6C, 7B), (1A, 2A, 3D, 4E, 5B, 6C, 7C), (1A, 2A, 3D, 4E, 5B, 6D, 7A), (1A, 2A, 3D, 4E, 5B, 6D, 7B), (1A, 2A, 3D, 4E, 5B, 6D, 7C), (1A, 2A, 3E, 4A, 5A, 6A, 7A), (1A, 2A, 3E, 4A, 5A, 6A, 7B), (1A, 2A, 3E, 4A, 5A, 6A, 7C), (1A, 2A, 3E, 4A, 5A, 6B, 7A), (1A, 2A, 3E, 4A, 5A, 6B, 7B), (1A, 2A, 3E, 4A, 5A, 6B, 7C), (1A, 2A, 3E, 4A, 5A, 6C, 7A), (1A, 2A, 3E, 4A, 5A, 6C, 7B), (1A, 2A, 3E, 4A, 5A, 6C, 7C), (1A, 2A, 3E, 4A, 5A, 6D, 7A), (1A, 2A, 3E, 4A, 5A, 6D, 7B), (1A, 2A, 3E, 4A, 5A, 6D, 7C), (1A, 2A, 3E, 4A, 5B, 6A, 7A), (1A, 2A, 3E, 4A, 5B, 6A, 7B), (1A, 2A, 3E, 4A, 5B, 6A, 7C), (1A, 2A, 3E, 4A, 5B, 6B, 7A), (1A, 2A, 3E, 4A, 5B, 6B, 7B), (1A, 2A, 3E, 4A, 5B, 6B, 7C), (1A, 2A, 3E, 4A, 5B, 6C, 7A), (1A, 2A, 3E, 4A, 5B, 6C, 7B), (1A, 2A, 3E, 4A, 5B, 6C, 7C), (1A, 2A, 3E, 4A, 5B, 6D, 7A), (1A, 2A, 3E, 4A, 5B, 6D, 7B), (1A, 2A, 3E, 4A, 5B, 6D, 7C), (1A, 2A, 3E, 4B, 5A, 6A, 7A), (1A, 2A, 3E, 4B, 5A, 6A, 7B), (1A, 2A, 3E, 4B, 5A, 6A, 7C), (1A, 2A, 3E, 4B, 5A, 6B, 7A), (1A, 2A, 3E, 4B, 5A, 6B, 7B), (1A, 2A, 3E, 4B, 5A, 6B, 7C), (1A, 2A, 3E, 4B, 5A, 6C, 7A), (1A, 2A, 3E, 4B, 5A, 6C, 7B), (1A, 2A, 3E, 4B, 5A, 6C, 7C), (1A, 2A, 3E, 4B, 5A, 6D, 7A), (1A, 2A, 3E, 4B, 5A, 6D, 7B), (1A, 2A, 3E, 4B, 5A, 6D, 7C), (1A, 2A, 3E, 4B, 5B, 6A, 7A), (1A, 2A, 3E, 4B, 5B, 6A, 7B), (1A, 2A, 3E, 4B, 5B, 6A, 7C), (1A, 2A, 3E, 4B, 5B, 6B, 7A), (1A, 2A, 3E, 4B, 5B, 6B, 7B), (1A, 2A, 3E, 4B, 5B, 6B, 7C), (1A, 2A, 3E, 4B, 5B, 6C, 7A), (1A, 2A, 3E, 4B, 5B, 6C, 7B), (1A, 2A, 3E, 4B, 5B, 6C, 7C), (1A, 2A, 3E, 4B, 5B, 6D, 7A), (1A, 2A, 3E, 4B, 5B, 6D, 7B), (1A, 2A, 3E, 4B, 5B, 6D, 7C), (1A, 2A, 3E, 4C, 5A, 6A, 7A), (1A, 2A, 3E, 4C, 5A, 6A, 7B), (1A, 2A, 3E, 4C, 5A, 6A, 7C), (1A, 2A, 3E, 4C, 5A, 6B, 7A), (1A, 2A, 3E, 4C, 5A, 6B, 7B), (1A, 2A, 3E, 4C, 5A, 6B, 7C), (1A, 2A, 3E, 4C, 5A, 6C, 7A), (1A, 2A, 3E, 4C, 5A, 6C, 7B), (1A, 2A, 3E, 4C, 5A, 6C, 7C), (1A, 2A, 3E, 4C, 5A, 6D, 7A), (1A, 2A, 3E, 4C, 5A, 6D, 7B), (1A, 2A, 3E, 4C, 5A, 6D, 7C), (1A, 2A, 3E, 4C, 5B, 6A, 7A), (1A, 2A, 3E, 4C, 5B, 6A, 7B), (1A, 2A, 3E, 4C, 5B, 6A, 7C), (1A, 2A, 3E, 4C, 5B, 6B, 7A), (1A, 2A, 3E, 4C, 5B, 6B, 7B), (1A, 2A, 3E, 4C, 5B, 6B, 7C), (1A, 2A, 3E, 4C, 5B, 6C, 7A), (1A, 2A, 3E, 4C, 5B, 6C, 7B), (1A, 2A, 3E, 4C, 5B, 6C, 7C), (1A, 2A, 3E, 4C, 5B, 6D, 7A), (1A, 2A, 3E, 4C, 5B, 6D, 7B), (1A, 2A, 3E, 4C, 5B, 6D, 7C), (1A, 2A, 3E, 4D, 5A, 6A, 7A), (1A, 2A, 3E, 4D, 5A, 6A, 7B), (1A, 2A, 3E, 4D, 5A, 6A, 7C), (1A, 2A, 3E, 4D, 5A, 6B, 7A), (1A, 2A, 3E, 4D, 5A, 6B, 7B), (1A, 2A, 3E, 4D, 5A, 6B, 7C), (1A, 2A, 3E, 4D, 5A, 6C, 7A), (1A, 2A, 3E, 4D, 5A, 6C, 7B), (1A, 2A, 3E, 4D, 5A, 6C, 7C), (1A, 2A, 3E, 4D, 5A, 6D, 7A), (1A, 2A, 3E, 4D, 5A, 6D, 7B), (1A, 2A, 3E, 4D, 5A, 6D, 7C), (1A, 2A, 3E, 4D, 5B, 6A, 7A), (1A, 2A, 3E, 4D, 5B, 6A, 7B), (1A, 2A, 3E, 4D, 5B, 6A, 7C), (1A, 2A, 3E, 4D, 5B, 6B, 7A), (1A, 2A, 3E, 4D, 5B, 6B, 7B), (1A, 2A, 3E, 4D, 5B, 6B, 7C), (1A, 2A, 3E, 4D, 5B, 6C, 7A), (1A, 2A, 3E, 4D, 5B, 6C, 7B), (1A, 2A, 3E, 4D, 5B, 6C, 7C), (1A, 2A, 3E, 4D, 5B, 6D, 7A), (1A, 2A, 3E, 4D, 5B, 6D, 7B), (1A, 2A, 3E, 4D, 5B, 6D, 7C), (1A, 2A, 3E, 4E, 5A, 6A, 7A), (1A, 2A, 3E, 4E, 5A, 6A, 7B), (1A, 2A, 3E, 4E, 5A, 6A, 7C), (1A, 2A, 3E, 4E, 5A, 6B, 7A), (1A, 2A, 3E, 4E, 5A, 6B, 7B), (1A, 2A, 3E, 4E, 5A, 6B, 7C), (1A, 2A, 3E, 4E, 5A, 6C, 7A), (1A, 2A, 3E, 4E, 5A, 6C, 7B), (1A, 2A, 3E, 4E, 5A, 6C, 7C), (1A, 2A, 3E, 4E, 5A, 6D, 7A), (1A, 2A, 3E, 4E, 5A, 6D, 7B), (1A, 2A, 3E, 5A, 6D, 7C), (1A, 2A, 3E, 4E, 5B, 6A, 7A), (1A, 2A, 3E, 4E, 5B, 6A, 7B), (1A, 2A, 3E, 4E, 5B, 6A, 7C), (1A, 2A, 3E, 4E, 5B, 6B, 7A), (1A, 2A, 3E, 4E, 5B, 6B, 7B), (1A, 2A, 3E, 4E, 5B, 6B, 7C), (1A, 2A, 3E, 4E, 5B, 6C, 7A), (1A, 2A, 3E, 4E, 5B, 6C, 7B), (1A, 2A, 3E, 4E, 5B, 6C, 7C), (1A, 2A, 3E, 4E, 5B, 6D, 7A), (1A, 2A, 3E, 4E, 5B, 6D, 7B), (1A, 2A, 3E, 4E, 5B, 6D, 7C), (1A, 2B, 3A, 4A, 5A, 6A, 7A), (1A, 2B, 3A, 4A, 5A, 6A, 7B), (1A, 2B, 3A, 4A, 5A, 6A, 7C), (1A, 2B, 3A, 4A, 5A, 6B, 7A), (1A, 2B, 3A, 4A, 5A, 6B, 7B), (1A, 2B, 3A, 4A, 5A, 6B, 7C), (1A, 2B, 3A, 4A, 5A, 6C, 7A), (1A, 2B, 3A, 4A, 5A, 6C, 7B), (1A, 2B, 3A, 4A, 5A, 6C, 7C), (1A, 2B, 3A, 4A, 5A, 6D, 7A), (1A, 2B, 3A, 4A, 5A, 6D, 7B), (1A, 2B, 3A, 4A, 5A, 6D, 7C), (1A, 2B, 3A, 4A, 5B, 6A, 7A), (1A, 2B, 3A, 4A, 5B, 6A, 7B), (1A, 2B, 3A, 4A, 5B, 6A, 7C), (1A, 2B, 3A, 4A, 5B, 6B, 7A), (1A, 2B, 3A, 4A, 5B, 6B, 7B), (1A, 2B, 3A, 4A, 5B, 6B, 7C), (1A, 2B, 3A, 4A, 5B, 6C, 7A), (1A, 2B, 3A, 4A, 5B, 6C, 7B), (1A, 2B, 3A, 4A, 5B, 6C, 7C), (1A, 2B, 3A, 4A, 5B, 6D, 7A), (1A, 2B, 3A, 4A, 5B, 6D, 7B), (1A, 2B, 3A, 4A, 5B, 6D, 7C), (1A, 2B, 3A, 4B, 5A, 6A, 7A), (1A, 2B, 3A, 4B, 5A, 6A, 7B), (1A, 2B, 3A, 4B, 5A, 6A, 7C), (1A, 2B, 3A, 4B, 5A, 6B, 7A), (1A, 2B, 3A, 4B, 5A, 6B, 7B), (1A, 2B, 3A, 4B, 5A, 6B, 7C), (1A, 2B, 3A, 4B, 5A, 6C, 7A), (1A, 2B, 3A, 4B, 5A, 6C, 7B), (1A, 2B, 3A, 4B, 5A, 6C, 7C), (1A, 2B, 3A, 4B, 5A, 6D, 7A), (1A, 2B, 3A, 4B, 5A, 6D, 7B), (1A, 2B, 3A, 4B, 5A, 6D, 7C), (1A, 2B, 3A, 4B, 5B, 6A, 7A), (1A, 2B, 3A, 4B, 5B, 6A, 7B), (1A, 2B, 3A, 4B, 5B, 6A, 7C), (1A, 2B, 3A, 4B, 5B, 6B, 7A), (1A, 2B, 3A, 4B, 5B, 6B, 7B), (1A, 2B, 3A, 4B, 5B, 6B, 7C), (1A, 2B, 3A, 4B, 5B, 6C, 7A), (1A, 2B, 3A, 4B, 5B, 6C, 7B), (1A, 2B, 3A, 4B, 5B, 6C, 7C), (1A, 2B, 3A, 4B, 5B, 6D, 7A), (1A, 2B, 3A, 4B, 5B, 6D, 7B), (1A, 2B, 3A, 4B, 5B, 6D, 7C), (1A, 2B, 3A, 4C, 5A, 6A, 7A), (1A, 2B, 3A, 4C, 5A, 6A, 7B), (1A, 2B, 3A, 4C, 5A, 6A, 7C), (1A, 2B, 3A, 4C, 5A, 6B, 7A), (1A, 2B, 3A, 4C, 5A, 6B, 7B), (1A, 2B, 3A, 4C, 5A, 6B, 7C), (1A, 2B, 3A, 4C, 5A, 6C, 7A), (1A, 2B, 3A, 4C, 5A, 6C, 7B), (1A, 2B, 3A, 4C, 5A, 6C, 7C), (1A, 2B, 3A, 4C, 5A, 6D, 7A), (1A, 2B, 3A, 4C, 5A, 6D, 7B), (1A, 2B, 3A, 4C, 5A, 6D, 7C), (1A, 2B, 3A, 4C, 5B, 6A, 7A), (1A, 2B, 3A, 4C, 5B, 6A, 7B), (1A, 2B, 3A, 4C, 5B, 6A, 7C), (1A, 2B, 3A, 4C, 5B, 6B, 7A), (1A, 2B, 3A, 4C, 5B, 6B, 7B), (1A, 2B, 3A, 4C, 5B, 6B, 7C), (1A, 2B, 3A, 4C, 5B, 6C, 7A), (1A, 2B, 3A, 4C, 5B, 6C, 7B), (1A, 2B, 3A, 4C, 5B, 6C, 7C), (1A, 2B, 3A, 4C, 5B, 6D, 7A), (1A, 2B, 3A, 4C, 5B, 6D, 7B), (1A, 2B, 3A, 4C, 5B, 6D, 7C), (1A, 2B, 3A, 4D, 5A, 6A, 7A), (1A, 2B, 3A, 4D, 5A, 6A, 7B), (1A, 2B, 3A, 4D, 5A, 6A, 7C), (1A, 2B, 3A, 4D, 5A, 6B, 7A), (1A, 2B, 3A, 4D, 5A, 6B, 7B), (1A, 2B, 3A, 4D, 5A, 6B, 7C), (1A, 2B, 3A, 4D, 5A, 6C, 7A), (1A, 2B, 3A, 4D, 5A, 6C, 7B), (1A, 2B, 3A, 4D, 5A, 6C, 7C), (1A, 2B, 3A, 4D, 5A, 6D, 7A), (1A, 2B, 3A, 4D, 5A, 6D, 7B), (1A, 2B, 3A, 4D, 5A, 6D, 7C), (1A, 2B, 3A, 4D, 5B, 6A, 7A), (1A, 2B, 3A, 4D, 5B, 6A, 7B), (1A, 2B, 3A, 4D, 5B, 6A, 7C), (1A, 2B, 3A, 4D, 5B, 6B, 7A), (1A, 2B, 3A, 4D, 5B, 6B, 7B), (1A, 2B, 3A, 4D, 5B, 6B, 7C), (1A, 2B, 3A, 4D, 5B, 6C, 7A), (1A, 2B, 3A, 4D, 5B, 6C, 7B), (1A, 2B, 3A, 4D, 5B, 6C, 7C), (1A, 2B, 3A, 4D, 5B, 6D, 7A), (1A, 2B, 3A, 4D, 5B, 6D, 7B), (1A, 2B, 3A, 4D, 5B, 6D, 7C), (1A, 2B, 3A, 4E, 5A, 6A, 7A), (1A, 2B, 3A, 4E, 5A, 6A, 7B), (1A, 2B, 3A, 4E, 5A, 6A, 7C), (1A, 2B, 3A, 4E, 5A, 6B, 7A), (1A, 2B, 3A, 4E, 5A, 6B, 7B), (1A, 2B, 3A, 4E, 5A, 6B, 7C), (1A, 2B, 3A, 4E, 5A, 6C, 7A), (1A, 2B, 3A, 4E, 5A, 6C, 7B), (1A, 2B, 3A, 4E, 5A, 6C, 7C), (1A, 2B, 3A, 4E, 5A, 6D, 7A), (1A, 2B, 3A, 4E, 5A, 6D, 7B), (1A, 2B, 3A, 4E, 5A, 6D, 7C), (1A, 2B, 3A, 4E, 5B, 6A, 7A), (1A, 2B, 3A, 4E, 5B, 6A, 7B), (1A, 2B, 3A, 4E, 5B, 6A, 7C), (1A, 2B, 3A, 4E, 5B, 6B, 7A), (1A, 2B, 3A, 4E, 5B, 6B, 7B), (1A, 2B, 3A, 4E, 5B, 6B, 7C), (1A, 2B, 3A, 4E, 5B, 6C, 7A), (1A, 2B, 3A, 4E, 5B, 6C, 7B), (1A, 2B, 3A, 4E, 5B, 6C, 7C), (1A, 2B, 3A, 4E, 5B, 6D, 7A), (1A, 2B, 3A, 4E, 5B, 6D, 7B), (1A, 2B, 3A, 4E, 5B, 6D, 7C), (1A, 2B, 3B, 4A, 5A, 6A, 7A), (1A, 2B, 3B, 4A, 5A, 6A, 7B), (1A, 2B, 3B, 4A, 5A, 6A, 7C), (1A, 2B, 3B, 4A, 5A, 6B, 7A), (1A, 2B, 3B, 4A, 5A, 6B, 7B), (1A, 2B, 3B, 4A, 5A, 6B, 7C), (1A, 2B, 3B, 4A, 5A, 6C, 7A), (1A, 2B, 3B, 4A, 5A, 6C, 7B), (1A, 2B, 3B, 4A, 5A, 6C, 7C), (1A, 2B, 3B, 4A, 5A, 6D, 7A), (1A, 2B, 3B, 4A, 5A, 6D, 7B), (1A, 2B, 3B, 4A, 5A, 6D, 7C), (1A, 2B, 3B, 4A, 5E, 6A, 7A), (1A, 2B, 3B, 4A, 5B, 6A, 7B), (1A, 2B, 3B, 4A, 5B, 6A, 7C), (1A, 2B, 3B, 4A, 5B, 6B, 7A), (1A, 2B, 3B, 4A, 5B, 6B, 7B), (1A, 2B, 3B, 4A, 5B, 6B, 7C), (1A, 2B, 3B, 4A, 5B, 6C, 7A), (1A, 2B, 3B, 4A, 5B, 6C, 7B), (1A, 2B, 3B, 4A, 5B, 6C, 7C), (1A, 2B, 3B, 4A, 5B, 6D, 7A), (1A, 2B, 3B, 4A, 5B, 6D, 7B), (1A, 2B, 3B, 4A, 5B, 6D, 7C), (1A, 2B, 3B, 4B, 5A, 6A, 7A), (1A, 2B, 3B, 4B, 5A, 6A, 7B), (1A, 2B, 3B, 4B, 5A, 6A, 7C), (1A, 2B, 3B, 4B, 5A, 6B, 7A), (1A, 2B, 3B, 4B, 5A, 6B, 7B), (1A, 2B, 3B, 4B, 5A, 6B, 7C), (1A, 2B, 3B, 4B, 5A, 6C, 7A), (1A, 2B, 3B, 4B, 5A, 6C, 7B), (1A, 2B, 3B, 4B, 5A, 6C, 7C), (1A, 2B, 3B, 4B, 5A, 6D, 7A), (1A, 2B, 3B, 4B, 5A, 6D, 7B), (1A, 2B, 3B, 4B, 5A, 6D, 7C), (1A, 2B, 3B, 4B, 5B, 6A, 7A), (1A, 2B, 3B, 4B, 5B, 6A, 7B), (1A, 2B, 3B, 4B, 5B, 6A, 7C), (1A, 2B, 3B, 4B, 5B, 6B, 7A), (1A, 2B, 3B, 4B, 5B, 6B, 7B), (1A, 2B, 3B, 4B, 5B, 6B, 7C), (1A, 2B, 3B, 4B, 5B, 6C, 7A), (1A, 2B, 3B, 4B, 5B, 6C, 7B), (1A, 2B, 3B, 4B, 5B, 6C, 7C), (1A, 2B, 3B, 4B, 5B, 6D, 7A), (1A, 2B, 3B, 4B, 5B, 6D, 7B), (1A, 2B, 3B, 4B, 5B, 6D, 7C), (1A, 2B, 3B, 4C, 5A, 6A, 7A), (1A, 2B, 3B, 4C, 5A, 6A, 7B), (1A, 2B, 3B, 4C, 5A, 6A, 7C), (1A, 2B, 3B, 4C, 5A, 6B, 7A), (1A, 2B, 3B, 4C, 5A, 6B, 7B), (1A, 2B, 3B, 4C, 5A, 6B, 7C), (1A, 2B, 3B, 4C, 5A, 6C, 7A), (1A, 2B, 3B, 4C, 5A, 6C, 7B), (1A, 2B, 3B, 4C, 5A, 6C, 7C), (1A, 2B, 3B, 4C, 5A, 6D, 7A), (1A, 2B, 3B, 4C, 5A, 6D, 7B), (1A, 2B, 3B, 4C, 5A, 6D, 7C), (1A, 2B, 3B, 4C, 5B, 6A, 7A), (1A, 2B, 3B, 4C, 5B, 6A, 7B), (1A, 2B, 3B, 4C, 5B, 6A, 7C), (1A, 2B, 3B, 4C, 5B, 6B, 7A), (1A, 2B, 3B, 4C, 5B, 6B, 7B), (1A, 2B, 3B, 4C, 5B, 6B, 7C), (1A, 2B, 3B, 4C, 5B, 6C, 7A), (1A, 2B, 3B, 4C, 5B, 6C, 7B), (1A, 2B, 3B, 4C, 5B, 6C, 7C), (1A, 2B, 3B, 4C, 5B, 6D, 7A), (1A, 2B, 3B, 4C, 5B, 6D, 7B), (1A, 2B, 3B, 4C, 5B, 6D, 7C), (1A, 2B, 3B, 4D, 5A, 6A, 7A), (1A, 2B, 3B, 4D, 5A, 6A, 7B), (1A, 2B, 3B, 4D, 5A, 6A, 7C), (1A, 2B, 3B, 4D, 5A, 6B, 7A), (1A, 2B, 3B, 4D, 5A, 6B, 7B), (1A, 2B, 3B, 4D, 5A, 6B, 7C), (1A, 2B, 3B, 4D, 5A, 6C, 7A), (1A, 2B, 3B, 4D, 5A, 6C, 7B), (1A, 2B, 3B, 4D, 5A, 6C, 7C), (1A, 2B, 3B, 4D, 5A, 6D, 7A), (1A, 2B, 3B, 4D, 5A, 6D, 7B), (1A, 2B, 3B, 4D, 5A, 6D, 7C), (1A, 2B, 3B, 4D, 5B, 6A, 7A), (1A, 2B, 3B, 4D, 5B, 6A, 7B), (A, 2B, 3B, 4D, 5B, 6A, 7C), (1A, 2B, 3B, 4D, 5B, 6B, 7A), (1A, 2B, 3B, 4D, 5B, 6B, 7B), (1A, 2B, 3B, 4D, 5B, 6B, 7C), (1A, 2B, 3B, 4D, 5B, 6C, 7A), (1A, 2B, 3B, 4D, 5B, 6C, 7B), (1A, 2B, 3B, 4D, 5B, 6C, 7C), (1A, 2B, 3B, 4D, 5B, 6D, 7A), (1A, 2B, 3B, 4D, 5B, 6D, 7B), (1A, 2B, 3B, 4D, 5B, 6D, 7C), (1A, 2B, 3B, 4E, 5A, 6A, 7A), (1A, 2B, 3B, 4E, 5A, 6A, 7B), (1A, 2B, 3B, 4E, 5A, 6A, 7C), (1A, 2B, 3B, 4E, 5A, 6B, 7A), (1A, 2B, 3B, 4E, 5A, 6B, 7B), (1A, 2B, 3B, 4E, 5A, 6B, 7C), (1A, 2B, 3B, 4E, 5A, 6C, 7A), (1A, 2B, 3B, 4E, 5A, 6C, 7B), (1A, 2B, 3B, 4E, 5A, 6C, 7C), (1A, 2B, 3B, 4E, 5A, 6D, 7A), (1A, 2B, 3B, 4E, 5A, 6D, 7B), (1A, 2B, 3B, 4E, 5A, 6D, 7C), (1A, 2B, 3B, 4E, 5B, 6A, 7A), (1A, 2B, 3B, 4E, 5B, 6A, 7B), (1A, 2B, 3B, 4E, 5B, 6A, 7C), (1A, 2B, 3B, 4E, 5B, 6B, 7A), (1A, 2B, 3B, 4E, 5B, 6B, 7B), (1A, 2B, 3B, 4E, 5B, 6B, 7C), (1A, 2B, 3B, 4E, 5B, 6C, 7A), (1A, 2B, 3B, 4E, 5B, 6C, 7B), (1A, 2B, 3B, 4E, 5B, 6C, 7C), (1A, 2B, 3B, 4E, 5B, 6D, 7A), (1A, 2B, 3B, 4E, 5B, 6D, 7B), (1A, 2B, 3B, 4E, 5B, 6D, 7C), (1A, 2B, 3C, 4A, 5A, 6A, 7A), (1A, 2B, 3C, 4A, 5A, 6A, 7B), (1A, 2B, 3C, 4A, 5A, 6A, 7C), (1A, 2B, 3C, 4A, 5A, 6B, 7A), (1A, 2B, 3C, 4A, 5A, 6B, 7B), (1A, 2B, 3C, 4A, 5A, 6B, 7C), (1A, 2B, 3C, 4A, 5A, 6C, 7A), (1A, 2B, 3C, 4A, 5A, 6C, 7B), (1A, 2B, 3C, 4A, 5A, 6C, 7C), (1A, 2B, 3C, 4A, 5A, 6D, 7A), (1A, 2B, 3C, 4A, 5A, 6D, 7B), (1A, 2B, 3C, 4A, 5A, 6D, 7C), (1A, 2B, 3C, 4A, 5B, 6A, 7A), (1A, 2B, 3C, 4A, 5B, 6A, 7B), (1A, 2B, 3C, 4A, 5B, 6A, 7C), (1A, 2B, 3C, 4A, 5B, 6B, 7A), (1A, 2B, 3C, 4A, 5B, 6B, 7B), (1A, 2B, 3C, 4A, 5B, 6B, 7C), (1A, 2B, 3C, 4A, 5B, 6C, 7A), (1A, 2B, 3C, 4A, 5B, 6C, 7B), (1A, 2B, 3C, 4A, 5B, 6C, 7C), (1A, 2B, 3C, 4A, 5B, 6D, 7A), (1A, 2B, 3C, 4A, 5B, 6D, 7B), (1A, 2B, 3C, 4A, 5B, 6D, 7C), (1A, 2B, 3C, 4B, 5A, 6A, 7A), (1A, 2B, 3C, 4B, 5A, 6A, 7B), (1A, 2B, 3C, 4B, 5A, 6A, 7C), (1A, 2B, 3C, 4B, 5A, 6B, 7A), (1A, 2B, 3C, 4B, 5A, 6B, 7B), (1A, 2B, 3C, 4B, 5A, 6B, 7C), (1A, 2B, 3C, 4B, 5A, 6C, 7A), (1A, 2B, 3C, 4B, 5A, 6C, 7B), (1A, 2B, 3C, 4B, 5A, 6C, 7C), (1A, 2B, 3C, 4B, 5A, 6D, 7A), (1A, 2B, 3C, 4B, 5A, 6D, 7B), (1A, 2B, 3C, 4B, 5A, 6D, 7C), (1A, 2B, 3C, 4B, 5B, 6A, 7A), (1A, 2B, 3C, 4B, 5B, 6A, 7B), (1A, 2B, 3C, 4B, 5B, 6A, 7C), (1A, 2B, 3C, 4B, 5B, 6B, 7A), (1A, 2B, 3C, 4B, 5B, 6B, 7B), (1A, 2B, 3C, 4B, 5B, 6B, 7C), (1A, 2B, 3C, 4B, 5B, 6C, 7A), (1A, 2B, 3C, 4B, 5B, 6C, 7B), (1A, 2B, 3C, 4B, 5B, 6C, 7C), (1A, 2B, 3C, 4B, 5B, 6D, 7A), (1A, 2B, 3C, 4B, 5B, 6D, 7B), (1A, 2B, 3C, 4B, 5B, 6D, 7C), (1A, 2B, 3C, 4C, 5A, 6A, 7A), (1A, 2B, 3C, 4C, 5A, 6A, 7B), (1A, 2B, 3C, 4C, 5A, 6A, 7C), (1A, 2B, 3C, 4C, 5A, 6B, 7A), (1A, 2B, 3C, 4C, 5A, 6B, 7B), (1A, 2B, 3C, 4C, 5A, 6B, 7C), (1A, 2B, 3C, 4C, 5A, 6C, 7A), (1A, 2B, 3C, 4C, 5A, 6C, 7B); (1A, 2B, 3C, 4C, 5A, 6C, 7C), (1A, 2B, 3C, 4C, 5A, 6D, 7A), (1A, 2B, 3C, 4C, 5A, 6D, 7B), (1A, 2B, 3C, 4C, 5A, 6D, 7C), (1A, 2B, 3C, 4C, 5B, 6A, 7A), (1A, 2B, 3C, 4C, 5B, 6A, 7B), (1A, 2B, 3C, 4C, 5B, 6A, 7C), (1A, 2B, 3C, 4C, 5B, 6B, 7A), (1A, 2B, 3C, 4C, 5B, 6B, 7B), (1A, 2B, 3C, 4C, 5B, 6B, 7C), (1A, 2B, 3C, 4C, 5B, 6C, 7A), (1A, 2B, 3C, 4C, 5B, 6C, 7B), (1A, 2B, 3C, 4C, 5B, 6C, 7C), (1A, 2B, 3C, 4C, 5B, 6D, 7A), (1A, 2B, 3C, 4C, 5B, 6D, 7B), (1A, 2B, 3C, 4C, 5B, 6D, 7C), (1A, 2B, 3C, 4D, 5A, 6A, 7A), (1A, 2B, 3C, 4D, 5A, 6A, 7B), (1A, 2B, 3C, 4D, 5A, 6A, 7C), (1A, 2B, 3C, 4D, 5A, 6B, 7A), (1A, 2B, 3C, 4D, 5A, 6B, 7B), (1A, 2B, 3C, 4D, 5A, 6B, 7C), (1A, 2B, 3C, 4D, 5A, 6C, 7A), (1A, 2B, 3C, 4D, 5A, 6C, 7B), (1A, 2B, 3C, 4D, 5A, 6C, 7C), (1A, 2B, 3C, 4D, 5A, 6D, 7A), (1A, 2B, 3C, 4D, 5A, 6D, 7B), (1A, 2B, 3C, 4D, 5A, 6D, 7C), (1A, 2B, 3C, 4D, 5B, 6A, 7A), (1A, 2B, 3C, 4D, 5B, 6A, 7B), (1A, 2B, 3C, 4D, 5B, 6A, 7C), (1A, 2B, 3C, 4D, 5B, 6B, 7A), (1A, 2B, 3C, 4D, 5B, 6B, 7B), (1A, 2B, 3C, 4D, 5B, 6B, 7C), (1A, 2B, 3C, 4D, 5B, 6C, 7A), (1A, 2B, 3C, 4D, 5B, 6C, 7B), (1A, 2B, 3C, 4D, 5B, 6C, 7C), (1A, 2B, 3C, 4D, 5B, 6A, 7A), (1A, 2B, 3C, 4D, 5B, 6D, 7B), (1A, 2B, 3C, 4D, 5B, 6D, 7C), (1A, 2B, 3C, 4E, 5A, 6A, 7A), (1A, 2B, 3C, 4E, 5A, 6A, 7B), (1A, 2B, 3C, 4E, 5A, 6A, 7C), (1A, 2B, 3C, 4E, 5A, 6B, 7A), (1A, 2B, 3C, 4E, 5A, 6B, 7B), (1A, 2B, 3C, 4E, 5A, 6B, 7C), (1A, 2B, 3C, 4E, 5A, 6C, 7A), (1A, 2B, 3C, 4E, 5A, 6C, 7B), (1A, 2B, 3C, 4E, 5A, 6C, 7C), (1A, 2B, 3C, 4E, 5A, 6D, 7A), (1A, 2B, 3C, 4E, 5A, 6D, 7B), (1A, 2B, 3C, 4E, 5A, 6D, 7C), (1A, 2B, 3C, 4E, 5B, 6A, 7A), (1A, 2B, 3C, 4E, 5B, 6A, 7B), (1A, 2B, 3C, 4E, 5B, 6A, 7C), (1A, 2B, 3C, 4E, 5B, 6B, 7A), (1A, 2B, 3C, 4E, 5B, 6B, 7B), (1A, 2B, 3C, 4E, 5B, 6B, 7C), (1A, 2B, 3C, 4E, 5B, 6C, 7A), (1A, 2B, 3C, 4E, 5B, 6C, 7B), (1A, 2B, 3C, 4E, 5B, 6C, 7C), (1A, 2B, 3C, 4E, 5B, 6D, 7A), (1A, 2B, 3C, 4E, 5B, 6D, 7B), (1A, 2B, 3C, 4E, 5B, 6D, 7C), (1A, 2B, 3D, 4A, 5A, 6A, 7A), (1A, 2B, 3D, 4A, 5A, 6A, 7B), (1A, 2B, 3D, 4A, 5A, 6A, 7C), (1A, 2B, 3D, 4A, 5A, 6B, 7A), (1A, 2B, 3D, 4A, 5A, 6B, 7B), (1A, 2B, 3D, 4A, 5A, 6B, 7C), (1A, 2B, 3D, 4A, 5A, 6C, 7A), (1A, 2B, 3D, 4A, 5A, 6C, 7B), (1A, 2B, 3D, 4A, 5A, 6C, 7C), (1A, 2B, 3D, 4A, 5A, 6D, 7A), (1A, 2B, 3D, 4A, 5A, 6D, 7B), (1A, 2B, 3D, 4A, 5A, 6D, 7C), (A, 2B, 3D, 4A, 5B, 6A, 7A), (1A, 2B, 3D, 4A, 5B, 6A, 7B), (1A, 2B, 3D, 4A, 5B, 6A, 7C), (1A, 2B, 3D, 4A, 5B, 6B, 7A), (1A, 2B, 3D, 4A, 5B, 6B, 7B), (1A, 2B, 3D, 4A, 5B, 6B, 7C), (1A, 2B, 3D, 4A, 5B, 6C, 7A), (1A, 2B, 3D, 4A, 5B, 6C, 7B), (1A, 2B, 3D, 4A, 5B, 6C, 7C), (1A, 2B, 3D, 4A, 5B, 6D, 7A), (1A, 2B, 3D, 4A, 5B, 6D, (B), (1A, 2B, 3D, 4A, 5B, 6D, 7C), (1A, 2B, 3D, 4B, 5A, 6A, 7A), (1A, 2B, 3D, 4B, 5A, 6A, 7B), (1A, 2B, 3D, 4B, 5A, 6A, 7C), (1A, 2B, 3D, 4B, 5A, 6B, 7A), (1A, 2B, 3D, 4B, 5A, 6B, 7B), (1A, 2B, 3D, 4B, 5A, 6B, (C), (1A, 2B, 3D, 4B, 5A, 6C, 7A), (1A, 2B, 3D, 4B, 5A, 6C, 7B), (1A, 2B, 3D, 4B, 5A, 6C, 7C), (1A, 2B, 3D, 4B, 5A, 6D, 7A), (1A, 2B, 3D, 4B, 5A, 6D, 7B), (1A, 2B, 3D, 4B, 5A, 6D, 7C), (1A, 2B, 3D, 4B, 5B, 6A, 7A), (1A, 2B, 3D, 4B, 5B, 6A, 7B), (1A, 2B, 3D, 4B, 5B, 6A, 7C), (1A, 2B, 3D, 4B, 5B, 6B, 7A), (1A, 2B, 3D, 4B, 5B, 6B, 7B), (1A, 2B, 3D, 4B, 5B, 6B, 7C), (1A, 2B, 3D, 4B, 5B, 6C, 7A), (1A, 2B, 3D, 4B, 5B, 6C, 7B), (1A, 2B, 3D, 4B, 5B, 6C, 7C), (1A, 2B, 3D, 4B, 5B, 6D, 7A), (1A, 2B, 3D, 4B, 5B, 6D, 7B), (1A, 2B, 3D, 4B, 5B, 6D, 7C), (1A, 2B, 3D, 4C, 5A, 6A, 7A), (1A, 2B, 3D, 4C, 5A, 6A, 7B), (1A, 2B, 3D, 4C, 5A, 6A, 7C), (1A, 2B, 3D, 4C, 5A, 6B, 7A), (1A, 2B, 3D, 4C, 5A, 6B, 7B), (1A, 2B, 3D, 4C, 5A, 6B, 7C), (1A, 2B, 3D, 4C, 5A, 6C, 7A), (1A, 2B, 3D, 4C, 5A, 6C, 7B), (1A, 2B, 3D, 4C, 5A, 6C, 7C), (1A, 2B, 3D, 4C, 5A, 6D, 7A), (1A, 2B, 3D, 4C, 5A, 6D, 7B), (1A, 2B, 3D, 4C, 5A, 6D, 7C), (1A, 2B, 3D, 4C, 5B, 6A, 7A), (1A, 2B, 3D, 4C, 5B, 6A, 7B), (1A, 2B, 3D, 4C, 5B, 6A, 7C), (1A, 2B, 3D, 4C, 5B, 6B, 7A), (1A, 2B, 3D, 4C, 5B, 6B, 7B), (1A, 2B, 3D, 4C, 5B, 6B, 7C), (1A, 2B, 3D, 4C, 5B, 6C, 7A), (1A, 2B, 3D, 4C, 5B, 6C, 7B), (1A, 2B, 3D, 4C, 5B, 6C, 7C), (1A, 2B, 3D, 4C, 5B, 6D, 7A), (1A, 2B, 3D, 4C, 5B, 6D, 7B), (1A, 2B, 3D, 4C, 5B, 6D, 7C), (1A, 2B, 3D, 4D, 5A, 6A, 7A), (1A, 2B, 3D, 4D, 5A, 6A, 7B), (1A, 2B, 3D, 4D, 5A, 6A, 7C), (1A, 2B, 3D, 4D, 5A, 6B, 7A), (1A, 2B, 3D, 4D, 5A, 6B, 7B), (1A, 2B, 3D, 4D, 5A, 6B, 7C), (1A, 2B, 3D, 4D, 5A, 6C, 7A), (1A, 2B, 3D, 4D, 5A, 6C, 7B), (1A, 2B, 3D, 4D, 5A, 6C, 7C), (1A, 2B, 3D, 4D, 5A, 6D, 7A), (1A, 2B, 3D, 4D, 5A, 6D, 7B), (1A, 2B, 3D, 4D, 5A, 6D, 7C), (1A, 2B, 3D, 4D, 5B, 6A, 7A), (1A, 2B, 3D, 4D, 5B, 6A, 7B), (1A, 2B, 3D, 4D, 5B, 6A, 7C), (1A, 2B, 3D, 4D, 5B, 6B, 7A), (1A, 2B, 3D, 4D, 5B, 6B, 7B), (1A, 2B, 3D, 4D, 5B, 6B, 7C), (1A, 2B, 3D, 4D, 5B, 6C, 7A), (1A, 2B, 3D, 4D, 5B, 6C, 7B), (1A, 2B, 3D, 4D, 5B, 6C, 7C), (1A, 2B, 3D, 4D, 5B, 6D, 7A), (1A, 2B, 3D, 4D, 5B, 6D, 7B), (1A, 2B, 3D, 4D, 5B, 6D, 7C), (1A, 2B, 3D, 4E, 5A, 6A, 7A), (1A, 2B, 3D, 4E, 5A, 6A, 7B), (1A, 2B, 3D, 4E, 5A, 6A, 7C), (1A, 2B, 3D, 4E, 5A, 6B, 7A), (1A, 2B, 3D, 4E, 5A, 6B, 7B), (1A, 2B, 3D, 4E, 5A, 6B, 7C), (1A, 2B, 3D, 4E, 5A, 6C, 7A), (1A, 2B, 3D, 4E, 5A, 6C, 7B), (1A, 2B, 3D, 4E, 5A, 6C, 7C), (1A, 2B, 3D, 4E, 5A, 6D, 7A), (1A, 2B, 3D, 4E, 5A, 6D, 7B), (1A, 2B, 3D, 4E, 5A, 6D, 7C), (1A, 2B, 3D, 4E, 5B, 6A, 7A), (1A, 2B, 3D, 4E, 5B, 6A, 7B), (1A, 2B, 3D, 4E, 5B, 6A, 7C), (1A, 2B, 3D, 4E, 5B, 6B, 7A), (1A, 2B, 3D, 4E, 5B, 6B, 7B), (1A, 2B, 3D, 4E, 5B, 6B, 7C), (1A, 2B, 3D, 4E, 5B, 6C, 7A), (1A, 2B, 3D, 4E, 5B, 6C, 7B), (1A, 2B, 3D, 4E, 5B, 6C, 7C), (1A, 2B, 3D, 4E, 5B, 6D, 7A), (1A, 2B, 3D, 4E, 5B, 6D, 7B), (1A, 2B, 3D, 4E, 5B, 6D, 7C), (1A, 2B, 3E, 4A, 5A, 6A, 7A), (1A, 2B, 3E, 4A, 5A, 6A, 7B), (1A, 2B, 3E, 4A, 5A, 6A, 7C), (1A, 2B, 3E, 4A, 5A, 6B, 7A), (1A, 2B, 3E, 4A, 5A, 6B, 7B), (1A, 2B, 3E, 4A, 5A, 6B, 7C), (1A, 2B, 3E, 4A, 5A, 6C, 7A), (1A, 2B, 3E, 4A, 5A, 6C, 7B), (1A, 2B, 3E, 4A, 5A, 6C, 7C), (1A, 2B, 3E, 4A, 5A, 6D, 7A), (1A, 2B, 3E, 4A, 5A, 6D, 7B), (1A, 2B, 3E, 4A, 5A, 6D, 7C), (1A, 2B, 3E, 4A, 5B, 6A, 7A), (1A, 2B, 3E, 4A, 5B, 6A, 7B), (1A, 2B, 3E, 4A, 5B, 6A, 7C), (1A, 2B, 3E, 4A, 5B, 6B, 7A), (1A, 2B, 3E, 4A, 5B, 6B, 7B), (1A, 2B, 3E, 4A, 5B, 6B, 7C), (1A, 2B, 3E, 4A, 5B, 6C, 7A), (1A, 2B, 3E, 4A, 5B, 6C, 7B), (1A, 2B, 3E, 4A, 5B, 6C, 7C), (1A, 2B, 3E, 4A, 5B, 6D, 7A), (1A, 2B, 3E, 4A, 5B, 6D, 7B), (1A, 2B, 3E, 4A, 5B, 6D, 7C), (1A, 2B, 3E, 4B, 5A, 6A, 7A), (1A, 2B, 3E, 4B, 5A, 6A, 7B), (1A, 2B, 3E, 4B, 5A, 6A, 7C), (1A, 2B, 3E, 4B, 5A, 6B, 7A), (1A, 2B, 3E, 4B, 5A, 6B, 7B), (1A, 2B, 3E, 4B, 5A, 6B, 7C), (1A, 2B, 3E, 4B, 5A, 6C, 7A), (1A, 2B, 3E, 4B, 5A, 6C, 7B), (1A, 2B, 3E, 4B, 5A, 6C, 7C), (1A, 2B, 3E, 4B, 5A, 6D, 7A), (1A, 2B, 3E, 4B, 5A, 6D, 7B), (1A, 2B, 3E, 4B, 5A, 6D, 7C), (1A, 2B, 3E, 4B, 5B, 6A, 7A), (1A, 2B, 3E, 4B, 5B, 6A, 7B), (1A, 2B, 3E, 4B, 5B, 6A, 7C), (1A, 2B, 3E, 4B, 5B, 6B, 7A), (1A, 2B, 3E, 4B, 5B, 6B, 7B), (1A, 2B, 3E, 4B, 5B, 6B, 7C), (1A, 2B, 3E, 4B, 5B, 6C, 7A), (1A, 2B, 3E, 4B, 5B, 6C, 7B), (1A, 2B, 3E, 4B, 5B, 6C, 7C), (1A, 2B, 3E, 4B, 5B, 6D, 7A), (1A, 2B, 3E, 4B, 5B, 6D, 7B), (1A, 2B, 3E, 4B, 5B, 6D, 7C), (1A, 2B, 3E, 4C, 5A, 6A, 7A), (1A, 2B, 3E, 4C, 5A, 6A, 7B), (1A, 2B, 3E, 4C, 5A, 6A, 7C), (1A, 2B, 3E, 4C, 5A, 6B, 7A), (1A, 2B, 3E, 4C, 5A, 6B, 7B), (1A, 2B, 3E, 4C, 5A, 6B, 7C), (1A, 2B, 3E, 4C, 5A, 6C, 7A), (1A, 2B, 3E, 4C, 5A, 6C, 7B), (1A, 2B, 3E, 4C, 5A, 6C, 7C), (1A, 2B, 3E, 4C, 5A, 6D, 7A), (1A, 2B, 3E, 4C, 5A, 6D, 7B), (1A, 2B, 3E, 4C, 5A, 6D, 7C), (1A, 2B, 3E, 4C, 5B, 6A, 7A), (1A, 2B, 3E, 4C, 5B, 6A, 7B), (1A, 2B, 3E, 4C, 5B, 6A, 7C), (1A, 2B, 3E, 4C, 5B, 6B, 7A), (1A, 2B, 3E, 4C, 5B, 6B, 7B), (1A, 2B, 3E, 4C, 5B, 6B, 7C), (1A, 2B, 3E, 4C, 5B, 6C, 7A), (1A, 2B, 3E, 4C, 5B, 6C, 7B), (1A, 2B, 3E, 4C, 5B, 6C, 7C), (1A, 2B, 3E, 4C, 5B, 6D, 7A), (1A, 2B, 3E, 4C, 5B, 6D, 7B), (1A, 2B, 3E, 4C, 5B, 6D, 7C), (1A, 2B, 3E, 4D, 5A, 6A, 7A), (1A, 2B, 3E, 4D, 5A, 6A, 7B), (1A, 2B, 3E, 4D, 5A, 6A, 7C), (1A, 2B, 3E, 4D, 5A, 6B, 7A), (1A, 2B, 3E, 4D, 5A, 6B, 7B), (1A, 2B, 3E, 4D, 5A, 6B, 7C), (1A, 2B, 3E, 4D, 5A, 6C, 7A), (1A, 2B, 3E, 4D, 5A, 6C, 7B), (1A, 2B, 3E, 4D, 5A, 6C, 7C), (1A, 2B, 3E, 4D, 5A, 6D, 7A), (1A, 2B, 3E, 4D, 5A, 6D, 7B), (1A, 2B, 3E, 4D, 5A, 6D, 7C), (1A, 2B, 3E, 4D, 5B, 6A, 7A), (1A, 2B, 3E, 4D, 5B, 6A, 7B), (1A, 2B, 3E, 4D, 5B, 6A, 7C), (1A, 2B, 3E, 4D, 5B, 6B, 7A), (1A, 2B, 3E, 4D, 5B, 6B, 7B), (1A, 2B, 3E, 4D, 5B, 6B, 7C), (1A, 2B, 3E, 4D, 5B, 6C, 7A), (1A, 2B, 3E, 4D, 5B, 6C, 7B), (1A, 2B, 3E, 4D, 5B, 6C, 7C), (1A, 2B, 3E, 4D, 5B, 6D, 7A), (1A, 2B, 3E, 4D, 5B, 6D, 7B), (1A, 2B, 3E, 4D, 5B, 6D, 7C), (1A, 2B, 3E, 4E, 5A, 6A, 7A), (1A, 2B, 3E, 4E, 5A, 6A, 7B), (1A, 2B, 3E, 4E, 5A, 6A, 7C), (1A, 2B, 3E, 4E, 5A, 6B, 7A), (1A, 2B, 3E, 4E, 5A, 6B, 7B), (1A, 2B, 3E, 4E, 5A, 6B, 7C), (1A, 2B, 3E, 4E, 5A, 6C, 7A), (1A, 2B, 3E, 4E, 5A, 6C, 7B), (1A, 2B, 3E, 4E, 5A, 6C, 7C), (1A, 2B, 3E, 4E, 5A, 6D, 7A), (1A, 2B, 3E, 4E, 5A, 6D, 7B), (1A, 2B, 3E, 4E, 5A, 6D, 7C), (1A, 2B, 3E, 4E, 5B, 6A, 7A), (1A, 2B, 3E, 4E, 5B, 6A, 7B), (1A, 2B, 3E, 4E, 5B, 6A, 7C), (1A, 2B, 3E, 4E, 5B, 6B, 7A), (1A, 2B, 3E, 4E, 5B, 6B, 7B), (1A, 2B, 3E, 4E, 5B, 6B, 7C), (1A, 2B, 3E, 4E, 5B, 6C, 7A), (A, 2B, 3E, 4E, 5B, 6C, 7B), (1A, 2B, 3E, 4E, 5B, 6C, 7C), (1A, 2B, 3E, 4E, 5B, 6D, 7A), (1A, 2B, 3E, 4E, 5B, 6D, 7B), (1A, 2B, 3E, 4E, 5B, 6D, 7C), (1A, 2C, 3A, 4A, 5A, 6A, 7A), (1A, 2C, 3A, 4A, 5A, 6A, 7B), (1A, 2C, 3A, 4A, 5A, 6A, 7C), (1A, 2C, 3A, 4A, 5A, 6B, 7A), (1A, 2C, 3A, 4A, 5A, 6B, 7B), (1A, 2C, 3A, 4A, 5A, 6B, 7C), (1A, 2C, 3A, 4A, 5A, 6C, 7A), (1A, 2C, 3A, 4A, 5A, 6C, 7B), (1A, 2C, 3A, 4A, 5A, 6C, 7C), (1A, 2C, 3A, 4A, 5A, 6D, 7A), (1A, 2C, 3A, 4A, 5A, 6D, 7B), (1A, 2C, 3A, 4A, 5A, 6D, 7C), (1A, 2C, 3A, 4A, 5B, 6A, 7A), (1A, 2C, 3A, 4A, 5B, 6A, 7B), (1A, 2C, 3A, 4A, 5B, 6A, 7C), (1A, 2C, 3A, 4A, 5B, 6B, 7A), (1A, 2C, 3A, 4A, 5B, 6B, 7B), (1A, 2C, 3A, 4A, 5B, 6B, 7C), (1A, 2C, 3A, 4A, 5B, 6C, 7A), (1A, 2C, 3A, 4A, 5B, 6C, 7B), (1A, 2C, 3A, 4A, 5B, 6C, 7C), (1A, 2C, 3A, 4A, 5B, 6D, 7A), (1A, 2C, 3A, 4A, 5B, 6D, 7B), (1A, 2C, 3A, 4A, 5B, 6D, 7C), (1A, 2C, 3A, 4B, 5A, 6A, 7A), (1A, 2C, 3A, 4B, 5A, 6A, 7B), (1A, 2C, 3A, 4B, 5A, 6A, 7C), (1A, 2C, 3A, 4B, 5A, 6B, 7A), (1A, 2C, 3A, 4B, 5A, 6B, 7B), (1A, 2C, 3A, 4B, 5A, 6B, 7C), (1A, 2C, 3A, 4B, 5A, 6C, 7A), (1A, 2C, 3A, 4B, 5A, 6C, 7B), (1A, 2C, 3A, 4B, 5A, 6C, 7C), (1A, 2C, 3A, 4B, 5A, 6D, 7A), (1A, 2C, 3A, 4B, 5A, 6D, 7B), (1A, 2C, 3A, 4B, 5A, 6D, 7C), (1A, 2C, 3A, 4B, 5B, 6A, 7A), (1A, 2C, 3A, 4B, 5B, 6A, 7B), (1A, 2C, 3A, 4B, 5B, 6A, 7C), (1A, 2C, 3A, 4B, 5B, 6B, 7A), (1A, 2C, 3A, 4B, 5B, 6B, 7B), (1A, 2C, 3A, 4B, 5B, 6B, 7C), (1A, 2C, 3A, 4B, 5B, 6C, 7A), (1A, 2C, 3A, 4B, 5B, 6C, 7B), (1A, 2C, 3A, 4B, 5B, 6C, 7C), (1A, 2C, 3A, 4B, 5B, 6D, 7A), (1A, 2C, 3A, 4B, 5B, 6D, 7B), (1A, 2C, 3A, 4B, 5B, 6D, 7C), (1A, 2C, 3A, 4C, 5A, 6A, 7A), (1A, 2C, 3A, 4C, 5A, 6A, 7B), (1A, 2C, 3A, 4C, 5A, 6A, 7C), (1A, 2C, 3A, 4C, 5A, 6B, 7A), (1A, 2C, 3A, 4C, 5A, 6B, 7B), (1A, 2C, 3A, 4C, 5A, 6B, 7C), (1A, 2C, 3A, 4C, 5A, 6C, 7A), (1A, 2C, 3A, 4C, 5A, 6C, 7B), (1A, 2C, 3A, 4C, 5A, 6C, 7C), (1A, 2C, 3A, 4C, 5A, 6D, 7A), (1A, 2C, 3A, 4C, 5A, 6D, 7B), (1A, 2C, 3A, 4C, 5A, 6D, 7C), (1A, 2C, 3A, 4C, 5B, 6A, 7A), (1A, 2C, 3A, 4C, 5B, 6A, 7B), (1A, 2C, 3A, 4C, 5B, 6A, 7C), (1A, 2C, 3A, 4C, 5B, 6B, 7A), (1A, 2C, 3A, 4C, 5B, 6B, 7B), (1A, 2C, 3A, 4C, 5B, 6B, 7C), (1A, 2C, 3A, 4C, 5B, 6C, 7A), (1A, 2C, 3A, 4C, 5B, 6C, 7B), (1A, 2C, 3A, 4C, 5B, 6C, 7C), (1A, 2C, 3A, 4C, 5B, 6D, 7A), (1A, 2C, 3A, 4C, 5B, 6D, 7B), (1A, 2C, 3A, 4C, 5B, 6D, 7C), (1A, 2C, 3A, 4D, 5A, 6A, 7A), (1A, 2C, 3A, 4D, 5A, 6A, 7B), (1A, 2C, 3A, 4D, 5A, 6A, 7C), (1A, 2C, 3A, 4D, 5A, 6B, 7A), (1A, 2C, 3A, 4D, 5A, 6B, 7B), (1A, 2C, 3A, 4D, 5A, 6B, 7C), (1A, 2C, 3A, 4D, 5A, 6C, 7A), (1A, 2C, 3A, 4D, 5A, 6C, 7B), (1A, 2C, 3A, 4D, 5A, 6C, 7C), (1A, 2C, 3A, 4D, 5A, 6D, 7A), (1A, 2C, 3A, 4D, 5A, 6D, 7B), (1A, 2C, 3A, 4D, 5A, 6D, 7C), (1A, 2C, 3A, 4D, 5B, 6A, 7A), (1A, 2C, 3A, 4D, 5B, 6A, 7B), (1A, 2C, 3A, 4D, 5B, 6A, 7C), (1A, 2C, 3A, 4D, 5B, 6B, 7A), (1A, 2C, 3A, 4D, 5B, 6B, 7B), (1A, 2C, 3A, 4D, 5B, 6B, 7C), (1A, 2C, 3A, 4D, 5B, 6C, 7A), (1A, 2C, 3A, 4D, 5B, 6C, 7B), (1A, 2C, 3A, 4D, 5B, 6C, 7C), (A, 2C, 3A, 4D, 5B, 6D, 7A), (1A, 2C, 3A, 4D, 5B, 6D, 7B), (1A, 2C, 3A, 4D, 5B, 6D, 7C), (1A, 2C, 3A, 4E, 5A, 6A, 7A), (1A, 2C, 3A, 4E, 5A, 6A, 7B), (1A, 2C, 3A, 4E, 5A, 6A, 7C), (1A, 2C, 3A, 4E, 5A, 6B, 7A), (1A, 2C, 3A, 4E, 5A, 6B, 7B), (1A, 2C, 3A, 4E, 5A, 6B, 7C), (1A, 2C, 3A, 4E, 5A, 6C, 7A), (1A, 2C, 3A, 4E, 5A, 6C, 7B), (1A, 2C, 3A, 4E, 5A, 6C, 7C), (1A, 2C, 3A, 4E, 5A, 6D, 7A), (1A, 2C, 3A, 4E, 5A, 6D, 7B), (1A, 2C, 3A, 4E, 5A, 6D, 7C), (1A, 2C, 3A, 4E, 5B, 6A, 7A), (1A, 2C, 3A, 4E, 5B, 6A, 7B), (1A, 2C, 3A, 4E, 5B, 6A, 7C), (1A, 2C, 3A, 4E, 5B, 6B, 7A), (1A, 2C, 3A, 4E, 5B, 6B, 7B), (1A, 2C, 3A, 4E, 5B, 6B, 7C), (1A, 2C, 3A, 4E, 5B, 6C, 7A), (1A, 2C, 3A, 4E, 5B, 6C, 7B), (1A, 2C, 3A, 4E, 5B, 6C, 7C), (1A, 2C, 3A, 4E, 5B, 6D, 7A), (1A, 2C, 3A, 4E, 5B, 6D, 7B), (1A, 2C, 3A, 4E, 5B, 6D, 7C), (1A, 2C, 3B, 4A, 5A, 6A, 7A), (1A, 2C, 3B, 4A, 5A, 6A, 7B), (1A, 2C, 3B, 4A, 5A, 6A, 7C), (1A, 2C, 3B, 4A, 5A, 6B, 7A), (1A, 2C, 3B, 4A, 5A, 6B, 7B), (1A, 2C, 3B, 4A, 5A, 6B, 7C), (1A, 2C, 3B, 4A, 5A, 6C, 7A), (1A, 2C, 3B, 4A, 5A, 6C, 7B), (1A, 2C, 3B, 4A, 5A, 6C, 7C), (1A, 2C, 3B, 4A, 5A, 6D, 7A), (1A, 2C, 3B, 4A, 5A, 6D, 7B), (1A, 2C, 3B, 4A, 5A, 6D, 7C), (1A, 2C, 3B, 4A, 5B, 6A, 7A), (1A, 2C, 3B, 4A, 5B, 6A, 7B), (1A, 2C, 3B, 4A, 5B, 6A, 7C), (1A, 2C, 3B, 4A, 5B, 6B, 7A), (1A, 2C, 3B, 4A, 5B, 6B, 7B), (1A, 2C, 3B, 4A, 5B, 6B, 7C), (1A, 2C, 3B, 4A, 5B, 6C, 7A), (1A, 2C, 3B, 4A, 5B, 6C, 7B), (1A, 2C, 3B, 4A, 5B, 6C, 7C), (1A, 2C, 3B, 4A, 5B, 6D, 7A), (1A, 2C, 3B, 4A, 5B, 6D, 7B), (1A, 2C, 3B, 4A, 5B, 6D, 7C), (1A, 2C, 3B, 4B, 5A, 6A, 7A), (1A, 2C, 3B, 4B, 5A, 6A, 7B), (1A, 2C, 3B, 4B, 5A, 6A, 7C), (1A, 2C, 3B, 4B, 5A, 6B, 7A), (1A, 2C, 3B, 4B, 5A, 6B, 7B), (1A, 2C, 3B, 4B, 5A, 6B, 7C), (1A, 2C, 3B, 4B, 5A, 6C, 7A), (1A, 2C, 3B, 4B, 5A, 6C, 7A), (1A, 2C, 3B, 4B, 5A, 6C, 7B), (1A, 2C, 3B, 4B, 5A, 6C, 7C), (1A, 2C, 3B, 4B, 5A, 6D, 7A), (1A, 2C, 3B, 4B, 5A, 6D, 7B), (1A, 2C, 3B, 4B, 5A, 6D, 7C), (1A, 2C, 3B, 4B, 5B, 6A, 7A), (1A, 2C, 3B, 4B, 5B, 6A, 7B), (1A, 2C, 3B, 4B, 5B, 6A, 7C), (1A, 2C, 3B, 4B, 5B, 6B, 7A), (1A, 2C, 3B, 4B, 5B, 6B, 7B), (1A, 2C, 3B, 4B, 5B, 6B, 7C), (1A, 2C, 3B, 4B, 5B, 6C, 7A), (1A, 2C, 3B, 4B, 5B, 6C, 7B), (1A, 2C, 3B, 4B, 5B, 6C, 7C), (1A, 2C, 3B, 4B, 5B, 6D, 7A), (1A, 2C, 3B, 4B, 5B, 6D, 7B), (1A, 2C, 3B, 4B, 5B, 6D, 7C), (1A, 2C, 3B, 4C, 5A, 6A, 7A), (1A, 2C, 3B, 4C, 5A, 6A, 7B), (1A, 2C, 3B, 4C, 5A, 6A, 7C), (1A, 2C, 3B, 4C, 5A, 6B, 7A), (1A, 2C, 3B, 4C, 5A, 6B, 7B), (1A, 2C, 3B, 4C, 5A, 6B, 7C), (1A, 2C, 3B, 4C, 5A, 6C, 7A), (1A, 2C, 3B, 4C, 5A, 6C, 7B), (1A, 2C, 3B, 4C, 5A, 6C, 7C), (1A, 2C, 3B, 4C, 5A, 6D, 7A), (1A, 2C, 3B, 4C, 5A, 6D, 7B), (1A, 2C, 3B, 4C, 5A, 6D, 7C), (1A, 2C, 3B, 4C, 5B, 6A, 7A), (1A, 2C, 3B, 4C, 5B, 6A, 7B), (1A, 2C, 3B, 4C, 5B, 6A, 7C), (1A, 2C, 3B, 4C, 5B, 6B, 7A), (1A, 2C, 3B, 4C, 5B, 6B, 7B), (1A, 2C, 3B, 4C, 5B, 6B, 7C), (1A, 2C, 3B, 4C, 5B, 6C, 7A), (1A, 2C, 3B, 4C, 5B, 6C, 7B), (1A, 2C, 3B, 4C, 5B, 6C, 7C), (1A, 2C, 3B, 4C, 5B, 6D, 7A), (1A, 2C, 3B, 4C, 5B, 6D, 7B), (1A, 2C, 3B, 4C, 5B, 6D, 7C), (1A, 2C, 3B, 4D, 5A, 6A, 7A), (1A, 2C, 3B, 4D, 5A, 6A, 7B), (1A, 2C, 3B, 4D, 5A, 6A, 7C), (1A, 2C, 3B, 4D, 5A, 6B, 7A), (1A, 2C, 3B, 4D, 5A, 6B, 7B), (1A, 2C, 3B, 4D, 5A, 6B, 7C), (1A, 2C, 3B, 4D, 5A, 6C, 7A), (1A, 2C, 3B, 4D, 5A, 6C, 7B), (1A, 2C, 3B, 4D, 5A, 6C, 7C), (1A, 2C, 3B, 4D, 5A, 6D, 7A), (1A, 2C, 3B, 4D, 5A, 6D, 7B), (1A, 2C, 3B, 4D, 5A, 6D, 7C), (1A, 2C, 3B, 4D, 5B, 6A, 7A), (1A, 2C, 3B, 4D, 5B, 6A, 7B), (1A, 2C, 3B, 4D, 5B, 6A, 7C), (1A, 2C, 3B, 4D, 5B, 6B, 7A), (1A, 2C, 3B, 4D, 5B, 6B, 7B), (1A, 2C, 3B, 4D, 5B, 6B, 7C), (1A, 2C, 3B, 4D, 5B, 6C, 7A), (1A, 2C, 3B, 4D, 5B, 6C, 7B), (1A, 2C, 3B, 4D, 5B, 6C, 7C), (1A, 2C, 3B, 4D, 5B, 6D, 7A), (1A, 2C, 3B, 4D, 5B, 6D, 7B), (1A, 2C, 3B, 4D, 5B, 6D, 7C), (1A, 2C, 3B, 4E, 5A, 6A, 7A), (1A, 2C, 3B, 4E, 5A, 6A, 7B), (1A, 2C, 3B, 4E, 5A, 6A, 7C), (1A, 2C, 3B, 4E, 5A, 6B, 7A), (1A, 2C, 3B, 4E, 5A, 6B, 7B), (1A, 2C, 3B, 4E, 5A, 6B, 7C), (1A, 2C, 3B, 4E, 5A, 6C, 7A), (1A, 2C, 3B, 4E, 5A, 6C, 7B), (1A, 2C, 3B, 4E, 5A, 6C, 7C), (1A, 2C, 3B, 4E, 5A, 6D, 7A), (1A, 2C, 3B, 4E, 5A, 6D, 7B), (1A, 2C, 3B, 4E, 5A, 6D, 7C), (1A, 2C, 3B, 4E, 5B, 6A, 7A), (1A, 2C, 3B, 4E, 5B, 6A, 7B), (1A, 2C, 3B, 4E, 5B, 6A, 7C), (1A, 2C, 3B, 4E, 5B, 6B, 7A), (1A, 2C, 3B, 4E, 5B, 6B, 7B), (1A, 2C, 3B, 4E, 5B, 6B, 7C), (1A, 2C, 3B, 4E, 5B, 6C, 7A), (1A, 2C, 3B, 4E, 5B, 6C, 7B), (1A, 2C, 3B, 4E, 5B, 6C, 7C), (1A, 2C, 3B, 4E, 5B, 6D, 7A), (1A, 2C, 3B, 4E, 5B, 6D, 7B), (1A, 2C, 3B, 4E, 5B, 6D, 7C), (1A, 2C, 3C, 4A, 5A, 6A, 7A), (1A, 2C, 3C, 4A, 5A, 6A, 7B), (1A, 2C, 3C, 4A, 5A, 6A, 7C), (1A, 2C, 3C, 4A, 5A, 6B, 7A), (1A, 2C, 3C, 4A, 5A, 6B, 7B), (1A, 2C, 3C, 4A, 5A, 6B, 7C), (1A, 2C, 3C, 4A, 5A, 6C, 7A), (1A, 2C, 3C, 4A, 5A, 6C, 7B), (1A, 2C, 3C, 4A, 5A, 6C, 7C), (1A, 2C, 3C, 4A, 5A, 6D, 7A), (1A, 2C, 3C, 4A, 5A, 6D, 7B), (1A, 2C, 3C, 4A, 5A, 6D, 7C), (1A, 2C, 3C, 4A, 5B, 6A, 7A), (1A, 2C, 3C, 4A, 5B, 6A, 7B), (1A, 2C, 3C, 4A, 5B, 6A, 7C), (1A, 2C, 3C, 4A, 5B, 6B, 7A), (1A, 2C, 3C, 4A, 5B, 6B, 7B), (1A, 2C, 3C, 4A, 5B, 6B, 7C), (1A, 2C, 3C, 4A, 5B, 6C, 7A), (1A, 2C, 3C, 4A, 5B, 6C, 7B), (A, 2C, 3C, 4A, 5B, 6C, 7C), (1A, 2C, 3C, 4A, 5B, 6D, 7A), (1A, 2C, 3C, 4A, 5B, 6D, 7B), (1A, 2C, 3C, 4A, 5B, 6D, 7C), (1A, 2C, 3C, 4B, 5A, 6A, 7A), (1A, 2C, 3C, 4B, 5A, 6A, 7B), (1A, 2C, 3C, 4B, 5A, 6A, 7C), (1A, 2C, 3C, 4B, 5A, 6B, 7A), (1A, 2C, 3C, 4B, 5A, 6B, 7B), (1A, 2C, 3C, 4B, 5A, 6B, 7C), (1A, 2C, 3C, 4B, 5A, 6C, 7A), (1A, 2C, 3C, 4B, 5A, 6C, 7B), (1A, 2C, 3C, 4B, 5A, 6C, 7C), (1A, 2C, 3C, 4B, 5A, 6D, 7A), (1A, 2C, 3C, 4B, 5A, 6D, 7B), (1A, 2C, 3C, 4B, 5A, 6D, 7C), (1A, 2C, 3C, 4B, 5B, 6A, 7A), (1A, 2C, 3C, 4B, 5B, 6A, 7B), (1A, 2C, 3C, 4B, 5B, 6A, 7C), (1A, 2C, 3C, 4B, 5B, 6B, 7A), (1A, 2C, 3C, 4B, 5B, 6B, 7B), (1A, 2C, 3C, 4B, 5B, 6B, 7C), (1A, 2C, 3C, 4B, 5B, 6C, 7A), (1A, 2C, 3C, 4B, 5B, 6C, 7B), (1A, 2C, 3C, 4B, 5B, 6C, 7C), (1A, 2C, 3C, 4B, 5B, 6D, 7A), (1A, 2C, 3C, 4B, 5B, 6D, 7B), (1A, 2C, 3C, 4B, 5B, 6D, 7C), (1A, 2C, 3C, 4C, 5A, 6A, 7A), (1A, 2C, 3C, 4C, 5A, 6A, 7B), (1A, 2C, 3C, 4C, 5A, 6A, 7C), (1A, 2C, 3C, 4C, 5A, 6B, 7A), (1A, 2C, 3C, 4C, 5A, 6B, 7B), (1A, 2C, 3C, 4C, 5A, 6B, 7C), (1A, 2C, 3C, 4C, 5A, 6C, 7A), (1A, 2C, 3C, 4C, 5A, 6C, 7B), (1A, 2C, 3C, 4C, 5A, 6C, 7C), (1A, 2C, 3C, 4C, 5A, 6D, 7A), (1A, 2C, 3C, 4C, 5A, 6D, 7B), (1A, 2C, 3C, 4C, 5A, 6D, 7C), (1A, 2C, 3C, 4C, 5B, 6A, 7A), (1A, 2C, 3C, 4C, 5B, 6A, 7B), (1A, 2C, 3C, 4C, 5B, 6A, 7C), (1A, 2C, 3C, 4C, 5B, 6B, 7A), (1A, 2C, 3C, 4C, 5B, 6B, 7B), (1A, 2C, 3C, 4C, 5B, 6B, 7C), (1A, 2C, 3C, 4C, 5B, 6C, 7A), (1A, 2C, 3C, 4C, 5B, 6C, 7B), (1A, 2C, 3C, 4C, 5B, 6C, 7C), (1A, 2C, 3C, 4C, 5B, 6D, 7A), (1A, 2C, 3C, 4C, 5B, 6D, 7B), (1A, 2C, 3C, 4C, 5B, 6D, 7C), (1A, 2C, 3C, 4D, 5A, 6A, 7A), (1A, 2C, 3C, 4D, 5A, 6A, 7B), (1A, 2C, 3C, 4D, 5A, 6A, 7C), (1A, 2C, 3C, 4D, 5A, 6B, 7A), (1A, 2C, 3C, 4D, 5A, 6B, 7B), (1A, 2C, 3C, 4D, 5A, 6B, 7C), (1A, 2C, 3C, 4D, 5A, 6C, 7A), (1A, 2C, 3C, 4D, 5A, 6C, 7B), (1A, 2C, 3C, 4D, 5A, 6C, 7C), (1A, 2C, 3C, 4D, 5A, 6D, 7A), (1A, 2C, 3C, 4D, 5A, 6D, 7B), (1A, 2C, 3C, 4D, 5A, 6D, 7C), (1A, 2C, 3C, 4D, 5B, 6A, 7A), (1A, 2C, 3C, 4D, 5B, 6A, 7B), (1A, 2C, 3C, 4D, 5B, 6A, 7C), (1A, 2C, 3C, 4D, 5B, 6B, 7A), (1A, 2C, 3C, 4D, 5B, 6B, 7B), (1A, 2C, 3C, 4D, 5B, 6B, 7C), (1A, 2C, 3C, 4D, 5B, 6C, 7A), (1A, 2C, 3C, 4D, 5B, 6C, 7B), (1A, 2C, 3C, 4D, 5B, 6C, 7C), (1A, 2C, 3C, 4D, 5B, 6D, 7A), (1A, 2C, 3C, 4D, 5B, 6D, 7B), (1A, 2C, 3C, 4D, 5B, 6D, 7C), (1A, 2C, 3C, 4E, 5A, 6A, 7A), (1A, 2C, 3C, 4E, 5A, 6A, 7B), (1A, 2C, 3C, 4E, 5A, 6A, 7C), (1A, 2C, 3C, 4E, 5A, 6B, 7A), (1A, 2C, 3C, 4E, 5A, 6B, 7B), (1A, 2C, 3C, 4E, 5A, 6B, 7C), (1A, 2C, 3C, 4E, 5A, 6C, 7A), (1A, 2C, 3C, 4E, 5A, 6C, 7B), (1A, 2C, 3C, 4E, 5A, 6C, 7C), (1A, 2C, 3C, 4E, 5A, 6D, 7A), (1A, 2C, 3C, 4E, 5A, 6D, 7B), (1A, 2C, 3C, 4E, 5A, 6D, 7C), (1A, 2C, 3C, 4E, 5B, 6A, 7A), (1A, 2C, 3C, 4E, 5B, 6A, 7B), (1A, 2C, 3C, 4E, 5B, 6A, 7C), (1A, 2C, 3C, 4E, 5B, 6B, 7A), (1A, 2C, 3C, 4E, 5B, 6B, 7B), (1A, 2C, 3C, 4E, 5B, 6B, 7C), (1A, 2C, 3C, 4E, 5B, 6C, 7A), (1A, 2C, 3C, 4E, 5B, 6C, 7B), (1A, 2C, 3C, 4E, 5B, 6C, 7C), (1A, 2C, 3C, 4E, 5B, 6D, 7A), (1A, 2C, 3C, 4E, 5B, 6D, 7B), (1A, 2C, 3C, 4E, 5B, 6D, 7C), (1A, 2C, 3D, 4A, 5A, 6A, 7A), (1A, 2C, 3D, 4A, 5A, 6A, 7B), (1A, 2C, 3D, 4A, 5A, 6A, 7C), (1A, 2C, 3D, 4A, 5A, 6B, 7A), (1A, 2C, 3D, 4A, 5A, 6B, 7B), (1A, 2C, 3D, 4A, 5A, 6B, 7C), (1A, 2C, 3D, 4A, 5A, 6C, 7A), (1A, 2C, 3D, 4A, 5A, 6C, 7B), (1A, 2C, 3D, 4A, 5A, 6C, 7C), (1A, 2C, 3D, 4A, 5A, 6D, 7A), (1A, 2C, 3D, 4A, 5A, 6D, 7B), (1A, 2C, 3D, 4A, 5A, 6D, 7C), (1A, 2C, 3D, 4A, 5B, 6A, 7A), (1A, 2C, 3D, 4A, 5B, 6A, 7B), (1A, 2C, 3D, 4A, 5B, 6A, 7C), (1A, 2C, 3D, 4A, 5B, 6B, 7A), (1A, 2C, 3D, 4A, 5B, 6B, 7B), (1A, 2C, 3D, 4A, 5B, 6B, 7C), (1A, 2C, 3D, 4A, 5B, 6C, 7A), (1A, 2C, 3D, 4A, 5B, 6C, 7B), (1A, 2C, 3D, 4A, 5B, 6C, 7C), (1A, 2C, 3D, 4A, 5B, 6D, 7A), (1A, 2C, 3D, 4A, 5B, 6D, 7B), (1A, 2C, 3D, 4A, 5B, 6D, 7C), (1A, 2C, 3D, 4B, 5A, 6A, 7A), (1A, 2C, 3D, 4B, 5A, 6A, 7B), (1A, 2C, 3D, 4B, 5A, 6A, 7C), (1A, 2C, 3D, 4B, 5A, 6B, 7A), (1A, 2C, 3D, 4B, 5A, 6B, 7B), (1A, 2C, 3D, 4B, 5A, 6B, 7C), (1A, 2C, 3D, 4B, 5A, 6C, 7A), (1A, 2C, 3D, 4B, 5A, 6C, 7B), (1A, 2C, 3D, 4B, 5A, 6C, 7C), (1A, 2C, 3D, 4B, 5A, 6D, 7A), (1A, 2C, 3D, 4B, 5A, 6D, 7B), (1A, 2C, 3D, 4B, 5A, 6D, 7C), (1A, 2C, 3D, 4B, 5B, 6A, 7A), (1A, 2C, 3D, 4B, 5B, 6A, 7B), (1A, 2C, 3D, 4B, 5B, 6A, 7C), (1A, 2C, 3D, 4B, 5B, 6B, 7A), (1A, 2C, 3D, 4B, 5B, 6B, 7B), (1A, 2C, 3D, 4B, 5B, 6B, 7C), (1A, 2C, 3D, 4B, 5B, 6C, 7A), (1A, 2C, 3D, 4B, 5B, 6C, 7B), (1A, 2C, 3D, 4B, 5B, 6C, 7C), (1A, 2C, 3D, 4B, 5B, 6D, 7A), (1A, 2C, 3D, 4B, 5B, 6D, 7B), (1A, 2C, 3D, 4B, 5B, 6D, 7C), (1A, 2C, 3D, 4C, 5A, 6A, 7A), (1A, 2C, 3D, 4C, 5A, 6A, 7B), (1A, 2C, 3D, 4C, 5A, 6A, 7C), (1A, 2C, 3D, 4C, 5A, 6B, 7A), (1A, 2C, 3D, 4C, 5A, 6B, 7B), (1A, 2C, 3D, 4C, 5A, 6B, 7C), (1A, 2C, 3D, 4C, 5A, 6C, 7A), (1A, 2C, 3D, 4C, 5A, 6C, 7B), (1A, 2C, 3D, 4C, 5A, 6C, 7C), (1A, 2C, 3D, 4C, 5A, 6D, 7A), (1A, 2C, 3D, 4C, 5A, 6D, 7B), (1A, 2C, 3D, 4C, 5A, 6D, 7C), (1A, 2C, 3D, 4C, 5B, 6A, 7A), (1A, 2C, 3D, 4C, 5B, 6A, 7B), (1A, 2C, 3D, 4C, 5B, 6A, 7C), (1A, 2C, 3D, 4C, 5B, 6B, 7A), (1A, 2C, 3D, 4C, 5B, 6B, 7B), (1A, 2C, 3D, 4C, 5B, 6B, 7C), (1A, 2C, 3D, 4C, 5B, 6C, 7A), (1A, 2C, 3D, 4C, 5B, 6C, 7B), (1A, 2C, 3D, 4C, 5B, 6C, 7C), (1A, 2C, 3D, 4C, 5B, 6D, 7A), (1A, 2C, 3D, 4C, 5B, 6D, 7B), (1A, 2C, 3D, 4C, 5B, 6D, 7C), (1A, 2C, 3D, 4D, 5A, 6A, 7A), (1A, 2C, 3D, 4D, 5A, 6A, 7B), (1A, 2C, 3D, 4D, 5A, 6A, 7C), (1A, 2C, 3D, 4D, 5A, 6B, 7A), (1A, 2C, 3D, 4D, 5A, 6B, 7B), (1A, 2C, 3D, 4D, 5A, 6B, 7C), (1A, 2C, 3D, 4D, 5A, 6C, 7A), (1A, 2C, 3D, 4D, 5A, 6C, 7B), (1A, 2C, 3D, 4D, 5A, 6C, 7C), (1A, 2C, 3D, 4D, 5A, 6D, 7A), (1A, 2C, 3D, 4D, 5A, 6D, 7B), (1A, 2C, 3D, 4D, 5A, 6D, 7C), (1A, 2C, 3D, 4D, 5B, 6A, 7A), (1A, 2C, 3D, 4D, 5B, 6A, 7B), (1A, 2C, 3D, 4D, 5B, 6A, 7C), (1A, 2C, 3D, 4D, 5B, 6B, 7A), (1A, 2C, 3D, 4D, 5B, 6B, 7B), (1A, 2C, 3D, 4D, 5B, 6B, 7C), (1A, 2C, 3D, 4D, 5B, 6C, 7A), (1A, 2C, 3D, 4D, 5B, 6C, 7B), (1A, 2C, 3D, 4D, 5B, 6C, 7C), (1A, 2C, 3D, 4D, 5B, 6D, 7A), (1A, 2C, 3D, 4D, 5B, 6D, 7B), (1A, 2C, 3D, 4D, 5B, 6D, 7C), (1A, 2C, 3D, 4E, 5A, 6A, 7A), (1A, 2C, 3D, 4E, 5A, 6A, 7B), (1A, 2C, 3D, 4E, 5A, 6A, 7C), (1A, 2C, 3D, 4E, 5A, 6B, 7A), (1A, 2C, 3D, 4E, 5A, 6B, 7B), (1A, 2C, 3D, 4E, 5A, 6B, 7C), (1A, 2C, 3D, 4E, 5A, 6C, 7A), (1A, 2C, 3D, 4E, 5A, 6C, 7B), (1A, 2C, 3D, 4E, 5A, 6C, 7C), (1A, 2C, 3D, 4E, 5A, 6D, 7A), (1A, 2C, 3D, 4E, 5A, 6D, 7B), (1A, 2C, 3D, 4E, 5A, 6D, 7C), (1A, 2C, 3D, 4E, 5B, 6A, 7A), (1A, 2C, 3D, 4E, 5B, 6A, 7B), (1A, 2C, 3D, 4E, 5B, 6A, 7C), (1A, 2C, 3D, 4E, 5B, 6B, 7A), (1A, 2C, 3D, 4E, 5B, 6B, 7B), (1A, 2C, 3D, 4E, 5B, 6B, 7C), (1A, 2C, 3D, 4E, 5B, 6C, 7A), (1A, 2C, 3D, 4E, 5B, 6C, 7B), (1A, 2C, 3D, 4E, 5B, 6C, 7C), (1A, 2C, 3D, 4E, 5B, 6D, 7A), (1A, 2C, 3D, 4E, 5B, 6D, 7B), (1A, 2C, 3D, 4E, 5B, 6D, 7C), (1A, 2C, 3E, 4A, 5A, 6A, 7A), (1A, 2C, 3E, 4A, 5A, 6A, 7B), (1A, 2C, 3E, 4A, 5A, 6A, 7C), (1A, 2C, 3E, 4A, 5A, 6B, 7A), (1A, 2C, 3E, 4A, 5A, 6B, 7B), (1A, 2C, 3E, 4A, 5A, 6B, 7C), (1A, 2C, 3E, 4A, 5A, 6C, 7A), (1A, 2C, 3E, 4A, 5A, 6C, 7B), (1A, 2C, 3E, 4A, 5A, 6C, 7C), (1A, 2C, 3E, 4A, 5A, 6D, 7A), (1A, 2C, 3E, 4A, 5A, 6D, 7B), (1A, 2C, 3E, 4A, 5A, 6D, 7C), (1A, 2C, 3E, 4A, 5B, 6A, 7A), (1A, 2C, 3E, 4A, 5B, 6A, 7B), (1A, 2C, 3E, 4A, 5B, 6A, 7C), (1A, 2C, 3E, 4A, 5B, 6B, 7A), (1A, 2C, 3E, 4A, 5B, 6B, 7B), (1A, 2C, 3E, 4A, 5B, 6B, 7C), (1A, 2C, 3E, 4A, 5B, 6C, 7A), (1A, 2C, 3E, 4A, 5B, 6C, 7B), (1A, 2C, 3E, 4A, 5B, 6C, 7C), (1A, 2C, 3E, 4A, 5B, 6D, 7A), (1A, 2C, 3E, 4A, 5B, 6D, 7B), (1A, 2C, 3E, 4A, 5B, 6D, 7C), (1A, 2C, 3E, 4B, 5A, 6A, 7A), (1A, 2C, 3E, 4B, 5A, 6A, 7B), (1A, 2C, 3E, 4B, 5A, 6A, 7C), (1A, 2C, 3E, 4B, 5A, 6B, 7A), (1A, 2C, 3E, 4B, 5A, 6B, 7B), (1A, 2C, 3E, 4B, 5A, 6B, 7C), (1A, 2C, 3E, 4B, 5A, 6C, 7A), (1A, 2C, 3E, 4B, 5A, 6C, 7B), (1A, 2C, 3E, 4B, 5A, 6C, 7C), (1A, 2C, 3E, 4B, 5A, 6D, 7A), (1A, 2C, 3E, 4B, 5A, 6D, 7B), (1A, 2C, 3E, 4B, 5A, 6D, 7C), (1A, 2C, 3E, 4B, 5B, 6A, 7A), (1A, 2C, 3E, 4B, 5B, 6A, 7B), (1A, 2C, 3E, 4B, 5B, 6A, 7C), (1A, 2C, 3E, 4B, 5B, 6B, 7A), (1A, 2C, 3E, 4B, 5B, 6B, 7B), (1A, 2C, 3E, 4B, 5B, 6B, 7C), (1A, 2C, 3E, 4B, 5B, 6C, 7A), (1A, 2C, 3E, 4B, 5B, 6C, 7B), (1A, 2C, 3E, 4B, 5B, 6C, 7C), (1A, 2C, 3E, 4B, 5B, 6D, 7A), (1A, 2C, 3E, 4B, 5B, 6D, 7B), (1A, 2C, 3E, 4B, 5B, 6D, 7C), (1A, 2C, 3E, 4C, 5A, 6A, 7A), (1A, 2C, 3E, 4C, 5A, 6A, 7B), (1A, 2C, 3E, 4C, 5A, 6A, 7C), (1A, 2C, 3E, 4C, 5A, 6B, 7A), (1A, 2C, 3E, 4C, 5A, 6B, 7B), (1A, 2C, 3E, 4C, 5A, 6B, 7C), (1A, 2C, 3E, 4C, 5A, 6C, 7A), (1A, 2C, 3E, 4C, 5A, 6C, 7B), (1A, 2C, 3E, 4C, 5A, 6C, 7C), (1A, 2C, 3E, 4C, 5A, 6D, 7A), (1A, 2C, 3E, 4C, 5A, 6D, 7B), (1A, 2C, 3E, 4C, 5A, 6D, 7C), (1A, 2C, 3E, 4C, 5B, 6A, 7A), (1A, 2C, 3E, 4C, 5B, 6A, 7B), (1A, 2C, 3E, 4C, 5B, 6A, 7C), (1A, 2C, 3E, 4C, 5B, 6B, 7A), (1A, 2C, 3E, 4C, 5B, 6B, 7B), (1A, 2C, 3E, 4C, 5B, 6B, 7C), (1A, 2C, 3E, 4C, 5B, 6C, 7A), (1A, 2C, 3E, 4C, 5B, 6C, 7B), (1A, 2C, 3E, 4C, 5B, 6C, 7C), (1A, 2C, 3E, 4C, 5B, 6D, 7A), (1A, 2C, 3E, 4C, 5B, 6D, 7B), (1A, 2C, 3E, 4C, 5B, 6D, 7C), (1A, 2C, 3E, 4D, 5A, 6A, 7A), (1A, 2C, 3E, 4D, 5A, 6A, 7B), (1A, 2C, 3E, 4D, 5A, 6A, 7C), (1A, 2C, 3E, 4D, 5A, 6B, 7A), (1A, 2C, 3E, 4D, 5A, 6B, 7B), (1A, 2C, 3E, 4D, 5A, 6B, 7C), (1A, 2C, 3E, 4D, 5A, 6C, 7A), (1A, 2C, 3E, 4D, 5A, 6C, 7B), (1A, 2C, 3E, 4D, 5A, 6C, 7C), (1A, 2C, 3E, 4D, 5A, 6D, 7A), (1A, 2C, 3E, 4D, 5A, 6D, 7B), (1A, 2C, 3E, 4D, 5A, 6D, 7C), (1A, 2C, 3E, 4D, 5B, 6A, 7A), (1A, 2C, 3E, 4D, 5B, 6A, 7B), (1A, 2C, 3E, 4D, 5B, 6A, 7C), (1A, 2C, 3E, 4D, 5B, 6B, 7A), (1A, 2C, 3E, 4D, 5B, 6B, 7B), (1A, 2C, 3E, 4D, 5B, 6B, 7C), (1A, 2C, 3E, 4D, 5B, 6C, 7A), (1A, 2C, 3E, 4D, 5B, 6C, 7B), (1A, 2C, 3E, 4D, 5B, 6C, 7C), (1A, 2C, 3E, 4D, 5B, 6D, 7A), (1A, 2C, 3E, 4D, 5B, 6D, 7B), (1A, 2C, 3E, 4D, 5B, 6D, 7C), (1A, 2C, 3E, 4E, 5A, 6A, 7A), (1A, 2C, 3E, 4E, 5A, 6A, 7B), (1A, 2C, 3E, 4E, 5A, 6A, 7C), (1A, 2C, 3E, 4E, 5A, 6B, 7A), (1A, 2C, 3E, 4E, 5A, 6B, 7B), (1A, 2C, 3E, 4E, 5A, 6B, 7C), (1A, 2C, 3E, 4E, 5A, 6C, 7A), (1A, 2C, 3E, 4E, 5A, 6C, 7B), (1A, 2C, 3E, 4E, 5A, 6C, 7C), (1A, 2C, 3E, 4E, 5A, 6D, 7A), (1A, 2C, 3E, 4E, 5A, 6D, 7B), (1A, 2C, 3E, 4E, 5A, 6D, 7C), (1A, 2C, 3E, 4E, 5B, 6A, 7A), (1A, 2C, 3E, 4E, 5B, 6A, 7B), (1A, 2C, 3E, 4E, 5B, 6A, 7C), (1A, 2C, 3E, 4E, 5B, 6B, 7A), (1A, 2C, 3E, 4E, 5B, 6B, 7B), (1A, 2C, 3E, 4E, 5B, 6B, 7C), (1A, 2C, 3E, 4E, 5B, 6C, 7A), (1A, 2C, 3E, 4E, 5B, 6C, 7B), (1A, 2C, 3E, 4E, 5B, 6C, 7C), (1A, 2C, 3E, 4E, 5B, 6D, 7A), (1A, 2C, 3E, 4E, 5B, 6D, 7B), (1A, 2C, 3E, 4E, 5B, 6D, 7C), (1A, 2D, 3A, 4A, 5A, 6A, 7A), (1A, 2D, 3A, 4A, 5A, 6A, 7B), (1A, 2D, 3A, 4A, 5A, 6A, 7C), (1A, 2D, 3A, 4A, 5A, 6B, 7A), (1A, 2D, 3A, 4A, 5A, 6B, 7B), (1A, 2D, 3A, 4A, 5A, 6B, 7C), (1A, 2D, 3A, 4A, 5A, 6C, 7A), (1A, 2D, 3A, 4A, 5A, 6C, 7B), (1A, 2D, 3A, 4A, 5A, 6C, 7C), (1A, 2D, 3A, 4A, 5A, 6D, 7A), (1A, 2D, 3A, 4A, 5A, 6D, 7B), (1A, 2D, 3A, 4A, 5A, 6D, 7C), (1A, 2D, 3A, 4A, 5B, 6A, 7A), (1A, 2D, 3A, 4A, 5B, 6A, 7B), (1A, 2D, 3A, 4A, 5B, 6A, 7C), (1A, 2D, 3A, 4A, 5B, 6B, 7A), (1A, 2D, 3A, 4A, 5B, 6B, 7B), (1A, 2D, 3A, 4A, 5B, 6B, 7C), (1A, 2D, 3A, 4A, 5B, 6C, 7A), (1A, 2D, 3A, 4A, 5B, 6C, 7B), (1A, 2D, 3A, 4A, 5B, 6C, 7C), (1A, 2D, 3A, 4A, 5B, 6D, 7A), (1A, 2D, 3A, 4A, 5B, 6D, 7B), (1A, 2D, 3A, 4A, 5B, 6D, 7C), (1A, 2D, 3A, 4B, 5A, 6A, 7A), (1A, 2D, 3A, 4B, 5A, 6A, 7B), (1A, 2D, 3A, 4B, 5A, 6A, 7C), (1A, 2D, 3A, 4B, 5A, 6B, 7A), (1A, 2D, 3A, 4B, 5A, 6B, 7B), (1A, 2D, 3A, 4B, 5A, 6B, 7C), (1A, 2D, 3A, 4B, 5A, 6C, 7A), (1A, 2D, 3A, 4B, 5A, 6C, 7B), (1A, 2D, 3A, 4B, 5A, 6C, 7C), (1A, 2D, 3A, 4B, 5A, 6D, 7A), (1A, 2D, 3A, 4B, 5A, 6D, 7B), (1A, 2D, 3A, 4B, 5A, 6D, 7C), (1A, 2D, 3A, 4B, 5B, 6A, 7A), (1A, 2D, 3A, 4B, 5B, 6A, 7B), (1A, 2D, 3A, 4B, 5B, 6A, 7C), (1A, 2D, 3A, 4B, 5B, 6B, 7A), (1A, 2D, 3A, 4B, 5B, 6B, 7B), (1A, 2D, 3A, 4B, 5B, 6B, 7C), (1A, 2D, 3A, 4B, 5B, 6C, 7A), (1A, 2D, 3A, 4B, 5B, 6C, 7B), (1A, 2D, 3A, 4B, 5B, 6C, 7C), (1A, 2D, 3A, 4B, 5B, 6D, 7A), (1A, 2D, 3A, 4B, 5B, 6D, 7B), (1A, 2D, 3A, 4B, 5B, 6D, 7C), (1A, 2D, 3A, 4C, 5A, 6A, 7A), (1A, 2D, 3A, 4C, 5A, 6A, 7B), (1A, 2D, 3A, 4C, 5A, 6A, 7C), (1A, 2D, 3A, 4C, 5A, 6B, 7A), (1A, 2D, 3A, 4C, 5A, 6B, 7B), (1A, 2D, 3A, 4C, 5A, 6B, 7C), (1A, 2D, 3A, 4C, 5A, 6C, 7A), (1A, 2D, 3A, 4C, 5A, 6C, 7B), (1A, 2D, 3A, 4C, 5A, 6C, 7C), (1A, 2D, 3A, 4C, 5A, 6D, 7A), (1A, 2D, 3A, 4C, 5A, 6D, 7B), (1A, 2D, 3A, 4C, 5A, 6D, 7C), (1A, 2D, 3A, 4C, 5B, 6A,

7A), (1A, 2D, 3A, 4C, 5B, 6A, 7B), (1A, 2D, 3A, 4C, 5B, 6A, 7C), (1A, 2D, 3A, 4C, 5B, 6B, 7A), (1A, 2D, 3A, 4C, 5B, 6B, 7B), (1A, 2D, 3A, 4C, 5B, 6B, 7C), (1A, 2D, 3A, 4C, 5B, 6C, 7A), (1A, 2D, 3A, 4C, 5B, 6C, 7B), (1A, 2D, 3A, 4C, 5B, 6C, 7C), (1A, 2D, 3A, 4C, 5B, 6D, 7A), (1A, 2D, 3A, 4C, 5B, 6D, 7B), (1A, 2D, 3A, 4C, 5B, 6D, 7C), (1A, 2D, 3A, 4D, 5A, 6A, 7A), (1A, 2D, 3A, 4D, 5A, 6A, 7B), (1A, 2D, 3A, 4D, 5A, 6A, 7C), (1A, 2D, 3A, 4D, 5A, 6B, 7A), (1A, 2D, 3A, 4D, 5A, 6B, 7B), (1A, 2D, 3A, 4D, 5A, 6B, 7C), (1A, 2D, 3A, 4D, 5A, 6C, 7A), (1A, 2D, 3A, 4D, 5A, 6C, 7B), (1A, 2D, 3A, 4D, 5A, 6C, 7C), (1A, 2D, 3A, 4D, 5A, 6D, 7A), (1A, 2D, 3A, 4D, 5A, 6D, 7B), (1A, 2D, 3A, 4D, 5A, 6D, 7C), (1A, 2D, 3A, 4D, 5B, 6A, 7A), (1A, 2D, 3A, 4D, 5B, 6A, 7B), (1A, 2D, 3A, 4D, 5B, 6A, 7C), (1A, 2D, 3A, 4D, 5B, 6B, 7A), (1A, 2D, 3A, 4D, 5B, 6B, 7B), (1A, 2D, 3A, 4D, 5B, 6B, 7C), (1A, 2D, 3A, 4D, 5B, 6C, 7A), (1A, 2D, 3A, 4D, 5B, 6C, 7B), (1A, 2D, 3A, 4D, 5B, 6C, 7C), (1A, 2D, 3A, 4D, 5B, 6D, 7A), (1A, 2D, 3A, 4D, 5B, 6D, 7B), (1A, 2D, 3A, 4D, 5B, 6D, 7C), (1A, 2D, 3A, 4E, 5A, 6A, 7A), (1A, 2D, 3A, 4E, 5A, 6A, 7B), (1A, 2D, 3A, 4E, 5A, 6A, 7C), (1A, 2D, 3A, 4E, 5A, 6B, 7A), (1A, 2D, 3A, 4E, 5A, 6B, 7B), (1A, 2D, 3A, 4E, 5A, 6B, 7C), (1A, 2D, 3A, 4E, 5A, 6C, 7A), (1A, 2D, 3A, 4E, 5A, 6C, 7B), (1A, 2D, 3A, 4E, 5A, 6C, 7C), (1A, 2D, 3A, 4E, 5A, 6D, 7A), (1A, 2D, 3A, 4E, 5A, 6D, 7B), (1A, 2D, 3A, 4E, 5A, 6D, 7C), (1A, 2D, 3A, 4E, 5B, 6A, 7A), (1A, 2D, 3A, 4E, 5B, 6A, 7B), (1A, 2D, 3A, 4E, 5B, 6A, 7C), (1A, 2D, 3A, 4E, 5B, 6B, 7A), (1A, 2D, 3A, 4E, 5B, 6B, 7B), (1A, 2D, 3A, 4E, 5B, 6B, 7C), (1A, 2D, 3A, 4E, 5B, 6C, 7A), (1A, 2D, 3A, 4E, 5B, 6C, 7B), (1A, 2D, 3A, 4E, 5B, 6C, 7C), (1A, 2D, 3A, 4E, 5B, 6D, 7A), (1A, 2D, 3A, 4E, 5B, 6D, 7B), (1A, 2D, 3A, 4E, 5B, 6D, 7C), (1A, 2D, 3B, 4A, 5A, 6A, 7A), (1A, 2D, 3B, 4A, 5A, 6A, 7B), (1A, 2D, 3B, 4A, 5A, 6A, 7C), (1A, 2D, 3B, 4A, 5A, 6B, 7A), (1A, 2D, 3B, 4A, 5A, 6B, 7B), (1A, 2D, 3B, 4A, 5A, 6B, 7C), (1A, 2D, 3B, 4A, 5A, 6C, 7A), (1A, 2D, 3B, 4A, 5A, 6C, 7B), (1A, 2D, 3B, 4A, 5A, 6C, 7C), (1A, 2D, 3B, 4A, 5A, 6D, 7A), (1A, 2D, 3B, 4A, 5A, 6D, 7B), (1A, 2D, 3B, 4A, 5A, 6D, 7C), (1A, 2D, 3B, 4A, 5B, 6A, 7A), (1A, 2D, 3B, 4A, 5B, 6A, 7B), (1A, 2D, 3B, 4A, 5B, 6A, 7C), (1A, 2D, 3B, 4A, 5B, 6B, 7A), (1A, 2D, 3B, 4A, 5B, 6B, 7B), (1A, 2D, 3B, 4A, 5B, 6B, 7C), (1A, 2D, 3B, 4A, 5B, 6C, 7A), (1A, 2D, 3B, 4A, 5B, 6C, 7B), (1A, 2D, 3B, 4A, 5B, 6C, 7C), (1A, 2D, 3B, 4A, 5B, 6D, 7A), (1A, 2D, 3B, 4A, 5B, 6D, 7B), (1A, 2D, 3B, 4A, 5B, 6D, 7C), (1A, 2D, 3B, 4B, 5A, 6A, 7A), (1A, 2D, 3B, 4B, 5A, 6A, 7B), (1A, 2D, 3B, 4B, 5A, 6A, 7C), (1A, 2D, 3B, 4B, 5A, 6B, 7A), (1A, 2D, 3B, 4B, 5A, 6B, 7B), (1A, 2D, 3B, 4B, 5A, 6B, 7C), (1A, 2D, 3B, 4B, 5A, 6C, 7A), (1A, 2D, 3B, 4B, 5A, 6C, 7B), (1A, 2D, 3B, 4B, 5A, 6C, 7C), (1A, 2D, 3B, 4B, 5A, 6D, 7A), (1A, 2D, 3B, 4B, 5A, 6D, 7B), (1A, 2D, 3B, 4B, 5A, 6D, 7C), (1A, 2D, 3B, 4B, 5B, 6A, 7A), (1A, 2D, 3B, 4B, 5B, 6A, 7B), (1A, 2D, 3B, 4B, 5B, 6A, 7C), (1A, 2D, 3B, 4B, 5B, 6B, 7A), (1A, 2D, 3B, 4B, 5B, 6B, 7B), (1A, 2D, 3B, 4B, 5B, 6B, 7C), (1A, 2D, 3B, 4B, 5B, 6C, 7A), (1A, 2D, 3B, 4B, 5B, 6C, 7B), (1A, 2D, 3B, 4B, 5B, 6C, 7C), (1A, 2D, 3B, 4B, 5B, 6D, 7A), (1A, 2D, 3B, 4B, 5B, 6D, 7B), (1A, 2D, 3B, 4B, 5B, 6D, 7C), (1A, 2D, 3B, 4C, 5A, 6A, 7A), (1A, 2D, 3B, 4C, 5A, 6A, 7B), (1A, 2D, 3B, 4C, 5A, 6A, 7C), (1A, 2D, 3B, 4C, 5A, 6B, 7A), (1A, 2D, 3B, 4C, 5A, 6B, 7B), (1A, 2D, 3B, 4C, 5A, 6B, 7C), (1A, 2D, 3B, 4C, 5A, 6C, 7A), (1A, 2D, 3B, 4C, 5A, 6C, 7B), (1A, 2D, 3B, 4C, 5A, 6C, 7C), (1A, 2D, 3B, 4C, 5A, 6D, 7A), (1A, 2D, 3B, 4C, 5A, 6D, 7B), (1A, 2D, 3B, 4C, 5A, 6D, 7C), (1A, 2D, 3B, 4C, 5B, 6A, 7A), (1A, 2D, 3B, 4C, 5B, 6A, 7B), (1A, 2D, 3B, 4C, 5B, 6A, 7C), (1A, 2D, 3B, 4C, 5B, 6B, 7A), (1A, 2D, 3B, 4C, 5B, 6B, 7B), (1A, 2D, 3B, 4C, 5B, 6B, 7C), (1A, 2D, 3B, 4C, 5B, 6C, 7A), (1A, 2D, 3B, 4C, 5B, 6C, 7B), (1A, 2D, 3B, 4C, 5B, 6C, 7C), (1A, 2D, 3B, 4C, 5B, 6D, 7A), (1A, 2D, 3B, 4C, 5B, 6D, 7B), (1A, 2D, 3B, 4C, 5B, 6D, 7C), (1A, 2D, 3B, 4D, 5A, 6A, 7A), (1A, 2D, 3B, 4D, 5A, 6A, 7B), (1A, 2D, 3B, 4D, 5A, 6A, 7C), (1A, 2D, 3B, 4D, 5A, 6B, 7A), (1A, 2D, 3B, 4D, 5A, 6B, 7B), (1A, 2D, 3B, 4D, 5A, 6B, 7C), (1A, 2D, 3B, 4D, 5A, 6C, 7A), (1A, 2D, 3B, 4D, 5A, 6C, 7B), (1A, 2D, 3B, 4D, 5A, 6C, 7C), (1A, 2D, 3B, 4D, 5A, 6D, 7A), (1A, 2D, 3B, 4D, 5A, 6D, 7B), (1A, 2D, 3B, 4D, 5A, 6D, 7C), (1A, 2D, 3B, 4D, 5B, 6A, 7A), (1A, 2D, 3B, 4D, 5B, 6A, 7B), (1A, 2D, 3B, 4D, 5B, 6A, 7C), (1A, 2D, 3B, 4D, 5B, 6B, 7A), (1A, 2D, 3B, 4D, 5B, 6B, 7B), (1A, 2D, 3B, 4D, 5B, 6B, 7C), (1A, 2D, 3B, 4D, 5B, 6C, 7A), (1A, 2D, 3B, 4D, 5B, 6C, 7B), (1A, 2D, 3B, 4D, 5B, 6C, 7C), (1A, 2D, 3B, 4D, 5B, 6D, 7A), (1A, 2D, 3B, 4D, 5B, 6D, 7B), (1A, 2D, 3B, 4D, 5B, 6D, 7C), (1A, 2D, 3B, 4E, 5A, 6A, 7A), (1A, 2D, 3B, 4E, 5A, 6A, 7B), (1A, 2D, 3B, 4E, 5A, 6A, 7C), (1A, 2D, 3B, 4E, 5A, 6B, 7A), (1A, 2D, 3B, 4E, 5A, 6B, 7B), (1A, 2D, 3B, 4E, 5A, 6B, 7C), (1A, 2D, 3B, 4E, 5A, 6C, 7A), (1A, 2D, 3B, 4E, 5A, 6C, 7B), (1A, 2D, 3B, 4E, 5A, 6C, 7C), (1A, 2D, 3B, 4E, 5A, 6D, 7A), (1A, 2D, 3B, 4E, 5A, 6D, 7B), (1A, 2D, 3B, 4E, 5A, 6D, 7C), (1A, 2D, 3B, 4E, 5B, 6A, 7A), (1A, 2D, 3B, 4E, 5B, 6A, 7B), (1A, 2D, 3B, 4E, 5B, 6A, 7C), (1A, 2D, 3B, 4E, 5B, 6B, 7A), (1A, 2D, 3B, 4E, 5B, 6B, 7B), (1A, 2D, 3B, 4E, 5B, 6B, 7C), (1A, 2D, 3B, 4E, 5B, 6C, 7A), (1A, 2D, 3B, 4E, 5B, 6C, 7B), (1A, 2D, 3B, 4E, 5B, 6C, 7C), (1A, 2D, 3B, 4E, 5B, 6D, 7A), (1A, 2D, 3B, 4E, 5B, 6D, 7B), (1A, 2D, 3B, 4E, 5B, 6D, 7C), (1A, 2D, 3C, 4A, 5A, 6A, 7A), (1A, 2D, 3C, 4A, 5A, 6A, 7B), (1A, 2D, 3C, 4A, 5A, 6A, 7C), (1A, 2D, 3C, 4A, 5A, 6B, 7A), (1A, 2D, 3C, 4A, 5A, 6B, 7B), (1A, 2D, 3C, 4A, 5A, 6B, 7C), (1A, 2D, 3C, 4A, 5A, 6C, 7A), (1A, 2D, 3C, 4A, 5A, 6C, 7B), (1A, 2D, 3C, 4A, 5A, 6C, 7C), (1A, 2D, 3C, 4A, 5A, 6D, 7A), (1A, 2D, 3C, 4A, 5A, 6D, 7B), (1A, 2D, 3C, 4A, 5A, 6D, 7C), (1A, 2D, 3C, 4A, 5B, 6A, 7A), (1A, 2D, 3C, 4A, 5B, 6A, 7B), (1A, 2D, 3C, 4A, 5B, 6A, 7C), (1A, 2D, 3C, 4A, 5B, 6B, 7A), (1A, 2D, 3C, 4A, 5B, 6B, 7B), (1A, 2D, 3C, 4A, 5B, 6B, 7C), (1A, 2D, 3C, 4A, 5B, 6C, 7A), (1A, 2D, 3C, 4A, 5B, 6C, 7B), (1A, 2D, 3C, 4A, 5B, 6C, 7C), (1A, 2D, 3C, 4A, 5B, 6D, 7A), (1A, 2D, 3C, 4A, 5B, 6D, 7B), (1A, 2D, 3C, 4A, 5B, 6D, 7C), (1A, 2D, 3C, 4B, 5A, 6A, 7A), (1A, 2D, 3C, 4B, 5A, 6A, 7B), (1A, 2D, 3C, 4B, 5A, 6A, 7C), (1A, 2D, 3C, 4B, 5A, 6B, 7A), (1A, 2D, 3C, 4B, 5A, 6B, 7B), (1A, 2D, 3C, 4B, 5A, 6B, 7C), (1A, 2D, 3C, 4B, 5A, 6C, 7A), (1A, 2D, 3C, 4B, 5A, 6C, 7B), (1A, 2D, 3C, 4B, 5A, 6C, 7C), (1A, 2D, 3C, 4B, 5A, 6D, 7A), (1A, 2D, 3C, 4B, 5A, 6D, 7B), (1A, 2D, 3C, 4B, 5A, 6D, 7C), (1A, 2D, 3C, 4B, 5B, 6A, 7A), (1A, 2D, 3C, 4B, 5B, 6A, 7B), (1A, 2D, 3C, 4B, 5B, 6A, 7C), (1A, 2D, 3C, 4B, 5B, 6B, 7A), (1A, 2D, 3C, 4B, 5B, 6B, 7B), (1A, 2D, 3C, 4B, 5B, 6B, 7C), (1A, 2D, 3C, 4B, 5B, 6C, 7A), (1A, 2D, 3C, 4B, 5B, 6C, 7B), (1A, 2D, 3C, 4B, 5B, 6C, 7C), (1A, 2D, 3C, 4B, 5B, 6D, 7A), (1A, 2D, 3C, 4B, 5B, 6D, 7B), (1A, 2D, 3C, 4B, 5B, 6D, 7C), (1A, 2D, 3C, 4C, 5A, 6A, 7A), (1A, 2D, 3C, 4C, 5A, 6A, 7B), (1A, 2D, 3C, 4C, 5A, 6A, 7C), (1A, 2D, 3C, 4C, 5A, 6B, 7A), (1A, 2D, 3C, 4C, 5A, 6B, 7B), (1A, 2D, 3C, 4C, 5A, 6B, 7C), (1A, 2D, 3C, 4C, 5A, 6C, 7A), (1A, 2D, 3C, 4C, 5A, 6C, 7B), (1A, 2D, 3C, 4C, 5A, 6C, 7C), (1A, 2D, 3C, 4C, 5A, 6D, 7A), (1A, 2D, 3C, 4C, 5A, 6D, 7B), (1A, 2D, 3C, 4C, 5A, 6D, 7C), (1A, 2D, 3C, 4C, 5B, 6A, 7A), (1A, 2D, 3C, 4C, 5B, 6A, 7B), (1A, 2D, 3C, 4C, 5B, 6A, 7C), (1A, 2D, 3C, 4C, 5B, 6B, 7A), (1A, 2D, 3C, 4C, 5B, 6B, 7B), (1A, 2D, 3C, 4C, 5B, 6B, 7C), (1A, 2D, 3C, 4C, 5B, 6C, 7A), (1A, 2D, 3C, 4C, 5B, 6C, 7B), (1A, 2D, 3C, 4C, 5B, 6C, 7C), (1A, 2D, 3C, 4C, 5B, 6D, 7A), (1A, 2D, 3C, 4C, 5B, 6D, 7B), (1A, 2D, 3C, 4C, 5B, 6D, 7C), (1A, 2D, 3C, 4D, 5A, 6A, 7A), (1A, 2D, 3C, 4D, 5A, 6A, 7B), (1A, 2D, 3C, 4D, 5A, 6A, 7C), (1A, 2D, 3C, 4D, 5A, 6B, 7A), (1A, 2D, 3C, 4D, 5A, 6B, 7B), (1A, 2D, 3C, 4D, 5A, 6B, 7C), (1A, 2D, 3C, 4D, 5A, 6C, 7A), (1A, 2D, 3C, 4D, 5A, 6C, 7B), (1A, 2D, 3C, 4D, 5A, 6C, 7C), (1A, 2D, 3C, 4D, 5A, 6D, 7A), (1A, 2D, 3C, 4D, 5A, 6D, 7B), (1A, 2D, 3C, 4D, 5A, 6D, 7C), (1A, 2D, 3C, 4D, 5B, 6A, 7A), (1A, 2D, 3C, 4D, 5B, 6A, 7B), (1A, 2D, 3C, 4D, 5B, 6A, 7C), (1A, 2D, 3C, 4D, 5B, 6B, 7A), (1A, 2D, 3C, 4D, 5B, 6B, 7B), (1A, 2D, 3C, 4D, 5B, 6B, 7C), (1A, 2D, 3C, 4D, 5B, 6C, 7A), (1A, 2D, 3C, 4D, 5B, 6C, 7B), (1A, 2D, 3C, 4D, 5B, 6C, 7C), (1A, 2D, 3C, 4D, 5B, 6D, 7A), (1A, 2D, 3C, 4D, 5B, 6D, 7B), (1A, 2D, 3C, 4D, 5B, 6D, 7C), (1A, 2D, 3C, 4E, 5A, 6A, 7A), (1A, 2D, 3C, 4E, 5A, 6A, 7B), (1A, 2D, 3C, 4E, 5A, 6A, 7C), (1A, 2D, 3C, 4E, 5A, 6B, 7A), (1A, 2D, 3C, 4E, 5A, 6B, 7B), (1A, 2D, 3C, 4E, 5A, 6B, 7C), (1A, 2D, 3C, 4E, 5A, 6C, 7A), (1A, 2D, 3C, 4E, 5A, 6C, 7B), (1A, 2D, 3C, 4E, 5A, 6C, 7C), (1A, 2D, 3C, 4E, 5A, 6D, 7A), (1A, 2D, 3C, 4E, 5A, 6D, 7B), (1A, 2D, 3C, 4E, 5A, 6D, 7C), (1A, 2D, 3C, 4E, 5B, 6A, 7A), (1A, 2D, 3C, 4E, 5B, 6A, 7B), (1A, 2D, 3C, 4E, 5B, 6A, 7C), (1A, 2D, 3C, 4E, 5B, 6B, 7A), (1A, 2D, 3C, 4E, 5B, 6B, 7B), (1A, 2D, 3C, 4E, 5B, 6B, 7C), (1A, 2D, 3C, 4E, 5B, 6C, 7A), (1A, 2D, 3C, 4E, 5B, 6C, 7B), (1A, 2D, 3C, 4E, 5B, 6C, 7C), (1A, 2D, 3C, 4E, 5B, 6D, 7A), (1A, 2D, 3C, 4E, 5B, 6D, 7B), (1A, 2D, 3C, 4E, 5B, 6D, 7C), (1A, 2D, 3D, 4A, 5A, 6A, 7A), (1A, 2D, 3D, 4A, 5A, 6A, 7B), (1A, 2D, 3D, 4A, 5A, 6A, 7C), (1A, 2D, 3D, 4A, 5A, 6B, 7A), (1A, 2D, 3D, 4A, 5A, 6B, 7B), (1A, 2D, 3D, 4A, 5A, 6B, 7C), (1A, 2D, 3D, 4A, 5A, 6C, 7A), (1A, 2D, 3D, 4A, 5A, 6C, 7B), (1A, 2D, 3D, 4A, 5A, 6C, 7C), (1A, 2D, 3D, 4A, 5A, 6D, 7A), (1A, 2D, 3D, 4A, 5A, 6D, 7B), (1A, 2D, 3D, 4A, 5A, 6D, 7C), (1A, 2D, 3D, 4A, 5B, 6A, 7A), (1A, 2D, 3D, 4A, 5B, 6A, 7B), (1A, 2D, 3D, 4A, 5B, 6A, 7C), (1A, 2D, 3D, 4A, 5B, 6B, 7A), (1A, 2D, 3D, 4A, 5B, 6B, 7B), (1A, 2D, 3D, 4A, 5B, 6B, 7C), (1A, 2D, 3D, 4A, 5B, 6C, 7A), (1A, 2D, 3D, 4A, 5B, 6C, 7B), (1A, 2D, 3D, 4A, 5B, 6C, 7C), (1A, 2D, 3D, 4A, 5B, 6D, 7A), (1A, 2D, 3D, 4A, 5B, 6D, 7B), (1A, 2D, 3D, 4A, 5B, 6D, 7C), (1A, 2D, 3D, 4B, 5A, 6A, 7A), (1A, 2D, 3D, 4B, 5A, 6A, 7B), (1A, 2D, 3D, 4B, 5A, 6A, 7C), (1A, 2D, 3D, 4B, 5A, 6B, 7A), (1A, 2D, 3D, 4B, 5A, 6B, 7B), (1A, 2D, 3D, 4B, 5A, 6B, 7C), (1A, 2D, 3D, 4B, 5A, 6C, 7A), (1A, 2D, 3D, 4B, 5A, 6C, 7B), (1A, 2D, 3D, 4B, 5A, 6C, 7C), (1A, 2D, 3D, 4B, 5A, 6D, 7A), (1A, 2D, 3D, 4B, 5A, 6D, 7B), (1A, 2D, 3D, 4B, 5A, 6D, 7C), (1A, 2D, 3D, 4B, 5B, 6A, 7A), (1A, 2D, 3D, 4B, 5B, 6A, 7B), (1A, 2D, 3D, 4B, 5B, 6A, 7C), (1A, 2D, 3D, 4B, 5B, 6B, 7A), (1A, 2D, 3D, 4B, 5B, 6B, 7B), (1A, 2D, 3D, 4B, 5B, 6B, 7C), (1A, 2D, 3D, 4B, 5B, 6C, 7A), (1A, 2D, 3D, 4B, 5B, 6C, 7B), (1A, 2D, 3D, 4B, 5B, 6C, 7C), (1A, 2D, 3D, 4B, 5B, 6D, 7A), (1A, 2D, 3D, 4B, 5B, 6D, 7B), (1A, 2D, 3D, 4B, 5B, 6D, 7C), (1A, 2D, 3D, 4C, 5A, 6A, 7A), (1A, 2D, 3D, 4C, 5A, 6A, 7B), (1A, 2D, 3D, 4C, 5A, 6A, 7C), (1A, 2D, 3D, 4C, 5A, 6B, 7A), (1A, 2D, 3D, 4C, 5A, 6B, 7B), (1A, 2D, 3D, 4C, 5A, 6B, 7C), (1A, 2D, 3D, 4C, 5A, 6C, 7A), (1A, 2D, 3D, 4C, 5A, 6C, 7B), (1A, 2D, 3D, 4C, 5A, 6C, 7C), (1A, 2D, 3D, 4C, 5A, 6D, 7A), (1A, 2D, 3D, 4C, 5A, 6D, 7B), (1A, 2D, 3D, 4C, 5A, 6D, 7C), (1A, 2D, 3D, 4C, 5B, 6A, 7A), (1A, 2D, 3D, 4C, 5B, 6A, 7B), (1A, 2D, 3D, 4C, 5B, 6A, 7C), (1A, 2D, 3D, 4C, 5B, 6B, 7A), (1A, 2D, 3D, 4C, 5B, 6B, 7B), (1A, 2D, 3D, 4C, 5B, 6B, 7C), (1A, 2D, 3D, 4C, 5B, 6C, 7A), (1A, 2D, 3D, 4C, 5B, 6C, 7B), (1A, 2D, 3D, 4C, 5B, 6C, 7C), (1A, 2D, 3D, 4C, 5B, 6D, 7A), (1A, 2D, 3D, 4C, 5B, 6D, 7B), (1A, 2D, 3D, 4C, 5B, 6D, 7C), (1A, 2D, 3D, 4D, 5A, 6A, 7A), (1A, 2D, 3D, 4D, 5A, 6A, 7B), (1A, 2D, 3D, 4D, 5A, 6A, 7C), (1A, 2D, 3D, 4D, 5A, 6B, 7A), (1A, 2D, 3D, 4D, 5A, 6B, 7B), (1A, 2D, 3D, 4D, 5A, 6B, 7C), (1A, 2D, 3D, 4D, 5A, 6C, 7A), (1A, 2D, 3D, 4D, 5A, 6C, 7B), (1A, 2D, 3D, 4D, 5A, 6C, 7C), (1A, 2D, 3D, 4D, 5A, 6D, 7A), (1A, 2D, 3D, 4D, 5A, 6D, 7B), (1A, 2D, 3D, 4D, 5A, 6D, 7C), (1A, 2D, 3D, 4D, 5B, 6A, 7A), (1A, 2D, 3D, 4D, 5B, 6A, 7B), (1A, 2D, 3D, 4D, 5B, 6A, 7C), (1A, 2D, 3D, 4D, 5B, 6B, 7A), (1A, 2D, 3D, 4D, 5B, 6B, 7B), (1A, 2D, 3D, 4D, 5B, 6B, 7C), (1A, 2D, 3D, 4D, 5B, 6C, 7A), (1A, 2D, 3D, 4D, 5B, 6C, 7B), (1A, 2D, 3D, 4D, 5B, 6C, 7C), (1A, 2D, 3D, 4D, 5B, 6D, 7A), (1A, 2D, 3D, 4D, 5B, 6D, 7B), (1A, 2D, 3D, 4D, 5B, 6D, 7C), (1A, 2D, 3D, 4E, 5A, 6A, 7A), (1A, 2D, 3D, 4E, 5A, 6A, 7B), (1A, 2D, 3D, 4E, 5A, 6A, 7C), (1A, 2D, 3D, 4E, 5A, 6B, 7A), (1A, 2D, 3D, 4E, 5A, 6B, 7B), (1A, 2D, 3D, 4E, 5A, 6B, 7C), (1A, 2D, 3D, 4E, 5A, 6C, 7A), (1A, 2D, 3D, 4E, 5A, 6C, 7B), (1A, 2D, 3D, 4E, 5A, 6C, 7C), (1A, 2D, 3D, 4E, 5A, 6D, 7A), (1A, 2D, 3D, 4E, 5A, 6D, 7B), (1A, 2D, 3D, 4E, 5A, 6D, 7C), (1A, 2D, 3D, 4E, 5B, 6A, 7A), (1A, 2D, 3D, 4E, 5B, 6A, 7B), (1A, 2D, 3D, 4E, 5B, 6A, 7C), (1A, 2D, 3D, 4E, 5B, 6B, 7A), (1A, 2D, 3D, 4E, 5B, 6B, 7B), (1A, 2D, 3D, 4E, 5B, 6B, 7C), (1A, 2D, 3D, 4E, 5B, 6C, 7A), (1A, 2D, 3D, 4E, 5B, 6C, 7B), (1A, 2D, 3D, 4E, 5B, 6C, 7C), (1A, 2D, 3D, 4E, 5B, 6D, 7A), (1A, 2D, 3D, 4E, 5B, 6D, 7B), (1A, 2D, 3D, 4E, 5B, 6D, 7C), (1A, 2D, 3E, 4A, 5A, 6A, 7A), (1A, 2D, 3E, 4A, 5A, 6A, 7B), (1A, 2D, 3E, 4A, 5A, 6A, 7C), (1A, 2D, 3E, 4A, 5A, 6B, 7A), (1A, 2D, 3E, 4A, 5A, 6B, 7B), (1A, 2D, 3E, 4A, 5A, 6B, 7C), (1A, 2D, 3E, 4A, 5A, 6C, 7A), (1A, 2D, 3E, 4A, 5A, 6C, 7B), (1A, 2D, 3E, 4A, 5A, 6C, 7C), (1A, 2D, 3E, 4A, 5A, 6D, 7A), (1A, 2D, 3E, 4A, 5A, 6D, 7B), (1A, 2D, 3E, 4A, 5A, 6D, 7C), (1A, 2D, 3E, 4A, 5B, 6A, 7A), (1A, 2D, 3E, 4A, 5B, 6A, 7B), (1A, 2D, 3E, 4A, 5B, 6A, 7C), (1A, 2D, 3E, 4A, 5B, 6B, 7A), (1A, 2D, 3E, 4A, 5B, 6B, 7B), (1A, 2D, 3E, 4A, 5B, 6B, 7C), (1A, 2D, 3E, 4A, 5B, 6C, 7A), (1A, 2D, 3E, 4A, 5B, 6C, 7B), (1A, 2D, 3E, 4A, 5B, 6C, 7C), (1A, 2D, 3E, 4A, 5B, 6D, 7A), (1A, 2D, 3E, 4A, 5B, 6D, 7B), (1A, 2D, 3E, 4A, 5B, 6D, 7C), (1A, 2D, 3E, 4B, 5A, 6A, 7A), (1A, 2D, 3E, 4B, 5A, 6A, 7B), (1A, 2D, 3E, 4B, 5A, 6A, 7C), (1A, 2D, 3E, 4B, 5A, 6B, 7A), (1A, 2D, 3E, 4B, 5A, 6B, 7B), (1A, 2D, 3E, 4B, 5A, 6B, 7C), (1A, 2D, 3E, 4B, 5A, 6C, 7A), (1A, 2D, 3E, 4B, 5A, 6C, 7B), (1A, 2D, 3E, 4B, 5A, 6C, 7C), (1A, 2D, 3E, 4B, 5A, 6D, 7A), (1A, 2D, 3E, 4B, 5A, 6D, 7B), (1A, 2D, 3E, 4B, 5A, 6D, 7C), (1A, 2D, 3E, 4B, 5B, 6A, 7A), (1A, 2D, 3E, 4B, 5B, 6A, 7B), (1A, 2D, 3E, 4B, 5B, 6A, 7C), (1A, 2D, 3E, 4B, 5B, 6B, 7A), (1A, 2D, 3E, 4B, 5B, 6B, 7B), (1A, 2D, 3E, 4B, 5B, 6B, 7C), (1A, 2D, 3E, 4B, 5B, 6C, 7A), (1A, 2D, 3E, 4B, 5B, 6C, 7B), (1A, 2D, 3E, 4B, 5B, 6C, 7C), (1A, 2D, 3E, 4B, 5B, 6D, 7A), (1A, 2D, 3E, 4B, 5B, 6D, 7B), (1A, 2D, 3E, 4B, 5B, 6D, 7C), (1A, 2D, 3E, 4C, 5A, 6A, 7A), (1A, 2D, 3E, 4C, 5A, 6A, 7B), (1A, 2D, 3E, 4C, 5A, 6A, 7C), (1A, 2D, 3E, 4C, 5A, 6B, 7A), (1A, 2D, 3E, 4C, 5A, 6B, 7B), (1A, 2D, 3E, 4C, 5A, 6B, 7C), (1A, 2D, 3E, 4C, 5A, 6C, 7A), (1A, 2D, 3E, 4C, 5A, 6C, 7B), (1A, 2D, 3E, 4C, 5A, 6C, 7C), (1A, 2D, 3E, 4C, 5A, 6D, 7A), (1A, 2D, 3E, 4C, 5A, 6D, 7B), (1A, 2D, 3E, 4C, 5A, 6D, 7C), (1A, 2D, 3E, 4C, 5B, 6A, 7A), (1A, 2D, 3E, 4C, 5B, 6A, 7B), (1A, 2D, 3E, 4C, 5B, 6A, 7C), (1A, 2D, 3E, 4C, 5B, 6B, 7A), (1A, 2D, 3E, 4C, 5B, 6B, 7B), (1A, 2D, 3E, 4C, 5B, 6B, 7C), (1A, 2D, 3E, 4C, 5B, 6C, 7A), (1A, 2D, 3E, 4C, 5B, 6C, 7B), (1A, 2D, 3E, 4C, 5B, 6C, 7C), (1A, 2D, 3E, 4C, 5B, 6D, 7A), (1A, 2D, 3E, 4C, 5B, 6D, 7B), (1A, 2D, 3E, 4C, 5B, 6D, 7C), (1A, 2D, 3E, 4D, 5A, 6A, 7A), (1A, 2D, 3E, 4D, 5A, 6A, 7B), (1A, 2D, 3E, 4D, 5A, 6A, 7C), (1A, 2D, 3E, 4D, 5A, 6B, 7A), (1A, 2D, 3E, 4D, 5A, 6B, 7B), (1A, 2D, 3E, 4D, 5A, 6B, 7C), (1A, 2D, 3E, 4D, 5A, 6C, 7A), (1A, 2D, 3E, 4D, 5A, 6C, 7B), (1A, 2D, 3E, 4D, 5A, 6C, 7C), (1A, 2D, 3E, 4D, 5A, 6D, 7A), (1A, 2D, 3E, 4D, 5A, 6D, 7B), (1A, 2D, 3E, 4D, 5A, 6D, 7C), (1A, 2D, 3E, 4D, 5B, 6A, 7A), (1A, 2D, 3E, 4D, 5B, 6A, 7B), (1A, 2D, 3E, 4D, 5B, 6A, 7C), (1A, 2D, 3E, 4D, 5B, 6B, 7A), (1A, 2D, 3E, 4D, 5B, 6B, 7B), (1A, 2D, 3E, 4D, 5B, 6C, 7A), (1A, 2D, 3E, 4D, 5B, 6C, 7B), (1A, 2D, 3E, 4D, 5B, 6C, 7C), (1A, 2D, 3E, 4D, 5B, 6D, 7A), (1A, 2D, 3E, 4D, 5B, 6D, 7B), (1A, 2D, 3E, 4D, 5B, 6D, 7C), (1A, 2D, 3E, 4E, 5A, 6A, 7A), (1A, 2D, 3E, 4E, 5A, 6A, 7B), (1A, 2D, 3E, 4E, 5A, 6A, 7C), (1A, 2D, 3E, 4E, 5A, 6B, 7A), (1A, 2D, 3E, 4E, 5A, 6B, 7B), (1A, 2D, 3E, 4E, 5A, 6B, 7C), (1A, 2D, 3E, 4E, 5A, 6C, 7A), (1A, 2D, 3E, 4E, 5A, 6C, 7B), (1A, 2D, 3E, 4E, 5A, 6C, 7C), (1A, 2D, 3E, 4E, 5A, 6D, 7A), (1A, 2D, 3E, 4E, 5A, 6D, 7B), (1A, 2D, 3E, 4E, 5A, 6D, 7C), (1A, 2D, 3E, 4E, 5B, 6A, 7A), (1A, 2D, 3E, 4E, 5B, 6A, 7B), (1A, 2D, 3E, 4E, 5B, 6A, 7C), (1A, 2D, 3E, 4E, 5B, 6B, 7A), (1A, 2D, 3E, 4E, 5B, 6B, 7B), (1A, 2D, 3E, 4E, 5B, 6B, 7C), (1A, 2D, 3E, 4E, 5B, 6C, 7A), (1A, 2D, 3E, 4E, 5B, 6C, 7B), (1A, 2D, 3E, 4E, 5B, 6C, 7C), (1A, 2D, 3E, 4E, 5B, 6D, 7A), (1A, 2D, 3E, 4E, 5B, 6D, 7B), (1A, 2D, 3E, 4E, 5B, 6D, 7C), (1A, 2E, 3A, 4A, 5A, 6A, 7A), (1A, 2E, 3A, 4A, 5A, 6A, 7B), (1A, 2E, 3A, 4A, 5A, 6A, 7C), (1A, 2E, 3A, 4A, 5A, 6B, 7A), (1A, 2E, 3A, 4A, 5A, 6B, 7B), (1A, 2E, 3A, 4A, 5A, 6B, 7C), (1A, 2E, 3A, 4A, 5A, 6C, 7A), (1A, 2E, 3A, 4A, 5A, 6C, 7B), (1A, 2E, 3A, 4A, 5A, 6C, 7C), (1A, 2E, 3A, 4A, 5A, 6D, 7A), (A, 2E, 3A, 4A, 5A, 6D, 7B), (1A, 2E, 3A, 4A, 5A, 6D, 7C), (1A, 2E, 3A, 4A, 5B, 6A, 7A), (1A, 2E, 3A, 4A, 5B, 6A, 7B), (1A, 2E, 3A, 4A, 5B, 6A, 7C), (1A, 2E, 3A, 4A, 5B, 6B, 7A), (1A, 2E, 3A, 4A, 5B, 6B, 7B), (1A, 2E, 3A, 4A, 5B, 6B, 7C), (1A, 2E, 3A, 4A, 5B, 6C, 7A), (1A, 2E, 3A, 4A, 5B, 6C, 7B), (1A, 2E, 3A, 4A, 5B, 6C, 7C), (1A, 2E, 3A, 4A, 5B, 6D, 7A), (1A, 2E, 3A, 4A, 5B, 6D, 7B), (1A, 2E, 3A, 4A, 5B, 6D, 7C), (1A, 2E, 3A, 4B, 5A, 6A, 7A), (1A, 2E, 3A, 4B, 5A, 6A, 7B), (1A, 2E, 3A, 4B, 5A, 6A, 7C), (1A, 2E, 3A, 4B, 5A, 6B, 7A), (1A, 2E, 3A, 4B, 5A, 6B, 7B), (1A, 2E, 3A, 4B, 5A, 6B, 7C), (1A, 2E, 3A, 4B, 5A, 6C, 7A), (1A, 2E, 3A, 4B, 5A, 6C, 7B), (1A, 2E, 3A, 4B, 5A, 6C, 7C), (1A, 2E, 3A, 4B, 5A, 6D, 7A), (1A, 2E, 3A, 4B, 5A, 6D, 7B), (1A, 2E, 3A, 4B, 5A, 6D, 7C), (1A, 2E, 3A, 4B, 5B, 6A, 7A), (1A, 2E, 3A, 4B, 5B, 6A, 7B), (1A, 2E, 3A, 4B, 5B, 6A, 7C), (1A, 2E, 3A, 4B, 5B, 6B, 7A), (1A, 2E, 3A, 4B, 5B, 6B, 7B), (1A, 2E, 3A, 4B, 5B, 6B, 7C), (1A, 2E, 3A, 4B, 5B, 6C, 7A), (1A, 2E, 3A, 4B, 5B, 6C, 7B), (1A, 2E, 3A, 4B, 5B, 6C, 7C), (1A, 2E, 3A, 4B, 5B, 6D, 7A), (1A, 2E, 3A, 4B, 5B, 6D, 7B), (1A, 2E, 3A, 4B, 5B, 6D, 7C), (1A, 2E, 3A, 4C, 5A, 6A, 7A), (1A, 2E, 3A, 4C, 5A, 6A, 7B), (1A, 2E, 3A, 4C, 5A, 6A, 7C), (1A, 2E, 3A, 4C, 5A, 6B, 7A), (1A, 2E, 3A, 4C, 5A, 6B, 7B), (1A, 2E, 3A, 4C, 5A, 6B, 7C), (1A, 2E, 3A, 4C, 5A, 6C, 7A), (1A, 2E, 3A, 4C, 5A, 6C, 7B), (1A, 2E, 3A, 4C, 5A, 6C, 7C), (1A, 2E, 3A, 4C, 5A, 6D, 7A), (1A, 2E, 3A, 4C, 5A, 6D, 7B), (1A, 2E, 3A, 4C, 5A, 6D, 7C), (1A, 2E, 3A, 4C, 5B, 6A, 7A), (1A, 2E, 3A, 4C, 5B, 6A, 7B), (1A, 2E, 3A, 4C, 5B, 6A, 7C), (1A, 2E, 3A, 4C, 5B, 6B, 7A), (1A, 2E, 3A, 4C, 5B, 6B, 7B), (1A, 2E, 3A, 4C, 5B, 6B, 7C), (1A, 2E, 3A, 4C, 5B, 6C, 7A), (1A, 2E, 3A, 4C, 5B, 6C, 7B), (1A, 2E, 3A, 4C, 5B, 6C, 7C), (1A, 2E, 3A, 4C, 5B, 6D, 7A), (1A, 2E, 3A, 4C, 5B, 6D, 7B), (1A, 2E, 3A, 4C, 5B, 6D, 7C), (1A, 2E, 3A, 4D, 5A, 6A, 7A), (1A, 2E, 3A, 4D, 5A, 6A, 7B), (1A, 2E, 3A, 4D, 5A, 6A, 7C), (1A, 2E, 3A, 4D, 5A, 6B, 7A), (1A, 2E, 3A, 4D, 5A, 6B, 7B), (1A, 2E, 3A, 4D, 5A, 6B, 7C), (1A, 2E, 3A, 4D, 5A, 6C, 7A), (1A, 2E, 3A, 4D, 5A, 6C, 7B), (1A, 2E, 3A, 4D, 5A, 6C, 7C), (1A, 2E, 3A, 4D, 5A, 6D, 7A), (1A, 2E, 3A, 4D, 5A, 6D, 7B), (1A, 2E, 3A, 4D, 5A, 6D, 7C), (1A, 2E, 3A, 4D, 5B, 6A, 7A), (1A, 2E, 3A, 4D, 5B, 6A, 7B), (1A, 2E, 3A, 4D, 5B, 6A, 7C), (1A, 2E, 3A, 4D, 5B, 6B, 7A), (1A, 2E, 3A, 4D, 5B, 6B, 7B), (1A, 2E, 3A, 4D, 5B, 6B, 7C), (1A, 2E, 3A, 4D, 5B, 6C, 7A), (1A, 2E, 3A, 4D, 5B, 6C, 7B), (1A, 2E, 3A, 4D, 5B, 6C, 7C), (1A, 2E, 3A, 4D, 5B, 6D, 7A), (1A, 2E, 3A, 4D, 5B, 6D, 7B), (1A, 2E, 3A, 4D, 5B, 6D, 7C), (1A, 2E, 3A, 4E, 5A, 6A, 7A), (1A, 2E, 3A, 4E, 5A, 6A, 7B), (1A, 2E, 3A, 4E, 5A, 6A, 7C), (1A, 2E, 3A, 4E, 5A, 6B, 7A), (1A, 2E, 3A, 4E, 5A, 6B, 7B), (1A, 2E, 3A, 4E, 5A, 6B, 7C), (1A, 2E, 3A, 4E, 5A, 6C, 7A), (1A, 2E, 3A, 4E, 5A, 6C, 7B), (1A, 2E, 3A, 4E, 5A, 6C, 7C), (A, 2E, 3A, 4E, 5A, 6D, 7A), (1A, 2E, 3A, 4E, 5A, 6D, 7B), (1A, 2E, 3A, 4E, 5A, 6D, 7C), (1A, 2E, 3A, 4E, 5B, 6A, 7A), (1A, 2E, 3A, 4E, 5B, 6A, 7B), (1A, 2E, 3A, 4E, 5B, 6A, 7C), (1A, 2E, 3A, 4E, 5B, 6B, 7A), (1A, 2E, 3A, 4E, 5B, 6B, 7B), (1A, 2E, 3A, 4E, 5B, 6B, 7C), (1A, 2E, 3A, 4E, 5B, 6C, 7A), (1A, 2E, 3A, 4E, 5B, 6C, 7B), (1A, 2E, 3A, 4E, 5B, 6C, 7C), (1A, 2E, 3A, 4E, 5B, 6D, 7A), (1A, 2E, 3A, 4E, 5B, 6D, 7B), (1A, 2E, 3A, 4E, 5B, 6D, 7C), (1A, 2E, 3B, 4A, 5A, 6A, 7A), (1A, 2E, 3B, 4A, 5A, 6A, 7B), (1A, 2E, 3B, 4A, 5A, 6A, 7C), (1A, 2E, 3B, 4A, 5A, 6B, 7A), (1A, 2E, 3B, 4A, 5A, 6B, 7B), (1A, 2E, 3B, 4A, 5A, 6B, 7C), (1A, 2E, 3B, 4A, 5A, 6C, 7A), (1A, 2E, 3B, 4A, 5A, 6C, 7B), (1A, 2E, 3B, 4A, 5A, 6C, 7C), (1A, 2E, 3B, 4A, 5A, 6D, 7A), (1A, 2E, 3B, 4A, 5A, 6D, 7B), (1A, 2E, 3B, 4A, 5A, 6D, 7C), (1A, 2E, 3B, 4A, 5B, 6A, 7A), (1A, 2E, 3B, 4A, 5B, 6A, 7B), (1A, 2E, 3B, 4A, 5B, 6A, 7C), (1A, 2E, 3B, 4A, 5B, 6B, 7A), (1A, 2E, 3B, 4A, 5B, 6B, 7B), (1A, 2E, 3B, 4A, 5B, 6B, 7C), (1A, 2E, 3B, 4A, 5B, 6C, 7A), (1A, 2E, 3B, 4A, 5B, 6C, 7B), (1A, 2E, 3B, 4A, 5B, 6C, 7C), (1A, 2E, 3B, 4A, 5B, 6D, 7A), (1A, 2E, 3B, 4A, 5B, 6D, 7B), (1A, 2E, 3B, 4A, 5B, 6D, 7C), (1A, 2E, 3B, 4B, 5A, 6A, 7A), (1A, 2E, 3B, 4B, 5A, 6A, 7B), (1A, 2E, 3B, 4B, 5A, 6A, 7C), (1A, 2E, 3B, 4B, 5A, 6B, 7A), (1A, 2E, 3B, 4B, 5A, 6B, 7B), (1A, 2E, 3B, 4B, 5A, 6B, 7C), (1A, 2E, 3B, 4B, 5A, 6C, 7A), (1A, 2E, 3B, 4B, 5A, 6C, 7B), (1A, 2E, 3B, 4B, 5A, 6C, 7C), (1A, 2E, 3B, 4B, 5A, 6D, 7A), (1A, 2E, 3B, 4B, 5A, 6D, 7B), (1A, 2E, 3B, 4B, 5A, 6D, 7C), (1A, 2E, 3B, 4B, 5B, 6A, 7A), (1A, 2E, 3B, 4B, 5B, 6A, 7B), (1A, 2E, 3B, 4B, 5B, 6A, 7C), (1A, 2E, 3B, 4B, 5B, 6B, 7A), (1A, 2E, 3B, 4B, 5B, 6B, 7B), (1A, 2E, 3B, 4B, 5B, 6B, 7C), (1A, 2E, 3B, 4B, 5B, 6C, 7A), (1A, 2E, 3B, 4B, 5B, 6C, 7B), (1A, 2E, 3B, 4B, 5B, 6C, 7C), (1A, 2E, 3B, 4B, 5B, 6D, 7A), (1A, 2E, 3B, 4B, 5B, 6D, 7B), (1A, 2E, 3B, 4B, 5B, 6D, 7C), (A, 2E, 3B, 4C, 5A, 6A, 7A), (1A, 2E, 3B, 4C, 5A, 6A, 7B), (1A, 2E, 3B, 4C, 5A, 6A, 7C), (1A, 2E, 3B, 4C, 5A, 6B, 7A), (1A, 2E, 3B, 4C, 5A, 6B, 7B), (1A, 2E, 3B, 4C, 5A, 6B, 7C), (1A, 2E, 3B, 4C, 5A, 6C, 7A), (1A, 2E, 3B, 4C, 5A, 6C, 7B), (1A, 2E, 3B, 4C, 5A, 6C, 7C), (1A, 2E, 3B, 4C, 5A, 6D, 7A), (1A, 2E, 3B, 4C, 5A, 6D, 7B), (1A, 2E, 3B, 4C, 5A, 6D, 7C), (1A, 2E, 3B, 4C, 5B, 6A, 7A), (1A, 2E, 3B, 4C, 5B, 6A, 7B), (1A, 2E, 3B, 4C, 5B, 6A, 7C), (1A, 2E, 3B, 4C, 5B, 6B, 7A), (1A, 2E, 3B, 4C, 5B, 6B, 7B), (1A, 2E, 3B, 4C, 5B, 6B, 7C), (1A, 2E, 3B, 4C, 5B, 6C, 7A), (1A, 2E, 3B, 4C, 5B, 6C, 7B), (1A, 2E, 3B, 4C, 5B, 6C, 7C), (1A, 2E, 3B, 4C, 5B, 6D, 7A), (1A, 2E, 3B, 4C, 5B, 6D, 7B), (1A, 2E, 3B, 4C, 5B, 6D, 7C), (1A, 2E, 3B, 4D, 5A, 6A, 7A), (1A, 2E, 3B, 4D, 5A, 6A, 7B), (1A, 2E, 3B, 4D, 5A, 6A, 7C), (1A, 2E, 3B, 4D, 5A, 6B, 7A), (1A, 2E, 3B, 4D, 5A, 6B, 7B), (1A, 2E, 3B, 4D, 5A, 6B, 7C), (1A, 2E, 3B, 4D, 5A, 6C, 7A), (1A, 2E, 3B, 4D, 5A, 6C, 7B), (1A, 2E, 3B, 4D, 5A, 6C, 7C), (1A, 2E, 3B, 4D, 5A, 6D, 7A), (1A, 2E, 3B, 4D, 5A, 6D, 7B), (1A, 2E, 3B, 4D, 5A, 6D, 7C), (1A, 2E, 3B, 4D, 5B, 6A, 7A), (1A, 2E, 3B, 4D, 5B, 6A, 7B), (1A, 2E, 3B, 4D, 5B, 6A, 7C), (1A, 2E, 3B, 4D, 5B, 6B, 7A), (1A, 2E, 3B, 4D, 5B, 6B, 7B), (1A, 2E, 3B, 4D, 5B, 6B, 7C), (1A, 2E, 3B, 4D, 5B, 6C, 7A), (1A, 2E, 3B, 4D, 5B, 6C, 7B), (1A, 2E, 3B, 4D, 5B, 6C, 7C), (1A, 2E, 3B, 4D, 5B, 6D, 7A), (1A, 2E, 3B, 4D, 5B, 6D, 7B), (1A, 2E, 3B, 4D, 5B, 6D, 7C), (1A, 2E, 3B, 4E, 5A, 6A, 7A), (1A, 2E, 3B, 4E, 5A, 6A, 7B), (1A, 2E, 3B, 4E, 5A, 6A, 7C), (1A, 2E, 3B, 4E, 5A, 6B, 7A), (1A, 2E, 3B, 4E, 5A, 6B, 7B), (1A, 2E, 3B, 4E, 5A, 6B, 7C), (1A, 2E, 3B, 4E, 5A, 6C, 7A), (1A, 2E, 3B, 4E, 5A, 6C, 7B), (1A, 2E, 3B, 4E, 5A, 6C, 7C), (1A, 2E, 3B, 4E, 5A, 6D, 7A), (1A, 2E, 3B, 4E, 5A, 6D, 7B), (1A, 2E, 3B, 4E, 5A, 6D, 7C), (1A, 2E, 3B, 4E, 5B, 6A, 7A), (1A, 2E, 3B, 4E, 5B, 6A, 7B), (1A, 2E, 3B, 4E, 5B, 6A, 7C), (1A, 2E, 3B, 4E, 5B, 6B, 7A), (1A, 2E, 3B, 4E, 5B, 6B, 7B), (1A, 2E, 3B, 4E, 5B, 6B, 7C), (1A, 2E, 3B, 4E, 5B, 6C, 7A), (1A, 2E, 3B, 4E, 5B, 6C, 7B), (1A, 2E, 3B, 4E, 5B, 6C, 7C), (1A, 2E, 3B, 4E, 5B, 6D, 7A), (1A, 2E, 3B, 4E, 5B, 6D, 7B), (1A, 2E, 3B, 4E, 5B, 6D, 7C), (1A, 2E, 3C, 4A, 5A, 6A, 7A), (1A, 2E, 3C, 4A, 5A, 6A, 7B), (1A, 2E, 3C, 4A, 5A, 6A, 7C), (1A, 2E, 3C, 4A, 5A, 6B, 7A), (1A, 2E, 3C, 4A, 5A, 6B, 7B), (1A, 2E, 3C, 4A, 5A, 6B, 7C), (1A, 2E, 3C, 4A, 5A, 6C, 7A), (1A, 2E, 3C, 4A, 5A, 6C, 7B), (1A, 2E, 3C, 4A, 5A, 6C, 7C), (1A, 2E, 3C, 4A, 5A, 6D, 7A), (1A, 2E, 3C, 4A, 5A, 6D, 7B), (1A, 2E, 3C, 4A, 5A, 6D, 7C), (1A, 2E, 3C, 4A, 5B, 6A, 7A), (1A, 2E, 3C, 4A, 5B, 6A, 7B), (1A, 2E, 3C, 4A, 5B, 6A, 7C), (1A, 2E, 3C, 4A, 5B, 6B, 7A), (1A, 2E, 3C, 4A, 5B, 6B, 7B), (1A, 2E, 3C, 4A, 5B, 6B, 7C), (1A, 2E, 3C, 4A, 5B, 6C, 7A), (1A, 2E, 3C, 4A, 5B, 6C, 7B), (1A, 2E, 3C, 4A, 5B, 6C, 7C), (1A, 2E, 3C, 4A, 5B, 6D, 7A), (1A, 2E, 3C, 4A, 5B, 6D, 7B), (1A, 2E, 3C, 4A, 5B, 6D, 7C), (1A, 2E, 3C, 4B, 5A, 6A, 7A), (1A, 2E, 3C, 4B, 5A, 6A, 7B), (1A, 2E, 3C, 4B, 5A, 6A, 7C), (1A, 2E, 3C, 4B, 5A, 6B, 7A), (1A, 2E, 3C, 4B, 5A, 6B, 7B), (1A, 2E, 3C, 4B, 5A, 6B, 7C), (1A, 2E, 3C, 4B, 5A, 6C, 7A), (1A, 2E, 3C, 4B, 5A, 6C, 7B), (1A, 2E, 3C, 4B, 5A, 6C, 7C), (1A, 2E, 3C, 4B, 5A, 6D, 7A), (1A, 2E, 3C, 4B, 5A, 6D, 7B), (1A, 2E, 3C, 4B, 5A, 6D, 7C), (1A, 2E, 3C, 4B, 5B, 6A, 7A), (1A, 2E, 3C, 4B, 5B, 6A, 7B), (1A, 2E, 3C, 4B, 5B, 6A, 7C), (1A, 2E, 3C, 4B, 5B, 6B, 7A), (1A, 2E, 3C, 4B, 5B, 6B, 7B), (1A, 2E, 3C, 4B, 5B, 6B, 7C), (1A, 2E, 3C, 4B, 5B, 6C, 7A), (1A, 2E, 3C, 4B, 5B, 6C, 7B), (1A, 2E, 3C, 4B, 5B, 6C, 7C), (1A, 2E, 3C, 4B, 5B, 6D, 7A), (1A, 2E, 3C, 4B, 5B, 6D, 7B), (1A, 2E, 3C, 4B, 5B, 6D, 7C), (1A, 2E, 3C, 4C, 5A, 6A, 7A), (1A, 2E, 3C, 4C, 5A, 6A, 7B), (1A, 2E, 3C, 4C, 5A, 6A, 7C), (1A, 2E, 3C, 4C, 5A, 6B, 7A), (1A, 2E, 3C, 4C, 5A, 6B, 7B), (1A, 2E, 3C, 4C, 5A, 6B, 7C), (1A, 2E, 3C, 4C, 5A, 6C, 7A), (1A, 2E, 3C, 4C, 5A, 6C, 7B), (1A, 2E, 3C, 4C, 5A, 6C, 7C), (1A, 2E, 3C, 4C, 5A, 6D, 7A), (1A, 2E, 3C, 4C, 5A, 6D, 7B), (1A, 2E, 3C, 4C, 5A, 6D, 7C), (1A, 2E, 3C, 4C, 5B, 6A, 7A), (1A, 2E, 3C, 4C, 5B, 6A, 7B), (1A, 2E, 3C, 4C, 5B, 6A, 7C), (1A, 2E, 3C, 4C, 5B, 6B, 7A), (1A, 2E, 3C, 4C, 5B, 6B, 7B), (1A, 2E, 3C, 4C, 5B, 6B, 7C), (1A, 2E, 3C, 4C, 5B, 6C, 7A), (1A, 2E, 3C, 4C, 5B, 6C, 7B), (1A, 2E, 3C, 4C, 5B, 6C, 7C), (1A, 2E, 3C, 4C, 5B, 6D, 7A), (1A, 2E, 3C, 4C, 5B, 6D, 7B), (1A, 2E, 3C, 4C, 5B, 6D, 7C), (1A, 2E, 3C, 4D, 5A, 6A, 7A), (1A, 2E, 3C, 4D, 5A, 6A, 7B), (1A, 2E, 3C, 4D, 5A, 6A, 7C), (1A, 2E, 3C, 4D, 5A, 6B, 7A), (1A, 2E, 3C, 4D, 5A, 6B, 7B), (1A, 2E, 3C, 4D, 5A, 6B, 7C), (1A, 2E, 3C, 4D, 5A, 6C, 7A), (1A, 2E, 3C, 4D, 5A, 6C, 7B), (1A, 2E, 3C, 4D, 5A, 6C, 7C), (1A, 2E, 3C, 4D, 5A, 6D, 7A), (1A, 2E, 3C, 4D, 5A, 6D, 7B), (1A, 2E, 3C, 4D, 5A, 6D, 7C), (1A, 2E, 3C, 4D, 5B, 6A, 7A), (1A, 2E, 3C, 4D, 5B, 6A, 7B), (1A, 2E, 3C, 4D, 5B, 6A, 7C), (1A, 2E, 3C, 4D, 5B, 6B, 7A), (1A, 2E, 3C, 4D, 5B, 6B, 7B), (1A, 2E, 3C, 4D, 5B, 6B, 7C), (1A, 2E, 3C, 4D, 5B, 6C, 7A), (1A, 2E, 3C, 4D, 5B, 6C, 7B), (1A, 2E, 3C, 4D, 5B, 6C, 7C), (1A, 2E, 3C, 4D, 5B, 6D, 7A), (1A, 2E, 3C, 4D, 5B, 6D, 7B), (1A, 2E, 3C, 4D, 5B, 6D, 7C), (1A, 2E, 3C, 4E, 5A, 6A, 7A), (1A, 2E, 3C, 4E, 5A, 6A, 7B), (1A, 2E, 3C, 4E, 5A, 6A, 7C), (1A, 2E, 3C, 4E, 5A, 6B, 7A), (1A, 2E, 3C, 4E, 5A, 6B, 7B), (1A, 2E, 3C, 4E, 5A, 6B, 7C), (1A, 2E, 3C, 4E, 5A, 6C, 7A), (1A, 2E, 3C, 4E, 5A, 6C, 7B), (1A, 2E, 3C, 4E, 5A, 6C, 7C), (1A, 2E, 3C, 4E, 5A, 6D, 7A), (1A, 2E, 3C, 4E, 5A, 6D, 7B), (1A, 2E, 3C, 4E, 5A, 6D, 7C), (1A, 2E, 3C, 4E, 5B, 6A, 7A), (1A, 2E, 3C, 4E, 5B, 6A, 7B), (1A, 2E, 3C, 4E, 5B, 6A, 7C), (1A, 2E, 3C, 4E, 5B, 6B, 7A), (1A, 2E, 3C, 4E, 5B, 6B, 7B), (1A, 2E, 3C, 4E, 5B, 6B, 7C), (1A, 2E, 3C, 4E, 5B, 6C, 7A), (1A, 2E, 3C, 4E, 5B, 6C, 7B), (1A, 2E, 3C, 4E, 5B, 6C, 7C), (1A, 2E, 3C, 4E, 5B, 6D, 7A), (1A, 2E, 3C, 4E, 5B, 6D, 7B), (1A, 2E, 3C, 4E, 5B, 6D, 7C), (1A, 2E, 3D, 4A, 5A, 6A, 7A), (1A, 2E, 3D, 4A, 5A, 6A, 7B), (1A, 2E, 3D, 4A, 5A, 6A, 7C), (1A, 2E, 3D, 4A, 5A, 6B, 7A), (1A, 2E, 3D, 4A, 5A, 6B, 7B), (1A, 2E, 3D, 4A, 5A, 6B, 7C), (1A, 2E, 3D, 4A, 5A, 6C, 7A), (1A, 2E, 3D, 4A, 5A, 6C, 7B), (1A, 2E, 3D, 4A, 5A, 6C, 7C), (1A, 2E, 3D, 4A, 5A, 6D, 7A), (1A, 2E, 3D, 4A, 5A, 6D, 7B), (1A, 2E, 3D, 4A, 5A, 6D, 7C), (1A, 2E, 3D, 4A, 5B, 6A, 7A), (1A, 2E, 3D, 4A, 5B, 6A, 7B), (1A, 2E, 3D, 4A, 5B, 6A, 7C), (1A, 2E, 3D, 4A, 5B, 6B, 7A), (1A, 2E, 3D, 4A, 5B, 6B, 7B), (1A, 2E, 3D, 4A, 5B, 6B, 7C), (1A, 2E, 3D, 4A, 5B, 6C, 7A), (1A, 2E, 3D, 4A, 5B, 6C, 7B), (1A, 2E, 3D, 4A, 5B, 6C, 7C), (1A, 2E, 3D, 4A, 5B, 6D, 7A), (1A, 2E, 3D, 4A, 5B, 6D, 7B), (1A, 2E, 3D, 4A, 5B, 6D, 7C), (1A, 2E, 3D, 4B, 5A, 6A, 7A), (1A, 2E, 3D, 4B, 5A, 6A, 7B), (1A, 2E, 3D, 4B, 5A, 6A, 7C), (1A, 2E, 3D, 4B, 5A, 6B, 7A), (1A, 2E, 3D, 4B, 5A, 6B, 7B), (1A, 2E, 3D, 4B, 5A, 6B, 7C), (1A, 2E, 3D, 4B, 5A, 6C, 7A), (1A, 2E, 3D, 4B, 5A, 6C, 7B), (1A, 2E, 3D, 4B, 5A, 6C, 7C), (1A, 2E, 3D, 4B, 5A, 6D, 7A), (1A, 2E, 3D, 4B, 5A, 6D, 7B), (1A, 2E, 3D, 4B, 5A, 6D, 7C), (1A, 2E, 3D, 4B, 5B, 6A, 7A), (1A, 2E, 3D, 4B, 5B, 6A, 7B), (1A, 2E, 3D, 4B, 5B, 6A, 7C), (1A, 2E, 3D, 4B, 5B, 6B, 7A), (1A, 2E, 3D, 4B, 5B, 6B, 7B), (1A, 2E, 3D, 4B, 5B, 6B, 7C), (1A, 2E, 3D, 4B, 5B, 6C, 7A), (1A, 2E, 3D, 4B, 5B, 6C, 7B), (1A, 2E, 3D, 4B, 5B, 6C, 7C), (1A, 2E, 3D, 4B, 5B, 6D, 7A), (1A, 2E, 3D, 4B, 5B, 6D, 7B), (1A, 2E, 3D, 4B, 5B, 6D, 7C), (1A, 2E, 3D, 4C, 5A, 6A, 7A), (1A, 2E, 3D, 4C, 5A, 6A, 7B), (1A, 2E, 3D, 4C, 5A, 6A, 7C), (1A, 2E, 3D, 4C, 5A, 6B, 7A), (1A, 2E, 3D, 4C, 5A, 6B, 7B), (1A, 2E, 3D, 4C, 5A, 6B, 7C), (1A, 2E, 3D, 4C, 5A, 6C, 7A), (1A, 2E, 3D, 4C, 5A, 6C, 7B), (1A, 2E, 3D, 4C, 5A, 6C, 7C), (1A, 2E, 3D, 4C, 5A, 6D, 7A), (1A, 2E, 3D, 4C, 5A, 6D, 7B), (1A, 2E, 3D, 4C, 5A, 6D, 7C), (1A, 2E, 3D, 4C, 5B, 6A, 7A), (1A, 2E, 3D, 4C, 5B, 6A, 7B), (1A, 2E, 3D, 4C, 5B, 6A, 7C), (1A, 2E, 3D, 4C, 5B, 6B, 7A), (1A, 2E, 3D, 4C, 5B, 6B, 7B), (1A, 2E, 3D, 4C, 5B, 6B, 7C), (1A, 2E, 3D, 4C, 5B, 6C, 7A), (1A, 2E, 3D, 4C, 5B, 6C, 7B), (1A, 2E, 3D, 4C, 5B, 6C, 7C), (1A, 2E, 3D, 4C, 5B, 6D, 7A), (1A, 2E, 3D, 4C, 5B, 6D, 7B), (1A, 2E, 3D, 4C, 5B, 6D, 7C), (1A, 2E, 3D, 4D, 5A, 6A, 7A), (1A, 2E, 3D, 4D, 5A, 6A, 7B), (1A, 2E, 3D, 4D, 5A, 6A, 7C), (1A, 2E, 3D, 4D, 5A, 6B, 7A), (1A, 2E, 3D, 4D, 5A, 6B, 7B), (1A, 2E, 3D, 4D, 5A, 6B, 7C), (1A, 2E, 3D, 4D, 5A, 6C, 7A), (1A, 2E, 3D, 4D, 5A, 6C, 7B), (1A, 2E, 3D, 4D, 5A, 6C, 7C), (1A, 2E, 3D, 4D, 5A, 6D, 7A), (1A, 2E, 3D, 4D, 5A, 6D, 7B), (1A, 2E, 3D, 4D, 5A, 6D, 7C), (1A, 2E, 3D, 4D, 5B, 6A, 7A), (1A, 2E, 3D, 4D, 5B, 6A, 7B), (1A, 2E, 3D, 4D, 5B, 6A, 7C), (1A, 2E, 3D, 4D, 5B, 6B, 7A), (1A, 2E, 3D, 4D, 5B, 6B, 7B), (1A, 2E, 3D, 4D, 5B, 6B, 7C), (1A, 2E, 3D, 4D, 5B, 6C, 7A), (1A, 2E, 3D, 4D, 5B, 6C, 7B), (1A, 2E, 3D, 4D, 5B, 6C, 7C), (1A, 2E, 3D, 4D, 5B, 6D, 7A), (1A, 2E, 3D, 4D, 5B, 6D, 7B), (1A, 2E, 3D, 4D, 5B, 6D, 7C), (1A, 2E, 3D, 4E, 5A, 6A, 7A), (1A, 2E, 3D, 4E, 5A, 6A, 7B), (1A, 2E, 3D, 4E, 5A, 6A, 7C), (1A, 2E, 3D, 4E, 5A, 6B, 7A), (1A, 2E, 3D, 4E, 5A, 6B, 7B), (1A, 2E, 3D, 4E, 5A, 6B, 7C), (1A, 2E, 3D, 4E, 5A, 6C, 7A), (1A, 2E, 3D, 4E, 5A, 6C, 7B), (1A, 2E, 3D, 4E, 5A, 6C, 7C), (1A, 2E, 3D, 4E, 5A, 6D, 7A), (1A, 2E, 3D, 4E, 5A, 6D, 7B), (1A, 2E, 3D, 4E, 5A, 6D, 7C), (1A, 2E, 3D, 4E, 5B, 6A, 7A), (1A, 2E, 3D, 4E, 5B, 6A, 7B), (1A, 2E, 3D, 4E, 5B, 6A, 7C), (1A, 2E, 3D, 4E, 5B, 6B, 7A), (1A, 2E, 3D, 4E, 5B, 6B, 7B), (1A, 2E, 3D, 4E, 5B, 6B, 7C), (1A, 2E, 3D, 4E, 5B, 6C, 7A), (1A, 2E, 3D, 4E, 5B, 6C, 7B), (A, 2E, 3D, 4E, 5B, 6C, 7C), (1A, 2E, 3D, 4E, 5B, 6D, 7A), (1A, 2E, 3D, 4E, 5B, 6D, 7B), (1A, 2E, 3D, 4E, 5B, 6D, 7C), (1A, 2E, 3E, 4A, 5A, 6A, 7A), (1A, 2E, 3E, 4A, 5A, 6A, 7B), (1A, 2E, 3E, 4A, 5A, 6A, 7C), (1A, 2E, 3E, 4A, 5A, 6B, 7A), (1A, 2E, 3E, 4A, 5A, 6B, 7B), (1A, 2E, 3E, 4A, 5A, 6B, 7C), (1A, 2E, 3E, 4A, 5A, 6C, 7A), (1A, 2E, 3E, 4A, 5A, 6C, 7B), (1A, 2E, 3E, 4A, 5A, 6C, 7C), (1A, 2E, 3E, 4A, 5A, 6D, 7A), (1A, 2E, 3E, 4A, 5A, 6D, 7B), (1A, 2E, 3E, 4A, 5A, 6D, 7C), (1A, 2E, 3E, 4A, 5B, 6A, 7A), (1A, 2E, 3E, 4A, 5B, 6A, 7B), (1A, 2E, 3E, 4A, 5B, 6A, 7C), (1A, 2E, 3E, 4A, 5B, 6B, 7A), (1A, 2E, 3E, 4A, 5B, 6B, 7B), (1A, 2E, 3E, 4A, 5B, 6B, 7C), (1A, 2E, 3E, 4A, 5B, 6C, 7A), (1A, 2E, 3E, 4A, 5B, 6C, 7B), (1A, 2E, 3E, 4A, 5B, 6C, 7C), (1A, 2E, 3E, 4A, 5B, 6D, 7A), (1A, 2E, 3E, 4A, 5B, 6D, 7B), (1A, 2E, 3E, 4A, 5B, 6D, 7A), (1A, 2E, 3E, 4B, 5A, 6A, 7A), (1A, 2E, 3E, 4B, 5A, 6A, 7B), (1A, 2E, 3E, 4B, 5A, 6A, 7C), (1A, 2E, 3E, 4B, 5A, 6B, 7A), (1A, 2E, 3E, 4B, 5A, 6B, 7B), (1A, 2E, 3E, 4B, 5A, 6B, 7C), (1A, 2E, 3E, 4B, 5A, 6C, 7A), (1A, 2E, 3E, 4B, 5A, 6C, 7B), (1A, 2E, 3E, 4B, 5A, 6C, 7C), (1A, 2E, 3E, 4B, 5A, 6D, 7A), (1A, 2E, 3E, 4B, 5A, 6D, 7B), (1A, 2E, 3E, 4B, 5A, 6D, 7C), (1A, 2E, 3E, 4B, 5B, 6A, 7A), (1A, 2E, 3E, 4B, 5B, 6A, 7B), (1A, 2E, 3E, 4B, 5B, 6A, 7C), (1A, 2E, 3E, 4B, 5B, 6B, 7A), (1A, 2E, 3E, 4B, 5B, 6B, 7B), (1A, 2E, 3E, 4B, 5B, 6B, 7C), (1A, 2E, 3E, 4B, 5B, 6C, 7A), (1A, 2E, 3E, 4B, 5B, 6C, 7B), (1A, 2E, 3E, 4B, 5B, 6C, 7C), (1A, 2E, 3E, 4B, 5B, 6D, 7A), (1A, 2E, 3E, 4B, 5B, 6D, 7B), (1A, 2E, 3E, 4B, 5B, 6D, 7C), (1A, 2E, 3E, 4C, 5A, 6A, 7A), (1A, 2E, 3E, 4C, 5A, 6A, 7B), (1A, 2E, 3E, 4C, 5A, 6A, 7C), (1A, 2E, 3E, 4C, 5A, 6B, 7A), (1A, 2E, 3E, 4C, 5A, 6B, 7B), (1A, 2E, 3E, 4C, 5A, 6B, 7C), (1A, 2E, 3E, 4C, 5A, 6C, 7A), (1A, 2E, 3E, 4C, 5A, 6C, 7B), (1A, 2E, 3E, 4C, 5A, 6C, 7C), (1A, 2E, 3E, 4C, 5A, 6D, 7A), (1A, 2E, 3E, 4C, 5A, 6D, 7B), (1A, 2E, 3E, 4C, 5A, 6D, 7C), (1A, 2E, 3E, 4C, 5B, 6A, 7A), (1A, 2E, 3E, 4C, 5B, 6A, 7B), (1A, 2E, 3E, 4C, 5B, 6A, 7C), (1A, 2E, 3E, 4C, 5B, 6B, 7A), (1A, 2E, 3E, 4C, 5B, 6B, 7B), (1A, 2E, 3E, 4C, 5B, 6B, 7C), (1A, 2E, 3E, 4C, 5B, 6C, 7A), (1A, 2E, 3E, 4C, 5B, 6C, 7B), (1A, 2E, 3E, 4C, 5B, 6C, 7C), (1A, 2E, 3E, 4C, 5B, 6D, 7A), (1A, 2E, 3E, 4C, 5B, 6D, 7B), (1A, 2E, 3E, 4C, 5B, 6D, 7C), (1A, 2E, 3E, 4D, 5A, 6A, 7A), (1A, 2E, 3E, 4D, 5A, 6A, 7B), (1A, 2E, 3E, 4D, 5A, 6A, 7C), (1A, 2E, 3E, 4D, 5A, 6B, 7A), (1A, 2E, 3E, 4D, 5A, 6B, 7B), (1A, 2E, 3E, 4D, 5A, 6B, 7C), (1A, 2E, 3E, 4D, 5A, 6C, 7A), (1A, 2E, 3E, 4D, 5A, 6C, 7B), (1A, 2E, 3E, 4D, 5A, 6C, 7C), (1A, 2E, 3E, 4D, 5A, 6D, 7A), (1A, 2E, 3E, 4D, 5A, 6D, 7B), (1A, 2E, 3E, 4D, 5A, 6D, 7C), (1A, 2E, 3E, 4D, 5B, 6A, 7A), (1A, 2E, 3E, 4D, 5B, 6A, 7B), (1A, 2E, 3E, 4D, 5B, 6A, 7C), (1A, 2E, 3E, 4D, 5B, 6B, 7A), (1A, 2E, 3E, 4D, 5B, 6B, 7B), (1A, 2E, 3E, 4D, 5B, 6B, 7C), (1A, 2E, 3E, 4D, 5B, 6C, 7A), (1A, 2E, 3E, 4D, 5B, 6C, 7B), (1A, 2E, 3E, 4D, 5B, 6C, 7C), (1A, 2E, 3E, 4D, 5B, 6D, 7A), (1A, 2E, 3E, 4D, 5B, 6D, 7B), (1A, 2E, 3E, 4D, 5B, 6D, 7C), (1A, 2E, 3E, 4E, 5A, 6A, 7A), (1A, 2E, 3E, 4E, 5A, 6A, 7B), (1A, 2E, 3E, 4E, 5A, 6A, 7C), (1A, 2E, 3E, 4E, 5A, 6B, 7A), (1A, 2E, 3E, 4E, 5A, 6B, 7B), (1A, 2E, 3E, 4E, 5A, 6B, 7C), (1A, 2E, 3E, 4E, 5A, 6C, 7A), (1A, 2E, 3E, 4E, 5A, 6C, 7B), (1A, 2E, 3E, 4E, 5A, 6C, 7C), (1A, 2E, 3E, 4E, 5A, 6D, 7A), (1A, 2E, 3E, 4E, 5A, 6D, 7B), (1A, 2E, 3E, 4E, 5A, 6D, 7C), (1A, 2E, 3E, 4E, 5B, 6A, 7A), (1A, 2E, 3E, 4E, 5B, 6A, 7B), (1A, 2E, 3E, 4E, 5B, 6A, 7C), (1A, 2E, 3E, 4E, 5B, 6B, 7A), (1A, 2E, 3E, 4E, 5B, 6B, 7B), (1A, 2E, 3E, 4E, 5B, 6B, 7C), (1A, 2E, 3E, 4E, 5B, 6C, 7A), (1A, 2E, 3E, 4E, 5B, 6C, 7B), (1A, 2E, 3E, 4E, 5B, 6C, 7C), (1A, 2E, 3E, 4E, 5B, 6D, 7A), (1A, 2E, 3E, 4E, 5B, 6D, 7C), (1B, 2A, 3A, 4A, 5A, 6A, 7A), (1B, 2A, 3A, 4A, 5A, 6A, 7B), (1B, 2A, 3A, 4A, 5A, 6A, 7C), (1B, 2A, 3A, 4A, 5A, 6B, 7A), (1B, 2A, 3A, 4A, 5A, 6B, 7B), (1B, 2A, 3A, 4A, 5A, 6B, 7C), (1B, 2A, 3A, 4A, 5A, 6C, 7A), (1B, 2A, 3A, 4A, 5A, 6C, 7B), (1B, 2A, 3A, 4A, 5A, 6C, 7C), (1B, 2A, 3A, 4A, 5A, 6D, 7A), (1B, 2A, 3A, 4A, 5A, 6D, 7B), (1B, 2A, 3A, 4A, 5B, 6A, 7A), (1B, 2A, 3A, 4A, 5B, 6A, 7B), (1B, 2A, 3A, 4A, 5B, 6A, 7C), (1B, 2A, 3A, 4A, 5B, 6B, 7A), (1B, 2A, 3A, 4A, 5B, 6B, 7B), (1B, 2A, 3A, 4A, 5B, 6B, 7C), (1B, 2A, 3A, 4A, 5B, 6C, 7A), (1B, 2A, 3A, 4A, 5B, 6C, 7B), (1B, 2A, 3A, 4A, 5B, 6C, 7C), (1B, 2A, 3A, 4A, 5B, 6D, 7A), (1B, 2A, 3A, 4A, 5B, 6D, 7B), (1B, 2A, 3A, 4A, 5B, 6D, 7C), (1B, 2A, 3A, 4B, 5A, 6A, 7A), (1B, 2A, 3A, 4B, 5A, 6A, 7B), (1B, 2A, 3A, 4B, 5A, 6A, 7C), (1B, 2A, 3A, 4B, 5A, 6B, 7A), (1B, 2A, 3A, 4B, 5A, 6B, 7B), (1B, 2A, 3A, 4B, 5A, 6B, 7C), (1B, 2A, 3A, 4B, 5A, 6C, 7A), (1B, 2A, 3A, 4B, 5A, 6C, 7B), (1B, 2A, 3A, 4B, 5A, 6C, 7C), (1B, 2A, 3A, 4B, 5A, 6D, 7A), (1B, 2A, 3A, 4B, 5A, 6D, 7B), (1B, 2A, 3A, 4B, 5A, 6D, 7C), (1B, 2A, 3A, 4B, 5B, 6A, 7A), (1B, 2A, 3A, 4B, 5B, 6A, 7B), (1B, 2A, 3A, 4B, 5B, 6A, 7C), (1B, 2A, 3A, 4B, 5B, 6B, 7A), (1B, 2A, 3A, 4B, 5B, 6B, 7B), (1B, 2A, 3A, 4B, 5B, 6B, 7C), (1B, 2A, 3A, 4B, 5B, 6C, 7A), (1B, 2A, 3A, 4B, 5B, 6C, 7B), (1B, 2A, 3A, 4B, 5B, 6C, 7C), (1B, 2A, 3A, 4B, 5B, 6D, 7A), (1B, 2A, 3A, 4B, 5B, 6D, 7B), (1B, 2A, 3A, 4B, 5B, 6D, 7C), (1B, 2A, 3A, 4C, 5A, 6A, 7A), (1B, 2A, 3A, 4C, 5A, 6A, 7B), (1E, 2A, 3A, 4C, 5A, 6A, 7C), (1B, 2A, 3A, 4C, 5A, 6B, 7A), (1B, 2A, 3A, 4C, 5A, 6B, 7B), (1B, 2A, 3A, 4C, 5A, 6B, 7C), (1B, 2A, 3A, 4C, 5A, 6C, 7A), (1B, 2A, 3A, 4C, 5A, 6C, 7B), (1B, 2A, 3A, 4C, 5A, 6C, 7C), (1B, 2A, 3A, 4C, 5A, 6D, 7A), (1B, 2A, 3A, 4C, 5A, 6D, 7B), (1B, 2A, 3A, 4C, 5A, 6D, 7C), (1B, 2A, 3A, 4C, 5B, 6A, 7A), (1B, 2A, 3A, 4C, 5B, 6A, 7B), (1B, 2A, 3A, 4C, 5B, 6A, 7C), (1B, 2A, 3A, 4C, 5B, 6B, 7A), (1B, 2A, 3A, 4C, 5B, 6B, 7B), (1B, 2A, 3A, 4C, 5B, 6B, 7C), (1B, 2A, 3A, 4C, 5B, 6C, 7A), (1B, 2A, 3A, 4C, 5B, 6C, 7B), (1B, 2A, 3A, 4C, 5B, 6C, 7C), (1B, 2A, 3A, 4C, 5B, 6D, 7A), (1B, 2A, 3A, 4C, 5B, 6D, 7B), (1B, 2A, 3A, 4C, 5B, 6D, 7C), (1B, 2A, 3A, 4D, 5A, 6A, 7A), (1B, 2A, 3A, 4D, 5A, 6A, 7B), (1B, 2A, 3A, 4D, 5A, 6A, 7C), (1B, 2A, 3A, 4D, 5A, 6B, 7A), (1B, 2A, 3A, 4D, 5A, 6B, 7B), (1B, 2A, 3A, 4D, 5A, 6B, 7C), (1B, 2A, 3A, 4D, 5A, 6C, 7A), (1B, 2A, 3A, 4D, 5A, 6C, 7B), (1B, 2A, 3A, 4D, 5A, 6C, 7C), (1B, 2A, 3A, 4D, 5A, 6D, 7A), (1B, 2A, 3A, 4D, 5A, 6D, 7B), (1B, 2A, 3A, 4D, 5A, 6D, 7C), (1B, 2A, 3A, 4D, 5B, 6A, 7A), (1B, 2A, 3A, 4D, 5B, 6A, 7B), (1B, 2A, 3A, 4D, 5B, 6A, 7C), (1B, 2A, 3A, 4D, 5B, 6B, 7A), (1B, 2A, 3A, 4D, 5B, 6B, 7B), (1B, 2A, 3A, 4D, 5B, 6B, 7C), (1B, 2A, 3A, 4D, 5B, 6C, 7A), (1B, 2A, 3A, 4D, 5B, 6C, 7B), (1B, 2A, 3A, 4D, 5B, 6C, 7C), (1B, 2A, 3A, 4D, 5B, 6D, 7A), (1B, 2A, 3A, 4D, 5B, 6D, 7B), (1B, 2A, 3A, 4D, 5B, 6D, 7C), (1B, 2A, 3A, 4E, 5A, 6A, 7A), (1B, 2A, 3A, 4E, 5A, 6A, 7B), (1B, 2A, 3A, 4E, 5A, 6A, 7C), (1B, 2A, 3A, 4E, 5A, 6B, 7A), (1B, 2A, 3A, 4E, 5A, 6B, 7B), (1B, 2A, 3A, 4E, 5A, 6B, 7C), (1B, 2A, 3A, 4E, 5A, 6C, 7A), (1B, 2A, 3A, 4E, 5A, 6C, 7B), (1B, 2A, 3A, 4E, 5A, 6C, 7C), (1B, 2A, 3A, 4E, 5A, 6D, 7A), (1B, 2A, 3A, 4E, 5A, 6D, 7B), (1B, 2A, 3A, 4E, 5A, 6D, 7C), (1B, 2A, 3A, 4E, 5B, 6A, 7A), (1B, 2A, 3A, 4E, 5B, 6A, 7B), (1B, 2A, 3A, 4E, 5B, 6A, 7C), (1B, 2A, 3A, 4E, 5B, 6B, 7A), (1B, 2A, 3A, 4E, 5B, 6B, 7B), (1B, 2A, 3A, 4E, 5B, 6B, 7C), (1B, 2A, 3A, 4E, 5B, 6C, 7A), (1B, 2A, 3A, 4E, 5B, 6C, 7B), (1B, 2A, 3A, 4E, 5B, 6C, 7C), (1B, 2A, 3A, 4E, 5B, 6D, 7A), (1B, 2A, 3A, 4E, 5B, 6D, 7B), (1B, 2A, 3A, 4E, 5B, 6D, 7C), (1B, 2A, 3B, 4A, 5A, 6A, 7A), (1B, 2A, 3B, 4A, 5A, 6A, 7B), (1B, 2A, 3B, 4A, 5A, 6A, 7C), (1B, 2A, 3B, 4A, 5A, 6B, 7A), (1B, 2A, 3B, 4A, 5A, 6B, 7B), (1B, 2A, 3B, 4A, 5A, 6B, 7C), (1B, 2A, 3B, 4A, 5A, 6C, 7A), (1B, 2A, 3B, 4A, 5A, 6C, 7B), (1B, 2A, 3B, 4A, 5A, 6C, 7C), (1B, 2A, 3B, 4A, 5A, 6D, 7A), (1B, 2A, 3B, 4A, 5A, 6D, 7B), (1B, 2A, 3B, 4A, 5A, 6D, 7C), (1B, 2A, 3B, 4A, 5B, 6A, 7A), (1B, 2A, 3B, 4A, 5B, 6A, 7B), (1B, 2A, 3B, 4A, 5B, 6A, 7C), (1B, 2A, 3B, 4A, 5B, 6B, 7A), (1B, 2A, 3B, 4A, 5B, 6B, 7B), (1B, 2A, 3B, 4A, 5B, 6B, 7C), (1B, 2A, 3B, 4A, 5B, 6C, 7A), (1B, 2A, 3B, 4A, 5B, 6C, 7B), (1B, 2A, 3B, 4A, 5B, 6C, 7C), (1B, 2A, 3B, 4A, 5B, 6D, 7A), (1B, 2A, 3B, 4A, 5B, 6D, 7B), (1B, 2A, 3B, 4A, 5B, 6D, 7C), (1B, 2A, 3B, 4B, 5A, 6A, 7A), (1B, 2A, 3B, 4B, 5A, 6A, 7B), (1B, 2A, 3B, 4B, 5A, 6A, 7C), (1B, 2A, 3B, 4B, 5A, 6B, 7A), (1B, 2A, 3B, 4B, 5A, 6B, 7B), (1B, 2A, 3B, 4B, 5A, 6B, 7C), (1B, 2A, 3B, 4B, 5A, 6C, 7A), (1B, 2A, 3B, 4B, 5A, 6C, 7B), (1B, 2A, 3B, 4B, 5A, 6C, 7C), (1B, 2A, 3B, 4B, 5A, 6D, 7A), (1B, 2A, 3B, 4B, 5A, 6D, 7B), (1B, 2A, 3B, 4B, 5A, 6D, 7C), (1B, 2A, 3B, 4B, 5B, 6A, 7A), (1B, 2A, 3B, 4B, 5B, 6A, 7B), (1B, 2A, 3B, 4B, 5B, 6A, 7C), (1B, 2A, 3B, 4B, 5B, 6B, 7A), (1B, 2A, 3B, 4B, 5B, 6B, 7B), (1B, 2A, 3B, 4B, 5B, 6B, 7C), (1B, 2A, 3B, 4B, 5B, 6C, 7A), (1B, 2A, 3B, 4B, 5B, 6C, 7B), (1B, 2A, 3B, 4B, 5B, 6C, 7C), (1B, 2A, 3B, 4B, 5B, 6D, 7A), (1B, 2A, 3B, 4B, 5B, 6D, 7B), (1B, 2A, 3B, 4B, 5B, 6D, 7C), (1B, 2A, 3B, 4C, 5A, 6A, 7A), (1B, 2A, 3B, 4C, 5A, 6A, 7B), (1B, 2A, 3B, 4C, 5A, 6A, 7C), (1B, 2A, 3B, 4C, 5A, 6B, 7A), (1B, 2A, 3B, 4C, 5A, 6B, 7B), (1B, 2A, 3B, 4C, 5A, 6B, 7C), (1B, 2A, 3B, 4C, 5A, 6C, 7A), (1B, 2A, 3B, 4C, 5A, 6C, 7B), (1B, 2A, 3B, 4C, 5A, 6C, 7C), (1B, 2A, 3B, 4C, 5A, 6D, 7A), (1B, 2A, 3B, 4C, 5A, 6D, 7B), (1B, 2A, 3B, 4C, 5A, 6D, 7C), (1B, 2A, 3B, 4C, 5B, 6A, 7A), (1B, 2A, 3B, 4C, 5B, 6A, 7B), (1B, 2A, 3B, 4C, 5B, 6A, 7C), (1B, 2A, 3B, 4C, 5B, 6B, 7A), (1B, 2A, 3B, 4C, 5B, 6B, 7B), (1B, 2A, 3B, 4C, 5B, 6B, 7C), (1B, 2A, 3B, 4C, 5B, 6C, 7A), (1B, 2A, 3B, 4C, 5B, 6C, 7B), (1B, 2A, 3B, 4C, 5B, 6C, 7C), (1B, 2A, 3B, 4C, 5B, 6D, 7A), (1B, 2A, 3B, 4C, 5B, 6D, 7B), (1B, 2A, 3B, 4C, 5B, 6D, 7C), (1B, 2A, 3B, 4D, 5A, 6A, 7A), (1B, 2A, 3B, 4D, 5A, 6A, 7B), (1B, 2A, 3B, 4D, 5A, 6A, 7C), (1B, 2A, 3B, 4D, 5A, 6B, 7A), (1B, 2A, 3B, 4D, 5A, 6B, 7B), (1B, 2A, 3B, 4D, 5A, 6B, 7C), (1B, 2A, 3B, 4D, 5A, 6C, 7A), (1B, 2A, 3B, 4D, 5A, 6C, 7B), (1B, 2A, 3B, 4D, 5A, 6C, 7C), (1B, 2A, 3B, 4D, 5A, 6D, 7A), (1B, 2A, 3B, 4D, 5A, 6D, 7B), (1B, 2A, 3B, 4D, 5A, 6D, 7C), (1B, 2A, 3B, 4D, 5B, 6A, 7A), (1B, 2A, 3B, 4D, 5B, 6A, 7B), (1B, 2A, 3B, 4D, 5B, 6A, 7C), (1B, 2A, 3B, 4D, 5B, 6B, 7A), (1B, 2A, 3B, 4D, 5B, 6B, 7B), (1B, 2A, 3B, 4D, 5B, 6B, 7C), (1B, 2A, 3B, 4D, 5B, 6C, 7A), (1B, 2A, 3B, 4D, 5B, 6C, 7B), (1B, 2A, 3B, 4D, 5B, 6C, 7C), (1B, 2A, 3B, 4D, 5B, 6D, 7A), (1B, 2A, 3B, 4D, 5B, 6D, 7B), (1B, 2A, 3B, 4D, 5B, 6D, 7C), (1B, 2A, 3B, 4E, 5A, 6A, 7A), (1B, 2A, 3B, 4E, 5A, 6A, 7B), (1B, 2A, 3B, 4E, 5A, 6A, 7C), (1B, 2A, 3B, 4E, 5A, 6B, 7A), (1B, 2A, 3B, 4E, 5A, 6B, 7B), (1B, 2A, 3B, 4E, 5A, 6B, 7C), (1B, 2A, 3B, 4E, 5A, 6C, 7A), (1B, 2A, 3B, 4E, 5A, 6C, 7B), (1B, 2A, 3B, 4E, 5A, 6C, 7C), (1B, 2A, 3B, 4E, 5A, 6D, 7A), (1B, 2A, 3B, 4E, 5A, 6D, 7B), (1B, 2A, 3B, 4E, 5A, 6D, 7C), (1B, 2A, 3B, 4E, 5B, 6A, 7A), (1B, 2A, 3B, 4E, 5B, 6A, 7B), (1B, 2A, 3B, 4E, 5B, 6A, 7C), (1B, 2A, 3B, 4E, 5B, 6B, 7A), (1B, 2A, 3B, 4E, 5B, 6B, 7B), (1B, 2A, 3B, 4E, 5B, 6B, 7C), (1B, 2A, 3B, 4E, 5B, 6C, 7A), (1B, 2A, 3B, 4E, 5B, 6C, 7B), (1B, 2A, 3B, 4E, 5B, 6C, 7C), (1B, 2A, 3B, 4E, 5B, 6D, 7A), (1B, 2A, 3B, 4E, 5B, 6D, 7B), (1B, 2A, 3B, 4E, 5B, 6D, 7C), (1B, 2A, 3C, 4A, 5A, 6A, 7A), (1B, 2A, 3C, 4A, 5A, 6A, 7B), (1B, 2A, 3C, 4A, 5A, 6A, 7C), (1B, 2A, 3C, 4A, 5A, 6B, 7A), (1B, 2A, 3C, 4A, 5A, 6B, 7B), (1B, 2A, 3C, 4A, 5A, 6B, 7C), (1B, 2A, 3C, 4A, 5A, 6C, 7A), (1B, 2A, 3C, 4A, 5A, 6C, 7B), (1B, 2A, 3C, 4A, 5A, 6C, 7C), (1B, 2A, 3C, 4A, 5A, 6D, 7A), (1B, 2A, 3C, 4A, 5A, 6D, 7B), (1B, 2A, 3C, 4A, 5A, 6D, 7C), (1B, 2A, 3C, 4A, 5B, 6A, 7A), (1B, 2A, 3C, 4A, 5B, 6A, 7B), (1B, 2A, 3C, 4A, 5B, 6A, 7C), (1B, 2A, 3C, 4A, 5B, 6B, 7A), (1B, 2A, 3C, 4A, 5B, 6B, 7B), (1B, 2A, 3C, 4A, 5B, 6B, 7C), (1B, 2A, 3C, 4A, 5B, 6C, 7A), (1B, 2A, 3C, 4A, 5B, 6C, 7B), (1B, 2A, 3C, 4A, 5B, 6C, 7C), (1B, 2A, 3C, 4A, 5B, 6D, 7A), (1B, 2A, 3C, 4A, 5B, 6D, 7B), (1B, 2A, 3C, 4A, 5B, 6D, 7C), (1B, 2A, 3C, 4B, 5A, 6A, 7A), (1B, 2A, 3C, 4B, 5A, 6A, 7B), (1B, 2A, 3C, 4B, 5A, 6A, 7C), (1B, 2A, 3C, 4B, 5A, 6B, 7A), (1B, 2A, 3C, 4B, 5A, 6B, 7B), (1B, 2A, 3C, 4B, 5A, 6B, 7C), (1B, 2A, 3C, 4B, 5A, 6C, 7A), (1B, 2A, 3C, 4B, 5A, 6C, 7B), (1B, 2A, 3C, 4B, 5A, 6C, 7C), (1B, 2A, 3C, 4B, 5A, 6D, 7A), (1B, 2A, 3C, 4B, 5A, 6D, 7B), (1B, 2A, 3C, 4B, 5A, 6D, 7C), (1B, 2A, 3C, 4B, 5B, 6A, 7A), (1B, 2A, 3C, 4B, 5B, 6A, 7B), (1B, 2A, 3C, 4B, 5B, 6A, 7C), (1B, 2A, 3C, 4B, 5B, 6B, 7A), (1B, 2A, 3C, 4B, 5B, 6B, 7B), (1B, 2A, 3C, 4B, 5B, 6B, 7C), (1B, 2A, 3C, 4B, 5B, 6C, 7A), (1B, 2A, 3C, 4B, 5B, 6C, 7B), (1B, 2A, 3C, 4B, 5B, 6C, 7C), (1B, 2A, 3C, 4B, 5B, 6D, 7A), (1B, 2A, 3C, 4B, 5B, 6D, 7B), (1B, 2A, 3C, 4B, 5B, 6D, 7C), (1B, 2A, 3C, 4C, 5A, 6A, 7A), (1B, 2A, 3C, 4C, 5A, 6A, 7B), (1B, 2A, 3C, 4C, 5A, 6A, 7C), (1B, 2A, 3C, 4C, 5A, 6B, 7A), (1B, 2A, 3C, 4C, 5A, 6B, 7B), (1B, 2A, 3C, 4C, 5A, 6B, 7C), (1B, 2A, 3C, 4C, 5A, 6C, 7A), (1B, 2A, 3C, 4C, 5A, 6C, 7B), (1B, 2A, 3C, 4C, 5A, 6C, 7C), (1B, 2A, 3C, 4C, 5A, 6D, 7A), (1B, 2A, 3C, 4C, 5A, 6D, 7B), (1B, 2A, 3C, 4C, 5A, 6D, 7C), (1B, 2A, 3C, 4C, 5B, 6A, 7A), (1B, 2A, 3C, 4C, 5B, 6A, 7B), (1B, 2A, 3C, 4C, 5B, 6A, 7C), (1B, 2A, 3C, 4C, 5B, 6B, 7A), (1B, 2A, 3C, 4C, 5B, 6B, 7B), (1B, 2A, 3C, 4C, 5B, 6B, 7C), (1B, 2A, 3C, 4C, 5B, 6C, 7A), (1B, 2A, 3C, 4C, 5B, 6C, 7B), (1B, 2A, 3C, 4C, 5B, 6C, 7C), (1B, 2A, 3C, 4C, 5B, 6D, 7A), (1B, 2A, 3C, 4C, 5B, 6D, 7B), (1B, 2A, 3C, 4C, 5B, 6D, 7C), (1B, 2A, 3C, 4D, 5A, 6A, 7A), (1B, 2A, 3C, 4D, 5A, 6A, 7B), (1B, 2A, 3C, 4D, 5A, 6A, 7C), (1B, 2A, 3C, 4D, 5A, 6B, 7A), (1B, 2A, 3C, 4D, 5A, 6B, 7B), (1B, 2A, 3C, 4D, 5A, 6B, 7C), (1B, 2A, 3C, 4D, 5A, 6C, 7A), (1B, 2A, 3C, 4D, 5A, 6C, 7B), (1B, 2A, 3C, 4D, 5A, 6C, 7C), (1B, 2A, 3C, 4D, 5A, 6D, 7A), (1B, 2A, 3C, 4D, 5A, 6D, 7B), (1B, 2A, 3C, 4D, 5A, 6D, 7C), (1B, 2A, 3C, 4D, 5B, 6A, 7A), (1B, 2A, 3C, 4D, 5B, 6A, 7B), (1B, 2A, 3C, 4D, 5B, 6A, 7C), (1B, 2A, 3C, 4D, 5B, 6B, 7A), (1B, 2A, 3C, 4D, 5B, 6B, 7B), (1B, 2A, 3C, 4D, 5B, 6B, 7C), (1B, 2A, 3C, 4D, 5B, 6C, 7A), (1B, 2A, 3C, 4D, 5B, 6C, 7B), (1B, 2A, 3C, 4D, 5B, 6C, 7C), (1B, 2A, 3C, 4D, 5B, 6D, 7A), (1B, 2A, 3C, 4D, 5B, 6D, 7B), (1B, 2A, 3C, 4D, 5B, 6D, 7C), (1B, 2A, 3C, 4E, 5A, 6A, 7A), (1B, 2A, 3C, 4E, 5A, 6A, 7B), (1B, 2A, 3C, 4E, 5A, 6A, 7C), (1B, 2A, 3C, 4E, 5A, 6B, 7A), (1B, 2A, 3C, 4E, 5A, 6B, 7B), (1B, 2A, 3C, 4E, 5A, 6B, 7C), (1B, 2A, 3C, 4E, 5A, 6C, 7A), (1B, 2A, 3C, 4E, 5A, 6C, 7B), (1B, 2A, 3C, 4E, 5A, 6C, 7C), (1B, 2A, 3C, 4E, 5A, 6D, 7A), (1B, 2A, 3C, 4E, 5A, 6D, 7B), (1B, 2A, 3C, 4E, 5A, 6D, 7C), (1B, 2A, 3C, 4E, 5B, 6A, 7A), (1B, 2A, 3C, 4E, 5B, 6A, 7B), (1B, 2A, 3C, 4E, 5B, 6A, 7C), (1B, 2A, 3C, 4E, 5B, 6B, 7A), (1B, 2A, 3C, 4E, 5B, 6B, 7B), (1B, 2A, 3C, 4E, 5B, 6B, 7C), (1B, 2A, 3C, 4E, 5B, 6C, 7A), (1B, 2A, 3C, 4E, 5B, 6C, 7B), (1B, 2A, 3C, 4E, 5B, 6C, 7C), (1B, 2A, 3C, 4E, 5B, 6D, 7A), (1B, 2A, 3C, 4E, 5B, 6D, 7B), (1B, 2A, 3C, 4E, 5B, 6D, 7C), (1B, 2A, 3D, 4A, 5A, 6A, 7A), (1B, 2A, 3D, 4A, 5A, 6A, 7B), (1B, 2A, 3D, 4A, 5A, 6A, 7C), (1B, 2A, 3D, 4A, 5A, 6B, 7A), (1B, 2A, 3D, 4A, 5A, 6B, 7B), (1B, 2A, 3D, 4A, 5A, 6B, 7C), (1B, 2A, 3D, 4A, 5A, 6C, 7A), (1B, 2A, 3D, 4A, 5A, 6C, 7B), (1B, 2A, 3D, 4A, 5A, 6C, 7C), (1B, 2A, 3D, 4A, 5A, 6D, 7A), (1B, 2A, 3D, 4A, 5A, 6D, 7B), (1B, 2A, 3D, 4A, 5A, 6D, 7C), (1B, 2A, 3D, 4A, 5B, 6A, 7A), (1B, 2A, 3D, 4A, 5B, 6A, 7B), (1B, 2A, 3D, 4A, 5B, 6A, 7C), (1B, 2A, 3D, 4A, 5B, 6B, 7A), (1B, 2A, 3D, 4A, 5B, 6B, 7B), (1B, 2A, 3D, 4A, 5B, 6B, 7C), (1B, 2A, 3D, 4A, 5B, 6C, 7A), (1B, 2A, 3D, 4A, 5B, 6C, 7B), (1B, 2A, 3D, 4A, 5B, 6C, 7C), (1B, 2A, 3D, 4A, 5B, 6D, 7A), (1B, 2A, 3D, 4A, 5B, 6D, 7B), (1B, 2A, 3D, 4A, 5B, 6D, 7C), (1B, 2A, 3D, 4B, 5A, 6A, 7A), (1B, 2A, 3D, 4B, 5A, 6A, 7B), (1B, 2A, 3D, 4B, 5A, 6A, 7C), (1B, 2A, 3D, 4B, 5A, 6B, 7A), (1B, 2A, 3D, 4B, 5A, 6B, 7B), (1B, 2A, 3D, 4B, 5A, 6B, 7C), (1B, 2A, 3D, 4B, 5A, 6C, 7A), (1B, 2A, 3D, 4B, 5A, 6C, 7B), (1B, 2A, 3D, 4B, 5A, 6C, 7C), (1B, 2A, 3D, 4B, 5A, 6D, 7A), (1B, 2A, 3D, 4B, 5A, 6D, 7B), (1B, 2A, 3D, 4B, 5A, 6D, 7C), (1B, 2A, 3D, 4B, 5B, 6A, 7A), (1B, 2A, 3D, 4B, 5B, 6A, 7B), (1B, 2A, 3D, 4B, 5B, 6A, 7C), (1B, 2A, 3D, 4B, 5B, 6B, 7A), (1B, 2A, 3D, 4B, 5B, 6B, 7B), (1B, 2A, 3D, 4B, 5B, 6B, 7C), (1B, 2A, 3D, 4B, 5B, 6C, 7A), (1B, 2A, 3D, 4B, 5B, 6C, 7B), (1B, 2A, 3D, 4B, 5B, 6C, 7C), (1B, 2A, 3D, 4B, 5B, 6D, 7A), (1B, 2A, 3D, 4B, 5B, 6D, 7B), (1B, 2A, 3D, 4B, 5B, 6D, 7C), (1B, 2A, 3D, 4C, 5A, 6A, 7A), (1B, 2A, 3D, 4C, 5A, 6A, 7B), (1B, 2A, 3D, 4C, 5A, 6A, 7C), (1B, 2A, 3D, 4C, 5A, 6B, 7A), (1B, 2A, 3D, 4C, 5A, 6B, 7B), (1B, 2A, 3D, 4C, 5A, 6B, 7C), (1B, 2A, 3D, 4C, 5A, 6C, 7A), (1B, 2A, 3D, 4C, 5A, 6C, 7B), (1B, 2A, 3D, 4C, 5A, 6C, 7C), (1B, 2A, 3D, 4C, 5A, 6D, 7A), (1B, 2A, 3D, 4C, 5A, 6D, 7B), (1B, 2A, 3D, 4C, 5A, 6D, 7C), (1B, 2A, 3D, 4C, 5B, 6A, 7A), (1B, 2A, 3D, 4C, 5B, 6A, 7B), (1B, 2A, 3D, 4C, 5B, 6A, 7C), (1B, 2A, 3D, 4C, 5B, 6B, 7A), (1B, 2A, 3D, 4C, 5B, 6B, 7B), (1B, 2A, 3D, 4C, 5B, 6B, 7C), (1B, 2A, 3D, 4C, 5B, 6C, 7A), (1B, 2A, 3D, 4C, 5B, 6C, 7B), (1B, 2A, 3D, 4C, 5B, 6C, 7C), (1B, 2A, 3D, 4C, 5B, 6D, 7A), (1B, 2A, 3D, 4C, 5B, 6D, 7B), (1B, 2A, 3D, 4C, 5B, 6D, 7C), (1B, 2A, 3D, 4D, 5A, 6A, 7A), (1B, 2A, 3D, 4D, 5A, 6A, 7B), (1B, 2A, 3D, 4D, 5A, 6A, 7C), (1B, 2A, 3D, 4D, 5A, 6B, 7A), (1B, 2A, 3D, 4D, 5A, 6B, 7B), (1B, 2A, 3D, 4D, 5A, 6B, 7C), (1B, 2A, 3D, 4D, 5A, 6C, 7A), (1B, 2A, 3D, 4D, 5A, 6C, 7B), (1B, 2A, 3D, 4D, 5A, 6C, 7C), (1B, 2A, 3D, 4D, 5A, 6D, 7A), (1B, 2A, 3D, 4D, 5A, 6D, 7B), (1B, 2A, 3D, 4D, 5A, 6D, 7C), (1B, 2A, 3D, 4D, 5B, 6A, 7A), (1B, 2A, 3D, 4D, 5B, 6A, 7B), (1B, 2A, 3D, 4D, 5B, 6A, 7C), (1B, 2A, 3D, 4D, 5B, 6B, 7A), (1B, 2A, 3D, 4D, 5B, 6B, 7B), (1B, 2A, 3D, 4D, 5B, 6B, 7C), (1B, 2A, 3D, 4D, 5B, 6C, 7A), (1B, 2A, 3D, 4D, 5B, 6C, 7B), (1B, 2A, 3D, 4D, 5B, 6C, 7C), (1B, 2A, 3D, 4D, 5B, 6D, 7A), (1B, 2A, 3D, 4D, 5B, 6D, 7B), (1B, 2A, 3D, 4D, 5B, 6D, 7C), (1B, 2A, 3D, 4E, 5A, 6A, 7A), (1B, 2A, 3D, 4E, 5A, 6A, 7B), (1B, 2A, 3D, 4E, 5A, 6A, 7C), (1B, 2A, 3D, 4E, 5A, 6B, 7A), (1B, 2A, 3D, 4E, 5A, 6B, 7B), (1B, 2A, 3D, 4E, 5A, 6B, 7C), (1B, 2A, 3D, 4E, 5A, 6C, 7A), (1B, 2A, 3D, 4E, 5A, 6C, 7B), (1B, 2A, 3D, 4E, 5A, 6C, 7C), (1B, 2A, 3D, 4E, 5A, 6D, 7A), (1B, 2A, 3D, 4E, 5A, 6D, 7B), (1B, 2A, 3D, 4E, 5A, 6D, 7C), (1B, 2A, 3D, 4E, 5B, 6A, 7A), (1B, 2A, 3D, 4E, 5B, 6A, 7B), (1B, 2A, 3D, 4E, 5B, 6A, 7C), (1B, 2A, 3D, 4E, 5B, 6B, 7A), (1B, 2A, 3D, 4E, 5B, 6B, 7B), (1B, 2A, 3D, 4E, 5B, 6B, 7C), (1B, 2A, 3D, 4E, 5B, 6C, 7A), (1B, 2A, 3D, 4E, 5B, 6C, 7B), (1B, 2A, 3D, 4E, 5B, 6C, 7C), (1B, 2A, 3D, 4E, 5B, 6D, 7A), (1B, 2A, 3D, 4E, 5B, 6D, 7B), (1B, 2A, 3D, 4E, 5B, 6D, 7C), (1B, 2A, 3E, 4A, 5A, 6A, 7A), (1B, 2A, 3E, 4A, 5A, 6A, 7B), (1B, 2A, 3E, 4A, 5A, 6A, 7C), (1B, 2A, 3E, 4A, 5A, 6B, 7A), (1B, 2A, 3E, 4A, 5A, 6B, 7B), (1B, 2A, 3E, 4A, 5A, 6B, 7C), (1B, 2A, 3E, 4A, 5A, 6C, 7A), (1B, 2A, 3E, 4A, 5A, 6C, 71B), (1B, 2A, 3E, 4A, 5A, 6C, 7C), (1B, 2A, 3E, 4A, 5A, 6D, 7A), (1B, 2A, 3E, 4A, 5A, 6D, 7B), (1B, 2A, 3E, 4A, 5A, 6D, 7C), (1B, 2A, 3E, 4A, 5B, 6A, 7A), (1B, 2A, 3E, 4A, 5B, 6A, 7B), (1B, 2A, 3E, 4A, 5B, 6A, 7C), (1B, 2A, 3E, 4A, 5B, 6B, 7A), (1B, 2A, 3E, 4A, 5B, 6B, 7B), (1B, 2A, 3E, 4A, 5B, 6B, 7C), (1B, 2A, 3E, 4A, 5B, 6C, 7A), (1B, 2A, 3E, 4A, 5B, 6C, 7B), (1B, 2A, 3E, 4A, 5B, 6C, 7C), (1B, 2A, 3E, 4A, 5B, 6D, 7A), (1B, 2A, 3E, 4A, 5B, 6D, 7B), (1B, 2A, 3E, 4A, 5B, 6D, 7C), (1B, 2A, 3E, 4B, 5A, 6A, 7A), (1B, 2A, 3E, 4B, 5A, 6A, 7B), (1B, 2A, 3E, 4B, 5A, 6A, 7C), (1B, 2A, 3E, 4B, 5A, 6B, 7A), (1B, 2A, 3E, 4B, 5A, 6B, 7B), (1B, 2A, 3E, 4B, 5A, 6B, 7C), (1B, 2A, 3E, 4B, 5A, 6C, 7A), (1B, 2A, 3E, 4B, 5A, 6C, 7B), (1B, 2A, 3E, 4B, 5A, 6C, 7C), (1B, 2A, 3E, 4B, 5A, 6D, 7A), (1B, 2A, 3E, 4B, 5A, 6D, 7B), (1B, 2A, 3E, 4B, 5A, 6D, 7C), (1B, 2A, 3E, 4B, 5B, 6A, 7A), (1B, 2A, 3E, 4B, 5B, 6A, 7B), (1B, 2A, 3E, 4B, 5B, 6A, 7C), (1B, 2A, 3E, 4B, 5B, 6B, 7A), (1B, 2A, 3E, 4B, 5B, 6B, 7B), (1B, 2A, 3E, 4B, 5B, 6B, 7C), (1B, 2A, 3E, 4B, 5B, 6C, 7A), (1B, 2A, 3E, 4B, 5B, 6C, 7B), (1B, 2A, 3E, 4B, 5B, 6C, 7C), (1B, 2A, 3E, 4B, 5B, 6D, 7A), (1B, 2A, 3E, 4B, 5B, 6D, 7B), (1B, 2A, 3E, 4B, 5B, 6D, 7C), (1B, 2A, 3E, 4C, 5A, 6A, 7A), (1B, 2A, 3E, 4C, 5A, 6A, 7B), (1B, 2A, 3E, 4C, 5A, 6A, 7C), (1B, 2A, 3E, 4C, 5A, 6B, 7A), (1B, 2A, 3E, 4C, 5A, 6B, 7B), (1B, 2A, 3E, 4C, 5A, 6B, 7C), (1B, 2A, 3E, 4C, 5A, 6C, 7A), (1B, 2A, 3E, 4C, 5A, 6C, 7B), (1B, 2A, 3E, 4C, 5A, 6C, 7C), (1B, 2A, 3E, 4C, 5A, 6D, 7A), (1B, 2A, 3E, 4C, 5A, 6D, 7B), (1B, 2A, 3E, 4C, 5A, 6D, 7C), (1B, 2A, 3E, 4C, 5B, 6A, 7A), (1B, 2A, 3E, 4C, 5B, 6A, 7B), (1B, 2A, 3E, 4C, 5B, 6A, 7C), (1B, 2A, 3E, 4C, 5B, 6B, 7A), (1B, 2A, 3E, 4C, 5B, 6B, 7B), (1B, 2A, 3E, 4C, 5B, 6B, 7C), (1B, 2A, 3E, 4C, 5B, 6C, 7A), (1B, 2A, 3E, 4C, 5B, 6C, 7B), (1B, 2A, 3E, 4C, 5B, 6C, 7C), (1B, 2A, 3E, 4C, 5B, 6D, 7A), (1B, 2A, 3E, 4C, 5B, 6D, 7B), (1B, 2A, 3E, 4C, 5B, 6D, 7C), (1B, 2A, 3E, 4D, 5A, 6A, 7A), (1B, 2A, 3E, 4D, 5A, 6A, 7B), (1B, 2A, 3E, 4D, 5A, 6A, 7C), (1B, 2A, 3E, 4D, 5A, 6B, 7A), (1B, 2A, 3E, 4D, 5A, 6B, 7B), (1B, 2A, 3E, 4D, 5A, 6B, 7C), (1B, 2A, 3E, 4D, 5A, 6C, 7A), (1B, 2A, 3E, 4D, 5A, 6C, 7B), (1B, 2A, 3E, 4D, 5A, 6C, 7C), (1B, 2A, 3E, 4D, 5A, 6D, 7A), (1B, 2A, 3E, 4D, 5A, 6D, 7B), (1B, 2A, 3E, 4D, 5A, 6D, 7C), (1B, 2A, 3E, 4D, 5B, 6A, 7A), (1B, 2A, 3E, 4D, 5B, 6A, 7B), (1B, 2A, 3E, 4D, 5B, 6A, 7C), (1B, 2A, 3E, 4D, 5B, 6B, 7A), (1B, 2A, 3E, 4D, 5B, 6B, 7B), (1B, 2A, 3E, 4D, 5B, 6B, 7C), (1B, 2A, 3E, 4D, 5B, 6C, 7A), (1B, 2A, 3E, 4D, 5B, 6C, 7B), (1B, 2A, 3E, 4D, 5B, 6C, 7C), (1B, 2A, 3E, 4D, 5B, 6D, 7A), (1B, 2A, 3E, 4D, 5B, 6D, 7B), (1B, 2A, 3E, 4D, 5B, 6D, 7C), (1B, 2A, 3E, 4E, 5A, 6A, 7A), (1B, 2A, 3E, 4E, 5A, 6A, 7B), (1B, 2A, 3E, 4E, 5A, 6A, 7C), (1B, 2A, 3E, 4E, 5A, 6B, 7A), (1B, 2A, 3E, 4E, 5A, 6B, 7B), (1B, 2A, 3E, 4E, 5A, 6B, 7C), (1B, 2A, 3E, 4E, 5A, 6C, 7A), (1B, 2A, 3E, 4E, 5A, 6C, 7B), (1B, 2A, 3E, 4E, 5A, 6C, 7C), (1B, 2A, 3E, 4E, 5A, 6D, 7A), (1B, 2A, 3E, 4E, 5A, 6D, 7B), (1B, 2A, 3E, 4E, 5A, 6D, 7C), (1B, 2A, 3E, 4E, 5B, 6A, 7A), (1B, 2A, 3E, 4E, 5B, 6A, 7B), (1B, 2A, 3E, 4E, 5B, 6A, 7C), (1B, 2A, 3E, 4E, 5B, 6B, 7A), (1B, 2A, 3E, 4E, 5B, 6B, 7B), (1B, 2A, 3E, 4E, 5B, 6B, 7C), (1B, 2A, 3E, 4E, 5B, 6C, 7A), (1B, 2A, 3E, 4E, 5B, 6C, 7B), (1B, 2A, 3E, 4E, 5B, 6C, 7C), (1B, 2A, 3E, 4E, 5B, 6D, 7A), (1B, 2A, 3E, 4E, 5B, 6D, 7B), (1B, 2A, 3E, 4E, 5B, 6D, 7C), (1B, 2B, 3A, 4A, 5A, 6A, 7A), (1B, 2B, 3A, 4A, 5A, 6A, 7B), (1B, 2B, 3A, 4A, 5A, 6A, 7C), (1B, 2B, 3A, 4A, 5A, 6B, 7A), (1B, 2B, 3A, 4A, 5A, 6B, 7B), (1B, 2B, 3A, 4A, 5A, 6B, 7C), (1B, 2B, 3A, 4A, 5A, 6C, 7A), (1B, 2B, 3A, 4A, 5A, 6C, 7B), (1B, 2B, 3A, 4A, 5A, 6C, 7C), (1B, 2B, 3A, 4A, 5A, 6D, 7A), (1B, 2B, 3A, 4A, 5A, 6D, 7B), (1B, 2B, 3A, 4A, 5A, 6D, 7C), (1B, 2B, 3A, 4A, 5B, 6A, 7A), (1B, 2B, 3A, 4A, 5B, 6A, 7B), (1B, 2B, 3A, 4A, 5B, 6A, 7C), (1B, 2B, 3A, 4A, 5B, 6B, 7A), (1B, 2B, 3A, 4A, 5B, 6B, 7B), (1B, 2B, 3A, 4A, 5B, 6B, 7C), (1B, 2B, 3A, 4A, 5B, 6C, 7A), (1B, 2B, 3A, 4A, 5B, 6C, 7B), (1B, 2B, 3A, 4A, 5B, 6C, 7C), (1B, 2B, 3A, 4A, 5B, 6D, 7A), (1B, 2B, 3A, 4A, 5B, 6D, 7B), (1B, 2B, 3A, 4A, 5B, 6D, 7C), (1B, 2B, 3A, 4B, 5A, 6A, 7A), (1B, 2B, 3A, 4B, 5A, 6A, 7B), (1B, 2B, 3A, 4B, 5A, 6A, 7C), (1B, 2B, 3A, 4B, 5A, 6B, 7A), (1B, 2B, 3A, 4B, 5A, 6B, 7B), (1B, 2B, 3A, 4B, 5A, 6B, 7C), (1B, 2B, 3A, 4B, 5A, 6C, 7A), (1B, 2B, 3A, 4B, 5A, 6C, 7B), (1B, 2B, 3A, 4B, 5A, 6C, 7C), (1B, 2B, 3A, 4B, 5A, 6D, 7A), (1B, 2B, 3A, 4B, 5A, 6D, 7B), (1B, 2B, 3A, 4B, 5A, 6D, 7C), (1B, 2B, 3A, 4B, 5B, 6A, 7A), (1B, 2B, 3A, 4B, 5B, 6A, 7B), (1B, 2B, 3A, 4B, 5B, 6A, 7C), (1B, 2B, 3A, 4B, 5B, 6B, 7A), (1B, 2B, 3A, 4B, 5B, 6B, 7B), (1B, 2B, 3A, 4B, 5B, 6B, 7C), (1B, 2B, 3A, 4B, 5B, 6C, 7A), (1B, 2B, 3A, 4B, 5B, 6C, 7B), (1B, 2B, 3A, 4B, 5B, 6C, 7C), (1B, 2B, 3A, 4B, 5B, 6D, 7A), (1B, 2B, 3A, 4B, 5B, 6D, 7B), (1B, 2B, 3A, 4B, 5B, 6D, 7C), (1B, 2B, 3A, 4C, 5A, 6A, 7A), (1B, 2B, 3A, 4C, 5A, 6A, 7B), (1B, 2B, 3A, 4C, 5A, 6A, 7C), (1B, 2B, 3A, 4C, 5A, 6B, 7A), (1B, 2B, 3A, 4C, 5A, 6B, 7B), (1B, 2B, 3A, 4C, 5A, 6B, 7C), (1B, 2B, 3A, 4C, 5A, 6C, 7A), (1B, 2B, 3A, 4C, 5A, 6C, 7B), (1B, 2B, 3A, 4C, 5A, 6C, 7C), (1B, 2B, 3A, 4C, 5A, 6D, 7A), (1B, 2B, 3A, 4C, 5A, 6D, 7B), (1B, 2B, 3A, 4C, 5A, 6D, 7C), (1B, 2B, 3A, 4C, 5B, 6A, 7A), (1B, 2B, 3A, 4C, 5B, 6A, 7B), (1B, 2B, 3A, 4C, 5B, 6A, 7C), (1B, 2B, 3A, 4C, 5B, 6B, 7A), (1B, 2B, 3A, 4C, 5B, 6B, 7B), (1B, 2B, 3A, 4C, 5B, 6B, 7C), (1B, 2B, 3A, 4C, 5B, 6C, 7A), (1B, 2B, 3A, 4C, 5B, 6C, 7B), (1B, 2B, 3A, 4C, 5B, 6C, 7C), (1B, 2B, 3A, 4C, 5B, 6D, 7A), (1B, 2B, 3A, 4C, 5B, 6D, 7B), (1B, 2B, 3A, 4C, 5B, 6D, 7C), (1B, 2B, 3A, 4D, 5A, 6A, 7A), (1B, 2B, 3A, 4D, 5A, 6A, 7B), (1B, 2B, 3A, 4D, 5A, 6A, 7C), (1B, 2B, 3A, 4D, 5A, 6B, 7A), (1B, 2B, 3A, 4D, 5A, 6B, 7B), (1B, 2B, 3A, 4D, 5A, 6B, 7C), (1B, 2B, 3A, 4D, 5A, 6C, 7A), (1B, 2B, 3A, 4D, 5A, 6C, 7B), (1B, 2B, 3A, 4D, 5A, 6C, 7C), (1B, 2B, 3A, 4D, 5A, 6D, 7A), (1B, 2B, 3A, 4D, 5A, 6D, 7B), (1B, 2B, 3A, 4D, 5A, 6D, 7C), (1B, 2B, 3A, 4D, 5B, 6A, 7A), (1B, 2B, 3A, 4D, 5B, 6A, 7B), (1B, 2B, 3A, 4D, 5B, 6A, 7C), (1B, 2B, 3A, 4D, 5B, 6B, 7A), (1B, 2B, 3A, 4D, 5B, 6B, 7B), (1B, 2B, 3A, 4D, 5B, 6B, 7C), (1B, 2B, 3A, 4D, 5B, 6C, 7A), (1B, 2B, 3A, 4D, 5B, 6C, 7B), (1B, 2B, 3A, 4D, 5B, 6C, 7C), (1B, 2B, 3A, 4D, 5B, 6D, 7A), (1B, 2B, 3A, 4D, 5B, 6D, 7B), (1B, 2B, 3A, 4D, 5B, 6D, 7C), (1B, 2B, 3A, 4E, 5A, 6A, 7A), (1B, 2B, 3A, 4E, 5A, 6A, 7B), (1B, 2B, 3A, 4E, 5A, 6A, 7C), (1B, 2B, 3A, 4E, 5A, 6B, 7A), (1B, 2B, 3A, 4E, 5A, 6B, 7B), (1B, 2B, 3A, 4E, 5A, 6B, 7C), (1B, 2B, 3A, 4E, 5A, 6C, 7A), (1B, 2B, 3A, 4E, 5A, 6C, 7B), (1B, 2B, 3A, 4E, 5A, 6C, 7C), (1B, 2B, 3A, 4E, 5A, 6D, 7A), (1B, 2B, 3A, 4E, 5A, 6D, 7B), (1B, 2B, 3A, 4E, 5A, 6D, 7C), (1B, 2B, 3A, 4E, 5B, 6A, 7A), (1B, 2B, 3A, 4E, 5B, 6A, 7B), (1B, 2B, 3A, 4E, 5B, 6A, 7C), (1B, 2B, 3A, 4E, 5B, 6B, 7A), (1B, 2B, 3A, 4E, 5B, 6B, 7B), (1B, 2B, 3A, 4E, 5B, 6B, 7C), (1B, 2B, 3A, 4E, 5B, 6C, 7A), (1B, 2B, 3A, 4E, 5B, 6C, 7B), (1B, 2B, 3A, 4E, 5B, 6C, 7C), (1B, 2B, 3A, 4E, 5B, 6D, 7A), (1B, 2B, 3A, 4E, 5B, 6D, 7B), (1B, 2B, 3A, 4E, 5B, 6D, 7C), (1B, 2B, 3B, 4A, 5A, 6A, 7A), (1B, 2B, 3B, 4A, 5A, 6A, 7B), (1B, 2B, 3B, 4A, 5A, 6A, 7C), (1B, 2B, 3B, 4A, 5A, 6B, 7A), (1B, 2B, 3B, 4A, 5A, 6B, 7B), (1B, 2B, 3B, 4A, 5A, 6B, 7C), (1B, 2B, 3B, 4A, 5A, 6C, 7A), (1B, 2B, 3B, 4A, 5A, 6C, 7B), (1B, 2B, 3B, 4A, 5A, 6C, 7C), (1B, 2B, 3B, 4A, 5A, 6D, 7A), (1B, 2B, 3B, 4A, 5A, 6D, 7B), (1B, 2B, 3B, 4A, 5A, 6D, 7C), (1B, 2B, 3B, 4A, 5B, 6A, 7A), (1B, 2B, 3B, 4A, 5B, 6A, 7B), (1B, 2B, 3B, 4A, 5B, 6A, 7C), (1B, 2B, 3B, 4A, 5B, 6B, 7A), (1B, 2B, 3B, 4A, 5B, 6B, 7B), (1B, 2B, 3B, 4A, 5B, 6B, 7C), (1B, 2B, 3B, 4A, 5B, 6C, 7A), (1B, 2B, 3B, 4A, 5B, 6C, 7B), (1B, 2B, 3B, 4A, 5B, 6C, 7C), (1B, 2B, 3B, 4A, 5B, 6D, 7A), (1B, 2B, 3B, 4A, 5B, 6D, 7B), (1B, 2B, 3B, 4A, 5B, 6D, 7C), (1B, 2B, 3B, 4B, 5A, 6A, 7A), (1B, 2B, 3B, 4B, 5A, 6A, 7B), (1B, 2B, 3B, 4B, 5A, 6A, 7C), (1B, 2B, 3B, 4B, 5A, 6B, 7A), (1B, 2B, 3B, 4B, 5A, 6B, 7B), (1B, 2B, 3B, 4B, 5A, 6B, 7C), (1B, 2B, 3B, 4B, 5A, 6C, 7A), (1B, 2B, 3B, 4B, 5A, 6C, 7B), (1B, 2B, 3B, 4B, 5A, 6C, 7C), (1B, 2B, 3B, 4B, 5A, 6D, 7A), (1B, 2B, 3B, 4B, 5A, 6D, 7B), (1B, 2B, 3B, 4B, 5A, 6D, 7C), (1B, 2B, 3B, 4B, 5B, 6A, 7A), (1B, 2B, 3B, 4B, 5B, 6A, 7B), (1B, 2B, 3B, 4B, 5B, 6A, 7C), (1B, 2B, 3B, 4B, 5B, 6B, 7A), (1B, 2B, 3B, 4B, 5B, 6B, 7B), (1B, 2B, 3B, 4B, 5B, 6B, 7C), (1B, 2B, 3B, 4B, 5B, 6C, 7A), (1B, 2B, 3B, 4B, 5B, 6C, 7B), (1B, 2B, 3B, 4B, 5B, 6C, 7C), (1B, 2B, 3B, 4B, 5B, 6D, 7A), (1B, 2B, 3B, 4B, 5B, 6D, 7B), (1B, 2B, 3B, 4B, 5B, 6D, 7C), (1B, 2B, 3B, 4C, 5A, 6A, 7A), (1B, 2B, 3B, 4C, 5A, 6A, 7B), (1B, 2B, 3B, 4C, 5A, 6A, 7C), (1B, 2B, 3B, 4C, 5A, 6B, 7A), (1B, 2B, 3B, 4C, 5A, 6B, 7B), (1B, 2B, 3B, 4C, 5A, 6B, 7C), (1B, 2B, 3B, 4C, 5A, 6C, 7A), (1B, 2B, 3B, 4C, 5A, 6C, 7B), (1B, 2B, 3B, 4C, 5A, 6C, 7C), (1B, 2B, 3B, 4C, 5A, 6D, 7A), (1B, 2B, 3B, 4C, 5A, 6D, 7B), (1B, 2B, 3B, 4C, 5A, 6D, 7C), (1B, 2B, 3B, 4C, 5B, 6A, 7A), (1B, 2B, 3B, 4C, 5B, 6A, 7B), (1B, 2B, 3B, 4C, 5B, 6A, 7C), (1B, 2B, 3B, 4C, 5B, 6B, 7A), (1B, 2B, 3B, 4C, 5B, 6B, 7B), (1B, 2B, 3B, 4C, 5B, 6B, 7C), (1B, 2B, 3B, 4C, 5B, 6C, 7A), (1B, 2B, 3B, 4C, 5B, 6C, 7B), (1B, 2B, 3B, 4C, 5B, 6C, 7C), (1B, 2B, 3B, 4C, 5B, 6D, 7A), (1B, 2B, 3B, 4C, 5B, 6D, 7B), (1B, 2B, 3B, 4C, 5B, 6D, 7C), (1B, 2B, 3B, 4D, 5A, 6A, 7A), (6B, 2B, 3B, 4D, 5A, 6A, 7B), (1B, 2B, 3B, 4D, 5A, 6A, 7C), (1B, 2B, 3B, 4D, 5A, 6B, 7A), (1B, 2B, 3B, 4D, 5A, 6B, 7B), (1B, 2B, 3B, 4D, 5A, 6B, 7C), (1B, 2B, 3B, 4D, 5A, 6C, 7A), (1B, 2B, 3B, 4D, 5A, 6C, 7B), (1B, 2B, 3B, 4D, 5A, 6C, 7C), (1B, 2B, 3B, 4D, 5A, 6D, 7A), (1B, 2B, 3B, 4D, 5A, 6D, 7B), (1B, 2B, 3B, 4D, 5A, 6D, 7C), (1B, 2B, 3B, 4D, 5B, 6A, 7A), (1B, 2B, 3B, 4D, 5B, 6A, 7B), (1B, 2B, 3B, 4D, 5B, 6A, 7C), (1B, 2B, 3B, 4D, 5B, 6B, 7A), (1B, 2B, 3B, 4D, 5B, 6B, 7B), (1B, 2B, 3B, 4D, 5B, 6B, 7C), (1B, 2B, 3B, 4D, 5B, 6C, 7A), (1B, 2B, 3B, 4D, 5B, 6C, 7B), (1B, 2B, 3B, 4D, 5B, 6C, 7C), (1B, 2B, 3B, 4D, 5B, 6D, 7A), (1B, 2B, 3B, 4D, 5B, 6D, 7B), (1B, 2B, 3B, 4D, 5B, 6D, 7C), (1B, 2B, 3B, 4E, 5A, 6A, 7A), (1B, 2B, 3B, 4E, 5A, 6A, 7B), (1B, 2B, 3B, 4E, 5A, 6A, 7C), (1B, 2B, 3B, 4E, 5A, 6B, 7A), (1B, 2B, 3B, 4E, 5A, 6B, 7B), (1B, 2B, 3B, 4E, 5A, 6B, 7C), (1B, 2B, 3B, 4E, 5A, 6C, 7A), (1B, 2B, 3B, 4E, 5A, 6C, 7B), (1B, 2B, 3B, 4E, 5A, 6C, 7C), (1B, 2B, 3B, 4E, 5A, 6D, 7A), (1B, 2B, 3B, 4E, 5A, 6D, 7B), (1B, 2B, 3B, 4E, 5A, 6D, 7C), (1B, 2B, 3B, 4E, 5B, 6A, 7A), (1B, 2B, 3B, 4E, 5B, 6A, 7B), (1B, 2B, 3B, 4E, 5B, 6A, 7C), (1B, 2B, 3B, 4E, 5B, 6B, 7A), (1B, 2B, 3B, 4E, 5B, 6B, 7B), (1B, 2B, 3B, 4E, 5B, 6B, 7C), (1B, 2B, 3B, 4E, 5B, 6C, 7A), (1B, 2B, 3B, 4E, 5B, 6C, 7B), (1B, 2B, 3B, 4E, 5B, 6C, 7C), (1B, 2B, 3B, 4E, 5B, 6D, 7A), (1B, 2B, 3B, 4E, 5B, 6D, 7B), (1B, 2B, 3B, 4E, 5B, 6D, 7C), (1B, 2B, 3C, 4A, 5A, 6A, 7A), (1B, 2B, 3C, 4A, 5A, 6A, 7B), (1B, 2B, 3C, 4A, 5A, 6A, 7C), (1B, 2B, 3C, 4A, 5A, 6B, 7A), (1B, 2B, 3C, 4A, 5A, 6B, 7B), (1B, 2B, 3C, 4A, 5A, 6B, 7C), (1B, 2B, 3C, 4A, 5A, 6C, 7A), (1B, 2B, 3C, 4A, 5A, 6C, 7B), (1B, 2B, 3C, 4A, 5A, 6C, 7C), (1B, 2B, 3C, 4A, 5A, 6D, 7A), (1B, 2B, 3C, 4A, 5A, 6D, 7B), (1B, 2B, 3C, 4A, 5A, 6D, 7C), (1B, 2B, 3C, 4A, 5B, 6A, 7A), (1B, 2B, 3C, 4A, 5B, 6A, 7B), (1B, 2B, 3C, 4A, 5B, 6A, 7C), (1B, 2B, 3C, 4A, 5B, 6B, 7A), (1B, 2B, 3C, 4A, 5B, 6B, 7B), (1B, 2B, 3C, 4A, 5B, 6B, 7C), (1B, 2B, 3C, 4A, 5B, 6C, 7A), (1B, 2B, 3C, 4A, 5B, 6C, 7B), (1B, 2B, 3C, 4A, 5B, 6C, 7C), (1B, 2B, 3C, 4A, 5B, 6D, 7A), (1B, 2B, 3C, 4A, 5B, 6D, 7B), (1B, 2B, 3C, 4A, 5B, 6D, 7C), (1B, 2B, 3C, 4B, 5A, 6A, 7A), (1B, 2B, 3C, 4B, 5A, 6A, 7B), (1B, 2B, 3C, 4B, 5A, 6A, 7C), (1B, 2B, 3C, 4B, 5A, 6B, 7A), (1B, 2B, 3C, 4B, 5A, 6B, 7B), (1B, 2B, 3C, 4B, 5A, 6B, 7C), (1B, 2B, 3C, 4B, 5A, 6C, 7A), (1B, 2B, 3C, 4B, 5A, 6C, 7B), (1B, 2B, 3C, 4B, 5A, 6C, 7C), (1B, 2B, 3C, 4B, 5A, 6D, 7A), (1B, 2B, 3C, 4B, 5A, 6D, 7B), (1B, 2B, 3C, 4B, 5A, 6D, 7C), (1B, 2B, 3C, 4B, 5B, 6A, 7A), (1B, 2B, 3C, 4B, 5B, 6A, 7B), (1B, 2B, 3C, 4B, 5B, 6A, 7C), (1B, 2B, 3C, 4B, 5B, 6B, 7A), (1B, 2B, 3C, 4B, 5B, 6B, 7B), (1B, 2B, 3C, 4B, 5B, 6B, 7C), (1B, 2B, 3C, 4B, 5B, 6C, 7A), (1B, 2B, 3C, 4B, 5B, 6C, 7B), (1B, 2B, 3C, 4B, 5B, 6C, 7C), (1B, 2B, 3C, 4B, 5B, 6D, 7A), (1B, 2B, 3C, 4B, 5B, 6D, 7B), (1B, 2B, 3C, 4B, 5B, 6D, 7C), (1B, 2B, 3C, 4C, 5A, 6A, 7A), (1B, 2B, 3C, 4C, 5A, 6A, 7B), (1B, 2B, 3C, 4C, 5A, 6A, 7C), (1B, 2B, 3C, 4C, 5A, 6B, 7A), (1B, 2B, 3C, 4C, 5A, 6B, 7B), (1B, 2B, 3C, 4C, 5A, 6B, 7C), (1B, 2B, 3C, 4C, 5A, 6C, 7A), (1B, 2B, 3C, 4C, 5A, 6C, 7B), (1B, 2B, 3C, 4C, 5A, 6C, 7C), (1B, 2B, 3C, 4C, 5A, 6D, 7A), (1B, 2B, 3C, 4C, 5A, 6D, 7B), (1B, 2B, 3C, 4C, 5A, 6D, 7C), (1B, 2B, 3C, 4C, 5B, 6A, 7A), (1B, 2B, 3C, 4C, 5B, 6A, 7B), (1B, 2B, 3C, 4C, 5B, 6A, 7C), (1B, 2B, 3C, 4C, 5B, 6B, 7A), (1B, 2B, 3C, 4C, 5B, 6B, 7B), (1B, 2B, 3C, 4C, 5B, 6B, 7C), (1B, 2B, 3C, 4C, 5B, 6C, 7A), (1B, 2B, 3C, 4C, 5B, 6C, 7B), (1B, 2B, 3C, 4C, 5B, 6C, 7C), (1B, 2B, 3C, 4C, 5B, 6D, 7A), (1B, 2B, 3C, 4C, 5B, 6D, 7B), (1B, 2B, 3C, 4C, 5B, 6D, 7C), (1B, 2B, 3C, 4D, 5A, 6A, 7A), (1B, 2B, 3C, 4D, 5A, 6A, 7B), (1B, 2B, 3C, 4D, 5A, 6A, 7C), (1B, 2B, 3C, 4D, 5A, 6B, 7A), (1B, 2B, 3C, 4D, 5A, 6B, 7B), (1B, 2B, 3C, 4D, 5A, 6B, 7C), (1B, 2B, 3C, 4D, 5A, 6C, 7A), (1B, 2B, 3C, 4D, 5A, 6C, 7B), (1B, 2B, 3C, 4D, 5A, 6C, 7C), (1B, 2B, 3C, 4D, 5A, 6D, 7A), (1B, 2B, 3C, 4D, 5A, 6D, 7B), (1B, 2B, 3C, 4D, 5A, 6D, 7C), (1B, 2B, 3C, 4D, 5B, 6A, 7A), (1B, 2B, 3C, 4D, 5B, 6A, 7B), (1B, 2B, 3C, 4D, 5B, 6A, 7C), (1B, 2B, 3C, 4D, 5B, 6B, 7A), (1B, 2B, 3C, 4D, 5B, 6B, 7B), (1B, 2B, 3C, 4D, 5B, 6B, 7C), (1B, 2B, 3C, 4D, 5B, 6C, 7A), (1B, 2B, 3C, 4D, 5B, 6C, 7B), (1B, 2B, 3C, 4D, 5B, 6C, 7C), (1B, 2B, 3C, 4D, 5B, 6D, 7A), (1B, 2B, 3C, 4D, 5B, 6D, 7B), (1B, 2B, 3C, 4D, 5B, 6D, 7C), (1B, 2B, 3C, 4E, 5A, 6A, 7A), (1B, 2B, 3C, 4E, 5A, 6A, 7B), (1B, 2B, 3C, 4E, 5A, 6A, 7C), (1B, 2B, 3C, 4E, 5A, 6B, 7A), (1B, 2B, 3C, 4E, 5A, 6B, 7B), (1B, 2B, 3C, 4E, 5A, 6B, 7C), (1B, 2B, 3C, 4E, 5A, 6C, 7A), (1B, 2B, 3C, 4E, 5A, 6C, 7B), (1B, 2B, 3C, 4E, 5A, 6C, 7C), (1B, 2B, 3C, 4E, 5A, 6D, 7A), (1B, 2B, 3C, 4E, 5A, 6D, 7B), (1B, 2B, 3C, 4E, 5A, 6D, 7C), (1B, 2B, 3C, 4E, 5B, 6A, 7A), (1B, 2B, 3C, 4E, 5B, 6A, 7B), (1B, 2B, 3C, 4E, 5B, 6A, 7C), (1B, 2B, 3C, 4E, 5B, 6B, 7A), (1B, 2B, 3C, 4E, 5B, 6B, 7B), (1B, 2B, 3C, 4E, 5B, 6B, 7C), (1B, 2B, 3C, 4E, 5B, 6C, 7A), (1B, 2B, 3C, 4E, 5B, 6C, 7B), (1B, 2B, 3C, 4E, 5B, 6C, 7C), (1B, 2B, 3C, 4E, 5B, 6D, 7A), (1B, 2B, 3C, 4E, 5B, 6D, 7B), (1B, 2B, 3C, 4E, 5B, 6D, 7C), (1B, 2B, 3D, 4A, 5A, 6A, 7A), (1B, 2B, 3D, 4A, 5A, 6A, 7B), (1B, 2B, 3D, 4A, 5A, 6A, 7C), (1B, 2B, 3D, 4A, 5A, 6B, 7A), (1B, 2B, 3D, 4A, 5A, 6B, 7B), (1B, 2B, 3D, 4A, 5A, 6B, 7C), (1B, 2B, 3D, 4A, 5A, 6C, 7A), (1B, 2B, 3D, 4A, 5A, 6C, 7B), (1B, 2B, 3D, 4A, 5A, 6C, 7C), (1B, 2B, 3D, 4A, 5A, 6D, 7A), (1B, 2B, 3D, 4A, 5A, 6D, 7B), (1B, 2B, 3D, 4A, 5A, 6D, 7C), (1B, 2B, 3D, 4A, 5B, 6A, 7A), (1B, 2B, 3D, 4A, 5B, 6A, 7B), (1B, 2B, 3D, 4A, 5B, 6A, 7C), (1B, 2B, 3D, 4A, 5B, 6B, 7A), (1B, 2B, 3D, 4A, 5B, 6B, 7B), (1B, 2B, 3D, 4A, 5B, 6B, 7C), (1B, 2B, 3D, 4A, 5B, 6C, 7A), (1B, 2B, 3D, 4A, 5B, 6C, 7B), (1B, 2B, 3D, 4A, 5B, 6C, 7C), (1B, 2B, 3D, 4A, 5B, 6D, 7A), (1B, 2B, 3D, 4A, 5B, 6D, 7B), (1B, 2B, 3D, 4A, 5B, 6D, 7C), (1B, 2B, 3D, 4B, 5A, 6A, 7A), (1B, 2B, 3D, 4B, 5A, 6A, 7B), (1B, 2B, 3D, 4B, 5A, 6A, 7C), (1B, 2B, 3D, 4B, 5A, 6B, 7A), (1B, 2B, 3D, 4B, 5A, 6B, 7B), (1B, 2B, 3D, 4B, 5A, 6B, 7C), (1B, 2B, 3D, 4B, 5A, 6C, 7A), (1B, 2B, 3D, 4B, 5A, 6C, 7B), (1B, 2B, 3D, 4B, 5A, 6C, 7C), (1B, 2B, 3D, 4B, 5A, 6D, 7A), (1B, 2B, 3D, 4B, 5A, 6D, 7B), (1B, 2B, 3D, 4B, 5A, 6D, 7C), (1B, 2B, 3D, 4B, 5B, 6A, 7A), (1B, 2B, 3D, 4B, 5B, 6A, 7B), (1B, 2B, 3D, 4B, 5B, 6A, 7C), (1B, 2B, 3D, 4B, 5B, 6B, 7A), (1B, 2B, 3D, 4B, 5B, 6B, 7B), (1B, 2B, 3D, 4B, 5B, 6B, 7C), (1B, 2B, 3D, 4B, 5B, 6C, 7A), (1B, 2B, 3D, 4B, 5B, 6C, 7B), (1B, 2B, 3D, 4B, 5B, 6C, 7C), (1B, 2B, 3D, 4B, 5B, 6D, 7A), (1B, 2B, 3D, 4B, 5B, 6D, 7B), (1B, 2B, 3D, 4B, 5B, 6D, 7C), (1B, 2B, 3D, 4C, 5A, 6A, 7A), (1B, 2B, 3D, 4C, 5A, 6A, 7B), (1B, 2B, 3D, 4C, 5A, 6A, 7C), (1B, 2B, 3D, 4C, 5A, 6B, 7A), (1B, 2B, 3D, 4C, 5A, 6B, 7B), (1B, 2B, 3D, 4C, 5A, 6B, 7C), (1B, 2B, 3D, 4C, 5A, 6C, 7A), (1B, 2B, 3D, 4C, 5A, 6C, 7B), (1B, 2B, 3D, 4C, 5A, 6C, 7C), (1B, 2B, 3D, 4C, 5A, 6D, 7A), (1B, 2B, 3D, 4C, 5A, 6D, 7B), (1B, 2B, 3D, 4C, 5A, 6D, 7C), (1B, 2B, 3D, 4C, 5B, 6A, 7A), (1B, 2B, 3D, 4C, 5B, 6A, 7B), (1B, 2B, 3D, 4C, 5B, 6A, 7C), (1B, 2B, 3D, 4C, 5B, 6B, 7A), (1B, 2B, 3D, 4C, 5B, 6B, 7B), (1B, 2B, 3D, 4C, 5B, 6B, 7C), (1B, 2B, 3D, 4C, 5B, 6C, 7A), (1B, 2B, 3D, 4C, 5B, 6C, 7B), (1B, 2B, 3D, 4C, 5B, 6C, 7C), (1B, 2B, 3D, 4C, 5B, 6D, 7A), (1B, 2B, 3D, 4C, 5B, 6D, 7B), (1B, 2B, 3D, 4C, 5B, 6D, 7C), (1B, 2B, 3D, 4D, 5A, 6A, 7A), (1B, 2B, 3D, 4D, 5A, 6A, 7B), (1B, 2B, 3D, 4D, 5A, 6A, 7C), (1B, 2B, 3D, 4D, 5A, 6B, 7A), (1B, 2B, 3D, 4D, 5A, 6B, 7B), (1B, 2B, 3D, 4D, 5A, 6B, 7C), (1B, 2B, 3D, 4D, 5A, 6C, 7A), (1B, 2B, 3D, 4D, 5A, 6C, 7B), (1B, 2B, 3D, 4D, 5A, 6C, 7C), (1B, 2B, 3D, 4D, 5A, 6D, 7A), (1B, 2B, 3D, 4D, 5A, 6D, 7B), (1B, 2B, 3D, 4D, 5A, 6D, 7C), (1B, 2B, 3D, 4D, 5B, 6A, 7A), (1B, 2B, 3D, 4D, 5B, 6A, 7B), (1B, 2B, 3D, 4D, 5B, 6A, 7C), (1B, 2B, 3D, 4D, 5B, 6B, 7A), (1B, 2B, 3D, 4D, 5B, 6B, 7B), (1B, 2B, 3D, 4D, 5B, 6B, 7C), (1B, 2B, 3D, 4D, 5B, 6C, 7A), (1B, 2B, 3D, 4D, 5B, 6C, 7B), (1B, 2B, 3D, 4D, 5B, 6C, 7C), (1B, 2B, 3D, 4D, 5B, 6D, 7A), (1B, 2B, 3D, 4D, 5B, 6D, 7B), (1B, 2B, 3D, 4D, 5B, 6D, 7C), (1B, 2B, 3D, 4E, 5A, 6A, 7A), (1B, 2B, 3D, 4E, 5A, 6A, 7B), (1B, 2B, 3D, 4E, 5A, 6A, 7C), (1B, 2B, 3D, 4E, 5A, 6B, 7A), (1B, 2B, 3D, 4E, 5A, 6B, 7B), (1B, 2B, 3D, 4E, 5A, 6B, 7C), (1B, 2B, 3D, 4E, 5A, 6C, 7A), (1B, 2B, 3D, 4E, 5A, 6C, 7B), (1B, 2B, 3D, 4E, 5A, 6C, 7C), (1B, 2B, 3D, 4E, 5A, 6D, 7A), (1B, 2B, 3D, 4E, 5A, 6D, 7B), (1B, 2B, 3D, 4E, 5A, 6D, 7C), (1B, 2B, 3D, 4E, 5B, 6A, 7A), (1B, 2B, 3D, 4E, 5B, 6A, 7B), (1B, 2B, 3D, 4E, 5B, 6A, 7C), (1B, 2B, 3D, 4E, 5B, 6B, 7A), (1B, 2B, 3D, 4E, 5B, 6B, 7B), (1B, 2B, 3D, 4E, 5B, 6B, 7C), (1B, 2B, 3D, 4E, 5B, 6C, 7A), (1B, 2B, 3D, 4E, 5B, 6C, 7B), (1B, 2B, 3D, 4E, 5B, 6C, 7C), (1B, 2B, 3D, 4E, 5B, 6D, 7A), (1B, 2B, 3D, 4E, 5B, 6D, 7B), (1B, 2B, 3D; 4E, 5B, 6D, 7C), (1B, 2B, 3E, 4A, 5A, 6A, 7A), (1B, 2B, 3E, 4A, 5A, 6A, 7B), (1B, 2B, 3E, 4A, 5A, 6A, 7C), (1B, 2B, 3E, 4A, 5A, 6B, 7A), (1B, 2B, 3E, 4A, 5A, 6B, 7B), (1B, 2B, 3E, 4A, 5A, 6B, 7C), (1B, 2B, 3E, 4A, 5A, 6C, 7A), (1B, 2B, 3E, 4A, 5A, 6C, 7B), (1B, 2B, 3E, 4A, 5A, 6C, 7C), (1B, 2B, 3E, 4A, 5A, 6D, 7A), (1B, 2B, 3E, 4A, 5A, 6D, 7B), (1B, 2B, 3E, 4A, 5A, 6D, 7C), (1B, 2B, 3E, 4A, 5B, 6A, 7A), (1B, 2B, 3E, 4A, 5B, 6A, 7B), (1B, 2B, 3E, 4A, 5B, 6A, 7C), (1B, 2B, 3E, 4A, 5B, 6B, 7A), (1B, 2B, 3E, 4A, 5B, 6B, 7B), (1B, 2B, 3E, 4A, 5B, 6B, 7C), (1B, 2B, 3E, 4A, 5B, 6C, 7A), (1B, 2B, 3E, 4A, 5B, 6C, 7B), (1B, 2B, 3E, 4A, 5B, 6C, 7C), (1B, 2B, 3E, 4A, 5B, 6D, 7A), (1B, 2B, 3E, 4A, 5B, 6D, 7B), (1B, 2B, 3E, 4A, 5B, 6D, 7C), (1B, 2B, 3E, 4B, 5A, 6A, 7A), (1B, 2B, 3E, 4B, 5A, 6A, 7B), (1B, 2B, 3E, 4B, 5A, 6A, 7C), (1B, 2B, 3E, 4B, 5A, 6B, 7A), (1B, 2B, 3E, 4B, 5A, 6B, 7B), (1B, 2B, 3E, 4B, 5A, 6B, 7C), (1B, 2B, 3E, 4B, 5A, 6C, 7A), (1B, 2B, 3E, 4B, 5A, 6C, 7B), (1B, 2B, 3E, 4B, 5A, 6C, 7C), (1B, 2B, 3E, 4B, 5A, 6D, 7A), (1B, 2B, 3E, 4B, 5A, 6D, 7B), (1B, 2B, 3E, 4B, 5A, 6D, 7C), (1B, 2B, 3E, 4B, 5B, 6A, 7A), (1B, 2B, 3E, 4B, 5B, 6A, 7B), (1B, 2B, 3E, 4B, 5B, 6A, 7C), (1B, 2B, 3E, 4B, 5B, 6B, 7A), (1B, 2B, 3E, 4B, 5B, 6B, 7B), (1B, 2B, 3E, 4B, 5B, 6B, 7C), (1B, 2B, 3E, 4B, 5B, 6C, 7A), (1B, 2B, 3E, 4B, 5B, 6C, 7B), (1B, 2B, 3E, 4B, 5B, 6C, 7C), (1B, 2B, 3E, 4B, 5B, 6D, 7A), (1B, 2B, 3E, 4B, 5B, 6D, 7B), (1B, 2B, 3E, 4B, 5B, 6D, 7C), (1B, 2B, 3E, 4C, 5A, 6A, 7A), (1B, 2B, 3E, 4C, 5A, 6A, 7B), (1B, 2B, 3E, 4C, 5A, 6A, 7C), (1B, 2B, 3E, 4C, 5A, 6B, 7A), (1B, 2B, 3E, 4C, 5A, 6B, 7B), (1B, 2B, 3E, 4C, 5A, 6B, 7C), (1B, 2B, 3E, 4C, 5A, 6A, 7A), (1B, 2B, 3E, 4C, 5A, 6C, 7B), (1B, 2B, 3E, 4C, 5A, 6C, 7C), (1B, 2B, 3E, 4C, 5A, 6D, 7A), (1B, 2B, 3E, 4C, 5A, 6D, 7B), (1B, 2B, 3E, 4C, 5A, 6D, 7C), (1B, 2B, 3E, 4C, 5B, 6A, 7A), (1B, 2B, 3E, 4C, 5B, 6A, 7B), (1B, 2B, 3E, 4C, 5B, 6A, 7C), (1B, 2B, 3E, 4C, 5B, 6B, 7A), (1B, 2B, 3E, 4C, 5B, 6B, 7B), (1B, 2B, 3E, 4C, 5B, 6B, 7C), (1B, 2B, 3E, 4C, 5B, 6C, 7A), (1B, 2B, 3E, 4C, 5B, 6C, 7B), (1B, 2B, 3E, 4C, 5B, 6C, 7C), (1B, 2B, 3E, 4C, 5B, 6D, 7A), (1B, 2B, 3E, 4C, 5B, 6D, 7B), (1B, 2B, 3E, 4C, 5B, 6D, 7C), (1B, 2B, 3E, 4D, 5A, 6A, 7A), (1B, 2B, 3E, 4D, 5A, 6A, 7B), (1B, 2B, 3E, 4D, 5A, 6A, 7C), (1B, 2B, 3E, 4D, 5A, 6B, 7A), (1B, 2B, 3E, 4D, 5A, 6B, 7B), (1B, 2B, 3E, 4D, 5A, 6B, 7C), (1B, 2B, 3E, 4D, 5A, 6C, 7A), (1B, 2B, 3E, 4D, 5A, 6C, 7B), (1B, 2B, 3E, 4D, 5A, 6C, 7C), (1B, 2B, 3E, 4D, 5A, 6D, 7A), (1B, 2B, 3E, 4D, 5A, 6D, 7B), (1B, 2B, 3E, 4D, 5A, 6D, 7C), (1B, 2B, 3E, 4D, 5B, 6A, 7A), (1B, 2B, 3E, 4D, 5B, 6A, 7B), (1B, 2B, 3E, 4D, 5B, 6A, 7C), (1B, 2B, 3E, 4D, 5B, 6B, 7A), (1B, 2B, 3E, 4D, 5B, 6B, 7B), (1B, 2B, 3E, 4D, 5B, 6B, 7C), (1B, 2B, 3E, 4D, 5B, 6C, 7A), (1B, 2B, 3E, 4D, 5B, 6C, 7B), (1B, 2B, 3E, 4D, 5B, 6C, 7C), (1B, 2B, 3E, 4D, 5B, 6D, 7A), (1B, 2B, 3E, 4D, 5B, 6D, 7B), (1B, 2B, 3E, 4D, 5B, 6D, 7C), (1B, 2B, 3E, 4E, 5A, 6A, 7A), (1B, 2B, 3E, 4E, 5A, 6A, 7B), (1B, 2B, 3E, 4E, 5A, 6A, 7C), (1B, 2B, 3E, 4E, 5A, 6B, 7A), (1B, 2B, 3E, 4E, 5A, 6B, 7B), (1B, 2B, 3E, 4E, 5A, 6B, 7C), (1B, 2B, 3E, 4E, 5A, 6C, 7A), (1B, 2B, 3E, 4E, 5A, 6C, 7B), (1B, 2B, 3E, 4E, 5A, 6C, 7C), (1B, 2B, 3E, 4E, 5A, 6D, 7A), (1B, 2B, 3E, 4E, 5A, 6D, 7B), (1B, 2B, 3E, 4E, 5A, 6D, 7C), (1B, 2B, 3E, 4E, 5B, 6A, 7A), (1B, 2B, 3E, 4E, 5B, 6A, 7B), (1B, 2B, 3E, 4E, 5B, 6A, 7A), (1B, 2B, 3E, 4E, 5B, 6B, 7A), (1B, 2B, 3E, 4E, 5B, 6B, 7B), (1B, 2B, 3E, 4E, 5B, 6B, 7C), (1B, 2B, 3E, 4E, 5B, 6C, 7A), (1B, 2B, 3E, 4E, 5B, 6C, 7B), (1B, 2B, 3E, 4E, 5B, 6C, 7C), (1B, 2B, 3E, 4E, 5B, 6D, 7A), (1B, 2B, 3E, 4E, 5B, 6D, 7B), (1B, 2B, 3E, 4E, 5B, 6D, 7C), (1B, 2C, 3A, 4A, 5A, 6A, 7A), (1B, 2C, 3A, 4A, 5A, 6A, 7B), (1B, 2C, 3A, 4A, 5A, 6A, 7C), (1B, 2C, 3A, 4A, 5A, 6B, 7A), (1B, 2C, 3A, 4A, 5A, 6B, 7B), (1B, 2C, 3A, 4A, 5A, 6B, 7C), (1B, 2C, 3A, 4A, 5A, 6C, 7A), (1B, 2C, 3A, 4A, 5A, 6C, 7B), (1B, 2C, 3A, 4A, 5A, 6C, 7C), (1B, 2C, 3A, 4A, 5A, 6D, 7A), (1B, 2C, 3A, 4A, 5A, 6D, 7B), (1E, 2C, 3A, 4A, 5A, 6D, 7C), (1B, 2C, 3A, 4A, 5B, 6A, 7A), (1B, 2C, 3A, 4A, 5B, 6A, 7B), (1B, 2C, 3A, 4A, 5B, 6A, 7C), (1B, 2C, 3A, 4A, 5B, 6B, 7A), (1B, 2C, 3A, 4A, 5B, 6B, 7B), (1B, 2C, 3A, 4A, 5B, 6B, 7C), (1B, 2C, 3A, 4A, 5B, 6C, 7A), (1B, 2C, 3A, 4A, 5B, 6C, 7B), (1B, 2C, 3A, 4A, 5B, 6C, 7C), (1B, 2C, 3A, 4A, 5B, 6D, 7A), (1B, 2C, 3A, 4A, 5B, 6D, 7B), (1B, 2C, 3A, 4A, 5B, 6D, 7C), (1B, 2C, 3A, 4B, 5A, 6A, 7A), (1B, 2C, 3A, 4B, 5A, 6A, 7B), (1B, 2C, 3A, 4B, 5A, 6A, 7C), (1B, 2C, 3A, 4B, 5A, 6B, 7A), (1B, 2C, 3A, 4B, 5A, 6B, 7B), (1B, 2C, 3A, 4B, 5A, 6B, 7C), (1B, 2C, 3A, 4B, 5A, 6C, 7A), (1B, 2C, 3A, 4B, 5A, 6C, 7B), (1B, 2C, 3A, 4B, 5A, 6C, 7C), (1B, 2C, 3A, 4B, 5A, 6D, 7A), (1B, 2C, 3A, 4B, 5A, 6D, 7B), (1B, 2C, 3A, 4B, 5A, 6D, 7C), (1B, 2C, 3A, 4B, 5B, 6A, 7A), (1B, 2C, 3A, 4B, 5B, 6A, 7B), (1B, 2C, 3A, 4B, 5B, 6A, 7C), (1B, 2C, 3A, 4B, 5B, 6B, 7A), (1B, 2C, 3A, 4B, 5B, 6B, 7B), (1B, 2C, 3A, 4B, 5B, 6B, 7C), (1B, 2C, 3A, 4B, 5B, 6C, 7A), (1B, 2C, 3A, 4B, 5B, 6C, 7B), (1B, 2C, 3A, 4B, 5B, 6C, 7C), (1B, 2C, 3A, 4B, 5B, 6D, 7A), (1B, 2C, 3A, 4B, 5B, 6D, 7B), (1B, 2C, 3A, 4B, 5B, 6D, 7C), (1B, 2C, 3A, 4C, 5A, 6A, 7A), (1B, 2C, 3A, 4C, 5A, 6A, 7B), (1B, 2C, 3A, 4C, 5A, 6A, 7C), (1B, 2C, 3A, 4C, 5A, 6B, 7A), (1B, 2C, 3A, 4C, 5A, 6B, 7B), (1B, 2C, 3A, 4C, 5A, 6B, 7C), (1B, 2C, 3A, 4C, 5A, 6C, 7A), (1B, 2C, 3A, 4C, 5A, 6C, 7B), (1B, 2C, 3A, 4C, 5A, 6C, 7C), (1B, 2C, 3A, 4C, 5A, 6D, 7A), (1B, 2C, 3A, 4C, 5A, 6D, 7B), (1B, 2C, 3A, 4C, 5A, 6D, 7C), (1B, 2C, 3A, 4C, 5B, 6A, 7A), (1B, 2C, 3A, 4C, 5B, 6A, 7B), (1B, 2C, 3A, 4C, 5B, 6A, 7C), (1B, 2C, 3A, 4C, 5B, 6B, 7A), (1B, 2C, 3A, 4C, 5B, 6B, 7B), (1B, 2C, 3A, 4C, 5B, 6B, 7C), (1B, 2C, 3A, 4C, 5B, 6C, 7A), (1B, 2C, 3A, 4C, 5B, 6C, 7B), (1B, 2C, 3A, 4C, 5B, 6C, 7C), (1B, 2C, 3A, 4C, 5B, 6D, 7A), (1B, 2C, 3A, 4C, 5B, 6D, 7B), (1B, 2C, 3A, 4C, 5B, 6D, 7C), (1B, 2C, 3A, 4D, 5A, 6A, 7A), (1B, 2C, 3A, 4D, 5A, 6A, 7B), (1B, 2C, 3A, 4D, 5A, 6A, 7C), (1B, 2C, 3A, 4D, 5A, 6B, 7A), (1B, 2C, 3A, 4D, 5A, 6B, 7B), (1B, 2C, 3A, 4D, 5A, 6B, 7C), (1B, 2C, 3A, 4D, 5A, 6C, 7A), (1B, 2C, 3A, 4D, 5A, 6C, 7B), (1B, 2C, 3A, 4D, 5A, 6C, 7C), (1B, 2C, 3A, 4D, 5A, 6D, 7A), (1B, 2C, 3A, 4D, 5A, 6D, 7B), (1B, 2C, 3A, 4D, 5A, 6D, 7C), (1B, 2C, 3A, 4D, 5B, 6A, 7A), (1B, 2C, 3A, 4D, 5B, 6A, 7B), (1B, 2C, 3A, 4D, 5B, 6A, 7C), (1B, 2C, 3A, 4D, 5B, 6B, 7A), (1B, 2C, 3A, 4D, 5B, 6B, 7B), (1B, 2C, 3A, 4D, 5B, 6B, 7C), (1B, 2C, 3A, 4D, 5B, 6C, 7A), (1B, 2C, 3A, 4D, 5B, 6C, 7B), (1B, 2C, 3A, 4D, 5B, 6C, 7C), (1B, 2C, 3A, 4D, 5B, 6D, 7A), (1B, 2C, 3A, 4D, 5B, 6D, 7B), (1B, 2C, 3A, 4D, 5B, 6D, 7C), (1B, 2C, 3A, 4E, 5A, 6A, 7A), (1B, 2C, 3A, 4E, 5A, 6A, 7B), (1B, 2C, 3A, 4E, 5A, 6A, 7C), (1B, 2C, 3A, 4E, 5A, 6B, 7A), (1B, 2C, 3A, 4E, 5A, 6B, 7B), (1B, 2C, 3A, 4E, 5A, 6B, 7C), (1B, 2C, 3A, 4E, 5A, 6C, 7A), (1B, 2C, 3A, 4E, 5A, 6C, 7B), (1B, 2C, 3A, 4E, 5A, 6C, 7C), (1B, 2C, 3A, 4E, 5A, 6D, 7A), (1B, 2C, 3A, 4E, 5A, 6D, 7B), (1B, 2C, 3A, 4E, 5A, 6D, 7C), (1B, 2C, 3A, 4E, 5B, 6A, 7A), (1B, 2C, 3A, 4E, 5B, 6A, 7B), (1B, 2C, 3A, 4E, 5B, 6A, 7C), (1B, 2C, 3A, 4E, 5B, 6B, 7A), (1B, 2C, 3A, 4E, 5B, 6B, 7B), (1B, 2C, 3A, 4E, 5B, 6B, 7C), (1B, 2C, 3A, 4E, 5B, 6C, 7A), (1B, 2C, 3A, 4E, 5B, 6C, 7B), (1B, 2C, 3A, 4E, 5B, 6C, 7C), (1B, 2C, 3A, 4E, 5B, 6D, 7A), (1B, 2C, 3A, 4E, 5B, 6D, 7B), (1B, 2C, 3A, 4E, 5B, 6D, 7C), (1B, 2C, 3B, 4A, 5A, 6A, 7A), (1B, 2C, 3B, 4A, 5A, 6A, 7B), (1B, 2C, 3B, 4A, 5A, 6A, 7C), (1B, 2C, 3B, 4A, 5A, 6B, 7A), (1B, 2C, 3B, 4A, 5A, 6B, 7B), (1B, 2C, 3B, 4A, 5A, 6B, 7C), (1B, 2C, 3B, 4A, 5A, 6C, 7A), (1B, 2C, 3B, 4A, 5A, 6C, 7B), (1B, 2C, 3B, 4A, 5A, 6C, 7C), (1B, 2C, 3B, 4A, 5A, 6D, 7A), (1B, 2C, 3B, 4A, 5A, 6D, 7B), (1B, 2C, 3B, 4A, 5A, 6D, 7C), (1B, 2C, 3B, 4A, 5B, 6A, 7A), (1B, 2C, 3B, 4A, 5B, 6A, 7B), (1B, 2C, 3B, 4A, 5B, 6A, 7C), (1B, 2C, 3B, 4A, 5B, 6B, 7A), (1B, 2C, 3B, 4A, 5B, 6B, 7B), (1B, 2C, 3B, 4A, 5B, 6B, 7C), (1B, 2C, 3B, 4A, 5B, 6C, 7A), (1B, 2C, 3B, 4A, 5B, 6C, 7B), (1B, 2C, 3B, 4A, 5B, 6C, 7C), (1B, 2C, 3B, 4A, 5B, 6D, 7A), (1B, 2C, 3B, 4A, 5B, 6D, 7B), (1B, 2C, 3B, 4A, 5B, 6D, 7C), (1B, 2C, 3B, 4B, 5A, 6A, 7A), (1B, 2C, 3B, 4B, 5A, 6A, 7B), (1B, 2C, 3B, 4B, 5A, 6A, 7C), (1B, 2C, 3B, 4B, 5A, 6B, 7A), (1B, 2C, 3B, 4B, 5A, 6B, 7B), (1B, 2C, 3B, 4B, 5A, 6B, 7C), (1B, 2C, 3B, 4B, 5A, 6C, 7A), (1B, 2C, 3B, 4B, 5A, 6C, 7B), (1B, 2C, 3B, 4B, 5A, 6C, 7C), (1B, 2C, 3B, 4B, 5A, 6D, 7A), (1B, 2C, 3B, 4B, 5A, 6D, 7B), (1B, 2C, 3B, 4B, 5A, 6D, 7C), (1B, 2C, 3B, 4B, 5B, 6A, 7A), (1B, 2C, 3B, 4B, 5B, 6A, 7B), (1B, 2C, 3B, 4B, 5B, 6A, 7C), (1B, 2C, 3B, 4B, 5B, 6B, 7A), (1B, 2C, 3B, 4B, 5B, 6B, 7B), (1B, 2C, 3B, 4B, 5B, 6B, 7C), (1B, 2C, 3B, 4B, 5B, 6C, 7A), (1B, 2C, 3B, 4B, 5B, 6C, 7B), (1B, 2C, 3B, 4B, 5B, 6C, 7C), (1B, 2C, 3B, 4B, 5B, 6D, 7A), (1B, 2C, 3B, 4B, 5B, 6D, 7B), (1B, 2C, 3B, 4B, 5B, 6D, 7C), (1B, 2C, 3B, 4C, 5A, 6A, 7A), (1B, 2C, 3B, 4C, 5A, 6A, 7B), (1B, 2C, 3B, 4C, 5A, 6A, 7C), (1B, 2C, 3B, 4C, 5A, 6B, 7A), (1B, 2C, 3B, 4C, 5A, 6B, 7B), (1B, 2C, 3B, 4C, 5A, 6B, 7C), (1B, 2C, 3B, 4C, 5A, 6C, 7A), (1B, 2C, 3B, 4C, 5A, 6C, 7B), (1B, 2C, 3B, 4C, 5A, 6C, 7C), (1B, 2C, 3B, 4C, 5A, 6D, 7A), (1B, 2C, 3B, 4C, 5A, 6D, 7B), (1B, 2C, 3B, 4C, 5A, 6D, 7C), (1B, 2C, 3B, 4C, 5B, 6A, 7A), (1B, 2C, 3B, 4C, 5B, 6A, 7B), (1B, 2C, 3B, 4C, 5B, 6A, 7C), (1B, 2C, 3B, 4C, 5B, 6B, 7A), (1B, 2C, 3B, 4C, 5B, 6B, 7B), (1B, 2C, 3B, 4C, 5B, 6B, 7C), (1B, 2C, 3B, 4C, 5B, 6C, 7A), (1B, 2C, 3B, 4C, 5B, 6C, 7B), (1B, 2C, 3B, 4C, 5B, 6C, 7C), (1B, 2C, 3B, 4C, 5B, 6D, 7A), (1B, 2C, 3B, 4C, 5B, 6D, 7B), (1B, 2C, 3B, 4C, 5B, 6D, 7C), (1B, 2C, 3B, 4D, 5A, 6A, 7A), (1B, 2C, 3B, 4D, 5A, 6A, 7B), (1B, 2C, 3B, 4D, 5A, 6A, 7C), (1B, 2C, 3B, 4D, 5A, 6B, 7A), (1B, 2C, 3B, 4D, 5A, 6B, 7B), (1B, 2C, 3B, 4D, 5A, 6B, 7C), (1B, 2C, 3B, 4D, 5A, 6C, 7A), (1B, 2C, 3B, 4D, 5A, 6C, 7B), (1B, 2C, 3B, 4D, 5A, 6C, 7C), (1B, 2C, 3B, 4D, 5A, 6D, 7A), (1B, 2C, 3B, 4D, 5A, 6D, 7B), (1B, 2C, 3B, 4D, 5A, 6D, 7C), (1B, 2C, 3B, 4D, 5B, 6A, 7A), (1B, 2C, 3B, 4D, 5B, 6A, 7B), (1B, 2C, 3B, 4D, 5B, 6A, 7C), (1B, 2C, 3B, 4D, 5B, 6B, 7A), (1B, 2C, 3B, 4D, 5B, 6B, 7B), (1B, 2C, 3B, 4D, 5B, 6B, 7C), (1B, 2C, 3B, 4D, 5B, 6C, 7A), (1B, 2C, 3B, 4D, 5B, 6C, 7B), (1B, 2C, 3B, 4D, 5B, 6C, 7C), (1B, 2C, 3B, 4D, 5B, 6D, 7A), (1B, 2C, 3B, 4D, 5B, 6D, 7B), (1B, 2C, 3B, 4D, 5B, 6D, 7C), (1B, 2C, 3B, 4E, 5A, 6A, 7A), (1B, 2C, 3B, 4E, 5A, 6A, 7B), (1B, 2C, 3B, 4E, 5A, 6A, 7C), (1B, 2C, 3B, 4E, 5A, 6B, 7A), (1B, 2C, 3B, 4E, 5A, 6B, 7B), (1B, 2C, 3B, 4E, 5A, 6B, 7C), (1B, 2C, 3B, 4E, 5A, 6C, 7A), (1B, 2C, 3B, 4E, 5A, 6C, 7B), (1B, 2C, 3B, 4E, 5A, 6C, 7C), (1B, 2C, 3B, 4E, 5A, 6D, 7A), (1B, 2C, 3B, 4E, 5A, 6D, 7B), (1B, 2C, 3B, 4E, 5A, 6D, 7C), (1B, 2C, 3B, 4E, 5B, 6A, 7A), (1B, 2C, 3B, 4E, 5B, 6A, 7B), (1B, 2C, 3B, 4E, 5B, 6A, 7C), (1B, 2C, 3B, 4E, 5B, 6B, 7A), (1B, 2C, 3B, 4E, 5B, 6B, 7B), (1B, 2C, 3B, 4E, 5B, 6B, 7C), (1B, 2C, 3B, 4E, 5B, 6C, 7A), (1B, 2C, 3B, 4E, 5B, 6C, 7B), (1B, 2C, 3B, 4E, 5B, 6C, 7C), (1B, 2C, 3B, 4E, 5B, 6D, 7A), (1B, 2C, 3B, 4E, 5B, 6D, 7B), (1B, 2C, 3B, 4E, 5B, 6D, 7C), (1B, 2C, 3C, 4A, 5A, 6A, 7A), (1B, 2C, 3C, 4A, 5A, 6A, 7B), (1B, 2C, 3C, 4A, 5A, 6A, 7C), (1B, 2C, 3C, 4A, 5A, 6B, 7A), (1B, 2C, 3C, 4A, 5A, 6B, 7B), (1B, 2C, 3C, 4A, 5A, 6B, 7C), (1B, 2C, 3C, 4A, 5A, 6C, 7A), (1B, 2C, 3C, 4A, 5A, 6C, 7B), (1B, 2C, 3C, 4A, 5A, 6C, 7C), (1B, 2C, 3C, 4A, 5A, 6D, 7A), (1B, 2C, 3C, 4A, 5A, 6D, 7B), (1B, 2C, 3C, 4A, 5A, 6D, 7C), (1B, 2C, 3C, 4A, 5B, 6A, 7A), (1B, 2C, 3C, 4A, 5B, 6A, 7B), (1B, 2C, 3C, 4A, 5B, 6A, 7C), (1B, 2C, 3C, 4A, 5B, 6B, 7A), (1B, 2C, 3C, 4A, 5B, 6B, 7B), (1B, 2C, 3C, 4A, 5B, 6B, 7C), (1B, 2C, 3C, 4A, 5B, 6C, 7A), (1B, 2C, 3C, 4A, 5B, 6C, 7B), (1B, 2C, 3C, 4A, 5B, 6C, 7C), (1B, 2C, 3C, 4A, 5B, 6D, 7A), (1B, 2C, 3C, 4A, 5B, 6D, 7B), (1B, 2C, 3C, 4A, 5B, 6D, 7C), (1B, 2C, 3C, 4B, 5A, 6A, 7A), (1B, 2C, 3C, 4B, 5A, 6A, 7B), (1B, 2C, 3C, 4B, 5A, 6A, 7C), (1B, 2C, 3C, 4B, 5A, 6B, 7A), (1B, 2C, 3C, 4B, 5A, 6B, 7B), (1B, 2C, 3C, 4B, 5A, 6B, 7C), (1B, 2C, 3C, 4B, 5A, 6C, 7A), (1B, 2C, 3C, 4B, 5A, 6C, 7B), (1B, 2C, 3C, 4B, 5A, 6C, 7C), (1B, 2C, 3C, 4B, 5A, 6D, 7A), (1B, 2C, 3C, 4B, 5A, 6D, 7B), (1B, 2C, 3C, 4B, 5A, 6D, 7C), (1B, 2C, 3C, 4B, 5B, 6A, 7A), (1B, 2C, 3C, 4B, 5B, 6A, 7B), (1B, 2C, 3C, 4B, 5B, 6A, 7C), (1B, 2C, 3C, 4B, 5B, 6B, 7A), (1B, 2C, 3C, 4B, 5B, 6B, 7B), (1B, 2C, 3C, 4B, 5B, 6B, 7C), (1B, 2C, 3C, 4B, 5B, 6C, 7A), (1B, 2C, 3C, 4B, 5B, 6C, 7B), (1B, 2C, 3C, 4B, 5B, 6C, 7C), (1B, 2C, 3C, 4B, 5B, 6D, 7A), (1B, 2C, 3C, 4B, 5B, 6D, 7B), (1B, 2C, 3C, 4B, 5B, 6D, 7C), (1B, 2C, 3C, 4C, 5A, 6A, 7A), (1B, 2C, 3C, 4C, 5A, 6A, 7B), (1B, 2C, 3C, 4C, 5A, 6A, 7C), (1B, 2C, 3C, 4C, 5A, 6B, 7A), (1B, 2C, 3C, 4C, 5A, 6B, 7B), (1B, 2C, 3C, 4C, 5A, 6B, 7C), (1B, 2C, 3C, 4C, 5A, 6C, 7A), (1B, 2C, 3C, 4C, 5A, 6C, 7B), (1B, 2C, 3C, 4C, 5A, 6C, 7C), (1B, 2C, 3C, 4C, 5A, 6D, 7A), (1B, 2C, 3C, 4C, 5A, 6D, 7B), (1B, 2C, 3C, 4C, 5A, 6D, 7C), (1B, 2C, 3C, 4C, 5B, 6A, 7A), (1B, 2C, 3C, 4C, 5B, 6A, 7B), (1B, 2C, 3C, 4C, 5B, 6A, 7C), (1B, 2C, 3C, 4C, 5B, 6B, 7A), (1B, 2C, 3C, 4C, 5B, 6B, 7B), (1B, 2C, 3C, 4C, 5B, 6B, 7C), (1B, 2C, 3C, 4C, 5B, 6C, 7A), (1B, 2C, 3C, 4C, 5B, 6C, 7B), (1B, 2C, 3C, 4C, 5B, 6C, 7C), (1B, 2C, 3C, 4C, 5B, 6D, 7A), (1B, 2C, 3C, 4C, 5B, 6D, 7B), (1B, 2C, 3C, 4C, 5B, 6D, 7C), (1B, 2C, 3C, 4D, 5A, 6A, 7A), (1B, 2C, 3C, 4D, 5A, 6A, 7B), (1B, 2C, 3C, 4D, 5A, 6A, 7C), (1B, 2C, 3C, 4D, 5A, 6B, 7A), (1B, 2C, 3C, 4D, 5A, 6B, 7B), (1B, 2C, 3C, 4D, 5A, 6B, 7C), (1B, 2C, 3C, 4D, 5A, 6C, 7A), (1B, 2C, 3C, 4D, 5A, 6C, 7B), (1B, 2C, 3C, 4D, 5A, 6C, 7C), (1B, 2C, 3C, 4D, 5A, 6D, 7A), (1B, 2C, 3C, 4D, 5A, 6D, 7B), (1B, 2C, 3C, 4D, 5A, 6D, 7C), (1B, 2C, 3C, 4D, 5B, 6A, 7A), (1B, 2C, 3C, 4D, 5B, 6A, 7B), (1B, 2C, 3C, 4D, 5B, 6A, 7C), (1B, 2C, 3C, 4D, 5B, 6B, 7A), (1B, 2C, 3C, 4D, 5B, 6B, 7B), (1B, 2C, 3C, 4D, 5B, 6B, 7C), (1B, 2C, 3C, 4D, 5B, 6C, 7A), (1B, 2C, 3C, 4D, 5B, 6C, 7B), (1B, 2C, 3C, 4D, 5B, 6C, 7C), (1B, 2C, 3C, 4D, 5B, 6D, 7A), (1B, 2C, 3C, 4D, 5B, 6D, 7B), (1B, 2C, 3C, 4D, 5B, 6D, 7C), (1B, 2C, 3C, 4E, 5A, 6A, 7A), (1B, 2C, 3C, 4E, 5A, 6A, 7B), (1B, 2C, 3C, 4E, 5A, 6A, 7C), (1B, 2C, 3C, 4E, 5A, 6B, 7A), (1B, 2C, 3C, 4E, 5A, 6B, 7B), (1B, 2C, 3C, 4E, 5A, 6B, 7C); (1B, 2C, 3C, 4E, 5A, 6C, 7A), (1B, 2C, 3C, 4E, 5A, 6C, 7B), (1B, 2C, 3C, 4E, 5A, 6C, 7C), (1B, 2C, 3C, 4E, 5A, 6D, 7A), (1B, 2C, 3C, 4E, 5A, 6D, 7B), (1B, 2C, 3C, 4E, 5A, 6D, 7C), (1B, 2C, 3C, 4E, 5B, 6A, 7A), (1B, 2C, 3C, 4E, 5B, 6A, 7B), (1B, 2C, 3C, 4E, 5B, 6A, 7C), (1B, 2C, 3C, 4E, 5B, 6B, 7A), (1B, 2C, 3C, 4E, 5B, 6B, 7B), (1B, 2C, 3C, 4E, 5B, 6B, 7C), (1B, 2C, 3C, 4E, 5B, 6C, 7A), (1B, 2C, 3C, 4E, 5B, 6C, 7B), (1B, 2C, 3C, 4E, 5B, 6C, 7C), (1B, 2C, 3C, 4E, 5B, 6D, 7A), (1B, 2C, 3C, 4E, 5B, 6D, 7B), (1B, 2C, 3C, 4E, 5B, 6D, 7C), (1B, 2C, 3D, 4A, 5A, 6A, 7A), (1B, 2C, 3D, 4A, 5A, 6A, 7B), (1B, 2C, 3D, 4A, 5A, 6A, 7C), (1B, 2C, 3D, 4A, 5A, 6B, 7A), (1B, 2C, 3D, 4A, 5A, 6B, 7B), (1B, 2C, 3D, 4A, 5A, 6B, 7C), (1B, 2C, 3D, 4A, 5A, 6C, 7A), (1B, 2C, 3D, 4A, 5A, 6C, 7B), (1B, 2C, 3D, 4A, 5A, 6C, 7C), (1B, 2C, 3D, 4A, 5A, 6D, 7A), (1B, 2C, 3D, 4A, 5A, 6D, 7B), (1B, 2C, 3D, 4A, 5A, 6D, 7C), (1B, 2C, 3D, 4A, 5B, 6A, 7A), (1B, 2C, 3D, 4A, 5B, 6A, 7B), (1B, 2C, 3D, 4A, 5B, 6A, 7C), (1B, 2C, 3D, 4A, 5B, 6B, 7A), (1B, 2C, 3D, 4A, 5B, 6B, 7B), (1B, 2C, 3D, 4A, 5B, 6B, 7C), (1B, 2C, 3D, 4A, 5B, 6C, 7A), (1B, 2C, 3D, 4A, 5B, 6C, 7B), (1B, 2C, 3D, 4A, 5B, 6C, 7C), (1B, 2C, 3D, 4A, 5B, 6D, 7A), (1B, 2C, 3D, 4A, 5B, 6D, 7B), (1B, 2C, 3D, 4A, 5B, 6D, 7C), (1B, 2C, 3D, 4B, 5A, 6A, 7A), (1B, 2C, 3D, 4B, 5A, 6A, 7B), (1B, 2C, 3D, 4B, 5A, 6A, 7C), (1B, 2C, 3D, 4B, 5A, 6B, 7A), (1B, 2C, 3D, 4B, 5A, 6B, 7B), (1B, 2C, 3D, 4B, 5A, 6B, 7C), (1B, 2C, 3D, 4B, 5A, 6C, 7A), (1B, 2C, 3D, 4B, 5A, 6C, 7B), (1B, 2C, 3D, 4B, 5A, 6C, 7C), (1B, 2C, 3D, 4B, 5A, 6D, 7A), (1B, 2C, 3D, 4B, 5A, 6D, 7B), (1B, 2C, 3D, 4B, 5A, 6D, 7C), (1B, 2C, 3D, 4B, 5B, 6A, 7A), (1B, 2C, 3D, 4B, 5B, 6A, 7B), (1B, 2C, 3D, 4B, 5B, 6A, 7C), (1B, 2C, 3D, 4B, 5B, 6B, 7A), (1B, 2C, 3D, 4B, 5B, 6B, 7B), (1B, 2C, 3D, 4B, 5B, 6B, 7C), (1B, 2C, 3D, 4B, 5B, 6C, 7A), (1B, 2C, 3D, 4B, 5B, 6C, 7B), (1B, 2C, 3D, 4B, 5B, 6C, 7C), (1B, 2C, 3D, 4B, 5B, 6D, 7A), (1B, 2C, 3D, 4B, 5B, 6D, 7B), (1B, 2C, 3D, 4B, 5B, 6D, 7C), (1B, 2C, 3D, 4C, 5A, 6A, 7A), (1B, 2C, 3D, 4C, 5A, 6A, 7B), (1B, 2C, 3D, 4C, 5A, 6A, 7C), (1B, 2C, 3D, 4C, 5A, 6B, 7A), (1B, 2C, 3D, 4C, 5A, 6B, 7B), (1B, 2C, 3D, 4C, 5A, 6B, 7C), (1B, 2C, 3D, 4C, 5A, 6C, 7A), (1B, 2C, 3D, 4C, 5A, 6C, 7B), (1B, 2C, 3D, 4C, 5A, 6C, 7C), (1B, 2C, 3D, 4C, 5A, 6D, 7A), (1B, 2C, 3D, 4C, 5A, 6D, 7B), (1B, 2C, 3D, 4C, 5A, 6D, 7C), (1B, 2C, 3D, 4C, 5B, 6A, 7A), (1B, 2C, 3D, 4C, 5B, 6A, 7B), (1B, 2C, 3D, 4C, 5B, 6A, 7C), (1B, 2C, 3D, 4C, 5B, 6B, 7A), (1B, 2C, 3D, 4C, 5B, 6B, 7B), (1B, 2C, 3D, 4C, 5B, 6B, 7C), (1B, 2C, 3D, 4C, 5B, 6C, 7A), (1B, 2C, 3D, 4C, 5B, 6C, 7B), (1B, 2C, 3D, 4C, 5B, 6C, 7C), (1B, 2C, 3D, 4C, 5B, 6D, 7A), (1B, 2C, 3D, 4C, 5B, 6D, 7B), (1B, 2C, 3D, 4C, 5B, 6D, 7C), (1B, 2C, 3D, 4D, 5A, 6A, 7A), (1B, 2C, 3D, 4D, 5A, 6A, 7B), (1B, 2C, 3D, 4D, 5A, 6A, 7C), (1B, 2C, 3D, 4D, 5A, 6B, 7A), (1B, 2C, 3D, 4D, 5A, 6B, 7B), (1B, 2C, 3D, 4D, 5A, 6B, 7C), (1B, 2C, 3D, 4D, 5A, 6C, 7A), (1B, 2C, 3D, 4D, 5A, 6C, 7B), (1B, 2C, 3D, 4D, 5A, 6C, 7C), (1B, 2C, 3D, 4D, 5A, 6D, 7A), (1B, 2C, 3D, 4D, 5A, 6D, 7B), (1B, 2C, 3D, 4D, 5A, 6D, 7C), (1B, 2C, 3D, 4 D, 5B, 6A, 7A), (1B, 2C, 3D, 4D, 5B, 6A, 7B), (1B, 2C, 3D, 4D, 5B, 6A, 7C), (1B, 2C, 3D, 4D, 5B, 6A, 7A), (1B, 2C, 3D, 4D, 5B, 6B, 7B), (1B, 2C, 3D, 4D, 5B, 6B, 7C), (1B, 2C, 3D, 4D, 5B, 6C, 7A), (1B, 2C, 3D, 4D, 5B, 6C, 7B), (1B, 2C, 3D, 4D, 5B, 6C, 7C), (1B, 2C, 3D, 4D, 5B, 6D, 7A), (1B, 2C, 3D, 4D, 5B, 6D, 7B), (1B, 2C, 3D, 4D, 5B, 6D, 7C), (1B, 2C, 3D, 4E, 5A, 6A, 7A), (1B, 2C, 3D, 4E, 5A, 6A, 7B), (1B, 2C, 3D, 4E, 5A, 6A, 7C), (1B, 2C, 3D, 4E, 5A, 6B, 7A), (1B, 2C, 3D, 4E, 5A, 6B, 7B), (1B, 2C, 3D, 4E, 5A, 6B, 7C), (1B, 2C, 3D, 4E, 5A, 6C, 7A), (1B, 2C, 3D, 4E, 5A, 6C, 7B), (1B, 2C, 3D, 4E, 5A, 6C, 7C), (1B, 2C, 3D, 4E, 5A, 6D, 7A), (1B, 2C, 3D, 4E, 5A, 6D, 7B), (1B, 2C, 3D, 4E, 5A, 6D, 7C), (1B, 2C, 3D, 4E, 5B, 6A, 7A), (1B, 2C, 3D, 4E, 5B, 6A, 7B), (1B, 2C, 3D, 4E, 5B, 6A, 7C), (1B, 2C, 3D, 4E, 5B, 6B, 7A), (1B, 2C, 3D, 4E, 5B, 6B, 7B), (1B, 2C, 3D, 4E, 5B, 6B, 7C), (1B, 2C, 3D, 4E, 5B, 6C, 7A), (1B, 2C, 3D, 4E, 5B, 6C, 7B), (1B, 2C, 3D, 4E, 5B, 6C, 7C), (1B, 2C, 3D, 4E, 5B, 6D, 7A), (1B, 2C, 3D, 4E, 5B, 6D, 7B), (1B, 2C, 3D, 4E, 5B, 6D, 7C), (1B, 2C, 3E, 4A, 5A, 6A, 7A), (1B, 2C, 3E, 4A, 5A, 6A, 7B), (1B, 2C, 3E, 4A, 5A, 6A, 7C), (1B, 2C, 3E, 4A, 5A, 6B, 7A), (1B, 2C, 3E, 4A, 5A, 6B, 7B), (1B, 2C, 3E, 4A, 5A, 6B, 7C), (1B, 2C, 3E, 4A, 5A, 6C, 7A), (1B, 2C, 3E, 4A, 5A, 6C, 7B), (1B, 2C, 3E, 4A, 5A, 6C, 7C), (1B, 2C, 3E, 4A, 5A, 6D, 7A), (1B, 2C, 3E, 4A, 5A, 6D, 7B), (1B, 2C, 3E, 4A, 5A, 6D, 7C), (1B, 2C, 3E, 4A, 5B, 6A, 7A), (1B, 2C, 3E, 4A, 5B, 6A, 7B), (1B, 2C, 3E, 4A, 5B, 6A, 7C), (1B, 2C, 3E, 4A, 5B, 6B, 7A), (1B, 2C, 3E, 4A, 5B, 6B, 7B), (1B, 2C, 3E, 4A, 5B, 6B, 7C), (1B, 2C, 3E, 4A, 5B, 6C, 7A), (1B, 2C, 3E, 4A, 5B, 6C, 7B), (1B, 2C, 3E, 4A, 5B, 6C, 7C), (1B, 2C, 3E, 4A, 5B, 6D, 7A), (1B, 2C, 3E, 4A, 5B, 6D, 7B), (1B, 2C, 3E, 4A, 5B, 6D, 7C), (1B, 2C, 3E, 4B, 5A, 6A, 7A), (1B, 2C, 3E, 4B, 5A, 6A, 7B), (1B, 2C, 3E, 4B, 5A, 6A, 7C), (1B, 2C, 3E, 4B, 5A, 6B, 7A), (1B, 2C, 3E, 4B, 5A, 6B, 7B), (1B, 2C, 3E, 4B, 5A, 6B, 7C), (1B, 2C, 3E, 4B, 5A, 6C, 7A), (1B, 2C, 3E, 4B, 5A, 6C, 7B), (1B, 2C, 3E, 4B, 5A, 6C, 7C), (1B, 2C, 3E, 4B, 5A, 6D, 7A), (1B, 2C, 3E, 4B, 5A, 6D, 7B), (1B, 2C, 3E, 4B, 5A, 6D, 7C), (1B, 2C, 3E, 4B, 5B, 6A, 7A), (1B, 2C, 3E, 4B, 5B, 6A, 7B), (1B, 2C, 3E, 4B, 5B, 6A, 7C), (1B, 2C, 3E, 4B, 5B, 6B, 7A), (1B, 2C, 3E, 4B, 5B, 6B, 7B), (1B, 2C, 3E, 4B, 5B, 6B, 7C), (1B, 2C, 3E, 4B, 5B, 6C, 7A), (1B, 2C, 3E, 4B, 5B, 6C, 7B), (1B, 2C, 3E, 4B, 5B, 6C, 7C), (1B, 2C, 3E, 4B, 5B, 6D, 7A), (1B, 2C, 3E, 4B, 5B, 6D, 7B), (1B, 2C, 3E, 4B, 5B, 6D, 7C), (1B, 2C, 3E, 4C, 5A, 6A, 7A), (1B, 2C, 3E, 4C, 5A, 6A, 7B), (1B, 2C, 3E, 4C, 5A, 6A, 7C), (1B, 2C, 3E, 4C, 5A, 6B, 7A), (1B, 2C, 3E, 4C, 5A, 6B, 7B), (1B, 2C, 3E, 4C, 5A, 6B, 7C), (1B, 2C, 3E, 4C, 5A, 6C, 7A), (1B, 2C, 3E, 4C, 5A, 6C, 7B), (1B, 2C, 3E, 4C, 5A, 6C, 7C), (1B, 2C, 3E, 4C, 5A, 6D, 7A), (1B, 2C, 3E, 4C, 5A, 6D, 7B), (1B, 2C, 3E, 4C, 5A, 6D, 7C), (1B, 2C, 3E, 4C, 5B, 6A, 7A), (1B, 2C, 3E, 4C, 5B, 6A, 7B), (1B, 2C, 3E, 4C, 5B, 6A, 7C), (1B, 2C, 3E, 4C, 5B, 6B, 7A), (1B, 2C, 3E, 4C, 5B, 6B, 7B), (1B, 2C, 3E, 4C, 5B, 6B, 7C), (1B, 2C, 3E, 4C, 5B, 6C, 7A), (1B, 2C, 3E, 4C, 5B, 6C, 7B), (1B, 2C, 3E, 4C, 5B, 6C, 7C), (1B, 2C, 3E, 4C, 5B, 6D, 7A), (1B, 2C, 3E, 4C, 5B, 6D, 7B), (1B, 2C, 3E, 4C, 5B, 6D, 7C), (1B, 2C, 3E, 4D, 5A, 6A, 7A), (1B, 2C, 3E, 4D, 5A, 6A, 7B), (1B, 2C, 3E, 4D, 5A, 6A, 7C), (1B, 2C, 3E, 4D, 5A, 6B, 7A), (1B, 2C, 3E, 4D, 5A, 6B, 7B), (1B, 2C, 3E, 4D, 5A, 6B, 7C), (1B, 2C, 3E, 4D, 5A, 6C, 7A), (1B, 2C, 3E, 4D, 5A, 6C, 7B), (1B, 2C, 3E, 4D, 5A, 6C, 7C), (1B, 2C, 3E, 4D, 5A, 6D, 7A), (1B, 2C, 3E, 4D, 5A, 6D, 7B), (1B, 2C, 3E, 4D, 5A, 6D, 7C), (1B, 2C, 3E, 4D, 5B, 6A, 7A), (1B, 2C, 3E, 4D, 5B, 6A, 7B), (1B, 2C, 3E, 4D, 5B, 6A, 7C), (1B, 2C, 3E, 4D, 5B, 6B, 7A), (1B, 2C, 3E, 4D, 5B, 6B, 7B), (1B, 2C, 3E, 4D, 5B, 6B, 7C), (1B, 2C, 3E, 4D, 5B, 6C, 7A), (1B, 2C, 3E, 4D, 5B, 6C, 7B), (1B, 2C, 3E, 4D, 5B, 6C, 7C), (1B, 2C, 3E, 4D, 5B, 6D, 7A), (1B, 2C, 3E, 4D, 5B, 6D, 7B), (1B, 2C, 3E, 4D, 5B, 6D, 7C), (1B, 2C, 3E, 4E, 5A, 6A, 7A), (1B, 2C, 3E, 4E, 5A, 6A, 7B), (1B, 2C, 3E, 4E, 5A, 6A, 7C), (1B, 2C, 3E, 4E, 5A, 6B, 7A), (1B, 2C, 3E, 4E, 5A, 6B, 7B), (1B, 2C, 3E, 4E, 5A, 6B, 7C), (1B, 2C, 3E, 4E, 5A, 6C, 7A), (1B, 2C, 3E, 4E, 5A, 6C, 7B), (1B, 2C, 3E, 4E, 5A, 6C, 7C), (1B, 2C, 3E, 4E, 5A, 6D, 7A), (1B, 2C, 3E, 4E, 5A, 6D, 7B), (1B, 2C, 3E, 4E, 5A, 6D, 7C), (1B, 2C, 3E, 4E, 5B, 6A, 7A), (1B, 2C, 3E, 4E, 5B, 6A, 7B), (1B, 2C, 3E, 4E, 5B, 6A, 7C), (1B, 2C, 3E, 4E, 5B, 6B, 7A), (1B, 2C, 3E, 4E, 5B, 6B, 7B), (1B, 2C, 3E, 4E, 5B, 6B, 7C), (1B, 2C, 3E, 4E, 5B, 6C, 7A), (1B, 2C, 3E, 4E, 5B, 6C, 7B), (1B, 2C, 3E, 4E, 5B, 6C, 7C), (1B, 2C, 3E, 4E, 5B, 6D, 7A), (1B, 2C, 3E, 4E, 5B, 6D, 7B), (1B, 2C, 3E, 4E, 5B, 6D, 7C), (1B, 2D, 3A, 4A, 5A, 6A, 7A), (1B, 2D, 3A, 4A, 5A, 6A, 7B), (1B, 2D, 3A, 4A, 5A, 6A, 7C), (1B, 2D, 3A, 4A, 5A, 6B, 7A), (1B, 2D, 3A, 4A, 5A, 6B, 7B), (1B, 2D, 3A, 4A, 5A, 6B, 7C), (1B, 2D, 3A, 4A, 5A, 6C, 7A), (1B, 2D, 3A, 4A, 5A, 6C, 7B), (1B, 2D, 3A, 4A, 5A, 6C, 7C), (1B, 2D, 3A, 4A, 5A, 6D, 7A), (1B, 2D, 3A, 4A, 5A, 6D, 7B), (1B, 2D, 3A, 4A, 5A, 6D, 7C), (1B, 2D, 3A, 4A, 5B, 6A, 7A), (1B, 2D, 3A, 4A, 5B, 6A, 7B), (1B, 2D, 3A, 4A, 5B, 6A, 7C), (1B, 2D, 3A, 4A, 5B, 6B, 7A), (1B, 2D, 3A, 4A, 5B, 6B, 7B), (1B, 2D, 3A, 4A, 5B, 6B, 7C), (1B, 2D, 3A, 4A, 5B, 6C, 7A), (1B, 2D, 3A, 4A, 5B, 6C, 7B), (1B, 2D, 3A, 4A, 5B, 6C, 7C), (1B, 2D, 3A, 4A, 5B, 6D, 7A), (1B, 2D, 3A, 4A, 5B, 6D, 7B), (1B, 2D, 3A, 4A, 5B, 6D, 7C), (1B, 2D, 3A, 4B, 5A, 6A, 7A), (1B, 2D, 3A, 4B, 5A, 6A, 7B), (1B, 2D, 3A, 4B, 5A, 6A, 7C), (1B, 2D, 3A, 4B, 5A, 6B, 7A), (1B, 2D, 3A, 4B, 5A, 6B, 7B), (1B, 2D, 3A, 4B, 5A, 6B, 7C), (1B, 2D, 3A, 4B, 5A, 6C, 7A), (1B, 2D, 3A, 4B, 5A, 6C, 7B), (1B, 2D, 3A, 4B, 5A, 6C, 7C), (1B, 2D, 3A, 4B, 5A, 6D, 7A), (1B, 2D, 3A, 4B, 5A, 6D, 7B), (1B, 2D, 3A, 4B, 5A, 6D, 7C), (1B, 2D, 3A, 4B, 5B, 6A, 7A), (1B, 2D, 3A, 4B, 5B, 6A, 7B), (1B, 2D, 3A, 4B, 5B, 6A, 7C), (1B, 2D, 3A, 4B, 5B, 6B, 7A), (1B, 2D, 3A, 4B, 5B, 6B, 7B), (1B, 2D, 3A, 4B, 5B, 6B, 7C), (1B, 2D, 3A, 4B, 5B, 6C, 7A), (1B, 2D, 3A, 4B, 5B, 6C, 7B), (1B, 2D, 3A, 4B, 5B, 6C, 7C), (1B, 2D, 3A, 4B, 5B, 6D, 7A), (1B, 2D, 3A, 4B, 5B, 6D, 7B), (1B, 2D, 3A, 4B, 5B, 6D, 7C), (1B, 2D, 3A, 4C, 5A, 6A, 7A), (1B, 2D, 3A, 4C, 5A, 6A, 7B), (1B, 2D, 3A, 4C, 5A, 6A, 7C), (1B, 2D, 3A, 4C, 5A, 6B, 7A), (1B, 2D, 3A, 4C, 5A, 6B, 7B), (1B, 2D, 3A, 4C, 5A, 6B, 7C), (1B, 2D, 3A, 4C, 5A, 6C, 7A), (1B, 2D, 3A, 4C, 5A, 6C, 7B), (1B, 2D, 3A, 4C, 5A, 6C, 7C), (1B, 2D, 3A, 4C, 5A, 6D, 7A), (1B, 2D, 3A, 4C, 5A, 6D, 7B), (1B, 2D, 3A, 4C, 5A, 6D, 7C), (1B, 2D, 3A, 4C, 5B, 6A, 7A), (1B, 2D, 3A, 4C, 5B, 6A, 7B), (1B, 2D, 3A, 4C, 5B, 6A, 7C), (1B, 2D, 3A, 4C, 5B, 6B, 7A), (1B, 2D, 3A, 4C, 5B, 6B, 7B), (1B, 2D, 3A, 4C, 5B, 6B, 7C), (1B, 2D, 3A, 4C, 5B, 6C, 7A), (1B, 2D, 3A, 4C, 5B, 6C, 7B), (1B, 2D, 3A, 4C, 5B, 6C, 7C), (1B, 2D, 3A, 4C, 5B, 6D, 7A), (1B, 2D, 3A, 4C, 5B, 6D, 7B), (1B, 2D, 3A, 4C, 5B, 6D, 7C), (1B, 2D, 3A, 4D, 5A, 6A, 7A), (1B, 2D, 3A, 4D, 5A, 6A, 7B), (1B, 2D, 3A, 4D, 5A, 6A, 7C), (1B, 2D, 3A, 4D, 5A, 6B, 7A), (1B, 2D, 3A, 4D, 5A, 6B, 7B), (1B, 2D, 3A, 4D, 5A, 6B, 7C), (1B, 2D, 3A, 4D, 5A, 6C, 7A), (1B, 2D, 3A, 4D, 5A, 6C, 7B), (1B, 2D, 3A, 4D, 5A, 6C, 7C), (1B, 2D, 3A, 4D, 5A, 6D, 7A), (1B, 2D, 3A, 4D, 5A, 6D, 7B), (1B, 2D, 3A, 4D, 5A, 6D, 7C), (1B, 2D, 3A, 4D, 5B, 6A, 7A), (1B, 2D, 3A, 4D, 5B, 6A, 7B), (1B, 2D, 3A, 4D, 5B, 6A, 7C), (1B, 2D, 3A, 4D, 5B, 6B, 7A), (1B, 2D, 3A, 4D, 5B, 6B, 7B), (1B, 2D, 3A, 4D, 5B, 6B, 7C), (1B, 2D, 3A, 4D, 5B, 6C, 7A), (1B, 2D, 3A, 4D, 5B, 6C, 7B), (1B, 2D, 3A, 4D, 5B, 6C, 7C), (1B, 2D, 3A, 4D, 5B, 6D, 7A), (1B, 2D, 3A, 4D, 5B, 6D, 7B), (1B, 2D, 3A, 4D, 5B, 6D, 7C), (1B, 2D, 3A, 4E, 5A, 6A, 7A), (1B, 2D, 3A, 4E, 5A, 6A, 7B), (1B, 2D, 3A, 4E, 5A, 6A, 7C), (1B, 2D, 3A, 4E, 5A, 6B, 7A), (1B, 2D, 3A, 4E, 5A, 6B, 7B), (1B, 2D, 3A, 4E, 5A, 6B, 7C), (1B, 2D, 3A, 4E, 5A, 6C, 7A), (1B, 2D, 3A, 4E, 5A, 6C, 7B), (1B, 2D, 3A, 4E, 5A, 6C, 7C), (1B, 2D, 3A, 4E, 5A, 6D, 7A), (1B, 2D, 3A, 4E, 5A, 6D, 7B), (1B, 2D, 3A, 4E, 5A, 6D, 7C), (1B, 2D, 3A, 4E, 5B, 6A, 7A), (1B, 2D, 3A, 4E, 5B, 6A, 7B), (1B, 2D, 3A, 4E, 5B, 6A, 7C), (1B, 2D, 3A, 4E, 5B, 6B, 7A), (1B, 2D, 3A, 4E, 5B, 6B, 7B), (1B, 2D, 3A, 4E, 5B, 6B, 7C), (1B, 2D, 3A, 4E, 5B, 6C, 7A), (1B, 2D, 3A, 4E, 5B, 6C, 7B), (1B, 2D, 3A, 4E, 5B, 6C, 7C), (1B, 2D, 3A, 4E, 5B, 6D, 7A), (1B, 2D, 3A, 4E, 5B, 6D, 7B), (1B, 2D, 3A, 4E, 5B, 6D, 7C), (1B, 2D, 3B, 4A, 5A, 6A, 7A), (1B, 2D, 3B, 4A, 5A, 6A, 7B), (1B, 2D, 3B, 4A, 5A, 6A, 7C), (1B, 2D, 3B, 4A, 5A, 6B, 7A), (1B, 2D, 3B, 4A, 5A, 6B, 7B), (1B, 2D, 3B, 4A, 5A, 6B, 7C), (1B, 2D, 3B, 4A, 5A, 6C, 7A), (1B, 2D, 3B, 4A, 5A, 6C, 7B), (1B, 2D, 3B, 4A, 5A, 6C, 7C), (1B, 2D, 3B, 4A, 5A, 6D, 7A), (1B, 2D, 3B, 4A, 5A, 6D, 7B), (1B, 2D, 3B, 4A, 5A, 6D, 7C), (1B, 2D, 3B, 4A, 5B, 6A, 7A), (1B, 2D, 3B, 4A, 5B, 6A, 7B), (1B, 2D, 3B, 4A, 5B, 6A, 7C), (1B, 2D, 3B, 4A, 5B, 6B, 7A), (1B, 2D, 3B, 4A, 5B, 6B, 7B), (1B, 2D, 3B, 4A, 5B, 6B, 7C), (1B, 2D, 3B, 4A, 5B, 6C, 7A), (1B, 2D, 3B, 4A, 5B, 6C, 7B), (1B, 2D, 3B, 4A, 5B, 6C, 7C), (1B, 2D, 3B, 4A, 5B, 6D, 7A), (1B, 2D, 3B, 4A, 5B, 6D, 7B), (1B, 2D, 3B, 4A, 5B, 6D, 7C), (1B, 2D, 3B, 4B, 5A, 6A, 7A), (1B, 2D, 3B, 4B, 5A, 6A, 7B), (1B, 2D, 3B, 4B, 5A, 6A, 7C), (1B, 2D, 3B, 4B, 5A, 6B, 7A), (1B, 2D, 3B, 4B, 5A, 6B, 7B), (1B, 2D, 3B, 4B, 5A, 6B, 7C), (1B, 2D, 3B, 4B, 5A, 6C, 7A), (1B, 2D, 3B, 4B, 5A, 6C, 7B), (1B, 2D, 3B, 4B, 5A, 6C, 7C), (1B, 2D, 3B, 4B, 5A, 6D, 7A), (1B, 2D, 3B, 4B, 5A, 6D, 7B), (1B, 2D, 3B, 4B, 5A, 6D, 7C), (1B, 2D, 3B, 4B, 5B, 6A, 7A), (1B, 2D, 3B, 4B, 5B, 6A, 7B), (1B, 2D, 3B, 4B, 5B, 6A, 7C), (1B, 2D, 3B, 4B, 5B, 6B, 7A), (1B, 2D, 3B, 4B, 5B, 6B, 7B), (1B, 2D, 3B, 4B, 5B, 6B, 7C), (1B, 2D, 3B, 4B, 5B, 6C, 7A), (1B, 2D, 3B, 4B, 5B, 6C, 7B), (1B, 2D, 3B, 4B, 5B, 6C, 7C), (1B, 2D, 3B, 4B, 5B, 6D, 7A), (1B, 2D, 3B, 4B, 5B, 6D, 7B), (1B, 2D, 3B, 4B, 5B, 6D, 7C), (1B, 2D, 3B, 4C, 5A, 6A, 7A), (1B, 2D, 3B, 4C, 5A, 6A, 7B), (1B, 2D, 3B, 4C, 5A, 6A, 7C), (1B, 2D, 3B, 4C, 5A, 6B, 7A), (1B, 2D, 3B, 4C, 5A, 6B, 7B), (1B, 2D, 3B, 4C, 5A, 6B, 7C), (1B, 2D, 3B, 4C, 5A, 6C, 7A), (1B, 2D, 3B, 4C, 5A, 6C, 7B), (1B, 2D, 3B, 4C, 5A, 6C, 7C), (1B, 2D, 3B, 4C, 5A, 6D, 7A), (1B, 2D, 3B, 4C, 5A, 6D, 7B), (1B, 2D, 3B, 4C, 5A, 6D, 7C), (1B, 2D, 3B, 4C, 5B, 6A, 7A), (1B, 2D, 3B, 4C, 5B, 6A, 7B), (1B, 2D, 3B, 4C, 5B, 6A, 7C), (1B, 2D, 3B, 4C, 5B, 6B, 7A), (1B, 2D, 3B, 4C, 5B, 6B, 7B), (1B, 2D, 3B, 4C, 5B, 6B, 7C), (1B, 2D, 3B, 4C, 5B, 6C, 7A), (1B, 2D, 3B, 4C, 5B, 6C, 7B), (1B, 2D, 3B, 4C, 5B, 6C, 7C), (1B, 2D, 3B, 4C, 5B, 6D, 7A), (1B, 2D, 3B, 4C, 5B, 6D, 7B), (1B, 2D, 3B, 4C, 5B, 6D, 7C), (1B, 2D, 3B, 4D, 5A, 6A, 7A), (1B, 2D, 3B, 4D, 5A, 6A, 7B), (1B, 2D, 3B, 4D, 5A, 6A, 7C), (1B, 2D, 3B, 4D, 5A, 6B, 7A), (1B, 2D, 3B, 4D, 5A, 6B, 7B), (1B, 2D, 3B, 4D, 5A, 6B, 7C), (1B, 2D, 3B, 4D, 5A, 6C, 7A), (1B, 2D, 3B, 4D, 5A, 6C, 7B), (1B, 2D, 3B, 4D, 5A, 6C, 7C), (1B, 2D, 3B, 4D, 5A, 6D, 7A), (1B, 2D, 3B, 4D, 5A, 6D, 7B), (1B, 2D, 3B, 4D, 5A, 6D, 7C), (1B, 2D, 3B, 4D, 5B, 6A, 7A), (1B, 2D, 3B, 4D, 5B, 6A, 7B), (1B, 2D, 3B, 4D, 5B, 6A, 7C), (1B, 2D, 3B, 4D, 5B, 6B, 7A), (1B, 2D, 3B, 4D, 5B, 6B, 7B), (1B, 2D, 3B, 4D, 5B, 6B, 7C), (1B, 2D, 3B, 4D, 5B, 6C, 7A), (1B, 2D, 3B, 4D, 5B, 6C, 7B), (1B, 2D, 3B, 4D, 5B, 6C, 7C), (1B, 2D, 3B, 4D, 5B, 6D, 7A), (1B, 2D, 3B, 4D, 5B, 6D, 7B), (1B, 2D, 3B, 4D, 5B, 6D, 7C), (1B, 2D, 3B, 4E, 5A, 6A, 7A), (1B, 2D, 3B, 4E, 5A, 6A, 7B), (1B, 2D, 3B, 4E, 5A, 6A, 7C), (1B, 2D, 3B, 4E, 5A, 6B, 7A), (1B, 2D, 3B, 4E, 5A, 6B, 7B), (1B, 2D, 3B, 4E, 5A, 6B, 7C), (1B, 2D, 3B, 4E, 5A, 6C, 7A), (1B, 2D, 3B, 4E, 5A, 6C, 7B), (1B, 2D, 3B, 4E, 5A, 6C, 7C), (1B, 2D, 3B, 4E, 5A, 6D, 7A), (1B, 2D, 3B, 4E, 5A, 6D, 7B), (1B, 2D, 3B, 4E, 5A, 6D, 7C), (1B, 2D, 3B, 4E, 5B, 6A, 7A), (1B, 2D, 3B, 4E, 5B, 6A, 7B), (1B, 2D, 3B, 4E, 5B, 6A, 7C), (1B, 2D, 3B, 4E, 5B, 6B, 7A), (1B, 2D, 3B, 4E, 5B, 6B, 7B), (1B, 2D, 3B, 4E, 5B, 6B, 7C), (1B, 2D, 3B, 4E, 5B, 6C, 7A), (1B, 2D, 3B, 4E, 5B, 6C, 7B), (1B, 2D, 3B, 4E, 5B, 6C, 7C), (1B, 2D, 3B, 4E, 5B, 6D, 7A), (1B, 2D, 3B, 4E, 5B, 6D, 7B), (1B, 2D, 3B, 4E, 5B, 6D, 7C), (1B, 2D, 3C, 4A, 5A, 6A, 7A), (1B, 2D, 3C, 4A, 5A, 6A, 7B), (1B, 2D, 3C, 4A, 5A, 6A, 7C), (1B, 2D, 3C, 4A, 5A, 6B, 7A), (1B, 2D, 3C, 4A, 5A, 6B, 7B), (1B, 2D, 3C, 4A, 5A, 6B, 7C), (1B, 2D, 3C, 4A, 5A, 6C, 7A), (1B, 2D, 3C, 4A, 5A, 6C, 7B), (1B, 2D, 3C, 4A, 5A, 6C, 7C), (1B, 2D, 3C, 4A, 5A, 6D, 7A), (1B, 2D, 3C, 4A, 5A, 6D, 7B), (1B, 2D, 3C, 4A, 5A, 6D, 7C), (1B, 2D, 3C, 4A, 5B, 6A, 7A), (1B, 2D, 3C, 4A, 5B, 6A, 7B), (1B, 2D, 3C, 4A, 5B, 6A, 7C), (1B, 2D, 3C, 4A, 5B, 6B, 7A), (1B, 2D, 3C, 4A, 5B, 6B, 7B), (1B, 2D, 3C, 4A, 5B, 6B, 7C), (1B, 2D, 3C, 4A, 5B, 6C, 7A), (1B, 2D, 3C, 4A, 5B, 6C, 7B), (1B, 2D, 3C, 4A, 5B, 6C, 7C), (1B, 2D, 3C, 4A, 5B, 6D, 7A), (1B, 2D, 3C, 4A, 5B, 6D, 7C), (1B, 2D, 3C, 4B, 5A, 6A, 7A), (1B, 2D, 3C, 4B, 5A, 6A, 7B), (1B, 2D, 3C, 4B, 5A, 6A, 7C), (1B, 2D, 3C, 4B, 5A, 6B, 7A), (1B, 2D, 3C, 4B, 5A, 6B, 7B), (1B, 2D, 3C, 4B, 5A, 6B, 7C), (1B, 2D, 3C, 4B, 5A, 6C, 7A), (1B, 2D, 3C, 4B, 5A, 6C, 7B), (1B, 2D, 3C, 4B, 5A, 6C, 7C), (1B, 2D, 3C, 4B, 5A, 6D, 7A), (1B, 2D, 3C, 4B, 5A, 6D, 7B), (1B, 2D, 3C, 4B, 5A, 6D, 7C), (1B, 2D, 3C, 4B, 5B, 6A, 7A), (1B, 2D, 3C, 4B, 5B, 6A, 7B), (1B, 2D, 3C, 4B, 5B, 6A, 7C), (1B, 2D, 3C, 4B, 5B, 6B, 7A), (1B, 2D, 3C, 4B, 5B, 6B, 7B), (1B, 2D, 3C, 4B, 5B, 6B, 7C), (1B, 2D, 3C, 4B, 5B, 6C, 7A), (1B, 2D, 3C, 4B, 5B, 6C, 7B), (1B, 2D, 3C, 4B, 5B, 6C, 7C), (1B, 2D, 3C, 4B, 5B, 6D, 7A), (1B, 2D, 3C, 4B, 5B, 6D, 7B), (1B, 2D, 3C, 4B, 5B, 6D, 7C), (1B, 2D, 3C, 4C, 5A, 6A, 7A), (1B, 2D, 3C, 4C, 5A, 6A, 7B), (1B, 2D, 3C, 4C, 5A, 6A, 7C), (1B, 2D, 3C, 4C, 5A, 6B, 7A), (1B, 2D, 3C, 4C, 5A, 6B, 7B), (1B, 2D, 3C, 4C, 5A, 6B, 7C), (1B, 2D, 3C, 4C, 5A, 6C, 7A), (1B, 2D, 3C, 4C, 5A, 6C, 7B), (1B, 2D, 3C, 4C, 5A, 6C, 7C), (1B, 2D, 3C, 4C, 5A, 6D, 7A), (1B, 2D, 3C, 4C, 5A, 6D, 7B), (1B, 2D, 3C, 4C, 5A, 6D, 7C), (1B, 2D, 3C, 4C, 5B, 6A, 7A), (1B, 2D, 3C, 4C, 5B, 6A, 7B), (1B, 2D, 3C, 4C, 5B, 6A, 7C), (1B, 2D, 3C, 4C, 5B, 6B, 7A), (1B, 2D, 3C, 4C, 5B, 6B, 7B), (1B, 2D, 3C, 4C, 5B, 6B, 7C), (1B, 2D, 3C, 4C, 5B, 6C, 7A), (1B, 2D, 3C, 4C, 5B, 6C, 7B), (1B, 2D, 3C, 4C, 5B, 6C, 7C), (1B, 2D, 3C, 4C, 5B, 6D, 7A), (1B, 2D, 3C, 4C, 5B, 6D, 7B), (1B, 2D, 3C, 4C, 5B, 6D, 7C), (1B, 2D, 3C, 4D, 5A, 6A, 7A), (1B, 2D, 3C, 4D, 5A, 6A, 7B), (1B, 2D, 3C, 4D, 5A, 6A, 7C), (1B, 2D, 3C, 4D, 5A, 6B, 7A), (1B, 2D, 3C, 4D, 5A, 6B, 7B), (1B, 2D, 3C, 4D, 5A, 6B, 7C), (1B, 2D, 3C, 4D, 5A, 6C, 7A), (1B, 2D, 3C, 4D, 5A, 6C, 7B), (1B, 2D, 3C, 4D, 5A, 6C, 7C), (1B, 2D, 3C, 4D, 5A, 6D, 7A), (1B, 2D, 3C, 4D, 5A, 6D, 7B), (1B, 2D, 3C, 4D, 5A, 6D, 7C), (1B, 2D, 3C, 4D, 5B, 6A, 7A), (1B, 2D, 3C, 4D, 5B, 6A, 7B), (1B, 2D, 3C, 4D, 5B, 6A, 7C), (1B, 2D, 3C, 4D, 5B, 6B, 7A), (1B, 2D, 3C, 4D, 5B, 6B, 7B), (1B, 2D, 3C, 4D, 5B, 6B, 7C), (1B, 2D, 3C, 4D, 5B, 6C, 7A), (1B, 2D, 3C, 4D, 5B, 6C, 7B), (1B, 2D, 3C, 4D, 5B, 6C, 7C), (1B, 2D, 3C, 4D, 5B, 6D, 7A), (1B, 2D, 3C, 4D, 5B, 6D, 7B), (1B, 2D, 3C, 4D, 5B, 6D, 7C), (1B, 2D, 3C, 4E, 5A, 6A, 7A), (1B, 2D, 3C, 4E, 5A, 6A, 7B), (1B, 2D, 3C, 4E, 5A, 6A, 7C), (1B, 2D, 3C, 4E, 5A, 6B, 7A), (1B, 2D, 3C, 4E, 5A, 6B, 7B), (1B, 2D, 3C, 4E, 5A, 6B, 7C), (1B, 2D, 3C, 4E, 5A, 6C, 7A), (1B, 2D, 3C, 4E, 5A, 6C, 7B), (1B, 2D, 3C, 4E, 5A, 6C, 7C), (1B, 2D, 3C, 4E, 5A, 6D, 7A), (1B, 2D, 3C, 4E, 5A, 6D, 7B), (1B, 2D, 3C, 4E, 5A, 6D, 7C), (1B, 2D, 3C, 4E, 5B, 6A, 7A), (1B, 2D, 3C, 4E, 5B, 6A, 7B), (1B, 2D, 3C, 4E, 5B, 6A, 7C), (1B, 2D, 3C, 4E, 5B, 6B, 7A), (1B, 2D, 3C, 4E, 5B, 6B, 7B), (1B, 2D, 3C, 4E, 5B, 6B, 7C), (1B, 2D, 3C, 4E, 5B, 6C, 7A), (1B, 2D, 3C, 4E, 5B, 6C, 7B), (1B, 2D, 3C, 4E, 5B, 6C, 7C), (1B, 2D, 3C, 4E, 5B, 6D, 7A), (1B, 2D, 3C, 4E, 5B, 6D, 7B), (1B, 2D, 3C, 4E, 5B, 6D, 7C), (1B, 2D, 3D, 4A, 5A, 6A, 7A), (1B, 2D, 3D, 4A, 5A, 6A, 7B), (1B, 2D, 3D, 4A, 5A, 6A, 7C), (1B, 2D, 3D, 4A, 5A, 6B, 7A), (1B, 2D, 3D, 4A, 5A, 6B, 7B), (1B, 2D, 3D, 4A, 5A, 6B, 7C), (1B, 2D, 3D, 4A, 5A, 6C, 7A), (1B, 2D, 3D, 4A, 5A, 6C, 7B), (1B, 2D, 3D, 4A, 5A, 6C, 7C), (1B, 2D, 3D, 4A, 5A, 6D, 7A), (1B, 2D, 3D, 4A, 5A, 6D, 7B), (1B, 2D, 3D, 4A, 5A, 6D, 7C), (1B, 2D, 3D, 4A, 5B, 6A, 7A), (1B, 2D, 3D, 4A, 5B, 6A, 7B), (1B, 2D, 3D, 4A, 5B, 6A, 7C), (1B, 2D, 3D, 4A, 5B, 6B, 7A), (1B, 2D, 3D, 4A, 5B, 6B, 7B), (1B, 2D, 3D, 4A, 5B, 6B, 7C), (1B, 2D, 3D, 4A, 5B, 6C, 7A), (1B, 2D, 3D, 4A, 5B, 6C, 7B), (1B, 2D, 3D, 4A, 5B, 6C, 7C), (1B, 2D, 3D, 4A, 5B, 6D, 7A), (1B, 2D, 3D, 4A, 5B, 6D, 7B), (1B, 2D, 3D, 4A, 5B, 6D, 7C), (1B, 2D, 3D, 4B, 5A, 6A, 7A), (1B, 2D, 3D, 4B, 5A, 6A, 7B), (1B, 2D, 3D, 4B, 5A, 6A, 7C), (1B, 2D, 3D, 4B, 5A, 6B, 7A), (1B, 2D, 3D, 4B, 5A, 6B, 7B), (1B, 2D, 3D, 4B, 5A, 6B, 7C), (1B, 2D, 3D, 4B, 5A, 6C, 7A), (1B, 2D, 3D, 4B, 5A, 6C, 7B), (1B, 2D, 3D, 4B, 5A, 6C, 7C), (1B, 2D, 3D, 4B, 5A, 6D, 7A), (1B, 2D, 3D, 4B, 5A, 6D, 7B), (1B, 2D, 3D, 4B, 5A, 6D, 7C), (1B, 2D, 3D, 4B, 5B, 6A, 7A), (1B, 2D, 3D, 4B, 5B, 6A, 7B), (1B, 2D, 3D, 4B, 5B, 6B, 7A), (1B, 2D, 3D, 4B, 5B, 6B, 7B), (1B, 2D, 3D, 4B, 5B, 6B, 7C), (1B, 2D, 3D, 4B, 5B, 6C, 7A), (1B, 2D, 3D, 4B, 5B, 6C, 7B), (1B, 2D, 3D, 4B, 5B, 6C, 7C), (1B, 2D, 3D, 4B, 5B, 6D,

7A), (1B, 2D, 3D, 4B, 5B, 6D, 7B), (1B, 2D, 3D, 4B, 5B, 6D, 7C), (1B, 2D, 3D, 4C, 5A, 6A, 7A), (1B, 2D, 3D, 4C, 5A, 6A, 7B), (1B, 2D, 3D, 4C, 5A, 6A, 7C), (1B, 2D, 3D, 4C, 5A, 6B, 7A), (1B, 2D, 3D, 4C, 5A, 6B, 7B), (1B, 2D, 3D, 4C, 5A, 6B, 7C), (1B, 2D, 3D, 4C, 5A, 6C, 7A), (1B, 2D, 3D, 4C, 5A, 6C, 7B), (1B, 2D, 3D, 4C, 5A, 6C, 7C), (1B, 2D, 3D, 4C, 5A, 6D, 7A), (1B, 2D, 3D, 4C, 5A, 6D, 7B), (1B, 2D, 3D, 4C, 5A, 6D, 7C), (1B, 2D, 3D, 4C, 5B, 6A, 7A), (1B, 2D, 3D, 4C, 5B, 6A, 7B), (1B, 2D, 3D, 4C, 5B, 6A, 7C), (1B, 2D, 3D, 4C, 5B, 6B, 7A), (1B, 2D, 3D, 4C, 5B, 6B, 7B), (1B, 2D, 3D, 4C, 5B, 6B, 7C), (1B, 2D, 3D, 4C, 5B, 6C, 7A), (1B, 2D, 3D, 4C, 5B, 6C, 7B), (1B, 2D, 3D, 4C, 5B, 6C, 7C), (1B, 2D, 3D, 4C, 5B, 6D, 7A), (1B, 2D, 3D, 4C, 5B, 6D, 7B), (1B, 2D, 3D, 4C, 5B, 6D, 7C), (1B, 2D, 3D, 4D, 5A, 6A, 7A), (1B, 2D, 3D, 4D, 5A, 6A, 7B), (1B, 2D, 3D, 4D, 5A, 6A, 7C), (1B, 2D, 3D, 4D, 5A, 6B, 7A), (1B, 2D, 3D, 4D, 5A, 6B, 7B), (1B, 2D, 3D, 4D, 5A, 6B, 7C), (1B, 2D, 3D, 4D, 5A, 6C, 7A), (1B, 2D, 3D, 4D, 5A, 6C, 7B), (1B, 2D, 3D, 4D, 5A, 6C, 7C), (1B, 2D, 3D, 4D, 5A, 6D, 7A), (1B, 2D, 3D, 4D, 5A, 6D, 7B), (1B, 2D, 3D, 4D, 5A, 6D, 7C), (1B, 2D, 3D, 4D, 5B, 6A, 7A), (1B, 2D, 3D, 4D, 5B, 6A, 7B), (1B, 2D, 3D, 4D, 5B, 6A, 7C), (1B, 2D, 3D, 4D, 5B, 6B, 7A), (1B, 2D, 3D, 4D, 5B, 6B, 7B), (1B, 2D, 3D, 4D, 5B, 6B, 7C), (1B, 2D, 3D, 4D, 5B, 6C, 7A), (1B, 2D, 3D, 4D, 5B, 6C, 7B), (1B, 2D, 3D, 4D, 5B, 6C, 7C), (1B, 2D, 3D, 4D, 5B, 6D, 7A), (1B, 2D, 3D, 4D, 5B, 6D, 7B), (1B, 2D, 3D, 4D, 5B, 6D, 7C), (1B, 2D, 3D, 4E, 5A, 6A, 7A), (1B, 2D, 3D, 4E, 5A, 6A, 7B), (1B, 2D, 3D, 4E, 5A, 6A, 7C), (1B, 2D, 3D, 4E, 5A, 6B, 7A), (1B, 2D, 3D, 4E, 5A, 6B, 7B), (1B, 2D, 3D, 4E, 5A, 6B, 7C), (1B, 2D, 3D, 4E, 5A, 6C, 7A), (1B, 2D, 3D, 4E, 5A, 6C, 7B), (1B, 2D, 3D, 4E, 5A, 6C, 7C), (1B, 2D, 3D, 4E, 5A, 6D, 7A), (1B, 2D, 3D, 4E, 5A, 6D, 7B), (1B, 2D, 3D, 4E, 5A, 6D, 7C), (1B, 2D, 3D, 4E, 5B, 6A, 7A), (1B, 2D, 3D, 4E, 5B, 6A, 7B), (1B, 2D, 3D, 4E, 5B, 6A, 7C), (1B, 2D, 3D, 4E, 5B, 6B, 7A), (1B, 2D, 3D, 4E, 5B, 6B, 7B), (1B, 2D, 3D, 4E, 5B, 6B, 7C), (1B, 2D, 3D, 4E, 5B, 6C, 7A), (1B, 2D, 3D, 4E, 5B, 6C, 7B), (1B, 2D, 3D, 4E, 5B, 6C, 7C), (1B, 2D, 3D, 4E, 5B, 6D, 7A), (1B, 2D, 3D, 4E, 5B, 6D, 7B), (1B, 2D, 3D, 4E, 5B, 6D, 7C), (1B, 2D, 3E, 4A, 5A, 6A, 7A), (1B, 2D, 3E, 4A, 5A, 6A, 7B), (1B, 2D, 3E, 4A, 5A, 6A, 7C), (1B, 2D, 3E, 4A, 5A, 6B, 7A), (1B, 2D, 3E, 4A, 5A, 6B, 7B), (1B, 2D, 3E, 4A, 5A, 6B, 7C), (1B, 2D, 3E, 4A, 5A, 6C, 7A), (1B, 2D, 3E, 4A, 5A, 6C, 7B), (1B, 2D, 3E, 4A, 5A, 6C, 7C), (1B, 2D, 3E, 4A, 5A, 6D, 7A), (1B, 2D, 3E, 4A, 5A, 6D, 7B), (1B, 2D, 3E, 4A, 5A, 6D, 7C), (1B, 2D, 3E, 4A, 5B, 6A, 7A), (1B, 2D, 3E, 4A, 5B, 6A, 7B), (1B, 2D, 3E, 4A, 5B, 6A, 7C), (1B, 2D, 3E, 4A, 5B, 6B, 7A), (1B, 2D, 3E, 4A, 5B, 6B, 7B), (1B, 2D, 3E, 4A, 5B, 6B, 7C), (1B, 2D, 3E, 4A, 5B, 6C, 7A), (1B, 2D, 3E, 4A, 5B, 6C, 7B), (1B, 2D, 3E, 4A, 5B, 6C, 7C), (1B, 2D, 3E, 4A, 5B, 6D, 7A), (1B, 2D, 3E, 4A, 5B, 6D, 7B), (1B, 2D, 3E, 4A, 5B, 6D, 7C), (1B, 2D, 3E, 4B, 5A, 6A, 7A), (1B, 2D, 3E, 4B, 5A, 6A, 7B), (1B, 2D, 3E, 4B, 5A, 6A, 7C), (1B, 2D, 3E, 4B, 5A, 6B, 7A), (1B, 2D, 3E, 4B, 5A, 6B, 7B), (1B, 2D, 3E, 4B, 5A, 6B, 7C), (1B, 2D, 3E, 4B, 5A, 6C, 7A), (1B, 2D, 3E, 4B, 5A, 6C, 7B), (1B, 2D, 3E, 4B, 5A, 6C, 7C), (1B, 2D, 3E, 4B, 5A, 6D, 7A), (1B, 2D, 3E, 4B, 5A, 6D, 7B), (1B, 2D, 3E, 4B, 5A, 6D, 7C), (1B, 2D, 3E, 4B, 5B, 6A, 7A), (1B, 2D, 3E, 4B, 5B, 6A, 7B), (1B, 2D, 3E, 4B, 5B, 6A, 7C), (1B, 2D, 3E, 4B, 5B, 6B, 7A), (1B, 2D, 3E, 4B, 5B, 6B, 7B), (1B, 2D, 3E, 4B, 5B, 6B, 7C), (1B, 2D, 3E, 4B, 5B, 6C, 7A), (1B, 2D, 3E, 4B, 5B, 6C, 7B), (1B, 2D, 3E, 4B, 5B, 6C, 7C), (1B, 2D, 3E, 4B, 5B, 6D, 7A), (1B, 2D, 3E, 4B, 5B, 6D, 7B), (1B, 2D, 3E, 4B, 5B, 6D, 7C), (1B, 2D, 3E, 4C, 5A, 6A, 7A), (1B, 2D, 3E, 4C, 5A, 6A, 7B), (1B, 2D, 3E, 4C, 5A, 6A, 7C), (1B, 2D, 3E, 4C, 5A, 6B, 7A), (1B, 2D, 3E, 4C, 5A, 6B, 7B), (1B, 2D, 3E, 4C, 5A, 6B, 7C), (1B, 2D, 3E, 4C, 5A, 6C, 7A), (1B, 2D, 3E, 4C, 5A, 6C, 7B), (1B, 2D, 3E, 4C, 5A, 6C, 7C), (1B, 2D, 3E, 4C, 5A, 6D, 7A), (1B, 2D, 3E, 4C, 5A, 6D, 7B), (1B, 2D, 3E, 4C, 5A, 6D, 7C), (1B, 2D, 3E, 4C, 5B, 6A, 7A), (1B, 2D, 3E, 4C, 5B, 6A, 7B), (1B, 2D, 3E, 4C, 5B, 6A, 7C), (1B, 2D, 3E, 4C, 5B, 6B, 7A), (1B, 2D, 3E, 4C, 5B, 6B, 7B), (1B, 2D, 3E, 4C, 5B, 6B, 7C), (1B, 2D, 3E, 4C, 5B, 6C, 7A), (1B, 2D, 3E, 4C, 5B, 6C, 7B), (1B, 2D, 3E, 4C, 5B, 6C, 7C), (1B, 2D, 3E, 4C, 5B, 6D, 7A), (1B, 2D, 3E, 4C, 5B, 6D, 7B), (1B, 2D, 3E, 4C, 5B, 6D, 7C), (1B, 2D, 3E, 4D, 5A, 6A, 7A), (1B, 2D, 3E, 4D, 5A, 6A, 7B), (1B, 2D, 3E, 4D, 5A, 6A, 7C), (1B, 2D, 3E, 4D, 5A, 6B, 7A), (1B, 2D, 3E, 4D, 5A, 6B, 7B), (1B, 2D, 3E, 4D, 5A, 6B, 7C), (1B, 2D, 3E, 4D, 5A, 6C, 7A), (1B, 2D, 3E, 4D, 5A, 6C, 7B), (1B, 2D, 3E, 4D, 5A, 6C, 7C), (1B, 2D, 3E, 4D, 5A, 6D, 7A), (1B, 2D, 3E, 4D, 5A, 6D, 7B), (1B, 2D, 3E, 4D, 5A, 6D, 7C), (1B, 2D, 3E, 4D, 5B, 6A, 7A), (1B, 2D, 3E, 4D, 5B, 6A, 7B), (1B, 2D, 3E, 4D, 5B, 6A, 7C), (1B, 2D, 3E, 4D, 5B, 6B, 7A), (1B, 2D, 3E, 4D, 5B, 6B, 7B), (1B, 2D, 3E, 4D, 5B, 6B, 7C), (1B, 2D, 3E, 4D, 5B, 6C, 7A), (1B, 2D, 3E, 4D, 5B, 6C, 7B), (1B, 2D, 3E, 4D, 5B, 6C, 7C), (1B, 2D, 3E, 4D, 5B, 6D, 7A), (1B, 2D, 3E, 4D, 5B, 6D, 7B), (1B, 2D, 3E, 4D, 5B, 6D, 7C), (1B, 2D, 3E, 4E, 5A, 6A, 7A), (1B, 2D, 3E, 4E, 5A, 6A, 7B), (1B, 2D, 3E, 4E, 5A, 6A, 7C), (1B, 2D, 3E, 4E, 5A, 6B, 7A), (1B, 2D, 3E, 4E, 5A, 6B, 7B), (1B, 2D, 3E, 4E, 5A, 6B, 7C), (1B, 2D, 3E, 4E, 5A, 6C, 7A), (1B, 2D, 3E, 4E, 5A, 6C, 7B), (1B, 2D, 3E, 4E, 5A, 6C, 7C), (1B, 2D, 3E, 4E, 5A, 6D, 7A), (1B, 2D, 3E, 4E, 5A, 6D, 7B), (1B, 2D, 3E, 4E, 5A, 6D, 7C), (1B, 2D, 3E, 4E, 5B, 6A, 7A), (1B, 2D, 3E, 4E, 5B, 6A, 7B), (1B, 2D, 3E, 4E, 5B, 6A, 7C), (1B, 2D, 3E, 4E, 5B, 6B, 7A), (1B, 2D, 3E, 4E, 5B, 6B, 7B), (1B, 2D, 3E, 4E, 5B, 6B, 7C), (1B, 2D, 3E, 4E, 5B, 6C, 7A), (1B, 2D, 3E, 4E, 5B, 6C, 7B), (1B, 2D, 3E, 4E, 5B, 6C, 7C), (1B, 2D, 3E, 4E, 5B, 6D, 7A), (1B, 2D, 3E, 4E, 5B, 6D, 7B), (1B, 2D, 3E, 4E, 5B, 6D, 7C), (1B, 2E, 3A, 4A, 5A, 6A, 7A), (1B, 2E, 3A, 4A, 5A, 6A, 7B), (1B, 2E, 3A, 4A, 5A, 6A, 7C), (1B, 2E, 3A, 4A, 5A, 6B, 7A), (1B, 2E, 3A, 4A, 5A, 6B, 7B), (1B, 2E, 3A, 4A, 5A, 6B, 7C), (1B, 2E, 3A, 4A, 5A, 6C, 7A), (1B, 2E, 3A, 4A, 5A, 6C, 7B), (1B, 2E, 3A, 4A, 5A, 6C, 7C), (1B, 2E, 3A, 4A, 5A, 6D, 7A), (1B, 2E, 3A, 4A, 5A, 6D, 7B), (1B, 2E, 3A, 4A, 5A, 6D, 7C), (1B, 2E, 3A, 4A, 5B, 6A, 7A), (1B, 2E, 3A, 4A, 5B, 6A, 7B), (1B, 2E, 3A, 4A, 5B, 6A, 7C), (1B, 2E, 3A, 4A, 5B, 6B, 7A), (1B, 2E, 3A, 4A, 5B, 6B, 7B), (1B, 2E, 3A, 4A, 5B, 6B, 7C), (1B, 2E, 3A, 4A, 5B, 6C, 7A), (1B, 2E, 3A, 4A, 5B, 6C, 7B), (1B, 2E, 3A, 4A, 5B, 6C, 7C), (1B, 2E, 3A, 4A, 5B, 6D, 7A), (1B, 2E, 3A, 4A, 5B, 6D, 7B), (1B, 2E, 3A, 4A, 5B, 6D, 7C), (1B, 2E, 3A, 4B, 5A, 6A, 7A), (1B, 2E, 3A, 4B, 5A, 6A, 7B), (1B, 2E, 3A, 4B, 5A, 6A, 7C), (1B, 2E, 3A, 4B, 5A, 6B, 7A), (1B, 2E, 3A, 4B, 5A, 6B, 7B), (1B, 2E, 3A, 4B, 5A, 6B, 7C), (1B, 2E, 3A, 4B, 5A, 6C, 7A), (1B, 2E, 3A, 4B, 5A, 6C, 7B), (1B, 2E, 3A, 4B, 5A, 6C, 7C), (1B, 2E, 3A, 4B, 5A, 6D, 7A), (1B, 2E, 3A, 4B, 5A, 6D, 7B), (1B, 2E, 3A, 4B, 5A, 6D, 7C), (1B, 2E, 3A, 4B, 5B, 6A, 7A), (1B, 2E, 3A, 4B, 5B, 6A, 7B), (1B, 2E, 3A, 4B, 5B, 6A, 7C), (1B, 2E, 3A, 4B, 5B, 6B, 7A), (1B, 2E, 3A, 4B, 5B, 6B, 7B), (1B, 2E, 3A, 4B, 5B, 6B, 7C), (1B, 2E, 3A, 4B, 5B, 6C, 7A), (1B, 2E, 3A, 4B, 5B, 6C, 7B), (1B, 2E, 3A, 4B, 5B, 6C, 7C), (1B, 2E, 3A, 4B, 5B, 6D, 7A), (1B, 2E, 3A, 4B, 5B, 6D, 7B), (1B, 2E, 3A, 4B, 5B, 6D, 7C), (1B, 2E, 3A, 4C, 5A, 6A, 7A), (1B, 2E, 3A, 4C, 5A, 6A, 7B), (1B, 2E, 3A, 4C, 5A, 6A, 7C), (1B, 2E, 3A, 4C, 5A, 6B, 7A), (1B, 2E, 3A, 4C, 5A, 6B, 7B), (1B, 2E, 3A, 4C, 5A, 6B, 7C), (1B, 2E, 3A, 4C, 5A, 6C, 7A), (1B, 2E, 3A, 4C, 5A, 6C, 7B), (1B, 2E, 3A, 4C, 5A, 6C, 7C), (1B, 2E, 3A, 4C, 5A, 6D, 7A), (1B, 2E, 3A, 4C, 5A, 6D, 7B), (1B, 2E, 3A, 4C, 5A, 6D, 7C), (1B, 2E, 3A, 4C, 5B, 6A, 7A), (1B, 2E, 3A, 4C, 5B, 6A, 7B), (1B, 2E, 3A, 4C, 5B, 6A, 7C), (1B, 2E, 3A, 4C, 5B, 6B, 7A), (1B, 2E, 3A, 4C, 5B, 6B, 7B), (1B, 2E, 3A, 4C, 5B, 6B, 7C), (1B, 2E, 3A, 4C, 5B, 6C, 7A), (1B, 2E, 3A, 4C, 5B, 6C, 7B), (1B, 2E, 3A, 4C, 5B, 6C, 7C), (1B, 2E, 3A, 4C, 5B, 6D, 7A), (1B, 2E, 3A, 4C, 5B, 6D, 7B), (1B, 2E, 3A, 4C, 5B, 6D, 7C), (1B, 2E, 3A, 4D, 5A, 6A, 7A), (1B, 2E, 3A, 4D, 5A, 6A, 7B), (1B, 2E, 3A, 4D, 5A, 6A, 7C), (1B, 2E, 3A, 4D, 5A, 6B, 7A), (1B, 2E, 3A, 4D, 5A, 6B, 7B), (1B, 2E, 3A, 4D, 5A, 6B, 7C), (1B, 2E, 3A, 4D, 5A, 6C, 7A), (1B, 2E, 3A, 4D, 5A, 6C, 7B), (1B, 2E, 3A, 4D, 5A, 6C, 7C), (1B, 2E, 3A, 4D, 5A, 6D, 7A), (1B, 2E, 3A, 4D, 5A, 6D, 7B), (1B, 2E, 3A, 4D, 5A, 6D, 7C), (1B, 2E, 3A, 4D, 5B, 6A, 7A), (1B, 2E, 3A, 4D, 5B, 6A, 7B), (1B, 2E, 3A, 4D, 5B, 6A, 7C), (1B, 2E, 3A, 4D, 5B, 6B, 7A), (1B, 2E, 3A, 4D, 5B, 6B, 7B), (1B, 2E, 3A, 4D, 5B, 6B, 7C), (1B, 2E, 3A, 4D, 5B, 6C, 7A), (1B, 2E, 3A, 4D, 5B, 6C, 7B), (1B, 2E, 3A, 4D, 5B, 6C, 7C), (1B, 2E, 3A, 4D, 5B, 6D, 7A), (1B, 2E, 3A, 4D, 5B, 6D, 7B), (1B, 2E, 3A, 4D, 5B, 6D, 7C), (1B, 2E, 3A, 4E, 5A, 6A, 7A), (1B, 2E, 3A, 4E, 5A, 6A, 7B), (1B, 2E, 3A, 4E, 5A, 6A, 7C), (1B, 2E, 3A, 4E, 5A, 6B, 7A), (1B, 2E, 3A, 4E, 5A, 6B, 7B), (1B, 2E, 3A, 4E, 5A, 6B, 7C), (1B, 2E, 3A, 4E, 5A, 6C, 7A), (1B, 2E, 3A, 4E, 5A, 6C, 7B), (1B, 2E, 3A, 4E, 5A, 6C, 7C), (1B, 2E, 3A, 4E, 5A, 6D, 7A), (1B, 2E, 3A, 4E, 5A, 6D, 7B), (1B, 2E, 3A, 4E, 5A, 6D, 7C), (1B, 2E, 3A, 4E, 5B, 6A, 7A), (1B, 2E, 3A, 4E, 5B, 6A, 7B), (1B, 2E, 3A, 4E, 5B, 6A, 7C), (1B, 2E, 3A, 4E, 5B, 6B, 7A), (1B, 2E, 3A, 4E, 5B, 6B, 7B), (1B, 2E, 3A, 4E, 5B, 6B, 7C), (1B, 2E, 3A, 4E, 5B, 6C, 7A), (1B, 2E, 3A, 4E, 5B, 6C, 7B), (1B, 2E, 3A, 4E, 5B, 6C, 7C), (1B, 2E, 3A, 4E, 5B, 6D, 7A), (1B, 2E, 3A, 4E, 5B, 6D, 7B), (1B, 2E, 3A, 4E, 5B, 6D, 7C), (1B, 2E, 3B, 4A, 5A, 6A, 7A), (1B, 2E, 3B, 4A, 5A, 6A, 7B), (1B, 2E, 3B, 4A, 5A, 6A, 7C), (1B, 2E, 3B, 4A, 5A, 6B, 7A), (1B, 2E, 3B, 4A, 5A, 6B, 7B), (1B, 2E, 3B, 4A, 5A, 6B, 7C), (1B, 2E, 3B, 4A, 5A, 6C, 7A), (1B, 2E, 3B, 4A, 5A, 6C, 7B), (1B, 2E, 3B, 4A, 5A, 6C, 7C), (1B, 2E, 3B, 4A, 5A, 6D, 7A), (1B, 2E, 3B, 4A, 5A, 6D, 7B), (1B, 2E, 3B, 4A, 5A, 6D, 7C), (1B, 2E, 3B, 4A, 5B, 6A, 7A), (1B, 2E, 3B, 4A, 5B, 6A, 7B), (1B, 2E, 3B, 4A, 5B, 6A, 7C), (1B, 2E, 3B, 4A, 5B, 6B, 7A), (1B, 2E, 3B, 4A, 5B, 6B, 7B), (1B, 2E, 3B, 4A, 5B, 6B, 7C), (1B, 2E, 3B, 4A, 5B, 6C, 7A), (1B, 2E, 3B, 4A, 5B, 6C, 7B), (1B, 2E, 3B, 4A, 5B, 6C, 7C), (1B, 2E, 3B, 4A, 5B, 6D, 7A), (1B, 2E, 3B, 4A, 5B, 6D, 7B), (1B, 2E, 3B, 4A, 5B, 6D, 7C), (1B, 2E, 3B, 4B, 5A, 6A, 7A), (1B, 2E, 3B, 4B, 5A, 6A, 7B), (1B, 2E, 3B, 4B, 5A, 6A, 7C), (1B, 2E, 3B, 4B, 5A, 6B, 7A), (1B, 2E, 3B, 4B, 5A, 6B, 7B), (1B, 2E, 3B, 4B, 5A, 6B, 7C), (1B, 2E, 3B, 4E, 5A, 6C, 7A), (1B, 2E, 3B, 4B, 5A, 6C, 7C), (1B, 2E, 3B, 4B, 5A, 6D, 7A), (1B, 2E, 3B, 4B, 5A, 6D, 7B), (1B, 2E, 3B, 4B, 5A, 6D, 7C), (1B, 2E, 3B, 4B, 5B, 6A, 7A), (1B, 2E, 3B, 4B, 5B, 6A, 7B), (1B, 2E, 3B, 4B, 5B, 6A, 7C), (1B, 2E, 3B, 4B, 5B, 6B, 7A), (1B, 2E, 3B, 4B, 5B, 6B, 7B), (1B, 2E, 3B, 4B, 5B, 6B, 7C), (1B, 2E, 3B, 4B, 5B, 6C, 7A), (1B, 2E, 3B, 4B, 5B, 6C, 7B), (1B, 2E, 3B, 4B, 5B, 6C, 7C), (1B, 2E, 3B, 4B, 5B, 6D, 7A), (1B, 2E, 3B, 4B, 5B, 6D, 7B), (1B, 2E, 3B, 4B, 5B, 6D, 7C), (1B, 2E, 3B, 4C, 5A, 6A, 7A), (1B, 2E, 3B, 4C, 5A, 6A, 7B), (1B, 2E, 3B, 4C, 5A, 6A, 7C), (1B, 2E, 3B, 4C, 5A, 6B, 7A), (1B, 2E, 3B, 4C, 5A, 6B, 7B), (1B, 2E, 3B, 4C, 5A, 6B, 7C), (1B, 2E, 3B, 4C, 5A, 6C, 7A), (1B, 2E, 3B, 4C, 5A, 6C, 7B), (1B, 2E, 3B, 4C, 5A, 6C, 7C), (1B, 2E, 3B, 4C, 5A, 6D, 7A), (1B, 2E, 3B, 4C, 5A, 6D, 7B), (1B, 2E, 3B, 4C, 5A, 6D, 7C), (1B, 2E, 3B, 4C, 5B, 6A, 7A), (1B, 2E, 3B, 4C, 5B, 6A, 7B), (1B, 2E, 3B, 4C, 5B, 6A, 7C), (1B, 2E, 3B, 4C, 5B, 6B, 7A), (1B, 2E, 3B, 4C, 5B, 6B, 7B), (1B, 2E, 3B, 4C, 5B, 6B, 7C), (1B, 2E, 3B, 4C, 5B, 6C, 7A), (1B, 2E, 3B, 4C, 5B, 6C, 7B), (1B, 2E, 3B, 4C, 5B, 6C, 7C), (1B, 2E, 3B, 4C, 5B, 6D, 7A), (1B, 2E, 3B, 4C, 5B, 6D, 7C), (1B, 2E, 3B, 4D, 5A, 6A, 7A), (1B, 2E, 3B, 4D, 5A, 6A, 7B), (1B, 2E, 3B, 4D, 5A, 6A, 7C), (1B, 2E, 3B, 4D, 5A, 6B, 7A), (1B, 2E, 3B, 4D, 5A, 6B, 7B), (1B, 2E, 3B, 4D, 5A, 6B, 7C), (1B, 2E, 3B, 4D, 5A, 6C, 7A), (1B, 2E, 3B, 4D, 5A, 6C, 7B), (1B, 2E, 3B, 4D, 5A, 6C, 7C), (1B, 2E, 3B, 4D, 5A, 6D, 7A), (1B, 2E, 3B, 4D, 5A, 6D, 7B), (1B, 2E, 3B, 4D, 5A, 6D, 7C), (1B, 2E, 3B, 4D, 5B, 6A, 7A), (1B, 2E, 3B, 4D, 5B, 6A, 7B), (1B, 2E, 3B, 4D, 5B, 6A, 7C), (1B, 2E, 3B, 4D, 5B, 6B, 7A), (1B, 2E, 3B, 4D, 5B, 6B, 7B), (1B, 2E, 3B, 4D, 5B, 6B, 7C), (1B, 2E, 3B, 4D, 5B, 6C, 7A), (1B, 2E, 3B, 4D, 5B, 6C, 7B), (1B, 2E, 3B, 4D, 5B, 6C, 7C), (1B, 2E, 3B, 4D, 5B, 6D, 7A), (1B, 2E, 3B, 4D, 5B, 6D, 7B), (1B, 2E, 3B, 4D, 5B, 6D, 7C), (1B, 2E, 3B, 4E, 5A, 6A, 7A), (1B, 2E, 3B, 4E, 5A, 6A, 7B), (1B, 2E, 3B, 4E, 5A, 6A, 7C), (1B, 2E, 3B, 4E, 5A, 6B, 7A), (1B, 2E, 3B, 4E, 5A, 6B, 7B), (1B, 2E, 3B, 4E, 5A, 6B, 7C), (1B, 2E, 3B, 4E, 5A, 6C, 7A), (1B, 2E, 3B, 4E, 5A, 6C, 7B), (1B, 2E, 3B, 4E, 5A, 6C, 7C), (1B, 2E, 3B, 4E, 5A, 6D, 7A), (1B, 2E, 3B, 4E, 5A, 6D, 7B), (1B, 2E, 3B, 4E, 5A, 6D, 7C), (1B, 2E, 3B, 4E, 5B, 6A, 7A), (1B, 2E, 3B, 4E, 5B, 6A, 7B), (1B, 2E, 3B, 4E, 5B, 6A, 7C), (1B, 2E, 3B, 4E, 5B, 6B, 7A), (1B, 2E, 3B, 4E, 5B, 6B, 7B), (1B, 2E, 3B, 4E, 5B, 6B, 7C), (1B, 2E, 3B, 4E, 5B, 6C, 7A), (1B, 2E, 3B, 4E, 5B, 6C, 7B), (1B, 2E, 3B, 4E, 5B, 6C, 7C), (1B, 2E, 3B, 4E, 5B, 6D, 7A), (1B, 2E, 3B, 4E, 5B, 6D, 7B), (1B, 2E, 3B, 4E, 5B, 6D, 7C), (1B, 2E, 3C, 4A, 5A, 6A, 7A), (1B, 2E, 3C, 4A, 5A, 6A, 7B), (1B, 2E, 3C, 4A, 5A, 6A, 7C), (1B, 2E, 3C, 4A, 5A, 6B, 7A), (1B, 2E, 3C, 4A, 5A, 6B, 7B), (1B, 2E, 3C, 4A, 5A, 6B, 7C), (1B, 2E, 3C, 4A, 5A, 6C, 7A), (1B, 2E, 3C, 4A, 5A, 6C, 7B), (1B, 2E, 3C, 4A, 5A, 6C, 7C), (1B, 2E, 3C, 4A, 5A, 6D, 7A), (1B, 2E, 3C, 4A, 5A, 6D, 7B), (1B, 2E, 3C, 4A, 5A, 6D, 7C), (1B, 2E, 3C, 4A, 5B, 6A, 7A), (1B, 2E, 3C, 4A, 5B, 6A, 7B), (1B, 2E, 3C, 4A, 5B, 6A, 7C), (1B, 2E, 3C, 4A, 5B, 6B, 7A), (1B, 2E, 3C, 4A, 5B, 6B, 7B), (1B, 2E, 3C, 4A, 5B, 6B, 7C), (1B, 2E, 3C, 4A, 5B, 6C, 7A), (1B, 2E, 3C, 4A, 5B, 6C, 7B), (1B, 2E, 3C, 4A, 5B, 6C, 7C), (1B, 2E, 3C, 4A, 5B, 6D, 7A), (1B, 2E, 3C, 4A, 5B, 6D, 7B), (1B, 2E, 3C, 4A, 5B, 6D, 7C), (1B, 2E, 3C, 4B, 5A, 6A, 7A), (1B, 2E, 3C, 4B, 5A, 6A, 7B), (1B, 2E, 3C, 4B, 5A, 6A, 7C), (1B, 2E, 3C, 4B, 5A, 6B, 7A), (1B, 2E, 3C, 4B, 5A, 6B, 7B), (1B, 2E, 3C, 4B, 5A, 6B, 7C), (1B, 2E, 3C, 4B, 5A, 6C, 7A), (1B, 2E, 3C, 4B, 5A, 6C, 7B), (1B, 2E, 3C, 4B, 5A, 6C, 7C), (1B, 2E, 3C, 4B, 5A, 6D, 7A), (1B, 2E, 3C, 4B, 5A, 6D, 7B), (1B, 2E, 3C, 4B, 5A, 6D, 7C), (1B, 2E, 3C, 4B, 5B, 6A, 7A), (1B, 2E, 3C, 4B, 5B, 6A, 7B), (1B, 2E, 3C, 4B, 5B, 6A, 7C), (1B, 2E, 3C, 4B, 5B, 6B, 7A), (1B, 2E, 3C, 4B, 5B, 6B, 7B), (1B, 2E, 3C, 4B, 5B, 6B, 7C), (1B, 2E, 3C, 4B, 5B, 6C, 7A), (1B, 2E, 3C, 4B, 5B, 6C, 7B), (1B, 2E, 3C, 4B, 5B, 6C, 7C), (1B, 2E, 3C, 4B, 5B, 6D, 7A), (1B, 2E, 3C, 4B, 5B, 6D, 7B), (1B, 2E, 3C, 4B, 5B, 6D, 7C), (1B, 2E, 3C, 4C, 5A, 6A, 7A), (1B, 2E, 3C, 4C, 5A, 6A, 7B), (1B, 2E, 3C, 4C, 5A, 6A, 7C), (1B, 2E, 3C, 4C, 5A, 6B, 7A), (1B, 2E, 3C, 4C, 5A, 6B, 7B), (1B, 2E, 3C, 4C, 5A, 6B, 7C), (1B, 2E, 3C, 4C, 5A, 6C, 7A), (1B, 2E, 3C, 4C, 5A, 6C, 7B), (1B, 2E, 3C, 4C, 5A, 6C, 7C), (1B, 2E, 3C, 4C, 5A, 6D, 7A), (1B, 2E, 3C, 4C, 5A, 6D, 7B), (1B, 2E, 3C, 4C, 5A, 6D, 7C), (1B, 2E, 3C, 4C, 5B, 6A, 7A), (1B, 2E, 3C, 4C, 5B, 6A, 7B), (1B, 2E, 3C, 4C, 5B, 6A, 7C), (1B, 2E, 3C, 4C, 5B, 6B, 7A), (1B, 2E, 3C, 4C, 5B, 6B, 7B), (1B, 2E, 3C, 4C, 5B, 6B, 7C), (1B, 2E, 3C, 4C, 5B, 6C, 7A), (1B, 2E, 3C, 4C, 5B, 6C, 7B), (1B, 2E, 3C, 4C, 5B, 6C, 7C), (1B, 2E, 3C, 4C, 5B, 6D, 7A), (1B, 2E, 3C, 4C, 5B, 6D, 7B), (1B, 2E, 3C, 4C, 5B, 6D, 7C), (1B, 2E, 3C, 4D, 5A, 6A, 7A), (1B, 2E, 3C, 4D, 5A, 6A, 7B), (1B, 2E, 3C, 4D, 5A, 6A, 7C), (1B, 2E, 3C, 4D, 5A, 6B, 7A), (1B, 2E, 3C, 4D, 5A, 6B, 7B), (1B, 2E, 3C, 4D, 5A, 6B, 7C), (1B, 2E, 3C, 4D, 5A, 6C, 7A), (1B, 2E, 3C, 4D, 5A, 6C, 7B), (1B, 2E, 3C, 4D, 5A, 6C, 7C), (1B, 2E, 3C, 4D, 5A, 6D, 7A), (1B, 2E, 3C, 4D, 5A, 6D, 7B), (1B, 2E, 3C, 4D, 5A, 6D, 7C), (1B, 2E, 3C, 4D, 5B, 6A, 7A), (1B, 2E, 3C, 4D, 5B, 6A, 7B), (1B, 2E, 3C, 4D, 5B, 6B, 7A), (1B, 2E, 3C, 4D, 5B, 6B, 7B), (1B, 2E, 3C, 4D, 5B, 6B, 7C), (1B, 2E, 3C, 4D, 5B, 6C, 7A), (1B, 2E, 3C, 4D, 5B, 6C, 7B), (1B, 2E, 3C, 4D, 5B, 6C, 7C), (1B, 2E, 3C, 4D, 5B, 6D, 7A), (1B, 2E, 3C, 4D, 5B, 6D, 7B), (1B, 2E, 3C, 4D, 5B, 6D, 7C), (1B, 2E, 3C, 4E, 5A, 6A, 7A), (1B, 2E, 3C, 4E, 5A, 6A, 7B), (1B, 2E, 3C, 4E, 5A, 6A, 7C), (1B, 2E, 3C, 4E, 5A, 6B, 7A), (1B, 2E, 3C, 4E, 5A, 6B, 7B), (1B, 2E, 3C, 4E, 5A, 6B, 7C), (1B, 2E, 3C, 4E, 5A, 6C, 7A), (1B, 2E, 3C, 4E, 5A, 6C, 7B), (1B, 2E, 3C, 4E, 5A, 6C, 7C), (1B, 2E, 3C, 4E, 5A, 6D, 7A), (1B, 2E, 3C, 4E, 5A, 6D, 7B), (1B, 2E, 3C, 4E, 5A, 6D, 7C), (1B, 2E, 3C, 4E, 5B, 6A, 7A), (1B, 2E, 3C, 4E, 5B, 6A, 7B), (1B, 2E, 3C, 4E, 5B, 6A, 7C), (1B, 2E, 3C, 4E, 5B, 6B, 7A), (1B, 2E, 3C, 4E, 5B, 6B, 7B), (1B, 2E, 3C, 4E, 5B, 6B, 7C), (1B, 2E, 3C, 4E, 5B, 6C, 7A), (1B, 2E, 3C, 4E, 5B, 6C, 7B), (1B, 2E, 3C, 4E, 5B, 6C, 7C), (1B, 2E, 3C, 4E, 5B, 6D, 7A), (1B, 2E, 3C, 4E, 5B, 6D, 7B), (1B, 2E, 3C, 4E, 5B, 6D, 7C), (1B, 2E, 3D, 4A, 5A, 6A, 7A), (1B, 2E, 3D, 4A, 5A, 6A, 7B), (1B, 2E, 3D, 4A, 5A, 6A, 7C), (1B, 2E, 3D, 4A, 5A, 6B, 7A), (1B, 2E, 3D, 4A, 5A, 6B, 7B), (1B, 2E, 3D, 4A, 5A, 6B, 7C), (1B, 2E, 3D, 4A, 5A, 6C, 7A), (1B, 2E, 3D, 4A, 5A, 6C, 7B), (1B, 2E, 3D, 4A, 5A, 6C, 7C), (1B, 2E, 3D, 4A, 5A, 6D, 7A), (1B, 2E, 3D, 4A, 5A, 6D, 7B), (1B, 2E, 3D, 4A, 5A, 6D, 7C), (1B, 2E, 3D, 4A, 5B, 6A, 7A), (1B, 2E, 3D, 4A, 5B, 6A, 7B), (1B, 2E, 3D, 4A, 5B, 6A, 7C), (1B, 2E, 3D, 4A, 5B, 6B, 7A), (1B, 2E, 3D, 4A, 5B, 6B, 7B), (1B, 2E, 3D, 4A, 5B, 6B, 7C), (1B, 2E, 3D, 4A, 5B, 6C, 7A), (1B, 2E, 3D, 4A, 5B, 6C, 7B), (1B, 2E, 3D, 4A, 5B, 6C, 7C), (1B, 2E, 3D, 4A, 5B, 6D, 7A), (1B, 2E, 3D, 4A, 5B, 6D, 7B), (1B, 2E, 3D, 4A, 5B, 6D, 7C), (1B, 2E, 3D, 4B, 5A, 6A, 7A), (1B, 2E, 3D, 4B, 5A, 6A, 7B), (1B, 2E, 3D, 4B, 5A, 6A, 7C), (1B, 2E, 3D, 4B, 5A, 6B, 7A), (1B, 2E, 3D, 4B, 5A, 6B, 7B), (1B, 2E, 3D, 4B, 5A, 6B, 7C), (1B, 2E, 3D, 4B, 5A, 6C, 7A), (1B, 2E, 3D, 4B, 5A, 6C, 7B), (1B, 2E, 3D, 4B, 5A, 6C, 7C), (1B, 2E, 3D, 4B, 5A, 6D, 7A), (1B, 2E, 3D, 4B, 5A, 6D, 7B), (1B, 2E, 3D, 4B, 5A, 6D, 7C), (1B, 2E, 3D, 4B, 5B, 6A, 7A), (1B, 2E, 3D, 4B, 5B, 6A, 7B), (1B, 2E, 3D, 4B, 5B, 6A, 7C), (1B, 2E, 3D, 4B, 5B, 6B, 7A), (1B, 2E, 3D, 4B, 5B, 6B, 7B), (1B, 2E, 3D, 4B, 5B, 6B, 7C), (1B, 2E, 3D, 4B, 5B, 6C, 7A), (1B, 2E, 3D, 4B, 5B, 6C, 7B), (1B, 2E, 3D, 4B, 5B, 6C, 7C), (1B, 2E, 3D, 4B, 5B, 6D, 7A), (1B, 2E, 3D, 4B, 5B, 6D, 7B), (1B, 2E, 3D, 4B, 5B, 6D, 7C), (1B, 2E, 3D, 4C, 5A, 6A, 7A), (1B, 2E, 3D, 4C, 5A, 6A, 7B), (1B, 2E, 3D, 4C, 5A, 6A, 7C), (1B, 2E, 3D, 4C, 5A, 6B, 7A), (1B, 2E, 3D, 4C, 5A, 6B, 7B), (1B, 2E, 3D, 4C, 5A, 6B, 7C), (1B, 2E, 3D, 4C, 5A, 6C, 7A), (1B, 2E, 3D, 4C, 5A, 6C, 7B), (1B, 2E, 3D, 4C, 5A, 6C, 7C), (1B, 2E, 3D, 4C, 5A, 6D, 7A), (1B, 2E, 3D, 4C, 5A, 6D, 7B), (1B, 2E, 3D, 4C, 5A, 6D, 7C), (1B, 2E, 3D, 4C, 5B, 6A, 7A), (1B, 2E, 3D, 4C, 5B, 6A, 7B), (1B, 2E, 3D, 4C, 5B, 6A, 7C), (1B, 2E, 3D, 4C, 5B, 6B, 7A), (1B, 2E, 3D, 4C, 5B, 6B, 7B), (1B, 2E, 3D, 4C, 5B, 6B, 7C), (1B, 2E, 3D, 4C, 5B, 6C, 7A), (1B, 2E, 3D, 4C, 5B, 6C, 7B), (1B, 2E, 3D, 4C, 5B, 6C, 7C), (1B, 2E, 3D, 4C, 5B, 6D, 7A), (1B, 2E, 3D, 4C, 5B, 6D, 7B), (1B, 2E, 3D, 4C, 5B, 6D, 7C), (1B, 2E, 3D, 4D, 5A, 6A, 7A), (1B, 2E, 3D, 4D, 5A, 6A, 7B), (1B, 2E, 3D, 4D, 5A, 6A, 7C), (1B, 2E, 3D, 4D, 5A, 6B, 7A), (1B, 2E, 3D, 4D, 5A, 6B, 7B), (1B, 2E, 3D, 4D, 5A, 6B, 7C), (1B, 2E, 3D, 4D, 5A, 6C, 7A), (1B, 2E, 3D, 4D, 5A, 6C, 7B), (1B, 2E, 3D, 4D, 5A, 6C, 7C), (1B, 2E, 3D, 4D, 5A, 6D, 7A), (1B, 2E, 3D, 4D, 5A, 6D, 7B), (1B, 2E, 3D, 4D, 5A, 6D, 7C), (1B, 2E, 3D, 4D, 5B, 6A, 7A), (1B, 2E, 3D, 4D, 5B, 6A, 7B), (1B, 2E, 3D, 4D, 5B, 6A, 7C), (1B, 2E, 3D, 4D, 5B, 6B, 7A), (1B, 2E, 3D, 4D, 5B, 6B, 7B), (1B, 2E, 3D, 4D, 5B, 6B, 7C), (1B, 2E, 3D, 4D, 5B, 6C, 7A), (1B, 2E, 3D, 4D, 5B, 6C, 7B), (1B, 2E, 3D, 4D, 5B, 6C, 7C), (1B, 2E, 3D, 4D, 5B, 6D, 7A), (1B, 2E, 3D, 4D, 5B, 6D, 7B), (1B, 2E, 3D, 4D, 5B, 6D, 7C), (1B, 2E, 3D, 4E, 5A, 6A, 7A), (1B, 2E, 3D, 4E, 5A, 6A, 7B), (1B, 2E, 3D, 4E, 5A, 6A, 7C), (1B, 2E, 3D, 4E, 5A, 6B, 7A), (1B, 2E, 3D, 4E, 5A, 6B, 7B), (1B, 2E, 3D, 4E, 5A, 6B, 7C), (1B, 2E, 3D, 4E, 5A, 6C, 7A), (1B, 2E, 3D, 4E, 5A, 6C, 7B), (1B, 2E, 3D, 4E, 5A, 6C, 7C), (1B, 2E, 3D, 4E, 5A, 6D, 7A), (1B, 2E, 3D, 4E, 5A, 6D, 7B), (1B, 2E, 3D, 4E, 5A, 6D, 7C), (1B, 2E, 3D, 4E, 5B, 6A, 7A), (1B, 2E, 3D, 4E, 5B, 6A, 7B), (1B, 2E, 3D, 4E, 5B, 6A, 7C), (1B, 2E, 3D, 4E, 5B, 6B, 7A), (1B, 2E, 3D, 4E, 5B, 6B, 7B), (1B, 2E, 3D, 4E, 5B, 6B, 7C), (1B, 2E, 3D, 4E, 5B, 6C, 7A), (1B, 2E, 3D, 4E, 5B, 6C, 7B), (1B, 2E, 3D, 4E, 5B, 6C, 7C), (1B, 2E, 3D, 4E, 5B, 6D, 7A), (1B, 2E, 3D, 4E, 5B, 6D, 7B), (1B, 2E, 3D, 4E, 5B, 6D, 7C), (1B, 2E, 3E, 4A, 5A, 6A, 7A), (1B, 2E, 3E, 4A, 5A, 6A, 7B), (1B, 2E, 3E, 4A, 5A, 6A, 7C), (1B, 2E, 3E, 4A, 5A, 6B, 7A), (1B, 2E, 3E, 4A, 5A, 6B, 7B), (1B, 2E, 3E, 4A, 5A, 6B, 7C), (1B, 2E, 3E, 4A, 5A, 6C, 7A), (1B, 2E, 3E, 4A, 5A, 6C, 7B), (1B, 2E, 3E, 4A, 5A, 6C, 7C), (1B, 2E, 3E, 4A, 5A, 6D, 7A), (1B, 2E, 3E, 4A, 5A, 6D, 7B), (1B, 2E, 3E, 4A, 5A, 6D, 7C), (1B, 2E, 3E, 4A, 5B, 6A, 7A), (1B, 2E, 3E, 4A, 5B, 6A, 7B), (1B, 2E, 3E, 4A, 5B, 6A, 7C), (1B, 2E, 3E, 4A, 5B, 6B, 7A), (1B, 2E, 3E, 4A, 5B, 6B, 7B), (1B, 2E, 3E, 4A, 5B, 6B, 7C), (1B, 2E, 3E, 4A, 5B, 6C, 7A), (1B, 2E, 3E, 4A, 5B, 6C, 7B), (1B, 2E, 3E, 4A, 5B, 6C, 7C), (1B, 2E, 3E, 4A, 5B, 6D, 7A), (1B, 2E, 3E, 4A, 5B, 6D, 7B), (1B, 2E, 3E, 4A, 5B, 6D, 7C), (1B, 2E, 3E, 4B, 5A, 6A, 7A), (1B, 2E, 3E, 4B, 5A, 6A, 7B), (1B, 2E, 3E, 4B, 5A, 6A, 7C), (1B, 2E, 3E, 4B, 5A, 6B, 7A), (1B, 2E, 3E, 4B, 5A, 6B, 7B), (1B, 2E, 3E, 4B, 5A, 6B, 7C), (1B, 2E, 3E, 4B, 5A, 6C, 7A), (1B, 2E, 3E, 4B, 5A, 6C, 7B), (1B, 2E, 3E, 4B, 5A, 6C, 7C), (1B, 2E, 3E, 4B, 5A, 6D, 7A), (1B, 2E, 3E, 4B, 5A, 6D, 7B), (1B, 2E, 3E, 4B, 5A, 6D, 7C), (1B, 2E, 3E, 4B, 5B, 6A, 7A), (1B, 2E, 3E, 4B, 5B, 6A, 7B), (1B, 2E, 3E, 4B, 5B, 6A, 7C), (1B, 2E, 3E, 4B, 5B, 6B, 7A), (1B, 2E, 3E, 4B, 5B, 6B, 7B), (1B, 2E, 3E, 4B, 5B, 6B, 7C), (1B, 2E, 3E, 4B, 5B, 6C, 7A), (1B, 2E, 3E, 4B, 5B, 6C, 7B), (1B, 2E, 3E, 4B, 5B, 6C, 7C), (1B, 2E, 3E, 4B, 5B, 6D, 7A), (1B, 2E, 3E, 4B, 5B, 6D, 7B), (1B, 2E, 3E, 4B, 5B, 6D, 7C), (1B, 2E, 3E, 4C, 5A, 6A, 7A), (1B, 2E, 3E, 4C, 5A, 6A, 7B), (1B, 2E, 3E, 4C, 5A, 6A, 7C), (1B, 2E, 3E, 4C, 5A, 6B, 7A), (1B, 2E, 3E, 4C, 5A, 6B, 7B), (1B, 2E, 3E, 4C, 5A, 6B, 7C), (1B, 2E, 3E, 4C, 5A, 6C, 7A), (1B, 2E, 3E, 4C, 5A, 6C, 7B), (1B, 2E, 3E, 4C, 5A, 6C, 7C), (1B, 2E, 3E, 4C, 5A, 6D, 7A), (1B, 2E, 3E, 4C, 5A, 6D, 7B), (1B, 2E, 3E, 4C, 5A, 6D, 7C), (1B, 2E, 3E, 4C, 5B, 6A, 7A), (1B, 2E, 3E, 4C, 5B, 6A, 7B), (1B, 2E, 3E, 4C, 5B, 6A, 7C), (1B, 2E, 3E, 4C, 5B, 6B, 7A), (1B, 2E, 3E, 4C, 5B, 6B, 7B), (1B, 2E, 3E, 4C, 5B, 6B, 7C), (1B, 2E, 3E, 4C, 5B, 6C, 7A), (1B, 2E, 3E, 4C, 5B, 6C, 7B), (1B, 2E, 3E, 4C, 5B, 6C, 7C), (1B, 2E, 3E, 4C, 5B, 6D, 7A), (1B, 2E, 3E, 4C, 5B, 6D, 7B), (1B, 2E, 3E, 4C, 5B, 6D, 7C), (1B, 2E, 3E, 4D, 5A, 6A, 7A), (1B, 2E, 3E, 4D, 5A, 6A, 7B), (1B, 2E, 3E, 4D, 5A, 6A, 7C), (1B, 2E, 3E, 4D, 5A, 6B, 7A), (1B, 2E, 3E, 4D, 5A, 6B, 7B), (1B, 2E, 3E, 4D, 5A, 6B, 7C), (1B, 2E, 3E, 4D, 5A, 6C, 7A), (1B, 2E, 3E, 4D, 5A, 6C, 7B), (1B, 2E, 3E, 4D, 5A, 6C, 7C), (1B, 2E, 3E, 4D, 5A, 6D, 7A), (1B, 2E, 3E, 4D, 5A, 6D, 7B), (1B, 2E, 3E, 4D, 5A, 6D, 7C), (1B, 2E, 3E, 4D, 5B, 6A, 7A), (1B, 2E, 3E, 4D, 5B, 6A, 7B), (1B, 2E, 3E, 4D, 5B, 6A, 7C), (1B, 2E, 3E, 4D, 5B, 6B, 7A), (1B, 2E, 3E, 4D, 5B, 6B, 7B), (1B, 2E, 3E, 4D, 5B, 6B, 7C), (1B, 2E, 3E, 4D, 5B, 6C, 7A), (1B, 2E, 3E, 4D, 5B, 6C, 7B), (1B, 2E, 3E, 4D, 5B, 6C, 7C), (1B, 2E, 3E, 4D, 5B, 6D, 7A), (1B, 2E, 3E, 4D, 5B, 6D, 7B), (1B, 2E, 3E, 4D, 5B, 6D, 7C), (1B, 2E, 3E, 4E, 5A, 6A, 7A), (1B, 2E, 3E, 4E, 5A, 6A, 7B), (1B, 2E, 3E, 4E, 5A, 6A, 7C), (1B, 2E, 3E, 4E, 5A, 6B, 7A), (1B, 2E, 3E, 4E, 5A, 6B, 7B), (1B, 2E, 3E, 4E, 5A, 6B, 7C), (1B, 2E, 3E, 4E, 5A, 6C, 7A), (1B, 2E, 3E, 4E, 5A, 6C, 7B), (1B, 2E, 3E, 4E, 5A, 6C, 7C), (1B, 2E, 3E, 4E, 5A, 6D, 7A), (1B, 2E, 3E, 4E, 5A, 6D, 7B), (1B, 2E, 3E, 4E, 5A, 6D, 7C), (1B, 2E, 3E, 4E, 5B, 6A, 7A), (1B, 2E, 3E, 4E, 5B, 6A, 7B), (1B, 2E, 3E, 4E, 5B, 6A, 7C), (1B, 2E, 3E, 4E, 5B, 6B, 7A), (1B, 2E, 3E, 4E, 5B, 6B, 7B), (1B, 2E, 3E, 4E, 5B, 6B, 7C), (1B, 2E, 3E, 4E, 5B, 6C, 7A), (1B, 2E, 3E, 4E, 5B, 6C, 7B), (1B, 2E, 3E, 4E, 5B, 6C, 7C), (1B, 2E, 3E, 4E, 5B, 6D, 7A), (1B, 2E, 3E, 4E, 5B, 6D, 7B), (1B, 2E, 3E, 4E, 5B, 6D, 7C), (1C, 2A, 3A, 4A, 5A, 6A, 7A), (1C, 2A, 3A, 4A, 5A, 6A, 7B), (1C, 2A, 3A, 4A, 5A, 6A, 7C), (1C, 2A, 3A, 4A, 5A, 6B, 7A), (1C, 2A, 3A, 4A, 5A, 6B, 7B), (1C, 2A, 3A, 4A, 5A, 6B, 7C), (1C, 2A, 3A, 4A, 5A, 6C, 7A), (1C, 2A, 3A, 4A, 5A, 6C, 7B), (1C, 2A, 3A, 4A, 5A, 6C, 7C), (1C, 2A, 3A, 4A, 5A, 6D, 7A), (1C, 2A, 3A, 4A, 5A, 6D, 7B), (1C, 2A, 3A, 4A, 5A, 6D, 7C), (1C, 2A, 3A, 4A, 5B, 6A, 7A), (1C, 2A, 3A, 4A, 5B, 6A, 7B), (1C, 2A, 3A, 4A, 5B, 6A, 7C), (1C, 2A, 3A, 4A, 5B, 6B, 7A), (1C, 2A, 3A, 4A, 5B, 6B, 7B), (1C, 2A, 3A, 4A, 5B, 6B, 7C), (1C, 2A, 3A, 4A, 5B, 6C, 7A), (1C, 2A, 3A, 4A, 5B, 6C, 7B), (1C, 2A, 3A, 4A, 5B, 6C, 7C), (1C, 2A, 3A, 4A, 5B, 6D, 7A), (1C, 2A, 3A, 4A, 5B, 6D, 7B), (1C, 2A, 3A, 4A, 5B, 6D, 7C), (1C, 2A, 3A, 4B, 5A, 6A, 7A), (1C, 2A, 3A, 4B, 5A, 6A, 7B), (1C, 2A, 3A, 4B, 5A, 6A, 7C), (1C, 2A, 3A, 4B, 5A, 6B, 7A), (1C, 2A, 3A, 4B, 5A, 6B, 7B), (1C, 2A, 3A, 4B, 5A, 6B, 7C), (1C, 2A, 3A, 4B, 5A, 6C, 7A), (1C, 2A, 3A, 4B, 5A, 6C, 7B), (1C, 2A, 3A, 4B, 5A, 6C, 7C), (1C, 2A, 3A, 4B, 5A, 6D, 7A), (1C, 2A, 3A, 4B, 5A, 6D, 7B), (1C, 2A, 3A, 4B, 5A, 6D, 7C), (1C, 2A, 3A, 4B, 5B, 6A, 7A), (1C, 2A, 3A, 4B, 5B, 6A, 7B), (1C, 2A, 3A, 4B, 5B, 6A, 7C), (1C, 2A, 3A, 4B, 5B, 6B, 7A), (1C, 2A, 3A, 4B, 5B, 6B, 7B), (1C, 2A, 3A, 4B, 5B, 6B, 7C), (1C, 2A, 3A, 4B, 5B, 6C, 7A), (1C, 2A, 3A, 4B, 5B, 6C, 7B), (1C, 2A, 3A, 4B, 5B, 6C, 7C), (1C, 2A, 3A, 4B, 5B, 6D, 7A), (1C, 2A, 3A, 4B, 5B, 6D, 7B), (1C, 2A, 3A, 4B, 5B, 6D, 7C), (1C, 2A, 3A, 4C, 5A, 6A, 7A), (1C, 2A, 3A, 4C, 5A, 6A, 7B), (1C, 2A, 3A, 4C, 5A, 6A, 7C), (1C, 2A, 3A, 4C, 5A, 6B, 7A), (1C, 2A, 3A, 4C, 5A, 6B, 7B), (1C, 2A, 3A, 4C, 5A, 6B, 7C), (1C, 2A, 3A, 4C, 5A, 6C, 7A), (1C, 2A, 3A, 4C, 5A, 6C, 7B), (1C, 2A, 3A, 4C, 5A, 6C, 7C), (1C, 2A, 3A, 4C, 5A, 6D, 7A), (1C, 2A, 3A, 4C, 5A, 6D, 7B), (1C, 2A, 3A, 4C, 5A, 6D, 7C), (1C, 2A, 3A, 4C, 5B, 6A, 7A), (1C, 2A, 3A, 4C, 5B, 6A, 7B), (1C, 2A, 3A, 4C, 5B, 6A, 7C), (1C, 2A, 3A, 4C, 5B, 6B, 7A), (1C, 2A, 3A, 4C, 5B, 6B, 7B), (1C, 2A, 3A, 4C, 5B, 6B, 7C), (1C, 2A, 3A, 4C, 5B, 6C, 7A), (1C, 2A, 3A, 4C, 5B, 6C, 7B), (1C, 2A, 3A, 4C, 5B, 6C, 7C), (1C, 2A, 3A, 4C, 5B, 6D, 7A), (1C, 2A, 3A, 4C, 5B, 6D, 7B), (1C, 2A, 3A, 4C, 5B, 6D, 7C), (1C, 2A, 3A, 4D, 5A, 6A, 7A), (1C, 2A, 3A, 4D, 5A, 6A, 7B), (1C, 2A, 3A, 4D, 5A, 6A, 7C), (1C, 2A, 3A, 4D, 5A, 6B, 7A), (1C, 2A, 3A, 4D, 5A, 6B, 7B), (1C, 2A, 3A, 4D, 5A, 6C, 7A), (1C, 2A, 3A, 4D, 5A, 6C, 7B), (1C, 2A, 3A, 4D, 5A, 6C, 7C), (1C, 2A, 3A, 4D, 5A, 6D, 7A), (1C, 2A, 3A, 4D, 5A, 6D, 7B), (1C, 2A, 3A, 4D, 5A, 6D, 7C), (1C, 2A, 3A, 4D, 5B, 6A, 7A), (1C, 2A, 3A, 4D, 5B, 6A, 7B), (1C, 2A, 3A, 4D, 5B, 6A, 7C), (1C, 2A, 3A, 4D, 5B, 6B, 7A), (1C, 2A, 3A, 4D, 5B, 6B, 7B), (1C, 2A, 3A, 4D, 5B, 6B, 7C), (1C, 2A, 3A, 4D, 5B, 6C, 7A), (1C, 2A, 3A, 4D, 5B, 6C, 7B), (1C, 2A, 3A, 4D, 5B, 6C, 7C), (1C, 2A, 3A, 4D, 5B, 6D, 7A), (1C, 2A, 3A, 4D, 5B, 6D, 7B), (1C, 2A, 3A, 4D, 5B, 6D, 7C), (1C, 2A, 3A, 4E, 5A, 6A, 7A), (1C, 2A, 3A, 4E, 5A, 6A, 7B), (1C, 2A, 3A, 4E, 5A, 6A, 7C), (1C, 2A, 3A, 4E, 5A, 6B, 7A), (1C, 2A, 3A, 4E, 5A, 6B, 7B), (1C, 2A, 3A, 4E, 5A, 6B, 7C), (1C, 2A, 3A, 4E, 5A, 6C, 7A), (1C, 2A, 3A, 4E, 5A, 6C, 7B), (1C, 2A, 3A, 4E, 5A, 6C, 7C), (1C, 2A, 3A, 4E, 5A, 6D, 7A), (1C, 2A, 3A, 4E, 5A, 6D, 7B), (1C, 2A, 3A, 4E, 5A, 6D, 7C), (1C, 2A, 3A, 4E, 5B, 6A, 7A), (1C, 2A, 3A, 4E, 5B, 6A, 7B), (1C, 2A, 3A, 4E, 5B, 6A, 7C), (1C, 2A, 3A, 4E, 5B, 6B, 7A), (1C, 2A, 3A, 4E, 5B, 6B, 7B), (1C, 2A, 3A, 4E, 5B, 6B, 7C), (1C, 2A, 3A, 4E, 5B, 6C, 7A), (1C, 2A, 3A, 4E, 5B, 6C, 7B), (1C, 2A, 3A, 4E, 5B, 6C, 7C), (1C, 2A, 3A, 4E, 5B, 6D, 7A), (1C, 2A, 3A, 4E, 5B, 6D, 7B), (1C, 2A, 3A, 4E, 5B, 6D, 7C), (1C, 2A, 3B, 4A, 5A, 6A, 7A), (1C, 2A, 3B, 4A, 5A, 6A, 7B), (1C, 2A, 3B, 4A, 5A, 6A, 7C), (1C, 2A, 3B, 4A, 5A, 6B, 7A), (1C, 2A, 3B, 4A, 5A, 6B, 7B), (1C, 2A, 3B, 4A, 5A, 6B, 7C), (1C, 2A, 3B, 4A, 5A, 6C, 7A), (1C, 2A, 3B, 4A, 5A, 6C, 7B), (1C, 2A, 3B, 4A, 5A, 6C, 7C), (1C, 2A, 3B, 4A, 5A, 6D, 7A), (1C, 2A, 3B, 4A, 5A, 6D, 7B), (1C, 2A, 3B, 4A, 5A, 6D, 7C), (1C, 2A, 3B, 4A, 5B, 6A, 7A), (1C, 2A, 3B, 4A, 5B, 6A, 7B), (1C, 2A, 3B, 4A, 5B, 6A, 7C), (1C, 2A, 3B, 4A, 5B, 6B, 7A), (1C, 2A, 3B, 4A, 5B, 6B, 7B), (1C, 2A, 3B, 4A, 5B, 6B, 7C), (1C, 2A, 3B, 4A, 5B, 6C, 7A), (1C, 2A, 3B, 4A, 5B, 6C, 7B), (1C, 2A, 3B, 4A, 5B, 6C, 7C), (1C, 2A, 3B, 4A, 5B, 6D, 7A), (1C, 2A, 3B, 4A, 5B, 6D, 7B), (1C, 2A, 3B, 4A, 5B, 6D, 7C), (1C, 2A, 3B, 4B, 5A, 6A, 7A), (1C, 2A, 3B, 4B, 5A, 6A, 7B), (1C, 2A, 3B, 4B, 5A, 6A, 7C), (1C, 2A, 3B, 4B, 5A, 6B, 7A), (1C, 2A, 3B, 4B, 5A, 6B, 7B), (1C, 2A, 3B, 4B, 5A, 6B, 7C), (1C, 2A, 3B, 4B, 5A, 6C, 7A), (1C, 2A, 3B, 4B, 5A, 6C, 7B), (1C, 2A, 3B, 4B, 5A, 6C, 7C), (1C, 2A, 3B, 4B, 5A, 6D, 7A), (1C, 2A, 3B, 4B, 5A, 6D, 7B), (1C, 2A, 3B, 4B, 5A, 6D, 7C), (1C, 2A, 3B, 4B, 5B, 6A, 7A), (1C, 2A, 3B, 4B, 5B, 6A, 7B), (1C, 2A, 3B, 4B, 5B, 6A, 7C), (1C, 2A, 3B, 4B, 5B, 6B, 7A), (1C, 2A, 3B, 4B, 5B, 6B, 7B), (1C, 2A, 3B, 4B, 5B, 6B, 7C), (1C, 2A, 3B, 4B, 5B, 6C, 7A), (1C, 2A, 3B, 4B, 5B, 6C, 7B), (1C, 2A, 3B, 4B, 5B, 6C, 7C), (1C, 2A, 3B, 4B, 5B, 6D, 7A), (1C, 2A, 3B, 4B, 5B, 6D, 7B), (1C, 2A, 3B, 4B, 5B, 6D, 7C), (1C, 2A, 3B, 4C, 5A, 6A, 7A), (1C, 2A, 3B, 4C, 5A, 6A, 7B), (1C, 2A, 3B, 4C, 5A, 6A, 7C), (1C, 2A, 3B, 4C, 5A, 6B, 7A), (1C, 2A, 3B, 4C, 5A, 6B, 7B), (1C, 2A, 3B, 4C, 5A, 6B, 7C), (1C, 2A, 3B, 4C, 5A, 6C, 7A), (1C, 2A, 3B, 4C, 5A, 6C, 7B), (1C, 2A, 3B, 4C, 5A, 6C, 7C), (1C, 2A, 3B, 4C, 5A, 6D, 7A), (1C, 2A, 3B, 4C, 5A, 6D, 7B), (1C, 2A, 3B, 4C, 5A, 6D, 7C), (1C, 2A, 3B, 4C, 5B, 6A, 7A), (1C, 2A, 3B, 4C, 5B, 6A, 7B), (1C, 2A, 3B, 4C, 5B, 6A, 7C), (1C, 2A, 3B, 4C, 5B, 6B, 7A), (1C, 2A, 3B, 4C, 5B, 6B, 7B), (1C, 2A, 3B, 4C, 5B, 6B, 7C), (1C, 2A, 3B, 4C, 5B, 6C, 7A), (1C, 2A, 3B, 4C, 5B, 6C, 7B), (1C, 2A, 3B, 4C, 5B, 6C, 7C), (1C, 2A, 3B, 4C, 5B, 6D, 7A), (1C, 2A, 3B, 4C, 5B, 6D, 7B), (1C, 2A, 3B, 4C, 5B, 6D, 7C), (1C, 2A, 3B, 4D, 5A, 6A, 7A), (1C, 2A, 3B, 4D, 5A, 6A, 7B), (1C, 2A, 3B, 4D, 5A, 6A, 7C), (1C, 2A, 3B, 4D, 5A, 6B, 7A), (1C, 2A, 3B, 4D, 5A, 6B, 7B), (1C, 2A, 3B, 4D, 5A, 6B, 7C), (1C, 2A, 3B, 4D, 5A, 6C, 7A), (1C, 2A, 3B, 4D, 5A, 6C, 7B), (1C, 2A, 3B, 4D, 5A, 6C, 7C), (1C, 2A, 3B, 4D, 5A, 6D, 7A), (1C, 2A, 3B, 4D, 5A, 6D, 7B), (1C, 2A, 3B, 4D, 5A, 6D, 7C), (1C, 2A, 3B, 4D, 5B, 6A, 7A), (1C, 2A, 3B, 4D, 5B, 6A, 7B), (1C, 2A, 3B, 4D, 5B, 6A, 7C), (1C, 2A, 3B, 4D, 5B, 6B, 7A), (1C, 2A, 3B, 4D, 5B, 6B, 7B), (1C, 2A, 3B, 4D, 5B, 6B, 7C), (1C, 2A, 3B, 4D, 5B, 6C, 7A), (1C, 2A, 3B, 4D, 5B, 6C, 7B), (1C, 2A, 3B, 4D, 5B, 6C, 7C), (1C, 2A, 3B, 4D, 5B, 6D, 7A), (1C, 2A, 3B, 4D, 5B, 6D, 7B), (1C, 2A, 3B, 4D, 5B, 6D, 7C), (1C, 2A, 3B, 4E, 5A, 6A, 7A), (1C, 2A, 3B, 4E, 5A, 6A, 7B), (1C, 2A, 3B, 4E, 5A, 6A, 7C), (1C, 2A, 3B, 4E, 5A, 6B, 7A), (1C, 2A, 3B, 4E, 5A, 6B, 7B), (1C, 2A, 3B, 4E, 5A, 6B, 7C), (1C, 2A, 3B, 4E, 5A, 6C, 7A), (1C, 2A, 3B, 4E, 5A, 6C, 7B), (1C, 2A, 3B, 4E, 5A, 6C, 7C), (1C, 2A, 3B, 4E, 5A, 6D, 7A), (1C, 2A, 3B, 4E, 5A, 6D, 7B), (1C, 2A, 3B, 4E, 5A, 6D, 7C), (1C, 2A, 3B, 4E, 5B, 6A, 7A), (1C, 2A, 3B, 4E, 5B, 6A, 7B), (1C, 2A, 3B, 4E, 5B, 6A, 7C), (1C, 2A, 3B, 4E, 5B, 6B, 7A), (1C, 2A, 3B, 4E, 5B, 6B, 7B), (1C, 2A, 3B, 4E, 5B, 6B, 7C), (1C, 2A, 3B, 4E, 5B, 6C, 7A), (1C, 2A, 3B, 4E, 5B, 6C, 7B), (1C, 2A, 3B, 4E, 5B, 6C, 7C), (1C, 2A, 3B, 4E, 5B, 6D, 7A), (1C, 2A, 3B, 4E, 5B, 6D, 7B), (1C, 2A, 3B, 4E, 5B, 6D, 7C), (1C, 2A, 3C, 4A, 5A, 6A, 7A), (1C, 2A, 3C, 4A, 5A, 6A, 7B), (1C, 2A, 3C, 4A, 5A, 6A, 7C), (1C, 2A, 3C, 4A, 5A, 6B, 7A), (1C, 2A, 3C, 4A, 5A, 6B, 7B), (1C, 2A, 3C, 4A, 5A, 6B, 7C), (1C, 2A, 3C, 4A, 5A, 6C, 7A), (1C, 2A, 3C, 4A, 5A, 6C, 7B), (1C, 2A, 3C, 4A, 5A, 6C, 7C), (1C, 2A, 3C, 4A, 5A, 6D, 7A), (1C, 2A, 3C, 4A, 5A, 6D, 7B), (1C, 2A, 3C, 4A, 5A, 6D, 7C), (1C, 2A, 3C, 4A, 5B, 6A, 7A), (1C, 2A, 3C, 4A, 5B, 6A, 7B), (1C, 2A, 3C, 4A, 5B, 6A, 7C), (1C, 2A, 3C, 4A, 5B, 6B, 7A), (1C, 2A, 3C, 4A, 5B, 6B, 7B), (1C, 2A, 3C, 4A, 5B, 6B, 7C), (1C, 2A, 3C, 4A, 5B, 6C, 7A), (1C, 2A, 3C, 4A, 5B, 6C, 7B), (1C, 2A, 3C, 4A, 5B, 6C, 7C), (1C, 2A, 3C, 4A, 5B, 6D, 7A), (1C, 2A, 3C, 4A, 5B, 6D, 7B), (1C, 2A, 3C, 4A, 5B, 6D, 7C), (1C, 2A, 3C, 4B, 5A, 6A, 7A), (1C, 2A, 3C, 4B, 5A, 6A, 7B), (1C, 2A, 3C, 4B, 5A, 6A, 7C), (1C, 2A, 3C, 4B, 5A, 6B, 7A), (1C, 2A, 3C, 4B, 5A, 6B, 7B), (1C, 2A, 3C, 4B, 5A, 6B, 7C), (1C, 2A, 3C, 4B, 5A, 6C, 7A), (1C, 2A, 3C, 4B, 5A, 6C, 7B), (1C, 2A, 3C, 4B, 5A, 6C, 7C), (1C, 2A, 3C, 4B, 5A, 6D, 7A), (1C, 2A, 3C, 4B, 5A, 6D, 7B), (1C, 2A, 3C, 4B, 5A, 6D, 7C), (1C, 2A, 3C, 4B, 5B, 6A, 7A), (1C, 2A, 3C, 4B, 5B, 6A, 7B), (1C, 2A, 3C, 4B, 5B, 6A, 7C), (1C, 2A, 3C, 4B, 5B, 6B, 7A), (1C, 2A, 3C, 4B, 5B, 6B, 7B), (1C, 2A, 3C, 4B, 5B, 6B, 7C), (1C, 2A, 3C, 4B, 5B, 6C, 7A), (1C, 2A, 3C, 4B, 5B, 6C, 7B), (1C, 2A, 3C, 4B, 5B, 6C, 7C), (1C, 2A, 3C, 4B, 5B, 6D, 7A), (1C, 2A, 3C, 4B, 5B, 6D, 7B), (1C, 2A, 3C, 4B, 5B, 6D, 7C), (1C, 2A, 3C, 4C, 5A, 6A, 7A), (1C, 2A, 3C, 4C, 5A, 6A, 7B), (1C, 2A, 3C, 4C, 5A, 6A, 7C), (1C, 2A, 3C, 4C, 5A, 6B, 7A), (1C, 2A, 3C, 4C, 5A, 6B, 7B), (1C, 2A, 3C, 4C, 5A, 6B, 7C), (1C, 2A, 3C, 4C, 5A, 6C, 7A), (1C, 2A, 3C, 4C, 5A, 6C, 7B), (1C, 2A, 3C, 4C, 5A, 6C, 7C), (1C, 2A, 3C, 4C, 5A, 6D, 7A), (1C, 2A, 3C, 4C, 5A, 6D, 7B), (1C, 2A, 3C, 4C, 5A, 6D, 7C), (1C, 2A, 3C, 4C, 5B, 6A, 7A), (1C, 2A, 3C, 4C, 5B, 6A, 7B), (1C, 2A, 3C, 4C, 5B, 6A, 7C), (1C, 2A, 3C, 4C, 5B, 6B, 7A), (1C, 2A, 3C, 4C, 5B, 6B, 7B), (1C, 2A, 3C, 4C, 5B, 6B, 7C), (1C, 2A, 3C, 4C, 5B, 6C, 7A), (1C, 2A, 3C, 4C, 5B, 6C, 7B), (1C, 2A, 3C, 4C, 5B, 6C, 7C), (1C, 2A, 3C, 4C, 5B, 6D, 7A), (1C, 2A, 3C, 4C, 5B, 6D, 7B), (1C, 2A, 3C, 4C, 5B, 6D, 7C), (1C, 2A, 3C, 4D, 5A, 6A, 7A), (1C, 2A, 3C, 4D, 5A, 6A, 7B), (1C, 2A, 3C, 4D, 5A, 6A, 7C), (1C, 2A, 3C, 4D, 5A, 6B, 7A), (1C, 2A, 3C, 4D, 5A, 6B, 7B), (1C, 2A, 3C, 4D, 5A, 6B, 7C), (1C, 2A, 3C, 4D, 5A, 6C, 7A), (1C, 2A, 3C, 4D, 5A, 6C, 7B), (1C, 2A, 3C, 4D, 5A, 6C, 7C), (1C, 2A, 3C, 4D, 5A, 6D, 7A), (1C, 2A, 3C, 4D, 5A, 6D, 7B), (1C, 2A, 3C, 4D, 5A, 6D, 7C), (1C, 2A, 3C, 4D, 5B, 6A, 7A), (1C, 2A, 3C, 4D, 5B, 6A, 7B), (1C, 2A, 3C, 4D, 5B, 6A, 7C), (1C, 2A, 3C, 4D, 5B, 6B, 7A), (1C, 2A, 3C, 4D, 5B, 6B, 7B), (1C, 2A, 3C, 4D, 5B, 6B, 7C), (1C, 2A, 3C, 4D, 5B, 6c, 7A), (1C, 2A, 3C, 4D, 5B, 6C, 7B), (1C, 2A, 3C, 4D, 5B, 6C, 7C), (1C, 2A, 3C, 4D, 5B, 6D, 7A), (1C, 2A, 3C, 4D, 5B, 6D, 7B), (1C, 2A, 3C, 4D, 5B, 6D, 7C), (1C, 2A, 3C, 4E, 5A, 6A, 7A), (1C, 2A, 3C, 4E, 5A, 6A, 7B), (1C, 2A, 3C, 4E, 5A, 6A, 7C), (1C, 2A, 3C, 4E, 5A, 6B, 7A), (1C, 2A, 3C, 4E, 5A, 6B, 7B), (1C, 2A, 3C, 4E, 5A, 6B, 7C), (1C, 2A, 3C, 4E, 5A, 6C, 7A), (1C, 2A, 3C, 4E, 5A, 6C, 7B), (1C, 2A, 3C, 4E, 5A, 6C, 7C), (1C, 2A, 3C, 4E, 5A, 6D, 7A), (1C, 2A, 3C, 4E, 5A, 6D, 7B), (1C, 2A, 3C, 4E, 5A, 6D, 7C), (1C, 2A, 3C, 4E, 5B, 6A, 7A), (1C, 2A, 3C, 4E, 5B, 6A, 7B), (1C, 2A, 3C, 4E, 5B, 6A, 7C), (1C, 2A, 3C, 4E, 5B, 6B, 7A), (1C, 2A, 3C, 4E, 5B, 6B, 7B), (1C, 2A, 3C, 4E, 5B, 6B, 7C), (1C, 2A, 3C, 4E, 5B, 6C, 7A), (1C, 2A, 3C, 4E, 5B, 6C, 7B), (1C, 2A, 3C, 4E, 5B, 6C, 7C), (1C, 2A, 3C, 4E, 5B, 6D, 7A), (1C, 2A, 3C, 4E, 5B, 6D, 7B), (1C, 2A, 3C, 4E, 5B, 6D, 7C), (1C, 2A, 3D, 4A, 5A, 6A, 7A), (1C, 2A, 3D, 4A, 5A, 6A, 7B), (1C, 2A, 3D, 4A, 5A, 6A, 7C), (1C, 2A, 3D, 4A, 5A, 6B, 7A), (1C, 2A, 3D, 4A, 5A, 6B, 7B), (1C, 2A, 3D, 4A, 5A, 6B, 7C), (1C, 2A, 3D, 4A, 5A, 6C, 7A), (1C, 2A, 3D, 4A, 5A, 6C, 7B), (1C, 2A, 3D, 4A, 5A, 6C, 7C), (1C, 2A, 3D, 4A, 5A, 6D, 7A), (1C, 2A, 3D, 4A, 5A, 6D, 7B), (1C, 2A, 3D, 4A, 5A, 6D, 7C), (1C, 2A, 3D, 4A, 5B, 6A, 7A), (1C, 2A, 3D, 4A, 5B, 6A, 7B), (1C, 2A, 3D, 4A, 5B, 6A, 7C), (1C, 2A, 3D, 4A, 5B, 6B, 7A), (1C, 2A, 3D, 4A, 5B, 6B, 7B), (1C, 2A, 3D, 4A, 5B, 6B, 7C), (1C, 2A, 3D, 4A, 5B, 6C, 7A), (1C, 2A, 3D, 4A, 5B, 6C, 7B), (1C, 2A, 3D, 4A, 5B, 6C, 7C), (1C, 2A, 3D, 4A, 5B, 6D, 7A), (1C, 2A, 3D, 4A, 5B, 6D, 7B), (1C, 2A, 3D, 4A, 5B, 6D, 7C), (1C, 2A, 3D, 4B, 5A, 6A, 7A), (1C, 2A, 3D, 4B, 5A, 6A, 7B), (1C, 2A, 3D, 4B, 5A, 6A, 7C), (1C, 2A, 3D, 4B, 5A, 6B, 7A), (1C, 2A, 3D, 4B, 5A, 6B, 7B), (1C, 2A, 3D, 4B, 5A, 6B, 7C), (1C, 2A, 3D, 4B, 5A, 6C, 7A), (1C, 2A, 3D, 4B, 5A, 6C, 7B), (1C, 2A, 3D, 4B, 5A, 6C, 7C), (1C, 2A, 3D, 4B, 5A, 6D, 7A), (1C, 2A, 3D, 4B, 5A, 6D, 7B), (1C, 2A, 3D, 4B, 5A, 6D, 7C), (1C, 2A, 3D, 4B, 5B, 6A, 7A), (1C, 2A, 3D, 4B, 5B, 6A, 7B), (1C, 2A, 3D, 4B, 5B, 6A, 7C), (1C, 2A, 3D, 4B, 5B, 6B, 7A), (1C, 2A, 3D, 4B, 5B, 6B, 7B), (1C, 2A, 3D, 4B, 5B, 6B, 7C), (1C, 2A, 3D, 4B, 5B, 6C, 7A), (1C, 2A, 3D, 4B, 5B, 6C, 7B), (1C, 2A, 3D, 4B, 5B, 6C, 7C), (1C, 2A, 3D, 4B, 5B, 6D, 7A), (1C, 2A, 3D, 4B, 5B, 6D, 7B), (1C, 2A, 3D, 4B, 5B, 6D, 7C), (1C, 2A, 3D, 4C, 5A, 6A, 7A), (1C, 2A, 3D, 4C, 5A, 6A, 7B), (1C, 2A, 3D, 4C, 5A, 6A, 7C), (1C, 2A, 3D, 4C, 5A, 6B, 7A), (1C, 2A, 3D, 4C, 5A, 6B, 7B), (1C, 2A, 3D, 4C, 5A, 6B, 7C), (1C, 2A, 3D, 4C, 5A, 6C, 7A), (1C, 2A, 3D, 4C, 5A, 6C, 7B), (1C, 2A, 3D, 4C, 5A, 6C, 7C), (1C, 2A, 3D, 4C, 5A, 6D, 7A), (1C, 2A, 3D, 4C, 5A, 6D, 7B), (1C, 2A, 3D, 4C, 5A, 6D, 7C), (1C, 2A, 3D, 4C, 5B, 6A, 7A), (1C, 2A, 3D, 4C, 5B, 6A, 7B), (1C, 2A, 3D, 4C, 5B, 6A, 7C), (1C, 2A, 3D, 4C, 5B, 6B, 7A), (1C, 2A, 3D, 4C, 5B, 6B, 7B), (1C, 2A, 3D, 4C, 5B, 6B, 7C), (1C, 2A, 3D, 4C, 5B, 6C, 7A), (1C, 2A, 3D, 4C, 5B, 6C, 7B), (1C, 2A, 3D, 4C, 5B, 6C, 7C), (1C, 2A, 3D, 4C, 5B, 6D, 7A), (1C, 2A, 3D, 4C, 5B, 6D, 7B), (1C, 2A, 3D, 4C, 5B, 6D, 7C), (1C, 2A, 3D, 4D, 5A, 6A, 7A), (1C, 2A, 3D, 4D, 5A, 6A, 7B), (1C, 2A, 3D, 4D, 5A, 6A, 7C), (1C, 2A, 3D, 4D, 5A, 6B, 7A), (1C, 2A, 3D, 4D, 5A, 6B, 7B), (1C, 2A, 3D, 4D, 5A, 6B, 7C), (1C, 2A, 3D, 4D, 5A, 6C, 7A), (1C, 2A, 3D, 4D, 5A, 6C, 7B), (1C, 2A, 3D, 4D, 5A, 6C, 7C), (1C, 2A, 3D, 4D, 5A, 6D, 7A), (1C, 2A, 3D, 4D, 5A, 6D, 7B), (1C, 2A, 3D, 4D, 5A, 6D, 7C), (1C, 2A, 3D, 4D, 5B, 6A, 7A), (1C, 2A, 3D, 4D, 5B, 6A, 7B), (1C, 2A, 3D, 4D, 5B, 6A, 7C), (1C, 2A, 3D, 4D, 5B, 6B, 7A), (1C, 2A, 3D, 4D, 5B, 6B, 7B), (1C, 2A, 3D, 4D, 5B, 6B, 7C), (1C, 2A, 3D, 4D, 5B, 6C, 7A), (1C, 2A, 3D, 4D, 5B, 6C, 7B), (1C, 2A, 3D, 4D, 5B, 6C, 7C), (1C, 2A, 3D, 4D, 5B, 6D, 7A), (1C, 2A, 3D, 4D, 5B, 6D, 7B), (1C, 2A, 3D, 4D, 5B, 6D, 7C), (1C, 2A, 3D, 4E, 5A, 6A, 7A), (1C, 2A, 3D, 4E, 5A, 6A, 7B), (1C, 2A, 3D, 4E, 5A, 6A, 7C), (1C, 2A, 3D, 4E, 5A, 6B, 7A), (1C, 2A, 3D, 4E, 5A, 6B, 7B), (1C, 2A, 3D, 4E, 5A, 6B, 7C), (1C, 2A, 3D, 4E, 5A, 6C, 7A), (1C, 2A, 3D, 4E, 5A, 6C, 7B), (1C, 2A, 3D, 4E, 5A, 6C, 7C), (1C, 2A, 3D, 4E, 5A, 6D, 7A), (1C, 2A, 3D, 4E, 5A, 6D, 7B), (1C, 2A, 3D, 4E, 5A, 6D, 7C), (1C, 2A, 3D, 4E, 5B, 6A, 7A), (1C, 2A, 3D, 4E, 5B, 6A, 7B), (1C, 2A, 3D, 4E, 5B, 6A, 7C), (1C, 2A, 3D, 4E, 5B, 6B, 7A), (1C, 2A, 3D, 4E, 5B, 6B, 7B), (1C, 2A, 3D, 4E, 5B, 6B, 7C), (1C, 2A, 3D, 4E, 5B, 6C, 7A), (1C, 2A, 3D, 4E, 5B, 6C, 7B), (1C, 2A, 3D, 4E, 5B, 6C, 7C), (1C, 2A, 3D, 4E, 5B, 6D, 7A), (1C, 2A, 3D, 4E, 5B, 6D, 7B), (1C, 2A, 3D, 4E, 5B, 6D, 7C), (1C, 2A, 3E, 4A, 5A, 6A, 7A), (1C, 2A, 3E, 4A, 5A, 6A, 7A), (1C, 2A, 3E, 4A, 5A, 6A, 7C), (1C, 2A, 3E, 4A, 5A, 6B, 7A), (1C, 2A, 3E, 4A, 5A, 6B, 7B), (1C, 2A, 3E, 4A, 5A, 6B, 7C), (1C, 2A, 3E, 4A, 5A, 6C, 7A), (1C, 2A, 3E, 4A, 5A, 6C, 7B), (1C, 2A, 3E, 4A, 5A, 6C, 7C), (1C, 2A, 3E, 4A, 5A, 6D, 7A), (1C, 2A, 3E, 4A, 5A, 6D, 7B), (1C, 2A, 3E, 4A, 5A, 6D, 7C), (1C, 2A, 3E, 4A, 5B, 6A, 7A), (1C, 2A, 3E, 4A, 5B, 6A, 7B), (1C, 2A, 3E, 4A, 5B, 6A, 7C), (1C, 2A, 3E, 4A, 5B, 6B, 7A), (1C, 2A, 3E, 4A, 5B, 6B, 7B), (1C, 2A, 3E, 4A, 5B, 6B, 7C), (1C, 2A, 3E, 4A, 5B, 6C, 7A), (1C, 2A, 3E, 4A, 5B, 6C, 7B), (1C, 2A, 3E, 4A, 5B, 6C, 7C), (1C, 2A, 3E, 4A, 5B, 6D, 7A), (1C, 2A, 3E, 4A, 5B, 6D, 7B), (1C, 2A, 3E, 4A, 5B, 6D, 7C), (1C, 2A, 3E, 4B, 5A, 6A, 7A), (1C, 2A, 3E, 4B, 5A, 6A, 7B), (1C, 2A, 3E, 4B, 5A, 6A, 7C), (1C, 2A, 3E, 4B, 5A, 6B, 7A), (1C, 2A, 3E, 4B, 5A, 6B, 7B), (1C, 2A, 3E, 4B, 5A, 6B, 7C), (1C, 2A, 3E, 4B, 5A, 6C, 7A), (1C, 2A, 3E, 4B, 5A, 6C, 7B), (1C, 2A, 3E, 4B, 5A, 6C, 7C), (1C, 2A, 3E, 4B, 5A, 6D, 7A), (1C, 2A, 3E, 4B, 5A, 6D, 7B), (1C, 2A, 3E, 4B, 5A, 6D, 7C), (1C, 2A, 3E, 4B, 5B, 6A, 7A), (1C, 2A, 3E, 4B, 5B, 6A, 7B), (1C, 2A, 3E, 4B, 5B, 6A, 7C), (1C, 2A, 3E, 4B, 5B, 6B, 7A), (1C, 2A, 3E, 4B, 5B, 6B, 7B), (1C, 2A, 3E, 4B, 5B, 6B, 7C), (1C, 2A, 3E, 4B, 5B, 6C, 7A), (1C, 2A, 3E, 4B, 5B, 6C, 7B), (1C, 2A, 3E, 4B, 5B, 6C, 7C), (1C, 2A, 3E, 4B, 5B, 6D, 7A), (1C, 2A, 3E, 4B, 5B, 6D, 7B), (1C, 2A, 3E, 4B, 5B, 6D, 7C), (1C, 2A, 3E, 4C, 5A, 6A, 7A), (1C, 2A, 3E, 4C, 5A, 6A, 7B), (1C, 2A, 3E, 4C, 5A, 6A, 7C), (1C, 2A, 3E, 4C, 5A, 6B, 7A), (1C, 2A, 3E, 4C, 5A, 6B, 7B), (1C, 2A, 3E, 4C, 5A, 6B, 7C), (1C, 2A, 3E, 4C, 5A, 6C, 7A), (1C, 2A, 3E, 4C, 5A, 6C, 7B), (1C, 2A, 3E, 4C, 5A, 6C, 7C), (1C, 2A, 3E, 4C, 5A, 6D, 7A), (1C, 2A, 3E, 4C, 5A, 6D, 7B), (1C, 2A, 3E, 4C, 5A, 6D, 7C), (1C, 2A, 3E, 4C, 5B, 6A, 7A), (1C, 2A, 3E, 4C, 5B, 6A, 7B), (1C, 2A, 3E, 4C, 5B, 6A, 7C), (1C, 2A, 3E, 4C, 5B, 6B, 7A), (1C, 2A, 3E, 4C, 5B, 6B, 7B), (1C, 2A, 3E, 4C, 5B, 6B, 7C), (1C, 2A, 3E, 4C, 5B, 6C, 7A), (1C, 2A, 3E, 4C, 5B, 6C, 7B), (1C, 2A, 3E, 4C, 5B, 6C, 7C), (1C, 2A, 3E, 4C, 5B, 6D, 7A), (1C, 2A, 3E, 4C, 5B, 6D, 7B), (1C, 2A, 3E, 4C, 5B, 6D, 7C), (1C, 2A, 3E, 4D, 5A, 6A, 7A), (1C, 2A, 3E, 4D, 5A, 6A, 7B), (1C, 2A, 3E, 4D, 5A, 6A, 7C), (1C, 2A, 3E, 4D, 5A, 6B, 7A), (1C, 2A, 3E, 4D, 5A, 6B, 7B), (1C, 2A, 3E, 4D, 5A, 6B, 7C), (1C, 2A, 3E, 4D, 5A, 6C, 7A), (1C, 2A, 3E, 4D, 5A, 6C, 7B), (1C, 2A, 3E, 4D, 5A, 6C, 7C), (1C, 2A, 3E, 4D, 5A, 6D, 7A), (1C, 2A, 3E, 4D, 5A, 6D, 7B), (1C, 2A, 3E, 4D, 5A, 6D, 7C), (1C, 2A, 3E, 4D, 5B, 6A, 7A), (1C, 2A, 3E, 4D, 5B, 6A, 7B), (1C, 2A, 3E, 4D, 5B, 6A, 7C), (1C, 2A, 3E, 4D, 5B, 6B, 7A), (1C, 2A, 3E, 4D, 5B, 6B, 7B), (1C, 2A, 3E, 4D, 5B, 6B, 7C), (1C, 2A, 3E, 4D, 5B, 6C, 7A), (1C, 2A, 3E, 4D, 5B, 6C, 7B), (1C, 2A, 3E, 4D, 5B, 6C, 7C), (1C, 2A, 3E, 4D, 5B, 6D, 7A), (1C, 2A, 3E, 4D, 5B, 6D, 7B), (1C, 2A, 3E, 4D, 5B, 6D, 7C), (1C, 2A, 3E, 4E, 5A, 6A, 7A), (1C, 2A, 3E, 4E, 5A, 6A, 7B), (1C, 2A, 3E, 4E, 5A, 6A, 7C), (1C, 2A, 3E, 4E, 5A, 6B, 7A), (1C, 2A, 3E, 4E, 5A, 6B, 7B), (1C, 2A, 3E, 4E, 5A, 6B, 7C), (1C, 2A, 3E, 4E, 5A, 6C, 7A), (1C, 2A, 3E, 4E, 5A, 6C, 7B), (1C, 2A, 3E, 4E, 5A, 6C, 7C), (1C, 2A, 3E, 4E, 5A, 6D, 7A), (1C, 2A, 3E, 4E, 5A, 6D, 7B), (1C, 2A, 3E, 4E, 5A, 6D, 7C), (1C, 2A, 3E, 4E, 5B, 6A, 7A), (1C, 2A, 3E, 4E, 5B, 6A, 7B), (1C, 2A, 3E, 4E, 5B, 6A, 7C), (1C, 2A, 3E, 4E, 5B, 6B, 7A), (1C, 2A, 3E, 4E, 5B, 6B, 7B), (1C, 2A, 3E, 4E, 5B, 6B, 7C), (1C, 2A, 3E, 4E, 5B, 6C, 7A), (1C, 2A, 3E, 4E, 5B, 6C, 7B), (1C, 2A, 3E, 4E, 5B, 6C, 7C), (1C, 2A, 3E, 4E, 5B, 6D, 7A), (1C, 2A, 3E, 4E, 5B, 6D, 7B), (1C, 2A, 3E, 4E, 5B, 6D, 7C), (1C, 2B, 3A, 4A, 5A, 6A, 7A), (1C, 2B, 3A, 4A, 5A, 6A, 7B), (1C, 2B, 3A, 4A, 5A, 6A, 7C), (1C, 2B, 3A, 4A, 5A, 6B, 7A), (1C, 2B, 3A, 4A, 5A, 6B, 7B), (1C, 2B, 3A, 4A, 5A, 6B, 7C), (1C, 2B, 3A, 4A, 5A, 6C, 7A), (1C, 2B, 3A, 4A, 5A, 6C, 7B), (1C, 2B, 3A, 4A, 5A, 6C, 7C), (1C, 2B, 3A, 4A, 5A, 6D, 7A), (1C, 2B, 3A, 4A, 5A, 6D, 7B), (1C, 2B, 3A, 4A, 5A, 6D, 7C), (1C, 2B, 3A, 4A, 5B, 6A, 7A), (1C, 2B, 3A, 4A, 5B, 6A, 7B), (1C, 2B, 3A, 4A, 5B, 6A, 7C), (1C, 2B, 3A, 4A, 5B, 6B, 7A), (1C, 2B, 3A, 4A, 5B, 6B, 7B), (1C, 2B, 3A, 4A, 5B, 6B, 7C), (1C, 2B, 3A, 4A, 5B, 6C, 7A), (1C, 2B, 3A, 4A, 5B, 6C, 7B), (1C, 2B, 3A, 4A, 5B, 6C, 7C), (1C, 2B, 3A, 4A, 5B, 6D, 7A), (1C, 2B, 3A, 4A, 5B, 6D, 7B), (1C, 2B, 3A, 4B, 5A, 6A, 7A), (1C, 2B, 3A, 4B, 5A, 6A, 7B), (1C, 2B, 3A, 4B, 5A, 6A, 7C), (1C, 2B, 3A, 4B, 5A, 6B, 7A), (1C, 2B, 3A, 4B, 5A, 6B, 7B), (1C, 2B, 3A, 4B, 5A, 6B, 7C), (1C, 2B, 3A, 4B, 5A, 6C, 7A), (1C, 2B, 3A, 4B, 5A, 6C, 7B), (1C, 2B, 3A, 4B, 5A, 6C, 7C), (1C, 2B, 3A, 4B, 5A, 6D, 7A), (1C, 2B, 3A, 4B, 5A, 6D, 7B), (1C, 2B, 3A, 4B, 5A, 6D, 7C), (1C, 2B, 3A, 4B, 5B, 6A, 7A), (1C, 2B, 3A, 4B, 5B, 6A, 7B), (1C, 2B, 3A, 4B, 5B, 6A, 7C), (1C, 2B, 3A, 4B, 5B, 6B, 7A), (1C, 2B, 3A, 4B, 5B, 6B, 7B), (1C, 2B, 3A, 4B, 5B, 6B, 7C), (1C, 2B, 3A, 4B, 5B, 6C, 7A), (1C, 2B, 3A, 4B, 5B, 6C, 7B), (1C, 2B, 3A, 4B, 5B, 6C, 7C), (1C, 2B, 3A, 4B, 5B, 6D, 7A), (1C, 2B, 3A, 4B, 5B, 6D, 7B), (1C, 2B, 3A, 4B, 5B, 6D, 7C), (1C, 2B, 3A, 4C, 5A, 6A, 7A), (1C, 2B, 3A, 4C, 5A, 6A, 7B), (1C, 2B, 3A, 4C, 5A, 6A, 7C), (1C, 2B, 3A, 4C, 5A, 6B, 7A), (1C, 2B, 3A, 4C, 5A, 6B, 7B), (1C, 2B, 3A, 4C, 5A, 6B, 7C), (1C, 2B, 3A, 4C, 5A, 6C, 7A), (1C, 2B, 3A, 4C, 5A, 6C, 7B), (1C, 2B, 3A, 4C, 5A, 6C, 7C), (1C, 2B, 3A, 4C, 5A, 6D, 7A), (1C, 2B, 3A, 4C, 5A, 6D, 7B), (1C, 2B, 3A, 4C, 5A, 6D, 7C), (1C, 2B, 3A, 4C, 5B, 6A, 7A), (1C, 2B, 3A, 4C, 5B, 6A, 7B), (1C, 2B, 3A, 4C, 5B, 6A, 7C), (1C, 2B, 3A, 4C, 5B, 6B, 7A), (1C, 2B, 3A, 4C, 5B, 6B, 7B), (1C, 2B, 3A, 4C, 5B, 6B, 7C), (1C, 2B, 3A, 4C, 5B, 6C, 7A), (1C, 2B, 3A, 4C, 5B, 6C, 7B), (1C, 2B, 3A, 4C, 5B, 6C, 7C), (1C, 2B, 3A, 4C, 5B, 6D, 7A), (1C, 2B, 3A, 4C, 5B, 6D, 7B), (1C, 2B, 3A, 4C, 5B, 6D, 7C), (1C, 2B, 3A, 4D, 5A, 6A, 7A), (1C, 2B, 3A, 4J, 5A, 6A, 7B), (1C, 2B, 3A, 4D, 5A, 6A, 7C), (1C, 2B, 3A, 4D, 5A, 6B, 7A), (1C, 2B, 3A, 4D, 5A, 6B, 7B), (1C, 2B, 3A, 4D, 5A, 6B, 7C), (1C, 2B, 3A, 4D, 5A, 6C, 7A), (1C, 2B, 3A, 4D, 5A, 6C, 7B), (1C, 2B, 3A, 4D, 5A, 6C, 7C), (1C, 2B, 3A, 4D, 5A, 6D, 7A), (C, 2B, 3A, 4D, 5A, 6D, 7B), (1C, 2B, 3A, 4D, 5A, 6D, 7C), (1C, 2B, 3A, 4D, 5B, 6A, 7A), (1C, 2B, 3A, 4D, 5B, 6A, 7B), (1C, 2B, 3A, 4D, 5B, 6A, 7C), (1C, 2B, 3A, 4D, 5B, 6B, 7A), (1C, 2B, 3A, 4D, 5B, 6B, 7B), (1C, 2B, 3A, 4D, 5B, 6B, 7C), (1C, 2B, 3A, 4D, 5B, 6C, 7A), (1C, 2B, 3A, 4D, 5B, 6C, 7B), (1C, 2B, 3A, 4D, 5B, 6C, 7C), (1C, 2B, 3A, 4D, 5B, 6D, 7A), (1C, 2B, 3A, 4D, 5B, 6D, 7B), (1C, 2B, 3A, 4D, 5B, 6D, 7C), (1C, 2B, 3A, 4E, 5A, 6A, 7A), (1C, 2B, 3A, 4E, 5A, 6A, 7B), (1C, 2B, 3A, 4E, 5A, 6A, 7C), (1C, 2B, 3A, 4E, 5A, 6B, 7A, (1C, 2B, 3A, 4E, 5A, 6B, 7B), (1C, 2B, 3A, 4E, 5A, 6B, 7C) (1C, 2B, 3A, 4E, 5A, 6C, 7A), (1C, 2B, 3A, 4E, 5A, 6C, 7B), (1C, 2B, 3A, 4E, 5A, 6C, 7C), (1C, 2B, 3A, 4E, 5A, 6D, 7A), (1C, 2B, 3A, 4E, 5A, 6D, 7B), (1C, 2B, 3A, 4E, 5A, 6D, 7C), (1C, 2B, 3A, 4E, 5B, 6A, 7A), (1C, 2B, 3A, 4E, 5B, 6A, 7B), (1C, 2B, 3A, 4E, 5B, 6A, 7C), (1C, 2B, 3A, 4E, 5B, 6B, 7A), (1C, 2B, 3A, 4E, 5B, 6B, 7B), (1C, 2B, 3A, 4E, 5B, 6B, 7C), (1C, 2B, 3A, 4E, 5B, 6C, 7A), (1C, 2B, 3A, 4E, 5B, 6C, 7B), (1C, 2B, 3A, 4E, 5B, 6C, 7C), (1C, 2B, 3A, 4E, 5B, 6D, 7A), (1C, 2B, 3A, 4E, 5B, 6D, 7B), (1C, 2B, 3A, 4E, 5B, 6D, 7C), (1C, 2B, 3B, 4A, 5A, 6A, 7A), (1C, 2B, 3B, 4A, 5A, 6A, 7B), (1C, 2B, 3B, 4A, 5A, 6A, 7C), (1C, 2B, 3B, 4A, 5A, 6B, 7A), (1C, 2B, 3B, 4A, 5A, 6B, 7B), (1C, 2B, 3B, 4A, 5A, 6B, 7C), (1C, 2B, 3B, 4A, 5A, 6C, 7A), (1C, 2B, 3B, 4A, 5A, 6C, 7B), (1C, 2B, 3B, 4A, 5A, 6C, 7C), (1C, 2B, 3B, 4A, 5A, 6D, 7A) (1C, 2B, 3B, 4A, 5A, 6D, 7B), (1C, 2B, 3B, 4A, 5A, 6D, 7C), (1C, 2B, 3B, 4A, 5B, 6A, 7A), (1C, 2B, 3B, 4A, 5B, 6A, 7B), (1C, 2B, 3B, 4A, 5B, 6A, 7C), (1C, 2B, 3B, 4A, 5B, 6B, 7A), (1C, 2B, 3B, 4A, 5B, 6B), (1C, 2B, 3B, 4A, 5B, 6B, 7C), (1C, 2B, 3B, 4A, 5B, 6C, 7A), (1C, 2B, 3B, 4A, 5B, 6C, 7B), (1C, 2B, 3B, 5B, 6C, 7C), (1C, 2B, 3B, 4A, 5B, 6D, 7A), (1C, 2B, 3B, 4A, 5B, 6D, 7B), (1C, 2B, 3B, 4A, 5B, 6D, 7C) (1C, 2B, 3B, 4B, 5A, 6A, 7A), (1C, 2B, 3B, 4B, 5A, 6A, 7B), (1C, 2B, 3B, 4B, 5A, 6A, 7C) (12B, 3B, 4B, 5A, 6B, 7A), (1C, 2B, 3B, 4B, 5A, 6B, 7B), (1C, 2B, 3B, 4B, 5A, 6B, 7C), (1C, 2B, 3B, 4B, 5A, 6C, 7A), (1C, 2B, 3B, 4B, 5A, 6C, 7B), (1C, 2B, 3B, 4B, 5A, 6C, 7C), (1C, 2B, 3B, 4B, 5A, 6D, 7A), (C, 2B, 3B, 4B, 5A, 6D, 7B), (1C, 2B, 3B, 4B, 5A, 6D, 7C), (1C, 2B, 3B, 4B, 5B, 6A, 7A), (1C, 2B, 3B, 4B, 5B, 6A, 7B), (1C, 2B, 3B, 4B, 5B, 6A, 7C), (1C, 2B, 3B, 4B, 5B, 6B, 7A), (1C, 2B, 3B, 4B, 5B, 6B, 7B), (1C, 2B, 3B, 4B, 5B, 6B, 7C), (1C, 2B, 3B, 4B, 5B, 6C, 7A), (1C, 2B, 3B, 4B, 5B, 6D,

7B), (1C, 2B, 3B, 4B, 5B, 6C, 7C) (1C, 2B, 3B, 4B, 5B, 6D, 7A), (1C, 2B, 3B, 4B, 5B, 6D, 7B), (1C, 2B, 3B, 4B, 5B, 6D, 7C), (1C, 2B, 3B, 4C, 5A, 6A, 7A), (1C, 2B, 3B, 4C, 5A, 6A, 7B), (1C, 2B, 3B, 4C, 5A, 6A, 7C), (1C, 2B, 3B, 4C, 5A, 6B, 7A), (1C, 2B, 3B, 4C, 5A, 6B, 7B), (1C, 2B, 3B, 4C, 5A, 6B, 7C), (1C, 2B, 3B, 4C, 5A, 6C, 7A), (1C, 2B, 3B, 4C, 5A, 6C, 7B), (1C, 2B, 3B, 4C, 5A, 6C, 7C), (1C, 2B, 3B, 4C, 5A, 6D, 7A), (1C, 2B, 3B, 4C, 5A, 6D, 7B), (1C, 2B, 3B, 4C, 5A, 6D, 7C), (1C, 2B, 3B, 4C, 5B, 6A, 7A), (1C, 2B, 3B, 4C, 5B, 6A, 7B), (1C, 2B, 3B, 4C, 5B, 6A, 7C), (1C, 2B, 3B, 4C, 5B, 6B, 7A), (1C, 2B, 3B, 4C, 5B, 6B, 7B), (1C, 2B, 3B, 4C, 5B, 6B, 7C), (1C, 2B, 3B, 4C, 5B, 6C, 7A), (1C, 2B, 3B, 4C, 5B, 6C, 7B), (1C, 2B, 3B, 4C, 5B, 6C, 7C), (1C, 2B, 3B, 4C, 5B, 6D, 7A), (1C, 2B, 3B, 4C, 5B, 6D, 7B), (1C, 2B, 3B, 4C, 5B, 6D, 7C), (1C, 2B, 3B, 4D, 5A, 6A, 7A), (1C, 2B, 3B, 4D, 5A, 6A, 7B), (1C, 2B, 3B, 4D, 5A, 6A, 7C), (1C, 2B, 3B, 4D, 5A, 6B, 7A), (1C, 2B, 3B, 4D, 5A, 6B, 7B), (1C, 2B, 3B, 4D, 5A, 6B, 7C), (1C, 2B, 3B, 4D, 5A, 6C, 7A), (1C, 2B, 3B, 4D, 5A, 6C, 7B), (1C, 2B, 3B, 4D, 5A, 6C, 7C), (1C, 2B, 3B, 4D, 5A, 6D, 7A), (1C, 2B, 3B, 4D, 5A, 6D, 7B), (1C, 2B, 3B, 4D, 5A, 6D, 7C), (1C, 2B, 3B, 4D, 5B, 6A, 7A), (1C, 2B, 3B, 4D, 5B, 6A, 7B), (1C, 2B, 3B, 4D, 5B, 6A, 7C), (1C, 2B, 3B, 4D, 5B, 6B, 7A), (1C, 2B, 3B, 4D, 5B, 6B, 7B), (1C, 2B, 3B, 4D, 5B, 6B, 7C), (1C, 2B, 3B, 4D, 5B, 6C, 7A), (1C, 2B, 3B, 4D, 5B, 6C, 7B), (1C, 2B, 3B, 4D, 5B, 6C, 7C), (1C, 2B, 3B, 4D, 5B, 6D, 7A), (1C, 2B, 3B, 4D, 5B, 6D, 7B), (1C, 2B, 3B, 4D, 5B, 6D, 7C), (1C, 2B, 3B, 4E, 5A, 6A, 7A), (1C, 2B, 3B, 4E, 5A, 6A, 7B), (1C, 2B, 3B, 4E, 5A, 6A, 7C), (1C, 2B, 3B, 4E, 5A, 6B, 7A), (1C, 2B, 3B, 4E, 5A, 6B, 7B), (1C, 2B, 3B, 4E, 5A, 6B, 7C), (1C, 2B, 3B, 4E, 5A, 6C, 7A), (1C, 2B, 3B, 4E, 5A, 6C, 7B), (1C, 2B, 3B, 4E, 5A, 6C, 7C), (1C, 2B, 3B, 4E, 5A, 6D, 7A), (1C, 2B, 3B, 4E, 5A, 6D, 7B), (1C, 2B, 3B, 4E, 5A, 6D, 7C), (1C, 2B, 3B, 4E, 5B, 6A, 7A), (1C, 2B, 3B, 4E, 5B, 6A, 7B), (1C, 2B, 3B, 4E, 5B, 6A, 7C), (1C, 2B, 3B, 4E, 5B, 6B, 7A), (1C, 2B, 3B, 4E, 5B, 6B, 7B), (1C, 2B, 3B, 4E, 5B, 6B, 7C), (1C, 2B, 3B, 4E, 5B, 6C, 7A), (1C, 2B, 3B, 4E, 5B, 6C, 7B), (1C, 2B, 3B, 4E, 5B, 6C, 7C), (1C, 2B, 3B, 4E, 5B, 6D, 7A), (1C, 2B, 3B, 4E, 5B, 6D, 7B), (1C, 2B, 3B, 4E, 5B, 6D, 7C), (1C, 2B, 3C, 4A, 5A, 6A, 7A), (1C, 2B, 3C, 4A, 5A, 6A, 7B), (1C, 2B, 3C, 4A, 5A, 6A, 7C), (1C, 2B, 3C, 4A, 5A, 6B, 7A), (1C, 2B, 3C, 4A, 5A, 6B, 7B), (1C, 2B, 3C, 4A, 5A, 6B, 7C), (1C, 2B, 3C, 4A, 5A, 6C, 7A), (1C, 2B, 3C, 4A, 5A, 6C, 7B), (1C, 2B, 3C, 4A, 5A, 6C, 7C), (1C, 2B, 3C, 4A, 5A, 6D, 7A), (1C, 2B, 3C, 4A, 5A, 6D, 7B), (1C, 2B, 3C, 4A, 5A, 6D, 7C), (1C, 2B, 3C, 4A, 5B, 6A, 7A), (1C, 2B, 3C, 4A, 5B, 6A, 7B), (1C, 2B, 3C, 4A, 5B, 6A, 7C), (1C, 2B, 3C, 4A, 5B, 6B, 7A), (1C, 2B, 3C, 4A, 5B, 6B, 7B), (1C, 2B, 3C, 4A, 5B, 6B, 7C), (1C, 2B, 3C, 4A, 5B, 6C, 7A), (1C, 2B, 3C, 4A, 5B, 6C, 7B), (1C, 2B, 3C, 4A, 5B, 6C, 7C), (1C, 2B, 3C, 4A, 5B, 6D, 7A), (1C, 2B, 3C, 4A, 5B, 6D, 7B), (1C, 2B, 3C, 4A, 5B, 6D, 7C), (1C, 2B, 3C, 4B, 5A, 6A, 7A), (1C, 2B, 3C, 4B, 5A, 6A, 7B), (1C, 2B, 3C, 4B, 5A, 6A, 7C), (1C, 2B, 3C, 4B, 5A, 6B, 7A), (1C, 2B, 3C, 4B, 5A, 6B, 7B), (1C, 2B, 3C, 4B, 5A, 6B, 7C), (1C, 2B, 3C, 4B, 5A, 6C, 7A), (1C, 2B, 3C, 4B, 5A, 6C, 7B), (1C, 2B, 3C, 4B, 5A, 6C, 7C), (1C, 2B, 3C, 4B, 5A, 6D, 7A), (1C, 2B, 3C, 4B, 5A, 6D, 7B), (1C, 2B, 3C, 4B, 5A, 6D, 7C), (1C, 2B, 3C, 4B, 5B, 6A, 7A), (1C, 2B, 3C, 4B, 5B, 6A, 7B), (1C, 2B, 3C, 4B, 5B, 6A, 7C), (1C, 2B, 3C, 4B, 5B, 6B, 7A), (1C, 2B, 3C, 4B, 5B, 6B, 7B), (1C, 2B, 3C, 4B, 5B, 6B, 7C), (1C, 2B, 3C, 4B, 5B, 6C, 7A), (1C, 2B, 3C, 4B, 5B, 6C, 7B), (1C, 2B, 3C, 4B, 5B, 6C, 7C), (1C, 2B, 3C, 4B, 5B, 6D, 7A), (1C, 2B, 3C, 4B, 5B, 6D, 7B), (1C, 2B, 3C, 4B, 5B, 6D, 7C), (1C, 2B, 3C, 4C, 5A, 6A, 7A), (1C, 2B, 3C, 4C, 5A, 6A, 7B), (1C, 2B, 3C, 4C, 5A, 6A, 7C), (1C, 2B, 3C, 4C, 5A, 6B, 7A), (1C, 2B, 3C, 4C, 5A, 6B, 7B), (1C, 2B, 3C, 4C, 5A, 6B, 7C), (1C, 2B, 3C, 4C, 5A, 6C, 7A), (1C, 2B, 3C, 4C, 5A, 6C, 7B), (1C, 2B, 3C, 4C, 5A, 6C, 7C), (1C, 2B, 3C, 4C, 5A, 6D, 7A), (1C, 2B, 3C, 4C, 5A, 6D, 7B), (1C, 2B, 3C, 4C, 5A, 6D, 7C), (1C, 2B, 3C, 4C, 5B, 6A, 7A), (1C, 2B, 3C, 4C, 5B, 6A, 7B), (1C, 2B, 3C, 4C, 5B, 6A, 7C), (1C, 2B, 3C, 4C, 5B, 6B, 7A), (1C, 2B, 3C, 4C, 5B, 6B, 7B), (1C, 2B, 3C, 4C, 5B, 6B, 7C), (1C, 2B, 3C, 4C, 5B, 6C, 7A), (1C, 2B, 3C, 4C, 5B, 6C, 7B), (1C, 2B, 3C, 4C, 5B, 6C, 7C), (1C, 2B, 3C, 4C; 5B, 6D, 7A), (1C, 2B, 3C, 4C, 5B, 6D, 7B), (1C, 2B, 3C, 4C, 5B, 6D, 7C), (1C, 2B, 3C, 4D, 5A, 6A, 7A), (1C, 2B, 3C, 4D, 5A, 6A, 7B), (1C, 2B, 3C, 4D, 5A, 6A, 7C), (1C, 2B, 3C, 4D, 5A, 6B, 7A), (1C, 2B, 3C, 4D, 5A, 6B, 7B), (1C, 2B, 3C, 4D, 5A, 6B, 7C), (1C, 2B, 3C, 4D, 5A, 6C, 7A), (1C, 2B, 3C, 4D, 5A, 6C, 7B), (1C, 2B, 3C, 4D, 5A, 6C, 7C), (1C, 2B, 3C, 4D, 5A, 6D, 7A), (1C, 2B, 3C, 4D, 5A, 6D, 7B), (1C, 2B, 3C, 4D, 5A, 6D, 7C), (1C, 2B, 3C, 4D, 5B, 6A, 7A), (1C, 2B, 3C, 4D, 5B, 6A, 7B), (1C, 2B, 3C, 4D, 5B, 6A, 7C), (1C, 2B, 3C, 4D, 5B, 6B, 7A), (1C, 2B, 3C, 4D, 5B, 6B, 7B), (1C, 2B, 3C, 4D, 5B, 6B, 7C), (1C, 2B, 3C, 4D, 5B, 6C, 7A), (1C, 2B, 3C, 4D, 5B, 6C, 7B), (1C, 2B, 3C, 4D, 5B, 6C, 7C), (1C, 2B, 3C, 4D, 5B, 6D, 7A), (1C, 2B, 3C, 4D, 5B, 6D, 7B), (1C, 2B, 3C, 4D, 5B, 6D, 7C), (1C, 2B, 3C, 4E, 5A, 6A, 7A), (1C, 2B, 3C, 4E, 5A, 6A, 7B), (1C, 2B, 3C, 4E, 5A, 6A, 7C), (1C, 2B, 3C, 4E, 5A, 6B, 7A), (1C, 2B, 3C, 4E, 5A, 6B, 7B), (1C, 2B, 3C, 4E, 5A, 6B, 7C), (1C, 2B, 3C, 4E, 5A, 6C, 7A), (1C, 2B, 3C, 4E, 5A, 6C, 7B), (1C, 2B, 3C, 4E, 5A, 6C, 7C), (1C, 2B, 3C, 4E, 5A, 6D, 7A), (1C, 2B, 3C, 4E, 5A, 6D, 7B), (1C, 2B, 3C, 4E, 5A, 6D, 7C), (1C, 2B, 3C, 4E, 5B, 6A, 7A), (1C, 2B, 3C, 4E, 5B, 6A, 7B), (1C, 2B, 3C, 4E, 5B, 6A, 7C), (1C, 2B, 3C, 4E, 5B, 6B, 7A), (1C, 2B, 3C, 4E, 5B, 6B, 7B), (1C, 2B, 3C, 4E, 5B, 6B, 7C), (1C, 2B, 3C, 4E, 5B, 6C, 7A), (1C, 2B, 3C, 4E, 5B, 6C, 7B), (1C, 2B, 3C, 4E, 5B, 6C, 7C), (1C, 2B, 3C, 4E, 5B, 6D, 7A), (1C, 2B, 3C, 4E, 5B, 6D, 7B), (1C, 2B, 3C, 4E, 5B, 6D, 7C), (1C, 2B, 3D, 4A, 5A, 6A, 7A), (1C, 2B, 3D, 4A, 5A, 6A, 7B), (1C, 2B, 3D, 4A, 5A, 6A, 7C), (1C, 2B, 3D, 4A, 5A, 6B, 7A), (1C, 2B, 3D, 4A, 5A, 6B, 7B), (1C, 2B, 3D, 4A, 5A, 6B, 7C), (1C, 2B, 3D, 4A, 5A, 6C, 7A), (1C, 2B, 3D, 4A, 5A, 6C, 7B), (1C, 2B, 3D, 4A, 5A, 6C, 7C), (1C, 2B, 3D, 4A, 5A, 6D, 7A), (1C, 2B, 3D, 4A, 5A, 6D, 7B), (1C, 2B, 3D, 4A, 5A, 6D, 7C), (1C, 2B, 3D, 4A, 5B, 6A, 7A), (1C, 2B, 3D, 4A, 5B, 6A, 7B), (1C, 2B, 3D, 4A, 5B, 6A, 7C), (1C, 2B, 3D, 4A, 5B, 6B, 7A), (1C, 2B, 3D, 4A, 5B, 6B, 7B), (1C, 2B, 3D, 4A, 5B, 6B, 7C), (1C, 2B, 3D, 4A, 5B, 6C, 7A), (1C, 2B, 3D, 4A, 5B, 6C, 7B), (1C, 2B, 3D, 4A, 5B, 6C, 7C), (1C, 2B, 3D, 4A, 5B, 6D, 7A), (1C, 2B, 3D, 4A, 5B, 6D, 7B), (1C, 2B, 3D, 4A, 5B, 6D, 7C), (1C, 2B, 3D, 4B, 5A, 6A, 7A), (1C, 2B, 3D, 4B, 5A, 6A, 7B), (1C, 2B, 3D, 4B, 5A, 6A, 7C), (1C, 2B, 3D, 4B, 5A, 6B, 7A), (1C, 2B, 3D, 4B, 5A, 6B, 7B), (1C, 2B, 3D, 4B, 5A, 6B, 7C), (1C, 2B, 3D, 4B, 5A, 6C, 7A), (1C, 2B, 3D, 4B, 5A, 6C, 7B), (1C, 2B, 3D, 4B, 5A, 6C, 7C), (1C, 2B, 3D, 4B, 5A, 6D, 7A), (1C, 2B, 3D, 4B, 5A, 6D, 7B), (1C, 2B, 3D, 4B, 5A, 6D, 7C), (1C, 2B, 3D, 4B, 5B, 6A, 7A), (1C, 2B, 3D, 4B, 5B, 6A, 7B), (1C, 2B, 3D, 4B, 5B, 6A, 7C), (1C, 2B, 3D, 4B, 5B, 6B, 7A), (1C, 2B, 3D, 4B, 5B, 6B, 7B), (1C, 2B, 3D, 4B, 5B, 6B, 7C), (1C, 2B, 3D, 4B, 5B, 6C, 7A), (1C, 2B, 3D, 4B, 5B, 6C, 7B), (1C, 2B, 3D, 4B, 5B, 6C, 7C), (1C, 2B, 3D, 4B, 5B, 6D, 7A), (1C, 2B, 3D, 4B, 5B, 6D, 7B), (1C, 2B, 3D, 4B, 5B, 6D, 7C), (1C, 2B, 3D, 4C, 5A, 6A, 7A), (1C, 2B, 3D, 4C, 5A, 6A, 7B), (1C, 2B, 3D, 4C, 5A, 6A, 7C), (1C, 2B, 3D, 4C, 5A, 6B, 7A), (1C, 2B, 3D, 4C, 5A, 6B, 7B), (1C, 2B, 3D, 4C, 5A, 6B, 7C), (1C, 2B, 3D, 4C, 5A, 6C, 7A), (1C, 2B, 3D, 4C, 5A, 6C, 7B), (1C, 2B, 3D, 4C, 5A, 6C, 7C), (1C, 2B, 3D, 4C, 5A, 6D, 7A), (1C, 2B, 3D, 4C, 5A, 6D, 7B), (1C, 2B, 3D, 4C, 5A, 6D, 7C), (1C, 2B, 3D, 4C, 5B, 6A, 7A), (1C, 2B, 3D, 4C, 5B, 6A, 7B), (1C, 2B, 3D, 4C, 5B, 6A, 7C), (1C, 2B, 3D, 4C, 5B, 6B, 7A), (1C, 2B, 3D, 4C, 5B, 6B, 7B), (1C, 2B, 3D, 4C, 5B, 6B, 7C), (1C, 2B, 3D, 4C, 5B, 6C, 7A), (C, 2B, 3D, 4C, 5B, 6C, 7B), (1C, 2B, 3D, 4C, 5B, 6C, 7C), (1C, 2B, 3D, 4C, 5B, 6D, 7A), (1C, 2B, 3D, 4C, 5B, 6D, 7B), (1C, 2B, 3D, 4C, 5B, 6D, 7C), (1C, 2B, 3D, 4D, 5A, 6A, 7A), (1C, 2B, 3D, 4D, 5A, 6A, 7B), (1C, 2B, 3D, 4D, 5A, 6A, 7C), (1C, 2B, 3D, 4D, 5A, 6B, 7A), (1C, 2B, 3D, 4D, 5A, 6B, 7B), (1C, 2B, 3D, 4D, 5A, 6B, 7C), (1C, 2B, 3D, 4D, 5A, 6C, 7A), (1C, 2B, 3D, 4D, 5A, 6C, 7B), (1C, 2B, 3D, 4D, 5A, 6C, 7C), (1C, 2B, 3D, 4D, 5A, 6D, 7A), (1C, 2B, 3D, 4D, 5A, 6D, 7B), (1C, 2B, 3D, 4D, 5A, 6D, 7C), (1C, 2B, 3D, 4D, 5B, 6A, 7A), (1C, 2B, 3D, 4D, 5B, 6A, 7B), (1C, 2B, 3D, 4D, 5B, 6A, 7C), (1C, 2B, 3D, 4D, 5B, 6B, 7A), (1C, 2B, 3D, 4D, 5B, 6B, 7B), (1C, 2B, 3D, 4D, 5B, 6B, 7C), (1C, 2B, 3D, 4D, 5B, 6C, 7A), (1C, 2B, 3D, 4D, 5B, 6C, 7C), (1C, 2B, 3D, 4D, 5B, 6C, 7C), (1C, 2B, 3D, 4D, 5B, 6D, 7A), (1C, 2B, 3D, 4D, 5B, 6D, 7B), (1C, 2B, 3D, 4D, 5B, 6D, 7C), (1C, 2B, 3D, 4E, 5A, 6A, 7A), (1C, 2B, 3D, 4E, 5A, 6A, 7B), (1C, 2B, 3D, 4E, 5A, 6A, 7C), (1C, 2B, 3D, 4E, 5A, 6B, 7A), (1C, 2B, 3D, 4E, 5A, 6B, 7B), (1C, 2B, 3D, 4E, 5A, 6B, 7C), (1C, 2B, 3D, 4E, 5A, 6C, 7A), (1C, 2B, 3D, 4E, 5A, 6C, 7B), (1C, 2B, 3D, 4E, 5A, 6C, 7C), (1C, 2B, 3D, 4E, 5A, 6D, 7A), (1C, 2B, 3D, 4E, 5A, 6D, 7B), (1C, 2B, 3D, 4E, 5A, 6D, 7C), (1C, 2B, 3D, 4E, 5B, 6A, 7A), (1C, 2B, 3D, 4E, 5B, 6A, 7B), (1C, 2B, 3D, 4E, 5B, 6A, 7C), (1C, 2B, 3D, 4E, 5B, 6B, 7A), (1C, 2B, 3D, 4E, 5B, 6B, 7B), (1C, 2B, 3D, 4E, 5B, 6B, 7C), (1C, 2B, 3D, 4E, 5B, 6C, 7A), (1C, 2B, 3D, 4E, 5B, 6C, 7B), (1C, 2B, 3D, 4E, 5B, 6C, 7C), (1C, 2B, 3D, 4E, 5B, 6D, 7A), (1C, 2B, 3D, 4E, 5B, 6D, 7B), (1C, 2B, 3D, 4E, 5B, 6D, 7C), (1C, 2B, 3E, 4A, 5A, 6A, 7A), (1C, 2B, 3E, 4A, 5A, 6A, 7B), (1C, 2B, 3E, 4A, 5A, 6A, 7C), (1C, 2B, 3E, 4A, 5A, 6B, 7A), (1C, 2B, 3E, 4A, 5A, 6B, 7B), (1C, 2B, 3E, 4A, 5A, 6B, 7C), (1C, 2B, 3E, 4A, 5A, 6C, 7A), (1C, 2B, 3E, 4A, 5A, 6C, 7B), (1C, 2B, 3E, 4A, 5A, 6C, 7C), (1C, 2B, 3E, 4A, 5A, 6D, 7A), (1C, 2B, 3E, 4A, 5A, 6D, 7B), (1C, 2B, 3E, 4A, 5A, 6D, 7C), (1C, 2B, 3E, 4A, 5B, 6A, 7A), (1C, 2B, 3E, 4A, 5B, 6A, 7B), (1C, 2B, 3E, 4A, 5B, 6A, 7C), (1C, 2B, 3E, 4A, 5B, 6B, 7A), (1C, 2B, 3E, 4A, 5B, 6B, 7B), (1C, 2B, 3E, 4A, 5B, 6B, 7C), (1C, 2B, 3E, 4A, 5B, 6C, 7A), (1C, 2B, 3E, 4A, 5B, 6C, 7B), (1C, 2B, 3E, 4A, 5B, 6C, 7C), (1C, 2B, 3E, 4A, 5B, 6D, 7A), (1C, 2B, 3E, 4A, 5B, 6D, 7B), (1C, 2B, 3E, 4A, 5B, 6D, 7C), (1C, 2B, 3E, 4B, 5A, 6A, 7A), (1C, 2B, 3E, 4B, 5A, 6A, 7B), (1C, 2B, 3E, 4B, 5A, 6A, 7C), (1C, 2B, 3E, 4B, 5A, 6B, 7A), (1C, 2B, 3E, 4B, 5A, 6B, 7B), (1C, 2B, 3E, 4B, 5A, 6B, 7C), (1C, 2B, 3E, 4B, 5A, 6C, 7A), (1C, 2B, 3E, 4B, 5A, 6C, 7B), (1C, 2B, 3E, 4B, 5A, 6C, 7C), (1C, 2B, 3E, 4B, 5A, 6D, 7A), (1C, 2B, 3E, 4B, 5A, 6D, 7B), (1C, 2B, 3E, 4B, 5A, 6D, 7C), (1C, 2B, 3E, 4B, 5B, 6A, 7A), (1C, 2B, 3E, 4B, 5B, 6A, 7B), (1C, 2B, 3E, 4B, 5B, 6A, 7C), (1C, 2B, 3E, 4B, 5B, 6B, 7A), (1C, 2B, 3E, 4B, 5B, 6B, 7B), (1C, 2B, 3E, 4B, 5B, 6B, 7C), (1C, 2B, 3E, 4B, 5B, 6C, 7A), (1C, 2B, 3E, 4B, 5B, 6C, 7B), (1C, 2B, 3E, 4B, 5B, 6C, 7C), (1C, 2B, 3E, 4B, 5B, 6D, 7A), (1C, 2B, 3E, 4B, 5B, 6D, 7B), (1C, 2B, 3E, 4B, 5B, 6D, 7C), (1C, 2B, 3E, 4C, 5A, 6A, 7A), (1C, 2B, 3E, 4C, 5A, 6A, 7B), (1C, 2B, 3E, 4C, 5A, 6A, 7C), (1C, 2B, 3E, 4C, 5A, 6B, 7A), (1C, 2B, 3E, 4C, 5A, 6B, 7B), (1C, 2B, 3E, 4C, 5A, 6B, 7C), (1C, 2B, 3E, 4C, 5A, 6C, 7A), (1C, 2B, 3E, 4C, 5A, 6C, 7B), (1C, 2B, 3E, 4C, 5A, 6C, 7C), (1C, 2B, 3E, 4C, 5A, 6D, 7A), (1C, 2B, 3E, 4C, 5A, 6D, 7B), (1C, 2B, 3E, 4C, 5A, 6D, 7C), (1C, 2B, 3E, 4C, 5B, 6A, 7A), (1C, 2B, 3E, 4C, 5B, 6A, 7B), (1C, 2B, 3E, 4C, 5B, 6A, 7C), (1C, 2B, 3E, 4C, 5B, 6B, 7A), (1C, 2B, 3E, 4C, 5B, 6B, 7B), (1C, 2B, 3E, 4C, 5B, 6B, 7C), (1C, 2B, 3E, 4C, 5B, 6C, 7A), (1C, 2B, 3E, 4C, 5B, 6C, 7B), (1C, 2B, 3E, 4C, 5B, 6C, 7C), (1C, 2B, 3E, 4C, 5B, 6D, 7A), (1C, 2B, 3E, 4C, 5B, 6D, 7B), (1C, 2B, 3E, 4C, 5B, 6D, 7C), (1C, 2B, 3E, 4D, 5A, 6A, 7A), (1C, 2B, 3E, 4D, 5A, 6A, 7B), (1C, 2B, 3E, 4D, 5A, 6A, 7C), (1C, 2B, 3E, 4D, 5A, 6B, 7A), (1C, 2B, 3E, 4D, 5A, 6B, 7B), (1C, 2B, 3E, 4D, 5A, 6B, 7C), (1C, 2B, 3E, 4D, 5A, 6C, 7A), (1C, 2B, 3E, 4D, 5A, 6C, 7B), (1C, 2B, 3E, 4D, 5A, 6C, 7C), (C, 2B, 3E, 4D, 5A, 6D, 7A), (1C, 2B, 3E, 4D, 5A, 6D, 7B), (1C, 2B, 3E, 4D, 5A, 6D, 7C), (1C, 2B, 3E, 4D, 5B, 6A, 7A), (1C, 2B, 3E, 4D, 5B, 6A, 7B), (1C, 2B, 3E, 4D, 5B, 6A, 7C), (1C, 2B, 3E, 4D, 5B, 6B, 7A), (1C, 2B, 3E, 4D, 5B, 6B, 7B), (1C, 2B, 3E, 4D, 5B, 6B, 7C), (1C, 2B, 3E, 4D, 5B, 6C, 7A), (1C, 2B, 3E, 4D, 5B, 6C, 7B), (1C, 2B, 3E, 4D, 5B, 6C, 7C), (1C, 2B, 3E, 4D, 5B, 6D, 7A), (1C, 2B, 3E, 4D, 5B, 6D, 7B), (1C, 2B, 3E, 4D, 5B, 6D, 7C), (1C, 2B, 3E, 4E, 5A, 6A, 7A), (1C, 2B, 3E, 4E, 5A, 6A, 7B), (1C, 2B, 3E, 4E, 5A, 6A, 7C), (1C, 2B, 3E, 4E, 5A, 6B, 7A), (1C, 2B, 3E, 4E, 5A, 6B, 7B), (1C, 2B, 3E, 4E, 5A, 6B, 7C), (1C, 2B, 3E, 4E, 5A, 6C, 7A), (1C, 2B, 3E, 4E, 5A, 6C, 7B), (1C, 2B, 3E, 4E, 5A, 6C, 7C), (1C, 2B, 3E, 4E, 5A, 6D, 7A), (1C, 2B, 3E, 4E, 5A, 6D, 7B), (1C, 2B, 3E, 4E, 5A, 6D, 7C), (1C, 2B, 3E, 4E, 5B, 6A, 7A), (1C, 2B, 3E, 4E, 5B, 6A, 7B), (1C, 2B, 3E, 4E, 5B, 6A, 7C), (1C, 2B, 3E, 4E, 5B, 6B, 7A), (1C, 2B, 3E, 4E, 5B, 6B, 7B), (1C, 2B, 3E, 4E, 5B, 6B, 7C), (1C, 2B, 3E, 4E, 5B, 6C, 7A), (1C, 2B, 3E, 4E, 5B, 6C, 7B), (1C, 2B, 3E, 4E, 5B, 6C, 7C), (1C, 2B, 3E, 4E, 5B, 6D, 7A), (1C, 2B, 3E, 4E, 5B, 6C, 7B), (1C, 2B, 3E, 4E, 5B, 6D, 7C), (1C, 2C, 3A, 4A, 5A, 6A, 7A), (1C, 2C, 3A, 4A, 5A, 6A, 7B), (1C, 2C, 3A, 4A, 5A, 6A, 7C), (1C, 2C, 3A, 4A, 5A, 6B, 7A), (1C, 2C, 3A, 4A, 5A, 6B, 7B), (1C, 2C, 3A, 4A, 5A, 6B, 7C), (1C, 2C, 3A, 4A, 5A, 6C, 7A), (1C, 2C, 3A, 4A, 5A, 6C, 7B), (1C, 2C, 3A, 4A, 5A, 6C, 7C), (1C, 2C, 3A, 4A, 5A, 6D, 7A), (1C, 2C, 3A, 4A, 5A, 6D, 7B), (1C, 2C, 3A, 4A, 5A, 6D, 7C), (1C, 2C, 3A, 4A, 5B, 6A, 7A), (1C, 2C, 3A, 4A, 5B, 6A, 7B), (1C, 2C, 3A, 4A, 5B, 6A, 7C), (1C, 2C, 3A, 4A, 5B, 6B, 7A), (1C, 2C, 3A, 4A, 5B, 6B, 7B), (1C, 2C, 3A, 4A, 5B, 6B, 7C), (1C, 2C, 3A, 4A, 5B, 6C, 7A), (1C, 2C, 3A, 4A, 5B, 6C, 7B), (1C, 2C, 3A, 4A, 5B, 6C, 7C), (1C, 2C, 3A, 4A, 5B, 6D, 7A), (1C, 2C, 3A, 4A, 5B, 6D, 7B), (1C, 2C, 3A, 4A, 5B, 6D, 7C), (1C, 2C, 3A, 4B, 5A, 6A, 7A), (1C, 2C, 3A, 4B, 5A, 6A, 7B), (1C, 2C, 3A, 4B, 5A, 6A, 7C), (1C, 2C, 3A, 4B, 5A, 6B, 7A), (1C, 2C, 3A, 4B, 5A, 6B, 7B), (1C, 2C, 3A, 4B, 5A, 6B, 7C), (1C, 2C, 3A, 4B, 5A, 6C, 7A), (1C, 2C, 3A, 4B, 5A, 6C, 7B), (1C, 2C, 3A, 4B, 5A, 6C, 7C), (1C, 2C, 3A, 4B, 5A, 6D, 7A), (1C, 2C, 3A, 4B, 5A, 6D, 7B), (1C, 2C, 3A, 4B, 5A, 6D, 7C), (1C, 2C, 3A, 4B, 5B, 6A, 7A), (1C, 2C, 3A, 4B, 5B, 6A, 7B), (1C, 2C, 3A, 4B, 5B, 6A, 7C), (1C, 2C, 3A, 4B, 5B, 6B, 7A), (1C, 2C, 3A, 4B, 5B, 6B, 7B), (1C, 2C, 3A, 4B, 5B, 6B, 7C), (1C, 2C, 3A, 4B, 5B, 6C, 7A), (1C, 2C, 3A, 4B, 5B, 6C, 7B), (1C, 2C, 3A, 4B, 5B, 6C, 7C), (1C, 2C, 3A, 4B, 5B, 6D, 7A), (1C, 2C, 3A, 4B, 5B, 6D, 7B), (1C, 2C, 3A, 4B, 5B, 6D, 7C), (1C, 2C, 3A, 4C, 5A, 6A, 7A), (1C, 2C, 3A, 4C, 5A, 6A, 7B), (1C, 2C, 3A, 4C, 5A, 6A, 7C), (1C, 2C, 3A, 4C, 5A, 6B, 7A), (1C, 2C, 3A, 4C, 5A, 6B, 7B), (1C, 2C, 3A, 4C, 5A, 6B, 7C), (1C, 2C, 3A, 4C, 5A, 6C, 7A), (1C, 2C, 3A, 4C, 5A, 6C, 7B), (1C, 2C, 3A, 4C, 5A, 6C, 7C), (1C, 2C, 3A, 4C, 5A, 6D, 7A), (1C, 2C, 3A, 4C, 5A, 6D, 7B), (1C, 2C, 3A, 4C, 5A, 6D, 7C), (1C, 2C, 3A, 4C, 5B, 6A, 7A), (1C, 2C, 3A, 4C, 5B, 6A, 7B), (1C, 2C, 3A, 4C, 5B, 6A, 7C), (1C, 2C, 3A, 4C, 5B, 6B, 7A), (1C, 2C, 3A, 4C, 5B, 6B, 7B), (1C, 2C, 3A, 4C, 5B, 6C, 7A), (1C, 2C, 3A, 4C, 5B, 6C, 7B), (1C, 2C, 3A, 4C, 5B, 6C, 7C), (1C, 2C, 3A, 4C, 5B, 6D, 7A), (1C, 2C, 3A, 4C, 5B, 6D, 7B), (1C, 2C, 3A, 4D, 5A, 6A, 7A), (1C, 2C, 3A, 4D, 5A, 6A, 7B), (1C, 2C, 3A, 4D, 5A, 6A, 7C), (1C, 2C, 3A, 4D, 5A, 6B, 7A), (1C, 2C, 3A, 4D, 5A, 6B, 7B), (1C, 2C, 3A, 4D, 5A, 6B, 7C), (1C, 2C, 3A, 4D, 5A, 6C, 7A), (1C, 2C, 3A, 4D, 5A, 6C, 7B), (1C, 2C, 3A, 4D, 5A, 6C, 7C), (1C, 2C, 3A, 4D, 5A, 6D, 7A), (1C, 2C, 3A, 4D, 5A, 6D, 7B), (1C, 2C, 3A, 4D, 5A, 6D, 7C), (1C, 2C, 3A, 4D, 5B, 6A, 7A), (1C, 2C, 3A, 4D, 5B, 6A, 7B), (1C, 2C, 3A, 4D, 5B, 6A, 7C), (1C, 2C, 3A, 4D, 5B, 6B, 7A), (1C, 2C, 3A, 4D, 5B, 6B, 7B), (1C, 2C, 3A, 4D, 5B, 6B, 7C), (1C, 2C, 3A, 4D, 5B, 6C, 7A), (1C, 2C, 3A, 4D, 5B, 6C, 7B), (1C, 2C, 3A, 4D, 5B, 6C, 7C), (1C, 2C, 3A, 4D, 5B, 6D, 7A), (1C, 2C, 3A, 4D, 5B, 6D, 7B), (1C, 2C, 3A, 4D, 5B, 6D, 7C), (1C, 2C, 3A, 4E, 5A, 6A, 7A), (1C, 2C, 3A, 4E, 5A, 6A, 7B), (1C, 2C, 3A, 4E, 5A, 6A, 7C), (1C, 2C, 3A, 4E, 5A, 6B, 7A), (1C, 2C, 3A, 4E, 5A, 6B, 7B), (1C, 2C, 3A, 4E, 5A, 6B, 7C), (1C, 2C, 3A, 4E, 5A, 6C, 7A), (1C, 2C, 3A, 4E, 5A, 6C, 7B), (1C, 2C, 3A, 4E, 5A, 6C, 7C), (1C, 2C, 3A, 4E, 5A, 6D, 7A), (1C, 2C, 3A, 4E, 5A, 6D, 7B), (1C, 2C, 3A, 4E, 5A, 6D, 7C), (1C, 2C, 3A, 4E, 5B, 6A, 7A), (1C, 2C, 3A, 4E, 5B, 6A, 7B), (1C, 2C, 3A, 4E, 5B, 6A, 7C), (1C, 2C, 3A, 4E, 5B, 6B, 7A), (1C, 2C, 3A, 4E, 5B, 6B, 7B), (1C, 2C, 3A, 4E, 5B, 6B, 7C), (1C, 2C, 3A, 4E, 5B, 6C, 7A), (1C, 2C, 3A, 4E, 5B, 6C, 7B), (1C, 2C, 3A, 4E, 5B, 6C, 7C), (1C, 2C, 3A, 4E, 5B, 6D, 7A), (1C, 2C, 3A, 4E, 5B, 6D, 7B), (1C, 2C, 3A, 4E, 5B, 6D, 7C), (1C, 2C, 3B, 4A, 5A, 6A, 7A), (1C, 2C, 3B, 4A, 5A, 6A, 7B), (1C, 2C, 3B, 4A, 5A, 6A, 7C), (1C, 2C, 3B, 4A, 5A, 6B, 7A), (1C, 2C, 3B, 4A, 5A, 6B, 7B), (1C, 2C, 3B, 4A, 5A, 6B, 7C), (1C, 2C, 3B, 4A, 5A, 6C, 7A), (1C, 2C, 3B, 4A, 5A, 6C, 7B), (1C, 2C, 3B, 4A, 5A, 6C, 7C), (1C, 2C, 3B, 4A, 5A, 6D, 7A), (1C, 2C, 3B, 4A, 5A, 6D, 7B), (1C, 2C, 3B, 4A, 5A, 6D, 7C), (1C, 2C, 3B, 4A, 5B, 6A, 7A), (1C, 2C, 3B, 4A, 5B, 6A, 7B), (1C, 2C, 3B, 4A, 5B, 6A, 7C), (1C, 2C, 3B, 4A, 5B, 6B, 7A), (1C, 2C, 3B, 4A, 5B, 6B, 7B), (1C, 2C, 3B, 4A, 5B, 6B, 7C), (1C, 2C, 3B, 4A, 5B, 6C, 7A), (1C, 2C, 3B, 4A, 5B, 6C, 7B), (1C, 2C, 3B, 4A, 5B, 6C, 7C), (1C, 2C, 3B, 4A, 5B, 6D, 7A), (1C, 2C, 3B, 4A, 5B, 6D, 7B), (1C, 2C, 3B, 4A, 5B, 6D, 7C), (1C, 2C, 3B, 4B, 5A, 6A, 7A), (1C, 2C, 3B, 4B, 5A, 6A, 7B), (1C, 2C, 3B, 4B, 5A, 6A, 7C), (1C, 2C, 3B, 4B, 5A, 6B, 7A), (1C, 2C, 3B, 4B, 5A, 6B, 7B), (1C, 2C, 3B, 4B, 5A, 6B, 7C), (1C, 2C, 3B, 4B, 5A, 6C, 7A), (1C, 2C, 3B, 4B, 5A, 6C, 7B), (1C, 2C, 3B, 4B, 5A, 6C, 7C), (1C, 2C, 3B, 4B, 5A, 6D, 7A), (1C, 2C, 3B, 4B, 5A, 6D, 7B), (1C, 2C, 3B, 4B, 5A, 6D, 7C), (1C, 2C, 3B, 4B, 5B, 6A, 7A), (1C, 2C, 3B, 4B, 5B, 6A, 7B), (1C, 2C, 3B, 4B, 5B, 6A, 7C), (1C, 2C, 3B, 4B, 5B, 6B, 7A), (1C, 2C, 3B, 4B, 5B, 6B, 7B), (1C, 2C, 3B, 4B, 5B, 6B, 7C), (1C, 2C, 3B, 4B, 5B, 6C, 7A), (1C, 2C, 3B, 4B, 5B, 6C, 7B), (1C, 2C, 3B, 4B, 5B, 6C, 7C), (1C, 2C, 3B, 4B, 5B, 6D, 7A), (1C, 2C, 3B, 4B, 5B, 6D, 7B), (1C, 2C, 3B, 4B, 5B, 6D, 7C), (1C, 2C, 3B, 4C, 5A, 6A, 7A), (1C, 2C, 3B, 4C, 5A, 6A, 7B), (1C, 2C, 3B, 4C, 5A, 6A, 7C), (1C, 2C, 3B, 4C, 5A, 6B, 7A), (1C, 2C, 3B, 4C, 5A, 6B, 7B), (1C, 2C, 3B, 4C, 5A, 6B, 7C), (1C, 2C, 3B, 4C, 5A, 6C, 7A), (1C, 2C, 3B, 4C, 5A, 6C, 7B), (1C, 2C, 3B, 4C, 5A, 6C, 7C), (1C, 2C, 3B, 4C, 5A, 6D, 7A), (1C, 2C, 3B, 4C, 5A, 6D, 7B), (1C, 2C, 3B, 4C, 5A, 6D, 7C), (1C, 2C, 3B, 4C, 5B, 6A, 7A), (1C, 2C, 3B, 4C, 5B, 6A, 7B), (1C, 2C, 3B, 4C, 5B, 6A, 7C), (1C, 2C, 3B, 4C, 5B, 6B, 7A), (1C, 2C, 3B, 4C, 5B, 6B, 7B), (1C, 2C, 3B, 4C, 5B, 6B, 7C), (1C, 2C, 3B, 4C, 5B, 6C, 7A), (1C, 2C, 3B, 4C, 5B, 6C, 7B), (1C, 2C, 3B, 4C, 5B, 6C, 7C), (1C, 2C, 3B, 4C, 5B, 6D, 7A), (1C, 2C, 3B, 4C, 5B, 6D, 7B), (1C, 2C, 3B, 4C, 5B, 6D, 7C), (1C, 2C, 3B, 4D, 5A, 6A, 7A), (1C, 2C, 3B, 4D, 5A, 6A, 7B), (1C, 2C, 3B, 4D, 5A, 6A, 7C), (1C, 2C, 3B, 4D, 5A, 6B, 7A), (1C, 2C, 3B, 4D, 5A, 6B, 7B), (1C, 2C, 3B, 4D, 5A, 6B, 7C), (1C, 2C, 3B, 4D, 5A, 6C, 7A), (1C, 2C, 3B, 4D, 5A, 6C, 7B), (1C, 2C, 3B, 4D, 5A, 6C, 7C), (1C, 2C, 3B, 4D, 5A, 6D, 7A), (1C, 2C, 3B, 4D, 5A, 6D, 7B), (1C, 2C, 3B, 4D, 5A, 6D, 7C), (1C, 2C, 3B, 4D, 5B, 6A, 7A), (1C, 2C, 3B, 4D, 5B, 6A, 7B), (1C, 2C, 3B, 4D, 5B, 6A, 7C), (1C, 2C, 3B, 4D, 5B, 6B, 7A), (1C, 2C, 3B, 4D, 5B, 6B, 7B), (1C, 2C, 3B, 4D, 5B, 6B, 7C), (1C, 2C, 3B, 4D, 5B, 6C, 7A), (1C, 2C, 3B, 4D, 5B, 6C, 7B), (1C, 2C, 3B, 4D, 5B, 6C, 7C), (1C, 2C, 3B, 4D, 5B, 6D, 7A), (1C, 2C, 3B, 4D, 5B, 6D, 7B), (1C, 2C, 3B, 4D, 5B, 6D, 7C), (1C, 2C, 3B, 4E, 5A, 6A, 7A), (1C, 2C, 3B, 4E, 5A, 6A, 7B), (1C, 2C, 3B, 4E, 5A, 6A, 7C), (1C, 2C, 3B, 4E, 5A, 6B, 7A), (1C, 2C, 3B, 4E, 5A, 6B, 7B), (1C, 2C, 3B, 4E, 5A, 6B, 7C), (1C, 2C, 3B, 4E, 5A, 6C, 7A), (1C, 2C, 3B, 4E, 5A, 6C, 7B), (1C, 2C, 3B, 4E, 5A, 6C, 7C), (1C, 2C, 3B, 4E, 5A, 6D, 7A), (1C, 2C, 3B, 4E, 5A, 6D, 7B), (1C, 2C, 3B, 4E, 5A, 6D, 7C), (1C, 2C, 3B, 4E, 5B, 6A, 7A), (1C, 2C, 3B, 4E, 5B, 6A, 7B), (1C, 2C, 3B, 4E, 5B, 6A, 7C), (1C, 2C, 3B, 4E, 5B, 6B, 7A), (1C, 2C, 3B, 4E, 5B, 6B, 7B), (1C, 2C, 3B, 4E, 5B, 6B, 7C), (1C, 2C, 3B, 4E, 5B, 6C, 7A), (1C, 2C, 3B, 4E, 5B, 6C, 7B), (1C, 2C, 3B, 4E, 5B, 6C, 7C), (1C, 2C, 3B, 4E, 5B, 6D, 7A), (1C, 2C, 3B, 4E, 5B, 6D, 7B), (1C, 2C, 3B, 4E, 5B, 6D, 7C), (1C, 2C, 3C, 4A, 5A, 6A, 7A), (1C, 2C, 3C, 4A, 5A, 6A, 7B), (1C, 2C, 3C, 4A, 5A, 6A, 7C), (1C, 2C, 3C, 4A, 5A, 6B, 7A), (1C, 2C, 3C, 4A, 5A, 6B, 7B), (1C, 2C, 3C, 4A, 5A, 6B, 7C), (1C, 2C, 3C, 4A, 5A, 6C, 7A), (1C, 2C, 3C, 4A, 5A, 6C, 7B), (1C, 2C, 3C, 4A, 5A, 6C, 7C), (1C, 2C, 3C, 4A, 5A, 6D, 7A), (1C, 2C, 3C, 4A, 5A, 6D, 7B), (1C, 2C, 3C, 4A, 5A, 6D, 7C), (1C, 2C, 3C, 4A, 5B, 6A, 7A), (1C, 2C, 3C, 4A, 5B, 6A, 7B), (1C, 2C, 3C, 4A, 5B, 6A, 7C), (1C, 2C, 3C, 4A, 5B, 6B, 7A), (1C, 2C, 3C, 4A, 5B, 6B, 7B), (1C, 2C, 3C, 4A, 5B, 6B, 7C), (1C, 2C, 3C, 4A, 5B, 6C, 7A), (1C, 2C, 3C, 4A, 5B, 6C, 7B), (1C, 2C, 3C, 4A, 5B, 6C, 7C), (1C, 2C, 3C, 4A, 5B, 6D, 7A), (1C, 2C, 3C, 4A, 5B, 6D, 7B), (1C, 2C, 3C, 4A, 5B, 6D, 7C), (1C, 2C, 3C, 4B, 5A, 6A, 7A), (1C, 2C, 3C, 4B, 5A, 6A, 7B), (1C, 2C, 3C, 4B, 5A, 6A, 7C), (1C, 2C, 3C, 4B, 5A, 6B, 7A), (1C, 2C, 3C, 4B, 5A, 6B, 7B), (1C, 2C, 3C, 4B, 5A, 6B, 7C), (1C, 2C, 3C, 4B, 5A, 6C, 7A), (1C, 2C, 3C, 4B, 5A, 6C, 7B), (1C, 2C, 3C, 4B, 5A, 6C, 7C), (1C, 2C, 3C, 4B, 5A, 6D, 7A), (1C, 2C, 3C, 4B, 5A, 6D, 7B), (1C, 2C, 3C, 4B, 5A, 6D, 7C), (1C, 2C, 3C, 4B, 5B, 6A, 7A), (1C, 2C, 3C, 4B, 5B, 6A, 7B), (1C, 2C, 3C, 4B, 5B, 6A, 7C), (1C, 2C, 3C, 4B, 5B, 6B, 7A), (1C, 2C, 3C, 4B, 5B, 6B, 7B), (1C, 2C, 3C, 4B, 5B, 6B, 7C), (1C, 2C, 3C, 4B, 5B, 6C, 7A), (1C, 2C, 3C, 4B, 5B, 6C, 7B), (1C, 2C, 3C, 4B, 5B, 6C, 7C), (1C, 2C, 3C, 4B, 5B, 6D, 7A), (1C, 2C, 3C, 4B, 5B, 6D, 7B), (1C, 2C, 3C, 4B, 5B, 6D, 7C), (1C, 2C, 3C, 4C, 5A, 6A, 7A), (1C, 2C, 3C, 4C, 5A, 6A, 7B), (1C, 2C, 3C, 4C, 5A, 6A, 7C), (1C, 2C, 3C, 4C, 5A, 6B, 7A), (1C, 2C, 3C, 4C, 5A, 6B, 7B), (1C, 2C, 3C, 4C, 5A, 6B, 7C), (1C, 2C, 3C, 4C, 5A, 6C, 7A), (1C, 2C, 3C, 4C, 5A, 6C, 7B), (1C, 2C, 3C, 4C, 5A, 6C, 7C), (1C, 2C, 3C, 4C, 5A, 6D, 7A), (1C, 2C, 3C, 4C, 5A, 6D, 7B), (1C, 2C, 3C, 4C, 5A, 6D, 7C), (1C, 2C, 3C, 4C, 5B, 6A, 7A), (1C, 2C, 3C, 4C, 5B, 6A, 7B), (1C, 2C, 3C, 4C, 5B, 6A, 7C), (1C, 2C, 3C, 4C, 5B, 6B, 7A), (1C, 2C, 3C, 4C, 5B, 6B, 7B), (1C, 2C, 3C, 4C, 5B, 6B, 7C), (1C, 2C, 3C, 4C, 5B, 6C, 7A), (1C, 2C, 3C, 4C, 5B, 6C, 7B), (1C, 2C, 3C, 4C, 5B, 6C, 7C), (1C, 2C, 3C, 4C, 5B, 6D, 7A), (1C, 2C, 3C, 4C, 5B, 6D, 7B), (1C, 2C, 3C, 4C, 5B, 6D, 7C), (1C, 2C, 3C, 4D, 5A, 6A, 7A), (1C, 2C, 3C, 4D, 5A, 6A, 7B), (1C, 2C, 3C, 4D, 5A, 6A, 7C), (1C, 2C, 3C, 4D, 5A, 6B, 7A), (1C, 2C, 3C, 4D, 5A, 6B, 7B), (1C, 2C, 3C, 4D, 5A, 6B, 7C), (1C, 2C, 3C, 4D, 5A, 6C, 7A), (1C, 2C, 3C, 4D, 5A, 6C, 7B), (1C, 2C, 3C, 4D, 5A, 6C, 7C), (1C, 2C, 3C, 4D, 5A, 6D, 7A), (1C, 2C, 3C, 4D, 5A, 6D, 7B), (1C, 2C, 3C, 4D, 5A, 6D, 7C), (1C, 2C, 3C, 4D, 5B, 6A, 7A), (1C, 2C, 3C, 4D, 5B, 6A, 7B), (1C, 2C, 3C, 4D, 5B, 6A, 7C), (1C, 2C, 3C, 4D, 5B, 6B, 7A), (1C, 2C, 3C, 4D, 5B, 6B, 7B), (1C, 2C, 3C, 4D, 5B, 6B, 7C), (1C, 2C, 3C, 4D, 5B, 6C, 7A), (1C, 2C, 3C, 4D, 5B, 6C, 7B), (1C, 2C, 3C, 4D, 5B, 6C, 7C), (1C, 2C, 3C, 4D, 5B, 6D, 7A), (1C, 2C, 3C, 4D, 5B, 6D, 7B), (1C, 2C, 3C, 4D, 5B, 6D, 7C), (1C, 2C, 3C, 4E, 5A, 6A, 7A), (1C, 2C, 3C, 4E, 5A, 6A, 7B), (1C, 2C, 3C, 4E, 5A, 6A, 7C), (1C, 2C, 3C, 4E, 5A, 6B, 7A), (1C, 2C, 3C, 4E, 5A, 6B, 7B), (1C, 2C, 3C, 4E, 5A, 6B, 7C), (1C, 2C, 3C, 4E, 5A, 6C, 7A), (1C, 2C, 3C, 4E, 5A, 6C, 7B), (1C, 2C, 3C, 4E, 5A, 6C, 7C), (1C, 2C, 3C, 4E, 5A, 6D, 7A), (1C, 2C, 3C, 4E, 5A, 6D, 7B), (1C, 2C, 3C, 4E, 5A, 6D, 7C), (1C, 2C, 3C, 4E, 5B, 6A, 7A), (1C, 2C, 3C, 4E, 5B, 6A, 7B), (1C, 2C, 3C, 4E, 5B, 6A, 7C), (1C, 2C, 3C, 4E, 5B, 6B, 7A), (1C, 2C, 3C, 4E, 5B, 6B, 7B), (1C, 2C, 3C, 4E, 5B, 6B, 7C), (1C, 2C, 3C, 4E, 5B, 6C, 7A), (1C, 2C, 3C, 4E, 5B, 6C, 7B), (1C, 2C, 3C, 4E, 5B, 6C, 7C), (1C, 2C, 3C, 4E, 5B, 6D, 7A), (1C, 2C, 3C, 4E, 5B, 6D, 7B), (1C, 2C, 3C, 4E, 5B, 6D, 7C), (1C, 2C, 3D, 4A, 5A, 6A, 7A), (1C, 2C, 3D, 4A, 5A, 6A, 7B), (1C, 2C, 3D, 4A, 5A, 6A, 7C), (1C, 2C, 3D, 4A, 5A, 6B, 7A), (1C, 2C, 3D, 4A, 5A, 6B, 7B), (1C, 2C, 3D, 4A, 5A, 6B, 7C), (1C, 2C, 3D, 4A, 5A, 6C, 7A), (1C, 2C, 3D, 4A, 5A, 6C, 7B), (1C, 2C, 3D, 4A, 5A, 6C, 7C), (1C, 2C, 3D, 4A, 5A, 6D, 7A), (1C, 2C, 3D, 4A, 5A, 6D, 7B), (1C, 2C, 3D, 4A, 5A, 6D, 7C), (1C, 2C, 3D, 4A, 5B, 6A, 7A), (1C, 2C, 3D, 4A, 5B, 6A, 7B), (1C, 2C, 3D, 4A, 5B, 6A, 7C), (1C, 2C, 3D, 4A, 5B, 6B, 7A), (1C, 2C, 3D, 4A, 5B, 6B, 7B), (1C, 2C, 3D, 4A, 5B, 6B, 7C), (1C, 2C, 3D, 4A, 5B, 6C, 7A), (1C, 2C, 3D, 4A, 5B, 6C, 7B), (1C, 2C, 3D, 4A, 5B, 6C, 7C), (1C, 2C, 3D, 4A, 5B, 6D, 7A), (1C, 2C, 3D, 4A, 5B, 6D, 7B), (1C, 2C, 3D, 4A, 5B, 6D, 7C), (1C, 2C, 3D, 4B, 5A, 6A, 7A), (1C, 2C, 3D, 4B, 5A, 6A, 7B), (1C, 2C, 3D, 4B, 5A, 6A, 7C), (1C, 2C, 3D, 4B, 5A, 6B, 7A), (1C, 2C, 3D, 4B, 5A, 6B, 7B), (1C, 2C, 3D, 4B, 5A, 6B, 7C), (1C, 2C, 3D, 4B, 5A, 6C, 7A), (1C, 2C, 3D, 4B, 5A, 6C, 7B), (1C, 2C, 3D, 4B, 5A, 6C, 7C), (1C, 2C, 3D, 4B, 5A, 6D, 7A), (1C, 2C, 3D, 4B, 5A, 6D, 7B), (1C, 2C, 3D, 4B, 5A, 6D, 7C), (1C, 2C, 3D, 4B, 5B, 6A, 7A), (1C, 2C, 3D, 4B, 5B, 6A, 7B), (1C, 2C, 3D, 4B, 5B, 6A, 7C), (1C, 2C, 3D, 4B, 5B, 6B, 7A), (1C, 2C, 3D, 4B, 5B, 6B, 7B), (1C, 2C, 3D, 4B, 5B, 6B, 7C), (1C, 2C, 3D, 4B, 5B, 6C, 7A), (1C, 2C, 3D, 4B, 5B, 6C, 7B), (1C, 2C, 3D, 4B, 5B, 6C, 7C), (1C, 2C, 3D, 4B, 5B, 6D, 7A), (1C, 2C, 3D, 4B, 5B, 6D, 7B), (1C, 2C, 3D, 4B, 5B, 6D, 7C), (1C, 2C, 3D, 4C, 5A, 6A, 7A), (1C, 2C, 3D, 4C, 5A, 6A, 7B), (1C, 2C, 3D, 4C, 5A, 6A, 7C), (1C, 2C, 3D, 4C, 5A, 6B, 7A), (1C, 2C, 3D, 4C, 5A, 6B, 7B), (1C, 2C, 3D, 4C, 5A, 6B, 7C), (1C, 2C, 3D, 4C, 5A, 6C, 7A), (1C, 2C, 3D, 4C, 5A, 6C, 7B), (1C, 2C, 3D, 4C, 5A, 6C, 7C), (1C, 2C, 3D, 4C, 5A, 6D, 7A), (1C, 2C, 3D, 4C, 5A, 6D, 7B), (1C, 2C, 3D, 4C, 5A, 6D, 7C), (1C, 2C, 3D, 4C, 5B, 6A, 7A), (1C, 2C, 3D, 4C, 5B, 6A, 7B), (1C, 2C, 3D, 4C, 5B, 6A, 7C), (1C, 2C, 3D, 4C, 5B, 6B, 7A), (1C, 2C, 3D, 4C, 5B, 6B, 7B), (1C, 2C, 3D, 4C, 5B, 6B, 7C), (1C, 2C, 3D, 4C, 5B, 6C, 7A), (1C, 2C, 3D, 4C, 5B, 6C, 7B), (1C, 2C, 3D, 4C, 5B, 6C, 7C), (1C, 2C, 3D, 4C, 5B, 6D, 7A), (1C, 2C, 3D, 4C, 5B, 6D, 7B), (1C, 2C, 3D, 4C, 5B, 6D, 7C), (1C, 2C, 3D, 4D, 5A, 6A, 7A), (1C, 2C, 3D, 4D, 5A, 6A, 7B), (1C, 2C, 3D, 4D, 5A, 6A, 7C), (1C, 2C, 3D, 4D, 5A, 6B, 7A), (1C, 2C, 3D, 4D, 5A, 6B, 7B), (1C, 2C, 3D, 4D, 5A, 6B, 7C), (1C, 2C, 3D, 4D, 5A, 6C, 7A), (1C, 2C, 3D, 4D, 5A, 6C, 7B), (1C, 2C, 3D, 4D, 5A, 6C, 7C), (1C, 2C, 3D, 4D, 5A, 6D, 7A), (1C, 2C, 3D, 4D, 5A, 6D, 7B), (1C, 2C, 3D, 4D, 5A, 6D, 7C), (1C, 2C, 3D, 4D, 5B, 6A, 7A), (1C, 2C, 3D, 4D, 5B, 6A, 7B), (1C, 2C, 3D, 4D, 5B, 6A, 7C), (1C, 2C, 3D, 4D, 5B, 6B, 7A), (1C, 2C, 3D, 4D, 5B, 6B, 7B), (1C, 2C, 3D, 4D, 5B, 6B, 7C), (1C, 2C, 3D, 4D, 5B, 6C, 7A), (1C, 2C, 3D, 4D, 5B, 6C, 7B), (1C, 2C, 3D, 4D, 5B, 6C, 7C), (1C, 2C, 3D, 4D, 5B, 6D, 7A), (1C, 2C, 3D, 4D, 5B, 6D, 7B), (1C, 2C, 3D, 4D, 5B, 6D, 7C), (1C, 2C, 3D, 4E, 5A, 6A, 7A), (1C, 2C, 3D, 4E, 5A, 6A, 7B), (1C, 2C, 3D, 4E, 5A, 6A, 7C), (1C, 2C, 3D, 4E, 5A, 6B, 7A), (1C, 2C, 3D, 4E, 5A, 6B, 7B), (1C, 2C, 3D, 4E, 5A, 6B, 7C), (1C, 2C, 3D, 4E, 5A, 6C, 7A), (1C, 2C, 3D, 4E, 5A, 6C, 7B), (1C, 2C, 3D, 4E, 5A, 6C, 7C), (1C, 2C, 3D, 4E, 5A, 6D, 7A), (1C, 2C, 3D, 4E, 5A, 6D, 7B), (1C, 2C, 3D, 4E, 5A, 6D, 7C), (1C, 2C, 3D, 4E, 5B, 6A, 7A), (1C, 2C, 3D, 4E, 5B, 6A, 7B), (1C, 2C, 3D, 4E, 5B, 6A, 7C), (1C, 2C, 3D, 4E, 5B, 6B, 7A), (1C, 2C, 3D, 4E, 5B, 6B, 7B), (1C, 2C, 3D, 4E, 5B, 6B, 7C), (1C, 2C, 3D, 4E, 5B, 6C, 7A), (1C, 2C, 3D, 4E, 5B, 6C, 7B), (1C, 2C, 3D, 4E, 5B, 6C, 7C), (1C, 2C, 3D, 4E, 5B, 6D, 7A), (1C, 2C, 3D, 4E, 5B, 6D, 7B), (1C, 2C, 3D, 4E, 5B, 6D, 7C), (1C, 2C, 3E, 4A, 5A, 6A, 7A), (1C, 2C, 3E, 4A, 5A, 6A, 7B), (1C, 2C, 3E, 4A, 5A, 6A, 7C), (1C, 2C, 3E, 4A, 5A, 6B, 7A), (1C, 2C, 3E, 4A, 5A, 6B, 7B), (1C, 2C, 3E, 4A, 5A, 6B, 7C), (1C, 2C, 3E, 4A, 5A, 6C, 7A), (1C, 2C, 3E, 4A, 5A, 6C, 7B), (1C, 2C, 3E, 4A, 5A, 6C, 7C), (1C, 2C, 3E, 4A, 5A, 6D, 7A), (1C, 2C, 3E, 4A, 5A, 6D, 7B), (1C, 2C, 3E, 4A, 5A, 6D, 7C), (1C, 2C, 3E, 4A, 5B, 6A, 7A), (1C, 2C, 3E, 4A, 5B, 6A, 7B), (1C, 2C, 3E, 4A, 5B, 6A, 7C), (1C, 2C, 3E, 4A, 5B, 6B, 7A), (1C, 2C, 3E, 4A, 5B, 6B, 7B), (1C, 2C, 3E, 4A, 5B, 6B, 7C), (1C, 2C, 3E, 4A, 5B, 6C, 7A), (1C, 2C, 3E, 4A, 5B, 6C, 7B), (1C, 2C, 3E, 4A, 5B, 6C, 7C), (1C, 2C, 3E, 4A, 5B, 6D, 7A), (1C, 2C, 3E, 4A, 5B, 6D, 7B), (1C, 2C, 3E, 4A, 5B, 6D, 7C), (1C, 2C, 3E, 4B, 5A, 6A, 7A), (1C, 2C, 3E, 4B, 5A, 6A, 7B), (1C, 2C, 3E, 4B, 5A, 6A, 7C), (1C, 2C, 3E, 4B, 5A, 6B, 7A), (1C, 2C, 3E, 4B, 5A, 6B, 7B), (1C, 2C, 3E, 4B, 5A, 6B, 7C), (1C, 2C, 3E, 4B, 5A, 6C, 7A), (1C, 2C, 3E, 4B, 5A, 6C, 7B), (1C, 2C, 3E, 4B, 5A, 6C, 7C), (1C, 2C, 3E, 4B, 5A, 6D, 7A), (1C, 2C, 3E, 4B, 5A, 6D, 7B), (1C, 2C, 3E, 4B, 5A, 6D, 7C), (1C, 2C, 3E, 4B, 5B, 6A, 7A), (1C, 2C, 3E, 4B, 5B, 6A, 7B), (1C, 2C, 3E, 4B, 5B, 6A, 7C), (1C, 2C, 3E, 4B, 5B, 6B, 7A), (1C, 2C, 3E, 4B, 5B, 6B, 7B), (1C, 2C, 3E, 4B, 5B, 6B, 7C), (1C, 2C, 3E, 4B, 5B, 6C, 7A), (1C, 2C, 3E, 4B, 5B, 6C, 7B), (1C, 2C, 3E, 4B, 5B, 6C, 7C), (1C, 2C, 3E, 4B, 5B, 6D, 7A), (1C, 2C, 3E, 4B, 5B, 6D, 7B), (1C, 2C, 3E, 4B, 5B, 6D, 7C), (1C, 2C, 3E, 4C, 5A, 6A, 7A), (1C, 2C, 3E, 4C, 5A, 6A, 7B), (1C, 2C, 3E, 4C, 5A, 6A, 7C), (1C, 2C, 3E, 4C, 5A, 6B, 7A), (1C, 2C, 3E, 4C, 5A, 6B, 7B), (1C, 2C, 3E, 4C, 5A, 6B, 7C), (1C, 2C, 3E, 4C, 5A, 6C, 7A), (1C, 2C, 3E, 4C, 5A, 6C, 7B), (1C, 2C, 3E, 4C, 5A, 6C, 7C), (1C, 2C, 3E, 4C, 5A, 6D, 7A), (1C, 2C, 3E, 4C, 5A, 6D, 7B), (1C, 2C, 3E, 4C, 5A, 6D, 7C), (1C, 2C, 3E, 4C, 5B, 6A, 7A), (1C, 2C, 3E, 4C, 5B, 6A, 7B), (1C, 2C, 3E, 4C, 5B, 6A, 7C), (1C, 2C, 3E, 4C, 5B, 6B, 7A), (1C, 2C, 3E, 4C, 5B, 6B, 7B), (1C, 2C, 3E, 4C, 5B, 6B, 7C), (1C, 2C, 3E, 4C, 5B, 6C, 7A), (1C, 2C, 3E, 4C, 5B, 6C, 7B), (1C, 2C, 3E, 4C, 5B, 6C, 7C), (1C, 2C, 3E, 4C, 5B, 6D, 7A), (1C, 2C, 3E, 4C, 5B, 6D, 7B), (1C, 2C, 3E, 4C, 5B, 6D, 7C), (1C, 2C, 3E, 4D, 5A, 6A, 7A), (1C, 2C, 3E, 4D, 5A, 6A, 7B), (1C, 2C, 3E, 4D, 5A, 6A, 7C), (1C, 2C, 3E, 4D, 5A, 6B, 7A), (1C, 2C, 3E, 4D, 5A, 6B, 7B), (1C, 2C, 3E, 4D, 5A, 6B, 7C), (1C, 2C, 3E, 4D, 5A, 6C, 7A), (1C, 2C, 3E, 4D, 5A, 6C, 7B), (1C, 2C, 3E, 4D, 5A, 6C, 7C), (1C, 2C, 3E, 4D, 5A, 6D, 7A), (1C, 2C, 3E, 4D, 5A, 6D, 7B), (1C, 2C, 3E, 4D, 5A, 6D, 7C), (1C, 2C, 3E, 4D, 5B, 6A, 7A), (1C, 2C, 3E, 4D, 5B, 6A, 7B), (1C, 2C, 3E, 4D, 5B, 6A, 7C), (1C, 2C, 3E, 4D, 5B, 6B, 7A), (1C, 2C, 3E, 4D, 5B, 6B, 7B), (1C, 2C, 3E, 4D, 5B, 6B, 7C), (1C, 2C, 3E, 4D, 5B, 6C, 7A), (1C, 2C, 3E, 4D, 5B, 6C, 7B), (1C, 2C, 3E, 4D, 5B, 6C, 7C), (1C, 2C, 3E, 4D, 5B, 6D, 7A), (1C, 2C, 3E, 4D, 5B, 6D, 7B), (1C, 2C, 3E, 4D, 5B, 6D, 7C), (1C, 2C, 3E, 4E, 5A, 6A, 7A), (1C, 2C, 3E, 4E, 5A, 6A, 7B), (1C, 2C, 3E, 4E, 5A, 6A, 7C), (1C, 2C, 3E, 4E, 5A, 6B, 7A), (1C, 2C, 3E, 4E, 5A, 6B, 7B), (1C, 2C, 3E, 4E, 5A, 6B, 7C), (1C, 2C, 3E, 4E, 5A, 6C, 7A), (1C, 2C, 3E, 4E, 5A, 6C, 7B), (1C, 2C, 3E, 4E, 5A, 6C, 7C), (1C, 2C, 3E, 4E, 5A, 6D, 7A), (1C, 2C, 3E, 4E, 5A, 6D, 7B), (1C, 2C, 3E, 4E, 5A, 6D, 7C), (1C, 2C, 3E, 4E, 5B, 6A, 7A), (1C, 2C, 3E, 4E, 5B, 6A, 7B), (1C, 2C, 3E, 4E, 5B, 6A, 7C), (1C, 2C, 3E, 4E, 5B, 6B, 7A), (1C, 2C, 3E, 4E, 5B, 6B, 7B), (1C, 2C, 3E, 4E, 5B, 6B, 7C), (1C, 2C, 3E, 4E, 5B, 6C, 7A), (1C, 2C, 3E, 4E, 5B, 6C, 7B), (1C, 2C, 3E, 4E, 5B, 6C, 7C), (1C, 2C, 3E, 4E, 5B, 6D, 7A), (1C, 2C, 3E, 4E, 5B, 6D, 7B), (1C, 2C, 3E, 4E, 5B, 6D, 7C), (1C, 2D, 3A, 4A, 5A, 6A, 7A), (1C, 2D, 3A, 4A, 5A, 6A, 7B), (1C, 2D, 3A, 4A, 5A, 6A, 7C). (1C, 2D, 3A, 4A, 5A, 6B, 7A), (1C, 2D, 3A, 4A, 5A, 6B, 7B), (1C, 2D, 3A, 4A, 5A, 6B, 7C), (1C, 2D, 3A, 4A, 5A, 6C, 7A), (1C, 2D, 3A, 4A, 5A, 6C, 7B), (1C, 2D, 3A, 4A, 5A, 6C, 7C), (1C, 2D, 3A, 4A, 5A, 6D, 7A), (1C, 2D, 3A, 4A, 5A, 6D, 7B), (1C, 2D, 3A, 4A, 5A, 6D, 7C), (1C, 2D, 3A, 4A, 5B, 6A, 7A), (1C, 2D, 3A, 4A, 5B, 6A, 7B), (1C, 2D, 3A, 4A, 5B, 6A, 7C), (1C, 2D, 3A, 4A, 5B, 6B, 7A), (1C, 2D, 3A, 4A, 5B, 6B, 7B), (1C, 2D, 3A, 4A, 5B, 6B, 7C), (1C, 2D, 3A, 4A, 5B, 6C, 7A), (1C, 2D, 3A, 4A, 5B, 6C, 7B), (1C, 2D, 3A, 4A, 5B, 6C, 7C), (1C, 2D, 3A, 4A, 5B, 6D, 7A), (1C, 2D, 3A, 4A, 5B, 6D, 7B), (1C, 2D, 3A, 4A, 5B, 6D, 7C), (1C, 2D, 3A, 4B, 5A, 6A, 7A), (1C, 2D, 3A, 4B, 5A, 6A, 7B), (1C, 2D, 3A, 4B, 5A, 6A, 7C), (1C, 2D, 3A, 4B, 5A, 6B, 7A), (1C, 2D, 3A, 4B, 5A, 6B, 7B), (1C, 2D, 3A, 4B, 5A, 6B, 7C), (1C, 2D, 3A, 4B, 5A, 6C, 7A), (1C, 2D, 3A, 4B, 5A, 6C, 7B), (1C, 2D, 3A, 4B, 5A, 6C, 7C), (1C, 2D, 3A, 4B, 5A, 6D, 7A), (1C, 2D, 3A, 4B, 5A, 6D, 7B), (1C, 2D, 3A, 4B, 5A, 6D, 7C), (1C, 2D, 3A, 4B, 5B, 6A, 7A), (1C, 2D, 3A, 4B, 5B, 6A, 7B), (1C, 2D, 3A, 4B, 5B, 6A, 7C), (1C, 2D, 3A, 4B, 5B, 6B, 7A), (1C, 2D, 3A, 4B, 5B, 6B, 7B), (1C, 2D, 3A, 4B, 5B, 6B, 7C), (1C, 2D, 3A, 4B, 5B, 6C, 7A), (1C, 2D, 3A, 4B, 5B, 6C, 7B), (1C, 2D, 3A, 4B, 5B, 6C, 7C), (1C, 2D, 3A, 4B, 5B, 6D, 7A), (1C, 2D, 3A, 4B, 5B, 6D, 7B), (1C, 2D, 3A, 4B, 5B, 6D, 7C), (1C, 2D, 3A, 4C, 5A, 6A, 7A), (1C, 2D, 3A, 4C, 5A, 6A, 7B), (1C, 2D, 3A, 4C, 5A, 6A, 7C), (1C, 2D, 3A, 4C, 5A, 6B, 7A), (1C, 2D, 3A, 4C, 5A, 6B, 7B), (1C, 2D, 3A, 4C, 5A, 6B, 7C), (1C, 2D, 3A, 4C, 5A, 6C, 7A), (1C, 2D, 3A, 4C, 5A, 6C, 7B), (1C, 2D, 3A, 4C, 5A, 6C, 7C), (1C, 2D, 3A, 4C, 5A, 6D, 7A), (1C, 2D, 3A, 4C, 5A, 6D, 7B), (1C, 2D, 3A, 4C, 5A, 6D, 7C), (1C, 2D, 3A, 4C, 5B, 6A, 7A), (1C, 2D, 3A, 4C, 5B, 6A, 7B), (1C, 2D, 3A, 4C, 5B, 6A, 7C), (1C, 2D, 3A, 4C, 5B, 6B, 7A), (1C, 2D, 3A, 4C, 5B, 6B, 7B), (1C, 2D, 3A, 4C, 5B, 6B, 7C), (1C, 2D, 3A, 4C, 5B, 6C, 7A), (1C, 2D, 3A, 4C, 5B, 6C, 7B), (1C, 2D, 3A, 4C, 5B, 6C, 7C), (1C, 2D, 3A, 4C, 5B, 6D, 7A), (1C, 2D, 3A, 4C, 5B, 6D, 7B), (1C, 2D, 3A, 4C, 5B, 6D, 7C), (1C, 2D, 3A, 4D, 5A, 6A, 7A), (1C, 2D, 3A, 4D, 5A, 6A, 7B), (1C, 2D, 3A, 4D, 5A, 6A, 7C), (1C, 2D, 3A, 4D, 5A, 6B, 7A), (1C, 2D, 3A, 4D, 5A, 6B, 7B), (1C, 2D, 3A, 4D, 5A, 6B, 7C), (1C, 2D, 3A, 4D, 5A, 6C, 7A), (1C, 2D, 3A, 4D, 5A, 6C, 7B), (1C, 2D, 3A, 4D, 5A, 6C, 7C), (1C, 2D, 3A, 4D, 5A, 6D, 7A), (1C, 2D, 3A, 4D, 5A, 6D, 7B), (1C, 2D, 3A, 4D, 5A, 6D, 7C), (1C, 2D, 3A, 4D, 5B, 6A, 7A), (1C, 2D, 3A, 4D, 5B, 6A, 7B), (1C, 2D, 3A, 4D, 5B, 6A, 7C), (1C, 2D, 3A, 4D, 5B, 6B, 7A), (1C, 2D, 3A, 4D, 5B, 6B, 7B), (1C, 2D, 3A, 4D, 5B, 6B, 7C), (1C, 2D, 3A, 4D, 5B, 6C, 7A), (1C, 2D, 3A, 4D, 5B, 6C, 7B), (1C, 2D, 3A, 4D, 5B, 6C, 7C), (1C, 2D, 3A, 4D, 5B, 6D, 7A), (1C, 2D, 3A, 4D, 5B, 6D, 7B), (1C, 2D, 3A, 4D, 5B, 6D, 7C), (1C, 2D, 3A, 4E, 5A, 6A, 7A), (1C, 2D, 3A, 4E, 5A, 6A, 7B), (1C, 2D, 3A, 4E, 5A, 6A, 7C), (1C, 2D, 3A, 4E, 5A, 6B, 7A), (1C, 2D, 3A, 4E, 5A, 6B, 7B), (1C, 2D, 3A, 4E, 5A, 6B, 7C), (1C, 2D, 3A, 4E, 5A, 6C, 7A), (1C, 2D, 3A, 4E, 5A, 6C, 7B), (1C, 2D, 3A, 4E, 5A, 6C, 7C), (1C, 2D, 3A, 4E, 5A, 6D, 7A), (1C, 2D, 3A, 4E, 5A, 6D, 7B), (1C, 2D, 3A, 4E, 5A, 6D, 7C), (1C, 2D, 3A, 4E, 5B, 6A, 7A), (1C, 2D, 3A, 4E, 5B, 6A, 7B), (1C, 2D, 3A, 4E, 5B, 6A, 7C), (1C, 2D, 3A, 4E, 5B, 6B, 7A), (1C, 2D, 3A, 4E, 5B, 6B, 7B), (1C, 2D, 3A, 4E, 5B, 6B, 7C), (1C, 2D, 3A, 4E, 5B, 6C, 7A), (1C, 2D, 3A, 4E, 5B, 6C, 7B), (1C, 2D, 3A, 4E, 5B, 6C, 7C), (1C, 2D, 3A, 4E, 5B, 6D, 7A), (1C, 2D, 3A, 4E, 5B, 6D, 7B), (1C, 2D, 3A, 4E, 5B, 6D, 7C), (1C, 2D, 3B, 4A, 5A, 6A, 7A), (1C, 2D, 3B, 4A, 5A, 6A, 7B), (1C, 2D, 3B, 4A, 5A, 6A, 7C), (1C, 2D, 3B, 4A, 5A, 6B, 7A), (1C, 2D, 3B, 4A, 5A, 6B, 7B), (1C, 2D, 3B, 4A, 5A, 6B, 7C), (1C, 2D, 3B, 4A, 5A, 6C, 7A), (1C, 2D, 3B, 4A, 5A, 6C, 7B), (1C, 2D, 3B, 4A, 5A, 6C, 7C), (1C, 2D, 3B, 4A, 5A, 6D, 7A), (1C, 2D, 3B, 4A, 5A, 6D, 7B), (1C, 2D, 3B, 4A, 5A, 6D, 7C), (1C, 2D, 3B, 4A, 5B, 6A, 7A), (1C, 2D, 3B, 4A, 5B, 6A, 7B), (1C, 2D, 3B, 4A, 5B, 6A, 7C), (1C, 2D, 3B, 4A, 5B, 6B, 7A), (1C, 2D, 3B, 4A, 5B, 6B, 7B), (1C, 2D, 3B, 4A, 5B, 6B, 7C), (1C, 2D, 3B, 4A, 5B, 6C, 7A), (1C, 2D, 3B, 4A, 5B, 6C, 7B), (1C, 2D, 3B, 4A, 5B, 6C, 7C), (1C, 2D, 3B, 4A, 5B, 6D, 7A), (1C, 2D, 3B, 4A, 5B, 6D, 7B), (1C, 2D, 3B, 4A, 5B, 6D, 7C), (1C, 2D, 3B, 4B, 5A, 6A, 7A), (1C, 2D, 3B, 4B, 5A, 6A, 7B), (1C, 2D, 3B, 4B, 5A, 6A, 7C), (1C, 2D, 3B, 4B, 5A, 6B, 7A), (1C, 2D, 3B, 4B, 5A, 6B, 7B), (1C, 2D, 3B, 4B, 5A, 6B, 7C), (1C, 2D, 3B, 4B, 5A, 6C, 7A), (1C, 2D, 3B, 4B, 5A, 6C, 7B), (1C, 2D, 3B, 4B, 5A, 6C, 7C), (1C, 2D, 3B, 4B, 5A, 6D, 7A), (1C, 2D, 3B, 4B, 5A, 6D, 7B), (1C, 2D, 3B, 4B, 5A, 6D, 7C), (1C, 2D, 3B, 4B, 5B, 6A, 7A), (1C, 2D, 3B, 4B, 5B, 6A, 7B), (1C, 2D, 3B, 4B, 5B, 6A, 7C), (1C, 2D, 3B, 4B, 5B, 6B, 7A), (1C, 2D, 3B, 4B, 5B, 6B, 7B), (1C, 2D, 3B, 4B, 5B, 6B, 7C), (1C, 2D, 3B, 4B, 5B, 6C, 7A), (1C, 2D, 3B, 4B, 5B, 6C, 7B), (1C, 2D, 3B, 4B, 5B, 6C, 7C), (1C, 2D, 3B, 4B, 5B, 6D, 7A), (1C, 2D, 3B, 4B, 5B, 6D, 7B), (1C, 2D, 3B, 4B, 5B, 6D, 7C), (1C, 2D, 3B, 4C, 5A, 6A, 7A), (1C, 2D, 3B, 4C, 5A, 6A, 7B), (1C, 2D, 3B, 4C, 5A, 6A, 7C), (1C, 2D, 3B, 4C, 5A, 6B, 7A), (1C, 2D, 3B, 4C, 5A, 6B, 7B), (1C, 2D, 3B, 4C, 5A, 6B, 7C), (1C, 2D, 3B, 4C, 5A, 6C, 7A), (1C, 2D, 3B, 4C, 5A, 6C, 7B), (1C, 2D, 3B, 4C, 5A, 6C, 7C), (1C, 2D, 3B, 4C, 5A, 6D, 7A), (1C, 2D, 3B, 4C, 5A, 6D, 7B), (1C, 2D, 3B, 4C, 5A, 6D, 7C), (1C, 2D, 3B, 4C, 5B, 6A, 7A), (1C, 2D, 3B, 4C, 5B, 6A, 7B), (1C, 2D, 3B, 4C, 5B, 6A, 7C), (1C, 2D, 3B, 4C, 5B, 6B, 7A), (1C, 2D, 3B, 4C, 5B, 6B, 7B), (1C, 2D, 3B, 4C, 5B, 6B, 7C), (1C, 2D, 3B, 4C, 5B, 6C, 7A), (1C, 2D, 3B, 4C, 5B, 6C, 7B), (1C, 2D, 3B, 4C, 5B, 6C, 7C), (1C, 2D, 3B, 4C, 5B, 6D, 7A), (1C, 2D, 3B, 4C, 5B, 6D, 7B), (1C, 2D, 3B, 4C, 5B, 6D, 7C), (1C, 2D, 3B, 4D, 5A, 6A, 7A), (1C, 2D, 3B, 4D, 5A, 6A, 7B), (1C, 2D, 3B, 4D, 5A, 6A, 7C), (1C, 2D, 3B, 4D, 5A, 6B, 7A), (1C, 2D, 3B, 4D, 5A, 6B, 7B), (1C, 2D, 3B, 4D, 5A, 6B, 7C), (1C, 2D, 3B, 4D, 5A, 6C, 7A), (1C, 2D, 3B, 4D, 5A, 6C, 7B), (1C, 2D, 3B, 4D, 5A, 6C, 7C), (1C, 2D, 3B, 4D, 5A, 6D, 7A), (1C, 2D, 3B, 4D, 5A, 6D, 7B), (1C, 2D, 3B, 4D, 5A, 6D, 7C), (1C, 2D, 3B, 4D, 5B, 6A, 7A), (1C, 2D, 3B, 4D, 5B, 6A, 7B), (1C, 2D, 3B, 4D, 5B, 6A, 7C), (1C, 2D, 3B, 4D, 5B, 6B, 7A), (1C, 2D, 3B, 4D, 5B, 6B, 7B), (1C, 2D, 3B, 4D, 5B, 6B, 7C), (1C, 2D, 3B, 4D, 5B, 6C, 7A), (1C, 2D, 3B, 4D, 5B, 6C, 7B), (1C, 2D, 3B, 4D, 5B, 6C, 7C), (1C, 2D, 3B, 4D, 5B, 6D, 7A), (1C, 2D, 3B, 4D, 5B, 6D, 7B), (1C, 2D, 3B, 4D, 5B, 6D, 7C), (1C, 2D, 3B, 4E, 5A, 6A, 7A), (1C, 2D, 3B, 4E, 5A, 6A, 7B), (1C, 2D, 3B, 4E, 5A, 6A, 7C), (1C, 2D, 3B, 4E, 5A, 6B, 7A), (1C, 2D, 3B, 4E, 5A, 6B, 7B), (1C, 2D, 3B, 4E, 5A, 6B, 7C), (1C, 2D, 3B, 4E, 5A, 6C, 7A), (1C, 2D, 3B, 4E, 5A, 6C, 7B), (1C, 2D, 3B, 4E, 5A, 6C, 7C), (1C, 2D, 3B, 4E, 5A, 6D, 7A), (1C, 2D, 3B, 4E, 5A, 6D, 7B), (C, 2D, 3B, 4E, 5A, 6D, 7C), (1C, 2D, 3B, 4E, 5B, 6A, 7A), (1C, 2D, 3B, 4E, 5B, 6A, 7B), (1C, 2D, 3B, 4E, 5B, 6A, 7C), (1C, 2D, 3B, 4E, 5B, 6B, 7A), (1C, 2D, 3B, 4E, 5B, 6B, 7B), (1C, 2D, 3B, 4E, 5B, 6B, 7C), (1C, 2D, 3B, 4E, 5B, 6C, 7A), (1C, 2D, 3B, 4E, 5B, 6C, 7B), (1C, 2D, 3B, 4E, 5B, 6C, 7C), (1C, 2D, 3B, 4E, 5B, 6D, 7A), (1C, 2D, 3B, 4E, 5B, 6D, 7B), (1C, 2D, 3B, 4E, 5B, 6D, 7C), (1C, 2D, 3C, 4A, 5A, 6A, 7A), (1C, 2D, 3C, 4A, 5A, 6A, 7B), (1C, 2D, 3C, 4A, 5A, 6A, 7C), (1C, 2D, 3C, 4A, 5A, 6B, 7A), (1C, 2D, 3C, 4A, 5A, 6B, 7B), (1C, 2D, 3C, 4A, 5A, 6B, 7C), (1C, 2D, 3C, 4A, 5A, 6C, 7A), (1C, 2D, 3C, 4A, 5A, 6C, 7B), (1C, 2D, 3C, 4A, 5A, 6C, 7C), (1C, 2D, 3C, 4A, 5A, 6D, 7A), (1C, 2D, 3C, 4A, 5A, 6D, 7B), (1C, 2D, 3C, 4A, 5A, 6D, 7C), (1C, 2D, 3C, 4A, 5B, 6A, 7A), (1C, 2D, 3C, 4A, 5B, 6A, 7B), (1C, 2D, 3C, 4A, 5B, 6A, 7C), (1C, 2D, 3C, 4A, 5B, 6B, 7A), (1C, 2D, 3C, 4A, 5B, 6B, 7B), (1C, 2D, 3C, 4A, 5B, 6B, 7C), (1C, 2D, 3C, 4A, 5B, 6C, 7A), (1C, 2D, 3C, 4A, 5B, 6C, 7B), (1C, 2D, 3C, 4A, 5B, 6C, 7C), (1C, 2D, 3C, 4A, 5B, 6D,

7A), (1C, 2D, 3C, 4A, 5B, 6D, 7B), (1C, 2D, 3C, 4A, 5B, 6D, 7C), (1C, 2D, 3C, 4B, 5A, 6A, 7A), (1C, 2B, 3C, 4B, 5A, 6A, 7B), (1C, 2D, 3C, 4B, 5A, 6A, 7C), (1C, 2D, 3C, 4B, 5A, 6B, 7A), (1C, 2D, 3C, 4B, 5A, 6B, 7B), (1C, 2D, 3C, 4B, 5A, 6B, 7C), (1C, 2D, 3C, 4B, 5A, 6C, 7A), (1C, 2D, 3C, 4B, 5A, 6C, 7B), (1C, 2D, 3C, 4B, 5A, 6C, 7C), (1C, 2D, 3C, 4B, 5A, 6D, 7A), (1C, 2D, 3C, 4B, 5A, 6D, 7B), (1C, 2D, 3C, 4B, 5A, 6D, 7C), (1C, 2D, 3C, 4B, 5B, 6A, 7A), (1C, 2D, 3C, 4B, 5B, 6A, 7B), (1C, 2D, 3C, 4B, 5B, 6A, 7C), (1C, 2D, 3C, 4B, 5B, 6B, 7A), (1C, 2D, 3C, 4B, 5B, 6B, 7B), (1C, 2D, 3C, 4B, 5B, 6B, 7C), (1C, 2D, 3C, 4B, 5B, 6C, 7A), (1C, 2D, 3C, 4B, 5B, 6C, 7B), (1C, 2D, 3C, 4B, 5B, 6C, 7C), (1C, 2D, 3C, 4B, 5B, 6D, 7A), (1C, 2D, 3C, 4B, 5B, 6D, 7B), (1C, 2D, 3C, 4B, 5B, 6D, 7C), (1C, 2D, 3C, 4C, 5A, 6A, 7A), (1C, 2D, 3C, 4C, 5A, 6A, 7B), (1C, 2D, 3C, 4C, 5A, 6A, 7C), (1C, 2D, 3C, 4C, 5A, 6B, 7A), (1C, 2D, 3C, 4C, 5A, 6B, 7B), (1C, 2D, 3C, 4C, 5A, 6B, 7C), (1C, 2D, 3C, 4C, 5A, 6C, 7A), (1C, 2D, 3C, 4C, 5A, 6C, 7B), (1C, 2D, 3C, 4C, 5A, 6C, 7C), (1C, 2D, 3C, 4C, 5A, 6D, 7A), (1C, 2D, 3C, 4C, 5A, 6D, 7B), (1C, 2D, 3C, 4C, 5A, 6D, 7C), (1C, 2D, 3C, 4C, 5B, 6A, 7A), (1C, 2D, 3C, 4C, 5B, 6A, 7B), (1C, 2D, 3C, 4C, 5B, 6A, 7C), (1C, 2D, 3C, 4C, 5B, 6B, 7A), (1C, 2D, 3C, 4C, 5B, 6B, 7B), (1C, 2D, 3C, 4C, 5B, 6B, 7C), (1C, 2D, 3C, 4C, 5B, 6C, 7A), (1C, 2D, 3C, 4C, 5B, 6C, 7B), (1C, 2D, 3C, 4C, 5B, 6C, 7C), (1C, 2D, 3C, 4C, 5B, 6D, 7A), (1C, 2D, 3C, 4C, 5B, 6D, 7B), (1C, 2D, 3C, 4C, 5B, 6D, 7C), (1C, 2D, 3C, 4D, 5A, 6A, 7A), (1C, 2D, 3C, 4D, 5A, 6A, 7B), (1C, 2D, 3C, 4D, 5A, 6A, 7C), (1C, 2D, 3C, 4D, 5A, 6B, 7A), (1C, 2D, 3C, 4D, 5A, 6B, 7B), (1C, 2D, 3C, 4D, 5A, 6B, 7C), (1C, 2D, 3C, 4D, 5A, 6C, 7A), (1C, 2D, 3C, 4D, 5A, 6C, 7B), (1C, 2D, 3C, 4D, 5A, 6C, 7C), (1C, 2D, 3C, 4D, 5A, 6D, 7A), (1C, 2D, 3C, 4D, 5A, 6D, 7B), (1C, 2D, 3C, 4D, 5A, 6D, 7C), (1C, 2D, 3C, 4D, 5B, 6A, 7A), (1C, 2D, 3C, 4D, 5B, 6A, 7B), (1C, 2D, 3C, 4D, 5B, 6A, 7C), (1C, 2D, 3C, 4D, 5B, 6B, 7A), (1C, 2D, 3C, 4D, 5B, 6B, 7B), (1C, 2D, 3C, 4D, 5B, 6B, 7C), (1C, 2D, 3C, 4D, 5B, 6C, 7A), (1C, 2D, 3C, 4D, 5B, 6C, 7B), (1C, 2D, 3C, 4D, 5B, 6C, 7C), (1C, 2D, 3C, 4D, 5B, 6D, 7A), (1C, 2D, 3C, 4D, 5B, 6D, 7B), (1C, 2D, 3C, 4D, 5B, 6D, 7C), (1C, 2D, 3C, 4E, 5A, 6A, 7A), (1C, 2D, 3C, 4E, 5A, 6A, 7B), (1C, 2D, 3C, 4E, 5A, 6A, 7C), (1C, 2D, 3C, 4E, 5A, 6B, 7A), (1C, 2D, 3C, 4E, 5A, 6B, 7B), (1C, 2D, 3C, 4E, 5A, 6B, 7C), (1C, 2D, 3C, 4E, 5A, 6C, 7A), (1C, 2D, 3C, 4E, 5A, 6C, 7B), (1C, 2D, 3C, 4E, 5A, 6C, 7C), (1C, 2D, 3C, 4E, 5A, 6D, 7A), (1C, 2D, 3C, 4E, 5A, 6D, 7B), (1C, 2D, 3C, 4E, 5A, 6D, 7C), (1C, 2D, 3C, 4E, 5B, 6A, 7A), (1C, 2D, 3C, 4E, 5B, 6A, 7B), (1C, 2D, 3C, 4E, 5B, 6A, 7C), (1C, 2D, 3C, 4E, 5B, 6B, 7A), (1C, 2D, 3C, 4E, 5B, 6B, 7B), (1C, 2D, 3C, 4E; 5B, 6B, 7C), (1C, 2D, 3C, 4E, 5B, 6C, 7A), (1C, 2D, 3C, 4E, 5B, 6C, 7B), (1C, 2D, 3C, 4E, 5B, 6C, 7C), (1C, 2D, 3C, 4E, 5B, 6D, 7A), (1C, 2D, 3C, 4E, 5B, 6D, 7B), (1C, 2D, 3C, 4E, 5B, 6D, 7C), (1C, 2D, 3D, 4A, 5A, 6A, 7A), (1C, 2D, 3D, 4A, 5A, 6A, 7B), (1C, 2D, 3D, 4A, 5A, 6A, 7C), (1C, 2D, 3D, 4A, 5A, 6B, 7A), (1C, 2D, 3D, 4A, 5A, 6B, 7B), (1C, 2D, 3D, 4A, 5A, 6B, 7C), (1C, 2D, 3D, 4A, 5A, 6C, 7A), (1C, 2D, 3D, 4A, 5A, 6C, 7E), (1C, 2D, 3D, 4A, 5A, 6C, 7C), (1C, 2D, 3D, 4A, 5A, 6D, 7A), (1C, 2D, 3D, 4A, 5A, 6D, 7B), (1C, 2D, 3D, 4A, 5A, 6D, 7C), (1C, 2D, 3D, 4A, 5B, 6A, 7A), (1C, 2D, 3D, 4A, 5B, 6A, 7B), (1C, 2D, 3D, 4A, 5B, 6A, 7C), (1C, 2D, 3D, 4A, 5B, 6B, 7A), (1C, 2D, 3D, 4A, 5B, 6B, 7B), (1C, 2D, 3D, 4A, 5B, 6B, 7C), (1C, 2D, 3D, 4A, 5B, 6C, 7A), (1C, 2D, 3D, 4A, 5B, 6C, 7B), (1C, 2D, 3D, 4A, 5B, 6C, 7C), (1C, 2D, 3D, 4A, 5B, 6D, 7A), (1C, 2D, 3D, 4A, 5B, 6D, 7C), (1C, 2D, 3D, 4B, 5A, 6A, 7A), (1C, 2D, 3D, 4B, 5A, 6A, 7B), (1C, 2D, 3D, 4B, 5A, 6A, 7C), (1C, 2D, 3D, 4B, 5A, 6B, 7A), (1C, 2D, 3D, 4B, 5A, 6B, 7B), (1C, 2D, 3D, 4B, 5A, 6B, 7C), (1C, 2D, 3D, 4B, 5A, 6C, 7A), (1C, 2D, 3D, 4B, 5A, 6C, 7B), (1C, 2D, 3D, 4B, 5A, 6C, 7C), (1C, 2D, 3D, 4B, 5A, 6D, 7A), (1C, 2D, 3D, 4B, 5A, 6D, 7B), (1C, 2D, 3D, 4B, 5A, 6D, 7C), (1C, 2D, 3D, 4B, 5B, 6A, 7A), (1C, 2D, 3D, 4B, 5B, 6A, 7B), (1C, 2D, 3D, 4B, 5B, 6A, 7C), (1C, 2D, 3D, 4B, 5B, 6B, 7A), (1C, 2D, 3D, 4B, 5B, 6B, 7B), (1C, 2D, 3D, 4B, 5B, 6B, 7C), (1C, 2D, 3D, 4B, 5B, 6C, 7A), (1C, 2D, 3D, 4B, 5B, 6C, 7B), (1C, 2D, 3D, 4B, 5B, 6C, 7C), (1C, 2D, 3D, 4B, 5B, 6D, 7A), (1C, 2D, 3D, 4B, 5B, 6D, 7B), (1C, 2D, 3D, 4B, 5B, 6D, 7C), (1C, 2D, 3D, 4C, 5A, 6A, 7A), (1C, 2D, 3D, 4C, 5A, 6A, 7B), (1C, 2D, 3D, 4C, 5A, 6A, 7C), (1C, 2D, 3D, 4C, 5A, 6B, 7A), (1C, 2D, 3D, 4C, 5A, 6B, 7B), (1C, 2D, 3D, 4C, 5A, 6B, 7C), (1C, 2D, 3D, 4C, 5A, 6C, 7A), (1C, 2D, 3D, 4C, 5A, 6C, 7B), (1C, 2D, 3D, 4C, 5A, 6C, 7C), (1C, 2D, 3D, 4C, 5A, 6D, 7A), (1C, 2D, 3D, 4C, 5A, 6D, 7B), (1C, 2D, 3D, 4C, 5A, 6D, 7C), (1C, 2D, 3D, 4C, 5B, 6A, 7A), (1C, 2D, 3D, 4C, 5B, 6A, 7B), (1C, 2D, 3D, 4C, 5B, 6A, 7C), (1C, 2D, 3D, 4C, 5B, 6B, 7A), (1C, 2D, 3D, 4C, 5B, 6B, 7B), (1C, 2D, 3D, 4C, 5B, 6B, 7C), (1C, 2D, 3D, 4C, 5B, 6C, 7A), (1C, 2D, 3D, 4C, 5B, 6C, 7B), (1C, 2D, 3D, 4C, 5B, 6C, 7C), (1C, 2D, 3D, 4C, 5B, 6D, 7A), (1C, 2D, 3D, 4C, 5B, 6D, 7B), (1C, 2D, 3D, 4C, 5B, 6D, 7C), (1C, 2D, 3D, 4D, 5A, 6A, 7A), (1C, 2D, 3D, 4D, 5A, 6A, 7B), (1C, 2D, 3D, 4D, 5A, 6A, 7C), (1C, 2D, 3D, 4D, 5A, 6B, 7A), (1C, 2D, 3D, 4D, 5A, 6B, 7B), (1C, 2D, 3D, 4D, 5A, 6B, 7C), (1C, 2D, 3D, 4D, 5A, 6C, 7A), (1C, 2D, 3D, 4D, 5A, 6C, 7B), (1C, 2D, 3D, 4D, 5A, 6C, 7C), (1C, 2D, 3D, 4D, 5A, 6D, 7A), (1C, 2D, 3D, 4D, 5A, 6D, 7B), (1C, 2D, 3D, 4D, 5A, 6D, 7C), (1C, 2D, 3D, 4D, 5B, 6A, 7A), (1C, 2D, 3D, 4D, 5B, 6A, 7B), (1C, 2D, 3D, 4D, 5B, 6A, 7C), (1C, 2D, 3D, 4D, 5B, 6B, 7A), (1C, 2D, 3D, 4D, 5B, 6B, 7B), (1C, 2D, 3D, 4D, 5B, 6B, 7C), (1C, 2D, 3D, 4D, 5B, 6C, 7A), (1C, 2D, 3D, 4D, 5B, 6C, 7B), (1C, 2D, 3D, 4D, 5B, 6C, 7C), (1C, 2D, 3D, 4D, 5B, 6D, 7A), (1C, 2D, 3D, 4D, 5B, 6D, 7B), (1C, 2D, 31D, 4D, 5B, 6D, 7C), (1C, 2D, 3D, 4E, 5A, 6A, 7A), (1C, 2D, 3D, 4E, 5A, 6A, 7B), (1C, 2D, 3D, 4E, 5A, 6A, 7C), (1C, 2D, 3D, 4E, 5A, 6B, 7A), (1C, 2D, 3D, 4E, 5A, 6B, 7B), (1C, 2D, 3D, 4E, 5A, 6B, 7C), (1C, 2D, 3D, 4E, 5A, 6C, 7A), (1C, 2D, 3D, 4E, 5A, 6C, 7B), (1C, 2D, 3D, 4E, 5A, 6C, 7C), (1C, 2D, 3D, 4E, 5A, 6D, 7A), (1C, 2D, 3D, 4E, 5A, 6D, 7B), (1C, 2D, 3D, 4E, 5A, 6D, 7C), (1C, 2D, 3D, 4E, 5B, 6A, 7A), (1C, 2D, 3D, 4E, 5B, 6A, 7B), (1C, 2D, 3D, 4E, 5B, 6A, 7C), (1C, 2D, 3D, 4E, 5B, 6B, 7A), (1C, 2D, 3D, 4E, 5B, 6B, 7B), (1C, 2D, 3D, 4E, 5B, 6B, 7C), (1C, 2D, 3D, 4E, 5B, 6C, 7A), (1C, 2D, 3D, 4E, 5B, 6C, 7B), (1C, 2D, 3D, 4E, 5B, 6C, 7C), (1C, 2D, 3D, 4E, 5B, 6D, 7A), (1C, 2D, 3D, 4E, 5B, 6D, 7B), (1C, 2D, 3D, 4E, 5B, 6D, 7C), (1C, 2D, 3E, 4A, 5A, 6A, 7A), (1C, 2D, 3E, 4A, 5A, 6A, 7B), (1C, 2D, 3E, 4A, 5A, 6A, 7C), (1C, 2D, 3E, 4A, 5A, 6B, 7A), (1C, 2D, 3E, 4A, 5A, 6B, 7B), (1C, 2D, 3E, 4A, 5A, 6B, 7C), (1C, 2D, 3E, 4A, 5A, 6C, 7A), (1C, 2D, 3E, 4A, 5A, 6C, 7B), (1C, 2D, 3E, 4A, 5A, 6C, 7C), (1C, 2D, 3E, 4A, 5A, 6D, 7A), (1C, 2D, 3E, 4A, 5A, 6D, 7B), (1C, 2D, 3E, 4A, 5A, 6D, 7C), (1C, 2D, 3E, 4A, 5B, 6A, 7A), (1C, 2D, 3E, 4A, 5B, 6A, 7B), (1C, 2D, 3E, 4A, 5B, 6A, 7C), (1C, 2D, 3E, 4A, 5B, 6B, 7A), (1C, 2D, 3E, 4A, 5B, 6B, 7B), (1C, 2D, 3E, 4A, 5B, 6B, 7C), (1C, 2D, 3E, 4A, 5B, 6C, 7A), (1C, 2D, 3E, 4A, 5B, 6C, 7B), (1C, 2D, 3E, 4A, 5B, 6C, 7C), (1C, 2D, 3E, 4A, 5B, 6D, 7A), (1C, 2D, 3E, 4A, 5B, 6D, 7B), (1C, 2D, 3E, 4A, 5B, 6D, 7C), (1C, 2D, 3E, 4B, 5A, 6A, 7A), (1C, 2D, 3E, 4B, 5A, 6A, 7B), (1C, 2D, 3E, 4B, 5A, 6A, 7C), (1C, 2D, 3E, 4B, 5A, 6B, 7A), (1C, 2D, 3E, 4B, 5A, 6B, 7B), (1C, 2D, 3E, 4B, 5A, 6B, 7C), (1C, 2D, 3E, 4B, 5A, 6C, 7A), (1C, 2D, 3E, 4B, 5A, 6C, 7B), (1C, 2D, 3E, 4B, 5A, 6C, 7C), (1C, 2D, 3E, 4B, 5A, 6D, 7A), (1C, 2D, 3E, 4B, 5A, 6D, 7B), (1C, 2D, 3E, 4B, 5A, 6D, 7C), (1C, 2D, 3E, 4B, 5B, 6A, 7A), (1C, 2D, 3E, 4B, 5B, 6A, 7B), (1C, 2D, 3E, 4B, 5B, 6A, 7C), (1C, 2D, 3E, 4B, 5B, 6B, 7A), (1C, 2D, 3E, 4B, 5B, 6B, 7B), (1C, 2D, 3E, 4B, 5B, 6B, 7C), (1C, 2D, 3E, 4B, 5B, 6C, 7A), (1C, 2D, 3E, 4B, 5B, 6C, 7B), (1C, 2D, 3E, 4B, 5B, 6C, 7C), (1C, 2D, 3E, 4B, 5B, 6D, 7A), (1C, 2D, 3E, 4B, 5B, 6D, 7B), (1C, 2D, 3E, 4B, 5B, 6D, 7C), (1C, 2D, 3E, 4C, 5A, 6A, 7A), (1C, 2D, 3E, 4C, 5A, 6A, 7B), (1C, 2D, 3E, 4C, 5A, 6A, 7C), (1C, 2D, 3E, 4C, 5A, 6B, 7A), (1C, 2D, 3E, 4C, 5A, 6B, 7B), (1C, 2D, 3E, 4C, 5A, 6B, 7C), (1C, 2D, 3E, 4C, 5A, 6C, 7A), (1C, 2D, 3E, 4C, 5A, 6C, 7B), (C, 2D, 3E, 4C, 5A, 6C, 7C), (1C, 2D, 3E, 4C, 5A, 6D, 7A), (1C, 2D, 3E, 4C, 5A, 6D, 7B), (1C, 2D, 3E, 4C, 5A, 6D, 7C), (1C, 2D, 3E, 4C, 5B, 6A, 7A), (1C, 2D, 3E, 4C, 5B, 6A, 7B), (1C, 2D, 3E, 4C, 5B, 6A, 7C), (1C, 2D, 3E, 4C, 5B, 6B, 7A), (1C, 2D, 3E, 4C, 5B, 6B, 7B), (1C, 2D, 3E, 4C, 5B, 6B, 7C), (1C, 2D, 3E, 4C, 5B, 6C, 7A), (1C, 2D, 3E, 4C, 5B, 6C, 7E), (1C, 2D, 3E, 4C, 5B, 6C, 7C), (1C, 2D, 3E, 4C, 5B, 6D, 7A), (1C, 2D, 3E, 4C, 5B, 6D, 7B), (1C, 2D, 3E, 4C, 5B, 6D, 7C), (1C, 2D, 3E, 4D, 5A, 6A, 7A), (1C, 2D, 3E, 4D, 5A, 6A, 7B), (1C, 2D, 3E, 4D, 5A, 6A, 7C), (1C, 2D, 3E, 4D, 5A, 6B, 7A), (1C, 2D, 3E, 4D, 5A, 6B, 7B), (1C, 2D, 3E, 4D, 5A, 6B, 7C), (1C, 2D, 3E, 4D, 5A, 6C, 7A), (1C, 2B, 3E, 4D, 5A, 6C, 7B), (1C, 2D, 3E, 4D, 5A, 6C, 7C), (1C, 2D, 3E, 4D, 5A, 6D, 7A), (1C, 2D, 3E, 4D, 5A, 6D, 7B), (1C, 2D, 3E, 4D, 5A, 6D, 7C), (1C, 2D, 3E, 4D, 5B, 6A, 7A), (1C, 2D, 3E, 4D, 5B, 6A, 7B), (1C, 2D, 3E, 4D, 5B, 6A, 7C), (1C, 2D, 3E, 4D, 5B, 6B, 7A), (1C, 2D, 3E, 4D, 5B, 6B, 7B), (1C, 2D, 3E, 4D, 5B, 6B, 7C), (1C, 2D, 3E, 4D, 5B, 6C, 7A), (1C, 2D, 3E, 4D, 5B, 6C, 7B), (1C, 2D, 3E, 4D, 5B, 6C, 7C), (1C, 2D, 3E, 4D, 5B, 6D, 7A), (1C, 2D, 3E, 4D, 5B, 6D, 7B), (1C, 2D, 3E, 4D, 5B, 6D, 7C), (1C, 2D, 3E, 4E, 5A, 6A, 7A), (1C, 2D, 3E, 4E, 5A, 6A, 7B), (1C, 2D, 3E, 4E, 5A, 6A, 7C), (1C, 2D, 3E, 4E, 5A, 6B, 7A), (1C, 2D, 3E, 4E, 5A, 6B, 7B), (1C, 2D, 3E, 4E, 5A, 6B, 7C), (1C, 2D, 3E, 4E, 5A, 6C, 7A), (1C, 2D, 3E, 4E, 5A, 6C, 7B), (1C, 2D, 3E, 4E, 5A, 6C, 7C), (1C, 2D, 3E, 4E, 5A, 6D, 7A), (1C, 2D, 3E, 4E, 5A, 6D, 7B), (1C, 2D, 3E, 4E, 5A, 6D, 7C), (1C, 2D, 3E, 4E, 5B, 6A, 7A), (1C, 2D, 3E, 4E, 5B, 6A, 7B), (1C, 2D, 3E, 4E, 5B, 6A, 7C), (1C, 2D, 3E, 4E, 5B, 6B, 7A), (1C, 2D, 3E, 4E, 5B, 6B, 7B), (1C, 2D, 3E, 4E, 5B, 6B, 7C), (1C, 2D, 3E, 4E, 5B, 6C, 7A), (1C, 2D, 3E, 4E, 5B, 6C, 7B), (1C, 2D, 3E, 4E, 5B, 6C, 7C), (1C, 2D, 3E, 4E, 5B, 6D, 7A), (1C, 2D, 3E, 4E, 5B, 6D, 7B), (1C, 2D, 3E, 4E, 5B, 6D, 7C), (1C, 2E, 3A, 4A, 5A, 6A, 7A), (1C, 2E, 3A, 4A, 5A, 6A, 7B), (1C, 2E, 3A, 4A, 5A, 6A, 7C), (1C, 2E, 3A, 4A, 5A, 6B, 7A), (1C, 2E, 3A, 4A, 5A, 6B, 7B), (1C, 2E, 3A, 4A, 5A, 6B, 7C), (1C, 2E, 3A, 4A, 5A, 6C, 7A), (1C, 2E, 3A, 4A, 5A, 6C, 7B), (1C, 2E, 3A, 4A, 5A, 6C, 7C), (1C, 2E, 3A, 4A, 5A, 6D, 7A), (1C, 2E, 3A, 4A, 5A, 6D, 7B), (1C, 2E, 3A, 4A, 5A, 6D, 7C), (1C, 2E, 3A, 4A, 5B, 6A, 7A), (1C, 2E, 3A, 4A, 5B, 6A, 7B), (1C, 2E, 3A, 4A, 5B, 6A, 7C), (1C, 2E, 3A, 4A, 5B, 6B, 7A), (1C, 2E, 3A, 4A, 5B, 6B, 7B), (1C, 2E, 3A, 4A, 5B, 6B, 7C), (1C, 2E, 3A, 4A, 5B, 6C, 7A), (1C, 2E, 3A, 4A, 5B, 6C, 7B), (1C, 2E, 3A, 4A, 5B, 6C, 7C), (1C, 2E, 3A, 4A, 5B, 6D, 7A), (1C, 2E, 3A, 4A, 5B, 6D, 7B), (1C, 2E, 3A, 4A, 5B, 6D, 7C), (1C, 2E, 3A, 4B, 5A, 6A, 7A), (1C, 2E, 3A, 4B, 5A, 6A, 7B), (1C, 2E, 3A, 4B, 5A, 6A, 7C), (1C, 2E, 3A, 4B, 5A, 6B, 7A), (1C, 2E, 3A, 41B, 5A, 6B, 7B), (1C, 2E, 3A, 4B, 5A, 6B, 7C), (1C, 2E, 3A, 4B, 5A, 6C, 7A), (1C, 2E, 3A, 4B, 5A, 6C, 7B), (1C, 2E, 3A, 4B, 5A, 6C, 7C), (1C, 2E, 3A, 4B, 5A, 6D, 7A), (1C, 2E, 3A, 4B, 5A, 6D, 7B), (1C, 2E, 3A, 4B, 5A, 6D, 7C), (1C, 2E, 3A, 4B, 5B, 6A, 7A), (1C, 2E, 3A, 4B, 5B, 6A, 7B), (1C, 2E, 3A, 4B, 5B, 6A, 7C), (1C, 2E, 3A, 4B, 5B, 6B, 7A), (1C, 2E, 3A, 4B, 5B, 6B, 7B), (1C, 2E, 3A, 4B, 5B, 6B, 7C), (1C, 2E, 3A, 4B, 5B, 6C, 7A), (1C, 2E, 3A, 4B, 5B, 6C, 7B), (1C, 2E, 3A, 4B, 5B, 6C, 7C), (1C, 2E, 3A, 4B, 5B, 6D, 7A), (1C, 2E, 3A, 4B, 5B, 6D, 7B), (1C, 2E, 3A, 4B, 5B, 6D, 7C), (1C, 2E, 3A, 4C, 5A, 6A, 7A), (1C, 2E, 3A, 4C, 5A, 6A, 7B), (1C, 2E, 3A, 4C, 5A, 6A, 7C), (1C, 2E, 3A, 4C, 5A, 6B, 7A), (1C, 2E, 3A, 4C, 5A, 6B, 7B), (1C, 2E, 3A, 4C, 5A, 6B, 7C), (1C, 2E, 3A, 4C, 5A, 6C, 7A), (1C, 2E, 3A, 4C, 5A, 6C, 7B), (1C, 2E, 3A, 4C, 5A, 6C, 7C), (1C, 2E, 3A, 4C, 5A, 6D, 7A), (1C, 2E, 3A, 4C, 5A, 6D, 7B), (1C, 2E, 3A, 4C, 5A, 6D, 7C), (1C, 2E, 3A, 4C, 5B, 6A, 7A), (1C, 2E, 3A, 4C, 5B, 6A, 7B), (1C, 2E, 3A, 4C, 5B, 6A, 7C), (1C, 2E, 3A, 4C, 5B, 6B, 7A), (1C, 2E, 3A, 4C, 5B, 6B, 7B), (1C, 2E, 3A, 4C, 5B, 6B, 7C), (1C, 2E, 3A, 4C, 5B, 6C, 7A), (1C, 2E, 3A, 4C, 5B, 6C, 7B), (1C, 2E, 3A, 4C, 5B, 6C, 7C), (1C, 2E, 3A, 4C, 5B, 6D, 7A), (1C, 2E, 3A, 4C, 5B, 6D, 7B), (1C, 2E, 3A, 4C, 5B, 6D, 7C), (1C, 2E, 3A, 4D, 5A, 6A, 7A), (1C, 2E, 3A, 4D, 5A, 6A, 7B), (1C, 2E, 3A, 4D, 5A, 6A, 7C), (1C, 2E, 3A, 4D, 5A, 6B, 7A), (1C, 2E, 3A, 4D, 5A, 6B, 7B), (1C, 2E, 3A, 4D, 5A, 6B, 7C), (1C, 2E, 3A, 4D, 5A, 6C, 7A), (1C, 2E, 3A, 4D, 5A, 6C, 7B), (1C, 2E, 3A, 4D, 5A, 6C, 7C), (1C, 2E, 3A, 4D, 5A, 6D, 7A), (1C, 2E, 3A, 4D, 5A, 6D, 7B), (1C, 2E, 3A, 4D, 5A, 6D, 7C), (1C, 2E, 3A, 4D, 5B, 6A, 7A), (1C, 2E, 3A, 4D, 5B, 6A, 7B), (1C, 2E, 3A, 4D, 5B, 6A, 7C), (1C, 2E, 3A, 4D, 5B, 6B, 7A), (1C, 2E, 3A, 4D, 5B, 6B, 7B), (1C, 2E, 3A, 4D, 5B, 6B, 7C), (1C, 2E, 3A, 4D, 5B, 6C, 7A), (1C, 2E, 3A, 4D, 5B, 6C, 7B), (1C, 2E, 3A, 4D, 5B, 6C, 7C), (1C, 2E, 3A, 4D, 5B, 6D, 7A), (1C, 2E, 3A, 4D, 5B, 6D, 7B), (1C, 2E, 3A, 4D, 5B, 6D, 7C), (1C, 2E, 3A, 4E, 5A, 6A, 7A), (1C, 2E, 3A, 4E, 5A, 6A, 7B), (1C, 2E, 3A, 4E, 5A, 6A, 7C), (1C, 2E, 3A, 4E, 5A, 6B, 7A), (1C, 2E, 3A, 4E, 5A, 6B, 7B), (1C, 2E, 3A, 4E, 5A, 6B, 7C), (1C, 2E, 3A, 4E, 5A, 6C, 7A), (1C, 2E, 3A, 4E, 5A, 6C, 7B), (1C, 2E, 3A, 4E, 5A, 6C, 7C), (1C, 2E, 3A, 4E, 5A, 6D, 7A), (1C, 2E, 3A, 4E, 5A, 6D, 7B), (1C, 2E, 3A, 4E, 5A, 6D, 7C), (1C, 2E, 3A, 4E, 5B, 6A, 7A), (1C, 2E, 3A, 4E, 5B, 6A, 7B), (1C, 2E, 3A, 4E, 5B, 6A, 7C), (1C, 2E, 3A, 4E, 5B, 6B, 7A), (1C, 2E, 3A, 4E, 5B, 6B, 7B), (1C, 2E, 3A, 4E, 5B, 6B, 7C), (1C, 2E, 3A, 4E, 5B, 6C, 7A), (1C, 2E, 3A, 4E, 5B, 6C, 7B), (1C, 2E, 3A, 4E, 5B, 6C, 7C), (1C, 2E, 3A, 4E, 5B, 6D, 7A), (1C, 2E, 3A, 4E, 5B, 6D, 7B), (1C, 2E, 3A, 4E, 5B, 6D, 7C), (1C, 2E, 3B, 4A, 5A, 6A, 7A), (1C, 2E, 3B, 4A, 5A, 6A, 7B), (1C, 2E, 3B, 4A, 5A, 6A, 7C), (1C, 2E, 3B, 4A, 5A, 6B, 7A), (1C, 2E, 3B, 4A, 5A, 6B, 7B), (1C, 2E, 3B, 4A, 5A, 6B, 7C), (1C, 2E, 3B, 4A, 5A, 6C, 7A), (1C, 2E, 3B, 4A, 5A, 6C, 7B), (1C, 2E, 3B, 4A, 5A, 6C, 7C), (1C, 2E, 3B, 4A, 5A, 6D, 7A), (1C, 2E, 3B, 4A, 5A, 6D, 7B), (1C, 2E, 3B, 4A, 5A, 6D, 7C), (1C, 2E, 3B, 4A, 5B, 6A, 7A), (1C, 2E, 3B, 4A, 5B, 6A, 7B), (1C, 2E, 3B, 4A, 5B, 6A, 7C), (1C, 2E, 3B, 4A, 5B, 6B, 7A), (1C, 2E, 3B, 4A, 5B, 6B, 7B), (1C, 2E, 3B, 4A, 5B, 6B, 7C), (1C, 2E, 3B, 4A, 5B, 6C, 7A), (1C, 2E, 3B, 4A, 5B, 6C, 7B), (1C, 2E, 3B, 4A, 5B, 6C, 7C), (1C, 2E, 3B, 4A, 5B, 6D, 7A), (1C, 2E, 3B, 4A, 5B, 6D, 7B), (1C, 2E, 3B, 4A, 5B, 6D, 7C), (1C, 2E, 3B, 4B, 5A, 6A, 7A), (1C, 2E, 3B, 4B, 5A, 6A, 7B), (1C, 2E, 3B, 4B, 5A, 6A, 7C), (1C, 2E, 3B, 4B, 5A, 6B, 7A), (1C, 2E, 3B, 4B, 5A, 6B, 7B), (1C, 2E, 3B, 4B, 5A, 6B, 7C), (1C, 2E, 3B, 4B, 5A, 6C, 7A), (1C, 2E, 3B, 4B, 5A, 6C, 7B), (1C, 2E, 3B, 4B, 5A, 6C, 7C), (1C, 2E, 3B, 4B, 5A, 6D, 7A), (1C, 2E, 3B, 4B, 5A, 6D, 7B), (1C, 2E, 3B, 4B, 5A, 6D, 7C), (1C, 2E, 3B, 4B, 5B, 6A, 7A), (1C, 2E, 3B, 4B, 5B, 6A, 7B), (1C, 2E, 3B, 4B, 5B, 6A, 7C), (1C, 2E, 3B, 4B, 5B, 6B, 7A), (1C, 2E, 3B, 4B, 5B, 6B, 7B), (1C, 2E, 3B, 4B, 5B, 6B, 7C), (1C, 2E, 3B, 4B, 5B, 6C, 7A), (1C, 2E, 3B, 4B, 5B, 6C, 7B), (1C, 2E, 3B, 4B, 5B, 6C, 7C), (1C, 2E, 3B, 4B, 5B, 6D, 7A), (1C, 2E, 3B, 4B, 5B, 6D, 7B), (1C, 2E, 3B, 4B, 5B, 6D, 7C), (1C, 2E, 3B, 4C, 5A, 6A, 7A), (1C, 2E, 3B, 4C, 5A, 6A, 7B), (1C, 2E, 3B, 4C, 5A, 6A, 7C), (1C, 2E, 3B, 4C, 5A, 6B, 7A), (1C, 2E, 3B, 4C, 5A, 6B, 7B), (1C, 2E, 3B, 4C, 5A, 6B, 7C), (1C, 2E, 3B, 4C, 5A, 6C, 7A), (1C, 2E, 3B, 4C, 5A, 6C, 7B), (1C, 2E, 3B, 4C, 5A, 6C, 7C), (1C, 2E, 3B, 4C, 5A, 6D, 7A), (1C, 2E, 3B, 4C, 5A, 6D, 7B), (1C, 2E, 3B, 4C, 5A, 6D, 7C), (1C, 2E, 3B, 4C, 5B, 6A, 7A), (1C, 2E, 3B, 4C, 5B, 6A, 7B), (1C, 2E, 3B, 4C, 5B, 6A, 7C), (1C, 2E, 3B, 4C, 5B, 6B, 7A), (1C, 2E, 3B, 4C, 5B, 6B, 7B), (1C, 2E, 3B, 4C, 5B, 6B, 7C), (1C, 2E, 3B, 4C, 5B, 6C, 7A), (1C, 2E, 3B, 4C, 5B, 6C, 7B), (1C, 2E, 3B, 4C, 5B, 6C, 7C), (1C, 2E, 3B, 4C, 5B, 6D, 7A), (1C, 2E, 3B, 4C, 5B, 6D, 7B), (1C, 2E, 3B, 4C, 5B, 6D, 7C), (1C, 2E, 3B, 4D, 5A, 6A, 7A), (1C, 2E, 3B, 4D, 5A, 6A, 7B), (1C, 2E, 3B, 4D, 5A, 6A, 7C), (1C, 2E, 3B, 4D, 5A, 6B, 7A), (1C, 2E, 3B, 4D, 5A, 6B, 7B), (1C, 2E, 3B, 4D, 5A, 6B, 7C), (1C, 2E, 3B, 4D, 5A, 6C, 7A), (1C, 2E, 3B, 4D, 5A, 6C, 7B), (1C, 2E, 3B, 4D, 5A, 6C, 7C), (1C, 2E, 3B, 4D, 5A, 6D, 7A), (1C, 2E, 3B, 4D, 5A, 6D, 7B), (1C, 2E, 3B, 4D, 5A, 6D, 7C), (1C, 2E, 3B, 4D, 5B, 6A, 7A), (1C, 2E, 3B, 4D, 5B, 6A, 7B), (1C, 2E, 3B, 4D, 5B, 6A, 7C), (1C, 2E, 3B, 4D, 5B, 6B, 7A), (1C, 2E, 3B, 4D, 5B, 6B, 7B), (1C, 2E, 3B, 4D, 5B, 6B, 7C), (1C, 2E, 3B, 4D, 5B, 6C, 7A), (1C, 2E, 3B, 4D, 5B, 6C, 7B), (1C, 2E, 3B, 4D, 5B, 6C, 7C), (1C, 2E, 3B, 4D, 5B, 6D, 7A), (1C, 2E, 3B, 4D, 5B, 6D, 7B), (1C, 2E, 3B, 4D, 5B, 6D, 7C), (1C, 2E, 3B, 4E, 5A, 6A, 7A), (1C, 2E, 3B, 4E, 5A, 6A, 7B), (1C, 2E, 3B, 4E, 5A, 6A, 7C), (1C, 2E, 3B, 4E, 5A, 6B, 7A), (1C, 2E, 3B, 4E, 5A, 6B, 7B), (1C, 2E, 3B, 4E, 5A, 6B, 7C), (1C, 2E, 3B, 4E, 5A, 6C, 7A), (1C, 2E, 3B, 4E, 5A, 6C, 7B), (1C, 2E, 3B, 4E, 5A, 6C, 7C), (1C, 2E, 3B, 4E, 5A, 6D, 7A), (1C, 2E, 3B, 4E, 5A, 6D, 7B), (1C, 2E, 3B, 4E, 5A, 6D, 7C), (1C, 2E, 3B, 4E, 5B, 6A, 7A), (1C, 2E, 3B, 4E, 5B, 6A, 7B), (1C, 2E, 3B, 4E, 5B, 6A, 7C), (1C, 2E, 3B, 4E, 5B, 6B, 7A), (1C, 2E, 3B, 4E, 5B, 6B, 7B), (1C, 2E, 3B, 4E, 5B, 6B, 7C), (1C, 2E, 3B, 4E, 5B, 6C, 7A), (1C, 2E, 3B, 4E, 5B, 6C, 7B), (1C, 2E, 3B, 4E, 5B, 6C, 7C), (1C, 2E, 3B, 4E, 5B, 6D, 7A), (1C, 2E, 3B, 4E, 5B, 6D, 7B), (1C, 2E, 3B, 4E, 5B, 6D, 7C), (1C, 2E, 3C, 4A, 5A, 6A, 7A), (1C, 2E, 3C, 4A, 5A, 6A, 7B), (1C, 2E, 3C, 4A, 5A, 6A, 7C), (1C, 2E, 3C, 4A, 5A, 6B, 7A), (1C, 2E, 3C, 4A, 5A, 6B, 7B), (1C, 2E, 3C, 4A, 5A, 6B, 7C), (1C, 2E, 3C, 4A, 5A, 6C, 7A), (1C, 2E, 3C, 4A, 5A, 6C, 7B), (1C, 2E, 3C, 4A, 5A, 6C, 7C), (1C, 2E, 3C, 4A, 5A, 6D, 7A), (1C, 2E, 3C, 4A, 5A, 6D, 7B), (1C, 2E, 3C, 4A, 5A, 6D, 7C), (1C, 2E, 3C, 4A, 5B, 6A, 7A), (1C, 2E, 3C, 4A, 5B, 6A, 7B), (1C, 2E, 3C, 4A, 5B, 6A, 7C), (1C, 2E, 3C, 4A, 5B, 6B, 7A), (1C, 2E, 3C, 4A, 5B, 6B, 7B), (1C, 2E, 3C, 4A, 5B, 6B, 7C), (1C, 2E, 3C, 4A, 5B, 6C, 7A), (1C, 2E, 3C, 4A, 5B, 6C, 7B), (1C, 2E, 3C, 4A, 5B, 6C, 7C), (1C, 2E, 3C, 4A, 5B, 6D, 7A), (1C, 2E, 3C, 4A, 5B, 6D, 7B), (1C, 2E, 3C, 4A, 5B, 6D, 7C), (1C, 2E, 3C, 4B, 5A, 6A, 7A), (1C, 2E, 3C, 4B, 5A, 6A, 7B), (1C, 2E, 3C, 4B, 5A, 6A, 7C), (1C, 2E, 3C, 4B, 5A, 6B, 7A), (1C, 2E, 3C, 4B, 5A, 6B, 7B), (1C, 2E, 3C, 4B, 5A, 6B, 7C), (1C, 2E, 3C, 4B, 5A, 6C, 7A), (1C, 2E, 3C, 4B, 5A, 6C, 7B), (1C, 2E, 3C, 4B, 5A, 6C, 7C), (1C, 2E, 3C, 4B, 5A, 6D, 7A), (1C, 2E, 3C, 4B, 5A, 6D, 7B), (1C, 2E, 3C, 4B, 5A, 6D, 7C), (1C, 2E, 3C, 4B, 5B, 6A, 7A), (1C, 2E, 3C, 4B, 5B, 6A, 7B), (1C, 2E, 3C, 4B, 5B, 6A, 7C), (1C, 2E, 3C, 4B, 5B, 6B, 7A), (1C, 2E, 3C, 4B, 5B, 6B, 7B), (1C, 2E, 3C, 4B, 5B, 6B, 7C), (1C, 2E, 3C, 4B, 5B, 6C, 7A), (1C, 2E, 3C, 4B, 5B, 6C, 7B), (1C, 2E, 3C, 4B, 5B, 6C, 7C), (1C, 2E, 3C, 4B, 5B, 6D, 7A), (1C, 2E, 3C, 4B, 5B, 6D, 7B), (1C, 2E, 3C, 4B, 5B, 6D, 7C), (1C, 2E, 3C, 4C, 5A, 6A, 7A), (1C, 2E, 3C, 4C, 5A, 6A, 7B), (1C, 2E, 3C, 4C, 5A, 6A, 7C), (1C, 2E, 3C, 4C, 5A, 6B, 7A), (1C, 2E, 3C, 4C, 5A, 6B, 7B), (1C, 2E, 3C, 4C, 5A, 6B, 7C), (1C, 2E, 3C, 4C, 5A, 6C, 7A), (1C, 2E, 3C, 4C, 5A, 6C, 7B), (1C, 2E, 3C, 4C, 5A, 6C, 7C), (1C, 2E, 3C, 4C, 5A, 6D, 7A), (1C, 2E, 3C, 4C, 5A, 6D, 7B), (1C, 2E, 3C, 4C, 5A, 6D, 7C), (1C, 2E, 3C, 4C, 5B, 6A, 7A), (1C, 2E, 3C, 4C, 5B, 6A, 7B), (1C, 2E, 3C, 4C, 5B, 6A, 7C), (1C, 2E, 3C, 4C, 5B, 6B, 7A), (1C, 2E, 3C, 4C, 5B, 6B, 7B), (1C, 2E, 3C, 4C, 5B, 6B, 7C), (1C, 2E, 3C, 4C, 5B, 6C, 7A), (1C, 2E, 3C, 4C, 5B, 6C, 7B), (1C, 2E, 3C, 4C, 5B, 6C, 7C), (1C, 2E, 3C, 4C, 5B, 6D, 7A), (1C, 2E, 3C, 4C, 5B, 6D, 7B), (1C, 2E, 3C, 4C, 5B, 6D, 7C), (1C, 2E, 3C, 4D, 5A, 6A, 7A), (1C, 2E, 3C, 4D, 5A, 6A, 7B), (1C, 2E, 3C, 4D, 5A, 6A, 7C), (1C, 2E, 3C, 4D, 5A, 6B, 7A), (1C, 2E, 3C, 4D, 5A, 6B, 7B), (1C, 2E, 3C, 4D, 5A, 6B, 7C), (1C, 2E, 3C, 4D, 5A, 6C, 7A), (1C, 2E, 3C, 4D, 5A, 6C, 7B), (1C, 2E, 3C, 4D, 5A, 6C, 7C), (1C, 2E, 3C, 4D, 5A, 6D, 7A), (1C, 2E, 3C, 4D, 5A, 6D, 7B), (1C, 2E, 3C, 4D, 5A, 6D, 7C), (1C, 2E, 3C, 4D, 5B, 6A, 7A), (1C, 2E, 3C, 4D, 5B, 6A, 7B), (1C, 2E, 3C, 4D, 5B, 6A, 7C), (1C, 2E, 3C, 4D, 5B, 6B, 7A), (1C, 2E, 3C, 4D, 5B, 6B, 7B), (1C, 2E, 3C, 4D, 5B, 6B, 7C), (1C, 2E, 3C, 4D, 5B, 6C, 7A), (1C, 2E, 3C, 4D, 5B, 6C, 7B), (1C, 2E, 3C, 4D, 5B, 6C, 7C), (1C, 2E, 3C, 4D, 5B, 6D, 7A), (1C, 2E, 3C, 4D, 5B, 6D, 7B), (1C, 2E, 3C, 4D, 5B, 6D, 7C), (1C, 2E, 3C, 4E, 5A, 6A, 7A), (1C, 2E, 3C, 4E, 5A, 6A, 7B), (1C, 2E, 3C, 4E, 5A, 6A, 7C), (1C, 2E, 3C, 4E, 5A, 6B, 7A), (1C, 2E, 3C, 4E, 5A, 6B, 7B), (1C, 2E, 3C, 4E, 5A, 6B, 7C), (1C, 2E, 3C, 4E, 5A, 6C, 7A), (1C, 2E, 3C, 4E, 5A, 6C, 7B), (1C, 2E, 3C, 4E, 5A, 6C, 7C), (1C, 2E, 3C, 4E, 5A, 6D, 7A), (1C, 2E, 3C, 4E, 5A, 6D, 7B), (1C, 2E, 3C, 4E, 5A, 6D, 7C), (1C, 2E, 3C, 4E, 5B, 6A, 7A), (1C, 2E, 3C, 4E, 5B, 6A, 7B), (1C, 2E, 3C, 4E, 5B, 6A, 7C), (1C, 2E, 3C, 4E, 5B, 6B, 7A), (1C, 2E, 3C, 4E, 5B, 6B, 7B), (1C, 2E, 3C, 4E, 5B, 6B, 7C), (1C, 2E, 3C, 4E, 5B, 6C, 7A), (1C, 2E, 3C, 4E, 5B, 6C, 7B), (1C, 2E, 3C, 4E, 5B, 6C, 7C), (1C, 2E, 3C, 4E, 5B, 6D, 7A), (1C, 2E, 3C, 4E, 5B, 6D, 7B), (1C, 2E, 3C, 4E, 5B, 6D, 7C), (1C, 2E, 3D, 4A, 5A, 6A, 7A), (1C, 2E, 3D, 4A, 5A, 6A, 7B), (1C, 2E, 3D, 4A, 5A, 6A, 7C), (1C, 2E, 3D, 4A, 5A, 6B, 7A), (1C, 2E, 3D, 4A, 5A, 6B, 7B), (1C, 2E, 3D, 4A, 5A, 6B, 7C), (1C, 2E, 3D, 4A, 5A, 6C, 7A), (1C, 2E, 3D, 4A, 5A, 6C, 7B), (1C, 2E, 3D, 4A, 5A, 6C, 7C), (1C, 2E, 3D, 4A, 5A, 6D, 7A), (1C, 2E, 3D, 4A, 5A, 6D, 7B), (1C, 2E, 3D, 4A, 5A, 6D, 7C), (1C, 2E, 3D, 4A, 5B, 6A, 7A), (1C, 2E, 3D, 4A, 5B, 6A, 7B), (C, 2E, 3D, 4A, 5B, 6A, 7C), (1C, 2E, 3D, 4A, 5B, 6B, 7A), (1C, 2E, 3D, 4A, 5B, 6B, 7B), (1C, 2E, 3D, 4A, 5B, 6B, 7C), (1C, 2E, 3D, 4A, 5B, 6C, 7A), (1C, 2E, 3D, 4A, 5B, 6C, 7B), (1C, 2E, 3D, 4A, 5B, 6C, 7C), (1C, 2E, 3D, 4A, 5B, 6D, 7A), (1C, 2E, 3D, 4A, 5B, 6D, 7B), (1C, 2E, 3D, 4A, 5B, 6D, 7C), (1C, 2E, 3D, 4B, 5A, 6A, 7A), (1C, 2E, 3D, 4B, 5A, 6A, 7B), (1C, 2E, 3D, 4B, 5A, 6A, 7C), (1C, 2E, 3D, 4B, 5A, 6B, 7A), (1C, 2E, 3D, 4B, 5A, 6B, 7B), (1C, 2E, 3D, 4B, 5A, 6B, 7C), (1C, 2E, 3D, 4B, 5A, 6C, 7A), (1C, 2E, 3D, 4B, 5A, 6C, 7B), (1C, 2E, 3D, 4B, 5A, 6C, 7C), (1C, 2E, 3D, 4B, 5A, 6D, 7A), (1C, 2E, 3D, 4B, 5A, 6D, 7B), (1C, 2E, 3D, 4B, 5A, 6D, 7C), (1C, 2E, 3D, 4B, 5B, 6A, 7A), (1C, 2E, 3D, 4B, 5B, 6A, 7B), (1C, 2E, 3D, 4B, 5B, 6A, 7C), (1C, 2E, 3D, 4B, 5B, 6B, 7A), (1C, 2E, 3D, 4B, 5B, 6B, 7B), (1C, 2E, 3D, 4B, 5B, 6B, 7C), (1C, 2E, 3D, 4B, 5B, 6C, 7A), (1C, 2E, 3D, 4B, 5B, 6C, 7B), (1C, 2E, 3D, 4B, 5B, 6C, 7C), (1C, 2E, 3D, 4B, 5B, 6D, 7A), (1C, 2E, 3D, 4B, 5B, 6D, 7B), (1C, 2E, 3D, 4B, 5B, 6D, 7C), (1C, 2E, 3D, 4C, 5A, 6A, 7A), (1C, 2E, 3D, 4C, 5A, 6A, 7B), (1C, 2E, 3D, 4C, 5A, 6A, 7C), (1C, 2E, 3D, 4C, 5A, 6B, 7A), (1C, 2E, 3D, 4C, 5A, 6B, 7B), (1C, 2E, 3D, 4C, 5A, 6B, 7C), (1C, 2E, 3D, 4C, 5A, 6C, 7A), (1C, 2E, 3D, 4C, 5A, 6C, 7B), (1C, 2E, 3D, 4C, 5A, 6C, 7C), (1C, 2E, 3D, 4C, 5A, 6D, 7A), (1C, 2E, 3D, 4C, 5A, 6D, 7B), (1C, 2E, 3D, 4C, 5A, 6D, 7C), (1C, 2E, 3D, 4C, 5B, 6A, 7A), (1C, 2E, 3D, 4C, 5B, 6A, 7B), (1C, 2E, 3D, 4C, 5B, 6A, 7C), (1C, 2E, 3D, 4C, 5B, 6B, 7A), (1C, 2E, 3D, 4C, 5B, 6B, 7B), (1C, 2E, 3D, 4C, 5B, 6B, 7C), (1C, 2E, 3D, 4C, 5B, 6C, 7A), (1C, 2E, 3D, 4C, 5B, 6C, 7B), (1C, 2E, 3D, 4C, 5B, 6C, 7C), (1C, 2E, 3D, 4C, 5B, 6D, 7A), (1C, 2E, 3D, 4C, 5B, 6D, 7B), (1C, 2E, 3D, 4C, 5B, 6D, 7C), (1C, 2E, 3D, 4D, 5A, 6A, 7A), (1C, 2E, 3D, 4D, 5A, 6A, 7B), (1C, 2E, 3D, 4D, 5A, 6A, 7C), (1C, 2E, 3D, 4D, 5A, 6B, 7A), (1C, 2E, 3D, 4D, 5A, 6B, 7B), (1C, 2E, 3D, 4D, 5A, 6B, 7C), (1C, 2E, 3D, 4D, 5A, 6C, 7A), (1C, 2E, 3D, 4D, 5A, 6C, 7B), (1C, 2E, 3D, 4D, 5A, 6C, 7C), (1C, 2E, 3D, 4D, 5A, 6D, 7A), (1C, 2E, 3D, 4D, 5A, 6D, 7B), (1C, 2E, 3D, 4D, 5A, 6D, 7C), (1C, 2E, 3D, 4D, 5B, 6A, 7A), (1C, 2E, 31D, 4D, 5B, 6A, 7B), (1C, 2E, 3D, 4D, 5B, 6A, 7C), (1C, 2E, 3D, 4D, 5B, 6B, 7A), (1C, 2E, 3D, 4D, 5B, 6B, 7B), (1C, 2E, 3D, 4D, 5B, 6B, 7C), (1C, 2E, 3D, 4D, 5B, 6C, 7A), (1C, 2E, 3D, 4D, 5B, 6C, 7B), (1C, 2E, 3D, 4D, 5B, 6C, 7C), (1C, 2E, 3D, 4D, 5B, 6D, 7A), (1C, 2E, 3D, 4D, 5B, 6D, 7B), (1C, 2E, 3D, 4D, 5B, 6D, 7C), (1C, 2E, 3D, 4E, 5A, 6A, 7A), (1C, 2E, 3D, 4E, 5A, 6A, 7B), (1C, 2E, 3D, 4E, 5A, 6A, 7C), (1C, 2E, 3D, 4E, 5A, 6B, 7A), (1C, 2E, 3D, 4E, 5A, 6B, 7B), (1C, 2E, 3D, 4E, 5A, 6B, 7C), (1C, 2E, 3D, 4E, 5A, 6C, 7A), (1C, 2E, 3D, 4E, 5A, 6C, 7B), (1C, 2E, 3D, 4E, 5A, 6C, 7C), (1C, 2E, 3D, 4E, 5A, 6D, 7A), (1C, 2E, 3D, 4E, 5A, 6D, 7B), (1C, 2E, 3D, 4E, 5A, 6D, 7C), (1C, 2E, 3D, 4E, 5B, 6A, 7A), (1C, 2E, 3D, 4E, 5B, 6A, 7B), (1C, 2E, 3D, 4E, 5B, 6A, 7C), (1C, 2E, 3D, 4E, 5B, 6B, 7A), (1C, 2E, 3D, 4E, 5B, 6B, 7B), (1C, 2E, 3D, 4E, 5B, 6B, 7C), (1C, 2E, 3D, 4E, 5B, 6C, 7A), (1C, 2E, 3D, 4E, 5B, 6C, 7B), (1C, 2E, 3D, 4E, 5B, 6C, 7C), (1C, 2E, 3D, 4E, 5B, 6D, 7A), (1C, 2E, 3D, 4E, 5B, 6D, 7B), (1C, 2E, 3D, 4E, 5B, 6D, 7C), (1C, 2E, 3E, 4A, 5A, 6A, 7A), (1C, 2E, 3E, 4A, 5A, 6A, 7B), (1C, 2E, 3E, 4A, 5A, 6A, 7C), (1C, 2E, 3E, 4A, 5A, 6B, 7A), (1C, 2E, 3E, 4A, 5A, 6B, 7B), (1C, 2E, 3E, 4A, 5A, 6B, 7C), (1C, 2E, 3E, 4A, 5A, 6C, 7A), (1C, 2E, 3E, 4A, 5A, 6C, 7B), (1C, 2E, 3E, 4A, 5A, 6C, 7C), (1C, 2E, 3E, 4A, 5A, 6D, 7A), (1C, 2E, 3E, 4A, 5A, 6D, 7B), (1C, 2E, 3E, 4A, 5A, 6D, 7C), (1C, 2E, 3E, 4A, 5B, 6A, 7A), (1C, 2E, 3E, 4A, 5B, 6A, 7B), (1C, 2E, 3E, 4A, 5B, 6A, 7C), (1C, 2E, 3E, 4A, 5B, 6B, 7A), (1C, 2E, 3E, 4A, 5B, 6B, 7B), (1C, 2E, 3E, 4A, 5B, 6B, 7C), (1C, 2E, 3E, 4A, 5B, 6C, 7A), (1C, 2E, 3E, 4A, 5B, 6C, 7B), (1C, 2E, 3E, 4A, 5B, 6C, 7C), (1C, 2E, 3E, 4A, 5B, 6D, 7A), (1C, 2E, 3E, 4A, 5B, 6D, 7B), (1C, 2E, 3E, 4A, 5B, 6D, 7C), (1C, 2E, 3E, 4B, 5A, 6A, 7A), (1C, 2E, 3E, 4B, 5A, 6A, 7B), (1C, 2E, 3E, 4B, 5A, 6A, 7C), (1C, 2E, 3E, 4B, 5A, 6B, 7A), (1C, 2E, 3E, 4B, 5A, 6B, 7B), (1C, 2E, 3E, 4B, 5A, 6B, 7C), (1C, 2E, 3E, 4B, 5A, 6C, 7A), (1C, 2E, 3E, 4B, 5A, 6C, 7B), (1C, 2E, 3E, 4B, 5A, 6C, 7C), (1C, 2E, 3E, 4B, 5A, 6D, 7A), (1C, 2E, 3E, 4B, 5A, 6D, 7B), (1C, 2E, 3E, 4B, 5A, 6D, 7C), (1C, 2E, 3E, 4B, 5B, 6A, 7A), (1C, 2E, 3E, 4B, 5B, 6A, 7B), (1C, 2E, 3E, 4B, 5B, 6A, 7C), (1C, 2E, 3E, 4B, 5B, 6B, 7A), (1C, 2E, 3E, 4B, 5B, 6B, 7B), (1C, 2E, 3E, 4B, 5B, 6B, 7C), (1C, 2E, 3E, 4B, 5B, 6C, 7A), (1C, 2E, 3E, 4B, 5B, 6C, 7B), (1C, 2E, 3E, 4B, 5B, 6C, 7C), (1C, 2E, 3E, 4B, 5B, 6D, 7A), (1C, 2E, 3E; 4B, 5B, 6D, 7B), (1C, 2E, 3E, 4B, 5B, 6D, 7C), (1C, 2E, 3E, 4C, 5A, 6A, 7A), (1C, 2E, 3E, 4C, 5A, 6A, 7B), (1C, 2E, 3E, 4C, 5A, 6A, 7C), (1C, 2E, 3E, 4C, 5A, 6B, 7A), (1C, 2E, 3E, 4C, 5A, 6B, 7B), (1C, 2E, 3E, 4C, 5A, 6B, 7C), (1C, 2E, 3E, 4C, 5A, 6C, 7A), (1C, 2E, 3E, 4C, 5A, 6C, 7B), (1C, 2E, 3E, 4C, 5A, 6C, 7C), (1C, 2E, 3E, 4C, 5A, 6D, 7A), (1C, 2E, 3E, 4C, 5A, 6D, 7B), (1C, 2E, 3E, 4C, 5A, 6D, 7C), (1C, 2E, 3E, 4C, 5B, 6A, 7A), (1C, 2E, 3E, 4C, 5B, 6A, 7B), (1C, 2E, 3E, 4C, 5B, 6A, 7C), (1C, 2E, 3E, 4C, 5B, 6B, 7A), (1C, 2E, 3E, 4C, 5B, 6B, 7B), (1C, 2E, 3E, 4C, 5B, 6B, 7C), (1C, 2E, 3E, 4C, 5B, 6C, 7A), (1C, 2E, 3E, 4C, 5B, 6C, 7B), (1C, 2E, 3E, 4C, 5B, 6C, 7C), (1C, 2E, 3E, 4C, 5B, 6D, 7A), (1C, 2E, 3E, 4C, 5B, 6D, 7B), (1C, 2E, 3E, 4C, 5B, 6D, 7C), (1C, 2E, 3E, 4D, 5A, 6A, 7A), (1C, 2E, 3E, 4D, 5A, 6A, 7B), (1C, 2E, 3E, 4D, 5A, 6A, 7C), (1C, 2E, 3E, 4D, 5A, 6B, 7A), (1C, 2E, 3E, 4D, 5A, 6B, 7B), (1C, 2E, 3E, 4D, 5A, 6B, 7C), (1C, 2E, 3E, 4D, 5A, 6C, 7A), (1C, 2E, 3E, 4D, 5A, 6C, 7B), (1C, 2E, 3E, 4D, 5A, 6C, 7C), (1C, 2E, 3E, 4D, 5A, 6D, 7A), (1C, 2E, 3E, 4D, 5A, 6D, 7B), (1C, 2E, 3E, 4D, 5A, 6D, 7C), (1C, 2E, 3E, 4D, 5B, 6A, 7A), (1C, 2E, 3E, 4D, 5B, 6A, 7B), (1C, 2E, 3E, 4D, 5B, 6A, 7C), (1C, 2E, 3E, 4D, 5B, 6B, 7A), (1C, 2E, 3E, 4D, 5B, 6B, 7B), (1C, 2E, 3E, 4D, 5B, 6B, 7C), (1C, 2E, 3E, 4D, 5B, 6C, 7A), (1C, 2E, 3E, 4D, 5B, 6C, 7B), (1C, 2E, 3E, 4D, 5B, 6C, 7C), (1C, 2E, 3E, 4D, 5B, 6D, 7A), (1C, 2E, 3E, 4D, 5B, 6D, 7B), (1C, 2E, 3E, 4D, 5B, 6D, 7C), (1C, 2E, 3E, 4E, 5A, 6A, 7A), (1C, 2E, 3E, 4E, 5A, 6A, 7B), (1C, 2E, 3E, 4E, 5A, 6A, 7C), (1C, 2E, 3E, 4E, 5A, 6B, 7A), (1C, 2E, 3E, 4E, 5A, 6B, 7B), (1C, 2E, 3E, 4E, 5A, 6B, 7C), (1C, 2E, 3E, 4E, 5A, 6C, 7A), (1C, 2E, 3E, 4E, 5A, 6C, 7B), (1C, 2E, 3E, 4E, 5A, 6C, 7C), (1C, 2E, 3E, 4E, 5A, 6D, 7A), (1C, 2E, 3E, 4E, 5A, 6D, 7B), (1C, 2E, 3E, 4E, 5A, 6D, 7C), (1C, 2E, 3E, 4E, 5B, 6A, 7A), (1C, 2E, 3E, 4E, 5B, 6A, 7B), (1C, 2E, 3E, 4E, 5B, 6A, 7C), (1C, 2E, 3E, 4E, 5B, 6B, 7A), (1C, 2E, 3E, 4E, 5B, 6B, 7B), (1C, 2E, 3E, 4E, 5B, 6B, 7C), (1C, 2E, 3E, 4E, 5B, 6C, 7A), (1C, 2E, 3E, 4E, 5B, 6C, 7B), (1C, 2E, 3E, 4E, 5B, 6C, 7C), (1C, 2E, 3E, 4E, 5B, 6D, 7A), (1C, 2E, 3E, 4E, 5B, 6D, 7B), (1C, 2E, 3E, 4E, 5B, 6D, 7C), (1D, 2A, 3A, 4A, 5A, 6A, 7A), (1D, 2A, 3A, 4A, 5A, 6A, 7B). (1D, 2A, 3A, 4A, 5A, 6A, 7C), (1D, 2A, 3A, 4A, 5A, 6B, 7A), (1D, 2A, 3A, 4A, 5A, 6B, 7B), (1D, 2A, 3A, 4A, 5A, 6B, 7C), (1D, 2A, 3A, 4A, 5A, 6C, 7A), (1D, 2A, 3A, 4A, 5A, 6C, 7B), (1D, 2A, 3A, 4A, 5A, 6C, 7C), (1D, 2A, 3A, 4A, 5A, 6D, 7A), (1D, 2A, 3A, 4A, 5A, 6D, 7B), (1D, 2A, 3A, 4A, 5A, 6D, 7C), (1D, 2A, 3A, 4A, 5B, 6A, 7A), (1D, 2A, 3A, 4A, 5B, 6A, 7B), (1D, 2A, 3A, 4A, 5B, 6A, 7C), (1D, 2A, 3A, 4A, 5B, 6B, 7A), (1D, 2A, 3A, 4A, 5B, 6B, 7B), (1D, 2A, 3A, 4A, 5B, 6B, 7C), (1D, 2A, 3A, 4A, 5B, 6C, 7A), (1D, 2A, 3A, 4A, 5B, 6C, 7B), (1D, 2A, 3A, 4A, 5B, 6C, 7C), (1D, 2A, 3A, 4A, 5B, 6D, 7A), (1D, 2A, 3A, 4A, 5B, 6D, 7B), (1D, 2A, 3A, 4A, 5B, 6D, 7C), (1D, 2A, 3A, 4B, 5A, 6A, 7A), (1D, 2A, 3A, 4B, 5A, 6A, 7B), (1D, 2A, 3A, 4B, 5A, 6A, 7C), (1D, 2A, 3A, 4B, 5A, 6B, 7A), (1D, 2A, 3A, 4B, 5A, 6B, 7B), (1D, 2A, 3A, 4B, 5A, 6B, 7C), (1D, 2A, 3A, 4B, 5A, 6C, 7A), (1D, 2A, 3A, 4B, 5A, 6C, 7B), (1D, 2A, 3A, 4B, 5A, 6C, 7C), (1D, 2A, 3A, 4B, 5A, 6D, 7A), (1D, 2A, 3A, 4B, 5A, 6D, 7B), (1D, 2A, 3A, 4B, 5A, 6D, 7C), (1D, 2A, 3A, 4B, 5B, 6A, 7A), (1D, 2A, 3A, 4B, 5B, 6A, 7B), (1D, 2A, 3A, 4B, 5B, 6A, 7C), (1D, 2A, 3A, 4B, 5B, 6B, 7A), (1D, 2A, 3A, 4B, 5B, 6B, 7B), (1D, 2A, 3A, 4B, 5B, 6B, 7C), (1D, 2A, 3A, 4B, 5B, 6C, 7A), (1D, 2A, 3A, 4B, 5B, 6C, 7B), (1D, 2A, 3A, 4B, 5B, 6C, 7C), (1D, 2A, 3A, 4B, 5B, 6D, 7A), (1D, 2A, 3A, 4B, 5B, 6D, 7B), (1D, 2A, 3A, 4B, 5B, 6D, 7C), (1D, 2A, 3A, 4C, 5A, 6A, 7A), (1D, 2A, 3A, 4C, 5A, 6A, 7B), (1D, 2A, 3A, 4C, 5A, 6A, 7C), (1D, 2A, 3A, 4C, 5A, 6B, 7A), (1D, 2A, 3A, 4C, 5A, 6B, 7B), (1D, 2A, 3A, 4C, 5A, 6B, 7C), (1D, 2A, 3A, 4C, 5A, 6C, 7A), (1D, 2A, 3A, 4C, 5A, 6C, 7B), (1D, 2A, 3A, 4C, 5A, 6C, 7C), (1D, 2A, 3A, 4C, 5A, 6D, 7A), (1D, 2A, 3A, 4C, 5A, 6D, 7B), (1D, 2A, 3A, 4C, 5A, 6D, 7C), (1D, 2A, 3A, 4C, 5B, 6A, 7A), (1D, 2A, 3A, 4C, 5B, 6A, 7B), (1D, 2A, 3A, 4C, 5B, 6A, 7C), (1D, 2A, 3A, 4C, 5B, 6B, 7A), (1D, 2A, 3A, 4C, 5B, 6B, 7B), (1D, 2A, 3A, 4C, 5B, 6B, 7C), (1D, 2A, 3A, 4C, 5B, 6C, 7A), (1D, 2A, 3A, 4C, 5B, 6C, 7B), (1D, 2A, 3A, 4C, 5B, 6C, 7C), (1D, 2A, 3A, 4C, 5B, 6D, 7A), (1D, 2A, 3A, 4C, 5B, 6D, 7B), (1D, 2A, 3A, 4C, 5B, 6D, 7C), (1D, 2A, 3A, 4D, 5A, 6A, 7A), (1D, 2A, 3A, 4D, 5A, 6A, 7B), (1D, 2A, 3A, 4D, 5A, 6A, 7C), (1D, 2A, 3A, 4D, 5A, 6B, 7A), (1D, 2A, 3A, 4D, 5A, 6B, 7B), (D, 2A, 3A, 4D, 5A, 6B, 7C), (1D, 2A, 3A, 4D, 5A, 6C, 7A), (1D, 2A, 3A, 4D, 5A, 6C, 7B), (1D, 2A, 3A, 4D, 5A, 6C, 7C), (1D, 2A, 3A, 4D, 5A, 6D, 7A), (1D, 2A, 3A, 4D, 5A, 6D, 7B), (1D, 2A, 3A, 4D, 5A, 6D, 7C), (1D, 2A, 3A, 4D, 5B, 6A, 7A), (1D, 2A, 3A, 4D, 5B, 6A, 7B), (1D, 2A, 3A, 4D, 5B, 6A, 7C), (1D, 2A, 3A, 4D, 5B, 6B, 7A), (1D, 2A, 3A, 4D, 5B, 6B, 7B), (1D, 2A, 3A, 4D, 5B, 6B, 7C), (1D, 2A, 3A, 4D, 5B, 6C, 7A), (1D, 2A, 3A, 4D, 5B, 6C, 7B), (1D, 2A, 3A, 4D, 5B, 6C, 7C), (1D, 2A, 3A, 4D, 5B, 6D, 7A), (1D, 2A, 3A, 4D, 5B, 6D, 7B), (1D, 2A, 3A, 4D, 5B, 6D, 7C), (1D, 2A, 3A, 4E, 5A, 6A, 7A), (1D, 2A, 3A, 4E, 5A, 6A, 7B), (1D, 2A, 3A, 4E, 5A, 6A, 7C), (1D, 2A, 3A, 4E, 5A, 6B, 7A), (1D, 2A, 3A, 4E, 5A, 6B, 7B), (1D, 2A, 3A, 4E, 5A, 6B, 7C), (1D, 2A, 3A, 4E, 5A, 6C, 7A), (1D, 2A, 3A, 4E, 5A, 6C, 7B), (1D, 2A, 3A, 4E, 5A, 6C, 7C), (1D, 2A, 3A, 4E, 5A, 6D, 7A), (1D, 2A, 3A, 4E, 5A, 6D, 7B), (1D, 2A, 3A, 4E, 5A, 6D, 7C), (1D, 2A, 3A, 4E, 5B, 6A, 7A), (1D, 2A, 3A, 4E, 5B, 6A, 7B), (1D, 2A, 3A, 4E, 5B, 6A, 7C), (1D, 2A, 3A, 4E, 5B, 6B, 7A), (1D, 2A, 3A, 4E, 5B, 6B, 7B), (1D, 2A, 3A, 4E, 5B, 6B, 7C), (1D, 2A, 3A, 4E, 5B, 6C, 7A), (1D, 2A, 3A, 4E, 5B, 6C, 7B), (1D, 2A, 3A, 4E, 5B, 6C, 7C), (1D, 2A, 3A, 4E, 5B, 6D, 7A), (1D, 2A, 3A, 4E, 5B, 6D, 7B), (1D, 2A, 3A, 4E, 5B, 6D, 7C), (1D, 2A, 3B, 4A, 5A, 6A, 7A), (1D, 2A, 3B, 4A, 5A, 6A, 7B), (1D, 2A, 3B, 4A, 5A, 6A, 7C), (1D, 2A, 3B, 4A, 5A, 6B, 7A), (1D, 2A, 3B, 4A, 5A, 6B, 7B), (1D, 2A, 3B, 4A, 5A, 6B, 7C), (1D, 2A, 3B, 4A, 5A, 6C, 7A), (1D, 2A, 3B, 4A, 5A, 6C, 7B), (1D, 2A, 3B, 4A, 5A, 6C, 7C), (1D, 2A, 3B, 4A, 5A, 6D, 7A), (1D, 2A, 3B, 4A, 5A, 6D, 7B), (1D, 2A, 3B, 4A, 5A, 6D, 7C), (1D, 2A, 3B, 4A, 5B, 6A, 7A), (1D, 2A, 3B, 4A, 5B, 6A, 7B), (1D, 2A, 3B, 4A, 5B, 6A, 7C), (1D, 2A, 3B, 4A, 5B, 6B, 7A), (1D, 2A, 3B, 4A, 5B, 6B, 7B), (1D, 2A, 3B, 4A, 5B, 6B, 7C), (1D, 2A, 3B, 4A, 5B, 6C, 7A), (1D, 2A, 3B, 4A, 5B, 6C, 7B), (1D, 2A, 3B, 4A, 5B, 6C, 7C), (1D, 2A, 3B, 4A, 5B, 6D, 7A), (1D, 2A, 3B, 4A, 5B, 6D, 7B), (1D, 2A, 3B, 4A, 5B, 6D, 7C), (1D, 2A, 3B, 4B, 5A, 6A, 7A), (1D, 2A, 3B, 4B, 5A, 6A, 7B), (1D, 2A, 3B, 4B, 5A, 6A, 7C), (1D, 2A, 3B, 4B, 5A, 6B, 7A), (1D, 2A, 3B, 4B, 5A, 6B, 7B), (1D, 2A, 3B, 4B, 5A, 6B, 7C), (1D, 2A, 3B, 4B, 5A, 6C, 7A), (1D, 2A, 3B, 4B, 5A, 6C, 7B), (1D, 2A, 3B, 4B, 5A, 6C, 7C), (1D, 2A, 3B, 4B, 5A, 6D, 7A), (1D, 2A, 3B, 4B, 5A, 6D, 7B), (1D, 2A, 3B, 4B, 5A, 6D, 7C), (1D, 2A, 3B, 4B, 5B, 6A, 7A), (1D, 2A, 3B, 4B, 5B, 6A, 7B), (1D, 2A, 3B, 4B, 5B, 6A, 7C), (1D, 2A, 3B, 4B, 5B, 6B, 7A), (1D, 2A, 3B, 4B, 5B, 6B, 7B), (1D, 2A, 3B, 4B, 5B, 6B, 7C), (1D, 2A, 3B, 4B, 5B, 6C, 7A), (1D, 2A, 3B, 4B, 5B, 6C, 7B), (1D, 2A, 3B, 4B, 5B, 6C, 7C), (1D, 2A, 3B, 4B, 5B, 6D, 7A), (1D, 2A, 3B, 4B, 5B, 6D, 7B), (1D, 2A, 3B, 4B, 5B, 6D, 7C), (1D, 2A, 3B, 4C, 5A, 6A, 7A), (1D, 2A, 3B, 4C, 5A, 6A, 7B), (1D, 2A, 3B, 4C, 5A, 6A, 7C), (1D, 2A, 3B, 4C, 5A, 6B, 7A), (1D, 2A, 3B, 4C, 5A, 6B, 7B), (1D, 2A, 3B, 4C, 5A, 6B, 7C), (1D, 2A, 3B, 4C, 5A, 6C, 7A), (1D, 2A, 3B, 4C, 5A, 6C, 7B), (1D, 2A, 3B, 4C, 5A, 6C, 7C), (1D, 2A, 3B, 4C, 5A, 6D, 7A), (1D, 2A, 3B, 4C, 5A, 6D, 7B), (1D, 2A, 3B, 4C, 5A, 6D, 7C), (1D, 2A, 3B, 4C, 5B, 6A, 7A), (1D, 2A, 3B, 4C, 5B, 6A, 7B), (1D, 2A, 3B, 4C, 5B, 6A, 7C), (1D, 2A, 3B, 4C, 5B, 6B, 7A), (1D, 2A, 3B, 4C, 5B, 6B, 7B), (1D, 2A, 3B, 4C, 5B, 6B, 7C), (1D, 2A, 3B, 4C, 5B, 6C, 7A), (1D, 2A, 3B, 4C, 5B, 6C, 7B), (1D, 2A, 3B, 4C, 5B, 6C, 7C), (1D, 2A, 3B, 4C, 5B, 6D, 7A), (1D, 2A, 3B, 4C, 5B, 6D, 7B), (1D, 2A, 3B, 4C, 5B, 6D, 7C), (1D, 2A, 3B, 4D, 5A, 6A, 7A), (1D, 2A, 3B, 4D, 5A, 6A, 7B), (1D, 2A, 3B, 4D, 5A, 6A, 7C), (1D, 2A, 3B, 4D, 5A, 6B, 7A), (1D, 2A, 3B, 4D, 5A, 6B, 7B), (1D, 2A, 3B, 4D, 5A, 6B, 7C), (1D, 2A, 3B, 4D, 5A, 6C, 7A), (1D, 2A, 3B, 4D, 5A, 6C, 7B), (1D, 2A, 3B, 4D, 5A, 6C, 7C), (1D, 2A, 3B, 4D, 5A, 6D, 7A), (1D, 2A, 3B, 4D, 5A, 6D, 7B), (1D, 2A, 3B, 4D, 5A, 6D, 7C), (1D, 2A, 3B, 4D, 5B, 6A, 7A), (1D, 2A, 3B, 4D, 5B, 6A, 7B), (1D, 2A, 3B, 4D, 5B, 6A, 7C), (1D, 2A, 3B, 4D, 5B, 6B, 7A), (1D, 2A, 3B, 4D, 5B, 6B, 7B), (1D, 2A, 3B, 4D, 5B, 6B, 7C), (1D, 2A, 3B, 4D, 5B, 6C, 7A), (1D, 2A, 3B, 4D, 5B, 6C, 7B), (1D, 2A, 3B, 4D, 5B, 6C, 7C), (1D, 2A, 3B, 4D, 5B, 6D, 7A), (1D, 2A, 3B, 4D, 5B, 6D, 7B), (1D, 2A, 3B, 4D, 5B, 6D, 7C), (1D, 2A, 3B, 4E, 5A, 6A, 7A), (1D, 2A, 3B, 4E, 5A, 6A, 7B), (1D, 2A, 3B, 4E, 5A, 6A, 7C), (1D, 2A, 3B, 4E, 5A, 6B, 7A), (1D, 2A, 3B, 4E, 5A, 6B, 7B), (1D, 2A, 3B, 4E, 5A, 6B, 7C), (1D, 2A, 3B, 4E, 5A, 6C, 7A), (1D, 2A, 3B, 4E, 5A, 6C, 7B), (1D, 2A, 3B, 4E, 5A, 6C, 7C), (1D, 2A, 3B, 4E, 5A, 6D, 7A), (1D, 2A, 3B, 4E, 5A, 6D, 7B), (1D, 2A, 3B, 4E, 5A, 6D, 7C), (1D, 2A, 3B, 4E, 5B, 6A, 7A), (1D, 2A, 3B, 4E, 5B, 6A, 7B), (1D, 2A, 3B, 4E, 5B, 6A, 7C), (1D, 2A, 3B, 4E, 5B, 6B, 7A), (1D, 2A, 3B, 4E, 5B, 6B, 7B), (1D, 2A, 3B, 4E, 5B, 6B, 7C), (1D, 2A, 3B, 4E, 5B, 6C, 7A), (1D, 2A, 3B, 4E, 5B, 6C, 7B), (1D, 2A, 3B, 4E, 5B, 6C, 7C), (1D, 2A, 3B, 4E, 5B, 6D, 7A), (1D, 2A, 3B, 4E, 5B, 6D, 7B), (1D, 2A, 3B, 4E, 5B, 6D, 7C), (1D, 2A, 3C, 4A, 5A, 6A, 7A), (1D, 2A, 3C, 4A, 5A, 6A, 7B), (1D, 2A, 3C, 4A, 5A, 6A, 7C), (1D, 2A, 3C, 4A, 5A, 6B, 7A), (1D, 2A, 3C, 4A, 5A, 6B, 7B), (1D, 2A, 3C, 4A, 5A, 6B, 7C), (1D, 2A, 3C, 4A, 5A, 6C, 7A), (1D, 2A, 3C, 4A, 5A, 6C, 7B), (1D, 2A, 3C, 4A, 5A, 6C, 7C), (1D, 2A, 3C, 4A, 5A, 6D, 7A), (1D, 2A, 3C, 4A, 5A, 6D, 7B), (1D, 2A, 3C, 4A, 5A, 6D, 7C), (1D, 2A, 3C, 4A, 5B, 6A, 7A), (1D, 2A, 3C, 4A, 5B, 6A, 7B), (1D, 2A, 3C, 4A, 5B, 6A, 7C), (1D, 2A, 3C, 4A, 5B, 6B, 7A), (1D, 2A, 3C, 4A, 5B, 6B, 7B), (1D, 2A, 3C, 4A, 5B, 6B, 7C), (1D, 2A, 3C, 4A, 5B, 6C, 7A), (1D, 2A, 3C, 4A, 5B, 6C, 7B), (1D, 2A, 3C, 4A, 5B, 6C, 7C), (1D, 2A, 3C, 4A, 5B, 6D, 7A), (1D, 2A, 3C, 4A, 5B, 6D, 7B), (1D, 2A, 3C, 4A, 5B, 6D, 7C), (1D, 2A, 3C, 4B, 5A, 6A, 7A), (1D, 2A, 3C, 4B, 5A, 6A, 7B), (1D, 2A, 3C, 4B, 5A, 6A, 7C), (1D, 2A, 3C, 4B, 5A, 6B, 7A), (1D, 2A, 3C, 4B, 5A, 6B, 7B), (1D, 2A, 3C, 4B, 5A, 6B, 7C), (1D, 2A, 3C, 4B, 5A, 6C, 7A), (1D, 2A, 3C, 4B, 5A, 6C, 7B), (1D, 2A, 3C, 4B, 5A, 6C, 7C), (1D, 2A, 3C, 4B, 5A, 6D, 7A), (1D, 2A, 3C, 4B, 5A, 6D, 7B), (1D, 2A, 3C, 4B, 5A, 6D, 7C), (1D, 2A, 3C, 4B, 5B, 6A, 7A), (1D, 2A, 3C, 4B, 5B, 6A, 7B), (1D, 2A, 3C, 4B, 5B, 6A, 7C), (1D, 2A, 3C, 4B, 5B, 6B, 7A), (1D, 2A, 3C, 4B, 5B, 6B, 7B), (1D, 2A, 3C, 4B, 5B, 6B, 7C), (1D, 2A, 3C, 4B, 5B, 6C, 7A), (1D, 2A, 3C, 4B, 5B, 6C, 7B), (1D, 2A, 3C, 4B, 5B, 6C, 7C), (1D, 2A, 3C, 4B, 5B, 6D, 7A), (1D, 2A, 3C, 4B, 5B, 6D, 7B), (1D, 2A, 3C, 4B, 5B, 6D, 7C), (1D, 2A, 3C, 4C, 5A, 6A, 7A), (1D, 2A, 3C, 4C, 5A, 6A, 7B), (1D, 2A, 3C, 4C, 5A, 6A, 7C), (1D, 2A, 3C, 4C, 5A, 6B, 7A), (1D, 2A, 3C, 4C, 5A, 6B, 7B), (1D, 2A, 3C, 4C, 5A, 6B, 7C), (1D, 2A, 3C, 4C, 5A, 6C, 7A), (1D, 2A, 3C, 4C, 5A, 6C, 7B), (1D, 2A, 3C, 4C, 5A, 6C, 7C), (1D, 2A, 3C, 4C, 5A, 6D, 7A), (1D, 2A, 3C, 4C, 5A, 6D, 7B), (1D, 2A, 3C, 4C, 5A, 6D, 7C), (1D, 2A, 3C, 4C, 5B, 6A, 7A), (1D, 2A, 3C, 4C, 5B, 6A, 7B), (1D, 2A, 3C, 4C, 5B, 6A, 7C), (1D, 2A, 3C, 4C, 5B, 6B, 7A), (1D, 2A, 3C, 4C, 5B, 6B, 7B), (1D, 2A, 3C, 4C, 5B, 6B, 7C), (1D, 2A, 3C, 4C, 5B, 6C, 7A), (1D, 2A, 3C, 4C, 5B, 6C, 7B), (1D, 2A, 3C, 4C, 5B, 6C, 7C), (1D, 2A, 3C, 4C, 5B, 6D, 7A), (1D, 2A, 3C, 4C, 5B, 6D, 7B), (1D, 2A, 3C, 4C, 5B, 6D, 7C), (1D, 2A, 3C, 4D, 5A, 6A, 7A), (1D, 2A, 3C, 4D, 5A, 6A, 7B), (1D, 2A, 3C, 4D, 5A, 6A, 7C), (1D, 2A, 3C, 4D, 5A, 6B, 7A), (1D, 2A, 3C, 4D, 5A, 6B, 7B), (1D, 2A, 3C, 4D, 5A, 6B, 7C), (1D, 2A, 3C, 4D, 5A, 6C, 7A), (1D, 2A, 3C, 4D, 5A, 6C, 7B), (1D, 2A, 3C, 4D, 5A, 6C, 7C), (1D, 2A, 3C, 4D, 5A, 6D, 7A), (1D, 2A, 3C, 4D, 5A, 6D, 7B), (1D, 2A, 3C, 4D, 5A, 6D, 7C), (1D, 2A, 3C, 4D, 5B, 6A, 7A), (1D, 2A, 3C, 4D, 5B, 6A, 7B), (1D, 2A, 3C, 4D, 5B, 6A, 7C), (1D, 2A, 3C, 4D, 5B, 6B, 7A), (1D, 2A, 3C, 4D, 5B, 6B, 7B), (1D, 2A, 3C, 4D, 5B, 6B, 7C), (1D, 2A, 3C, 4D, 5B, 6C, 7A), (1D, 2A, 3C, 4D, 5B, 6C, 7B), (1D, 2A, 3C, 4D, 5B, 6C, 7C), (1D, 2A, 3C, 4D, 5B, 6D, 7A), (1D, 2A, 3C, 4D, 5B, 6D, 7B), (1D, 2A, 3C, 4D, 5B, 6D, 7C), (1D, 2A, 3C, 4E, 5A, 6A, 7A), (1D, 2A, 3C, 4E, 5A, 6A, 7B), (1D, 2A, 3C, 4E, 5A, 6A, 7C), (1D, 2A, 3C, 4E, 5A, 6B, 7A), (1D, 2A, 3C, 4E, 5A, 6B, 7B), (1D, 2A, 3C, 4E, 5A, 6B, 7C), (1D, 2A, 3C, 4E, 5A, 6C, 7A), (1D, 2A, 3C, 4E, 5A, 6C, 7B), (1D, 2A, 3C, 4E, 5A, 6C, 7C), (1D, 2A, 3C, 4E, 5A, 6D, 7A), (1D, 2A, 3C, 4E, 5A, 6D, 7B), (1D, 2A, 3C, 4E, 5A, 6D, 7C), (1D, 2A, 3C, 4E, 5B, 6A, 7A), (1D, 2A, 3C, 4E, 5B, 6A, 7B), (1D, 2A, 3C, 4E, 5B, 6A, 7C), (1D, 2A, 3C, 4E, 5B, 6B, 7A), (1D, 2A, 3C, 4E, 5B, 6B, 7B), (1D, 2A, 3C, 4E, 5B, 6B, 7C), (1D, 2A, 3C, 4E, 5B, 6C, 7A), (1D, 2A, 3C, 4E, 5B, 6C, 7B), (1D, 2A, 3C, 4E, 5B, 6C, 7C), (1D, 2A, 3C, 4E, 5B, 6D, 7A), (1D, 2A, 3C, 4E, 5B, 6D, 7B), (1D, 2A, 3C, 4E, 5B, 6D, 7C), (1D, 2A, 3D, 4A, 5A, 6A, 7A), (1D, 2A, 3D, 4A, 5A, 6A, 7B), (1D, 2A, 3D, 4A, 5A, 6A, 7C), (1D, 2A, 3D, 4A, 5A, 6B, 7A), (1D, 2A, 3D, 4A, 5A, 6B, 7B), (1D, 2A, 3D, 4A, 5A, 6B, 7C), (1D, 2A, 3D, 4A, 5A, 6C, 7A), (1D, 2A, 3D, 4A, 5A, 6C, 7B), (1D, 2A, 3D, 4A, 5A, 6C, 7C), (1D, 2A, 3D, 4A, 5A, 6D, 7A), (1D, 2A, 3D, 4A, 5A, 6D, 7B), (1D, 2A, 3D, 4A, 5A, 6D, 7C), (1D, 2A, 3D, 4A, 5B, 6A, 7A), (1D, 2A, 3D, 4A, 5B, 6A, 7B), (1D, 2A, 3D, 4A, 5B, 6A, 7C), (1D, 2A, 3D, 4A, 5B, 6B, 7A), (1D, 2A, 3D, 4A, 5B, 6B, 7B), (1D, 2A, 3D, 4A, 5B, 6B, 7C), (1D, 2A, 3D, 4A, 5B, 6C, 7A), (1D, 2A, 3D, 4A, 5B, 6C, 7B), (1D, 2A, 3D, 4A, 5B, 6C, 7C), (1D, 2A, 3D, 4A, 5B, 6D, 7A), (1D, 2A, 3D, 4A, 5B, 6D, 7B), (1D, 2A, 3D, 4A, 5B, 6D, 7C), (1D, 2A, 3D, 4B, 5A, 6A, 7A), (1D, 2A, 3D, 4B, 5A, 6A, 7B), (1D, 2A, 3D, 4B, 5A, 6A, 7C), (1D, 2A, 3D, 4B, 5A, 6B, 7A), (1D, 2A, 3D, 4B, 5A, 6B, 7B), (1D, 2A, 3D, 4B, 5A, 6B, 7C), (1D, 2A, 3D, 4B, 5A, 6C, 7A), (1D, 2A, 3D, 4B, 5A, 6C, 7B), (1D, 2A, 3D, 4B, 5A, 6C, 7C), (1D, 2A, 3D, 4B, 5A, 6D, 7A), (1D, 2A, 3D, 4B, 5A, 6B, 7B), (1D, 2A, 3D, 4B, 5A, 6D, 7C), (1D, 2A, 3D, 4B, 5B, 6A, 7A), (1D, 2A, 3D, 4B, 5B, 6A, 7B), (1D, 2A, 3D, 4B, 5B, 6A, 7C), (1D, 2A, 3D, 4B, 5B, 6B, 7A), (1D, 2A, 3D, 4B, 5B, 6B, 7B), (1D, 2A, 3D, 4B, 5B, 6B, 7C), (1D, 2A, 3D, 4B, 5B, 6C, 7A), (1D, 2A, 3D, 4B, 5B, 6C, 7B), (1D, 2A, 3D, 4B, 5B, 6C, 7C), (1D, 2A, 3D, 4B, 5B, 6D, 7A), (1D, 2A, 3D, 4B, 5B, 6D, 7B), (1D, 2A, 3D, 4B, 5B, 6D, 7C), (1D, 2A, 3D, 4C, 5A, 6A, 7A), (1D, 2A, 3D, 4C, 5A, 6A, 7B), (1D, 2A, 3D, 4C, 5A, 6A, 7C), (1D, 2A, 3D, 4C, 5A, 6B, 7A), (1D, 2A, 3D, 4C, 5A, 6B, 7B), (1D, 2A, 3D, 4C, 5A, 6B, 7C), (1D, 2A, 3D, 4C, 5A, 6C, 7A), (1D, 2A, 3D, 4C, 5A, 6C, 7B), (1D, 2A, 3D, 4C, 5A, 6C, 7C), (1D, 2A, 3D, 4C, 5A, 6D, 7A), (1D, 2A, 3D, 4C, 5A, 6D, 7B), (1D, 2A, 3D, 4C, 5A, 6D, 7C), (1D, 2A, 3D, 4C, 5B, 6A, 7A), (1D, 2A, 3D, 4C, 5B, 6A, 7B), (1D, 2A, 3D, 4C, 5B, 6A, 7C), (1D, 2A, 3D, 4C, 5B, 6B, 7A), (1D, 2A, 3D, 4C, 5B, 6B, 7B), (1D, 2A, 3D, 4C, 5B, 6B, 7C), (1D, 2A, 3D, 4C, 5B, 6C, 7A), (1D, 2A, 3D, 4C, 5B, 6C, 7B), (1D, 2A, 3D, 4C, 5B, 6C, 7C), (1D, 2A, 3D, 4C, 5B, 6D, 7A), (1D, 2A, 3D, 4C, 5B, 6D, 7B), (1D, 2A, 3D, 4C, 5B, 6D, 7C), (1D, 2A, 3D, 4D, 5A, 6A, 7A), (1D, 2A, 3D, 4D, 5A, 6A, 7B), (1D, 2A, 3D, 4D, 5A, 6A, 7C), (1D, 2A, 3D, 4D, 5A, 6B, 7A), (1D, 2A, 3D, 4D, 5A, 6B, 7B), (1D, 2A, 3D, 4D, 5A, 6B, 7C), (1D, 2A, 3D, 4D, 5A, 6C, 7A), (1D, 2A, 3D, 4D, 5A, 6C, 7B), (1D, 2A, 3D, 4D, 5A, 6C, 7C), (1D, 2A, 3D, 4D, 5A, 6D, 7A), (1D, 2A, 3D, 4D, 5A, 6D, 7B), (1D, 2A, 3D, 4D, 5A, 6D, 7C), (1D, 2A, 3D, 4D, 5B, 6A, 7A), (1D, 2A, 3D, 4D, 5B, 6A, 7B), (1D, 2A, 3D, 4D, 5B, 6A, 7C), (1D, 2A, 3D, 4D, 5B, 6B, 7A), (1D, 2A, 3D, 4D, 5B, 6B, 7B), (1D, 2A, 3D, 4D, 5B, 6B, 7C), (1D, 2A, 3D, 4D, 5B, 6C, 7A), (1D, 2A, 3D, 4D, 5B, 6C, 7B), (1D, 2A, 3D, 4D, 5B, 6C, 7C), (1D, 2A, 3D, 4D, 5B, 6D, 7A), (1D, 2A, 3D, 4D, 5B, 6D, 7B), (1D, 2A, 3D, 4D, 5B, 6D, 7C), (1D, 2A, 3D, 4E, 5A, 6A, 7A), (1D, 2A, 3D, 4E, 5A, 6A, 7B), (1D, 2A, 3D, 4E, 5A, 6A, 7C), (1D, 2A, 3D, 4E, 5A, 6B, 7A), (1D, 2A, 3D, 4E, 5A, 6B, 7B), (1D, 2A, 3D, 4E, 5A, 6B, 7C), (1D, 2A, 3D, 4E, 5A, 6C, 7A), (1D, 2A, 3D, 4E, 5A, 6C, 7B), (1D, 2A, 3D, 4E, 5A, 6C, 7C), (1D, 2A, 3D, 4E, 5A, 6D, 7A), (1D, 2A, 3D, 4E, 5A, 6D, 7B), (1D, 2A, 3D, 4E, 5A, 6D, 7C), (1D, 2A, 3D, 4E, 5B, 6A, 7A), (1D, 2A, 3D, 4E, 5B, 6A, 7B), (1D, 2A, 3D, 4E, 5B, 6A, 7C), (1D, 2A, 3D, 4E, 5B, 6B, 7A), (1D, 2A, 3D, 4E, 5B, 6B, 7B), (1D, 2A, 3D, 4E, 5B, 6B, 7C), (1D, 2A, 3D, 4E, 5B, 6C, 7A), (1D, 2A, 3D, 4E, 5B, 6C, 7B), (1D, 2A, 3D, 4E, 5B, 6C, 7C), (1D, 2A, 3D, 4E, 5B, 6D, 7A), (1D, 2A, 3D, 4E, 5B, 6D, 7B), (1D, 2A, 3D, 4E, 5B, 6D, 7C), (1D, 2A, 3E, 4A, 5A, 6A, 7A), (1D, 2A, 3E, 4A, 5A, 6A, 7B), (1D, 2A, 3E, 4A, 5A, 6A, 7C), (1D, 2A, 3E, 4A, 5A, 6B, 7A), (1D, 2A, 3E, 4A, 5A, 6B, 7B), (1D, 2A, 3E, 4A, 5A, 6B, 7C), (1D, 2A, 3E, 4A, 5A, 6C, 7A), (1D, 2A, 3E, 4A, 5A, 6C, 7B), (1D, 2A, 3E, 4A, 5A, 6C, 7C), (1D, 2A, 3E, 4A, 5A, 6D, 7A), (1D, 2A, 3E, 4A, 5A, 6D, 7B), (1D, 2A, 3E, 4A, 5A, 6D, 7C), (1D, 2A, 3E, 4A, 5B, 6A, 7A), (1D, 2A, 3E, 4A, 5B, 6A, 7B), (1D, 2A, 3E, 4A, 5B, 6A, 7C), (1D, 2A, 3E, 4A, 5B, 6B, 7A), (1D, 2A, 3E, 4A, 5B, 6B, 7B), (1D, 2A, 3E, 4A, 5B, 6B, 7C), (1D, 2A, 3E, 4A, 5B, 6C, 7A), (1D, 2A, 3E, 4A, 5B, 6C, 7B), (1D, 2A, 3E, 4A, 5B, 6C, 7C), (1D, 2A, 3E, 4A, 5B, 6D, 7A), (1D, 2A, 3E, 4A, 5B, 6D, 7B), (1D, 2A, 3E, 4A, 5B, 6D, 7C), (1D, 2A, 3E, 4B, 5A, 6A, 7A), (1D, 2A, 3E, 4B, 5A, 6A, 7B), (1D, 2A, 3E, 4B, 5A, 6A, 7C), (1D, 2A, 3E, 4B, 5A, 6B, 7A), (1D, 2A, 3E, 4B, 5A, 6B, 7B), (1D, 2A, 3E, 4B, 5A, 6B, 7C), (1D, 2A, 3E, 4B, 5A, 6C, 7A), (1D, 2A, 3E, 4B, 5A, 6C, 7B), (1D, 2A, 3E, 4B, 5A, 6C, 7C), (1D, 2A, 3E, 4B, 5A, 6D, 7A), (1D, 2A, 3E, 4B, 5A, 6D, 7B), (1D, 2A, 3E, 4B, 5A, 6D, 7C), (1D, 2A, 3E, 4B, 5B, 6A, 7A), (1D, 2A, 3E, 4B, 5B, 6A, 7B), (1D, 2A, 3E, 4B, 5B, 6A, 7C), (1D, 2A, 3E, 4B, 5B, 6B, 7A), (1D, 2A, 3E, 4B, 5B, 6B, 7B), (1D, 2A, 3E, 4B, 5B, 6B, 7C), (1D, 2A, 3E, 4B, 5B, 6C, 7A), (1D, 2A, 3E, 4B, 5B, 6C, 7B), (1D, 2A, 3E, 4B, 5B, 6C, 7C), (1D, 2A, 3E, 4B, 5B, 6D, 7A), (1D, 2A, 3E, 4B, 5B, 6D, 7B), (1D, 2A, 3E, 4B, 5B, 6D, 7C), (1D, 2A, 3E, 4C, 5A, 6A, 7A), (1D, 2A, 3E, 4C, 5A, 6A, 7B), (1D, 2A, 3E, 4C, 5A, 6A, 7C), (1D, 2A, 3E, 4C, 5A, 6B, 7A), (1D, 2A, 3E, 4C, 5A, 6B, 7B), (1D, 2A, 3E, 4C, 5A, 6B, 7C), (1D, 2A, 3E, 4C, 5A, 6C, 7A), (1D, 2A, 3E, 4C, 5A, 6C, 7B), (1D, 2A, 3E, 4C, 5A, 6C, 7C), (1D, 2A, 3E, 4C, 5A, 6D, 7A), (1D, 2A, 3E, 4C, 5A, 6D, 7B), (1D, 2A, 3E, 4C, 5A, 6D, 7C), (1D, 2A, 3E, 4C, 5B, 6A, 7A), (1D, 2A, 3E, 4C, 5B, 6A, 7B), (1D, 2A, 3E, 4C, 5B, 6A, 7C), (1D, 2A, 3E, 4C, 5B, 6B, 7A), (1D, 2A, 3E, 4C, 5B, 6B, 7B), (1D, 2A, 3E, 4C, 5B, 6B, 7C), (1D, 2A, 3E, 4C, 5B, 6C, 7A), (1D, 2A, 3E, 4C, 5B, 6C, 7B), (1D, 2A, 3E, 4C, 5B, 6C, 7C), (1D, 2A, 3E, 4C, 5B, 6D, 7A), (1D, 2A, 3E, 4C, 5B, 6D, 7B), (1D, 2A, 3E, 4C, 5B, 6D, 7C), (1D, 2A, 3E, 4D, 5A, 6A, 7A), (1D, 2A, 3E, 4D, 5A, 6A, 7B), (1D, 2A, 3E, 4D, 5A, 6A, 7C), (1D, 2A, 3E, 4D, 5A, 6B, 7A), (1D, 2A, 3E, 4D, 5A, 6B, 7B), (1D, 2A, 3E, 4D, 5A, 6B, 7C), (1D, 2A, 3E, 4D, 5A, 6C, 7A), (1D, 2A, 3E, 4D, 5A, 6C, 7B), (1D, 2A, 3E, 4D, 5A, 6C, 7C), (1D, 2A, 3E, 4D, 5A, 6D, 7A), (1D, 2A, 3E, 4D, 5A, 6D, 7B), (1D, 2A, 3E, 4D, 5A, 6D, 7C), (1D, 2A, 3E, 4D, 5B, 6A, 7A), (1D, 2A, 3E, 4D, 5B, 6A, 7B), (1D, 2A, 3E, 4D, 5B, 6A, 7C), (1D, 2A, 3E, 4D, 5B, 6B, 7A), (1D, 2A, 3E, 4D, 5B, 6B, 7B), (1D, 2A, 3E, 4D, 5B, 6B, 7C), (1D, 2A, 3E, 4D, 5B, 6C, 7A), (1D, 2A, 3E, 4D, 5B, 6C, 7B), (1D, 2A, 3E, 4D, 5B, 6C, 7C), (1D, 2A, 3E, 4D, 5B, 6D, 7A), (1D, 2A, 3E, 4D, 5B, 6D, 7B), (1D, 2A, 3E, 4D, 5B, 6D, 7C), (1D, 2A, 3E, 4E, 5A, 6A, 7A), (1D, 2A, 3E, 4E, 5A, 6A, 7B), (1D, 2A, 3E, 4E, 5A, 6A, 7C), (1D, 2A, 3E, 4E, 5A, 6B, 7A), (1D, 2A, 3E, 4E, 5A, 6B, 7B), (1D, 2A, 3E, 41E, 5A, 6B, 7C), (1D, 2A, 3E, 4E, 5A, 6C, 7A), (1D, 2A, 3E, 4E, 5A, 6C, 7B), (1D, 2A, 3E, 4E, 5A, 6C, 7C), (1D, 2A, 3E, 4E, 5A, 6D, 7A), (1D, 2A, 3E, 4E, 5A, 6D, 7B), (1D, 2A, 3E, 4E, 5A, 6D, 7C), (1D, 2A, 3E, 4E, 5B, 6A, 7A), (1D, 2A, 3E, 4E, 5B, 6A, 7B), (1D, 2A, 3E, 4E, 5B, 6A, 7C), (1D, 2A, 3E, 4E, 5B, 6B, 7A), (1D, 2A, 3E, 4E, 5B, 6B, 7B), (1D, 2A, 3E, 4E, 5B, 6B, 7C), (1D, 2A, 3E, 4E, 5B, 6C, 7A), (1D, 2A, 3E, 4E, 5B, 6C, 7B), (1D, 2A, 3E, 4E, 5B, 6C, 7C), (1D, 2A, 3E, 4E, 5B, 6D, 7A), (1D, 2A, 3E, 4E, 5B, 6D, 7B), (1D, 2A, 3E, 4E, 5B, 6D, 7C), (1D, 2B, 3A, 4A, 5A, 6A, 7A), (1D, 2B, 3A, 4A, 5A, 6A, 7B), (1D, 2B, 3A, 4A, 5A, 6A, 7C), (1D, 2B, 3A, 4A, 5A, 6B, 7A), (1D, 2B, 3A, 4A, 5A, 6B, 7B), (1D, 2B, 3A, 4A, 5A, 6B, 7C), (1D, 2B, 3A, 4A, 5A, 6C, 7A), (1D, 2B, 3A, 4A, 5A, 6C, 7B), (1D, 2B, 3A, 4A, 5A, 6C, 7C), (1D, 2B, 3A, 4A, 5A, 6D, 7A), (1D, 2B, 3A, 4A, 5A, 6D, 7B), (D, 2B, 3A, 4A, 5A, 6D, 7C), (1D, 2B, 3A, 4A, 5B, 6A, 7A), (1D, 2B, 3A, 4A, 5B, 6A, 7B), (1D, 2B, 3A, 4A, 5B, 6A, 7C), (1D, 2B, 3A, 4A, 5B, 6B, 7A), (1D, 2B, 3A, 4A, 5B, 6B, 7B), (1D, 2B, 3A, 4A, 5B, 6B, 7C), (1D, 2B, 3A, 4A, 5B, 6C, 7A), (1D, 2B, 3A, 4A, 5B, 6C, 7B), (1D, 2B, 3A, 4A, 5B, 6C, 7C), (1D, 2B, 3A, 4A, 5B, 6D, 7A), (1D, 2B, 3A, 4A, 5B, 6D, 7B), (1D, 2B, 3A, 4A, 5B, 6D, 7C), (1D, 2B, 3A, 4B, 5A, 6A, 7A), (1D, 2B, 3A, 4B, 5A, 6A, 7B), (1D, 2B, 3A, 4B, 5A, 6A, 7C), (1D, 2B, 3A, 4B, 5A, 6B, 7A), (1D, 2B, 3A, 4B, 5A, 6B, 7B), (1D, 2B, 3A, 4B, 5A, 6B, 7C), (1D, 2B, 3A, 4B, 5A, 6C, 7A), (1D, 2B, 3A, 4B, 5A, 6C, 7B), (1D, 2B, 3A, 4B, 5A, 6C, 7C), (1D, 2B, 3A, 4B, 5A, 6D, 7A), (1D, 2B, 3A, 4B, 5A, 6D, 7B), (1D, 2B, 3A, 4B, 5A, 6D, 7C), (1D, 2B, 3A, 4B, 5B, 6A, 7A), (1D, 2B, 3A, 4B, 5B, 6A, 7B), (1D, 2B, 3A, 4B, 5B, 6A, 7C), (1D, 2B, 3A, 4B, 5B, 6B, 7A), (1D, 2B, 3A, 4B, 5B, 6B, 7B), (1D, 2B, 3A, 4B, 5B, 6B, 7C), (1D, 2B, 3A, 4B, 5B, 6C, 7A), (1D, 2B, 3A, 4B, 5B, 6C, 7B), (1D, 2B, 3A, 4B, 5B, 6C, 7C), (1D, 2B, 3A, 4B, 5B, 6D, 7A), (1D, 2B, 3A, 4B, 5B, 6D, 7B), (1D, 2B, 3A, 4B, 5B, 6D, 7C), (1D, 2B, 3A, 4C, 5A, 6A, 7A), (1D, 2B, 3A, 4C, 5A, 6A, 7B), (1D, 2B, 3A, 4C, 5A, 6A, 7C), (1D, 2B, 3A, 4C, 5A, 6B, 7A), (1D, 2B, 3A, 4C, 5A, 6B, 7B), (1D, 2B, 3A, 4C, 5A, 6B, 7C), (1D, 2B, 3A, 4C, 5A, 6C, 7A), (1D, 2B, 3A, 4C, 5A, 6C, 7B), (1D, 2B, 3A, 4C, 5A, 6C, 7C), (1D, 2B, 3A, 4C, 5A, 6D, 7A), (1D, 2B, 3A, 4C, 5A, 6D, 7B), (1D, 2B, 3A, 4C, 5A, 6D, 7C), (1D, 2B, 3A, 4C, 5B, 6A, 7A), (1D, 2B, 3A, 4C, 5B, 6A, 7B), (1D, 2B, 3A, 4C, 5B, 6A, 7C), (1D, 2B, 3A, 4C, 5B, 6B, 7A), (1D, 2B, 3A, 4C, 5B, 6B, 7B), (1D, 2B, 3A, 4C, 5B, 6B, 7C), (1D, 2B, 3A, 4C, 5B, 6C, 7A), (1D, 2B, 3A, 4C, 5B, 6C, 7B), (1D, 2B, 3A, 4C, 5B, 6C, 7C), (1D, 2B, 3A, 4C, 5B, 6D, 7A), (1D, 2B, 3A, 4C, 5B, 6D, 7B), (1D, 2B, 3A, 4C, 5B, 6D, 7C), (1D, 2B, 3A, 4D, 5A, 6A, 7A), (1D, 2B, 3A, 4D, 5A, 6A, 7B), (1D, 2B, 3A, 4D, 5A, 6A, 7C), (1D, 2B, 3A, 4D, 5A, 6B, 7A), (1D, 2B, 3A, 4D, 5A, 6B, 7B), (1D, 2B, 3A, 4D, 5A, 6B, 7C), (1D, 2B, 3A, 4D, 5A, 6C, 7A), (1D, 2B, 3A, 4D, 5A, 6C, 7B), (1D, 2B, 3A, 4D, 5A, 6C, 7C), (1D, 2B, 3A, 4D, 5A, 6D, 7A), (1D, 2B, 3A, 4D, 5A, 6D, 7B), (1D, 2B, 3A, 4D, 5A, 6D, 7C), (1D, 2B, 3A, 4D, 5B, 6A, 7A), (1D, 2B, 3A, 4D, 5B, 6A, 7B), (1D, 2B, 3A, 4D, 5B, 6A, 7C), (1D, 2B, 3A, 4D, 5B, 6B, 7A), (1D, 2B, 3A, 4D, 5B, 6B, 7B), (1D, 2B, 3A, 4D, 5B, 6B, 7C), (1D, 2B, 3A, 4D, 5B, 6C, 7A), (1D, 2B, 3A, 4D, 5B, 6C, 7B), (1D, 2B, 3A, 4D, 5B, 6C, 7C), (1D, 2B, 3A, 4D, 5B, 6D, 7A), (1D, 2B, 3A, 4D, 5B, 6D, 7B), (1D, 2B, 3A, 4D, 5B, 6D, 7C), (1D, 2B, 3A, 4E, 5A, 6A, 7A), (1D, 2B, 3A, 4E, 5A, 6A, 7B), (1D, 2B, 3A, 4E, 5A, 6A, 7C), (1D, 2B, 3A, 4E, 5A, 6B, 7A), (1D, 2B, 3A, 4E, 5A, 6B, 7B), (1D, 2B, 3A, 4E, 5A, 6B, 7C), (1D, 2B, 3A, 4E, 5A, 6C, 7A), (1D, 2B, 3A, 4E, 5A, 6C, 7B), (1D, 2B, 3A, 4E, 5A, 6C, 7C), (1D, 2B, 3A, 4E, 5A, 6D, 7A), (1D, 2B, 3A, 4E, 5A, 6D, 7B), (1D, 2B, 3A, 4E, 5A, 6D, 7C), (1D, 2B, 3A, 4E, 5B, 6A, 7A), (1D, 2B, 3A, 4E, 5B, 6A, 7B), (1D, 2B, 3A, 4E, 5B, 6A, 7C), (1D, 2B, 3A, 4E, 5B, 6B, 7A), (1D, 2B, 3A, 4E, 5B, 6B, 7B), (1D, 2B, 3A, 4E, 5B, 6B, 7C), (1D, 2B, 3A, 4E, 5B, 6C, 7A), (1D, 2B, 3A, 4E, 5B, 6C, 7B), (1D, 2B, 3A, 4E, 5B, 6C, 7C), (1D, 2B, 3A, 4E, 5B, 6D, 7A), (1D, 2B, 3A, 4E, 5B, 6D, 7B), (1D, 2B, 3A, 4E, 5B, 6D, 7C), (1D, 2B, 3B, 4A, 5A, 6A, 7A), (1D, 2B, 3B, 4A, 5A, 6A, 7B), (1D, 2B, 3B, 4A, 5A, 6A, 7C), (1D, 2B, 3B, 4A, 5A, 6B, 7A), (1D, 2B, 3B, 4A, 5A, 6B, 7B), (1D, 2B, 3B, 4A, 5A, 6B, 7C), (1D, 2B, 3B, 4A, 5A, 6C, 7A), (1D, 2B, 3B, 4A, 5A, 6C, 7B), (1D, 2B, 3B, 4A, 5A, 6C, 7C), (1D, 2B, 3B, 4A, 5A, 6D, 7A), (1D, 2B, 3B, 4A, 5A, 6D, 7B), (1D, 2B, 3B, 4A, 5A, 6D, 7C), (1D, 2B, 3B, 4A, 5B, 6A, 7A), (1D, 2B, 3B, 4A, 5B, 6A, 7B), (1D, 2B, 3B, 4A, 5B, 6A, 7C), (1D, 2B, 3B, 4A, 5B, 6B, 7A), (1D, 2B, 3B, 4A, 5B, 6B, 7B), (1D, 2B, 3B, 4A, 5B, 6B, 7C), (1D, 2B, 3B, 4A, 5B, 6C, 7A), (1D, 2B, 3B, 4A, 5B, 6C, 7B), (1D, 2B, 3B, 4A, 5B, 6C, 7C), (1D, 2B, 3B, 4A, 5B, 6D, 7A), (1D, 2B, 3B, 4A, 5B, 6D, 7B), (1D, 2B, 3B, 4A, 5B, 6D, 7C), (1D, 2B, 3B, 4B, 5A, 6A, 7A), (1D, 2B, 3B, 4B, 5A, 6A, 7B), (1D, 2B, 3B, 4B, 5A, 6A, 7C), (1D, 2B, 3B, 4B, 5A, 6B, 7A), (1D, 2B, 3B, 4B, 5A, 6B, 7B), (1D, 2B, 3B, 4B, 5A, 6B, 7C), (1D, 2B, 3B, 4B, 5A, 6C, 7A), (1D, 2B, 3B, 4B, 5A, 6C, 7B), (1D, 2B, 3B, 4B, 5A, 6C, 7C), (1D, 2B, 3B, 4B, 5A, 6D, 7A), (1D, 2B, 3B, 4B, 5A, 6D, 7B), (1D, 2B, 3B, 4B, 5A, 6D, 7C), (1D, 2B, 3B, 4B, 5B, 6A, 7A), (1D, 2B, 3B, 4B, 5B, 6A, 7B), (1D, 2B, 3B, 4B, 5B, 6A, 7C), (1D, 2B, 3B, 4B, 5B, 6B, 7A), (1D, 2B, 3B, 4B, 5B, 6B, 7B), (1D, 2B, 3B, 4B, 5B, 6B, 7C), (1D, 2B, 3B, 4B, 5B, 6C, 7A), (1D, 2B, 3B, 4B, 5B, 6C, 7B), (1D, 2B, 3B, 4B, 5B, 6C, 7C), (1B, 2B, 3B, 4B, 5B, 6D, 7A), (1D, 2B, 3B, 4B, 5B, 6D, 7B), (1D, 2B, 3B, 4B, 5B, 6D, 7C), (1D, 2B, 3B, 4C, 5A, 6A, 7A), (1D, 2B, 3B, 4C, 5A, 6A, 7B), (1D, 2B, 3B, 4C, 5A, 6A, 7C), (1D, 2B, 3B, 4C, 5A, 6B, 7A), (1D, 2B, 3B, 4C, 5A, 6B, 7B), (1D, 2B, 3B, 4C, 5A, 6B, 7C), (1D, 2B, 3B, 4C, 5A, 6C, 7A), (1D, 2B, 3B, 4C, 5A, 6C, 7B), (1D, 2B, 3B, 4C, 5A, 6C, 7C), (1D, 2B, 3B, 4C, 5A, 6D, 7A), (1D, 2B, 3B, 4C, 5A, 6D, 7B), (1D, 2B, 3B, 4C, 5A, 6D, 7C), (1D, 2B, 3B, 4C, 5B, 6A, 7A), (1D, 2B, 3B, 4C, 5B, 6A, 7B), (1D, 2B, 3B, 4C, 5B, 6A, 7C), (1D, 2B, 3B, 4C, 5B, 6B, 7A), (1D, 2B, 3B, 4C, 5B, 6B, 7B), (1D, 2B, 3B, 4C, 5B, 6B, 7C), (1D, 2B, 3B, 4C, 5B, 6C, 7A), (1D, 2B, 3B, 4C, 5B, 6C, 7B), (1D, 2B, 3B, 4C, 5B, 6C, 7C), (1D, 2B, 3B, 4C, 5B, 6D, 7A), (1D, 2B, 3B, 4C, 5B, 6D, 7B), (1D, 2B, 3B, 4C, 5B, 6D, 7C), (1D, 2B, 3B, 4D, 5A, 6A, 7A), (1D, 2B, 3B, 4D, 5A, 6A, 7B), (1D, 2B, 3B, 4D, 5A, 6A, 7C), (1D, 2B, 3B, 4D, 5A, 6B, 7A), (1D, 2B, 3B, 4D, 5A, 6B, 7B), (1D, 2B, 3B, 4D, 5A, 6B, 7C), (1D, 2B, 3B, 4D, 5A, 6C, 7A), (1D, 2B, 3B, 4D, 5A, 6C, 7B), (1D, 2B, 3B, 4D, 5A, 6C, 7C), (1D, 2B, 3B, 4D, 5A, 6D, 7A), (1D, 2B, 3B, 4D, 5A, 6D, 7B), (1D, 2B, 3B, 4D, 5A, 6D, 7C), (1D, 2B, 3B, 4D, 5B, 6A, 7A), (1D, 2B, 3B, 4D, 5B, 6A, 7B), (1D, 2B, 3B, 4D, 5B, 6A, 7C), (1D, 2B, 3B, 4D, 5B, 6B, 7A), (1D, 2B, 3B, 4D, 5B, 6B, 7B), (1D, 2B, 3B, 4D, 5B, 6B, 7C), (1D, 2B, 3B, 4D, 5B, 6C, 7A), (1D, 2B, 3B, 4D, 5B, 6C, 7B), (1D, 2B, 3B, 4D, 5B, 6C, 7C), (1D, 2B, 3B, 4D, 5B, 6D, 7A), (1D, 2B, 3B, 4D, 5B, 6D, 7B), (1D, 2B, 3B, 4D, 5B, 6D, 7C), (1D, 2B, 3B, 4E, 5A, 6A, 7A), (1D, 2B, 3B, 4E, 5A, 6A, 7B), (1D, 2B, 3B, 4E, 5A, 6A, 7C), (1D, 2B, 3B, 4E, 5A, 6B, 7A), (1D, 2B, 3B, 4E, 5A, 6B, 7B), (1D, 2B, 3B, 4E, 5A, 6B, 7C), (1D, 2B, 3B, 4E, 5A, 6C, 7A), (1D, 2B, 3B, 4E, 5A, 6C, 7B), (1D, 2B, 3B, 4E, 5A, 6C, 7C), (1D, 2B, 3B, 4E, 5A, 6D, 7A), (1D, 2B, 3B, 4E, 5A, 6D, 7B), (1D, 2B, 3B, 4E, 5A, 6D, 7C), (1D, 2B, 3B, 4E, 5B, 6A, 7A), (1D, 2B, 3B, 4E, 5B, 6A, 7B), (1D, 2B, 3B, 4E, 5B, 6A, 7C), (1D, 2B, 3B, 4E, 5B, 6B, 7A), (1D, 2B, 3B, 4E, 5B, 6B, 7B), (1D, 2B, 3B, 4E, 5B, 6B, 7C), (1D, 2B, 3B, 4E, 5B, 6C, 7A), (1D, 2B, 3B, 4E, 5B, 6C, 7B), (1D, 2B, 3B, 4E, 5B, 6C, 7C), (1D, 2B, 3B, 4E, 5B, 6D, 7A), (1D, 2B, 3B, 4E, 5B, 6D, 7B), (1D, 2B, 3B, 4E, 5B, 6D, 7C), (1D, 2B, 3C, 4A, 5A, 6A, 7A), (1D, 2B, 3C, 4A, 5A, 6A, 7B), (1D, 2B, 3C, 4A, 5A, 6A, 7C), (1D, 2B, 3C, 4A, 5A, 6B, 7A), (1D, 2B, 3C, 4A, 5A, 6B, 7B), (1D, 2B, 3C, 4A, 5A, 6B, 7C), (1D, 2B, 3C, 4A, 5A, 6C, 7A), (1D, 2B, 3C, 4A, 5A, 6C, 7B), (1D, 2B, 3C, 4A, 5A, 6C, 7C), (1D, 2B, 3C, 4A, 5A, 6D, 7A), (1D, 2B, 3C, 4A, 5A, 6D, 7B), (1D, 2B, 3C, 4A, 5A, 6D, 7C), (1D, 2B, 3C, 4A, 5B, 6A, 7A), (1D, 2B, 3C, 4A, 5B, 6A, 7B), (1D, 2B, 3C, 4A, 5B, 6A, 7C), (1D, 2B, 3C, 4A, 5B, 6B, 7A), (1D, 2B, 3C, 4A, 5B, 6B, 7B), (1D, 2B, 3C, 4A, 5B, 6B, 7C), (1D, 2B, 3C, 4A, 5B, 6C, 7A), (1D, 2B, 3C, 4A, 5B, 6C, 7B), (1D, 2B, 3C, 4A, 5B, 6C, 7C), (1D, 2B, 3C, 4A, 5B, 6D, 7A), (1D, 2B, 3C, 4A, 5B, 6D, 7B), (1D, 2B, 3C, 4A, 5B, 6D, 7C), (1D, 2B, 3C, 4B, 5A, 6A, 7A), (1D, 2B, 3C, 4B, 5A, 6A, 7B), (1D, 2B, 3C, 4B, 5A, 6A, 7C), (1D, 2B, 3C, 4B, 5A, 6B, 7A), (1D, 2B, 3C, 4B, 5A, 6B, 7B), (1D, 2B, 3C, 4B, 5A, 6B, 7C), (1D, 2B, 3C, 4B, 5A, 6C, 7A), (1D, 2B, 3C, 4B, 5A, 6C, 7B), (1D, 2B, 3C, 4B, 5A, 6C, 7C), (1D, 2B, 3C, 4B, 5A, 6D, 7A), (1D, 2B, 3C, 4B, 5A, 6D, 7B), (1D, 2B, 3C, 4B, 5A, 6D, 7C), (1D, 2B, 3C, 4B, 5B, 6A, 7A), (1D, 2B, 3C, 4B, 5B, 6A, 7B), (1D, 2B, 3C, 4B, 5B, 6A, 7C), (1D, 2B, 3C, 4B, 5B, 6B, 7A), (1D, 2B, 3C, 4B, 5B, 6B, 7B), (1D, 2B, 3C, 4B, 5B, 6B, 7C), (1D, 2B, 3C, 4B, 5B, 6C, 7A), (1D, 2B, 3C, 4B, 5B, 6C, 7B), (1D, 2B, 3C, 4B, 5B, 6C, 7C), (1D, 2B, 3C, 4B, 5B, 6D, 7A), (1D, 2B, 3C, 4B, 5B, 6D, 7B), (1D, 2B, 3C, 4B, 5B, 6D, 7C), (1D, 2B, 3C, 4C, 5A, 6A, 7A), (1D, 2B, 3C, 4C, 5A, 6A, 7B), (1D, 2B, 3C, 4C, 5A, 6A, 7C), (1D, 2B, 3C, 4C, 5A, 6B, 7A), (1D, 2B, 3C, 4C, 5A, 6B, 7B), (1D, 2B, 3C, 4C, 5A, 6B, 7C), (1D, 2B, 3C, 4C, 5A, 6C, 7A), (1D, 2B, 3C, 4C, 5A, 6C, 7B), (1D, 2B, 3C, 4C, 5A, 6C, 7C), (1D, 2B, 3C, 4C, 5A, 6D, 7A), (1D, 2B, 3C, 4C, 5A, 6D, 7B), (1D, 2B, 3C, 4C, 5A, 6D, 7C), (1D, 2B, 3C, 4C, 5B, 6A, 7A), (1D, 2B, 3C, 4C, 5B, 6A, 7B), (1D, 2B, 3C, 4C, 5B, 6A, 7C), (1D, 2B, 3C, 4C, 5B, 6B, 7A), (1D, 2B, 3C, 4C, 5B, 6B, 7B), (1D, 2B, 3C, 4C, 5B, 6B, 7C), (1D, 2B, 3C, 4C, 5B, 6C, 7A), (1D, 2B, 3C, 4C, 5B, 6C, 7B), (1D, 2B, 3C, 4C, 5B, 6C, 7C), (1D, 2B, 3C, 4C, 5B, 6D, 7A), (1D, 2B, 3C, 4C, 5B, 6D, 7B), (1D, 2B, 3C, 4C, 5B, 6D, 7C), (1D, 2B, 3C, 4D, 5A, 6A, 7A), (1D, 2B, 3C, 4D, 5A, 6A, 7B), (1D, 2B, 3C, 4D, 5A, 6A, 7C), (1D, 2B, 3C, 4D, 5A, 6B, 7A), (1D, 2B, 3C, 4D, 5A, 6B, 7B), (1D, 2B, 3C, 4D, 5A, 6B, 7C), (1D, 2B, 3C, 4D, 5A, 6C, 7A), (1D, 2B, 3C, 4D, 5A, 6C, 7B), (1D, 2B, 3C, 4D, 5A, 6C, 7C), (1D, 2B, 3C, 4D, 5A, 6D, 7A), (1D, 2B, 3C, 4D, 5A, 6D, 7B), (1D, 2B, 3C, 4D, 5A, 6D, 7C), (1D, 2B, 3C, 4D, 5B, 6A, 7A), (1D, 2B, 3C, 4D, 5B, 6A, 7B), (1D, 2B, 3C, 4D, 5B, 6A, 7C), (1D, 2B, 3C, 4D, 5B, 6B, 7A), (1D, 2B, 3C, 4D, 5B, 6B, 7B), (1D, 2B, 3C, 4D, 5B, 6B, 7C), (1D, 2B, 3C, 4D, 5B, 6C, 7A), (1D, 2B, 3C, 4D, 5B, 6C, 7B), (1D, 2B, 3C, 4D, 5B, 6C, 7C), (1D, 2B, 3C, 4D, 5B, 6D, 7A), (1D, 2B, 3C, 4D, 5B, 6D, 7B), (1D, 2B, 3C, 4D, 5B, 6D, 7C), (1D, 2B, 3C, 4E, 5A, 6A, 7A), (1D, 2B, 3C, 4E, 5A, 6A, 7B), (1D, 2B, 3C, 4E, 5A, 6A, 7C), (1D, 2B, 3C, 4E, 5A, 6B, 7A), (1D, 2B, 3C, 4E, 5A, 6B, 7B), (1D, 2B, 3C, 4E, 5A, 6B, 7C), (1D, 2B, 3C, 4E, 5A, 6C, 7A), (1D, 2B, 3C, 4E, 5A, 6C, 7B), (1D, 2B, 3C, 4E, 5A, 6C, 7C), (1D, 2B, 3C, 4E, 5A, 6D, 7A), (1D, 2B, 3C, 4E, 5A, 6D, 7B), (1D, 2B, 3C, 4E, 5A, 6D, 7C), (1D, 2B, 3C, 4E, 5B, 6A, 7A), (1D, 2B, 3C, 4E, 5B, 6A, 7B), (1D, 2B, 3C, 4E, 5B, 6A, 7C), (1D, 2B, 3C, 4E, 5B, 6B, 7A), (1D, 2B, 3C, 4E, 5B, 6B, 7B), (1D, 2B, 3C, 4E, 5B, 6B, 7C), (1D, 2B, 3C, 4E, 5B, 6C, 7A), (1D, 2B, 3C, 4E, 5B, 6C, 7B), (1D, 2B, 3C, 4E, 5B, 6C, 7C), (1D, 2B, 3C, 4E, 5B, 6D, 7A), (1D, 2B, 3C, 4E, 5B, 6D, 7B), (1D, 2B, 3C, 4E, 5B, 6D, 7C), (1D, 2B, 3D, 4A, 5A, 6A, 7A), (1D, 2B, 3D, 4A, 5A, 6A, 7B), (1D, 2B, 3D, 4A, 5A, 6A, 7C), (1D, 2B, 3D, 4A, 5A, 6B, 7A), (1D, 2B, 3D, 4A, 5A, 6B, 7B), (1D, 2B, 3D, 4A, 5A, 6B, 7C), (1D, 2B, 3D, 4A, 5A, 6C, 7A), (1D, 2B, 3D, 4A, 5A, 6C, 7B), (1D, 2B, 3D, 4A, 5A, 6C, 7C), (1D, 2B, 3D, 4A, 5A, 6D, 7A), (1D, 2B, 3D, 4A, 5A, 6D, 7B), (1D, 2B, 3D, 4A, 5A, 6D, 7C), (1D, 2B, 3D, 4A, 5B, 6A, 7A), (1D, 2B, 3D, 4A, 5B, 6A, 7B), (1D, 2B, 3D, 4A, 5B, 6A, 7C), (1D, 2B, 3D, 4A, 5B, 6B, 7A), (1D, 2B, 3D, 4A, 5B, 6B, 7B), (1D, 2B, 3D, 4A, 5B, 6B, 7C), (1D, 2B, 3D, 4A, 5B, 6C, 7A), (1D, 2B, 3D, 4A, 5B, 6C, 7B), (1D, 2B, 3D, 4A, 5B, 6C, 7C), (1D, 2B, 3D, 4A, 5B, 6D, 7A), (1D, 2B, 3D, 4A, 5B, 6D, 7B), (1D, 2B, 3D, 4A, 5B, 6D, 7C), (1D, 2B, 3D, 4B, 5A, 6A, 7A), (1D, 2B, 3D, 4B, 5A, 6A, 7B), (1D,
2B, 3D, 4B, 5A, 6B, 7B), (1D, 2B, 3D, 4B, 5A, 6B, 7C), (1D, 2B, 3D, 4B, 5A, 6C, 7A), (1D, 2B, 3D, 4B, 5A, 6C, 7B), (1D, 2B, 3D, 4B, 5A, 6C, 7C), (1D, 2B, 3D, 4B, 5A, 6D, 7A), (1D, 2B, 3D, 4B, 5A, 6D, 7B), (1D, 2B, 3D, 4B, 5A, 6D, 7C), (1D, 2B, 3D, 4B, 5B, 6A, 7A), (1D, 2B, 3D, 4B, 5B, 6A, 7B), (1D, 2B, 3D, 4B, 5B, 6A, 7C), (1D, 2B, 3D, 4B, 5B, 6B, 7A), (1D, 2B, 3D, 4B, 5B, 6B, 7B), (1D, 2B, 3D, 4B, 5B, 6B, 7C), (1D, 2B, 3D, 4B, 5B, 6C, 7A), (1D, 2B, 3D, 4B, 5B, 6C, 7B), (1D, 2B, 3D, 4B, 5B, 6C, 7C), (1D, 2B, 3D, 4B, 5B, 6D, 7A), (1D, 2B, 3D, 4B, 5B, 6D, 7B), (1D, 2B, 3D, 4B, 5B, 6D, 7C), (1D, 2B, 3D, 4C, 5A, 6A, 7A), (1D, 2B, 3D, 4C, 5A, 6A, 7B), (1D, 2B, 3D, 4C, 5A, 6A, 7C), (1D, 2B, 3D, 4C, 5A, 6B, 7A), (1D, 2B, 3D, 4C, 5A, 6B, 7B), (1D, 2B, 3D, 4C, 5A, 6B, 7C), (1D, 2B, 3D, 4C, 5A, 6C, 7A), (1D, 2B, 3D, 4C, 5A, 6C, 7B), (1D, 2B, 3D, 4C, 5A, 6C, 7C), (1D, 2B, 3D, 4C, 5A, 6D, 7A), (1D, 2B, 3D, 4C, 5A, 6D, 7B), (1D, 2B, 3D, 4C, 5A, 6D, 7C), (1D, 2B, 3D, 4C, 5B, 6A, 7A), (1D, 2B, 3D, 4C, 5B, 6A, 7B), (1D, 2B, 3D, 4C, 5B, 6A, 7C), (1D, 2B, 3D, 4C, 5B, 6B, 7A), (1D, 2B, 3D, 4C, 5B, 6B, 7B), (1D, 2B, 3D, 4C, 5B, 6B, 7C), (1D, 2B, 3D, 4C, 5B, 6C, 7A), (1D, 2B, 3D, 4C, 5B, 6C, 7B), (1D, 2B, 3D, 4C, 5B, 6C, 7C), (1D, 2B, 3D, 4C, 5B, 6D, 7A), (1D, 2B, 3D, 4C, 5B, 6D, 7B), (1D, 2B, 3D, 4C, 5B, 6D, 7C), (1D, 2B, 3D, 4D, 5A, 6A, 7A), (1D, 2B, 3D, 4D, 5A, 6A, 7B), (1D, 2B, 3D, 4D, 5A, 6A, 7C), (1D, 2B, 3D, 4D, 5A, 6B, 7A), (1D, 2B, 3D, 4D, 5A, 6B, 7B), (D, 2B, 3D, 4D, 5A, 6B, 7C), (1D, 2B, 3D, 4D, 5A, 6C, 7A), (1D, 2B, 3D, 4D, 5A, 6C, 7B), (1D, 2B, 3D, 4D, 5A, 6C, 7C), (1D, 2B, 3D, 4D, 5A, 6D, 7A), (1D, 2B, 3D, 4D, 5A, 6D, 7B), (1D, 2B, 3D, 4D, 5A, 6D, 7C), (1D, 2B, 3D, 4D, 5B, 6A, 7A), (1D, 2B, 3D, 4D, 5B, 6A, 7B), (1D, 2B, 3D, 4D, 5B, 6A, 7C), (1D, 2B, 3D, 4D, 5B, 6B, 7A), (1D, 2B, 3D, 4D, 5B, 6B, 7B), (1D, 2B, 3D, 4D, 5B, 6B, 7C), (1D, 2B, 3D, 4D, 5B, 6C, 7A), (1D, 2B, 3D, 4D, 5B, 6C, 7B), (1D, 2B, 3D, 4D, 5B, 6C, 7C), (1D, 2B, 3D, 4D, 5B, 6D, 7A), (1D, 2B, 3D, 4D, 5B, 6D, 7B), (1D, 2B, 3D, 4D, 5B, 6D, 7C), (1D, 2B, 3D, 4E, 5A, 6A, 7A), (1D, 2B, 3D, 4E, 5A, 6A, 7B), (1D, 2B, 3D, 4E, 5A, 6A, 7C, (1D, 2B, 3D, 4E, 5A, 6B, 7A), (1D, 2B, 3D, 4E, 5A, 6B, 7B), (1D, 2B, 3D, 4E, 5A, 6B, 7C), (1D, 2B, 3D, 4E, 5A, 6C, 7A), (1D, 2B, 3D, 4E, 5A, 6C, 7B), (1D, 2B, 3D, 4E, 5A, 6C, 7C), (1D, 2B, 3D, 4E, 5A, 6D, 7A), (1D, 2B, 3D, 4E, 5A, 6D, 7B), (1D, 2B, 3D, 4E, 5A, 6D, 7C), (1D, 2B, 3D, 4E, 5B, 6A, 7A), (1D, 2B, 3D, 4E, 5B, 6A, 7B), (1D, 2B, 3D, 4E, 5B, 6A, 7C), (1D, 2B, 3D, 4E, 5B, 6B, 7A), (1D, 2B, 3D, 4E, 5B, 6B, 7B), (1D, 2B, 3D, 4E, 5B, 6B, 7C), (1D, 2B, 3D, 4E, 5B, 6C, 7A), (1D, 2B, 3D, 4E, 5B, 6C, 7B), (1D, 2B, 3D, 4E, 5B, 6C, 7C), (1D, 2B, 3D, 4E, 5B, 6D, 7A), (1D, 2B, 3D, 4E, 5B, 6D, 7B), (1D, 2B, 3D, 4E, 5B, 6D, 7C), (1D, 2B, 3E, 4A, 5A, 6A, 7A), (1D, 2B, 3E, 4A, 5A, 6A, 7B), (1D, 2B, 3E, 4A, 5A, 6A, 7C), (1D, 2B, 3E, 4A, 5A, 6B, 7A), (1D, 2B, 3E, 4A, 5A, 6B, 7B), (1D, 2B, 3E, 4A, 5A, 6B, 7C), (1D, 2B, 3E, 4A, 5A, 6C, 7A), (1D, 2B, 3E, 4A, 5A, 6C, 7B), (1D, 2B, 3E, 4A, 5A, 6C, 7C), (1D, 2B, 3E, 4A, 5A, 6D, 7A), (1D, 2B, 3E, 4A, 5A, 6D, 7B), (1D, 2B, 3E, 4A, 5A, 6D, 7C), (1D, 2B, 3E, 4A, 5B, 6A, 7A), (1D, 2B, 3E, 4A, 5B, 6A, 7B), (1D, 2B, 3E, 4A, 5B, 6A, 7C), (1D, 2B, 3E, 4A, 5B, 6B, 7A), (1D, 2B, 3E, 4A, 5B, 6B, 7B), (1D, 2B, 3E, 4A, 5B, 6B, 7C), (1D, 2B, 3E, 4A, 5B, 6C, 7A), (1D, 2B, 3E, 4A, 5B, 6C, 7B), (1D, 2B, 3E, 4A, 5B, 6C, 7C), (1D, 2B, 3E, 4A, 5B, 6D, 7A), (1D, 2B, 3E, 4A, 5B, 6D, 7B), (1D, 2B, 3E, 4A, 5B, 6D, 7C), (1D, 2B, 3E, 4B, 5A, 6A, 7A), (1D, 2B, 3E, 4B, 5A, 6A, 7B), (1D, 2B, 3E, 4B, 5A, 6A, 7C), (1D, 2B, 3E, 4B, 5A, 6B, 7A), (1D, 2B, 3E, 4B, 5A, 6B, 7B), (1D, 2B, 3E, 4B, 5A, 6C, 7A), (1D, 2B, 3E, 4B, 5A, 6C, 7B), (1D, 2B, 3E, 4B, 5A, 6C, 7C), (1D, 2B, 3E, 4B, 5A, 6D, 7A), (1D, 2B, 3E, 4B, 5A, 6D, 7B), (1D, 2B, 3E, 4B, 5A, 6D, 7C), (1D, 2B, 3E, 4B, 5B, 6A, 7A), (1D, 2B, 3E, 4B, 5B, 6A, 7B), (1D, 2B, 3E, 4B, 5B, 6A, 7C), (1D, 2B, 3E, 4B, 5B, 6B, 7A), (1D, 2B, 3E, 4B, 5B, 6B, 7B), (1D, 2B, 3E, 4B, 5B, 6B, 7C), (1D, 2B, 3E, 4B, 5B, 6C, 7A), (1D, 2B, 3E, 4B, 5B, 6C, 7B), (1D, 2B, 3E, 4B, 5B, 6C, 7C), (1D, 2B, 3E, 4B, 5B, 6D, 7A), (1D, 2B, 3E, 4B, 5B, 6D, 7B), (1D, 2B, 3E, 4B, 5B, 6D, 7C), (1D, 2B, 3E, 4C, 5A, 6A, 7A), (1D, 2B, 3E, 4C, 5A, 6A, 7B), (1D, 2B, 3E, 4C, 5A, 6A, 7C), (1D, 2B, 3E, 4C, 5A, 6B, 7A), (1D, 2B, 3E, 4C, 5A, 6B, 7B), (1D, 2B, 3E, 4C, 5A, 6B, 7C), (1D, 2B, 3E, 4C, 5A, 6C, 7A), (1D, 2B, 3E, 4C, 5A, 6C, 7B), (1D, 2B, 3E, 4C, 5A, 6C, 7C), (1D, 2B, 3E, 4C, 5A, 6D, 7A), (1D, 2B, 3E, 4C, 5A, 6D, 7B), (1D, 2B, 3E, 4C, 5A, 6D, 7C), (1D, 2B, 3E, 4C, 5B, 6A, 7A), (1D, 2B, 3E, 4C, 5B, 6A, 7B), (1D, 2B, 3E, 4C, 5B, 6A, 7C), (1D, 2B, 3E, 4C, 5B, 6B, 7A), (1D, 2B, 3E, 4C, 5B, 6B, 7B), (1D, 2B, 3E, 4C, 5B, 6B, 7C), (1D, 2B, 3E, 4C, 5B, 6C, 7A), (1D, 2B, 3E, 4C, 5B, 6C, 7B), (1D, 2B, 3E, 4C, 5B, 6C, 7C), (1D, 2B, 3E, 4C, 5B, 6D, 7A), (1D, 2B, 3E, 4C, 5B, 6D, 7B), (1D, 2B, 3E, 4C, 5B, 6D, 7C), (1D, 2B, 3E, 4D, 5A, 6A, 7A), (1D, 2B, 3E, 4D, 5A, 6A, 7B), (1D, 2B, 3E, 4D, 5A, 6A, 7C), (1D, 2B, 3E, 4D, 5A, 6B, 7A), (1D, 2B, 3E, 4D, 5A, 6B, 7B), (1D, 2B, 3E, 4D, 5A, 6B, 7C), (1D, 2B, 3E, 4D, 5A, 6C, 7A), (1D, 2B, 3E, 4D, 5A, 6C, 7B), (1D, 2B, 3E, 4D, 5A, 6C, 7C), (1D, 2B, 3E, 4D, 5A, 6D, 7A), (1D, 2B, 3E, 4D, 5A, 6D, 7B), (1D, 2B, 3E, 4D, 5A, 6D, 7C), (1D, 2B, 3E, 4D, 5B, 6A, 7A), (1D, 2B, 3E, 4D, 5B, 6A, 7B), (1D, 2B, 3E, 4D, 5B, 6A, 7C), (1D, 2B, 3E, 4D, 5B, 6B, 7A), (1D, 2B, 3E, 4D, 5B, 6B, 7B), (1D, 2B, 3E, 4D, 5B, 6B, 7C), (1D, 2B, 3E, 4D, 5B, 6C, 7A), (1D, 2B, 3E, 4D, 5B, 6C, 7B), (1D, 2B, 3E, 4D, 5B, 6C, 7C), (1D, 2B, 3E, 4D, 5B, 6D, 7A), (1D, 2B, 3E, 4D, 5B, 6D, 7B), (1D, 2B, 3E, 4D, 5B, 6D, 7C), (1D, 2B, 3E, 4E, 5A, 6A, 7A), (1D, 2B, 3E, 4E, 5A, 6A, 7B), (1D, 2B, 3E, 4E, 5A, 6A, 7C), (1D, 2B, 3E, 4E, 5A, 6B, 7A), (1D, 2B, 3E, 4E, 5A, 6B, 7B), (1D, 2B, 3E, 4E, 5A, 6B, 7C), (1D, 2B, 3E, 4E, 5A, 6C, 7A), (1D, 2B, 3E, 4E, 5A, 6C, 7B), (1D, 2B, 3E, 4E, 5A, 6C, 7C), (1D, 2B, 3E, 4E, 5A, 6D, 7A), (1D, 2B, 3E, 4E, 5A, 6D, 7B), (1D, 2B, 3E, 4E, 5A, 6D, 7C), (1D, 2B, 3E, 4E, 5B, 6A, 7A), (1D, 2B, 3E, 4E, 5B, 6A, 7B), (1D, 2B, 3E, 4E, 5B, 6A, 7C), (1D, 2B, 3E, 4E, 5B, 6B, 7A), (1D, 2B, 3E, 4E, 5B, 6B, 7B), (1D, 2B, 3E, 4E, 5B, 6B, 7C), (1D, 2B, 3E, 4E, 5B, 6C, 7A), (1D, 2B, 3E, 4E, 5B, 6C, 7B), (1D, 2B, 3E, 4E, 5B, 6C, 7C), (1D, 2B, 3E, 4E, 5B, 6D, 7A), (1D, 2B, 3E, 4E, 5B, 6D, 7B), (1D, 2B, 3E, 4E, 5B, 6D, 7C), (1D, 2C, 3A, 4A, 5A, 6A, 7A), (1D, 2C, 3A, 4A, 5A, 6A, 7B), (1D, 2C, 3A, 4A, 5A, 6A, 7C), (1D, 2C, 3A, 4A, 5A, 6B, 7A), (1D, 2C, 3A, 4A, 5A, 6B, 7B), (1D, 2C, 3A, 4A, 5A, 6B, 7C), (1D, 2C, 3A, 4A, 5A, 6C, 7A), (1D, 2C, 3A, 4A, 5A, 6C, 7B), (1D, 2C, 3A, 4A, 5A, 6C, 7C), (1D, 2C, 3A, 4A, 5A, 6D, 7A), (1D, 2C, 3A, 4A, 5A, 6D, 7B), (1D, 2C, 3A, 4A, 5A, 6D, 7C), (1D, 2C, 3A, 4A, 5B, 6A, 7A), (1D, 2C, 3A, 4A, 5B, 6A, 7B), (1D, 2C, 3A, 4A, 5B, 6A, 7C), (1D, 2C, 3A, 4A, 5B, 6B, 7A), (1D, 2C, 3A, 4A, 5B, 6B, 7B), (1D, 2C, 3A, 4A, 5B, 6B, 7C), (1D, 2C, 3A, 4A, 5B, 6C, 7A), (1D, 2C, 3A, 4A, 5B, 6C, 7B), (1D, 2C, 3A, 4A, 5B, 6C, 7C), (1D, 2C, 3A, 4A, 5B, 6D, 7A), (1D, 2C, 3A, 4A, 5B, 6D, 7B), (1D, 2C, 3A, 4A, 5B, 6D, 7C), (1D, 2C, 3A, 4B, 5A, 6A, 7A), (1D, 2C, 3A, 4B, 5A, 6A, 7B), (1D, 2C, 3A, 4B, 5A, 6A, 7C), (1D, 2C, 3A, 4B, 5A, 6B, 7A), (1D, 2C, 3A, 4B, 5A, 6B, 7B), (1D, 2C, 3A, 4B, 5A, 6B, 7C), (1D, 2C, 3A, 4B, 5A, 6C, 7A), (1D, 2C, 3A, 4B, 5A, 6C, 7B), (1D, 2C, 3A, 4B, 5A, 6C, 7C), (1D, 2C, 3A, 4B, 5A, 6D, 7A), (1D, 2C, 3A, 4B, 5A, 6D, 7B), (1D, 2C, 3A, 4B, 5A, 6D, 7C), (1D, 2C, 3A, 4B, 5B, 6A, 7A), (1D, 2C, 3A, 4B, 5B, 6A, 7B), (1D, 2C, 3A, 4B, 5B, 6A, 7C), (1D, 2C, 3A, 4B, 5B, 6B, 7A), (1D, 2C, 3A, 4B, 5B, 6B, 7B), (1D, 2C, 3A, 4B, 5B, 6B, 7C), (1D, 2C, 3A, 4B, 5B, 6C, 7A), (1D, 2C, 3A, 4B, 5B, 6C, 7B), (1D, 2C, 3A, 4B, 5B, 6C, 7C), (1D, 2C, 3A, 4B, 5B, 6D, 7A), (1D, 2C, 3A, 4B, 5B, 6D, 7B), (1D, 2C, 3A, 4B, 5B, 6D, 7C), (1D, 2C, 3A, 4C, 5A, 6A, 7A), (1D, 2C, 3A, 4C, 5A, 6A, 7B), (1D, 2C, 3A, 4C, 5A, 6A, 7C), (1D, 2C, 3A, 4C, 5A, 6B, 7A), (1D, 2C, 3A, 4C, 5A, 6B, 7B), (1D, 2C, 3A, 4C, 5A, 6B, 7C), (1D, 2C, 3A, 4C, 5A, 6C, 7A), (1D, 2C, 3A, 4C, 5A, 6C, 7B), (1D, 2C, 3A, 4C, 5A, 6C, 7C), (1D, 2C, 3A, 4C, 5A, 6D, 7A), (1D, 2C, 3A, 4C, 5A, 6D, 7E), (1D, 2C, 3A, 4C, 5A, 6D, 7C), (1D, 2C, 3A, 4C, 5B, 6A, 7A), (1D, 2C, 3A, 4C, 5B, 6A, 7B), (1D, 2C, 3A, 4C, 5B, 6A, 7C), (1D, 2C, 3A, 4C, 5B, 6B, 7A), (1D, 2C, 3A, 4C, 5B, 6B, 7B), (1D, 2C, 3A, 4C, 5B, 6B, 7C), (1D, 2C, 3A, 4C, 5B, 6C, 7A), (1D, 2C, 3A, 4C, 5B, 6C, 7B), (1D, 2C, 3A, 4C, 5B, 6C, 7C), (1D, 2C, 3A, 4C, 5B, 6D, 7A), (1D, 2C, 3A, 4C, 5B, 6D, 7B), (1D, 2C, 3A, 4C, 5B, 6D, 7C), (1D, 2C, 3A, 4D, 5A, 6A, 7A), (1D, 2C, 3A, 4D, 5A, 6A, 7B), (1D, 2C, 3A, 4D, 5A, 6A, 7C), (1D, 2C, 3A, 4D, 5A, 6B, 7A), (1D, 2C, 3A, 4D, 5A, 6B, 7B), (1D, 2C, 3A, 4D, 5A, 6B, 7C), (1D, 2C, 3A, 4D, 5A, 6C, 7A), (1D, 2C, 3A, 4D, 5A, 6C, 7B), (1D, 2C, 3A, 4D, 5A, 6C, 7C), (1D, 2C, 3A, 4D, 5A, 6D, 7A), (1D, 2C, 3A, 4D, 5A, 6D, 7B), (1D, 2C, 3A, 4D, 5A, 6D, 7C), (1D, 2C, 3A, 4D, 5B, 6A, 7A), (1D, 2C, 3A, 4D, 5B, 6A, 7B), (1D, 2C, 3A, 4D, 5B, 6A, 7C), (1D, 2C, 3A, 4D, 5B, 6B, 7A), (1D, 2C, 3A, 4D, 5B, 6B, 7B), (1D, 2C, 3A, 4D, 5B, 6B, 7C), (1D, 2C, 3A, 4D, 5B, 6C, 7A), (1D, 2C, 3A, 4D, 5B, 6C, 7B), (1D, 2C, 3A, 4D, 5B, 6C, 7C), (1D, 2C, 3A, 4D, 5B, 6D, 7A), (1D, 2C, 3A, 4D, 5B, 6D, 7B), (1D, 2C, 3A, 4D, 5B, 6D, 7C), (1D, 2C, 3A, 4E, 5A, 6A, 7A), (1D, 2C, 3A, 4E, 5A, 6A, 7B), (1D, 2C, 3A, 4E, 5A, 6A, 7C), (1D, 2C, 3A, 4E, 5A, 6B, 7A), (1D, 2C, 3A, 4E, 5A, 6B, 7B), (1D, 2C, 3A, 4E, 5A, 6B, 7C), (1D, 2C, 3A, 4E, 5A, 6C, 7A), (1D, 2C, 3A, 4E, 5A, 6C, 7B), (1D, 2C, 3A, 4E, 5A, 6C, 7C), (1D, 2C, 3A, 4E, 5A, 6D, 7A), (1D, 2C, 3A, 4E, 5A, 6D, 7B), (1D, 2C, 3A, 4E, 5A, 6D, 7C), (1D, 2C, 3A, 4E, 5B, 6A, 7A), (1D, 2C, 3A, 4E, 5B, 6A, 7B), (1D, 2C, 3A, 4E, 5B, 6A, 7C), (1D, 2C, 3A, 4E, 5B, 6B, 7A), (1D, 2C, 3A, 4E, 5B, 6B, 7B), (1D, 2C, 3A, 4E, 5B, 6B, 7C), (1D, 2C, 3A, 4E, 5B, 6C, 7A), (1D, 2C, 3A, 4E, 5B, 6C, 7B), (1D, 2C, 3A, 4E, 5B, 6C, 7C), (1D, 2C, 3A, 4E, 5B, 6D, 7A), (1D, 2C, 3A, 4E, 5B, 6D, 7B), (1D, 2C, 3A, 4E, 5B, 6D, 7C), (1D, 2C, 3B, 4A, 5A, 6A, 7A), (1D, 2C, 3B, 4A, 5A, 6A, 7B), (1D, 2C, 3B, 4A, 5A, 6A, 7C), (1D, 2C, 3B, 4A, 5A, 6B, 7A), (1D, 2C, 3B, 4A, 5A, 6B, 7B), (1D, 2C, 3B, 4A, 5A, 6B, 7C), (1D, 2C, 3B, 4A, 5A, 6C, 7A), (1D, 2C, 3B, 4A, 5A, 6C, 7B), (1D, 2C, 3B, 4A, 5A, 6C, 7C), (1D, 2C, 3B, 4A, 5A, 6D, 7A), (1D, 2C, 3B, 4A, 5A, 6D, 7B), (1D, 2C, 3B, 4A, 5A, 6D, 7C), (1D, 2C, 3B, 4A, 5B, 6A, 7A), (1D, 2C, 3B, 4A, 5B, 6A, 7B), (1D, 2C, 3B, 4A, 5B, 6A, 7C), (1D, 2C, 3B, 4A, 5B, 6B, 7A), (1D, 2C, 3B, 4A, 5B, 6B, 7B), (1D, 2C, 3B, 4A, 5B, 6B, 7C), (1D, 2C, 3B, 4A, 5B, 6C, 7A), (1D, 2C, 3B, 4A, 5B, 6C, 7B), (1D, 2C, 3B, 4A, 5B, 6C, 7C), (1D, 2C, 3B, 4A, 5B, 6D, 7A), (1D, 2C, 3B, 4A, 5B, 6D, 7B), (1D, 2C, 3B, 4A, 5B, 6D, 7C), (1D, 2C, 3B, 4B, 5A, 6A, 7A), (1D, 2C, 3B, 4B, 5A, 6A, 7B), (1D, 2C, 3B, 4B, 5A, 6A, 7C), (1D, 2C, 3B, 4B, 5A, 6B, 7A), (1D, 2C, 3B, 4B, 5A, 6B, 7B), (1D, 2C, 3B, 4B, 5A, 6B, 7C), (1D, 2C, 3B, 4B, 5A, 6C, 7A), (1D, 2C, 3B, 4B, 5A, 6C, 7B), (1D, 2C, 3B, 4B, 5A, 6C, 7C), (1D, 2C, 3B, 4B, 5A, 6D, 7A), (1D, 2C, 3B, 4B, 5A, 6D, 7B), (1D, 2C, 3B, 4B, 5A, 6D, 7C), (1D, 2C, 3B, 4B, 5B, 6A, 7A), (1D, 2C, 3B, 4B, 5B, 6A, 7B), (1D, 2C, 3B, 4B, 5B, 6A, 7C), (1D, 2C, 3B, 4B, 5B, 6B, 7A), (1D, 2C, 3B, 4B, 5B, 6B, 7B), (1D, 2C, 3B, 4B, 5B, 6B, 7C), (1D, 2C, 3B, 4B, 5B, 6C, 7A), (1D, 2C, 3B, 4B, 5B, 6C, 7B), (1D, 2C, 3B, 4B, 5B, 6C, 7C), (1D, 2C, 3B, 4B, 5B, 6D, 7A), (1D, 2C, 3B, 4B, 5B, 6D, 7B), (1D, 2C, 3B, 4B, 5B, 6D, 7C), (1D, 2C, 3B, 4C, 5A, 6A, 7A), (1D, 2C, 3B, 4C, 5A, 6A, 7B), (1D, 2C, 3B, 4C, 5A, 6A, 7C), (1D, 2C, 3B, 4C, 5A, 6B, 7A), (1D, 2C, 3B, 4C, 5A, 6B, 7B), (1D, 2C, 3B, 4C, 5A, 6B, 7C), (1D, 2C, 3B, 4C, 5A, 6C, 7A), (1D, 2C, 3B, 4C, 5A, 6C, 7B), (1D, 2C, 3B, 4C, 5A, 6C, 7C), (1D, 2C, 3B, 4C, 5A, 6D, 7A), (1D, 2C, 3B, 4C, 5A, 6D, 7B), (1D, 2C, 3B, 4C, 5A, 6D, 7C), (1D, 2C, 3B, 4C, 5B, 6A, 7A), (1D, 2C, 3B, 4C, 5B, 6A, 7B), (1D, 2C, 3B, 4C, 5B, 6A, 7C), (1D, 2C, 3B, 4C, 5B, 6B, 7A), (1D, 2C, 3B, 4C, 5B, 6B, 7B), (1D, 2C, 3B, 4C, 5B, 6B, 7C), (1D, 2C, 3B, 4C, 5B, 6C, 7A), (1D, 2C, 3B, 4C, 5B, 6C, 7B), (1D, 2C, 3B, 4C, 5B, 6C, 7C), (1D, 2C, 3B, 4C, 5B, 6D, 7A), (1D, 2C, 3B, 4C, 5B, 6D, 7B), (1D, 2C, 3B, 4C, 5B, 6D, 7C), (1D, 2C, 3B, 4D, 5A, 6A, 7A), (1D, 2C, 3B, 4D, 5A, 6A, 7B), (1D, 2C, 3B, 4D, 5A, 6A, 7C), (1D, 2C, 3B, 4D, 5A, 6B, 7A), (1D, 2C, 3B, 4D, 5A, 6B, 7B), (1D, 2C, 3B, 4D, 5A, 6B, 7C), (1D, 2C, 3B, 4D, 5A, 6C, 7A), (1D, 2C, 3B, 4D, 5A, 6C, 7B), (1D, 2C, 3B, 4D, 5A, 6C, 7C), (1D, 2C, 3B, 4D, 5A, 6D, 7A), (1D, 2C, 3B, 4D, 5A, 6D, 7B), (1D, 2C, 3B, 4D, 5A, 6D, 7C), (1D, 2C, 3B, 4D, 5B, 6A, 7A), (1D, 2C, 3B, 4D, 5B, 6A, 7B), (1D, 2C, 3B, 4D, 5B, 6A, 7C), (1D, 2C, 3B, 4D, 5B, 6B, 7A), (1D, 2C, 3B, 4D, 5B, 6B, 7B), (1D, 2C, 3B, 4D, 5B, 6B, 7C), (1D, 2C, 3B, 4D, 5B, 6C, 7A), (1D, 2C, 3B, 4D, 5B, 6C, 7B), (1D, 2C, 3B, 4D, 5B, 6C, 7C), (1D, 2C, 3B, 4D, 5B, 6D, 7A), (1D, 2C, 3B, 4D, 5B, 6D, 7B), (1D, 2C, 3B, 4D, 5B, 6D, 7C), (1D, 2C, 3B, 4E, 5A, 6A, 7A), (1D, 2C, 3B, 4E, 5A, 6A, 7B), (1D, 2C, 3B, 4E, 5A, 6A, 7C), (1D, 2C, 3B, 4E, 5A, 6B, 7A), (1D, 2C, 3B, 4E, 5A, 6B, 7B), (1D, 2C, 3B, 4E, 5A, 6B, 7C), (1D, 2C, 3B, 4E, 5A, 6C, 7A), (1D, 2C, 3B, 4E, 5A, 6C, 7B), (1D, 2C, 3B, 4E, 5A, 6C, 7C), (1D, 2C, 3B, 4E, 5A, 6D, 7A), (1D, 2C, 3B, 4E, 5A, 6D, 7B), (1D, 2C, 3B, 4E, 5A, 6D, 7C), (1D, 2C, 3B, 4E, 5B, 6A, 7A), (1D, 2C, 3B, 4E, 5B, 6A, 7B), (1D, 2C, 3B, 4E, 5B, 6A, 7C), (1D, 2C, 3B, 4E, 5B, 6B, 7A), (1D, 2C, 3B, 4E, 5B, 6B, 7B), (1D, 2C, 3B, 4E, 5B, 6B, 7C), (1D, 2C, 3B, 4E, 5B, 6C, 7A), (1D, 2C, 3B, 4E, 5B, 6C, 7B), (1D, 2C, 3B, 4E, 5B, 6C, 7C), (1D, 2C, 3B, 4E, 5B, 6D, 7A), (1D, 2C, 3B, 4E, 5B, 6D, 7B), (1D, 2C, 3B, 4E, 5B, 6D, 7C), (1D, 2C, 3C, 4A, 5A, 6A, 7A), (1D, 2C, 3C, 4A, 5A, 6A, 7B), (1D, 2C, 3C, 4A, 5A, 6A, 7C), (1D, 2C, 3C, 4A, 5A, 6B, 7A), (1D, 2C, 3C, 4A, 5A, 6B, 7B), (1D, 2C, 3C, 4A, 5A, 6B, 7C), (1D, 2C, 3C, 4A, 5A, 6C, 7A), (1D, 2C, 3C, 4A, 5A, 6C, 7B), (1D, 2C, 3C, 4A, 5A, 6C, 7C), (1D, 2C, 3C, 4A, 5A, 6D, 7A), (1D, 2C, 3C, 4A, 5A, 6D, 7B), (1D, 2C, 3C, 4A, 5A, 6D, 7C), (1D, 2C, 3C, 4A, 5B, 6A, 7A), (1D, 2C, 3C, 4A, 5B, 6A, 7B), (1D, 2C, 3C, 4A, 5B, 6A, 7C), (1D, 2C, 3C, 4A, 5B, 6B, 7A), (1D, 2C, 3C, 4A, 5B, 6B, 7B), (1D, 2C, 3C, 4A, 5B, 6B, 7C), (1D, 2C, 3C, 4A, 5B, 6C, 7A), (1D, 2C, 3C, 4A, 5B, 6C, 7B), (1D, 2C, 3C, 4A, 5B, 6C, 7C), (1D, 2C, 3C, 4A, 5B, 6D, 7A), (1D, 2C, 3C, 4A, 5B, 6D, 7B), (1D, 2C, 3C, 4A, 5B, 6D, 7C), (1D, 2C, 3C, 4B, 5A, 6A, 7A), (1D, 2C, 3C, 4B, 5A, 6A, 7B), (1D, 2C, 3C, 4B, 5A, 6A, 7C), (1D, 2C, 3C, 4B, 5A, 6B, 7A), (1D, 2C, 3C, 4B, 5A, 6B, 7B), (1D, 2C, 3C, 4B, 5A, 6B, 7C), (1D, 2C, 3C, 4B, 5A, 6C, 7A), (1D, 2C, 3C, 4B, 5A, 6C, 7B), (1D, 2C, 3C, 4B, 5A, 6C, 7C), (1D, 2C, 3C, 4B, 5A, 6D, 7A), (1D, 2C, 3C, 4B, 5A, 6D, 7B), (1D, 2C, 3C, 4B, 5A, 6D, 7C), (1D, 2C, 3C, 4B, 5B, 6A, 7A), (1D, 2C, 3C, 4B, 5B, 6A, 7B), (1D, 2C, 3C, 4B, 5B, 6A, 7C), (1D, 2C, 3C, 4B, 5B, 6B, 7A), (1D, 2C, 3C, 4B, 5B, 6B, 7B), (1D, 2C, 3C, 4B, 5B, 6B, 7C), (1D, 2C, 3C, 4B, 5B, 6C, 7A), (1D, 2C, 3C, 4B, 5B, 6C, 7B), (1D, 2C, 3C, 4B, 5B, 6C, 7C), (1D, 2C, 3C, 4B, 5B, 6D, 7A), (1D, 2C, 3C, 4B, 5B, 6D, 7B), (1D, 2C, 3C, 4B, 5B, 6D, 7C), (1D, 2C, 3C, 4C, 5A, 6A, 7A), (1D, 2C, 3C, 4C, 5A, 6A, 7B), (1D, 2C, 3C, 4C, 5A, 6A, 7C), (1D, 2C, 3C, 4C, 5A, 6B, 7A), (1D, 2C, 3C, 4C, 5A, 6B, 7B), (1D, 2C, 3C, 4C, 5A, 6B, 7C), (1D, 2C, 3C, 4C, 5A, 6C, 7A), (1D, 2C, 3C, 4C, 5A, 6C, 7B), (1D, 2C, 3C, 4C, 5A, 6C, 7C), (1D, 2C, 3C, 4C, 5A, 6D, 7A), (1D, 2C, 3C, 4C, 5A, 6D, 7B), (1D, 2C, 3C, 4C, 5A, 6D, 7C), (1D, 2C, 3C, 4C, 5B, 6A, 7A), (1D, 2C, 3C, 4C, 5B, 6A, 7B), (1D, 2C, 3C, 4C, 5B, 6A, 7C), (1D, 2C, 3C, 4C, 5B, 6B, 7A), (1D, 2C, 3C, 4C, 5B, 6B, 7B), (1D, 2C, 3C, 4C, 5B, 6B, 7C), (1D, 2C, 3C, 4C, 5B, 6C, 7A), (1D, 2C, 3C, 4C, 5B, 6C, 7B), (1D, 2C, 3C, 4C, 5B, 6C, 7C), (1D, 2C, 3C, 4C, 5B, 6D, 7A), (1D, 2C, 3C, 4C, 5B, 6D, 7B), (1D, 2C, 3C, 4C, 5B, 6D, 7C), (1D, 2C, 3C, 4D, 5A, 6A, 7A), (1D, 2C, 3C, 4D, 5A, 6A, 7B), (1D, 2C, 3C, 4D, 5A, 6A, 7C), (1D, 2C, 3C, 4D, 5A, 6B, 7A), (1D, 2C, 3C, 4D, 5A, 6B, 7B), (1D, 2C, 3C, 4D, 5A, 6B, 7C), (1D, 2C, 3C, 4D, 5A, 6C, 7A), (1D, 2C, 3C, 4D, 5A, 6C, 7B), (1D, 2C, 3C, 4D, 5A, 6C, 7C), (1D, 2C, 3C, 4D, 5A, 6D, 7A), (1D, 2C, 3C, 4D, 5A, 6D, 7B), (1D, 2C, 3C, 4D, 5A, 6D, 7C), (1D, 2C, 3C, 4D, 5B, 6A, 7A), (1D, 2C, 3C, 4D, 5B, 6A, 7B), (1D, 2C, 3C, 4D, 5B, 6A, 7C), (1D, 2C, 3C, 4D, 5B, 6B, 7A), (1D, 2C, 3C, 4D, 5B, 6B, 7B), (1D, 2C, 3C, 4D, 5B, 6B, 7C), (1D, 2C, 3C, 4D, 5B, 6C, 7A), (1D, 2C, 3C, 4D, 5B, 6C, 7B), (1D, 2C, 3C, 4D, 5B, 6C, 7C), (1D, 2C, 3C, 4D, 5B, 6D, 7A), (1D, 2C, 3C, 4D, 5B, 6D, 7B), (1D, 2C, 3C, 4D, 5B, 6D, 7C), (1D, 2C, 3C, 4E, 5A, 6A, 7A), (1D, 2C, 3C, 4E, 5A, 6A, 7C), (1D, 2C, 3C, 4E, 5A, 6A, 7C), (1D, 2C, 3C, 4E, 5A, 6B, 7A), (1D, 2C, 3C, 4E, 5A, 6B, 7B), (1D, 2C, 3C, 4E, 5A, 6B, 7C), (1D, 2C, 3C, 4E, 5A, 6C, 7A), (1D, 2C, 3C, 4E, 5A, 6C, 7B), (1D, 2C, 3C, 4E, 5A, 6C, 7C), (1D, 2C, 3C, 4E, 5A, 6D, 7A), (1D, 2C, 3C, 4E, 5A, 6D, 7B), (1D, 2C, 3C, 4E, 5A, 6D, 7C), (1D, 2C, 3C, 4E, 5B, 6A, 7A), (1D, 2C, 3C, 4E, 5B, 6A, 7B), (1D, 2C, 3C, 4E, 5B, 6A, 7C), (1D, 2C, 3C, 4E, 5B, 6B, 7A), (1D, 2C, 3C, 4E, 5B, 6B, 7B), (1D, 2C, 3C, 4E, 5B, 6B, 7C), (1D, 2C, 3C, 4E, 5B, 6C, 7A), (1D, 2C, 3C, 4E, 5B, 6C, 7B), (1D, 2C, 3C, 4E, 5B, 6C, 7C), (1D, 2C, 3C, 4E, 5B, 6D, 7A), (1D, 2C, 3C, 4E, 5B, 6D, 7B), (1D, 2C, 3C, 4E, 5B, 6D, 7C), (1D, 2C, 3D, 4A, 5A, 6A, 7A), (1D, 2C, 3D, 4A, 5A, 6A, 7B), (1D, 2C, 3D, 4A, 5A, 6A, 7C), (1D, 2C, 3D, 4A, 5A, 6B, 7A), (1D, 2C, 3D, 4A, 5A, 6B, 7B), (1D, 2C, 3D, 4A, 5A, 6B, 7C), (1D, 2C, 3D, 4A, 5A, 6C, 7A), (1D, 2C, 3D, 4A, 5A, 6C, 7B), (1D, 2C, 3D, 4A, 5A, 6C, 7C), (1D, 2C, 3D, 4A, 5A, 6D, 7A), (1D, 2C, 3D, 4A, 5A, 6D, 7B), (1D, 2C, 3D, 4A, 5A, 6D, 7C), (1D, 2C, 3D, 4A, 5B, 6A, 7A), (1D, 2C, 3D, 4A, 5B, 6A, 7B), (1D, 2C, 3D, 4A, 5B, 6A, 7C), (1D, 2C, 3D, 4A, 5B, 6B, 7A), (1D, 2C, 3D, 4A, 5B, 6B, 7B), (1D, 2C, 3D, 4A, 5B, 6B, 7C), (1D, 2C, 3D, 4A, 5B, 6C, 7A), (1D, 2C, 3D, 4A, 5B, 6C, 7B), (1D, 2C, 3D, 4A, 5B, 6C, 7C), (1D, 2C, 3D, 4A, 5B, 6D, 7A), (1D, 2C, 3D, 4A, 5B, 6D, 7B), (1D, 2C, 3D, 4A, 5B, 6D, 7C), (1D, 2C, 3D, 4B, 5A, 6A, 7A), (1D, 2C, 3D, 4B, 5A, 6A, 7B), (1D, 2C, 3D, 4B, 5A, 6A, 7C), (1D, 2C, 3D, 4B, 5A, 6B, 7A), (1D, 2C, 3D, 4B, 5A, 6B, 7B), (1D, 2C, 3D, 4B, 5A, 6B, 7C), (1D, 2C, 3D, 4B, 5A, 6C, 7A), (1D, 2C, 3D, 4B, 5A, 6C, 7B), (1D, 2C, 3D, 4B, 5A, 6C, 7C), (1D, 2C, 3D, 4B, 5A, 6D, 7A), (1D, 2C, 3D, 4B, 5A, 6D, 7E), (1D, 2C, 31D, 4B, 5A, 6D, 7C), (1D, 2C, 3D, 4B, 5B, 6A, 7A), (1D, 2C, 3D, 4B, 5B, 6A, 7B), (1D, 2C, 3D, 4B, 5B, 6A, 7C), (1D, 2C, 3D, 4B, 5B, 6B, 7A), (1D, 2C, 3D, 4B, 5B, 6B, 7B), (1D, 2C, 3D, 4B, 5B, 6B, 7C), (1D, 2C, 3D, 4B, 5B, 6C, 7A), (1D, 2C, 3D, 4B, 5B, 6C, 7B), (1D, 2C, 3D, 4B, 5B, 6C, 7C), (1D, 2C, 3D, 4B, 5B, 6D, 7A), (1D, 2C, 3D, 4B, 5B, 6D, 7B), (1D, 2C, 3D, 4B, 5B, 6D, 7C), (1D, 2C, 3D, 4C, 5A, 6A, 7A), (1D, 2C, 3D, 4C, 5A, 6A, 7B), (1D, 2C, 3D, 4C, 5A, 6A, 7C), (1D, 2C, 3D, 4C, 5A, 6B, 7A), (1D, 2C, 3D, 4C, 5A, 6B, 7B), (1D, 2C, 3D, 4C, 5A, 6B, 7C), (1D, 2C, 3D, 4C, 5A, 6C, 7A), (1D, 2C, 3D, 4C, 5A, 6C, 7B), (1D, 2C, 3D, 4C, 5A, 6C, 7C), (1D, 2C, 3D, 4C, 5A, 6D, 7A), (1D, 2C, 3D, 4C, 5A, 6D, 7B), (1D, 2C, 3D, 4C, 5A, 6D, 7C), (1D, 2C, 3D, 4C, 5B, 6A, 7A), (1D, 2C, 3D, 4C, 5B, 6A, 7B), (1D, 2C, 3D, 4C, 5B, 6A, 7C), (1D, 2C, 3D, 4C, 5B, 6B, 7A), (1D, 2C, 3D, 4C, 5B, 6B, 7B), (1D, 2C, 3D, 4C, 5B, 6B, 7C), (1D, 2C, 3D, 4C, 5B, 6C, 7A), (1D, 2C, 3D, 4C, 5B, 6C, 7B), (1D, 2C, 3D, 4C, 5B, 6C, 7C), (1D, 2C, 3D, 4C, 5B, 6D, 7A), (1D, 2C, 3D, 4C, 5B, 6D, 7B), (1D, 2C, 3D, 4C, 5B, 6D, 7C), (1D, 2C, 3D, 4C, 5B, 6A, 7A), (1D, 2C, 3D, 4D, 5A, 6A, 7B), (1D, 2C, 3D, 4D, 5A, 6A, 7C), (1D, 2C, 3D, 4D, 5A, 6B, 7A), (1D, 2C, 3D, 4D, 5A, 6B, 7B), (1D, 2C, 3D, 4D, 5A, 6B, 7C), (1D, 2C, 3D, 4D, 5A, 6C, 7A), (1D, 2C, 3D, 4D, 5A, 6C, 7B), (1D, 2C, 3D, 4D, 5A, 6C, 7C), (1D, 2C, 3D, 4D, 5A, 6D, 7A), (1D, 2C, 3D, 4D, 5A, 6D, 7B), (1D, 2C, 3D, 4D, 5A, 6D, 7C), (1D, 2C, 3D, 4D, 5B, 6A, 7A), (1D, 2C, 3D, 4D, 5B, 6A, 7B), (1D, 2C, 3D, 4D, 5B, 6A, 7C), (1D, 2C, 3D, 4D, 5B, 6B, 7A), (1D, 2C, 3D, 4D, 5B, 6B, 7B), (1D, 2C, 3D, 4D, 5B, 6B, 7C), (1D, 2C, 3D, 4D, 5B, 6C, 7A), (1D, 2C, 3D, 4D, 5B, 6C, 7B), (1D, 2C, 3D, 4D, 5B, 6C, 7C), (1D, 2C, 3D, 4D, 5B, 6D, 7A), (1D, 2C, 3D, 4D, 5B, 6D, 7B), (1D, 2C, 3D, 4D, 5B, 6D, 7C), (1D, 2C, 3D, 4E, 5A, 6A, 7A), (1D, 2C, 3D, 4E, 5A, 6A, 7B), (1D, 2C, 3D, 4E, 5A, 6A, 7C), (1D, 2C, 3D, 4E, 5A, 6B, 7A), (1D, 2C, 3D, 4E, 5A, 6B, 7B), (1D, 2C, 3D, 4E, 5A, 6B, 7C), (1D, 2C, 3D, 4E, 5A, 6C, 7A), (1D, 2C, 3D, 4E, 5A, 6C, 7B), (1D, 2C, 3D, 4E, 5A, 6C, 7C), (1D, 2C, 3D, 4E, 5A, 6D, 7A), (1D, 2C, 3D, 4E, 5A, 6D, 7B), (1D, 2C, 3D, 4E, 5A, 6D, 7C), (1D, 2C, 3D, 4E, 5B, 6A, 7A), (1D, 2C, 3D, 4E, 5B, 6A, 7B), (1D, 2C, 3D, 4E, 5B, 6A, 7C), (1D, 2C, 3D, 4E, 5B, 6B, 7A), (1D, 2C, 3D, 4E, 5B, 6B, 7B), (1D, 2C, 3D, 4E, 5B, 6B, 7C), (1D, 2C, 3D, 4E, 5B, 6C, 7A), (1D, 2C, 3D, 4E, 5B, 6C, 7B), (1D, 2C, 3D, 4E, 5B, 6C, 7C), (1D, 2C, 3D, 4E, 5B, 6D, 7A), (1D, 2C, 3D, 4E, 5B, 6D, 7B), (1D, 2C, 3D, 4E, 5B, 6D, 7C), (1D, 2C, 3E, 4A, 5A, 6A, 7A), (1D, 2C, 3E, 4A, 5A, 6A, 7B), (1D, 2C, 3E, 4A, 5A, 6A, 7C), (1D, 2C, 3E, 4A, 5A, 6B, 7A), (1D, 2C, 3E, 4A, 5A, 6B, 7B), (1D, 2C, 3E, 4A, 5A, 6B, 7C), (1D, 2C, 3E, 4A, 5A, 6C, 7A), (1D, 2C, 3E, 4A, 5A, 6C, 7B), (1D, 2C, 3E, 4A, 5A, 6C, 7C), (1D, 2C, 3E, 4A, 5A, 6D, 7A), (1D, 2C, 3E, 4A, 5A, 6D, 7B), (1D, 2C, 3E, 4A, 5A, 6D, 7C), (1D, 2C, 3E, 4A, 5B, 6A, 7A), (1D, 2C, 3E, 4A, 5B, 6A, 7B), (1D, 2C, 3E, 4A, 5B, 6A, 7C), (1D, 2C, 3E, 4A, 5B, 6B, 7A), (1D, 2C, 3E, 4A, 5B, 6B, 7B), (1D, 2C, 3E, 4A, 5B, 6B, 7C), (1D, 2C, 3E, 4A, 5B, 6C, 7A), (1D, 2C, 3E, 4A, 5B, 6C, 7B), (1D, 2C, 3E, 4A, 5B, 6C, 7C), (1D, 2C, 3E, 4A, 5B, 6D, 7A), (1D, 2C, 3E, 4A, 5B, 6D, 7B), (1D, 2C, 3E, 4A, 5B, 6D, 7C), (1D, 2C, 3E, 4B, 5A, 6A, 7A), (1D, 2C, 3E, 4B, 5A, 6A, 7B), (1D, 2C, 3E, 4B, 5A, 6A, 7C), (1D, 2C, 3E, 4B, 5A, 6B, 7A), (1D, 2C, 3E, 4B, 5A, 6B, 7B), (1D, 2C, 3E, 4B, 5A, 6B, 7C), (1D, 2C, 3E, 4B, 5A, 6C, 7A), (1D, 2C, 3E, 4B, 5A, 6C, 7B), (1D, 2C, 3E, 4B, 5A, 6C, 7C), (1D, 2C, 3E, 4B, 5A, 6D, 7A), (1D, 2C, 3E, 4B, 5A, 6D, 7B), (1D, 2C, 3E, 4B, 5A, 6D, 7C), (1D, 2C, 3E, 4B, 5B, 6A, 7A), (1D, 2C, 3E, 4B, 5B, 6A, 7B), (1D, 2C, 3E, 4B, 5B, 6A, 7C), (1D, 2C, 3E, 4B, 5B, 6B, 7A), (1D, 2C, 3E, 4B, 5B, 6B, 7B), (1D, 2C, 3E, 4B, 5B, 6B, 7C), (1D, 2C, 3E, 4B, 5B, 6C, 7A), (1D, 2C, 3E, 4B, 5B, 6C, 7B), (1D, 2C, 3E, 4B, 5B, 6C, 7C), (1D, 2C, 3E, 4B, 5B, 6D, 7A), (1D, 2C, 3E, 4B, 5B, 6D, 7B), (1D, 2C, 3E, 4B, 5B, 6D, 7C), (1D, 2C, 3E, 4C, 5A, 6A, 7A), (1D, 2C, 3E, 4C, 5A, 6A, 7B), (1D, 2C, 3E, 4C, 5A, 6A, 7C), (1D, 2C, 3E, 4C, 5A, 6B, 7A), (1D, 2C, 3E, 4C, 5A, 6B, 7B), (1D, 2C, 3E, 4C, 5A, 6B, 7C), (1D, 2C, 3E, 4C, 5A, 6C, 7A), (1D, 2C, 3E, 4C, 5A, 6C, 7B), (1D, 2C, 3E, 4C, 5A, 6C, 7C), (1D, 2C, 3E, 4C, 5A, 6D, 7A), (1D, 2C, 3E, 4C, 5A, 6D, 7B), (1D, 2C, 3E, 4C, 5A, 6D, 7C), (1D, 2C, 3E, 4C, 5B, 6A, 7A), (1D, 2C, 3E, 4C, 5B, 6A, 7B), (1D, 2C, 3E, 4C, 5B, 6A, 7C), (1D, 2C, 3E, 4C, 5B, 6B, 7A), (1D, 2C, 3E, 4C, 5B, 6B, 7B), (1D, 2C, 3E, 4C, 5B, 6B, 7C), (1D, 2C, 3E, 4C, 5B, 6C, 7A), (1D, 2C, 3E, 4C, 5B, 6C, 7B), (1D, 2C, 3E, 4C, 5B, 6C, 7C), (1D, 2C, 3E, 4C, 5B, 6D, 7A), (1D, 2C, 3E, 4C, 5B, 6D, 7B), (1D, 2C, 3E, 4C, 5B, 6D, 7C), (1D, 2C, 3E, 4D, 5A, 6A, 7A), (1D, 2C, 3E, 4D, 5A, 6A, 7B), (1D, 2C, 3E, 4D, 5A, 6A, 7C), (1D, 2C, 3E, 4D, 5A, 6B, 7A), (1D, 2C, 3E, 4D, 5A, 6B, 7B), (1D, 2C, 3E, 4D, 5A, 6B, 7C), (1D, 2C, 3E, 4D, 5A, 6C, 7A), (1D, 2C, 3E, 4D, 5A, 6C, 7B), (1D, 2C, 3E, 4D, 5A, 6C, 7C), (1D, 2C, 3E, 4D, 5A, 6D, 7A), (1D, 2C, 3E, 4D, 5A, 6D, 7B), (1D, 2C, 3E, 4D, 5A, 6D, 7C), (1D, 2C, 3E, 4D, 5B, 6A, 7A), (1D, 2C, 3E, 4D, 5B, 6A, 7B), (1D, 2C, 3E, 4D, 5B, 6A, 7C), (1D, 2C, 3E, 4D, 5B, 6B, 7A), (1D, 2C, 3E, 4D, 5B, 6B, 7B), (1D, 2C, 3E, 4D, 5B, 6B, 7C), (1D, 2C, 3E, 4D, 5B, 6C, 7A), (1D, 2C, 3E, 4D, 5B, 6C, 7B), (1D, 2C, 3E, 4D, 5B, 6C, 7C), (1D, 2C, 3E, 4D, 5B, 6D, 7A), (1D, 2C, 3E, 4D, 5B, 6D, 7B), (1D, 2C, 3E, 4D, 5B, 6D, 7C), (1D, 2C, 3E, 4E, 5A, 6A, 7A), (1D, 2C, 3E, 4E, 5A, 6A, 7B), (1D, 2C, 3E, 4E, 5A, 6A, 7C), (1D, 2C, 3E, 4E, 5A, 6B, 7A), (1D, 2C, 3E, 4E, 5A, 6B, 7B), (1D, 2C, 3E, 4E, 5A, 6B, 7C), (1D, 2C, 3E, 4E, 5A, 6C, 7A), (1D, 2C, 3E, 4E, 5A, 6C, 7B), (1D, 2C, 3E, 4E, 5A, 6C, 7C), (1D, 2C, 3E, 4E, 5A, 6D, 7A), (1D, 2C, 3E, 4E, 5A, 6D, 7B), (1D, 2C, 3E, 4E, 5A, 6D, 7C), (1D, 2C, 3E, 4E, 5B, 6A, 7A), (1D, 2C, 3E, 4E, 5B, 6A, 7B), (1D, 2C, 3E, 4E, 5B, 6A, 7C), (1D, 2C, 3E, 4E, 5B, 6B, 7A), (1D, 2C, 3E, 4E, 5B, 6B, 7B), (1D, 2C, 3E, 4E, 5B, 6B, 7C), (1D, 2C, 3E, 4E, 5B, 6C, 7A), (1D, 2C, 3E, 4E, 5B, 6C, 7B), (1D, 2C, 3E, 4E, 5B, 6C, 7C), (1D, 2C, 3E, 4E, 5B, 6D, 7A), (1D, 2C, 3E, 4E, 5B, 6D, 7B), (1D, 2C, 3E, 4E, 5B, 6D, 7C), (1D, 2D, 3A, 4A, 5A, 6A, 7A), (1D, 2D, 3A, 4A, 5A, 6A, 7B), (1D, 2D, 3A, 4A, 5A, 6A, 7C), (1D, 2D, 3A, 4A, 5A, 6B, 7A), (1D, 2D, 3A, 4A, 5A, 6B, 7B), (1D, 2D, 3A, 4A, 5A, 6B, 7C), (1D, 2D, 3A, 4A, 5A, 6C, 7A), (1D, 2D, 3A, 4A, 5A, 6C, 7B), (1D, 2D, 3A, 4A, 5A, 6C, 7C), (1D, 2D, 3A, 4A, 5A, 6D, 7A), (1D, 2D, 3A, 4A, 5A, 6D, 7B), (1D, 2D, 3A, 4A, 5A, 6D, 7C), (1D, 2D, 3A, 4A, 5B, 6A, 7A), (1D, 2D, 3A, 4A, 5B, 6A, 7B), (1D, 2D, 3A, 4A, 5B, 6A, 7C), (1D, 2D, 3A, 4A, 5B, 6B, 7A), (1D, 2D, 3A, 4A, 5B, 6B, 7B), (1D, 2D, 3A, 4A, 5B, 6B, 7C), (1D, 2D, 3A, 4A, 5B, 6C, 7A), (1D, 2D, 3A, 4A, 5B, 6C, 7B), (1D, 2D, 3A, 4A, 5B, 6C, 7C), (1D, 2D, 3A, 4A, 5B, 6D, 7A), (1D, 2D, 3A, 4A, 5B, 6D, 7B), (1D, 2D, 3A, 4A, 5B, 6D, 7C), (1D, 2D, 3A, 4B, 5A, 6A, 7A), (1D, 2D, 3A, 4B, 5A, 6A, 7B), (1D, 2D, 3A, 4B, 5A, 6A, 7C), (1D, 2D, 3A, 4B, 5A, 6B, 7A), (1D, 2D, 3A, 4B, 5A, 6B, 7B), (1D, 2D, 3A, 4B, 5A, 6B, 7C), (1D, 2D, 3A, 4B, 5A, 6C, 7A), (1D, 2D, 3A, 4B, 5A, 6C, 7B), (1D, 2D, 3A, 4B, 5A, 6C, 7C), (1D, 2D, 3A, 4B, 5A, 6D, 7A), (1D, 2D, 3A, 4B, 5A, 6D, 7B), (1D, 2D, 3A, 4B, 5A, 6D, 7C), (1D, 2D, 3A, 4B, 5B, 6A, 7A), (1D, 2D, 3A, 4B, 5B, 6A, 7B), (1D, 2D, 3A, 4B, 5B, 6A, 7C), (1D, 2D, 3A, 4B, 5B, 6B, 7A), (1D, 2D, 3A, 4B, 5B, 6B, 7B), (1D, 2D, 3A, 4B, 5B, 6B, 7C), (1D, 2D, 3A, 4B, 5B, 6C, 7A), (1D, 2D, 3A, 4B, 5B, 6C, 7B), (1D, 2D, 3A, 4B, 5B, 6C, 7C), (1D, 2D, 3A, 4B, 5B, 6D, 7A), (1D, 2D, 3A, 4B, 5B, 6D, 7B), (1D, 2D, 3A, 4B, 5B, 6D, 7C), (1D, 2D, 3A, 4C, 5A, 6A, 7A), (1D, 2D, 3A, 4C, 5A, 6A, 7B), (1D, 2D, 3A, 4C, 5A, 6A, 7C), (1D, 2D, 3A, 4C, 5A, 6B, 7A), (1D, 2D, 3A, 4C, 5A, 6B, 7B), (1D, 2D, 3A, 4C, 5A, 6B, 7C), (1D, 2D, 3A, 4C, 5A, 6C, 7A), (1D, 2D, 3A, 4C, 5A, 6C, 7B), (1D, 2D, 3A, 4C, 5A, 6C, 7C), (1D, 2D, 3A, 4C, 5A, 6D, 7A), (1D, 2D, 3A, 4C, 5A, 6D, 7B), (1D, 2D, 3A, 4C, 5A, 6D, 7C), (1D, 2D, 3A, 4C, 5B, 6A, 7A), (1D, 2D, 3A, 4C, 5B, 6A, 7B), (1D, 2D, 3A, 4C, 5B, 6A, 7C), (1D, 2D, 3A, 4C, 5B, 6B, 7A), (1D, 2D, 3A, 4C, 5B, 6B, 7B), (1D, 2D, 3A, 4C, 5B, 6B, 7C), (1D, 2D, 3A, 4C, 5B, 6C, 7A), (1D, 2D, 3A, 4C, 5B, 6C, 7B), (1D, 2D, 3A, 4C, 5B, 6C, 7C), (1D, 2D, 3A, 4C, 5B, 6D, 7A), (1D, 2D, 3A, 4C, 5B, 6D, 7B), (1D, 2D, 3A, 4C, 5B, 6D, 7C), (1D, 2D, 3A, 4D, 5A, 6A, 7A), (D, 2D, 3A, 4D, 5A, 6A, 7B), (1D, 2D, 3A, 4D, 5A, 6A, 7C), (1D, 2D, 3A, 4D, 5A, 6B, 7A), (1D, 2D, 3A, 4D, 5A, 6B, 7B), (1D, 2D, 3A, 4D, 5A, 6B, 7C), (1D, 2D, 3A, 4D, 5A, 6C, 7A), (1D, 2D, 3A, 4D, 5A, 6C, 7B), (1D, 2D, 3A, 4D, 5A, 6C, 7C), (1D, 2D, 3A, 4D, 5A, 6D, 7A), (1D, 2D, 3A, 4D, 5A, 6D, 7B), (1D, 2D, 3A, 4D, 5A, 6D, 7C), (1D, 2D, 3A, 4D, 5B, 6A, 7A), (1D, 2D, 3A, 4D, 5B, 6A, 7B), (1D, 2D, 3A, 4D, 5B, 6A, 7C), (1D, 2D, 3A, 4D, 5B, 6B, 7A), (1D, 2D, 3A, 4D, 5B, 6B, 7B), (1D, 2D, 3A, 4D, 5B, 6B, 7C), (1D, 2D, 3A, 4D, 5B, 6C, 7A), (1D, 2D, 3A, 4D, 5B, 6C, 7B), (1D, 2D, 3A, 4D, 5B, 6C, 7C), (1D, 2D, 3A, 4D, 5B, 6D, 7A), (1D, 2D, 3A, 4D, 5B, 6D, 7B), (1D, 2D, 3A, 4D, 5B, 6D, 7C), (1D, 2D, 3A, 4E, 5A, 6A, 7A), (1D, 2D, 3A, 4E, 5A, 6A, 7B), (1D, 2D, 3A, 4E, 5A, 6A, 7C), (1D, 2D, 3A, 4E, 5A, 6B, 7A), (1D, 2D, 3A, 4E, 5A, 6B, 7B), (1D, 2D, 3A, 4E, 5A, 6B, 7C), (1D, 2D, 3A, 4E, 5A, 6C, 7A), (1D, 2D, 3A, 4E, 5A, 6C, 7B), (1D, 2D, 3A, 4E, 5A, 6C, 7C), (1D, 2D, 3A, 4E, 5A, 6D, 7A), (1D, 2D, 3A, 4E, 5A, 6D, 7B), (1D, 2D, 3A, 4E, 5A, 6D, 7C), (1D, 2D, 3A, 4E, 5B, 6A, 7A), (1D, 2D, 3A, 4E, 5B, 6A, 7B), (1D, 2D, 3A, 4E, 5B, 6A, 7C), (1D, 2D, 3A, 4E, 5B, 6B, 7A), (1D, 2D, 3A, 4E, 5B, 6B, 7B), (1D, 2D, 3A, 4E, 5B, 6B, 7C), (1D, 2D, 3A, 4E, 5B, 6C, 7A), (1D, 2D, 3A, 4E, 5B, 6C, 7B), (1D, 2D, 3A, 4E, 5B, 6C, 7C), (1D, 2D, 3A, 4E, 5B, 6D, 7A), (1D, 2D, 3A, 4E, 5B, 6D, 7B), (1D, 2D, 3A, 4E, 5B, 6D, 7C), (1D, 2D, 3B, 4A, 5A, 6A, 7A), (1D, 2D, 3B, 4A, 5A, 6A, 7B), (1D, 2D, 3B, 4A, 5A, 6A, 7C), (1D, 2D, 3B, 4A, 5A, 6B, 7A), (1D, 2D, 3B, 4A, 5A, 6B, 7B), (1D, 2D, 3B, 4A, 5A, 6B, 7C), (1D, 2D, 3B, 4A, 5A, 6C, 7A), (1D, 2D, 3B, 4A, 5A, 6C, 7B), (1D, 2D, 3B, 4A, 5A, 6C, 7C), (1D, 2D, 3B, 4A, 5A, 6D, 7A), (1D, 2D, 3B, 4A, 5A, 6D, 7B), (1D, 2D, 3B, 4A, 5A, 6D, 7C), (1D, 2D, 3B, 4A, 5B, 6A, 7A), (1D, 2D, 3B, 4A, 5B, 6A, 7B), (1D, 2D, 3B, 4A, 5B, 6A, 7C), (1D, 2D, 3B, 4A, 5B, 6B, 7A), (1D, 2D, 3B, 4A, 5B, 6B, 7B), (1D, 2D, 3B, 4A, 5B, 6B, 7C), (1D, 2D, 3B, 4A, 5B, 6C, 7A), (1D, 2D, 3B, 4A, 5B, 6C, 7B), (1D, 2D, 3B, 4A, 5B, 6C, 7C), (1D, 2D, 3B, 4A, 5B, 6D, 7A), (1D, 2D, 3B, 4A, 5B, 6D, 7B), (1D, 2D, 3B, 4A, 5B, 6D, 7C), (1D, 2D, 3B, 4B, 5A, 6A, 7A), (1D, 2D, 3B, 4B, 5A, 6A, 7B), (1D, 2D, 3B, 4B, 5A, 6A, 7C), (1D, 2D, 3B, 4B, 5A, 6B, 7A), (1D, 2D, 3B, 4B, 5A, 6B, 7B), (1D, 2D, 3B, 4B, 5A, 6B, 7C), (1D, 2D, 3B, 4B, 5A, 6C, 7A), (1D, 2D, 3B, 4B, 5A, 6C, 7B), (1D, 2D, 3B, 4B, 5A, 6C, 7C), (1D, 2D, 3B, 4B, 5A, 6D, 7A), (1D, 2D, 3B, 4B, 5A, 6D, 7B), (1D, 2D, 3B, 4B, 5A, 6D, 7C), (1D, 2D, 3B, 4B, 5B, 6A, 7A), (1D, 2D, 3B, 4B, 5B, 6A, 7B), (1D, 2D, 3B, 4B, 5B, 6A, 7C), (1D, 2D, 3B, 4B, 5B, 6B, 7A), (1D, 2D, 3B, 4B, 5B, 6B, 7B), (D, 2D, 3B, 4B, 5B, 6B, 7C), (1D, 2D, 3B, 4B, 5B, 6C, 7A), (1D, 2D, 3B, 4B, 5B, 6C, 7B), (1D, 2D, 3B, 4B, 5B, 6C, 7C), (1D, 2D, 3B, 4B, 5B, 6D, 7A), (1D, 2D, 3B, 4B, 5B, 6D, 7B), (1D, 2D, 3B, 4B, 5B, 6D, 7C), (1D, 2D, 3B, 4C, 5A, 6A, 7A), (1D, 2D, 3B, 4C, 5A, 6A, 7B), (1D, 2D, 3B, 4C, 5A, 6A, 7C), (1D, 2D, 3B, 4C, 5A, 6B, 7A), (1D, 2D, 3B, 4C, 5A, 6B, 7B), (1D, 2D, 3B, 4C, 5A, 6B, 7C), (1D, 2D, 3B, 4C, 5A, 6C, 7A), (1D, 2D, 3B, 4C, 5A, 6C, 7B), (1D, 2D, 3B, 4C, 5A, 6C, 7C), (1D, 2D, 3B, 4C, 5A, 6D, 7A), (1D, 2D, 3B, 4C, 5A, 6D, 7B), (1D, 2D, 3B, 4C, 5A, 6D, 7C), (1D, 2D, 3B, 4C, 5B, 6A, 7A), (1D, 2D, 3B, 4C, 5B, 6A, 7B), (1D, 2D, 3B, 4C, 5B, 6A, 7C), (1D, 2D, 3B, 4C, 5B, 6B, 7A), (1D, 2D, 3B, 4C, 5B, 6B, 7B), (1D, 2D, 3B, 4C, 5B, 6B, 7C), (1D, 2D, 3B, 4C, 5B, 6C, 7A), (1D, 2D, 3B, 4C, 5B, 6C, 7B), (1D, 2D, 3B, 4C, 5B, 6C, 7C), (1D, 2D, 3B, 4C, 5B, 6D, 7A), (1D, 2D, 3B, 4C, 5B, 6D, 7B), (1D, 2D, 3B, 4C, 5B, 6D, 7C), (1D, 2D, 3B, 4D, 5A, 6A, 7A), (1D, 2D, 3B, 4D, 5A, 6A, 7B), (1D, 2D, 3B, 4D, 5A, 6A, 7C), (1D, 2D, 3B, 4D, 5A, 6B, 7A), (1D, 2D, 3B, 4D, 5A, 6B, 7B), (1D, 2D, 3B, 4D, 5A, 6B, 7C), (1D, 2D, 3B, 4D, 5A, 6C, 7A), (1D, 2D, 3B, 4D, 5A, 6C, 7B), (1D, 2D, 3B, 4D, 5A, 6C, 7C), (1D, 2D, 3B, 4D, 5A, 6D, 7A), (1D, 2D, 3B, 4D, 5A, 6D, 7B), (1D, 2D, 3B, 4D, 5A, 6D, 7C), (1D, 2D, 3B, 4D, 5B, 6A, 7A), (1D, 2D, 3B, 4D, 5B, 6A, 7B), (1D, 2D, 3B, 4D, 5B, 6A, 7C), (1D, 2D, 3B, 4D, 5B, 6B, 7A), (1D, 2D, 3B, 4D, 5B, 6B, 7B), (1D, 2D, 3B, 4D, 5B, 6B, 7C), (1D, 2D, 3B, 4D, 5B, 6C, 7A), (1D, 2D, 3B, 4D, 5B, 6C, 7B), (1D, 2D, 3B, 4D, 5B, 6C, 7C), (1D, 2D, 3B, 4D, 5B, 6D, 7A), (1D, 2D, 3B, 41D, 5B, 6D, 7B), (1D, 2D, 3B, 4D, 5B, 6D, 7C), (1D, 2D, 3B, 4E, 5A, 6A, 7A), (1D, 2D, 3B, 4E, 5A, 6A, 7B), (1D, 2D, 3B, 4E, 5A, 6A, 7C), (1D, 2D, 3B, 4E, 5A, 6B, 7A), (1D, 2D, 3B, 4E, 5A, 6B, 7B), (1D, 2D, 3B, 4E, 5A, 6B, 7C), (1D, 2D, 3B, 4E, 5A, 6C, 7A), (1D, 2D, 3B, 4E, 5A, 6C, 7B), (1D, 2D, 3B, 4E, 5A, 6C, 7C), (1D, 2D, 3B, 4E, 5A, 6D, 7A), (1D, 2D, 3B, 4E, 5A, 6D, 7B), (1D, 2D, 3B, 4E, 5A, 6D, 7C), (1D, 2D, 3B, 4E, 5B, 6A, 7A), (1D, 2D, 3B, 4E, 5B, 6A, 7B), (1D, 2D, 3B, 4E, 5B, 6A, 7C), (1D, 2D, 3B, 4E, 5B, 6B, 7A), (1D, 2D, 3B, 4E, 5B, 6B, 7B), (1D, 2D, 3B, 4E, 5B, 6B, 7C), (1D, 2D, 3B, 4E, 5B, 6C, 7A), (1D, 2D, 3B, 4E, 5B, 6C, 7B), (1D, 2B, 3B, 4E, 5B, 6C, 7C), (1D, 2D, 3B, 4E, 5B, 6D, 7A), (1D, 2D, 3B, 4E, 5B, 6D, 7B), (1D, 2D, 3B, 4E, 5B, 6D, 7C), (1D, 2D, 3C, 4A, 5A, 6A, 7A), (1D, 2D, 3C, 4A, 5A, 6A, 7B), (1D, 2D, 3C, 4A, 5A, 6A, 7C), (1D, 2D, 3C, 4A, 5A, 6B, 7A), (1D, 2D, 3C, 4A, 5A, 6B, 7B), (1D, 2D, 3C, 4A, 5A, 6B, 7C), (1D, 2D, 3C, 4A, 5A, 6C, 7A), (1D, 2D, 3C, 4A, 5A, 6C, 7B), (1D, 2D, 3C, 4A, 5A, 6C, 7C), (1D, 2D, 3C, 4A, 5A, 6D, 7A), (1D, 2D, 3C, 4A, 5A, 6D, 7B), (1D, 2D, 3C, 4A, 5A, 6D, 7C), (1D, 2D, 3C, 4A, 5B, 6A, 7A), (1D, 2D, 3C, 4A, 5B, 6A, 7B), (1D, 2D, 3C, 4A, 5B, 6A, 7C), (1D, 2D, 3C, 4A, 5B, 6B, 7A), (1D, 2D, 3C, 4A, 5B, 6B, 7B), (1D, 2D, 3C, 4A, 5B, 6B, 7C), (1D, 2D, 3C, 4A, 5B, 6C, 7A), (1D, 2D, 3C, 4A, 5B, 6C, 7B), (1D, 2D, 3C, 4A, 5B, 6C, 7C), (1D, 2D, 3C, 4A, 5B, 6D, 7A), (1D, 2D, 3C, 4A, 5B, 6D, 7B), (1D, 2D, 3C, 4A, 5B, 6D, 7C), (1D, 2D, 3C, 4B, 5A, 6A, 7A), (1D, 2D, 3C, 4B, 5A, 6A, 7B), (1D, 2D, 3C, 4B, 5A, 6A, 7C), (1D, 2D, 3C, 4B, 5A, 6B, 7A), (1D, 2D, 3C, 4B, 5A, 6B, 7B), (1D, 2D, 3C, 4B, 5A, 6B, 7C), (1D, 2D, 3C, 4B, 5A, 6C, 7A), (1D, 2D, 3C, 4B, 5A, 6C, 7B), (1D, 2D, 3C, 4B, 5A, 6C, 7C), (1D, 2D, 3C, 4B, 5A, 6D, 7A), (1D, 2D, 3C, 4B, 5A, 6D, 7B), (1D, 2D, 3C, 4B, 5A, 6D, 7C), (1D, 2D, 3C, 4B, 5B, 6A, 7A), (1D, 2D, 3C, 4B, 5B, 6A, 7B), (1D, 2D, 3C, 4B, 5B, 6A, 7C), (1D, 2D, 3C, 4B, 5B, 6B, 7A), (1D, 2D, 3C, 4B, 5B, 6B, 7B), (1D, 2D, 3C, 4B, 5B, 6B, 7C), (1D, 2D, 3C, 4B, 5B, 6C, 7A), (1D, 2D, 3C, 4B, 5B, 6C, 7B), (1D, 2D, 3C, 4B, 5B, 6C, 7C), (1D, 2D, 3C, 4B, 5B, 6D, 7A), (1D, 2D, 3C, 4B, 5B, 6D, 7B), (1D, 2D, 3C, 4B, 5B, 6D, 7C), (1D, 2D, 3C, 4C, 5A, 6A, 7A), (1D, 2D, 3C, 4C, 5A, 6A, 7B), (1D, 2D, 3C, 4C, 5A, 6A, 7C), (1D, 2D, 3C, 4C, 5A, 6B, 7A), (1D, 2D, 3C, 4C, 5A, 6B, 7B), (1D, 2D, 3C, 4C, 5A, 6B, 7C), (1D, 2D, 3C, 4C, 5A, 6C, 7A), (1D, 2D, 3C, 4C, 5A, 6C, 7B), (1D, 2D, 3C, 4C, 5A, 6C, 7C), (1D, 2D, 3C, 4C, 5A, 6D, 7A), (1D, 2D, 3C, 4C, 5A, 6D, 7B), (1D, 2D, 3C, 4C, 5A, 6D, 7C), (1D, 2D, 3C, 4C, 5B, 6A, 7A), (1D, 2D, 3C, 4C, 5B, 6A, 7B), (1D, 2D, 3C, 4C, 5B, 6A, 7C), (1D, 2D, 3C, 4C, 5B, 6B, 7A), (1D, 2D, 3C, 4C, 5B, 6B, 7B), (1D, 2D, 3C, 4C, 5B, 6B, 7C), (1D, 2D, 3C, 4C, 5B, 6C, 7A), (1D, 2D, 3C, 4C, 5B, 6C, 7B), (1D, 2D, 3C, 4C, 5B, 6C, 7C), (1D, 2D, 3C, 4C, 5B, 6D, 7A), (1D, 2D, 3C, 4C, 5B, 6D, 7B), (1D, 2D, 3C, 4C, 5B, 6D, 7C), (1D, 2D, 3C, 4D, 5A, 6A, 7A), (1D, 2D, 3C, 4D, 5A, 6A, 7B), (1D, 2D, 3C, 4D, 5A, 6A, 7C), (1D, 2D, 3C, 4D, 5A, 6B, 7A), (1D, 2D, 3C, 4D, 5A, 6B, 7B), (1D, 2D, 3C, 4D, 5A, 6B, 7C), (1D, 2D, 3C, 4D, 5A, 6C, 7A), (1D, 2D, 3C, 4D, 5A, 6C, 7B), (1D, 2D, 3C, 4D, 5A, 6C, 7C), (1D, 2D, 3C, 4D, 5A, 6D, 7A), (1D, 2D, 3C, 4D, 5A, 6D, 7B), (1D, 2D, 3C, 4D, 5A, 6D, 7C), (1D, 2D, 3C, 4D, 5B, 6A, 7A), (1D, 2D, 3C, 4D, 5B, 6A, 7B), (1D, 2D, 3C, 4D, 5B, 6A, 7C), (1D, 2D, 3C, 4D, 5B, 6B, 7A), (1D, 2D, 3C, 4D, 5B, 6B, 7B), (1D, 2D, 3C, 4D, 5B, 6B, 7C), (1D, 2D, 3C, 4D, 5B, 6C, 7A), (1D, 2D, 3C, 4D, 5B, 6C, 7B), (1D, 2D, 3C, 4D, 5B, 6C, 7C), (1D, 2D, 3C, 4D, 5B, 6D, 7A), (1D, 2D, 3C, 4D, 5B, 6D, 7B), (1D, 2D, 3C, 4D, 5B, 6D, 7C), (1D, 2D, 3C, 4E, 5A, 6A, 7A), (1D, 2D, 3C, 4E, 5A, 6A, 7B), (1D, 2D, 3C, 4E, 5A, 6A, 7C), (1D, 2D, 3C, 4E, 5A, 6B, 7A), (1D, 2D, 3C, 4E, 5A, 6B, 7B), (1D, 2D, 3C, 4E, 5A, 6B, 7C), (1D, 2D, 3C, 4E, 5A, 6C, 7A), (1D, 2D, 3C, 4E, 5A, 6C, 7B), (1D, 2D, 3C, 4E, 5A, 6C, 7C), (1D, 2D, 3C, 4E, 5A, 6D, 7A), (1D, 2D, 3C, 4E, 5A, 6D, 7B), (1D, 2D, 3C, 4E, 5A, 6D, 7C), (1D, 2D, 3C, 4E, 5B, 6A, 7A), (1D, 2D, 3C, 4E, 5B, 6A, 7B), (1D, 2D, 3C, 4E, 5B, 6A, 7C), (1D, 2D, 3C, 4E, 5B, 6B, 7A), (1D, 2D, 3C, 4E, 5B, 6B, 7B), (1D, 2D, 3C, 4E, 5B, 6B, 7C), (1D, 2D, 3C, 4E, 5B, 6C, 7A), (1D, 2D, 3C, 4E, 5B, 6C, 7B), (1D, 2D, 3C, 4E, 5B, 6C, 7C), (1D, 2D, 3C, 4E, 5B, 6D, 7A), (1D, 2D, 3C, 4E, 5B, 6D, 7B), (1D, 2D, 3C, 4E, 5B, 6D, 7C), (1D, 2D, 3D, 4A, 5A, 6A, 7A), (1D, 2D, 3D, 4A, 5A, 6A, 7B), (1D, 2D, 3D, 4A, 5A, 6A, 7C), (1D, 2D, 3D, 4A, 5A, 6B, 7A), (1D, 2D, 3D, 4A, 5A, 6B, 7B), (1D, 2D, 3D, 4A, 5A, 6B, 7C), (1D, 2D, 3D, 4A, 5A, 6C, 7A), (1D, 2D, 3D, 4A, 5A, 6C, 7B), (1D, 2D, 3D, 4A, 5A, 6C, 7C), (1D, 2D, 3D, 4A, 5A, 6D, 7A), (1D, 2D, 3D, 4A, 5A, 6D, 7B), (1D, 2D, 3D, 4A, 5A, 6D, 7C), (1D, 2D, 3D, 4A, 5B, 6A, 7A), (1D, 2D, 3D, 4A, 5B, 6A, 7B), (1D, 2D, 3D, 4A, 5B, 6A, 7C), (1D, 2D, 3D, 4A, 5B, 6B, 7A), (1D, 2D, 3D, 4A, 5B, 6B, 7B), (1D, 2D, 3D, 4A, 5B, 6B, 7C), (1D, 2D, 3D, 4A, 5B, 6C, 7A), (1D, 2D, 3D, 4A, 5B, 6C, 7B), (1D, 2D, 3D, 4A, 5B, 6C, 7C), (1D, 2D, 3D, 4A, 5B, 6D, 7A), (1D, 2D, 3D, 4A, 5B, 6D, 7B), (1D, 2D, 3D, 4A, 5B, 6D, 7C), (1D, 2D, 3D, 4B, 5A, 6A, 7A), (1D, 2D, 3D, 4B, 5A, 6A, 7B), (1D, 2D, 3D, 4B, 5A, 6A, 7C), (1D, 2D, 3D, 4B, 5A, 6B, 7A), (1D, 2D, 3D, 4B, 5A, 6B, 7B), (1D, 2D, 3D, 4B, 5A, 6B, 7C), (1D, 2D, 3D, 4B, 5A, 6C, 7A), (1D, 2D, 3D, 4B, 5A, 6C, 7B), (1D, 2D, 3D, 4B, 5A, 6C, 7C), (1D, 2D, 3D, 4B, 5A, 6D, 7A), (1D, 2D, 3D, 4B, 5A, 6D, 7B), (1D, 2D, 3D, 4B, 5A, 6D, 7C), (1D, 2D, 3D, 4B, 5B, 6A, 7A), (1D, 2D, 3D, 4B, 5B, 6A, 7B), (1D, 2D, 3D, 4B, 5B, 6A, 7C), (1D, 2D, 3D, 4B, 5B, 6B, 7A), (1D, 2D, 3D, 4B, 5B, 6B, 7B), (1D, 2D, 3D, 4B, 5B, 6B, 7C), (1D, 2D, 3D, 4B, 5B, 6C, 7A), (1D, 2D, 3D, 4B, 5B, 6C, 7B), (1D, 2D, 3D, 4B, 5B, 6C, 7C), (1D, 2D, 3D, 4B, 5B, 6D, 7A), (1D, 2D, 3D, 4B, 5B, 6D, 7B), (1D, 2D, 3D, 4B, 5B, 6D, 7C), (1D, 2D, 3D, 4C, 5A, 6A, 7A), (1D, 2D, 3D, 4C, 5A, 6A, 7B), (1D, 2D, 3D, 4C, 5A, 6A, 7C), (1D, 2D, 3D, 4C, 5A, 6B, 7A), (1D, 2D, 3D, 4C, 5A, 6B, 7B), (1D, 2D, 3D, 4C, 5A, 6B, 7C), (1D, 2D, 3D, 4C, 5A, 6C, 7A), (1D, 2D, 3D, 4C, 5A, 6C, 7B), (1D, 2D, 3D, 4C, 5A, 6C, 7C), (1D, 2D, 3D, 4C, 5A, 6D, 7A), (1D, 2D, 3D, 4C, 5A, 6D, 7B), (1D, 2D, 3D, 4C, 5A, 6D, 7C), (1D, 2D, 3D, 4C, 5B, 6A, 7A), (1D, 2D, 3D, 4C, 5B, 6A, 7B), (1D, 2D, 3D, 4C, 5B, 6A, 7C), (1D, 2D, 3D, 4C, 5B, 6B, 7A), (1D, 2D, 3D, 4C, 5B, 6B, 7B), (1D, 2D, 3D, 4C, 5B, 6B, 7C), (1D, 2D, 3D, 4C, 5B, 6C, 7A), (1D, 2D, 3D, 4C, 5B, 6C, 7B), (1D, 2D, 3D, 4C, 5B, 6C, 7C), (1D, 2D, 3D, 4C, 5B, 6D, 7A), (1D, 2D, 3D, 4C, 5B, 6D, 7B), (1D, 2D, 3D, 4C, 5B, 6D, 7C), (1D, 2D, 3D, 4D, 5A, 6A, 7A), (1D, 2D, 3D, 4D, 5A, 6A, 7B), (1D, 2D, 3D, 4D, 5A, 6A, 7C), (1D, 2D, 3D, 4D, 5A, 6B, 7A), (1D, 2D, 3D, 4D, 5A, 6B, 7B), (1D, 2D, 3D, 4D, 5A, 6B, 7C), (1D, 2D, 3D, 4D, 5A, 6C, 7A), (1D, 2D, 3D, 4D, 5A, 6C, 7B), (1D, 2D, 3D, 4D, 5A, 6C, 7C), (1D, 2D, 3D, 4D, 5A, 6D, 7A), (1D, 2D, 3D, 4D, 5A, 6D, 7B), (1D, 2D, 3D, 4D, 5A, 6D, 7C), (1D, 2D, 3D, 4D, 5B, 6A, 7A), (1D, 2D, 3D, 4D, 5B, 6A, 7B), (1D, 2D, 3D, 4D, 5B, 6A, 7C), (1D, 2D, 3D, 4D, 5B, 6B, 7A), (1D, 2D, 3D, 4D, 5B, 6B, 7B), (1D, 2D, 3D, 4D, 5B, 6B, 7C), (1D, 2D, 3D, 4D, 5B, 6C, 7A), (1D, 2D, 3D, 4D, 5B, 6C, 7B), (1D, 2D, 3D, 4D, 5B, 6C, 7C), (D, 2D, 3D, 4D, 5B, 6D, 7A), (1D, 2D, 3D, 4D, 5B, 6D, 7B), (1D, 2D, 3D, 4D, 5B, 6D, 7C), (1D, 2D, 3D, 4E, 5A, 6A, 7A), (1D, 2D, 3D, 4E, 5A, 6A, 7B), (1D, 2D, 3D, 4E, 5A, 6A, 7C), (1D, 2D, 3D, 4E, 5A, 6B, 7A), (1D, 2D, 3D, 4E, 5A, 6B, 7B), (1D, 2D, 3D, 4E, 5A, 6B, 7C), (1D, 2D, 3D, 4E, 5A, 6C, 7A), (1D, 2D, 3D, 4E, 5A, 6C, 7B), (1D, 2D, 3D, 4E, 5A, 6C, 7C), (1D, 2D, 3D, 4E, 5A, 6D, 7A), (1D, 2D, 3D, 4E, 5A, 6D, 7B), (1D, 2D, 3D, 4E, 5A, 6D, 7C), (1D, 2D, 3D, 4E, 5B, 6A, 7A), (1D, 2D, 3D, 4E, 5B, 6A, 7B), (1D, 2D, 3D, 4E, 5B, 6A, 7C), (1D, 2D, 3D, 4E, 5B, 6B, 7A), (1D, 2D, 3D, 4E, 5B, 6B, 7B), (1D, 2D, 3D, 4E, 5B, 6B, 7C), (1D, 2D, 3D, 4E, 5B, 6C, 7A), (1D, 2D, 3D, 4E, 5B, 6C, 7B), (1D, 2D, 3D, 4E, 5B, 6C, 7C), (1D, 2D, 3D, 4E, 5B, 6D, 7A), (1D, 2D, 3D, 4E, 5B, 6D, 7B), (1D, 2D, 3D, 4E, 5B, 6D, 7C, (1D, 2D, 3E, 4A, 5A, 6A, 7A), (1D, 2D, 3E, 4A, 5A, 6A, 7B), (1D, 2D, 3E, 4A, 5A, 6A, 7C), (1D, 2D, 3E, 4A, 5A, 6B, 7A), (1D, 2D, 3E, 4A, 5A, 6B, 7B), (1D, 2D, 3E, 4A, 5A, 6B, 7C), (1D, 2D, 3E, 4A, 5A, 6C, 7A), (1D, 2D, 3E, 4A, 5A, 6C, 7B), (1D, 2D, 3E, 4A, 5A, 6C, 7C), (1D, 2D, 3E, 4A, 5A, 6D, 7A), (1D, 2D, 3E, 4A, 5A, 6D, 7B), (1D, 2D, 3E, 4A, 5A, 6D, 7C), (1D, 2D, 3E, 4A, 5B, 6A, 7A), (1D, 2D, 3E, 4A, 5B, 6A, 7B), (1D, 2D, 3E, 4A, 5B, 6A, 7C), (1D, 2D, 3E, 4A, 5B, 6B, 7A), (1D, 2B, 3E, 4A, 5B, 6B, 7B), (1D, 2D, 3E, 4A, 5B, 6B, 7C), (1D, 2D, 3E, 4A, 5B, 6C, 7A), (1D, 2D, 3E, 4A, 5B, 6C, 7B), (1D, 2D, 3E, 4A, 5B, 6C, 7C), (1D, 2D, 3E, 4A, 5B, 6D, 7A), (1D, 2D, 3E, 4A, 5B, 6D, 7B), (1D, 2D, 3E, 4A, 5B, 6D, 7C), (1D, 2D, 3E, 4B, 5A, 6A, 7A), (1D, 2D, 3E, 4B, 5A, 6A, 7B), (1D, 2D, 3E, 4B, 5A, 6A, 7C), (1D, 2D, 3E, 4B, 5A, 6B, 7A), (1D, 2D, 3E, 4B, 5A, 6B, 7B), (1D, 2D, 3E, 4B, 5A, 6B, 7C), (1D, 2D, 3E, 4B, 5A, 6C, 7A), (1D, 2D, 3E, 4B, 5A, 6C, 7B), (1D, 2D, 3E, 4B, 5A, 6C, 7C), (1D, 2D, 3E, 4B, 5A, 6D, 7A), (1D, 2D, 3E, 4B, 5A, 6D, 7B), (1D, 2D, 3E, 4B, 5A, 6D, 7C), (1D, 2D, 3E, 4B, 5B, 6A, 7A), (1D, 2D, 3E, 4B, 5B, 6A, 7B), (1D, 2D, 3E, 4B, 5B, 6A, 7C), (1D, 2D, 3E, 4B, 5B, 6B, 7A), (1D, 2D, 3E, 4B, 5B, 6B, 7B), (1D, 2D, 3E, 4B, 5B, 6B, 7C), (1D, 2D, 3E, 4B, 5B, 6C, 7A), (1D, 2D, 3E, 4B, 5B, 6C, 7B), (1D, 2D, 3E, 4B, 5B, 6C, 7C), (1D, 2D, 3E, 4B, 5B, 6D, 7A), (1D, 2D, 3E, 4B, 5B, 6D, 7B), (1D, 2D, 3E, 4B, 5B, 6D, 7C), (1D, 2D, 3E, 4C, 5A, 6A, 7A), (1D, 2D, 3E, 4C, 5A, 6A, 7B), (1D, 2D, 3E, 4C, 5A, 6A, 7C), (1D, 2D, 3E, 4C, 5A, 6B, 7A), (1D, 2D, 3E, 4C, 5A, 6B, 7B), (1D, 2D, 3E, 4C, 5A, 6B, 7C), (1D, 2D, 3E, 4C, 5A, 6C, 7A), (1D, 2D, 3E, 4C, 5A, 6C, 7B), (1D, 2D, 3E, 4C, 5A, 6C, 7C), (1D, 2D, 3E, 4C, 5A, 6D, 7A), (1D, 2D, 3E, 4C, 5A, 6D, 7B), (1D, 2D, 3E, 4C, 5A, 6D, 7C), (1D, 2D, 3E, 4C, 5B, 6A, 7A), (1D, 2D, 3E, 4C, 5B, 6A, 7B), (1D, 2D, 3E, 4C, 5B, 6A, 7C), (1D, 2D, 3E, 4C, 5B, 6B, 7A), (1D, 2D, 3E, 4C, 5B, 6B, 7B), (1D, 2D, 3E, 4C, 5B, 6B, 7C), (1D, 2D, 3E, 4C, 5B, 6C, 7A), (1D, 2D, 3E, 4C, 5B, 6C, 7B), (1D, 2D, 3E, 4C, 5B, 6C, 7C), (1D, 2D, 3E, 4C, 5B, 6D, 7A), (1D, 2D, 3E, 4C, 5B, 6D, 7B), (1D, 2D, 3E, 4C, 5B, 6D, 7C), (1D, 2D, 3E, 4D, 5A, 6A, 7A), (1D, 2D, 3E, 4D, 5A, 6A, 7B), (1D, 2D, 3E, 4D, 5A, 6A, 7C), (1D, 2D, 3E, 4D, 5A, 6B, 7A), (1D, 2D, 3E, 4D, 5A, 6B, 7B), (1D, 2D, 3E, 4D, 5A, 6B, 7C), (1D, 2D, 3E, 4D, 5A, 6C, 7A), (1D, 2D, 3E, 4D, 5A, 6C, 7B), (1D, 2D, 3E, 4D, 5A, 6C, 7C), (1D, 2D, 3E, 4D, 5A, 6D, 7A), (1D, 2D, 3E, 4D, 5A, 6D, 7B), (1D, 2D, 3E, 4D, 5A, 6D, 7C), (1D, 2D, 3E, 4D, 5B, 6A, 7A), (1D, 2D, 3E, 4D, 5B, 6A, 7B), (1D, 2D, 3E, 4D, 5B, 6A, 7C), (1D, 2D, 3E, 4D, 5B, 6B, 7A), (1D, 2D, 3E, 4D, 5B, 6B, 7B), (1D, 2D, 3E, 4D, 5B, 6B, 7C), (1D, 2D, 3E, 4D, 5B, 6C, 7A), (1D, 2D, 3E, 4D, 5B, 6C, 7B), (1D, 2D, 3E, 4D, 5B, 6C, 7C), (1D, 2D, 3E, 4D, 5B, 6D, 7A), (1D, 2D, 3E, 4D, 5B, 6D, 7B), (1D, 2D, 3E, 4D, 5B, 6D, 7C), (1D, 2D, 3E, 4E, 5A, 6A, 7A), (1D, 2D, 3E, 4E, 5A, 6A, 7B), (1D, 2D, 3E, 4E, 5A, 6A, 7C), (1D, 2D, 3E, 4E, 5A, 6B, 7A), (1D, 2D, 3E, 4E, 5A, 6B, 7B), (1D, 2D, 3E, 4E, 5A, 6B, 7C), (1D, 2D, 3E, 4E, 5A, 6C, 7A), (1D, 2D, 3E, 4E, 5A, 6C, 7B), (1D, 2D, 3E, 4E, 5A, 6C, 7C), (1D, 2D, 3E, 4E, 5A, 6D, 7A), (1D, 2D, 3E, 4E, 5A, 6D, 7B), (1D, 2D, 3E, 4E, 5A, 6D, 7C), (1D, 2D, 3E, 4E, 5B, 6A, 7A), (1D, 2D, 3E, 4E, 5B, 6A, 7B), (1D, 2D, 3E, 4E, 5B, 6A, 7C), (1D, 2D, 3E, 4E, 5B, 6B, 7A), (1D, 2D, 3E, 4E, 5B, 6B, 7B), (1D, 2D, 3E, 4E, 5B, 6B, 7C), (1D, 2D, 3E, 4E, 5B, 6C, 7A), (1D, 2D, 3E, 4E, 5B, 6C, 7B), (1D, 2D, 3E, 4E, 5B, 6C, 7C), (1D, 2D, 3E, 4E, 5B, 6D, 7A), (1D, 2D, 3E, 4E, 5B, 6D, 7B), (1D, 2D, 3E, 4E, 5B, 6D, 7C), (1D, 2E, 3A, 4A, 5A, 6A, 7A), (1D, 2E, 3A, 4A, 5A, 6A, 7B), (1D, 2E, 3A, 4A, 5A, 6A, 7C), (1D, 2E, 3A, 4A, 5A, 6B, 7A), (1D, 2E, 3A, 4A, 5A, 6B, 7B), (1D, 2E, 3A, 4A, 5A, 6B, 7C), (1D, 2E, 3A, 4A, 5A, 6C, 7A), (1D, 2E, 3A, 4A, 5A, 6C, 7B), (1D, 2E, 3A, 4A, 5A, 6C, 7C), (1D, 2E, 3A, 4A, 5A, 6D, 7A), (1D, 2E, 3A, 4A, 5A, 6D, 7B), (1D, 2E, 3A, 4A, 5A, 6D, 7C), (1D, 2E, 3A, 4A, 5B, 6A, 7A), (1D, 2E, 3A, 4A, 5B, 6A, 7B), (1D, 2E, 3A, 4A, 5B, 6A, 7C), (1D, 2E, 3A, 4A, 5B, 6B, 7A), (1D, 2E, 3A, 4A, 5B, 6B, 7B), (1D, 2E, 3A, 4A, 5B, 6B, 7C), (1D, 2E, 3A, 4A, 5B, 6C, 7A), (1D, 2E, 3A, 4A, 5B, 6C, 7B), (1D, 2E, 3A, 4A, 5B, 6C, 7C), (1D, 2E, 3A, 4A, 5B, 6D, 7A), (1D, 2E, 3A, 4A, 5B, 6D, 7B), (1D, 2E, 3A, 4A, 5B, 6D, 7C), (1D, 2E, 3A, 4B, 5A, 6A, 7A), (1D, 2E, 3A, 4B, 5A, 6A, 7B), (1D, 2E, 3A, 4B, 5A, 6A, 7C), (1D, 2E, 3A, 4B, 5A, 6B, 7A), (1D, 2E, 3A, 4B, 5A, 6B, 7B), (1D, 2E, 3A, 4B, 5A, 6B, 7C), (1D, 2E, 3A, 4B, 5A, 6C, 7A), (1D, 2E, 3A, 4B, 5A, 6C, 7B), (1D, 2E, 3A, 4B, 5A, 6C, 7C), (1D, 2E, 3A, 4B, 5A, 6D, 7A), (1D, 2E, 3A, 4B, 5A, 6D, 7B), (1D, 2E, 3A, 4B, 5A, 6D, 7C), (1D, 2E, 3A, 4B, 5B, 6A, 7A), (1D, 2E, 3A, 4B, 5B, 6A, 7B), (1D, 2E, 3A, 4B, 5B, 6A, 7C), (1D, 2E, 3A, 4B, 5B, 6B, 7A), (1D, 2E, 3A, 4B, 5B, 6B, 7B), (1D, 2E, 3A, 4B, 5B, 6B, 7C), (1D, 2E, 3A, 4B, 5B, 6C, 7A), (1D, 2E, 3A, 4B, 5B, 6C, 7B), (1D, 2E, 3A, 4B, 5B, 6C, 7C), (1D, 2E, 3A, 4B, 5B, 6D, 7A), (1D, 2E, 3A, 4B, 5B, 6D, 7B), (1D, 2E, 3A, 4B, 5B, 6D, 7C), (1D, 2E, 3A, 4C, 5A, 6A, 7A), (1D, 2E, 3A, 4C, 5A, 6A, 7B), (1D, 2E, 3A, 4C, 5A, 6A, 7C), (1D, 2E, 3A, 4C, 5A, 6B, 7A), (1D, 2E, 3A, 4C, 5A, 6B, 7B), (1D, 2E, 3A, 4C, 5A, 6B, 7C), (1D, 2E, 3A, 4C, 5A, 6C, 7A), (1D, 2E, 3A, 4C, 5A, 6C, 7B), (1D, 2E, 3A, 4C, 5A, 6C, 7C), (1D, 2E, 3A, 4C, 5A, 6D, 7A), (1D, 2E, 3A, 4C, 5A, 6D, 7B), (1D, 2E, 3A, 4C, 5A, 6D, 7C), (1D, 2E, 3A, 4C, 5B, 6A, 7A), (1D, 2E, 3A, 4C, 5B, 6A, 7B), (1D, 2E, 3A, 4C, 5B, 6A, 7C), (1D, 2E, 3A, 4C, 5B, 6B, 7A), (1D, 2E, 3A, 4C, 5B, 6B, 7B), (1D, 2E, 3A, 4C, 5B, 6B, 7C), (1D, 2E, 3A, 4C, 5B, 6C, 7A), (1D, 2E, 3A, 4C, 5B, 6C, 7B), (1D, 2E, 3A, 4C, 5B, 6C, 7C), (1D, 2E, 3A, 4C, 5B, 6D, 7A), (1D, 2E, 3A, 4C, 5B, 6D, 7B), (1D, 2E, 3A, 4C, 5B, 6D, 7C), (1D, 2E, 3A, 4D, 5A, 6A, 7A), (1D, 2E, 3A, 4D, 5A, 6A, 7B), (1D, 2E, 3A, 4D, 5A, 6A, 7C), (1D, 2E, 3A, 4D, 5A, 6B, 7A), (1D, 2E, 3A, 4D, 5A, 6B, 7B), (1D, 2E, 3A, 4D, 5A, 6B, 7C), (1D, 2E, 3A, 4D, 5A, 6C, 7A), (1D, 2E, 3A, 4D, 5A, 6C, 7B), (1D, 2E, 3A, 4D, 5A, 6C, 7C), (1D, 2E, 3A, 4D, 5A, 6D, 7A), (1D, 2E, 3A, 4D, 5A, 6D, 7B), (1D, 2E, 3A, 4D, 5A, 6C, 7C), (1D, 2E, 3A, 4D, 5B, 6A, 7A), (1D, 2E, 3A, 4D, 5B, 6A, 7B), (1D, 2E, 3A, 4D, 5B, 6A, 7C), (1D, 2E, 3A, 4D, 5B, 6B, 7A), (1D, 2E, 3A, 4D, 5B, 6B, 7B), (1D, 2E, 3A, 4D, 5B, 6B, 7C), (1D, 2E, 3A, 4D, 5B, 6C, 7A), (1D, 2E, 3A, 4D, 5B, 6C, 7B), (1D, 2E, 3A, 4D, 5B, 6C, 7C), (1D, 2E, 3A, 4D, 5B, 6D, 7A), (1D, 2E, 3A, 4D, 5B, 6D, 7B), (1D, 2E, 3A, 4D, 5B, 6D, 7C), (1D, 2E, 3A, 4E, 5A, 6A, 7A), (1D, 2E, 3A, 4E, 5A, 6A, 7B), (1D, 2E, 3A, 4E, 5A, 6A, 7C), (1D, 2E, 3A, 4E, 5A, 6B, 7A), (1D, 2E, 3A, 4E, 5A, 6B, 7B), (1D, 2E, 3A, 4E, 5A, 6B, 7C), (1D, 2E, 3A, 4E, 5A, 6C, 7A), (1D, 2E, 3A, 4E, 5A, 6C, 7B), (1D, 2E, 3A, 4E, 5A, 6C, 7C), (1D, 2E, 3A, 4E, 5A, 6D, 7A), (1D, 2E, 3A, 4E, 5A, 6D, 7B), (1D, 2E, 3A, 4E, 5A, 6D, 7C), (1D, 2E, 3A, 4E, 5B, 6A, 7A), (1D, 2E, 3A, 4E, 5B, 6A, 7B), (D, 2E, 3A, 4E, 6A, 7C), (1D, 2E, 3A, 4E, 5B, 6B, 7A), (1D, 2E, 3A, 4E, 5B, 6B, 7B), (1D, 2E, 3A, 4E, 5B, 6B, 7C) (1D, 2E, 3A, 4E, 5B, 6C, 7A), (1D, 2E, 3A, 4E, 5B, 6C, 7B), (1D, 2E, 3A, 4E, 5B, 6C, 7C), (1D, 2E, 3A, 4E, 5B, 6D, 7A), (1D, 2E, 3A, 4E, 5B, 6D, 7B), (1D, 2E, 3A, 4E, 5B, 6D, 70, (1D, 2E, 3B, 4A, 5A, 6A, 7A) (1D, 2E, 3B, 4A, 5A, 6A, 7B), (1D, 2E, 3B, 4A, 5A, 6A, 7C), (1D, 2E, 3B, 4A, 5A, 6B, 7A), (1D, 2E, 3B, 4A, 5A, 6B, 7C), (1D, 2E, 3B, 4A, 5A, 6B, 7C), (1D, 2E, 3B, 4A, 5A, 6C, 7A), (1D, 2E, 3B, 4A, 5A, 6B, 7B), (1D, 2E, 3B, 4A, 5A, 6C, 7C), (1D, 2E, 3B, 4A, 5A, 6D, 7A), (1D, 2E, 3B, 4A, 5A, 6D, 7B), (1D, 2E, 3B, 4A, 5A, 6D 7C), (1D, 2E, 3B, 4A, 5B, 6A, 7A), (1D, 2E, 3B, 4A, 5B, 6A, 7B), (1D, 2E, 3B, 4A, 5B, 6A, 7A), (1D, 2E, 3B, 4A, 5B, 6B, 7A), (1D, 2E, 3B, 4A, 5B, 6B, 7B), (1D, 2E, 3B, 4A, 5B, 6B, 7C), (1D, 2E, 3B, 4A, 5B, 6C, 7A), (1D, 2E, 3B, 4A, 5B, 6C, 7B), (1D, 2E, 3B, 4A, 5B, 6C, 7C), (1D, 2E, 3B, 4A, 5B, 6D, 7A), (1D, 2E, 3B, 4A, 5B, 6D, 7B), (1D, 2E, 3B, 4A, 5B, 6D, 7C), (1D, 2E, 3B, 4B, 5A, 6A, 7A), (1D, 2E, 3B, 4B, 5A, 6A, 7B), (1D, 2E, 3B, 4B, 5A, 6A, 7C), (1D, 2E, 3B, 4B, 5A, 6B, 7A), (D, 2E, 3B, 4B, 5A, 6B, 7B), (1D, 2E, 3B, 4B, 5A, 6B, 7C), (1D, 2E, 3B, 4B, 5A, 6C, 7A), (1D, 2E, 3B, 4B, 5A, 6B, 7B), (1D, 2E, 3B, 4B, 5A, 6C, 7C) (1D, 2E, 3B, 4B, 5A, 6D, 7A), (1D, 2E, 3B, 4B, 5A, 6D, 7B), (1D, 2E, 3B, 4B, 5A, 6D, 7C), (1D, 2E, 3B, 4B, 5B, 6A, 7A), (1D, 2E, 3B, 4B, 5B, 6A, 7B), (1D, 2E, 3B, 4B, 5B, 6A, 7C), (1D, 2E, 3B, 4B, 5B, 6A, 7A), (1D, 2E, 3B, 4B, 5B, 6B, 7B), (1D, 2E, 3B, 4B, 5B, 6B, 7C), (1D, 2E, 3B, 4B, 5B, 6B, 7A), (1D, 2E, 3B, 4B, 5B, 6C, 7B), (1D, 2E, 3B, 4B, 5B, 6C, 7C), (1D, 2E, 3B, 4B, 5B, 6D, 7A), (1D, 2E, 3B, 4B, 5B, 6D, 7B), (1D, 2E, 3B, 4B, 5B, 6D, 7C), (1D, 2E, 3B, 4C, 5A, 6A, 7A), (1D, 2E, 3B, 4C, 5A, 6A, 7B), (1D, 2E, 3B, 4C, 5A, 6A, 7C), (1D, 2E, 3B, 4C, 5A, 6B, 7A), (1D, 2E, 3B, 4C, 5A, 6B, 7B), (1D, 2E, 3B, 405A, 6B, 7C) (1D, 2E, 3B, 4C, 5A, 6C, 7A), (1D, 2E, 3B, 4C, 5A, 6C, 7B), (1D, 2E, 3B, 4C, 5A, 6C, 7C), (1D, 2E, 3B, 4C, 5A, 6D, 7A), (1D, 2E, 3B, 4C, 5A, 6D, 7B), (1D, 2E, 3B, 4C, 5A, 6D, 7C), (1D, 2E, 3B, 4B, 6A, 7A), (1D, 2E, 3B, 4C, 5B, 6A, 7B), (1D, 2E, 3B, 4C, 5B, 6A, 7C), (1D, 2E, 3B, 4C, 5B, 6B, 7A), (1D, 2E, 3B, 4C, 5B, 6B, 7B), (1D, 2E, 3B, 4C, 5B, 6B, 7C), (1D, 2E, 3B, 4B, 5B, 6C, 7A), (1D, 2E, 3B, 4C, 5B, 6C, 7B), (1D, 2E, 3B, 4C, 5B, 6C, 7C), (1D, 2E, 3B, 4C, 5B, 6D, 7A), (1D, 2E, 3B, 4C, 5B, 6D, 7C), (1D, 2E, 3B, 4C, 5B, 6D, 7C), (1D, 2E, 3B, 4D, 5A, 6A, 7A), (1D, 2E, 3B, 4D, 5A, 6A, 7B), (1D, 2E, 3B, 4D, 5A, 6A, 7C), (1D, 2E, 3B, 4D, 5A, 6B, 7A), (1D, 2E, 3B, 4D, 5A, 6B, 7B), (1D, 2E, 3B, 4D, 5A, 6B, 7C), (1D, 23B, 4D, 5A, 6C, 7A), (1D, 2E, 3B, 4D, 5A, 6C, 7B), (1D, 2E, 3B, 4D, 5A, 6C, 7C), (1D, 2E, 3B, 4D, 5A, 6D, 7A), (1D, 2E, 3B, 4D, 5A, 6D, 7B), (1D, 2E, 3B, 4D, 5A, 6D, 7C), (1D, 2E, 3B, 4D, 5B, 6A, 7A), (1D, 2E, 3B, 4D, 5B, 6A, 7B), (1D, 2E, 3B, 4D, 5B, 6A, 7C), (1D, 2E, 3B, 4D, 5B, 6B, 7A), (1D, 2E, 3B, 4D, 5B, 6B, 7B), (1D, 2E, 3B, 4D, 5B, 6B, 7C), (1D, 2E, 3B, 4D, 5B, 6C, 7A), (1D, 2E, 3B, 4D, 5B, 6C, 7B), (1D, 2E, 3B, 4D, 5B, 6C, 7C), (1D, 2E, 3B, 4D, 5B, 6D, 7A), (1D, 2E, 3B, 4D, 5B, 6D, 7B), (1D, 2E, 3B, 4D, 5B, 6D, 7C), (1D, 2E, 3B, 4E, 5A, 6A, 7A), (1D, 2E, 3B, 4E, 5A, 6A, 7B), (1D, 2E, 3B, 4E, 5A, 6A, 7C), (1D, 2E, 3B, 4E, 5A, 6B, 7A), (1D, 2E, 3B, 4E, 5A, 6B, 7B), (1D, 2E, 3B, 4E, 5A, 6B, 7C), (1D, 2E, 3B, 4E, 5A, 6C, 7A), (1D, 2E, 3B, 4E, 5A, 6C, 7B), (1D, 2E, 3B, 4E, 5A, 6C, 7C), (1D, 2E, 3B, 4E, 5A, 6D, 7A), (1D, 2E, 3B, 4E, 5A, 6D, 7B), (1D, 2E, 3B, 4E, 5A, 6D, 7C), (1D, 2E, 3B, 4E, 5B, 6A, 7A), (1D, 2E, 3B, 4E, 5B, 6A, 7B), (1D, 2E, 3B, 4E, 5B, 6A, 7C), (1D, 2E, 3B, 4E, 5B, 6B, 7A), (1D, 2E, 3B, 4E, 5B, 6B, 7B), (1D, 2E, 3B, 4E, 5B, 6B, 7C), (1D, 2E, 3B, 4E, 5B, 6C, 7A), (1D, 2E, 3B, 4E, 5B, 6C, 7B), (1D, 2E, 3B, 4E, 5B, 6C, 7C), (1D, 2E, 3B, 4E, 5B, 6D, 7A), (1D, 2E, 3B, 4E, 5B, 6D, 7B), (1D, 2E, 3B, 4E, 5B, 6D, 7C), (1D, 2E, 3C, 4A, 5A, 6A, 7A), (1D, 2E, 3C, 4A, 5A, 6A, 7B), (1D, 2E, 3C, 4A, 5A, 6A,

7C), (1D, 2E, 3C, 4A, 5A, 6B, 7A), (1D, 2E, 3C, 4A, 5A, 6B, 7B), (1D, 2E, 3C, 4A, 5A, 6B, 7C), (1D, 2E, 3C, 4A, 5A, 6C, 7A), (1D, 2E, 3C, 4A, 5A, 6C, 7B), (1D, 2E, 3C, 4A, 5A, 6C, 7C), (1D, 2E, 3C, 4A, 5A, 6D, 7A), (1D, 2E, 3C, 4A, 5A, 6D, 7B), (1D, 2E, 3C, 4A, 5A, 6D, 7C), (1D, 2E, 3C, 4A, 5B, 6A, 7A), (1D, 2E, 3C, 4A, 5B, 6A, 7B), (1D, 2E, 3C, 4A, 5B, 6A, 7C), (1D, 2E, 3C, 4A, 5B, 6B, 7A), (1D, 2E, 3C, 4A, 5B, 6B, 7B), (1D, 2E, 3C, 4A, 5B, 6B, 7C), (1D, 2E, 3C, 4A, 5B, 6C, 7A), (1D, 2E, 3C, 4A, 5B, 6C, 7B), (1D, 2E, 3C, 4A, 5B, 6C, 7C), (1D, 2E, 3C, 4A, 5B, 6D, 7A), (1D, 2E, 3C, 4A, 5B, 6D, 7B), (1D, 2E, 3C, 4A, 5B, 6D, 7C), (1D, 2E, 3C, 4B, 5A, 6A, 7A), (1D, 2E, 3C, 4B, 5A, 6A, 7B), (1D, 2E, 3C, 4B, 5A, 6A, 7C), (1D, 2E, 3C, 4B, 5A, 6B, 7A), (1D, 2E, 3C, 4B, 5A, 6B, 7B), (1D, 2E, 3C, 4B, 5A, 6B, 7C), (1D, 2E, 3C, 4B, 5A, 6C, 7A), (1D, 2E, 3C, 4B, 5A, 6C, 7B), (1D, 2E, 3C, 4B, 5A, 6C, 7C), (1D, 2E, 3C, 4B, 5A, 6D, 7A), (1D, 2E, 3C, 4B, 5A, 6D, 7B), (1D, 2E, 3C, 4B, 5A, 6D, 7C), (1D, 2E, 3C, 4B, 5B, 6A, 7A), (1D, 2E, 3C, 4B, 5B, 6A, 7B), (1D, 2E, 3C, 4B, 5B, 6A, 7C), (1D, 2E, 3C, 4B, 5B, 6B, 7A), (1D, 2E, 3C, 4B, 5B, 6B, 7B), (1D, 2E, 3C, 4B, 5B, 6B, 7C), (1D, 2E, 3C, 4B, 5B, 6C, 7A), (1D, 2E, 3C, 4B, 5B, 6C, 7B), (1D, 2E, 3C, 4B, 5B, 6C, 7C), (1D, 2E, 3C, 4B, 5B, 6D, 7A), (1D, 2E, 3C, 4B, 5B, 6D, 7B), (1D, 2E, 3C, 4B, 5B, 6D, 7C), (1D, 2E, 3C, 4C, 5A, 6A, 7A), (1D, 2E, 3C, 4C, 5A, 6A, 7B), (1D, 2E, 3C, 4C, 5A, 6A, 7C), (1D, 2E, 3C, 4C, 5A, 6B, 7A), (1D, 2E, 3C, 4C, 5A, 6B, 7B), (1D, 2E, 3C, 4C, 5A, 6B, 7C), (1D, 2E, 3C, 4C, 5A, 6C, 7A), (1D, 2E, 3C, 4C, 5A, 6C, 7B), (1D, 2E, 3C, 4C, 5A, 6C, 7C), (1D, 2E, 3C, 4C, 5A, 6D, 7A), (1D, 2E, 3C, 4C, 5A, 6D, 7B), (1D, 2E, 3C, 4C, 5A, 6D, 7C), (1D, 2E, 3C, 4C, 5B, 6A, 7A), (1D, 2E, 3C, 4C, 5B, 6A, 7B), (1D, 2E, 3C, 4C, 5B, 6A, 7C), (1D, 2E, 3C, 4C, 5B, 6B, 7A), (1D, 2E, 3C, 4C, 5B, 6B, 7B), (1D, 2E, 3C, 4C, 5B, 6B, 7C), (1D, 2E, 3C, 4C, 5B, 6C, 7A), (1D, 2E, 3C, 4C, 5B, 6C, 7B), (1D, 2E, 3C, 4C, 5B, 6C, 7C), (1D, 2E, 3C, 4C, 5B, 6D, 7A), (1D, 2E, 3C, 4C, 5B, 6D, 7B), (1D, 2E, 3C, 4C, 5B, 6D, 7C), (1D, 2E, 3C, 4D, 5A, 6A, 7A), (1D, 2E, 3C, 4D, 5A, 6A, 7B), (1D, 2E, 3C, 4D, 5A, 6A, 7C), (1D, 2E, 3C, 4D, 5A, 6B, 7A), (1D, 2E, 3C, 4D, 5A, 6B, 7B), (1D, 2E, 3C, 4D, 5A, 6B, 7C), (1D, 2E, 3C, 4D, 5A, 6C, 7A), (1D, 2E, 3C, 4D, 5A, 6C, 7B), (D, 2E, 3C, 4D, 5A, 6C, 7C), (1D, 2E, 3C, 4D, 5A, 6D, 7A), (1D, 2E, 3C, 4D, 5A, 6D, 7B), (1D, 2E, 3C, 4D, 5A, 6D, 7C), (1D, 2E, 3C, 4D, 5B, 6A, 7A), (1D, 2E, 3C, 4D, 5B, 6A, 7B), (1D, 2E, 3C, 4D, 5B, 5A, 7C), (1D, 2E, 3C, 4D, 5B, 6B, 7A), (1D, 2E, 3C, 4D, 5B, 6B, 7B), (1D, 2E, 3C, 4D, 5B, 6B, 7C), (1D, 2E, 3C, 4D, 5B, 6C, 7A) (1D, 2E, 3C, 4D, 5B, 6C, 7B), (1D, 2E, 3C, 4D, 5B, 6C, 7C), (1D, 2E, 3C, 4D, 5B, 6D, 7A), (1D, 2E, 3C, 4D, 5B, 6D, 7B), (1D, 2E, 3C, 4D, 5B, 6D, 7C), (1D, 2E, 3C, 4E, 5A, 6A, 7A), (1D, 2E, 3C, 4E, 5A, 6A), (1D, 2E, 3C, 4E, 5A, 6A, 7C), (1D, 2E, 3C, 4E, 5A, 6B, 7A), (1D, 2E, 3C, 4E, 5A, 6B, 7B), (1D, 2E, 3C, 4E, 5A, 6B, 7C), (1D, 2E, 3C, 4E, 5A, 6C, 7A), (1D, 2E, 3C, 4E, 5A, 6C, 7B), (1D, 2E, 3C, 4E, 5A, 6C, 7C), (1D, 2E, 3C, 4E, 5A, 6D, 7A), (1D, 2E, 3C, 4E, 5A, 6D, 7B), (1D, 2E, 3C, 4E, 5A, 6D, 7C), (1D, 2E, 3C, 4E, 5B, 6A, 7A), (1D, 2E, 3C, 4E, 5B, 6A, 7B), (1D, 2E, 3C, 4E, 5B, 6A, 7C), (1D, 2E, 3C, 4E, 5B, 6B, 7A), (1D, 2E, 3C, 4E, 5B, 6B, 7B), (1D, 2E, 3C, 4E, 5B, 6B, 7C), (1D, 2E, 3C, 4E, 5B, 6C, 7A), (1D, 2E, 3C, 4E, 5B, 6C, 7B), (1D, 2E, 3C, 4E, 5B, 6C, 7C), (1D, 2E, 3C, 4E, 5B, 6D, 7A), (1D, 2E, 3C, 4E, 5B, 6D, 7B), (1D, 2E, 3C, 4E, 5B, 6D, 7C), (1D, 2E, 3D, 4A, 5A, 6A, 7A), (1D, 2E, 3D, 4A, 5A, 6A, 7B), (1D, 2E, 3D, 4A, 5A, 6A, 7C), (1D, 2E, 3D, 4A, 5A, 6B, 7A), (1D, 2E, 3D, 4A, 5A, 6B, 7B), (1D, 2E, 3D, 4A, 5A, 6B, 7C), (1D, 2E, 3D, 4A, 5A, 6C, 7A), (1D, 2E, 3D, 4A, 5A, 6C, 7B), (1D, 2E, 3D, 4A, 5A, 6C, 7C), (1D, 2E, 3D, 4A, 5A, 6D, 7A), (1D, 2E, 3D, 4A, 5A, 6D, 7B), (1D, 2E, 3D, 4A, 5A, 6D, 7C), (1D, 2E, 3D, 4A, 5B, 6A, 7A), (1D, 2E, 3D, 4A, 5B, 6A, 7B), (1D, 2E, 3D, 4A, 5B, 6A, 7C), (1D, 2E, 3D, 4A, 5B, 6B, 7A), (1D, 2E, 3D, 4A, 5B, 6B, 7B), (1D, 2E, 3D, 4A, 5B, 6B, 7C), (1D, 2E, 3D, 4A, 5B, 6C, 7A), (1D, 2E, 3D, 4A, 5B, 6C, 7B), (1D, 2E, 3D, 4A, 5B, 6C, 7C), (1D, 2E, 3D, 4A, 5B, 6D, 7A), (1D, 2E, 3D, 4A, 5B, 6D, 7B), (1D, 2E, 3D 5B, 6D, 7C), (1D, 2E, 3D, 4B, 5A, 6A, 7A), (1D, 2E, 3D, 4B, 5A, 6A, 7B), (1D, 2E, 3D, 4B, 5A, 6A, 7C), (1D, 2E, 3D, 4B, 5A, 6B, 7A), (1D, 2E, 3D, 4B, 5A, 6B, 7B), (1D, 2E, 3D, 4B, 5A, 6B, 7C), (1D, 2E, 3D, 4B, 5A, 6C, 7A), (1D, 2E, 3D, 4B, 5A, 6C, 7B), (1D, 2E, 3D, 4B, 5A, 6C, 7C), (1D, 2E, 3D, 4B, 5A, 6D, 7A), (1D, 2E, 3D, 4B, 5A, 6D, 7B), (1D, 2E, 3D, 4B, 5A, 6D, 7C), (1D, 2E, 3D, 4B, 5B, 6A, 7A), (1D, 2E, 3D, 4B, 5B, 6A, 7B), (1D, 2E, 3D, 4B, 5B, 6A, 7C), (1D, 2E, 3D, 4B, 5B, 6B, 7A), (1D, 2E, 3D, 4B, 5B, 6B, 7B), (1D, 2E, 3D, 4B, 5B, 6B, 7C), (1D, 2E, 3D, 4B, 5B, 6C, 7A), (1D, 2E, 3D, 4B, 5B, 6C, 7B), (1D, 2E, 3D, 4B, 5B, 6C, 7C), (1D, 2E, 3D, 4B, 5B, 6D, 7A), (1D, 2E, 3D, 4B, 5B, 6D, 7B), (1D, 2E, 3D, 4B, 5B, 6D, 7C), (1D, 2E, 3D, 4C, 5A, 6A, 7A), (1D, 2E, 3D, 4C, 5A, 6A, 7B), (1D, 2E, 3D, 4B, 5A, 6A, 7C), (1D, 2E, 3D, 4C, 5A, 6B, 7A), (1D, 2E, 3D, 4C, 5A, 6B, 7B), (1D, 2E, 3D, 4C, 5A, 6B, 7C), (1D, 2E, 3D, 4C, 5A, 6C, 7A), (1D, 2E, 3D, 4C, 5A, 6C, 7B), (1D, 2E, 3D, 4C, 5A, 6C, 7C), (1D, 2E, 3D, 4C, 5A, 6D, 7A), (1D, 2E, 3D, 4C, 5A, 6D, 7B), (1D, 2E, 3D, 4C, 5A, 6D, 7C), (1D, 2E, 3D, 4C, 5B, 6A, 7A), (1D, 2E, 3D, 4C, 5B, 6A, 7B), (1D, 2E, 3D, 4C, 5B, 6A, 7C), (1D, 2E, 3D, 4C, 5B, 6B, 7A), (1D, 2E, 3D, 4C, 5B, 6B, 7B), (1D, 2E, 3D, 4C, 5B, 6B, 7C), (1D, 2E, 3D, 4C, 5B, 6C, 7A), (1D, 2E, 3D, 4C, 5B, 6C, 7B), (1D, 2E, 3D, 4C, 5B, 6C, 7C), (1D, 2E, 3D, 4C, 5B, 6D, 7A), (1D, 2E, 3D, 4C, 5B, 6D, 7B), (1D, 2E, 3D, 4C, 5B, 6D, 7C), (1D, 2E, 3D, 4D, 5A, 6A, 7A), (1D, 2E, 3D, 4D, 5A, 6A, 7B), (1D, 2E, 3D, 4D, 5A, 6A, 7C), (1D, 2E, 3D, 4D, 5A, 6B, 7A), (1D, 2E, 3D, 4D, 5A, 6B, 7B), (1D, 2E, 3D, 4D, 5A, 6B, 7C), (1D, 2E, 3D, 4D, 5A, 6C, 7A), (1D, 2E, 3D, 4D, 5A, 6C, 7B), (1D, 2E, 3D, 4D, 5A, 6C, 7C), (1D, 2E, 3D, 4D, 5A, 6D, 7A), (1D, 2E, 3D, 4D, 5A, 6D, 7B), (1D, 2E, 3D, 4D, 5A, 6D, 7C), (1D, 2E, 3D, 4D, 5B, 6A, 7A), (1D, 2E, 3D, 4D, 5B, 6A, 7B), (1D, 2E, 3D, 4D, 5B, 6A, 7C), (1D, 2E, 3D, 4D, 5B, 6B, 7A), (1D, 2E, 3D, 4D, 5B, 6B, 7B), (1D, 2E, 3D, 4D, 5B, 6B, 7C), (1D, 2E, 3D, 4D, 5B, 6C, 7A), (1D, 2E, 3D, 4D, 5B, 6C, 7B), (1D, 2E, 3D, 4D, 5B, 6C, 7C), (1D, 2E, 3D, 4D, 5B, 6D, 7A), (1D, 2E, 3D, 4D, 5B, 6D, 7B), (1D, 2E, 3D, 4E, 5A, 6A, 7A), (1D, 2E, 3D, 4E, 5A, 6A, 7B), (1D, 2E, 3D, 4E, 5A, 6A, 7C), (1D, 2E, 3D, 4E, 5A, 6B, 7A), (1D, 2E, 3D, 4E, 5A, 6B, 7B), (1D, 2E, 3D, 4E, 5A, 6B, 7C), (1D, 2E, 3D, 4E, 5A, 6C, 7A), (1D, 2E, 3D, 4E, 5A, 6C, 7B), (1D, 2E, 3D, 4E, 5A, 6C, 7C), (1D, 2E, 3D, 4E, 5A, 6D, 7A), (1D, 2E, 3D, 4E, 5A, 6D, 7B), (1D, 2E, 3D, 4E, 5A, 6D, 7C), (1D, 2E, 3D, 4E, 5B, 6A, 7A), (1D, 2E, 3D, 4E, 5B, 6A, 7B), (1D, 2E, 3D, 4E, 5B, 6A, 7C), (1D, 2E, 3D, 4E, 5B, 6B, 7A), (1D, 2E, 3D, 4E, 5B, 6B, 7B), (1D, 2E, 3D, 4E, 5B, 6B, 7C), (1D, 2E, 3D, 4E, 5B, 6C, 7A), (1D, 2E, 3D, 4E, 5B, 6C, 7B), (1D, 2E, 3D, 4E, 5B, 6C, 7C), (1D, 2E, 3D, 4E, 5B, 6D, 7A), (1D, 2E, 3D, 4E, 5B, 6D, 7B), (1D, 2E, 3D, 4E, 5B, 6D, 7C), (1D, 2E, 3E, 4A, 5A, 6A, 7A), (1D, 2E, 3E, 4A, 5A, 6A, 7B), (1D, 2E, 3E, 4A, 5A, 6A, 7C), (1D, 2E, 3E, 4A, 5A, 6B, 7A), (1D, 2E, 3E, 4A, 5A, 6B, 7B), (1D, 2E, 3E, 4A, 5A, 6B, 7C), (1D, 2E, 3E, 4A, 5A, 6C, 7A), (1D, 2E, 3E, 4A, 5A, 6C, 7B), (1D, 2E, 3E, 4A, 5A, 6C, 7C), (1D, 2E, 3E, 4A, 5A, 6D, 7A), (1D, 2E, 3E, 4A, 5A, 6D, 7B), (1D, 2E, 3E, 4A, 5A, 6D, 7C), (1D, 2E, 3E, 4A, 5B, 6A, 7A), (1D, 2E, 3E, 4A, 5B, 6A, 7B), (1D, 2E, 3E, 4A, 5B, 6A, 7C), (1D, 2E, 3E, 4A, 5B, 6B, 7A), (1D, 2E, 3E, 4A, 5B, 6B, 7B), (1D, 2E, 3E, 4A, 5B, 6B, 7C), (1D, 2E, 3E, 4A, 5B, 6C, 7A), (1D, 2E, 3E, 4A, 5B, 6C, 7B), (1D, 2E, 3E, 4A, 5B, 6C, 7C), (1D, 2E, 3E, 4A, 5B, 6D, 7A), (1D, 2E, 3E, 4A, 5B, 6D, 7B), (1D, 2E, 3E, 4A, 5B, 6D, 7C), (1D, 2E, 3E, 4B, 5A, 6A, 7A), (1D, 2E, 3E, 4B, 5A, 6A, 7B), (1D, 2E, 3E, 4B, 5A, 6A, 7C), (1D, 2E, 3E, 4B, 5A, 6B, 7A), (1D, 2E, 3E, 4B, 5A, 6B, 7B), (1D, 2E, 3E, 4B, 5A, 6B, 7C), (1D, 2E, 3E, 4B, 5A, 6C, 7A), (1D, 2E, 3E, 4B, 5A, 6C, 7B), (1D, 2E, 3E, 4B, 5A, 6C, 7C), (1D, 2E, 3E, 4B, 5A, 6D, 7A), (1D, 2E, 3E, 4B, 5A, 6D, 7B), (1D, 2E, 3E, 4B, 5A, 6D, 7C), (1D, 2E, 3E, 4B, 5B, 6A, 7A), (1D, 2E, 3E, 4B, 5B, 6A, 7B), (1D, 2E, 3E, 4B, 5B, 6A, 7C), (1D, 2E, 3E, 4B, 5B, 6B, 7A), (1D, 2E, 3E, 4B, 5B, 6B, 7B), (1D, 2E, 3E, 4B, 5B, 6B, 7C), (1D, 2E, 3E, 4B, 5B, 6C, 7A), (1D, 2E, 3E, 4B, 5B, 6C, 7B), (1D, 2E, 3E, 4B, 5B, 6C, 7C), (1D, 2E, 3E, 4B, 5B, 6D, 7A), (1D, 2E, 3E, 4B, 5B, 6D, 7B), (1D, 2E, 3E, 4B, 5B, 6D, 7C), (1D, 2E, 3E, 4C, 5A, 6A, 7A), (1D, 2E, 3E, 4C, 5A, 6A, 7B), (1D, 2E, 3E, 4C, 5A, 6A, 7C), (1D, 2E, 3E, 4C, 5A, 6B, 7A), (1D, 2E, 3E, 4C, 5A, 6B, 7B), (1D, 2E, 3E, 4C, 5A, 6B, 7C), (1D, 2E, 3E, 4C, 5A, 6C, 7A), (1D, 2E, 3E, 4C, 5A, 6C, 7B), (1D, 2E, 3E, 4C, 5A, 6C, 7C), (1D, 2E, 3E, 4C, 5A, 6D, 7A), (1D, 2E, 3E, 4C, 5A, 6D, 7B), (1D, 2E, 3E, 4C, 5A, 6D, 7C), (1D, 2E, 3E, 4C, 5B, 6A, 7A), (1D, 2E, 3E, 4C, 5B, 6A, 7B), (1D, 2E, 3E, 4C, 5B, 6A, 7C), (1D, 2E, 3E, 4C, 5B, 6B, 7A), (1D, 2E, 3E, 4C, 5B, 6B, 7B), (1D, 2E, 3E, 4C, 5B, 6B, 7C), (1D, 2E, 3E, 4C, 5B, 6C, 7A), (1D, 2E, 3E, 4C, 5B, 6C, 7B), (1D, 2E, 3E, 4C, 5B, 6C, 7C), (1D, 2E, 3E, 4C, 5B, 6D, 7A), (1D, 2E, 3E, 4C, 5B, 6D, 7B), (1D, 2E, 3E, 4C, 5B, 6D, 7C), (1D, 2E, 3E, 4D, 5A, 6A, 7A), (1D, 2E, 3E, 4D, 5A, 6A, 7B), (1D, 2E, 3E, 4D, 5A, 6A, 7C), (1D, 2E, 3E, 4D, 5A, 6B, 7A), (1D, 2E, 3E, 4D, 5A, 6B, 7B), (1D, 2E, 3E, 4D, 5A, 6B, 7C), (1D, 2E, 3E, 4D, 5A, 6C, 7A), (1D, 2E, 3E, 4D, 5A, 6C, 7B), (1D, 2E, 3E, 4D, 5A, 6C, 7C), (1D, 2E, 3E, 4D, 5A, 6D, 7A), (1D, 2E, 3E, 4D, 5A, 6D, 7B), (1D, 2E, 3E, 4D, 5A, 6D, 7C), (1D, 2E, 3E, 4D, 5B, 6A, 7A), (1D, 2E, 3E, 4D, 5B, 6A, 7B), (1D, 2E, 3E, 4D, 5B, 6A, 7C), (1D, 2E, 3E, 4D, 5B, 6B, 7A), (1D, 2E, 3E, 4D, 5B, 6B, 7B), (1D, 2E, 3E, 4D, 5B, 6B, 7C), (1D, 2E, 3E, 4D, 5B, 6C, 7A), (1D, 2E, 3E, 4D, 5B, 6C, 7B), (1D, 2E, 3E, 4D, 5B, 6C, 7C), (1D, 2E, 3E, 4D, 5B, 6D, 7A), (1D, 2E, 3E, 4D, 5B, 6D, 7B), (1D, 2E, 3E, 4D, 5B, 6D, 7C), (1D, 2E, 3E, 4E, 5A, 6A, 7A), (1D, 2E, 3E, 4E, 5A, 6A, 7B), (1D, 2E, 3E, 4E, 5A, 6A, 7C), (1D, 2E, 3E, 4E, 5A, 6B, 7A), (1D, 2E, 3E, 4E, 5A, 6B, 7B), (1D, 2E, 3E, 4E, 5A, 6B, 7C), (1D, 2E, 3E, 4E, 5A, 6C, 7A), (1D, 2E, 3E, 4E, 5A, 6C, 7B), (1D, 2E, 3E, 4E, 5A, 6C, 7C), (1D, 2E, 3E, 4E, 5A, 6D, 7A), (1D, 2E, 3E, 4E, 5A, 6D, 7B), (1D, 2E, 3E, 4E, 5A, 6D, 7C), (1D, 2E, 3E, 4E, 5B, 6A, 7A), (1D, 2E, 3E, 4E, 5B, 6A, 7B), (1D, 2E, 3E, 4E, 5B, 6A, 7C), (1D, 2E, 3E, 4E, 5B, 6B, 7A), (1D, 2E, 3E, 4E, 5B, 6B, 7B), (1D, 2E, 3E, 4E, 5B, 6B, 7C), (1D, 2E, 3E, 4E, 5B, 6C, 7A), (1D, 2E, 3E, 4E, 5B, 6C, 7B), (1D, 2E, 3E, 4E, 5B, 6C, 7C), (1D, 2E, 3E, 4E, 5B, 6D, 7A), (1D, 2E, 3E, 4E, 5B, 6D, 7B), (1D, 2E, 3E, 4E, 5B, 6D, 7C), (1E, 2A, 3A, 4A, 5A, 6A, 7A), (1E, 2A, 3A, 4A, 5A, 6A, 7B), (1E, 2A, 3A, 4A, 5A, 6A, 7C), (1E, 2A, 3A, 4A, 5A, 6B, 7A), (1E, 2A, 3A, 4A, 5A, 6B, 7B), (1E, 2A, 3A, 4A, 5A, 6B, 7C), (1E, 2A, 3A, 4A, 5A, 6C, 7A), (1E, 2A, 3A, 4A, 5A, 6C, 7B), (1E, 2A, 3A, 4A, 5A, 6C, 7C), (1E, 2A, 3A, 4A, 5A, 6D, 7A), (1E, 2A, 3A, 4A, 5A, 6D, 7B), (1E, 2A, 3A, 4A, 5A, 6D, 7C), (1E, 2A, 3A, 4A, 5B, 6A, 7A), (1E, 2A, 3A, 4A, 5B, 6A, 7B), (1E, 2A, 3A, 4A, 5B, 6A, 7C), (1E, 2A, 3A, 4A, 5B, 6B, 7A), (1E, 2A, 3A, 4A, 5B, 6B, 7B), (1E, 2A, 3A, 4A, 5B, 6B, 7C), (1E, 2A, 3A, 4A, 5B, 6C, 7A), (1E, 2A, 3A, 4A, 5B, 6C, 7B), (1E, 2A, 3A, 4A, 5B, 6C, 7C), (1E, 2A, 3A, 4A, 5B, 6D, 7A), (1E, 2A, 3A, 4A, 5B, 6D, 7B), (1E, 2A, 3A, 4A, 5B, 6D, 7C), (1E, 2A, 3A, 4B, 5A, 6A, 7A), (1E, 2A, 3A, 4B, 5A, 6A, 7B), (1E, 2A, 3A, 4B, 5A, 6A, 7C), (1E, 2A, 3A, 4B, 5A, 6B, 7A), (1E, 2A, 3A, 4B, 5A, 6B, 7B), (1E, 2A, 3A, 4B, 5A, 6B, 7C), (1E, 2A, 3A, 4B, 5A, 6C, 7A), (1E, 2A, 3A, 4B, 5A, 6C, 7B), (1E, 2A, 3A, 4B, 5A, 6C, 7C), (1E, 2A, 3A, 4B, 5A, 6D, 7A), (1E, 2A, 3A, 4B, 5A, 6D, 7B), (1E, 2A, 3A, 4B, 5A, 6D, 7C), (1E, 2A, 3A, 4B, 5B, 6A, 7A), (1E, 2A, 3A, 4B, 5B, 6A, 7B), (1E, 2A, 3A, 4B, 5B, 6A, 7C), (1E, 2A, 3A, 4B, 5B, 6B, 7A), (1E, 2A, 3A, 4B, 5B, 6B, 7B), (1E, 2A, 3A, 4B, 5B, 6B, 7C), (1E, 2A, 3A, 4B, 5B, 6C, 7A), (1E, 2A, 3A, 4B, 5B, 6C, 7B), (1E, 2A, 3A, 4B, 5B, 6C, 7C), (1E, 2A, 3A, 4B, 5B, 6D, 7A), (1E, 2A, 3A, 4B, 5B, 6D, 7B), (1E, 2A, 3A, 4B, 5B, 6D, 7C), (1E, 2A, 3A, 4C, 5A, 6A, 7A), (1E, 2A, 3A, 4C, 5A, 6A, 7B), (1E, 2A, 3A, 4C, 5A, 6A, 7C), (1E, 2A, 3A, 4C, 5A, 6B, 7A), (1E, 2A, 3A, 4C, 5A, 6B, 7B), (1E, 2A, 3A, 4C, 5A, 6B, 7C), (1E, 2A, 3A, 4C, 5A, 6C, 7A), (1E, 2A, 3A, 4C, 5A, 6C, 7B), (1E, 2A, 3A, 4C, 5A, 6C, 7C), (1E, 2A, 3A, 4C, 5A, 6D, 7A), (1E, 2A, 3A, 4C, 5A, 6D, 7B), (1E, 2A, 3A, 4C, 5A, 6D, 7C), (1E, 2A, 3A, 4C, 5B, 6A, 7A), (1E, 2A, 3A, 4C, 5B, 6A, 7B), (1E, 2A, 3A, 4C, 5B, 6A, 7C), (1E, 2A, 3A, 4C, 5B, 6B, 7A), (1E, 2A, 3A, 4C, 5B, 6B, 7B), (1E, 2A, 3A, 4C, 5B, 6B, 7C), (1E, 2A, 3A, 4C, 5B, 6C, 7A), (1E, 2A, 3A, 4C, 5B, 6C, 7B), (1E, 2A, 3A, 4C, 5B, 6C, 7C), (1E, 2A, 3A, 4C, 5B, 6D, 7A), (1E, 2A, 3A, 4C, 5B, 6D, 7B), (1E, 2A, 3A, 4C, 5B, 6D, 7C), (1E, 2A, 3A, 4D, 5A, 6A, 7A), (1E, 2A, 3A, 4D, 5A, 6A, 7B), (1E, 2A, 3A, 4D, 5A, 6A, 7C), (1E, 2A, 3A, 4D, 5A, 6B, 7A), (1E, 2A, 3A, 4D, 5A, 6B, 7B), (1E, 2A, 3A, 4D, 5A, 6B, 7C), (1E, 2A, 3A, 4D, 5A, 6C, 7A), (1E, 2A, 3A, 4D, 5A, 6C, 7B), (1E, 2A, 3A, 4D, 5A, 6C, 7C), (1E, 2A, 3A, 4D, 5A, 6D, 7A), (1E, 2A, 3A, 4D, 5A, 6D, 7B), (1E, 2A, 3A, 4D, 5A, 6D, 7C), (1E, 2A, 3A, 4D, 5B, 6A, 7A), (1E, 2A, 3A, 4D, 5B, 6A, 7B), (1E, 2A, 3A, 4D, 5B, 6A, 7C), (1E, 2A, 3A, 4D, 5B, 6B, 7A), (1E, 2A, 3A, 4D, 5B, 6B, 7B), (1E, 2A, 3A, 4D, 5B, 6B, 7C), (1E, 2A, 3A, 4D, 5B, 6C, 7A), (1E, 2A, 3A, 4D, 5B, 6C, 7B), (1E, 2A, 3A, 4D, 5B, 6C, 7C), (1E, 2A, 3A, 4D, 5B, 6D, 7A), (1E, 2A, 3A, 4D, 5B, 6D, 7B), (1E, 2A, 3A, 4D, 5B, 6D, 7C), (1E, 2A, 3A, 4E, 5A, 6A, 7A), (1E, 2A, 3A, 4E, 5A, 6A, 7B), (1E, 2A, 3A, 4E, 5A, 6A, 7C), (1E, 2A, 3A, 4E, 5A, 6B, 7A), (1E, 2A, 3A, 4E, 5A, 6B, 7B), (1E, 2A, 3A, 4E, 5A, 6B, 7C), (1E, 2A, 3A, 4E, 5A, 6C, 7A), (1E, 2A, 3A, 4E, 5A, 6C, 7B), (1E, 2A, 3A, 4E, 5A, 6C, 7C), (1E, 2A, 3A, 4E, 5A, 6D, 7A), (1E, 2A, 3A, 4E, 5A, 6D, 7B), (1E, 2A, 3A, 4E, 5A, 6D, 7C), (1E, 2A, 3A, 4E, 5B, 6A, 7A), (1E, 2A, 3A, 4E, 5B, 6A, 7B), (1E, 2A, 3A, 4E, 5B, 6A, 7C), (1E, 2A, 3A, 4E, 5B, 6B, 7A), (1E, 2A, 3A, 4E, 5B, 6B, 7B), (1E, 2A, 3A, 4E, 5B, 6B, 7C), (1E, 2A, 3A, 4E, 5B, 6C, 7A), (1E, 2A, 3A, 4E, 5B, 6C, 7B), (1E, 2A, 3A, 4E, 5B, 6C, 7C), (1E, 2A, 3A, 4E, 5B, 6D, 7A), (1E, 2A, 3A, 4E, 5B, 6D, 7B), (1E, 2A, 3A, 4E, 5B, 6D, 7C), (1E, 2A, 3B, 4A, 5A, 6A, 7A), (1E, 2A, 3B, 4A, 5A, 6A, 7B), (1E, 2A, 3B, 4A, 5A, 6A, 7C), (1E, 2A, 3B, 4A, 5A, 6B, 7A), (1E, 2A, 3B, 4A, 5A, 6B, 7B), (1E, 2A, 3B, 4A, 5A, 6B, 7C), (1E, 2A, 3B, 4A, 5A, 6C, 7A), (1E, 2A, 3B, 4A, 5A, 6C, 7B), (1E, 2A, 3B, 4A, 5A, 6C, 7C), (1E, 2A, 3B, 4A, 5A, 6D, 7A), (1E, 2A, 3B, 4A, 5A, 6D, 7B), (1E, 2A, 3B, 4A, 5A, 6D, 7C), (1E, 2A, 3B, 4A, 5B, 6A, 7A), (1E, 2A, 3B, 4A, 5B, 6A, 7B), (1E, 2A, 3B, 4A, 5B, 6A, 7C), (1E, 2A, 3B, 4A, 5B, 6B, 7A), (1E, 2A, 3B, 4A, 5B, 6B, 7B), (1E, 2A, 3B, 4A, 5B, 6B, 7C), (1E, 2A, 3B, 4A, 5B, 6C, 7A), (1E, 2A, 3B, 4A, 5B, 6C, 7B), (1E, 2A, 3B, 4A, 5B, 6C, 7C), (1E, 2A, 3B, 4A, 5B, 6D, 7A), (1E, 2A, 3B, 4A, 5B, 6D, 7B), (1E, 2A, 3B, 4A, 5B, 6D, 7C), (1E, 2A, 3B, 4B, 5A, 6A, 7A), (1E, 2A, 3B, 4B, 5A, 6A, 7B), (1E, 2A, 3B, 4B, 5A, 6A, 7C), (1E, 2A, 3B, 4B, 5A, 6B, 7A), (1E, 2A, 3B, 4B, 5A, 6B, 7B), (1E, 2A, 3B, 4B, 5A, 6B, 7C), (1E, 2A, 3B, 4B, 5A, 6C, 7A), (1E, 2A, 3B, 4B, 5A, 6C, 7B), (1E, 2A, 3B, 4B, 5A, 6C, 7C), (1E, 2A, 3B, 4B, 5A, 6D, 7A), (1E, 2A, 3B, 4B, 5A, 6D, 7B), (1E, 2A, 3B, 4B, 5A, 6D, 7C), (1E, 2A, 3B, 4B, 5B, 6A, 7A), (1E, 2A, 3B, 4B, 5B, 6A, 7B), (1E, 2A, 3B, 4B, 5B, 6A, 7C), (1E, 2A, 3B, 4B, 5B, 6B, 7A), (1E, 2A, 3B, 4B, 5B, 6B, 7B), (1E, 2A, 3B, 4B, 5B, 6B, 7C) (1E, 2A, 3B, 4B, 5B, 6C, 7A), (1E, 2A, 3B, 4B, 5B, 6C, 7B), (1E, 2A, 3B, 4B, 6C, 7C), (1E, 2A, 3B, 4B, 5B, 6D, 7A), (1E, 2A, 3B, 4B, 5B, 6D, 7B), (1E, 2A, 3B, 4B, 5B, 6D, 7C), (1E, 2A, 3B, 4C, 5A, 6A, 7A), (1E, 2A, 3B, 4C, 5A, 6A, 7B), (1E, 2A, 3B, 4C, 5A, 6A, 7C), (1E, 2A, 3B, 4C, 5A, 6B, 7A), (1E, 2A, 3B, 4C, 5A, 6B, 7B), (1E, 2A, 3B, 4C, 5A, 6B, 7C), (1E, 2A, 3B, 4C, 5A, 6C, 7A), (1E, 2A, 3B, 4C, 5A, 6C, 7B), (1E, 2A, 3B, 4C, 5A, 6C, 7C), (1E, 2A, 3B, 4C, 5A, 6D, 7A), (1E, 2A, 3B, 4C, 5A, 6D, 7B), (1E, 2A, 3B, 4C, 5A, 6D, 7C), (1E, 2A, 3B, 4C, 5B, 6A, 7A), (1E, 2A, 3B, 4C, 5B, 6A, 7B), (1E, 2A, 3B, 4C, 5B, 6A, 7C), (1E, 2A, 3B, 4C, 5B, 6B, 7A), (1E, 2A, 3B, 4C, 5B, 6B, 7B), (1E, 2A, 3B, 4C, 5B, 6B, 7C), (1E, 2A, 3B, 4C, 5B, 6C, 7A), (1E, 2A, 3B, 4C, 5B, 6C, 7B), (1E, 2A, 3B, 4C, 5B, 6C, 7C), (1E, 2A, 3B, 4C, 5B, 6D, 7A), (1E, 2A, 3B, 4C, 5B, 6D, 7B), (1E, 2A, 3B, 4C, 5B, 6D, 7C), (1E, 2A, 3B, 4D, 5A, 6A, 7A), (1E, 2A, 3B, 4D, 5A, 6A, 7B), (1E, 2A, 3B, 4D, 5A, 6A, 7C), (1E, 2A, 3B, 4D, 5A, 6B, 7A), (1E, 2A, 3B, 4D, 5A, 6B, 7B), (1E, 2A, 3B, 4D, 5A, 6B, 7C), (1E, 2A, 3B, 4D, 5A, 6C, 7A), (1E, 2A, 3B, 4D, 5A, 6C, 7B), (1E, 2A, 3B, 4D, 5A, 6C, 7C), (1E, 2A, 3B, 4D, 5A, 6D, 7A), (1E, 2A, 3B, 4D, 5A, 6D, 7B), (1E, 2A, 3B, 4D, 5A, 6D, 7C), (1E, 2A, 3B, 4D, 5B, 6A, 7A), (1E, 2A, 3B, 4D, 5B, 6A, 7B), (1E, 2A, 3B, 4D, 5B, 6A, 7C), (1E, 2A, 3B, 4D, 5B, 6B, 7A), (1E, 2A, 3B, 4D, 5B, 6B, 7B), (1E, 2A, 3B, 4D, 5B, 6B, 7C), (1E, 2A, 3B, 4D, 5B, 6C, 7A), (1E, 2A, 3B, 4D, 5B, 6C, 7B), (1E, 2A, 3B, 4D, 5B, 6C, 7C), (1E, 2A, 3B, 4D, 5B, 6D, 7A), (1E, 2A, 3B, 4D, 5B, 6D, 7B), (1E, 2A, 3B, 4D, 5B, 6D, 7C), (1E, 2A, 3B, 4E, 5A, 6A, 7A), (1E, 2A, 3B, 4E, 5A, 6A, 7B), (1E, 2A, 3B, 4E, 5A, 6A, 7C), (1E, 2A, 3B, 4E, 5A, 6B, 7A), (1E, 2A, 3B, 4E, 5A, 6B, 7B), (1E, 2A, 3B, 4E, 5A, 6B, 7C), (1E, 2A, 3B, 4E, 5A, 6C, 7A), (1E, 2A, 3B, 4E, 5A, 6C, 7B), (1E, 2A, 3B, 4E, 5A, 6C, 7C), (1E, 2A, 3B, 4E, 5A, 6D, 7A), (1E, 2A, 3B, 4E, 5A, 6D, 7B), (1E, 2A, 3B, 4E, 5A, 6D, 7C), (1E, 2A, 3B, 4E, 5B, 6A, 7A), (1E, 2A, 3B, 4E, 5B, 6A, 7B), (1E, 2A, 3B, 4E, 5B, 6A, 7C), (1E, 2A, 3B, 4E, 5B, 6B, 7A), (1E, 2A, 3B, 4E, 5B, 6B, 7B), (1E, 2A, 3B, 4E, 5B, 6B, 7C), (1E, 2A, 3B, 4E, 5B, 6C, 7A), (1E, 2A, 3B, 4E, 5B, 6C, 7B), (1E, 2A, 3B, 4E, 5B, 6C, 7C), (1E, 2A, 3B, 4E, 5B, 6D, 7A), (1E, 2A, 3B, 4E, 5B, 6D, 7B), (1E, 2A, 3B, 4E, 5B, 6D, 7C), (1E, 2A, 3C, 4A, 5A, 6A, 7A), (1E, 2A, 3C, 4A, 5A, 6A, 7B), (1E, 2A, 3C, 4A, 5A, 6A, 7C), (1E, 2A, 3C, 4A, 5A, 6B, 7A), (1E, 2A, 3C, 4A, 5A, 6B, 7B), (1E, 2A, 3C, 4A, 5A, 6B, 7C), (1E, 2A, 3C, 4A, 5A, 6C, 7A), (1E, 2A, 3C, 4A, 5A, 6C, 7B), (1E, 2A, 3C, 4A, 5A, 6C, 7C), (1E, 2A, 3C, 4A, 5A, 6D, 7A), (1E, 2A, 3C, 4A, 5A, 6D, 7B), (1E, 2A, 3C, 4A, 5A, 6D, 7C), (1E, 2A, 3C, 4A, 5B, 6A, 7A), (1E, 2A, 3C, 4A, 5B, 6A, 7B), (1E, 2A, 3C, 4A, 5B, 6A, 7C), (1E, 2A, 3C, 4A, 5B, 6B, 7A), (1E, 2A, 3C, 4A, 5B, 6B, 7B), (1E, 2A, 3C, 4A, 5B, 6C, 7A), (1E, 2A, 3C, 4A, 5B, 6C, 7B), (1E, 2A, 3C, 4A, 5B, 6C, 7C), (1E, 2A, 3C, 4A, 5B, 6D, 7A), (1E, 2A, 3C, 4A, 5B, 6D, 7B), (1E, 2A, 3C, 4A, 5B, 6D, 7C), (1E, 2A, 3C, 4B, 5A, 6A, 7A), (1E, 2A, 3C, 4B, 5A, 6A, 7B), (1E, 2A, 3C, 4B, 5A, 6A, 7C), (1E, 2A, 3C, 4B, 5A, 6B, 7A), (1E, 2A, 3C, 4B, 5A, 6B, 7B), (1E, 2A, 3C, 4B, 5A, 6B, 7C), (1E, 2A, 3C, 4B, 5A, 6C, 7A), (1E, 2A, 3C, 4B, 5A, 6C, 7B), (1E, 2A, 3C, 4B, 5A, 6C, 7C), (1E, 2A, 3C, 4B, 5A, 6D, 7A), (1E, 2A, 3C, 4B, 5A, 6D, 7B), (1E, 2A, 3C, 4B, 5A, 6D, 7C), (1E, 2A, 3C, 4B, 5B, 6A, 7A), (1E, 2A, 3C, 4B, 5B, 6A, 7B), (1E, 2A, 3C, 4B, 5B, 6A, 7C), (1E, 2A, 3C, 4B, 5B, 6B, 7A), (1E, 2A, 3C, 4B, 5B, 6B, 7B), (1E, 2A, 3C, 4B, 5B, 6B, 7C), (1E, 2A, 3C, 4B, 5B, 6C, 7A), (1E, 2A, 3C, 4B, 5B, 6C, 7B), (1E, 2A, 3C, 4B, 5B, 6C, 7C), (1E, 2A, 3C, 4B, 5B, 6D, 7A), (1E, 2A, 3C, 4B, 5B, 6D, 7B), (1E, 2A, 3C, 4B, 5B, 6D, 7C), (1E, 2A, 3C, 4C, 5A, 6A, 7A), (1E, 2A, 3C, 4C, 5A, 6A, 7B), (1E, 2A, 3C, 4C, 5A, 6A, 7C), (1E, 2A, 3C, 4C, 5A, 6B, 7A), (1E, 2A, 3C, 4C, 5A, 6B, 7B), (1E, 2A, 3C, 4C, 5A, 6B, 7C), (1E, 2A, 3C, 4C, 5A, 6C, 7A), (1E, 2A, 3C, 4C, 5A, 6C, 7B), (1E, 2A, 3C, 4C, 5A, 6C, 7C), (1E, 2A, 3C, 4C, 5A, 6D, 7A), (1E, 2A, 3C, 4C, 5A, 6D, 7B), (1E, 2A, 3C, 4C, 5A, 6D, 7C), (1E, 2A, 3C, 4C, 5B, 6A, 7A), (1E, 2A, 3C, 4C, 5B, 6A, 7B), (1E, 2A, 3C, 4C, 5B, 6A, 7C), (1E, 2A, 3C, 4C, 5B, 6B, 7A), (1E, 2A, 3C, 4C, 5B, 6B, 7B), (1E, 2A, 3C, 4C, 5B, 6B, 7C), (1E, 2A, 3C, 4C, 5B, 6C, 7A), (1E, 2A, 3C, 4C, 5B, 6C, 7B), (1E, 2A, 3C, 4C, 5B, 6C, 7C), (1E, 2A, 3C, 4C, 5B, 6D, 7A), (1E, 2A, 3C, 4C, 5B, 6D, 7B), (1E, 2A, 3C, 4C, 5B, 6D, 7C), (1E, 2A, 3C, 4D, 5A, 6A, 7A), (1E, 2A, 3C, 4D, 5A, 6A, 7B), (1E, 2A, 3C, 4D, 5A, 6A, 7C), (1E, 2A, 3C, 4D, 5A, 6B, 7A), (1E, 2A, 3C, 4D, 5A, 6B, 7B), (1E, 2A, 3C, 4D, 5A, 6B, 7C), (1E, 2A, 3C, 4D, 5A, 6C, 7A), (1E, 2A, 3C, 4D, 5A, 6C, 7B), (1E, 2A, 3C, 4D, 5A, 6C, 7C), (1E, 2A, 3C, 4D, 5A, 6D, 7A), (1E, 2A, 3C, 4D, 5A, 6D, 7B), (1E, 2A, 3C, 4D, 5A, 6D, 7C), (1E, 2A, 3C, 4D, 5B, 6A, 7A), (1E, 2A, 3C, 4D, 5B, 6A, 7B), (1E, 2A, 3C, 4D, 5B, 6A, 7C), (1E, 2A, 3C, 4D, 5B, 6B, 7A), (1E, 2A, 3C, 4D, 5B, 6B, 7B), (1E, 2A, 3C, 4D, 5B, 6B, 7C), (1E, 2A, 3C, 4D, 5B, 6C, 7A), (1E, 2A, 3C, 4D, 5B, 6C, 7B), (1E, 2A, 3C, 4D, 5B, 6C, 7C), (1E, 2A, 3C, 4D, 5B, 6D, 7A), (1E, 2A, 3C, 4D, 5B, 6D, 7B), (1E, 2A, 3C, 4D, 5B, 6D, 7C), (1E, 2A, 3C, 4E, 5A, 6A, 7A), (1E, 2A, 3C, 4E, 5A, 6A, 7B), (1E, 2A, 3C, 4E, 5A, 6A, 7C), (1E, 2A, 3C, 4E, 5A, 6B, 7A), (1E, 2A, 3C, 4E, 5A, 6B, 7B), (1E, 2A, 3C, 4E, 5A, 6B, 7C), (1E, 2A, 3C, 4E, 5A, 6C, 7A), (1E, 2A, 3C, 4E, 5A, 6C, 7B), (1E, 2A, 3C, 4E, 5A, 6C, 7C), (1E, 2A, 3C, 4E, 5A, 6D, 7A), (1E, 2A, 3C, 4E, 5A, 6D, 7B), (1E, 2A, 3C, 4E, 5A, 6D, 7C), (1E, 2A, 3C, 4E, 5B, 6A, 7A), (1E, 2A, 3C, 4E, 5B, 6A, 7B), (1E, 2A, 3C, 4E, 5B, 6A, 7C), (1E, 2A, 3C, 4E, 5B, 6B, 7A), (1E, 2A, 3C, 4E, 5B, 6B, 7B), (1E, 2A, 3C, 4E, 5B, 6B, 7C), (1E, 2A, 3C, 4E, 5B, 6C, 7A), (1E, 2A, 3C, 4E, 5B, 6C, 7B), (1E, 2A, 3C, 4E, 5B, 6C, 7C), (1E, 2A, 3C, 4E, 5B, 6D, 7A), (1E, 2A, 3C, 4E, 5B, 6D, 7B), (1E, 2A, 3C, 4E, 5B, 6D, 7C), (1E, 2A, 3D, 4A, 5A, 6A, 7A), (1E, 2A, 3D, 4A, 5A, 6A, 7B), (1E, 2A, 3D, 4A, 5A, 6A, 7C), (1E, 2A, 3D, 4A, 5A, 6B, 7A), (1E, 2A, 3D, 4A, 5A, 6B, 7B), (1E, 2A, 3D, 4A, 5A, 6B, 7C), (1E, 2A, 3D, 4A, 5A, 6C, 7A), (1E, 2A, 3D, 4A, 5A, 6C, 7B), (1E, 2A, 3D, 4A, 5A, 6C, 7C), (1E, 2A, 3D, 4A, 5A, 6D, 7A), (1E, 2A, 3D, 4A, 5A, 6D, 7B), (1E, 2A, 3D, 4A, 5A, 6D, 7C), (1E, 2A, 3D, 4A, 5B, 6A, 7A), (1E, 2A, 3D, 4A, 5B, 6A, 7B), (1E, 2A, 3D, 4A, 5B, 6A, 7C), (1E, 2A, 3D, 4A, 5B, 6B, 7A), (1E, 2A, 3D, 4A, 5B, 6B, 7B), (1E, 2A, 3D, 4A, 5B, 6B, 7C), (1E, 2A, 3D, 4A, 5B, 6C, 7A), (1E, 2A, 3D, 4A, 5B, 6C, 7B), (1E, 2A, 3D, 4A, 5B, 6C, 7C), (1E, 2A, 3D, 4A, 5B, 6D, 7A), (1E, 2A, 3D, 4A, 5B, 6D, 7B), (1E, 2A, 3D, 4A, 5B, 6D, 7C), (1E, 2A, 3D, 4B, 5A, 6A, 7A), (1E, 2A, 3D, 4B, 5A, 6A, 7B), (1E, 2A, 3D, 4B, 5A, 6A, 7C), (1E, 2A, 3D, 4B, 5A, 6B, 7A), (1E, 2A, 3D, 4B, 5A, 6B, 7B), (1E, 2A, 3D, 4B, 5A, 6B, 7C), (1E, 2A, 3D, 4B, 5A, 6C, 7A), (1E, 2A, 3D, 4B, 5A, 6C, 7B), (1E, 2A, 3D, 4B, 5A, 6C, 7C), (1E, 2A, 3D, 4B, 5A, 6D, 7A), (1E, 2A, 3D, 4B, 5A, 6D, 7B), (1E, 2A, 3D, 4B, 5A, 6D, 7C) (1E, 2A, 3D, 4B, 5B, 6A, 7A), (1E, 2A, 3D, 4B, 5B, 6A, 7B), (1E, 2A, 3D, 4B, 5B, 6A, 7C), (1E, 2A, 3D, 4B, 5B, 6B, 7A), (1E, 2A, 3D, 4B, 5B, 6B, 7B), (1E, 2A, 3D, 4B, 5B, 6B, 7C), (1E, 2A, 3D, 4B, 5B, 6C, 7A), (1E, 2A, 3D, 4B, 5B, 6C, 7B), (1E, 2A, 3D, 4B, 5B, 6C, 7C), (1E, 2A, 3D, 4B, 5B, 6D, 7A), (1E, 2A, 3D, 4B, 5B, 6D, 7B), (1E, 2A, 3D, 4B, 5B, 6D, 7C), (1E, 2A, 3D, 4C, 5A, 6A, 7A), (1E, 2A, 3D, 4C, 5A, 6A, 7B), (1E, 2A, 3D, 4C, 5A, 6A, 7C), (1E, 2A, 3D, 4C, 5A, 6B, 7A), (1E, 2A, 3D, 4C, 5A, 6B, 7B), (1E, 2A, 3D, 4C, 5A, 6B, 7C), (1E, 2A, 3D, 4C, 5A, 6C, 7A), (1E, 2A, 3D, 4C, 5A, 6C, 7B), (1E, 2A, 3D, 4C, 5A, 6C, 7C), (1E, 2A, 3D, 4C, 5A, 6D, 7A), (1E, 2A, 3D, 4C, 5A, 6D, 7B), (1E, 2A, 3D, 4C, 5A, 6D, 7C), (1E, 2A, 3D, 4C, 5B, 6A, 7A), (1E, 2A, 3D, 4C, 5B, 6A, 7B), (1E, 2A, 3D, 4C, 5B, 6A, 7C), (1E, 2A, 3D, 4C, 5B, 6B, 7A), (1E, 2A, 3D, 4C, 5B, 6B, 7B), (1E, 2A, 3D, 4C, 5B, 6B, 7C), (1E, 2A, 3D, 4C, 5B, 6C, 7A), (1E, 2A, 3D, 4C, 5B, 6C, 7B), (1E, 2A, 3D, 4C, 5B, 6C, 7C), (1E, 2A, 3D, 4C, 5B, 6D, 7A), (1E, 2A, 3D, 4C, 5B, 6D, 7B), (1E, 2A, 3D, 4C, 5B, 6D, 7C), (1E, 2A, 3D, 4C, 5A, 6A, 7A), (1E, 2A, 3D, 4D, 5A, 6A, 7B), (1E, 2A, 3D, 4D, 5A, 6A, 7C), (1E, 2A, 3D, 4D, 5A, 6B, 7A), (1E, 2A, 3D, 4D, 5A, 6B, 7B), (1E, 2A, 3D, 4D, 5A, 6B, 7C), (1E, 2A, 3D, 4D, 5A, 6C, 7A), (1E, 2A, 3D, 4D, 5A, 6C, 7B), (1E, 2A, 3D, 4D, 5A, 6C, 7C), (1E, 2A, 3D, 4D, 5A, 6D, 7A), (1E, 2A, 3D, 4D, 5A, 6D, 7B), (1E, 2A, 3D, 4D, 5A, 6D, 7C), (1E, 2A, 3D, 4D, 5B, 6A, 7A), (1E, 2A, 3D, 4D, 5B, 6A, 7B), (1E, 2A, 3D, 4D, 5B, 6A, 7C), (1E, 2A, 3D, 4D, 5B, 6B, 7A), (1E, 2A, 3D, 4D, 5B, 6B, 7B), (1E, 2A, 3D, 4D, 5B, 6B, 7C), (1E, 2A, 3D, 4D, 5B, 6C, 7A), (1E, 2A, 3D, 4D, 5B, 6C, 7B), (1E, 2A, 3D, 4D, 5B, 6C, 7C), (1E, 2A, 3D, 4D, 5B, 6D, 7A), (1E, 2A, 3D, 4D, 5B, 6D, 7B), (1E, 2A, 3D, 4D, 5B, 6D, 7C), (1E, 2A, 3D, 4E, 5A, 6A, 7A), (1E, 2A, 3D, 4E, 5A, 6A, 7B), (1E, 2A, 3D, 4E, 5A, 6A, 7C), (1E, 2A, 3D, 4E, 5A, 6B, 7A), (1E, 2A, 3D, 4E, 5A, 6B, 7B), (1E, 2A, 3D, 4E, 5A, 6B, 7C), (1E, 2A, 3D, 4E, 5A, 6C, 7A), (1E, 2A, 3D, 4E, 5A, 6C, 7B), (1E, 2A, 3D, 4E, 5A, 6C, 7C), (1E, 2A, 3D, 4E, 5A, 6D, 7A), (1E, 2A, 3D, 4E, 5A, 6D, 7B), (1E, 2A, 3D, 4E, 5A, 6D, 7C), (1E, 2A, 3D, 4E, 5B, 6A, 7A), (1E, 2A, 3D, 4E, 5B, 6A, 7B), (1E, 2A, 3D, 4E, 5B, 6A, 7C), (1E, 2A, 3D, 4E, 5B, 6B, 7A), (1E, 2A, 3D, 4E, 5B, 6B, 7B), (1E, 2A, 3D, 4E, 5B, 6B, 7C), (1E, 2A, 3D, 4E, 5B, 6C, 7A), (1E, 2A, 3D, 4E, 5B, 6C, 7B), (1E, 2A, 3D, 4E, 5B, 6C, 7C), (1E, 2A, 3D, 4E, 5B, 6D, 7A), (1E, 2A, 3D, 4E, 5B, 6D, 7B), (1E, 2A, 3D, 4E, 5B, 6D, 7C), (1E, 2A, 3E, 4A, 5A, 6A, 7A), (1E, 2A, 3E, 4A, 5A, 6A, 7B), (1E, 2A, 3E, 4A, 5A, 6A, 7C), (1E, 2A, 3E, 4A, 5A, 6B, 7A), (1E, 2A, 3E, 4A, 5A, 6B, 7B), (1E, 2A, 3E, 4A, 5A, 6B, 7C), (1E, 2A, 3E, 4A, 5A, 6C, 7A), (1E, 2A, 3E, 4A, 5A, 6C, 7B), (1E, 2A, 3E, 4A, 5A, 6C, 7C), (1E, 2A, 3E, 4A, 5A, 6D, 7A), (1E, 2A, 3E, 4A, 5A, 6D, 7B), (1E, 2A, 3E, 4A, 5A, 6D, 7C), (1E, 2A, 3E, 4A, 5B, 6A, 7A), (1E, 2A, 3E, 4A, 5B, 6A, 7B), (1E, 2A, 3E, 4A, 5B, 6A, 7C), (1E, 2A, 3E, 4A, 5B, 6B, 7A), (1E, 2A, 3E, 4A, 5B, 6B, 7B), (1E, 2A, 3E, 4A, 5B, 6B, 7C), (1E, 2A, 3E, 4A, 5B, 6C, 7A), (1E, 2A, 3E, 4A, 5B, 6C, 7B), (1E, 2A, 3E, 4A, 5B, 6C, 7C), (1E, 2A, 3E, 4A, 5B, 6D, 7A), (1E, 2A, 3E, 4A, 5B, 6D, 7B), (1E, 2A, 3E, 4A, 5B, 6D, 7C), (1E, 2A, 3E, 4B, 5A, 6A, 7A), (1E, 2A, 3E, 4B, 5A, 6A, 7B), (1E, 2A, 3E, 4B, 5A, 6A, 7C), (1E, 2A, 3E, 4B, 5A, 6B, 7A), (1E, 2A, 3E, 4B, 5A, 6B, 7B), (1E, 2A, 3E, 4B, 5A, 6B, 7C), (1E, 2A, 3E, 4B, 5A, 6C, 7A), (1E, 2A, 3E, 4B, 5A, 6C, 7B), (1E, 2A, 3E, 4B, 5A, 6C, 7C), (1E, 2A, 3E, 4B, 5A, 6D, 7A), (1E, 2A, 3E, 4B, 5A, 6D, 7B), (1E, 2A, 3E, 4B, 5A, 6D, 7C), (1E, 2A, 3E, 4B, 5B, 6A, 7A), (1E, 2A, 3E, 4B, 5B, 6A, 7B), (1E, 2A, 3E, 4B, 5B, 6A, 7C), (1E, 2A, 3E, 4B, 5B, 6B, 7A), (1E, 2A, 3E, 4B, 5B, 6B, 7B), (1E, 2A, 3E, 4B, 5B, 6B, 7C), (1E, 2A, 3E, 4B, 5B, 6C, 7A), (1E, 2A, 3E, 4B, 5B, 6C, 7B), (1E, 2A, 3E, 4B, 5B, 6C, 7C), (1E, 2A, 3E, 4B, 5B, 6D, 7A), (1E, 2A, 3E, 4B, 5B, 6D, 7B), (1E, 2A, 3E, 4B, 5B, 6D, 7C), (1E, 2A, 3E, 4C, 5A, 6A, 7A), (1E, 2A, 3E, 4C, 5A, 6A, 7B), (1E, 2A, 3E, 4C, 5A, 6A, 7C), (1E, 2A, 3E, 4C, 5A, 6B, 7A), (1E, 2A, 3E, 4C, 5A, 6B, 7B), (1E, 2A, 3E, 4C, 5A, 6C, 7A), (1E, 2A, 3E, 4C, 5A, 6C, 7B), (1E, 2A, 3E, 4C, 5A, 6C, 7C), (1E, 2A, 3E, 4C, 5A, 6D, 7A), (1E, 2A, 3E, 4C, 5A, 6D, 7B), (1E, 2A, 3E, 4C, 5A, 6D, 7C), (1E, 2A, 3E, 4C, 5B, 6A, 7A), (1E, 2A, 3E, 4C, 5B, 6A, 7B), (1E, 2A, 3E, 4C, 5B, 6A, 7C), (1E, 2A, 3E, 4C, 5B, 6B, 7A), (1E, 2A, 3E, 4C, 5B, 6B, 7B), (1E, 2A, 3E, 4C, 5B, 6B, 7C), (1E, 2A, 3E, 4C, 5B, 6C, 7A), (1E, 2A, 3E, 4C, 5B, 6C, 7B), (1E, 2A, 3E, 4C, 5B, 6C, 7C), (1E, 2A, 3E, 4C, 5B, 6D, 7A), (1E, 2A, 3E, 4C, 5B, 6D, 7B), (1E, 2A, 3E, 4C, 5B, 6D, 7C), (1E, 2A, 3E, 4D, 5A, 6A, 7A), (1E, 2A, 3E, 4D, 5A, 6A, 7B), (1E, 2A, 3E, 4D, 5A, 6A, 7C), (1E, 2A, 3E, 4D, 5A, 6B, 7A), (1E, 2A, 3E, 4D, 5A, 6B, 7B), (1E, 2A, 3E, 4D, 5A, 6B, 7C), (1E, 2A, 3E, 4D, 5A, 6C, 7A), (1E, 2A, 3E, 4D, 5A, 6C, 7B), (1E, 2A, 3E, 4D, 5A, 6C, 7C), (1E, 2A, 3E, 4D, 5A, 6D, 7A), (1E, 2A, 3E, 4D, 5A, 6D, 7B), (1E, 2A, 3E, 4D, 5A, 6D, 7C), (1E, 2A, 3E, 4D, 5B, 6A, 7B), (1E, 2A, 3E, 4D, 5B, 6A, 7C), (1E, 2A, 3E, 4D, 5B, 6B, 7A), (1E, 2A, 3E, 4D, 5B, 6B, 7B), (1E, 2A, 3E, 4D, 5B, 6B, 7C), (1E, 2A, 3E, 4D, 5B, 6C, 7A), (1E, 2A, 3E, 4D, 5B, 6C, 7B), (1E, 2A, 3E, 4D, 5B, 6C, 7C), (1E, 2A, 3E, 4D, 5B, 6D, 7A), (1E, 2A, 3E, 4D, 5B, 6D, 7B), (1E, 2A, 3E, 4D, 5B, 6D, 7C), (1E, 2A, 3E, 4E, 5A, 6A, 7A), (1E, 2A, 3E, 4E, 5A, 6A, 7B), (1E, 2A, 3E, 4E, 5A, 6A, 7C), (1E, 2A, 3E, 4E, 5A, 6B, 7A), (1E, 2A, 3E, 4E, 5A, 6B, 7B), (1E, 2A, 3E, 4E, 5A, 6B, 7C), (1E, 2A, 3E, 4E, 5A, 6C, 7A), (1E, 2A, 3E, 4E, 5A, 6C, 7B), (1E, 2A, 3E, 4E, 5A, 6C, 7C), (1E, 2A, 3E, 4E, 5A, 6D, 7A), (1E, 2A, 3E, 4E, 5A, 6D, 7B), (1E, 2A, 3E, 4E, 5A, 6D, 7C), (1E, 2A, 3E, 4E, 5B, 6A, 7A), (1E, 2A, 3E, 4E, 5B, 6A, 7B), (1E, 2A, 3E, 4E, 5B, 6A, 7C), (1E, 2A, 3E, 4E, 5B, 6B, 7A), (1E, 2A, 3E, 4E, 5B, 6B, 7B), (1E, 2A, 3E, 4E, 5B, 6B, 7C), (1E, 2A, 3E, 4E, 5B, 6C, 7A), (1E, 2A, 3E, 4E, 5B, 6C, 7B), (1E, 2A, 3E, 4E, 5B, 6C, 7C), (1E, 2A, 3E, 4E, 5B, 6D, 7A), (1E, 2A, 3E, 4E, 5B, 6D, 7B), (1E, 2A, 3E, 4E, 5B, 6D, 7C), (1E, 2B, 3A, 4A, 5A, 6A, 7A), (1E, 2B, 3A, 4A, 5A, 6A, 7B), (1E, 2B, 3A, 4A, 5A, 6A, 7C), (1E, 2B, 3A, 4A, 5A, 6B, 7A), (1E, 2B, 3A, 4A, 5A, 6B, 7B), (1E, 2B, 3A, 4A, 5A, 6B, 7C), (1E, 2B, 3A, 4A, 5A, 6C, 7A), (1E, 2B, 3A, 4A, 5A, 6C, 7B), (1E, 2B, 3A, 4A, 5A, 6C, 7C), (1E, 2B, 3A, 4A, 5A, 6D, 7A), (1E, 2B, 3A, 4A, 5A, 6D, 7B), (1E, 2B, 3A, 4A, 5A, 6D, 7C), (1E, 2B, 3A, 4A, 5B, 6A, 7A), (1E, 2B, 3A, 4A, 5B, 6A, 7B), (1E, 2B, 3A, 4A, 5B, 6A, 7C), (1E, 2B, 3A, 4A, 5B, 6B, 7A), (1E, 2B, 3A, 4A, 5B, 6B, 7B), (1E, 2B, 3A, 4A, 5B, 6B, 7C), (1E, 2B, 3A, 4A, 5B, 6C, 7A), (1E, 2B, 3A, 4A, 5B, 6C, 7B), (1E, 2B, 3A, 4A, 5B, 6C, 7C), (1E, 2B, 3A, 4A, 5B, 6D, 7A), (1E, 2B, 3A, 4A, 5B, 6D, 7B), (1E, 2B, 3A, 4A, 5B, 6D, 7C), (1E, 2B, 3A, 4B, 5A, 6A, 7A), (1E, 2B, 3A, 4B, 5A, 6A, 7B), (1E, 2B, 3A, 4B, 5A, 6A, 7C), (1E, 2B, 3A, 4B, 5A, 6B, 7A), (1E, 2B, 3A, 4B, 5A, 6B, 7B), (1B, 2B, 3A, 4B, 5A, 6B, 7C), (1E, 2B, 3A, 4B, 5A, 6C, 7A), (1E, 2B, 3A, 4B, 5A, 6C, 7B), (1E, 2B, 3A, 4B, 5A, 6C, 7C), (1E, 2B, 3A, 4B, 5A, 6D, 7A), (1E, 2B, 3A, 4B, 5A, 6D, 7B), (1E, 2B, 3A, 4B, 5A, 6D, 7C), (1E, 2B, 3A, 4B, 5B, 6A, 7A), (1E, 2B, 3A, 4B, 5B, 6A, 7B), (1E, 2B, 3A, 4B, 5B, 6A, 7C), (1E, 2B, 3A, 4B, 5B, 6B, 7A), (1E, 2B, 3A, 4B, 5B, 6B, 7B), (1E, 2B, 3A, 4B, 5B, 6B, 7C), (1E, 2B, 3A, 4B, 5B, 6C, 7A), (1E, 2B, 3A, 4B, 5B, 6C, 7B), (1E, 2B, 3A, 4B, 5B, 6C, 7C), (1E, 2B, 3A, 4B, 5B, 6D, 7A), (1E, 2B, 3A, 4B, 5B, 6D, 7B), (1E, 2B, 3A, 4B, 5B, 6D, 7C), (1E, 2B, 3A, 4C, 5A, 6A, 7A), (1E, 2B, 3A, 4C, 5A, 6A, 7B), (1E, 2B, 3A, 4C, 5A, 6A, 7C), (1E, 2B, 3A, 4C, 5A, 6B, 7A), (1E, 2B, 3A, 4C, 5A, 6B, 7B), (1E, 2B, 3A, 4C, 5A, 6B, 7C), (1E, 2B, 3A, 4C, 5A, 6C, 7A), (1E, 2B, 3A, 4C, 5A, 6C, 7B), (1E, 2B, 3A, 4C, 5A, 6C, 7C), (1E, 2B, 3A, 4C, 5A, 6D, 7A), (1E, 2B, 3A, 4C, 5A, 6D, 7B), (1E, 2B, 3A, 4C, 5A, 6D, 7C), (1E, 2B, 3A, 4C, 5B, 6A, 7A), (1E, 2B, 3A, 4C, 5B, 6A, 7B), (1E, 2B, 3A, 4C, 5B, 6A, 7C), (1E, 2B, 3A, 4C, 5B, 6B, 7A), (1E, 2B, 3A, 4C, 5B, 6B, 7B), (1E, 2B, 3A, 4C, 5B, 6B, 7C), (1E, 2B, 3A, 4C, 5B, 6C, 7A), (1E, 2B, 3A, 4C, 5B, 6C, 7B), (1E, 2B, 3A, 4C, 5B, 6C, 7C), (1E, 2B, 3A, 4C, 5B, 6D, 7A), (1E, 2B, 3A, 4C, 5B, 6D, 7B), (1E, 2B, 3A, 4C, 5B, 6D, 7C), (1E, 2B, 3A, 4D, 5A, 6A, 7A), (1E, 2B, 3A, 4D, 5A, 6A, 7B), (1E, 2B, 3A, 4D, 5A, 6A, 7C), (1E, 2B, 3A, 4D, 5A, 6B, 7A), (1E, 2B, 3A, 4D, 5A, 6B, 7B), (1E, 2B, 3A, 4D, 5A, 6B, 7C), (1E, 2B, 3A, 4D, 5A, 6C, 7A), (1E, 2B, 3A, 4D, 5A, 6C, 7B), (1E, 2B, 3A, 4D, 5A, 6C, 7C), (1E, 2B, 3A, 4D, 5A, 6D, 7A), (1E, 2B, 3A, 4D, 5A, 6D, 7B), (1E, 2B, 3A, 4D, 5A, 6D, 7C), (1E, 2B, 3A, 4D, 5B, 6A, 7A), (1E, 2B, 3A, 4D, 5B, 6A, 7B), (1E, 2B, 3A, 4D, 5B, 6A, 7C), (1E, 2B, 3A, 4D, 5B, 6B, 7A), (1E, 2B, 3A, 4D, 5B, 6B, 7B), (1E, 2B, 3A, 4D, 5B, 6B, 7C), (1E, 2B, 3A, 4D, 5B, 6C, 7A), (1E, 2B, 3A, 4D, 5B, 6C, 7B), (1E, 2B, 3A, 4D, 5B, 6C, 7C), (1E, 2B, 3A, 4D, 5B, 6D, 7A), (1E, 2B, 3A, 4D, 5B, 6D, 7B), (1E, 2B, 3A, 4D, 5B, 6D, 7C), (1E, 2B, 3A, 4E, 5A, 6A, 7A), (1E, 2B, 3A, 4E, 5A, 6A, 7B), (1E, 2B, 3A, 4E, 5A, 6A, 7C), (1E, 2B, 3A, 4E, 5A, 6B, 7A), (1E, 2B, 3A, 4E, 5A, 6B, 7B), (1E, 2B, 3A, 4E, 5A, 6B, 7C), (1E, 2B, 3A, 4E, 5A, 6C, 7A), (1E, 2B, 3A, 4E, 5A, 6C, 7B), (1E, 2B, 3A, 4E, 5A, 6C, 7C), (1E, 2B, 3A, 4E, 5A, 6D, 7A), (1E, 2B, 3A, 4E, 5A, 6D, 7B), (1E, 2B, 3A, 4E, 5A, 6D, 7C), (1E, 2B, 3A, 4E, 5B, 6A, 7A), (1E, 2B, 3A, 4E, 5B, 6A, 7B), (1E, 2B, 3A, 4E, 5B, 6A, 7C), (1E, 2B, 3A, 4E, 5B, 6B, 7A), (1E, 2B, 3A, 4E, 5B, 6B, 7B), (1E, 2B, 3A, 4E, 5B, 6B, 7C), (1E, 2B, 3A, 4E, 5B, 6C, 7A), (1E, 2B, 3A, 4E, 5B, 6C, 7B), (1E, 2B, 3A, 4E, 5B, 6C, 7C), (1E, 2B, 3A, 4E, 5B, 6D, 7A), (1E, 2B, 3A, 4E, 5B, 6D, 7B), (1E, 2B, 3A, 4E, 5B, 6D, 7C), (1E, 2B, 3B, 4A, 5A, 6A, 7A), (1E, 2B, 3B, 4A, 5A, 6A, 7B), (1E, 2B, 3B, 4A, 5A, 6A, 7C), (1E, 2B, 3B, 4A, 5A, 6B, 7A), (1E, 2B, 3B, 4A, 5A, 6B, 7B), (1E, 2B, 3B, 4A, 5A, 6B, 7C), (1E, 2B, 3B, 4A, 5A, 6C, 7A), (1E, 2B, 3B, 4A, 5A, 6C, 7B), (1E, 2B, 3B, 4A, 5A, 6C, 7C), (1E, 2B, 3B, 4A, 5A, 6D, 7A), (1E, 2B, 3B, 4A, 5A, 6D, 7B), (1E, 2B, 3B, 4A, 5A, 6D, 7C), (1E, 2B, 3B, 4A, 5B, 6A, 7A), (1E, 2B, 3B, 4A, 5B, 6A, 7B), (1E, 2B, 3B, 4A, 5B, 6A, 7C), (1E, 2B, 3B, 4A, 5B, 6B, 7A), (1E, 2B, 3B, 4A, 5B, 6B, 7B), (1E, 2B, 3B, 4A, 5B, 6B, 7C), (1E, 2B, 3B, 4A, 5B, 6C, 7A), (1E, 2B, 3B, 4A, 5B, 6C, 7B), (1E, 2B, 3B, 4A, 5B, 6C, 7C), (1E, 2B, 3B, 4A, 5B, 6D, 7A), (1E, 2B, 3B, 4A, 5B, 6D, 7B), (1E, 2B, 3B, 4A, 5B, 6D, 7C), (1E, 2B, 3B, 4B, 5A, 6A, 7A), (1E, 2B, 3B, 4B, 5A, 6A, 7B), (1E, 2B, 3B, 4B, 5A, 6A, 7C), (1E, 2B, 3B, 4B, 5A, 6B, 7A), (1E, 2B, 3B, 4B, 5A, 6B, 7B), (1E, 2B, 3B, 4B, 5A, 6B, 7C), (1E, 2B, 3B, 4B, 5A, 6C, 7A), (1E, 2B, 3B, 4B, 5A, 6C, 7B), (1E, 2B, 3B, 4B, 5A, 6C, 7C), (1E, 2B, 3B, 4B, 5A, 6D, 7A), (1E, 2B, 3B, 4B, 5A, 6D, 7B), (1E, 2B, 3B, 4B, 5A, 6D, 7C), (1E, 2B, 3B, 4B, 5B, 6A, 7A), (1E, 2B, 3B, 4B, 5B, 6A, 7B), (1E, 2B, 3B, 4B, 5B, 6A, 7C), (1E, 2B, 3B, 4B, 5B, 6B, 7A), (1E, 2B, 3B, 4B, 5B, 6B, 7B), (1E, 2B, 3B, 4B, 5B, 6B, 7C), (1E, 2B, 3B, 4B, 5B, 6C, 7A), (1E, 2B, 3B, 4B, 5B, 6C, 7B), (1E, 2B, 3B, 4B, 5B, 6C, 7C), (1E, 2B, 3B, 4B, 5B, 6D, 7A), (1E, 2B, 3B, 4B, 5B, 6D, 7B), (1E, 2B, 3B, 4B, 5B, 6D, 7C), (1E, 2B, 3B, 4C, 5A, 6A, 7A), (1E, 2B, 3B, 4C, 5A, 6A, 7B), (1E, 2B, 3B, 4C, 5A, 6A, 7C), (1E, 2B, 3B, 4C, 5A, 6B, 7A), (1E, 2B, 3B, 4C, 5A, 6B, 7B), (1E, 2B, 3B, 4C, 5A, 6B, 7C), (1E, 2B, 3B, 4C, 5A, 6C, 7A), (1E, 2B, 3B, 4C, 5A, 6C, 7B), (1E, 2B, 3B, 4C, 5A, 6C, 7C), (1E, 2B, 3B, 4C, 5A, 6D, 7A), (1E, 2B, 3B, 4C, 5A, 6D, 7B), (1E, 2B, 3B, 4C, 5A, 6D, 7C), (1E, 2B, 3B, 4C, 5B, 6A, 7A), (1E, 2B, 3B, 4C, 5B, 6A, 7B), (1E, 2B, 3B, 4C, 5B, 6A, 7C), (1E, 2B, 3B, 4C, 5B, 6B, 7A), (1E, 2B, 3B, 4C, 5B, 6B, 7B), (1E, 2B, 3B, 4C, 5B, 6B, 7C), (1E, 2B, 3B, 4C, 5B, 6C, 7A), (1E, 2B, 3B, 4C, 5B, 6C, 7B), (1E, 2B, 3B, 4C, 5B, 6C, 7C), (1E, 2B, 3B, 4C, 5B, 6D, 7A), (1E, 2B, 3B, 4C, 5B, 6D, 7B), (1E, 2B, 3B, 4C, 5B, 6D, 7C), (1E, 2B, 3B, 4D, 5A, 6A, 7A), (1E, 2B, 3B, 4D, 5A, 6A, 7B), (1E, 2B, 3B, 4D, 5A, 6A, 7C), (1E, 2B, 3B, 4D, 5A, 6B, 7A), (1E, 2B, 3B, 4D, 5A, 6B, 7B), (1E, 2B, 3B, 4D, 5A, 6B, 7C), (1E, 2B, 3B, 4D, 5A, 6C, 7A), (1E, 2B, 3B, 4D, 5A, 6C, 7B), (1E, 2B, 3B, 4D, 5A, 6C, 7C), (1E, 2B, 3B, 4D, 5A, 6D, 7A), (1E, 2B, 3B, 4D, 5A, 6D, 7B), (1E, 2B, 3B, 4D, 5A, 6D, 7C), (1E, 2B, 3B, 4D, 5B, 6A, 7A), (1E, 2B, 3B, 4D, 5B, 6A, 7B), (1E, 2B, 3B, 4D, 5B, 6A, 7C), (1E, 2B, 3B, 4D, 5B, 6B, 7A), (1E, 2B, 3B, 4D, 5B, 6B, 7B), (1E, 2B, 3B, 4D, 5B, 6B, 7C), (1E, 2B, 3B, 4D, 5B, 6C, 7A), (1E, 2B, 3B, 4D, 5B, 6C, 7B), (1E, 2B, 3B, 4D, 5B, 6C, 7C), (1E, 2B, 3B, 4D, 5B, 6D, 7A), (1E, 2B, 3B, 4D, 5B, 6D, 7B), (1E, 2B, 3B, 4D, 5B, 6D, 7C), (1E, 2B, 3B, 4E, 5A, 6A, 7A), (1E, 2B, 3B, 4E, 5A, 6A, 7B), (1E, 2B, 3B, 4E, 5A, 6A, 7C), (1E, 2B, 3B, 4E, 5A, 6B, 7A), (1E, 2B, 3B, 4E, 5A, 6B, 7B), (1E, 2B, 3B, 4E, 5A, 6B, 7C), (1E, 2B, 3B, 4E, 5A, 6C, 7A), (1E, 2B, 3B, 4E, 5A, 6C, 7B), (1E, 2B, 3B, 4E, 5A, 6C, 7C), (1E, 2B, 3B, 4E, 5A, 6D, 7A), (1E, 2B, 3B, 4E, 5A, 6D, 7B), (1E, 2B, 3B, 4E, 5A, 6D, 7C), (1E, 2B, 3B, 4E, 5B, 6A, 7A), (1E, 2B, 3B, 4E, 5B, 6A, 7B), (1E, 2B, 3B, 4E, 5B, 6A, 7C), (1E, 2B, 3B, 4E, 5B, 6B, 7A), (1E, 2B, 3B, 4E, 5B, 6B, 7B), (1E, 2B, 3B, 4E, 5B, 6B, 7C), (1E, 2B, 3B, 4E, 5B, 6C, 7A), (1E, 2B, 3B, 4E, 5B, 6C, 7B), (1E, 2B, 3B, 4E, 5B, 6C, 7C), (1E, 2B, 3B, 4E, 5B, 6D, 7A), (1E, 2B, 3B, 4E, 5B, 6D, 7B), (1E, 2B, 3B, 4E, 5B, 6D, 7C), (1E, 2B, 3C, 4A, 5A, 6A, 7A), (1E, 2B, 3C, 4A, 5A, 6A, 7B), (1E, 2B, 3C, 4A, 5A, 6A, 7C), (1E, 2B, 3C, 4A, 5A, 6B, 7A), (1E, 2B, 3C, 4A, 5A, 6B, 7B), (1E, 2B, 3C, 4A, 5A, 6B, 7C), (1E, 2B, 3C, 4A, 5A, 6C, 7A), (1E, 2B, 3C, 4A, 5A, 6C, 7B), (1E, 2B, 3C, 4A, 5A, 6C, 7C), (1E, 2B, 3C, 4A, 5A, 6D, 7A), (1E, 2B, 3C, 4A, 5A, 6D, 7B), (1E, 2B, 3C, 4A, 5A, 6D, 7C), (1E, 2B, 3C, 4A, 5B, 6A, 7A), (1E, 2B, 3C, 4A, 5B, 6A, 7B), (1E, 2B, 3C, 4A, 5B, 6A, 7C), (1E, 2B, 3C, 4A, 5B, 6B, 7A), (1E, 2B, 3C, 4A, 5B, 6B, 7B), (1E, 2B, 3C, 4A, 5B, 6B, 7C), (1E, 2B, 3C, 4A, 5B, 6C, 7A), (1E, 2B, 3C, 4A, 5B, 6C, 7B), (1E, 2B, 3C, 4A, 5B, 6C, 7C), (1E, 2B, 3C, 4A, 5B, 6D, 7A), (1E, 2B, 3C, 4A, 5B, 6D, 7B), (1E, 2B, 3C, 4A, 5B, 6D, 7C), (1E, 2B, 3C, 4B, 5A, 6A, 7A), (1E, 2B, 3C, 4B, 5A, 6A, 7B), (1E, 2B, 3C, 4B, 5A, 6A, 7C), (1E, 2B, 3C, 4B, 5A, 6B, 7A), (1E, 2B, 3C, 4B, 5A, 6B, 7B), (1E, 2B, 3C, 4B, 5A, 6B, 7C), (1E, 2B, 3C, 4B, 5A, 6C, 7A), (1E, 2B, 3C, 4B, 5A, 6C, 7B), (1E, 2B, 3C, 4B, 5A, 6C, 7C), (1E, 2B, 3C, 4B, 5A, 6D, 7A), (1E, 2B, 3C, 4B, 5A, 6D, 7B), (1E, 2B, 3C, 4B, 5A, 6D, 7C), (1E, 2B, 3C, 4B, 5B, 6A, 7A), (1E, 2B, 3C, 4B, 5B, 6A, 7B), (1E, 2B, 3C, 4B, 5B, 6A, 7C), (1E, 2B, 3C, 4B, 5B, 6B, 7A), (1E, 2B, 3C, 4B, 5B, 6B, 7B), (1E, 2B, 3C, 4B, 5B, 6B, 7C), (1E, 2B, 3C, 4B, 5B, 6C, 7A), (1E, 2B, 3C, 4B, 5B, 6C, 7B), (1E, 2B, 3C, 4B, 5B, 6C, 7C), (1E, 2B, 3C, 4B, 5B, 6D, 7A), (1E, 2B, 3C, 4B, 5B, 6D, 7B), (1E, 2B, 3C, 4B, 5B, 6D, 7C), (1E, 2B, 3C, 4C, 5A, 6A, 7A), (1E, 2B, 3C, 4C, 5A, 6A, 7B), (1E, 2B, 3C, 4C, 5A, 6A, 7C), (1E, 2B, 3C, 4C, 5A, 6B, 7A), (1E, 2B, 3C, 4C, 5A, 6B, 7B), (1E, 2B, 3C, 4C, 5A, 6B, 7C), (1E, 2B, 3C, 4C, 5A, 6C, 7A), (1E, 2B, 3C, 4C, 5A, 6C, 7B), (1E, 2B, 3C, 4C, 5A, 6C, 7C), (1E, 2B, 3C, 4C, 5A, 6D, 7A), (1E, 2B, 3C, 4C, 5A, 6D, 7B), (1E, 2B, 3C, 4C, 5A, 6D, 7C), (1E, 2B, 3C, 4C, 5B, 6A, 7A), (1E, 2B, 3C, 4C, 5B, 6A, 7B), (1E, 2B, 3C, 4C, 5B, 6A, 7C), (1E, 2B, 3C, 4C, 5B, 6B, 7A), (1E, 2B, 3C, 4C, 5B, 6B, 7B), (1E, 2B, 3C, 4C, 5B, 6B, 7C), (1E, 2B, 3C, 4C, 5B, 6C, 7A), (1E, 2B, 3C, 4C, 5B, 6C, 7B), (1E, 2B, 3C, 4C, 5B, 6C, 7C), (1E, 2B, 3C, 4C, 5B, 6D, 7A), (1E, 2B, 3C, 4C, 5B, 6D, 7B), (1E, 2B, 3C, 4C, 5B, 6D, 7C), (1E, 2B, 3C, 4D, 5A, 6A, 7A), (1E, 2B, 3C, 4D, 5A, 6A, 7B), (1E, 2B, 3C, 4D, 5A, 6A, 7C), (1E, 2B, 3C, 4D, 5A, 6B, 7A), (1E, 2B, 3C, 4D, 5A, 6B, 7B), (1E, 2B, 3C, 4D, 5A, 6B, 7C), (1E, 2B, 3C, 4D, 5A, 6C, 7A), (1E, 2B, 3C, 4D, 5A, 6C, 7B), (1E, 2B, 3C, 4D, 5A, 6C, 7C), (1E, 2B, 3C, 4D, 5A, 6D, 7A), (1E, 2B, 3C, 4D, 5A, 6D, 7B), (1E, 2B, 3C, 4D, 5A, 6D, 7C), (1E, 2B, 3C, 4D, 5B, 6A, 7A), (1E, 2B, 3C, 4D, 5B, 6A, 7B), (1E, 2B, 3C, 4D, 5B, 6A, 7C), (1E, 2B, 3C, 4D, 5B, 6B, 7A), (1E, 2B, 3C, 4D, 5B, 6B, 7B), (1E, 2B, 3C, 4D, 5B, 6B, 7C), (1E, 2B, 3C, 4D, 5B, 6C, 7A), (1E, 2B, 3C, 4D, 5B, 6C, 7B), (1E, 2B, 3C, 4D, 5B, 6C, 7C), (1E, 2B, 3C, 4D, 5B, 6D, 7A), (1E, 2B, 3C, 4D, 5B, 6D, 7B), (1E, 2B, 3C, 4D, 5B, 6D, 7C), (1E, 2B, 3C, 4E, 5A, 6A, 7A), (1E, 2B, 3C, 4E, 5A, 6A, 7B), (1E, 2B, 3C, 4E, 5A, 6A, 7C), (1E, 2B, 3C, 4E, 5A, 6B, 7A), (1E, 2B, 3C, 4E, 5A, 6B, 7B), (1E, 2B, 3C, 4E, 5A, 6B, 7C), (1E, 2B, 3C, 4E, 5A, 6C, 7A), (1E, 2B, 3C, 4E, 5A, 6C, 7B), (1E, 2B, 3C, 4E, 5A, 6C, 7C), (1E, 2B, 3C, 4E, 5A, 6D, 7A), (1E, 2B, 3C, 4E, 5A, 6D, 7B), (1E, 2B, 3C, 4E, 5A, 6D, 7C), (1E, 2B, 3C, 4E, 5B, 6A, 7A), (1E, 2B, 3C, 4E, 5B, 6A, 7B), (1E, 2B, 3C, 4E, 5B, 6A, 7C), (1E, 2B, 3C, 4E, 5B, 6B, 7A), (1E, 2B, 3C, 4E, 5B, 6B, 7B), (1E, 2B, 3C, 4E, 5B, 6B, 7C), (1E, 2B, 3C, 4E, 5B, 6C, 7A), (1E, 2B, 3C, 4E, 5B, 6C, 7B), (1E, 2B, 3C, 4E, 5B, 6C, 7C), (1E, 2B, 3C, 4E, 5B, 6D, 7A), (1E, 2B, 3C, 4E, 5B, 6D, 7B), (1E, 2B, 3C, 4E, 5B, 6D, 7C), (1E, 2B, 3D, 4A, 5A, 6A, 7A), (1E, 2B, 3D, 4A, 5A, 6A, 7B), (1E, 2B, 3D, 4A, 5A, 6A, 7C), (1E, 2B, 3D, 4A, 5A, 6B, 7A), (1E, 2B, 3D, 4A, 5A, 6B, 7B), (1E, 2B, 3D, 4A, 5A, 6B, 7C), (1E, 2B, 3D, 4A, 5A, 6C, 7A), (1E, 2B, 3D, 4A, 5A, 6C, 7B), (1E, 2B, 3D, 4A, 5A, 6C, 7C), (1E, 2B, 3D, 4A, 5A, 6D, 7A), (1E, 2B, 3D, 4A, 5A, 6D, 7B), (1E, 2B, 3D, 4A, 5A, 6D, 7C), (1E, 2B, 3D, 4A, 5B, 6A, 7A), (1E, 2B, 3D, 4A, 5B, 6A, 7B), (1E, 2B, 3D, 4A, 5B, 6A, 7C), (1E, 2B, 3D, 4A, 5B, 6B, 7A), (1E, 2B, 3D, 4A, 5B, 6B, 7B), (1E, 2B, 3D, 4A, 5B, 6B, 7C), (1E, 2B, 3D, 4A, 5B, 6C, 7A), (1E, 2B, 3D, 4A, 5B, 6C, 7B), (1E, 2B, 3D, 4A, 5B, 6C, 7C), (1E, 2B, 3D, 4A, 5B, 6D, 7A), (1E, 2B, 3D, 4A, 5B, 6D, 7B), (1E, 2B, 3D, 4A, 5B, 6D, 7C), (1E, 2B, 3D, 4B, 5A, 6A, 7A), (1E, 2B, 3D, 4B, 5A, 6A, 7B), (1E, 2B, 3D, 4B, 5A, 6A, 7C), (1E, 2B, 3D, 4B, 5A, 6B, 7A), (1E, 2B, 3D, 4B, 5A, 6B, 7B), (1E, 2B, 3D, 4B, 5A, 6B, 7C), (1E, 2B, 3D, 4B, 5A, 6C, 7A), (1E, 2B, 3D, 4B, 5A, 6C, 7B), (1E, 2B, 3D, 4B, 5A, 6C, 7C), (1E, 2B, 3D, 4B, 5A, 6D, 7A), (1E, 2B, 3D, 4B, 5A, 6D, 7B), (1E, 2B, 3D, 4B, 5A, 6D, 7C), (1E, 2B, 3D, 4B, 5B, 6A, 7A), (1E, 2B, 3D, 4B, 5B, 6A, 7B), (1E, 2B, 3D, 4B, 5B, 6A, 7C), (1E, 2B, 3D, 4B, 5B, 6B, 7A), (1E, 2B, 3D, 4B, 5B, 6B, 7B), (1E, 2B, 3D, 4B, 5B, 6B, 7C), (1E, 2B, 3D, 4B, 5B, 6C, 7A), (1E, 2B, 3D, 4B, 5B, 6C, 7B), (1E, 2B, 3D, 4B, 5B, 6C, 7C), (1E, 2B, 3D, 4B, 5B, 6D, 7A), (1E, 2B, 3D, 4B, 5B, 6D, 7B), (1E, 2B, 3D, 4B, 5B, 6D, 7C), (1E, 2B, 3D, 4C, 5A, 6A, 7A), (1E, 2B, 3D, 4C, 5A, 6A, 7B), (1E, 2B, 3D, 4C, 5A, 6A, 7C), (1E, 2B, 3D, 4C, 5A, 6B, 7A), (1E, 2B, 3D, 4C, 5A, 6B, 7B), (1E, 2B, 3D, 4C, 5A, 6B, 7C), (1E, 2B, 3D, 4C, 5A, 6C, 7A), (1E, 2B, 3D, 4C, 5A, 6C, 7B), (1E, 2B, 3D, 4C, 5A, 6C, 7C), (1E, 2B, 3D, 4C, 5A, 6D, 7A), (1E, 2B, 3D, 4C, 5A, 6D, 7B), (1E, 2B, 3D, 4C, 5A, 6D, 7C), (1E, 2B, 3D, 4C, 5B, 6A, 7A), (1E, 2B, 3D, 4C, 5B, 6A, 7B), (1E, 2B, 3D, 4C, 5B, 6A, 7C), (1E, 2B, 3D, 4C, 5B, 6B, 7A), (1E, 2B, 3D, 4C, 5B, 6B, 7B), (1E, 2B, 3D, 4C, 5B, 6B, 7C), (1E, 2B, 3D, 4C, 5B, 6C, 7A), (1E, 2B, 3D, 4C, 5B, 6C, 7B), (1E, 2B, 3D, 4C, 5B, 6C, 7C), (1E, 2B, 3D, 4C, 5B, 6D, 7A), (1E, 2B, 3D, 4C, 5B, 6D, 7B), (1E, 2B, 3D, 4C, 5B, 6D, 7C), (1E, 2B, 3D, 4D, 5A, 6A, 7A), (1E, 2B, 3D, 4D, 5A, 6A, 7B), (1E, 2B, 3D, 4D, 5A, 6A, 7C), (1E, 2B, 3D, 4D, 5A, 6B, 7A), (1E, 2B, 3D, 4D, 5A, 6B, 7B), (1E, 2B, 3D, 4D, 5A, 6B, 7C), (1E, 2B, 3D, 4D, 5A, 6C, 7A), (1E, 2B, 3D, 4D, 5A, 6C, 7B), (1E, 2B, 3D, 4D, 5A, 6C, 7C), (1E, 2B, 3D, 4D, 5A, 6D, 7A), (1E, 2B, 3D, 4D, 5A, 6D, 7B), (1E, 2B, 3D, 4D, 5A, 6D, 7C), (1E, 2B, 3D, 4D, 5B, 6A, 7A), (1E, 2B, 3D, 4D, 5B, 6A, 7B), (1E, 2B, 3D, 4D, 5B, 6A, 7C), (1E, 2B, 3D, 4D, 5B, 6B, 7A), (1E, 2B, 3D, 4D, 5B, 6B, 7B), (1E, 2B, 3D, 4D, 5B, 6B, 7C), (1E, 2B, 3D, 4D, 5B, 6C, 7A), (1E, 2B, 3D, 4D, 5B, 6C, 7B), (1E, 2B, 3D, 4D, 5B, 6C, 7C), (1E, 2B, 3D, 4D, 5B, 6D, 7A), (1E, 2B, 3D, 4D, 5B, 6D, 7B), (1E, 2B, 3D, 4D, 5B, 6D, 7C), (1E, 2B, 3D, 4E, 5A, 6A, 7A), (1E, 2B, 3D, 4E, 5A, 6A, 7B), (1E, 2B, 3D, 4E, 5A, 6A, 7C), (1E, 2B, 3D, 4E, 5A, 6B, 7A), (1E, 2B, 3D, 4E, 5A, 6B, 7B), (1E, 2B, 3D, 4E, 5A, 6B, 7C), (1E, 2B, 3D, 4E, 5A, 6C, 7A), (1E, 2B, 3D, 4E, 5A, 6C, 7B), (1E, 2B, 3D, 4E, 5A, 6C, 7C), (1E, 2B, 3D, 4E, 5A, 6D, 7A), (1E, 2B, 3D, 4E, 5A, 6D, 7B), (1E, 2B, 3D, 4E, 5A, 6D, 7C), (1E, 2B, 3D, 4E, 5B, 6A, 7A), (1E, 2B, 3D, 4E, 5B, 6A, 7B), (1E, 2B, 3D, 4E, 5B, 6A, 7C), (1E, 2B, 3D, 4E, 5B, 6B, 7A), (1E, 2B, 3D, 4E, 5B, 6B, 7B), (1E, 2B, 3D, 4E, 5B, 6B, 7C), (1E, 2B, 3D, 4E, 5B, 6C, 7A), (1E, 2B, 3D, 4E, 5B, 6C, 7B), (1E, 2B, 3D, 4E, 5B, 6C, 7C), (1E, 2B, 3D, 4E, 5B, 6D, 7A), (1E, 2B, 3D, 4E, 5B, 6D, 7B), (1E, 2B, 3D, 4E, 5B, 6D, 7C), (1E, 2B, 3E, 4A, 5A, 6A, 7A), (1E, 2B, 3E, 4A, 5A, 6A, 7B), (1E, 2B, 3E, 4A, 5A, 6B, 7A), (1E, 2B, 3E, 4A, 5A, 6B, 7B), (1E, 2B, 3E, 4A, 5A, 6B, 7C), (1E, 2B, 3E, 4A, 5A, 6C, 7A), (1E, 2B, 3E, 4A, 5A, 6C, 7B), (1E, 2B, 3E, 4A, 5A, 6C, 7C), (1E, 2B, 3E, 4A, 5A, 6D, 7A), (1E, 2B, 3E, 4A, 5A, 6D, 7B), (1E, 2B, 3E, 4A, 5A, 6D, 7C), (1E, 2B, 3E, 4A, 5B, 6A, 7A), (1E, 2B, 3E, 4A, 5B, 6A, 7B), (1E, 2B, 3E, 4A, 5B, 6A, 7C), (1E, 2B, 3E, 4A, 5B, 6B, 7A), (1E, 2B, 3E, 4A, 5B, 6B, 7B), (1E, 2B, 3E, 4A, 5B, 6B, 7C), (1E, 2B, 3E, 4A, 5B, 6C, 7A), (1E, 2B, 3E, 4A, 5B, 6C, 7B), (1E, 2B, 3E, 4A, 5B, 6C, 7C), (1E, 2B, 3E, 4A, 5B, 6D, 7A), (1E, 2B, 3E, 4A, 5B, 6D, 7B), (1E, 2B, 3E, 4A, 5B, 6D, 7C), (1E, 2B, 3E, 4B, 5A, 6A, 7A), (1E, 2B, 3E, 4B, 5A, 6A, 7B), (1E, 2B, 3E, 4B, 5A, 6A, 7C), (1E, 2B, 3E, 4B, 5A, 6B, 7A), (1E, 2B, 3E, 4B, 5A, 6B, 7B), (1E, 2B, 3E, 4B, 9A, 6B, 7C), (1E, 2B, 3E, 4B, 5A, 6C, 7A), (1E, 2B, 3E, 4B, 5A, 6C, 7B), (1E, 2B, 3E, 4B, 5A, 6C, 7C), (1E, 2B, 3E, 4B, 5A, 6D, 7A), (1E, 2B, 3E, 4B, 5A, 6D, 7B), (1E, 2B, 3E, 4B, 5A, 6D, 7C), (1E, 2B, 3E, 4B, 5B, 6A, 7A), (1E, 2B, 3E, 4B, 5B, 6A, 7B), (1E, 2B, 3E, 4B, 5B, 6A, 7C), (1E, 2B, 3E, 4B, 5B, 6B, 7A), (1E, 2B, 3E, 4B, 5B, 6B, 7B), (1E, 2B, 3E, 4B, 5B, 6B, 7C), (1E, 2B, 3E, 4B, 5B, 6C, 7A), (1E, 2B, 3E, 4B, 5B, 6C, 7B), (1E, 2B, 3E, 4B, 5B, 6C, 7C), (1E, 2B, 3E, 4B, 5B, 6D, 7A), (1E, 2B, 3E, 4B, 5B, 6D, 7B), (1E, 2B, 3E, 4B, 5B, 6D, 7C), (1E, 2B, 3E, 4C, 5A, 6A, 7A), (1E, 2B, 3E, 4C, 5A, 6A, 7B), (1E, 2B, 3E, 4C, 5A, 6A, 7C), (1E, 2B, 3E, 4C, 5A, 6B, 7A), (1E, 2B, 3E, 4C, 5A, 6B, 7B), (1E, 2B, 3E, 4C, 5A, 6B, 7C), (1E, 2B, 3E, 4C, 5A, 6C, 7A), (1E, 2B, 3E, 4C, 5A, 6C, 7B), (1E, 2B, 3E, 4C, 5A, 6C, 7C), (1E, 2B, 3E, 4C, 5A, 6D, 7A), (1E, 2B, 3E, 4C, 5A, 6D, 7B), (1E, 2B, 3E, 4C, 5A, 6D, 7C), (1E, 2B, 3E, 4C, 5B, 6A, 7A), (1E, 2B, 3E, 4C, 5B, 6A, 7B), (1E, 2B, 3E, 4C, 5B, 6A, 7C), (1E, 2B, 3E, 4C, 5B, 6B, 7A), (1E, 2B, 3E, 4C, 5B, 6B, 7B), (1E, 2B, 3E, 4C, 5B, 6B, 7C), (1E, 2B, 3E, 4C, 5B, 6C, 7A), (1E, 2B, 3E, 4C, 5B, 6C, 7B), (1E, 2B, 3E, 4C, 5B, 6C, 7C), (1E, 2B, 3E, 4C, 5B, 6D, 7A), (1E, 2B, 3E, 4C, 5B, 6D, 7B), (1E, 2B, 3E, 4C, 5B, 6D, 7C), (1E, 2B, 3E, 4D, 5A, 6A, 7A), (1E, 2B, 3E, 4D, 5A, 6A, 7B), (1E, 2B, 3E, 4D, 5A, 6A, 7C), (1E, 2B, 3E, 4D, 5A, 6B, 7A), (1E, 2B, 3E, 4D, 5A, 6B, 7B), (1E, 2B, 3E, 4D, 5A, 6B, 7C), (1E, 2B, 3E, 4D, 5A, 6C, 7A), (1E, 2B, 3E, 4D, 5A, 6C, 7B), (1E, 2B, 3E, 4D, 5A, 6C, 7C), (1E, 2B, 3E, 4D, 5A, 6D, 7A), (1E, 2B, 3E, 4D, 5A, 6D, 7B), (1E, 2B, 3E, 4D, 5A, 6D, 7C), (1E, 2B, 3E, 4D, 5B, 6A, 7A), (1E, 2B, 3E, 4D, 5B, 6A, 7B), (1E, 2B, 3E, 4D, 5B, 6A, 7C), (1E, 2B, 3E, 4D, 5B, 6B, 7A), (1E, 2B, 3E, 4D, 5B, 6B, 7B), (1E, 2B, 3E, 4D, 5B, 6B, 7C), (1E, 2B, 3E, 4D, 5B, 6C, 7A), (1E, 2B, 3E, 4D, 5B, 6C, 7B), (1E, 2B, 3E, 4D, 5B, 6C, 7C), (1E, 2B, 3E, 4D, 5B, 6D, 7A), (1E, 2B, 3E, 4D, 5B, 6D, 7B), (1E, 2B, 3E, 4D, 5B, 6D, 7C), (1E, 2B, 3E, 4E, 5A, 6A, 7A), (1E, 2B, 3E, 4E, 5A, 6A, 7B), (1E, 2B, 3E, 4E, 5A, 6A, 7C), (1E, 2B, 3E, 4E, 5A, 6B, 7A), (1E, 2B, 3E, 4E, 5A, 6B, 7B), (1E, 2B, 3E, 4E, 5A, 6B, 7C), (1E, 2B, 3E, 4E, 5A, 6C, 7A), (1E, 2B, 3E, 4E, 5A, 6C, 7B), (1E, 2B, 3E, 4E, 5A, 6C, 7C), (1E, 2B, 3E, 4E, 5A, 6D, 7A), (1E, 2B, 3E, 4E, 5A, 6D, 7B), (1E, 2B, 3E, 4E, 5A, 6D, 7C), (1E, 2B, 3E, 4E, 5B, 6A, 7A), (1E, 2B, 3E, 4E, 5B, 6A, 7B), (1E, 2B, 3E, 4E, 5B, 6A, 7C), (1E, 2B, 3E, 4E, 5B, 6B, 7A), (1E, 2B, 3E, 4E, 5B, 6B, 7B), (1E, 2B, 3E, 4E, 5B, 6B, 7C), (1E, 2B, 3E, 4E, 5B, 6C, 7A), (1E, 2B, 3E, 4E, 5B, 6C, 7B), (1E, 2B, 3E, 4E, 5B, 6C, 7C), (1E, 2B, 3E, 4E, 5B, 6D, 7A), (1E, 2B, 3E, 4E, 5B, 6D, 7B), (1E, 2B, 3E, 4E, 5B, 6D, 7C), (1E, 2C, 3A, 4A, 5A, 6A, 7A), (1E, 2C, 3A, 4A, 5A, 6A, 7B), (1E, 2C, 3A, 4A, 5A, 6A, 7C), (1E, 2C, 3A, 4A, 5A, 6B, 7A), (1E, 2C, 3A, 4A, 5A, 6B, 7B), (1E, 2C, 3A, 4A, 5A, 6B, 7C), (1E, 2C, 3A, 4A, 5A, 6C, 7A), (1E, 2C, 3A, 4A, 5C, 6C, 7B), (1E, 2C, 3A, 4A, 5A, 6C, 7C), (1E, 2C, 3A, 4A, 5A, 6D, 7A), (1E, 2C, 3A, 4A, 5A, 6D, 7B), (1E, 2C, 3A, 4A, 5A, 6D, 7C), (1E, 2C, 3A, 4A, 5B, 6A, 7A), (1E, 2C, 3A, 4A, 5B, 6A, 7B), (1E, 2C, 3A, 4A, 5B, 6A, 7C), (1E, 2C, 3A, 4A, 5B, 6B, 7A), (1E, 2C, 3A, 4A, 5B, 6B, 7B), (1E, 2C, 3A, 4A, 5B, 6B, 7C), (1E, 2C, 3A, 4A, 5B, 6C, 7A), (1E, 2C, 3A, 4A, 5B, 6C, 7B), (1E, 2C, 3A, 4A, 5B, 6C, 7C), (1E, 2C, 3A, 4A, 5B, 6D, 7A), (1E, 2C, 3A, 4A, 5B, 6D, 7B), (1E, 2C, 3A, 4A, 5B, 6D, 7C), (1E, 2C, 3A, 4B, 5A, 6A, 7A), (1E, 2C, 3A, 4B, 5A, 6A, 7B), (1E, 2C, 3A, 4B, 5A, 6A, 7C), (1E, 2C, 3A, 4B, 5A, 6B, 7A), (1E, 2C, 3A, 4B, 5A, 6B, 7B), (1E, 2C, 3A, 4B, 5A, 6B, 7C), (1E, 2C, 3A, 4B, 5A, 6C, 7A), (1E, 2C, 3A, 4B, 5A, 6C, 7B), (1E, 2C, 3A, 4B, 5A, 6C, 7C), (1E, 2C, 3A, 4B, 5A, 6D, 7A), (1E, 2C, 3A, 4B, 5A, 6D, 7B), (1E, 2C, 3A, 4B, 5A, 6D, 7C), (1E, 2C, 3A, 4B, 5B, 6A, 7A), (1E, 2C, 3A, 4B, 5B, 6A, 7B), (1E, 2C, 3A, 4B, 5B, 6A, 7C), (1E, 2C, 3A, 4B, 5B, 6B, 7A), (1E, 2C, 3A, 4B, 5B, 6B, 7B), (1E, 2C, 3A, 4B, 5B, 6B, 7C), (1E, 2C, 3A, 4B, 5B, 6C, 7A), (1E, 2C, 3A, 4B, 5B, 6C, 7B), (1E, 2C, 3A, 4B, 5B, 6C, 7C), (1E, 2C, 3A, 4B, 5B, 6D, 7A), (1E, 2C, 3A, 4B, 5B, 6D, 7B), (1E, 2C, 3A, 4B, 5B, 6D, 7C), (1E, 2C, 3A, 4C, 5A, 6A, 7A), (1E, 2C, 3A, 4C, 5A, 6A, 7B), (1E, 2C, 3A, 4C, 5A, 6A, 7C), (1E, 2C, 3A, 4C, 5A, 6B, 7A), (1E, 2C, 3A, 4C, 5A, 6B, 7B), (1E, 2C, 3A, 4C, 5A, 6B, 7C), (1E, 2C, 3A, 4C, 5A, 6C, 7A), (1E, 2C, 3A, 4C, 5A, 6C, 7B), (1E, 2C, 3A, 4C, 5A, 6C, 7C), (1E, 2C, 3A, 4C, 5A, 6D, 7A), (1E, 2C, 3A, 4C, 5A, 6D, 7B), (1E, 2C, 3A, 4C, 5A, 6D, 7C), (1E, 2C, 3A, 4C, 5B, 6A, 7A), (1E, 2C, 3A, 4C, 5B, 6A, 7B), (1E, 2C, 3A, 4C, 5B, 6A, 7C), (1E, 2C, 3A, 4C, 5B, 6B, 7A), (1E, 2C, 3A, 4C, 5B, 6B, 7B), (1E, 2C, 3A, 4C, 5B, 6B, 7C), (1E, 2C, 3A, 4C, 5B, 6C, 7A), (1E, 2C, 3A, 4C, 5B, 6C, 7B), (1E, 2C, 3A, 4C, 5B, 6C, 7C), (1E, 2C, 3A, 4C, 5B, 6D, 7A), (1E, 2C, 3A, 4C, 5B, 6D, 7B), (1E, 2C, 3A, 4C, 5B, 6D, 7C), (1E, 2C, 3A, 4D, 5A, 6A, 7A), (1E, 2C, 3A, 4D, 5A, 6A, 7B), (1E, 2C, 3A, 4D, 5A, 6A, 7C), (1E, 2C, 3A, 4D, 5A, 6B, 7A), (1E, 2C, 3A, 4D, 5A, 6B, 7B), (1E, 2C, 3A, 4D, 5A, 6B, 7C), (1E, 2C, 3A, 4D, 5A, 6C, 7A), (1E, 2C, 3A, 4D, 5A, 6C, 7B), (1E, 2C, 3A, 4D, 5A, 6C, 7C), (1E, 2C, 3A, 4D, 5A, 6D, 7A), (1E, 2C, 3A, 4D, 5A, 6D, 7B), (1E, 2C, 3A, 4D, 5A, 6D, 7C), (1E, 2C, 3A, 4D, 5B, 6A, 7A), (1E, 2C, 3A, 4D, 5B, 6A, 7B), (1E, 2C, 3A, 4D, 5B, 6A, 7C), (1E, 2C, 3A, 4D, 5B, 6B, 7A), (1E, 2C, 3A, 4D, 5B, 6B, 7B), (1E, 2C, 3A, 4D, 5B, 6B, 7C), (1E, 2C, 3A, 4D, 5B, 6C, 7A), (1E, 2C, 3A, 4D, 5B, 6C, 7B), (1E, 2C, 3A, 4D, 5B, 6C, 7C), (1E, 2C, 3A, 4D, 5B, 6D, 7A), (1E, 2C, 3A, 4D, 5B, 6D, 7B), (1E, 2C, 3A, 4D, 5B, 6D, 7C), (1E, 2C, 3A, 4E, 5A, 6A, 7A), (1E, 2C, 3A, 4E, 5A, 6A, 7B), (1E, 2C, 3A, 4E, 5A, 6A, 7C), (1E, 2C, 3A, 4E, 5A, 6B, 7A), (1E, 2C, 3A, 4E, 5A, 6B, 7B), (1E, 2C, 3A, 4E, 5A, 6B, 7C), (1E, 2C, 3A, 4E, 5A, 6C, 7A), (1E, 2C, 3A, 4E, 5A, 6C, 7B), (1E, 2C, 3A, 4E, 5A, 6C, 7C), (1E, 2C, 3A, 4E, 5A, 6D, 7A), (1E, 2C, 3A, 4E, 5A, 6D, 7B), (1E, 2C, 3A, 4E, 5A, 6D, 7C), (1E, 2C, 3A, 4E, 5B, 6A, 7A), (1E, 2C, 3A, 4E, 5B, 6A, 7B), (1E, 2C, 3A, 4E, 5B, 6A, 7C), (1E, 2C, 3A, 4E, 5B, 6B, 7A), (1E, 2C, 3A, 4E, 5B, 6B, 7B), (1E, 2C, 3A, 4E, 5B, 6B, 7C), (1E, 2C, 3A, 4E, 5B, 6C, 7A), (1E, 2C, 3A, 4E, 5B, 6C, 7B), (1E, 2C, 3A, 4E, 5B, 6C, 7C), (1E, 2C, 3A, 4E, 5B, 6D, 7A), (1E, 2C, 3A, 4E, 5B, 6D, 7B), (1E, 2C, 3A, 4E, 5B, 6D, 7C), (1E, 2C, 3B, 4A, 5A, 6A, 7A), (1E, 2C, 3B, 4A, 5A, 6A, 7B), (1E, 2C, 3B, 4A, 5A, 6A, 7C), (1E, 2C, 3B, 4A, 5A, 6B, 7A), (1E, 2C, 3B, 4A, 5A, 6B, 7B), (1E, 2C, 3B, 4A, 5A, 6B, 7C), (1E, 2C, 3B, 4A, 5A, 6C, 7A), (1E, 2C, 3B, 4A, 5A, 6C, 7B), (1E, 2C, 3B, 4A, 5A, 6C, 7C), (1E, 2C, 3B, 4A, 5A, 6D, 7A), (1E, 2C, 3B, 4A, 5A, 6D, 7B), (1E, 2C, 3B, 4A, 5A, 6D, 7C), (1E, 2C, 3B, 4A, 5B, 6A, 7A), (1E, 2C, 3B, 4A, 5B, 6A, 7B), (1E, 2C, 3B, 4A, 5B, 6A, 7C), (1E, 2C, 3B, 4A, 5B, 6B, 7A), (1E, 2C, 3B, 4A, 5B, 6B, 7B), (1E, 2C, 3B, 4A, 5B, 6B, 7C), (1E, 2C, 3B, 4A, 5B, 6C, 7A), (1E, 2C, 3B, 4A, 5B, 6C, 7B), (1E, 2C, 3B, 4A, 5B, 6C, 7C), (1E, 2C, 3B, 4A, 5B, 6D, 7A), (1E, 2C, 3B, 4A, 5B, 6D, 7B), (1E, 2C, 3B, 4A, 5B, 6D, 7C), (1E, 2C, 3B, 4B, 5A, 6A, 7A), (1E, 2C, 3B, 4B, 5A, 6A, 7B), (1E, 2C, 3B, 4B, 5A, 6A, 7C), (1E, 2C, 3B, 4B, 5A, 6B, 7A), (1E, 2C, 3B, 4B, 5A, 6B, 7B), (1E, 2C, 3B, 4B, 5A, 6B, 7C), (1E, 2C, 3B, 4B, 5A, 6C, 7A), (1E, 2C, 3B, 4B, 5A, 6C, 7B), (1E, 2C, 3B, 4B, 5A, 6C, 7C), (1E, 2C, 3B, 4B, 5A, 6D, 7A), (1E, 2C, 3B, 4B, 5A, 6D, 7B), (1E, 2C, 3B, 4B, 5A, 6D, 7C), (1E, 2C, 3B, 4B, 5B, 6A, 7A), (1E, 2C, 3B, 4B, 5B, 6A, 7B), (1E, 2C, 3B, 4B, 5B, 6A, 7C), (1E, 2C, 3B, 4B, 5B, 6B, 7A), (1E, 2C, 3B, 4B, 5B, 6B, 7B), (1E, 2C, 3B, 4B, 5B, 6B, 7C), (1E, 2C, 3B, 4B, 5B, 6C, 7A), (1E, 2C, 3B, 4B, 5B, 6C, 7B), (1E, 2C, 3B, 4B, 5B, 6C, 7C), (1E, 2C, 3B, 4B, 5B, 6D, 7A), (1E, 2C, 3B, 4B, 5B, 6D, 7B), (1E, 2C, 3B, 4B, 5B, 6D, 7C), (1E, 2C, 3B, 4C, 5A, 6A, 7A), (1E, 2C, 3B, 4C, 5A, 6A, 7B), (1E, 2C, 3B, 4C, 5A, 6A, 7C), (1E, 2C, 3B, 4C, 5A, 6B, 7A), (1E, 2C, 3B, 4C, 5A, 6B, 7B), (1E, 2C, 3B, 4C, 5A, 6B, 7C), (1E, 2C, 3B, 4C, 5A, 6C, 7A), (1E, 2C, 3B, 4C, 5A, 6C, 7B), (1E, 2C, 3B, 4C, 5A, 6C, 7C), (1E, 2C, 3B, 4C, 5A, 6D, 7A), (1E, 2C, 3B, 4C, 5A, 6D, 7B), (1E, 2C, 3B, 4C, 5A, 6D, 7C), (1E, 2C, 3B, 4C, 5B, 6A, 7A), (1E, 2C, 3B, 4C, 5B, 6A, 7B), (1E, 2C, 3B, 4C, 5B, 6A, 7C), (1E, 2C, 3B, 4C, 5B, 6B, 7A), (1E, 2C, 3B, 4C, 5B, 6B, 7B), (1E, 2C, 3B, 4C, 5B, 6B, 7C), (1E, 2C, 3B, 4C, 5B, 6C, 7A), (1E, 2C, 3B, 4C, 5B, 6C, 7B), (1E, 2C, 3B, 4C, 5B, 6C, 7C), (1E, 2C, 3B, 4C, 5B, 6D, 7A), (1E, 2C, 3B, 4C, 5B, 6D, 7B), (1E, 2C, 3B, 4C, 5B, 6D, 7C), (1E, 2C, 3B, 4D, 5A, 6A, 7A), (1E, 2C, 3B, 4D, 5A, 6A, 7B), (1E, 2C, 3B, 4D, 5A, 6A, 7C), (1E, 2C, 3B, 4D, 5A, 6B, 7A), (1E, 2C, 3B, 4D, 5A, 6B, 7B), (1E, 2C, 3B, 4D, 5A, 6B, 7C), (1E, 2C, 3B, 4D, 5A, 6C, 7A), (1E, 2C, 3B, 4D, 5A, 6C, 7B), (1E, 2C, 3B, 4D, 5A, 6C, 7C), (1E, 2C, 3B, 4D, 5A, 6D, 7A), (1E, 2C, 3B, 4D, 5A, 6D, 7B), (1E, 2C, 3B, 4D, 5A, 6D, 7C), (1E, 2C, 3B, 4D, 5B, 6A, 7A), (1E, 2C, 3B, 4D, 5B, 6A, 7B), (1E, 2C, 3B, 4D, 5B, 6A, 7C), (1E, 2C, 3B, 4D, 5B, 6B, 7A), (1E, 2C, 3B, 4D, 5B, 6B, 7B), (1E, 2C, 3B, 4D, 5B, 6B, 7C), (1E, 2C, 3B, 4D, 5B, 6C, 7A), (1E, 2C, 3B, 4D, 5B, 6C, 7B), (1E, 2C, 3B, 4D, 5B, 6C, 7C), (1E, 2C, 3B, 4D, 5B, 6D, 7A), (1E, 2C, 3B, 4D, 5B, 6D, 7B), (1E, 2C, 3B, 4D, 5B, 6D, 7C), (1E, 2C, 3B, 4E, 5A, 6A, 7A), (1E, 2C, 3B, 4E, 5A, 6A, 7B), (1E, 2C, 3B, 4E, 5A, 6A, 7C), (1E, 2C, 3B, 4E, 5A, 6B, 7A), (1E, 2C, 3B, 4E, 5A, 6B, 7B), (1E, 2C, 3B, 4E, 5A, 6B, 7C), (1E, 2C, 3B, 4E, 5A, 6C, 7A), (1E, 2C, 3B, 4E, 5A, 6C, 7B), (1E, 2C, 3B, 4E, 5A, 6C, 7C), (1E, 2C, 3B, 4E, 5A, 6D, 7A), (1E, 2C, 3B, 4E, 5A, 6D, 7B), (1E, 2C, 3B, 4E, 5A, 6D, 7C), (1E, 2C, 3B, 4E, 5B, 6A, 7A), (1E, 2C, 3B, 4E, 5B, 6A, 7B), (1E, 2C, 3B, 4E, 5B, 6A, 7C), (1E, 2C, 3B, 4E, 5B, 6B, 7A), (1E, 2C, 3B, 4E, 5B, 6B, 7B), (1E, 2C, 3B, 4E, 5B, 6B, 7C), (1E, 2C, 3B, 4E, 5B, 6C, 7A), (1E, 2C, 3B, 4E, 5B, 6C, 7B), (1E, 2C, 3B, 4E, 5B, 6C, 7C), (1E, 2C, 3B, 4E, 5B, 6D, 7A), (1E, 2C, 3B, 4E, 5B, 6D, 7B), (1E, 2C, 3B, 4E, 5B, 6D, 7C), (1E, 2C, 3C, 4A, 5A, 6A, 7A), (1E, 2C, 3C, 4A, 5A, 6A, 7B), (1E, 2C, 3C, 4A, 5A, 6A, 7C), (1E, 2C, 3C, 4A, 5A, 6B, 7A), (1E, 2C, 3C, 4A, 5A, 6B, 7B), (1E, 2C, 3C, 4A, 5A, 6B, 7C), (1E, 2C, 3C, 4A, 5A, 6C, 7A), (1E, 2C, 3C, 4A, 5A, 6C, 7B), (1E, 2C, 3C, 4A, 5A, 6C, 7C), (1E, 2C, 3C, 4A, 5A, 6D, 7A), (1E, 2C, 3C, 4A, 5A, 6D, 7B), (1E, 2C, 3C, 4A, 5A, 6D, 7C), (1E, 2C, 3C, 4A, 5B, 6A, 7A), (1E, 2C, 3C, 4A, 5B, 6A, 7B), (1E, 2C, 3C, 4A, 5B, 6A, 7C), (1E, 2C, 3C, 4A, 5B, 6B, 7A), (1E, 2C, 3C, 4A, 5B, 6B, 7B), (1E, 2C, 3C, 4A, 5B, 6B, 7C), (1E, 2C, 3C, 4A, 5B, 6C, 7A), (1E, 2C, 3C, 4A, 5B, 6C, 7B), (1E, 2C, 3C, 4A, 5B, 6C, 7C), (1E, 2C, 3C, 4A, 5B, 6D, 7A), (1E, 2C, 3C, 4A, 5B, 6D, 7B), (1E, 2C, 3C, 4A, 5B, 6D, 7C), (1E, 2C, 3C, 4B, 5A, 6A, 7A), (1E, 2C, 3C, 4B, 5A, 6A, 7B), (1E, 2C, 3C, 4B, 5A, 6A, 7C), (1E, 2C, 3C, 4B, 5A, 6B, 7A), (1E, 2C, 3C, 4B, 5A, 6B, 7B), (1E, 2C, 3C, 4B, 5A, 6B, 7C), (1E, 2C, 3C, 4B, 5A, 6C, 7A), (1E, 2C, 3C, 4B, 5A, 6C, 7B), (1E, 2C, 3C, 4B, 5A, 6C, 7C), (1E, 2C, 3C, 4B, 5A, 6D, 7A) (1E, 2C, 3C, 4B, 5A, 6D, 7B), (1E, 2C, 3C, 4B, 5A, 6D, 7C), (1E, 2C, 3C, 4B, 5B, 6A, 7A), (1E, 2C, 3C, 4B, 5B, 6A, 7B), (1E, 2C, 3C, 4B, 5B, 6A, 7C), (1E, 2C, 3C, 4B, 5B, 6B, 7A), (1E, 2C, 3C, 4B, 5B, 6B, 7B), (1E, 2C, 3C, 4B, 5B, 6B, 7C), (1E, 2C, 3C, 4B, 5B, 6C, 7A), (1E, 2C, 3C, 4B, 5B, 6C, 7B), (1E, 2C, 3C, 4B, 5B, 6C, 7C), (1E, 2C, 3C, 4B, 5B, 6D, 7A), (1E, 2C, 3C, 4B, 5B, 6D, 7B), (1E, 2C, 3C, 4B, 5B, 6D, 7C), (1E, 2C, 3C, 4C, 5A, 6A, 7A), (1E, 2C, 3C, 4C, 5A, 6A, 7B), (1E, 2C, 3C, 4C, 5A, 6A, 7C), (1E, 2C, 3C, 4C, 5A, 6B, 7A), (1E, 2C, 3C, 4C, 5A, 6B, 7B), (1E, 2C, 3C, 4C, 5A, 6B, 7C), (1E, 2C, 3C, 4C, 5A, 6C, 7A), (1E, 2C, 3C, 4C, 5A, 6C, 7B), (1E, 2C, 3C, 4C, 5A, 6C, 7C), (1E, 2C, 3C, 4C, 5A, 6D, 7A), (1E, 2C, 3C, 4C, 5A, 6D, 7B), (1E, 2C, 3C, 4C, 5A, 6D, 7C), (1E, 2C, 3C, 4C, 5B, 6A, 7A), (1E, 2C, 3C, 4C, 5B, 6A, 7B), (1B, 2C, 3C, 4C, 5B, 6A, 7C), (1E, 2C, 3C, 4C, 5B, 6B, 7A), (1E, 2C, 3C, 4C, 5B, 6B, 7B), (1E, 2C, 3C, 4C, 5B, 6B, 7C), (1E, 2C, 3C, 4C, 5B, 6C, 7A), (1E, 2C, 3C, 4C, 5B, 6C, 7B), (1E, 2C, 3C, 4C, 5B, 6C, 7C), (1E, 2C, 3C, 4C, 5B, 6D, 7A), (1E, 2C, 3C, 4C, 5B, 6D, 7B), (1E, 2C, 3C, 4C, 5B, 6D, 7C), (1E, 2C, 3C, 4D, 5A, 6A, 7A), (1E, 2C, 3C, 4D, 5A, 6A, 7B), (1E, 2C, 3C, 4D, 5A, 6A, 7C), (1E, 2C, 3C, 4D, 5A, 6B, 7A), (1E, 2C, 3C, 4D, 5A, 6B, 7B), (1E, 2C, 3C, 4D, 5A, 6B, 7C), (1E, 2C, 3C, 4D, 5A, 6C, 7A), (1E, 2C, 3C, 4D, 5A, 6C, 7B), (1E, 2C, 3C, 4D, 5A, 6C, 7C), (1E, 2C, 3C, 4D, 5A, 6D, 7A), (1E, 2C, 3C, 4D, 5A, 6D, 7B), (1E, 2C, 3C, 4D, 5A, 6D, 7C), (1E, 2C, 3C, 4D, 5B, 6A, 7A), (1E, 2C, 3C, 4D, 5B, 6A, 7B), (1E, 2C, 3C, 4D, 5B, 6A, 7C), (1E, 2C, 3C, 4D, 5B, 6B, 7A), (1E, 2C, 3C, 4D, 5B, 6B, 7B), (1E, 2C, 3C, 4D, 5B, 6B, 7C), (1E, 2C, 3C, 4D, 5B, 6C, 7A), (1E, 2C, 3C, 4D, 5B, 6C, 7B), (1E, 2C, 3C, 4D, 5B, 6C, 7C), (1E, 2C, 3C, 4D, 5B, 6D, 7A), (1E, 2C, 3C, 4D, 5B, 6D, 7B), (1E, 2C, 3C, 4D, 5B, 6D, 7C), (1E, 2C, 3C, 4E, 5A, 6A, 7A), (1E, 2C, 3C, 4E, 5A, 6A, 7B), (1E, 2C, 3C, 4E, 5A, 6A, 7C), (1E, 2C, 3C, 4E, 5A, 6B, 7A), (1E, 2C, 3C, 4E, 5A, 6B, 7B), (1E, 2C, 3C, 4E, 5A, 6B, 7C), (1E, 2C, 3C, 4E, 5A, 6C, 7A), (1E, 2C, 3C, 4E, 5A, 6C, 7B), (1E, 2C, 3C, 4E, 5A, 6C, 7C), (1E, 2C, 3C, 4E, 5A, 6D, 7A), (1E, 2C, 3C, 4E, 5A, 6D, 7B), (1E, 2C, 3C, 4E, 5A, 6D, 7C), (1E, 2C, 3C, 4E, 5B, 6A, 7A), (1E, 2C, 3C, 4E, 5B, 6A, 7B), (1E, 2C, 3C, 4E, 5B, 6A, 7C), (1E, 2C, 3C, 4E, 5B, 6B, 7A), (1E, 2C, 3C, 4E, 5B, 6B, 7B), (1E, 2C, 3C, 4E, 5B, 6B, 7C), (1E, 2C, 3C, 4E, 5B, 6C, 7A), (1E, 2C, 3C, 4E, 5B, 6C, 7B), (1E, 2C, 3C, 4E, 5B, 6C, 7C), (1E, 2C, 3C, 4E, 5B, 6D, 7A), (1E, 2C, 3C, 4E, 5B, 6D, 7B), (1E, 2C, 3C, 4E, 5B, 6D, 7C), (1E, 2C, 3D, 4A, 5A, 6A, 7A), (1E, 2C, 3D, 4A, 5A, 6A, 7B), (1E, 2C, 3D, 4A, 5A, 6A, 7C), (1E, 2C, 3D, 4A, 5A, 6B, 7A), (1E, 2C, 3D, 4A, 5A, 6B, 7B), (1E, 2C, 3D, 4A, 5A, 6B, 7C), (1E, 2C, 3D, 4A, 5A, 6C, 7A), (1E, 2C, 3D, 4A, 5A, 6C, 7B), (1E, 2C, 3D, 4A, 5A, 6C, 7C), (1E, 2C, 3D, 4A, 5A, 6D, 7A), (1E, 2C, 3D, 4A, 5A, 6D, 7B), (1E, 2C, 3D, 4A, 5A, 6D, 7C), (1E, 2C, 3D, 4A, 5B, 6A, 7A), (1E, 2C, 3D, 4A, 5B, 6A, 7B), (1E, 2C, 3D, 4A, 5B, 6A, 7C), (1E, 2C, 3D, 4A, 5B, 6B, 7A), (1E, 2C, 3D, 4A, 5B, 6B, 7B), (1E, 2C, 3D, 4A, 5B, 6B, 7C), (1E, 2C, 3D, 4A, 5B, 6C, 7A), (1E, 2C, 3D, 4A, 5B, 6C, 7B), (1E, 2C, 3D, 4A, 5B, 6C, 7C), (1E, 2C, 3D, 4A, 5B, 6D, 7A), (1E, 2C, 3D, 4A, 5B, 6D, 7B), (1E, 2C, 3D, 4A, 5B, 6D, 7C), (1E, 2C, 3D, 4B, 5A, 6A, 7A), (1E, 2C, 3D, 4B, 5A, 6A, 7B), (1E, 2C, 3D, 4B, 5A, 6A, 7C), (1E, 2C, 3D, 4B, 5A, 6B, 7A), (1E, 2C, 3D, 4B, 5A, 6B, 7B), (1E, 2C, 3D, 4B, 5A, 6B; 7C), (1E, 2C, 3D, 4B, 5A, 6C, 7A), (1E, 2C, 3D, 4B, 5A, 6C, 7B), (1E, 2C, 3D, 4B, 5A, 6C, 7C), (1E, 2C, 3D, 4B, 5A, 6D, 7A), (1E, 2C, 3D, 4B, 5A, 6D, 7B), (1E, 2C, 3D, 4B, 5A, 6D, 7C), (1E, 2C, 3D, 4B, 5B, 6A, 7A), (1E, 2C, 3D, 4B, 5B, 6A, 7B), (1E, 2C, 3D, 4B, 5B, 6A, 7C), (1E, 2C, 3D, 4B, 5B, 6B, 7A), (1E, 2C, 3D, 4B, 5B, 6B, 7B), (1E, 2C, 3D, 4B, 5B, 6B, 7C), (1E, 2C, 3D, 4B, 5B, 6C, 7A), (1E, 2C, 3D, 4B, 5B, 6C, 7B), (1E, 2C, 3D, 4B, 5B, 6C, 7C), (1E, 2C, 3D, 4B, 5B, 6D, 7A), (1E, 2C, 3D, 4B, 5B, 6D, 7B), (1E, 2C, 3D, 4B, 5B, 6D, 7C), (1E, 2C, 3D, 4C, 5A, 6A, 7A), (1E, 2C, 3D, 4C, 5A, 6A, 7B), (1E, 2C, 3D, 4C, 5A, 6A, 7C), (1E, 2C, 3D, 4C, 5A, 6B, 7A), (1E, 2C, 3D, 4C, 5A, 6B, 7B), (1E, 2C, 3D, 4C, 5A, 6B, 7C), (1E, 2C, 3D, 4C, 5A, 6C, 7A), (1E, 2C, 3D, 4C, 5A, 6C, 7B), (1E, 2C, 3D, 4C, 5A, 6C, 7C), (1E, 2C, 3D, 4C, 5A, 6D, 7A), (1E, 2C, 3D, 4C, 5A, 6D, 7B), (1E, 2C, 3D, 4C, 5A, 6D, 7C), (1E, 2C, 3D, 4C, 5B, 6A, 7A), (1E, 2C, 3D, 4C, 5B, 6A, 7B), (1E, 2C, 3D, 4C, 5B, 6A, 7C), (1E, 2C, 3D, 4C, 5B, 6B, 7A), (1E, 2C, 3D, 4C, 5B, 6B, 7B), (1E, 2C, 3D, 4C, 5B, 6C, 7A), (1E, 2C, 3D, 4C, 5B, 6C, 7B), (1E, 2C, 3D, 4C, 5B, 6C, 7C), (1E, 2C, 3D, 4C, 5B, 6D, 7A), (1E, 2C, 3D, 4C, 5B, 6D, 7B), (1E, 2C, 3D, 4C, 5B, 6D, 7C), (1E, 2C, 3D, 4D, 5A, 6A, 7A), (1E, 2C, 3D, 4D, 5A, 6A, 7B), (1E, 2C, 3D, 4D, 5A, 6A, 7C), (1E, 2C, 3D, 4D, 5A, 6B, 7A), (1E, 2C, 3D, 4D, 5A, 6B, 7B), (1E, 2C, 3D, 4D, 5A, 6B, 7C), (1E, 2C, 3D, 4D, 5A, 6C, 7A), (1E, 2C, 3D, 4D, 5A, 6C, 7B), (1E, 2C, 3D, 4D, 5A, 6C, 7C), (1E, 2C, 3D, 4D, 5A, 6D, 7A), (1E, 2C, 3D, 4D, 5A, 6D, 7B), (1E, 2C, 3D, 4D, 5A, 6D, 7C), (1E, 2C, 3D, 4D, 5B, 6A, 7A), (1E, 2C, 3D, 4D, 5B, 6A, 7B), (1E, 2C, 3D, 4D, 5B, 6A, 7C), (1E, 2C, 3D, 4D, 5B, 6B, 7A), (1E, 2C, 3D, 4D, 5B, 6B, 7B), (1E, 2C, 3D, 4D, 5B, 6B, 7C), (1E, 2C, 3D, 4D, 5B, 6C, 7A), (1E, 2C, 3D, 4D, 5B, 6C, 7B), (1E, 2C, 3D, 4D, 5B, 6C, 7C), (1E, 2C, 3D, 4D, 5B, 6D, 7A), (1E, 2C, 3D, 4D, 5B, 6D, 7B), (1E, 2C, 3D, 4D, 5B, 6D, 7C), (1E, 2C, 3D, 4E, 5A, 6A, 7A), (1E, 2C, 3D, 4E, 5A, 6A, 7B), (1E, 2C, 3D, 4E, 5A, 6A, 7C), (1E, 2C, 3D, 4E, 5A, 6B, 7A), (1E, 2C, 3D, 4E, 5A, 6B, 7B), (1E, 2C, 3D, 4E, 5A, 6B, 7C), (1E, 2C, 3D, 4E, 5A, 6C, 7A), (1E, 2C, 3D, 4E, 5A, 6C, 7B), (1E, 2C, 3D, 4E, 5A, 6C, 7C), (1E, 2C, 3D, 4E, 5A, 6D, 7A), (1E, 2C, 3D, 4E, 5A, 6D, 7B), (1E, 2C, 3D, 4E, 5A, 6D, 7C), (1E, 2C, 3D, 4E, 5B, 6A, 7A), (1E, 2C, 3D, 4E, 5B, 6A, 7B), (1E, 2C, 3D, 4E, 5B, 6A, 7C), (1E, 2C, 3D, 4E, 5B, 6B, 7A), (1E, 2C, 3D, 4E, 5B, 6B, 7B), (1E, 2C, 3D, 4E, 5B, 6B, 7C), (1E, 2C, 3D, 4E, 5B, 6C, 7A), (1E, 2C, 3D, 4E, 5B, 6C, 7B), (1E, 2C, 3D, 4E, 5B, 6C, 7C), (1E, 2C, 3D, 4E, 5B, 6D, 7A), (1E, 2C, 3D, 4E, 5B, 6D, 7B), (1E, 2C, 3D, 4E, 5B, 6D, 7C), (1E, 2C, 3E, 4A, 5A, 6A, 7A), (1E, 2C, 3E, 4A, 5A, 6A, 7B), (1E, 2C, 3E, 4A, 5A, 6A, 7C), (1E, 2C, 3E, 4A, 5A, 6B, 7A), (1E, 2C, 3E, 4A, 5A, 6B, 7B), (1E, 2C, 3E, 4A, 5A, 6B, 7C), (1E, 2C, 3E, 4A, 5A, 6C, 7A), (1E, 2C, 3E, 4A, 5A, 6C, 7B), (1E, 2C, 3E, 4A, 5A, 6C, 7C), (1E, 2C, 3E, 4A, 5A, 6D, 7A), (1E, 2C, 3E, 4A, 5A, 6D, 7B), (1E, 2C, 3E, 4A, 5A, 6D, 7C), (1E, 2C, 3E, 4A, 5B, 6A, 7A), (1E, 2C, 3E, 4A, 5B, 6A, 7B), (1E, 2C, 3E, 4A, 5B, 6A, 7C), (1E, 2C, 3E, 4A, 5B, 6B, 7A), (1E, 2C, 3E, 4A, 5B, 6B, 7B), (1E, 2C, 3E, 4A, 5B, 6B, 7C), (1E, 2C, 3E, 4A, 5B, 6C, 7A), (1E, 2C, 3E, 4A, 5B, 6C, 7B), (1E, 2C, 3E, 4A, 5B, 6C, 7C), (1E, 2C, 3E, 4A, 5B, 6D, 7A), (1E, 2C, 3E, 4A, 5B, 6D, 7B), (1E, 2C, 3E, 4A, 5B, 6D, 7C), (1E, 2C, 3E, 4B, 5A, 6A, 7A), (1E, 2C, 3E, 4B, 5A, 6A, 7B), (1E, 2C, 3E, 4B, 5A, 6A, 7C), (1E, 2C, 3E, 4B, 5A, 6B, 7A), (1E, 2C, 3E, 4B, 5A, 6B, 7B), (1E, 2C, 3E, 4B, 5A, 6B, 7C), (1E, 2C, 3E, 4B, 5A, 6C, 7A), (1E, 2C, 3E, 4B, 5A, 6C, 7B), (1E, 2C, 3E, 4B, 5A, 6C, 7C), (1E, 2C, 3E, 4B, 5A, 6D, 7A), (1E, 2C, 3E, 4B, 5A, 6D, 7B), (1E, 2C, 3E, 4B, 5A, 6D, 7C), (1E, 2C, 3E, 4B, 5B, 6A, 7A), (1E, 2C, 3E, 4B, 5B, 6A, 7B), (1E, 2C, 3E, 4B, 5B, 6A, 7C), (1E, 2C, 3E, 4B, 5B, 6B, 7A), (1E, 2C, 3E, 4B, 5B, 6B, 7B), (1E, 2C, 3E, 4B, 5B, 6B, 7C), (1E, 2C, 3E, 4B, 5B, 6C, 7A), (1E, 2C, 3E, 4B, 5B, 6C, 7B), (1E, 2C, 3E, 4B, 5B, 6C, 7C), (1E, 2C, 3E, 4B, 5B, 6D, 7A), (1E, 2C, 3E, 4B, 5B, 6D, 7B), (1E, 2C, 3E, 4B, 5B, 6D, 7C), (1E, 2C, 3E, 4C, 5A, 6A, 7A), (1E, 2C, 3E, 4C, 5A, 6A, 7B), (1E, 2C, 3E, 4C, 5A, 6A, 7C), (1E, 2C, 3E, 4C, 5A, 6B, 7A), (1E, 2C, 3E, 4C, 5A, 6B, 7B), (1E, 2C, 3E, 4C, 5A, 6B, 7C), (1E, 2C, 3E, 4C, 5A, 6C, 7A), (1E, 2C, 3E, 4C, 5A, 6C, 7B), (1E, 2C, 3E, 4C, 5A, 6C, 7C), (1E, 2C, 3E, 4C, 5A, 6D, 7A), (1E, 2C, 3E, 4C, 5A, 6D, 7B), (1E, 2C, 3E, 4C, 5A, 6D, 7C), (1E, 2C, 3E, 4C, 5B, 6A, 7A), (1E, 2C, 3E, 4C, 5B, 6A, 7B), (1E, 2C, 3E, 4C, 5B, 6A, 7C), (1E, 2C, 3E, 4C, 5B, 6B, 7A), (1E, 2C, 3E, 4C, 5B, 6B, 7B), (1E, 2C, 3E, 4C, 5B, 6B, 7C), (1E, 2C, 3E, 4C, 5B, 6C, 7A), (1E, 2C, 3E, 4C, 5B, 6C, 7B), (1E, 2C, 3E, 4C, 5B, 6C, 7C), (1E, 2C, 3E, 4C, 5B, 6D, 7A), (1E, 2C, 3E, 4C, 5B, 6D, 7B), (1E, 2C, 3E, 4C, 5B, 6D, 7C), (1E, 2C, 3E, 4D, 5A, 6A, 7A), (1E, 2C, 3E, 4D, 5A, 6A, 7B), (1E, 2C, 3E, 4D, 5A, 6A, 7C), (1E, 2C, 3E, 4D, 5A, 6B, 7A), (1E, 2C, 3E, 4D, 5A, 6B, 7B), (1E, 2C, 3E, 4D, 5A, 6B, 7C), (1E, 2C, 3E, 4D, 5A, 6C, 7A), (1E, 2C, 3E, 4D, 5A, 6C, 7B), (1E, 2C, 3E, 4D, 5A, 6C, 7C), (1E, 2C, 3E, 4D, 5A, 6D, 7A), (1E, 2C, 3E, 4D, 5A, 6D, 7B), (1E, 2C, 3E, 4D, 5A, 6D, 7C), (1E, 2C, 3E, 4D, 5B, 6A, 7A), (1E, 2C, 3E, 4D, 5B, 6A, 7B), (1E, 2C, 3E, 4D, 5B, 6A, 7C), (1E, 2C, 3E, 4D, 5B, 6B, 7A), (1E, 2C, 3E, 4D, 5B, 6B, 7B), (1E, 2C, 3E, 4D, 5B, 6B, 7C), (1E, 2C, 3E, 4D, 5B, 6C, 7A), (1E, 2C, 3E, 4D, 5B, 6C, 7B), (1E, 2C, 3E, 4D, 5B, 6C, 7C), (1E, 2C, 3E, 4D, 5B, 6D, 7A), (1E, 2C, 3E, 4D, 5B, 6D, 7B), (1E, 2C, 3E, 4D, 5B, 6D, 7C), (1E, 2C, 3E, 4E, 5A, 6A, 7A), (1E, 2C, 3E, 4E, 5A, 6A, 7B), (1E, 2C, 3E, 4E, 5A, 6A, 7C), (1E, 2C, 3E, 4E, 5A, 6B, 7A), (1E, 2C, 3E, 4E, 5A, 6B, 7B), (1E, 2C, 3E, 4E, 5A, 6B, 7C), (1E, 2C, 3E, 4E, 5A, 6C, 7A), (1E, 2C, 3E, 4E, 5A, 6C, 7B), (1E, 2C, 3E, 4E, 5A, 6C, 7C), (1E, 2C, 3E, 4E, 5A, 6D, 7A), (1E, 2C, 3E, 4E, 5A, 6D, 7B), (1E, 2C, 3E, 4E, 5A, 6D, 7C), (1E, 2C, 3E, 4E, 5B, 6A, 7A), (1E, 2C, 3E, 4E, 5B, 6A, 7B), (1E, 2C, 3E, 4E, 5B, 6A, 7C), (1E, 2C, 3E, 4E, 5B, 6B, 7A), (1E, 2C, 3E, 4E, 5B, 6B, 7B), (1E, 2C, 3E, 4E, 5B, 6B, 7C), (1E, 2C, 3E, 4E, 5B, 6C, 7A), (1E, 2C, 3E, 4E, 5B, 6C, 7B), (1E, 2C, 3E, 4E, 5B, 6C, 7C), (1E, 2C, 3E, 4E, 5B, 6D, 7A), (1E, 2C, 3E, 4E, 5B, 6D, 7B), (1E, 2C, 3E, 4E, 5B, 6D, 7C), (1E, 2D, 3A, 4A, 5A, 6A, 7A), (1E, 2D, 3A, 4A, 5A, 6A, 7B), (1E, 2D, 3A, 4A, 5A, 6A, 7C), (1E, 2D, 3A, 4A, 5A, 6B, 7A), (1E, 2D, 3A, 4A, 5A, 6B, 7B), (1E, 2D, 3A, 4A, 5A, 6B, 7C), (1E, 2D, 3A, 4A, 5A, 6C, 7A), (1E, 2D, 3A, 4A, 5A, 6C, 7B), (1E, 2D, 3A, 4A, 5A, 6C, 7C), (1E, 2D, 3A, 4A, 5A, 6D, 7A), (1E, 2D, 3A, 4A, 5A, 6D, 7B), (1E, 2D, 3A, 4A, 5A, 6D, 7C), (1E, 2D, 3A, 4A, 5B, 6A, 7A), (1E, 2D, 3A, 4A, 5B, 6A, 7B), (1E, 2D, 3A, 4A, 5B, 6A, 7C), (1E, 2D, 3A, 4A, 5B, 6B, 7A), (1E, 2D, 3A, 4A, 5B, 6B, 7B), (1E, 2D, 3A, 4A, 5B, 6B, 7C), (1E, 2D, 3A, 4A, 5B, 6C, 7A), (1E, 2D, 3A, 4A, 5B, 6C, 7B), (1E, 2D, 3A, 4A, 5B, 6C, 7C), (1E, 2D, 3A, 4A, 5B, 6D, 7A), (1E, 2D, 3A, 4A, 5B, 6D, 7B), (1E, 2D, 3A, 4A, 5B, 6D, 7C), (1E, 2D, 3A, 4B, 5A, 6A, 7A), (1E, 2D, 3A, 4B, 5A, 6A, 7B), (1E, 2D, 3A, 4B, 5A, 6A, 7C), (1E, 2D, 3A, 4B, 5A, 6B, 7A), (1E, 2D, 3A, 4B, 5A, 6B, 7B), (1E, 2D, 3A, 4B, 5A, 6B, 7C), (1E, 2D, 3A, 4B, 5A, 6C, 7A), (1E, 2D, 3A, 4B, 5A, 6C, 7B), (1E, 2D, 3A, 4B, 5A, 6C, 7C), (1E, 2D, 3A, 4B, 5A, 6D, 7A), (1E, 2D, 3A, 4B, 5A, 6D, 7B), (1E, 2D, 3A, 4B, 5A, 6D, 7C), (1E, 2D, 3A, 4B, 5B, 6A, 7A), (1E, 2D, 3A, 4B, 5B, 6A, 7B), (1E, 2D, 3A, 4B, 5B, 6A, 7C), (1E, 2D, 3A, 4B, 5B, 6B, 7A), (1E, 2D, 3A, 4B, 5B, 6B, 7B), (1E, 2D, 3A, 4B, 5B, 6B, 7C), (1E, 2D, 3A, 4B, 5B, 6C, 7A), (1E, 2D, 3A, 4B, 5B, 6C, 7B), (1E, 2D, 3A, 4B, 5B, 6C, 7C), (1E, 2D, 3A, 4B, 5B, 6D, 7A), (1E, 2D, 3A, 4B, 5B, 6D, 7B), (1E, 2D, 3A, 4B, 5B, 6D, 7C), (1E, 2D, 3A, 4C, 5A, 6A, 7A), (1E, 2D, 3A, 4C, 5A, 6A, 7B), (1E, 2D, 3A, 4C, 5A, 6A, 7C), (1E, 2D, 3A, 4C, 5A, 6B, 7A), (1E, 2D, 3A, 4C, 5A, 6B, 7B), (1E, 2D, 3A, 4C, 5A, 6B, 7C), (1E, 2D, 3A, 4C, 5A, 6C, 7A), (1E, 2D, 3A, 4C, 5A, 6C, 7B), (1E, 2D, 3A, 4C, 5A, 6C, 7C), (1E, 2D, 3A, 4C, 5A, 6D, 7A), (1E, 2D, 3A, 4C, 5A, 6D, 7B), (1E, 2D, 3A, 4C, 5A, 6D, 7C), (1E, 2D, 3A, 4C, 5B, 6A, 7A), (1E, 2D, 3A, 4C, 5B, 6A, 7C), (1E, 2D, 3A, 4C, 5B, 6A, 7C), (1E, 2D, 3A, 4C, 5B, 6B, 7A), (1E, 2D, 3A, 4C, 5B, 6B, 7B), (1E, 2D, 3A, 4C, 5B, 6B, 7C), (1E, 2D, 3A, 4C, 5B, 6C, 7A), (1E, 2D, 3A, 4C, 5B, 6C, 7B), (1E, 2D, 3A, 4C, 5B, 6C, 7C), (1E, 2D, 3A, 4C, 5B, 6D, 7A), (1E, 2D, 3A, 4C, 5B, 6D, 7B), (1E, 2D, 3A, 4C, 5B, 6D, 7C), (1E, 2D, 3A, 4D, 5A, 6A, 7A), (1E, 2D, 3A, 4D, 5A, 6A, 7B), (1E, 2D, 3A, 4D, 5A, 6A, 7C), (1E, 2D, 3A, 4D, 5A, 6B, 7A), (1E, 2D, 3A, 4D, 5A, 6B, 7B), (1E, 2D, 3A, 4D, 5A, 6B, 7C), (1E, 2D, 3A, 4D, 5A, 6C, 7A), (1E, 2D, 3A, 4D, 5A, 6C, 7B), (1E, 2D, 3A, 4D, 5A, 6C, 7C), (1E, 2D, 3A, 4D, 5A, 6D, 7A), (1E, 2D, 3A, 4D, 5A, 6D, 7B), (1E, 2D, 3A, 4D, 5A, 6D, 7C), (1E, 2D, 3A, 4D, 5B, 6A, 7A), (1E, 2D, 3A, 4D, 5B, 6A, 7B), (1E, 2D, 3A, 4D, 5B, 6A, 7C), (1E, 2D, 3A, 4D, 5B, 6B, 7A), (1E, 2D, 3A, 4D, 5B, 6B, 7B), (1E, 2D, 3A, 4D, 5B, 6B, 7C), (1E, 2D, 3A, 4D, 5B, 6C, 7A), (1E, 2D, 3A, 4D, 5B, 6C, 7B), (1E, 2D, 3A, 4D, 5B, 6C, 7C), (1E, 2D, 3A, 4D, 5B, 6D, 7A), (1E, 2D, 3A, 4D, 5B, 6D, 7B), (1E, 2D, 3A, 4D, 5B, 6D, 7C), (1E, 2D, 3A, 4E, 5A, 6A, 7A), (1E, 2D, 3A, 4E, 5A, 6A, 7B), (1E, 2D, 3A, 4E, 5A, 6A, 7C), (1E, 2D, 3A, 4E, 5A, 6B, 7A), (1E, 2D, 3A, 4E, 5A, 6B, 7B), (1E, 2D, 3A, 4E, 5A, 6B, 7C), (1E, 2D, 3A, 4E, 5A, 6C, 7A), (1E, 2D, 3A, 4E, 5A, 6C, 7B), (1E, 2D, 3A, 4E, 5A, 6C, 7C), (1E, 2D, 3A, 4E, 5A, 6D, 7A), (1E, 2D, 3A, 4E, 5A, 6D, 7B), (1E, 2D, 3A, 4E, 5A, 6D, 7C), (1E, 2D, 3A, 4E, 5B, 6A, 7A), (1E, 2D, 3A, 4E, 5B, 6A, 7B), (1E, 2D, 3A, 4E, 5B, 6A, 7C), (1E, 2D, 3A, 4E, 5B, 6B, 7A), (1E, 2D, 3A, 4E, 5B, 6B, 7B), (1E, 2D, 3A, 4E, 5B, 6B, 7C), (1E, 2D, 3A, 4E, 5B, 6C, 7A), (1E, 2D, 3A, 4E, 5B, 6C, 7B), (1E, 2D, 3A, 4E, 5B, 6C, 7C), (1E, 2D, 3A, 4E, 5B, 6D, 7A), (1E, 2D, 3A, 4E, 5B, 6D, 7B), (1E, 2D, 3A, 4E, 5B, 6D, 7C), (1E, 2D, 3B, 4A, 5A, 6A, 7A), (1E, 2D, 3B, 4A, 5A, 6A, 7B), (1E, 2D, 3B, 4A, 5A, 6A, 7C), (1E, 2D, 3B, 4A, 5A, 6B, 7A), (1E, 2D, 3B, 4A, 5A, 6B, 7B), (1E, 2D, 3B, 4A, 5A, 6B, 7C), (1E, 2D, 3B, 4A, 5A, 6C, 7A), (1E, 2D, 3B, 4A, 5A, 6C, 7B), (1E, 2D, 3B, 4A, 5A, 6C, 7C), (1E, 2D, 3B, 4A, 5A, 6D, 7A), (1E, 2D, 3B, 4A, 5A, 6D, 7B), (1E, 2D, 3B, 4A, 5A, 6D, 7C), (1E, 2D, 3B, 4A, 5B, 6A, 7A), (1E, 2D, 3B, 4A, 5B, 6A, 7B), (1E, 2D, 3B, 4A, 5B, 6A, 7C), (1E, 2D, 3B, 4A, 5B, 6B, 7A), (1E, 2D, 3B, 4A, 5B, 6B, 7B), (1E, 2D, 3B, 4A, 5B, 6B, 7C), (1E, 2D, 3B, 4A, 5B, 6C, 7A), (1E, 2D, 3B, 4A, 5B, 6C, 7B), (1E, 2D, 3B, 4A, 5B, 6C, 7C), (1E, 2D, 3B, 4A, 5B, 6D, 7A), (1E, 2D, 3B, 4A, 5B, 6D, 7B), (1E, 2D, 3B, 4A, 5B, 6D, 7C), (1E, 2D, 3B, 4B, 5A, 6A, 7A), (1E, 2D, 3B, 4B, 5A, 6A, 7B), (1E, 2D, 3B, 4B, 5A, 6A, 7C), (1E, 2D, 3B, 4B, 5A, 6B, 7A), (1E, 2D, 3B, 4B, 5A, 6B, 7B), (1E, 2D, 3B, 4B, 5A, 6B, 7C), (1E, 2D, 3B, 4B, 5A, 6C, 7A), (1E, 2D, 3B, 4B, 5A, 6C, 7B), (1E, 2D, 3B, 4B, 5A, 6C, 7C), (1E, 2D, 3B, 4B, 5A, 6D, 7A), (1E, 2D, 3B, 4B, 5A, 6D, 7B), (1E, 2D, 3B, 4B, 5A, 6D, 7C), (1E, 2D, 3B, 4B, 5B, 6A, 7A), (1E, 2D, 3B, 4B, 5B, 6A, 7B), (1E, 2D, 3B, 4B, 5B, 6A, 7C), (1E, 2D, 3B, 4B, 5B, 6B, 7A), (1E, 2D, 3B, 4B, 5B, 6B, 7B), (1E, 2D, 3B, 4B, 5B, 6B, 7C), (1E, 2D, 3B, 4B, 5B, 6C, 7A), (1E, 2D, 3B, 4B, 5B, 6C, 7B), (1E, 2D, 3B, 4B, 5B, 6C, 7C), (1E, 2D, 3B, 4B, 5B, 6D, 7A), (1E, 2D, 3B, 4B, 5B, 6D, 7B), (1E, 2D, 3B, 4B, 5B, 6D, 7C), (1E, 2D, 3B, 4C, 5A, 6A, 7A), (1E, 2D, 3B, 4C, 5A, 6A, 7B), (1E, 2D, 3B, 4C, 5A, 6A, 7C), (1E, 2D, 3B, 4C, 5A, 6B, 7A), (1E, 2D, 3B, 4C, 5A, 6B, 7B), (1E, 2D, 3B, 4C, 5A, 6B, 7C), (1E, 2D, 3B, 4C, 5A, 6C, 7A), (1E, 2D, 3B, 4C, 5A, 6C, 7B), (1E, 2D, 3B, 4C, 5A, 6C, 7C), (1E, 2D, 3B, 4C, 5A, 6D, 7A), (1E, 2D, 3B, 4C, 5A, 6D, 7B), (1E, 2D, 3B, 4C, 5A, 6D, 7C), (1E, 2D, 3B, 4C, 5B, 6A, 7A), (1E, 2D, 3B, 4C, 5B, 6A, 7B), (1E, 2D, 3B, 4C, 5B, 6A, 7C), (1E, 2D, 3B, 4C, 5B, 6B, 7A), (1E, 2D, 3B, 4C, 5B, 6B, 7B), (1E, 2D, 3B, 4C, 5B, 6B, 7C), (1E, 2D, 3B, 4C, 5B, 6C, 7A), (1E, 2D, 3B, 4C, 5B, 6C, 7B), (1E, 2D, 3B, 4C, 5B, 6C, 7C), (1E, 2D, 3B, 4C, 5B, 6D, 7A), (1E, 2D, 3B, 4C, 5B, 6D, 7B), (1E, 2D, 3B, 4C, 5B, 6D, 7C), (1E, 2D, 3B, 4D, 5A, 6A, 7A), (1E, 2D, 3B, 4D, 5A, 6A, 7B), (1E, 2D, 3B, 4D, 5A, 6A, 7C), (1E, 2D, 3B, 4D, 5A, 6B, 7A), (1E, 2D, 3B, 4D, 5A, 6B, 7B), (1E, 2D, 3B, 4D, 5A, 6B, 7C), (1E, 2D, 3B, 4D, 5A, 6C, 7A), (1E, 2D, 3B, 4D, 5A, 6C, 7B), (1E, 2D, 3B, 4D, 5A, 6C, 7C), (1E, 2D, 3B, 4D, 5A, 6D, 7A), (1E, 2D, 3B, 4D, 5A, 6D, 7B), (1E, 2D, 3B, 4D, 5A, 6D, 7C), (1E, 2D, 3B, 4D, 5B, 6A, 7A), (1E, 2D, 3B, 4D, 5B, 6A, 7B), (1E, 2D, 3B, 4D, 5B, 6A, 7C), (1E, 2D, 3B, 4D, 5B, 6B, 7A), (1E, 2D, 3B, 4D, 5B, 6B, 7B), (1E, 2D, 3B, 4D, 5B, 6B, 7C), (1E, 2D, 3B, 4D, 5B, 6C, 7A), (1E, 2D, 3B, 4D, 5B, 6C, 7B), (1E, 2D, 3B, 4D, 5B, 6C, 7C), (1E, 2D, 3B, 4D, 5B, 6D, 7A), (1E, 2D, 3B, 4D, 5B, 6D, 7B), (1E, 2D, 3B, 4D, 5B, 6D, 7C), (1E, 2D, 3B, 4E, 5A, 6A, 7A), (1E, 2D, 3B, 4E, 5A, 6A, 7B), (1E, 2D, 3B, 4E, 5A, 6A, 7C), (1E, 2D, 3B, 4E, 5A, 6B, 7A), (1E, 2D, 3B, 4E, 5A, 6B, 7B), (1E, 2D, 3B, 4E, 5A, 6B, 7C), (1B, 2D, 3B, 4E, 5A, 6C, 7A), (1E, 2D, 3B, 4E, 5A, 6C, 7B), (1E, 2D, 3B, 4E, 5A, 6C, 7C), (1E, 2D, 3B, 4E, 5A, 6D, 7A), (1E, 2D, 3B, 4E, 5A, 6D, 7B), (1E, 2D, 3B, 4E, 5A, 6D, 7C), (1E, 2D, 3B, 4E, 5B, 6A, 7A), (1E, 2D, 3B, 4E, 5B, 6A, 7B), (1E, 2D, 3B, 4E, 5B, 6A, 7C), (1E, 2D, 3B, 4E, 5B, 6B, 7A), (1E, 2D, 3B, 4E, 5B, 6B, 7B), (1E, 2D, 3B, 4E, 5B, 6B, 7C), (1E, 2D, 3B, 4E, 5B, 6C, 7A), (1E, 2D, 3B, 4E, 5B, 6C, 7B), (1E, 2D, 3B, 4E, 5B, 6C, 7C), (1E, 2D, 3B, 4E, 5B, 6D, 7A), (1E, 2D, 3B, 4E, 5B, 6D, 7B), (1E, 2D, 3B, 4E, 5B, 6D, 7C), (1E, 2D, 3C, 4A, 5A, 6A, 7A), (1E, 2D, 3C, 4A, 5A, 6A, 7B), (1E, 2D, 3C, 4A, 5A, 6A, 7C), (1E, 2D, 3C, 4A, 5A, 6B, 7A), (1E, 2D, 3C, 4A, 5A, 6B, 7B), (1E, 2D, 3C, 4A, 5A, 6B, 7C), (1E, 2D, 3C, 4A, 5A, 6C, 7A), (1E, 2D, 3C, 4A, 5A, 6C, 7B), (1E, 2D, 3C, 4A, 5A, 6C, 7C), (1E, 2D, 3C, 4A, 5A, 6D, 7A), (1E, 2D, 3C, 4A, 5A, 6D, 7B), (1E, 2D, 3C, 4A, 5A, 6D, 7C), (1E, 2D, 3C, 4A, 5B, 6A, 7A), (1E, 2D, 3C, 4A, 5B, 6A, 7B), (1E, 2D, 3C, 4A, 5B, 6A, 7C), (1E, 2D, 3C, 4A, 5B, 6B, 7A), (1E, 2D, 3C, 4A, 5B, 6B, 7B), (1E, 2D, 3C, 4A, 5B, 6B, 7C), (1E, 2D, 3C, 4A, 5B, 6C, 7A), (1E, 2D, 3C, 4A, 5B, 6C, 7B), (1E, 2D, 3C, 4A, 5B, 6C, 7C), (1E, 2D, 3C, 4A, 5B, 6D, 7A), (1E, 2D, 3C, 4A, 5B, 6D, 7B), (1E, 2D, 3C, 4A, 5B, 6D, 7C), (1E, 2D, 3C, 4B, 5A, 6A, 7A), (1E, 2D, 3C, 4B, 5A, 6A, 7B), (1E, 2D, 3C, 4B, 5A, 6A, 7C), (1E, 2D, 3C, 4B, 5A, 6B, 7A), (1E, 2D, 3C, 4B, 5A, 6B, 7B), (1E, 2D, 3C, 4B, 5A, 6B, 7C), (1E, 2D, 3C, 4B, 5A, 6C, 7A), (1E, 2D, 3C, 4B, 5A, 6C, 7B), (1E, 2D, 3C, 4B, 5A, 6C, 7C), (1E, 2D, 3C, 4B, 5A, 6D, 7A), (1E, 2D, 3C, 4B, 5A, 6D, 7B), (1E, 2D, 3C, 4B, 5A, 6D, 7C), (1E, 2D, 3C, 4B, 5B, 6A, 7A), (1E, 2D, 3C, 4B, 5B, 6A, 7B), (1E, 2D, 3C, 4B, 5B, 6A, 7C), (1E, 2D, 3C, 4B, 5B, 6B, 7A), (1E, 2D, 3C, 4B, 5B, 6B, 7B), (1E, 2D, 3C, 4B, 5B, 6B, 7C), (1E, 2D, 3C, 4B, 5B, 6C, 7A), (1E, 2D, 3C, 4B, 5B, 6C, 7B), (1E, 2D, 3C, 4B, 5B, 6C, 7C), (1E, 2D, 3C, 4B, 5B, 6D, 7A), (1E, 2D, 3C, 4B, 5B, 6D, 7B), (1E, 2D, 3C, 4B, 5B, 6D, 7C), (1E, 2D, 3C, 4C, 5A, 6A, 7A), (1E, 2D, 3C, 4C, 5A, 6A, 7B), (1E, 2D, 3C, 4C, 5A, 6A, 7C), (1E, 2D, 3C, 4C, 5A, 6B, 7A), (1E, 2D, 3C, 4C, 5A, 6B, 7B), (1E, 2D, 3C, 4C, 5A, 6B, 7C), (1E, 2D, 3C, 4C, 5A, 6C, 7A), (1E, 2D, 3C, 4C, 5A, 6C, 7B), (1E, 2D, 3C, 4C, 5A, 6C, 7C), (1E, 2D, 3C, 4C, 5A, 6D, 7A), (1E, 2D, 3C, 4C, 5A, 6D, 7B), (1E, 2D, 3C, 4C, 5A, 6D, 7C), (1E, 2D, 3C, 4C, 5B, 6A, 7A), (1E, 2D, 3C, 4C, 5B, 6A, 7B), (1E, 2D, 3C, 4C, 5B, 6A, 7C), (1E, 2D, 3C, 4C, 5B, 6B, 7A), (1E, 2D, 3C, 4C, 5B, 6B, 7B), (1E, 2D, 3C, 4C, 5B, 6B, 7C), (1E, 2D, 3C, 4C, 5B, 6C, 7A), (1E, 2D, 3C, 4C, 5B, 6C, 7B), (1E, 2D, 3C, 4C, 5B, 6C, 7C), (1E, 2D, 3C, 4C, 5B, 6D, 7A), (1E, 2D, 3C, 4C, 5B, 6D, 7B), (1E, 2D, 3C, 4C, 5B, 6D, 7C), (1E, 2D, 3C, 4D, 5A, 6A, 7A), (1E, 2D, 3C, 4D, 5A, 6A, 7B), (1E, 2D, 3C, 4D, 5A, 6A, 7C), (1E, 2D, 3C, 4D, 5A, 6B, 7A), (1E, 2D, 3C, 4D, 5A, 6B, 7B), (1E, 2D, 3C, 4D, 5A, 6B, 7C), (1E, 2D, 3C, 4D, 5A, 6C, 7A), (1E, 2D, 3C, 4D, 5A, 6C, 7B), (1E, 2D, 3C, 4D, 5A, 6C, 7C), (1E, 2D, 3C, 4D, 5A, 6D, 7A), (1E, 2D, 3C, 4D, 5A, 6D, 7B), (1E, 2D, 3C, 4D, 5A, 6D, 7C), (1E, 2D, 3C, 4D, 5B, 6A, 7A), (1E, 2D, 3C, 4D, 5B, 6A, 7B), (1E, 2D, 3C, 4D, 5B, 6A, 7C), (1E, 2D, 3C, 4D, 5B, 6B, 7A), (1E, 2D, 3C, 4D, 5B, 6B, 7B), (1E, 2D, 3C, 4D, 5B, 6B, 7C), (1E, 2D, 3C, 4D, 5B, 6C, 7A), (1E, 2D, 3C, 4D, 5B, 6C, 7B), (1E, 2D, 3C, 4D, 5B, 6C, 7C), (1E, 2D, 3C, 4D, 5B, 6D, 7A), (1E, 2D, 3C, 4D, 5B, 6D, 7B), (1E, 2D, 3C, 4D, 5B, 6D, 7C), (1E, 2D, 3C, 4E, 5A, 6A, 7A), (1E, 2D, 3C, 4E, 5A, 6A, 7B), (1E, 2D, 3C, 4E, 5A, 6A, 7C), (1E, 2D, 3C, 4E, 5A, 6B, 7A), (1E, 2D, 3C, 4E, 5A, 6B, 7B), (1E, 2D, 3C, 4E, 5A, 6B, 7C), (1E, 2D, 3C, 4E, 5A, 6C, 7A), (1E, 2D, 3C, 4E, 5A, 6C, 7B), (1E, 2D, 3C, 4E, 5A, 6C, 7C), (1E, 2D, 3C, 4E, 5A, 6D, 7A), (1E, 2D, 3C, 4E, 5A, 6D, 7B), (1E, 2D, 3C, 4E, 5A, 6D, 7C), (1E, 2D, 3C, 4E, 5B, 6A, 7A), (1E, 2D, 3C, 4E, 5B, 6A, 7B), (1E, 2D, 3C, 4E, 5B, 6A, 7C), (1E, 2D, 3C, 4E, 5B, 6B, 7A), (1E, 2D, 3C, 4E, 5B, 6B, 7B), (1E, 2D, 3C, 4E, 5B, 6B, 7C), (1E, 2D, 3C, 4E, 5B, 6C, 7A), (1E, 2D, 3C, 4E, 5B, 6C, 7B), (1E, 2D, 3C, 4E, 5B, 6C, 7C), (1E, 2D, 3C, 4E, 5B, 6D, 7A), (1E, 2D, 3C, 4E, 5B, 6D, 7B), (1E, 2D, 3C, 4E, 5B, 6D, 7C), (1E, 2D, 3D, 4A, 5A, 6A, 7A), (1E, 2D, 3D, 4A, 5A, 6A, 7B), (1E, 2D, 3D, 4A, 5A, 6A, 7C), (1E, 2D, 3D, 4A, 5A, 6B, 7A), (1E, 2D, 3D, 4A, 5A, 6B, 7B), (1E, 2D, 3D, 4A, 5A, 6B, 7C), (1E, 2D, 3D, 4A, 5A, 6C, 7A), (1E, 2D, 3D, 4A, 5A, 6C, 7B), (1E, 2D, 3D, 4A, 5A, 6C, 7C), (1E, 2D, 3D, 4A, 5A, 6D, 7A), (1E, 2D, 3D, 4A, 5A, 6D, 7B), (1E, 2D, 3D, 4A, 5A, 6D, 7C), (1E, 2D, 3D, 4A, 5B, 6A, 7A), (1E, 2D, 3D, 4A, 5B, 6A, 7B), (1E, 2D, 3D, 4A, 5B, 6A, 7C), (1E, 2D, 3D, 4A, 5B, 6B, 7A), (1E, 2D, 3D, 4A, 5B, 6B, 7B), (1E, 2D, 3D, 4A, 5B, 6B, 7C), (1E, 2D, 3D, 4A, 5B, 6C, 7A), (1E, 2D, 3D, 4A, 5B, 6C, 7B), (1E, 2D, 3D, 4A, 5B, 6C, 7C), (1E, 2D, 3D, 4A, 5B, 6D, 7A), (1E, 2D, 3D, 4A, 5B, 6D, 7B), (1E, 2D, 3D, 4A, 5B, 6D, 7C), (1E, 2D, 3D, 4B, 5A, 6A, 7A), (1E, 2D, 3D, 4B, 5A, 6A, 7B), (1E, 2D, 3D, 4B, 5A, 6A, 7C), (1E, 2D, 3D, 4B, 5A, 6B, 7A), (1E, 2D, 3D, 4B, 5A, 6B, 7B), (1E, 2D, 3D, 4B, 5A, 6B, 7C), (1E, 2D, 3D, 4B, 5A, 6C, 7A), (1E, 2D, 3D, 4B, 5A, 6C, 7B), (1E, 2D, 3D, 4B, 5A, 6C, 7C), (1E, 2D, 3D, 4B, 5A, 6D, 7A), (1E, 2D, 3D, 4B, 5A, 6D, 7B), (1E, 2D, 3D, 4B, 5A, 6D, 7C), (1E, 2D, 3D, 4B, 5B, 6A, 7A), (1E, 2D, 3D, 4B, 5B, 6A, 7B), (1E, 2D, 3D, 4B, 5B, 6A, 7C), (1E, 2D, 3D, 4B, 5B, 6B, 7A), (1E, 2D, 3D, 4B, 5B, 6B, 7B), (1E, 2D, 3D, 4B, 5B, 6B, 7C), (1E, 2D, 3D, 4B, 5B, 6C, 7A), (1E, 2D, 3D, 4B, 5B, 6C, 7B), (1E, 2D, 3D, 4B, 5B, 6C, 7C), (1E, 2D, 3D, 4B, 5B, 6D, 7A), (1E, 2D, 3D, 4B, 5B, 6D, 7B), (1E, 2D, 3D, 4B, 5B, 6D, 7C), (1E, 2D, 3D, 4C, 5A, 6A, 7A), (1E, 2D, 3D, 4C, 5A, 6A, 7B), (1E, 2D, 3D, 4C, 5A, 6A, 7C), (1E, 2D, 3D, 4C, 5A, 6B, 7A), (1E, 2D, 3D, 4C, 5A, 6B, 7B), (1E, 2D, 3D, 4C, 5A, 6B, 7C), (1E, 2D, 3D, 4C, 5A, 6C, 7A), (1E, 2D, 3D, 4C, 5A, 6C, 7B), (1E, 2D, 3D, 4C, 5A, 6C, 7C), (1E, 2D, 3D, 4C, 5A, 6D, 7A), (1E, 2D, 3D, 4C, 5A, 6D, 7B), (1E, 2D, 3D, 4C, 5A, 6D, 7C), (1E, 2D, 3D, 4C, 5B, 6A, 7A), (1E, 2D, 3D, 4C, 5B, 6A, 7B), (1E, 2D, 3D, 4C, 5B, 6A, 7C), (1E, 2D, 3D, 4C, 5B, 6B, 7A), (1E, 2D, 3D, 4C, 5B, 6B, 7B), (1E, 2D, 3D, 4C, 5B, 6B, 7C), (1E, 2D, 3D, 4C, 5B, 6C, 7A), (1E, 2D, 3D, 4C, 5B, 6C, 7B), (1E, 2D, 3D, 4C, 5B, 6C, 7C), (1E, 2D, 3D, 4C, 5B, 6D, 7A), (1E, 2D, 3D, 4C, 5B, 6D, 7B), (1E, 2D, 3D, 4C, 5B, 6D, 7C), (1E, 2D, 3D, 4D, 5A, 6A, 7A), (1E, 2D, 3D, 4D, 5A, 6A, 7B), (1E, 2D, 3D, 4D, 5A, 6A, 7C), (1E, 2D, 3D, 4D, 5A, 6B, 7A), (1E, 2D, 3D, 4D, 5A, 6B, 7B), (1E, 2D, 3D, 4D, 5A, 6B, 7C), (1E, 2D, 3D, 4D, 5A, 6C, 7A), (1E, 2D, 3D, 4D, 5A, 6C, 7B), (1E, 2D, 3D, 4D, 5A, 6C, 7C), (1E, 2D, 3D, 4D, 5A, 6D, 7A), (1E, 2D, 3D, 4D, 5A, 6D, 7B), (1E, 2D, 3D, 4D, 5A, 6D, 7C), (1E, 2D, 3D, 4D, 5B, 6A, 7A), (1E, 2D, 3D, 4D, 5B, 6A, 7B), (1E, 2D, 3D, 4D, 5B, 6A, 7C), (1E, 2D, 3D, 4D, 5B, 6B, 7A), (1E, 2D, 3D, 4D, 5B, 6B, 7B), (1E, 2D, 3D, 4D, 5B, 6B, 7C), (1E, 2D, 3D, 4D, 5B, 6C, 7A), (1E, 2D, 3D, 4D, 5B, 6C, 7B), (1E, 2D, 3D, 4D, 5B, 6C, 7C), (1E, 2D, 3D, 4D, 5B, 6D, 7A), (1E, 2D, 3D, 4D, 5B, 6D, 7B), (1E, 2D, 3D, 4D, 5B, 6D, 7C), (1E, 2D, 3D, 4E, 5A, 6A, 7A), (1E, 2D, 3D, 4E, 5A, 6A, 7B), (1E, 2D, 3D, 4E, 5A, 6A, 7C), (1E, 2D, 3D, 4E, 5A, 6B, 7A), (1E, 2D, 3D, 4E, 5A, 6B, 7B), (1E, 2D, 3D, 4E, 5A, 6B, 7C), (1E, 2D, 3D, 4E, 5A, 6C, 7A), (1E, 2D, 3D, 4E, 5A, 6C, 7B), (1E, 2D, 3D, 4E, 5A, 6C, 7C), (1E, 2D, 3D, 4E, 5A, 6D, 7A), (1E, 2D, 3D, 4E, 5A, 6D, 7B), (1E, 2D, 3D, 4E, 5A, 6D, 7C), (1E, 2D, 3D, 4E, 5B, 6A, 7A), (1E, 2D, 3D, 4E, 5B, 6A, 7B), (1E, 2D, 3D, 4E, 5B, 6A, 7C), (1E, 2D, 3D, 4E, 5B, 6B, 7A), (1E, 2D, 3D, 4E, 5B, 6B, 7B), (1E, 2D, 3D, 4E, 5B, 6B, 7C), (1E, 2D, 3D, 4E, 5B, 6C, 7A), (1E, 2D, 3D, 4E, 5B, 6C, 7B), (1E, 2D, 3D, 4E, 5B, 6C, 7C), (1E, 2D, 3D, 4E, 5B, 6D, 7A), (1E, 2D, 3D, 4E, 5B, 6D, 7B), (1E, 2D, 3D, 4E, 5B, 6D, 7C), (1E, 2D, 3E, 4A, 5A, 6A, 7A), (1E, 2D, 3E, 4A, 5A, 6A, 7B), (1E, 2D, 3E, 4A, 5A, 6A, 7C), (1E, 2D, 3E, 4A, 5A, 6B, 7A), (1E, 2D, 3E, 4A, 5A, 6B, 7B), (1E, 2D, 3E, 4A, 5A, 6B, 7C), (1E, 2D, 3E, 4A, 5A, 6C, 7A), (1E, 2D, 3E, 4A, 5A, 6C, 7B), (1E, 2D, 3E, 4A, 5A, 6C, 7C), (1E, 2D, 3E, 4A, 5A, 6D, 7A), (1E, 2D, 3E, 4A, 5A, 6D, 7B), (1E, 2D, 3E, 4A, 5A, 6D, 7C), (1E, 2D, 3E, 4A, 5B, 6A, 7A), (1E, 2D, 3E, 4A, 5B, 6A, 7B), (1E, 2D, 3E, 4A, 5B, 6A, 7C), (1E, 2D, 3E, 4A, 5B, 6B, 7A), (1E, 2D, 3E, 4A, 5B, 6B, 7B), (1E, 2D, 3E, 4A, 5B, 6B, 7C), (1E, 2D, 3E, 4A, 5B, 6C, 7A), (1E, 2D, 3E, 4A, 5B, 6C, 7B), (1E, 2D, 3E, 4A, 5B, 6C, 7C), (1E, 2D, 3E, 4A, 5B, 6D, 7A), (1E, 2D, 3E, 4A, 5B, 6D, 7B), (1E, 2D, 3E, 4A, 5B, 6D, 7C), (1E, 2D, 3E, 4B, 5A, 6A, 7A), (1E, 2D, 3E, 4B, 5A, 6A, 7B), (1E, 2D, 3E, 4B, 5A, 6A, 7C), (1E, 2D, 3E, 4B, 5A, 6B, 7A), (1E, 2D, 3E, 4B, 5A, 6B, 7B), (1E, 2D, 3E, 4B, 5A, 6B, 7C), (1E, 2D, 3E, 4B, 5A, 6C, 7A), (1E, 2D, 3E, 4B, 5A, 6C, 7B), (1E, 2D, 3E, 4B, 5A, 6C, 7C), (1E, 2D, 3E, 4B, 5A, 6D, 7A), (1E, 2D, 3E, 4B, 5A, 6D, 7B), (1E, 2D, 3E, 4B, 5A, 6D, 7C), (1E, 2D, 3E, 4B, 5B, 6A, 7A), (1E, 2D, 3E, 4B, 5B, 6A, 7B), (1E, 2D, 3E, 4B, 5B, 6A, 7C), (1E, 2D, 3E, 4B, 5B, 6B, 7A), (1E, 2D, 3E, 4B, 5B, 6B, 7B), (1E, 2D, 3E, 4B, 5B, 6B, 7C), (1E, 2D, 3E, 4B, 5B, 6C, 7A), (1E, 2D, 3E, 4B, 5B, 6C, 7B), (1E, 2D, 3E, 4B, 5B, 6C, 7C), (1E, 2D, 3E, 4B, 5B, 6D, 7A), (1E, 2D, 3E, 4B, 5B, 6D, 7B), (1E, 2D, 3E, 4B, 5B, 6D, 7C), (1E, 2D, 3E, 4C, 5A, 6A, 7A), (1E, 2D, 3E, 4C, 5A, 6A, 7B), (1E, 2D, 3E, 4C, 5A, 6A, 7C), (1E, 2D, 3E, 4C, 5A, 6B, 7A), (1E, 2D, 3E, 4C, 5A, 6B, 7B), (1E, 2D, 3E, 4C, 5A, 6B, 7C), (1E, 2D, 3E, 4C, 5A, 6C, 7A), (1E, 2D, 3E, 4C, 5A, 6C, 7B), (1E, 2D, 3E, 4C, 5A, 6C, 7C), (1E, 2D, 3E, 4C, 5A, 6D, 7A), (1E, 2D, 3E, 4C, 5A, 6D, 7B), (1E, 2D, 3E, 4C, 5A, 6D, 7C), (1E, 2D, 3E, 4C, 5B, 6A, 7A), (1E, 2D, 3E, 4C, 5B, 6A, 7B), (1E, 2D, 3E, 4C, 5B, 6A, 7C), (1E, 2D, 3E, 4C, 5B, 6B, 7A), (1E, 2D, 3E, 4C, 5B, 6B, 7B), (1E, 2D, 3E, 4C, 5B, 6B, 7C), (1E, 2D, 3E, 4C, 5B, 6C, 7A), (1E, 2D, 3E, 4C, 5B, 6C, 7B), (1E, 2D, 3E, 4C, 5B, 6C, 7C), (1E, 2D, 3E, 4C, 5B, 6D, 7A), (1E, 2D, 3E, 4C, 5B, 6D, 7B), (1E, 2D, 3E, 4C, 5B, 6D, 7C), (1E, 2D, 3E, 4D, 5A, 6A, 7A), (1E, 2D, 3E, 4D, 5A, 6A, 7B), (1E, 2D, 3E, 4D, 5A, 6A, 7C), (1E, 2D, 3E, 4D, 5A, 6B, 7A), (1E, 2D, 3E, 4D, 5A, 6B, 7B), (1E, 2D, 3E, 4D, 5A, 6B, 7C), (1E, 2D, 3E, 4D, 5A, 6C, 7A), (1E, 2D, 3E, 4D, 5A, 6C, 7B), (1E, 2D, 3E, 4D, 5A, 6C, 7C), (1E, 2D, 3E, 4D, 5A, 6D, 7A), (1E, 2D, 3E, 4D, 5A, 6D, 7B), (1E, 2D, 3E, 4D, 5A, 6D, 7C), (1E, 2D, 3E, 4D, 5B, 6A, 7A), (1E, 2D, 3E, 4D, 5B, 6A, 7B), (1E, 2D, 3E, 4D, 5B, 6A, 7C), (1E, 2D, 3E, 4D, 5B, 6B, 7A), (1E, 2D, 3E, 4D, 5B, 6B, 7B), (1E, 2D, 3E, 4D, 5B, 6B, 7C), (1E, 2D, 3E, 4D, 5B, 6C, 7A), (1E, 2D, 3E, 4D, 5B, 6C, 7B), (1E, 2D, 3E, 4D, 5B, 6C, 7C), (1E, 2D, 3E, 4D, 5B, 6D, 7A), (1E, 2D, 3E, 4D, 5B, 6D, 7B), (1E, 2D, 3E, 4D, 5B, 6D, 7C), (1E, 2D, 3E, 4E, 5A, 6A, 7A), (1E, 2D, 3E, 4E, 5A, 6A, 7B), (1E, 2D, 3E, 4E, 5A, 6A, 7C), (1E, 2D, 3E, 4E, 5A, 6B, 7A), (1E, 2D, 3E, 4E, 5A, 6B, 7B), (1E, 2D, 3E, 4E, 5A, 6B, 7C), (1E, 2D, 3E, 4E, 5A, 6C, 7A), (1E, 2D, 3E, 4E, 5A, 6C, 7B), (1E, 2D, 3E, 4E, 5A, 6C, 7C), (1E, 2D, 3E, 4E, 5A, 6D, 7A), (1E, 2D, 3E, 4E, 5A, 6D, 7B), (1E, 2D, 3E, 4E, 5A, 6D, 7C), (1E, 2D, 3E, 4E, 5B, 6A, 7A), (1E, 2D, 3E, 4E, 5B, 6A, 7B), (1E, 2D, 3E, 4E, 5B, 6A, 7C), (1E, 2D, 3E, 4E, 5B, 6B, 7A), (1E, 2D, 3E, 4E, 5B, 6B, 7B), (1E, 2D, 3E, 4E, 5B, 6B, 7C), (1E, 2D, 3E, 4E, 5B, 6C, 7A), (1E, 2D, 3E, 4E, 5B, 6C, 7B), (1E, 2D, 3E, 4E, 5B, 6C, 7C), (1E, 2D, 3E, 4E, 5B, 6D, 7A), (1E, 2D, 3E, 4E, 5B, 6D, 7B), (1E, 2D, 3E, 4E, 5B, 6D, 7C), (1E, 2E, 3A, 4A, 5A, 6A, 7A), (1E, 2E, 3A, 4A, 5A, 6A, 7B), (1E, 2E, 3A, 4A, 5A, 6A, 7C), (1E, 2E, 3A, 4A, 5A, 6B, 7A), (1E, 2E, 3A, 4A, 5A, 6B, 7B), (1E, 2E, 3A, 4A, 5A, 6B, 7C), (1E, 2E, 3A, 4A, 5A, 6C, 7A), (1E, 2E, 3A, 4A, 5A, 6C, 7B), (1E, 2E, 3A, 4A, 5A, 6C, 7C), (1E, 2E, 3A, 4A, 5A, 6D, 7A), (1E, 2E, 3A, 4A, 5A, 6D, 7B), (1E, 2E, 3A, 4A, 5A, 6D, 7C), (1E, 2E, 3A, 4A, 5B, 6A, 7A), (1E, 2E, 3A, 4A, 5B, 6A, 7B), (1E, 2E, 3A, 4A, 5B, 6A, 7C), (1E, 2E, 3A, 4A, 5B, 6B, 7A), (1E, 2E, 3A, 4A, 5B, 6B, 7B), (1E, 2E, 3A, 4A, 5B, 6B, 7C), (1E, 2E, 3A, 4A, 5B, 6C, 7A), (1E, 2E, 3A, 4A, 5B, 6C, 7B), (1E, 2E, 3A, 4A, 5B, 6C, 7C), (1E, 2E, 3A, 4A, 5B, 6D, 7A), (1E, 2E, 3A, 4A, 5B, 6D, 7B), (1E, 2E, 3A, 4A, 5B, 6D, 7C), (1E, 2E, 3A, 4B, 5A, 6A, 7A), (1E, 2E, 3A, 4B, 5A, 6A, 7B), (1E, 2E, 3A, 4B, 5A, 6A, 7C), (1E, 2E, 3A, 4B, 5A, 6B, 7A), (1E, 2E, 3A, 4B, 5A, 6B, 7B) (1E, 2E, 3A, 4B, 5A, 6B, 7C), (1E, 2E, 3A, 4B, 5A, 6C, 7A), (1E, 2E, 3A, 4B, 5A, 6C, 7B), (1E, 2E, 3A, 4B, 5A, 6C, 7C), (1E, 2E, 3A, 4B, 5A, 6D, 7A), (1E, 2E, 3A, 4B, 5A, 6D, 7B), (1E, 2E, 3A, 4B, 5A, 6D, 7C), (1E, 2E, 3A, 4B, 5B, 6A, 7A), (1E, 2E, 3A, 4B, 5B, 6A, 7B), (1E, 2E, 3A, 4B, 5B, 6A, 7C), (1E, 2E, 3A, 4B, 5B, 6B, 7A), (1E, 2E, 3A, 4B, 5B, 6B, 7B), (1E, 2E, 3A, 4B, 5B, 6B, 7C), (1E, 2E, 3A, 4B, 5B, 6C, 7A), (1E, 2E, 3A, 4B, 5B, 6C, 7B), (1E, 2E, 3A, 4B, 5B, 6C, 7C), (1E, 2E, 3A, 4B, 5B, 6D, 7A), (1E, 2E, 3A, 4B, 5B, 6D, 7B), (1E, 2E, 3A, 4B, 5B, 6D, 7C), (1E, 2E, 3A, 4C, 5A, 6A, 7A), (1E, 2E, 3A, 4C, 5A, 6A, 7B), (1E, 2E, 3A, 4C, 5A, 6A, 7C), (1E, 2E, 3A, 4C, 5A, 6B, 7A), (1E, 2E, 3A, 4C, 5A, 6B, 7B), (1E, 2E, 3A, 4C, 5A, 6C, 7A), (1E, 2E, 3A, 4C, 5A, 6C, 7B), (1E, 2E, 3A, 4C, 5A, 6C, 7C), (1E, 2E, 3A, 4C, 5A, 6D, 7A), (1E, 2E, 3A, 4C, 5A, 6D, 7B), (1E, 2E, 3A, 4C, 5A, 6D, 7C), (1E, 2E, 3A, 4C, 5B, 6A, 7A), (1E, 2E, 3A, 4C, 5B, 6A, 7B), (1E, 2E, 3A, 4C, 5B, 6A, 7C), (1E, 2E, 3A, 4C, 5B, 6B, 7A), (1E, 2E, 3A, 4C, 5B, 6B, 7B), (1E, 2E, 3A, 4C, 5B, 6B, 7C), (1E)2E, 3A, 4C, 5B, 6C, 7A), (1E, 2E, 3A, 4C, 5B, 6C, 7B), (1E, 2E, 3A, 4C, 5B, 6C, 7C), (1E, 2E, 3A, 4C, 5B, 6D, 7A), (1E, 2E, 3A, 4C, 5B, 6D, 7B), (1E, 2E, 3A, 4C, 5B, 6D, 7C), (1E, 2E, 3A, 4D, 5A, 6A, 7A), (1E, 2E, 3A, 4D, 5A, 6A, 7B), (1E, 2E, 3A, 4D, 5A, 6A, 7C), (1E, 2E, 3A, 4D, 5A, 6B, 7A), (1E, 2E, 3A, 4D, 5A, 6B, 7B), (1E, 2E, 3A, 4D, 5A, 6B, 7C), (1E, 2E, 3A, 4D, 5A, 6C, 7A), (1E, 2E, 3A, 4D, 5A, 6C, 7B), (1E, 2E, 3A, 4D, 5A, 6C, 7C), (1E, 2E, 3A, 4D, 5A, 6D, 7A), (1E, 2E, 3A, 4D, 5A, 6D, 7B), (1E, 2E, 3A, 4D, 5A, 6D, 7C), (1E, 2E, 3A, 4D, 5B, 6A, 7A), (1E, 2E, 3A, 4D, 5B, 6A, 7B), (1E, 2E, 3A, 4D, 5B, 6A, 7C), (1E, 2E, 3A, 4D, 5B, 6B, 7A), (1E, 2E, 3A, 4D, 5B, 6B, 7B), (1E, 2E, 3A, 4D, 5B, 6B, 7C), (1E, 2E, 3A, 4D, 5B, 6C, 7A), (1E, 2E, 3A, 4D, 5B, 6C, 7B), (1E, 2E, 3A, 4D, 5B, 6C, 7C), (1E, 2E, 3A, 4D, 5B, 6D, 7A), (1E, 2E, 3A, 4D, 5B, 6D, 7B), (1E, 2E, 3A, 4D, 5B, 6D, 7C), (1E, 2E, 3A, 4E, 5A, 6A, 7A), (1E, 2E, 3A, 4E, 5A, 6A, 7B), (1E, 2E, 3A, 4E, 5A, 6A, 7C), (1E, 2E, 3A, 4E, 5A, 6B, 7A), (1E, 2E, 3A, 4E, 5A, 6B, 7B), (1E, 2E, 3A, 4E, 5A, 6B, 7C), (1E, 2E, 3A, 4E, 5A, 6C, 7A), (1E, 2E, 3A, 4E, 5A, 6C, 7B), (1E, 2E, 3A, 4E, 5A, 6C, 7C), (1E, 2E, 3A, 4E, 5A, 6D, 7A), (1E, 2E, 3A, 4E, 5A, 6D, 7B), (1E, 2E, 3A, 4E, 5A, 6D, 7C), (1E, 2E, 3A, 4E, 5B, 6A, 7A), (1E, 2E, 3A, 4E, 5B, 6A, 7B), (1E, 2E, 3A, 4E, 5B, 6A, 7C), (1E, 2E, 3A, 4E, 5B, 6B, 7A), (1E, 2E, 3A, 4E, 5B, 6B, 7B), (1E, 2E, 3A, 4E, 5B, 6B, 7C), (1E, 2E, 3A, 4E, 5B, 6C, 7A), (1E, 2E, 3A, 4E, 5B, 6C, 7B), (1E, 2E, 3A, 4E, 5B, 6C, 7C), (1E, 2E, 3A, 4E, 5B, 6D, 7A), (1E, 2E, 3A, 4E, 5B, 6D, 7B), (1E, 2E, 3A, 4E, 5B, 6D, 7C), (1E, 2E, 3B, 4A, 5A, 6A, 7A), (1E, 2E, 3B, 4A, 5A, 6A, 7B), (1E, 2E, 3B, 4A, 5A, 6A, 7C), (1E, 2E, 3B, 4A, 5A, 6B, 7A), (1E, 2E, 3B, 4A, 5A, 6B, 7B), (1E, 2E, 3B, 4A, 5A, 6B, 7C), (1E, 2E, 3B, 4A, 5A, 6C, 7A), (1E, 2E, 3B, 4A, 5A, 6C, 7B), (1E, 2E, 3B, 4A, 5A, 6C, 7C), (1E, 2E, 3B, 4A, 5A, 6D, 7A), (1E, 2E, 3B, 4A, 5A, 6D, 7B), (1E, 2E, 3B, 4A, 5A, 6D, 7C), (1E, 2E, 3B, 4A, 5B, 6A, 7A), (1E, 2E, 3B, 4A, 5B, 6A, 7B), (1E, 2E, 3B, 4A, 5B, 6A, 7C), (1E, 2E, 3B, 4A, 5B, 6B, 7A), (1E, 2E, 3B, 4A, 5B, 6B, 7B), (1E, 2E, 3B, 4A, 5B, 6B, 7C), (1E, 2E, 3B, 4A, 5B, 6C,

7A), (1E, 2E, 3B, 4A, 5B, 6C, 7B), (1E, 2E, 3B, 4A, 5B, 6C, 7C), (1E, 2E, 3B, 4A, 5B, 6D, 7A), (1E, 2E, 3B, 4A, 5B, 6D, 7B), (1E, 2E, 3B, 4A, 5B, 6D, 7C), (1E, 2E, 3B, 4B, 5A, 6A, 7A), (1E, 2E, 3B, 4B, 5A, 6A, 7B), (1E, 2E, 3B, 4B, 5A, 6A, 7C), (1E, 2E, 3B, 4B, 5A, 6B, 7A), (1E, 2E, 3B, 4B, 5A, 6B, 7B), (1E, 2E, 3B, 4B, 5A, 6B, 7C), (1E, 2E, 3B, 4B, 5A, 6C, 7A), (1E, 2E, 3B, 4B, 5A, 6C, 7B), (1E, 2E, 3B, 4B, 5A, 6C, 7C), (1E, 2C, 3B, 4B, 5A, 6D, 7A), (1E, 2E, 3B, 4B, 5A, 6D, 7B), (1E, 2E, 3B, 4B, 5A, 6D, 7C), (1E, 2E, 3B, 4B, 5B, 6A, 7A), (1E, 2E, 3B, 4B, 5B, 6A, 7B), (1E, 2E, 3B, 4B, 5B, 6A, 7C), (1E, 2E, 3B, 4B, 5B, 6B, 7A), (1E, 2E, 3B, 4B, 5B, 6B, 7B), (1E, 2E, 3B, 4B, 5B, 6B, 7C), (1E, 2E, 3B, 4B, 5B, 6C, 7A), (1E, 2E, 3B, 4B, 5B, 6C, 7B), (1E, 2E, 3B, 4B, 5B, 6C, 7C), (1E, 2E, 3B, 4B, 5B, 6D, 7A), (1E, 2E, 3B, 4B, 5B, 6D, 7B), (1E, 2E, 3B, 4B, 5B, 6D, 7C), (1E, 2E, 3B, 4C, 5A, 6A, 7A), (1E, 2E, 3B, 4C, 5A, 6A, 7B), (1E, 2E, 3B, 4C, 5A, 6A, 7C), (1E, 2E, 3B, 4C, 5A, 6B, 7A), (1E, 2E, 3B, 4C, 5A, 6B, 7B), (1E, 2E, 3B, 4C, 5A, 6B, 7C), (1E, 2E, 3B, 4C, 5A, 6C, 7A), (1E, 2E, 3B, 4C, 5A, 6C, 7B), (1E, 2E, 3B, 4C, 5A, 6C, 7C), (1E, 2E, 3B, 4C, 5A, 6D, 7A), (1E, 2E, 3B, 4C, 5A, 6D, 7B), (1E, 2E, 3B, 4C, 5A, 6D, 7C), (1E, 2E, 3B, 4C, 5B, 6A, 7A), (1E, 2E, 3B, 4C, 5B, 6A, 7B), (1E, 2E, 3B, 4C, 5B, 6A, 7C), (1E, 2E, 3B, 4C, 5B, 6B, 7A), (1E, 2E, 3B, 4C, 5B, 6B, 7B), (1E, 2E, 3B, 4C, 5B, 6B, 7C), (1E, 2E, 3B, 4C, 5B, 6C, 7A), (1E, 2E, 3B, 4C, 5B, 6C, 7B), (1E, 2E, 3B, 4C, 5B, 6C, 7C), (1E, 2E, 3B, 4C, 5B, 6D, 7A), (1E, 2E, 3B, 4C, 5B, 6D, 7B), (1E, 2E, 3B, 4C, 5B, 6D, 7C), (1E, 2E, 3B, 4D, 5A, 6A, 7A), (1E, 2E, 3B, 4D, 5A, 6A, 7B), (1E, 2E, 3B, 4D, 5A, 6A, 7C), (1E, 2E, 3B, 4D, 5A, 6B, 7A), (1E, 2E, 3B, 4D, 5A, 6B, 7B), (1E, 2E, 3B, 4D, 5A, 6B, 7C), (1E, 2E, 3B, 4D, 5A, 6C, 7A), (1E, 2E, 3B, 4D, 5A, 6C, 7B), (1E, 2E, 3B, 4D, 5A, 6C, 7C), (1E, 2E, 3B, 4D, 5A, 6D, 7A), (1E, 2E, 3B, 4D, 5A, 6D, 7B), (1E, 2E, 3B, 4D, 5A, 6D, 7C), (1E, 2E, 3B, 4D, 5B, 6A, 7A), (1E, 2E, 3B, 4D, 5B, 6A, 7B), (1E, 2E, 3B, 4D, 5B, 6A, 7C), (1E, 2E, 3B, 4D, 5B, 6B, 7A), (1E, 2E, 3B, 4D, 5B, 6B, 7B, (1E, 2E, 3B, 4D, 5B, 6B, 7C), (1E, 2E, 3B, 4D, 5B, 6C, 7A), (1E, 2E, 3B, 4D, 5B, 6C, 7B), (1E, 2E, 3B, 4D, 5B, 6C, 7C), (1E, 2E, 3B, 4D, 5B, 6D, 7A), (1E, 2E, 3B, 4D, 5B, 6D, 7B), (1E, 2E, 3B, 4D, 5B, 6D, 7C), (1E, 2E, 3B, 4E, 5A, 6A, 7A), (1E, 2E, 3B, 4E, 5A, 6A, 7B), (1E, 2E, 3B, 4E, 5A, 6A, 7C), (1E, 2E, 3B, 4E, 5A, 6B, 7A), (1E, 2E, 3B, 4E, 5A, 6B, 7B), (1E, 2E, 3B, 4E, 5A, 6B, 7C), (1E, 2E, 3B, 4E, 5A, 6C, 7A), (1E, 2E, 3B, 4E, 5A, 6C, 7B), (1E, 2E, 3B, 4E, 5A, 6C, 7C), (1E, 2E, 3B, 4E, 5A, 6D, 7A), (1E, 2E, 3B, 4E, 5A, 6D, 7B), (1E, 2E, 3B, 4E, 5A, 6D, 7C), (1E, 2E, 3B, 4E, 5B, 6A, 7A), (1E, 2E, 3B, 4E, 5B, 6A, (B), (1E, 2E, 3B, 4E, 5B, 6A, 7C), (1E, 2E, 3B, 4E, 5B, 6B, 7A), (1E, 2E, 3B, 4E, 5B, 6B, 7B), (1E, 2E, 3B, 4E, 5B, 6B, 7C), (1E, 2E, 3B, 4E, 5B, 6C, 7A), (1E, 2E, 3B, 4E, 5B, 6C, 7B), (1E, 2E, 3B, 4E, 5B, 6C, 7C), (1E, 2E, 3B, 4E, 5B, 6D, 7A), (1E, 2E, 3B, 4E, 5B, 6D, 7B), (1E, 2E, 3B, 4E, 5B, 6D, 7C), (1E, 2E, 3C, 4A, 5A, 6A, 7A), (1E, 2E, 3C, 4A, 5A, 6A, 7B), (1E, 2E, 3C, 4A, 5A, 6A, 7C), (1E, 2E, 3C, 4A, 5A, 6B, 7A), (1E, 2E, 3C, 4A, 5A, 6B, 7B), (1E, 2E, 3C, 4A, 5A, 6B, 7C), (1E, 2E, 3C, 4A, 5A, 6C, 7A), (1E, 2E, 3C, 4A, 5A, 6C, 7B), (1E, 2E, 3C, 4A, 5A, 6C, 7C), (1E, 2E, 3C, 4A, 5A, 6D, 7A), (1E, 2E, 3C, 4A, 5A, 6D, 7B), (1E, 2E, 3C, 4A, 5A, 6D, 7C), (1E, 2E, 3C, 4A, 5B, 6A, 7A), (1E, 2E, 3C, 4A, 5B, 6A, 7B), (1E, 2E, 3C, 4A, 5B, 6A, 7C), (1E, 2E, 3C, 4A, 5B, 6B, 7A), (1E, 2E, 3C, 4A, 5B, 6B, 7B), (1E, 2E, 3C, 4A, 5B, 6B, 7C), (1E, 2E, 3C, 4A, 5B, 6C, 7A), (1E, 2E, 3C, 4A, 5B, 6C, 7B), (1E, 2E, 3C, 4A, 5B, 6C, 7C), (1E, 2E, 3C, 4A, 5B, 6D, 7A), (1E, 2E, 3C, 4A, 5B, 6D, 7B), (1E, 2E, 3C, 4A, 5B, 6D, 7C), (1E, 2E, 3C, 4B, 5A, 6A, 7A), (1E, 2E, 3C, 4B, 5A, 6A, 7B), (1E, 2E, 3C, 4B, 5A, 6A, 7C), (1E, 2E, 3C, 4B, 5A, 6B, 7A), (1E, 2E, 3C, 4B, 5A, 6B, 7B), (1E, 2E, 3C, 4B, 5A, 6B, 7C), (1E, 2E, 3C, 4B, 5A, 6C, 7A), (1E, 2E, 3C, 4B, 5A, 6C, 7B), (1E, 2E, 3C, 4B, 5A, 6C, 7C), (1E, 2E, 3C, 4B, 5A, 6D, 7A), (1E, 2E, 3C, 4B, 5A, 6D, 7B), (1E, 2E, 3C, 4B, 5A, 6D, 7C), (1E, 2E, 3C, 4B, 5B, 6A, 7A), (1E, 2E, 3C, 4B, 5B, 6A, 7B), (1E, 2E, 3C, 4B, 5B, 6A, 7C), (1E, 2E, 3C, 4B, 5B, 6B, 7A), (1E, 2E, 3C, 4B, 5B, 6B, 7B), (1E, 2E, 3C, 4B, 5B, 6B, 7C), (1E, 2E, 3C, 4B, 5B, 6C, 7A), (1E, 2E, 3C, 4B, 5B, 6C, 7B), (1E, 2E, 3C, 4B, 5B, 6C, 7C), (1E, 2E, 3C, 4B, 5B, 6D, 7A), (1E, 2E, 3C, 4B, 5B, 6D, 7B), (1E, 2E, 3C, 4B, 5B, 6D, 7C), (1E, 2E, 3C, 4C, 5A, 6A, 7A), (1E, 2E, 3C, 4C, 5A, 6A, 7B), (1E, 2E, 3C, 4C, 5A, 6A, 7C), (1E, 2E, 3C, 4C, 5A, 6B, 7A), (1E, 2E, 3C, 4C, 5A, 6B, 7B), (1E, 2E, 3C, 4C, 5A, 6B, 7C), (1E, 2E, 3C, 4C, 5A, 6C, 7A), (1E, 2E, 3C, 4C, 5A, 6C, 7B), (1E, 2E, 3C, 4C, 5A, 6C, 7C), (1E, 2E, 3C, 4C, 5A, 6D, 7A), (1E, 2E, 3C, 4C, 5A, 6D, 7B), (1E, 2E, 3C, 4C, 5A, 6D, 7C), (1E, 2E, 3C, 4C, 5B, 6A, 7A), (1E, 2E, 3C, 4C, 5B, 6A, 7B), (1E, 2E, 3C, 4C, 5B, 6A, 7C), (1E, 2E, 3C, 4C, 5B, 6B, 7A), (1E, 2E, 3C, 4C, 5B, 6B, 7B), (1E, 2E, 3C, 4C, 5B, 6B, 7C), (1E, 2E, 3C, 4C, 5B, 6C, 7A), (1E, 2E, 3C, 4C, 5B, 6C, 7B), (1E, 2E, 3C, 4C, 5B, 6C, 7C), (1E, 2E, 3C, 4C, 5B, 6D, 7A), (1E, 2E, 3C, 4C, 5B, 6D, 7B), (1E, 2E, 3C, 4C, 5B, 6D, 7C), (1E, 2E, 3C, 4D, 5A, 6A, 7A), (1E, 2E, 3C, 4D, 5A, 6A, 7B), (1E, 2E, 3C, 4D, 5A, 6A, 7C), (1E, 2E, 3C, 4D, 5A, 6B, 7A), (1E, 2E, 3C, 4D, 5A, 6B, 7B), (1E, 2E, 3C, 4D, 5A, 6B, 7C), (1E, 2E, 3C, 4D, 5A, 6C, 7A), (1E, 2E, 3C, 4D, 5A, 6C, 7B), (1E, 2E, 3C, 4D, 5A, 6C, 7C), (1E, 2E, 3C, 4D, 5A, 6D, 7A), (1E, 2E, 3C, 4D, 5A, 6D, 7B), (1E, 2E, 3C, 4D, 5A, 6D, 7C), (1E, 2E, 3C, 4D, 5B, 6A, 7A), (1E, 2E, 3C, 4D, 5B, 6A, 7B), (1E, 2E, 3C, 4D, 5B, 6A, 7C), (1E, 2E, 3C, 4D, 5B, 6B, 7A), (1E, 2E, 3C, 4D, 5B, 6B, 7B), (1E, 2E, 3C, 4D, 5B, 6B, 7C), (1E, 2E, 3C, 4D, 5B, 6C, 7A), (1E, 2E, 3C, 4D, 5B, 6C, 7B), (1E, 2E, 3C, 4D, 5B, 6C, 7C), (1E, 2E, 3C, 4D, 5B, 6D, 7A), (1E, 2E, 3C, 4D, 5B, 6D, 7B), (1E, 2E, 3C, 4D, 5B, 6D, 7C), (1E, 2E, 3C, 4E, 5A, 6A, 7A), (1E, 2E, 3C, 4E, 5A, 6A, 7B), (1E, 2E, 3C, 4E, 5A, 6A, 7C), (1E, 2E, 3C, 4E, 5A, 6B, 7A), (1E, 2E, 3C, 4E, 5A, 6B, 7B), (1E, 2E, 3C, 4E, 5A, 6B, 7C), (1E, 2E, 3C, 4E, 5A, 6C, 7A), (1E, 2E, 3C, 4E, 5A, 6C, 7B), (1E, 2E, 3C, 4E, 5A, 6C, 7C), (1E, 2E, 3C, 4E, 5A, 6D, 7A), (1E, 2E, 3C, 4E, 5A, 6D, 7B), (1E, 2E, 3C, 4E, 5A, 6D, 7C), (1E, 2E, 3C, 4E, 5B, 6A, 7A), (1E, 2E, 3C, 4E, 5B, 6A, 7B), (1E, 2E, 3C, 4E, 5B, 6A, 7C), (1E, 2E, 3C, 4E, 5B, 6B, 7A), (1E, 2E, 3C, 4E, 5B, 6B, 7B), (1E, 2E, 3C, 4E, 5B, 6B, 7C), (1E, 2E, 3C, 4E, 5B, 6C, 7A), (1E, 2E, 3C, 4E, 5B, 6C, 7B), (1E, 2E, 3C, 4E, 5B, 6C, 7C), (1E, 2E, 3C, 4E, 5B, 6D, 7A), (1E, 2E, 3C, 4E, 5B, 6D, 7B), (1E, 2E, 3C, 4E, 5B, 6D, 7C), (1E, 2E, 3D, 4A, 5A, 6A, 7A), (1E, 2E, 3D, 4A, 5A, 6A, 7B), (1E, 2E, 3D, 4A, 5A, 6A, 7C), (1E, 2E, 3D, 4A, 5A, 6B, 7A), (1E, 2E, 3D, 4A, 5A, 6B, 7B), (1E, 2E, 3D, 4A, 5A, 6B, 7C), (1E, 2E, 3D, 4A, 5A, 6C, 7A), (1E, 2E, 3D, 4A, 5A, 6C, 7B), (1E, 2E, 3D, 4A, 5A, 6C, 7C), (1E, 2E, 3D, 4A, 5A, 6D, 7A), (1E, 2E, 3D, 4A, 5A, 6D, 7B), (1E, 2E, 3D, 4A, 5A, 6D, 7C), (1E, 2E, 3D, 4A, 5B, 6A, 7A), (1E, 2E, 3D, 4A, 5B, 6A, 7B), (1E, 2E, 3D, 4A, 5B, 6A, 7C), (1E, 2E, 3D, 4A, 5B, 6B, 7A), (1E, 2E, 3D, 4A, 5B, 6B, 7B), (1E, 2E, 3D, 4A, 5B, 6B, 7C), (1E, 2E, 3D, 4A, 5B, 6C, 7A), (1E, 2E, 3D, 4A, 5B, 6C, 7B), (1E, 2E, 3D, 4A, 5B, 6C, 7C), (1E, 2E, 3D, 4A, 5B, 6D, 7A), (1E, 2E, 3D, 4A, 5B, 6D, 7B), (1E, 2E, 3D, 4A, 5B, 6D, 7C), (1E, 2E, 3D, 4B, 5A, 6A, 7A), (1E, 2E, 3D, 4B, 5A, 6A, 7B), (1E, 2E, 3D, 4B, 5A, 6A, 7C), (1E, 2E, 3D, 4B, 5A, 6B, 7A), (1E, 2E, 3D, 4B, 5A, 6B, 7B), (1E, 2E, 3D, 4B, 5A, 6B, 7C), (1E, 2E, 3D, 4B, 5A, 6C, 7A), (1E, 2E, 3D, 4B, 5A, 6C, 7B), (1E, 2E, 3D, 4B, 5A, 6C, 7C), (1E, 2E, 3D, 4B, 5A, 6D, 7A), (1E, 2E, 3D, 4B, 5A, 6D, 7B), (1E, 2E, 3D, 4B, 5A, 6D, 7C), (1E, 2E, 3D, 4B, 5B, 6A, 7A), (1E, 2E, 3D, 4B, 5B, 6A, 7B), (1E, 2E, 3D, 4B, 5B, 6A, 7C), (1E, 2E, 3D, 4B, 5B, 6B, 7A), (1E, 2E, 3D, 4B, 5B, 6B, 7B), (1E, 2E, 3D, 4B, 5B, 6B, 7C), (1E, 2E, 3D, 4B, 5B, 6C, 7A), (1E, 2E, 3D, 4B, 5B, 6C, 7B), (1E, 2E, 3D, 4B, 5B, 6C, 7C), (1E, 2E, 3D, 4B, 5B, 6D, 7A), (1E, 2E, 3D, 4B, 5B, 6D, 7B), (1E, 2E, 3D, 4B, 5B, 6D, 7C), (1E, 2E, 3D, 4C, 5A, 6A, 7A), (1E, 2E, 3D, 4C, 5A, 6A, 7B), (1E, 2E, 3D, 4C, 5A, 6A, 7C), (1E, 2E, 3D, 4C, 5A, 6B, 7A), (1E, 2E, 3D, 4C, 5A, 6B, 7B), (1E, 2E, 3D, 4C, 5A, 6B, 7C), (1E, 2E, 3D, 4C, 5A, 6C, 7A), (1E, 2E, 3D, 4C, 5A, 6C, 7B), (1E, 2E, 3D, 4C, 5A, 6C, 7C), (1E, 2E, 3D, 4C, 5A, 6D, 7A), (1E, 2E, 3D, 4C, 5A, 6D, 7B), (1E, 2E, 3D, 4C, 5A, 6D, 7C), (1E, 2E, 3D, 4C, 5B, 6A, 7A), (1E, 2E, 3D, 4C, 5B, 6A, 7B), (1E, 2E, 3D, 4C, 5B, 6A, 7C), (1E, 2E, 3D, 4C, 5B, 6B, 7A), (1E, 2E, 3D, 4C, 5B, 6B, 7B), (1E, 2E, 3D, 4C, 5B, 6B, 7C), (1E, 2E, 3D, 4C, 5B, 6C, 7A), (1E, 2E, 3D, 4C, 5B, 6C, 7B), (1E, 2E, 3D, 4C, 5B, 6C, 7C), (1E, 2E, 3D, 4C, 5B, 6D, 7A), (1E, 2E, 3D, 4C, 5B, 6D, 7B), (1E, 2E, 3D, 4C, 5B, 6D, 7C), (1E, 2E, 3D, 4D, 5A, 6A, 7A), (1E, 2E, 3D, 4D, 5A, 6A, 7B), (1E, 2E, 3D, 4D, 5A, 6A, 7C), (1E, 2E, 3D, 4D, 5A, 6B, 7A), (1E, 2E, 3D, 4D, 5A, 6B, 7B), (1E, 2E, 3D, 4D, 5A, 6B, 7C), (1E, 2E, 3D, 4D, 5A, 6C, 7A), (1E, 2E, 3D, 4D, 5A, 6C, 7B), (1E, 2E, 3D, 4D, 5A, 6C, 7C), (1E, 2E, 3D, 4D, 5A, 6D, 7A), (1E, 2E, 3D, 4D, 5A, 6D, 7B), (1E, 2E, 3D, 4D, 5A, 6D, 7C), (1E, 2E, 3D, 4D, 5B, 6A, 7A), (1E, 2E, 3D, 4D, 5B, 6A, 7B), (1E, 2E, 3D, 4D, 5B, 6A, 7C), (1E, 2E, 3D, 4D, 5B, 6B, 7A), (1E, 2E, 3D, 4D, 5B, 6B, 7B), (1E, 2E, 3D, 4D, 5B, 6B, 7C), (1E, 2E, 3D, 4D, 5B, 6C, 7A), (1E, 2E, 3D, 4D, 5B, 6C, 7B), (1E, 2E, 3D, 4D, 5B, 6C, 7C), (1E, 2E, 3D, 4D, 5B, 6D, 7A), (1E, 2E, 3D, 4D, 5B, 6D, 7B), (1E, 2E, 3D, 4D, 5B, 6D, 7C), (1E, 2E, 3D, 4E, 5A, 6A, 7A), (1E, 2E, 3D, 4E, 5A, 6A, 7B), (1E, 2E, 3D, 4E, 5A, 6A, 7C), (1E, 2E, 3D, 4E, 5A, 6B, 7A), (1E, 2E, 3D, 4E, 5A, 6B, 7B), (1E, 2E, 3D, 4E, 5A, 6B, 7C), (1E, 2E, 3D, 4E, 5A, 6C, 7A), (1E, 2E, 3D, 4E, 5A, 6C, 7B), (1E, 2E, 3D, 4E, 5A, 6C, 7C), (1E, 2E, 3D, 4E, 5A, 6D, 7A), (1E, 2E, 3D, 4E, 5A, 6D, 7B), (1E, 2E, 3D, 4E, 5A, 6D, 7C), (1E, 2E, 3D, 4E, 5B, 6A, 7A), (1E, 2E, 3D, 4E, 5B, 6A, 7B), (1E, 2E, 3D, 4E, 5B, 6A, 7C), (1E, 2E, 3D, 4E, 5B, 6B, 7A), (1E, 2E, 3D, 4E, 5B, 6B, 7B), (1E, 2E, 3D, 4E, 5B, 6B, 7C), (1E, 2E, 3D, 4E, 5B, 6C, 7A), (1E, 2E, 3D, 4E, 5B, 6C, 7B), (1E, 2E, 3D, 4E, 5B, 6C, 7C), (1E, 2E, 3D, 4E, 5B, 6D, 7A), (1E, 2E, 3D, 4E, 5B, 6D, 7B), (1E, 2E, 3D, 4E, 5B, 6D, 7C), (1E, 2E, 3E, 4A, 5A, 6A, 7A), (1E, 2E, 3E, 4A, 5A, 6A, 7B), (1E, 2E, 3E, 4A, 5A, 6A, 7C), (1E, 2E, 3E, 4A, 5A, 6B, 7A), (1E, 2E, 3E, 4A, 5A, 6B, 7B), (1E, 2E, 3E, 4A, 5A, 6B, 7C), (1E, 2E, 3E, 4A, 5A, 6C, 7A), (1E, 2E, 3E, 4A, 5A, 6C, 7B), (1E, 2E, 3E, 4A, 5A, 6C, 7C), (1E, 2E, 3E, 4A, 5A, 6D, 7A), (1E, 2E, 3E, 4A, 5A, 6D, 7B), (1E, 2E, 3E, 4A, 5A, 6D, 7C), (1E, 2E, 3E, 4A, 5B, 6A, 7A), (1E, 2E, 3E, 4A, 5B, 6A, 7B), (1E, 2E, 3E, 4A, 5B, 6A, 7C), (1E, 2E, 3E, 4A, 5B, 6B, 7A), (1E, 2E, 3E, 4A, 5B, 6B, 7B), (1E, 2E, 3E, 4A, 5B, 6B, 7C), (1E, 2E, 3E, 4A, 5B, 6C, 7A), (1E, 2E, 3E, 4A, 5B, 6C, 7B), (1E, 2E, 3E, 4A, 5B, 6C, 7C), (1E, 2E, 3E, 4A, 5B, 6D, 7A), (1E, 2E, 3E, 4A, 5B, 6D, 7B), (1E, 2E, 3E, 4A, 5B, 6D, 7C), (1E, 2E, 3E, 4B, 5A, 6A, 7A), (1E, 2E, 3E, 4B, 5A, 6A, 7B), (1E, 2E, 3E, 4B, 5A, 6A, 7C), (1E, 2E, 3E, 4B, 5A, 6B, 7A), (1E, 2E, 3E, 4B, 5A, 6B, 7B), (1E, 2E, 3E, 4B, 5A, 6B, 7C), (1E, 2E, 3E, 4B, 5A, 6C, 7A), (1E, 2E, 3E, 4B, 5A, 6C, 7B), (1E, 2E, 3E, 4B, 5A, 6C, 7C), (1E, 2E, 3E, 4B, 5A, 6D, 7A), (1E, 2E, 3E, 4B, 5A, 6D, 7B), (1E, 2E, 3E, 4B, 5A, 6D, 7C), (1E, 2E, 3E, 4B, 5B, 6A, 7A), (1E, 2E, 3E, 4B, 5B, 6A, 7B), (1E, 2E, 3E, 4B, 5B, 6A, 7C), (1E, 2E, 3E, 4B, 5B, 6B, 7A), (1E, 2E, 3E, 4B, 5B, 6B, 7B), (1E, 2E, 3E, 4B, 5B, 6B, 7C), (1E, 2E, 3E, 4B, 5B, 6C, 7A), (1E, 2E, 3E, 4B, 5B, 6C, 7B), (1E, 2E, 3E, 4B, 5B, 6C, 7C), (1E, 2E, 3E, 4B, 5B, 6D, 7A), (1E, 2E, 3E, 4B, 5B, 6D, 7B), (1E, 2E, 3E, 4B, 5B, 6D, 7C), (1E, 2E, 3E, 4C, 5A, 6A, 7A), (1E, 2E, 3E, 4C, 5A, 6A, 7B), (1E, 2E, 3E, 4C, 5A, 6A, 7C), (1E, 2E, 3E, 4C, 5A, 6B, 7A), (1E, 2E, 3E, 4C, 5A, 6B, 7B), (1E, 2E, 3E, 4C, 5A, 6B, 7C), (1E, 2E, 3E, 4C, 5A, 6C, 7A), (1E, 2E, 3E, 4C, 5A, 6C, 7B), (1E, 2E, 3E, 4C, 5A, 6C, 7C), (1E, 2E, 3E, 4C, 5A, 6D, 7A), (1E, 2E, 3E, 4C, 5A, 6D, 7B), (1E, 2E, 3E, 4C, 5A, 6D, 7C), (1E, 2E, 3E, 4C, 5B, 6A, 7A), (1E, 2E, 3E, 4C, 5B, 6A, 7B), (1E, 2E, 3E, 4C, 5B, 6A, 7C), (1E, 2E, 3E, 4C, 5B, 6B, 7A), (1E, 2E, 3E, 4C, 5B, 6B, 7B), (1E, 2E, 3E, 4C, 5B, 6B, 7C), (1E, 2E, 3E, 4C, 5B, 6C, 7A), (1E, 2E, 3E, 4C, 5B, 6C, 7B), (1E, 2E, 3E, 4C, 5B, 6C, 7C), (1E, 2E, 3E, 4C, 5B, 6D, 7A), (1E, 2E, 3E, 4C, 5B, 6D, 7B), (1E, 2E, 3E, 4C, 5B, 6D, 7C), (1E, 2E, 3E, 4D, 5A, 6A, 7A), (1E, 2E, 3E, 4D, 5A, 6A, 7B), (1E, 2E, 3E, 4D, 5A, 6A, 7C), (1E, 2E, 3E, 4D, 5A, 6B, 7A), (1E, 2E, 3E, 4D, 5A, 6B, 7B), (1E, 2E, 3E, 4D, 5A, 6B, 7C), (1E, 2E, 3E, 4D, 5A, 6C, 7A), (1E, 2E, 3E, 4D, 5A, 6C, 7B), (1E, 2E, 3E, 4D, 5A, 6C, 7C), (1E, 2E, 3E, 4D, 5A, 6D, 7A), (1E, 2E, 3E, 4D, 5A, 6D, 7B), (1E, 2E, 3E, 4D, 5A, 6D, 7C), (1E, 2E, 3E, 4D, 5B, 6A, 7A), (1E, 2E, 3E, 4D, 5B, 6A, 7B), (1E, 2E, 3E, 4D, 5B, 6A, 7C), (1E, 2E, 3E, 4D, 5B, 6B, 7A), (1E, 2E, 3E, 4D, 5B, 6B, 7B), (1E, 2E, 3E, 4D, 5B, 6B, 7C), (1E, 2E, 3E, 4D, 5B, 6C, 7A), (1E, 2E, 3E, 4D, 5B, 6C, 7B), (1E, 2E, 3E, 4D, 5B, 6C, 7C), (1E, 2E, 3E, 4D, 5B, 6D, 7A), (1E, 2E, 3E, 4D, 5B, 6D, 7B), (1E, 2E, 3E, 4D, 5B, 6D, 7C), (1E, 2E, 3E, 4E, 5A, 6A, 7A), (1E, 2E, 3E, 4E, 5A, 6A, 7B), (1E, 2E, 3E, 4E, 5A, 6A, 7C), (1E, 2E, 3E, 4E, 5A, 6B, 7A), (1E, 2E, 3E, 4E, 5A, 6B, 7B), (1E, 2E, 3E, 4E, 5A, 6B, 7C), (1E, 2E, 3E, 4E, 5A, 6C, 7A), (1E, 2E, 3E, 4E, 5A, 6C, 7B), (1E, 2E, 3E, 4E, 5A, 6C, 7C), (1E, 2E, 3E, 4E, 5A, 6D, 7A), (1E, 2E, 3E, 4E, 5A, 6D, 7B), (1E, 2E, 3E, 4E, 5A, 6D, 7C), (1E, 2E, 3E, 4E, 5B, 6A, 7A), (1E, 2E, 3E, 4E, 5B, 6A, 7B), (1E, 2E, 3E, 4E, 5B, 6A, 7C), (1E, 2E, 3E, 4E, 5B, 6B, 7A), (1E, 2E, 3E, 4E, 5B, 6B, 7B), (1E, 2E, 3E, 4E, 5B, 6B, 7C), (1E, 2E, 3E, 4E, 5B, 6C, 7A), (1E, 2E, 3E, 4E, 5B, 6C, 7B), (1E, 2E, 3E, 4E, 5B, 6C, 7C), (1E, 2E, 3E, 4E, 5B, 6D, 7A), (1E, 2E, 3E, 4E, 5B, 6D, 7B), (1E, 2E, 3E, 4E, 5B, 6D, 7C)

And $(R^1, R^2, R^3, R^4, X, R^6, R^7,)$=(1A, 2A, 3A, 4A, 5A, 6A, 7A) is the compound which $R^1$ is 1A, $R^2$ is 2A, $R^3$ is 3A, $R^4$ is 4A, X is 5A, $R^6$ is 6A and $R^7$ is 7A. The other combinations are the same.

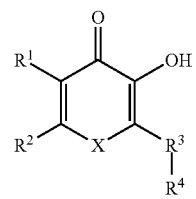

The substituents of $R^1$, $R^2$, X, $R^3$ and $R^4$ of above compound include the following substitution group.
$R^1$=H (1A), Me(1B), $CH_2OH$(1C), $CH_2OMe$(1D), COOH (1E), COOMe(1F), CONHMe(1G)
$R^2$=H (2A), Me(2B), $CH_2OH$(2C), $CH_2OMe$(2D), COOH (2E), COOMe(2F), CONHMe(2G)
X=O(XA), NH(XB)

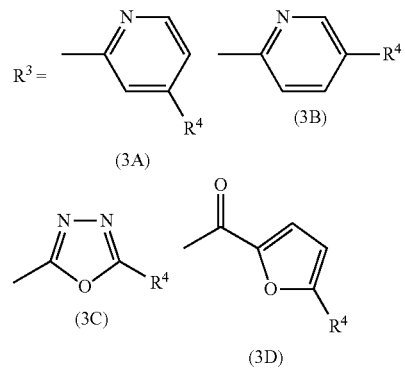

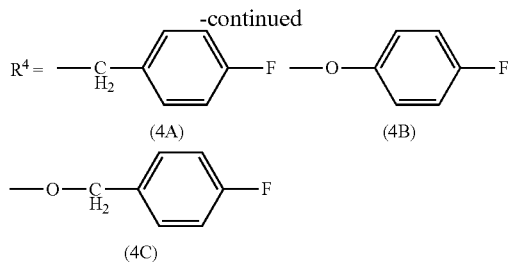

(4A)　(4B)

(4C)

The preferable combinations ($R^1$, $R^2$, X, $R^3$, $R^4$) of the substituents of above compound include the followings.
(1A, 2A, XA, 3A, 4A), (1A, 2A, XA, 3A, 4B), (1A, 2A, XA, 3A, 4C), (1A, 2A, XA, 3B, 4A), (1A, 2A, XA, 3B, 4B), (1A, 2A, XA, 3B, 4C), (1A, 2A, XA, 3C, 4A), (1A, 2A, XA, 3C, 4B), (1A, 2A, XA, 3C, 4C), (1A, 2A, XA, 3D, 4A), (1A, 2A, XA, 3D, 4B), (1A, 2A, XA, 3D, 4C), (1A, 2A, XB, 3A, 4A), (1A, 2A, XB, 3A, 4B), (1A, 2A, XB, 3A, 4C), (1A, 2A, XB, 3B, 4A), (1A, 2A, XB, 3B, 4B), (1A, 2A, XB, 3B, 4C), (1A, 2A, XB, 3C, 4A), (1A, 2A, XB, 3C, 4B), (1A, 2A, XB, 3C, 4C), (1A, 2A, XB, 3D, 4A), (1A, 2A, XB, 3D, 4B), (1A, 2A, XB, 3D, 4C), (1A, 2B, XA, 3A, 4A), (1A, 2B, XA, 3A, 4B), (1A, 2B, XA, 3A, 4C), (1A, 2B, XA, 3B, 4A), (1A, 2B, XA, 3B, 4B), (1A, 2B, XA, 3B, 4C), (1A, 2B, XA, 3C, 4A), (1A, 2B, XA, 3C, 4B), (1A, 2B, XA, 3C, 4C), (1A, 2B, XA, 3D, 4A), (1A, 2B, XA, 3D, 4B), (1A, 2B, XA, 3D, 4C), (1A, 2B, XB, 3A, 4A), (1A, 2B, XB, 3A, 4B), (1A, 2B, XB, 3A, 4C), (1A, 2B, XB, 3B, 4A), (1A, 2B, XB, 3B, 4B), (1A, 2B, XB, 3B, 4C), (1A, 2B, XB, 3C, 4A), (1A, 2B, XB, 3C, 4B), (1A, 2B, XB, 3C, 4C), (1A, 2B, XB, 3D, 4A), (1A, 2B, XB, 3D, 4B), (1A, 2B, XB, 3D, 4C), (1A, 2C, XA, 3A, 4A), (1A, 2C, XA, 3A, 4B), (1A, 2C, XA, 3A, 4C), (1A, 2C, XA, 3B, 4A), (1A, 2C, XA, 3B, 4B), (1A, 2C, XA, 3B, 4C), (1A, 2C, XA, 3C, 4A), (1A, 2C, XA, 3C, 4B), (1A, 2C, XA, 3C, 4C), (1A, 2C, XA, 3D, 4A), (1A, 2C, XA, 3D, 4B), (1A, 2C, XA, 3D, 4C), (1A, 2C, XB, 3A, 4A), (1A, 2C, XB, 3A, 4B), (1A, 2C, XB, 3A, 4C), (1A, 2C, XB, 3B, 4A), (1A, 2C, XB, 3B, 4B), (1A, 2C, XB, 3B, 4C), (1A, 2C, XB, 3C, 4A), (1A, 2C, XB, 3C, 4B), (1A, 2C, XB, 3C, 4C), (1A, 2C, XB, 3D, 4A), (1A, 2C, XB, 3D, 4B), (1A, 2C, XB, 3D, 4C), (1A, 2D, XA, 3A, 4A), (1A, 2D, XA, 3A, 4B), (1A, 2D, XA, 3A, 4C), (1A, 2D, XA, 3B, 4A), (1A, 2D, XA, 3B, 4B), (1A, 2D, XA, 3B, 4C), (1A, 2D, XA, 3C, 4A), (1A, 2D, XA, 3C, 4B), (1A, 2D, XA, 3C, 4C), (1A, 2D, XA, 3D, 4A), (1A, 2D, XA, 3D, 4B), (1A, 2D, XA, 3D, 4C), (1A, 2D, XB, 3A, 4A), (1A, 2D, XB, 3A, 4B), (1A, 2D, XB, 3A, 4C), (1A, 2D, XB, 3B, 4A), (1A, 2D, XB, 3B, 4B), (1A, 2D, XB, 3B, 4C), (1A, 2D, XB, 3C, 4A), (1A, 2D, XB, 3C, 4B), (1A, 2D, XB, 3C, 4C), (1A, 2D, XB, 3D, 4A), (1A, 2D, XB, 3D, 4B), (1A, 2D, XB, 3D, 4C), (1A, 2E, XA, 3A, 4A), (1A, 2E, XA, 3A, 4B), (1A, 2E, XA, 3A, 4C), (1A, 2E, XA, 3B, 4A), (1A, 2E, XA, 3B, 4B), (1A, 2E, XA, 3B, 4C), (1A, 2E, XA, 3C, 4A), (1A, 2E, XA, 3C, 4B), (1A, 2E, XA, 3C, 4C), (1A, 2E, XA, 3D, 4A), (1A, 2E, XA, 3D, 4B), (1A, 2E, XA, 3D, 4C), (1A, 2E, XB, 3A, 4A), (1A, 2E, XB, 3A, 4B), (1A, 2E, XB, 3A, 4C), (1A, 2E, XB, 3B, 4A), (1A, 2E, XB, 3B, 4B), (1A, 2E, XB, 3B, 4C), (1A, 2E, XB, 3C, 4A), (1A, 2E, XB, 3C, 4B), (1A, 2E, XB, 3C, 4C), (1A, 2E, XB, 3D, 4A), (1A, 2E, XB, 3D, 4B), (1A, 2E, XB, 3D, 4C), (1A, 2F, XA, 3A, 4A), (1A, 2F, XA, 3A, 4B), (1A, 2F, XA, 3A, 4C), (1A, 2F, XA, 3B, 4A), (1A, 2F, XA, 3B, 4B), (1A, 2F, XA, 3B, 4C), (1A, 2F, XA, 3C, 4A), (1A, 2F, XA, 3C, 4B), (1A, 2F, XA, 3C, 4C), (1A, 2F, XA, 3D, 4A), (1A, 2F, XA, 3D, 4B), (1A, 2F, XA, 3D, 4C), (1A, 2F, XB, 3A, 4A), (1A, 2F, XB, 3A, 4B), (1A, 2F, XB, 3A, 4C), (1A, 2F, XB, 3B, 4A), (1A, 2F, XB, 3B, 4B), (1A, 2F, XB, 3B, 4C), (1A, 2F, XB, 3C, 4A), (1A, 2F, XB, 3C, 4B), (1A, 2F, XB, 3C, 4C), (1A, 2F, XB, 3D, 4A), (1A, 2F, XB, 3D, 4B), (1A, 2F, XB, 3D, 4C), (1A, 2G, XA, 3A, 4A), (1A, 2G, XA, 3A, 4B), (1A, 2G, XA, 3A, 4C), (1A, 2G, XA, 3B, 4A), (1A, 2G, XA, 3B, 4B), (1A, 2G, XA, 3B, 4C), (1A, 2G, XA, 3C, 4A), (1A, 2G, XA, 3C, 4B), (1A, 2G, XA, 3C, 4C), (1A, 2G, XA, 3D, 4A), (1A, 2G, XA, 3D, 4B), (1A, 2G, XA, 3D, 4C), (1A, 2G, XB, 3A, 4A), (1A, 2G, XB, 3A, 4B), (1A, 2G, XB, 3A, 4C), (1A, 2G, XB, 3B, 4A), (1A, 2G, XB, 3B, 4B), (1A, 2G, XB, 3B, 4C), (1A, 2G, XB, 3C, 4A), (1A, 2G, XB, 3C, 4B), (1A, 2G, XB, 3C, 4C), (1A, 2G, XB, 3D, 4A), (1A, 2G, XB, 3D, 4B), (1A, 2G, XB, 3D, 4C), (1B, 2A, XA, 3A, 4A), (1B, 2A, XA, 3A, 4B), (1B, 2A, XA, 3A, 4C), (1B, 2A, XA, 3B, 4A), (1B, 2A, XA, 3B, 4B), (1B, 2A, XA, 3B, 4C), (1B, 2A, XA, 3C, 4A), (1B, 2A, XA, 3C, 4B), (1B, 2A, XA, 3C, 4C), (1B, 2A, XA, 3D, 4A), (1B, 2A, XA, 3D, 4B), (1B, 2A, XA, 3D, 4C), (1B, 2A, XB, 3A, 4A), (1B, 2A, XB, 3A, 4B), (1B, 2A, XB, 3A, 4C), (1B, 2A, XB, 3B, 4A), (1B, 2A, XB, 3B, 4B), (1B, 2A, XB, 3B, 4C), (1B, 2A, XB, 3C, 4A), (1B, 2A, XB, 3C, 4B), (1B, 2A, XB, 3C, 4C), (1B, 2A, XB, 3D, 4A), (1B, 2A, XB, 3D, 4B); (1B, 2A, XB, 3D, 4C), (1B, 2B, XA, 3A, 4A), (1B, 2B, XA, 3A, 4B), (1B, 2B, XA, 3A, 4C), (1B, 2B, XA, 3B, 4A), (1B, 2B, XA, 3B, 4B), (1B, 2B, XA, 3B, 4C), (1B, 2B, XA, 3C, 4A), (1B, 2B, XA, 3C, 4B), (1B, 2B, XA, 3C, 4C), (1B, 2B, XA, 3D, 4A), (1B, 2B, XA, 3D, 4B), (1B, 2B, XA, 3D, 4C), (1B, 2B, XB, 3A, 4A), (1B, 2B, XB, 3A, 4B), (1B, 2B, XB, 3A, 4C), (1B, 2B, XB, 3B, 4A), (1B, 2B, XB, 3B, 4B), (1B, 2B, XB, 3B, 4C), (1B, 2B, XB, 3C, 4A), (1B, 2B, XB, 3C, 4B), (1B, 2B, XB, 3C, 4C), (1B, 2B, XB, 3D, 4A), (1B, 2B, XB, 3D, 4B), (1B, 2B, XB, 3D, 4C), (1B, 2C, XA, 3A, 4A), (1B, 2C, XA, 3A, 4B), (1B, 2C, XA, 3A, 4C), (1B, 2C, XA, 3B, 4A), (1B, 2C, XA, 3B, 4B), (1B, 2C, XA, 3B, 4C), (1B, 2C, XA, 3C, 4A), (1B, 2C, XA, 3C, 4B), (1B, 2C, XA, 3C, 4C), (1B, 2C, XA, 3D, 4A), (1B, 2C, XA, 3D, 4B), (1B, 2C, XA, 3D, 4C), (1B, 2C, XB, 3A, 4A), (1B, 2C, XB, 3A, 4B), (1B, 2C, XB, 3A, 4C), (1B, 2C, XB, 3B, 4A), (1B, 2C, XB, 3B, 4B), (1B, 2C, XB, 3B, 4C), (1B, 2C, XB, 3C, 4A), (1B, 2C, XB, 3C, 4B), (1B, 2C, XB, 3C, 4C), (1B, 2C, XB, 3D, 4A), (1B, 2C, XB, 3D, 4B), (1B, 2C, XB, 3D, 4C), (1B, 2D, XA, 3A, 4A), (1B, 2D, XA, 3A, 4B), (1B, 2D, XA, 3A, 4C), (1B, 2D, XA, 3B, 4A), (1B, 2D, XA, 3B, 4B), (1B, 2D, XA, 3B, 4C), (1B, 2D, XA, 3C, 4A), (1B, 2D, XA, 3C, 4B), (1B, 2D, XA, 3C, 4C), (1B, 2D, XA, 3D, 4A), (1B, 2D, XA, 3D, 4B), (1B, 2D, XA, 3D, 4C), (1B, 2D, XB, 3A, 4A), (1B, 2D, XB, 3A, 4B), (1B, 2D, XB, 3A, 4C), (1B, 2D, XB, 3B, 4A), (1B, 2D, XB, 3B, 4B), (1B, 2D, XB, 3B, 4C), (1B, 2D, XB, 3C, 4A), (1B, 2D, XB, 3C, 4B), (1B, 2D, XB, 3C, 4C), (1B, 2D, XB, 3D, 4A), (1B, 2D, XB, 3D, 4B), (1B, 2D, XB, 3D, 4C), (1B, 2E, XA, 3A, 4A), (1B, 2E, XA, 3A, 4B), (1B, 2E, XA, 3A, 4C), (1B, 2E, XA, 3B, 4A), (1B, 2E, XA, 3B, 4B), (1B, 2E, XA, 3B, 4C), (1B, 2E, XA, 3C, 4A), (1B, 2E, XA, 3C, 4B), (1B, 2E, XA, 3C, 4C), (1B, 2E, XA, 3D, 4A), (1B, 2E, XA, 3D, 4B), (1B, 2E, XA, 3D, 4C), (1B, 2E, XB, 3A, 4A), (1B, 2E, XB, 3A, 4B), (1B, 2E, XB, 3A, 4C), (1B, 2E, XB, 3B, 4A), (1B, 2E, XB, 3B, 4B), (1B, 2E, XB, 3B, 4C), (1B, 2E, XB, 3C, 4A), (1B, 2E, XB, 3C, 4B), (1B, 2E, XB, 3C, 4C), (1B, 2E, XB, 3D, 4A), (1B, 2E, XB, 3D, 4B), (1B, 2E, XB, 3D, 4C), (1B, 2F, XA, 3A, 4A), (1B, 2F, XA, 3A, 4B), (1B, 2F, XA, 3A, 4C), (1B, 2F, XA, 3B, 4A), (1B, 2F, XA, 3B, 4B), (1B, 2F, XA, 3B, 4C), (1B, 2F, XA, 3C, 4A), (1B, 2F, XA, 3C, 4B), (1B, 2F, XA, 3C, 4C), (1B, 2F, XA, 3D, 4A), (1B, 2F, XA, 3D, 4B), (1B, 2F, XA, 3D, 4C), (1B, 2F, XB, 3A, 4A), (1B, 2F, XB, 3A, 4B), (1B, 2F, XB, 3A, 4C), (1B, 2F, XB, 3B, 4A), (1B, 2F, XB, 3B, 4B), (1B, 2F, XB, 3B, 4C), (1B, 2F, XB, 3C, 4A), (1B, 2F, XB, 3C, 4B), (1B, 2F, XB, 3C, 4C), (1B, 2F, XB, 3D, 4A), (1B, 2F, XB, 3D, 4B), (1B, 2F, XB, 3D, 4C), (1B, 2G, XA, 3A, 4A), (1B, 2G, XA, 3A, 4B), (1B, 2G, XA, 3A, 4C), (1B, 2G, XA, 3B, 4A), (1B, 2G, XA, 3B, 4B), (1B, 2G, XA, 3B, 4C), (1B, 2G, XA, 3C, 4A), (1B, 2G, XA, 3C, 4B), (1B, 2G, XA, 3C, 4C), (1B, 2G, XA, 3D, 4A), (1B, 2G, XA, 3D, 4B), (1B, 2G, XA, 3D, 4C), (1B, 2G, XB, 3A, 4A), (1B, 2G, XB, 3A, 4B), (1B, 2G, XB, 3A, 4C), (1B, 2G, XB, 3B, 4A), (1B, 2G, XB, 3B, 4B), (1B, 2G, XB, 3B, 4C), (1B, 2G, XB, 3C, 4A), (1B, 2G, XB, 3C, 4B), (1B, 2G, XB, 3C, 4C), (1B, 2G, XB, 3D, 4A), (1B, 2G, XB, 3D, 4B), (1B, 2G, XB, 3D, 4C), (1C, 2A, XA, 3A, 4A), (1C, 2A, XA, 3A, 4B), (1C, 2A, XA, 3A, 4C), (1C, 2A, XA, 3B, 4A), (1C, 2A, XA, 3B, 4B), (1C, 2A, XA, 3B, 4C), (1C, 2A, XA, 3C, 4A), (1C, 2A, XA, 3C, 4B), (1C, 2A, XA, 3C, 4C), (1C, 2A, XA, 3D, 4A), (1C, 2A, XA, 3D, 4B), (1C, 2A, XA, 3D, 4C), (1C, 2A, XB, 3A, 4A), (1C, 2A, XB, 3A, 4B), (1C, 2A, XB, 3A, 4C), (1C, 2A, XB, 3B, 4A), (1C, 2A, XB, 3B, 4B), (1C, 2A, XB, 3B, 4C), (1C, 2A, XB, 3C, 4A), (1C, 2A, XB, 3C, 4B), (1C, 2A, XB, 3C, 4C), (1C, 2A, XB, 3D, 4A), (1C, 2A, XB, 3D, 4B), (1C, 2A, XB, 3D, 4C), (1C, 2B, XA, 3A, 4A), (1C, 2B, XA, 3A, 4B), (1C, 2B, XA, 3A, 4C), (1C, 2B, XA, 3B, 4A), (1C, 2B, XA, 3B, 4B), (1C, 2B, XA, 3B, 4C), (1C, 2B, XA, 3C, 4A), (1C, 2B, XA, 3C, 4B), (1C, 2B, XA, 3C, 4C), (1C, 2B, XA, 3D, 4A), (1C, 2B, XA, 3D, 4B), (1C, 2B, XA, 3D, 4C), (1C, 2B, XB, 3A, 4A), (1C, 2B, XB, 3A, 4B), (1C, 2B, XB, 3A, 4C), (1C, 2B, XB, 3B, 4A), (1C, 2B, XB, 3B, 4B), (1C, 2B, XB, 3B, 4C), (1C, 2B, XB, 3C, 4A), (1C, 2B, XB, 3C, 4B), (1C, 2B, XB, 3C, 4C), (1C, 2B, XB, 3D, 4A), (1C, 2B, XB, 3D, 4B), (1C, 2B, XB, 3D, 4C), (1C, 2C, XA, 3A, 4A), (1C, 2C, XA, 3A, 4B), (1C, 2C, XA, 3A, 4C), (1C, 2C, XA, 3B, 4A), (1C, 2C, XA, 3B, 4B), (1C, 2C, XA, 3B, 4C), (1C, 2C, XA, 3C, 4A), (1C, 2C, XA, 3C, 4B), (1C, 2C, XA, 3C, 4C), (1C, 2C, XA, 3D, 4A), (1C, 2C, XA, 3D, 4B), (1C, 2C, XA, 3D, 4C), (1C, 2C, XB, 3A, 4A), (1C, 2C, XB, 3A, 4B), (1C, 2C, XB, 3A, 4C), (1C, 2C, XB, 3B, 4A), (1C, 2C, XB, 3B, 4B), (1C, 2C, XB, 3B, 4C), (1C, 2C, XB, 3C, 4A), (1C, 2C, XB, 3C, 4B), (1C, 2C, XB, 3C, 4C), (1C, 2C, XB, 3D, 4A), (1C, 2C, XB, 3D, 4B), (1C, 2C, XB, 3D, 4C), (1C, 2D, XA, 3A, 4A), (1C, 2D, XA, 3A, 4B), (1C, 2D, XA, 3A, 4C), (1C, 2D, XA, 3B, 4A), (1C, 2D, XA, 3B, 4B), (1C, 2D, XA, 3B, 4C), (1C, 2D, XA, 3C, 4A), (1C, 2D, XA, 3C, 4B), (1C, 2D, XA, 3C, 4C), (1C, 2D, XA, 3D, 4A), (1C, 2D, XA, 3D, 4B), (1C, 2D, XA, 3D, 4C), (1C, 2D, XB, 3A, 4A), (1C, 2D, XB, 3A, 4B), (1C, 2D, XB, 3A, 4C), (1C, 2D, XB, 3B, 4A), (1C, 2D, XB, 3B, 4B), (1C, 2D, XB, 3B, 4C), (1C, 2D, XB, 3C, 4A), (1C, 2D, XB, 3C, 4B), (1C, 2D, XB, 3C, 4C), (1C, 2D, XB, 3D, 4A), (1C, 2D, XB, 3D, 4B), (1C, 2D, XB, 3D, 4C), (1C, 2E, XA, 3A, 4A), (1C, 2E, XA, 3A, 4B), (1C, 2E, XA, 3A, 4C), (1C, 2E, XA, 3B, 4A), (1C, 2E, XA, 3B, 4B), (1C, 2E, XA, 3B, 4C), (1C, 2E, XA, 3C, 4A), (1C, 2E, XA, 3C, 4B), (1C, 2E, XA, 3C, 4C), (1C, 2E, XA, 3D, 4A), (1C, 2E, XA, 3D, 4B), (1C, 2E, XA, 3D, 4C), (1C, 2E, XB, 3A, 4A), (1C, 2E, XB, 3A, 4B), (1C, 2E, XB, 3A, 4C), (1C, 2E, XB, 3B, 4A), (1C, 2E, XB, 3B, 4B), (1C, 2E, XB, 3B, 4C), (1C, 2E, XB, 3C, 4A), (1C, 2E, XB, 3C, 4B), (1C, 2E, XB, 3C, 4C), (1C, 2E, XB, 3D, 4A), (1C, 2E, XB, 3D, 4B), (1C, 2E, XB, 3D, 4C), (1C, 2F, XA, 3A, 4A), (1C, 2F, XA, 3A, 4B), (1C, 2F, XA, 3A, 4C), (1C, 2F, XA, 3B, 4A), (1C, 2F, XA, 3B, 4B), (1C, 2F, XA, 3B, 4C), (1C, 2F, XA, 3C, 4A), (1C, 2F, XA, 3C, 4B), (1C, 2F, XA, 3C, 4C), (1C, 2F, XA, 3D, 4A), (1C, 2F, XA, 3D, 4B), (1C, 2F, XA, 3D, 4C), (1C, 2F, XB, 3A, 4A), (1C, 2F, XB, 3A, 4B), (1C, 2F, XB, 3A, 4C), (1C, 2F, XB, 3B, 4A), (1C, 2F, XB, 3B, 4B), (1C, 2F, XB, 3B, 4C), (1C, 2F, XB, 3C, 4A), (1C, 2F, XB, 3C, 4B), (1C, 2F, XB, 3C, 4C), (1C, 2F, XB, 3D, 4A), (1C, 2F, XB, 3D, 4B), (1C, 2F, XB, 3D, 4C), (1C, 2G, XA, 3A, 4A), (1C, 2G, XA, 3A, 4B), (1C, 2G, XA, 3A, 4C), (1C, 2G, XA, 3B, 4A), (1C, 2G, XA, 3B, 4B), (1C, 2G, XA, 3B, 4C), (1C, 2G, XA, 3C, 4A), (1C, 2G, XA, 3C, 4B), (1C, 2G, XA, 3C, 4C), (1C, 2G, XA, 3D, 4A), (1C, 2G, XA, 3D, 4B), (1C, 2G, XA, 3D, 4C), (1C, 2G, XB, 3A, 4A), (1C, 2G, XB, 3A, 4B), (1C, 2G, XB, 3A, 4C), (1C, 2G, XB, 3B, 4A), (1C, 2G, XB, 3B, 4B), (1C, 2G, XB, 3B, 4C), (1C, 2G, XB, 3C, 4A), (1C, 2G, XB, 3C, 4B), (1C, 2G, XB, 3C, 4C), (1C, 2G, XB, 3D, 4A), (1C, 2G, XB, 3D, 4B), (1C, 2G, XB, 3D, 4C), (1D, 2A, XA, 3A, 4A), (1D, 2A, XA, 3A, 4B), (1D, 2A, XA, 3A, 4C), (1D, 2A, XA, 3B, 4A), (1D, 2A, XA, 3B, 4B), (1D, 2A, XA, 3B, 4C), (1D, 2A, XA, 3C, 4A), (1D, 2A, XA, 3C, 4B), (1D, 2A, XA, 3C, 4C), (1D, 2A, XA, 3D, 4A), (1D, 2A, XA, 3D, 4B), (1D, 2A, XA, 3D, 4C), (1D, 2A, XB, 3A, 4A), (1D, 2A, XB, 3A, 4B), (1D, 2A, XB, 3A, 4C), (1D, 2A, XB, 3B, 4A), (1D, 2A, XB, 3B, 4B), (1D, 2A, XB, 3B, 4C), (1D, 2A, XB, 3C, 4A), (1D, 2A, XB, 3C, 4B), (1D, 2A, XB, 3C, 4C), (1D, 2A, XB, 3D, 4A), (1D, 2A, XB, 3D, 4B), (1D, 2A, XB, 3D, 4C), (1D, 2B, XA, 3A, 4A), (1D, 2B, XA, 3A, 4B), (1D, 2B, XA, 3A, 4C), (1D, 2B, XA, 3B, 4A), (1D, 2B, XA, 3B, 4B), (1D, 2B, XA, 3B, 4C), (1D, 2B, XA, 3C, 4A), (1D, 2B, XA, 3C, 4B), (1D, 2B, XA, 3C, 4C), (1D, 2B, XA, 3D, 4A), (1D, 2B, XA, 3D, 4B), (1D, 2B, XA, 3D, 4C), (1D, 2B, XB, 3A, 4A), (1D, 2B, XB, 3A, 4B), (1D, 2B, XB, 3A, 4C), (1D, 2B, XB, 3B, 4A), (1D, 2B, XB, 3B, 4B), (1D, 2B, XB, 3B, 4C), (1D, 2B, XB, 3C, 4A), (1D, 2B, XB, 3C, 4B), (1D, 2B, XB, 3C, 4C), (1D, 2B, XB, 3D, 4A), (1D, 2B, XB, 3D, 4B), (1D, 2B, XB, 3D, 4C), (1D, 2C, XA, 3A, 4A), (1D, 2C, XA, 3A, 4B), (1D, 2C, XA, 3A, 4C), (1D, 2C, XA, 3B, 4A), (1D, 2C, XA, 3B, 4B), (1D, 2C, XA, 3B, 4C), (1D, 2C, XA, 3C, 4A), (1D, 2C, XA, 3C, 4B), (1D, 2C, XA, 3C, 4C), (1D, 2C, XA, 3D, 4A), (1D, 2C, XA, 3D, 4B), (1D, 2C, XA, 3D, 4C), (1D, 2C, XB, 3A, 4A), (1D, 2C, XB, 3A, 4B), (1D, 2C, XB, 3A, 4C), (1D, 2C, XB, 3B, 4A), (1D, 2C, XB, 3B, 4B), (1D, 2C, XB, 3B, 4C), (1D, 2C, XB, 3C, 4A), (1D, 2C, XB, 3C, 4B), (1D, 2C, XB, 3C, 4C), (1D, 2C, XB, 3D, 4A), (1D, 2C, XB, 3D, 4B), (1D, 2C, XB, 3D, 4C), (1D, 2D, XA, 3A, 4A), (1D, 2D, XA, 3A, 4B), (1D, 2D, XA, 3A, 4C), (1D, 2D, XA, 3B, 4A), (1D, 2D, XA, 3B, 4B), (1D, 2D, XA, 3B, 4C), (1D, 2D, XA, 3C, 4A), (1D, 2D, XA, 3C, 4B), (1D, 2D, XA, 3C, 4C), (1D, 2D, XA, 3D, 4A), (1D, 2D, XA, 3D, 4B), (1D, 2D, XA, 3D, 4C), (1D, 2D, XB, 3A, 4A), (1D, 2D, XB, 3A, 4B), (1D, 2D, XB, 3A, 4C), (1D, 2D, XB, 3B, 4A), (1D, 2D, XB, 3B, 4B), (1D, 2D, XB, 3B, 4C), (1D, 2D, XB, 3C, 4A), (1D, 2D, XB, 3C, 4B), (1D, 2D, XB, 3C, 4C), (1D, 2D, XB, 3D, 4A), (1D, 2D, XB, 3D, 4B), (1D, 2D, XB, 3D, 4C), (1D, 2E, XA, 3A, 4A), (1D, 2E, XA, 3A, 4B), (1D, 2E, XA, 3A, 4C), (1D, 2E, XA, 3B, 4A), (1D, 2E, XA, 3B, 4B), (1D, 2E, XA, 3B, 4C), (1D, 2E, XA, 3C, 4A), (1D, 2E, XA, 3C, 4B), (1D, 2E, XA, 3C, 4C), (1D, 2E, XA, 3D, 4A), (1D, 2E, XA, 3D, 4B), (1D, 2E, XA, 3D, 4C), (1D, 2E, XB, 3A, 4A), (1D, 2E, XB, 3A, 4B), (1D, 2E, XB, 3A, 4C), (1D, 2E, XB, 3B, 4A), (1D, 2E, XB, 3B, 4B), (1D, 2E, XB, 3B, 4C), (1D, 2E, XB, 3C, 4A), (1D, 2E, XB, 3C, 4B), (1D, 2E, XB, 3C, 4C), (1D, 2E, XB, 3D, 4A), (1D, 2E, XB, 3D, 4B), (1D, 2E, XB, 3D, 4C), (1D, 2F, XA, 3A, 4A), (1D, 2F, XA, 3A, 4B), (1D, 2F, XA, 3A, 4C), (1D, 2F, XA, 3B, 4A), (1D, 2F, XA, 3B, 4B), (1D, 2F, XA, 3B, 4C), (1D, 2F, XA, 3C, 4A), (1D, 2F, XA, 3C, 4B), (1D, 2F, XA, 3C, 4C), (1D, 2F, XA, 3D, 4A), (1D, 2F, XA, 3D, 4B), (1D, 2F, XA, 3D, 4C), (1D, 2F, XB, 3A, 4A), (1D, 2F, XB, 3A, 4B), (1D, 2F, XB, 3A, 4C), (1D, 2F, XB, 3B, 4A), (1D, 2F, XB, 3B, 4B), (1D, 2F, XB, 3B, 4C), (1D, 2F, XB, 3C, 4A), (1D, 2F, XB, 3C, 4B), (1D, 2F, XB, 3C, 4C), (1D, 2F, XB, 3D, 4A), (1D, 2F, XB, 3D, 4B), (1D, 2F, XB, 3D, 4C), (1D, 2G, XA, 3A, 4A), (1D, 2G, XA, 3A, 4B), (1D, 2G, XA, 3A, 4C), (1D, 2G, XA, 3B, 4A), (1D, 2G, XA, 3B, 4B), (1D, 2G, XA, 3B, 4C), (1D, 2G, XA, 3C, 4A), (1D, 2G, XA, 3C, 4B), (1D, 2G, XA, 3C, 4C), (1D, 2G, XA, 3D, 4A), (1D, 2G, XA, 3D, 4B), (1D, 2G, XA, 3D, 4C), (1D, 2G, XB, 3A, 4A), (1D, 2G, XB, 3A, 4B), (1D, 2G, XB, 3A, 4C), (1D, 2G, XB, 3B, 4A), (1D, 2G, XB, 3B, 4B), (1D, 2G, XB, 3B, 4C), (1D, 2G, XB, 3C, 4A), (1D, 2G, XB, 3C, 4B), (1D, 2G, XB, 3C, 4C), (1D, 2G, XB, 3D, 4A), (1D, 2G, XB, 3D, 4B), (1D, 2G, XB, 3D, 4C), (1E, 2A, XA, 3A, 4A), (1E, 2A, XA, 3A, 4B), (1E, 2A, XA, 3A, 4C), (1E, 2A, XA, 3B, 4A), (1E, 2A, XA, 3B, 4B), (1E, 2A, XA, 3B, 4C), (1E, 2A, XA, 3C, 4A), (1E, 2A, XA, 3C, 4B), (1E, 2A, XA, 3C, 4C), (1E, 2A, XA, 3D, 4A), (1E, 2A, XA, 3D, 4B), (1E, 2A, XA, 3D, 4C), (1E, 2A, XB, 3A, 4A), (1E, 2A, XB, 3A, 4B), (1E, 2A, XB, 3A, 4C), (1E, 2A, XB, 3B, 4A), (1E, 2A, XB, 3B, 4B), (1E, 2A, XB, 3B, 4C), (1E, 2A, XB, 3C, 4A), (1E, 2A, XB, 3C, 4B), (1E, 2A, XB, 3C, 4C), (1E, 2A, XB, 3D, 4A), (1E, 2A, XB, 3D, 4B), (1E, 2A, XB, 3D, 4C), (1E, 2B, XA, 3A, 4A), (1E, 2B, XA, 3A, 4B), (1E, 2B, XA, 3A, 4C), (1E, 2B, XA, 3B, 4A), (1E, 2B, XA, 3B, 4B), (1E, 2B, XA, 3B, 4C), (1E, 2B, XA, 3C, 4A), (1E, 2B, XA, 3C, 4B), (1E, 2B, XA, 3C, 4C), (1E, 2B, XA, 3D, 4A), (1E, 2B, XA, 3D, 4B), (1E, 2B, XA, 3D, 4C), (1E, 2B, XB, 3A, 4A), (1E, 2B, XB, 3A, 4B), (1E, 2B, XB, 3A, 4C), (1E, 2B, XB, 3B, 4A), (1E, 2B, XB, 3B, 4B), (1E, 2B, XB, 3B, 4C), (1E, 2B, XB, 3C, 4A), (1E, 2B, XB, 3C, 4B), (1E, 2B, XB, 3C, 4C), (1E, 2B, XB, 3D, 4A), (1E, 2B, XB, 3D, 4B), (1E, 2B, XB, 3D, 4C), (1E, 2C, XA, 3A, 4A), (1E, 2C, XA, 3A, 4B), (1E, 2C, XA, 3A, 4C), (1E, 2C, XA, 3B, 4A), (1E, 2C, XA, 3B, 4B), (1E, 2C, XA, 3B, 4C), (1E, 2C, XA, 3C, 4A), (1E, 2C, XA, 3C, 4B), (1E, 2C, XA, 3C, 4C), (1E, 2C, XA, 3D, 4A), (1E, 2C, XA, 3D, 4B), (1E, 2C, XA, 3D, 4C), (1E, 2C, XB, 3A, 4A), (1E, 2C, XB, 3A, 4B), (1E, 2C, XB, 3A, 4C), (1E, 2C, XB, 3B, 4A), (1E, 2C, XB, 3B, 4B), (1E, 2C, XB, 3B, 4C), (1E, 2C, XB, 3C, 4A), (1E, 2C, XB, 3C, 4B), (1E, 2C, XB, 3C, 4C), (1E, 2C, XB, 3D, 4A), (1E, 2C, XB, 3D, 4B), (1E, 2C, XB, 3D, 4C), (1E, 2D, XA, 3A, 4A), (1E, 2D, XA, 3A, 4B), (1E, 2D, XA, 3A, 4C), (1E, 2D, XA, 3B, 4A), (1E, 2D, XA, 3B, 4B), (1E, 2D, XA, 3B, 4C), (1E, 2D, XA, 3C; 4A), (1E, 2D, XA, 3C, 4B), (1E, 2D, XA, 3C, 4C), (1E, 2D, XA, 3D, 4A), (1E, 2D, XA, 3D, 4B), (1E, 2D, XA, 3D, 4C), (1E, 2D, XB, 3A, 4A), (1E, 2D, XB, 3A, 4B), (1E, 2D, XB, 3A, 4C), (1E, 2D, XB, 3B, 4A), (1E, 2D, XB, 3B, 4B), (1E, 2D, XB, 3B, 4C), (1E, 2D, XB, 3C, 4A), (1E, 2D, XB, 3C, 4B), (1E, 2D, XB, 3C, 4C), (1E, 2D, XB, 3D, 4A), (1E, 2D, XB, 3D, 4B), (1E, 2D, XB, 3D, 4C), (1E, 2E, XA, 3A, 4A), (1E, 2E, XA, 3A, 4B), (1E, 2E, XA, 3A, 4C), (1E, 2E, XA, 3B, 4A), (1E, 2E, XA, 3B, 4B), (1E, 2E, XA, 3B, 4C), (1E, 2E, XA, 3C, 4A), (1E, 2E, XA, 3C, 4B), (1E, 2E, XA, 3C, 4C), (1E, 2E, XA, 3D, 4A), (1E, 2E, XA, 3D, 4B), (1E, 2E, XA, 3D, 4C), (1E, 2E, XB, 3A, 4A), (1E, 2E, XB, 3A, 4B), (1E, 2E, XB, 3A, 4C), (1E, 2E, XB, 3B, 4A), (1E, 2E, XB, 3B, 4B), (1E, 2E, XB, 3B, 4C), (1E, 2E, XB, 3C, 4A), (1E, 2E, XB, 3C, 4B), (1E, 2E, XB, 3C, 4C), (1E, 2E, XB, 3D, 4A), (1E, 2E, XB, 3D, 4B), (1E, 2E, XB, 3D, 4C), (1E, 2F, XA, 3A, 4A), (1E, 2F, XA, 3A, 4B), (1E, 2F, XA, 3A, 4C), (1E, 2F, XA, 3B, 4A), (1E, 2F, XA, 3B, 4B), (1E, 2F, XA, 3B, 4C), (1E, 2F, XA, 3C, 4A), (1E, 2F, XA, 3C, 4B), (1E, 2F, XA, 3C, 4C), (1E, 2F, XA, 3D, 4A), (1E, 2F, XA, 3D, 4B), (1E, 2F, XA, 3D, 4C), (1E, 2F, XB, 3A, 4A), (1E, 2F, XB, 3A, 4B), (1E, 2F, XB, 3A, 4C), (1E, 2F, XB, 3B, 4A), (1E, 2F, XB, 3B, 4B), (1E, 2F, XB, 3B, 4C), (1E, 2F, XB, 3C, 4A), (1E, 2F, XB, 3C, 4B), (1E, 2F, XB, 3C, 4C), (1E, 2F, XB, 3D, 4A), (1E, 2F, XB, 3D, 4B), (1E, 2F, XB, 3D, 4C), (1E, 2G, XA, 3A, 4A), (1E, 2G; XA, 3A, 4B), (1E, 2G, XA, 3A, 4C), (1E, 2G, XA, 3B, 4A), (1E, 2G, XA, 3B, 4B), (1E, 2G, XA, 3B, 4C), (1E, 2G, XA, 3C, 4A), (1E, 2G, XA, 3C, 4B), (1E, 2G, XA, 3C, 4C), (1E, 2G, XA, 3D, 4A), (1E, 2G, XA, 3D, 4B), (1E, 2G, XA, 3D, 4C), (1E, 2G, XB, 3A, 4A), (1E, 2G, XB, 3A, 4B), (1E, 2G, XB, 3A, 4C), (1E, 2G, XB, 3B, 4A), (1E, 2G, XB, 3B, 4B), (1E, 2G, XB, 3B, 4C), (1E, 2G, XB, 3C, 4A), (1E, 2G, XB, 3C, 4B), (1E, 2G, XB, 3C, 4C), (1E, 2G, XB, 3D, 4A), (1E, 2G, XB, 3D, 4B), (1E, 2G, XB, 3D, 4C), (1F, 2A, XA, 3A, 4A), (1F, 2A, XA, 3A, 4B), (1F, 2A, XA, 3A, 4C), (1F, 2A, XA, 3B, 4A), (1F, 2A, XA, 3B, 4B), (1F, 2A, XA, 3B, 4C), (1F, 2A, XA, 3C, 4A), (1F, 2A, XA, 3C, 4B), (1F, 2A, XA, 3C, 4C), (1F, 2A, XA, 3D, 4A), (1F, 2A, XA, 3D, 4B), (1F, 2A, XA, 3D, 4C), (1F, 2A, XB, 3A, 4A), (1F, 2A, XB, 3A, 4B), (1F, 2A, XB, 3A, 4C), (1F, 2A, XB, 3B, 4A), (1F, 2A, XB, 3B, 4B), (1F, 2A, XB, 3B, 4C), (1F, 2A, XB, 3C, 4A), (1F, 2A, XB, 3C, 4B), (1F, 2A, XB, 3C, 4C), (1F, 2A, XB, 3D, 4A), (1F, 2A, XB, 3D, 4B), (1F, 2A, XB, 3D, 4C), (1F, 2B, XA, 3A, 4A), (1F, 2B, XA, 3A, 4B), (1F, 2B, XA, 3A, 4C), (1F, 2B, XA, 3B, 4A), (1F, 2B, XA, 3B, 4B), (1F, 2B, XA, 3B, 4C), (1F, 2B, XA, 3C, 4A), (1F, 2B, XA, 3C, 4B), (1F, 2B, XA, 3C, 4C), (1F, 2B, XA, 3D, 4A), (1F, 2B, XA, 3D, 4B), (1F, 2B, XA, 3D, 4C), (1F, 2B, XB, 3A, 4A), (1F, 2B, XB, 3A, 4B), (1F, 2B, XB, 3A, 4C), (1F, 2B, XB, 3B, 4A), (1F, 2B, XB, 3B, 4B), (1F, 2B, XB, 3B, 4C), (1F, 2B, XB, 3C, 4A), (1F, 2B, XB, 3C, 4B), (1F, 2B, XB, 3C, 4C), (1F, 2B, XB, 3D, 4A), (1F, 2B, XB, 3D, 4B), (1F, 2B, XB, 3D, 4C), (1F, 2C, XA, 3A, 4A), (1F, 2C, XA, 3A, 4B), (1F, 2C, XA, 3A, 4C), (1F, 2C, XA, 3B, 4A), (1F, 2C, XA, 3B, 4B), (1F, 2C, XA, 3B, 4C), (1F, 2C, XA, 3C, 4A), (1F, 2C, XA, 3C, 4B), (1F, 2C, XA, 3C, 4C), (1F, 2C, XA, 3D, 4A), (1F, 2C, XA, 3D, 4B), (1F, 2C, XA, 3D, 4C), (1F, 2C, XB, 3A, 4A), (1F, 2C, XB, 3A, 4B), (1F, 2C, XB, 3A, 4C), (1F, 2C, XB, 3B, 4A), (1F, 2C, XB, 3B, 4B), (1F, 2C, XB, 3B, 4C), (1F, 2C, XB, 3C, 4A), (1F, 2C, XB, 3C, 4B), (1F, 2C, XB, 3C, 4C), (1F, 2C, XB, 3D, 4A), (1F, 2C, XB, 3D, 4B), (1F, 2C, XB, 3D, 4C), (1F, 2D, XA, 3A, 4A), (1F, 2D, XA, 3A, 4B), (1F, 2D, XA, 3A, 4C), (1F, 2D, XA, 3B, 4A), (1F, 2D, XA, 3B, 4B), (1F, 2D, XA, 3B, 4C), (1F, 2D, XA, 3C, 4A), (1F, 2D, XA, 3C, 4B), (1F, 2D, XA, 3C, 4C), (1F, 2D, XA, 3D, 4A), (1F, 2D, XA, 3D, 4B), (1F, 2D, XA, 3D, 4C), (1F, 2D, XB, 3A, 4A), (1F, 2D, XB, 3A, 4B), (1F, 2D, XB, 3A, 4C), (1F, 2D, XB, 3B, 4A), (1F, 2D, XB, 3B, 4B), (1F, 2D, XB, 3B, 4C), (1F, 2D, XB, 3C, 4A), (1F, 2D, XB, 3C, 4B), (1F, 2D, XB, 3C, 4C), (1F, 2D, XB, 3D, 4A), (1F, 2D, XB, 3D, 4B), (1F, 2D, XB, 3D, 4C), (1F, 2E, XA, 3A, 4A), (1F, 2E, XA, 3A, 4B), (1F, 2E, XA, 3A, 4C), (1F, 2E, XA, 3B, 4A), (1F, 2E, XA, 3B, 4B), (1F, 2E, XA, 3B, 4C), (1F, 2E, XA, 3C, 4A), (1F, 2E, XA, 3C, 4B), (1F, 2E, XA, 3C, 4C), (1F, 2E, XA, 3D, 4A), (1F, 2E, XA, 3D, 4B), (1F, 2E, XA, 3D, 4C), (1F, 2E, XB, 3A, 4A), (1F, 2E, XB, 3A, 4B), (1F, 2E, XB, 3A, 4C), (1F, 2E, XB, 3B, 4A), (1F, 2E, XB, 3B, 4B), (1F, 2E, XB, 3B, 4C), (1F, 2E, XB, 3C, 4A), (1F, 2E, XB, 3C, 4B), (1F, 2E, XB, 3C, 4C), (1F, 2E, XB, 3D, 4A), (1F, 2E, XB, 3D, 4B), (1F, 2E, XB, 3D, 4C), (1F, 2F, XA, 3A, 4A), (1F, 2F, XA, 3A, 4B), (1F, 2F, XA, 3A, 4C), (1F, 2F, XA, 3B, 4A), (1F, 2F, XA, 3B, 4B), (1F, 2F, XA, 3B, 4C), (1F, 2F, XA, 3C, 4A), (1F, 2F, XA, 3C, 4B), (1F, 2F, XA, 3C, 4C), (1F, 2F, XA, 3D, 4A), (1F, 2F, XA, 3D, 4B), (1F, 2F, XA, 3D, 4C), (1F, 2F, XB, 3A, 4A), (1F, 2F, XB, 3A, 4B), (1F, 2F, XB, 3A, 4C), (1F, 2F, XB, 3B, 4A), (1F, 2F, XB, 3B, 4B), (1F, 2F, XB, 3B, 4C), (1F, 2F, XB, 3C, 4A), (1F, 2F, XB, 3C, 4B), (1F, 2F, XB, 3C, 4C), (1F, 2F, XB, 3D, 4A), (1F, 2F, XB, 3D, 4B), (1F, 2F, XB, 3D, 4C), (1F, 2G, XA, 3A, 4A), (1F, 2G, XA, 3A, 4B), (1F, 2G, XA, 3A, 4C), (1F, 2G, XA, 3B, 4A), (1F, 2G, XA, 3B, 4B), (1F, 2G, XA, 3B, 4C), (1F, 2G, XA, 3C, 4A), (1F, 2G, XA, 3C, 4B), (1F, 2G, XA, 3C, 4C), (1F, 2G, XA, 3D, 4A), (1F, 2G, XA, 3D, 4B), (1F, 2G, XA, 3D, 4C), (1F, 2G, XB, 3A, 4A), (1F, 2G, XB, 3A, 4B), (1F, 2G, XB, 3A, 4C), (1F, 2G, XB, 3B, 4A), (1F, 2G, XB, 3B, 4B), (1F, 2G, XB, 3B, 4C), (1F, 2G, XB, 3C, 4A), (1F, 2G, XB, 3C, 4B), (1F, 2G, XB, 3C, 4C), (1F, 2G, XB, 3D, 4A), (1F, 2G, XB, 3D, 4B), (1F, 2G, XB, 3D, 4C), (1G, 2A, XA, 3A, 4A), (1G, 2A, XA, 3A, 4B), (1G, 2A, XA, 3A, 4C), (1G, 2A, XA, 3B, 4A), (1G, 2A, XA, 3B, 4B), (1G, 2A, XA, 3B, 4C), (1G, 2A, XA, 3C, 4A), (1G, 2A, XA, 3C, 4B), (1G, 2A, XA, 3C, 4C), (1G, 2A, XA, 3D, 4A), (1G, 2A, XA, 3D, 4B), (1G, 2A, XA, 3D, 4C), (1G, 2A, XB, 3A, 4A), (1G, 2A, XB, 3A, 4B), (1G, 2A, XB, 3A, 4C), (1G, 2A, XB, 3B, 4A), (1G, 2A, XB, 3B, 4B), (1G, 2A, XB, 3B, 4C), (1G, 2A, XB, 3C, 4A), (1G, 2A, XB, 3C, 4B), (1G, 2A, XB, 3C, 4C), (1G, 2A, XB, 3D, 4A), (1G, 2A, XB, 3D, 4B), (1G, 2A, XB, 3D, 4C), (1G, 2B, XA, 3A, 4A), (1G, 2B, XA, 3A, 4B), (1G, 2B, XA, 3A, 4C), (1G, 2B, XA, 3B, 4A), (1G, 2B, XA, 3B, 4B), (1G, 2B, XA, 3B, 4C), (1G, 2B, XA, 3C, 4A), (1G, 2B, XA, 3C, 4B), (1G, 2B, XA, 3C, 4C), (1G, 2B, XA, 3D, 4A), (1G, 2B, XA, 3D, 4B), (1G, 2B, XA, 3D, 4C), (1G, 2B, XB, 3A, 4A), (1G, 2B, XB, 3A, 4B), (1G, 2B, XB, 3A, 4C), (1G, 2B, XB, 3B, 4A), (1G, 2B, XB, 3B, 4B), (1G, 2B, XB, 3B, 4C), (1G, 2B, XB, 3C, 4A), (1G, 2B, XB, 3C, 4B), (1G, 2B, XB, 3C, 4C), (1G, 2B, XB, 3D, 4A), (1G, 2B, XB, 3D, 4B), (1G, 2B, XB, 3D, 4C), (1G, 2C, XA, 3A, 4A), (1G, 2C, XA, 3A, 4B), (1G, 2C, XA, 3A, 4C), (1G, 2C, XA, 3B, 4A), (1G, 2C, XA, 3B, 4B), (1G, 2C, XA, 3B, 4C), (1G, 2C, XA, 3C, 4A), (1G, 2C, XA, 3C, 4B), (1G, 2C, XA, 3C, 4C), (1G, 2C, XA, 3D, 4A), (1G, 2C, XA, 3D, 4B), (1G, 2C, XA, 3D, 4C), (1G, 2C, XB, 3A, 4A), (1G, 2C, XB, 3A, 4B), (1G, 2C, XB, 3A, 4C), (1G, 2C, XB, 3B, 4A), (1G, 2C, XB, 3B, 4B), (1G, 2C, XB, 3B, 4C), (1G, 2C, XB, 3C, 4A), (1G, 2C, XB, 3C, 4B), (1G, 2C, XB, 3C, 4C), (1G, 2C, XB, 3D, 4A), (1G, 2C, XB, 3D, 4B), (1G, 2C, XB, 3D, 4C), (1G, 2D, XA, 3A, 4A), (1G, 2D, XA, 3A, 4B), (1G, 2D, XA, 3A, 4C), (1G, 2D, XA, 3B, 4A), (1G, 2D, XA, 3B, 4B), (1G, 2D, XA, 3B, 4C), (1G, 2D, XA, 3C, 4A), (1G, 2D, XA, 3C, 4B), (1G, 2D, XA, 3C, 4C), (1G, 2D, XA, 3D, 4A), (1G, 2D, XA, 3D, 4B), (1G, 2D, XA, 3D, 4C), (1G, 2D, XB, 3A, 4A), (1G, 2D, XB, 3A, 4B), (1G, 2D, XB, 3A, 4C), (1G, 2D, XB, 3B, 4A), (1G, 2D, XB, 3B, 4B), (1G, 2D, XB, 3B, 4C), (1G, 2D, XB, 3C, 4A), (1G, 2D, XB, 3C, 4B), (1G, 2D, XB, 3C, 4C), (1G, 2D, XB, 3D, 4A), (1G, 2D, XB, 3D, 4B), (1G, 2D, XB, 3D, 4C), (1G, 2E, XA, 3A, 4A), (1G, 2E, XA, 3A, 4B), (1G, 2E, XA, 3A, 4C), (1G, 2E, XA, 3B, 4A), (1G; 2E, XA, 3B, 4B), (1G, 2E, XA, 3B, 4C), (1G, 2E, XA, 3C, 4A), (1G, 2E, XA, 3C, 4B), (1G, 2E, XA, 3C, 4C), (1G, 2E, XA, 3D, 4A), (1G, 2E, XA, 3D, 4B), (1G, 2E, XA, 3D, 4C), (1G, 2E, XB, 3A, 4A), (1G, 2E, XB, 3A, 4B), (1G, 2E, XB, 3A, 4C), (1G, 2E, XB, 3B, 4A), (1G, 2E, XB, 3B, 4B), (1G, 2E, XB, 3B, 4C), (1G, 2E, XB, 3C, 4A), (1G, 2E, XB, 3C, 4B), (1G, 2E, XB, 3C, 4C), (1G, 2E, XB, 3D, 4A), (1G, 2E, XB, 3D, 4B), (1G, 2E, XB, 3D, 4C), (1G, 2F, XA, 3A, 4A), (1G, 2F, XA, 3A, 4B), (1G, 2F, XA, 3A, 4C), (1G, 2F, XA, 3B, 4A), (1G, 2F, XA, 3B, 4B), (1G, 2F, XA, 3B, 4C), (1G, 2F, XA, 3C, 4A), (1G, 2F, XA, 3C, 4B), (1G, 2F, XA, 3C, 4C), (1G, 2F, XA, 3D, 4A), (1G, 2F, XA, 3D, 4B), (1G, 2F, XA, 3D, 4C), (1G, 2F, XB, 3A, 4A), (1G, 2F, XB, 3A, 4B), (1G, 2F, XB, 3A, 4C), (1G, 2F, XB, 3B, 4A), (1G, 2F, XB, 3B, 4B), (1G, 2F, XB, 3B, 4C), (1G, 2F, XB, 3C, 4A), (1G, 2F, XB, 3C, 4B), (1G, 2F, XB, 3C, 4C), (1G, 2F, XB, 3D, 4A), (1G, 2F, XB, 3D, 4B), (1G, 2F, XB, 3D, 4C), (1G, 2G, XA, 3A, 4A), (1G, 2G, XA, 3A, 4B), (1G, 2G, XA, 3A, 4C), (1G, 2G, XA, 3B, 4A), (1G, 2G, XA, 3B, 4B), (1G, 2G, XA, 3B, 4C), (1G, 2G, XA, 3C, 4A), (1G, 2G, XA, 3C, 4B), (1G, 2G, XA, 3C, 4C), (1G, 2G, XA, 3D, 4A), (1G, 2G, XA, 3D, 4B), (1G, 2G, XA, 3D, 4C), (1G, 2G, XB, 3A, 4A), (1G, 2G, XB, 3A, 4B), (1G, 2G, XB, 3A, 4C), (1G, 2G, XB, 3B, 4A), (1G, 2G, XB, 3B, 4B), (1G, 2G, XB, 3B, 4C), (1G, 2G, XB, 3C, 4A), (1G, 2G, XB, 3C, 4B), (1G, 2G, XB, 3C, 4C), (1G, 2G, XB, 3D, 4A), (1G, 2G, XB, 3D, 4B), (1G, 2G, XB, 3D, 4C)

And ($R^1$, $R^2$, X, $R^3$, $R^4$)=(1A, 2A, XA, 3A, 4A) is the compound which $R^1$ is 1A, $R^2$ is 2A, X is XA, $R^3$ is 3A and $R^4$ is 4A. The other combinations are the same.

Experimental Example

The inhibitory activities against integrase of the compounds in the present invention have been determined by the assay described below.

(1) Preparation of DNA Solutions.

Substrate DNA and target DNA, which sequences were indicated below, were synthesized by Amersham Pharmacia Biotech and dissolved in KTE buffer (composition: 100 mM KCl, 1 mM EDTA, 10 mM Tris-HCl (pH 7.6)) at concentration of 2 pmol/µl and 0.5 pmol/µl, respectively. The DNA solutions were annealed with each complement by slowly cooling after heating.

(Substrate DNA)

5'-Biotin-ACC CTT TTA GTC AGT GTG GAA AAT CTC TAG CAG T-3'

3'-GAA AAT CAG TCA CAC CTT TTA GAG ATC GTC A-5'

(Target DNA)

5'-TGA CCA AGG GCT AAT TCA CT-Dig-3'

3'-Dig-ACT GGT TCC CGA TTA AGT GA-5'

(2) Calculations of the Percent Inhibitions (the $IC_{50}$ Values of Test Compounds)

Streptavidin, obtained from Vector Laboratories, was dissolved in 0.1 M carbonate buffer (composition: 90 mM $Na_2CO_3$, 10 mM $NaHCO_3$) at concentration of 40 g/ml. After coating each well of microtiter plates (obtained from NUNC) with 50 µL of the above solution at 4° C. over night, each well was washed twice with PBS (composition: 13.7 mM NaCl, 0.27 mM KCl, 0.43 mM $Na_2HPO_4$, 0.14 mM $KH_2PO_4$) and blocked with 300 µl of 1% skim milk in PBS for 30 min. Additionally, each well was washed twice with PBS and added 50 µl of substrate DNA solution (0.04 pmol/µl) diluted to one fiftieth with NTE buffer (composition: 1M NaCl, 10 mM Tris-HCl (pH8.0), 1 mM EDTA). The microtiter plates were kept at room temperature for 30 min. Then, each well was washed twice with PBS and once with $H_2O$.

Subsequently, in the each well prepared above were added 45 µl of the reaction buffer prepared from 12 µl of the buffer (composition: 150 mM MOPS (pH 7.2), 75 mM $MnCl_2$, 50 mM 2-mercaptoethanol, 25% glycerol, 500 µg/ml bovine serum albumin-fraction V), 1 µl of target DNA (5 pmol/µl), and 32 µl of the distilled water. Additionally, 6 µl of either a test compound in DMSO or DMSO for positive control (PC) was mixed with the above reaction buffer, then 9 µl of an integrase solution (30 pmol) was added and mixed well. In the well of negative control (NC) was added 9 µl of the integrase dilution buffer (composition: Hepes (pH7.6), 400 mM potassium glutamate, 1 mM EDTA, 0.1% NP-40, 20% glycerol, 1 mM DTT, 4M urea).

The microtiter plates were incubated at 30° C. for 1 hour. The reaction solution was removed and each well was washed twice with PBS. Subsequently, each well of the microtiter plates was filled with 100 µl of anti-digoxigenin antibody labeled with alkaline phosphatase (Sheep Fab fragment: obtained from Boehringer) and incubated at 30° C. for 1 hour. Then, each well was washed twice with 0.05% Tween20 in PBS and once with PBS. Next, 150 µl of the Alkaline phosphatase reaction buffer (composition: 10 mM p-Nitrophenylphosphate (obtained from Vector Laboratories), 5 mM MgCl$_2$, 100 mM NaCl, 100 mM Tris-HCl (pH 9.5)) was added in each well. The microtiter plates were incubated at 30° C. for 2 hours. The optical density (OD) at 405 nm of each well was measured and the percent inhibition was determined by the following expression.

The percent inhibition (%)=100[1−{(C abs.−NC abs.)/(PC abs.−NC abs.)}]

C abs.; the OD of the well of the
NC abs.: the OD of the negative control (NC)
PC abs.: the OD of the positive control (PC)

When the percent inhibition (%) is X % at the concentration of x μg/ml and the percent inhibition (%) is Y % at the concentration of y μg/ml, one of which is more than 50% and the other is less than 50%, IC$_{50}$ can be determined by the following expression.

IC$_{50}$(μg/ml)=x−{(X−50),(x−y)/(X−Y)}

The IC$_{50}$ values, the concentration of the compounds at percent inhibition 50%, are shown in the following Table 1. Compound No. in the Table 1 is the same as compound No. of the above example.

TABLE 1

| compound No. | IC$_{50}$ (μg/ml) |
| --- | --- |
| A-7 | 0.76 |
| A-12-a | 0.33 |
| A-17 | 0.80 |
| A-17-c | 0.94 |
| A-50 | 0.16 |
| A-141-k | 0.68 |
| A-158 | 0.67 |
| B-6-a | 1.6 |
| B-6-d | 2.4 |
| B-12 | 0.29 |
| B-12-b | 0.21 |
| B-29 | 0.12 |
| B-68 | 0.22 |
| C-22 | 0.48 |
| C-26 | 0.36 |
| C-39 | 0.23 |
| D-5 | 0.45 |
| E-8 | 0.14 |
| E-16 | 0.12 |
| F-4 | 0.57 |
| G-7 | 0.48 |
| H-7 | 0.68 |
| I-4 | 0.50 |
| J-4 | 0.26 |
| K-4 | 0.57 |
| L-4 | 0.49 |
| M-6 | 2.9 |

The compounds of the present invention except the above compounds had the same or more integrase inhibitory activities.

And the compounds of the present invention have high stability against metabolism and they are superior inhibitory agents against integrase.

Formulation Example

It is to be noted that the following Formulation Examples 1 to 8 are mere illustration, but not intended to limit the scope of the invention. The term "active ingredient" means the compounds of the present invention, the tautomers, the prodrugs thereof, their pharmaceutical acceptable salts, or their solvate.

Formulation Example 1

Hard gelatin capsules are prepared using of the following ingredients:

| | Dose (mg/capsule) |
| --- | --- |
| Active ingredient | 250 |
| Starch, dried | 200 |
| Magnesium stearate | 10 |
| Total | 460 mg |

Formulation Example 2

A tablet is prepared using of the following ingredients:

| | Dose (mg/tablet) |
| --- | --- |
| Active ingredient | 250 |
| Cellulose, microcrystals | 400 |
| Silicon dioxide, fumed | 10 |
| Stearic acid | 5 |
| Total | 665 mg |

The components are blended and compressed to form tablets each weighing 665 mg.

Formulation Example 3

An aerosol solution is prepared containing the following components:

| | Weight |
| --- | --- |
| Active ingredient | 0.25 |
| Ethanol | 25.75 |
| Propellant 22 (chlorodifluoromethane) | 74.00 |
| Total | 100.00 |

The active ingredient is mixed with ethanol and the admixture added to a portion of the propellant 22, cooled to −30° C. and transferred to a filling device. The required amount is then fed to a stainless steel container and diluted with the reminder of the propellant. The valve units are then fitted to the container.

Formulation Example 4

Tablets, each containing 60 mg of active ingredient, are made as follows.

| | |
| --- | --- |
| Active ingredient | 60 mg |
| Starch | 45 mg |
| Microcrystals cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve, and the mixed thoroughly. The aqueous solution containing polyvinylpyrrolidone is mixed with the resultant powder, and the admixture then is passed through a No. 14 mesh U.S. sieve. The granules so produced are dried at 50° C. and passed through a No. 18 mesh U.S. sieve. The sodium carboxymethyl starch, magnesium stearate, and talc, previously passed through No. 60 mesh U.S. sieve, are then added to the granules which, after mixing, are compressed on a tablet machine to yield tablets each weighing 150 mg.

Formulation Example 5

Capsules, each containing 80 mg of active ingredient, are made as follows:

| | |
|---|---|
| Active ingredient | 80 mg |
| Starch | 59 mg |
| Microcrystals cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation Example 6

Suppositories, each containing 225 mg of active ingredient, are made as follows:

| | |
|---|---|
| Active ingredient | 225 mg |
| Saturated fatty acid glycerides | 2000 mg |
| Total | 2225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation Example 7

Suspensions, each containing 50 mg of active ingredient, are made as follows:

| | |
|---|---|
| Active ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 U.S. sieve, and mixed with the sodium carboxymethyl cellulose and syrup to form a smooth paste. The benzoic acid solution, flavor and color are diluted with a portion of the water and added, with stirring. Sufficient water is then added to produce the required volume.

Formulation Example 8

An intravenous formulation may be prepared as follows:

| | |
|---|---|
| Active ingredient | 100 mg |
| Isotonic saline | 1000 ml |

The solution of the above ingredients is generally administered intravenously to a subject at a rate of 1 ml per minute.

INDUSTRIAL APPLICABILITY

The compounds of the present invention have inhibitory activities against integrase and useful for treatment of AIDS as an antiviral agent and an anti-HIV agent.

The invention claimed is:

1. A method of inhibiting HIV integrase activity, the method comprising contacting an HIV integrase protein with an effective amount of a compound of Formula (I-z):

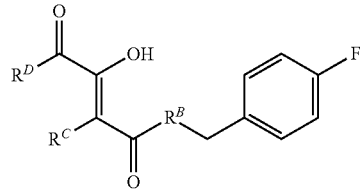

(I-z)

wherein
$R^C$ and $R^D$ taken together with the neighboring carbon atoms form a 5- to 6-membered heterocycle which contains heteroatom(s) of O and/or N and which is optionally condensed with a benzene ring;
$R^B$ is 2-furyl; and
the ring formed by $R^C$ and $R^D$ and the neighboring carbon atoms is optionally substituted with —$Z^1$—$Z^2$—$Z^3$—$R^1$ and/or $C_1$-$C_6$ alkyl, wherein
$Z^1$ and $Z^3$ are independently a bond or $C_1$-$C_6$ alkylene;
$Z^2$ is a bond, —$NR^2SO_2$—, —$NR^2CO$—, or —$CONR^2$;
$R^2$ is hydrogen; and
$R^1$ is aryl or heteroaryl, each of which is optionally substituted with $C_1$-$C_6$ alkyl;
or a salt thereof.

2. The method of claim 1, wherein $R^C$ and $R^D$ taken together with the neighboring carbon atoms form a 6-membered N-containing heterocycle.

3. The method of claim 1, wherein the ring formed by $R^C$ and $R^D$ is substituted with $C_1$-$C_6$ alkyl.

4. The method of claim 1, wherein the ring formed by $R^C$ and $R^D$ is substituted with —$Z^1$—$Z^2$—$Z^3$—$R^1$, wherein
$Z^1$ is $C_1$-$C_6$ alkylene;
$Z^2$ is —$NR^2CO$—;
$Z^3$ is a bond;
$R^2$ is hydrogen; and
$R^1$ is heteroaryl optionally substituted with $C_1$-$C_6$ alkyl.

5. The method of claim 2, wherein the ring formed by $R^C$ and $R^D$ and the neighboring carbon atoms is substituted with $C_1$-$C_6$ alkyl.

6. The method of claim 1, wherein the ring formed by $R^C$ and $R^D$ and the neighboring carbon atoms is substituted with —$Z^1$—$Z^2$—$Z^3$—$R^1$, wherein
$Z^1$ and $Z^3$ are independently a bond or $C_1$-$C_6$ alkylene;
$Z^2$ is a bond, —$NR^2SO_2$—, —$NR^2CO$—, or —$CONR^2$;
$R^2$ is hydrogen; and
$R^1$ is aryl or heteroaryl, each of which is optionally substituted with $C_1$-$C_6$ alkyl.

7. The method of claim 2, wherein the ring formed by $R^C$ and $R^D$ and the neighboring carbon atoms is substituted with methyl.

8. The method of claim 7, wherein the ring formed by $R^C$ and $R^D$ and the neighboring carbon atoms is substituted with —$Z^1$—$Z^2$—$Z^3$—$R^1$, wherein
$Z^1$ is $C_1$-$C_6$ alkylene;
$Z^2$ is a bond, —$NR^2SO_2$—, —$NR^2CO$—, or —$CONR^2$—;
$Z^3$ is a bond;
$R^2$ is hydrogen; and
$R^1$ is aryl or heteroaryl, each of which is optionally substituted with $C_1$-$C_6$ alkyl.

9. The method of claim 8, wherein
$Z^2$ is —$NR^2CO$—; and
$R^1$ is heteroaryl, which is optionally substituted with $C_1$-$C_6$ alkyl.

10. The method of claim 9, wherein $R^1$ is 1,3,4-oxadiazol-2-yl optionally substituted with $C_1$-$C_6$ alkyl.

11. The method of claim 10, wherein $R^1$ is 1,3,4-oxadiazol-2-yl substituted with $C_1$-$C_6$ alkyl.

* * * * *